(12) United States Patent
Buckley et al.

(10) Patent No.: US 12,023,385 B2
(45) Date of Patent: Jul. 2, 2024

(54) TUNABLE ENDOGENOUS PROTEIN DEGRADATION WITH HETEROBIFUNCTIONAL COMPOUNDS

(71) Applicant: DANA-FARBER CANCER INSTITUTE, INC., Boston, MA (US)

(72) Inventors: Dennis Buckley, Jamaica Plain, MA (US); Georg Winter, Vienna (AT); Andrew J. Phillips, Cambridge, MA (US); Timothy P. Heffernan, Cambridge, MA (US); James Bradner, Weston, MA (US); Justin Roberts, Cambridge, MA (US); Behnam Nabet, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 1328 days.

(21) Appl. No.: 16/483,209

(22) PCT Filed: Feb. 8, 2018

(86) PCT No.: PCT/US2018/017468
§ 371 (c)(1),
(2) Date: Aug. 2, 2019

(87) PCT Pub. No.: WO2018/148443
PCT Pub. Date: Aug. 16, 2018

(65) Prior Publication Data
US 2019/0374657 A1    Dec. 12, 2019

Related U.S. Application Data

(60) Provisional application No. 62/457,127, filed on Feb. 9, 2017, provisional application No. 62/456,654, filed on Feb. 8, 2017.

(51) Int. Cl.
| | | |
|---|---|---|
| C12N 15/90 | (2006.01) | |
| A61K 35/12 | (2015.01) | |
| A61K 35/407 | (2015.01) | |
| A61K 38/46 | (2006.01) | |
| A61K 47/55 | (2017.01) | |
| A61K 48/00 | (2006.01) | |
| C12N 9/10 | (2006.01) | |
| C12N 9/22 | (2006.01) | |
| C12N 9/90 | (2006.01) | |

(52) U.S. Cl.
CPC ........ *A61K 48/0058* (2013.01); *A61K 35/407* (2013.01); *A61K 38/465* (2013.01); *A61K 48/0025* (2013.01); *A61K 48/0083* (2013.01); *C12N 9/104* (2013.01); *C12N 9/22* (2013.01); *C12N 9/90* (2013.01); *C07K 2319/20* (2013.01); *C07K 2319/95* (2013.01); *C12Y 502/01008* (2013.01)

(58) Field of Classification Search
None
See application file for complete search history.

(56) References Cited

U.S. PATENT DOCUMENTS

| 2004/0072319 A1 | 4/2004 | Nash et al. |
| 2016/0235730 A1 | 8/2016 | Bradner et al. |

FOREIGN PATENT DOCUMENTS

| CN | 108350062 A | 7/2018 | |
| EP | 3331906 A1 | 6/2018 | |
| EP | 3445357 A1 | 2/2019 | |
| WO | WO-2012078559 A2 * | 6/2012 | ....... A61K 47/48015 |
| WO | WO-2013106643 A2 * | 7/2013 | ........... A61K 31/422 |
| WO | 2016/105518 A1 | 6/2016 | |
| WO | 2016/197032 A1 | 12/2016 | |
| WO | 2016/205764 A1 | 12/2016 | |
| WO | 2017/007612 A1 | 1/2017 | |
| WO | 2017/024319 A1 | 2/2017 | |
| WO | 2017024319 A1 | 2/2017 | |
| WO | 2017/185036 A1 | 10/2017 | |

OTHER PUBLICATIONS

Bondeson et al. Lessons in PROTAC design from selective degradation with a promiscuous warhead (Cell Chem Biol, 2018, 25:78-87) (Year: 2018).*
Mohanty et al. Hydrophobic Core Variations Provide a Structural Framework for Tyrosine Kinase Evolution and Functional Specialization (PLoS Genet, 2016, 12:e1005885) (Year: 2016).*
Buckley, Dennis L., et al., "HaloPROTACS: Use of Small Molecule PROTACs to Induce Degradation of HaloTag Fusion Proteins", ACS Chem. Biol., 2015, vol. 10, pp. 1831-1837.
Neklesa, Taavi K., et al., "Small-Molecule Hydrophobic Tagging Induced Degradation of HaloTag Fusion Proteins", Nat. Chem. Biol., 2012, vol. 7, No. 8, pp. 538-543.
Bondeson, Daniel P., et al., "Catalytic in Vivo Protein Knockdown by Small-Molecule PROTACs", Nat. Chem. Biol., Jun. 10, 2015, vol. 11, No. 8, pp. 611-617.

(Continued)

*Primary Examiner* — Arthur S Leonard
(74) *Attorney, Agent, or Firm* — BURNS & LEVINSON, LLP; Daniel W. Clarke; Shawn P. Foley

(57) ABSTRACT

The present invention provides a means to modulate gene expression in vivo in a manner that avoids problems associated with CRISPR endogenous protein knock-out or knock-in strategies and strategies that provide for correction, or alteration, of single nucleotides. The invention includes inserting into the genome a nucleotide encoding a heterobifunctional compound targeting protein (dTAG) in-frame with the nucleotide sequence of a gene encoding an endogenously expressed protein of interest which, upon expression, produces an endogenous protein-dTAG hybrid protein. This allows for targeted protein degradation of the dTAG and the fused endogenous protein using a heterobifunctional compound.

24 Claims, 130 Drawing Sheets
Specification includes a Sequence Listing.

(56) References Cited

OTHER PUBLICATIONS

Bondeson, Daniel P., et al., "Targeted Protein Degradation by Small Molecules", Ann. Rev. Pharmacol. Toxicol., Oct. 12, 2016, vol. 57, No. 1, pp. 107-123.
Buckley, Dennis L., et al., "Small-Molecule Control of Intracellular Protein Levels through Modulation of the Ubiquitin Proteasome System", Angew. Chem. Int. Ed., Jan. 23, 2014, vol. 53, No. 9, pp. 2312-2330.
Li, H., et al., "TGF-B Induces Degradation of PTHrP Through Ubiquitin-Proteasome System in Hepatocellular Carcinoma", Journal of Cancer; Apr. 5, 2015, vol. 6, pp. 511-518.
Robers et al., "Fluorescent Labeling of Proteins in Living Cells Using the FKBP12(F36V) Tag", Cytometry Part A, 2009, vol. 75A, pp. 207-224.

\* cited by examiner

| | |
|---|---|
|  | dBET15 |
|  | dBET16 |
|  | dBET17 |
|  | dBET18 |
|  | dGR1 |
|  | dGR2 |

| Cmpd. No. | Structure |
|---|---|
| dBET19 | 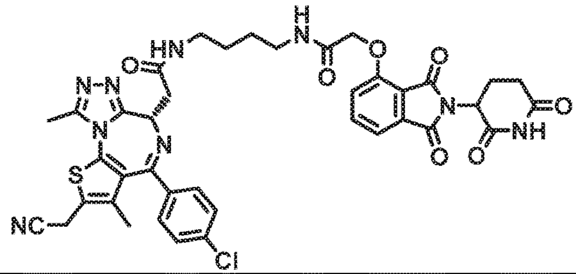 |
| dBET20 | 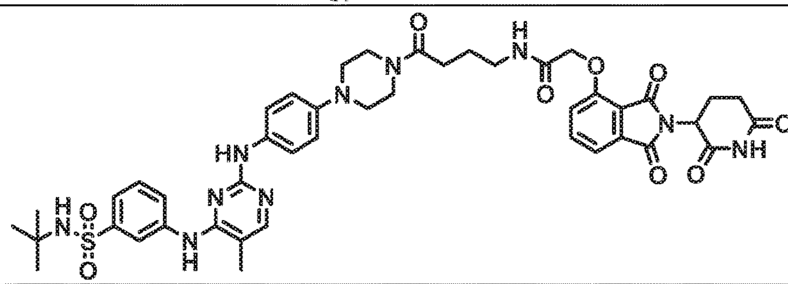 |
| dBET21 | 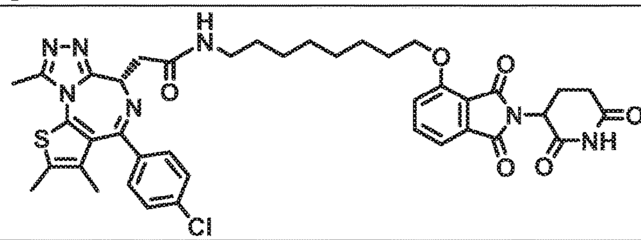 |
| dBET22 | 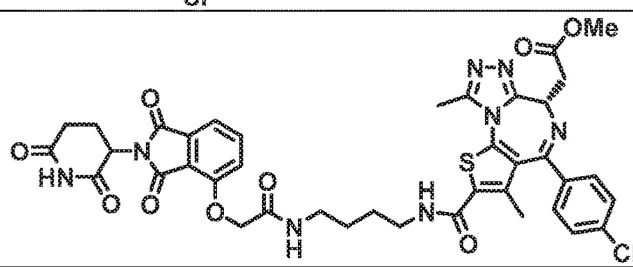 |
| dBET23 | 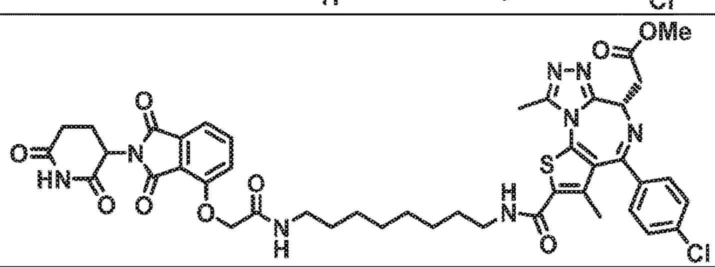 |

| | |
|---|---|
| dBET24 |  |
| dBET25 |  |
| dBET26 |  |
| dBET27 |  |
| dBET28 |  |

| | |
|---|---|
| dBET29 |  |
| dBET30 |  |
| dBET31 |  |
| dBET32 |  |
| dBET33 |  |

| | |
|---|---|
| dBET34 |  |
| dBET35 |  |
| dBET36 |  |
| dBET37 |  |
| dBET38 |  |
| dBET39 |  |

| | |
|---|---|
| dBET40 |  |
| dBET41 |  |
| dBET42 |  |
| dBET43 |  |
| dBET44 |  |

| | |
|---|---|
| dBET45 |  |
| dBET46 |  |
| dBET50 |  |
| dBET51 |  |
| dBET52 |  |

| dBET100 |  |
| --- | --- |
| dBET101 |  |
| dBET102 |  |
| dBET103 |  |
| dBET104 |  |

| | |
|---|---|
| dBET105 |  |
| dBET106 |  |
| dBET107 |  |
| dFKBP-14 |  |

| | |
|---|---|
| dFKBP-18 |  |
| dFKBP-19 |  |
| dFKBP-20 |  |

| | |
|---|---|
| dFKBP-36 |  |
| dFKBP-37 |  |
| dFKBP-38 |  |
| dFKBP100 |  |

| Cmpd. No. | Structure |
|---|---|
| dBET200 | 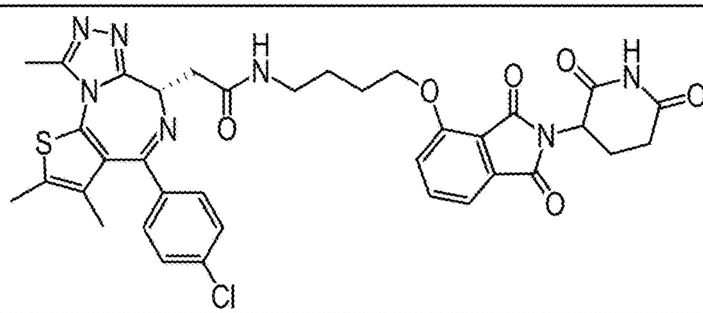 |
| dBET201 | 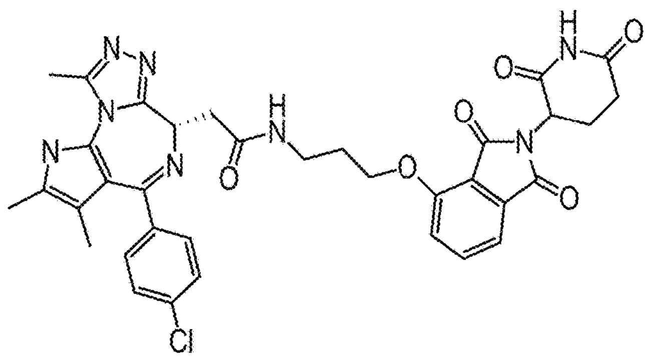 |
| dBET202 | 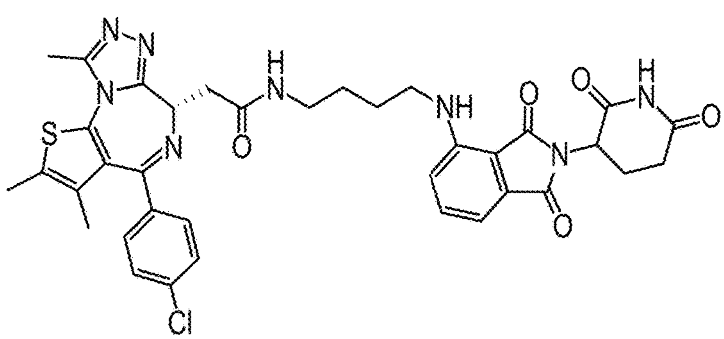 |
| dBET203 | 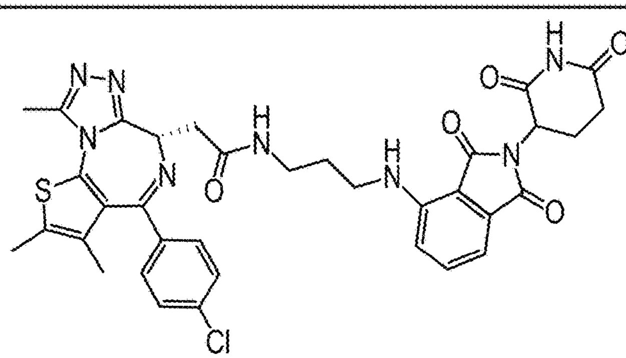 |

FIG. 32A

| | | |
|---|---|---|
| dFKBP-2-I-m″ |  |  |
| dFKBP-2-I-o |  |  |
| dFKBP-2-I-o″ |  |  |
| dFKBP-2-I-p |  |  |
| dFKBP-2-I-p″ |  |  |
| dFKBP-3-I-m |  |  |
| dFKBP-3-I-m″ |  |  |

| | | |
|---|---|---|
| dFKBP-17-I-o |  |  |
| dFKBP-17-I-o″ |  |  |
| dFKBP-17-I-p |  |  |
| dFKBP-17-I-p″ |  |  |
| dFKBP-26-I-m |  |  |
| dFKBP-26-I-m″ |  |  |
| dFKBP-26-I-o |  |  |

| | | |
|---|---|---|
| dFKBP-26-I-o'' |  |  |
| dFKBP-26-I-p |  |  |
| dFKBP-26-I-p'' |  |  |
| dFKBP-24-I-m |  |  |
| dFKBP-24-I-m'' |  |  |
| dFKBP-24-I-o |  |  |
| dFKBP-24-I-o'' |  |  |

| | | |
|---|---|---|
| dFKBP-24-I-p |  |  |
| dFKBP-24-I-p″ |  |  |
| dFKBP-27-I-m |  |  |
| dFKBP-27-I-m″ |  |  |
| dFKBP-27-I-o |  |  |
| dFKBP-27-I-o″ |  |  |

FIG. 32L

| | | |
|---|---|---|
| dFKBP-16-I-m |  |  |
| dFKBP-16-I-m" |  |  |
| dFKBP-16-I-o |  |  |
| dFKBP-16-I-o" |  |  |
| dFKBP-16-I-p |  |  |

| | | |
|---|---|---|
| dFKBP-18-I-m |  |  |
| dFKBP-18-I-m″ |  |  |
| dFKBP-18-I-o |  |  |
| dFKBP-18-I-o″ |  |  |
| dFKBP-18-I-p |  |  |
| dFKBP-18-I-p″ |  |  |

| | | |
|---|---|---|
| dFKBP -14-I- m″ |  |  |
| dFKBP -14-I-o |  |  |
| dFKBP -14-I- o″ |  |  |
| dFKBP -14-I-p |  |  |
| dFKBP -14-I- p″ |  |  |
| dFKBP -19-I- m |  |  |

FIG. 32U

| | | |
|---|---|---|
| dFKBP-15-I-o |  |  |
| dFKBP-15-I-o″ |  |  |
| dFKBP-15-I-p |  |  |
| dFKBP-15-I-p″ |  |  |
| dFKBP-A-m |  |  |
| dFKBP-A-m″ |  |  |

FIG. 32W

| | | |
|---|---|---|
| dFKBP-34-I-o″ |  |  |
| dFKBP-34-I-p |  |  |
| dFKBP-34-I-p″ |  |  |
| dFKBP-36-I-m |  |  |
| dFKBP-36-I-m″ |  |  |
| dFKBP-36-I-o |  |  |
| dFKBP-36-I-o″ |  |  |

FIG. 32Y

| | | |
|---|---|---|
| dFKBP-35-I-p″ |  |  |
| dFKBP-37-I-m |  |  |
| dFKBP-37-I-m″ |  |  |
| dFKBP-37-I-o |  |  |
| dFKBP-37-I-o″ |  |  |
| dFKBP-37-I-p |  |  |
| dFKBP-37-I-p″ |  |  |

| | | |
|---|---|---|
| dFKBP-30-I-m |  |  |
| dFKBP-30-I-m″ |  |  |
| dFKBP-30-I-o |  |  |
| dFKBP-30-I-o″ |  |  |
| dFKBP-30-I-p |  |  |
| dFKBP-30-I-p″ |  |  |

| | | |
|---|---|---|
| dFKBP-32-I-m |  |  |
| dFKBP-32-I-m″ |  |  |
| dFKBP-32-I-o |  |  |
| dFKBP-32-I-o″ |  |  |
| dFKBP-32-I-p |  |  |
| dFKBP-32-I-p″ |  |  |

FIG. 32DD

| | | |
|---|---|---|
| dFKBP-38-I-m" |  |  |
| dFKBP-38-I-o |  |  |
| dFKBP-38-I-o" |  |  |
| dFKBP-38-I-p |  |  |
| dFKBP-38-I-p" |  |  | dFKBP-1-o dFKBP-1-p dFKBP-2-o dFKBP-2-*p* dFKBP*6-*o* dFKBP*6-*p* dFKBP*7-*o* dFKBP*7-p dFKBP*8-o dFKBP*9-o dFKBP*9-p

X2-o

X2-p dFKBP13-o dFKBP13-p dFKBP14-o dFKBP16-o dFKBP16-p dFKBP17-o dFKBP17-p dFKBP18-o dFKBP18-p dFKBP27-o dFKBP27-p dFKBP28-o dFKBP30-o dFKBP30-p dFKBP31-o dFKBP31-p dFKBP32-o dFKBP32-p dFKBP33-o dFKBP33-p dFKBP34-o dFKBP49-p dFKBP49-m dFKBP49-o

SEQUENCE LISTING

<160> NUMBER OF SEQ ID NOS: 63

<210> SEQ ID NO 1
<211> LENGTH: 107
<212> TYPE: PRT
<213> ORGANISM: Homo sapiens

<400> SEQUENCE: 1

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
                100                 105

<210> SEQ ID NO 2
<211> LENGTH: 107
<212> TYPE: PRT
<213> ORGANISM: Artificial Sequence
<220> FEATURE:
<223> OTHER INFORMATION: FKBP12 derived amino acid sequence with a
      mutation of the phenylalanine (F) at amino acid position 35 to
      valine (V) (F36V)

<400> SEQUENCE: 2

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
                100                 105

<210> SEQ ID NO 3
<211> LENGTH: 1362
<212> TYPE: PRT
<213> ORGANISM: Homo sapiens

<400> SEQUENCE: 3

Met Ser Ala Glu Ser Gly Pro Gly Thr Arg Leu Arg Asn Leu Pro Val
1               5                   10                  15

Met Gly Asp Gly Leu Glu Thr Ser Gln Met Ser Thr Thr Gln Ala Gln
            20                  25                  30

Ala Gln Pro Gln Pro Ala Asn Ala Ala Ser Thr Asn Pro Pro Pro Pro
            35                  40                  45

Glu Thr Ser Asn Pro Asn Lys Pro Lys Arg Gln Thr Asn Gln Leu Gln
    50                  55                  60

Tyr Leu Leu Arg Val Val Leu Lys Thr Leu Trp Lys His Gln Phe Ala
65                  70                  75                  80

Trp Pro Phe Gln Gln Pro Val Asp Ala Val Lys Leu Asn Leu Pro Asp
                85                  90                  95
```

```
Tyr Tyr Lys Ile Ile Lys Thr Pro Met Asp Met Gly Thr Ile Lys Lys
            100                 105                 110

Arg Leu Glu Asn Asn Tyr Tyr Trp Asn Ala Gln Glu Cys Ile Gln Asp
            115                 120                 125

Phe Asn Thr Met Phe Thr Asn Cys Tyr Ile Tyr Asn Lys Pro Gly Asp
            130                 135                 140

Asp Ile Val Leu Met Ala Glu Ala Leu Glu Lys Leu Phe Leu Gln Lys
145                 150                 155                 160

Ile Asn Glu Leu Pro Thr Glu Thr Glu Ile Met Ile Val Gln Ala
                    165                 170                 175

Lys Gly Arg Gly Arg Gly Arg Lys Glu Thr Gly Thr Ala Lys Pro Gly
            180                 185                 190

Val Ser Thr Val Pro Asn Thr Thr Gln Ala Ser Thr Pro Pro Gln Thr
            195                 200                 205

Gln Thr Pro Gln Pro Asn Pro Pro Val Gln Ala Thr Pro His Pro
            210                 215                 220

Phe Pro Ala Val Thr Pro Asp Leu Ile Val Gln Thr Pro Val Met Thr
225                 230                 235                 240

Val Val Pro Pro Gln Pro Leu Gln Thr Pro Pro Val Pro Pro Gln
                    245                 250                 255

Pro Gln Pro Pro Pro Ala Pro Ala Pro Gln Pro Val Gln Ser His Pro
            260                 265                 270

Pro Ile Ile Ala Ala Thr Pro Gln Pro Val Lys Thr Lys Lys Gly Val
            275                 280                 285

Lys Arg Lys Ala Asp Thr Thr Thr Pro Thr Thr Ile Asp Pro Ile His
290                 295                 300

Glu Pro Pro Ser Leu Pro Pro Glu Pro Lys Thr Thr Lys Leu Gly Gln
305                 310                 315                 320

Arg Arg Glu Ser Ser Arg Pro Val Lys Pro Pro Lys Lys Asp Val Pro
                    325                 330                 335

Asp Ser Gln Gln His Pro Ala Pro Glu Lys Ser Ser Lys Val Ser Glu
            340                 345                 350

Gln Leu Lys Cys Cys Ser Gly Ile Leu Lys Glu Met Phe Ala Lys Lys
            355                 360                 365

His Ala Ala Tyr Ala Trp Pro Phe Tyr Lys Pro Val Asp Val Glu Ala
            370                 375                 380

Leu Gly Leu His Asp Tyr Cys Asp Ile Ile Lys His Pro Met Asp Met
385                 390                 395                 400

Ser Thr Ile Lys Ser Lys Leu Glu Ala Arg Glu Tyr Arg Asp Ala Gln
                    405                 410                 415

Glu Phe Gly Ala Asp Val Arg Leu Met Phe Ser Asn Cys Tyr Lys Tyr
            420                 425                 430

Asn Pro Pro Asp His Glu Val Val Ala Met Ala Arg Lys Leu Gln Asp
            435                 440                 445

Val Phe Glu Met Arg Phe Ala Lys Met Pro Asp Glu Pro Glu Glu Pro
450                 455                 460

Val Val Ala Val Ser Ser Pro Ala Val Pro Pro Thr Lys Val Val
                    470                 475                 480

Ala Pro Pro Ser Ser Ser Asp Ser Ser Asp Ser Ser Ser Asp Ser
            485                 490                 495

Asp Ser Ser Thr Asp Asp Ser Glu Glu Glu Arg Ala Gln Arg Leu Ala
            500                 505                 510
```

-continued

Glu Leu Gln Glu Gln Leu Lys Ala Val His Glu Gln Leu Ala Ala Leu
        515                 520                 525

Ser Gln Pro Gln Gln Asn Lys Pro Lys Lys Glu Lys Asp Lys Lys
530                 535                 540

Glu Lys Lys Lys Glu Lys His Lys Arg Lys Glu Glu Val Glu Glu Asn
545                 550                 555                 560

Lys Lys Ser Lys Ala Lys Glu Pro Pro Lys Lys Thr Lys Lys Asn
            565                 570                 575

Asn Ser Ser Asn Ser Asn Val Ser Lys Lys Glu Pro Ala Pro Met Lys
                580                 585                 590

Ser Lys Pro Pro Thr Tyr Glu Ser Glu Glu Glu Asp Lys Cys Lys
        595                 600                 605

Pro Met Ser Tyr Glu Glu Lys Arg Gln Leu Ser Leu Asp Ile Asn Lys
610                 615                 620

Leu Pro Gly Glu Lys Leu Gly Arg Val Val His Ile Ile Gln Ser Arg
625                 630                 635                 640

Glu Pro Ser Leu Lys Asn Ser Asn Pro Asp Glu Ile Glu Ile Asp Phe
                645                 650                 655

Glu Thr Leu Lys Pro Ser Thr Leu Arg Glu Leu Glu Arg Tyr Val Thr
            660                 665                 670

Ser Cys Leu Arg Lys Lys Arg Lys Pro Gln Ala Glu Lys Val Asp Val
        675                 680                 685

Ile Ala Gly Ser Ser Lys Met Lys Gly Phe Ser Ser Ser Glu Ser Glu
690                 695                 700

Ser Ser Ser Glu Ser Ser Ser Ser Asp Ser Glu Asp Ser Glu Thr Glu
705                 710                 715                 720

Met Ala Pro Lys Ser Lys Lys Lys Gly His Pro Gly Arg Glu Gln Lys
                725                 730                 735

Lys His His His His His His Gln Gln Met Gln Gln Ala Pro Ala Pro
            740                 745                 750

Val Pro Gln Gln Pro Pro Pro Pro Gln Gln Pro Pro Pro Pro Pro
        755                 760                 765

Pro Pro Gln Gln Gln Gln Gln Pro Pro Pro Pro Pro Pro Pro Ser
770                 775                 780

Met Pro Gln Gln Ala Ala Pro Ala Met Lys Ser Ser Pro Pro Pro Phe
785                 790                 795                 800

Ile Ala Thr Gln Val Pro Val Leu Glu Pro Gln Leu Pro Gly Ser Val
                805                 810                 815

Phe Asp Pro Ile Gly His Phe Thr Gln Pro Ile Leu His Leu Pro Gln
            820                 825                 830

Pro Glu Leu Pro Pro His Leu Pro Gln Pro Pro Glu His Ser Thr Pro
        835                 840                 845

Pro His Leu Asn Gln His Ala Val Val Ser Pro Pro Ala Leu His Asn
850                 855                 860

Ala Leu Pro Gln Gln Pro Ser Arg Pro Ser Asn Arg Ala Ala Ala Leu
865                 870                 875                 880

Pro Pro Lys Pro Ala Arg Pro Pro Ala Val Ser Pro Ala Leu Thr Gln
                885                 890                 895

Thr Pro Leu Leu Pro Gln Pro Pro Met Ala Gln Pro Pro Gln Val Leu
            900                 905                 910

Leu Glu Asp Glu Glu Pro Pro Ala Pro Pro Leu Thr Ser Met Gln Met
        915                 920                 925

Gln Leu Tyr Leu Gln Gln Leu Gln Lys Val Gln Pro Pro Thr Pro Leu

```
                  930             935             940
Leu Pro Ser Val Lys Val Gln Ser Gln Pro Pro Pro Leu Pro Pro
945                 950             955                 960

Pro Pro His Pro Ser Val Gln Gln Leu Gln Gln Gln Pro Pro Pro
            965             970             975

Pro Pro Pro Pro Gln Pro Gln Pro Pro Gln Gln His Gln Pro
        980             985             990

Pro Pro Arg Pro Val His Leu Gln Pro Met Gln Phe Ser Thr His Ile
        995             1000            1005

Gln Gln Pro Pro Pro Pro Gln Gly Gln Gln Pro Pro His Pro Pro
    1010            1015            1020

Pro Gly Gln Gln Pro Pro Pro Gln Pro Ala Lys Pro Gln Gln
    1025            1030            1035

Val Ile Gln His His His Ser Pro Arg His His Lys Ser Asp Pro
    1040            1045            1050

Tyr Ser Thr Gly His Leu Arg Glu Ala Pro Ser Pro Leu Met Ile
    1055            1060            1065

His Ser Pro Gln Met Ser Gln Phe Gln Ser Leu Thr His Gln Ser
    1070            1075            1080

Pro Pro Gln Gln Asn Val Gln Pro Lys Lys Gln Glu Leu Arg Ala
    1085            1090            1095

Ala Ser Val Val Gln Pro Gln Pro Leu Val Val Lys Glu Glu
    1100            1105            1110

Lys Ile His Ser Pro Ile Ile Arg Ser Glu Pro Phe Ser Pro Ser
    1115            1120            1125

Leu Arg Pro Glu Pro Pro Lys His Pro Glu Ser Ile Lys Ala Pro
    1130            1135            1140

Val His Leu Pro Gln Arg Pro Glu Met Lys Pro Val Asp Val Gly
    1145            1150            1155

Arg Pro Val Ile Arg Pro Pro Glu Gln Asn Ala Pro Pro Pro Gly
    1160            1165            1170

Ala Pro Asp Lys Asp Lys Gln Lys Gln Glu Pro Lys Thr Pro Val
    1175            1180            1185

Ala Pro Lys Lys Asp Leu Lys Ile Lys Asn Met Gly Ser Trp Ala
    1190            1195            1200

Ser Leu Val Gln Lys His Pro Thr Thr Pro Ser Ser Thr Ala Lys
    1205            1210            1215

Ser Ser Ser Asp Ser Phe Glu Gln Phe Arg Arg Ala Ala Arg Glu
    1220            1225            1230

Lys Glu Glu Arg Glu Lys Ala Leu Lys Ala Gln Ala Glu His Ala
    1235            1240            1245

Glu Lys Glu Lys Glu Arg Leu Arg Gln Glu Arg Met Arg Ser Arg
    1250            1255            1260

Glu Asp Glu Asp Ala Leu Glu Gln Ala Arg Arg Ala His Glu Glu
    1265            1270            1275

Ala Arg Arg Arg Gln Glu Gln Gln Gln Gln Gln Arg Gln Glu Gln
    1280            1285            1290

Gln Gln Gln Gln Gln Gln Ala Ala Ala Val Ala Ala Ala Ala
    1295            1300            1305

Thr Pro Gln Ala Gln Ser Ser Gln Pro Gln Ser Met Leu Asp Gln
    1310            1315            1320

Gln Arg Glu Leu Ala Arg Lys Arg Glu Gln Glu Arg Arg Arg
    1325            1330            1335
```

-continued

Glu Ala Met Ala Ala Thr Ile Asp Met Asn Phe Gln Ser Asp Leu
    1340                1345                1350

Leu Ser Ile Phe Glu Glu Asn Leu Phe
    1355                1360

<210> SEQ ID NO 4
<211> LENGTH: 595
<212> TYPE: PRT
<213> ORGANISM: Homo sapiens

<400> SEQUENCE: 4

Met Thr Met Thr Leu His Thr Lys Ala Ser Gly Met Ala Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg

```
                 340                 345                 350
Glu Leu Val His Met Ile Asn Trp Ala Lys Arg Val Pro Gly Phe Val
            355                 360                 365

Asp Leu Thr Leu His Asp Gln Val His Leu Leu Glu Cys Ala Trp Leu
370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
            405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
        450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
            530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 5
<211> LENGTH: 245
<212> TYPE: PRT
<213> ORGANISM: Artificial Sequence
<220> FEATURE:
<223> OTHER INFORMATION: estrogen receptor ligand-binding domain

<400> SEQUENCE: 5

Ser Leu Ala Leu Ser Leu Thr Ala Asp Gln Met Val Ser Ala Leu Leu
1               5                   10                  15

Asp Ala Glu Pro Pro Ile Leu Tyr Ser Glu Tyr Asp Pro Thr Arg Pro
            20                  25                  30

Phe Ser Glu Ala Ser Met Met Gly Leu Leu Thr Asn Leu Ala Asp Arg
        35                  40                  45

Glu Leu Val His Met Ile Asn Trp Ala Lys Arg Val Pro Gly Phe Val
    50                  55                  60

Asp Leu Thr Leu His Asp Gln Val His Leu Leu Glu Cys Ala Trp Leu
65                  70                  75                  80

Glu Ile Leu Met Ile Gly Leu Val Trp Arg Ser Met Glu His Pro Gly
                85                  90                  95

Lys Leu Leu Phe Ala Pro Asn Leu Leu Leu Asp Arg Asn Gln Gly Lys
```

```
                100                 105                 110
Cys Val Glu Gly Met Val Glu Ile Phe Asp Met Leu Leu Ala Thr Ser
            115                 120                 125

Ser Arg Phe Arg Met Met Asn Leu Gln Gly Glu Phe Val Cys Leu
130                 135                 140

Lys Ser Ile Ile Leu Leu Asn Ser Gly Val Tyr Thr Phe Leu Ser Ser
145                 150                 155                 160

Thr Leu Lys Ser Leu Glu Glu Lys Asp His Ile His Arg Val Leu Asp
            165                 170                 175

Lys Ile Thr Asp Thr Leu Ile His Leu Met Ala Lys Ala Gly Leu Thr
            180                 185                 190

Leu Gln Gln Gln His Gln Arg Leu Ala Gln Leu Leu Leu Ile Leu Ser
            195                 200                 205

His Ile Arg His Met Ser Asn Lys Gly Met Glu His Leu Tyr Ser Met
            210                 215                 220

Lys Cys Lys Asn Val Val Pro Leu Tyr Asp Leu Leu Leu Glu Met Leu
225                 230                 235                 240

Asp Ala His Arg Leu
            245

<210> SEQ ID NO 6
<211> LENGTH: 920
<212> TYPE: PRT
<213> ORGANISM: Homo sapiens

<400> SEQUENCE: 6

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
            85                  90                  95

Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
            115                 120                 125

Arg Gly Cys Val Pro Glu Pro Gly Ala Ala Val Ala Ala Ser Lys Gly
            130                 135                 140

Leu Pro Gln Gln Leu Pro Ala Pro Pro Asp Glu Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
                180                 185                 190

Leu Leu Gln Gln Gln Gln Gln Glu Ala Val Ser Glu Gly Ser Ser Ser
            195                 200                 205

Gly Arg Ala Arg Glu Ala Ser Gly Ala Pro Thr Ser Ser Lys Asp Asn
            210                 215                 220
```

-continued

```
Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
            245                 250                 255

Leu Ser Pro Gly Glu Gln Leu Arg Gly Asp Cys Met Tyr Ala Pro Leu
        260                 265                 270

Leu Gly Val Pro Pro Ala Val Arg Pro Thr Pro Cys Ala Pro Leu Ala
    275                 280                 285

Glu Cys Lys Gly Ser Leu Leu Asp Asp Ser Ala Gly Lys Ser Thr Glu
290                 295                 300

Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Ala Gly Ser Ser
            325                 330                 335

Gly Thr Leu Glu Leu Pro Ser Thr Leu Ser Leu Tyr Lys Ser Gly Ala
        340                 345                 350

Leu Asp Glu Ala Ala Ala Tyr Gln Ser Arg Asp Tyr Tyr Asn Phe Pro
    355                 360                 365

Leu Ala Leu Ala Gly Pro Pro Pro Pro Pro Pro Pro His Pro His
370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
            405                 410                 415

Ala Gly Ala Ala Gly Pro Gly Ser Gly Ser Pro Ser Ala Ala Ala Ser
        420                 425                 430

Ser Ser Trp His Thr Leu Phe Thr Ala Glu Glu Gly Gln Leu Tyr Gly
    435                 440                 445

Pro Cys Gly Gly Gly Gly Gly Gly Gly Gly Gly Gly Gly Gly Gly Gly
450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
            485                 490                 495

Phe Thr Ala Pro Asp Val Trp Tyr Pro Gly Gly Met Val Ser Arg Val
        500                 505                 510

Pro Tyr Pro Ser Pro Thr Cys Val Lys Ser Glu Met Gly Pro Trp Met
    515                 520                 525

Asp Ser Tyr Ser Gly Pro Tyr Gly Asp Met Arg Leu Glu Thr Ala Arg
530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
            565                 570                 575

Cys Gly Ser Cys Lys Val Phe Phe Lys Arg Ala Ala Glu Gly Lys Gln
        580                 585                 590

Lys Tyr Leu Cys Ala Ser Arg Asn Asp Cys Thr Ile Asp Lys Phe Arg
    595                 600                 605

Arg Lys Asn Cys Pro Ser Cys Arg Leu Arg Lys Cys Tyr Glu Ala Gly
610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
```

645                 650                 655
Thr Gln Lys Leu Thr Val Ser His Ile Glu Gly Tyr Glu Cys Gln Pro
                660                 665                 670

Ile Phe Leu Asn Val Leu Glu Ala Ile Glu Pro Gly Val Val Cys Ala
                675                 680                 685

Gly His Asp Asn Asn Gln Pro Asp Ser Phe Ala Ala Leu Leu Ser Ser
            690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
                725                 730                 735

Val Ile Gln Tyr Ser Trp Met Gly Leu Met Val Phe Ala Met Gly Trp
                740                 745                 750

Arg Ser Phe Thr Asn Val Asn Ser Arg Met Leu Tyr Phe Ala Pro Asp
                755                 760                 765

Leu Val Phe Asn Glu Tyr Arg Met His Lys Ser Arg Met Tyr Ser Gln
            770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
                820                 825                 830

Met Asn Tyr Ile Lys Glu Leu Asp Arg Ile Ile Ala Cys Lys Arg Lys
                835                 840                 845

Asn Pro Thr Ser Cys Ser Arg Arg Phe Tyr Gln Leu Thr Lys Leu Leu
            850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
                900                 905                 910

Lys Pro Ile Tyr Phe His Thr Gln
                915                 920

<210> SEQ ID NO 7
<211> LENGTH: 462
<212> TYPE: PRT
<213> ORGANISM: Homo sapiens

<400> SEQUENCE: 7

Met Asp Thr Lys His Phe Leu Pro Leu Asp Phe Ser Thr Gln Val Asn
1               5                   10                  15

Ser Ser Leu Thr Ser Pro Thr Gly Arg Gly Ser Met Ala Ala Pro Ser
                20                  25                  30

Leu His Pro Ser Leu Gly Pro Gly Ile Gly Ser Pro Gly Gln Leu His
            35                  40                  45

Ser Pro Ile Ser Thr Leu Ser Ser Pro Ile Asn Gly Met Gly Pro Pro
        50                  55                  60

Phe Ser Val Ile Ser Ser Pro Met Gly Pro His Ser Met Ser Val Pro
65                  70                  75                  80

Thr Thr Pro Thr Leu Gly Phe Ser Thr Gly Ser Pro Gln Leu Ser Ser
                85                  90                  95

```
Pro Met Asn Pro Val Ser Ser Glu Asp Ile Lys Pro Leu Gly
            100                 105                 110

Leu Asn Gly Val Leu Lys Val Pro Ala His Pro Ser Gly Asn Met Ala
        115                 120                 125

Ser Phe Thr Lys His Ile Cys Ala Ile Cys Gly Asp Arg Ser Ser Gly
    130                 135                 140

Lys His Tyr Gly Val Tyr Ser Cys Glu Gly Cys Lys Gly Phe Phe Lys
145                 150                 155                 160

Arg Thr Val Arg Lys Asp Leu Thr Tyr Thr Cys Arg Asp Asn Lys Asp
                165                 170                 175

Cys Leu Ile Asp Lys Arg Gln Arg Asn Arg Cys Gln Tyr Cys Arg Tyr
                180                 185                 190

Gln Lys Cys Leu Ala Met Gly Met Lys Arg Glu Ala Val Gln Glu Glu
            195                 200                 205

Arg Gln Arg Gly Lys Asp Arg Asn Glu Asn Glu Val Glu Ser Thr Ser
            210                 215                 220

Ser Ala Asn Glu Asp Met Pro Val Glu Arg Ile Leu Glu Ala Glu Leu
225                 230                 235                 240

Ala Val Glu Pro Lys Thr Glu Thr Tyr Val Glu Ala Asn Met Gly Leu
                245                 250                 255

Asn Pro Ser Ser Pro Asn Asp Pro Val Thr Asn Ile Cys Gln Ala Ala
            260                 265                 270

Asp Lys Gln Leu Phe Thr Leu Val Glu Trp Ala Lys Arg Ile Pro His
            275                 280                 285

Phe Ser Glu Leu Pro Leu Asp Asp Gln Val Ile Leu Leu Arg Ala Gly
        290                 295                 300

Trp Asn Glu Leu Leu Ile Ala Ser Phe Ser His Arg Ser Ile Ala Val
305                 310                 315                 320

Lys Asp Gly Ile Leu Leu Ala Thr Gly Leu His Val His Arg Asn Ser
                325                 330                 335

Ala His Ser Ala Gly Val Gly Ala Ile Phe Asp Arg Val Leu Thr Glu
            340                 345                 350

Leu Val Ser Lys Met Arg Asp Met Gln Met Asp Lys Thr Glu Leu Gly
        355                 360                 365

Cys Leu Arg Ala Ile Val Leu Phe Asn Pro Asp Ser Lys Gly Leu Ser
370                 375                 380

Asn Pro Ala Glu Val Glu Ala Leu Arg Glu Lys Val Tyr Ala Ser Leu
385                 390                 395                 400

Glu Ala Tyr Cys Lys His Lys Tyr Pro Glu Gln Pro Gly Arg Phe Ala
                405                 410                 415

Lys Leu Leu Leu Arg Leu Pro Ala Leu Arg Ser Ile Gly Leu Lys Cys
                420                 425                 430

Leu Glu His Leu Phe Phe Phe Lys Leu Ile Gly Asp Thr Pro Ile Asp
            435                 440                 445

Thr Phe Leu Met Glu Met Leu Glu Ala Pro His Gln Met Thr
        450                 455                 460

<210> SEQ ID NO 8
<211> LENGTH: 165
<212> TYPE: PRT
<213> ORGANISM: Escherichia coli

<400> SEQUENCE: 8

Met Asn Ser Glu Ser Val Arg Ile Tyr Leu Val Ala Ala Met Gly Ala
1               5                   10                  15
```

```
Asn Arg Val Ile Gly Asn Gly Pro Asn Ile Pro Trp Lys Ile Pro Gly
            20                  25                  30

Glu Gln Lys Ile Phe Arg Arg Leu Thr Glu Gly Lys Val Val Met
        35                  40                  45

Gly Arg Lys Thr Phe Glu Ser Ile Gly Lys Pro Leu Pro Asn Arg His
 50                  55                  60

Thr Leu Val Ile Ser Arg Gln Ala Asn Tyr Arg Ala Thr Gly Cys Val
65                  70                  75                  80

Val Val Ser Thr Leu Ser His Ala Ile Ala Leu Ala Ser Glu Leu Gly
                85                  90                  95

Asn Glu Leu Tyr Val Ala Gly Ala Glu Ile Tyr Thr Leu Ala Leu
            100                 105                 110

Pro His Ala His Gly Val Phe Leu Ser Glu Val His Gln Thr Phe Glu
            115                 120                 125

Gly Asp Ala Phe Phe Pro Met Leu Asn Glu Thr Glu Phe Glu Leu Val
130                 135                 140

Ser Thr Glu Thr Ile Gln Ala Val Ile Pro Tyr Thr His Ser Val Tyr
145                 150                 155                 160

Ala Arg Arg Asn Gly
            165

<210> SEQ ID NO 9
<211> LENGTH: 297
<212> TYPE: PRT
<213> ORGANISM: Artificial Sequence
<220> FEATURE:
<223> OTHER INFORMATION: bacterial dehalogenase

<400> SEQUENCE: 9

Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
 50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
            115                 120                 125

Met Glu Phe Ile Arg Pro Ile Pro Thr Trp Asp Glu Trp Pro Glu Phe
130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
            165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
            195                 200                 205
```

```
Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
                260                 265                 270

Leu Leu Gln Glu Asp Asn Pro Asp Leu Ile Gly Ser Glu Ile Ala Arg
            275                 280                 285

Trp Leu Ser Thr Leu Glu Ile Ser Gly
    290                 295

<210> SEQ ID NO 10
<211> LENGTH: 229
<212> TYPE: PRT
<213> ORGANISM: Artificial Sequence
<220> FEATURE:
<223> OTHER INFORMATION: androgen receptor ligand-binding domain

<400> SEQUENCE: 10

Asp Asn Asn Gln Pro Asp Ser Phe Ala Ala Leu Leu Ser Ser Leu Asn
1               5                   10                  15

Glu Leu Gly Glu Arg Gln Leu Val His Val Val Lys Trp Ala Lys Ala
            20                  25                  30

Leu Pro Gly Phe Arg Asn Leu His Val Asp Asp Gln Met Ala Val Ile
        35                  40                  45

Gln Tyr Ser Trp Met Gly Leu Met Val Phe Ala Met Gly Trp Arg Ser
    50                  55                  60

Phe Thr Asn Val Asn Ser Arg Met Leu Tyr Phe Ala Pro Asp Leu Val
65                  70                  75                  80

Phe Asn Glu Tyr Arg Met His Lys Ser Arg Met Tyr Ser Gln Cys Val
                85                  90                  95

Arg Met Arg His Leu Ser Gln Glu Phe Gly Trp Leu Gln Ile Thr Pro
            100                 105                 110

Gln Glu Phe Leu Cys Met Lys Ala Leu Leu Leu Phe Ser Ile Ile Pro
        115                 120                 125

Val Asp Gly Leu Lys Asn Gln Lys Phe Phe Asp Glu Leu Arg Met Asn
    130                 135                 140

Tyr Ile Lys Glu Leu Asp Arg Ile Ile Ala Cys Lys Arg Lys Asn Pro
145                 150                 155                 160

Thr Ser Cys Ser Arg Arg Phe Tyr Gln Leu Thr Lys Leu Leu Asp Ser
                165                 170                 175

Val Gln Pro Ile Ala Arg Glu Leu His Gln Phe Thr Phe Asp Leu Leu
            180                 185                 190

Ile Lys Ser His Met Val Ser Val Asp Phe Pro Glu Met Met Ala Glu
        195                 200                 205

Ile Ile Ser Val Gln Val Pro Lys Ile Leu Ser Gly Lys Val Lys Pro
    210                 215                 220

Ile Tyr Phe His Thr
225

<210> SEQ ID NO 11
<211> LENGTH: 238
<212> TYPE: PRT
<213> ORGANISM: Artificial Sequence
```

<220> FEATURE:
<223> OTHER INFORMATION: Retinoic Receptor ligand-binding domain

<400> SEQUENCE: 11

```
Ser Ala Asn Glu Asp Met Pro Val Glu Arg Ile Leu Glu Ala Glu Leu
1               5                   10                  15

Ala Val Glu Pro Lys Thr Glu Thr Tyr Val Glu Ala Asn Met Gly Leu
            20                  25                  30

Asn Pro Ser Ser Pro Asn Asp Pro Val Thr Asn Ile Cys Gln Ala Ala
        35                  40                  45

Asp Lys Gln Leu Phe Thr Leu Val Glu Trp Ala Lys Arg Ile Pro His
    50                  55                  60

Phe Ser Glu Leu Pro Leu Asp Asp Gln Val Ile Leu Leu Arg Ala Gly
65                  70                  75                  80

Trp Asn Glu Leu Leu Ile Ala Ser Phe Ser His Arg Ser Ile Ala Val
                85                  90                  95

Lys Asp Gly Ile Leu Leu Ala Thr Gly Leu His Val His Arg Asn Ser
            100                 105                 110

Ala His Ser Ala Gly Val Gly Ala Ile Phe Asp Arg Val Leu Thr Glu
        115                 120                 125

Leu Val Ser Lys Met Arg Asp Met Gln Met Asp Lys Thr Glu Leu Gly
    130                 135                 140

Cys Leu Arg Ala Ile Val Leu Phe Asn Pro Asp Ser Lys Gly Leu Ser
145                 150                 155                 160

Asn Pro Ala Glu Val Glu Ala Leu Arg Glu Lys Val Tyr Ala Ser Leu
                165                 170                 175

Glu Ala Tyr Cys Lys His Lys Tyr Pro Glu Gln Pro Gly Arg Phe Ala
            180                 185                 190

Lys Leu Leu Leu Arg Leu Pro Ala Leu Arg Ser Ile Gly Leu Lys Cys
        195                 200                 205

Leu Glu His Leu Phe Phe Phe Lys Leu Ile Gly Asp Thr Pro Ile Asp
    210                 215                 220

Thr Phe Leu Met Glu Met Leu Glu Ala Pro His Gln Met Thr
225                 230                 235
```

<210> SEQ ID NO 12
<211> LENGTH: 110
<212> TYPE: PRT
<213> ORGANISM: Artificial Sequence
<220> FEATURE:
<223> OTHER INFORMATION: N-terminus of MDM2

<400> SEQUENCE: 12

```
Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

Thr Met Lys Glu Val Leu Phe Tyr Leu Gly Gln Tyr Ile Met Thr Lys
    50                  55                  60

Arg Leu Tyr Asp Glu Lys Gln Gln His Ile Val Tyr Cys Ser Asn Asp
65                  70                  75                  80

Leu Leu Gly Asp Leu Phe Gly Val Pro Ser Phe Ser Val Lys Glu His
                85                  90                  95

Arg Lys Ile Tyr Thr Met Ile Tyr Arg Asn Leu Val Val Val
```

<210> SEQ ID NO 13
<211> LENGTH: 801
<212> TYPE: PRT
<213> ORGANISM: Homo sapiens

<400> SEQUENCE: 13

```
Met Leu Gln Asn Val Thr Pro His Asn Lys Leu Pro Gly Glu Gly Asn
1               5                   10                  15

Ala Gly Leu Leu Gly Leu Gly Pro Glu Ala Ala Pro Gly Lys Arg
            20                  25                  30

Ile Arg Lys Pro Ser Leu Leu Tyr Glu Gly Phe Glu Ser Pro Thr Met
        35                  40                  45

Ala Ser Val Pro Ala Leu Gln Leu Thr Pro Ala Asn Pro Pro Pro
50                  55                  60

Glu Val Ser Asn Pro Lys Lys Pro Gly Arg Val Thr Asn Gln Leu Gln
65                  70                  75                  80

Tyr Leu His Lys Val Val Met Lys Ala Leu Trp Lys His Gln Phe Ala
                85                  90                  95

Trp Pro Phe Arg Gln Pro Val Asp Ala Val Lys Leu Gly Leu Pro Asp
            100                 105                 110

Tyr His Lys Ile Ile Lys Gln Pro Met Asp Met Gly Thr Ile Lys Arg
        115                 120                 125

Arg Leu Glu Asn Asn Tyr Tyr Trp Ala Ala Ser Glu Cys Met Gln Asp
130                 135                 140

Phe Asn Thr Met Phe Thr Asn Cys Tyr Ile Tyr Asn Lys Pro Thr Asp
145                 150                 155                 160

Asp Ile Val Leu Met Ala Gln Thr Leu Glu Lys Ile Phe Leu Gln Lys
                165                 170                 175

Val Ala Ser Met Pro Gln Glu Glu Gln Glu Leu Val Val Thr Ile Pro
            180                 185                 190

Lys Asn Ser His Lys Lys Gly Ala Lys Leu Ala Ala Leu Gln Gly Ser
        195                 200                 205

Val Thr Ser Ala His Gln Val Pro Ala Val Ser Val Ser His Thr
210                 215                 220

Ala Leu Tyr Thr Pro Pro Glu Ile Pro Thr Thr Val Leu Asn Ile
225                 230                 235                 240

Pro His Pro Ser Val Ile Ser Ser Pro Leu Leu Lys Ser Leu His Ser
                245                 250                 255

Ala Gly Pro Pro Leu Leu Ala Val Thr Ala Ala Pro Ala Gln Pro
            260                 265                 270

Leu Ala Lys Lys Lys Gly Val Lys Arg Lys Ala Asp Thr Thr Thr Pro
        275                 280                 285

Thr Pro Thr Ala Ile Leu Ala Pro Gly Ser Pro Ala Ser Pro Pro Gly
290                 295                 300

Ser Leu Glu Pro Lys Ala Ala Arg Leu Pro Pro Met Arg Arg Glu Ser
305                 310                 315                 320

Gly Arg Pro Ile Lys Pro Pro Arg Lys Asp Leu Pro Asp Ser Gln Gln
                325                 330                 335

Gln His Gln Ser Ser Lys Lys Gly Lys Leu Ser Glu Gln Leu Lys His
            340                 345                 350

Cys Asn Gly Ile Leu Lys Glu Leu Leu Ser Lys Lys His Ala Ala Tyr
        355                 360                 365
```

```
Ala Trp Pro Phe Tyr Lys Pro Val Asp Ala Ser Ala Leu Gly Leu His
    370             375             380

Asp Tyr His Asp Ile Ile Lys His Pro Met Asp Leu Ser Thr Val Lys
385             390             395             400

Arg Lys Met Glu Asn Arg Asp Tyr Arg Asp Ala Gln Glu Phe Ala Ala
                405             410             415

Asp Val Arg Leu Met Phe Ser Asn Cys Tyr Lys Tyr Asn Pro Pro Asp
            420             425             430

His Asp Val Val Ala Met Ala Arg Lys Leu Gln Asp Val Phe Glu Phe
        435             440             445

Arg Tyr Ala Lys Met Pro Asp Glu Pro Leu Glu Pro Gly Pro Leu Pro
450             455             460

Val Ser Thr Ala Met Pro Pro Gly Leu Ala Lys Ser Ser Glu Ser
465             470             475             480

Ser Ser Glu Glu Ser Ser Glu Ser Ser Glu Glu Glu Glu
                485             490             495

Glu Asp Glu Glu Asp Glu Glu Glu Glu Ser Glu Ser Ser Asp Ser
            500             505             510

Glu Glu Glu Arg Ala His Arg Leu Ala Glu Leu Gln Glu Gln Leu Arg
        515             520             525

Ala Val His Glu Gln Leu Ala Ala Leu Ser Gln Gly Pro Ile Ser Lys
530             535             540

Pro Lys Arg Lys Arg Glu Lys Lys Glu Lys Lys Lys Arg Lys Ala
545             550             555             560

Glu Lys His Arg Gly Arg Ala Gly Ala Asp Glu Asp Asp Lys Gly Pro
                565             570             575

Arg Ala Pro Arg Pro Pro Gln Pro Lys Lys Ser Lys Lys Ala Ser Gly
            580             585             590

Ser Gly Gly Gly Ser Ala Ala Leu Gly Pro Ser Gly Phe Gly Pro Ser
        595             600             605

Gly Gly Ser Gly Thr Lys Leu Pro Lys Lys Ala Thr Lys Thr Ala Pro
610             615             620

Pro Ala Leu Pro Thr Gly Tyr Asp Ser Glu Glu Glu Glu Glu Ser Arg
625             630             635             640

Pro Met Ser Tyr Asp Glu Lys Arg Gln Leu Ser Leu Asp Ile Asn Lys
                645             650             655

Leu Pro Gly Glu Lys Leu Gly Arg Val Val His Ile Ile Gln Ala Arg
            660             665             670

Glu Pro Ser Leu Arg Asp Ser Asn Pro Glu Glu Ile Glu Ile Asp Phe
        675             680             685

Glu Thr Leu Lys Pro Ser Thr Leu Arg Glu Leu Glu Arg Tyr Val Leu
690             695             700

Ser Cys Leu Arg Lys Lys Pro Arg Lys Pro Tyr Thr Ile Lys Lys Pro
705             710             715             720

Val Gly Lys Thr Lys Glu Glu Leu Ala Leu Glu Lys Lys Arg Glu Leu
                725             730             735

Glu Lys Arg Leu Gln Asp Val Ser Gly Gln Leu Asn Ser Thr Lys Lys
            740             745             750

Pro Pro Lys Lys Ala Asn Glu Lys Thr Glu Ser Ser Ala Gln Gln
        755             760             765

Val Ala Val Ser Arg Leu Ser Ala Ser Ser Ser Ser Asp Ser Ser
770             775             780

Ser Ser Ser Ser Ser Ser Ser Ser Ser Asp Thr Ser Asp Ser Asp Ser
```

```
                        785                 790                 795                 800
Gly

<210> SEQ ID NO 14
<211> LENGTH: 726
<212> TYPE: PRT
<213> ORGANISM: Homo sapiens

<400> SEQUENCE: 14

Met Ser Thr Ala Thr Thr Val Ala Pro Ala Gly Ile Pro Ala Thr Pro
1               5                   10                  15

Gly Pro Val Asn Pro Pro Pro Glu Val Ser Asn Pro Ser Lys Pro
            20                  25                  30

Gly Arg Lys Thr Asn Gln Leu Gln Tyr Met Gln Asn Val Val Lys
        35                  40                  45

Thr Leu Trp Lys His Gln Phe Ala Trp Pro Phe Tyr Gln Pro Val Asp
    50                  55                  60

Ala Ile Lys Leu Asn Leu Pro Asp Tyr His Lys Ile Ile Lys Asn Pro
65                  70                  75                  80

Met Asp Met Gly Thr Ile Lys Lys Arg Leu Glu Asn Asn Tyr Tyr Trp
                85                  90                  95

Ser Ala Ser Glu Cys Met Gln Asp Phe Asn Thr Met Phe Thr Asn Cys
            100                 105                 110

Tyr Ile Tyr Asn Lys Pro Thr Asp Asp Ile Val Leu Met Ala Gln Ala
        115                 120                 125

Leu Glu Lys Ile Phe Leu Gln Lys Val Ala Gln Met Pro Gln Glu Glu
130                 135                 140

Val Glu Leu Leu Pro Pro Ala Pro Lys Gly Lys Gly Arg Lys Pro Ala
145                 150                 155                 160

Ala Gly Ala Gln Ser Ala Gly Thr Gln Gln Val Ala Ala Val Ser Ser
                165                 170                 175

Val Ser Pro Ala Thr Pro Phe Gln Ser Val Pro Pro Thr Val Ser Gln
            180                 185                 190

Thr Pro Val Ile Ala Ala Thr Pro Val Pro Thr Ile Thr Ala Asn Val
        195                 200                 205

Thr Ser Val Pro Val Pro Pro Ala Ala Pro Pro Pro Pro Ala Thr
210                 215                 220

Pro Ile Val Pro Val Val Pro Pro Thr Pro Pro Val Val Lys Lys Lys
225                 230                 235                 240

Gly Val Lys Arg Lys Ala Asp Thr Thr Thr Pro Thr Thr Ser Ala Ile
                245                 250                 255

Thr Ala Ser Arg Ser Glu Ser Pro Pro Pro Leu Ser Asp Pro Lys Gln
            260                 265                 270

Ala Lys Val Val Ala Arg Arg Glu Ser Gly Gly Arg Pro Ile Lys Pro
        275                 280                 285

Pro Lys Lys Asp Leu Glu Asp Gly Glu Val Pro Gln His Ala Gly Lys
290                 295                 300

Lys Gly Lys Leu Ser Glu His Leu Arg Tyr Cys Asp Ser Ile Leu Arg
305                 310                 315                 320

Glu Met Leu Ser Lys His Ala Ala Tyr Ala Trp Pro Phe Tyr Lys
                325                 330                 335

Pro Val Asp Ala Glu Ala Leu Glu Leu His Asp Tyr His Asp Ile Ile
            340                 345                 350

Lys His Pro Met Asp Leu Ser Thr Val Lys Arg Lys Met Asp Gly Arg
```

```
                355                 360                 365
Glu Tyr Pro Asp Ala Gln Gly Phe Ala Ala Asp Val Arg Leu Met Phe
        370                 375                 380

Ser Asn Cys Tyr Lys Tyr Asn Pro Pro Asp His Glu Val Val Ala Met
385                 390                 395                 400

Ala Arg Lys Leu Gln Asp Val Phe Glu Met Arg Phe Ala Lys Met Pro
                405                 410                 415

Asp Glu Pro Val Glu Ala Pro Ala Leu Pro Ala Pro Ala Ala Pro Met
            420                 425                 430

Val Ser Lys Gly Ala Glu Ser Ser Arg Ser Ser Glu Glu Ser Ser Ser
        435                 440                 445

Asp Ser Gly Ser Ser Asp Ser Glu Glu Arg Ala Thr Arg Leu Ala
    450                 455                 460

Glu Leu Gln Glu Gln Leu Lys Ala Val His Gln Leu Ala Ala Leu
465                 470                 475                 480

Ser Gln Ala Pro Val Asn Lys Pro Lys Lys Lys Glu Lys Lys Glu
                485                 490                 495

Lys Glu Lys Lys Lys Asp Lys Glu Lys Lys Glu Lys His Lys
            500                 505                 510

Val Lys Ala Glu Glu Lys Lys Ala Lys Val Ala Pro Ala Lys
        515                 520                 525

Gln Ala Gln Gln Lys Lys Ala Pro Ala Lys Lys Ala Asn Ser Thr Thr
530                 535                 540

Thr Ala Gly Arg Gln Leu Lys Lys Gly Gly Lys Gln Ala Ser Ala Ser
545                 550                 555                 560

Tyr Asp Ser Glu Glu Glu Glu Gly Leu Pro Met Ser Tyr Asp Glu
                565                 570                 575

Lys Arg Gln Leu Ser Leu Asp Ile Asn Arg Leu Pro Gly Glu Lys Leu
            580                 585                 590

Gly Arg Val Val His Ile Ile Gln Ser Arg Glu Pro Ser Leu Arg Asp
        595                 600                 605

Ser Asn Pro Asp Glu Ile Glu Ile Asp Phe Glu Thr Leu Lys Pro Thr
610                 615                 620

Thr Leu Arg Glu Leu Glu Arg Tyr Val Lys Ser Cys Leu Gln Lys Lys
625                 630                 635                 640

Gln Arg Lys Pro Phe Ser Ala Ser Gly Lys Lys Gln Ala Ala Lys Ser
                645                 650                 655

Lys Glu Glu Leu Ala Gln Glu Lys Lys Lys Glu Leu Glu Lys Arg Leu
            660                 665                 670

Gln Asp Val Ser Gly Gln Leu Ser Ser Lys Lys Pro Ala Arg Lys
        675                 680                 685

Glu Lys Pro Gly Ser Ala Pro Ser Gly Pro Ser Arg Leu Ser Ser
        690                 695                 700

Ser Ser Ser Ser Glu Ser Gly Ser Ser Ser Ser Gly Ser Ser Ser
705                 710                 715                 720

Asp Ser Ser Asp Ser Glu
                725

<210> SEQ ID NO 15
<211> LENGTH: 947
<212> TYPE: PRT
<213> ORGANISM: Homo sapiens

<400> SEQUENCE: 15
```

```
Met Ser Leu Pro Ser Arg Gln Thr Ala Ile Ile Val Asn Pro Pro
1               5                   10                  15

Pro Glu Tyr Ile Asn Thr Lys Lys Asn Gly Arg Leu Thr Asn Gln Leu
            20                  25                  30

Gln Tyr Leu Gln Lys Val Val Leu Lys Asp Leu Trp Lys His Ser Phe
        35                  40                  45

Ser Trp Pro Phe Gln Arg Pro Val Asp Ala Val Lys Leu Gln Leu Pro
    50                  55                  60

Asp Tyr Tyr Thr Ile Ile Lys Asn Pro Met Asp Leu Asn Thr Ile Lys
65                  70                  75                  80

Lys Arg Leu Glu Asn Lys Tyr Tyr Ala Lys Ala Ser Glu Cys Ile Glu
                85                  90                  95

Asp Phe Asn Thr Met Phe Ser Asn Cys Tyr Leu Tyr Asn Lys Pro Gly
            100                 105                 110

Asp Asp Ile Val Leu Met Ala Gln Ala Leu Glu Lys Leu Phe Met Gln
        115                 120                 125

Lys Leu Ser Gln Met Pro Gln Glu Glu Gln Val Val Gly Val Lys Glu
    130                 135                 140

Arg Ile Lys Lys Gly Thr Gln Gln Asn Ile Ala Val Ser Ser Ala Lys
145                 150                 155                 160

Glu Lys Ser Ser Pro Ser Ala Thr Glu Lys Val Phe Lys Gln Gln Glu
                165                 170                 175

Ile Pro Ser Val Phe Pro Lys Thr Ser Ile Ser Pro Leu Asn Val Val
            180                 185                 190

Gln Gly Ala Ser Val Asn Ser Ser Gln Thr Ala Ala Gln Val Thr
        195                 200                 205

Lys Gly Val Lys Arg Lys Ala Asp Thr Thr Thr Pro Ala Thr Ser Ala
210                 215                 220

Val Lys Ala Ser Ser Glu Phe Ser Pro Thr Phe Thr Glu Lys Ser Val
225                 230                 235                 240

Ala Leu Pro Pro Ile Lys Glu Asn Met Pro Lys Asn Val Leu Pro Asp
            245                 250                 255

Ser Gln Gln Gln Tyr Asn Val Val Lys Thr Val Lys Val Thr Glu Gln
        260                 265                 270

Leu Arg His Cys Ser Glu Ile Leu Lys Glu Met Leu Ala Lys Lys His
    275                 280                 285

Phe Ser Tyr Ala Trp Pro Phe Tyr Asn Pro Val Asp Val Asn Ala Leu
290                 295                 300

Gly Leu His Asn Tyr Tyr Asp Val Val Lys Asn Pro Met Asp Leu Gly
305                 310                 315                 320

Thr Ile Lys Glu Lys Met Asp Asn Gln Glu Tyr Lys Asp Ala Tyr Lys
                325                 330                 335

Phe Ala Ala Asp Val Arg Leu Met Phe Met Asn Cys Tyr Lys Tyr Asn
            340                 345                 350

Pro Pro Asp His Glu Val Val Thr Met Ala Arg Met Leu Gln Asp Val
        355                 360                 365

Phe Glu Thr His Phe Ser Lys Ile Pro Ile Glu Pro Val Glu Ser Met
    370                 375                 380

Pro Leu Cys Tyr Ile Lys Thr Asp Ile Thr Glu Thr Thr Gly Arg Glu
385                 390                 395                 400

Asn Thr Asn Glu Ala Ser Ser Glu Gly Asn Ser Ser Asp Asp Ser Glu
                405                 410                 415

Asp Glu Arg Val Lys Arg Leu Ala Lys Leu Gln Glu Gln Leu Lys Ala
```

-continued

```
                420                 425                 430
Val His Gln Gln Leu Gln Val Leu Ser Gln Val Pro Phe Arg Lys Leu
            435                 440                 445
Asn Lys Lys Lys Glu Lys Ser Lys Lys Glu Lys Lys Lys Glu Lys Val
        450                 455                 460
Asn Asn Ser Asn Glu Asn Pro Arg Lys Met Cys Glu Gln Met Arg Leu
465                 470                 475                 480
Lys Glu Lys Ser Lys Arg Asn Gln Pro Lys Lys Arg Lys Gln Gln Phe
                485                 490                 495
Ile Gly Leu Lys Ser Glu Asp Glu Asp Asn Ala Lys Pro Met Asn Tyr
            500                 505                 510
Asp Glu Lys Arg Gln Leu Ser Leu Asn Ile Asn Lys Leu Pro Gly Asp
        515                 520                 525
Lys Leu Gly Arg Val Val His Ile Ile Gln Ser Arg Glu Pro Ser Leu
    530                 535                 540
Ser Asn Ser Asn Pro Asp Glu Ile Glu Ile Asp Phe Glu Thr Leu Lys
545                 550                 555                 560
Ala Ser Thr Leu Arg Glu Leu Glu Lys Tyr Val Ser Ala Cys Leu Arg
                565                 570                 575
Lys Arg Pro Leu Lys Pro Ala Lys Lys Ile Met Met Ser Lys Glu
            580                 585                 590
Glu Leu His Ser Gln Lys Lys Gln Glu Leu Glu Lys Arg Leu Leu Asp
        595                 600                 605
Val Asn Asn Gln Leu Asn Ser Arg Lys Arg Gln Thr Lys Ser Asp Lys
    610                 615                 620
Thr Gln Pro Ser Lys Ala Val Glu Asn Val Ser Arg Leu Ser Glu Ser
625                 630                 635                 640
Ser Ser Ser Ser Ser Ser Ser Glu Ser Glu Ser Ser Ser Ser Ser Asp
                645                 650                 655
Leu Ser Ser Ser Asp Ser Ser Asp Ser Glu Ser Glu Met Phe Pro Lys
            660                 665                 670
Phe Thr Glu Val Lys Pro Asn Asp Ser Pro Ser Lys Glu Asn Val Lys
        675                 680                 685
Lys Met Lys Asn Glu Cys Ile Pro Pro Glu Gly Arg Thr Gly Val Thr
    690                 695                 700
Gln Ile Gly Tyr Cys Val Gln Asp Thr Thr Ser Ala Asn Thr Thr Leu
705                 710                 715                 720
Val His Gln Thr Thr Pro Ser His Val Met Pro Pro Asn His His Gln
                725                 730                 735
Leu Ala Phe Asn Tyr Gln Glu Leu Glu His Leu Gln Thr Val Lys Asn
            740                 745                 750
Ile Ser Pro Leu Gln Ile Leu Pro Pro Ser Gly Asp Ser Glu Gln Leu
        755                 760                 765
Ser Asn Gly Ile Thr Val Met His Pro Ser Gly Asp Ser Asp Thr Thr
    770                 775                 780
Met Leu Glu Ser Glu Cys Gln Ala Pro Val Gln Lys Asp Ile Lys Ile
785                 790                 795                 800
Lys Asn Ala Asp Ser Trp Lys Ser Leu Gly Lys Pro Val Lys Pro Ser
                805                 810                 815
Gly Val Met Lys Ser Ser Asp Glu Leu Phe Asn Gln Phe Arg Lys Ala
            820                 825                 830
Ala Ile Glu Lys Glu Val Lys Ala Arg Thr Gln Glu Leu Ile Arg Lys
        835                 840                 845
```

```
His Leu Glu Gln Asn Thr Lys Glu Leu Lys Ala Ser Gln Glu Asn Gln
    850                 855                 860

Arg Asp Leu Gly Asn Gly Leu Thr Val Glu Ser Phe Ser Asn Lys Ile
865                 870                 875                 880

Gln Asn Lys Cys Ser Gly Glu Glu Lys Glu His Gln Gln Ser Ser
                885                 890                 895

Glu Ala Gln Asp Lys Ser Lys Leu Trp Leu Leu Lys Asp Arg Asp Leu
                900                 905                 910

Ala Arg Gln Lys Glu Gln Glu Arg Arg Arg Glu Ala Met Val Gly
                915                 920                 925

Thr Ile Asp Met Thr Leu Gln Ser Asp Ile Met Thr Met Phe Glu Asn
                930                 935                 940

Asn Phe Asp
945

<210> SEQ ID NO 16
<211> LENGTH: 233
<212> TYPE: PRT
<213> ORGANISM: Homo sapiens

<400> SEQUENCE: 16

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
                20                  25                  30

Asn Arg Thr Glu Ala Pro Glu Gly Thr Glu Ser Glu Met Glu Thr Pro
            35                  40                  45

Ser Ala Ile Asn Gly Asn Pro Ser Trp His Leu Ala Asp Ser Pro Ala
        50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
                100                 105                 110

His Ile Thr Pro Gly Thr Ala Tyr Gln Ser Phe Glu Gln Val Val Asn
            115                 120                 125

Glu Leu Phe Arg Asp Gly Val Asn Trp Gly Arg Ile Val Ala Phe Phe
130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
                180                 185                 190

Glu Leu Tyr Gly Asn Asn Ala Ala Ala Glu Ser Arg Lys Gly Gln Glu
            195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230

<210> SEQ ID NO 17
<211> LENGTH: 404
<212> TYPE: PRT
```

<213> ORGANISM: Homo sapiens

<400> SEQUENCE: 17

Met Ser Asp Ser Lys Glu Pro Arg Leu Gln Gln Leu Gly Leu Leu Glu
1               5                   10                  15

Glu Glu Gln Leu Arg Gly Leu Gly Phe Arg Gln Thr Arg Gly Tyr Lys
            20                  25                  30

Ser Leu Ala Gly Cys Leu Gly His Gly Pro Leu Val Leu Gln Leu Leu
        35                  40                  45

Ser Phe Thr Leu Leu Ala Gly Leu Leu Val Gln Val Ser Lys Val Pro
    50                  55                  60

Ser Ser Ile Ser Gln Glu Gln Ser Arg Gln Asp Ala Ile Tyr Gln Asn
65                  70                  75                  80

Leu Thr Gln Leu Lys Ala Ala Val Gly Glu Leu Ser Glu Lys Ser Lys
                85                  90                  95

Leu Gln Glu Ile Tyr Gln Glu Leu Thr Gln Leu Lys Ala Ala Val Gly
            100                 105                 110

Glu Leu Pro Glu Lys Ser Lys Leu Gln Glu Ile Tyr Gln Glu Leu Thr
        115                 120                 125

Arg Leu Lys Ala Ala Val Gly Glu Leu Pro Glu Lys Ser Lys Leu Gln
    130                 135                 140

Glu Ile Tyr Gln Glu Leu Thr Trp Leu Lys Ala Ala Val Gly Glu Leu
145                 150                 155                 160

Pro Glu Lys Ser Lys Met Gln Glu Ile Tyr Gln Glu Leu Thr Arg Leu
                165                 170                 175

Lys Ala Ala Val Gly Glu Leu Pro Glu Lys Ser Lys Gln Gln Glu Ile
            180                 185                 190

Tyr Gln Glu Leu Thr Arg Leu Lys Ala Ala Val Gly Glu Leu Pro Glu
        195                 200                 205

Lys Ser Lys Gln Gln Glu Ile Tyr Gln Glu Leu Thr Arg Leu Lys Ala
    210                 215                 220

Ala Val Gly Glu Leu Pro Glu Lys Ser Lys Gln Gln Glu Ile Tyr Gln
225                 230                 235                 240

Glu Leu Thr Gln Leu Lys Ala Ala Val Glu Arg Leu Cys His Pro Cys
                245                 250                 255

Pro Trp Glu Trp Thr Phe Phe Gln Gly Asn Cys Tyr Phe Met Ser Asn
            260                 265                 270

Ser Gln Arg Asn Trp His Asp Ser Ile Thr Ala Cys Lys Glu Val Gly
        275                 280                 285

Ala Gln Leu Val Val Ile Lys Ser Ala Glu Glu Gln Asn Phe Leu Gln
    290                 295                 300

Leu Gln Ser Ser Arg Ser Asn Arg Phe Thr Trp Met Gly Leu Ser Asp
305                 310                 315                 320

Leu Asn Gln Glu Gly Thr Trp Gln Trp Val Asp Gly Ser Pro Leu Leu
                325                 330                 335

Pro Ser Phe Lys Gln Tyr Trp Asn Arg Gly Glu Pro Asn Asn Val Gly
            340                 345                 350

Glu Glu Asp Cys Ala Glu Phe Ser Gly Asn Gly Trp Asn Asp Asp Lys
        355                 360                 365

Cys Asn Leu Ala Lys Phe Trp Ile Cys Lys Lys Ser Ala Ala Ser Cys
    370                 375                 380

Ser Arg Asp Glu Glu Gln Phe Leu Ser Pro Ala Pro Ala Thr Pro Asn
385                 390                 395                 400

Pro Pro Pro Ala

<210> SEQ ID NO 18
<211> LENGTH: 497
<212> TYPE: PRT
<213> ORGANISM: Homo sapiens

<400> SEQUENCE: 18

Met Thr Phe Asn Ser Phe Glu Gly Ser Lys Thr Cys Val Pro Ala Asp
1               5                   10                  15

Ile Asn Lys Glu Glu Glu Phe Val Glu Phe Asn Arg Leu Lys Thr
            20                  25                  30

Phe Ala Asn Phe Pro Ser Gly Ser Pro Val Ser Ala Ser Thr Leu Ala
            35                  40                  45

Arg Ala Gly Phe Leu Tyr Thr Gly Glu Gly Asp Thr Val Arg Cys Phe
50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser Arg Asp His Phe Ala
            115                 120                 125

Leu Asp Arg Pro Ser Glu Thr His Ala Asp Tyr Leu Leu Arg Thr Gly
130                 135                 140

Gln Val Val Asp Ile Ser Asp Thr Ile Tyr Pro Arg Asn Pro Ala Met
145                 150                 155                 160

Tyr Ser Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ile Gly Asp Gln Val Gln Cys Phe Cys Cys Gly Gly Lys Leu Lys
            195                 200                 205

Asn Trp Glu Pro Cys Asp Arg Ala Trp Ser Glu His Arg Arg His Phe
210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
            260                 265                 270

Gly Thr Trp Ile Tyr Ser Val Asn Lys Glu Gln Leu Ala Arg Ala Gly
            275                 280                 285

Phe Tyr Ala Leu Gly Glu Gly Asp Lys Val Lys Cys Phe His Cys Gly
290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
                325                 330                 335

Glu Tyr Ile Asn Asn Ile His Leu Thr His Ser Leu Glu Glu Cys Leu
            340                 345                 350

Val Arg Thr Thr Glu Lys Thr Pro Ser Leu Thr Arg Arg Ile Asp Asp
            355                 360                 365

```
Thr Ile Phe Gln Asn Pro Met Val Gln Glu Ala Ile Arg Met Gly Phe
        370                 375                 380
Ser Phe Lys Asp Ile Lys Lys Ile Met Glu Glu Lys Ile Gln Ile Ser
385                 390                 395                 400
Gly Ser Asn Tyr Lys Ser Leu Glu Val Leu Val Ala Asp Leu Val Asn
                    405                 410                 415
Ala Gln Lys Asp Ser Met Gln Asp Glu Ser Ser Gln Thr Ser Leu Gln
                420                 425                 430
Lys Glu Ile Ser Thr Glu Glu Gln Leu Arg Arg Leu Gln Glu Glu Lys
            435                 440                 445
Leu Cys Lys Ile Cys Met Asp Arg Asn Ile Ala Ile Val Phe Val Pro
450                 455                 460
Cys Gly His Leu Val Thr Cys Lys Gln Cys Ala Glu Ala Val Asp Lys
465                 470                 475                 480
Cys Pro Met Cys Tyr Thr Val Ile Thr Phe Lys Gln Lys Ile Phe Met
                485                 490                 495
Ser
```

<210> SEQ ID NO 19
<211> LENGTH: 618
<212> TYPE: PRT
<213> ORGANISM: Homo sapiens

<400> SEQUENCE: 19

```
Met His Lys Thr Ala Ser Gln Arg Leu Phe Pro Gly Pro Ser Tyr Gln
1               5                   10                  15
Asn Ile Lys Ser Ile Met Glu Asp Ser Thr Ile Leu Ser Asp Trp Thr
            20                  25                  30
Asn Ser Asn Lys Gln Lys Met Lys Tyr Asp Phe Ser Cys Glu Leu Tyr
        35                  40                  45
Arg Met Ser Thr Tyr Ser Thr Phe Pro Ala Gly Val Pro Val Ser Glu
    50                  55                  60
Arg Ser Leu Ala Arg Ala Gly Phe Tyr Tyr Thr Gly Val Asn Asp Lys
65                  70                  75                  80
Val Lys Cys Phe Cys Cys Gly Leu Met Leu Asp Asn Trp Lys Leu Gly
                85                  90                  95
Asp Ser Pro Ile Gln Lys His Lys Gln Leu Tyr Pro Ser Cys Ser Phe
            100                 105                 110
Ile Gln Asn Leu Val Ser Ala Ser Leu Gly Ser Thr Ser Lys Asn Thr
        115                 120                 125
Ser Pro Met Arg Asn Ser Phe Ala His Ser Leu Ser Pro Thr Leu Glu
    130                 135                 140
His Ser Ser Leu Phe Ser Gly Ser Tyr Ser Ser Leu Ser Pro Asn Pro
145                 150                 155                 160
Leu Asn Ser Arg Ala Val Glu Asp Ile Ser Ser Ser Arg Thr Asn Pro
                165                 170                 175
Tyr Ser Tyr Ala Met Ser Thr Glu Glu Ala Arg Phe Leu Thr Tyr His
            180                 185                 190
Met Trp Pro Leu Thr Phe Leu Ser Pro Ser Glu Leu Ala Arg Ala Gly
        195                 200                 205
Phe Tyr Tyr Ile Gly Pro Gly Asp Arg Val Ala Cys Phe Ala Cys Gly
    210                 215                 220
Gly Lys Leu Ser Asn Trp Glu Pro Lys Asp Asp Ala Met Ser Glu His
225                 230                 235                 240
```

```
Arg Arg His Phe Pro Asn Cys Pro Phe Leu Glu Asn Ser Leu Glu Thr
            245                 250                 255
Leu Arg Phe Ser Ile Ser Asn Leu Ser Met Gln Thr His Ala Ala Arg
        260                 265                 270
Met Arg Thr Phe Met Tyr Trp Pro Ser Ser Val Pro Val Gln Pro Glu
    275                 280                 285
Gln Leu Ala Ser Ala Gly Phe Tyr Val Gly Arg Asn Asp Asp Val
290                 295                 300
Lys Cys Phe Cys Cys Asp Gly Gly Leu Arg Cys Trp Glu Ser Gly Asp
305                 310                 315                 320
Asp Pro Trp Val Glu His Ala Lys Trp Phe Pro Arg Cys Glu Phe Leu
                325                 330                 335
Ile Arg Met Lys Gly Gln Glu Phe Val Asp Glu Ile Gln Gly Arg Tyr
            340                 345                 350
Pro His Leu Leu Glu Gln Leu Leu Ser Thr Ser Asp Thr Thr Gly Glu
        355                 360                 365
Glu Asn Ala Asp Pro Pro Ile Ile His Phe Gly Pro Gly Glu Ser Ser
    370                 375                 380
Ser Glu Asp Ala Val Met Met Asn Thr Pro Val Val Lys Ser Ala Leu
385                 390                 395                 400
Glu Met Gly Phe Asn Arg Asp Leu Val Lys Gln Thr Val Gln Ser Lys
                405                 410                 415
Ile Leu Thr Thr Gly Glu Asn Tyr Lys Thr Val Asn Asp Ile Val Ser
            420                 425                 430
Ala Leu Leu Asn Ala Glu Asp Glu Lys Arg Glu Glu Lys Glu Lys
        435                 440                 445
Gln Ala Glu Glu Met Ala Ser Asp Asp Leu Ser Leu Ile Arg Lys Asn
    450                 455                 460
Arg Met Ala Leu Phe Gln Gln Leu Thr Cys Val Leu Pro Ile Leu Asp
465                 470                 475                 480
Asn Leu Leu Lys Ala Asn Val Ile Asn Lys Gln Glu His Asp Ile Ile
                485                 490                 495
Lys Gln Lys Thr Gln Ile Pro Leu Gln Ala Arg Glu Leu Ile Asp Thr
            500                 505                 510
Ile Leu Val Lys Gly Asn Ala Ala Ala Asn Ile Phe Lys Asn Cys Leu
        515                 520                 525
Lys Glu Ile Asp Ser Thr Leu Tyr Lys Asn Leu Phe Val Asp Lys Asn
    530                 535                 540
Met Lys Tyr Ile Pro Thr Glu Asp Val Ser Gly Leu Ser Leu Glu Glu
545                 550                 555                 560
Gln Leu Arg Arg Leu Gln Glu Glu Arg Thr Cys Lys Val Cys Met Asp
                565                 570                 575
Lys Glu Val Ser Val Val Phe Ile Pro Cys Gly His Leu Val Val Cys
            580                 585                 590
Gln Glu Cys Ala Pro Ser Leu Arg Lys Cys Pro Ile Cys Arg Gly Ile
        595                 600                 605
Ile Lys Gly Thr Val Arg Thr Phe Leu Ser
    610                 615

<210> SEQ ID NO 20
<211> LENGTH: 199
<212> TYPE: PRT
<213> ORGANISM: Homo sapiens

<400> SEQUENCE: 20
```

Met Pro Asn Tyr Lys Leu Thr Tyr Phe Asn Met Arg Gly Arg Ala Glu
1               5                   10                  15

Ile Ile Arg Tyr Ile Phe Ala Tyr Leu Asp Ile Gln Tyr Glu Asp His
            20                  25                  30

Arg Ile Glu Gln Ala Asp Trp Pro Glu Ile Lys Ser Thr Leu Pro Phe
        35                  40                  45

Gly Lys Ile Pro Ile Leu Glu Val Asp Gly Leu Thr Leu His Gln Ser
    50                  55                  60

Leu Ala Ile Ala Arg Tyr Leu Thr Lys Asn Thr Asp Leu Ala Gly Asn
65                  70                  75                  80

Thr Glu Met Glu Gln Cys His Val Asp Ala Ile Val Asp Thr Leu Asp
                85                  90                  95

Asp Phe Met Ser Cys Phe Pro Trp Ala Glu Lys Lys Gln Asp Val Lys
                100                 105                 110

Glu Gln Met Phe Asn Glu Leu Leu Thr Tyr Asn Ala Pro His Leu Met
            115                 120                 125

Gln Asp Leu Asp Thr Tyr Leu Gly Gly Arg Glu Trp Leu Ile Gly Asn
        130                 135                 140

Ser Val Thr Trp Ala Asp Phe Tyr Trp Glu Ile Cys Ser Thr Thr Leu
145                 150                 155                 160

Leu Val Phe Lys Pro Asp Leu Leu Asp Asn His Pro Arg Leu Val Thr
                165                 170                 175

Leu Arg Lys Lys Val Gln Ala Ile Pro Ala Val Ala Asn Trp Ile Lys
            180                 185                 190

Arg Arg Pro Gln Thr Lys Leu
            195

<210> SEQ ID NO 21
<211> LENGTH: 189
<212> TYPE: PRT
<213> ORGANISM: Homo sapiens

<400> SEQUENCE: 21

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys

```
                        165                 170                 175
Thr Pro Gly Cys Val Lys Ile Lys Lys Cys Ile Ile Met
                180                 185

<210> SEQ ID NO 22
<211> LENGTH: 678
<212> TYPE: PRT
<213> ORGANISM: Homo sapiens

<400> SEQUENCE: 22

Met Ala Ala Pro Gly Pro Leu Pro Ala Ala Leu Ser Pro Gly Ala
1               5                   10                  15

Pro Thr Pro Arg Glu Leu Met His Gly Val Ala Gly Val Thr Ser Arg
                20                  25                  30

Ala Gly Arg Asp Arg Glu Ala Gly Ser Val Leu Pro Ala Gly Asn Arg
            35                  40                  45

Gly Ala Arg Lys Ala Ser Arg Arg Ser Ser Arg Ser Met Ser Arg
        50                  55                  60

Asp Asn Lys Phe Ser Lys Lys Asp Cys Leu Ser Ile Arg Asn Val Val
65                  70                  75                  80

Ala Ser Ile Gln Thr Lys Glu Gly Leu Asn Leu Lys Leu Ile Ser Gly
                85                  90                  95

Asp Val Leu Tyr Ile Trp Ala Asp Val Ile Val Asn Ser Val Pro Met
            100                 105                 110

Asn Leu Gln Leu Gly Gly Gly Pro Leu Ser Arg Ala Phe Leu Gln Lys
        115                 120                 125

Ala Gly Pro Met Leu Gln Lys Glu Leu Asp Asp Arg Arg Arg Glu Thr
    130                 135                 140

Glu Glu Lys Val Gly Asn Ile Phe Met Thr Ser Gly Cys Asn Leu Asp
145                 150                 155                 160

Cys Lys Ala Val Leu His Ala Val Ala Pro Tyr Trp Asn Asn Gly Ala
                165                 170                 175

Glu Thr Ser Trp Gln Ile Met Ala Asn Ile Ile Lys Lys Cys Leu Thr
            180                 185                 190

Thr Val Glu Val Leu Ser Phe Ser Ser Ile Thr Phe Pro Met Ile Gly
        195                 200                 205

Thr Gly Ser Leu Gln Phe Pro Lys Ala Val Phe Ala Lys Leu Ile Leu
    210                 215                 220

Ser Glu Val Phe Glu Tyr Ser Ser Ser Thr Arg Pro Ile Thr Ser Pro
225                 230                 235                 240

Leu Gln Glu Val His Phe Leu Val Tyr Thr Asn Asp Asp Glu Gly Cys
                245                 250                 255

Gln Ala Phe Leu Asp Glu Phe Thr Asn Trp Ser Arg Ile Asn Pro Asn
            260                 265                 270

Lys Ala Arg Ile Pro Met Ala Gly Asp Thr Gln Gly Val Val Gly Thr
        275                 280                 285

Val Ser Lys Pro Cys Phe Thr Ala Tyr Glu Met Lys Ile Gly Ala Ile
    290                 295                 300

Thr Phe Gln Val Ala Thr Gly Asp Ile Ala Thr Glu Gln Val Asp Val
305                 310                 315                 320

Ile Val Asn Ser Thr Ala Arg Thr Phe Asn Arg Lys Ser Gly Val Ser
                325                 330                 335

Arg Ala Ile Leu Glu Gly Ala Gly Gln Ala Val Glu Ser Glu Cys Ala
            340                 345                 350
```

```
Val Leu Ala Ala Gln Pro His Arg Asp Phe Ile Ile Thr Pro Gly Gly
            355                 360                 365

Cys Leu Lys Cys Lys Ile Ile Ile His Val Pro Gly Gly Lys Asp Val
370                 375                 380

Arg Lys Thr Val Thr Ser Val Leu Glu Glu Cys Glu Gln Arg Lys Tyr
385                 390                 395                 400

Thr Ser Val Ser Leu Pro Ala Ile Gly Thr Gly Asn Ala Gly Lys Asn
                405                 410                 415

Pro Ile Thr Val Ala Asp Asn Ile Asp Ala Ile Val Asp Phe Ser
                420                 425                 430

Ser Gln His Ser Thr Pro Ser Leu Lys Thr Val Lys Val Val Ile Phe
            435                 440                 445

Gln Pro Glu Leu Leu Asn Ile Phe Tyr Asp Ser Met Lys Lys Arg Asp
450                 455                 460

Leu Ser Ala Ser Leu Asn Phe Gln Ser Thr Phe Ser Met Thr Thr Cys
465                 470                 475                 480

Asn Leu Pro Glu His Trp Thr Asp Met Asn His Gln Leu Phe Cys Met
                485                 490                 495

Val Gln Leu Glu Pro Gly Gln Ser Glu Tyr Asn Thr Ile Lys Asp Lys
            500                 505                 510

Phe Thr Arg Thr Cys Ser Ser Tyr Ala Ile Glu Lys Ile Glu Arg Ile
            515                 520                 525

Gln Asn Ala Phe Leu Trp Gln Ser Tyr Gln Val Lys Lys Arg Gln Met
530                 535                 540

Asp Ile Lys Asn Asp His Lys Asn Asn Glu Arg Leu Leu Phe His Gly
545                 550                 555                 560

Thr Asp Ala Asp Ser Val Pro Tyr Val Asn Gln His Gly Phe Asn Arg
                565                 570                 575

Ser Cys Ala Gly Lys Asn Ala Val Ser Tyr Gly Lys Gly Thr Tyr Phe
            580                 585                 590

Ala Val Asp Ala Ser Tyr Ser Ala Lys Asp Thr Tyr Ser Lys Pro Asp
            595                 600                 605

Ser Asn Gly Arg Lys His Met Tyr Val Val Arg Val Leu Thr Gly Val
610                 615                 620

Phe Thr Lys Gly Arg Ala Gly Leu Val Thr Pro Pro Lys Asn Pro
625                 630                 635                 640

His Asn Pro Thr Asp Leu Phe Asp Ser Val Thr Asn Thr Arg Ser
                645                 650                 655

Pro Lys Leu Phe Val Val Phe Asp Asn Gln Ala Tyr Pro Glu Tyr
            660                 665                 670

Leu Ile Thr Phe Thr Ala
            675

<210> SEQ ID NO 23
<211> LENGTH: 1801
<212> TYPE: PRT
<213> ORGANISM: Homo sapiens

<400> SEQUENCE: 23

Met Ala Val Pro Gly Ser Phe Pro Leu Leu Val Glu Gly Ser Trp Gly
1               5                   10                  15

Pro Asp Pro Pro Lys Asn Leu Asn Thr Lys Leu Gln Met Tyr Phe Gln
                20                  25                  30

Ser Pro Lys Arg Ser Gly Gly Gly Glu Cys Glu Val Arg Gln Asp Pro
            35                  40                  45
```

```
Arg Ser Pro Ser Arg Phe Leu Val Phe Phe Tyr Pro Glu Asp Val Arg
     50                  55                  60

Gln Lys Val Leu Glu Arg Lys Asn His Glu Leu Val Trp Gln Gly Lys
 65                  70                  75                  80

Gly Thr Phe Lys Leu Thr Val Gln Leu Pro Ala Thr Pro Asp Glu Ile
                     85                  90                  95

Asp His Val Phe Glu Glu Leu Leu Thr Lys Glu Ser Lys Thr Lys
                100                 105                 110

Glu Asp Val Lys Glu Pro Asp Val Ser Glu Glu Leu Asp Thr Lys Leu
            115                 120                 125

Pro Leu Asp Gly Gly Leu Asp Lys Met Glu Asp Ile Pro Glu Glu Cys
    130                 135                 140

Glu Asn Ile Ser Ser Leu Val Ala Phe Glu Asn Leu Lys Ala Asn Val
145                 150                 155                 160

Thr Asp Ile Met Leu Ile Leu Leu Val Glu Asn Ile Ser Gly Leu Ser
                165                 170                 175

Asn Asp Asp Phe Gln Val Glu Ile Ile Arg Asp Phe Asp Val Ala Val
                180                 185                 190

Val Thr Phe Gln Lys His Ile Asp Thr Ile Arg Phe Val Asp Asp Cys
        195                 200                 205

Thr Lys His His Ser Ile Lys Gln Leu Gln Leu Ser Pro Arg Leu Leu
    210                 215                 220

Glu Val Thr Asn Thr Ile Arg Val Glu Asn Leu Pro Pro Gly Ala Asp
225                 230                 235                 240

Asp Tyr Ser Leu Lys Leu Phe Phe Glu Asn Pro Tyr Asn Gly Gly Gly
                245                 250                 255

Arg Val Ala Asn Val Glu Tyr Phe Pro Glu Glu Ser Ser Ala Leu Ile
            260                 265                 270

Glu Phe Phe Asp Arg Lys Val Leu Asp Thr Ile Met Ala Thr Lys Leu
    275                 280                 285

Asp Phe Asn Lys Met Pro Leu Ser Val Phe Pro Tyr Tyr Ala Ser Leu
    290                 295                 300

Gly Thr Ala Leu Tyr Gly Lys Glu Lys Pro Leu Ile Lys Leu Pro Ala
305                 310                 315                 320

Pro Phe Glu Glu Ser Leu Asp Leu Pro Leu Trp Lys Phe Leu Gln Lys
                325                 330                 335

Lys Asn His Leu Ile Glu Glu Ile Asn Asp Glu Met Arg Arg Cys His
            340                 345                 350

Cys Glu Leu Thr Trp Ser Gln Leu Ser Gly Lys Val Thr Ile Arg Pro
    355                 360                 365

Ala Ala Thr Leu Val Asn Glu Gly Arg Pro Arg Ile Lys Thr Trp Gln
    370                 375                 380

Ala Asp Thr Ser Thr Thr Leu Ser Ser Ile Arg Ser Lys Tyr Lys Val
385                 390                 395                 400

Asn Pro Ile Lys Val Asp Pro Thr Met Trp Asp Thr Ile Lys Asn Asp
                405                 410                 415

Val Lys Asp Asp Arg Ile Leu Ile Glu Phe Asp Thr Leu Lys Glu Met
            420                 425                 430

Val Ile Leu Ala Gly Lys Ser Glu Asp Val Gln Ser Ile Glu Val Gln
        435                 440                 445

Val Arg Glu Leu Ile Glu Ser Thr Thr Gln Lys Ile Lys Arg Glu Glu
    450                 455                 460
```

```
Gln Ser Leu Lys Glu Lys Met Ile Ile Ser Pro Gly Arg Tyr Phe Leu
465                 470                 475                 480

Leu Cys His Ser Ser Leu Leu Asp His Leu Leu Thr Glu Cys Pro Glu
            485                 490                 495

Ile Glu Ile Cys Tyr Asp Arg Val Thr Gln His Leu Cys Leu Lys Gly
            500                 505                 510

Pro Ser Ala Asp Val Tyr Lys Ala Lys Cys Glu Ile Gln Glu Lys Val
            515                 520                 525

Tyr Thr Met Ala Gln Lys Asn Ile Gln Val Ser Pro Glu Ile Phe Gln
    530                 535                 540

Phe Leu Gln Gln Val Asn Trp Lys Glu Phe Ser Lys Cys Leu Phe Ile
545                 550                 555                 560

Ala Gln Lys Ile Leu Ala Leu Tyr Glu Leu Glu Gly Thr Thr Val Leu
                565                 570                 575

Leu Thr Ser Cys Ser Ser Glu Ala Leu Leu Glu Ala Glu Lys Gln Met
            580                 585                 590

Leu Ser Ala Leu Asn Tyr Lys Arg Ile Glu Val Glu Asn Lys Glu Val
            595                 600                 605

Leu His Gly Lys Lys Trp Lys Gly Leu Thr His Asn Leu Leu Lys Lys
        610                 615                 620

Gln Asn Ser Ser Pro Asn Thr Val Ile Ile Asn Glu Leu Thr Ser Glu
625                 630                 635                 640

Thr Thr Ala Glu Val Ile Ile Thr Gly Cys Val Lys Glu Val Asn Glu
                645                 650                 655

Thr Tyr Lys Leu Leu Phe Asn Phe Val Glu Gln Asn Met Lys Ile Glu
            660                 665                 670

Arg Leu Val Glu Val Lys Pro Ser Leu Val Ile Asp Tyr Leu Lys Thr
        675                 680                 685

Glu Lys Lys Leu Phe Trp Pro Lys Ile Lys Lys Val Asn Val Gln Val
        690                 695                 700

Ser Phe Asn Pro Glu Asn Lys Gln Lys Gly Ile Leu Leu Thr Gly Ser
705                 710                 715                 720

Lys Thr Glu Val Leu Lys Ala Val Asp Ile Val Lys Gln Val Trp Asp
            725                 730                 735

Ser Val Cys Val Lys Ser Val His Thr Asp Lys Pro Gly Ala Lys Gln
            740                 745                 750

Phe Phe Gln Asp Lys Ala Arg Phe Tyr Gln Ser Glu Ile Lys Arg Leu
        755                 760                 765

Phe Gly Cys Tyr Ile Glu Leu Gln Glu Asn Glu Val Met Lys Glu Gly
        770                 775                 780

Gly Ser Pro Ala Gly Gln Lys Cys Phe Ser Arg Thr Val Leu Ala Pro
785                 790                 795                 800

Gly Val Val Leu Ile Val Gln Gln Gly Asp Leu Ala Arg Leu Pro Val
                805                 810                 815

Asp Val Val Asn Ala Ser Asn Glu Asp Leu Lys His Tyr Gly Gly
            820                 825                 830

Leu Ala Ala Ala Leu Ser Lys Ala Ala Gly Pro Glu Leu Gln Ala Asp
            835                 840                 845

Cys Asp Gln Ile Val Lys Arg Glu Gly Arg Leu Pro Gly Asn Ala
        850                 855                 860

Thr Ile Ser Lys Ala Gly Lys Leu Pro Tyr His His Val Ile His Ala
865                 870                 875                 880

Val Gly Pro Arg Trp Ser Gly Tyr Glu Ala Pro Arg Cys Val Tyr Leu
```

```
                  885                 890                 895
Leu Arg Arg Ala Val Gln Leu Ser Leu Cys Leu Ala Glu Lys Tyr Lys
            900                 905                 910

Tyr Arg Ser Ile Ala Ile Pro Ala Ile Ser Ser Gly Val Phe Gly Phe
            915                 920                 925

Pro Leu Gly Arg Cys Val Glu Thr Ile Val Ser Ala Ile Lys Glu Asn
            930                 935                 940

Phe Gln Phe Lys Lys Asp Gly His Cys Leu Lys Glu Ile Tyr Leu Val
945                 950                 955                 960

Asp Val Ser Glu Lys Thr Val Glu Ala Phe Ala Glu Ala Val Lys Thr
            965                 970                 975

Val Phe Lys Ala Thr Leu Pro Asp Thr Ala Ala Pro Pro Gly Leu Pro
            980                 985                 990

Pro Ala Ala Ala Gly Pro Gly Lys Thr Ser Trp Glu Lys Gly Ser Leu
            995                 1000                1005

Val Ser Pro Gly Gly Leu Gln Met Leu Leu Val Lys Glu Gly Val
    1010                1015                1020

Gln Asn Ala Lys Thr Asp Val Val Asn Ser Val Pro Leu Asp
    1025                1030                1035

Leu Val Leu Ser Arg Gly Pro Leu Ser Lys Ser Leu Leu Glu Lys
    1040                1045                1050

Ala Gly Pro Glu Leu Gln Glu Glu Leu Asp Thr Val Gly Gln Gly
    1055                1060                1065

Val Ala Val Ser Met Gly Thr Val Leu Lys Thr Ser Ser Trp Asn
    1070                1075                1080

Leu Asp Cys Arg Tyr Val Leu His Val Val Ala Pro Glu Trp Arg
    1085                1090                1095

Asn Gly Ser Thr Ser Ser Leu Lys Ile Met Glu Asp Ile Ile Arg
    1100                1105                1110

Glu Cys Met Glu Ile Thr Glu Ser Leu Ser Leu Lys Ser Ile Ala
    1115                1120                1125

Phe Pro Ala Ile Gly Thr Gly Asn Leu Gly Phe Pro Lys Asn Ile
    1130                1135                1140

Phe Ala Glu Leu Ile Ile Ser Glu Val Phe Lys Phe Ser Ser Lys
    1145                1150                1155

Asn Gln Leu Lys Thr Leu Gln Glu Val His Phe Leu Leu His Pro
    1160                1165                1170

Ser Asp His Glu Asn Ile Gln Ala Phe Ser Asp Glu Phe Ala Arg
    1175                1180                1185

Arg Ala Asn Gly Asn Leu Val Ser Asp Lys Ile Pro Lys Ala Lys
    1190                1195                1200

Asp Thr Gln Gly Phe Tyr Gly Thr Val Ser Pro Asp Ser Gly
    1205                1210                1215

Val Tyr Glu Met Lys Ile Gly Ser Ile Ile Phe Gln Val Ala Ser
    1220                1225                1230

Gly Asp Ile Thr Lys Glu Glu Ala Asp Val Ile Val Asn Ser Thr
    1235                1240                1245

Ser Asn Ser Phe Asn Leu Lys Ala Gly Val Ser Lys Ala Ile Leu
    1250                1255                1260

Glu Cys Ala Gly Gln Asn Val Glu Arg Glu Cys Ser Gln Gln Ala
    1265                1270                1275

Gln Gln Arg Lys Asn Asp Tyr Ile Ile Thr Gly Gly Gly Phe Leu
    1280                1285                1290
```

-continued

```
Arg Cys Lys Asn Ile Ile His Val Ile Gly Gly Asn Asp Val Lys
1295                1300                1305

Ser Ser Val Ser Ser Val Leu Gln Glu Cys Glu Lys Lys Asn Tyr
1310                1315                1320

Ser Ser Ile Cys Leu Pro Ala Ile Gly Thr Gly Asn Ala Lys Gln
1325                1330                1335

His Pro Asp Lys Val Ala Glu Ala Ile Ile Asp Ala Ile Glu Asp
1340                1345                1350

Phe Val Gln Lys Gly Ser Ala Gln Ser Val Lys Lys Val Lys Val
1355                1360                1365

Val Ile Phe Leu Pro Gln Val Leu Asp Val Phe Tyr Ala Asn Met
1370                1375                1380

Lys Lys Arg Glu Gly Thr Gln Leu Ser Ser Gln Gln Ser Val Met
1385                1390                1395

Ser Lys Leu Ala Ser Phe Leu Gly Phe Ser Lys Gln Ser Pro Gln
1400                1405                1410

Lys Lys Asn His Leu Val Leu Glu Lys Lys Thr Glu Ser Ala Thr
1415                1420                1425

Phe Arg Val Cys Gly Glu Asn Val Thr Cys Val Glu Tyr Ala Ile
1430                1435                1440

Ser Trp Leu Gln Asp Leu Ile Glu Lys Glu Gln Cys Pro Tyr Thr
1445                1450                1455

Ser Glu Asp Glu Cys Ile Lys Asp Phe Asp Glu Lys Glu Tyr Gln
1460                1465                1470

Glu Leu Asn Glu Leu Gln Lys Lys Leu Asn Ile Asn Ile Ser Leu
1475                1480                1485

Asp His Lys Arg Pro Leu Ile Lys Val Leu Gly Ile Ser Arg Asp
1490                1495                1500

Val Met Gln Ala Arg Asp Glu Ile Glu Ala Met Ile Lys Arg Val
1505                1510                1515

Arg Leu Ala Lys Glu Gln Glu Ser Arg Ala Asp Cys Ile Ser Glu
1520                1525                1530

Phe Ile Glu Trp Gln Tyr Asn Asp Asn Asn Thr Ser His Cys Phe
1535                1540                1545

Asn Lys Met Thr Asn Leu Lys Leu Glu Asp Ala Arg Arg Glu Lys
1550                1555                1560

Lys Lys Thr Val Asp Val Lys Ile Asn His Arg His Tyr Thr Val
1565                1570                1575

Asn Leu Asn Thr Tyr Thr Ala Thr Asp Thr Lys Gly His Ser Leu
1580                1585                1590

Ser Val Gln Arg Leu Thr Lys Ser Lys Val Asp Ile Pro Ala His
1595                1600                1605

Trp Ser Asp Met Lys Gln Gln Asn Phe Cys Val Val Glu Leu Leu
1610                1615                1620

Pro Ser Asp Pro Glu Tyr Asn Thr Val Ala Ser Lys Phe Asn Gln
1625                1630                1635

Thr Cys Ser His Phe Arg Ile Glu Lys Ile Glu Arg Ile Gln Asn
1640                1645                1650

Pro Asp Leu Trp Asn Ser Tyr Gln Ala Lys Lys Thr Met Asp
1655                1660                1665

Ala Lys Asn Gly Gln Thr Met Asn Glu Lys Gln Leu Phe His Gly
1670                1675                1680
```

-continued

```
Thr Asp Ala Gly Ser Val Pro His Val Asn Arg Asn Gly Phe Asn
    1685                1690                1695

Arg Ser Tyr Ala Gly Lys Asn Ala Val Ala Tyr Gly Lys Gly Thr
1700                1705                1710

Tyr Phe Ala Val Asn Ala Asn Tyr Ser Ala Asn Asp Thr Tyr Ser
    1715                1720                1725

Arg Pro Asp Ala Asn Gly Arg Lys His Val Tyr Val Arg Val
    1730                1735                1740

Leu Thr Gly Ile Tyr Thr His Gly Asn His Ser Leu Ile Val Pro
    1745                1750                1755

Pro Ser Lys Asn Pro Gln Asn Pro Thr Asp Leu Tyr Asp Thr Val
    1760                1765                1770

Thr Asp Asn Val His His Pro Ser Leu Phe Val Ala Phe Tyr Asp
    1775                1780                1785

Tyr Gln Ala Tyr Pro Glu Tyr Leu Ile Thr Phe Arg Lys
    1790                1795                1800
```

<210> SEQ ID NO 24
<211> LENGTH: 154
<212> TYPE: PRT
<213> ORGANISM: Homo sapiens

<400> SEQUENCE: 24

```
Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
                20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
        50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150
```

<210> SEQ ID NO 25
<211> LENGTH: 150
<212> TYPE: PRT
<213> ORGANISM: Homo sapiens

<400> SEQUENCE: 25

```
Met Ser Ala Lys Asp Glu Arg Ala Arg Glu Ile Leu Arg Gly Phe Lys
1               5                   10                  15

Leu Asn Trp Met Asn Leu Arg Asp Ala Glu Thr Gly Lys Ile Leu Trp
                20                  25                  30

Gln Gly Thr Glu Asp Leu Ser Val Pro Gly Val Glu His Glu Ala Arg
            35                  40                  45
```

```
Val Pro Lys Lys Ile Leu Lys Cys Lys Ala Val Ser Arg Glu Leu Asn
 50                  55                  60

Phe Ser Ser Thr Glu Gln Met Glu Lys Phe Arg Leu Glu Gln Lys Val
 65                  70                  75                  80

Tyr Phe Lys Gly Gln Cys Leu Glu Glu Trp Phe Phe Glu Phe Gly Phe
                 85                  90                  95

Val Ile Pro Asn Ser Thr Asn Thr Trp Gln Ser Leu Ile Glu Ala Ala
                100                 105                 110

Pro Glu Ser Gln Met Met Pro Ala Ser Val Leu Thr Gly Asn Val Ile
            115                 120                 125

Ile Glu Thr Lys Phe Phe Asp Asp Leu Leu Val Ser Thr Ser Arg
130                 135                 140

Val Arg Leu Phe Tyr Val
145                 150

<210> SEQ ID NO 26
<211> LENGTH: 350
<212> TYPE: PRT
<213> ORGANISM: Homo sapiens

<400> SEQUENCE: 26

Met Phe Gly Leu Lys Arg Asn Ala Val Ile Gly Leu Asn Leu Tyr Cys
 1               5                  10                  15

Gly Gly Ala Gly Leu Gly Ala Gly Ser Gly Ala Thr Arg Pro Gly
                20                  25                  30

Gly Arg Leu Leu Ala Thr Glu Lys Glu Ala Ser Ala Arg Arg Glu Ile
            35                  40                  45

Gly Gly Gly Glu Ala Gly Ala Val Ile Gly Ser Ala Gly Ala Ser
 50                  55                  60

Pro Pro Ser Thr Leu Thr Pro Asp Ser Arg Arg Val Ala Arg Pro Pro
 65                  70                  75                  80

Pro Ile Gly Ala Glu Val Pro Asp Val Thr Ala Thr Pro Ala Arg Leu
                 85                  90                  95

Leu Phe Phe Ala Pro Thr Arg Arg Ala Ala Pro Leu Glu Glu Met Glu
                100                 105                 110

Ala Pro Ala Ala Asp Ala Ile Met Ser Pro Glu Glu Leu Asp Gly
            115                 120                 125

Tyr Glu Pro Glu Pro Leu Gly Lys Arg Pro Ala Val Leu Pro Leu Leu
130                 135                 140

Glu Leu Val Gly Glu Ser Gly Asn Asn Thr Ser Thr Asp Gly Ser Leu
145                 150                 155                 160

Pro Ser Thr Pro Pro Ala Glu Glu Glu Asp Glu Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
            195                 200                 205

Ala Leu Glu Thr Leu Arg Arg Val Gly Asp Gly Val Gln Arg Asn His
 210                 215                 220

Glu Thr Ala Phe Gln Gly Met Leu Arg Lys Leu Asp Ile Lys Asn Glu
225                 230                 235                 240

Asp Asp Val Lys Ser Leu Ser Arg Val Met Ile His Val Phe Ser Asp
                245                 250                 255

Gly Val Thr Asn Trp Gly Arg Ile Val Thr Leu Ile Ser Phe Gly Ala
                260                 265                 270
```

```
Phe Val Ala Lys His Leu Lys Thr Ile Asn Gln Glu Ser Cys Ile Glu
        275                 280                 285

Pro Leu Ala Glu Ser Ile Thr Asp Val Leu Val Arg Thr Lys Arg Asp
    290                 295                 300

Trp Leu Val Lys Gln Arg Gly Trp Asp Gly Phe Val Glu Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
                340                 345                 350

<210> SEQ ID NO 27
<211> LENGTH: 239
<212> TYPE: PRT
<213> ORGANISM: Homo sapiens

<400> SEQUENCE: 27

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
                20                  25                  30

Gly Asp Val Gly Ala Ala Pro Pro Gly Ala Ala Pro Ala Pro Gly Ile
            35                  40                  45

Phe Ser Ser Gln Pro Gly His Thr Pro His Pro Ala Ala Ser Arg Asp
        50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
                100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
        130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 28
<211> LENGTH: 163
<212> TYPE: PRT
<213> ORGANISM: Homo sapiens

<400> SEQUENCE: 28

Met Ala Asp Glu Glu Lys Leu Pro Pro Gly Trp Glu Lys Arg Met Ser
1               5                   10                  15
```

```
Arg Ser Ser Gly Arg Val Tyr Tyr Phe Asn His Ile Thr Asn Ala Ser
            20                  25                  30

Gln Trp Glu Arg Pro Ser Gly Asn Ser Ser Gly Gly Lys Asn Gly
        35                  40                  45

Gln Gly Glu Pro Ala Arg Val Arg Cys Ser His Leu Leu Val Lys His
 50                  55                  60

Ser Gln Ser Arg Arg Pro Ser Ser Trp Arg Gln Glu Lys Ile Thr Arg
 65                  70                  75                  80

Thr Lys Glu Glu Ala Leu Glu Leu Ile Asn Gly Tyr Ile Gln Lys Ile
                85                  90                  95

Lys Ser Gly Glu Glu Asp Phe Glu Ser Leu Ala Ser Gln Phe Ser Asp
                100                 105                 110

Cys Ser Ser Ala Lys Ala Arg Gly Asp Leu Gly Ala Phe Ser Arg Gly
            115                 120                 125

Gln Met Gln Lys Pro Phe Glu Asp Ala Ser Phe Ala Leu Arg Thr Gly
130                 135                 140

Glu Met Ser Gly Pro Val Phe Thr Asp Ser Gly Ile His Ile Ile Leu
145                 150                 155                 160

Arg Thr Glu

<210> SEQ ID NO 29
<211> LENGTH: 1327
<212> TYPE: PRT
<213> ORGANISM: Homo sapiens

<400> SEQUENCE: 29

Met Ala Ala Ser Arg Arg Ser Gln His His His His His Gln Gln
 1               5                  10                  15

Gln Leu Gln Pro Ala Pro Gly Ala Ser Ala Pro Pro Pro Pro Pro
                20                  25                  30

Pro Pro Leu Ser Pro Gly Leu Ala Pro Gly Thr Thr Pro Ala Ser Pro
            35                  40                  45

Thr Ala Ser Gly Leu Ala Pro Phe Ala Ser Pro Arg His Gly Leu Ala
 50                  55                  60

Leu Pro Glu Gly Asp Gly Ser Arg Asp Pro Pro Asp Arg Pro Arg Ser
 65                  70                  75                  80

Pro Asp Pro Val Asp Gly Thr Ser Cys Cys Ser Thr Thr Ser Thr Ile
                85                  90                  95

Cys Thr Val Ala Ala Ala Pro Val Val Pro Ala Val Ser Thr Ser Ser
                100                 105                 110

Ala Ala Gly Val Ala Pro Asn Pro Ala Gly Ser Gly Ser Asn Asn Ser
            115                 120                 125

Pro Ser Ser Ser Ser Ser Pro Thr Ser Ser Ser Ser Ser Ser Pro Ser
130                 135                 140

Ser Pro Gly Ser Ser Leu Ala Glu Ser Pro Glu Ala Ala Gly Val Ser
145                 150                 155                 160

Ser Thr Ala Pro Leu Gly Pro Gly Ala Ala Gly Pro Gly Thr Gly Val
                165                 170                 175

Pro Ala Val Ser Gly Ala Leu Arg Glu Leu Leu Glu Ala Cys Arg Asn
            180                 185                 190

Gly Asp Val Ser Arg Val Lys Arg Leu Val Asp Ala Ala Asn Val Asn
                195                 200                 205

Ala Lys Asp Met Ala Gly Arg Lys Ser Ser Pro Leu His Phe Ala Ala
210                 215                 220
```

```
Gly Phe Gly Arg Lys Asp Val Val Glu His Leu Leu Gln Met Gly Ala
225                 230                 235                 240

Asn Val His Ala Arg Asp Asp Gly Gly Leu Ile Pro Leu His Asn Ala
                245                 250                 255

Cys Ser Phe Gly His Ala Glu Val Val Ser Leu Leu Leu Cys Gln Gly
            260                 265                 270

Ala Asp Pro Asn Ala Arg Asp Asn Trp Asn Tyr Thr Pro Leu His Glu
        275                 280                 285

Ala Ala Ile Lys Gly Lys Ile Asp Val Cys Ile Val Leu Leu Gln His
    290                 295                 300

Gly Ala Asp Pro Asn Ile Arg Asn Thr Asp Gly Lys Ser Ala Leu Asp
305                 310                 315                 320

Leu Ala Asp Pro Ser Ala Lys Ala Val Leu Thr Gly Glu Tyr Lys Lys
                325                 330                 335

Asp Glu Leu Leu Glu Ala Ala Arg Ser Gly Asn Glu Glu Lys Leu Met
            340                 345                 350

Ala Leu Leu Thr Pro Leu Asn Val Asn Cys His Ala Ser Asp Gly Arg
        355                 360                 365

Lys Ser Thr Pro Leu His Leu Ala Ala Gly Tyr Asn Arg Val Arg Ile
    370                 375                 380

Val Gln Leu Leu Leu Gln His Gly Ala Asp Val His Ala Lys Asp Lys
385                 390                 395                 400

Gly Gly Leu Val Pro Leu His Asn Ala Cys Ser Tyr Gly His Tyr Glu
                405                 410                 415

Val Thr Glu Leu Leu Lys His Gly Ala Cys Val Asn Ala Met Asp
            420                 425                 430

Leu Trp Gln Phe Thr Pro Leu His Glu Ala Ala Ser Lys Asn Arg Val
        435                 440                 445

Glu Val Cys Ser Leu Leu Leu Ser His Gly Ala Asp Pro Thr Leu Val
    450                 455                 460

Asn Cys His Gly Lys Ser Ala Val Asp Met Ala Pro Thr Pro Glu Leu
465                 470                 475                 480

Arg Glu Arg Leu Thr Tyr Glu Phe Lys Gly His Ser Leu Leu Gln Ala
                485                 490                 495

Ala Arg Glu Ala Asp Leu Ala Lys Val Lys Lys Thr Leu Ala Leu Glu
            500                 505                 510

Ile Ile Asn Phe Lys Gln Pro Gln Ser His Glu Thr Ala Leu His Cys
        515                 520                 525

Ala Val Ala Ser Leu His Pro Lys Arg Lys Gln Val Thr Glu Leu Leu
    530                 535                 540

Leu Arg Lys Gly Ala Asn Val Asn Glu Lys Asn Lys Asp Phe Met Thr
545                 550                 555                 560

Pro Leu His Val Ala Ala Glu Arg Ala His Asn Asp Val Met Glu Val
                565                 570                 575

Leu His Lys His Gly Ala Lys Met Asn Ala Leu Asp Thr Leu Gly Gln
            580                 585                 590

Thr Ala Leu His Arg Ala Ala Leu Ala Gly His Leu Gln Thr Cys Arg
        595                 600                 605

Leu Leu Leu Ser Tyr Gly Ser Asp Pro Ser Ile Ile Ser Leu Gln Gly
    610                 615                 620

Phe Thr Ala Ala Gln Met Gly Asn Glu Ala Val Gln Gln Ile Leu Ser
625                 630                 635                 640
```

```
Glu Ser Thr Pro Ile Arg Thr Ser Asp Val Asp Tyr Arg Leu Leu Glu
                645                 650                 655

Ala Ser Lys Ala Gly Asp Leu Glu Thr Val Lys Gln Leu Cys Ser Ser
            660                 665                 670

Gln Asn Val Asn Cys Arg Asp Leu Glu Gly Arg His Ser Thr Pro Leu
        675                 680                 685

His Phe Ala Ala Gly Tyr Asn Arg Val Ser Val Val Glu Tyr Leu Leu
    690                 695                 700

His His Gly Ala Asp Val His Ala Lys Asp Lys Gly Gly Leu Val Pro
705                 710                 715                 720

Leu His Asn Ala Cys Ser Tyr Gly His Tyr Glu Val Ala Glu Leu Leu
                725                 730                 735

Val Arg His Gly Ala Ser Val Asn Val Ala Asp Leu Trp Lys Phe Thr
            740                 745                 750

Pro Leu His Glu Ala Ala Ala Lys Gly Lys Tyr Glu Ile Cys Lys Leu
        755                 760                 765

Leu Leu Lys His Gly Ala Asp Pro Thr Lys Lys Asn Arg Asp Gly Asn
    770                 775                 780

Thr Pro Leu Asp Leu Val Lys Glu Gly Asp Thr Asp Ile Gln Asp Leu
785                 790                 795                 800

Leu Arg Gly Asp Ala Ala Leu Leu Asp Ala Ala Lys Lys Gly Cys Leu
                805                 810                 815

Ala Arg Val Gln Lys Leu Cys Thr Pro Glu Asn Ile Asn Cys Arg Asp
            820                 825                 830

Thr Gln Gly Arg Asn Ser Thr Pro Leu His Leu Ala Ala Gly Tyr Asn
        835                 840                 845

Asn Leu Glu Val Ala Glu Tyr Leu Leu Glu His Gly Ala Asp Val Asn
    850                 855                 860

Ala Gln Asp Lys Gly Gly Leu Ile Pro Leu His Asn Ala Ala Ser Tyr
865                 870                 875                 880

Gly His Val Asp Ile Ala Ala Leu Leu Ile Lys Tyr Asn Thr Cys Val
                885                 890                 895

Asn Ala Thr Asp Lys Trp Ala Phe Thr Pro Leu His Glu Ala Ala Gln
            900                 905                 910

Lys Gly Arg Thr Gln Leu Cys Ala Leu Leu Leu Ala His Gly Ala Asp
        915                 920                 925

Pro Thr Met Lys Asn Gln Glu Gly Gln Thr Pro Leu Asp Leu Ala Thr
    930                 935                 940

Ala Asp Asp Ile Arg Ala Leu Leu Ile Asp Ala Met Pro Pro Glu Ala
945                 950                 955                 960

Leu Pro Thr Cys Phe Lys Pro Gln Ala Thr Val Val Ser Ala Ser Leu
                965                 970                 975

Ile Ser Pro Ala Ser Thr Pro Ser Cys Leu Ser Ala Ala Ser Ser Ile
            980                 985                 990

Asp Asn Leu Thr Gly Pro Leu Ala Glu Leu Ala Val Gly Gly Ala Ser
        995                1000                1005

Asn Ala Gly Asp Gly Ala Ala Gly Thr Glu Arg Lys Glu Gly Glu
    1010                1015                1020

Val Ala Gly Leu Asp Met Asn Ile Ser Gln Phe Leu Lys Ser Leu
    1025                1030                1035

Gly Leu Glu His Leu Arg Asp Ile Phe Glu Thr Glu Gln Ile Thr
    1040                1045                1050

Leu Asp Val Leu Ala Asp Met Gly His Glu Glu Leu Lys Glu Ile
```

```
            1055                1060                1065

Gly Ile Asn Ala Tyr Gly His Arg His Lys Leu Ile Lys Gly Val
        1070                1075                1080

Glu Arg Leu Leu Gly Gly Gln Gln Gly Thr Asn Pro Tyr Leu Thr
        1085                1090                1095

Phe His Cys Val Asn Gln Gly Thr Ile Leu Leu Asp Leu Ala Pro
        1100                1105                1110

Glu Asp Lys Glu Tyr Gln Ser Val Glu Glu Met Gln Ser Thr
        1115                1120                1125

Ile Arg Glu His Arg Asp Gly Gly Asn Ala Gly Gly Ile Phe Asn
        1130                1135                1140

Arg Tyr Asn Val Ile Arg Ile Gln Lys Val Val Asn Lys Lys Leu
        1145                1150                1155

Arg Glu Arg Phe Cys His Arg Gln Lys Glu Val Ser Glu Glu Asn
        1160                1165                1170

His Asn His His Asn Glu Arg Met Leu Phe His Gly Ser Pro Phe
        1175                1180                1185

Ile Asn Ala Ile Ile His Lys Gly Phe Asp Glu Arg His Ala Tyr
        1190                1195                1200

Ile Gly Gly Met Phe Gly Ala Gly Ile Tyr Phe Ala Glu Asn Ser
        1205                1210                1215

Ser Lys Ser Asn Gln Tyr Val Tyr Gly Ile Gly Gly Gly Thr Gly
        1220                1225                1230

Cys Pro Thr His Lys Asp Arg Ser Cys Tyr Ile Cys His Arg Gln
        1235                1240                1245

Met Leu Phe Cys Arg Val Thr Leu Gly Lys Ser Phe Leu Gln Phe
        1250                1255                1260

Ser Thr Met Lys Met Ala His Ala Pro Pro Gly His His Ser Val
        1265                1270                1275

Ile Gly Arg Pro Ser Val Asn Gly Leu Ala Tyr Ala Glu Tyr Val
        1280                1285                1290

Ile Tyr Arg Gly Glu Gln Ala Tyr Pro Glu Tyr Leu Ile Thr Tyr
        1295                1300                1305

Gln Ile Met Lys Pro Glu Ala Pro Ser Gln Thr Ala Thr Ala Ala
        1310                1315                1320

Glu Gln Lys Thr
        1325

<210> SEQ ID NO 30
<211> LENGTH: 1166
<212> TYPE: PRT
<213> ORGANISM: Homo sapiens

<400> SEQUENCE: 30

Met Ser Gly Arg Arg Cys Ala Gly Gly Ala Ala Cys Ala Ser Ala
1               5                   10                  15

Ala Ala Glu Ala Val Glu Pro Ala Ala Arg Glu Leu Phe Glu Ala Cys
                20                  25                  30

Arg Asn Gly Asp Val Glu Arg Val Lys Arg Leu Val Thr Pro Glu Lys
            35                  40                  45

Val Asn Ser Arg Asp Thr Ala Gly Arg Lys Ser Thr Pro Leu His Phe
        50                  55                  60

Ala Ala Gly Phe Gly Arg Lys Asp Val Val Glu Tyr Leu Leu Gln Asn
65                  70                  75                  80
```

```
Gly Ala Asn Val Gln Ala Arg Asp Asp Gly Leu Ile Pro Leu His
             85                  90                  95

Asn Ala Cys Ser Phe Gly His Ala Glu Val Val Asn Leu Leu Leu Arg
            100                 105                 110

His Gly Ala Asp Pro Asn Ala Arg Asp Asn Trp Asn Tyr Thr Pro Leu
            115                 120                 125

His Glu Ala Ala Ile Lys Gly Lys Ile Asp Val Cys Ile Val Leu Leu
            130                 135                 140

Gln His Gly Ala Glu Pro Thr Ile Arg Asn Thr Asp Gly Arg Thr Ala
145                 150                 155                 160

Leu Asp Leu Ala Asp Pro Ser Ala Lys Ala Val Leu Thr Gly Glu Tyr
                165                 170                 175

Lys Lys Asp Glu Leu Leu Glu Ser Ala Arg Ser Gly Asn Glu Glu Lys
                180                 185                 190

Met Met Ala Leu Leu Thr Pro Leu Asn Val Asn Cys His Ala Ser Asp
            195                 200                 205

Gly Arg Lys Ser Thr Pro Leu His Leu Ala Ala Gly Tyr Asn Arg Val
            210                 215                 220

Lys Ile Val Gln Leu Leu Leu Gln His Gly Ala Asp Val His Ala Lys
225                 230                 235                 240

Asp Lys Gly Asp Leu Val Pro Leu His Asn Ala Cys Ser Tyr Gly His
                245                 250                 255

Tyr Glu Val Thr Glu Leu Leu Val Lys His Gly Ala Cys Val Asn Ala
            260                 265                 270

Met Asp Leu Trp Gln Phe Thr Pro Leu His Glu Ala Ala Ser Lys Asn
            275                 280                 285

Arg Val Glu Val Cys Ser Leu Leu Leu Ser Tyr Gly Ala Asp Pro Thr
            290                 295                 300

Leu Leu Asn Cys His Asn Lys Ser Ala Ile Asp Leu Ala Pro Thr Pro
305                 310                 315                 320

Gln Leu Lys Glu Arg Leu Ala Tyr Glu Phe Lys Gly His Ser Leu Leu
            325                 330                 335

Gln Ala Ala Arg Glu Ala Asp Val Thr Arg Ile Lys Lys His Leu Ser
            340                 345                 350

Leu Glu Met Val Asn Phe Lys His Pro Gln Thr His Glu Thr Ala Leu
            355                 360                 365

His Cys Ala Ala Ala Ser Pro Tyr Pro Lys Arg Lys Gln Ile Cys Glu
            370                 375                 380

Leu Leu Leu Arg Lys Gly Ala Asn Ile Asn Glu Lys Thr Lys Glu Phe
385                 390                 395                 400

Leu Thr Pro Leu His Val Ala Ser Glu Lys Ala His Asn Asp Val Val
                405                 410                 415

Glu Val Val Lys His Glu Ala Lys Val Asn Ala Leu Asp Asn Leu
            420                 425                 430

Gly Gln Thr Ser Leu His Arg Ala Ala Tyr Cys Gly His Leu Gln Thr
            435                 440                 445

Cys Arg Leu Leu Leu Ser Tyr Gly Cys Asp Pro Asn Ile Ile Ser Leu
450                 455                 460

Gln Gly Phe Thr Ala Leu Gln Met Gly Asn Glu Asn Val Gln Gln Leu
465                 470                 475                 480

Leu Gln Glu Gly Ile Ser Leu Gly Asn Ser Glu Ala Asp Arg Gln Leu
                485                 490                 495

Leu Glu Ala Ala Lys Ala Gly Asp Val Glu Thr Val Lys Lys Leu Cys
```

```
                500             505                 510
Thr Val Gln Ser Val Asn Cys Arg Asp Ile Glu Gly Arg Gln Ser Thr
            515                 520                 525
Pro Leu His Phe Ala Ala Gly Tyr Asn Arg Val Ser Val Val Glu Tyr
            530                 535                 540
Leu Leu Gln His Gly Ala Asp Val His Ala Lys Asp Lys Gly Gly Leu
545                 550                 555                 560
Val Pro Leu His Asn Ala Cys Ser Tyr Gly His Tyr Glu Val Ala Glu
                565                 570                 575
Leu Leu Val Lys His Gly Ala Val Val Asn Val Ala Asp Leu Trp Lys
                580                 585                 590
Phe Thr Pro Leu His Glu Ala Ala Lys Gly Lys Tyr Glu Ile Cys
            595                 600                 605
Lys Leu Leu Leu Gln His Gly Ala Asp Pro Thr Lys Lys Asn Arg Asp
            610                 615                 620
Gly Asn Thr Pro Leu Asp Leu Val Lys Asp Gly Asp Thr Asp Ile Gln
625                 630                 635                 640
Asp Leu Leu Arg Gly Asp Ala Ala Leu Leu Asp Ala Ala Lys Lys Gly
                645                 650                 655
Cys Leu Ala Arg Val Lys Lys Leu Ser Ser Pro Asp Asn Val Asn Cys
                660                 665                 670
Arg Asp Thr Gln Gly Arg His Ser Thr Pro Leu His Leu Ala Ala Gly
            675                 680                 685
Tyr Asn Asn Leu Glu Val Ala Glu Tyr Leu Leu Gln His Gly Ala Asp
            690                 695                 700
Val Asn Ala Gln Asp Lys Gly Gly Leu Ile Pro Leu His Asn Ala Ala
705                 710                 715                 720
Ser Tyr Gly His Val Asp Val Ala Ala Leu Leu Ile Lys Tyr Asn Ala
                725                 730                 735
Cys Val Asn Ala Thr Asp Lys Trp Ala Phe Thr Pro Leu His Glu Ala
                740                 745                 750
Ala Gln Lys Gly Arg Thr Gln Leu Cys Ala Leu Leu Leu Ala His Gly
            755                 760                 765
Ala Asp Pro Thr Leu Lys Asn Gln Glu Gly Gln Thr Pro Leu Asp Leu
            770                 775                 780
Val Ser Ala Asp Asp Val Ser Ala Leu Leu Thr Ala Ala Met Pro Pro
785                 790                 795                 800
Ser Ala Leu Pro Ser Cys Tyr Lys Pro Gln Val Leu Asn Gly Val Arg
                805                 810                 815
Ser Pro Gly Ala Thr Ala Asp Ala Leu Ser Ser Gly Pro Ser Ser Pro
                820                 825                 830
Ser Ser Leu Ser Ala Ala Ser Ser Leu Asp Asn Leu Ser Gly Ser Phe
                835                 840                 845
Ser Glu Leu Ser Ser Val Val Ser Ser Ser Gly Thr Glu Gly Ala Ser
            850                 855                 860
Ser Leu Glu Lys Lys Glu Val Pro Gly Val Asp Phe Ser Ile Thr Gln
865                 870                 875                 880
Phe Val Arg Asn Leu Gly Leu Glu His Leu Met Asp Ile Phe Glu Arg
                885                 890                 895
Glu Gln Ile Thr Leu Asp Val Leu Val Glu Met Gly His Lys Glu Leu
            900                 905                 910
Lys Glu Ile Gly Ile Asn Ala Tyr Gly His Arg His Lys Leu Ile Lys
            915                 920                 925
```

Gly Val Glu Arg Leu Ile Ser Gly Gln Gln Gly Leu Asn Pro Tyr Leu
            930                 935                 940

Thr Leu Asn Thr Ser Gly Ser Gly Thr Ile Leu Ile Asp Leu Ser Pro
945                 950                 955                 960

Asp Asp Lys Glu Phe Gln Ser Val Glu Glu Met Gln Ser Thr Val
                965                 970                 975

Arg Glu His Arg Asp Gly Gly His Ala Gly Gly Ile Phe Asn Arg Tyr
                980                 985                 990

Asn Ile Leu Lys Ile Gln Lys Val Cys Asn Lys Lys Leu Trp Glu Arg
            995                 1000                1005

Tyr Thr His Arg Arg Lys Glu Val Ser Glu Glu Asn His Asn His
    1010                1015                1020

Ala Asn Glu Arg Met Leu Phe His Gly Ser Pro Phe Val Asn Ala
    1025                1030                1035

Ile Ile His Lys Gly Phe Asp Glu Arg His Ala Tyr Ile Gly Gly
    1040                1045                1050

Met Phe Gly Ala Gly Ile Tyr Phe Ala Glu Asn Ser Ser Lys Ser
    1055                1060                1065

Asn Gln Tyr Val Tyr Gly Ile Gly Gly Gly Thr Gly Cys Pro Val
    1070                1075                1080

His Lys Asp Arg Ser Cys Tyr Ile Cys His Arg Gln Leu Leu Phe
    1085                1090                1095

Cys Arg Val Thr Leu Gly Lys Ser Phe Leu Gln Phe Ser Ala Met
    1100                1105                1110

Lys Met Ala His Ser Pro Pro Gly His His Ser Val Thr Gly Arg
    1115                1120                1125

Pro Ser Val Asn Gly Leu Ala Leu Ala Glu Tyr Val Ile Tyr Arg
    1130                1135                1140

Gly Glu Gln Ala Tyr Pro Glu Tyr Leu Ile Thr Tyr Gln Ile Met
    1145                1150                1155

Arg Pro Glu Gly Met Val Asp Gly
    1160                1165

<210> SEQ ID NO 31
<211> LENGTH: 197
<212> TYPE: PRT
<213> ORGANISM: Homo sapiens

<400> SEQUENCE: 31

Met Tyr Trp Ser Asn Gln Ile Thr Arg Arg Leu Gly Glu Arg Val Gln
1               5                   10                  15

Gly Phe Met Ser Gly Ile Ser Pro Gln Gln Met Gly Glu Pro Glu Gly
            20                  25                  30

Ser Trp Ser Gly Lys Asn Pro Gly Thr Met Gly Ala Ser Arg Leu Tyr
        35                  40                  45

Thr Leu Val Leu Val Leu Gln Pro Gln Arg Val Leu Leu Gly Met Lys
    50                  55                  60

Lys Arg Gly Phe Gly Ala Gly Arg Trp Asn Gly Phe Gly Gly Lys Val
65                  70                  75                  80

Gln Glu Gly Glu Thr Ile Glu Asp Gly Ala Arg Arg Glu Leu Gln Glu
                85                  90                  95

Glu Ser Gly Leu Thr Val Asp Ala Leu His Lys Val Gly Gln Ile Val
            100                 105                 110

Phe Glu Phe Val Gly Glu Pro Glu Leu Met Asp Val His Val Phe Cys

```
            115                 120                 125
Thr Asp Ser Ile Gln Gly Thr Pro Val Glu Ser Asp Glu Met Arg Pro
130                 135                 140

Cys Trp Phe Gln Leu Asp Gln Ile Pro Phe Lys Asp Met Trp Pro Asp
145                 150                 155                 160

Asp Ser Tyr Trp Phe Pro Leu Leu Leu Gln Lys Lys Phe His Gly
                    165                 170                 175

Tyr Phe Lys Phe Gln Gly Gln Asp Thr Ile Leu Asp Tyr Thr Leu Arg
                180                 185                 190

Glu Val Asp Thr Val
            195

<210> SEQ ID NO 32
<211> LENGTH: 536
<212> TYPE: PRT
<213> ORGANISM: Homo sapiens

<400> SEQUENCE: 32

Met Gly Ser Asn Lys Ser Lys Pro Lys Asp Ala Ser Gln Arg Arg Arg
1               5                   10                  15

Ser Leu Glu Pro Ala Glu Asn Val His Gly Ala Gly Gly Gly Ala Phe
            20                  25                  30

Pro Ala Ser Gln Thr Pro Ser Lys Pro Ala Ser Ala Asp Gly His Arg
        35                  40                  45

Gly Pro Ser Ala Ala Phe Ala Pro Ala Ala Glu Pro Lys Leu Phe
    50                  55                  60

Gly Gly Phe Asn Ser Ser Asp Thr Val Thr Ser Pro Gln Arg Ala Gly
65                  70                  75                  80

Pro Leu Ala Gly Gly Val Thr Thr Phe Val Ala Leu Tyr Asp Tyr Glu
                85                  90                  95

Ser Arg Thr Glu Thr Asp Leu Ser Phe Lys Lys Gly Glu Arg Leu Gln
            100                 105                 110

Ile Val Asn Asn Thr Glu Gly Asp Trp Trp Leu Ala His Ser Leu Ser
        115                 120                 125

Thr Gly Gln Thr Gly Tyr Ile Pro Ser Asn Tyr Val Ala Pro Ser Asp
    130                 135                 140

Ser Ile Gln Ala Glu Glu Trp Tyr Phe Gly Lys Ile Thr Arg Arg Glu
145                 150                 155                 160

Ser Glu Arg Leu Leu Leu Asn Ala Glu Asn Pro Arg Gly Thr Phe Leu
                165                 170                 175

Val Arg Glu Ser Glu Thr Thr Lys Gly Ala Tyr Cys Leu Ser Val Ser
            180                 185                 190

Asp Phe Asp Asn Ala Lys Gly Leu Asn Val Lys His Tyr Lys Ile Arg
        195                 200                 205

Lys Leu Asp Ser Gly Gly Phe Tyr Ile Thr Ser Arg Thr Gln Phe Asn
    210                 215                 220

Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
                245                 250                 255

Gly Leu Ala Lys Asp Ala Trp Glu Ile Pro Arg Glu Ser Leu Arg Leu
            260                 265                 270

Glu Val Lys Leu Gly Gln Gly Cys Phe Gly Glu Val Trp Met Gly Thr
        275                 280                 285
```

```
Trp Asn Gly Thr Thr Arg Val Ala Ile Lys Thr Leu Lys Pro Gly Thr
    290                 295                 300
Met Ser Pro Glu Ala Phe Leu Gln Glu Ala Gln Val Met Lys Lys Leu
305                 310                 315                 320
Arg His Glu Lys Leu Val Gln Leu Tyr Ala Val Val Ser Glu Pro
                325                 330                 335
Ile Tyr Ile Val Thr Glu Tyr Met Ser Lys Gly Ser Leu Leu Asp Phe
            340                 345                 350
Leu Lys Gly Glu Thr Gly Lys Tyr Leu Arg Leu Pro Gln Leu Val Asp
        355                 360                 365
Met Ala Ala Gln Ile Ala Ser Gly Met Ala Tyr Val Glu Arg Met Asn
370                 375                 380
Tyr Val His Arg Asp Leu Arg Ala Ala Asn Ile Leu Val Gly Glu Asn
385                 390                 395                 400
Leu Val Cys Lys Val Ala Asp Phe Gly Leu Ala Arg Leu Ile Glu Asp
                405                 410                 415
Asn Glu Tyr Thr Ala Arg Gln Gly Ala Lys Phe Pro Ile Lys Trp Thr
            420                 425                 430
Ala Pro Glu Ala Ala Leu Tyr Gly Arg Phe Thr Ile Lys Ser Asp Val
        435                 440                 445
Trp Ser Phe Gly Ile Leu Leu Thr Glu Leu Thr Thr Lys Gly Arg Val
450                 455                 460
Pro Tyr Pro Gly Met Val Asn Arg Glu Val Leu Asp Gln Val Glu Arg
465                 470                 475                 480
Gly Tyr Arg Met Pro Cys Pro Pro Glu Cys Pro Glu Ser Leu His Asp
                485                 490                 495
Leu Met Cys Gln Cys Trp Arg Lys Glu Pro Glu Glu Arg Pro Thr Phe
            500                 505                 510
Glu Tyr Leu Gln Ala Phe Leu Glu Asp Tyr Phe Thr Ser Thr Glu Pro
        515                 520                 525
Gln Tyr Gln Pro Gly Glu Asn Leu
530                 535

<210> SEQ ID NO 33
<211> LENGTH: 152
<212> TYPE: PRT
<213> ORGANISM: Homo sapiens

<400> SEQUENCE: 33

Met Pro Ala His Ser Leu Val Met Ser Ser Pro Ala Leu Pro Ala Phe
1               5                   10                  15
Leu Leu Cys Ser Thr Leu Leu Val Ile Lys Met Tyr Val Val Ala Ile
                20                  25                  30
Ile Thr Gly Gln Val Arg Leu Arg Lys Lys Ala Phe Ala Asn Pro Glu
            35                  40                  45
Asp Ala Leu Arg His Gly Gly Pro Gln Tyr Cys Arg Ser Asp Pro Asp
        50                  55                  60
Val Glu Arg Cys Leu Arg Ala His Arg Asn Asp Met Glu Thr Ile Tyr
65                  70                  75                  80
Pro Phe Leu Phe Leu Gly Phe Val Tyr Ser Phe Leu Gly Pro Asn Pro
                85                  90                  95
Phe Val Ala Trp Met His Phe Leu Val Phe Leu Val Gly Arg Val Ala
                100                 105                 110
His Thr Val Ala Tyr Leu Gly Lys Leu Arg Ala Pro Ile Arg Ser Val
            115                 120                 125
```

```
Thr Tyr Thr Leu Ala Gln Leu Pro Cys Ala Ser Met Ala Leu Gln Ile
    130                 135                 140

Leu Trp Glu Ala Ala Arg His Leu
145                 150

<210> SEQ ID NO 34
<211> LENGTH: 161
<212> TYPE: PRT
<213> ORGANISM: Homo sapiens

<400> SEQUENCE: 34

Met Asp Gln Glu Thr Val Gly Asn Val Val Leu Leu Ala Ile Val Thr
1               5                   10                  15

Leu Ile Ser Val Val Gln Asn Gly Phe Phe Ala His Lys Val Glu His
                20                  25                  30

Glu Ser Arg Thr Gln Asn Gly Arg Ser Phe Gln Arg Thr Gly Thr Leu
            35                  40                  45

Ala Phe Glu Arg Val Tyr Thr Ala Asn Gln Asn Cys Val Asp Ala Tyr
        50                  55                  60

Pro Thr Phe Leu Ala Val Leu Trp Ser Ala Gly Leu Leu Cys Ser Gln
65                  70                  75                  80

Val Pro Ala Ala Phe Ala Gly Leu Met Tyr Leu Phe Val Arg Gln Lys
                85                  90                  95

Tyr Phe Val Gly Tyr Leu Gly Glu Arg Thr Gln Ser Thr Pro Gly Tyr
            100                 105                 110

Ile Phe Gly Lys Arg Ile Ile Leu Phe Leu Phe Leu Met Ser Val Ala
        115                 120                 125

Gly Ile Phe Asn Tyr Tyr Leu Ile Phe Phe Gly Ser Asp Phe Glu
    130                 135                 140

Asn Tyr Ile Lys Thr Ile Ser Thr Thr Ile Ser Pro Leu Leu Leu Ile
145                 150                 155                 160

Pro

<210> SEQ ID NO 35
<211> LENGTH: 132
<212> TYPE: PRT
<213> ORGANISM: Homo sapiens

<400> SEQUENCE: 35

Met Cys Asp Ala Phe Val Gly Thr Trp Lys Leu Val Ser Ser Glu Asn
1               5                   10                  15

Phe Asp Asp Tyr Met Lys Glu Val Gly Val Gly Phe Ala Thr Arg Lys
                20                  25                  30

Val Ala Gly Met Ala Lys Pro Asn Met Ile Ile Ser Val Asn Gly Asp
            35                  40                  45

Val Ile Thr Ile Lys Ser Glu Ser Thr Phe Lys Asn Thr Glu Ile Ser
        50                  55                  60

Phe Ile Leu Gly Gln Glu Phe Asp Glu Val Thr Ala Asp Asp Arg Lys
65                  70                  75                  80

Val Lys Ser Thr Ile Thr Leu Asp Gly Gly Val Leu Val His Val Gln
                85                  90                  95

Lys Trp Asp Gly Lys Ser Thr Thr Ile Lys Arg Lys Arg Glu Asp Asp
            100                 105                 110

Lys Leu Val Val Glu Cys Val Met Lys Gly Val Thr Ser Thr Arg Val
        115                 120                 125
```

<210> SEQ ID NO 36
<211> LENGTH: 1821
<212> TYPE: PRT
<213> ORGANISM: Homo sapiens

<400> SEQUENCE: 36

```
Met Ser Cys Glu Arg Lys Gly Leu Ser Glu Leu Arg Ser Glu Leu Tyr
1               5                   10                  15

Phe Leu Ile Ala Arg Phe Leu Glu Asp Gly Pro Cys Gln Gln Ala Ala
            20                  25                  30

Gln Val Leu Ile Arg Glu Val Ala Glu Lys Glu Leu Leu Pro Arg Arg
        35                  40                  45

Thr Asp Trp Thr Gly Lys Glu His Pro Arg Thr Tyr Gln Asn Leu Val
    50                  55                  60

Lys Tyr Tyr Arg His Leu Ala Pro Asp His Leu Leu Gln Ile Cys His
65                  70                  75                  80

Arg Leu Gly Pro Leu Leu Glu Gln Glu Ile Pro Gln Ser Val Pro Gly
                85                  90                  95

Val Gln Thr Leu Leu Gly Ala Gly Arg Gln Ser Leu Leu Arg Thr Asn
            100                 105                 110

Lys Ser Cys Lys His Val Val Trp Lys Gly Ser Ala Leu Ala Ala Leu
        115                 120                 125

His Cys Gly Arg Pro Pro Glu Ser Pro Val Asn Tyr Gly Ser Pro Pro
    130                 135                 140

Ser Ile Ala Asp Thr Leu Phe Ser Arg Lys Leu Asn Gly Lys Tyr Arg
145                 150                 155                 160

Leu Glu Arg Leu Val Pro Thr Ala Val Tyr Gln His Met Lys Met His
                165                 170                 175

Lys Arg Ile Leu Gly His Leu Ser Ser Val Tyr Cys Val Thr Phe Asp
            180                 185                 190

Arg Thr Gly Arg Arg Ile Phe Thr Gly Ser Asp Asp Cys Leu Val Lys
        195                 200                 205

Ile Trp Ala Thr Asp Asp Gly Arg Leu Leu Ala Thr Leu Arg Gly His
    210                 215                 220

Ala Ala Glu Ile Ser Asp Met Ala Val Asn Tyr Glu Asn Thr Met Ile
225                 230                 235                 240

Ala Ala Gly Ser Cys Asp Lys Met Ile Arg Val Trp Cys Leu Arg Thr
                245                 250                 255

Cys Ala Pro Leu Ala Val Leu Gln Gly His Ser Ala Ser Ile Thr Ser
            260                 265                 270

Leu Gln Phe Ser Pro Leu Cys Ser Gly Ser Lys Arg Tyr Leu Ser Ser
        275                 280                 285

Thr Gly Ala Asp Gly Thr Ile Cys Phe Trp Leu Trp Asp Ala Gly Thr
    290                 295                 300

Leu Lys Ile Asn Pro Arg Pro Ala Lys Phe Thr Glu Arg Pro Arg Pro
305                 310                 315                 320

Gly Val Gln Met Ile Cys Ser Ser Phe Ser Ala Gly Gly Met Phe Leu
                325                 330                 335

Ala Thr Gly Ser Thr Asp His Ile Ile Arg Val Tyr Phe Phe Gly Ser
            340                 345                 350

Gly Gln Pro Glu Lys Ile Ser Glu Leu Glu Phe His Thr Asp Lys Val
        355                 360                 365
```

Asp Ser Ile Gln Phe Ser Asn Thr Ser Asn Arg Phe Val Gly Ser
    370             375             380

Arg Asp Gly Thr Ala Arg Ile Trp Gln Phe Lys Arg Glu Trp Lys
385             390             395             400

Ser Ile Leu Leu Asp Met Ala Thr Arg Pro Ala Gly Gln Asn Leu Gln
        405             410             415

Gly Ile Glu Asp Lys Ile Thr Lys Met Lys Val Thr Met Val Ala Trp
            420             425             430

Asp Arg His Asp Asn Thr Val Ile Thr Ala Val Asn Asn Met Thr Leu
        435             440             445

Lys Val Trp Asn Ser Tyr Thr Gly Gln Leu Ile His Val Leu Met Gly
    450             455             460

His Glu Asp Glu Val Phe Val Leu Glu Pro His Pro Phe Asp Pro Arg
465             470             475             480

Val Leu Phe Ser Ala Gly His Asp Gly Asn Val Ile Val Trp Asp Leu
        485             490             495

Ala Arg Gly Val Lys Ile Arg Ser Tyr Phe Asn Met Ile Glu Gly Gln
            500             505             510

Gly His Gly Ala Val Phe Asp Cys Lys Cys Ser Pro Asp Gly Gln His
        515             520             525

Phe Ala Cys Thr Asp Ser His Gly His Leu Leu Ile Phe Gly Phe Gly
    530             535             540

Ser Ser Ser Lys Tyr Asp Lys Ile Ala Asp Gln Met Phe Phe His Ser
545             550             555             560

Asp Tyr Arg Pro Leu Ile Arg Asp Ala Asn Asn Phe Val Leu Asp Glu
            565             570             575

Gln Thr Gln Gln Ala Pro His Leu Met Pro Pro Pro Phe Leu Val Asp
        580             585             590

Val Asp Gly Asn Pro His Pro Ser Arg Tyr Gln Arg Leu Val Pro Gly
            595             600             605

Arg Glu Asn Cys Arg Glu Glu Gln Leu Ile Pro Gln Met Gly Val Thr
    610             615             620

Ser Ser Gly Leu Asn Gln Val Leu Ser Gln Gln Ala Asn Gln Glu Ile
625             630             635             640

Ser Pro Leu Asp Ser Met Ile Gln Arg Leu Gln Gln Glu Gln Asp Leu
            645             650             655

Arg Arg Ser Gly Glu Ala Val Ile Ser Asn Thr Ser Arg Leu Ser Arg
        660             665             670

Gly Ser Ile Ser Ser Thr Ser Glu Val His Ser Pro Pro Asn Val Gly
    675             680             685

Leu Arg Arg Ser Gly Gln Ile Glu Gly Val Arg Gln Met His Ser Asn
690             695             700

Ala Pro Arg Ser Glu Ile Ala Thr Glu Arg Asp Leu Val Ala Trp Ser
705             710             715             720

Arg Arg Val Val Val Pro Glu Leu Ser Ala Gly Val Ala Ser Arg Gln
            725             730             735

Glu Glu Trp Arg Thr Ala Lys Gly Glu Glu Ile Lys Thr Tyr Arg
        740             745             750

Ser Glu Glu Lys Arg Lys His Leu Thr Val Pro Lys Glu Asn Lys Ile
    755             760             765

Pro Thr Val Ser Lys Asn His Ala His Glu His Phe Leu Asp Leu Gly
770             775             780

```
Glu Ser Lys Lys Gln Gln Thr Asn Gln His Asn Tyr Arg Thr Arg Ser
785                 790                 795                 800

Ala Leu Glu Glu Thr Pro Arg Pro Ser Glu Glu Ile Glu Asn Gly Ser
            805                 810                 815

Ser Ser Ser Asp Glu Gly Glu Val Val Ala Val Ser Gly Gly Thr Ser
        820                 825                 830

Glu Glu Glu Glu Arg Ala Trp His Ser Asp Gly Ser Ser Ser Asp Tyr
    835                 840                 845

Ser Ser Asp Tyr Ser Asp Trp Thr Ala Asp Ala Gly Ile Asn Leu Gln
850                 855                 860

Pro Pro Lys Lys Val Pro Lys Asn Lys Thr Lys Lys Ala Glu Ser Ser
865                 870                 875                 880

Ser Asp Glu Glu Glu Ser Glu Lys Gln Lys Gln Lys Gln Ile Lys
        885                 890                 895

Lys Glu Lys Lys Lys Val Asn Glu Glu Lys Asp Gly Pro Ile Ser Pro
                900                 905                 910

Lys Lys Lys Lys Pro Lys Glu Arg Lys Gln Lys Arg Leu Ala Val Gly
            915                 920                 925

Glu Leu Thr Glu Asn Gly Leu Thr Leu Glu Glu Trp Leu Pro Ser Thr
930                 935                 940

Trp Ile Thr Asp Thr Ile Pro Arg Arg Cys Pro Phe Val Pro Gln Met
945                 950                 955                 960

Gly Asp Glu Val Tyr Tyr Phe Arg Gln Gly His Glu Ala Tyr Val Glu
                965                 970                 975

Met Ala Arg Lys Asn Lys Ile Tyr Ser Ile Asn Pro Lys Lys Gln Pro
        980                 985                 990

Trp His Lys Met Glu Leu Arg Glu Gln Glu Leu Met Lys Ile Val Gly
        995                 1000                1005

Ile Lys Tyr Glu Val Gly Leu Pro Thr Leu Cys Cys Leu Lys Leu
    1010                1015                1020

Ala Phe Leu Asp Pro Asp Thr Gly Lys Leu Thr Gly Gly Ser Phe
    1025                1030                1035

Thr Met Lys Tyr His Asp Met Pro Asp Val Ile Asp Phe Leu Val
    1040                1045                1050

Leu Arg Gln Gln Phe Asp Asp Ala Lys Tyr Arg Arg Trp Asn Ile
    1055                1060                1065

Gly Asp Arg Phe Arg Ser Val Ile Asp Asp Ala Trp Trp Phe Gly
    1070                1075                1080

Thr Ile Glu Ser Gln Glu Pro Leu Gln Leu Glu Tyr Pro Asp Ser
    1085                1090                1095

Leu Phe Gln Cys Tyr Asn Val Cys Trp Asp Asn Gly Asp Thr Glu
    1100                1105                1110

Lys Met Ser Pro Trp Asp Met Glu Leu Ile Pro Asn Asn Ala Val
    1115                1120                1125

Phe Pro Glu Glu Leu Gly Thr Ser Val Pro Leu Thr Asp Gly Glu
    1130                1135                1140

Cys Arg Ser Leu Ile Tyr Lys Pro Leu Asp Gly Glu Trp Gly Thr
    1145                1150                1155

Asn Pro Arg Asp Glu Glu Cys Glu Arg Ile Val Ala Gly Ile Asn
    1160                1165                1170

Gln Leu Met Thr Leu Asp Ile Ala Ser Ala Phe Val Ala Pro Val
    1175                1180                1185

Asp Leu Gln Ala Tyr Pro Met Tyr Cys Thr Val Val Ala Tyr Pro
```

```
                1190                1195                1200
Thr Asp Leu Ser Thr Ile Lys Gln Arg Leu Glu Asn Arg Phe Tyr
    1205                1210                1215
Arg Arg Val Ser Ser Leu Met Trp Glu Val Arg Tyr Ile Glu His
    1220                1225                1230
Asn Thr Arg Thr Phe Asn Glu Pro Gly Ser Pro Ile Val Lys Ser
    1235                1240                1245
Ala Lys Phe Val Thr Asp Leu Leu Leu His Phe Ile Lys Asp Gln
    1250                1255                1260
Thr Cys Tyr Asn Ile Ile Pro Leu Tyr Asn Ser Met Lys Lys Lys
    1265                1270                1275
Val Leu Ser Asp Ser Glu Asp Glu Lys Asp Ala Asp Val Pro
    1280                1285                1290
Gly Thr Ser Thr Arg Lys Arg Lys Asp His Gln Pro Arg Arg Arg
    1295                1300                1305
Leu Arg Asn Arg Ala Gln Ser Tyr Asp Ile Gln Ala Trp Lys Lys
    1310                1315                1320
Gln Cys Glu Glu Leu Leu Asn Leu Ile Phe Gln Cys Glu Asp Ser
    1325                1330                1335
Glu Pro Phe Arg Gln Pro Val Asp Leu Leu Glu Tyr Pro Asp Tyr
    1340                1345                1350
Arg Asp Ile Ile Asp Thr Pro Met Asp Phe Ala Thr Val Arg Glu
    1355                1360                1365
Thr Leu Glu Ala Gly Asn Tyr Glu Ser Pro Met Glu Leu Cys Lys
    1370                1375                1380
Asp Val Arg Leu Ile Phe Ser Asn Ser Lys Ala Tyr Thr Pro Ser
    1385                1390                1395
Lys Arg Ser Arg Ile Tyr Ser Met Ser Leu Arg Leu Ser Ala Phe
    1400                1405                1410
Phe Glu Glu His Ile Ser Ser Val Leu Ser Asp Tyr Lys Ser Ala
    1415                1420                1425
Leu Arg Phe His Lys Arg Asn Thr Ile Thr Lys Arg Arg Lys Lys
    1430                1435                1440
Arg Asn Arg Ser Ser Ser Val Ser Ser Ser Ala Ala Ser Ser Pro
    1445                1450                1455
Glu Arg Lys Lys Arg Ile Leu Lys Pro Gln Leu Lys Ser Glu Ser
    1460                1465                1470
Ser Thr Ser Ala Phe Ser Thr Pro Thr Arg Ser Ile Pro Pro Arg
    1475                1480                1485
His Asn Ala Ala Gln Ile Asn Gly Lys Thr Glu Ser Ser Ser Val
    1490                1495                1500
Val Arg Thr Arg Ser Asn Arg Val Val Val Asp Pro Val Val Thr
    1505                1510                1515
Glu Gln Pro Ser Thr Ser Ser Ala Ala Lys Thr Phe Ile Thr Lys
    1520                1525                1530
Ala Asn Ala Ser Ala Ile Pro Gly Lys Thr Ile Leu Glu Asn Ser
    1535                1540                1545
Val Lys His Ser Lys Ala Leu Asn Thr Leu Ser Ser Pro Gly Gln
    1550                1555                1560
Ser Ser Phe Ser His Gly Thr Arg Asn Asn Ser Ala Lys Glu Asn
    1565                1570                1575
Met Glu Lys Glu Lys Pro Val Lys Arg Lys Met Lys Ser Ser Val
    1580                1585                1590
```

```
Leu Pro Lys Ala Ser Thr Leu Ser Lys Ser Ser Ala Val Ile Glu
    1595                1600                1605

Gln Gly Asp Cys Lys Asn Asn Ala Leu Val Pro Gly Thr Ile Gln
    1610                1615                1620

Val Asn Gly His Gly Gly Gln Pro Ser Lys Leu Val Lys Arg Gly
    1625                1630                1635

Pro Gly Arg Lys Pro Lys Val Glu Val Asn Thr Asn Ser Gly Glu
    1640                1645                1650

Ile Ile His Lys Lys Arg Gly Arg Lys Pro Lys Lys Leu Gln Tyr
    1655                1660                1665

Ala Lys Pro Glu Asp Leu Glu Gln Asn Asn Val His Pro Ile Arg
    1670                1675                1680

Asp Glu Val Leu Pro Ser Ser Thr Cys Asn Phe Leu Ser Glu Thr
    1685                1690                1695

Asn Asn Val Lys Glu Asp Leu Leu Gln Lys Lys Asn Arg Gly Gly
    1700                1705                1710

Arg Lys Pro Lys Arg Lys Met Lys Thr Gln Lys Leu Asp Ala Asp
    1715                1720                1725

Leu Leu Val Pro Ala Ser Val Lys Val Leu Arg Arg Ser Asn Arg
    1730                1735                1740

Lys Lys Ile Asp Asp Pro Ile Asp Glu Glu Glu Phe Glu Glu
    1745                1750                1755

Leu Lys Gly Ser Glu Pro His Met Arg Thr Arg Asn Gln Gly Arg
    1760                1765                1770

Arg Thr Ala Phe Tyr Asn Glu Asp Asp Ser Glu Glu Glu Gln Arg
    1775                1780                1785

Gln Leu Leu Phe Glu Asp Thr Ser Leu Thr Phe Gly Thr Ser Ser
    1790                1795                1800

Arg Gly Arg Val Arg Lys Leu Thr Glu Lys Ala Lys Ala Asn Leu
    1805                1810                1815

Ile Gly Trp
    1820

<210> SEQ ID NO 37
<211> LENGTH: 158
<212> TYPE: PRT
<213> ORGANISM: Homo sapiens

<400> SEQUENCE: 37

Met Ser Gly Ile Ala Leu Ser Arg Leu Ala Gln Glu Arg Lys Ala Trp
1               5                   10                  15

Arg Lys Asp His Pro Phe Gly Phe Val Ala Val Pro Thr Lys Asn Pro
                20                  25                  30

Asp Gly Thr Met Asn Leu Met Asn Trp Glu Cys Ala Ile Pro Gly Lys
            35                  40                  45

Lys Gly Thr Pro Trp Glu Gly Gly Leu Phe Lys Leu Arg Met Leu Phe
        50                  55                  60

Lys Asp Asp Tyr Pro Ser Ser Pro Pro Lys Cys Lys Phe Glu Pro Pro
65                  70                  75                  80

Leu Phe His Pro Asn Val Tyr Pro Ser Gly Thr Val Cys Leu Ser Ile
                85                  90                  95

Leu Glu Glu Asp Lys Asp Trp Arg Pro Ala Ile Thr Ile Lys Gln Ile
                100                 105                 110

Leu Leu Gly Ile Gln Glu Leu Leu Asn Glu Pro Asn Ile Gln Asp Pro
```

```
                    115                 120                 125
Ala Gln Ala Glu Ala Tyr Thr Ile Tyr Cys Gln Asn Arg Val Glu Tyr
            130                 135                 140

Glu Lys Arg Val Arg Ala Gln Ala Lys Lys Phe Ala Pro Ser
145                 150                 155
```

<210> SEQ ID NO 38
<211> LENGTH: 101
<212> TYPE: PRT
<213> ORGANISM: Homo sapiens

<400> SEQUENCE: 38

```
Met Ser Asn Thr Gln Ala Glu Arg Ser Ile Ile Gly Met Ile Asp Met
1               5                   10                  15

Phe His Lys Tyr Thr Arg Arg Asp Asp Lys Ile Glu Lys Pro Ser Leu
                20                  25                  30

Leu Thr Met Met Lys Glu Asn Phe Pro Asn Phe Leu Ser Ala Cys Asp
            35                  40                  45

Lys Lys Gly Thr Asn Tyr Leu Ala Asp Val Phe Glu Lys Lys Asp Lys
        50                  55                  60

Asn Glu Asp Lys Lys Ile Asp Phe Ser Glu Phe Leu Ser Leu Leu Gly
65                  70                  75                  80

Asp Ile Ala Thr Asp Tyr His Lys Gln Ser His Gly Ala Ala Pro Cys
                85                  90                  95

Ser Gly Gly Ser Gln
            100
```

<210> SEQ ID NO 39
<211> LENGTH: 144
<212> TYPE: PRT
<213> ORGANISM: Homo sapiens

<400> SEQUENCE: 39

```
Met Lys Thr Leu Leu Leu Ala Val Ile Met Ile Phe Gly Leu Leu Leu
1               5                   10                  15

Gln Ala His Gly Asn Leu Val Asn Phe His Arg Met Ile Lys Leu Thr
                20                  25                  30

Thr Gly Lys Glu Ala Ala Leu Ser Tyr Gly Phe Tyr Gly Cys His Cys
            35                  40                  45

Gly Val Gly Gly Arg Gly Ser Pro Lys Asp Ala Thr Asp Arg Cys Cys
        50                  55                  60

Val Thr His Asp Cys Cys Tyr Lys Arg Leu Glu Lys Arg Gly Cys Gly
65                  70                  75                  80

Thr Lys Phe Leu Ser Tyr Lys Phe Ser Asn Ser Gly Ser Arg Ile Thr
                85                  90                  95

Cys Ala Lys Gln Asp Ser Cys Arg Ser Gln Leu Cys Glu Cys Asp Lys
            100                 105                 110

Ala Ala Ala Thr Cys Phe Ala Arg Asn Lys Thr Thr Tyr Asn Lys Lys
        115                 120                 125

Tyr Gln Tyr Tyr Ser Asn Lys His Cys Arg Gly Ser Thr Pro Arg Cys
130                 135                 140
```

<210> SEQ ID NO 40
<211> LENGTH: 1215
<212> TYPE: PRT
<213> ORGANISM: Homo sapiens

<400> SEQUENCE: 40

```
Met Thr Ser Thr Gly Gln Asp Ser Thr Thr Arg Gln Arg Ser
1               5                   10                  15

Arg Gln Asn Pro Gln Ser Pro Gln Asp Ser Ser Val Thr Ser Lys
            20              25                  30

Arg Asn Ile Lys Lys Gly Ala Val Pro Arg Ser Ile Pro Asn Leu Ala
            35              40                  45

Glu Val Lys Lys Lys Gly Lys Met Lys Lys Leu Gly Gln Ala Met Glu
    50              55                  60

Glu Asp Leu Ile Val Gly Leu Gln Gly Met Asp Leu Asn Leu Glu Ala
65              70                  75                  80

Glu Ala Leu Ala Gly Thr Gly Leu Val Leu Asp Glu Gln Leu Asn Glu
                85                  90                  95

Phe His Cys Leu Trp Asp Asp Ser Phe Pro Glu Gly Pro Glu Arg Leu
                100                 105                 110

His Ala Ile Lys Glu Gln Leu Ile Gln Glu Gly Leu Leu Asp Arg Cys
            115                 120                 125

Val Ser Phe Gln Ala Arg Phe Ala Glu Lys Glu Glu Leu Met Leu Val
        130                 135                 140

His Ser Leu Glu Tyr Ile Asp Leu Met Glu Thr Thr Gln Tyr Met Asn
145                 150                 155                 160

Glu Gly Glu Leu Arg Val Leu Ala Asp Thr Tyr Asp Ser Val Tyr Leu
                165                 170                 175

His Pro Asn Ser Tyr Ser Cys Ala Cys Leu Ala Ser Gly Ser Val Leu
            180                 185                 190

Arg Leu Val Asp Ala Val Leu Gly Ala Glu Ile Arg Asn Gly Met Ala
        195                 200                 205

Ile Ile Arg Pro Pro Gly His His Ala Gln His Ser Leu Met Asp Gly
210                 215                 220

Tyr Cys Met Phe Asn His Val Ala Val Ala Ala Arg Tyr Ala Gln Gln
225                 230                 235                 240

Lys His Arg Ile Arg Arg Val Leu Ile Val Asp Trp Asp Val His His
            245                 250                 255

Gly Gln Gly Thr Gln Phe Thr Phe Asp Gln Asp Pro Ser Val Leu Tyr
                260                 265                 270

Phe Ser Ile His Arg Tyr Glu Gln Gly Arg Phe Trp Pro His Leu Lys
            275                 280                 285

Ala Ser Asn Trp Ser Thr Thr Gly Phe Gly Gln Gly Gln Gly Tyr Thr
        290                 295                 300

Ile Asn Val Pro Trp Asn Gln Val Gly Met Arg Asp Ala Asp Tyr Ile
305                 310                 315                 320

Ala Ala Phe Leu His Val Leu Leu Pro Val Ala Leu Glu Phe Gln Pro
                325                 330                 335

Gln Leu Val Leu Val Ala Ala Gly Phe Asp Ala Leu Gln Gly Asp Pro
            340                 345                 350

Lys Gly Glu Met Ala Ala Thr Pro Ala Gly Phe Ala Gln Leu Thr His
        355                 360                 365

Leu Leu Met Gly Leu Ala Gly Gly Lys Leu Ile Leu Ser Leu Glu Gly
370                 375                 380

Gly Tyr Asn Leu Arg Ala Leu Ala Glu Gly Val Ser Ala Ser Leu His
385                 390                 395                 400

Thr Leu Leu Gly Asp Pro Cys Pro Met Leu Glu Ser Pro Gly Ala Pro
                405                 410                 415
```

```
Cys Arg Ser Ala Gln Ala Ser Val Ser Cys Ala Leu Glu Ala Leu Glu
                420                 425                 430

Pro Phe Trp Glu Val Leu Val Arg Ser Thr Glu Thr Val Glu Arg Asp
        435                 440                 445

Asn Met Glu Glu Asp Asn Val Glu Glu Ser Glu Glu Glu Gly Pro Trp
    450                 455                 460

Glu Pro Pro Val Leu Pro Ile Leu Thr Trp Pro Val Leu Gln Ser Arg
465                 470                 475                 480

Thr Gly Leu Val Tyr Asp Gln Asn Met Met Asn His Cys Asn Leu Trp
                485                 490                 495

Asp Ser His His Pro Glu Val Pro Gln Arg Ile Leu Arg Ile Met Cys
                500                 505                 510

Arg Leu Glu Glu Leu Gly Leu Ala Gly Arg Cys Leu Thr Leu Thr Pro
            515                 520                 525

Arg Pro Ala Thr Glu Ala Glu Leu Leu Thr Cys His Ser Ala Glu Tyr
            530                 535                 540

Val Gly His Leu Arg Ala Thr Glu Lys Met Lys Thr Arg Glu Leu His
545                 550                 555                 560

Arg Glu Ser Ser Asn Phe Asp Ser Ile Tyr Ile Cys Pro Ser Thr Phe
                565                 570                 575

Ala Cys Ala Gln Leu Ala Thr Gly Ala Ala Cys Arg Leu Val Glu Ala
            580                 585                 590

Val Leu Ser Gly Glu Val Leu Asn Gly Ala Ala Val Val Arg Pro Pro
            595                 600                 605

Gly His His Ala Glu Gln Asp Ala Ala Cys Gly Phe Cys Phe Phe Asn
610                 615                 620

Ser Val Ala Val Ala Ala Arg His Ala Gln Thr Ile Ser Gly His Ala
625                 630                 635                 640

Leu Arg Ile Leu Ile Val Asp Trp Asp Val His His Gly Asn Gly Thr
                645                 650                 655

Gln His Met Phe Glu Asp Asp Pro Ser Val Leu Tyr Val Ser Leu His
            660                 665                 670

Arg Tyr Asp His Gly Thr Phe Phe Pro Met Gly Asp Glu Gly Ala Ser
        675                 680                 685

Ser Gln Ile Gly Arg Ala Ala Gly Thr Gly Phe Thr Val Asn Val Ala
    690                 695                 700

Trp Asn Gly Pro Arg Met Gly Asp Ala Asp Tyr Leu Ala Ala Trp His
705                 710                 715                 720

Arg Leu Val Leu Pro Ile Ala Tyr Glu Phe Asn Pro Glu Leu Val Leu
                725                 730                 735

Val Ser Ala Gly Phe Asp Ala Ala Arg Gly Asp Pro Leu Gly Gly Cys
            740                 745                 750

Gln Val Ser Pro Glu Gly Tyr Ala His Leu Thr His Leu Leu Met Gly
        755                 760                 765

Leu Ala Ser Gly Arg Ile Ile Leu Ile Leu Glu Gly Gly Tyr Asn Leu
    770                 775                 780

Thr Ser Ile Ser Glu Ser Met Ala Ala Cys Thr Arg Ser Leu Leu Gly
785                 790                 795                 800

Asp Pro Pro Pro Leu Thr Leu Pro Arg Pro Pro Leu Ser Gly Ala
                805                 810                 815

Leu Ala Ser Ile Thr Glu Thr Ile Gln Val His Arg Arg Tyr Trp Arg
            820                 825                 830

Ser Leu Arg Val Met Lys Val Glu Asp Arg Glu Gly Pro Ser Ser Ser
```

```
                835                 840                 845
Lys Leu Val Thr Lys Lys Ala Pro Gln Pro Ala Lys Pro Arg Leu Ala
    850                 855                 860
Glu Arg Met Thr Thr Arg Glu Lys Lys Val Leu Glu Ala Gly Met Gly
865                 870                 875                 880
Lys Val Thr Ser Ala Ser Phe Gly Glu Glu Ser Thr Pro Gly Gln Thr
                885                 890                 895
Asn Ser Glu Thr Ala Val Val Ala Leu Thr Gln Asp Gln Pro Ser Glu
            900                 905                 910
Ala Ala Thr Gly Gly Ala Thr Leu Ala Gln Thr Ile Ser Glu Ala Ala
            915                 920                 925
Ile Gly Gly Ala Met Leu Gly Gln Thr Thr Ser Glu Glu Ala Val Gly
        930                 935                 940
Gly Ala Thr Pro Asp Gln Thr Thr Ser Glu Glu Thr Val Gly Gly Ala
945                 950                 955                 960
Ile Leu Asp Gln Thr Thr Ser Glu Asp Ala Val Gly Gly Ala Thr Leu
                965                 970                 975
Gly Gln Thr Thr Ser Glu Glu Ala Val Gly Gly Ala Thr Leu Ala Gln
            980                 985                 990
Thr Thr Ser Glu Ala Ala Met Glu Gly Ala Thr Leu Asp Gln Thr Thr
        995                 1000                1005
Ser Glu Glu Ala Pro Gly Gly Thr Glu Leu Ile Gln Thr Pro Leu
    1010                1015                1020
Ala Ser Ser Thr Asp His Gln Thr Pro Pro Thr Ser Pro Val Gln
    1025                1030                1035
Gly Thr Thr Pro Gln Ile Ser Pro Ser Thr Leu Ile Gly Ser Leu
    1040                1045                1050
Arg Thr Leu Glu Leu Gly Ser Glu Ser Gln Gly Ala Ser Glu Ser
    1055                1060                1065
Gln Ala Pro Gly Glu Glu Asn Leu Leu Gly Glu Ala Ala Gly Gly
    1070                1075                1080
Gln Asp Met Ala Asp Ser Met Leu Met Gln Gly Ser Arg Gly Leu
    1085                1090                1095
Thr Asp Gln Ala Ile Phe Tyr Ala Val Thr Pro Leu Pro Trp Cys
    1100                1105                1110
Pro His Leu Val Ala Val Cys Pro Ile Pro Ala Ala Gly Leu Asp
    1115                1120                1125
Val Thr Gln Pro Cys Gly Asp Cys Gly Thr Ile Gln Glu Asn Trp
    1130                1135                1140
Val Cys Leu Ser Cys Tyr Gln Val Tyr Cys Gly Arg Tyr Ile Asn
    1145                1150                1155
Gly His Met Leu Gln His His Gly Asn Ser Gly His Pro Leu Val
    1160                1165                1170
Leu Ser Tyr Ile Asp Leu Ser Ala Trp Cys Tyr Tyr Cys Gln Ala
    1175                1180                1185
Tyr Val His His Gln Ala Leu Leu Asp Val Lys Asn Ile Ala His
    1190                1195                1200
Gln Asn Lys Phe Gly Glu Asp Met Pro His Pro His
    1205                1210                1215

<210> SEQ ID NO 41
<211> LENGTH: 524
<212> TYPE: PRT
<213> ORGANISM: Homo sapiens
```

```
<400> SEQUENCE: 41

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
        275                 280                 285

Ser Lys Asn Val Ile Pro Ala Leu Glu Leu Val Glu Pro Ile Lys Lys
    290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
        355                 360                 365

Leu Ser Ile Leu Leu Glu Glu Val Ser Pro Glu Leu Val Cys Ser Met
    370                 375                 380

Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
```

```
                    405                 410                 415
Gly Tyr Leu Asp Arg Asn Leu Glu Lys Asn Ser Thr Lys Gln Glu Ile
                420                 425                 430

Leu Ala Ala Leu Glu Lys Gly Cys Ser Phe Leu Pro Asp Pro Tyr Gln
            435                 440                 445

Lys Gln Cys Asp Gln Phe Val Ala Glu Tyr Glu Pro Val Leu Ile Glu
        450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
                485                 490                 495

Trp Gly Pro Ser Tyr Trp Cys Gln Asn Thr Glu Thr Ala Ala Gln Cys
            500                 505                 510

Asn Ala Val Glu His Cys Lys Arg His Val Trp Asn
        515                 520

<210> SEQ ID NO 42
<211> LENGTH: 4548
<212> TYPE: PRT
<213> ORGANISM: Homo sapiens

<400> SEQUENCE: 42

Met Glu His Lys Glu Val Val Leu Leu Leu Leu Phe Leu Lys Ser
1               5                   10                  15

Ala Ala Pro Glu Gln Ser His Val Val Gln Asp Cys Tyr His Gly Asp
                20                  25                  30

Gly Gln Ser Tyr Arg Gly Thr Tyr Ser Thr Thr Val Thr Gly Arg Thr
            35                  40                  45

Cys Gln Ala Trp Ser Ser Met Thr Pro His Gln His Asn Arg Thr Thr
        50                  55                  60

Glu Asn Tyr Pro Asn Ala Gly Leu Ile Met Asn Tyr Cys Arg Asn Pro
65                  70                  75                  80

Asp Ala Val Ala Ala Pro Tyr Cys Tyr Thr Arg Asp Pro Gly Val Arg
                85                  90                  95

Trp Glu Tyr Cys Asn Leu Thr Gln Cys Ser Asp Ala Glu Gly Thr Ala
            100                 105                 110

Val Ala Pro Pro Thr Val Thr Pro Val Pro Ser Leu Glu Ala Pro Ser
        115                 120                 125

Glu Gln Ala Pro Thr Glu Gln Arg Pro Gly Val Gln Glu Cys Tyr His
130                 135                 140

Gly Asn Gly Gln Ser Tyr Arg Gly Thr Tyr Ser Thr Thr Val Thr Gly
145                 150                 155                 160

Arg Thr Cys Gln Ala Trp Ser Ser Met Thr Pro His Ser His Ser Arg
                165                 170                 175

Thr Pro Glu Tyr Tyr Pro Asn Ala Gly Leu Ile Met Asn Tyr Cys Arg
            180                 185                 190

Asn Pro Asp Ala Val Ala Ala Pro Tyr Cys Tyr Thr Arg Asp Pro Gly
        195                 200                 205

Val Arg Trp Glu Tyr Cys Asn Leu Thr Gln Cys Ser Asp Ala Glu Gly
210                 215                 220

Thr Ala Val Ala Pro Pro Thr Val Thr Pro Val Pro Ser Leu Glu Ala
225                 230                 235                 240

Pro Ser Glu Gln Ala Pro Thr Glu Gln Arg Pro Gly Val Gln Glu Cys
                245                 250                 255
```

```
Tyr His Gly Asn Gly Gln Ser Tyr Arg Gly Thr Tyr Ser Thr Thr Val
            260                 265                 270

Thr Gly Arg Thr Cys Gln Ala Trp Ser Ser Met Thr Pro His Ser His
        275                 280                 285

Ser Arg Thr Pro Glu Tyr Tyr Pro Asn Ala Gly Leu Ile Met Asn Tyr
    290                 295                 300

Cys Arg Asn Pro Asp Ala Val Ala Ala Pro Tyr Cys Tyr Thr Arg Asp
305                 310                 315                 320

Pro Gly Val Arg Trp Glu Tyr Cys Asn Leu Thr Gln Cys Ser Asp Ala
                325                 330                 335

Glu Gly Thr Ala Val Ala Pro Pro Thr Val Thr Pro Val Pro Ser Leu
            340                 345                 350

Glu Ala Pro Ser Glu Gln Ala Pro Thr Glu Gln Arg Pro Gly Val Gln
        355                 360                 365

Glu Cys Tyr His Gly Asn Gly Gln Ser Tyr Arg Gly Thr Tyr Ser Thr
    370                 375                 380

Thr Val Thr Gly Arg Thr Cys Gln Ala Trp Ser Ser Met Thr Pro His
385                 390                 395                 400

Ser His Ser Arg Thr Pro Glu Tyr Tyr Pro Asn Ala Gly Leu Ile Met
                405                 410                 415

Asn Tyr Cys Arg Asn Pro Asp Ala Val Ala Ala Pro Tyr Cys Tyr Thr
            420                 425                 430

Arg Asp Pro Gly Val Arg Trp Glu Tyr Cys Asn Leu Thr Gln Cys Ser
        435                 440                 445

Asp Ala Glu Gly Thr Ala Val Ala Pro Pro Thr Val Thr Pro Val Pro
    450                 455                 460

Ser Leu Glu Ala Pro Ser Glu Gln Ala Pro Thr Glu Gln Arg Pro Gly
465                 470                 475                 480

Val Gln Glu Cys Tyr His Gly Asn Gly Gln Ser Tyr Arg Gly Thr Tyr
                485                 490                 495

Ser Thr Thr Val Thr Gly Arg Thr Cys Gln Ala Trp Ser Ser Met Thr
            500                 505                 510

Pro His Ser His Ser Arg Thr Pro Glu Tyr Tyr Pro Asn Ala Gly Leu
        515                 520                 525

Ile Met Asn Tyr Cys Arg Asn Pro Asp Ala Val Ala Ala Pro Tyr Cys
    530                 535                 540

Tyr Thr Arg Asp Pro Gly Val Arg Trp Glu Tyr Cys Asn Leu Thr Gln
545                 550                 555                 560

Cys Ser Asp Ala Glu Gly Thr Ala Val Ala Pro Pro Thr Val Thr Pro
                565                 570                 575

Val Pro Ser Leu Glu Ala Pro Ser Glu Gln Ala Pro Thr Glu Gln Arg
            580                 585                 590

Pro Gly Val Gln Glu Cys Tyr His Gly Asn Gly Gln Ser Tyr Arg Gly
        595                 600                 605

Thr Tyr Ser Thr Thr Val Thr Gly Arg Thr Cys Gln Ala Trp Ser Ser
    610                 615                 620

Met Thr Pro His Ser His Ser Arg Thr Pro Glu Tyr Tyr Pro Asn Ala
625                 630                 635                 640

Gly Leu Ile Met Asn Tyr Cys Arg Asn Pro Asp Ala Val Ala Ala Pro
                645                 650                 655

Tyr Cys Tyr Thr Arg Asp Pro Gly Val Arg Trp Glu Tyr Cys Asn Leu
            660                 665                 670

Thr Gln Cys Ser Asp Ala Glu Gly Thr Ala Val Ala Pro Pro Thr Val
```

```
                        675                 680                 685
Thr Pro Val Pro Ser Leu Glu Ala Pro Ser Glu Gln Ala Pro Thr Glu
    690                 695                 700

Gln Arg Pro Gly Val Gln Glu Cys Tyr His Gly Asn Gly Gln Ser Tyr
705                 710                 715                 720

Arg Gly Thr Tyr Ser Thr Thr Val Thr Gly Arg Thr Cys Gln Ala Trp
                725                 730                 735

Ser Ser Met Thr Pro His Ser His Ser Arg Thr Pro Glu Tyr Tyr Pro
            740                 745                 750

Asn Ala Gly Leu Ile Met Asn Tyr Cys Arg Asn Pro Asp Ala Val Ala
        755                 760                 765

Ala Pro Tyr Cys Tyr Thr Arg Asp Pro Gly Val Arg Trp Glu Tyr Cys
    770                 775                 780

Asn Leu Thr Gln Cys Ser Asp Ala Glu Gly Thr Ala Val Ala Pro Pro
785                 790                 795                 800

Thr Val Thr Pro Val Pro Ser Leu Glu Ala Pro Ser Glu Gln Ala Pro
                805                 810                 815

Thr Glu Gln Arg Pro Gly Val Gln Glu Cys Tyr His Gly Asn Gly Gln
            820                 825                 830

Ser Tyr Arg Gly Thr Tyr Ser Thr Thr Val Thr Gly Arg Thr Cys Gln
        835                 840                 845

Ala Trp Ser Ser Met Thr Pro His Ser His Ser Arg Thr Pro Glu Tyr
    850                 855                 860

Tyr Pro Asn Ala Gly Leu Ile Met Asn Tyr Cys Arg Asn Pro Asp Ala
865                 870                 875                 880

Val Ala Ala Pro Tyr Cys Tyr Thr Arg Asp Pro Gly Val Arg Trp Glu
                885                 890                 895

Tyr Cys Asn Leu Thr Gln Cys Ser Asp Ala Glu Gly Thr Ala Val Ala
            900                 905                 910

Pro Pro Thr Val Thr Pro Val Pro Ser Leu Glu Ala Pro Ser Glu Gln
        915                 920                 925

Ala Pro Thr Glu Gln Arg Pro Gly Val Gln Glu Cys Tyr His Gly Asn
    930                 935                 940

Gly Gln Ser Tyr Arg Gly Thr Tyr Ser Thr Thr Val Thr Gly Arg Thr
945                 950                 955                 960

Cys Gln Ala Trp Ser Ser Met Thr Pro His Ser His Ser Arg Thr Pro
                965                 970                 975

Glu Tyr Tyr Pro Asn Ala Gly Leu Ile Met Asn Tyr Cys Arg Asn Pro
            980                 985                 990

Asp Ala Val Ala Ala Pro Tyr Cys Tyr Thr Arg Asp Pro Gly Val Arg
        995                1000                1005

Trp Glu Tyr Cys Asn Leu Thr Gln Cys Ser Asp Ala Glu Gly Thr
    1010                1015                1020

Ala Val Ala Pro Pro Thr Val Thr Pro Val Pro Ser Leu Glu Ala
    1025                1030                1035

Pro Ser Glu Gln Ala Pro Thr Glu Gln Arg Pro Gly Val Gln Glu
    1040                1045                1050

Cys Tyr His Gly Asn Gly Gln Ser Tyr Arg Gly Thr Tyr Ser Thr
    1055                1060                1065

Thr Val Thr Gly Arg Thr Cys Gln Ala Trp Ser Ser Met Thr Pro
    1070                1075                1080

His Ser His Ser Arg Thr Pro Glu Tyr Tyr Pro Asn Ala Gly Leu
    1085                1090                1095
```

```
Ile Met Asn Tyr Cys Arg Asn Pro Asp Ala Val Ala Ala Pro Tyr
    1100            1105                1110
Cys Tyr Thr Arg Asp Pro Gly Val Arg Trp Glu Tyr Cys Asn Leu
    1115            1120                1125
Thr Gln Cys Ser Asp Ala Glu Gly Thr Ala Val Ala Pro Pro Thr
    1130            1135                1140
Val Thr Pro Val Pro Ser Leu Glu Ala Pro Ser Glu Gln Ala Pro
    1145            1150                1155
Thr Glu Gln Arg Pro Gly Val Gln Glu Cys Tyr His Gly Asn Gly
    1160            1165                1170
Gln Ser Tyr Arg Gly Thr Tyr Ser Thr Thr Val Thr Gly Arg Thr
    1175            1180                1185
Cys Gln Ala Trp Ser Ser Met Thr Pro His Ser His Ser Arg Thr
    1190            1195                1200
Pro Glu Tyr Tyr Pro Asn Ala Gly Leu Ile Met Asn Tyr Cys Arg
    1205            1210                1215
Asn Pro Asp Ala Val Ala Ala Pro Tyr Cys Tyr Thr Arg Asp Pro
    1220            1225                1230
Gly Val Arg Trp Glu Tyr Cys Asn Leu Thr Gln Cys Ser Asp Ala
    1235            1240                1245
Glu Gly Thr Ala Val Ala Pro Pro Thr Val Thr Pro Val Pro Ser
    1250            1255                1260
Leu Glu Ala Pro Ser Glu Gln Ala Pro Thr Glu Gln Arg Pro Gly
    1265            1270                1275
Val Gln Glu Cys Tyr His Gly Asn Gly Gln Ser Tyr Arg Gly Thr
    1280            1285                1290
Tyr Ser Thr Thr Val Thr Gly Arg Thr Cys Gln Ala Trp Ser Ser
    1295            1300                1305
Met Thr Pro His Ser His Ser Arg Thr Pro Glu Tyr Tyr Pro Asn
    1310            1315                1320
Ala Gly Leu Ile Met Asn Tyr Cys Arg Asn Pro Asp Ala Val Ala
    1325            1330                1335
Ala Pro Tyr Cys Tyr Thr Arg Asp Pro Gly Val Arg Trp Glu Tyr
    1340            1345                1350
Cys Asn Leu Thr Gln Cys Ser Asp Ala Glu Gly Thr Ala Val Ala
    1355            1360                1365
Pro Pro Thr Val Thr Pro Val Pro Ser Leu Glu Ala Pro Ser Glu
    1370            1375                1380
Gln Ala Pro Thr Glu Gln Arg Pro Gly Val Gln Glu Cys Tyr His
    1385            1390                1395
Gly Asn Gly Gln Ser Tyr Arg Gly Thr Tyr Ser Thr Thr Val Thr
    1400            1405                1410
Gly Arg Thr Cys Gln Ala Trp Ser Ser Met Thr Pro His Ser His
    1415            1420                1425
Ser Arg Thr Pro Glu Tyr Tyr Pro Asn Ala Gly Leu Ile Met Asn
    1430            1435                1440
Tyr Cys Arg Asn Pro Asp Ala Val Ala Ala Pro Tyr Cys Tyr Thr
    1445            1450                1455
Arg Asp Pro Gly Val Arg Trp Glu Tyr Cys Asn Leu Thr Gln Cys
    1460            1465                1470
Ser Asp Ala Glu Gly Thr Ala Val Ala Pro Pro Thr Val Thr Pro
    1475            1480                1485
```

```
Val Pro Ser Leu Glu Ala Pro Ser Glu Gln Ala Pro Thr Glu Gln
1490                1495                1500

Arg Pro Gly Val Gln Glu Cys Tyr His Gly Asn Gly Gln Ser Tyr
1505                1510                1515

Arg Gly Thr Tyr Ser Thr Thr Val Thr Gly Arg Thr Cys Gln Ala
1520                1525                1530

Trp Ser Ser Met Thr Pro His Ser His Ser Arg Thr Pro Glu Tyr
1535                1540                1545

Tyr Pro Asn Ala Gly Leu Ile Met Asn Tyr Cys Arg Asn Pro Asp
1550                1555                1560

Ala Val Ala Ala Pro Tyr Cys Tyr Thr Arg Asp Pro Gly Val Arg
1565                1570                1575

Trp Glu Tyr Cys Asn Leu Thr Gln Cys Ser Asp Ala Glu Gly Thr
1580                1585                1590

Ala Val Ala Pro Pro Thr Val Thr Pro Val Pro Ser Leu Glu Ala
1595                1600                1605

Pro Ser Glu Gln Ala Pro Thr Glu Gln Arg Pro Gly Val Gln Glu
1610                1615                1620

Cys Tyr His Gly Asn Gly Gln Ser Tyr Arg Gly Thr Tyr Ser Thr
1625                1630                1635

Thr Val Thr Gly Arg Thr Cys Gln Ala Trp Ser Ser Met Thr Pro
1640                1645                1650

His Ser His Ser Arg Thr Pro Glu Tyr Tyr Pro Asn Ala Gly Leu
1655                1660                1665

Ile Met Asn Tyr Cys Arg Asn Pro Asp Ala Val Ala Ala Pro Tyr
1670                1675                1680

Cys Tyr Thr Arg Asp Pro Gly Val Arg Trp Glu Tyr Cys Asn Leu
1685                1690                1695

Thr Gln Cys Ser Asp Ala Glu Gly Thr Ala Val Ala Pro Pro Thr
1700                1705                1710

Val Thr Pro Val Pro Ser Leu Glu Ala Pro Ser Glu Gln Ala Pro
1715                1720                1725

Thr Glu Gln Arg Pro Gly Val Gln Glu Cys Tyr His Gly Asn Gly
1730                1735                1740

Gln Ser Tyr Arg Gly Thr Tyr Ser Thr Thr Val Thr Gly Arg Thr
1745                1750                1755

Cys Gln Ala Trp Ser Ser Met Thr Pro His Ser His Ser Arg Thr
1760                1765                1770

Pro Glu Tyr Tyr Pro Asn Ala Gly Leu Ile Met Asn Tyr Cys Arg
1775                1780                1785

Asn Pro Asp Ala Val Ala Ala Pro Tyr Cys Tyr Thr Arg Asp Pro
1790                1795                1800

Gly Val Arg Trp Glu Tyr Cys Asn Leu Thr Gln Cys Ser Asp Ala
1805                1810                1815

Glu Gly Thr Ala Val Ala Pro Pro Thr Val Thr Pro Val Pro Ser
1820                1825                1830

Leu Glu Ala Pro Ser Glu Gln Ala Pro Thr Glu Gln Arg Pro Gly
1835                1840                1845

Val Gln Glu Cys Tyr His Gly Asn Gly Gln Ser Tyr Arg Gly Thr
1850                1855                1860

Tyr Ser Thr Thr Val Thr Gly Arg Thr Cys Gln Ala Trp Ser Ser
1865                1870                1875

Met Thr Pro His Ser His Ser Arg Thr Pro Glu Tyr Tyr Pro Asn
```

```
                 1880            1885           1890
Ala Gly Leu Ile Met Asn Tyr Cys Arg Asn Pro Asp Ala Val Ala
    1895            1900           1905
Ala Pro Tyr Cys Tyr Thr Arg Asp Pro Gly Val Arg Trp Glu Tyr
    1910            1915           1920
Cys Asn Leu Thr Gln Cys Ser Asp Ala Glu Gly Thr Ala Val Ala
    1925            1930           1935
Pro Pro Thr Val Thr Pro Val Pro Ser Leu Glu Ala Pro Ser Glu
    1940            1945           1950
Gln Ala Pro Thr Glu Gln Arg Pro Gly Val Gln Glu Cys Tyr His
    1955            1960           1965
Gly Asn Gly Gln Ser Tyr Arg Gly Thr Tyr Ser Thr Thr Val Thr
    1970            1975           1980
Gly Arg Thr Cys Gln Ala Trp Ser Ser Met Thr Pro His Ser His
    1985            1990           1995
Ser Arg Thr Pro Glu Tyr Tyr Pro Asn Ala Gly Leu Ile Met Asn
    2000            2005           2010
Tyr Cys Arg Asn Pro Asp Ala Val Ala Ala Pro Tyr Cys Tyr Thr
    2015            2020           2025
Arg Asp Pro Gly Val Arg Trp Glu Tyr Cys Asn Leu Thr Gln Cys
    2030            2035           2040
Ser Asp Ala Glu Gly Thr Ala Val Ala Pro Pro Thr Val Thr Pro
    2045            2050           2055
Val Pro Ser Leu Glu Ala Pro Ser Glu Gln Ala Pro Thr Glu Gln
    2060            2065           2070
Arg Pro Gly Val Gln Glu Cys Tyr His Gly Asn Gly Gln Ser Tyr
    2075            2080           2085
Arg Gly Thr Tyr Ser Thr Thr Val Thr Gly Arg Thr Cys Gln Ala
    2090            2095           2100
Trp Ser Ser Met Thr Pro His Ser His Ser Arg Thr Pro Glu Tyr
    2105            2110           2115
Tyr Pro Asn Ala Gly Leu Ile Met Asn Tyr Cys Arg Asn Pro Asp
    2120            2125           2130
Ala Val Ala Ala Pro Tyr Cys Tyr Thr Arg Asp Pro Gly Val Arg
    2135            2140           2145
Trp Glu Tyr Cys Asn Leu Thr Gln Cys Ser Asp Ala Glu Gly Thr
    2150            2155           2160
Ala Val Ala Pro Pro Thr Val Thr Pro Val Pro Ser Leu Glu Ala
    2165            2170           2175
Pro Ser Glu Gln Ala Pro Thr Glu Gln Arg Pro Gly Val Gln Glu
    2180            2185           2190
Cys Tyr His Gly Asn Gly Gln Ser Tyr Arg Gly Thr Tyr Ser Thr
    2195            2200           2205
Thr Val Thr Gly Arg Thr Cys Gln Ala Trp Ser Ser Met Thr Pro
    2210            2215           2220
His Ser His Ser Arg Thr Pro Glu Tyr Tyr Pro Asn Ala Gly Leu
    2225            2230           2235
Ile Met Asn Tyr Cys Arg Asn Pro Asp Ala Val Ala Ala Pro Tyr
    2240            2245           2250
Cys Tyr Thr Arg Asp Pro Gly Val Arg Trp Glu Tyr Cys Asn Leu
    2255            2260           2265
Thr Gln Cys Ser Asp Ala Glu Gly Thr Ala Val Ala Pro Pro Thr
    2270            2275           2280
```

-continued

Val Thr Pro Val Pro Ser Leu Glu Ala Pro Ser Glu Gln Ala Pro
    2285            2290            2295

Thr Glu Gln Arg Pro Gly Val Gln Glu Cys Tyr His Gly Asn Gly
    2300            2305            2310

Gln Ser Tyr Arg Gly Thr Tyr Ser Thr Thr Val Thr Gly Arg Thr
    2315            2320            2325

Cys Gln Ala Trp Ser Ser Met Thr Pro His Ser His Ser Arg Thr
    2330            2335            2340

Pro Glu Tyr Tyr Pro Asn Ala Gly Leu Ile Met Asn Tyr Cys Arg
    2345            2350            2355

Asn Pro Asp Ala Val Ala Pro Tyr Cys Tyr Thr Arg Asp Pro
    2360            2365            2370

Gly Val Arg Trp Glu Tyr Cys Asn Leu Thr Gln Cys Ser Asp Ala
    2375            2380            2385

Glu Gly Thr Ala Val Ala Pro Pro Thr Val Thr Pro Val Pro Ser
    2390            2395            2400

Leu Glu Ala Pro Ser Glu Gln Ala Pro Thr Glu Gln Arg Pro Gly
    2405            2410            2415

Val Gln Glu Cys Tyr His Gly Asn Gly Gln Ser Tyr Arg Gly Thr
    2420            2425            2430

Tyr Ser Thr Thr Val Thr Gly Arg Thr Cys Gln Ala Trp Ser Ser
    2435            2440            2445

Met Thr Pro His Ser His Ser Arg Thr Pro Glu Tyr Tyr Pro Asn
    2450            2455            2460

Ala Gly Leu Ile Met Asn Tyr Cys Arg Asn Pro Asp Ala Val Ala
    2465            2470            2475

Ala Pro Tyr Cys Tyr Thr Arg Asp Pro Gly Val Arg Trp Glu Tyr
    2480            2485            2490

Cys Asn Leu Thr Gln Cys Ser Asp Ala Glu Gly Thr Ala Val Ala
    2495            2500            2505

Pro Pro Thr Val Thr Pro Val Pro Ser Leu Glu Ala Pro Ser Glu
    2510            2515            2520

Gln Ala Pro Thr Glu Gln Arg Pro Gly Val Gln Glu Cys Tyr His
    2525            2530            2535

Gly Asn Gly Gln Ser Tyr Arg Gly Thr Tyr Ser Thr Thr Val Thr
    2540            2545            2550

Gly Arg Thr Cys Gln Ala Trp Ser Ser Met Thr Pro His Ser His
    2555            2560            2565

Ser Arg Thr Pro Glu Tyr Tyr Pro Asn Ala Gly Leu Ile Met Asn
    2570            2575            2580

Tyr Cys Arg Asn Pro Asp Ala Val Ala Ala Pro Tyr Cys Tyr Thr
    2585            2590            2595

Arg Asp Pro Gly Val Arg Trp Glu Tyr Cys Asn Leu Thr Gln Cys
    2600            2605            2610

Ser Asp Ala Glu Gly Thr Ala Val Ala Pro Pro Thr Val Thr Pro
    2615            2620            2625

Val Pro Ser Leu Glu Ala Pro Ser Glu Gln Ala Pro Thr Glu Gln
    2630            2635            2640

Arg Pro Gly Val Gln Glu Cys Tyr His Gly Asn Gly Gln Ser Tyr
    2645            2650            2655

Arg Gly Thr Tyr Ser Thr Thr Val Thr Gly Arg Thr Cys Gln Ala
    2660            2665            2670

-continued

Trp Ser Ser Met Thr Pro His Ser His Ser Arg Thr Pro Glu Tyr
2675                2680                2685

Tyr Pro Asn Ala Gly Leu Ile Met Asn Tyr Cys Arg Asn Pro Asp
2690                2695                2700

Ala Val Ala Ala Pro Tyr Cys Tyr Thr Arg Asp Pro Gly Val Arg
2705                2710                2715

Trp Glu Tyr Cys Asn Leu Thr Gln Cys Ser Asp Ala Glu Gly Thr
2720                2725                2730

Ala Val Ala Pro Pro Thr Val Thr Pro Val Pro Ser Leu Glu Ala
2735                2740                2745

Pro Ser Glu Gln Ala Pro Thr Glu Gln Arg Pro Gly Val Gln Glu
2750                2755                2760

Cys Tyr His Gly Asn Gly Gln Ser Tyr Arg Gly Thr Tyr Ser Thr
2765                2770                2775

Thr Val Thr Gly Arg Thr Cys Gln Ala Trp Ser Ser Met Thr Pro
2780                2785                2790

His Ser His Ser Arg Thr Pro Glu Tyr Tyr Pro Asn Ala Gly Leu
2795                2800                2805

Ile Met Asn Tyr Cys Arg Asn Pro Asp Ala Val Ala Ala Pro Tyr
2810                2815                2820

Cys Tyr Thr Arg Asp Pro Gly Val Arg Trp Glu Tyr Cys Asn Leu
2825                2830                2835

Thr Gln Cys Ser Asp Ala Glu Gly Thr Ala Val Ala Pro Pro Thr
2840                2845                2850

Val Thr Pro Val Pro Ser Leu Glu Ala Pro Ser Glu Gln Ala Pro
2855                2860                2865

Thr Glu Gln Arg Pro Gly Val Gln Glu Cys Tyr His Gly Asn Gly
2870                2875                2880

Gln Ser Tyr Arg Gly Thr Tyr Ser Thr Thr Val Thr Gly Arg Thr
2885                2890                2895

Cys Gln Ala Trp Ser Ser Met Thr Pro His Ser His Ser Arg Thr
2900                2905                2910

Pro Glu Tyr Tyr Pro Asn Ala Gly Leu Ile Met Asn Tyr Cys Arg
2915                2920                2925

Asn Pro Asp Ala Val Ala Ala Pro Tyr Cys Tyr Thr Arg Asp Pro
2930                2935                2940

Gly Val Arg Trp Glu Tyr Cys Asn Leu Thr Gln Cys Ser Asp Ala
2945                2950                2955

Glu Gly Thr Ala Val Ala Pro Pro Thr Val Thr Pro Val Pro Ser
2960                2965                2970

Leu Glu Ala Pro Ser Glu Gln Ala Pro Thr Glu Gln Arg Pro Gly
2975                2980                2985

Val Gln Glu Cys Tyr His Gly Asn Gly Gln Ser Tyr Arg Gly Thr
2990                2995                3000

Tyr Ser Thr Thr Val Thr Gly Arg Thr Cys Gln Ala Trp Ser Ser
3005                3010                3015

Met Thr Pro His Ser His Ser Arg Thr Pro Glu Tyr Tyr Pro Asn
3020                3025                3030

Ala Gly Leu Ile Met Asn Tyr Cys Arg Asn Pro Asp Ala Val Ala
3035                3040                3045

Ala Pro Tyr Cys Tyr Thr Arg Asp Pro Gly Val Arg Trp Glu Tyr
3050                3055                3060

Cys Asn Leu Thr Gln Cys Ser Asp Ala Glu Gly Thr Ala Val Ala

```
                3065                3070                3075
Pro Pro Thr Val Thr Pro Val Pro Ser Leu Glu Ala Pro Ser Glu
    3080                3085                3090
Gln Ala Pro Thr Glu Gln Arg Pro Gly Val Gln Glu Cys Tyr His
    3095                3100                3105
Gly Asn Gly Gln Ser Tyr Arg Gly Thr Tyr Ser Thr Thr Val Thr
    3110                3115                3120
Gly Arg Thr Cys Gln Ala Trp Ser Ser Met Thr Pro His Ser His
    3125                3130                3135
Ser Arg Thr Pro Glu Tyr Tyr Pro Asn Ala Gly Leu Ile Met Asn
    3140                3145                3150
Tyr Cys Arg Asn Pro Asp Ala Val Ala Ala Pro Tyr Cys Tyr Thr
    3155                3160                3165
Arg Asp Pro Gly Val Arg Trp Glu Tyr Cys Asn Leu Thr Gln Cys
    3170                3175                3180
Ser Asp Ala Glu Gly Thr Ala Val Ala Pro Pro Thr Val Thr Pro
    3185                3190                3195
Val Pro Ser Leu Glu Ala Pro Ser Glu Gln Ala Pro Thr Glu Gln
    3200                3205                3210
Arg Pro Gly Val Gln Glu Cys Tyr His Gly Asn Gly Gln Ser Tyr
    3215                3220                3225
Arg Gly Thr Tyr Ser Thr Thr Val Thr Gly Arg Thr Cys Gln Ala
    3230                3235                3240
Trp Ser Ser Met Thr Pro His Ser His Ser Arg Thr Pro Glu Tyr
    3245                3250                3255
Tyr Pro Asn Ala Gly Leu Ile Met Asn Tyr Cys Arg Asn Pro Asp
    3260                3265                3270
Ala Val Ala Ala Pro Tyr Cys Tyr Thr Arg Asp Pro Gly Val Arg
    3275                3280                3285
Trp Glu Tyr Cys Asn Leu Thr Gln Cys Ser Asp Ala Glu Gly Thr
    3290                3295                3300
Ala Val Ala Pro Pro Thr Val Thr Pro Val Pro Ser Leu Glu Ala
    3305                3310                3315
Pro Ser Glu Gln Ala Pro Thr Glu Gln Arg Pro Gly Val Gln Glu
    3320                3325                3330
Cys Tyr His Gly Asn Gly Gln Ser Tyr Arg Gly Thr Tyr Ser Thr
    3335                3340                3345
Thr Val Thr Gly Arg Thr Cys Gln Ala Trp Ser Ser Met Thr Pro
    3350                3355                3360
His Ser His Ser Arg Thr Pro Glu Tyr Tyr Pro Asn Ala Gly Leu
    3365                3370                3375
Ile Met Asn Tyr Cys Arg Asn Pro Asp Pro Val Ala Ala Pro Tyr
    3380                3385                3390
Cys Tyr Thr Arg Asp Pro Ser Val Arg Trp Glu Tyr Cys Asn Leu
    3395                3400                3405
Thr Gln Cys Ser Asp Ala Glu Gly Thr Ala Val Ala Pro Pro Thr
    3410                3415                3420
Ile Thr Pro Ile Pro Ser Leu Glu Ala Pro Ser Glu Gln Ala Pro
    3425                3430                3435
Thr Glu Gln Arg Pro Gly Val Gln Glu Cys Tyr His Gly Asn Gly
    3440                3445                3450
Gln Ser Tyr Gln Gly Thr Tyr Phe Ile Thr Val Thr Gly Arg Thr
    3455                3460                3465
```

```
Cys Gln Ala Trp Ser Ser Met Thr Pro His Ser His Ser Arg Thr
3470                3475                3480

Pro Ala Tyr Tyr Pro Asn Ala Gly Leu Ile Lys Asn Tyr Cys Arg
3485                3490                3495

Asn Pro Asp Pro Val Ala Ala Pro Trp Cys Tyr Thr Thr Asp Pro
3500                3505                3510

Ser Val Arg Trp Glu Tyr Cys Asn Leu Thr Arg Cys Ser Asp Ala
3515                3520                3525

Glu Trp Thr Ala Phe Val Pro Pro Asn Val Ile Leu Ala Pro Ser
3530                3535                3540

Leu Glu Ala Phe Phe Glu Gln Ala Leu Thr Glu Glu Thr Pro Gly
3545                3550                3555

Val Gln Asp Cys Tyr Tyr His Tyr Gly Gln Ser Tyr Arg Gly Thr
3560                3565                3570

Tyr Ser Thr Thr Val Thr Gly Arg Thr Cys Gln Ala Trp Ser Ser
3575                3580                3585

Met Thr Pro His Gln His Ser Arg Thr Pro Glu Asn Tyr Pro Asn
3590                3595                3600

Ala Gly Leu Thr Arg Asn Tyr Cys Arg Asn Pro Asp Ala Glu Ile
3605                3610                3615

Arg Pro Trp Cys Tyr Thr Met Asp Pro Ser Val Arg Trp Glu Tyr
3620                3625                3630

Cys Asn Leu Thr Gln Cys Leu Val Thr Glu Ser Ser Val Leu Ala
3635                3640                3645

Thr Leu Thr Val Val Pro Asp Pro Ser Thr Glu Ala Ser Ser Glu
3650                3655                3660

Glu Ala Pro Thr Glu Gln Ser Pro Gly Val Gln Asp Cys Tyr His
3665                3670                3675

Gly Asp Gly Gln Ser Tyr Arg Gly Ser Phe Ser Thr Thr Val Thr
3680                3685                3690

Gly Arg Thr Cys Gln Ser Trp Ser Ser Met Thr Pro His Trp His
3695                3700                3705

Gln Arg Thr Thr Glu Tyr Tyr Pro Asn Gly Gly Leu Thr Arg Asn
3710                3715                3720

Tyr Cys Arg Asn Pro Asp Ala Glu Ile Ser Pro Trp Cys Tyr Thr
3725                3730                3735

Met Asp Pro Asn Val Arg Trp Glu Tyr Cys Asn Leu Thr Gln Cys
3740                3745                3750

Pro Val Thr Glu Ser Ser Val Leu Ala Thr Ser Thr Ala Val Ser
3755                3760                3765

Glu Gln Ala Pro Thr Glu Gln Ser Pro Thr Val Gln Asp Cys Tyr
3770                3775                3780

His Gly Asp Gly Gln Ser Tyr Arg Gly Ser Phe Ser Thr Thr Val
3785                3790                3795

Thr Gly Arg Thr Cys Gln Ser Trp Ser Ser Met Thr Pro His Trp
3800                3805                3810

His Gln Arg Thr Thr Glu Tyr Tyr Pro Asn Gly Gly Leu Thr Arg
3815                3820                3825

Asn Tyr Cys Arg Asn Pro Asp Ala Glu Ile Arg Pro Trp Cys Tyr
3830                3835                3840

Thr Met Asp Pro Ser Val Arg Trp Glu Tyr Cys Asn Leu Thr Gln
3845                3850                3855
```

-continued

Cys Pro Val Met Glu Ser Thr Leu Leu Thr Pro Thr Val Val
3860             3865             3870

Pro Val Pro Ser Thr Glu Leu Pro Ser Glu Glu Ala Pro Thr Glu
3875             3880             3885

Asn Ser Thr Gly Val Gln Asp Cys Tyr Arg Gly Asp Gly Gln Ser
3890             3895             3900

Tyr Arg Gly Thr Leu Ser Thr Thr Ile Thr Gly Arg Thr Cys Gln
3905             3910             3915

Ser Trp Ser Ser Met Thr Pro His Trp His Arg Arg Ile Pro Leu
3920             3925             3930

Tyr Tyr Pro Asn Ala Gly Leu Thr Arg Asn Tyr Cys Arg Asn Pro
3935             3940             3945

Asp Ala Glu Ile Arg Pro Trp Cys Tyr Thr Met Asp Pro Ser Val
3950             3955             3960

Arg Trp Glu Tyr Cys Asn Leu Thr Arg Cys Pro Val Thr Glu Ser
3965             3970             3975

Ser Val Leu Thr Thr Pro Thr Val Ala Pro Val Pro Ser Thr Glu
3980             3985             3990

Ala Pro Ser Glu Gln Ala Pro Pro Glu Lys Ser Pro Val Val Gln
3995             4000             4005

Asp Cys Tyr His Gly Asp Gly Arg Ser Tyr Arg Gly Ile Ser Ser
4010             4015             4020

Thr Thr Val Thr Gly Arg Thr Cys Gln Ser Trp Ser Ser Met Ile
4025             4030             4035

Pro His Trp His Gln Arg Thr Pro Glu Asn Tyr Pro Asn Ala Gly
4040             4045             4050

Leu Thr Glu Asn Tyr Cys Arg Asn Pro Asp Ser Gly Lys Gln Pro
4055             4060             4065

Trp Cys Tyr Thr Thr Asp Pro Cys Val Arg Trp Glu Tyr Cys Asn
4070             4075             4080

Leu Thr Gln Cys Ser Glu Thr Glu Ser Gly Val Leu Glu Thr Pro
4085             4090             4095

Thr Val Val Pro Val Pro Ser Met Glu Ala His Ser Glu Ala Ala
4100             4105             4110

Pro Thr Glu Gln Thr Pro Val Val Arg Gln Cys Tyr His Gly Asn
4115             4120             4125

Gly Gln Ser Tyr Arg Gly Thr Phe Ser Thr Thr Val Thr Gly Arg
4130             4135             4140

Thr Cys Gln Ser Trp Ser Ser Met Thr Pro His Arg His Gln Arg
4145             4150             4155

Thr Pro Glu Asn Tyr Pro Asn Asp Gly Leu Thr Met Asn Tyr Cys
4160             4165             4170

Arg Asn Pro Asp Ala Asp Thr Gly Pro Trp Cys Phe Thr Met Asp
4175             4180             4185

Pro Ser Ile Arg Trp Glu Tyr Cys Asn Leu Thr Arg Cys Ser Asp
4190             4195             4200

Thr Glu Gly Thr Val Val Ala Pro Pro Thr Val Ile Gln Val Pro
4205             4210             4215

Ser Leu Gly Pro Pro Ser Glu Gln Asp Cys Met Phe Gly Asn Gly
4220             4225             4230

Lys Gly Tyr Arg Gly Lys Lys Ala Thr Thr Val Thr Gly Thr Pro
4235             4240             4245

Cys Gln Glu Trp Ala Ala Gln Glu Pro His Arg His Ser Thr Phe

-continued

```
            4250            4255            4260
Ile Pro Gly Thr Asn Lys Trp Ala Gly Leu Glu Lys Asn Tyr Cys
        4265            4270            4275

Arg Asn Pro Asp Gly Asp Ile Asn Gly Pro Trp Cys Tyr Thr Met
        4280            4285            4290

Asn Pro Arg Lys Leu Phe Asp Tyr Cys Asp Ile Pro Leu Cys Ala
        4295            4300            4305

Ser Ser Ser Phe Asp Cys Gly Lys Pro Gln Val Glu Pro Lys Lys
        4310            4315            4320

Cys Pro Gly Ser Ile Val Gly Gly Cys Val Ala His Pro His Ser
        4325            4330            4335

Trp Pro Trp Gln Val Ser Leu Arg Thr Arg Phe Gly Lys His Phe
        4340            4345            4350

Cys Gly Gly Thr Leu Ile Ser Pro Glu Trp Val Leu Thr Ala Ala
        4355            4360            4365

His Cys Leu Lys Lys Ser Ser Arg Pro Ser Ser Tyr Lys Val Ile
        4370            4375            4380

Leu Gly Ala His Gln Glu Val Asn Leu Glu Ser His Val Gln Glu
        4385            4390            4395

Ile Glu Val Ser Arg Leu Phe Leu Glu Pro Thr Gln Ala Asp Ile
        4400            4405            4410

Ala Leu Leu Lys Leu Ser Arg Pro Ala Val Ile Thr Asp Lys Val
        4415            4420            4425

Met Pro Ala Cys Leu Pro Ser Pro Asp Tyr Met Val Thr Ala Arg
        4430            4435            4440

Thr Glu Cys Tyr Ile Thr Gly Trp Gly Glu Thr Gln Gly Thr Phe
        4445            4450            4455

Gly Thr Gly Leu Leu Lys Glu Ala Gln Leu Leu Val Ile Glu Asn
        4460            4465            4470

Glu Val Cys Asn His Tyr Lys Tyr Ile Cys Ala Glu His Leu Ala
        4475            4480            4485

Arg Gly Thr Asp Ser Cys Gln Gly Asp Ser Gly Gly Pro Leu Val
        4490            4495            4500

Cys Phe Glu Lys Asp Lys Tyr Ile Leu Gln Gly Val Thr Ser Trp
        4505            4510            4515

Gly Leu Gly Cys Ala Arg Pro Asn Lys Pro Gly Val Tyr Ala Arg
        4520            4525            4530

Val Ser Arg Phe Val Thr Trp Ile Glu Gly Met Met Arg Asn Asn
        4535            4540            4545

<210> SEQ ID NO 43
<211> LENGTH: 184
<212> TYPE: PRT
<213> ORGANISM: Homo sapiens

<400> SEQUENCE: 43

Met Ala Glu Pro Gln Pro Pro Ser Gly Gly Leu Thr Asp Glu Ala Ala
1               5                   10                  15

Leu Ser Cys Cys Ser Asp Ala Asp Pro Ser Thr Lys Asp Phe Leu Leu
            20                  25                  30

Gln Gln Thr Met Leu Arg Val Lys Asp Pro Lys Lys Ser Leu Asp Phe
        35                  40                  45

Tyr Thr Arg Val Leu Gly Met Thr Leu Ile Gln Lys Cys Asp Phe Pro
    50                  55                  60
```

```
Ile Met Lys Phe Ser Leu Tyr Phe Leu Ala Tyr Glu Asp Lys Asn Asp
 65                  70                  75                  80

Ile Pro Lys Glu Lys Asp Glu Lys Ile Ala Trp Ala Leu Ser Arg Lys
                 85                  90                  95

Ala Thr Leu Glu Leu Thr His Asn Trp Gly Thr Glu Asp Asp Glu Thr
            100                 105                 110

Gln Ser Tyr His Asn Gly Asn Ser Asp Pro Arg Gly Phe Gly His Ile
        115                 120                 125

Gly Ile Ala Val Pro Asp Val Tyr Ser Ala Cys Lys Arg Phe Glu Glu
    130                 135                 140

Leu Gly Val Lys Phe Val Lys Lys Pro Asp Asp Gly Lys Met Lys Gly
145                 150                 155                 160

Leu Ala Phe Ile Gln Asp Pro Asp Gly Tyr Trp Ile Glu Ile Leu Asn
                165                 170                 175

Pro Asn Lys Met Ala Thr Leu Met
                180

<210> SEQ ID NO 44
<211> LENGTH: 1824
<212> TYPE: PRT
<213> ORGANISM: Homo sapiens

<400> SEQUENCE: 44

Met Ser Ala Gly Gly Arg Asp Glu Glu Arg Arg Lys Leu Ala Asp Ile
  1               5                  10                  15

Ile His His Trp Asn Ala Asn Arg Leu Asp Leu Phe Glu Ile Ser Gln
                 20                  25                  30

Pro Thr Glu Asp Leu Glu Phe His Gly Val Met Arg Phe Tyr Phe Gln
             35                  40                  45

Asp Lys Ala Ala Gly Asn Phe Ala Thr Lys Cys Ile Arg Val Ser Ser
        50                  55                  60

Thr Ala Thr Thr Gln Asp Val Ile Glu Thr Leu Ala Glu Lys Phe Arg
 65                  70                  75                  80

Pro Asp Met Arg Met Leu Ser Ser Pro Lys Tyr Ser Leu Tyr Glu Val
                 85                  90                  95

His Val Ser Gly Glu Arg Arg Leu Asp Ile Asp Glu Lys Pro Leu Val
            100                 105                 110

Val Gln Leu Asn Trp Asn Lys Asp Asp Arg Glu Gly Arg Phe Val Leu
        115                 120                 125

Lys Asn Glu Asn Asp Ala Ile Pro Pro Lys Lys Ala Gln Ser Asn Gly
    130                 135                 140

Pro Glu Lys Gln Glu Lys Glu Gly Val Ile Gln Asn Phe Lys Arg Thr
145                 150                 155                 160

Leu Ser Lys Lys Glu Lys Lys Glu Lys Lys Arg Glu Lys Glu Ala
                165                 170                 175

Leu Arg Gln Ala Ser Asp Lys Asp Arg Pro Phe Gln Gly Glu Asp
    180                 185                 190

Val Glu Asn Ser Arg Leu Ala Ala Glu Val Tyr Lys Asp Met Pro Glu
                195                 200                 205

Thr Ser Phe Thr Arg Thr Ile Ser Asn Pro Glu Val Val Met Lys Arg
            210                 215                 220

Arg Arg Gln Gln Lys Leu Glu Lys Arg Met Gln Glu Phe Arg Ser Ser
225                 230                 235                 240

Asp Gly Arg Pro Asp Ser Gly Gly Thr Leu Arg Ile Tyr Ala Asp Ser
                245                 250                 255
```

-continued

Leu Lys Pro Asn Ile Pro Tyr Lys Thr Ile Leu Leu Ser Thr Thr Asp
            260                 265                 270

Pro Ala Asp Phe Ala Val Ala Glu Ala Leu Glu Lys Tyr Gly Leu Glu
        275                 280                 285

Lys Glu Asn Pro Lys Asp Tyr Cys Ile Ala Arg Val Met Leu Pro Pro
    290                 295                 300

Gly Ala Gln His Ser Asp Glu Lys Gly Ala Lys Glu Ile Ile Leu Asp
305                 310                 315                 320

Asp Asp Glu Cys Pro Leu Gln Ile Phe Arg Glu Trp Pro Ser Asp Lys
                325                 330                 335

Gly Ile Leu Val Phe Gln Leu Lys Arg Arg Pro Pro Asp His Ile Pro
            340                 345                 350

Lys Lys Thr Lys Lys His Leu Glu Gly Lys Thr Pro Lys Gly Lys Glu
        355                 360                 365

Arg Ala Asp Gly Ser Gly Tyr Gly Ser Thr Leu Pro Pro Glu Lys Leu
    370                 375                 380

Pro Tyr Leu Val Glu Leu Ser Pro Gly Arg Arg Asn His Phe Ala Tyr
385                 390                 395                 400

Tyr Asn Tyr His Thr Tyr Glu Asp Gly Ser Asp Ser Arg Asp Lys Pro
                405                 410                 415

Lys Leu Tyr Arg Leu Gln Leu Ser Val Thr Glu Val Gly Thr Glu Lys
            420                 425                 430

Leu Asp Asp Asn Ser Ile Gln Leu Phe Gly Pro Gly Ile Gln Pro His
        435                 440                 445

His Cys Asp Leu Thr Asn Met Asp Gly Val Val Thr Val Thr Pro Arg
    450                 455                 460

Ser Met Asp Ala Glu Thr Tyr Val Glu Gly Gln Arg Ile Ser Glu Thr
465                 470                 475                 480

Thr Met Leu Gln Ser Gly Met Lys Val Gln Phe Gly Ala Ser His Val
                485                 490                 495

Phe Lys Phe Val Asp Pro Ser Gln Asp His Ala Leu Ala Lys Arg Ser
            500                 505                 510

Val Asp Gly Gly Leu Met Val Lys Gly Pro Arg His Lys Pro Gly Ile
        515                 520                 525

Val Gln Glu Thr Thr Phe Asp Leu Gly Gly Asp Ile His Ser Gly Thr
    530                 535                 540

Ala Leu Pro Thr Ser Lys Ser Thr Thr Arg Leu Asp Ser Asp Arg Val
545                 550                 555                 560

Ser Ser Ala Ser Ser Thr Ala Glu Arg Gly Met Val Lys Pro Met Ile
                565                 570                 575

Arg Val Glu Gln Gln Pro Asp Tyr Arg Arg Gln Glu Ser Arg Thr Gln
            580                 585                 590

Asp Ala Ser Gly Pro Glu Leu Ile Leu Pro Ala Ser Ile Glu Phe Arg
        595                 600                 605

Glu Ser Ser Glu Asp Ser Phe Leu Ser Ala Ile Ile Asn Tyr Thr Asn
    610                 615                 620

Ser Ser Thr Val His Phe Lys Leu Ser Pro Thr Tyr Val Leu Tyr Met
625                 630                 635                 640

Ala Cys Arg Tyr Val Leu Ser Asn Gln Tyr Arg Pro Asp Ile Ser Pro
                645                 650                 655

Thr Glu Arg Thr His Lys Val Ile Ala Val Val Asn Lys Met Val Ser
            660                 665                 670

```
Met Met Glu Gly Val Ile Gln Lys Gln Lys Asn Ile Ala Gly Ala Leu
            675                 680                 685

Ala Phe Trp Met Ala Asn Ala Ser Glu Leu Leu Asn Phe Ile Lys Gln
        690                 695                 700

Asp Arg Asp Leu Ser Arg Ile Thr Leu Asp Ala Gln Asp Val Leu Ala
705                 710                 715                 720

His Leu Val Gln Met Ala Phe Lys Tyr Leu Val His Cys Leu Gln Ser
                725                 730                 735

Glu Leu Asn Asn Tyr Met Pro Ala Phe Leu Asp Asp Pro Glu Glu Asn
                740                 745                 750

Ser Leu Gln Arg Pro Lys Ile Asp Asp Val Leu His Thr Leu Thr Gly
            755                 760                 765

Ala Met Ser Leu Leu Arg Arg Cys Arg Val Asn Ala Ala Leu Thr Ile
        770                 775                 780

Gln Leu Phe Ser Gln Leu Phe His Phe Ile Asn Met Trp Leu Phe Asn
785                 790                 795                 800

Arg Leu Val Thr Asp Pro Asp Ser Gly Leu Cys Ser His Tyr Trp Gly
                805                 810                 815

Ala Ile Ile Arg Gln Gln Leu Gly His Ile Glu Ala Trp Ala Glu Lys
                820                 825                 830

Gln Gly Leu Glu Leu Ala Ala Asp Cys His Leu Ser Arg Ile Val Gln
            835                 840                 845

Ala Thr Thr Leu Leu Thr Met Asp Lys Tyr Ala Pro Asp Asp Ile Pro
        850                 855                 860

Asn Ile Asn Ser Thr Cys Phe Lys Leu Asn Ser Leu Gln Leu Gln Ala
865                 870                 875                 880

Leu Leu Gln Asn Tyr His Cys Ala Pro Asp Glu Pro Phe Ile Pro Thr
                885                 890                 895

Asp Leu Ile Glu Asn Val Val Thr Val Ala Glu Asn Thr Ala Asp Glu
                900                 905                 910

Leu Ala Arg Ser Asp Gly Arg Glu Val Gln Leu Glu Glu Asp Pro Asp
            915                 920                 925

Leu Gln Leu Pro Phe Leu Leu Pro Glu Asp Gly Tyr Ser Cys Asp Val
        930                 935                 940

Val Arg Asn Ile Pro Asn Gly Leu Gln Glu Phe Leu Asp Pro Leu Cys
945                 950                 955                 960

Gln Arg Gly Phe Cys Arg Leu Ile Pro His Thr Arg Ser Pro Gly Thr
                965                 970                 975

Trp Thr Ile Tyr Phe Glu Gly Ala Asp Tyr Glu Ser His Leu Leu Arg
                980                 985                 990

Glu Asn Thr Glu Leu Ala Gln Pro Leu Arg Lys Glu Pro Glu Ile Ile
            995                 1000                1005

Thr Val Thr Leu Lys Lys Gln Asn Gly Met Gly Leu Ser Ile Val
    1010                1015                1020

Ala Ala Lys Gly Ala Gly Gln Asp Lys Leu Gly Ile Tyr Val Lys
    1025                1030                1035

Ser Val Val Lys Gly Gly Ala Ala Asp Val Asp Gly Arg Leu Ala
    1040                1045                1050

Ala Gly Asp Gln Leu Leu Ser Val Asp Gly Arg Ser Leu Val Gly
    1055                1060                1065

Leu Ser Gln Glu Arg Ala Ala Glu Leu Met Thr Arg Thr Ser Ser
    1070                1075                1080

Val Val Thr Leu Glu Val Ala Lys Gln Gly Ala Ile Tyr His Gly
```

-continued

```
            1085                1090                1095

Leu Ala Thr Leu Leu Asn Gln Pro Ser Pro Met Met Gln Arg Ile
            1100                1105                1110

Ser Asp Arg Arg Gly Ser Gly Lys Pro Arg Pro Lys Ser Glu Gly
            1115                1120                1125

Phe Glu Leu Tyr Asn Asn Ser Thr Gln Asn Gly Ser Pro Glu Ser
            1130                1135                1140

Pro Gln Leu Pro Trp Ala Glu Tyr Ser Glu Pro Lys Lys Leu Pro
            1145                1150                1155

Gly Asp Asp Arg Leu Met Lys Asn Arg Ala Asp His Arg Ser Ser
            1160                1165                1170

Pro Asn Val Ala Asn Gln Pro Pro Ser Pro Gly Gly Lys Ser Ala
            1175                1180                1185

Tyr Ala Ser Gly Thr Thr Ala Lys Ile Thr Ser Val Ser Thr Gly
            1190                1195                1200

Asn Leu Cys Thr Glu Glu Gln Thr Pro Pro Arg Pro Glu Ala
            1205                1210                1215

Tyr Pro Ile Pro Thr Gln Thr Tyr Thr Arg Glu Tyr Phe Thr Phe
            1220                1225                1230

Pro Ala Ser Lys Ser Gln Asp Arg Met Ala Pro Pro Gln Asn Gln
            1235                1240                1245

Trp Pro Asn Tyr Glu Glu Lys Pro His Met His Thr Asp Ser Asn
            1250                1255                1260

His Ser Ser Ile Ala Ile Gln Arg Val Thr Arg Ser Gln Glu Glu
            1265                1270                1275

Leu Arg Glu Asp Lys Ala Tyr Gln Leu Glu Arg His Arg Ile Glu
            1280                1285                1290

Ala Ala Met Asp Arg Lys Ser Asp Ser Asp Met Trp Ile Asn Gln
            1295                1300                1305

Ser Ser Ser Leu Asp Ser Ser Thr Ser Ser Gln Glu His Leu Asn
            1310                1315                1320

His Ser Ser Lys Ser Val Thr Pro Ala Ser Thr Leu Thr Lys Ser
            1325                1330                1335

Gly Pro Gly Arg Trp Lys Thr Pro Ala Ala Ile Pro Ala Thr Pro
            1340                1345                1350

Val Ala Val Ser Gln Pro Ile Arg Thr Asp Leu Pro Pro Pro Pro
            1355                1360                1365

Pro Pro Pro Pro Val His Tyr Ala Gly Asp Phe Asp Gly Met Ser
            1370                1375                1380

Met Asp Leu Pro Leu Pro Pro Pro Ser Ala Asn Gln Ile Gly
            1385                1390                1395

Leu Pro Ser Ala Gln Val Ala Ala Ala Glu Arg Arg Lys Arg Glu
            1400                1405                1410

Glu His Gln Arg Trp Tyr Glu Lys Glu Lys Ala Arg Leu Glu Glu
            1415                1420                1425

Glu Arg Glu Arg Lys Arg Arg Glu Gln Glu Arg Lys Leu Gly Gln
            1430                1435                1440

Met Arg Thr Gln Ser Leu Asn Pro Ala Pro Phe Ser Pro Leu Thr
            1445                1450                1455

Ala Gln Gln Met Lys Pro Glu Lys Pro Ser Thr Leu Gln Arg Pro
            1460                1465                1470

Gln Glu Thr Val Ile Arg Glu Leu Gln Pro Gln Gln Gln Pro Arg
            1475                1480                1485
```

Thr Ile Glu Arg Arg Asp Leu Gln Tyr Ile Thr Val Ser Lys Glu
    1490                1495                1500

Glu Leu Ser Ser Gly Asp Ser Leu Ser Pro Asp Pro Trp Lys Arg
    1505                1510                1515

Asp Ala Lys Glu Lys Leu Glu Lys Gln Gln Gln Met His Ile Val
    1520                1525                1530

Asp Met Leu Ser Lys Glu Ile Gln Glu Leu Gln Ser Lys Pro Asp
    1535                1540                1545

Arg Ser Ala Glu Glu Ser Asp Arg Leu Arg Lys Leu Met Leu Glu
    1550                1555                1560

Trp Gln Phe Gln Lys Arg Leu Gln Glu Ser Lys Gln Lys Asp Glu
    1565                1570                1575

Asp Asp Glu Glu Glu Asp Asp Val Asp Thr Met Leu Ile
    1580                1585                1590

Met Gln Arg Leu Glu Ala Glu Arg Arg Ala Arg Leu Gln Asp Glu
    1595                1600                1605

Glu Arg Arg Arg Gln Gln Gln Leu Glu Glu Met Arg Lys Arg Glu
    1610                1615                1620

Ala Glu Asp Arg Ala Arg Gln Glu Glu Glu Arg Arg Arg Gln Glu
    1625                1630                1635

Glu Glu Arg Thr Lys Arg Asp Ala Glu Glu Lys Arg Arg Gln Glu
    1640                1645                1650

Glu Gly Tyr Tyr Ser Arg Leu Glu Ala Glu Arg Arg Arg Gln His
    1655                1660                1665

Asp Glu Ala Ala Arg Arg Leu Leu Glu Pro Glu Ala Pro Gly Leu
    1670                1675                1680

Cys Arg Pro Pro Leu Pro Arg Asp Tyr Glu Pro Ser Pro Ser
    1685                1690                1695

Pro Ala Pro Gly Ala Pro Pro Pro Pro Gln Arg Asn Ala Ser
    1700                1705                1710

Tyr Leu Lys Thr Gln Val Leu Ser Pro Asp Ser Leu Phe Thr Ala
    1715                1720                1725

Lys Phe Val Ala Tyr Asn Glu Glu Glu Glu Glu Asp Cys Ser
    1730                1735                1740

Leu Ala Gly Pro Asn Ser Tyr Pro Gly Ser Thr Gly Ala Ala Val
    1745                1750                1755

Gly Ala His Asp Ala Cys Arg Asp Ala Lys Glu Lys Arg Ser Lys
    1760                1765                1770

Ser Gln Asp Ala Asp Ser Pro Gly Ser Ser Gly Ala Pro Glu Asn
    1775                1780                1785

Leu Thr Phe Lys Glu Arg Gln Arg Leu Phe Ser Gln Gly Gln Asp
    1790                1795                1800

Val Ser Asn Lys Val Lys Ala Ser Arg Lys Leu Thr Glu Leu Glu
    1805                1810                1815

Asn Glu Leu Asn Thr Lys
    1820

<210> SEQ ID NO 45
<211> LENGTH: 23
<212> TYPE: DNA
<213> ORGANISM: Artificial Sequence
<220> FEATURE:
<223> OTHER INFORMATION: PCSK9 sgRNA target

<400> SEQUENCE: 45

```
gagggagatt tgacacacac agg                                              23
```

<210> SEQ ID NO 46
<211> LENGTH: 6
<212> TYPE: PRT
<213> ORGANISM: Artificial Sequence
<220> FEATURE:
<223> OTHER INFORMATION: 2X glycine linker

<400> SEQUENCE: 46

```
Gly Gly Gly Gly Gly Gly
1               5
```

<210> SEQ ID NO 47
<211> LENGTH: 3564
<212> TYPE: DNA
<213> ORGANISM: Artificial Sequence
<220> FEATURE:
<223> OTHER INFORMATION: targeted PCSK9 genomic locus

<400> SEQUENCE: 47

```
gtgtggggct gcctccccga gcttccatct gccgctgggg ccacacccca ggcccaggga     60
tgggacccca cagtggtcac atcatcttgc agcagaaccc aggtacagct cctggagcag    120
atggtggtcc caagcacggg tgggaccaga aggactctc acctgggcta actcagctgc     180
agcctcagtt ccctcctcac acacgacgag gaacatggac tggaagcctg cccagcaggc    240
cttctgctcg atgtgcgttg tgtggcttac gtccaggag ggaagcagcc tctgtgctgt      300
cttctagata agcctgtatt ccccgggctg tctgccaatg tatccagttg tcccgtcagc    360
ctggaagctc tgagggaaaa ccttgggctg cttcctgagc acctgtatcc cctgcagcca    420
gcccggggcc tctgctagga gcagactgag catggcttat gggcctggca ccatctggcc    480
tctgcccacc ttgctggcct tgtcttgtgt ctgccccttc gacattccat agcccagctc    540
aatatctagt ggttcctcta gggtggcgag cactgtttgg tctccagatg tcttcaggtc    600
ggagctcaca gcgctctcag ccaccccttc ccagtgtagc accgggcaca tggtagatgc    660
ctattgatga gtgaaagctc ctaacacact cagagagcaa ggactccgcc tcatcccaca    720
gcctgggagg agaggcagac tgccaaggac ctgctcagca tgctacagaa gaaaccaaag    780
tgcccacggg actgatcagt ggagcttcct gccgagactg gaggccttag ggcagggtag    840
acagtgtgtg tgcaggctgg ggactcacag ttcggactgt gcccagacct actagcatag    900
tgggtgggtg ggaggatgcg ggactggggg ccgaccttgc ctgaaattca tgtgggatct    960
cagagcagcc actgaattgc tctgtagggg gctaaatagt ggcccccaca gatacacaca   1020
cccagacaga gcctgtgagc cagaccttat ttggagaaaa ggtctttgta gatgtaatta   1080
agcatctcaa gatggcatca tctggattat gcggtgggct gtaagtcctg tgatgtgtct   1140
ttatgagaga aaggcagagg gagatttgac acacacagga ggggccacgt ggagacagag   1200
gtggagattg gagaaatgtg gccacaagcc agggaacacc agcagccacc agaagccgga   1260
agacgtgagg cagggttctt cccagagcct tcgctgctga gtctgggaat tgtgaccga    1320
agccataaga agtgggtaca cgccctgagc ctcccacact tgctcacctg tcctgagatg   1380
agaatctcta ctctgcagca tatttggagg atcactgcgg gggccacaga ggtgctgttc   1440
agatggcact tcagaagact caggagaccc tgggcagga gcagtttgac tgacagccca    1500
gagggctgcc ctctgattcc acctgaggcc ctgcttttcc tggctgcagg ggttccaggg   1560
ccaggccatt tccgctggcg caggactctg ctagcagcaa cctgcctgaa gtcttccttt   1620
```

```
ggcctggctg agagtttctg agacctgcgc tggagcggag gtgcttcctt ccttgcttcc      1680
tttcttcctc tctcccttct ccatccagca ggctggacct gcctggcatc tgtgagctct      1740
ccctactttc tcctataccc taacctttgt cctgcatggg cgactccccc agtgagtctc      1800
ttgcagcttt taccccagtg cctgcttctt ggagaatcca aactgatcca gttagggatg      1860
ataaagtgta gggtaggcgc tcggtgactg ttttctctga ggttgtgact cgtgtgaggc      1920
agaagcagtc cccgtgagcc ctcctggtat cttgtggagt ggagaacgct tggacctgga      1980
gccaggaggc ccagacatac atcctgtccg agctgcagct tcctgtctct aaaatgagcc      2040
ggccagcgca ggtggccaga catcactgtt attctccttt gagtctttaa atcttgttgt      2100
ctttcttgca gactcggtga gctgtgaaag gctataatag gggctttatt ttacactttg      2160
atactatttt ttgaacattc atattattgt tagatattga tattcatatg aaggagcagg      2220
atgacttggg tccttcttgg cagtagcatt gccagctgat ggccttggac agttacctgc      2280
cctctctagg cctcccttc cttgtctatg aaatacatta tagaatagga tgtagtgtgt      2340
gaggattttt tggaggttaa acgagtgaat atatttaagg cgctttcacc agtgcctggg      2400
atgtgctctg tagtttctgt gtgttaacta taaggttgac tttatgctca ttccctcctc      2460
tcccacaaat gtcgccttgg aaagacggag gcagcctggt ggaggtgtat ctcctagaca      2520
ccagcataca gagtgaccac cgggaaatcg agggcagggt catggtcacc gacttcgaga      2580
atgtgcccga ggaggacggg acccgcttcc acagacaggt aagcacggcc gtctgatggg      2640
agggctgcct ctgcccatat ccccatcctg gaggtgggtg gggactgcca ccccagagcg      2700
ttgcagctgt actcctgggt tgcaccccc ccagctgtca ctgtcccctc cctgccatca      2760
gttgtgggaa gggcgttcat ccatccagcc acctgctgat tgttataggt gtggagggg      2820 ggtctttctc atgtggtcct tgtgttcgtc gagcaggcca gcaagtgtga cagtcatggc      2880
acccacctgg caggggtggt cagcggccgg gatgccggcg tggccaaggg tgccagcatg      2940
cgcagcctgc gcgtgctcaa ctgccaaggg aagggcacgg ttagcggcac cctcataggt      3000
aagtgatggc cccagacgct ggtctctctc catctggacc tggcctggga ggtggcttgg      3060
gctgggccca gggagagcta atgtctccta accaagaatg ctgtggcagc ctctgccgca      3120
gagccagaga accagagtgc caaggctggc agggttccca gtggccacga gtgcagatga      3180
agaaacccag gccccaagag ggtcatgcag gtagcccagg gagttcagcc ttgaccctgg      3240
gtcaatgacc tttccacagt tccacactgc tccccttta aaatccggtg atgtctttat      3300
gtcttttgtt atgttatctt caatgtggag ggactcgagg tgatctaagc aaactttttc      3360
tatcttctgc ttgcatacct ctgagaccag gggactcact cacttgcatg actgggccct      3420
gcaggtcaca ctggccaggc agatgtggtg gaggaactgg cagaggactt tttctagact      3480
gtgactacat ttagtccacc cagcggcccc cctatgaagt ccagttgaga actaggactc      3540
tgggggccgg tggacagaga agag                                             3564
```

<210> SEQ ID NO 48
<211> LENGTH: 3888
<212> TYPE: DNA
<213> ORGANISM: Artificial Sequence
<220> FEATURE:
<223> OTHER INFORMATION: PCSK9-dTAG hybrid

<400> SEQUENCE: 48

```
gtgtggggct gcctccccga gcttccatct gccgctgggg ccacacccca ggcccaggga       60
```

-continued

```
tgggacccca cagtggtcac atcatcttgc agcagaaccc aggtacagct cctggagcag      120
atggtggtcc caagcacggg tgggaccaga aaggactctc acctgggcta actcagctgc      180
agcctcagtt ccctcctcac acacgacgag gaacatggac tggaagcctg cccagcaggc      240
cttctgctcg atgtgcgttg tgtggcttac gtccagggag ggaagcagcc tctgtgctgt      300
cttctagata agcctgtatt ccccgggctg tctgccaatg tatccagttg tcccgtcagc      360
ctggaagctc tgagggaaaa ccttgggctg cttcctgagc acctgtatcc cctgcagcca      420
gcccggggcc tctgctagga gcagactgag catggcttat gggcctggca ccatctggcc      480
tctgcccacc ttgctggcct tgtcttgtgt ctgccccttc gacattccat agcccagctc      540
aatatctagt ggttcctcta gggtggcgag cactgtttgg tctccagatg tcttcaggtc      600
ggagctcaca gcgctctcag ccaccccttc ccagtgtagc accgggcaca tggtagatgc      660
ctattgatga gtgaaagctc ctaacacact cagagagcaa ggactccgcc tcatcccaca      720
gcctgggagg agaggcagac tgccaaggac ctgctcagca tgctacagaa gaaaccaaag      780
tgcccacggg actgatcagt ggagcttcct gccgagactg gaggccttag ggcagggtag      840
acagtgtgtg tgcaggctgg ggactcacag ttcggactgt gcccagacct actagcatag      900
tgggtgggtg ggaggatgcg ggactggggg ccgaccttgc ctgaaattca tgtgggatct      960
cagagcagcc actgaattgc tctgtagggg gctaaatagt ggcccccaca gatacacaca     1020
cccagacaga gcctgtgagc cagaccttat ttggagaaaa ggtctttgta gatgtaatta     1080
agcatctcaa gatggcatca tctggattat gcggtgggct gtaagtcctg tgatgtgtct     1140
ttatgggagt gcaggtggaa accatctccc caggagacgg gcgcaccttc cccaagcgcg     1200
gccagacctg cgtggtgcac tacaccggga tgcttgaaga tggaaagaaa gttgattcct     1260
cccgggacag aaacaagccc tttaagttta tgctaggcaa gcaggaggtg atccgaggct     1320
gggaagaagg ggttgcccag atgagtgtgg gtcagagagc caaactgact atatctccag     1380
attatgccta tggtgccact gggcacccag gcatcatccc accacatgcc actctcgtct     1440
tcgatgtgga gcttctaaaa ctggggggga gagaaaggca gagggagatt tgacacacac     1500
aggaggggcc acgtggagac agaggtggag attggagaaa tgtggccaca agccagggaa     1560
caccagcagc caccagaagc cggaagacgt gaggcagggt tcttcccaga gccttcgctg     1620
ctgagtctgg gaatttgtga ccgaagccat aagaagtggg tacacgccct gagcctccca     1680
cacttgctca cctgtcctga gatgagaatc tctactctgc agcatatttg gaggatcact     1740
gcggggggcca cagaggtgct gttcagatgg cacttcagaa gactcaggag accctggggc     1800
aggagcagtt tgactgacag cccagagggc tgccctctga ttccacctga ggccctgctt     1860
ttcctggctg caggggttcc agggccaggc catttccgct ggcgcaggac tctgctagca     1920
gcaacctgcc tgaagtcttc ctttggcctg gctgagagtt tctgagacct cgcgctggagc     1980
ggaggtgctt ccttccttgc ttcctttctt cctctctccc ttctccatcc agcaggctgg     2040
acctgcctgg catctgtgag ctctccctac tttctcctat accctaacct ttgtcctgca     2100
tgggcgactc ccccagtgag tctcttgcag cttttacccc agtgcctgct tcttggagaa     2160
tccaaactga tccagttagg gatgataaag tgtagggtag gcgctcggtg actgttttct     2220
ctgaggttgt gactcgtgtg aggcagaagc agtccccgtg agccctcctg gtatcttgtg     2280
gagtggagaa cgcttggacc tggagccagg aggcccagac atacatcctg tccgagctgc     2340
agcttcctgt ctctaaaatg agccggccag cgcaggtggc cagacatcac tgttattctc     2400
ctttgagtct ttaaatcttg ttgtctttct tgcagactcg gtgagctgtg aaaggctata     2460
```

```
ataggggctt tattttacac tttgatacta tttttttgaac attcatatta ttgttagata    2520
ttgatattca tatgaaggag caggatgact tgggtccttc ttggcagtag cattgccagc    2580
tgatggcctt ggacagttac ctgccctctc taggcctccc tttccttgtc tatgaaatac    2640
attatagaat aggatgtagt gtgtgaggat tttttggagg ttaaacgagt gaatatattt    2700
aaggcgcttt caccagtgcc tgggatgtgc tctgtagttt ctgtgtgtta actataaggt    2760
tgactttatg ctcattccct cctctcccac aaatgtcgcc ttggaaagac ggaggcagcc    2820
tggtggaggt gtatctccta gacaccagca tacagagtga ccaccgggaa atcgagggca    2880
gggtcatggt caccgacttc gagaatgtgc ccgaggagga cgggacccgc ttccacagac    2940
aggtaagcac ggccgtctga tgggagggct gcctctgccc atatccccat cctggaggtg    3000
ggtggggact gccaccccag agcgttgcag ctgtactcct gggttgcacc ccccccagct    3060
gtcactgtcc cctccctgcc atcagttgtg ggaagggcgt tcatccatcc agccacctgc    3120
tgatttgtta tagggtggag ggggggtctt tctcatgtgg tccttgtgtt cgtcgagcag    3180
gccagcaagt gtgacagtca tggcacccac ctggcagggg tggtcagcgg ccgggatgcc    3240
ggcgtggcca agggtgccag catgcgcagc ctgcgcgtgc tcaactgcca agggaagggc    3300
acggttagcg gcaccctcat aggtaagtga tggccccaga cgctggtctc tctccatctg    3360
gacctggcct gggaggtggc ttgggctggg cccaggagaa gctaatgtct cctaaccaag    3420
aatgctgtgg cagcctctgc cgcagagcca gagaaccaga gtgccaaggc tggcagggtt    3480
cccagtggcc acgagtgcag atgaagaaac ccaggcccca agagggtcat gcaggtagcc    3540
cagggagttc agccttgacc ctgggtcaat gacctttcca cagttccaca ctgctcccct    3600
tttaaaatcc ggtgatgtct ttatgtcttt tgttatgtta tcttcaatgt ggagggactc    3660
gaggtgatct aagcaaactt tttctatctt ctgcttgcat acctctgaga ccaggggact    3720
cactcacttg catgactggg ccctgcaggt cacactggcc aggcagatgt ggtggaggaa    3780
ctggcagagg acttttttcta gactgtgact acatttagtc cacccagcgg cccccctatg    3840
aagtccagtt gagaactagg actctggggg ccggtggaca gagaagag              3888
```

<210> SEQ ID NO 49
<211> LENGTH: 24
<212> TYPE: DNA
<213> ORGANISM: Artificial Sequence
<220> FEATURE:
<223> OTHER INFORMATION: CTNNB1 sgRNA target

<400> SEQUENCE: 49

```
taccacagct ccttctctga gtgg                                            24
```

<210> SEQ ID NO 50
<211> LENGTH: 1650
<212> TYPE: DNA
<213> ORGANISM: Artificial Sequence
<220> FEATURE:
<223> OTHER INFORMATION: CTNNB1 genomic locus

<400> SEQUENCE: 50

```
aaataatttt tgatggcact atatcagaaa acaacttgtt aaagaaaatg tggagttttt     60
aaaatcccac tgtacctctg ttatccaaag gggatctgtg aattttctg tgaaaggtta    120 aaaaaggaga gacctttagg aattcagaga gcagctgatt tttgaatagt gtttccccct    180
ccctggcttt tattattaca actctgtgct ttttcatcac catcctgaat atctataatt    240
```

```
aatatttata ctattaataa aaagacattt ttggtaagga ggagttttca ctgaagttca      300
gcagtgatgg agctgtggtt gaggtgtctg gaggagacca tgaggtctgc gtttcactaa      360
cctggtaaaa gaggatatgg gtttttttg tgggtgtaat agtgacattt aacaggtatc       420
ccagtgactt aggagtatta atcaagctaa atttaaatcc taatgacttt tgattaactt      480
tttttagggt atttgaagta taccatacaa ctgttttgaa atccagcgt ggacaatggc       540 tactcaaggt ttgtgtcatt aaatctttag ttactgaatt ggggctctgc ttcgttgcca      600
ttaagccagt ctggctgaga tccccctgct ttcctctctc cctgcttact tgtcaggcta      660
ccttttgctc cattttctgc tcactcctcc taatggcttg gtgaaatagc aaacaagcca      720
ccagcaggaa tctagtctgg atgactgctt ctggagcctg gatgcagtac cattcttcca      780
ctgattcagt gagtaactgt taggtggttc cctaagggat taggtatttc atcactgagc      840
taaccctggc tatcattctg ctttcttgg ctgtctttca gatttgactt tatttctaaa       900
aatatttcaa tgggtcatat cacagattct ttttttttaa attaaagtaa catttccaat      960
ctactaatgc taatactgtt tcgtatttat agctgatttg atggagttgg acatggccat     1020
ggaaccagac agaaaagcgg ctgttagtca ctggcagcaa cagtcttacc tggactctgg     1080
aatccattct ggtgccacta ccacagctcc ttctctgagt ggtaaaggca atcctgagga     1140
agaggatgtg gatacctccc aagtcctgta tgagtgggaa cagggatttt ctcagtcctt     1200
cactcaagaa caagtagctg gtaagagtat tatttttcat tgccttactg aaagtcagaa     1260
tgcagttttg agaactaaaa agttagtgta taatagttta ataaaatgt tgtggtgaag      1320 aaaagagagt aatagcaatg tcactttac catttaggat agcaaatact taggtaaatg      1380
ctgaactgtg gatagtgagt gttgaattaa cctttccag atattgatgg acagtatgca      1440
atgactcgag ctcagagggt acgagctgct atgttccctg agacattaga tgagggcatg     1500
cagatcccat ctacacagtt tgatgctgct catcccacta atgtccagcg tttggctgaa     1560
ccatcacaga tgctgaaaca tgcagttgta aacttgatta ctatcaaga tgatgcagaa      1620 cttgccacac gtgcaatccc tgaactgaca                                      1650
```

<210> SEQ ID NO 51
<211> LENGTH: 1977
<212> TYPE: DNA
<213> ORGANISM: Artificial Sequence
<220> FEATURE:
<223> OTHER INFORMATION: CTNNB1-dTAG hybrid
<400> SEQUENCE: 51

```
aaataattt tgatggcact atatcagaaa acaacttgtt aaagaaaatg tggagttttt       60
aaaatcccac tgtacctctg ttatccaaag gggatctgtg aattttctg tgaaaggtta      120 aaaaaggaga gacctttagg aattcagaga gcagctgatt tttgaatagt gttttcccct     180
ccctggcttt tattattaca actctgtgct tttcatcac catcctgaat atctataatt      240
aatatttata ctattaataa aaagacattt ttggtaagga ggagttttca ctgaagttca     300
gcagtgatgg agctgtggtt gaggtgtctg gaggagacca tgaggtctgc gtttcactaa     360
cctggtaaaa gaggatatgg gtttttttg tgggtgtaat agtgacattt aacaggtatc      420
ccagtgactt aggagtatta atcaagctaa atttaaatcc taatgacttt tgattaactt     480
tttttagggt atttgaagta taccatacaa ctgttttgaa atccagcgt ggacaatggg      540 agtgcaggtg gaaccatct ccccaggaga cgggcgcacc ttccccaagc gcggccagac      600
ctgcgtggtg cactacaccg ggatgcttga agatggaaag aaagttgatt cctcccggga     660
```

```
cagaaacaag cccttttaagt ttatgctagg caagcaggag gtgatccgag gctgggaaga    720 agggggttgcc cagatgagtg tgggtcagag agccaaactg actatatctc cagattatgc    780
ctatggtgcc actgggcacc caggcatcat cccaccacat gccactctcg tcttcgatgt    840
ggagcttcta aaactggggg gatggctac tcaaggtttg tgtcattaaa tctttagtta    900
ctgaattggg gctctgcttc gttgccatta agccagtctg gctgagatcc ccctgctttc    960
ctctctccct gcttacttgt caggctacct tttgctccat tttctgctca ctcctcctaa   1020
tggcttggtg aaatagcaaa caagccacca gcaggaatct agtctggatg actgcttctg   1080
gagcctggat gcagtaccat tcttccactg attcagtgag taactgttag gtggttccct   1140
aagggattag gtatttcatc actgagctaa ccctggctat cattctgctt tcttggctg    1200 tctttcagat ttgactttat ttctaaaaat atttcaatgg gtcatatcac agattctttt   1260
tttttaaatt aaagtaacat ttcaatctac taatgctaat actgtttcgt atttatagcc   1320
tgatttgatg gagttggaca tggccatgga accagacaga aaagcggctg ttagtcactg   1380
gcagcaacag tcttacctgg actctggaat ccattctggt gccactacca cagctccttc   1440
tctgagtggt aaaggcaatc ctgaggaaga ggatgtggaa acctcccaag tcctgtatga   1500
gtgggaacag ggatttttctc agtccttcac tcaagaacaa gtagctggta agagtattat   1560
ttttcattgc cttactgaaa gtcagaatgc agttttgaga actaaaaagt tagtgtataa   1620
tagtttaaat aaaatgttgt ggtgaagaaa agagagtaat agcaatgtca cttttaccat   1680
ttaggatagc aaatacttag gtaaatgctg aactgtggat agtgagtgtt gaattaacct   1740
tttccagata ttgatggaca gtatgcaatg actcgagctc agagggtacg agctgctatg   1800
ttccctgaga cattagatga gggcatgcag atcccatcta cacagtttga tgctgctcat   1860
cccactaatg tccagcgttt ggctgaacca tcacagatgc tgaaacatgc agttgtaaac   1920
ttgattaact atcaagatga tgcagaactt gccacacgtg caatccctga actgaca      1977
```

<210> SEQ ID NO 52
<211> LENGTH: 1368
<212> TYPE: PRT
<213> ORGANISM: Artificial Sequence
<220> FEATURE:
<223> OTHER INFORMATION: Cas-9 nuclease

<400> SEQUENCE: 52

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125
```

-continued

```
His Glu Lys Tyr Pro Thr Ile Tyr His Leu Arg Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
```

```
            545                 550                 555                 560
        Val Lys Gln Leu Lys Glu Asp Tyr Phe Lys Ile Glu Cys Phe Asp
                        565                 570                 575
        Ser Val Glu Ile Ser Gly Val Glu Asp Arg Phe Asn Ala Ser Leu Gly
                        580                 585                 590
        Thr Tyr His Asp Leu Leu Lys Ile Ile Lys Asp Lys Asp Phe Leu Asp
                        595                 600                 605
        Asn Glu Glu Asn Glu Asp Ile Leu Glu Asp Ile Val Leu Thr Leu Thr
                    610                 615                 620
        Leu Phe Glu Asp Arg Glu Met Ile Glu Glu Arg Leu Lys Thr Tyr Ala
        625                 630                 635                 640
        His Leu Phe Asp Asp Lys Val Met Lys Gln Leu Lys Arg Arg Arg Tyr
                        645                 650                 655
        Thr Gly Trp Gly Arg Leu Ser Arg Lys Leu Ile Asn Gly Ile Arg Asp
                        660                 665                 670
        Lys Gln Ser Gly Lys Thr Ile Leu Asp Phe Leu Lys Ser Asp Gly Phe
                        675                 680                 685
        Ala Asn Arg Asn Phe Met Gln Leu Ile His Asp Asp Ser Leu Thr Phe
        690                 695                 700
        Lys Glu Asp Ile Gln Lys Ala Gln Val Ser Gly Gln Gly Asp Ser Leu
        705                 710                 715                 720
        His Glu His Ile Ala Asn Leu Ala Gly Ser Pro Ala Ile Lys Lys Gly
                        725                 730                 735
        Ile Leu Gln Thr Val Lys Val Val Asp Glu Leu Val Lys Val Met Gly
                        740                 745                 750
        Arg His Lys Pro Glu Asn Ile Val Ile Glu Met Ala Arg Glu Asn Gln
                        755                 760                 765
        Thr Thr Gln Lys Gly Gln Lys Asn Ser Arg Glu Arg Met Lys Arg Ile
                770                 775                 780
        Glu Glu Gly Ile Lys Glu Leu Gly Ser Gln Ile Leu Lys Glu His Pro
        785                 790                 795                 800
        Val Glu Asn Thr Gln Leu Gln Asn Glu Lys Leu Tyr Leu Tyr Tyr Leu
                        805                 810                 815
        Gln Asn Gly Arg Asp Met Tyr Val Asp Gln Glu Leu Asp Ile Asn Arg
                        820                 825                 830
        Leu Ser Asp Tyr Asp Val Asp His Ile Val Pro Gln Ser Phe Leu Lys
                    835                 840                 845
        Asp Asp Ser Ile Asp Asn Lys Val Leu Thr Arg Ser Asp Lys Asn Arg
                850                 855                 860
        Gly Lys Ser Asp Asn Val Pro Ser Glu Glu Val Val Lys Lys Met Lys
        865                 870                 875                 880
        Asn Tyr Trp Arg Gln Leu Leu Asn Ala Lys Leu Ile Thr Gln Arg Lys
                        885                 890                 895
        Phe Asp Asn Leu Thr Lys Ala Glu Arg Gly Gly Leu Ser Glu Leu Asp
                        900                 905                 910
        Lys Ala Gly Phe Ile Lys Arg Gln Leu Val Glu Thr Arg Gln Ile Thr
                        915                 920                 925
        Lys His Val Ala Gln Ile Leu Asp Ser Arg Met Asn Thr Lys Tyr Asp
                    930                 935                 940
        Glu Asn Asp Lys Leu Ile Arg Glu Val Lys Val Ile Thr Leu Lys Ser
        945                 950                 955                 960
        Lys Leu Val Ser Asp Phe Arg Lys Asp Phe Gln Phe Tyr Lys Val Arg
                        965                 970                 975
```

```
Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365
```

<210> SEQ ID NO 53
<211> LENGTH: 327
<212> TYPE: PRT
<213> ORGANISM: Homo sapiens

<400> SEQUENCE: 53

Gly Glu Ala Pro Asn Gln Ala Leu Leu Arg Ile Leu Lys Glu Thr Glu
1               5                   10                  15

Phe Lys Lys Ile Lys Val Leu Gly Ser Gly Ala Phe Gly Thr Val Tyr
                20                  25                  30

Lys Gly Leu Trp Ile Pro Glu Gly Glu Lys Val Lys Ile Pro Val Ala
            35                  40                  45

Ile Lys Glu Leu Arg Glu Ala Thr Ser Pro Lys Ala Asn Lys Glu Ile
50                  55                  60

Leu Asp Glu Ala Tyr Val Met Ala Ser Val Asp Asn Pro His Val Cys
65                  70                  75                  80

Arg Leu Leu Gly Ile Cys Leu Thr Ser Thr Val Gln Leu Ile Thr Gln
                85                  90                  95

Leu Met Pro Phe Gly Cys Leu Leu Asp Tyr Val Arg Glu His Lys Asp
                100                 105                 110

Asn Ile Gly Ser Gln Tyr Leu Leu Asn Trp Cys Val Gln Ile Ala Lys
            115                 120                 125

Gly Met Asn Tyr Leu Glu Asp Arg Arg Leu Val His Arg Asp Leu Ala
130                 135                 140

Ala Arg Asn Val Leu Val Lys Thr Pro Gln His Val Lys Ile Thr Asp
145                 150                 155                 160

Phe Gly Arg Ala Lys Leu Leu Gly Ala Glu Glu Lys Glu Tyr His Ala
                165                 170                 175

Glu Gly Gly Lys Val Pro Ile Lys Trp Met Ala Leu Glu Ser Ile Leu
            180                 185                 190

His Arg Ile Tyr Thr His Gln Ser Asp Val Trp Ser Tyr Gly Val Thr
        195                 200                 205

Val Trp Glu Leu Met Thr Phe Gly Ser Lys Pro Tyr Asp Gly Ile Pro
210                 215                 220

Ala Ser Glu Ile Ser Ser Ile Leu Glu Lys Gly Glu Arg Leu Pro Gln
225                 230                 235                 240

Pro Pro Ile Cys Thr Ile Asp Val Tyr Met Ile Met Val Lys Cys Trp
                245                 250                 255

Met Ile Asp Ala Asp Ser Arg Pro Lys Phe Arg Glu Leu Ile Ile Glu
            260                 265                 270

Phe Ser Lys Met Ala Arg Asp Pro Gln Arg Tyr Leu Val Ile Gln Gly
        275                 280                 285

Asp Glu Arg Met His Leu Pro Ser Pro Thr Asp Ser Asn Phe Tyr Arg
290                 295                 300

Ala Leu Met Asp Glu Glu Asp Met Asp Asp Val Val Asp Ala Asp Glu
305                 310                 315                 320

Tyr Leu Ile Pro Gln Gln Gly
                325

<210> SEQ ID NO 54
<211> LENGTH: 327
<212> TYPE: PRT
<213> ORGANISM: Artificial Sequence
<220> FEATURE:
<223> OTHER INFORMATION: epidermal growth factor receptor T790M dTAG

<400> SEQUENCE: 54

```
Gly Glu Ala Pro Asn Gln Ala Leu Leu Arg Ile Leu Lys Glu Thr Glu
1               5                   10                  15

Phe Lys Lys Ile Lys Val Leu Gly Ser Gly Ala Phe Gly Thr Val Tyr
            20                  25                  30

Lys Gly Leu Trp Ile Pro Glu Gly Glu Lys Val Lys Ile Pro Val Ala
        35                  40                  45

Ile Lys Glu Leu Arg Glu Ala Thr Ser Pro Lys Ala Asn Lys Glu Ile
    50                  55                  60

Leu Asp Glu Ala Tyr Val Met Ala Ser Val Asp Asn Pro His Val Cys
65                  70                  75                  80

Arg Leu Leu Gly Ile Cys Leu Thr Ser Thr Val Gln Leu Ile Met Gln
                85                  90                  95

Leu Met Pro Phe Gly Cys Leu Leu Asp Tyr Val Arg Glu His Lys Asp
            100                 105                 110

Asn Ile Gly Ser Gln Tyr Leu Leu Asn Trp Cys Val Gln Ile Ala Lys
        115                 120                 125

Gly Met Asn Tyr Leu Glu Asp Arg Arg Leu Val His Arg Asp Leu Ala
    130                 135                 140

Ala Arg Asn Val Leu Val Lys Thr Pro Gln His Val Lys Ile Thr Asp
145                 150                 155                 160

Phe Gly Arg Ala Lys Leu Leu Gly Ala Glu Glu Lys Glu Tyr His Ala
                165                 170                 175

Glu Gly Gly Lys Val Pro Ile Lys Trp Met Ala Leu Glu Ser Ile Leu
            180                 185                 190

His Arg Ile Tyr Thr His Gln Ser Asp Val Trp Ser Tyr Gly Val Thr
        195                 200                 205

Val Trp Glu Leu Met Thr Phe Gly Ser Lys Pro Tyr Asp Gly Ile Pro
    210                 215                 220

Ala Ser Glu Ile Ser Ser Ile Leu Glu Lys Gly Glu Arg Leu Pro Gln
225                 230                 235                 240

Pro Pro Ile Cys Thr Ile Asp Val Tyr Met Ile Met Val Lys Cys Trp
                245                 250                 255

Met Ile Asp Ala Asp Ser Arg Pro Lys Phe Arg Glu Leu Ile Ile Glu
            260                 265                 270

Phe Ser Lys Met Ala Arg Asp Pro Gln Arg Tyr Leu Val Ile Gln Gly
        275                 280                 285

Asp Glu Arg Met His Leu Pro Ser Pro Thr Asp Ser Asn Phe Tyr Arg
    290                 295                 300

Ala Leu Met Asp Glu Glu Asp Met Asp Val Val Asp Ala Asp Glu
305                 310                 315                 320

Tyr Leu Ile Pro Gln Gln Gly
                325
```

<210> SEQ ID NO 55
<211> LENGTH: 327
<212> TYPE: PRT
<213> ORGANISM: Artificial Sequence
<220> FEATURE:
<223> OTHER INFORMATION: C797S dTAG

<400> SEQUENCE: 55

```
Gly Glu Ala Pro Asn Gln Ala Leu Leu Arg Ile Leu Lys Glu Thr Glu
1               5                   10                  15

Phe Lys Lys Ile Lys Val Leu Gly Ser Gly Ala Phe Gly Thr Val Tyr
```

20                  25                  30
Lys Gly Leu Trp Ile Pro Glu Gly Glu Lys Val Lys Ile Pro Val Ala
            35                  40                  45
Ile Lys Glu Leu Arg Glu Ala Thr Ser Pro Lys Ala Asn Lys Glu Ile
 50                  55                  60
Leu Asp Glu Ala Tyr Val Met Ala Ser Val Asp Asn Pro His Val Cys
 65                  70                  75                  80
Arg Leu Leu Gly Ile Cys Leu Thr Ser Thr Val Gln Leu Ile Met Gln
                85                  90                  95
Leu Met Pro Phe Gly Ser Leu Leu Asp Tyr Val Arg Glu His Lys Asp
            100                 105                 110
Asn Ile Gly Ser Gln Tyr Leu Leu Asn Trp Cys Val Gln Ile Ala Lys
            115                 120                 125
Gly Met Asn Tyr Leu Glu Asp Arg Arg Leu Val His Arg Asp Leu Ala
            130                 135                 140
Ala Arg Asn Val Leu Val Lys Thr Pro Gln His Val Lys Ile Thr Asp
145                 150                 155                 160
Phe Gly Arg Ala Lys Leu Leu Gly Ala Glu Glu Lys Glu Tyr His Ala
                165                 170                 175
Glu Gly Gly Lys Val Pro Ile Lys Trp Met Ala Leu Glu Ser Ile Leu
            180                 185                 190
His Arg Ile Tyr Thr His Gln Ser Asp Val Trp Ser Tyr Gly Val Thr
            195                 200                 205
Val Trp Glu Leu Met Thr Phe Gly Ser Lys Pro Tyr Asp Gly Ile Pro
            210                 215                 220
Ala Ser Glu Ile Ser Ser Ile Leu Glu Lys Gly Glu Arg Leu Pro Gln
225                 230                 235                 240
Pro Pro Ile Cys Thr Ile Asp Val Tyr Met Ile Met Val Lys Cys Trp
                245                 250                 255
Met Ile Asp Ala Asp Ser Arg Pro Lys Phe Arg Glu Leu Ile Ile Glu
            260                 265                 270
Phe Ser Lys Met Ala Arg Asp Pro Gln Arg Tyr Leu Val Ile Gln Gly
            275                 280                 285
Asp Glu Arg Met His Leu Pro Ser Pro Thr Asp Ser Asn Phe Tyr Arg
            290                 295                 300
Ala Leu Met Asp Glu Glu Asp Met Asp Asp Val Val Asp Ala Asp Glu
305                 310                 315                 320
Tyr Leu Ile Pro Gln Gln Gly
                325

<210> SEQ ID NO 56
<211> LENGTH: 327
<212> TYPE: PRT
<213> ORGANISM: Artificial Sequence
<220> FEATURE:
<223> OTHER INFORMATION: C790G dTAG

<400> SEQUENCE: 56

Gly Glu Ala Pro Asn Gln Ala Leu Leu Arg Ile Leu Lys Glu Thr Glu
1               5                   10                  15
Phe Lys Lys Ile Lys Val Leu Gly Ser Gly Ala Phe Gly Thr Val Tyr
                20                  25                  30
Lys Gly Leu Trp Ile Pro Glu Gly Glu Lys Val Lys Ile Pro Val Ala
            35                  40                  45
Ile Lys Glu Leu Arg Glu Ala Thr Ser Pro Lys Ala Asn Lys Glu Ile
 50                  55                  60

```
            50                  55                  60
Leu Asp Glu Ala Tyr Val Met Ala Ser Val Asp Asn Pro His Val Cys
65                  70                  75                  80

Arg Leu Leu Gly Ile Cys Leu Thr Ser Thr Val Gln Leu Ile Met Gln
                85                  90                  95

Leu Met Pro Phe Gly Cys Gly Leu Asp Tyr Val Arg Glu His Lys Asp
                100                 105                 110

Asn Ile Gly Ser Gln Tyr Leu Leu Asn Trp Cys Val Gln Ile Ala Lys
                115                 120                 125

Gly Met Asn Tyr Leu Glu Asp Arg Arg Leu Val His Arg Asp Leu Ala
                130                 135                 140

Ala Arg Asn Val Leu Val Lys Thr Pro Gln His Val Lys Ile Thr Asp
145                 150                 155                 160

Phe Gly Arg Ala Lys Leu Leu Gly Ala Glu Lys Glu Tyr His Ala
                165                 170                 175

Glu Gly Gly Lys Val Pro Ile Lys Trp Met Ala Leu Glu Ser Ile Leu
                180                 185                 190

His Arg Ile Tyr Thr His Gln Ser Asp Val Trp Ser Tyr Gly Val Thr
                195                 200                 205

Val Trp Glu Leu Met Thr Phe Gly Ser Lys Pro Tyr Asp Gly Ile Pro
210                 215                 220

Ala Ser Glu Ile Ser Ser Ile Leu Glu Lys Gly Glu Arg Leu Pro Gln
225                 230                 235                 240

Pro Pro Ile Cys Thr Ile Asp Val Tyr Met Ile Met Val Lys Cys Trp
                245                 250                 255

Met Ile Asp Ala Asp Ser Arg Pro Lys Phe Arg Glu Leu Ile Ile Glu
                260                 265                 270

Phe Ser Lys Met Ala Arg Asp Pro Gln Arg Tyr Leu Val Ile Gln Gly
                275                 280                 285

Asp Glu Arg Met His Leu Pro Ser Pro Thr Asp Ser Asn Phe Tyr Arg
                290                 295                 300

Ala Leu Met Asp Glu Glu Asp Met Asp Val Val Asp Ala Asp Glu
305                 310                 315                 320

Tyr Leu Ile Pro Gln Gln Gly
                325

<210> SEQ ID NO 57
<211> LENGTH: 272
<212> TYPE: PRT
<213> ORGANISM: Artificial Sequence
<220> FEATURE:
<223> OTHER INFORMATION: epidermal growth factor receptor (BCR-ABL)

<400> SEQUENCE: 57

Ser Pro Asn Tyr Asp Lys Trp Glu Met Glu Arg Thr Asp Ile Thr Met
1               5                   10                  15

Lys His Lys Leu Gly Gly Gly Gln Tyr Gly Glu Val Tyr Glu Gly Val
                20                  25                  30

Trp Lys Lys Tyr Ser Leu Thr Val Ala Val Lys Thr Leu Lys Glu Asp
                35                  40                  45

Thr Met Glu Val Glu Glu Phe Leu Lys Glu Ala Ala Val Met Lys Glu
                50                  55                  60

Ile Lys His Pro Asn Leu Val Gln Leu Leu Gly Val Cys Thr Arg Glu
65                  70                  75                  80

Pro Pro Phe Tyr Ile Ile Ile Glu Phe Met Thr Tyr Gly Asn Leu Leu
```

```
                    85                  90                  95
Asp Tyr Leu Arg Glu Cys Asn Arg Gln Glu Val Asn Ala Val Val Leu
                100                 105                 110

Leu Tyr Met Ala Thr Gln Ile Ser Ser Ala Met Glu Tyr Leu Glu Lys
            115                 120                 125

Lys Asn Phe Ile His Arg Asp Leu Ala Ala Arg Asn Cys Leu Val Gly
        130                 135                 140

Glu Asn His Leu Val Lys Val Ala Asp Phe Gly Leu Ser Arg Leu Met
145                 150                 155                 160

Thr Gly Asp Thr Tyr Thr Ala His Ala Gly Ala Lys Phe Pro Ile Lys
                165                 170                 175

Trp Thr Ala Pro Glu Ser Leu Ala Tyr Asn Lys Phe Ser Ile Lys Ser
            180                 185                 190

Asp Val Trp Ala Phe Gly Val Leu Leu Trp Glu Ile Ala Thr Tyr Gly
        195                 200                 205

Met Ser Pro Tyr Pro Gly Ile Asp Leu Ser Gln Val Tyr Glu Leu Leu
    210                 215                 220

Glu Lys Asp Tyr Arg Met Glu Arg Pro Glu Gly Cys Pro Glu Lys Val
225                 230                 235                 240

Tyr Glu Leu Met Arg Ala Cys Trp Gln Trp Asn Pro Ser Asp Arg Pro
                245                 250                 255

Ser Phe Ala Glu Ile His Gln Ala Phe Glu Thr Met Phe Gln Glu Ser
            260                 265                 270

<210> SEQ ID NO 58
<211> LENGTH: 272
<212> TYPE: PRT
<213> ORGANISM: Artificial Sequence
<220> FEATURE:
<223> OTHER INFORMATION: BCR-ABL

<400> SEQUENCE: 58

Ser Pro Asn Tyr Asp Lys Trp Glu Met Glu Arg Thr Asp Ile Thr Met
1               5                   10                  15

Lys His Lys Leu Gly Gly Gly Gln Tyr Gly Glu Val Tyr Glu Gly Val
            20                  25                  30

Trp Lys Lys Tyr Ser Leu Thr Val Ala Val Lys Thr Leu Lys Glu Asp
        35                  40                  45

Thr Met Glu Val Glu Glu Phe Leu Lys Glu Ala Ala Val Met Lys Glu
    50                  55                  60

Ile Lys His Pro Asn Leu Val Gln Leu Leu Gly Val Cys Thr Arg Glu
65                  70                  75                  80

Pro Pro Phe Tyr Ile Ile Thr Glu Phe Met Thr Tyr Gly Asn Leu Leu
                85                  90                  95

Asp Tyr Leu Arg Glu Cys Asn Arg Gln Glu Val Asn Ala Val Val Leu
                100                 105                 110

Leu Tyr Met Ala Thr Gln Ile Ser Ser Ala Met Glu Tyr Leu Glu Lys
            115                 120                 125

Lys Asn Phe Ile His Arg Asp Leu Ala Ala Arg Asn Cys Leu Val Gly
        130                 135                 140

Glu Asn His Leu Val Lys Val Ala Asp Phe Gly Leu Ser Arg Leu Met
145                 150                 155                 160

Thr Gly Asp Thr Tyr Thr Ala His Ala Gly Ala Lys Phe Pro Ile Lys
                165                 170                 175

Trp Thr Ala Pro Glu Ser Leu Ala Tyr Asn Lys Phe Ser Ile Lys Ser
```

```
                180                185                190
Asp Val Trp Ala Phe Gly Val Leu Leu Trp Glu Ile Ala Thr Tyr Gly
            195                200                205
Met Ser Pro Tyr Pro Gly Ile Asp Leu Ser Gln Val Tyr Glu Leu Leu
        210                215                220
Glu Lys Asp Tyr Arg Met Glu Arg Pro Glu Gly Cys Pro Glu Lys Val
225                230                235                240
Tyr Glu Leu Met Arg Ala Cys Trp Gln Trp Asn Pro Ser Asp Arg Pro
                245                250                255
Ser Phe Ala Glu Ile His Gln Ala Phe Glu Thr Met Phe Gln Glu Ser
            260                265                270

<210> SEQ ID NO 59
<211> LENGTH: 339
<212> TYPE: PRT
<213> ORGANISM: Homo sapiens

<400> SEQUENCE: 59

Glu Leu Gln Ser Pro Glu Tyr Lys Leu Ser Lys Leu Arg Thr Ser Thr
1               5                  10                 15
Ile Met Thr Asp Tyr Asn Pro Asn Tyr Cys Phe Ala Gly Lys Thr Ser
            20                 25                 30
Ser Ile Ser Asp Leu Lys Glu Val Pro Arg Lys Asn Ile Thr Leu Ile
        35                 40                 45
Arg Gly Leu Gly His Gly Ala Phe Gly Glu Val Tyr Glu Gly Gln Val
    50                 55                 60
Ser Gly Met Pro Asn Asp Pro Ser Pro Leu Gln Val Ala Val Lys Thr
65                 70                 75                 80
Leu Pro Glu Val Cys Ser Glu Gln Asp Glu Leu Asp Phe Leu Met Glu
                85                 90                 95
Ala Leu Ile Ile Ser Lys Phe Asn His Gln Asn Ile Val Arg Cys Ile
            100                105                110
Gly Val Ser Leu Gln Ser Leu Pro Arg Phe Ile Met Leu Glu Leu Met
        115                120                125
Ala Gly Gly Asp Leu Lys Ser Phe Leu Arg Glu Thr Arg Pro Arg Pro
    130                135                140
Ser Gln Pro Ser Ser Leu Ala Met Leu Asp Leu Leu His Val Ala Arg
145                150                155                160
Asp Ile Ala Cys Gly Cys Gln Tyr Leu Glu Glu Asn His Phe Ile His
                165                170                175
Arg Asp Ile Ala Ala Arg Asn Cys Leu Leu Thr Cys Pro Gly Pro Gly
            180                185                190
Arg Val Ala Lys Ile Gly Asp Phe Gly Met Ala Arg Asp Ile Tyr Arg
        195                200                205
Ala Gly Tyr Tyr Arg Lys Gly Gly Cys Ala Met Leu Pro Val Lys Trp
    210                215                220
Met Pro Pro Glu Ala Phe Met Glu Gly Ile Phe Thr Ser Lys Thr Asp
225                230                235                240
Thr Trp Ser Phe Gly Val Leu Leu Trp Glu Ile Phe Ser Leu Gly Tyr
                245                250                255
Met Pro Tyr Pro Ser Lys Ser Asn Gln Glu Val Leu Glu Phe Val Thr
            260                265                270
Ser Gly Gly Arg Met Asp Pro Pro Lys Asn Cys Pro Gly Pro Val Tyr
        275                280                285
```

```
Arg Ile Met Thr Gln Cys Trp Gln His Gln Pro Glu Asp Arg Pro Asn
    290                 295                 300
Phe Ala Ile Ile Leu Glu Arg Ile Glu Tyr Cys Thr Gln Asp Pro Asp
305                 310                 315                 320
Val Ile Asn Thr Ala Leu Pro Ile Glu Tyr Gly Pro Leu Val Glu Glu
                    325                 330                 335
Glu Glu Lys

<210> SEQ ID NO 60
<211> LENGTH: 277
<212> TYPE: PRT
<213> ORGANISM: Homo sapiens

<400> SEQUENCE: 60

Val Phe His Lys Ile Arg Asn Glu Asp Leu Ile Phe Asn Glu Ser Leu
1               5                   10                  15
Gly Gln Gly Thr Phe Thr Lys Ile Phe Lys Gly Val Arg Arg Glu Val
                20                  25                  30
Gly Asp Tyr Gly Gln Leu His Glu Thr Glu Val Leu Leu Lys Val Leu
            35                  40                  45
Asp Lys Ala His Arg Asn Tyr Ser Glu Ser Phe Phe Glu Ala Ala Ser
50                  55                  60
Met Met Ser Lys Leu Ser His Lys His Leu Val Leu Asn Tyr Gly Val
65                  70                  75                  80
Cys Phe Cys Gly Asp Glu Asn Ile Leu Val Gln Glu Phe Val Lys Phe
                85                  90                  95
Gly Ser Leu Asp Thr Tyr Leu Lys Asn Lys Asn Cys Ile Asn Ile
                100                 105                 110
Leu Trp Lys Leu Glu Val Ala Lys Gln Leu Ala Trp Ala Met His Phe
            115                 120                 125
Leu Glu Glu Asn Thr Leu Ile His Gly Asn Val Cys Ala Lys Asn Ile
130                 135                 140
Leu Leu Ile Arg Glu Glu Asp Arg Lys Thr Gly Asn Pro Pro Phe Ile
145                 150                 155                 160
Lys Leu Ser Asp Pro Gly Ile Ser Ile Thr Val Leu Pro Lys Asp Ile
                165                 170                 175
Leu Gln Glu Arg Ile Pro Trp Val Pro Pro Glu Cys Ile Glu Asn Pro
            180                 185                 190
Lys Asn Leu Asn Leu Ala Thr Asp Lys Trp Ser Phe Gly Thr Thr Leu
            195                 200                 205
Trp Glu Ile Cys Ser Gly Gly Asp Lys Pro Leu Ser Ala Leu Asp Ser
210                 215                 220
Gln Arg Lys Leu Gln Phe Tyr Glu Asp Arg His Gln Leu Pro Ala Pro
225                 230                 235                 240
Lys Ala Ala Glu Leu Ala Asn Leu Ile Asn Asn Cys Met Asp Tyr Glu
                245                 250                 255
Pro Asp His Arg Pro Ser Phe Arg Ala Ile Ile Arg Asp Leu Asn Ser
            260                 265                 270
Leu Phe Thr Pro Asp
        275

<210> SEQ ID NO 61
<211> LENGTH: 272
<212> TYPE: PRT
<213> ORGANISM: Homo sapiens
```

<400> SEQUENCE: 61

Asp Trp Glu Ile Pro Asp Gly Gln Ile Thr Val Gly Gln Arg Ile Gly
1               5                   10                  15

Ser Gly Ser Phe Gly Thr Val Tyr Lys Gly Lys Trp His Gly Asp Val
            20                  25                  30

Ala Val Lys Met Leu Asn Val Thr Ala Pro Thr Pro Gln Gln Leu Gln
        35                  40                  45

Ala Phe Lys Asn Glu Val Gly Val Leu Arg Lys Thr Arg His Val Asn
    50                  55                  60

Ile Leu Leu Phe Met Gly Tyr Ser Thr Ala Pro Gln Leu Ala Ile Val
65                  70                  75                  80

Thr Gln Trp Cys Glu Gly Ser Ser Leu Tyr His His Leu His Ala Ser
                85                  90                  95

Glu Thr Lys Phe Glu Met Lys Lys Leu Ile Asp Ile Ala Arg Gln Thr
            100                 105                 110

Ala Arg Gly Met Asp Tyr Leu His Ala Lys Ser Ile Ile His Arg Asp
        115                 120                 125

Leu Lys Ser Asn Asn Ile Phe Leu His Glu Asp Asn Thr Val Lys Ile
    130                 135                 140

Gly Asp Phe Gly Leu Ala Thr Glu Lys Ser Arg Trp Ser Gly Ser His
145                 150                 155                 160

Gln Phe Glu Gln Leu Ser Gly Ser Ile Leu Trp Met Ala Pro Glu Val
                165                 170                 175

Ile Arg Met Gln Asp Ser Asn Pro Tyr Ser Phe Gln Ser Asp Val Tyr
            180                 185                 190

Ala Phe Gly Ile Val Leu Tyr Glu Leu Met Thr Gly Gln Leu Pro Tyr
        195                 200                 205

Ser Asn Ile Asn Asn Arg Asp Gln Ile Ile Glu Met Val Gly Arg Gly
    210                 215                 220

Ser Leu Ser Pro Asp Leu Ser Lys Val Arg Ser Asn Cys Pro Lys Arg
225                 230                 235                 240

Met Lys Arg Leu Met Ala Glu Cys Leu Lys Lys Arg Asp Glu Arg
                245                 250                 255

Pro Ser Phe Pro Arg Ile Leu Ala Glu Ile Glu Leu Ala Arg Glu
            260                 265                 270

<210> SEQ ID NO 62
<211> LENGTH: 254
<212> TYPE: PRT
<213> ORGANISM: Artificial Sequence
<220> FEATURE:
<223> OTHER INFORMATION: dTAG sequence

<400> SEQUENCE: 62

Leu Arg Leu Glu Val Lys Leu Gly Gln Gly Cys Phe Gly Glu Val Trp
1               5                   10                  15

Met Gly Thr Trp Asn Gly Thr Thr Arg Val Ala Ile Lys Thr Leu Lys
            20                  25                  30

Pro Gly Thr Met Ser Pro Glu Ala Phe Leu Gln Glu Ala Gln Val Met
        35                  40                  45

Lys Lys Leu Arg His Glu Lys Leu Val Gln Leu Tyr Ala Val Val Ser
    50                  55                  60

Glu Glu Pro Ile Tyr Ile Val Thr Glu Tyr Gly Ser Lys Gly Ser Leu
65                  70                  75                  80

Leu Asp Phe Leu Lys Gly Glu Thr Gly Lys Tyr Leu Arg Leu Pro Gln

```
              85                  90                  95
Leu Val Asp Met Ala Ala Gln Ile Ala Ser Gly Met Ala Tyr Val Glu
            100                 105                 110
Arg Met Asn Tyr Val His Arg Asp Leu Arg Ala Ala Asn Ile Leu Val
            115                 120                 125
Gly Glu Asn Leu Val Cys Lys Val Ala Asp Phe Gly Leu Ala Arg Leu
        130                 135                 140
Ile Glu Asp Asn Glu Tyr Thr Ala Arg Gln Gly Ala Lys Phe Pro Ile
145                 150                 155                 160
Lys Trp Thr Ala Pro Glu Ala Ala Leu Tyr Gly Arg Phe Thr Ile Lys
                165                 170                 175
Ser Asp Val Trp Ser Phe Gly Ile Leu Leu Thr Glu Leu Thr Thr Lys
                180                 185                 190
Gly Arg Val Pro Tyr Pro Gly Met Val Asn Arg Glu Val Leu Asp Gln
            195                 200                 205
Val Glu Arg Gly Tyr Arg Met Pro Cys Pro Pro Glu Cys Pro Glu Ser
        210                 215                 220
Leu His Asp Leu Met Cys Gln Cys Trp Arg Lys Glu Pro Glu Glu Arg
225                 230                 235                 240
Pro Thr Phe Glu Tyr Leu Gln Ala Phe Leu Glu Asp Tyr Phe
                245                 250

<210> SEQ ID NO 63
<211> LENGTH: 254
<212> TYPE: PRT
<213> ORGANISM: Artificial Sequence
<220> FEATURE:
<223> OTHER INFORMATION: dTAG sequence

<400> SEQUENCE: 63

Leu Arg Leu Glu Val Lys Leu Gly Gln Gly Cys Phe Gly Glu Val Trp
1               5                   10                  15
Met Gly Thr Trp Asn Gly Thr Thr Arg Val Ala Ile Lys Thr Leu Lys
            20                  25                  30
Pro Gly Thr Met Ser Pro Glu Ala Phe Leu Gln Glu Ala Gln Val Met
        35                  40                  45
Lys Lys Leu Arg His Glu Lys Leu Val Gln Leu Tyr Ala Val Val Ser
    50                  55                  60
Glu Glu Pro Ile Tyr Ile Val Thr Glu Tyr Ala Ser Lys Gly Ser Leu
65                  70                  75                  80
Leu Asp Phe Leu Lys Gly Glu Thr Gly Lys Tyr Leu Arg Leu Pro Gln
                85                  90                  95
Leu Val Asp Met Ala Ala Gln Ile Ala Ser Gly Met Ala Tyr Val Glu
            100                 105                 110
Arg Met Asn Tyr Val His Arg Asp Leu Arg Ala Ala Asn Ile Leu Val
            115                 120                 125
Gly Glu Asn Leu Val Cys Lys Val Ala Asp Phe Gly Leu Ala Arg Leu
        130                 135                 140
Ile Glu Asp Asn Glu Tyr Thr Ala Arg Gln Gly Ala Lys Phe Pro Ile
145                 150                 155                 160
Lys Trp Thr Ala Pro Glu Ala Ala Leu Tyr Gly Arg Phe Thr Ile Lys
                165                 170                 175
Ser Asp Val Trp Ser Phe Gly Ile Leu Leu Thr Glu Leu Thr Thr Lys
                180                 185                 190
Gly Arg Val Pro Tyr Pro Gly Met Val Asn Arg Glu Val Leu Asp Gln
```

```
                195                 200                 205
Val Glu Arg Gly Tyr Arg Met Pro Cys Pro Pro Glu Cys Pro Glu Ser
    210                 215                 220

Leu His Asp Leu Met Cys Gln Cys Trp Arg Lys Glu Pro Glu Glu Arg
225                 230                 235                 240

Pro Thr Phe Glu Tyr Leu Gln Ala Phe Leu Glu Asp Tyr Phe
                245                 250
```

TUNABLE ENDOGENOUS PROTEIN DEGRADATION WITH HETEROBIFUNCTIONAL COMPOUNDS

RELATED APPLICATIONS

This application is a national stage application, filed under 35 U.S.C. § 371, of International Application No. PCT/US2018/017468, filed Feb. 8, 2018, which claims the benefit of provisional U.S. Application No. 62/456,654, filed Feb. 8, 2017, and provisional U.S. application No. 62/457,127, filed Feb. 9, 2017. The entirety of these applications are hereby incorporated by reference for all purposes.

INCORPORATION BY REFERENCE

The contents of the text file named "16010-025WO1_sequencelisting_ST25.txt" which was created on Jan. 26, 2018, and is 287 kilobytes in size, are hereby incorporated by reference in their entirety.

FIELD OF THE INVENTION

This invention describes methods, compounds, and compositions to modulate an endogenously expressed protein using targeted protein degradation.

BACKGROUND

Many tools have been developed to manipulate gene expression to interrogate the function of a gene or protein of interest. For example, techniques such as RNA interference and antisense deoxyoligonucleotides are commonly used to disrupt protein expression at the RNA and DNA level. Homologous recombination or loss-of-function mutations can be accomplished using site-specific double-strand breaks using zinc-finger nucleases, transcription activator-like effector nucleases (TALENs), or clustered regulatory interspaced short palindromic repeat (CRISPR)-Cas9 (Cheng, J. K. and Alper, H. S., "The genome editing toolbox: a spectrum of approaches for targeted modification" *Curr. Opin. Biotechnol.*, 30C, (2014): 87-94; and Graham et al., *Gen Biol*, (2015): 16:260). The CRISPR-Cas9 system has been used to modulate endogenous gene expression by incorporating specific mutations into a gene of interest (see, for example, Lo et al., Genetics, 2013; 195(2): 331-348; Yu et al., Biology Open, 2014; 3:271-280; Park et al., PLOS One, 2013; 9(4):e95101; Lackner et al., Nature Communications, 2015; 17(6): 1-7; U.S. Pat. Nos. 8,771,945 and 9,228,208; WO 2014/204729; and U.S. Publication 2014/0273235).

For example, the CRISPR-Cas9 system was employed to mutate the human PCSK9 gene in chimeric liver-humanized mice bearing human hepatocytes (Wang, X., et al. "CRISPR-Cas9 Targeting of PCSK9 in Human Hepatocytes In Vivo." *Arteriosclerosis, Thrombosis, and Vascular Biology*, (2016).). PCSK9 was successfully mutated and the CRISPR-Cas9 system has been proposed to be useful as a way to treat human disorders in vivo. However, the long-term implications of permanent genome modification are unknown and concerns exist over the imperfect precision of genome editing, the continuous activity of virally-delivered CRISPR-Cas9, and the impact of direct correction in adults where biological compensation mechanisms may exist (Kormann et al., "Expression of therapeutic proteins after delivery of chemically modified mRNA in mice" *Nat. Biotechnol.*, 29, (2011):154-157; Cho et al., "Analysis of off-target effects of CRISPR/Cas-derived RNA-guided endonucleases and nickases." *Genome Res.*, 24, (2014):132-141). Furthermore, CRISPR knock-out strategies may be undesirable where the protein expressed, even if imperfect, is essential for cellular function.

Efforts have been made to modulate gene expression in vitro using inducible degradation systems. For example, the auxin-inducible degradation (AID) system in plants has enabled controlled protein depletion in yeast and cultured vertebrate cells. This system relies on expression of a plant-specific F-box protein, TIR1, which regulates diverse aspects of plant growth and morphogenesis in response to the phytohormone auxin. TIR1 is the substrate recognition component of a Skp1-Cullin-F-box E3 ubiquitin ligase complex, which recognizes substrates only in the presence of auxin and targets them for degradation by the proteasome. This system has been manipulated and shown to enable conditional auxin-dependent protein depletion in *Caenorhabditis elegans* as well as in human HCT116 cells (see, for example, Zhang et al., Development, 2015; 142: 4374-4384 and Natsume et al., Cell Reports, 2016; 15: 210-218). However, this approach is impractical as an in vivo modulation system due to the toxicity of auxin.

An alternative approach to reversibly controlling gene expression has been the use of ligand-dependent destabilization domains and the Shield-1 ligand, which allows for reversible stabilization and destabilization of a tagged protein of interest in a dose-dependent manner (see, for example, Rakhit et al., Chemistry & Biology, 2014; 21: 1238-1252). Fusing the destabilizing domain to a gene of interest results in the expression a fused protein that is degraded by the proteasome. Shield-1 binds specifically to the destabilization domain and inactivates protein degradation. However, this system is also not viable as an in vivo modulation strategy due to the requirement for the presence of Sield-1 in the cell cytoplasm in order to avoid degradation. Such an approach would require a constant administration of Shield-1 to maintain protein stability.

Thus, there remains an unmet need for improved systems that allow for reversible control of endogenous gene expression in vivo while providing improved treatment modalities in subjects suffering from disorders such as proteopathies.

It is therefore an object of the present invention to provide methods, compounds, and compositions to modulate gene expression in vivo in a manner that avoids problems associated with CRISPR endogenous protein knock-out or knock-in strategies.

SUMMARY OF THE INVENTION

The present invention provides a means to modulate gene expression in vivo in a manner that avoids problems associated with CRISPR endogenous protein knock-out or knock-in strategies and strategies that provide for correction, or alteration, of single nucleotides. The invention includes inserting into the genome a nucleotide encoding a heterobifunctional compound targeting protein (dTAG) in-frame with the nucleotide sequence of a gene encoding an endogenously expressed protein of interest which, upon expression, produces an endogenous protein-dTAG hybrid protein. This allows for targeted protein degradation of the dTAG and the fused endogenous protein using a heterobifunctional compound in a controlled, tunable fashion.

A heterobifunctional compound, as contemplated herein, is a compound that binds to an ubiquitin ligase through a ubiquitin ligase binding moiety and also binds to the dTAG through its dTAG Targeting Ligand in vivo, as defined in more detail below. Heterobifunctional compounds are capable of induced proteasome-mediated degradation of the fused endogenous proteins via recruitment to E3 ubiquitin ligase and subsequent ubiquitination. These drug-like molecules offer the possibility of reversible, dose-responsive, tunable, temporal control over protein levels.

Compared to CRISPR-Cas9 genome editing that incorporates irreversible changes into a gene of interest, the use of a heterobifunctional compound to target endogenously expressed proteins with a dTAG allows for reversible control of the endogenously expressed protein of interest. Accordingly, the heterobifunctional compound can be used as a rheostat of protein expression affording the ability to turn endogenous protein expression on and off upon titration of the heterobifunctional compound. Furthermore, by genomically and stably incorporating a nucleic acid sequence encoding a dTAG in frame, either 5'- or 3'- to the gene of the endogenous protein, side effects associated with CRISPR-Cas9 such as negative downstream consequences associated with permanently editing a gene can be avoided.

The invention provides a mechanism to control the degradation of endogenous proteins that mediate a disease by combining genome engineering with small molecule activation/modulation of degradation. The methods and compositions described herein are particularly useful for targeting endogenous proteins associated with disease due to a gain of function, toxic accumulation, overexpression, or downstream enzymatic process the protein may be involved in. Applications of this technology include, but are not limited to 1) targeted degradation of proteins where pathology is a result of gain of function mutation(s), 2) targeted degradation of proteins where pathology is a function of amplification or increased expression, 3) targeted degradation of proteins that are manifestations of monogenetic disease, 4) targeted degradation of proteins where genetic predisposition manifests over longer periods and often after alternative biological compensatory mechanisms are no longer adequate, for example, but not limited to, hypercholesterolemia and proteinopathies.

Therefore, in one embodiment, a method is provided that includes at least the steps of:

(i) transforming relevant cells of a subject, typically a human, with a nucleic acid sequence encoding a dTAG, wherein the nucleic acid sequence is integrated genomically in-frame with a nucleic acid sequence of an endogenous protein which is acting as a mediator of disease, wherein insertion of the nucleic acid encoding the dTAG into the genomic sequence results in an endogenous protein-dTAG hybrid or fusion protein upon expression; and (ii) administering to the subject, as needed, a heterobifunctional compound which binds to a) the inserted dTAG and b) a ubiquitin ligase in a manner that brings the dTAG (and thus the endogenous protein-dTAG hybrid protein) into proximity of the ubiquitin ligase, such that the endogenous protein-dTAG hybrid protein is ubiquitinated, and then degraded by the proteasome.

In one embodiment, the subject's cell is transformed in vivo. In one embodiment, the subject's cell is transformed ex vivo and administered back to the subject. In one embodiment, the subject's cell is a liver cell.

In one embodiment, a method is provided that includes the steps of:

administering to the subject, as needed, a heterobifunctional compound, wherein the subject has one or more cells which have been transformed with a nucleic acid sequence encoding a dTAG, wherein the nucleic acid sequence is integrated genomically in-frame in a 5' or 3' orientation with a nucleic acid sequence of an endogenous protein which is acting as a mediator of disease, wherein insertion of the nucleic acid encoding the dTAG into the genomic sequence results in an endogenous protein-dTAG hybrid or fusion protein upon expression of the protein; and wherein the heterobifunctional compound binds to a) the inserted dTAG and b) a ubiquitin ligase in a manner that brings the dTAG (and thus the endogenous protein-dTAG hybrid protein) into proximity of the ubiquitin ligase, such that the endogenous protein-dTAG hybrid protein is ubiquitinated, and then degraded by the proteasome.

As contemplated herein, the synthetic gene encoding the endogenous protein of interest-dTAG hybrid is derived in vivo through the targeted insertion of a nucleic acid encoding the dTAG in-frame either 5'- or 3'- to the nucleic acid encoding the protein of interest. This results in an in-frame gene fusion that is susceptible to proteasome mediated degradation upon treatment with a heterobifunctional compound that is capable of binding the dTAG. In a main embodiment, the dTAG does not substantially interfere with the function of the endogenously expressed protein. In one embodiment, the dTAG is a non-endogenous peptide, which allows for heterobifunctional compound selectivity and minimizes off target effects upon administration of the heterobifunctional compound. In one embodiment, the dTAG is an amino acid sequence derived from an endogenous protein which has been modified, for example through a "bump" strategy (see, for example, (see Clackson et al., "Redesigning an FKBP-ligand interface to generate chemical dimerizers with novel specificity", *PNAS* 95 (1998): 10437-10442, incorporated herein by reference), so that the heterobifunctional compound binds only to or preferentially to the modified amino acid sequence of the dTAG and not the corresponding endogenously expressed protein.

Also contemplated herein is a method for the in vitro allele-specific regulation of an endogenous protein through the targeted insertion of a nucleic acid sequence encoding a dTAG in frame either 5'- or 3'- to the genomic sequence encoding a protein of interest, wherein insertion of the nucleic acid encoding the dTAG into the genomic sequence results in an endogenous protein-dTAG hybrid or fusion protein upon expression, wherein the endogenous protein-dTAG is capable of being degraded by a heterobifunctional compound which binds to a) the inserted dTAG and b) a ubiquitin ligase in a manner that brings the dTAG (and thus the endogenous protein-dTAG hybrid protein) into proximity of a ubiquitin ligase, such that the endogenous protein-dTAG hybrid protein is ubiquitinated, and then degraded by the proteasome. By using the methods described herein to insert a nucleic acid encoding a dTAG in frame with a gene encoding an endogenous protein of interest, the expression of the resultant protein can be tightly controlled through the introduction of a heterobifunctional compound capable of binding the dTAG, resulting in the degradation of the endogenous protein. Importantly, by using a heterobifunctional compound, expression of the endogenous protein can be reversibly controlled, allowing for the examination of the effects of protein expression on the cell.

Accordingly, by regulating expression of endogenous proteins in this manner, downstream effects of modulating protein expression can be examined across a wide variety of proteins and cell types, and in various physiological conditions. Because the heterobifunctional compound concentration within the cell can be titrated, protein-dTAG hybrid protein concentrations within the cell can be finely tuned, allowing for the conditional alteration of protein abundance within the cell and the ability to alter phenotype within the cell on demand. In one embodiment, provided herein is a method of assessing protein expression attenuation in a cell comprising inserting a nucleic acid sequence encoding a dTAG in frame either 5'- or 3'- to a genomic sequence encoding a protein of interest, wherein insertion of the nucleic acid encoding the dTAG into the genomic sequence results in an endogenous protein-dTAG hybrid or fusion protein upon expression, wherein the endogenous protein-dTAG is capable of being degraded by a heterobifunctional compound which binds to a) the inserted dTAG and b) a ubiquitin ligase in a manner that brings the dTAG (and thus the endogenous protein-dTAG hybrid protein) into proximity of a ubiquitin ligase, such that the endogenous protein-dTAG hybrid protein is ubiquitinated, and then degraded by the proteasome. In one embodiment, the heterobifunctional compound is administered to the cell so that the concentration of the protein-dTAG hybrid protein in the cell is partially degraded. In one embodiment, the heterobifunctional compound is administered to the cell so that the concentration of the endogenous protein-dTAG hybrid protein in the cell is completely degraded.

In one embodiment, provided herein is a method of identifying a protein target associated with a disease or disorder comprising inserting a nucleic acid sequence encoding a dTAG in frame either 5'- or 3'- to the genomic sequence encoding a protein of interest, wherein insertion of the nucleic acid encoding the dTAG into the genomic sequence results in an endogenous protein-dTAG hybrid or fusion protein upon expression, wherein the endogenous protein-dTAG is capable of being degraded by a heterobifunctional compound which binds to a) the inserted dTAG and b) a ubiquitin ligase in a manner that brings the dTAG (and thus the endogenous protein-dTAG hybrid protein) into proximity of a ubiquitin ligase, such that the endogenous protein-dTAG hybrid protein is ubiquitinated, and then degraded by the proteasome, and measuring the effects of protein degradation on the disorder or disease state of the cell. By using the methods described herein to insert nucleic acids encoding dTAGs in frame with a gene encoding an endogenous protein of interest, downregulation of various proteins can be examined and potential targets for treating disorders associated with a particular disease state can be identified. In addition, the current methods can be utilized to validate a potential protein being targeted as associated with a disease state.

In a particular embodiment, the dTAGs for use in the present invention include an amino acid sequence derived from an endogenous protein kinase. In one embodiment, the endogenous protein kinase amino acid sequence includes a mutation rendering the kinase inactive. In one embodiment, the mutation in the protein kinase occurs within a conserved kinase catalytic triad amino acid sequence. In one embodiment, the conserved kinase catalytic triad amino acid sequence is TVS. In one embodiment, the conserved kinase catalytic triad amino acid sequence is HRD. In one embodiment, the conserved kinase catalytic triad amino acid sequence is DFG. In one embodiment, the conserved kinase catalytic triad amino acid sequence is TRD. See Kornev et al., "Surface comparison of active and inactive protein kinases identifies a conserved activation mechanism," PNAS 2006; 103(47):17783-17788, incorporated herein by reference. In one embodiment, at least one of the catalytic triad amino acids is substituted for an alanine. In one embodiment, at least one of the catalytic triad amino acids is substituted for a glycine. In one embodiment, the heterobifunctional compound contains an allelic-specific ligand capable of selectively binding the mutant protein kinase sequence. In one embodiment, the mutant kinase is as described in Roskoski et al., "Classification of small molecule protein kinase inhibitors based upon the structures of their drug-enzyme complexes," Pharmacological Research dx.doi.org/10.1016/j.phrs.2015.10.021, incorporated herein by reference and/or Roskoski et al.," A historical overview of protein kinases and their targeted small molecule inhibitors," Pharmaceutical Research (2015), dx.doi.org/10.1016/j.phrs.2015.07.010, incorporated herein by reference. In one embodiment, the dTAG is derived from a kinase that is an analog-sensitive kinase. In one embodiment, the mutant kinase is as described in Zhang et al., "Structure-guided inhibitor design expands the scope of analog-sensitive kinase technology," ACS Chem Biol. 2013:8(9); 1931-1938, incorporated herein by reference. In alternative embodiments, the dTAGs for use in the present invention include, but are not limited to, amino acid sequences derived from proteins selected from EGFR, BCR-ABL, ALK, JAK2, BRAF, LRRK2, PDGFRα, and RET. In one embodiment, the proteins contain one or more mutations. In one embodiment, the one or more mutations render the protein inactive.

In alternative embodiments, the dTAGs for use in the present invention include, but are not limited to, amino acid sequences derived from proteins selected from Src, Src, Pkd1, Kit, Jak2, Abl, Mek1, HIV integrase, and HIV reverse transcriptase.

In particular embodiments, the dTAGs for use in the present invention include, but are not limited to, amino acid sequences derived from endogenously expressed proteins such as FK506 binding protein-12 (FKBP12), bromodomain-containing protein 4 (BRD4), CREB binding protein (CREBBP), or transcriptional activator BRG1 (SMARCA4). In other embodiments, dTAGs for use in the present invention may include, for example, a hormone receptor e.g. estrogen-receptor protein, androgen receptor protein, retinoid x receptor (RXR) protein, or dihydrofolate reductase (DHFR), including bacterial DHFR. In other embodiments, the dTAG may include, for example, an amino acid sequence derived from a bacterial dehalogenase. In other embodiments, the dTAG, may include, amino acid sequences derived from 7,8-dihydro-8-oxoguanin triphosphatase, AFAD, Arachidonate 5-lipoxygenase activating protein, apolipoprotein, ASH1L, ATAD2, baculoviral IAP repeat-containing protein 2, BAZ1A, BAZ1B, BAZ2A, BAZ2B, Bcl-2, Bcl-xL, BRD1, BRD2, BRD3, BRD4, BRD5, BRD6, BRD7, BRD8, BRD9, BRD10, BRDT, BRPF1, BRPF3, BRWD3, CD209, CECR2, CREBBP, E3 ligase XIAP, EP300, FALZ, fatty acid binding protein from adipocytes 4 (FABP4), GCN5L2, GTPase k-RAS, HDAC6, hematopoietic prostaglandin D synthase, KIAA1240, lactoglutathione lyase, LOC93349, Mcl-1, MLL, PA2GA, PB1, PCAF, peptidyl-prolyl cis-trans isomerase NIMA-interacting 1, PHIP, poly-ADP-ribose polymerase 14, poly-ADP-ribose polymerase 15, PRKCBP1, prosaposin, prostaglandin E synthase, retinal rod rhodopsin-sensitive cGMP 3',5-cyclic phosphodiesterase subunit delta, S100-A7, SMARCA2, SMARCA4, SP100, SP110, SP140, Src, Sumo-conjugating enzyme UBC9, superoxide dismutase, TAF1, TAF1L, tankyrase 1, tankyrase 2, TIFla, TRIM28, TRIM33, TRIM66, WDR9, ZMYND11, or MLL4. In yet further embodiments, the dTAG may include, for example, an amino acid sequence derived from MDM2.

In a particular embodiment, the dTAG is derived from BRD2, BRD3, BRD4, or BRDT. In certain embodiments, the dTAG is a modified or mutant BRD2, BRD3, BRD4, or BRDT protein. In certain embodiments, the one or more mutations of BRD2 include a mutation of the Tryptophan (W) at amino acid position 97, a mutation of the Valine (V) at amino acid position 103, a mutation of the Leucine (L) at amino acid position 110, a mutation of the W at amino acid position 370, a mutation of the V at amino acid position 376, or a mutation of the L at amino acid position 381.

In certain embodiments, the one or more mutations of BRD3 include a mutation of the W at amino acid position 57, a mutation of the V at amino acid position 63, a mutation of the L at amino acid position 70, a mutation of the W at amino acid position 332, a mutation of the V at amino acid position 338, or a mutation of the L at amino acid position 345. In certain embodiments, the one or more mutations of BRD4 include a mutation of the W at amino acid position 81, a mutation of the V at amino acid position 87, a mutation of the L at amino acid position 94, a mutation of the W at amino acid position 374, a mutation of the V at amino acid position 380, or a mutation of the L at amino acid position 387. In certain embodiments, the one or more mutations of BRDT include a mutation of the W at amino acid position 50, a mutation of the V at amino acid position 56, a mutation of the L at amino acid position 63, a mutation of the W at amino acid position 293, a mutation of the V at amino acid position 299, or a mutation of the L at amino acid position 306.

In a particular embodiment, the dTAG is derived from cytosolic signaling protein FKBP12. In certain embodiments, the dTAG is a modified or mutant cytosolic signaling protein FKBP12. In certain embodiments, the modified or mutant cytosolic signaling protein FKBP12 contains one or more mutations that create an enlarged binding pocket for FKBP12 ligands. In certain embodiments, the one or more mutations include a mutation of the phenylalanine (F) at amino acid position 36 to valine (V) (F36V) (referred to interchangeably herein as FKBP* or FKBP12*).

In one embodiment, the dTAG is derived from an amino acid sequence, or fragment thereof from any of SEQ. ID. NOs.: 1-44. In a particular embodiment, the dTAG is derived from an amino acid sequence, or fragment thereof of SEQ. ID. NO.: 1. In a particular embodiment, the dTAG is derived from an amino acid sequence, or fragment thereof of SEQ. ID. NO.: 2. In a particular embodiment, the dTAG is derived from an amino acid sequence, or fragment thereof of SEQ. ID. NO.: 3. In a particular embodiment, the dTAG is derived from an amino acid sequence, or fragment thereof of SEQ. ID. NO.: 4. In a particular embodiment, the dTAG is derived from an amino acid sequence, or fragment thereof of SEQ. ID. NO.: 5. In a particular embodiment, the dTAG is derived from an amino acid sequence, or fragment thereof of SEQ. ID. NO.: 6. In a particular embodiment, the dTAG is derived from an amino acid sequence, or fragment thereof of SEQ. ID. NO.: 7. In a particular embodiment, the dTAG is derived from an amino acid sequence, or fragment thereof of SEQ. ID. NO.: 8. In a particular embodiment, the dTAG is derived from an amino acid sequence, or fragment thereof of SEQ. ID. NO.: 9. In a particular embodiment, the dTAG is derived from an amino acid sequence, or fragment thereof of SEQ. ID. NO.: 10. In a particular embodiment, the dTAG is derived from an amino acid sequence, or fragment thereof of SEQ. ID. NO.: 11. In a particular embodiment, the dTAG is derived from an amino acid sequence, or fragment thereof of SEQ. ID. NO.: 12. In a particular embodiment, the dTAG is derived from an amino acid sequence, or fragment thereof of SEQ. ID. NO.: 13. In a particular embodiment, the dTAG is derived from an amino acid sequence, or fragment thereof of SEQ. ID. NO.: 14. In a particular embodiment, the dTAG is derived from an amino acid sequence, or fragment thereof of SEQ. ID. NO.: 15. In a particular embodiment, the dTAG is derived from an amino acid sequence, or fragment thereof of SEQ. ID. NO.: 16. In a particular embodiment, the dTAG is derived from an amino acid sequence, or fragment thereof of SEQ. ID. NO.: 17. In a particular embodiment, the dTAG is derived from an amino acid sequence, or fragment thereof of SEQ. ID. NO.: 18. In a particular embodiment, the dTAG is derived from an amino acid sequence, or fragment thereof of SEQ. ID. NO.: 19. In a particular embodiment, the dTAG is derived from an amino acid sequence, or fragment thereof of SEQ. ID. NO.: 20. In a particular embodiment, the dTAG is derived from an amino acid sequence, or fragment thereof of SEQ. ID. NO.: 21. In a particular embodiment, the dTAG is derived from an amino acid sequence, or fragment thereof of SEQ. ID. NO.: 22. In a particular embodiment, the dTAG is derived from an amino acid sequence, or fragment thereof of SEQ. ID. NO.: 23. In a particular embodiment, the dTAG is derived from an amino acid sequence, or fragment thereof of SEQ. ID. NO.: 24. In a particular embodiment, the dTAG is derived from an amino acid sequence, or fragment thereof of SEQ. ID. NO.: 25. In a particular embodiment, the dTAG is derived from an amino acid sequence, or fragment thereof of SEQ. ID. NO.: 26. In a particular embodiment, the dTAG is derived from an amino acid sequence, or fragment thereof of SEQ. ID. NO.: 27. In a particular embodiment, the dTAG is derived from an amino acid sequence, or fragment thereof of SEQ. ID. NO.: 28. In a particular embodiment, the dTAG is derived from an amino acid sequence, or fragment thereof of SEQ. ID. NO.: 29. In a particular embodiment, the dTAG is derived from an amino acid sequence, or fragment thereof of SEQ. ID. NO.: 30. In a particular embodiment, the dTAG is derived from an amino acid sequence, or fragment thereof of SEQ. ID. NO.: 31. In a particular embodiment, the dTAG is derived from an amino acid sequence, or fragment thereof of SEQ. ID. NO.: 32. In a particular embodiment, the dTAG is derived from an amino acid sequence, or fragment thereof of SEQ. ID. NO.: 33. In a particular embodiment, the dTAG is derived from an amino acid sequence, or fragment thereof of SEQ. ID. NO.: 34. In a particular embodiment, the dTAG is derived from an amino acid sequence, or fragment thereof of SEQ. ID. NO.: 35. In a particular embodiment, the dTAG is derived from an amino acid sequence, or fragment thereof of SEQ. ID. NO.: 36. In a particular embodiment, the dTAG is derived from an amino acid sequence, or fragment thereof of SEQ. ID. NO.: 37. In a particular embodiment, the dTAG is derived from an amino acid sequence, or fragment thereof of SEQ. ID. NO.: 38. In a particular embodiment, the dTAG is derived from an amino acid sequence, or fragment thereof of SEQ. ID. NO.: 39. In a particular embodiment, the dTAG is derived from an amino acid sequence, or fragment thereof of SEQ. ID. NO.: 40. In a particular embodiment, the dTAG is derived from an amino acid sequence, or fragment thereof of SEQ. ID. NO.: 41. In a particular embodiment, the dTAG is derived from an amino acid sequence, or fragment thereof of SEQ. ID. NO.: 42. In a particular embodiment, the dTAG is derived from an amino acid sequence, or fragment thereof of SEQ. ID. NO.: 43. In a particular embodiment, the dTAG is derived from an amino acid sequence, or fragment thereof of SEQ. ID. NO.: 44. In a particular embodiment, the fragment thereof refers to the minimum amino acid sequence need to be bound by the heterobifunctional compound. In a particular embodiment, the dTAG is derived from an amino acid sequence, or fragment thereof of SEQ. ID. NO.: 62. In a particular embodiment, the dTAG is derived from an amino acid sequence, or fragment thereof of SEQ. ID. NO.: 63. In a particular embodiment, the fragment thereof refers to the minimum amino acid sequence needed to be bound by the heterobifunctional compound.

In a particular embodiment, the dTAG is derived from an amino acid sequence or fragment thereof of SEQ. ID. NO.: 1 and the dTAG is capable of being bound by a heterobifunctional compound selected from any of dFKBP-1-dFKBP-5. In a particular embodiment, the dTAG is derived from an amino acid sequence or fragment thereof of SEQ. ID. NO.: 2 and the dTAG is capable of being bound by a heterobifunctional compound selected from any of dFKBP-6-dFKBP-13. In a particular embodiment, the dTAG is derived from an amino acid sequence or fragment thereof of SEQ. ID. NO.: 3 and the dTAG is capable of being bound by a heterobifunctional compound selected from any of dBET1-dBET18. In a particular embodiment, the dTAG is derived from an amino acid sequence or fragment thereof of SEQ. ID. NO.: 3 and the dTAG is capable of being bound by a heterobifunctional compound selected from any of dBromo1-dBromo34. In a particular embodiment, the dTAG is derived from an amino acid sequence or fragment thereof of SEQ. ID. NO.: 9 and the dTAG is capable of being bound by a heterobifunctional compound selected from any of dHalo1-dHalo2.

In one embodiment, the dTAG is derived from any amino acid sequence described herein, or a fragment thereof, and the dTAG is capable of being bound by a corresponding heterobifunctional compound comprising a dTAG Targeting Ligand capable of binding the dTAG described herein. In one embodiment, the dTAG is amino acid sequence capable of being bound by a heterobifunctional compound described in FIG. 29, FIG. 30, FIG. 31, FIG. 32, and FIG. 33, or any other heterobifunctional compound described herein. In one embodiment, the dTAG is amino acid sequence capable of being bound by a heterobifunctional compound comprising a dTAG Targeting Ligand described in Table T. In a particular embodiment, the dTAG is derived from an amino acid sequence or fragment thereof of SEQ. ID. NO.: 1 and the dTAG is capable of being bound by a heterobifunctional compound selected from any of dFKBP-1-dFKBP-5. In a particular embodiment, the dTAG is derived from an amino acid sequence or fragment thereof of SEQ. ID. NO.: 2 and the dTAG is capable of being bound by a heterobifunctional compound selected from any of dFKBP-6-dFKBP-13. In a particular embodiment, the dTAG is derived from an amino acid sequence or fragment thereof of SEQ. ID. NO.: 3 and the dTAG is capable of being bound by a heterobifunctional compound selected from any of dBET1-dBET18. In a particular embodiment, the dTAG is derived from an amino acid sequence or fragment thereof of SEQ. ID. NO.: 3 and the dTAG is capable of being bound by a heterobifunctional compound selected from any of dBromo1-dBromo34. In a particular embodiment, the dTAG is derived from an amino acid sequence or fragment thereof of SEQ. ID. NO.: 9 and the dTAG is capable of being bound by a heterobifunctional compound selected from any of dHalo1-dHalo2. In a particular embodiment, the dTAG is derived from CREBBP and the heterobifunctional compound contains a CREBBP dTAG Targeting Ligand selected from Table T. In a particular embodiment, the dTAG is derived from SMARCA4, PB1, or SMARCA2 and the heterobifunctional compound contains a SMARCA4/PB1/SMARCA2 dTAG Targeting Ligand selected from Table T. In a particular embodiment, the dTAG is derived from TRIM24 or BRPF1 and the heterobifunctional compound contains a TRIM24/BRPF1 dTAG Targeting Ligand selected from Table T. In a particular embodiment, the dTAG is derived from a glucocorticoid receptor and the heterobifunctional compound contains a glucocorticoid dTAG Targeting Ligand selected from Table T. In a particular embodiment, the dTAG is derived from an estrogen or androgen receptor and the heterobifunctional compound contains an estrogen/androgen receptor dTAG Targeting Ligand selected from Table T. In a particular embodiment, the dTAG is derived from DOT1L and the heterobifunctional compound contains a DOT1L dTAG Targeting Ligand selected from Table T. In a particular embodiment, the dTAG is derived from Ras and the heterobifunctional compound contains a Ras dTAG Targeting Ligand selected from Table T. In a particular embodiment, the dTAG is derived from RasG12C and the heterobifunctional compound contains a RasG12C dTAG Targeting Ligand selected from Table T. In a particular embodiment, the dTAG is derived from HER3 and the heterobifunctional compound contains a HER3 dTAG Targeting Ligand selected from Table T. In a particular embodiment, the dTAG is derived from Bcl-2 or Bcl-XL and the heterobifunctional compound contains a Bcl-2/Bcl-XL dTAG Targeting Ligand selected from Table T. In a particular embodiment, the dTAG is derived from HDAC and the heterobifunctional compound contains a HDAC dTAG Targeting Ligand selected from Table T. In a particular embodiment, the dTAG is derived from PPAR and the heterobifunctional compound contains a PPAR dTAG Targeting Ligand selected from Table T. In a particular embodiment, the dTAG is derived from DHFR and the heterobifunctional compound contains a DHFR dTAG Targeting Ligand selected from Table T.

In one aspect, the synthetic gene of the present invention includes a gene of interest that is implicated in a genetic disorder. By way of a non-limiting example, a mutated gene, for example, encoding alpha-1 antitrypsin (A1AT), may be targeted for dTAG in frame insertion in a cell to produce a synthetic gene which encodes a hybrid protein capable of being degraded by a heterobifunctional compound that targets the dTAG of the endogenous A1AT-dTAG hybrid protein. By generating an A1AT-dTAG hybrid, the function of the mutated A1AT can be regulated or modulated through heterobifunctional compound administration, allowing the cell to maintain some function of the A1AT endogenous protein while reducing the effects of A1AT overexpression. Other non-limiting examples of proteins that may be targeted include β-catenin (CTNNB1), apolipoprotein B (APOB), angiopoietin-like protein 3 (ANGPTL3), proprotein convertase subtilisin/kexin type 9 (PCSK9), apolipoprotein C3 (APOC3), low density lipoprotein receptor (LDLR), C-reactive protein (CRP), apolipoprotein a (Apo (a)), Factor VII, Factor XI, antithrombin III (SERPINC1), phosphatidylinositol glycan class A (PIG-A), C5, alpha-1 antitrypsin (SERPINA1), hepcidin regulation (TMPRSS6), (delta-aminolevulinate synthase 1 (ALAS-1), acylCaA:diacylglycerol acyltransferase (DGAT), miR-122, miR-21, miR-155, miR-34a, prekallikrein (KLKB1), connective tissue growth factor (CCN2), intercellular adhesion molecule 1 (ICAM-1), glucagon receptor (GCGR), glucorticoid receptor (GCCR), protein tyrosine phosphatase (PTP-1B), c-Raf kinase (RAF1), fibroblast growth factor receptor 4 (FGFR4), vascular adhesion molecule-1 (VCAM-1), very late antigen-4 (VLA-4), transthyretin (TTR), survival motor neuron 2 (SMN2), growth hormone receptor (GHR), dystophia myotonic protein kinase (DMPK), cellular nucleic acid-binding protein (CNBP or ZNF9), clusterin (CLU), eukaryotic translation initiation factor 4E (eIF-4e), MDM2, MDM4, heat shock protein 27 (HSP 27), signal transduction and activator of transcription 3 protein (STAT3), vascular endothelial growth factor (VEGF), kinesin spindle protein (KIF 11), hepatitis B genome, the androgen receptor (AR), Atonal homolog 1 (ATOH1), vascular endothelial growth factor receptor 1 (FLT1), retinoschism 1 (RS1), retinal pigment epithelium-specific 65 kDa protein (RPE65), Rab escort protein 1 (CHM), and the sodium channel, voltage gated, type X, alpha subunit (PN3 or SCN10A). The genetic disorders include but are not limited to homozygous familial hypercholesterolemia, AGS1-AGS7, PRAAS/CANDLE, SAVI, ISG15 def, SPENCDI, hemophagocytic lymphohistiocytosis, NLRC4-MAS, CAMPS, DADA2, PLAID, Tyrosinemia type I, BSEP deficiency, MRD3 gene defect, glycogen storage disease types IV, I, Crigler-Najjar syndrome, Ornithine transcarbamylase deficiency, primary hyperoxaluria, Wilson disease, Cystic fibrosis, FIC1 deficiency, citrullinemia, cystinosis, propionic academia, ADA-SCID, X-linked SCID, lipoprotein lipase deficiency, Leber's congenital amaurosis, and adrenoleukodystrophy.

Also contemplated herein is the use of heterobifunctional compounds capable of binding to the dTAG of the endogenous protein-dTAG hybrid of the present invention and inducing degradation through ubiquination. By administering to a subject a heterobifunctional compound directed to a dTAG, the endogenous protein-dTAG hybrid can be modulated in a subject suffering from a disease or disorder as a result of the target protein's expression. The heterobifunctional compounds for use in the present invention are small molecule antagonists capable of disabling the biological function of the endogenous protein through degradation of the endogenous protein-dTAG hybrid. They provide prompt ligand-dependent target protein degradation via chemical conjugation with, for example, derivatized phthalimides that hijack the function of the Cereblon E3 ubiquitin ligase complex. Using this approach, the endogenous protein-dTAG hybrid of the present invention can be degraded rapidly with a high specificity and efficiency.

The heterobifunctional compounds that can be used in the present invention include those that include a small molecule E3 ligase ligand which is covalently linked to a dTAG Targeting Ligand through a Linker of varying length and/or functionality as described in more detail below. The heterobifunctional compound is able to bind to the dTAG and recruit an E3 ligase, for example, by binding to a Cereblon (CRBN) containing ligase or Von Hippel-Lindau tumor suppressor (VHL) to the endogenous-dTAG hybrid for ubiquitination and subsequent proteasomal degradation.

Moreover, by combining the chemical strategy of protein degradation via the bifunctional molecules of the present application with the effectiveness of gene therapy, the activity of the endogenously expressed protein, and thus the side effects, can be regulated in a precise, temporal manner by rapidly turning on and off ubiquitination, and proteasomal degradation of the endogenous protein-dTAG hybrid.

Examples of heterobifunctional compounds useful in the present invention are exemplified further below.

In one aspect, the genomic nucleic acid sequence encodes a synthetic gene comprising an endogenous gene of interest having a 5'- or 3'-in-frame insertion of a nucleic acid encoding a dTAG which, when expressed, results in an endogenous protein-dTAG hybrid protein wherein the dTAG is capable of being bound by a heterobifunctional compound. Cells and animals, including in particular non-human animals, bearing such genetic modifications are part of the invention.

In a particular embodiment, the genomic nucleic acid sequence encodes a synthetic gene comprising an endogenous gene of interest having a 5'- or 3'-in-frame insertion of a nucleic acid encoding a dTAG wherein the dTAG is derived from an amino acid sequence or fragment thereof of SEQ. ID. NO.: 1 and the dTAG is capable of being bound by a heterobifunctional compound selected from any of dFKBP-1-dFKBP-5. In a particular embodiment, the genomic nucleic acid sequence encodes a synthetic gene comprising an endogenous gene of interest having a 5'- or 3'-in-frame insertion of a nucleic acid encoding a dTAG wherein the dTAG is derived from an amino acid sequence or fragment thereof of SEQ. ID. NO.: 2 and the dTAG is capable of being bound by a heterobifunctional compound selected from any of dFKBP-6-dFKBP-13. In a particular embodiment, the genomic nucleic acid sequence encodes a synthetic gene comprising an endogenous gene of interest having a 5'- or 3'-in-frame insertion of a nucleic acid encoding a dTAG wherein the dTAG is derived from an amino acid sequence or fragment thereof of SEQ. ID. NO.: 3 and the dTAG is capable of being bound by a heterobifunctional compound selected from any of dBET1-dBET18. In a particular embodiment, the genomic nucleic acid sequence encodes a synthetic gene comprising an endogenous gene of interest having a 5'- or 3'-in-frame insertion of a nucleic acid encoding a dTAG wherein the dTAG is derived from an amino acid sequence or fragment thereof of SEQ. ID. NO.: 3 and the dTAG is capable of being bound by a heterobifunctional compound selected from any of dBromo1-dBromo34. In a particular embodiment, the genomic nucleic acid sequence encodes a synthetic gene comprising an endogenous gene of interest having a 5'- or 3'-in-frame insertion of a nucleic acid encoding a dTAG wherein the dTAG is derived from an amino acid sequence or fragment thereof of SEQ. ID. NO.: 9 and the dTAG is capable of being bound by a heterobifunctional compound selected from dHalo1 and dHalo2.

In one aspect, an amino acid encoded by a synthetic gene comprising an endogenous gene of interest having a 5'- or 3'-in-frame insertion of a nucleic acid encoding a dTAG is provided, wherein the amino acid being an endogenous protein-dTAG hybrid protein wherein the dTAG is capable of being bound by a heterobifunctional compound.

In one aspect, provided herein is a transformed cell comprising a genomic nucleic acid sequence encoding a synthetic gene comprising an endogenous gene of interest having a 5'- or 3'-in-frame insertion of a nucleic acid encoding a dTAG which, when expressed, results in an endogenous protein-dTAG hybrid protein wherein the dTAG is capable of being bound by a heterobifunctional compound.

In one aspect, provided herein is a cell expressing a synthetic gene comprising an endogenous gene of interest having a 5'- or 3'-in-frame insertion of a nucleic acid encoding a dTAG which, when expressed, results in an endogenous protein-dTAG hybrid protein wherein the dTAG is capable of being bound by a heterobifunctional compound.

In a particular aspect, a method of modulating the activity of an endogenous protein by genomically inserting in frame a nucleic acid sequence encoding a dTAG is provided which, when expressed, results in an endogenous protein-dTAG hybrid protein wherein the dTAG is capable of being bound by a heterobifunctional compound, and administering to a subject a heterobifunctional compound capable of binding the dTAG and degrading the endogenous protein-dTAG hybrid.

In a particular aspect, a method of identifying an endogenous protein associated with a disease state is provided wherein the activity of the endogenous protein is modulated by genomically inserting in frame a nucleic acid sequence encoding a dTAG which, when expressed, results in an endogenous protein-dTAG hybrid protein wherein the dTAG is capable of being bound by a heterobifunctional compound, and administering a heterobifunctional compound capable of binding the dTAG and degrading the endogenous protein-dTAG hybrid, wherein degradation of the protein results in the alteration of the disease state.

In one embodiment, provided herein is a transformed cell comprising a nucleic acid encoding SEQ. ID. NO.: 52 and a nucleic acid encoding a dTAG. In one embodiment, provided herein is a transformed cell comprising a nucleic acid encoding SEQ. ID. NO.: 52 and a nucleic acid encoding dTAG derived from an amino acid sequence, or fragment thereof, selected from SEQ. ID. NOs.: 1-44.

In one embodiment, provided herein is a first nucleic acid encoding SEQ. ID. NO.: 52 and a second nucleic acid encoding a dTAG. In one embodiment, provided herein is a first nucleic acid encoding SEQ. ID. NO.: 52 and a second nucleic acid encoding a dTAG derived from an amino acid sequence, or fragment thereof, selected from SEQ. ID. NO.: 1-44.

Other aspects of the invention include polynucleotide sequences, plasmids, and vectors encoding the synthetic genes of the present invention, and host cells expressing the synthetic genes of the present invention.

In an alternative embodiment, the dTAG for use in the present invention is an amino acid sequence derived from EGFR. In certain embodiments, the dTAG is a modified or mutant EGFR protein or fragment thereof. In certain embodiments, the one or more mutations of EGFR include a substitution of Leucine (L) with Arginine (R) at amino acid position 858, a deletion of the amino acid sequence LREA in exon 19, an insertion of amino acids VAIKEL in exon 19, a substitution of Glycine (G) with Alanine (A), Cysteine (C), or Serine (S) at amino acid position 719, a substitution of Leucine (L) with Alanine (A), Cysteine (C), or Serine (S) at amino acid position 861, a substitution of Valine (V) with Alanine (A) at amino acid position 765, a substitution of Threonine (T) with Alanine (A) at amino acid position 783, a substitution of Serine (S) with Proline (P) at amino acid position 784, a substitution of Threonine (T) with Methionine (M) at amino acid position 790 M, a substitution of Threonine (T) with Alanine (A) at amino acid position 854, a substitution of Aspartic Acid (D) with Tyrosine (Y) at amino acid 761, a substitution of Leucine (L) with Serine (S) at amino acid position 747, a substitution of Cysteine (C) with Serine (S) or Glycine (G) at amino acid position 797. In one embodiment, the dTAG is an amino acid sequence derived from, or a fragment thereof, of SEQ. ID. NO.: 53. In one embodiment, the dTAG is an amino acid sequence derived from, or a fragment thereof, of SEQ. ID. NO.: 54. In one embodiment, SEQ. ID. NO.: 54 has a Leucine at position 163. In one embodiment, the dTAG is an amino acid sequence derived from, or a fragment thereof, of SEQ. ID. NO.: 55. In one embodiment, SEQ. ID. NO.: 55 has a Leucine at position 163. In one embodiment, SEQ. ID. No.: 55 has a Threonine at position 95. In one embodiment, SEQ. ID. NO.: 55 has a Leucine at position 163 and a Threonine at position 95. In one embodiment, the dTAG is an amino acid sequence derived from, or a fragment thereof, of SEQ. ID. NO.: 56. In one embodiment, SEQ. ID. NO.: 56 has a Leucine at position 163. In one embodiment, SEQ. ID. NO.: 56 has a Threonine at position 95. In one embodiment, SEQ. ID. NO.: 56 has a Leucine at position 163 and a Threonine at position 95.

In an alternative embodiment, the dTAG for use in the present invention is an amino acid sequence derived from BCR-ABL. In certain embodiments, the dTAG is a modified or mutant BCR-ABL protein or fragment thereof. In certain embodiments, the one or more mutations of BCR-ABL include a substitution of Tyrosine (T) with Isoleucine (I) at amino acid position 315. In one embodiment, the dTAG is an amino acid sequence derived from, or a fragment thereof, of SEQ. ID. NO.: 57. In one embodiment, the dTAG is an amino acid sequence derived from, or a fragment thereof, of SEQ. ID. NO.: 58.

In an alternative embodiment, the dTAGs for use in the present invention is an amino acid sequence derived from ALK. In certain embodiments, the dTAG is a modified or mutant ALK protein or fragment thereof. In certain embodiments, the one or more mutations of ALK include a substitution of Leucine (L) with Methionine at amino acid position 1196. In one embodiment, the dTAG is an amino acid sequence derived from, or a fragment thereof, of SEQ. ID. NO.: 59.

In an alternative embodiment, the dTAGs for use in the present invention is an amino acid sequence derived from JAK2. In certain embodiments, the dTAG is a modified or mutant JAK2 protein or fragment thereof. In certain embodiments, the one or more mutations of JAK2 include a substitution of Valine (V) with Phenylalanine (F) at amino acid position 617. In one embodiment, the dTAG is an amino acid sequence derived from, or a fragment thereof, of SEQ. ID. NO.: 60.

In an alternative embodiment, the dTAGs for use in the present invention is an amino acid sequence derived from BRAF. In certain embodiments, the dTAG is a modified or mutant BRAF protein or fragment thereof. In certain embodiments, the one or more mutations of BRAF include a substitution of Valine (V) with Glutamic Acid (E) at amino acid position 600. In one embodiment, the dTAG is an amino acid sequence derived from, or a fragment thereof, of SEQ. ID. NO.: 61.

In alternative embodiments, the dTAGs for use in the present invention include, but are not limited to, amino acid sequences derived from proteins selected from EGFR, BCR-ABL, ALK, JAK2, and BRAF. In one embodiment, the proteins contain one or more mutations. In one embodiment, the one or more mutations render the protein inactive.

In an alternative embodiment, the dTAG for use in the present invention is an amino acid sequence derived from Src. In certain embodiments, the dTAG is a modified or mutant Src protein or fragment thereof. In certain embodiments, the one or more mutations or modifications of Src include a substitution of Threonine (T) with Glycine (G) or Alanine (A) at amino acid position 341. In one embodiment, the dTAG is an amino acid sequence derived from, or a fragment thereof, of SEQ. ID. NO.: 62. In one embodiment, the dTAG is an amino acid sequence derived from, or a fragment thereof, of SEQ. ID. NO.: 63.

In an alternative embodiment, the dTAG for use in the present invention is an amino acid sequence derived from LKKR2. In certain embodiments, the dTAG is a modified or mutant LKKR2 protein or fragment thereof. In certain embodiments, the one or more mutations of LKKR2 include a substitution of Arginine (R) with Cysteine (C) at amino acid 1441, a substitution of Glycine (G) with Serine (S) at amino acid 2019, a substitution of Isoleucine (I) with Threonine (T) at amino acid 2020.

In an alternative embodiment, the dTAG for use in the present invention is an amino acid sequence derived from PDGFRα. In certain embodiments, the dTAG is a modified or mutant PDGFRa protein or fragment thereof. In certain embodiments, the one or more mutations of PDGFRa include a substitution of Threonine (T) with Isoleucine (I) at amino acid 674.

In an alternative embodiment, the dTAG for use in the present invention is an amino acid sequence derived from RET. In certain embodiments, the dTAG is a modified or mutant RET protein or fragment thereof. In certain embodiments, the one or more mutations of RET include a substitution of Glycine (G) with Serine (S) at amino acid 691. In certain embodiments, the one or more mutations of RET include a substitution of Arginine (R) with Threonine (T) at amino acid 749. In certain embodiments, the one or more mutations of RET include a substitution of Glutamic acid (E) with Glutamine (Q) at amino acid 762. In certain embodiments, the one or more mutations of RET include a substitution of Tyrosine (Y) with Phenylalanine (F) at amino acid 791. In certain embodiments, the one or more mutations of RET include a substitution of Valine (V) with Methionine (M) at amino acid 804. In certain embodiments, the one or more mutations of RET include a substitution of Methionine (M) with Threonine (T) at amino acid 918.

In alternative embodiments, the dTAGs for use in the present invention include, but are not limited to, amino acid sequences derived from proteins selected from Kit, Jak3, Abl, Mek1, HIV reverse transcriptase, and HIV integrase.

In an alternative embodiment, the dTAG for use in the present invention is an amino acid sequence derived from LKKR2. In certain embodiments, the dTAG is a modified or mutant LKKR2 protein or fragment thereof. In certain embodiments, the one or more mutations of LKKR2 include a substitution of Arginine (R) with Cysteine (C) at amino acid 1441, a substitution of Glycine (G) with Serine (S) at amino acid 2019, a substitution of Isoleucine (I) with Threonine (T) at amino acid 2020.

In one embodiment, the dTAG has an amino acid sequence derived from a LRRK2 protein (UniProtKB-Q5S007 (LRKK2_HUMAN) incorporated herein by reference), or variant thereof. In one embodiment, the dTAG is derived from amino acid 1328 to 1511 of Q5S007. In one embodiment, the dTAG is derived from amino acid 1328 to 1511 of Q5S007, wherein amino acid 1441 is Cysteine. In one embodiment, the dTAG is derived from amino acid 1328 to 1511 of Q5S007 and the dTAG Targeting Ligand in the heterobifunctional compound is selected from a ligand in Table T-U1. In one embodiment, the dTAG is derived from amino acid 1328 to 1511 of Q5S007, wherein amino acid 1441 is Cysteine and the dTAG Targeting Ligand in the heterobifunctional compound is selected from a ligand in Table T-U1. In one embodiment, the dTAG is derived from amino acid 1879 to 2138 of Q5S007. In one embodiment, the dTAG is derived from amino acid 1879 to 2138 of Q5S007, wherein amino acid 2019 is Serine. In on embodiment, the dTAG is derived from amino acid 1879 to 2138 of Q5S007, wherein amino acid 2020 is Threonine. In one embodiment, the dTAG is derived from amino acid 1879 to 2138 of Q5S007 and the dTAG Targeting Ligand in the heterobifunctional compound is selected from a ligand in Table T-U2 or U3. In one embodiment, the dTAG is derived from amino acid 1879 to 2138 of Q5S007, wherein amino acid 2019 is Serine and the dTAG Targeting Ligand in the heterobifunctional compound is selected from a ligand in Table T-U2. In one embodiment, the dTAG is derived from amino acid 1879 to 2138 of Q5 S007, wherein amino acid 2020 is Threonine and the dTAG Targeting Ligand in the heterobifunctional compound is selected from a ligand in Table T-U3.

In an alternative embodiment, the dTAG for use in the present invention is an amino acid sequence derived from PDGFRα. In certain embodiments, the dTAG is a modified or mutant PDGFRa protein or fragment thereof. In certain embodiments, the one or more mutations of PDGFRa include a substitution of Threonine (T) with Isoleucine (I) at amino acid 6741.

In one embodiment, the dTAG has an amino acid sequence derived from a PDGFRa protein (UniProtKB-P09619 (PDGFR_HUMAN) incorporated herein by reference), or variant thereof. In one embodiment, the dTAG is derived from amino acid 600 to 692 of P09619. In one embodiment, the dTAG is derived from amino acid 600 to 692 of P09619, wherein amino acid 660 is Alanine. In one embodiment, the dTAG is derived from amino acid 600 to 692 of P09619 and the dTAG Targeting Ligand in the heterobifunctional compound is selected from a ligand in Table T-V1. In one embodiment, the dTAG is derived from amino acid 600 to 692 of P09619, wherein amino acid 660 is Alanine and the dTAG Targeting Ligand in the heterobifunctional compound is selected from a ligand in Table T-V1.

In an alternative embodiment, the dTAG for use in the present invention is an amino acid sequence derived from RET. In certain embodiments, the dTAG is a modified or mutant RET protein or fragment thereof. In certain embodiments, the one or more mutations of RET include a substitution of Glycine (G) with Serine (S) at amino acid 691. In certain embodiments, the one or more mutations of RET include a substitution of Arginine (R) with Threonine (T) at amino acid 691. In certain embodiments, the one or more mutations of RET include a substitution of Glutamic acid (E) with Glutamine (Q) at amino acid 691. In certain embodiments, the one or more mutations of RET include a substitution of Tyrosine (Y) with Phenylalanine (F) at amino acid 691. In certain embodiments, the one or more mutations of RET include a substitution of Valine (V) with Methionine (M) at amino acid 691. In certain embodiments, the one or more mutations of RET include a substitution of Methionine (M) with Threonine (T) at amino acid 691.

In one embodiment, the dTAG has an amino acid sequence derived from a PDGFRa protein (UniProtKB-P07949 (RET_HUMAN) incorporated herein by reference), or variant thereof. In one embodiment, the dTAG is derived from amino acid 724 to 1016 of P07949. In one embodiment, the dTAG is derived from amino acid 724 to 1016 of P07949, wherein amino acid 940 is Isoleucine. In one embodiment, the dTAG is derived from amino acid 724 to 1016 of P07949 and the dTAG Targeting Ligand in the heterobifunctional compound is selected from a ligand in Table T-W1. In one embodiment, the dTAG is derived from amino acid 724 to 1016 of P07949, wherein amino acid 940 is Isoleucine and the dTAG Targeting Ligand in the heterobifunctional compound is selected from a ligand in Table T-W1. In one embodiment, the dTAG is derived from amino acid 724 to 1016 of P07949 and the dTAG Targeting Ligand in the heterobifunctional compound is selected from a ligand in Table T-W2. In one embodiment, the dTAG is derived from amino acid 724 to 1016 of P07949 and the dTAG Targeting Ligand in the heterobifunctional compound is selected from a ligand in Table T-W3. In one embodiment, the dTAG is derived from amino acid 724 to 1016 of P07949 and the dTAG Targeting Ligand in the heterobifunctional compound is selected from a ligand in Table T-W4. In one embodiment, the dTAG is derived from amino acid 724 to 1016 of P07949 and the dTAG Targeting Ligand in the heterobifunctional compound is selected from a ligand in Table T-W5. In one embodiment, the dTAG is derived from amino acid 724 to 1016 of P07949 and the dTAG Targeting Ligand in the heterobifunctional compound is selected from a ligand in Table T-W6.

In a particular embodiment, the dTAG is derived from an amino acid sequence or fragment thereof of SEQ. ID. NO.: 53 and the dTAG is capable of being bound by a heterobifunctional compound that contains an EGFR dTAG Targeting Ligand selected from Table T-P1. In a particular embodiment, the dTAG is derived from an amino acid sequence or fragment thereof of SEQ. ID. NO.: 54 and the dTAG is capable of being bound by a heterobifunctional compound that contains an EGFR dTAG Targeting Ligand selected from Table T-P2. In a particular embodiment, the dTAG is derived from an amino acid sequence or fragment thereof of SEQ. ID. NO.: 55 and the dTAG is capable of being bound by a heterobifunctional compound that contains an EGFR dTAG Targeting Ligand selected from Table T-P3. In a particular embodiment, the dTAG is derived from an amino acid sequence or fragment thereof of SEQ. ID. NO.: 56 and the dTAG is capable of being bound by a heterobifunctional compound that contains an EGFR dTAG Targeting Ligand selected from Table T-P. In a particular embodiment, the dTAG is derived from an amino acid sequence or fragment thereof of SEQ. ID. NO.: 57 and the dTAG is capable of being bound by a heterobifunctional compound that contains a BCR-ABL dTAG Targeting Ligand selected from Table T-Q1. In a particular embodiment, the dTAG is derived from an amino acid sequence or fragment thereof of SEQ. ID. NO.: 58 and the dTAG is capable of being bound by a heterobifunctional compound that contains a BCR-ABL dTAG Targeting Ligand selected from Table T-Q1. In a particular embodiment, the dTAG is derived from an amino acid sequence or fragment thereof of SEQ. ID. NO.: 59 and the dTAG is capable of being bound by a heterobifunctional compound that contains a ALK dTAG Targeting Ligand selected from Table T-R1. In a particular embodiment, the dTAG is derived from an amino acid sequence or fragment thereof of SEQ. ID. NO.: 60 and the dTAG is capable of being bound by a heterobifunctional compound that contains a JAK2 dTAG Targeting Ligand selected from Table T-S1. In a particular embodiment, the dTAG is derived from an amino acid sequence or fragment thereof of SEQ. ID. NO.: 61 and the dTAG is capable of being bound by a heterobifunctional compound that contains a BRAF dTAG Targeting Ligand selected from Table T-T1.

In one embodiment, the dTAG is derived from LRRK2 amino acid 1328 to 1511 (UnitPro-Q5S007) and the dTAG Targeting Ligand in the heterobifunctional compound is selected from a ligand in Table T-U1. In one embodiment, the dTAG is derived from LRRK2 amino acid 1328 to 1511 (UniProt-Q5S007), wherein amino acid 1441 is Cysteine and the dTAG Targeting Ligand in the heterobifunctional compound is selected from a ligand in Table T-U1. In one embodiment, the dTAG is derived from LRRK2 amino acid 1879 to 2138 (UniProt-Q5S007. In one embodiment, the dTAG is derived from LRRK2 amino acid 1879 to 2138 (UniProt-Q5S007), wherein amino acid 2019 is Serine. In on embodiment, the dTAG is derived from amino acid 1879 to 2138 (UniProt-Q5S007), wherein amino acid 2020 is Threonine. In one embodiment, the dTAG is derived from LRRK2 amino acid 1879 to 2138 (UniProt-Q5S007) and the dTAG Targeting Ligand in the heterobifunctional compound is selected from a ligand in Table T-U2 or U3. In one embodiment, the dTAG is derived from LRRK2 amino acid 1879 to 2138 (UniProt-Q5S007), wherein amino acid 2019 is Serine and the dTAG Targeting Ligand in the heterobifunctional compound is selected from a ligand in Table T-U2. In one embodiment, the dTAG is derived from LRRK2 amino acid 1879 to 2138 (UniProt-Q5S007), wherein amino acid 2020 is Threonine and the dTAG Targeting Ligand in the heterobifunctional compound is selected from a ligand in Table T-U3. In one embodiment, the dTAG is derived from PDGFR amino acid 600 to 692 (UniProt-P09619) and the dTAG Targeting Ligand in the heterobifunctional compound is selected from a ligand in Table T-V1. In one embodiment, the dTAG is derived from PDGFR amino acid 600 to 692 (UniProt-P09619), wherein amino acid 674 is Isoleucine and the dTAG Targeting Ligand in the heterobifunctional compound is selected from a ligand in Table T-V1. In one embodiment, the dTAG is derived from RET amino acid 724 to 1016 (UniProtKB-P07949), and the dTAG Targeting Ligand in the heterobifunctional compound is selected from a ligand in Table T-W1-W6. In one embodiment, the dTAG is derived from RET amino acid 724 to 1016 (UniProtKB P07949), wherein amino acid 691 is Serine and the dTAG Targeting Ligand in the heterobifunctional compound is selected from a ligand in Table T-W1. In one embodiment, the dTAG is derived from RET amino acid 724 to 1016 (UniProtKB-P07949), wherein amino acid 749 is Threonine and the dTAG Targeting Ligand in the heterobifunctional compound is selected from a ligand in Table T-W2. In one embodiment, the dTAG is derived from RET amino acid 724 to 1016 (UniProtKB-P07949), wherein amino acid 762 is Glutamine and the dTAG Targeting Ligand in the heterobifunctional compound is selected from a ligand in Table T-W3. In one embodiment, the dTAG is derived from RET amino acid 724 to 1016 (UniProtKB-P07949), wherein amino acid 791 is Phenylalanine and the dTAG Targeting Ligand in the heterobifunctional compound is selected from a ligand in Table T-W4. In one embodiment, the dTAG is derived from RET amino acid 724 to 1016 (UniProtKB-P07949), wherein amino acid 804 is Methionine and the dTAG Targeting Ligand in the heterobifunctional compound is selected from a ligand in Table T-W5. In one embodiment, the dTAG is derived from RET amino acid 724 to 1016 (UniProtKB-P07949), wherein amino acid 918 is Threonine and the dTAG Targeting Ligand in the heterobifunctional compound is selected from a ligand in Table T-W6. In one embodiment, the dTAG is derived from an JAK2, and the dTAG Targeting Ligand in the heterobifunctional compound is selected from a ligand in Table T-JJJ1. In one embodiment, the dTAG is derived from an Abl, and the dTAG Targeting Ligand in the heterobifunctional compound is selected from a ligand in Table T-KKK1. In one embodiment, the dTAG is derived from an MEK1, and the dTAG Targeting Ligand in the heterobifunctional compound is selected from a ligand in Table T-LLL1. In one embodiment, the dTAG is derived from an KIT, and the dTAG Targeting Ligand in the heterobifunctional compound is selected from a ligand in Table T-MMM1. In one embodiment, the dTAG is derived from an HIV reverse transcriptase, and the dTAG Targeting Ligand in the heterobifunctional compound is selected from a ligand in Table T-NNN1. In one embodiment, the dTAG is derived from an HIV integrase, and the dTAG Targeting Ligand in the heterobifunctional compound is selected from a ligand in Table T-OOO1.

In a particular embodiment, the dTAG is derived from a protein selected from EGFR, ErbB2, ErbB4, VEGFR1, VEGFR2, VEGFR3, Kit, BCR-Abl, Src, Lyn, Hck, RET, c-Met, TrkB, Flt3, Axl, Tie2, ALK, IGF-1R, InsR, ROS1, MST1R, B-Raf, Lck, Yes, Fyn, HER2-breast cancer, PNET, RCC, RAML, SEGA, BTK, FGFR1/2/3/4, DDR1, PDGFRα, PDGFRP3, CDK4, CDK6, Fms, Itk, T315I, Eph2A, JAK1, JAK2, JAK3 CDK8, CSF-1R, FKBP12/mTOR, MEK1, MEK2, Brk, EphR, A-Raf, B-Raf, C-Raf and the heterobifunctional compound contains a dTAG Targeting Ligand selected from Table Z.

Heterobifunctional compounds capable of binding to the amino acid sequences, or a fragment thereof, described above can be generated using the dTAG Targeting Ligands described in Table T. In one embodiment, a nucleic acid sequence encoding a dTAG derived from an amino acid sequence described above, or a fragment thereof, is genomically inserted into a gene encoding an endogenous protein of interest which, upon expression, results in an endogenous protein-dTAG hybrid protein and is degraded by administering to the subject a heterobifunctional compound comprising a dTAG Targeting Ligand described in Table T. In one embodiment, a nucleic acid sequence encoding a dTAG derived from an amino acid sequence described above, or a fragment thereof, is genomically inserted into a gene encoding an endogenous protein of interest which, upon expression, results in an endogenous protein-dTAG hybrid protein and is degraded by administering to the subject its corresponding heterobifunctional compound, which is capable of binding to the dTAG, for example a heterobifunctional compound described in FIG. 29, FIG. 30, FIG. 31, FIG. 32, and FIG. 33, or any other heterobifunctional compound described herein.

BRIEF DESCRIPTION OF THE FIGURES

Figure 32F:
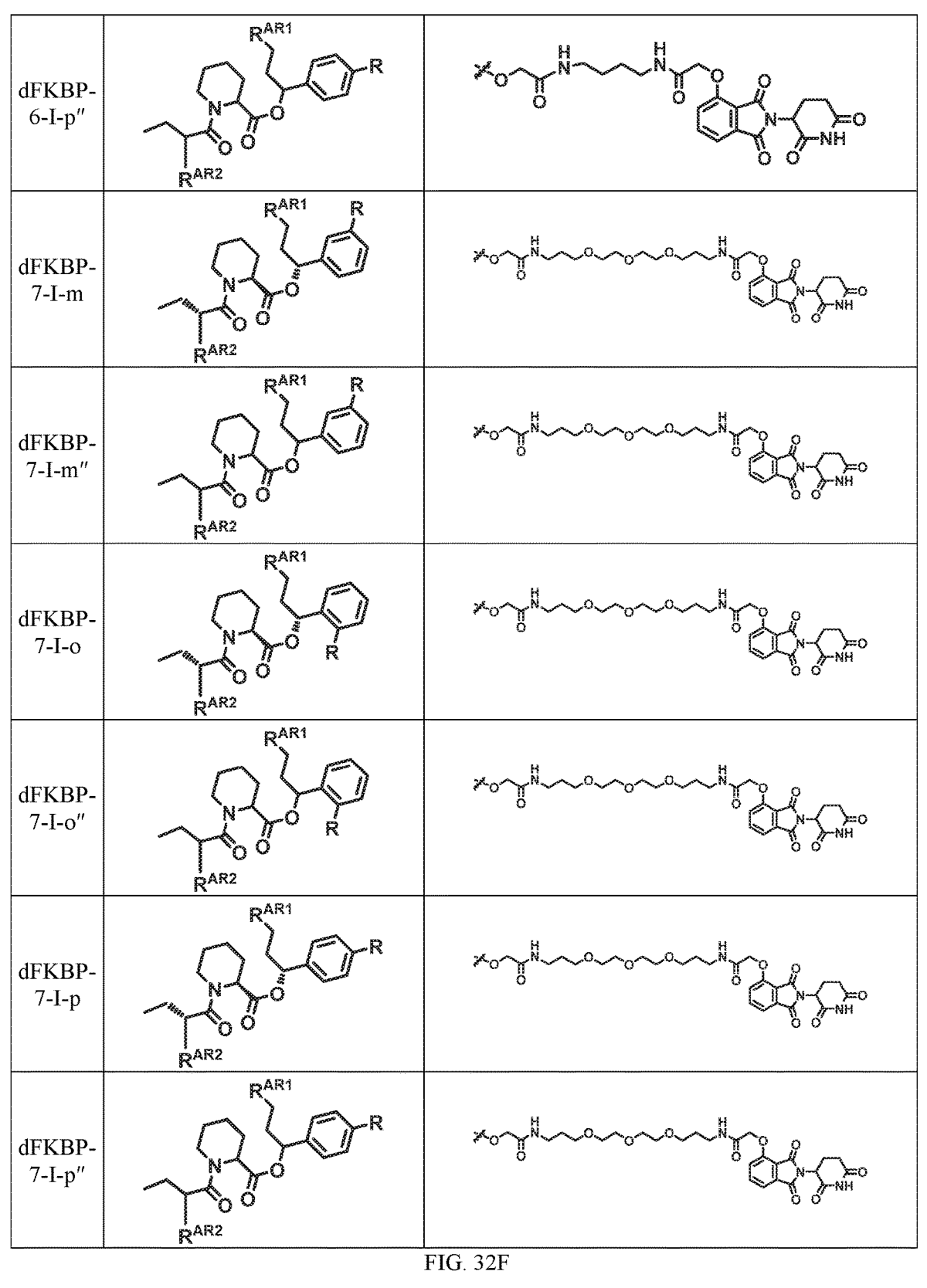
Figure 32G:
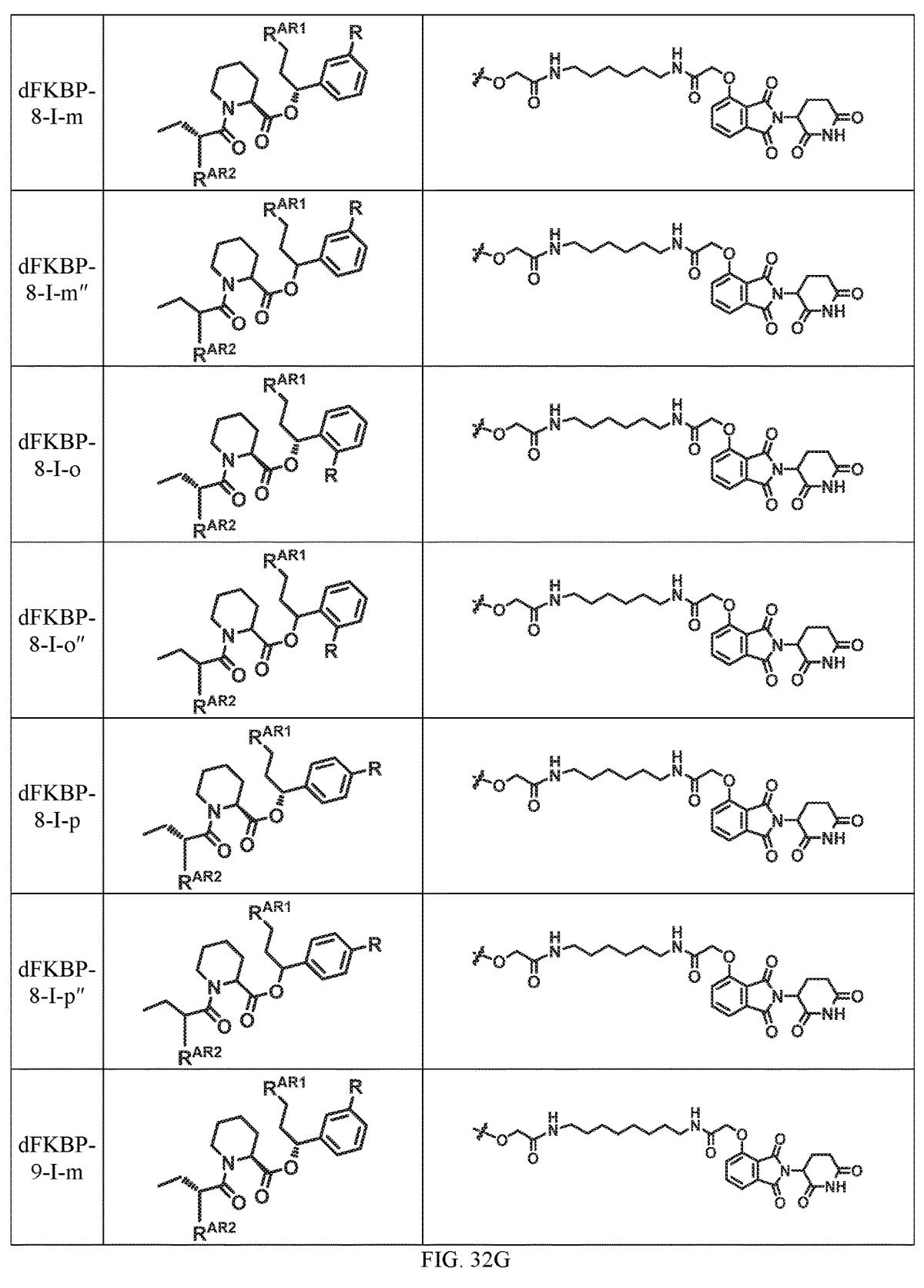
Figure 32H:
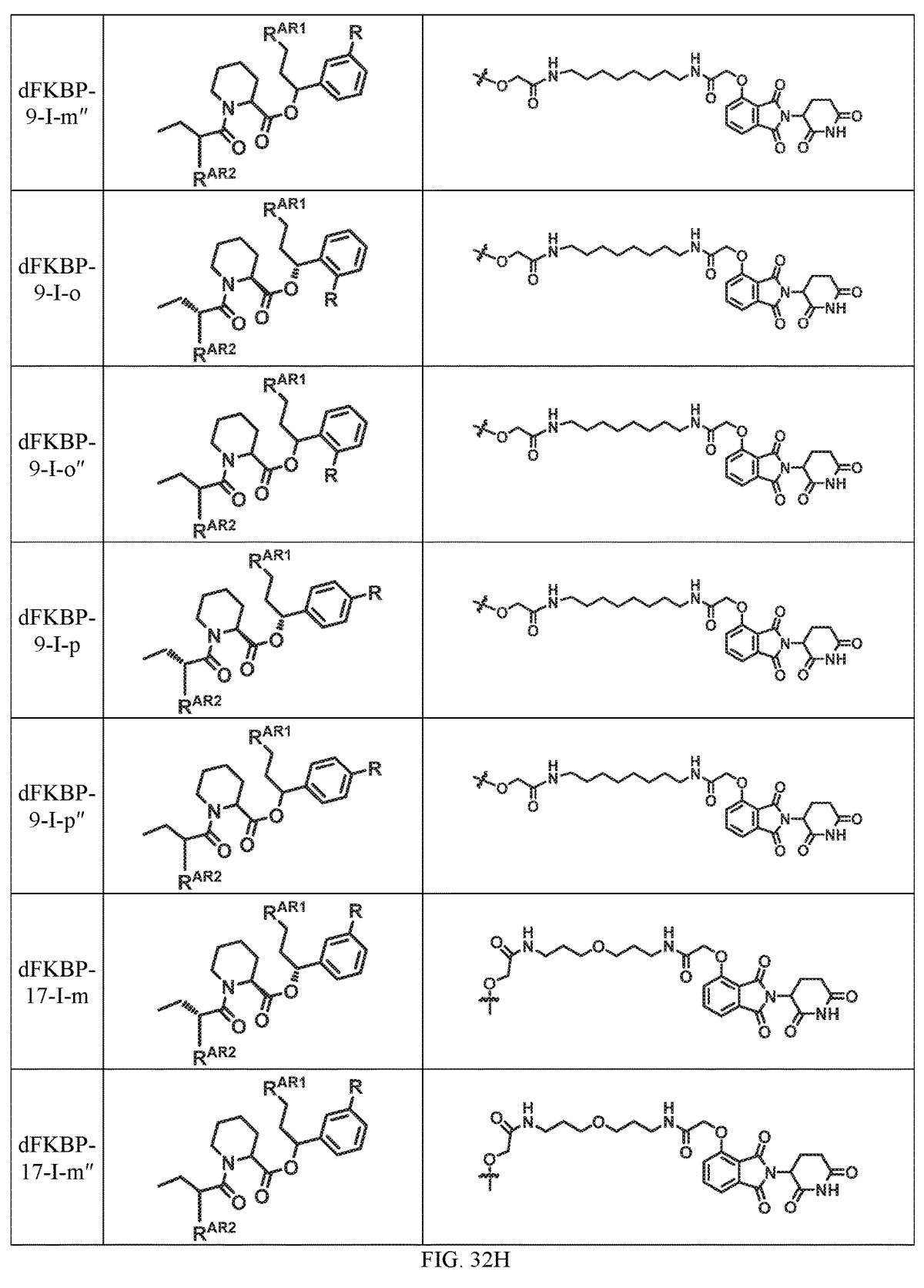
Figure 32L:
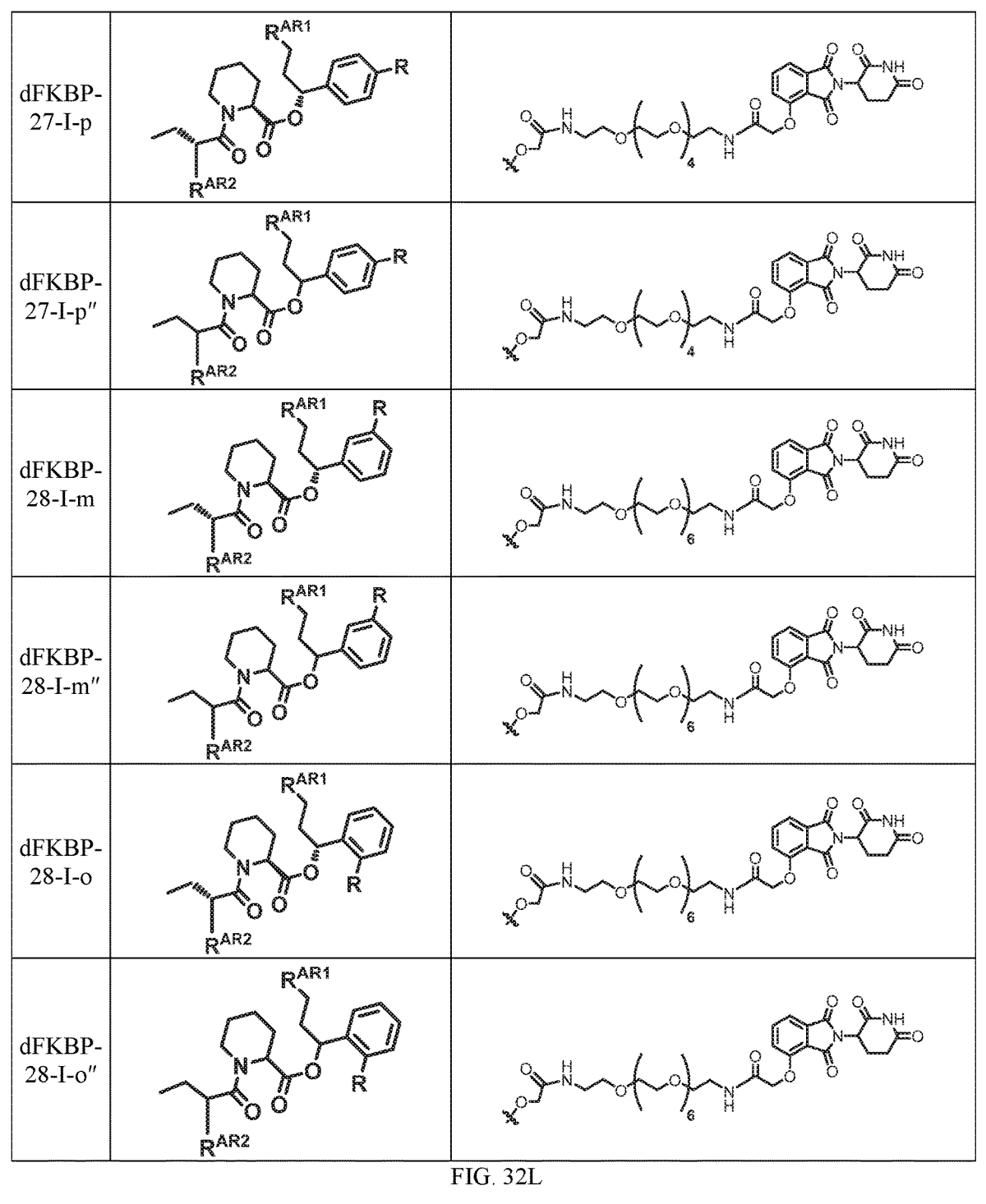
Figure 32U:
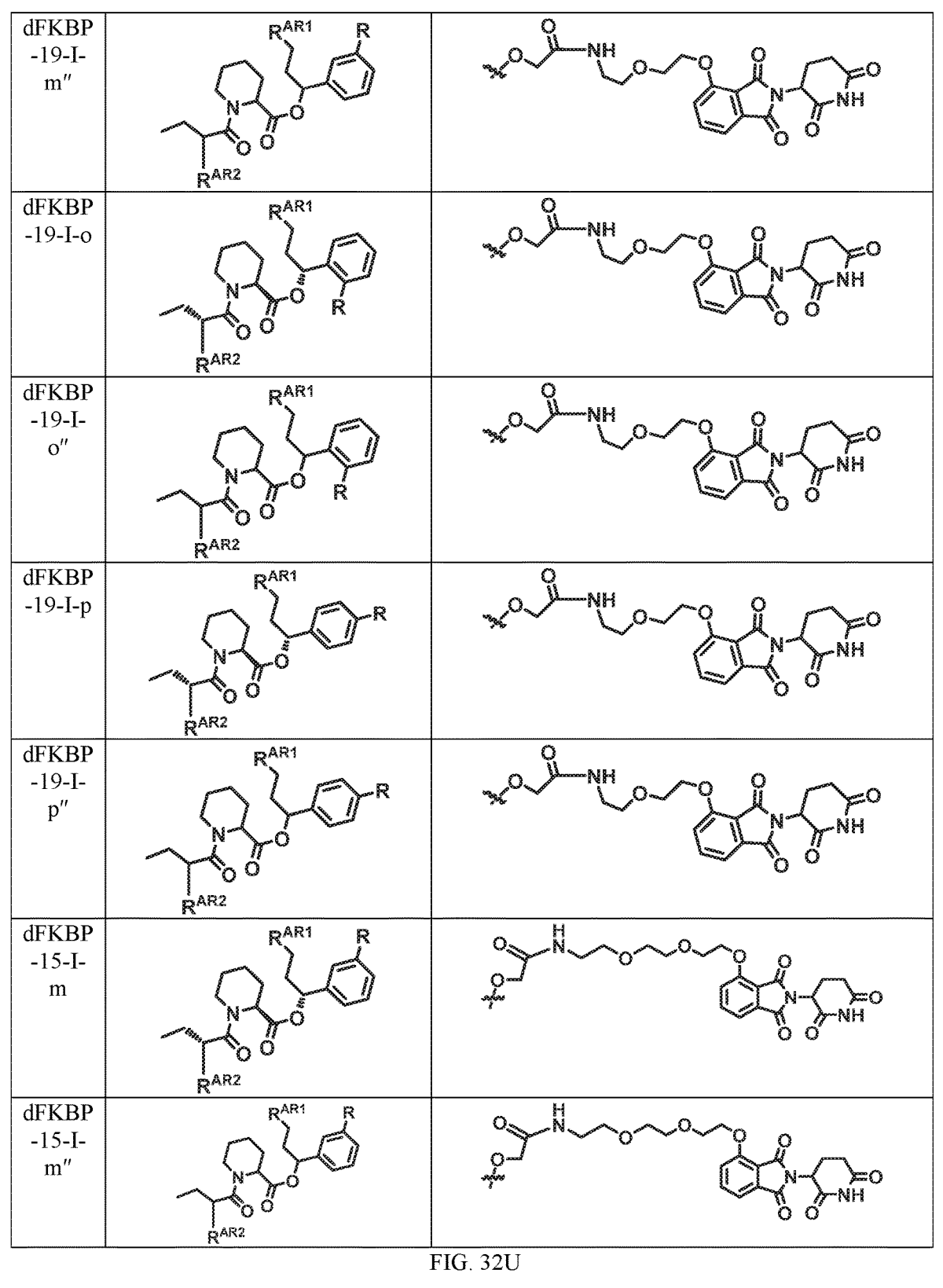
Figure 32W:
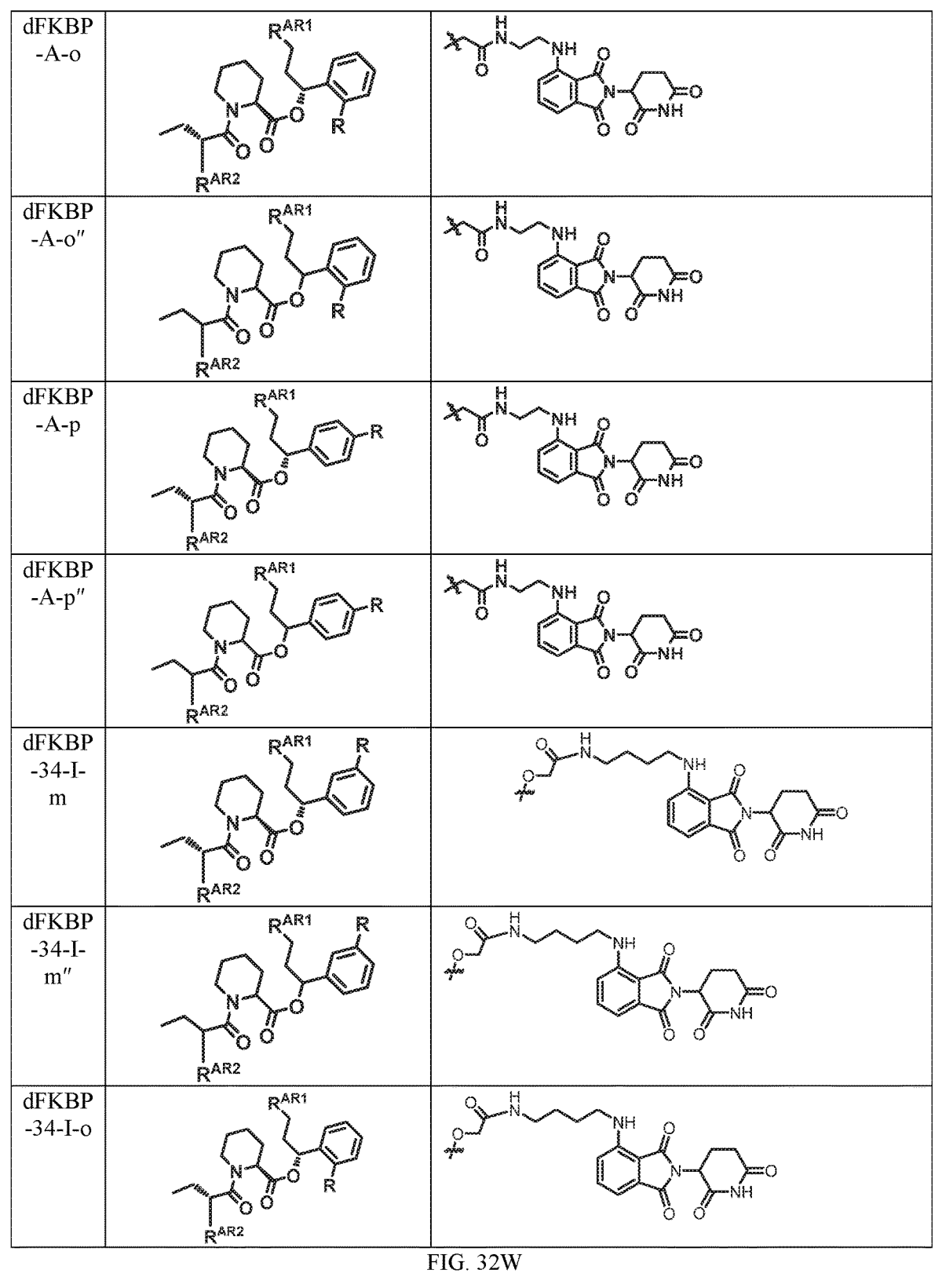
Figure 32Y:
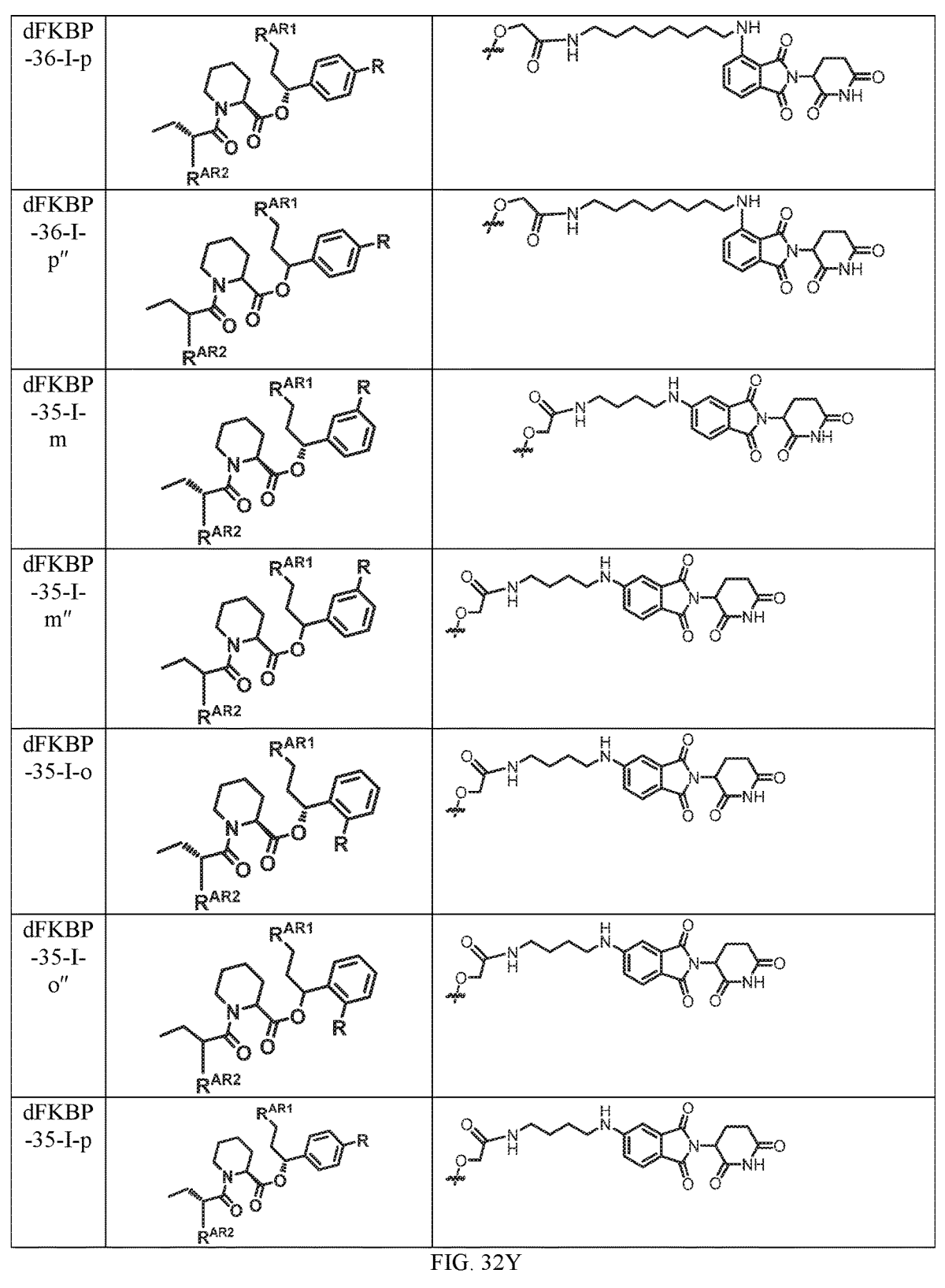

FIG. 32A, FIG. 32B, FIG. 32C, FIG. 32D, FIG. 32E, FIG. 32F, FIG. 32G, FIG. 32H, FIG. 32I, FIG. 32J, FIG. 32K, FIG. 32L, FIG. 32M, FIG. 32N, FIG. 32O, FIG. 32P, FIG. 32Q, FIG. 32R, FIG. 32S, FIG. 32T, FIG. 32U, FIG. 32V, FIG. 32W, FIG. 32X, FIG. 32Y, FIG. 32Z, FIG. 32AA, FIG. 32BB, FIG. 32CC, FIG. 32DD, and FIG. 32EE provide specific heterobifunctional compounds for use in the present invention, wherein $R^{AR1}$ and $R^{AR2}$ are described herein.

DETAILED DESCRIPTION OF THE INVENTION

Figure 1:
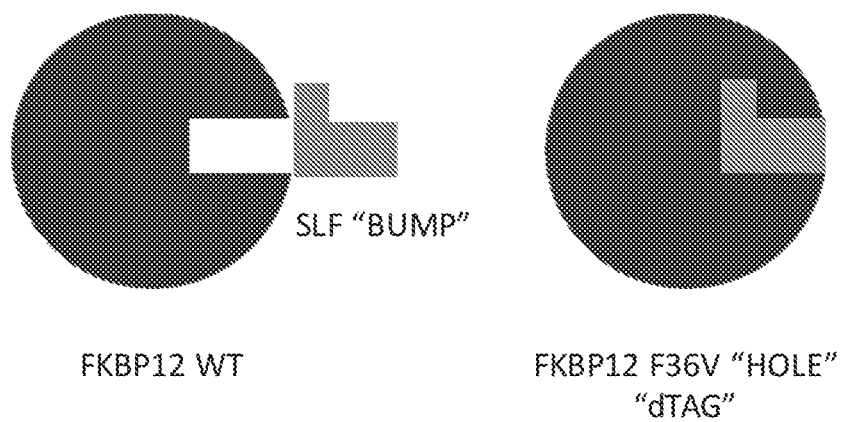
FIG. 1 is a schematic representing a "bump-hole" approach for selective degradation of a dTAG fusion protein. For example, the dTAG fusion can be a version of the FK506- and Rapamycin-binding protein FKBP12 engineered with a cavity forming "hole" via an amino acid mutation (F36V). This mutant FKBP12 ("bumped" FKBP, aka FKBP* or FKBP12* (SEQ. ID. NO.: 2)) can then be selectively targeted by a heterobifunctional compound possessing a synthetic "bump" in the FKBP12 binding domain, a linker, and a cereblon targeting domain. This heterobifunctional compound does not target native FKBP12 and thus offers selectivity against wildtype variants of the tag naturally present in human cells.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Here, we describe a method that takes advantage of both gene and protein disruption to provide a highly selective and reversible method for promoting protein degradation. This methodology is of value for precise, temporal, small-molecule controlled target validation and the exploration of cellular and in vivo effects of protein of interest degradation.

In this method, a region of the target gene of interest is targeted by a guide RNA and Cas9 in order to insert (knock-in) an expression cassette for dTAG present in a homologous recombination (HR) targeting vector. The HR targeting vector contains homology arms at the 5' and 3' end of the expression cassette homologous to the genomic DNA surrounding the targeting gene of interest locus. By fusing dTAG in frame with the target gene of interest, the resulting fusion protein upon expression will be made susceptible to proteasome mediated degradation upon treatment with a bioinert small molecule heterobifunctional compound.

Genome editing in mammalian cells offers much potential for the treatment and correction of human disease. By using short single-guide RNAs (sgRNAs) the Cas9 endonuclease can be directed to genomic positions of interest whereupon it induces DNA double strand breaks. These breaks are repaired by non-homologous end joining, which can be leveraged to produce insertions or deletions (indels) that inactivate genes. In vivo genome editing can be accomplished with CRISPR/Cas9 delivery by adeno-associated virus (AAV-), lentivirus-, particle-, hydrodynamic injection- or electroporation-mediated methods, or combinations thereof (see, for example, Kumar et al., *Hum. Gene Ther.* 12, (2001):1893-1905; Wu et al., *Mol. Ther.* 18, (2010):80-86; Ran et al., Nature 520, (2015): 186-191; Swiech et al., *Nat. Biotechnol.* 33, (2015):102-105; Zuris et al., *Nat. Biotechnol.* 33, (2015):73-80; Kauffman et al., *Nano. Lett.* 15, (2015):7300-7306; Ding et al., *Circ. Res.* 115, (2014):488-492; Maresch et al., *Nat. Commun.* 7, (2016):10770; Khorsandi et al., *Cancer Gene Ther.* 15, (2008):225-230; Yin et al., *Nat. Rev. Genet.* 15, (2014):541-555; Yin et al., *Nat. Biotechnol.* 34, (2016):328-333; and Xue et al., *Nature* 514, (2014):380-384, incorporated herein by reference) and somatic genome editing has been applied to mouse organs such as the lung, liver, brain, and pancreas (see, for example, Xue et al., Nature 514, (2014):380-384; Sanchez-Rivera et al., *Nature* 516, (2014):428-431; Platt et al., Cell 159, (2014):440-455; Yin et al., *Nat. Biotechnol.* 32, (2014):551-553; Zuckermann et al., *Nat. Commun.* 6, (2015):7391; Chiou et al., *Genes Dev.* 29, (2015):1576-1585; and Mazur et al., *Nat. Med.* 21, (2015):1163-1171, incorporated herein by reference). However, the long-term implications of permanent genome modification are unknown and concerns exist over the imperfect precision of genome editing and the impact of direct correction in adults where biological compensation mechanisms may exist (see, for example, Fu et al., Nat. Biotechnol. 31(9), (2013):822-826, and Cho et al., Genome Res. 24, (2014):132-141, incorporated herein by reference).

Here we describe a strategy for widespread therapeutic use that is based on in vivo genome engineering to produce knock-in fusion proteins that are produced from the endogenous locus and are readily degraded in a ligand-dependent, reversible, and dose-responsive, fashion. The fusion protein contains a dTAG that is targeted by a bi- or polyvalent heterobifunctional compound. The heterobifunctional compound has the ability to bind the dTAG and recruit an E3 ligase e.g. the cereblon-containing CRL4A E3 ubiquitin ligase complex. This recruitment induces ubiquitination of the fusion protein (on either the dTAG domain or on the cognate protein) and subsequent degradation via the UPP. Through this approach a protein of interest can be targeted for rapid ubiquitin mediated degradation with high specificity and high specificity without requiring the discovery of a de novo ligand for the protein of interest. In light of the combined use of a small molecule and genome engineering for in vivo use.

A variety of dTAGs can be used, including, but not limited to, bromodomains e.g. the first bromodomain of BRD4; hormone receptors e.g. ER, AR, RXR; FKBP12; DHFR, esp. bacterial DHFR, and other commonly used protein fusion tags that can be bound by a ligand that can be converted to a heterobifunctional compound. In some cases, there will be an advantage to using a dTAG that leverages a "bump-hole" strategy conceptually related to that developed to selectively target the ATP binding site of protein kinases. In such a case, the dTAG fusion is a version of the FK506- and Rapamycin-binding protein FKBP12 engineered with a cavity forming "hole" via an amino acid mutation (F36V). This mutant FKBP12 ("bumped" FKBP, aka FKBP* (SEQ. ID. NO.: 2) is then targeted by a heterobifunctional compound (or similar molecule) possessing a synthetic "bump" in the FKBP12 binding domain, a linker, and a cereblon targeting domain (e.g. an IMID derivative). This molecule does not target native FKBP12 and thus offers selectivity of the heterobifunctional compound against wildtype variants of the tag naturally present in human cells. An illustration representing the exemplified "bump-hole" strategy is provided for in FIG. 1.

The invention described herein provides a mechanism to control the degradation of endogenous proteins of relevance to disease by combining genome engineering with small molecule activation/modulation of degradation. Applications of this technology include, but are not limited to 1) targeted degradation of proteins where pathology is a function of gain of function mutation(s), 2) targeted degradation of proteins where pathology is a function of amplification or increased expression, 3) targeted degradation of proteins that are manifestations of monogenetic disease, 4) targeted degradation of proteins where genetic predisposition manifests over longer periods and often after alternative biological compensatory mechanisms are no longer adequate, e.g. hypercholesterolemia, proteinopathies.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide," and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid) or a macromolecule and a small molecule (e.g. between a protein and a drug). Not all components of a binding interaction need be sequence-specific (e.g., contacts with phosphate residues in a DNA backbone), as long as the interaction as a whole is sequence-specific.

"Recombination" refers to a process of exchange of genetic information between two polynucleotides. For the purposes of this disclosure, "homologous recombination" (HR) refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and leads to the transfer of genetic information from the donor to the target.

One or more targeted nucleases as described herein create a double-stranded break in the target sequence (e.g., cellular chromatin) at a predetermined site, and a "donor" polynucleotide, encoding a dTAG, having homology to the nucleotide sequence in the region of the break, can be introduced into the cell. The presence of the double-stranded break has been shown to facilitate integration of the donor sequence. The donor sequence may be physically integrated, resulting in the introduction of all or part of the nucleotide sequence as in the donor into the cellular chromatin. Thus, a first sequence in cellular chromatin can be altered and converted into a sequence present in a donor polynucleotide.

In certain methods for targeted recombination and/or replacement and/or alteration of a sequence in a region of interest in cellular chromatin, a chromosomal sequence is altered by homologous recombination with an exogenous "donor" nucleotide sequence encoding a dTAG. Such homologous recombination is stimulated by the presence of a double-stranded break in cellular chromatin, if sequences homologous to the region of the break are present.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence, i.e., the nucleic acid sequence encoding a dTAG, in the region of interest. Thus portions of the donor sequence that are homologous to sequences in the region of interest exhibit between about 80 to 99% (or any integer there between) sequence identity to the genomic sequence that is replaced. In other embodiments, the homology between the donor and genomic sequence is higher than 99%, for example if only 1 nucleotide differs as between donor and genomic sequences of over 100 contiguous base pairs. A non-homologous portion of the donor sequence contains nucleic sequences not present in the region of interest, e.g., a sequence encoding a dTAG, such that new sequences are introduced into the region of interest. In these instances, the non-homologous sequence is generally flanked by sequences of 50-1,000 base pairs (or any integral value there between) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

An "exogenous" molecule is a molecule that is not normally present in a cell, for example, certain dTAGs but can be introduced into a cell by one or more genetic, biochemical or other methods. An exogenous molecule can comprise, for example, a synthetic endogenous protein-dTAG hybrid.

An "endogenous" protein is one that is normally present in a particular cell at a particular developmental stage under particular environmental conditions. For example, an endogenous protein, for example, may be a transcription factor or enzyme or any other type of naturally expressed protein.

A "fusion" or "hybrid" protein is a protein in which two or more polypeptides are linked, preferably covalently. Examples of fusion proteins, for example, include a fusion between an endogenous protein and a dTAG.

A "gene," for the purposes of the present disclosure, includes a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of protein expression refers to a change in the activity of a protein. Modulation of expression can include, but is not limited to, reduced protein activity or increased protein activity. For example, as contemplated herein, exposing an endogenous protein-dTAG hybrid to a heterobifunctional compound, resulting in the degradation of the endogenous protein-dTAG hybrid, may modulate the activity of the endogenous protein. Thus, protein inactivation may be partial or complete.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, rabbits and other animals. Accordingly, the term "subject" or "patient" as used herein means any patient or subject (e.g., mammalian) having a disorder.

A. Heterobifunctional Compound Targeting Protein (dTAGs)

The present invention provides method for making knock-in fusion proteins that are produced from the endogenous locus and are readily degraded in a ligand-dependent, reversible, and dose-responsive, fashion. Specifically, a nucleic acid encoding a dTAG is inserted in frame with a target gene of interest, wherein upon expression, the resulting fusion protein contains a dTAG that is targeted by a bi- or polyvalent heterobifunctional compound. The heterobifunctional compound has the ability to bind the target protein and recruit an E3 ligase e.g. the cereblon-containing CRL4A E3 ubiquitin ligase complex. This recruitment induces ubiquitination of the fusion protein (on either the dTAG or on the cognate protein) and subsequent degradation via the ubiquitin proteasome pathway (UPP). Through this approach a protein of interest can be targeted for rapid ubiquitin mediated degradation with high specificity without requiring the discovery of a de novo ligand for the POI.

The heterobifunctional compound targeting protein of the synthetic gene is any amino acid sequence to which a heterobifunctional compound can be bound, leading to the ubiquitination and degradation of the expressed endogenous protein-dTAG hybrid protein when in contact with the heterobifunctional compound. Preferably, the dTAG should not interfere with the function of the endogenously expressed protein. In one embodiment, the dTAG is a non-endogenous peptide, leading to heterobifunctional compound selectivity and allowing for the avoidance of off target effects upon administration of the heterobifunctional compound. In one embodiment, the dTAG is an amino acid sequence derived from an endogenous protein or fragment thereof which has been modified so that the heterobifunctional compound binds only to the modified amino acid sequence and not the endogenously expressed protein. In one embodiment, the dTAG is an endogenously expressed protein or a fragment of an endogenously expressed protein. Any amino acid sequence domain that can be bound by a ligand for use in a heterobifunctional compound can be used as a dTAG as contemplated herewith. In certain embodiments, it is preferred that the smallest amino acid sequence capable of being bound by a particular heterobifunctional compound be utilized as a dTAG.

In particular embodiments, the dTAG for use in the present invention include, but are not limited to, an amino acid sequence derived from an endogenously expressed protein such as FK506 binding protein-12 (FKBP12), bromodomain-containing protein 4 (BRD4), CREB binding protein (CREBBP), and transcriptional activator BRG1 (SMARCA4), or a variant thereof. As contemplated herein, "variant" means any variant comprising a substitution, deletion, or addition of one or a few to plural amino acids, provided that the variant substantially retains the same function as the original sequence, which in this case is providing a ligand for a heterobifunctional compound. In other embodiments, a dTAG for use in the present invention may include, for example, a hormone receptor e.g. estrogen-receptor protein, androgen receptor protein, retinoid x receptor (RXR) protein, and dihydrofolate reductase (DHFR), including bacterial DHFR, bacterial dehydrogenase, and variants.

Some embodiments of dTAGs can be, but are not limited to, those derived from Hsp90 inhibitors, kinase inhibitors, MDM2 inhibitors, compounds targeting Human BET Bromodomain-containing proteins, compounds targeting cytosolic signaling protein FKBP12, HDAC inhibitors, human lysine methyltransferase inhibitors, angiogenesis inhibitors, immunosuppressive compounds, and compounds targeting the aryl hydrocarbon receptor (AHR).

In certain embodiments, the dTAG is derived from, a kinase, a BET bromodomain-containing protein, a cytosolic signaling protein (e.g., FKBP12), a nuclear protein, a histone deacetylase, a lysine methyltransferase, a protein regulating angiogenesis, a protein regulating immune response, an aryl hydrocarbon receptor (AHR), an estrogen receptor, an androgen receptor, a glucocorticoid receptor, or a transcription factor (e.g., SMARCA4, SMARCA2, TRIM24).

In certain embodiments, the dTAG is derived from a kinase, for example, but not limited to, a tyrosine kinase (e.g., AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, IRAK4, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDGFRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES 1, or ZAP70), a serine/threonine kinase (e.g., casein kinase 2, protein kinase A, protein kinase B, protein kinase C, Raf kinases, CaM kinases, AKT 1, AKT2, AKT3, ALK1, ALK2, ALK3, ALK4, Aurora A, Aurora B, Aurora C, CHK1, CHK2, CLK1, CLK2, CLK3, DAPK1, DAPK2, DAPK3, DMPK, ERK1, ERK2, ERK5, GCK, GSK3, HIPK, KHS1, LKB1, LOK, MAPKAPK2, MAPKAPK, MNK1, MSSK1, MST1, MST2, MST4, NDR, NEK2, NEK3, NEK6, NEK7, NEK9, NEK11, PAK1, PAK2, PAK3, PAK4, PAK5, PAK6, PIM1, PIM2, PLK1, RIP2, RIP5, RSK1, RSK2, SGK2, SGK3, SIK1, STK33, TAO1, TAO2, TGF-beta, TLK2, TSSK1, TSSK2, ULK1, or ULK2), a cyclin dependent kinase (e.g., Cdk1-Cdk11), and a leucine-rich repeat kinase (e.g., LRRK2).

In certain embodiments, the dTAG is derived from a BET bromodomain-containing protein, for example, but not limited to, ASH1L, ATAD2, BAZ1A, BAZ1B, BAZ2A, BAZ2B, BRD1, BRD2, BRD3, BRD4, BRD5, BRD6, BRD7, BRD8, BRD9, BRD10, BRDT, BRPF1, BRPF3, BRWD3, CECR2, CREBBP, EP300, FALZ, GCN5L2, KIAA1240, LOC93349, MLL, PB1, PCAF, PHIP, PRKCBP1, SMARCA2, SMARCA4, SP100, SP110, SP140, TAF1, TAF1L, TIFla, TRIM28, TRIM33, TRIM66, WDR9, ZMYND11, and MLL4. In certain embodiments, a BET bromodomain-containing protein is BRD4.

In certain embodiments, the dTAG is derived from, but not limited to, 7,8-dihydro-8-oxoguanin triphosphatase, AFAD, Arachidonate 5-lipoxygenase activating protein, apolipoprotein, baculoviral IAP repeat-containing protein 2, Bcl-2, Bcl-xL, E3 ligase XIAP, fatty acid binding protein from adipocytes 4 (FABP4), GTPase k-RAS, HDAC6, hematopoietic prostaglandin D synthase, lactoglutathione lyase, Mcl-1, PA2GA, peptidyl-prolyl cis-trans isomerase NIMA-interacting 1, poly-ADP-ribose polymerase 14, poly-ADP-ribose polymerase 15, prosaposin, prostaglandin E synthase, retinal rod rhodopsin-sensitive cGMP 3',5-cyclic phosphodiesterase subunit delta, S100-A7, Src, Sumo-conjugating enzyme UBC9, superoxide dismutase, tankyrase 1, or tankyrase 2.

In certain embodiments, the dTAG is derived from a nuclear protein including, but not limited to, BRD2, BRD3, BRD4, Antennapedia Homeodomain Protein, BRCA1, BRCA2, CCAAT-Enhanced-Binding Proteins, histones, Polycomb-group proteins, High Mobility Group Proteins, Telomere Binding Proteins, FANCA, FANCD2, FANCE, FANCF, hepatocyte nuclear factors, Mad2, NF-kappa B, Nuclear Receptor Coactivators, CREB-binding protein, p55, p107, p130, Rb proteins, p53, c-fos, c-jun, c-mdm2, c-myc, and c-rel.

In a particular embodiment, the dTAG has an amino acid sequence derived from BRD2 ((Universal Protein Resource Knowledge Base (UniProtKB)-P25440 (BRD2_HUMAN) incorporated herein by reference), BRD3 (UniProtKB-Q15059 (BRD3_HUMAN) incorporated herein by reference), BRD4 (UniProtKB-O60885 (BRD4_HUMAN) incorporated herein by reference), or BRDT (UniProtKB-Q58F21 (BRDT_HUMAN) incorporated herein by reference) (see Baud et al., "A bump-and-hole approach to engineer controlled selectivity of BET bromodomains chemical probes", *Science* 346(6209) (2014):638-641; and Baud et al., "New Synthetic Routes to Triazolo-benzodiazepine Analogues: Expanding the Scope of the Bump-and-Hole Approach for Selective Bromo and Extra-Terminal (BET) Bromodomain Inhibition", *JMC* 59 (2016): 1492-1500, both incorporated herein by reference). In certain embodiments, the dTAG is a modified or mutant BRD2, BRD3, BRD4, or BRDT protein (see Baud et al., "A bump-and-hole approach to engineer controlled selectivity of BET bromodomains chemical probes", *Science* 346(6209) (2014):638-641; and Baud et al., "New Synthetic Routes to Triazolo-benzodiazepine Analogues: Expanding the Scope of the Bump-and-Hole Approach for Selective Bromo and Extra-Terminal (BET) Bromodomain Inhibition", *JMC* 59 (2016):1492-1500, both incorporated herein by reference). In certain embodiments, the one or more mutations of BRD2 include a mutation of the Tryptophan (W) at amino acid position 97, a mutation of the Valine (V) at amino acid position 103, a mutation of the Leucine (L) at amino acid position 110, a mutation of the W at amino acid position 370, a mutation of the V at amino acid position 376, or a mutation of the L at amino acid position 381. In certain embodiments, the one or more mutations of BRD3 include a mutation of the W at amino acid position 57, a mutation of the V at amino acid position 63, a mutation of the L at amino acid position 70, a mutation of the W at amino acid position 332, a mutation of the V at amino acid position 338, or a mutation of the L at amino acid position 345. In certain embodiments, the one or more mutations of BRD4 include a mutation of the W at amino acid position 81, a mutation of the V at amino acid position 87, a mutation of the L at amino acid position 94, a mutation of the W at amino acid position 374, a mutation of the V at amino acid position 380, or a mutation of the L at amino acid position 387. In certain embodiments, the one or more mutations of BRDT include a mutation of the W at amino acid position 50, a mutation of the V at amino acid position 56, a mutation of the L at amino acid position 63, a mutation of the W at amino acid position 293, a mutation of the V at amino acid position 299, or a mutation of the L at amino acid position 306.

In certain embodiments, the dTAG is derived from a kinase inhibitor, a BET bromodomain-containing protein inhibitor, cytosolic signaling protein FKBP12 ligand, an HDAC inhibitor, a lysine methyltransferase inhibitor, an angiogenesis inhibitor, an immunosuppressive compound, and an aryl hydrocarbon receptor (AHR) inhibitor.

In a particular embodiment, the dTAG is derived from cytosolic signaling protein FKBP12. In certain embodiments, the dTAG is a modified or mutant cytosolic signaling protein FKBP12. In certain embodiments, the modified or mutant cytosolic signaling protein FKBP12 contains one or more mutations that create an enlarged binding pocket for FKBP12 ligands. In certain embodiments, the one or more mutations include a mutation of the phenylalanine (F) at amino acid position 36 to valine (V) (F36V) (as counted without the methionine start codon) (referred to interchangeably herein as FKBP* or FKBP12*) (see Clackson et al., "Redesigning an FKBP-ligand interface to generate chemical dimerizers with novel specificity", PNAS 95 (1998): 10437-10442) (incorporated herein by reference).

In a particular embodiment, the dTAG has an amino acid sequence derived from an FKBP12 protein (UniProtKB-P62942 (FKB1A_HUMAN) incorporated herein by reference), or variant thereof. In one embodiment, the dTAG is derived from the amino acid sequence: (SEQ. ID. NO.: 1) GVQVETISP GDGRTFPKRG QTCVVHYTGM LEDGKKFDSS RDRNKPFKFM LGKQEVIRGW EEGVAQMSVG QRAKLTISPD YAYGATGHPG IIPPHATLVF DVELLKLE.

In one embodiment, the dTAG is a FKBP12 derived amino acid sequence with a mutation of the phenylalanine (F) at amino acid position 36 (as counted without the methionine) to valine (V) (F36V) (FKBP*) having the amino acid sequence: (SEQ. ID. NO.: 2) GVQVETISPGDGRTFPKRGQTCVVHYTGMLEDGKKFDSSR-DRNKPFKFMLGKQEVIRG WEEGVAQMSVGQRAK-LTISPDYAYGATGHPGIIPPHATLVFDVELLKLE.

In one embodiment, the dTAG has an amino acid sequence derived from a BRD4 protein (UniProtKB-O60885 (BRD4_HUMAN) incorporated herein by reference), or variant thereof. In one embodiment, the dTAG is derived from the amino acid sequence:

```
                                    (SEQ. ID. NO.: 3)
MSAESGPGTRLRNLPVMGDGLETSQMSTTQAQAQPQPANAASTNPPPPET

SNPNKPKRQTNQLQYLLRVVLKTLWKHQFAWPFQQPVDAVKLNLPDYYKI

IKTPMDMGTIKKRLENNYYWNAQECIQDFNTMFTNCYIYNKPGDDIVLMA

EALEKLFLQKINELPTEETEIMIVQAKGRGRGRKETGTAKPGVSTVPNTT

QASTPPQTQTPQPNPPPVQATPFIPFPAVTPDLIVQTPVMTVVPPQPLQT

PPPVPPQPQPPPAPAPQPVQSHPPIIAATPQPVKTKKGVKRKADTTTPTT

IDPIHEPPSLPPEPKTTKLGQRRESSRPVKPPKKDVPDSQQHPAPEKSSK

VSEQLKCCSGILKEMFAKKHAAYAWPFYKPVDVEALGLHDYCDIIKHPMD

MSTIKSKLEAREYRDAQEFGADVRLMFSNCYKYNPPDHEVVAMARKLQDV

FEMRFAKMPDEPEEPVVAVSSPAVPPPTKVVAPPSSSDSSSDSSSDSDSS

TDDSEEERAQRLAELQEQLKAVHEQLAALSQPQQNKPKKKEKDKKEKKKE
```

```
KHKRKEEVEENKKSKAKEPPPKKTKKNNSSNSNVSKKEPAPMKSKPPPTY

ESEEEDKCKPMSYEEKRQLSLDINKLPGEKLGRVVHIIQSREPSLKNSNP

DEIEIDFETLKPSTLRELERYVTSCLRKKRKPQAEKVDVIAGSSKMKGFS

SSESESSSESSSSDSEDSETEMAPKSKKKGHPGREQKKHHHHHHQQMQQA

PAPVPQQPPPPPQQPPPPPPPQQQQQPPPPPPPSMPQQAAPAMKSSPPP

FIATQWVLEPQLPGSVFDPIGHFTQPILHLPQPELPPHLPQPPEHSTPPH

LNQHAVVSPPALHNALPQQPSRPSNRAAALPPKPARPPAVSPALTQTPLL

PQPPMAQPPQVLLEDEEPPAPPLTSMQMQLYLQQLQKVQPPTPLLPSVKV

QSQPPPPLPPPPHPSVQQQLQQQPPPPPPPQPQPPPQQQHQPPPRPVHLQ

PMQFSTHIQQPPPPQGQQPPHPPPGQQPPPPQPAKPQQVIQHHHSPRHHK

SDPYSTGHLREAPSPLMIHSPQMSQFQSLTHQSPPQQNVQPKKQELRAAS

VVQPQPLVVVKEEKIHSPIIRSEPFSPSLRPEPPKHPESIKAPVHLPQRP

EMKPVDVGRPVIRPPEQNAPPPGAPDKDKQKQEPKTPVAPKKDLKIKNMG

SWASLVQKHPTTPSSTAKSSSDSFEQFRRAAREKEEREKALKAQAEHAEK

EKERLRQERMRSREDEDALEQARRAHEEARRRQEQQQQQRQEQQQQQQQQ

AAAVAAAATPQAQSSQPQSMLDQQRELARKREQERRRREAMAATIDMNFQ

SDLLSIFEENLF.
```

In one embodiment, the dTAG is derived from amino acid 75-147 of SEQ. ID. NO.: 3.

In one embodiment, the dTAG has an amino acid sequence derived from a ASH1L protein (UniProtKB-Q9NR48 (ASH1L_HUMAN) incorporated herein by reference), or variant thereof. In one embodiment, the dTAG is derived from amino acid 2463-2533 of Q9NR48.

In one embodiment, the dTAG has an amino acid sequence derived from a ATAD2 protein (UniProtKB-Q6PL18 (ATAD2_HUMAN) incorporated herein by reference), or variant thereof. In one embodiment, the dTAG is derived from amino acid 1001-1071 of Q6PL18.

In one embodiment, the dTAG has an amino acid sequence derived from a BAZ1A protein (UniProtKB-Q9NRL2 (BAZ1A_HUMAN) incorporated herein by reference), or variant thereof. In one embodiment, the dTAG is derived from amino acid 1446-1516 of Q9NRL2.

In one embodiment, the dTAG has an amino acid sequence derived from a BAZ1B protein (UniProtKB-Q9UIG0 (BAZ1B_HUMAN) incorporated herein by reference), or variant thereof. In one embodiment, the dTAG is derived from amino acid 1356-1426 of Q9UIG0.

In one embodiment, the dTAG has an amino acid sequence derived from a BAZ2A protein (UniProtKB-Q9UIF9 (BAZ2A_HUMAN) incorporated herein by reference), or variant thereof. In one embodiment, the dTAG is derived from amino acid 1810-1880 of Q9UIF9.

In one embodiment, the dTAG has an amino acid sequence derived from a BAZ2B protein (UniProtKB-Q9UIF8 (BAZ2B_HUMAN) incorporated herein by reference), or variant thereof. In one embodiment, the dTAG is derived from amino acid 2077-2147 of Q9UIF8.

In one embodiment, the dTAG has an amino acid sequence derived from a BRD1 protein (UniProtKB-O95696 (BRD1_HUMAN) incorporated herein by reference), or variant thereof. In one embodiment, the dTAG is derived from amino acid 579-649 of O95696.

In one embodiment, the dTAG has an amino acid sequence derived from a BRD2 protein (UniProtKB-P25440 (BRD2_HUMAN) incorporated herein by reference), or variant thereof. In one embodiment, the dTAG is derived from the amino acid sequence:

```
                                       (SEQ. ID. NO.: 13)
MLQNVTPHNKLPGEGNAGLLGLGPEAAAPGKRIRKPSLLYEGFESPTMAS

VPALQLTPANPPPPEVSNPKKPGRVTNQLQYLHKVVMKALWKHQFAWPFR

QPVDAVKLGLPDYHKIIKQPMDMGTIKRRLENNYYWAASECMQDFNTMTT

NCYIYNKPTDDIVLMAQTLEKIFLQKVASMPQEEQELVVTIPKNSHKKGA

KLAALQGSVTSAHQVPAVSSVSHTALYTPPPEIPTTVLNIPHPSVISSPL

LKSLHSAGPPLLAVTAAPPAQPLAKKKGVKRKADTTTPTPTAILAPGSPA

SPPGSLEPKAARLPPMRRESGRPIKPPRKDLPDSQQQHQSSKKGKLSEQL

KHCNGILKELLSKKHAAYAWPFYKPVDASALGLHDYHDIIKHPMDLSTVK

RKMENRDYRDAQEFAADVRLMFSNCYKYNPPDHDVVAMARKLQDVFEFRY

AKMPDEPLEPGPLPVSTAMPPGLAKSSSESSSEESSSESSSEEEEEEDEE

DEEEEESESSDSEEERAHRLAELQEQLRAVEMQLAALSQGPISKPKRKRE

KKEKKKKRKAEKHRGRAGADEDDKGPRAPRPPQPKKSKKASGSGGGSAAL

GPSGFGPSGGSGTKLPKKATKTAPPALPTGYDSEEEEESRPMSYDEKRQL

SLDINKLPGEKLGRVVHIIQAREPSLRDSNPEEIEIDFETLKPSTLRELE

RYVLSCLRKKPRKPYTIKKPVGKTKEELALEKKRELEKRLQDVSGQLNST

KKPPKKANEKTESSSAQQVAVSRLSASSSSSDSSSSSSSSSSSDTSDSDS

G.
```

In one embodiment, the dTAG is derived from amino acid 91-163 or 364-436 of SEQ. ID. NO.: 13.

In one embodiment, the dTAG has an amino acid sequence derived from a BRD3 protein (UniProtKB-Q15059 (BRD3_HUMAN) incorporated herein by reference), or variant thereof. In one embodiment, the dTAG is derived from the amino acid sequence:

```
                                       (SEQ. ID. NO.: 14)
MSTATTVAPAGIPATPGPVNPPPPEVSNPSKPGRKTNQLQYMQNVVVKTL

WKHQFAWPFYQPVDAIKLNLPDYHKIIKNPMDMGTIKKRLENNVSASECM

QDFNTMFTNCYIYNKPTDDIVLMAQALEKIFLQKVAQMPQEEVELLPPAP

KGKGRKPAAGAQSAGTQQVAAVSSVSPATPFQSVPPTVSQTPVIAATPVP

TITANVTSVPVPPAAAPPPPATPIVPVVPPTPPVVKKKGVKRKADTTTPT

TSAITASRSESPPPLSDPKQAKVVARRESGGRPIKPPKKDLEDGEVPQHA

GKKGKLSEHLRYCDSILREMLSKKHAAYAWPFYKPVDAEALELEIDYHDI

IKHPMDLSTVKRKMDGREYPDAQGFAADVRLMFSNCYKYNPPDHEVVAMA

RKLQDVFEMRFAKMPDEPVEAPALPAPAAPMVSKGAESSRSSEESSSDSG

SSDSEEERATRLAELQEQLKAVHEQLAALSQAPVNKPKKKKEKKEKEKKK

KDKEKEKEKHKVKAEEEKKAKVAPPAKQAQQKKAPAKKANSTTTAGRQLK

KGGKQASASYDSEEEEEGLPMSYDEKRQLSLDINRLPGEKLGRVVHIIQS

REPSLRDSNPDEIEIDFETLKPTTLRELERYVKSCLQKKQRKPFSASGKK

QAAKSKEELAQEKKKELEKRLQDVSGQLSSSKKPARKEKPGSAPSGGPSR

LSSSSSSESGSSSSSGSSSDSSDSE.
```

In one embodiment, the dTAG is derived from amino acid 51-123 or 326-398 of SEQ. ID. NO.: 14.

In one embodiment, the dTAG has an amino acid sequence derived from a BRD7 protein (UniProtKB-Q9NPI1 (BRD7_HUMAN) incorporated herein by reference), or variant thereof. In one embodiment, the dTAG is derived from amino acid 148-218 of Q9NPI1.

In one embodiment, the dTAG has an amino acid sequence derived from a BRD8 protein (UniProtKB-Q9HOE9 (BRD8_HUMAN) incorporated herein by reference), or variant thereof. In one embodiment, the dTAG is derived from amino acid 724-794 or 1120-1190 of Q9HOE9.

In one embodiment, the dTAG has an amino acid sequence derived from a BRD9 protein (UniProtKB-Q9H8M2 (BRD9_HUMAN) incorporated herein by reference), or variant thereof. In one embodiment, the dTAG is derived from amino acid 153-223 of Q9H8M2.

In one embodiment, the dTAG has an amino acid sequence derived from a BRDT protein (UniProtKB-Q58F21 (BRDT_HUMAN) incorporated herein by reference), or variant thereof. In one embodiment, the dTAG is derived from the amino acid sequence:

(SEQ. ID. NO.: 15)
MSLPSRQTAIIVNPPPPEYINTKKNGRLTNQLQYLQKVVLKDLWKHSFSW

PFQRPVDAVKLQLPDYYTIIKNPMDLNTIKKRLENKYYAKASECIEDFNT

MFSNCYLYNKPGDDIVLMAQALEKLFMQKLSQMPQEEQVVGVKERIKKGT

QQNIAVSSAKEKSSPSATEKVFKQQEIPSVFPKTSISPLNVVQGASVNSS

SQTAAQVTKGVKRKADTTTPATSAVKASSEFSPTFTEKSVALPPIKENMP

KNVLPDSQQQYNVVKTVKVTEQLRHCSEILKEMLAKKHFSYAWPFYNPVD

VNALGLHNYYDVVKNPMDLGTIKEKMDNQEYKDAYKFAADVRLMFMNCYK

YNPPDHEVVTMARMLQDVFETHFSKIPIEPVESMPLCYIKTDITETTGRE

NTNEASSEGNSSDDSEDERVKRLAKLQEQLKAVHQQLQVLSQVPFRKLNK

KKEKSKKEKKKEKVNNSNENPRKMCEQMRLKEKSKRNQPKKRKQQFIGLK

SEDEDNAKPMNYDEKRQLSLNINKLPGDKLGRVVHIIQSREPSLSNSNPD

EIEIDFETLKASTLRELEKYVSACLRKRPLKPPAKKIMINISKEELHSQK

KQELEKRLLDVNNQLNSRKRQTKSDKTQPSKAVENVSRLSESSSSSSSSS

ESESSSSDLSSSDSSDSESEMFPKFTEVKPNDSPSKENVKKMKNECIPPE

GRTGVTQIGYCVQDTTSANTTLVHQTTPSHVMPPNHHQLAFNYQELEHLQ

TVKNISPLQILPPSGDSEQLSNGITVMHPSGDSDTTMLESECQAPVQKDI

KIKNADSWKSLGKPVKPSGVMKSSDELFNQFRKAAIEKEVKARTQELIRK

HLEQNTKELKASQENQRDLGNGLTVESFSNKIQNKCSGEEQKEHQQSSEA

QDKSKLWLLKDRDLARQKEQERRREAMVGTIDMTLQSDIMTMFENNFD.

In one embodiment, the dTAG is derived from amino acid 44-116 or 287-359 of SEQ. ID. NO.: 15.

In one embodiment, the dTAG has an amino acid sequence derived from a BRPF1 protein (UniProtKB-P55201 (BRPF1_HUMAN) incorporated herein by reference), or variant thereof. In one embodiment, the dTAG is derived from amino acid 645-715 of P55201.

In one embodiment, the dTAG has an amino acid sequence derived from a BRPF3 protein (UniProtKB-Q9ULD4 (BRPF3_HUMAN) incorporated herein by reference), or variant thereof. In one embodiment, the dTAG is derived from amino acid 606-676 of Q9ULD4.

In one embodiment, the dTAG has an amino acid sequence derived from a BRWD3 protein (UniProtKB-Q6RI45 (BRWD3_HUMAN) incorporated herein by reference), or variant thereof. In one embodiment, the dTAG is derived from amino acid 1158-1228 or 1317-1412 of Q6RI45.

In one embodiment, the dTAG has an amino acid sequence derived from a CECR2 protein (UniProtKB-Q9BXF3 (CECR2_HUMAN) incorporated herein by reference), or variant thereof. In one embodiment, the dTAG is derived from amino acid 451-521 of Q9BXF3.

In one embodiment, the dTAG has an amino acid sequence derived from a CREBBP protein (UniProtKB-Q92793 (CBP_HUMAN) incorporated herein by reference), or variant thereof. In one embodiment, the dTAG is derived from amino acid 1103-1175 of Q92793.

In one embodiment, the dTAG has an amino acid sequence derived from a EP300 protein (UniProtKB-Q09472 (EP300_HUMAN) incorporated herein by reference), or variant thereof. In one embodiment, the dTAG is derived from amino acid 1067-1139 of Q09472.

In one embodiment, the dTAG has an amino acid sequence derived from a FALZ protein (UniProtKB-Q12830 (BPTF_HUMAN) incorporated herein by reference), or variant thereof. In one embodiment, the dTAG is derived from amino acid 2944-3014 of Q12830.

In one embodiment, the dTAG has an amino acid sequence derived from a GCN5L2 protein (UniProtKB-Q92830 (KAT2A_HUMAN) incorporated herein by reference), or variant thereof. In one embodiment, the dTAG is derived from amino acid 745-815 of Q92830.

In one embodiment, the dTAG has an amino acid sequence derived from a KIAA1240 protein (UniProtKB-Q9ULI0 (ATD2B_HUMAN) incorporated herein by reference), or variant thereof. In one embodiment, the dTAG is derived from amino acid 975-1045 of Q9ULI0.

In one embodiment, the dTAG has an amino acid sequence derived from a LOC93349 protein (UniProtKB-Q13342 (SP140_HUMAN) incorporated herein by reference), or variant thereof. In one embodiment, the dTAG is derived from amino acid 796-829 of Q13342.

In one embodiment, the dTAG has an amino acid sequence derived from a MLL protein (UniProtKB-Q03164 (KMT2A_HUMAN) incorporated herein by reference), or variant thereof. In one embodiment, the dTAG is derived from amino acid 1703-1748 of Q03164.

In one embodiment, the dTAG has an amino acid sequence derived from a PB1 protein (UniProtKB-Q86U86 (PB_HUMAN) incorporated herein by reference), or variant thereof. In one embodiment, the dTAG is derived from amino acid 63-134, 200-270, 400-470, 538-608, 676-746, or 792-862 of Q86U86.

In one embodiment, the dTAG has an amino acid sequence derived from a PCAF protein (UniProtKB-Q92831 (KAT2B_HUMAN) incorporated herein by reference), or variant thereof. In one embodiment, the dTAG is derived from amino acid 740-810 of Q92831.

In one embodiment, the dTAG has an amino acid sequence derived from a PHIP protein (UniProtKB-Q8WWQ0 (PHIP_HUMAN) incorporated herein by reference), or variant thereof. In one embodiment, the dTAG is derived from amino acid 1176-1246 or 1333-1403 of Q8WWQ0.

In one embodiment, the dTAG has an amino acid sequence derived from a PRKCBP1 protein (UniProtKB-Q9ULU4 (PKCB1_HUMAN) incorporated herein by reference), or variant thereof. In one embodiment, the dTAG is derived from amino acid 165-235 of Q9ULU4.

In one embodiment, the dTAG has an amino acid sequence derived from a SMARCA2 protein (UniProtKB-P51531 (SMCA2_HUMAN) incorporated herein by reference), or variant thereof. In one embodiment, the dTAG is derived from amino acid 1419-1489 of P51531.

In one embodiment, the dTAG has an amino acid sequence derived from a SMARCA4 protein (UniProtKB-P51532 (SMCA4_HUMAN) incorporated herein by reference), or variant thereof. In one embodiment, the dTAG is derived from amino acid 1477-1547 of P51532.

In one embodiment, the dTAG has an amino acid sequence derived from a SP100 protein (UniProtKB-P23497 (SP100_HUMAN) incorporated herein by reference), or variant thereof. In one embodiment, the dTAG is derived from amino acid 761-876 of P23497.

In one embodiment, the dTAG has an amino acid sequence derived from a SP110 protein (UniProtKB-Q9HB58 (SP110_HUMAN) incorporated herein by reference), or variant thereof. In one embodiment, the dTAG is derived from amino acid 581-676 of Q9HB58.

In one embodiment, the dTAG has an amino acid sequence derived from a SP140 protein (UniProtKB-Q13342 (SP140_HUMAN) incorporated herein by reference), or variant thereof. In one embodiment, the dTAG is derived from amino acid 796-829 of Q13342.

In one embodiment, the dTAG has an amino acid sequence derived from a TAF1 protein (UniProtKB-P21675 (TAF1_HUMAN) incorporated herein by reference), or variant thereof. In one embodiment, the dTAG is derived from amino acid 1397-1467 or 1520-1590 of P21675.

In one embodiment, the dTAG has an amino acid sequence derived from a TAF1L protein (UniProtKB-Q8IZX4 (TAF1L_HUMAN) incorporated herein by reference), or variant thereof. In one embodiment, the dTAG is derived from amino acid 1416-1486 or 1539-1609 of Q8IZX4.

In one embodiment, the dTAG has an amino acid sequence derived from a TIF1A protein (UniProtKB-O15164 (TIF1A_HUMAN) incorporated herein by reference), or variant thereof. In one embodiment, the dTAG is derived from amino acid 932-987 of O15164.

In one embodiment, the dTAG has an amino acid sequence derived from a TRIM28 protein (UniProtKB-Q13263 (TIF1B_HUMAN) incorporated herein by reference), or variant thereof. In one embodiment, the dTAG is derived from amino acid 697-801 of Q13263.

In one embodiment, the dTAG has an amino acid sequence derived from a TRIM33 protein (UniProtKB-Q9UPN9 (TRI33_HUMAN) incorporated herein by reference), or variant thereof. In one embodiment, the dTAG is derived from amino acid 974-1046 of Q9UPN9.

In one embodiment, the dTAG has an amino acid sequence derived from a TRIM66 protein (UniProtKB-O15016 (TRI66_HUMAN) incorporated herein by reference), or variant thereof. In one embodiment, the dTAG is derived from amino acid 1056-1128 of O15016.

In one embodiment, the dTAG has an amino acid sequence derived from a WDR9 protein (UniProtKB-Q9NSI6 (BRWD1_HUMAN) incorporated herein by reference), or variant thereof. In one embodiment, the dTAG is derived from amino acid 1177-1247 or 1330-1400 of Q9NSI6.

In one embodiment, the dTAG has an amino acid sequence derived from a ZMYND11 protein (UniProtKB-Q15326 (ZMY1_HUMAN) incorporated herein by reference), or variant thereof. In one embodiment, the dTAG is derived from amino acid 168-238 of Q15326.

In one embodiment, the dTAG has an amino acid sequence derived from a MLL4 protein (UniProtKB-Q9UMN6 (KMT2B_HUMAN) incorporated herein by reference), or variant thereof. In one embodiment, the dTAG is derived from amino acid 1395-1509 of Q9UMN6.

In one embodiment, the dTAG has an amino acid sequence derived from an estrogen receptor, human (UniProtKB-P03372-1) (incorporated herein by reference), or a variant thereof. In one embodiment, the dTAG is derived from the amino acid sequence:

```
                                       (SEQ. ID. NO.: 4)
MTMTLHTKASGMALLHQIQGNELEPLNRPQLKIPLERPLGEVYLDSSKPA

VYNYPEGAAYEFNAAAAANAQVYGQTGLPYGPGSEAAAFGSNGLGGFPPL

NSVSPSPLMLLHPPPQLSPFLQPHGQQVPYYLENEPSGYTVREAGPPAFY

RPNSDNRRQGGRERLASTNDKGSMAMESAKETRYCAVCNDYASGYHYGVW

SCEGCKAFFKRSIQGHNDYMCPATNQCTIDKNRRKSCQACRLRKCYEVGM

MKGGIRKDRRGGRMLKHKRQRDDGEGRGEVGSAGDMRAANLWPSPLMIKR

SKKNSLALSLTADQMVSALLDAEPPILYSEYDPTRPFSEASMMGLLTNLA

DRELVHMINWAKRVPGFVDLTLHDQVHLLECAWLEILMIGLVWRSMEHPG

KLLFAPNLLLDRNQGKCVEGMVEIFDMLLATSSRFRMMNLQGEEFVCLKS

IILLNSGVYTFLSSTLKSLEEKDHIHRVLDKITDTLIHLMAKAGLTLQQQ

HQRLAQLLLILSHIRHMSNKGMEHLYSMKCKNVVPLYDLLLEMLDAHRLH

APTSRGGASVEETDQSHLATAGSTSSHSLQKYYITGEAEGFPATV.
```

In one embodiment, the dTAG has an amino acid sequence derived from an estrogen receptor ligand-binding domain, or a variant thereof. In one embodiment, the dTAG is derived from the amino acid sequence:

```
                                       (SEQ. ID. NO.: 5)
SLALSLTADQMVSALLDAEPPILYSEYDPTRPFSEASMMGLLTNLADREL

VHMINWAKRVPGFVDLTLHDQVHLLECAWLEILMIGLVWRSMEHPGKLLF

APNLLLDRNQGKCVEGMVEIFDMLLATSSRFRMMNLQGEEFVCLKSIILL

NSGVYTFLSSTLKSLEEKDHIHRVLDKITDTLIHLMAKAGLTLQQQHQRL

AQLLLILSHIRHIVISNKGMEHLYSMKCKNVVPLYDLLLEMLDAHRL.
```

In one embodiment, the dTAG has an amino acid sequence derived from an androgen receptor, UniProtKB-P10275 (ANDR_HUMAN) (incorporated herein by reference), or a variant thereof. In one embodiment, the dTAG is derived from the amino acid sequence:

```
                                       (SEQ. ID. NO.: 6)
MEVQLGLGRVYPRPPSKTYRGAFQNLFQSVREVIQNPGPRHPEAASAAPP

GASLLLLQQQQQQQQQQQQQQQQQQQQQQQQETSPRQQQQQQGEDGSPQAH

RRGPTGYLVLDEEQQPSQPQSALECHPERGCVPEPGAAVAASKGLPQQLP

APPDEDDSAAPSTLSLLGPTFPGLSSCSADLKDILSEASTMQLLQQQQQE

AVSEGSSSGRAREASGAPTSSKDNYLGGTSTISDNAKELCKAVSVSMGLG

VEALEHLSPGEQLRGDCMYAPLLGVPPAVRPTPCAPLAECKGSLLDDSAG
```

```
KSTEDTAEYSPFKGGYTKGLEGESLGCSGSAAAGSSGTLELPSTLSLYKS

GALDEAAAYQSRDYYNFPLALAGPPPPPPPPHPHARIKLENPLDYGSAWA

AAAAQCRYGDLASLHGAGAAGPGSGSPSAAASSSWHTLFTAEEGQLYGPC

GGGGGGGGGGGGGGGGGGGGGGEAGAVAPYGYTRPPQGLAGQESDFTAP

DVWYPGGMVSRVPYPSPTCVKSEMGPWMDSYSGPYGDMRLETARDHVLPI

DYYFPPQKTCLICGDEASGCHYGALTCGSCKVFFKRAAEGKQKYLCASRN

DCTIDKFRRKNCPSCRLRKCYEAGMTLGARKLKKLGNLKLQEEGEASSTT

SPTEETTQKLTVSHIEGYECQPIFLNVLEAIEPGVVCAGHDNNQPDSFAA

LLSSLNELGERQLVHVVKWAKALPGFRNLHVDDQMAVIQYSWMGLMVFAM

GWRSFTNVNSRMLYFAPDLVFNEYRMHKSRMYSQCVRMRHLSQEFGWLQI

TPQEFLCMKALLLFSIIPVDGLKNQKFFDELRMNYIKELDRIIACKRKNP

TSCSRRFYQLTKLLDSVQPIARELHQFTFDLLIKSHMVSVDFPEMMAEII

SVQVPKILSGKVKPIYFHTQ.
```

In one embodiment, the dTAG has an amino acid sequence derived from an androgen receptor ligand-binding domain, or a variant thereof. In one embodiment, the dTAG is derived from the amino acid sequence:

```
                                       (SEQ. ID. NO.: 10)
DNNQPDSFAALLSSLNELGERQLVHVVKWAKALPGFRNLHVDDQMAVI

QYSWMGLMVFAMGWRSFTNVNSRMLYFAPDLVFNEYRMHKSRMYSQCV

RMRHLSQEFGWLQITPQEFLCMKALLLFSIIPVDGLKNQKFFDELRMN

YIKELDRIIACKRKNPTSCSRRFYQLTKLLDSVQPIARELHQFTFDLL

IKSHMVSVDFPEMMAEIISVQVPKILSGKVKPIYFHT.
```

In one embodiment, the dTAG has an amino acid sequence derived from a Retinoic Receptor, (UniProtKB-P19793) (RXRA_HUMAN) (incorporated herein by reference), or a variant thereof. In one embodiment, the dTAG is derived from the amino acid sequence:

```
                                       (SEQ. ID. NO.: 7)
MDTKHFLPLDFSTQVNSSLTSPTGRGSMAAPSLHPSLGPGIGSPGQLH

SPISTLSSPINGMGPPFSVISSPMGPHSMSVPTTPTLGFSTGSPQLSS

PMNPVSSSEDIKPPLGLNGVLKVPAHPSGNMASFTKHICAICGDRSSG

KHYGVYSCEGCKGFFKRTVRKDLTYTCRDNKDCLIDKRQRNRCQYCRY

QKCLAMGMKREAVQEERQRGKDRNENEVESTSSANEDMPVERILEAEL

AVEPKTETYVEANMGLNPSSPNDPVTNICQAADKQLFTLVEWAKRIPH

FSELPLDDQVILLRAGWNELLIASFSHRSIAVKDGILLATGLHVHRNS

AHSAGVGAIFDRVLTELVSKMRDMQMDKTELGCLRAIVLFNPDSKGLS

NPAEVEALREKVYASLEAYCKHKYPEQPGRFAKLLLRLPALRSIGLKC

LEHLFFFKLIGDTPIDTFLMEMLEAPHQMT.
```

In one embodiment, the dTAG has an amino acid sequence derived from a Retinoic Receptor ligand-binding domain, or a variant thereof. In one embodiment, the dTAG is derived from the amino acid sequence:

```
                                       (SEQ. ID. NO.: 11)
SANEDMPVERILEAELAVEPKTETYVEANMGLNPSSPNDPVTNICQAA

DKQLFTLVEWAKRIPHFSELPLDDQVILLRAGWNELLIASFSHRSIAV

KDGILLATGLHVHRNSAHSAGVGAIFDRVLTELVSKMRDMQMDKTELG

CLRAIVLFNPDSKGLSNPAEVEALREKVYASLEAYCKHKYPEQPGRFA

KLLLRLPALRSIGLKCLEHLFFFKLIGDTPIDTFLMEMLEAPHQMT.
```

In one embodiment, the dTAG has an amino acid sequence derived from a DHFR, E. coli, UniProtKB-Q79DQ2 (Q79DQ2_ECOLX) (incorporated herein by reference), or a variant thereof. In one embodiment, the dTAG is derived from the amino acid sequence:

```
                                       (SEQ. ID. NO.: 8)
MNSESVRIYLVAAMGANRVIGNGPNIPWKIPGEQKIFRRLTEGKVVVM

GRKTFESIGKPLPNRHTLVISRQANYRATGCVVVSTLSHAIALASELG

NELYVAGGAEIYTLALPHAHGVFLSEVHQTFEGDAFFPMLNETEFELV

STETIQAVIPYTHSVYARRNG.
```

In one embodiment, the dTAG has an amino acid sequence derived from a bacterial dehalogenase, or variant thereof. In one embodiment, the dTAG is derived from the amino acid sequence:

```
                                       (SEQ. ID. NO.: 9)
MAEIGTGFPFDPHYVEVLGERMHYVDVGPRDGTPVLFLHGNPTSSYVW

RNIIPHVAPTHRCIAPDLIGMGKSDKPDLGYFFDDHVRFMDAFIEALG

LEEVVLVIHDWGSALGFHWAKRNPERVKGIAFMEFIRPIPTWDEWPEF

ARETFQAFRTTDVGRKLIIDQNVFIEGTLPMGVVRPLTEVEMDHYREP

FLNPVDREPLWRFPNELPIAGEPANIVALVEEYMDWLHQSPVPKLLFW

GTPGVLIPPAEAARLAKSLPNCKAVDIGPGLNLLQEDNPDLIGSEIAR

WLSTLEISG.
```

In one embodiment, the dTAG has an amino acid sequence derived from the N-terminus of MDM2, or variants thereof. In one embodiment, the dTAG is derived from the amino acid sequence:

```
                                       (SEQ. ID. NO.: 12)
MCNTNMSVPTDGAVTTSQIPASEQETLVRPKPLLLKLLKSVGAQKDTY

TMKEVLFYLGQYIMTKRLYDEKQQHIVYCSNDLLGDLFGVPSFSVKEH

RKIYTMIYRNLVVV.
```

In one embodiment, the dTAG has an amino acid sequence derived from apoptosis regulator Bcl-xL protein, UniProtKB-Q07817 (B2CL1_HUMAN) (incorporated herein by reference), or a variant thereof. In one embodiment, the dTAG is derived from the amino acid sequence:

```
                                       (SEQ. ID. NO.: 16)
MSQSNRELVVDFLSYKLSQKGYSWSQFSDVEENRTEAPEGTESEMETP

SAINGNPSWHLADSPAVNGATGHSSSLDAREVIPMAAVKQALREAGDE

FELRYRRAFSDLTSQLHITPGTAYQSFEQVVNELFRDGVNWGRIVAFF
```

SFGGALCVESVDKEMQVLVSRIAAWMATYLNDHLEPWIQENGGWDTFV

ELYGNNAAAESRKGQERFNRWFLTGMTVAGVVLLGSLFSRK.

In one embodiment, the dTAG has an amino acid sequence derived from the CD209 antigen, UniProtKB-Q9NNX6 (CD209_HUMAN) (incorporated herein by reference), or a variant thereof. In one embodiment, the dTAG is derived from the amino acid sequence:

(SEQ. ID. NO.: 17)
MSDSKEPRLQQLGLLEEEQLRGLGFRQTRGYKSLAGCLGHGPLVLQLL

SFTLLAGLLVQVSKVPSSISQEQSRQDAIYQNLTQLKAAVGELSEKSK

LQEIYQELTQLKAAVGELPEKSKLQEIYQELTRLKAAVGELPEKSKLQ

EIYQELTWLKAAVGELPEKSKMQEIYQELTRLKAAVGELPEKSKQQEI

YQELTRLKAAVGELPEKSKQQEIYQELTRLKAAVGELPEKSKQQEIYQ

ELTQLKAAVERLCHPCPWEWTFFQGNCYFMSNSQRNWHDSITACKEVG

AQLVVIKSAEEQNFLQLQSSRSNRFTWMGLSDLNQEGTWQWVDGSPLL

PSFKQYWNRGEPNNVGEEDCAEFSGNGWNDDKCNLAKFWICKKSAASC

SRDEEQFLSPAPATPNPPPA.

In one embodiment, the dTAG has an amino acid sequence derived from E3 ligase XIAP, UniProtKB-P98170 (XIAP_HUMAN) (incorporated herein by reference), or a variant thereof. In one embodiment, the dTAG is derived from the amino acid sequence:

(SEQ. ID. NO.: 18)
MTFNSFEGSKTCVPADINKEEEFVEEFNRLKTFANFPSGSPVSASTLA

RAGFLYTGEGDTVRCFSCHAAVDRWQYGDSAVGRHRKVSPNCRFINGF

YLENSATQSTNSGIQNGQYKVENYLGSRDHFALDRPSETHADYLLRTG

QVVDISDTIYPRNPAMYSEEARLKSFQNWPDYAHLTPRELASAGLYYT

GIGDQVQCFCCGGKLKNWEPCDRAWSEHRRHFPNCFFVLGRNLNIRSE

SDAVSSDRNFPNSTNLPRNPSMADYEARIFTFGTWIYSVNKEQLARAG

FYALGEGDKVKCFHCGGGLTDWKPSEDPWEQHAKWYPGCKYLLEQKGQ

EYINNIHLTHSLEECLVRTTEKTPSLTRRIDDTIFQNPMVQEAIRMGF

SFKDIKKIMEEKIQISGSNYKSLEVLVADLVNAQKDSMQDESSQTSLQ

KEISTEEQLRRLQEEKLCKICMDRNIAIVFVPCGHLVTCKQCAEAVDK

CPMCYTVITFKQKIFMS.

In one embodiment, the dTAG has an amino acid sequence derived from baculoviral IAP repeat-containing protein 2, UniProtKB-Q13490 (BIRC2_HUMAN) (incorporated herein by reference) or a variant thereof. In one embodiment, the dTAG is derived from the amino acid sequence:

(SEQ. ID. NO.: 19)
MHKTASQRLFPGPSYQNIKSIMEDSTILSDWTNSNKQKMKYDFSCELY

RMSTYSTFPAGVPVSERSLARAGFYYTGVNDKVKCFCCGLMLDNWKLG

DSPIQKEIKQLYPSCSFIQNLVSASLGSTSKNTSPMRNSFAHSLSPTL

EHSSLFSGSYSSLSPNPLNSRAVEDISSSRTNPYSYAMSTEEARFLTY

HMWPLTFLSPSELARAGFYYIGPGDRVACFACGGKLSNWEPKDDAMSE

HRRHFPNCPFLENSLETLRFSISNLSMQTHAARMRTFMYWPSSVPVQP

EQLASAGFYYVGRNDDVKCFCCDGGLRCWESGDDPWVEHAKWFPRCEF

LIRMKGQEFVDEIQGRYPHLLEQLLSTSDTTGEENADPPIIHFGPGES

SSEDAVMMNTPVVKSALEMGFNRDLVKQTVQSKILTTGENYKTVNDIV

SALLNAEDEKREEEKEKQAEEMASDDLSLIRKNRMALFQQLTCVLPIL

DNLLKANVINKQEHDIIKQKTQIPLQARELIDTILVKGNAAANIFKNC

LKEIDSTLYKNLFVDKNMKYIPTEDVSGLSLEEQLRRLQEERTCKVCM

DKEVSVVFIPCGHLVVCQECAPSLRKCPICRGIIKGTVRTFLS.

In one embodiment, the dTAG has an amino acid sequence derived from hematopoietic prostaglandin D synthase, UniProtKB-O60760 (HPGDS_HUMAN) (incorporated herein by reference), or a variant thereof. In one embodiment, the dTAG is derived from the amino acid sequence:

(SEQ. ID. NO.: 20)
MPNYKLTYFNMRGRAEIIRYIFAYLDIQYEDHRIEQADWPEIKSTLPF

GKIPILEVDGLTLHQSLAIARYLTKNTDLAGNTEMEQCHVDAIVDTLD

DFMSCFPWAEKKQDVKEQMFNELLTYNAPHLMQDLDTYLGGREWLIGN

SVTWADFYWEICSTTLLVFKPDLLDNHPRLVTLRKKVQAIPAVANWIK

RRPQTKL.

In one embodiment, the dTAG has an amino acid sequence derived from GTPase k-RAS, UniProtKB-P01116 (RASK_HUMAN) (incorporated herein by reference), or a variant thereof. In one embodiment, the dTAG is derived from the amino acid sequence:

(SEQ. ID. NO.: 21)
MTEYKLVVVGAGGVGKSALTIQLIQNHFVDEYDPTIEDSYRKQVVIDG

ETCLLDILDTAGQEEYSAMRDQYMRTGEGFLCVFAINNTKSFEDIHHY

REQIKRVKDSEDVPMVLVGNKCDLPSRTVDTKQAQDLARSYGIPFIET

SAKTRQRVEDAFYTLVREIRQYRLKKISKEEKTPGCVKIKKCIIM.

In one embodiment, the dTAG has an amino acid sequence derived from Poly-ADP-ribose polymerase 15, UniProtKB-Q460N3 (PAR15_HUMAN) (incorporated herein by reference), or a variant thereof. In one embodiment, the dTAG is derived from the amino acid sequence:

(SEQ. ID. NO.: 22)
MAAPGPLPAAALSPGAPTPRELMHGVAGVTSRAGRDREAGSVLPAGNR

GARKASRRSSSRSMSRDNKFSKKDCLSIRNVVASIQTKEGLNLKLISG

DVLYIWADVIVNSVPMNLQLGGGPLSRAFLQKAGPMLQKELDDRRRET

EEKVGNIFMTSGCNLDCKAVLHAVAPYWNNGAETSWQIMANIIKKCLT

TVEVLSFSSITFPMIGTGSLQFPKAVFAKLILSEVFEYSSSTRPITSP

LQEVHFLVYTNDDEGCQAFLDEFTNWSRINPNKARIPMAGDTQGVVGT

VSKPCFTAYEMKIGAITFQVATGDIATEQVDVIVNSTARTFNRKSGVS

```
RAILEGAGQAVESECAVLAAQPHRDFIITPGGCLKCKIIIHVPGGKDV

RKTVTSVLEECEQRKYTSVSLPAIGTGNAGKNPITVADNIIDAIVDFS

SQHSTPSLKTVKVVIFQPELLNIFYDSMKKRDLSASLNFQSTFSMTTC

NLPEHWTDMNHQLFCMVQLEPGQSEYNTIKDKFTRTCSSYAIEKIERI

QNAFLWQSYQVKKRQMDIKNDHKNNERLLFHGTDADSVPYVNQHGFNR

SCAGKNAVSYGKGTYFAVDASYSAKDTYSKPDSNGRKHMYVVRVLTGV

FTKGRAGLVTPPPKNPHNPTDLFDSVTNNTRSPKLFVVFFDNQAYPEY

LITFTA.
```

In one embodiment, the dTAG has an amino acid sequence derived from Poly-ADP-ribose polymerase 14, UniProtKB Q460N5 (PAR14_HUMAN) (incorporated herein by reference), or a variant thereof. In one embodiment, the dTAG is derived from the amino acid sequence:

```
                                          (SEQ. ID. NO.: 23)
MAVPGSFPLLVEGSWGPDPPKNLNTKLQMYFQSPKRSGGGECEVRQDP

RSPSRFLVFFYPEDVRQKVLERKNHELVWQGKGTFKLTVQLPATPDEI

DHVFEEELLTKESKTKEDVKEPDVSEELDTKLPLDGGLDKMEDIPEEC

ENISSLVAFENLKANVTDIMLILLVENISGLSNDDFQVEIIRDFDVAV

VTFQKHIDTIRFVDDCTKHHSIKQLQLSPRLLEVTNTIRVENLPPGAD

DYSLKLFFENPYNGGGRVANVEYFPEESSALIEFFDRKVLDTIMATKL

DFNKMPLSVFPYYASLGTALYGKEKPLIKLPAPFEESLDLPLWKFLQK

KNHLIEEINDEMRRCHCELTWSQLSGKVTIRPAATLVNEGRPRIKTWQ

ADTSTTLSSIRSKYKVNPIKVDPTMWDTIKNDVKDDRILIEFDTLKEM

VILAGKSEDVQSIEVQVRELIESTTQKIKREEQSLKEKMIISPGRYFL

LCHSSLLDHLLTECPEIEICYDRVTQHLCLKGPSADVYKAKCEIQEKV

YTMAQKNIQVSPEIFQFLQQVNWKEFSKCLFIAQKILALYELEGTTVL

LTSCSSEALLEAEKQMLSALNYKRIEVENKEVLHGKKWKGLTHNLLKK

QNSSPNTVIINELTSETTAEVIITGCVKEVNETYKLLFNFVEQNMKIE

RLVEVKPSLVIDYLKTEKKLFWPKIKKVNVQVSFNPENKQKGILLTGS

KTEVLKAVDIVKQVWDSVCVKSVHTDKPGAKQFFQDKARFYQSEIKRL

FGCYIELQENEVMKEGGSPAGQKCFSRTVLAPGVVLIVQQGDLARLPV

DVVVNASNEDLKHYGGLAAALSKAAGPELQADCDQIVKREGRLLPGNA

TISKAGKLPYHHVIHAVGPRWSGYEAPRCVYLLRRAVQLSLCLAEKYK

YRSIAIPAISSGVFGFPLGRCVETIVSAIKENFQFKKDGHCLKEIYLV

DVSEKTVEAFAEAVKTVFKATLPDTAAPPGLPPAAAGPGKTSWEKGSL

VSPGGLQMLLVKEGVQNAKTDVVVNSVPLDLVLSRGPLSKSLLEKAGP

ELQEELDTVGQGVAVSMGTVLKTSSWNLDCRYVLHVVAPEWRNGSTSS

LKIMEDIIRECMEITESLSLKSIAFPAIGTGNLGFPKNIFAELIISEV

FKFSSKNQLKTLQEVHFLLHPSDHENIQAFSDEFARRANGNLVSDKIP

KAKDTQGFYGTVSSPDSGVYEMKIGSIIFQVASGDITKEEADVIVNST

SNSFNLKAGVSKAILECAGQNVERECSQQAQQRKNDYIITGGGFLRCK

NIIHVIGGNDVKSSVSSVLQECEKKNYSSICLPAIGTGNAKQHPDKVA

EAIIDAIEDFVQKGSAQSVKKVKVVIFLPQVLDVFYANMKKREGTQLS

SQQSVMSKLASFLGFSKQSPQKKNHLVLEKKTESATFRVCGENVTCVE

YAISWLQDLIEKEQCPYTSEDECIKDFDEKEYQELNELQKKLNINISL

DHKRPLIKVLGISRDVMQARDEIEAMIKRVRLAKEQESRADCISEFIE

WQYNDNNTSHCFNKMTNLKLEDARREKKKTVDVKINHRHYTVNLNTYT

ATDTKGHSLSVQRLTKSKVDIPAHWSDMKQQNFCVVELLPSDPEYNTV

ASKFNQTCSHFRIEKIERIQNPDLWNSYQAKKKTMDAKNGQTMNEKQL

FHGTDAGSVPHVNRNGFNRSYAGKNAVAYGKGTYFAVNANYSANDTYS

RPDANGRKHVYYVRVLTGIYTHGNHSLIVPPSKNPQNPTDLYDTVTDN

VHHPSLFVAFYDYQAYPEYLITFRK.
```

In one embodiment, the dTAG has an amino acid sequence derived from superoxide dismutase, UniProtKB-P00441 (SODC_HUMAN) (incorporated herein by reference), or a variant thereof. In one embodiment, the dTAG is derived from the amino acid sequence:

```
                                          (SEQ. ID. NO.: 24)
MATKAVCVLKGDGPVQGIINFEQKESNGPVKVWGSIKGLTEGLHGFHV

HEFGDNTAGCTSAGPHFNPLSRKHGGPKDEERHVGDLGNVTADKDGVA

DVSIEDSVISLSGDHCIIGRTLVVHEKADDLGKGGNEESTKTGNAGSR

LACGVIGIAQ.
```

In one embodiment, the dTAG has an amino acid sequence derived from retinal rod rhodopsin-sensitive cGMP 3',5'-cyclic phosphodiesterase subunit delta, UniProtKB-O43924 (PDE6D HUMAN) (incorporated herein by reference), or a variant thereof. In one embodiment, the dTAG is derived from the amino acid sequence:

```
                                          (SEQ. ID. NO.: 25)
MSAKDERAREILRGFKLNWMNLRDAETGKILWQGTEDLSVPGVEHEARVP

KKILKCKAVSRELNFSSTEQMEKFRLEQKVYFKGQCLEEWFFEFGFVIPN

STNTWQSLIEAAPESQMMPASVLTGNVIIETKFFDDDLLVSTSRVRLFYV.
```

In one embodiment, the dTAG has an amino acid sequence derived from induced myeloid leukemia cell differentiation protein Mcl-1, UniProtKB-Q07820 (MCL1_HUMAN) (incorporated herein by reference), or a variant thereof. In one embodiment, the dTAG is derived from the amino acid sequence:

```
                                          (SEQ. ID. NO.: 26)
MFGLKRNAVIGLNLYCGGAGLGAGSGGATRPGGRLLATEKEASARREIGG

GEAGAVIGGSAGASPPSTLTPDSRRVARPPPIGAEVPDVTATPARLLFFA

PTRRAAPLEEMEAPAADAIMSPEEELDGYEPEPLGKRPAVLPLLELVGES

GNNTSTDGSLPSTPPPAEEEEDELYRQSLEIISRYLREQATGAKDTKPMG

RSGATSRKALETLRRVGDGVQRNEHETAFQGMLRKLDIKNEDDVKSLSRV

MIHVFSDGVTNWGRIVTLISFGAFVAKHLKTINQESCIEPLAESITDVLV

RTKRDWLVKQRGWDGFVEFFHVEDLEGGIRNVLLAFAGVAGVGAGLAYL

IR.
```

In one embodiment, the dTAG has an amino acid sequence derived from apoptosis regulator Bcl-2, UniProtKB-Q07820 (BCL2_HUMAN) (incorporated herein by reference), or a variant thereof. In one embodiment, the dTAG is derived from the amino acid sequence:

(SEQ. ID. NO. : 27)
MAHAGRTGYDNREIVMKYIHYKLSQRGYEWDAGDVGAAPPGAAPAPGIFS

SQPGHTPHPAASRDPVARTSPLQTPAAPGAAAGPALSPVPPVVHLTLRQA

GDDFSRRYRRDFAEMSSQLHLTPFTARGRFATVVEELFRDGVNWGRIVAF

FEFGGVMCVESVNREMSPLVDNIALWMTEYLNRHLHTWIQDNGGWDAFVE

LYGPSMRPLFDFSWLSLKTLLSLALVGACITLGAYLGHK.

In one embodiment, the dTAG has an amino acid sequence derived from peptidyl-prolyl cis-trans isomerase NIMA-interacting 1, UniProtKB-Q13526 (PIN1_HUMAN) (incorporated herein by reference), or a variant thereof. In one embodiment, the dTAG is derived from the amino acid sequence:

(SEQ. ID. NO.: 28)
MADEEKLPPGWEKRMSRSSGRVYYFNHITNASQWERPSGNSSSGGKNGQG

EPARVRCSHLLVKHSQSRRPSSWRQEKITRTKEEALELINGYIQKIKSGE

EDFESLASQFSDCSSAKARGDLGAFSRGQMQKPFEDASFALRTGEMSGPV

FTDSGIHIILRTE.

In one embodiment, the dTAG has an amino acid sequence derived from tankyrase 1, UniProtKB-095271 (TNKS1_HUMAN) (incorporated herein by reference), or a variant thereof. In one embodiment, the dTAG is derived from the amino acid sequence:

(SEQ. ID. NO.: 29)
MAASRRSQHHHHHHQQQLQPAPGASAPPPPPPPPLSPGLAPGTTPASPTA

SGLAPFASPRHGLALPEGDGSRDPPDRPRSPDPVDGTSCCSTTSTICTVA

AAPVVPAVSTSSAAGVAPNPAGSGSNNSPSSSSSPTSSSSSSPSSPGSSL

AESPEAAGVSSTAPLGPGAAGPGTGVPAVSGALRELLEACRNGDVSRVKR

LVDAANVNAKDMAGRKSSPLHFAAGFGRKDVVEHLLQMGANVHARDDGGL

IPLHNACSFGHAEVVSLLLCQGADPNARDNWNYTPLHEAAIKGKIDVCIV

LLQHGADPNIRNTDGKSALDLADPSAKAVLTGEYKKDELLEAARSGNEEK

LMALLTPLNVNCHASDGRKSTPLHLAAGYNRVRIVQLLLQHGADVHAKDK

GGLVPLHNACSYGHYEVTELLLKHGACVNAMDLWQFTPLHEAASKNRVEV

CSLLLSHGADPTLVNCHGKSAVDMAPTPELRERLTYEFKGHSLLQAAREA

DLAKVKKTLALEIINFKQPQSHETALHCAVASLHPKRKQVTELLLRKGAN

VNEKNKDFMTPLHVAAERAHNDVMEVLHKHGAKMNALDTLGQTALHRAAL

AGHLQTCRLLLSYGSDPSIISLQGFTAAQMGNEAVQQILSESTPIRTSDV

DYRLLEASKAGDLETVKQLCSSQNVNCRDLEGRHSTPLHFAAGYNRVSVV

EYLLHHGADVHAKDKGGLVPLHNACSYGHYEVAELLVRHGASVNVADLWK

FTPLHEAAAKGKYEICKLLLKHGADPTKKNRDGNTPLDLVKEGDTDIQDL

LRGDAALLDAAKKGCLARVQKLCTPENINCRDTQGRNSTPLHLAAGYNNL

EVAEYLLEHGADVNAQDKGGLIPLHNAASYGHVDIAALLIKYNTCVNATD

KWAFTPLHEAAQKGRTQLCALLLAHGADPTMKNQEGQTPLDLATADDIRA

LLIDAMPPEALPTCFKPQATVVSASLISPASTPSCLSAASSIDNLTGPLA

ELAVGGASNAGDGAAGTERKEGEVAGLDMNISQFLKSLGLEHLRDIFETE

QITLDVLADMGHEELKEIGINAYGHRHKLIKGVERLLGGQQGTNPYLTFH

CVNQGTILLDLAPEDKEYQSVEEEMQSTIREHRDGGNAGGIFNRYNVIRI

QKVVNKKLRERFCHRQKEVSEENHNHHNERMLFHGSPFINAIIHKGFDER

HAYIGGMFGAGIYFAENSSKSNQYVYGIGGGTGCPTHKDRSCYICHRQML

FCRVTLGKSFLQFSTMKMAHAPPGHHSVIGRPSVNGLAYAEYVIYRGEQA

YPEYLITYQIMKPEAPSQTATAAEQKT.

In one embodiment, the dTAG has an amino acid sequence derived from tankyrase 2, UniProtKB-09H2K2 (TNKS2_HUMAN) (incorporated herein by reference), or a variant thereof. In one embodiment, the dTAG is derived from the amino acid sequence:

(SEQ. ID. NO.: 30)
MSGRRCAGGGAACASAAAEAVEPAARELFEACRNGDVERVKRLVTPEKVN

SRDTAGRKSTPLHFAAGFGRKDVVEYLLQNGANVQARDDGGLIPLHNACS

FGHAEVVNLLLRHGADPNARDNWNYTPLHEAAIKGKIDVCIVLLQHGAEP

TIRNTDGRTALDLADPSAKAVLTGEYKKDELLESARSGNEEKMMALLTPL

NVNCHASDGRKSTPLHLAAGYNRVKIVQLLLQHGADVHAKDKGDLVPLHN

ACSYGHYEVTELLVKHGACVNAMDLWQFTPLHEAASKNRVEVCSLLLSYG

ADPTLLNCHNKSAIDLAPTPQLKERLAYEFKGHSLLQAAREADVTRIKKH

LSLEMVNFKHPQTHETALHCAAASPYPKRKQICELLLRKGANINEKTKEF

LTPLHVASEKAHNDVVEVVVKHEAKVNALDNLGQTSLHRAAYCGHLQTCR

LLLSYGCDPNIISLQGFTALQMGNENVQQLLQEGISLGNSEADRQLLEAA

KAGDVETVKKLCTVQSVNCRDIEGRQSTPLHFAAGYNRVSVVEYLLQHGA

DVHAKDKGGLVPLHNACSYGHYEVAELLVKHGAVVNVADLWKFTPLHEAA

AKGKYEICKLLLQHGADPTKKNRDGNTPLDLVKDGDTDIQDLLRGDAALL

DAAKKGCLARVKKLSSPDNVNCRDTQGRHSTPLHLAAGYNNLEVAEYLLQ

HGADVNAQDKGGLIPLHNAASYGHVDVAALLIKYNACVNATDKWAFTPLH

EAAQKGRTQLCALLLAHGADPTLKNQEGQTPLDLVSADDVSALLTAAMPP

SALPSCYKPQVLNGVRSPGATADALSSGPSSPSSLSAASSLDNLSGSFSE

LSSVVSSSGTEGASSLEKKEVPGVDFSITQFVRNLGLEHLMDIFEREQIT

LDVLVEMGHKELKEIGINAYGHRHKLIKGVERLISGQQGLNPYLTLNTSG

SGTILIDLSPDDKEFQSVEEEMQSTVREHRDGGHAGGIFNRYNILKIQKV

CNKKLWERYTHRRKEVSEENHNHANERMLFHGSPFVNAIIHKGFDERHAY

IGGMFGAGIYFAENSSKSNQYVYGIGGGTGCPVHKDRSCYICHRQLLFCR

VTLGKSFLQFSAMKMAHSPPGHHSVTGRPSVNGLALAEYVIYRGEQAYPE

YLITYQIMRPEGMVDG.

In one embodiment, the dTAG has an amino acid sequence derived from 7,8-dihydro-8-oxoguanin triphosphatase, UniProtKB-P36639 (8ODP_HUMAN) (incorporated herein by reference), or a variant thereof. In one embodiment, the dTAG is derived from the amino acid sequence:

(SEQ. ID. NO.: 31)
MYWSNQITRRLGERVQGFMSGISPQQMGEPEGSWSGKNPGTMGASRLYTL

VLVLQPQRVLLGMKKRGFGAGRWNGFGGKVQEGETIEDGARRELQEESGL

TVDALHKVGQIVFEFVGEPELMDVHVFCTDSIQGTPVESDEMRPCWFQLD

QIPFKDMWPDDSWFPLLLQKKKFHGYFKFQGQDTILDYTLREVDTV.

In one embodiment, the dTAG has an amino acid sequence derived from Proto-oncogene tyrosine protein kinase Src, UniProtKB-P12931 (SRC_HUMAN) (incorporated herein by reference), or a variant thereof. In one embodiment, the dTAG is derived from the amino acid sequence:

(SEQ. ID. NO.: 32)
MGSNKSKPKDASQRRRSLEPAENVHGAGGGAFPASQTPSKPASADGHRGP

SAAFAPAAAEPKLFGGFNSSDTVTSPQRAGPLAGGVTTFVALYDYESRTE

TDLSFKKGERLQIVNNTEGDWWLAHSLSTGQTGYIPSNYVAPSDSIQAEE

WYFGKITRRESERLLLNAENPRGTFLVRESETTKGAYCLSVSDFDNAKGL

NVKHYKIRKLDSGGFYITSRTQFNSLQQLVAYYSKHADGLCHRLTTVCPT

SKPQTQGLAKDAWEIPRESLRLEVKLGQGCFGEVWMGTWNGTTRVAIKTL

KPGTMSPEAFLQEAQVMKKLRHEKLVQLYAVVSEEPIYIVTEYMSKGSLL

DFLKGETGKYLRLPQLVDMAAQIASGMAYVERMNYVHRDLRAANILVGEN

LVCKVADFGLARLIEDNEYTARQGAKFPIKWTAPEAALYGRFTIKSDVWS

FGILLTELTTKGRVPYPGMVNREVLDQVERGYRMPCPPECPESLHDLMCQ

CWRKEPEERPTFEYLQAFLEDYFTSTEPQYQPGENL.

In one embodiment, the dTAG includes a substitution of Threonine (T) with Glycine (G) or Alanine (A) at amino acid position 341. In one embodiment, the dTAG is an amino acid sequence derived from, or a fragment thereof, of SEQ. ID. NO.: 62.
LRLEVKLGQGCFGEVWMGTWNGTTRVAIKTLKPGT-MSPEAFLQEAQVMKKLRHEKLV QLYAVVSEEPIYI-VTEYGSKGSLLDFLKGETGKYLRLPQLVDMAAQ-IASGMAYVERMN YVHRDLRAANILVGENLVCKVAD-FGLARLIEDNEYTARQGAKFPIKWTAPEAALYGRF TIKSDVWSFGILLTELTTKGRVPYPGMVNREVLDQV-ERGYRMPCPPECPESLHDLMCQC WRKEPEERPTFE-YLQAFLEDYF.

In one embodiment, the dTAG is an amino acid sequence derived from, or a fragment thereof, of SEQ. ID. NO.: 63.
LRLEVKLGQGCFGEVWMGTWNGTTRVAIKTLKP-GTMSPEAFLQEAQVMKKLRHEKLV QLYAVVSEEPIY-IVTEYASKGSLLDFLKGETGKYLRLPQLVDMAAQI-ASGMAYVERMN YVHRDLRAANILVGENLVCKVAD-FGLARLIEDNEYTARQGAKFPIKWTAPEAALYGRF TIKSDVWSFGILLTELTTKGRVPYPGMVNREVLDQV-ERGYRMPCPPECPESLHDLMCQC WRKEPEERPTFE-YLQAFLEDYF In one embodiment, the dTAG has an amino acid sequence derived from prostaglandin E synthase, UniProtKB-O14684 (PTGES_HUMAN) (incorporated herein by reference), or a variant thereof. In one embodiment, the dTAG is derived from the amino acid sequence:

(SEQ. ID. NO.: 33)
MPAHSLVMSSPALPAFLLCSTLLVIKMYVVAIITGQVRLRKKAFANPEDA

LRHGGPQYCRSDPDVERCLRAHRNDMETIYPFLFLGFVYSFLGPNPFVAW

MHFLVFLVGRVAHTVAYLGKLRAPIRSVTYTLAQLPCASMALQILWEAAR

HL.

In one embodiment, the dTAG has an amino acid sequence derived from Arachidonate 5-lipoxygenase activating protein, UniProtKB-P20292 (AL5AP_HUMAN) (incorporated herein by reference), or a variant thereof. In one embodiment, the dTAG is derived from the amino acid sequence:

(SEQ. ID. NO.: 34)
MDQETVGNVVLLAIVTLISVVQNGFFAHKVEHESRTQNGRSFQRTGTLAF

ERVYTANQNCVDAYPTFLAVLWSAGLLCSQVPAAFAGLMYLFVRQKYFVG

YLGERTQSTPGYIFGKRIILFLFLMSVAGIFNYYLIFFFGSDFENYIKTI

STTISPLLLIP.

In one embodiment, the dTAG has an amino acid sequence derived from fatty acid binding protein from adipocyte, UniProtKB-P15090 (FABP4_HUMAN) (incorporated herein by reference), or a variant thereof. In one embodiment, the dTAG is derived from the amino acid sequence:

(SEQ. ID. NO.: 35)
MCDAFVGTWKLVSSENFDDYMKEVGVGFATRKVAGMAKPNMIISVNGDVI

TIKSESTFKNTEISFILGQEFDEVTADDRKVKSTITLDGGVLVHVQKWDG

KSTTIKRKREDDKLVVECVMKGVTSTRVYERA.

In one embodiment, the dTAG has an amino acid sequence derived from PH-interacting protein, UniProtKB Q8WWQ0 (PHIP_HUMAN) (incorporated herein by reference), or a variant thereof. In one embodiment, the dTAG is derived from the amino acid sequence:

(SEQ. ID. NO.: 36)
MSCERKGLSELRSELYFLIARFLEDGPCQQAAQVLIREVAEKELLPRRTD

WTGKEHPRTYQNLVKYYRHLAPDHLLQICHRLGPLLEQEIPQSVPGVQTL

LGAGRQSLLRTNKSCKHVVWKGSALAALHCGRPPESPVNYGSPPSIADTL

FSRKLNGKYRLERLVPTAVYQHMKMHKRILGHLSSVYCVTFDRTGRRIFT

GSDDCLVKIWATDDGRLLATLRGHAAEISDMAVNYENTMIAAGSCDKMIR

VWCLRTCAPLAVLQGHSASITSLQFSPLCSGSKRYLSSTGADGTICFWLW

DAGTLKINPRPAKFTERPRPGVQMICSSFSAGGMFLATGSTDHIIRVYFF

GSGQPEKISELEFHTDKVDSIQFSNTSNRFVSGSRDGTARIWQFKRREWK

SILLDMATRPAGQNLQGIEDKITKMKVTMVAWDRHDNTVITAVNNMTLKV

WNSYTGQLIHVLMGHEDEVFVLEPHPFDPRVLFSAGHDGNVIVWDLARGV

KIRSYFNMIEGQGHGAVFDCKCSPDGQHFACTDSHGHLLIFGFGSSSKYD

KIADQMFFHSDYRPLIRDANNFVLDEQTQQAPHLMPPPFLVDVDGNPHPS

RYQRLVPGRENCREEQLIPQMGVTSSGLNQVLSQQANQEISPLDSMIQRL

QQEQDLRRSGEAVISNTSRLSRGSISSTSEVHSPPNVGLRRSGQIEGVRQ

-continued

MHSNAPRSEIATERDLVAWSRRVVVPELSAGVASRQEEWRTAKGEEEIKT

YRSEEKRKHLTVPKENKIPTVSKNHAHEHFLDLGESKKQQTNQHNYRTRS

ALEETPRPSEEIENGSSSSDEGEVVAVSGGTSEEEERAWHSDGSSSDYSS

DYSDWTADAGINLQPPKKVPKNKTKKAESSSDEEEESEKQKQKQIKKEKK

KVNEEKDGPISPKKKKPKERKQKRLAVGELTENGLTLEEWLPSTWITDTI

PRRCPFVPQMGDEVYYFRQGHEAYVEMARKNKIYSINPKKQPWHKMELRE

QELMKIVGIKYEVGLPTLCCLKLAFLDPDTGKLTGGSFTMKYHDMPDVID

FLVLRQQFDDAKYRRWNIGDRFRSVIDDAWWFGTIESQEPLQLEYPDSLF

QCYNVCWDNGDTEKMSPWDMELIPNNAVFPEELGTSVPLTDGECRSLIYK

PLDGEWGTNPRDEECERIVAGINQLMTLDIASAFVAPVDLQAYPMYCTVV

AYPTDLSTIKQRLENRFYRRVSSLMWEVRYIEHNTRTFNEPGSPIVKSAK

FVTDLLLHFIKDQTCYNIIPLYNSMKKKVLSDSEDEEKDADVPGTSTRKR

KDHQPRRRLRNRAQSYDIQAWKKQCEELLNLIFQCEDSEPFRQPVDLLEY

PDYRDIIDTPMDFATVRETLEAGNYESPMELCKDVRLIFSNSKAYTPSKR

SRIYSMSLRLSAFFEEHISSVLSDYKSALRFHKRNTITKRRKKRNRSSSV

SSSAASSPERKKRILKPQLKSESSTSAFSTPTRSIPPRHNAAQINGKTES

SSVVRTRSNRVVVDPVVTEQPSTSSAAKTFITKANASAIPGKTILENSVK

HSKALNTLSSPGQSSFSHGTRNNSAKENMEKEKPVKRKMKSSVLPKASTL

SKSSAVIEQGDCKNNALVPGTIQVNGHGGQPSKLVKRGPGRKPKVEVNTN

SGEIIHKKRGRKPKKLQYAKPEDLEQNNVHPIRDEVLPSSTCNFLSETNN

VKEDLLQKKNRGGRKPKRKMKTQKLDADLLVPASVKVLRRSNRKKIDDPI

DEEEEFEELKGSEPHMRTRNQGRRTAFYNEDDSEEEQRQLLFEDTSLTFG

TSSRGRVRKLTEKAKANLIGW.

In one embodiment, the dTAG has an amino acid sequence derived from SUMO-conjugating enzyme UBC9, UniProtKB-P63279 (UBC9_HUMAN) (incorporated herein by reference), or a variant thereof. In one embodiment, the dTAG is derived from the amino acid sequence:

(SEQ. ID. NO.: 37)
MSGIALSRLAQERKAWRKDHPFGFVAVPTKNPDGTMNLMNWECAIPGKKG

TPWEGGLFKLRMLFKDDYPSSPPKCKFEPPLFHPNVYPSGTVCLSILEED

KDWRPAITIKQILLGIQELLNEPNIQDPAQAEAYTIYCQNRVEYEKRVRA

QAKKFAPS.

In one embodiment, the dTAG has an amino acid sequence derived from Protein S100-A7, UniProtKB-P31151 (S10A7_HUMAN) (incorporated herein by reference), or a variant thereof. In one embodiment, the dTAG is derived from the amino acid sequence:

(SEQ. ID. NO.: 38)
MSNTQAERSIIGMIDMFHKYTRRDDKIEKPSLLTMMKENFPNFLSACDKK

GTNYLADVFEKKDKNEDKKIDFSEFLSLLGDIATDYHKQSHGAAPCSGG

SQ.

In one embodiment, the dTAG has an amino acid sequence derived from phospholipase A2, membrane associated, UniProtKB-P14555 (PA2GA HUMAN) (incorporated herein by reference), or a variant thereof. In one embodiment, the dTAG is derived from the amino acid sequence:

(SEQ. ID. NO.: 39)
MKTLLLLAVIMIFGLLQAHGNLVNFHRMIKLTTGKEAALSYGFYGCHCGV

GGRGSPKDATDRCCVTHDCCYKRLEKRGCGTKFLSYKFSNSGSRITCAKQ

DSCRSQLCECDKAAATCFARNKTTYNKKYQYYSNKHCRGSTPRC.

In one embodiment, the dTAG has an amino acid sequence derived from histone deacetylase 6, UniProtKB-Q9UBN7 (HDAC6_HUMAN) (incorporated herein by reference), or a variant thereof. In one embodiment, the dTAG is derived from the amino acid sequence:

(SEQ. ID. NO.: 40)
MTSTGQDSTTTRQRRSRQNPQSPPQDSSVTSKRNIKKGAVPRSIPNLAEV

KKKGKMKKLGQAMEEDLIVGLQGMDLNLEAEALAGTGLVLDEQLNEFHCL

WDDSFPEGPERLHAIKEQLIQEGLLDRCVSFQARFAEKEELMLVHSLEYI

DLMETTQYMNEGELRVLADTYDSVYLHPNSYSCACLASGSVLRLVDAVLG

AEIRNGMAIIRPPGHHAQHSLMDGYCMFNHVAVAARYAQQKHRIRRVLIV

DWDVHHGQGTQFTFDQDPSVLYFSIHRYEQGRFWPHLKASNWSTTGFGQG

QGYTINVPWNQVGMRDADYIAAFLHVLLPVALEFQPQLVLVAAGFDALQG

DPKGEMAATPAGFAQLTHLLMGLAGGKLILSLEGGYNLRALAEGVSASLH

TLLGDPCPMILESPGAPCRSAQASVSCALEALEPFWEVLVRSTETVERDN

MEEDNVEESEEEGPWEPPVLPILTWPVLQSRTGLVYDQNMMNHCNLWDSH

HPEVPQRILRIMCRLEELGLAGRCLTLTPRPATEAELLTCHSAEYVGHLR

ATEKMKTRELHRESSNFDSIYICPSTFACAQLATGAACRLVEAVLSGEVL

NGAAVVRPPGHHAEQDAACGFCFFNSVAVAARHAQTISGHALRILIVDWD

VHHGNGTQHMFEDDPSVLYVSLHRYDHGTFFPMGDEGASSQIGRAAGTGF

TVNVAWNGPRMGDADYLAAWHRLVLPIAYEFNPELVLVSAGFDAARGDPL

GGCQVSPEGYAHLTHLLMGLASGRIILILEGGYNLTSISESMAACTRSLL

GDPPPLLTLPRPPLSGALASITETIQVHRRYWRSLRVMKVEDREGPSSSK

LVTKKAPQPAKPRLAERMTTREKKVLEAGMGKVTSASFGEESTPGQTNSE

TAVVALTQDQPSEAATGGATLAQTISEAAIGGAMLGQTTSEEAVGGATPD

QTTSEETVGGAILDQTTSEDAVGGATLGQTTSEEAVGGATLAQTTSEAAM

EGATLDQTTSEEAPGGTELIQTPLASSTDHQTPPTSPVQGTTPQISPSTL

IGSLRTLELGSESQGASESQAPGEENLLGEAAGGQDMADSMLMQGSRGLT

DQAIFYAVTPLPWCNILVAVCPIPAAGLDVTQPCGDCGTIQENWVCLSCY

QVYCGRYINGHMLQHHGNSGHPLVLSYIDLSAWCYYCQAYVHHQALLDVK

NIAHQNKFGEDMPHPH.

In one embodiment, the dTAG has an amino acid sequence derived from prosaposin, UniProtKB-P07602 (SAP HUMAN) (incorporated herein by reference), or a variant thereof. In one embodiment, the dTAG is derived from the amino acid sequence:

```
                                         (SEQ. ID. NO.: 41)
MYALFLLASLLGAALAGPVLGLKECTRGSAVWCQNVKTASDCGAVKHCLQ
TVWNKPTVKSLPCDICKDVVTAAGDMLKDNATEEEILVYLEKTCDWLPKP
NMSASCKEIVDSYLPVILDIIKGEMSRPGEVCSALNLCESLQKHLAELNH
QKQLESNKIPELDMTEVVAPFMANIPLLLYPQDGPRSKPQPKDNGDVCQD
CIQMVTDIQTAVRTNSTFVQALVEHVKEECDRLGPGMADICKNYISQYSE
IAIQMMMHMQPKEICALVGFCDEVKEMPMQTLVPAKVASKNVIPALELVE
PIKKHEVPAKSDVYCEVCEFLVKEVTKLIDNNKTEKEILDAFDKMCSKLP
KSLSEECQEVVDTYGSSILSILLEEVSPELVCSMLHLCSGTRLPALTVHV
TQPKDGGFCEVCKKLVGYLDRNLEKNSTKQEILAALEKGCSFLPDPYQKQ
CDQFVAEYEPVLIEILVEVMDPSFVCLKIGACPSAHKPLLGTEKCIWGPS
YWCQNTETAAQCNAVEHCKRHVWN.
```

In one embodiment, the dTAG has an amino acid sequence derived from apolipoprotein a, UniProtKB-P08519 (APOA_HUMAN) (incorporated herein by reference), or a variant thereof. In one embodiment, the dTAG is derived from the amino acid sequence:

```
                                         (SEQ. ID. NO.: 42)
MEHKEVVLLLLLFLKSAAPEQSHVVQDCYHGDGQSYRGTYSTTVTGRTCQ
AWSSMTPHQHNRTTENYPNAGLIMNYCRNPDAVAAPYCYTRDPGVRWEYC
NLTQCSDAEGTAVAPPTVTPVPSLEAPSEQAPTEQRPGVQECYHGNGQSY
RGTYSTTVTGRTCQAWSSMTPHSHSRTPEYYPNAGLIMNYCRNPDAVAAP
YCYTRDPGVRWEYCNLTQCSDAEGTAVAPPTVTPVPSLEAPSEQAPTEQR
PGVQECYHGNGQSYRGTYSTTVTGRTCQAWSSMTPHSHSRTPEYYPNAGL
IMNYCRNPDAVAAPYCYTRDPGVRWEYCNLTQCSDAEGTAVAPPTVTPVP
SLEAPSEQAPTEQRPGVQECYHGNGQSYRGTYSTTVTGRTCQAWSSMTPH
SHSRTPEYYPNAGLIMNYCRNPDAVAAPYCYTRDPGVRWEYCNLTQCSDA
EGTAVAPPTVTPVPSLEAPSEQAPTEQRPGVQECYHGNGQSYRGTYSTTV
TGRTCQAWSSMTPHSHSRTPEYYPNAGLIMNYCRNPDAVAAPYCYTRDPG
VRWEYCNLTQCSDAEGTAVAPPTVTPVPSLEAPSEQAPTEQRPGVQECYH
GNGQSYRGTYSTTVTGRTCQAWSSMTPHSHSRTPEYYPNAGLIMNYCRNP
DAVAAPYCYTRDPGVRWEYCNLTQCSDAEGTAVAPPTVTPVPSLEAPSEQ
APTEQRPGVQECYHGNGQSYRGTYSTTVTGRTCQAWSSMTPHSHSRTPEY
YPNAGLIMNYCRNPDAVAAPYCYTRDPGVRWEYCNLTQCSDAEGTAVAPP
TVTPVPSLEAPSEQAPTEQRPGVQECYHGNGQSYRGTYSTTVTGRTCQAW
SSMTPHSHSRTPEYYPNAGLIMNYCRNPDAVAAPYCYTRDPGVRWEYCNL
TQCSDAEGTAVAPPTVTPVPSLEAPSEQAPTEQRPGVQECYHGNGQSYRG
TYSTTVTGRTCQAWSSMTPHSHSRTPEYYPNAGLIMNYCRNPDAVAAPYC
YTRDPGVRWEYCNLTQCSDAEGTAVAPPTVTPVPSLEAPSEQAPTEQRPG
VQECYHGNGQSYRGTYSTTVTGRTCQAWSSMTPHSHSRTPEYYPNAGLIM
NYCRNPDAVAAPYCYTRDPGVRWEYCNLTQCSDAEGTAVAPPTVTPVPSL
EAPSEQAPTEQRPGVQECYHGNGQSYRGTYSTTVTGRTCQAWSSMTPHSH
SRTPEYYPNAGLIMNYCRNPDAVAAPYCYTRDPGVRWEYCNLTQCSDAEG
TAVAPPTVTPVPSLEAPSEQAPTEQRPGVQECYHGNGQSYRGTYSTTVTG
RTCQAWSSMTPHSHSRTPEYYPNAGLIMNYCRNPDAVAAPYCYTRDPGVR
WEYCNLTQCSDAEGTAVAPPTVTPVPSLEAPSEQAPTEQRPGVQECYHGN
GQSYRGTYSTTVTGRTCQAWSSMTPHSHSRTPEYYPNAGLIMNYCRNPDA
VAAPYCYTRDPGVRWEYCNLTQCSDAEGTAVAPPTVTPVPSLEAPSEQAP
TEQRPGVQECYHGNGQSYRGTYSTTVTGRTCQAWSSMTPHSHSRTPEYYP
NAGLIMNYCRNPDAVAAPYCYTRDPGVRWEYCNLTQCSDAEGTAVAPPTV
TPVPSLEAPSEQAPTEQRPGVQECYHGNGQSYRGTYSTTVTGRTCQAWSS
MTPHSHSRTPEYYPNAGLIMNYCRNPDAVAAPYCYTRDPGVRWEYCNLTQ
CSDAEGTAVAPPTVTPVPSLEAPSEQAPTEQRPGVQECYHGNGQSYRGTY
STTVTGRTCQAWSSMTPHSHSRTPEYYPNAGLIMNYCRNPDAVAAPYCYT
RDPGVRWEYCNLTQCSDAEGTAVAPPTVTPVPSLEAPSEQAPTEQRPGVQ
ECYHGNGQSYRGTYSTTVTGRTCQAWSSMTPHSHSRTPEYYPNAGLIMNY
CRNPDAVAAPYCYTRDPGVRWEYCNLTQCSDAEGTAVAPPTVTPVPSLEA
PSEQAPTEQRPGVQECYHGNGQSYRGTYSTTVTGRTCQAWSSMTPHSHSR
TPEYYPNAGLIMNYCRNPDAVAAPYCYTRDPGVRWEYCNLTQCSDAEGTA
VAPPTVTPVPSLEAPSEQAPTEQRPGVQECYHGNGQSYRGTYSTTVTGRT
CQAWSSMTPHSHSRTPEYYPNAGLIMNYCRNPDAVAAPYCYTRDPGVRWE
YCNLTQCSDAEGTAVAPPTVTPVPSLEAPSEQAPTEQRPGVQECYHGNGQ
SYRGTYSTTVTGRTCQAWSSMTPHSHSRTPEYYPNAGLIMNYCRNPDAVA
APYCYTRDPGVRWEYCNLTQCSDAEGTAVAPPTVTPVPSLEAPSEQAPTE
QRPGVQECYHGNGQSYRGTYSTTVTGRTCQAWSSMTPHSHSRTPEYYPNA
GLIMNYCRNPDAVAAPYCYTRDPGVRWEYCNLTQCSDAEGTAVAPPTVTP
VPSLEAPSEQAPTEQRPGVQECYHGNGQSYRGTYSTTVTGRTCQAWSSMT
PHSHSRTPEYYPNAGLIMNYCRNPDAVAAPYCYTRDPGVRWEYCNLTQCS
DAEGTAVAPPTVTPVPSLEAPSEQAPTEQRPGVQECYHGNGQSYRGTYST
TVTGRTCQAWSSMTPHSHSRTPEYYPNAGLIMNYCRNPDAVAAPYCYTRD
PGVRWEYCNLTQCSDAEGTAVAPPTVTPVPSLEAPSEQAPTEQRPGVQEC
YHGNGQSYRGTYSTTVTGRTCQAWSSMTPHSHSRTPEYYPNAGLIMNYCR
NPDAVAAPYCYTRDPGVRWEYCNLTQCSDAEGTAVAPPTVTPVPSLEAPS
EQAPTEQRPGVQECYHGNGQSYRGTYSTTVTGRTCQAWSSMTPHSHSRTP
EYYPNAGLIMNYCRNPDAVAAPYCYTRDPGVRWEYCNLTQCSDAEGTAVA
PPTVTPVPSLEAPSEQAPTEQRPGVQECYHGNGQSYRGTYSTTVTGRTCQ
AWSSMTPHSHSRTPEYYPNAGLIMNYCRNPDAVAAPYCYTRDPGVRWEYC
NLTQCSDAEGTAVAPPTVTPVPSLEAPSEQAPTEQRPGVQECYHGNGQSY
RGTYSTTVTGRTCQAWSSMTPHSHSRTPEYYPNAGLIMNYCRNPDAVAAP
YCYTRDPGVRWEYCNLTQCSDAEGTAVAPPTVTPVPSLEAPSEQAPTEQR
PGVQECYHGNGQSYRGTYSTTVTGRTCQAWSSMTPHSHSRTPEYYPNAGL
```

-continued
IMNYCRNPDAVAAPYCYTRDPGVRWEYCNLTQCSDAEGTAVAPPTVTPVP
SLEAPSEQAPTEQRPGVQECYHGNGQSYRGTYSTTVTGRTCQAWSSMTPH
SHSRTPEYYPNAGLIMNYCRNPDAVAAPYCYTRDPGVRWEYCNLTQCSDA
EGTAVAPPTVTPVPSLEAPSEQAPTEQRPGVQECYHGNGQSYRGTYSTTV
TGRTCQAWSSMTPHSHSRTPEYYPNAGLIMNYCRNPDPVAAPYCYTRDPS
VRWEYCNLTQCSDAEGTAVAPPTITPIPSLEAPSEQAPTEQRPGVQECYH
GNGQSYQGTYFITVTGRTCQAWSSMTPHSHSRTPAYYPNAGLIKNYCRNP
DPVAAPWCYTTDPSVRWEYCNLTRCSDAEWTAFVPPNVILAPSLEAFFEQ
ALTEETPGVQDCYYHYGQSYRGTYSTTVTGRTCQAWSSMTPHQHSRTPEN
YPNAGLTRNYCRNPDAEIRPWCYTMDPSVRWEYCNLTQCLVTESSVLATL
TVVPDPSTEASSEEAPTEQSPGVQDCYHGDGQSYRGSFSTTVTGRTCQSW
SSMTPHWHQRTTEYYPNGGLTRNYCRNPDAEISPWCYTMDPNVRWEYCNL
TQCPVTESSVLATSTAVSEQAPTEQSPTVQDCYHGDGQSYRGSFSTTVTG
RTCQSWSSMTPHWHQRTTEYYPNGGLTRNYCRNPDAEIRPWCYTMDPSVR
WEYCNLTQCPVMESTLLTTPTVVPVPSTELPSEEAPTENSTGVQDCYRGD
GQSYRGTLSTTITGRTCQSWSSMTPHWHRRIPLYYPNAGLTRNYCRNPDA
EIRPWCYTMDPSVRWEYCNLTRCPVTESSVLTTPTVAPVPSTEAPSEQAP
PEKSPVVQDCYHGDGRSYRGISSTTVTGRTCQSWSSMIPHWHQRTPENYP
NAGLTENYCRNPDSGKQPWCYTTDPCVRWEYCNLTQCSETESGVLETPTV
VPVPSMEAHSEAAPTEQTPVVRQCYHGNGQSYRGTFSTTVTGRTCQSWSS
MTPHRHQRTPENYPNDGLTMNYCRNPDADTGPWCFTMDPSIRWEYCNLTR
CSDTEGTVVAPPTVIQVPSLGPPSEQDCMFGNGKGYRGKKATTVTGTPCQ
EWAAQEPHRHSTFIPGTNKWAGLEKNYCRNPDGDINGPWCYTMNPRKLFD
YCDIPLCASSSFDCGKPQVEPKKCPGSIVGGCVAHPSWPWQVSLRTRFG
KEIFCGGTLISPEWVLTAAHCLKKSSRPSSYKVILGAHQEVNLESHVQEI
EVSRLFLEPTQADIALLKLSRPAVITDKVMPACLPSPDYMVTARTECYIT
GWGETQGTFGTGLLKEAQLLVIENEVCNHYKYICAEHLARGTDSCQGDSG
GPLVCFEKDKYILQGVTSWGLGCARPNKPGVYARVSRFVTWIEGMMRNN In one embodiment, the dTAG has an amino acid sequence derived from lactoglutathione lyase, UniProtKB-Q04760 (LGUL_HUMAN) (incorporated herein by reference), or a variant thereof. In one embodiment, the dTAG is derived from the amino acid sequence:

(SEQ. ID. NO.: 43)
MAEPQPPSGGLTDEAALSCCSDADPSTKDFLLQQTMLRVKDPKKSLDFYT
RVLGMTLIQKCDFPIMKFSLYFLAYEDKNDIPKEKDEKIAWALSRKATLE
LTHNWGTEDDETQSYHNGNSDPRGFGHIGIAVPDVYSACKRFEELGVKFV
KKPDDGKMKGLAFIQDPDGYWIEILNPNKMATLM.

In one embodiment, the dTAG has an amino acid sequence derived from protein afadin, UniProtKB-P55196 (AFAD_HUMAN) (incorporated herein by reference), or a variant thereof. In one embodiment, the dTAG is derived from the amino acid sequence:

(SEQ. ID. NO.: 44)
MSAGGRDEERRKLADIIHHWNANRLDLFEISQPTEDLEFHGVMRFYFQDK
AAGNFATKCIRVSSTATTQDVIETLAEKFRPDMRMLSSPKYSLYEVHVSG
ERRLDIDEKPLVVQLNWNKDDREGRFVLKNENDAIPPKKAQSNGPEKQEK
EGVIQNFKRTLSKKEKKEKKKREKEALRQASDKDDRPFQGEDVENSRLAA
EVYKDMPETSFTRTISNPEVVMKRRRQQKLEKRMQEFRSSDGRPDSGGTL
RIYADSLKPNIPYKTILLSTTDPADFAVAEALEKYGLEKENPKDYCIARV
MLPPGAQHSDEKGAKEIILDDDECPLQIFREWPSDKGILVFQLKRRPPDH
IPKKTKKHLEGKTPKGKERADGSGYGSTLPPEKLPYLVELSPGRRNHFAY
YNYHTYEDGSDSRDKPKLYRLQLSVTEVGTEKLDDNSIQLFGPGIQPHHC
DLTNMDGVVTVTPRSMDAETYVEGQRISETTMLQSGMKVQFGASHVFKFV
DPSQDHALAKRSVDGGLMVKGPRHKPGIVQETTFDLGGDIHSGTALPTSK
STTRLDSDRVSSASSTAERGMVKPMIRVEQQPDYRRQESRTQDASGPELI
LPASIEFRESSEDSFLSAIINYTNSSTVHFKLSPTYVLYMACRYVLSNQY
RPDISPTERTHKVIAVVNKMVSMMEGVIQKQKNIAGALAFWMANASELLN
FIKQDRDLSRITLDAQDVLAHLVQMAFKYLVHCLQSELNNYMPAFLDDPE
ENSLQRPKIDDVLHTLTGAMSLLRRCRVNAALTIQLFSQLFHFINMWLFN
RLVTDPDSGLCSHYWGAIIRQQLGHIEAWAEKQGLELAADCHLSRIVQAT
TLLTMDKYAPDDIPNINSTCFKLNSLQLQALLQNYHCAPDEPFIPTDLIE
NVVTVAENTADELARSDGREVQLEEDPDLQLPFLLPEDGYSCDVVRNIPN
GLQEFLDPLCQRGFCRLIPHTRSPGTWTIYFEGADYESEILLRENTELAQ
PLRKEPEIITVTLKKQNGMGLSIVAAKGAGQDKLGIYVKSVVKGGAADVD
GRLAAGDQLLSVDGRSLVGLSQERAAELMTRTSSVVTLEVAKQGAIYHGL
ATLLNQPSPMMQRISDRRGSGKPRPKSEGFELYNNSTQNGSPESPQLPWA
EYSEPKKLPGDDRLMKNRADHRSSPNVANQPPSPGGKSAYASGTTAKITS
VSTGNLCTEEQTPPPRPEAYPIPTQTYTREYFTFPASKSQDRMAPPQNQW
PNYEEKPHMHTDSNHSSIAIQRVTRSQEELREDKAYQLERHRIEAAMDRK
SDSDMWINQSSSLDSSTSSQEHLNHSSKSVTPASTLTKSGPGRWKTPAAI
PATPVAVSQPIRTDLPPPPPPPPVHYAGDFDGMSMDLPLPPPPSANQIGL
PSAQVAAAERRKREEHQRWYEKEKARLEEERERKRREQERKLGQMRTQSL
NPAPFSPLTAQQMKPEKPSTLQRPQETVIRELQPQQQPRTIERRDLQYIT
VSKEELSSGDSLSPDPWKRDAKEKLEKQQQMHIVDMLSKEIQELQSKPDR
SAEESDRLRKLMLEWQFQKRLQESKQKDEDDEEEEDDDVDTMLEVIQRLE
AERRARLQDEERRRQQQLEEMRKREAEDRARQEEERRRQEEEERTKRDAEE
KRRQEEGYYSRLEAERRRQHDEAARRLLEPEAPGLCRPPLPRDYEPPSPS
PAPGAPPPPPQRNASYLKTQVLSPDSLFTAKFVAYNEEEEEEDCSLAGPN
SYPGSTGAAVGAHDACRDAKEKRSKSQDADSPGSSGAPENLTFKERQRLF
SQGQDVSNKVKASRKLTELENELNTK.

In one embodiment, the dTAG has an amino acid sequence derived from epidermal growth factor receptor (EGFR, UniProtKB P00533(EGFR_HUMAN) incorporated herein by reference, or a variant thereof. In one embodiment, the dTAG is derived from, includes, or is the amino acid sequence:

(SEQ. ID. NO.: 53): (L858R)
GEAPNQALLRILKETEFKKIKVLGSGAFGTVYKGLWIPEGEKVKIPVAIK

ELREATSPKANKEILDEAYVMASVDNPHVCRLLGICLTSTVQLITQLMPF

GCLLDYVREHKDNIGSQYLLNWCVQIAKGMNYLEDRRLVHRDLAARNVLV

KTPQHVKITDFGRAKLLGAEEKEYHAEGGKVPIKWMALESILHRIYTHQS

DVWSYGVTVWELMTFGSKPYDGIPASEISSILEKGERLPQPPICTIDVYM

IMVKCWMIDADSRPKFRELIIEFSKMARDPQRYLVIQGDERMHLPSPTDS

NFYRALMDEEDMDDVVDADEYLIPQQG.

In one embodiment, the dTAG is derived from, includes, or is the amino acid sequence:

(SEQ. ID. NO.: 54): (T790M)
GEAPNQALLRILKETEFKKIKVLGSGAFGTVYKGLWIPEGEKVKIPVAIK

ELREATSPKANKEILDEAYVMASVDNPHVCRLLGICLTSTVQLIMQLMPF

GCLLDYVREHKDNIGSQYLLNWCVQIAKGMNYLEDRRLVHRDLAARNVLV

KTPQHVKITDFGRAKLLGAEEKEYHAEGGKVPIKWMALESILHRIYTHQS

DVWSYGVTVWELMTFGSKPYDGIPASEISSILEKGERLPQPPICTIDVYM

IMVKCWMIDADSRPKFRELIIEFSKMARDPQRYLVIQGDERMHLPSPTDS

NFYRALMDEEDMDDVVDADEYLIPQQG.

In one embodiment, SEQ. ID. NO.: 54 has a Leucine at position 163.

In one embodiment, the dTAG is derived from, includes, or is the amino acid sequence:

(SEQ. ID. NO.: 55): (C797S)
GEAPNQALLRILKETEFKKIKVLGSGAFGTVYKGLWIPEGEKVKIPVAIK

ELREATSPKANKEILDEAYVMASVDNPHVCRLLGICLTSTVQLIMQLMPF

GSLLDYVREHKDNIGSQYLLNWCVQIAKGMNYLEDRRLVHRDLAARNVLV

KTPQHVKITDFGRAKLLGAEEKEYHAEGGKVPIKWMALESILHRIYTHQS

DVWSYGVTVWELMTFGSKPYDGIPASEISSILEKGERLPQPPICTIDVYM

IMVKCWMIDADSRPKFRELIIEFSKMARDPQRYLVIQGDERMHLPS.

In one embodiment, SEQ. ID. NO.: 55 has a Leucine at position 163. In one embodiment, SEQ. ID. NO.: 55 has a Threonine at position 95. In one embodiment, SEQ. II). NO.: 55 has a Leucine at position 163 and a Threonine at position 95. In one embodiment, the dTAG is derived from, includes, or is the amino acid sequence:

(SEQ. ID. NO.: 56): (C790G)
GEAPNQALLRILKETEFKKIKVLGSGAFGTVYKGLWIPEGEKVKIPVAIK

ELREATSPKANKEILDEAYVMASVDNPHVCRLLGICLTSTVQLIMQLMPF

GCGLDYVREHKDNIGSQYLLNWCVQIAKGMNYLEDRRLVHRDLAARNVLV

KTPQHVKITDFGRAKLLGAEEKEYHAEGGKVPIKWMALESILHRIYTHQS

DVWSYGVTVWELMTFGSKPYDGIPASEISSILEKGERLPQPPICTIDVYM

IMVKCWMIDADSRPKFRELIIEFSKMARDPQRYLVIQGDERMHLPSPTDS

NFYRALMDEEDMDDVVDADEYLIPQQG.

In one embodiment, SEQ. ID. NO.: 56 has a Leucine at position 163. In one embodiment, SEQ. ID. NO.: 56 has a Threonine at position 95. In one embodiment, SEQ. ID. NO.: 56 has a Leucine at position 163 and a Threonine at position 95.

In one embodiment, the dTAG has an amino acid sequence derived from epidermal growth factor receptor (BCR-ABL, or a variant thereof. In one embodiment, the dTAG is derived from, includes, or is the amino acid sequence:

(SEQ. ID. NO.: 57): (T315I)
SPNYDKWEMERTDITMKHKLGGGQYGEVYEGVWKKYSLTVAVKTLKEDTM

EVEEFLKEAAVMKEIKHPNLVQLLGVCTREPPFYIIIEFMTYGNLLDYLR

ECNRQEVNAVVLLYMATQISSAMEYLEKKNFIHRDLAARNCLVGENHLVK

VADFGLSRLMTGDTYTAHAGAKFPIKWTAPESLAYNKFSIKSDVWAFGVL

LWEIATYGMSPYPGIDLSQVYELLEKDYRMERPEGCPEKVYELMRACWQW

NPSDRPSFAFIHQAFETMFQES.

In one embodiment, SEQ. ID. NO.: 57 has a Threonine at position 87.

In one embodiment, the dTAG has an amino acid sequence derived from BCR-ABL (BCR-ABL) or a variant thereof. In one embodiment, the dTAG is derived from, includes, or is the amino acid sequence:

(SEQ. ID. NO.: 58):
SPNYDKWEMERTDITMKHKLGGGQYGEVYEGVWKKYSLTVAVKTLKEDTM

EVEEFLKEAAVMKEIKHPNLVQLLGVCTREPPFYIITEFMTYGNLLDYLR

ECNRQEVNAWLLYMATQISSAMEYLEKKNFIHRDLAARNCLVGENHLVKV

ADFGLSRLMTGDTYTAHAGAKFPIKWTAPESLAYNKFSIKSDVWAFGVLL

WEIATYGMSPYPGIDLSQVYELLEKDYRMERPEGCPEKVYELMRACWQWN

PSDRPSFAEIHQAFETMFQES.

In one embodiment, the dTAG has an amino acid sequence derived from ALK (ALK, UniProtKB Q9UM73 (ALK_HUMAN) incorporated herein by reference, or a variant thereof. In one embodiment, the dTAG is derived from, includes, or is the amino acid sequence:

(SEQ ID NO.: 59) (L1196M):
ELQSPEYKLSKLRTSTIMTDYNPNYCFAGKTSSISDLKEVPRKNITLIRG

LGHGAFGEVYEGQVSGMPNDPSPLQVAVKTLPEVCSEQDELDFLMEALII

SKFNHQNIVRCIGVSLQSLPRFIMLELMAGGDLKSFLRETRPRPSQPSSL

AMLDLLHVARDIACGCQYLEENHFIHRDIAARNCLLTCPGPGRVAKIGDF

GMARDIYRAGYYRKGGCAVILPVKWMPPEAFMEGIFTSKTDTWSFGVLLW

EIFSLGYMPYPSKSNQEVLEFVTSGGRMDPPKNCPGPVYRIMTQCVVQHQ

PEDRPNFAIILERIEYCTQDPDVINTALPIEYGPLVEEEEK.

In one embodiment, SEQ. ID. NO.: 59 has a Leucine at position 136.

In one embodiment, the dTAG has an amino acid sequence derived from JAK2 (JAK2, UniProtKB O60674 (JAK2_HUMAN) incorporated herein by reference, or a variant thereof. In one embodiment, the dTAG is derived from, includes, or is the amino acid sequence:

(SEQ. ID. NO.: 60) (V617F):
VFHKIRNEDLIFNESLGQGTFTKIFKGVRREVGDYGQLHETEVLLKVLDK

AHRNYSESFFEAASMNISKLSHKHLVLNYGVCFCGDENILVQEFVKFGSL

DTYLKKNKNCINILWKLEVAKQLAWAMHFLEENTLIHGNVCAKNILLIRE

EDRKTGNPPFIKLSDPGISITVLPKDILQERIPWVPPECIENPKNLNLAT

DKWSFGTTLWEICSGGDKPLSALDSQRKLQFYEDRHQLPAPKAAELANLI

NNCMDYEPDEIRPSFRAIIRDLNSLFTPD.

In one embodiment, SEQ. ID. NO.: 60 has a valine at position 82.

In one embodiment, the dTAG has an amino acid sequence derived from BRAF (BRAF, UniProtKB P15056 (BRAF HUMAN) incorporated herein by reference, or a variant thereof. In one embodiment, the dTAG is derived from, includes, or is the amino acid sequence:

(SEQ. ID. NO 61) (V600E)
DWEIPDGQITVGQRIGSGSFGTVYKGKWHGDVAVKMLNVTAPTPQQLQAF

KNEVGVLRKTRHVNILLFMGYSTAPQLAIVTQWCEGSSLYHHLHASETKF

EMKKLIDIARQTARGMDYLHAKSIIHRDLKSNNIFLHEDNTVKIGDFGLA

TEKSRWSGSHQFEQLSGSILWMAPEVIRMQDSNPYSFQSDVYAFGIVLYE

LMTGQLPYSNINNRDQIIEMVGRGSLSPDLSKVRSNCPKRMKRLMAECLK

KKRDERPSFPRILAEIEELARE.

In one embodiment, SEQ. ID. NO.: 61 has a Valine at position 152. In one embodiment, SEQ. ID. NO. 61 has a Tyrosine at position 153. In one embodiment, SEQ. ID. NO.: 61 has a Valine at position 152. In one embodiment, SEQ. ID. NO. 61 has a Lysine at position 153. In one embodiment, SEQ. ID. NO.: 61 has a Valine at position 152 and a Lysine at position 153.

In one embodiment, the dTAG has an amino acid sequence derived from a LRRK2 protein (UniProtKB Q5S007 (LRRK2_HUMAN) incorporated herein by reference), or variant thereof. In one embodiment, the dTAG is derived from LRRK2 amino acid 1328 to 1511. In one embodiment, the dTAG is derived from LRRK2 amino acid 1328 to 1511, wherein amino acid 1441 is Cysteine In one embodiment, the dTAG has an amino acid sequence derived from a PDGFRa protein (UniProtKB-P09619 (PDGFRHUMAN) incorporated herein by reference), or variant thereof. In one embodiment, the dTAG is derived from amino acid 600 to 692 of P09619. In one embodiment, the dTAG is derived from amino acid 600 to 692 of P09619, wherein amino acid 674 is Isoleucine.

In one embodiment, the dTAG has an amino acid sequence derived from a RET protein (UniProtKB-P07949 (RET_HUMAN) incorporated herein by reference), or variant thereof. In one embodiment, the dTAG is derived from amino acid 724 to 1016 of P07949. In one embodiment, the dTAG is derived from amino acid 724 to 1016 of P07949, wherein amino acid 691 is Serine. In one embodiment, the dTAG is derived from amino acid 724 to 1016 of P07949, wherein amino acid 749 is Threonine. In one embodiment, the dTAG is derived from amino acid 724 to 1016 of P07949, wherein amino acid 762 is Glutamine. In one embodiment, the dTAG is derived from amino acid 724 to 1016 of P07949, wherein amino acid 791 is Phenylalanine. In one embodiment, the dTAG is derived from amino acid 724 to 1016 of P07949, wherein amino acid 804 is Methionine. In one embodiment, the dTAG is derived from amino acid 724 to 1016 of P07949, wherein amino acid 918 is Threonine.

In one embodiment, the dTAG has an amino acid sequence derived from a JAK3 protein (UniProtKB-P52333 (JAK3_HUMAN) incorporated herein by reference), or variant thereof.

In one embodiment, the dTAG has an amino acid sequence derived from a ABL protein (UniProtKB-P00519 (ABL_HUMAN) incorporated herein by reference), or variant thereof.

In one embodiment, the dTAG has an amino acid sequence derived from a MEK1 protein (UniProtKB-Q02750 (MP2K1_HUMAN) incorporated herein by reference), or variant thereof.

In one embodiment, the dTAG has an amino acid sequence derived from a KIT protein (UniProtKB-P10721 (KIT_HUMAN) incorporated herein by reference), or variant thereof.

In one embodiment, the dTAG has an amino acid sequence derived from a KIT protein (UniProtKB-P10721 (KIT_HUMAN) incorporated herein by reference), or variant thereof.

In one embodiment, the dTAG has an amino acid sequence derived from a HIV reverse transcriptase protein (UniProtKB-P04585 (POL_HV1H2) incorporated herein by reference), or variant thereof.

In one embodiment, the dTAG has an amino acid sequence derived from a HIV integrase protein (UniProtKB-Q76353 (Q76353_9HIV1)) incorporated herein by reference), or variant thereof.

B. Proteins of Interest

As contemplated herein, the dTAG strategy can be utilized to produce a stably expressed, endogenous protein-dTAG hybrid in vivo, or as the case may be ex vivo or in vitro, by genomic insertion of the dTAG nucleic acid sequence either 5'- or 3' in-frame with the nucleic acid sequence encoding the protein of interest. Following the insertion of the in-frame dTAG nucleic acid sequence, the cell expresses the endogenous protein-dTAG hybrid, allowing for the modulation of the activity of the endogenous protein-dTAG hybrid through the administration of a heterobifunctional compound that is capable of binding the dTAG and thus degrading the endogenous protein-dTAG hybrid. In one embodiment, the activity of the endogenous protein-dTAG hybrid is reduced.

In certain embodiments, a nucleic acid encoding a dTAG can be genomically inserted in-frame with a gene encoding a protein that is involved in a disorder. Non-limiting examples of particular genes involved in disorders that may be targeted for dTAG insertion include by way of non-limiting example, alpha-1 antitrypsin (A1AT), apolipoprotein B (APOB), angiopoietin-like protein 3 (ANGPTL3), proprotein convertase subtilisin/kexin type 9 (PCSK9), apolipoprotein C3 (APOC3), catenin (CTNNB1), low density lipoprotein receptor (LDLR), C-reactive protein (CRP), apolipoprotein a (Apo(a)), Factor VII, Factor XI, antithrombin III (SERPINC1), phosphatidylinositol glycan class A (PIG-A), C5, alpha-1 antitrypsin (SERPINA1), hepcidin regulation (TMPRSS6), (delta-aminolevulinate synthase 1 (ALAS-1), acylCaA:diacylglycerol acyltransferase (DGAT), miR-122, miR-21, miR-155, miR-34a, prekallikrein (KLKB1), connective tissue growth factor (CCN2), intercellular adhesion molecule 1 (ICAM-1), glucagon receptor (GCGR), glucorticoid receptor (GCCR), protein tyrosine phosphatase (PTP-1B), c-Raf kinase (RAF1), fibroblast growth factor receptor 4 (FGFR4), vascular adhesion molecule-1 (VCAM-1), very late antigen-4 (VLA-4), transthyretin (TTR), survival motor neuron 2 (SMN2), growth hormone receptor (GHR), dystophia myotonic protein kinase (DMPK), cellular nucleic acid-binding protein (CNBP or ZNF9), clusterin (CLU), eukaryotic translation initiation factor 4E (eIF-4e), MDM2, MDM4, heat shock protein 27 (HSP 27), signal transduction and activator of transcription 3 protein (STAT3), vascular endothelial growth factor (VEGF), kinesin spindle protein (KIF11), hepatitis B genome, the androgen receptor (AR), Atonal homolog 1 (ATOH1), vascular endothelial growth factor receptor 1 (FLT1), retinoschism 1 (RS1), retinal pigment epithelium-specific 65 kDa protein (RPE65), Rab escort protein 1 (CHM), and the sodium channel, voltage gated, type X, alpha subunit (PN3 or SCN10A). Additional proteins of interest that may be targeted by dTAG insertion include proteins associated with gain of function mutations, for example, cancer causing proteins.

In particular embodiments, the protein of interest for targeting is apoB-100, ANGPTL3, PCSK9, APOC3, CRP, ApoA, Factor XI, Factor VII, antithrombin III, phosphatidylinositol glycan class A (PIG-A), the C5 component of complement, Alpha-1-antitrypsin (A1AT), TMPRSS6, ALAS-1, DGAT-2, KLB1, CCN2, ICAM, glucagon receptor, glucocorticoid receptor, PTP-1B, FGFR4, VCAM-1, VLA-4, GCCR, TTR, SMN1, GHR, DMPK, or NAV1.8.

In one embodiment, the dTAG is genomically integrated in-frame, either 5' or 3', into the gene encoding for an endogenous protein associated with a proteopathy. In one embodiment the dTAG is genomically integrated in-frame, either 5' or 3', into the gene encoding for an endogenous protein associated with a disorder selected from is genomically inserted in-frame, either 5' or 3', into the gene encoding for an endogenous protein associated with Alzheimer's disease (Amyloid β peptide (Aβ); Tau protein), Cerebral β-amyloid angiopathy (Amyloid β peptide (A13)), Retinal ganglion cell degeneration in glaucoma (Amyloid β peptide (Aβ)), Prion diseases (Prion protein), Parkinson's disease and other synucleinopathies (α-Synuclein), Tauopathies (Microtubule-associated protein tau (Tau protein)), Fronto-temporal lobar degeneration (FTLD) (Ubi+, Tau−) (TDP-43), FTLD-FUS (Fused in sarcoma (FUS) protein), Amyotrophic lateral sclerosis (ALS) (Superoxide dismutase, TDP-43, FUS), Huntington's disease and other triplet repeat disorders (Proteins with tandem glutamine expansions), Familial British dementia (ABri), Familial Danish dementia (Adan), Hereditary cerebral hemorrhage with amyloidosis (Icelandic) (HCHWA-I) (Cystatin C), CADASIL (Notch3), Alexander disease (Glial fibrillary acidic protein (GFAP)), Seipinopathies (Seipin), Familial amyloidotic neuropathy, Senile systemic amyloidosis (Transthyretin), Serpinopathies (Serpins), AL (light chain) amyloidosis (primary systemic amyloidosis) (Monoclonal immunoglobulin light chains), AH (heavy chain) amyloidosis (Immunoglobulin heavy chains), AA (secondary) amyloidosis (Amyloid A protein), Type II diabetes (Islet amyloid polypeptide (IAPP; amylin)), Aortic medial amyloidosis (Medin (lactadherin)), ApoAI amyloidosis (Apolipoprotein AI), ApoAII amyloidosis (Apolipoprotein AII), ApoAIV amyloidosis (Apolipoprotein AIV), Familial amyloidosis of the Finnish type (FAF) (Gelsolin), Lysozyme amyloidosis (Lysozyme), Fibrinogen amyloidosis (Fibrinogen), Dialysis amyloidosis (Beta-2 microglobulin), Inclusion body myositis/myopathy (Amyloid β peptide (Aβ)), Cataracts (Crystallins), Retinitis pigmentosa with rhodopsin mutations (rhodopsin), Medullary thyroid carcinoma (Calcitonin), Cardiac atrial amyloidosis (Atrial natriuretic factor), Pituitary prolactinoma (Prolactin), Hereditary lattice corneal dystrophy (Keratoepithelin), Cutaneous lichen amyloidosis (Keratins), Mallory bodies (Keratin intermediate filament proteins), Corneal lactoferrin amyloidosis (Lactoferrin), Pulmonary alveolar proteinosis (Surfactant protein C (SP-C)), Odontogenic (Pindborg) tumor amyloid (Odontogenic ameloblast-associated protein), Seminal vesicle amyloid (Semenogelin I), Cystic Fibrosis (cystic fibrosis transmembrane conductance regulator (CFTR) protein), Sickle cell disease (Hemoglobin), and Critical illness myopathy (CIM) (Hyperproteolytic state of myosin ubiquitination).

As contemplated herein, by genomically inserting a nucleic acid encoding a dTAG in frame with particular proteins of interest, modulation of the protein of interest can be achieved by administering a heterobifunctional compound specific for the dTAG, which binds to the protein-dTAG hybrid, leading to its degradation. Because of the ability to modulate a particular protein of interest in this manner, such a strategy can be used to treat disorders wherein expression of a protein above certain threshold levels within the cell leads to a diseased state. Other applications of this technology include, but are not limited to 1.) targeted degradation of proteins where pathology is a function of gain of function mutation(s), 2) targeted degradation of proteins where pathology is a function of amplification or increased expression, 3) targeted degradation of proteins that are manifestations of monogenetic disease, 4) targeted degradation of proteins where genetic predisposition manifests over longer periods and often after alternative biological compensatory mechanisms are no longer adequate, for example, but not limited to, hypercholesterolemia and proteinopathies.

By controlled degradation of the endogenous protein-dTAG hybrid, a favorable change in protein expression or activity kinetics may result in prevention and/or treatment of a disorder in a subject in need thereof.

Exemplary diseases and disorders capable of being treated by the currently contemplated methods are described, for example, in U.S. Application No. 20150329875 titled "Methods and Compositions for Prevention of Treatment of a Disease," incorporated herein by reference.

In certain embodiments, the target proteins are involved in lipid metabolism. For example, hypercholesterolemia is a condition characterized by very high levels of cholesterol in the blood which is known to increase the risk of coronary artery disease. Familial hypercholesterolemia, hyperlipidemia, and familial chylomicronemia are genetic conditions passed through families where an aberrant gene causes the observed symptomology. Mutations in genes encoding the LDL receptor (LDLR), Apolipoprotein B (APOB), angiopoietin-like protein 3 (ANGPTL3) and proprotein convertase subtilisin/kexin type 9 (PCSK9) are involved in these diseases. The LDLR serves to remove LDL from the plasma for internalization into the cell. The LDLR is a transmembrane protein that localizes to clathrin-coated pits where it forms a complex with ApoB-100 (the longer gene product of APOB) and apoE enriched lipoproteins. Following endocytosis of this complex, it moves to the endosome where the lipoproteins are released from the complex for eventual degradation by the lysosome. The LDLR can then be recycled back to the cell surface.

Patients with defective apoB-100, termed 'Familial defective apolipoprotein B' (FDB), frequently carry a R3500Q mutation in APOB which makes LDL with reduced ability to bind to the LDLR, reducing plasma clearance, thus raising plasma levels of fatty acids (Innerarity et al, (1987) PNAS USA 84:6919). FDB is generally recognized as an autosomal dominant condition, and occurs in approximately 1:700 people of European descent (Ginsburg and Willard (2012) Genomic and Personalized Medicine, volumes 1 and 2. Academic Press, London. p. 507). Thus, in FDB patients that are heterozygous for the mutation at apoB-100, specific degradation of the defective apoB-100 allele by inserting a dTAG in-frame in the allele in liver cells and administering a heterobifunctional compound, resulting in the gene product of an apo-100 defective protein-dTAG hybrid, can cause correction of the disease.

Similarly, angiopoietin-like protein 3 (ANGPTL3) overexpression mutations that cause elevated levels of ANGPTL3 can cause hyperlipidemia in subjects. ANGPTL3 also acts as dual inhibitor of lipoprotein lipase (LPL) and endothelial lipase (EL), and increases plasma triglyceride and HDL cholesterol in rodents. ANGPTL3 is expressed primarily in the liver and secreted, and normally acts to increase plasma levels of triglycerides, LDL cholesterol and HDL cholesterol where it acts directly on the liver to regulate hepatocellular lipoprotein secretion and clearance (Musunuru et at (2010) N Engl J Med 363:23 p. 2220). Thus, the method of the invention can be used to treat hyperlipidemia related to ANGPTL3 overexpression through the targeted degradation of the protein using the dTAG insertion strategy described herein.

PCSK9 is another gene encoding a protein that plays a major regulatory role in cholesterol homeostasis. PCSK9 binds to the epidermal growth factor-like repeat A (EGF-A) domain of LDLR, and induces LDLR degradation. Autosomal dominant, toxic gain of function mutations in PCSK9 (e.g. S127R, P216L, D374Y and N157K) have been described and are associated with hyperlipidemia and Familial hypercholesterolemia (FH) as a result of an increased rate of LDLR degradation leading to a corresponding increase in plasma LDL cholesterol (Abifadel et at (2003) Nat Gen 34(2):154). In addition, loss of function PCSK9 mutations have been identified (e.g. Y142X, C679X and R46L) that cause an increase in hepatic LDLR levels, with an associated substantial decrease in the amount of plasma LDL cholesterol, leading to an 88% reduction in the incidence of coronary heart disease (Cohen et at (2003) New Eng J Med 354(12): 1264). Thus the methods and compositions of the invention can be used to treat or prevent hyperlipidemia and/or FH through the targeted degradation of the PCSK9 protein using the dTAG insertion strategy described herein.

Familial chylomicronemia syndrome, or FCS, is characterized by extremely high levels of plasma triglycerides and lead to a number of health problems such as abdominal pain, enlargement of the liver and spleen and recurrent acute pancreatitis. In addition, there are subjects with high triglyceride levels that do not have FCS, but, due to the elevated triglycerides, have similar health issues. Apolipoprotein C3, or apo-CIII, encoded by the APOC3 gene, is a component of very low lipoprotein (VLDL), LDL, HDL and chylomicrons, and normally inhibits lipolysis by inhibiting lipoprotein lipase and hepatic lipase. Apo-CIII inhibits hepatic uptake of triglyceride-rich particles and can be elevated in patients with hyperlipidemia (Bobik, (2008) Circulation 118:702) and is an independent cardiovascular disease risk factor. Knocking out the APOC3 agene in mice results in animals with reduced plasma triglyceride levels as compared to normal (Maeda et al (1994) J Biol Chem 269(38):23610). Thus, the methods and compositions of the invention can be used to prevent or treat a subject with lipid metabolism disorders (e.g., familial hypercholesterolemia, hyperlipidemia, and familial chylomicronemia) by targeted degradation of the APOC3 protein through use of the dTAG insertion strategy described herein.

In other embodiments, the target protein(s) are involved in vascular diseases such as cardiovascular disease and coronary artery disease. Similar to the lipid metabolism disorders discussed above, coronary artery diseases can also be caused by specific genes. For example, C-reactive protein (CRP) is a protein produced in the liver that has been associated with inflammatory disease. It is an acute phase protein that binds to phosphocholine expressed on the surface of dead or dying cells where its job is to activate the complement system to help clear the cell. In chronic inflammatory disease, increased levels of CRP may exacerbate disease symptoms by contributing and amplifying an overall chronic inflammatory state. In addition, it has been shown in rat models that CRP increases myocardial and cerebral infarct size, which, when translated into human patients, maybe predicative of a more negative prognosis following heart attack. When inhibitors of CRP are introduced into these rat models, infarct size and cardiac dysfunction are decreased (Pepys et at (2005) Nature 440(27):1217). Inhibition of CRP thus may be beneficial both in inflammatory diseases and in coronary artery disease. The methods and compositions of the invention may be used to cause modulation of CRP expression by targeted degradation of the CRP protein through use of the dTAG insertion strategy described herein.

Plasma lipoprotein (Lp(a)) is a low density lipoprotein particle comprising Apolipoprotein(a) (apo(a)), and is also an independent risk factor for cardiovascular disease including atherosclerosis. Apo(a) contacts the surface of LDL through apoB-100, linked by a disulfide bond, and it has been reported that genetic polymorphisms associated with elevated Apo(a) levels are associated with an excessive rate of myocardial infarction (Chasman et at (2009) Atherosclerosis 203(2):371). Lp(a) concentration in the plasma varies widely in concentration between individuals, where these concentration differences appear to be genetically determined. The apo(a) gene comprises a number of plasminogen kringle 4-like repeats, and the number of these kringle repeats is inversely related to plasma concentration of Lp(a). A DNA-vaccine approach, designed to mount an immune response to apo(a) and cause antibody-mediated clearance of Lp(a), demonstrated a reduction in the proatherosclerotic activity of Lp(a) in mice (Kyutoku et at (2013) Sci Rep 3 doi: 10.1038/srep1600). Thus the methods and compositions of the invention can be used to reduce the expression of the ApoA protein, resulting in a decrease in plasma concentration of Lp(a), by targeted degradation of the ApoA protein through use of the dTAG insertion strategy described herein.

Clotting disorders, often referred to as thrombophilia, can have ramifications in vascular diseases. The complex network of biochemical events regulating mammalian coagulation comprises 5 proteases (factors II, VII, IX, and X and protein C) that interface with 5 cofactors (tissue factor, factor V, factor VIII, thrombomodulin, and surface membrane proteins) to generate fibrin, which is the main component of a clot. A delicate balance exists between powerful endogenous procoagulant and thromboresistant forces to ensure the fluidity of blood and maintain the readiness of these factors to induce a blood clot if an injury occurs. High plasma activity of both Factor XI and Factor VII are associated with hypercoagulation and thrombotic disease (coronary infarcts, stroke, deep vein thrombosis, pulmonary embolism) and with poor patient prognosis. It has been demonstrated that people that with severe Factor XI deficiency are protected from ischemic brain injury and stroke (Saloman et at (2008) Blood 111:4113). At the same time, it has been shown that high levels of FXI are associated with higher rates of stroke incidents in patients (Yang et at (2006) Am J Clin Path 126: 411). Similarly, high Factor VII levels are also associated with coronary artery disease although this is complicated by other considerations such as how the Factor VII is measured, and which form of the protein is analyzed (Chan et at (2008) Circulation 118:2286). Thus, the methods and compositions of the invention can be used to prevent or treat subjects with hyperthrombotic disease through selective degradation of clotting factors associated with the disease (for example, Factor VII and Factor XI) by targeted degradation of Factor XI and/or Factor VII through use of the dTAG insertion strategy described herein.

As described above, the balance of the clotting cascade is crucial. Thus, in addition to the importance of the clotting factors, the inhibitors of these factors are also critical. Patients with hemophilias are deficient in one or more components of the clotting cascade, and have a reduced clotting capacity as a consequence. In one of the last steps of this cascade, thrombin acts on fibrinogen to create fibrin which is the main component of the clot. The cascade leads up to the production of active thrombin to allow this to occur. To keep the system balanced, antithrombin (also known as antithrombin III, encoded by the SERPINC1 gene) acts upon thrombin to inhibit its action. In many hemophilias, the factor deficiency is not absolute and there is some degree of clotting that occurs. Thus an approach based on degradation of antithrombin could allow the clotting cascade to produce sufficient clotting when the upstream factors are limited, potentially regardless of which factor is deficient. This has been demonstrated using blood derived from hemophilia A patients (see Di Micco et at (2000) Eur J Pharmacol. March 10; 391(1-2): 1-9.). The methods and compositions of the invention can be used to treat patients with hemophilias such as Hemophilia A and Hemophilia B by targeted degradation of the antithrombin III protein through use of the dTAG insertion strategy described herein.

The target protein(s) may also be involved in blood disorders (hematological conditions). The complement system is a pivotal player in multiple hematological conditions. Paroxysmal nocturnal hemoglobinuria (PNH) is a hemolytic disease caused by a defect in the PIG-A gene (see Brodsky (2008) Blood Rev 22(2):65). The PIG-A gene product phosphatidylinositol glycan class A is required for the first step in the synthesis of GPI-anchored proteins. PIG-A is found on the X chromosome and mutations in PIG-A result in red blood cells that are sensitive to hemolysis by complement. Notably, these mutant cells lack the GPI-anchored proteins CD55 and CD59. CD59 interacts directly with the complement related membrane attack complex (or MAC) to prevent lytic pore formation by blocking the aggregation of C9, a vital step in the assembly of the pore. CD55 functions to accelerate the destruction of the C3 convertase, so in the absence of CD55, there is more of the C3 convertase enzyme, leading to more MAC formation. Thus, the lack of both of these proteins leads to increases lysis of the mutant red blood cells. For patients with PNH, complications due to increased thrombosis are the greatest concern (Brodsky (2008) Blood Rev 22(2):65). 40% of PNH patients have ongoing thrombosis which can lead to stroke and acute cardiovascular disease. Thus, the methods and compositions of the inventions can be used to treat and/or prevent PHN in a subject by targeted degradation of the phosphatidylinositol glycan class A (PIG A) through use of the dTAG insertion strategy described herein.

Inhibition of the C5 component of complement has been approved as a treatment for both PNH and atypical hemolytic-uremic syndrome (aHUS), validating C5 as an important therapeutic target. The hemolysis of red blood cells associated with aHUS occurs when the cells are targeted for destruction by the alternative pathway due to a dysregulation of the complement system (part of innate immunity). Normally the destructive C3bBb complex is formed on the surface of an invading cell (e.g. a bacterium) to hasten its destruction as part of the alternative pathway in the complement system. The C3bBb complex can bind another C3b to form a C3bBbC3b complex which then acts as a C5 convertase. C5 convertase cleaves C5 to C5a and C5b, and C5b recruits C6, C7, C8 and C9 to form the MAC. A set of complement regulatory proteins (e.g. CD35, CD46, CD55 and CD59) are located on the body's own cells to inhibit the activity of these proteins and thus protect them. However, when there is an imbalance of these regulatory proteins, the C3bBb complex can form inappropriately (de Jorge et at (2011) J Am Soc Nephrol 22:137). This syndrome, in addition to the premature destruction of red blood cells can also lead to kidney disease as a result of the damaging and clogging of the glomerular filtering apparatus. C5 negative mice were shown to be protected when crossed with mice with complement regulator protein mutations, data that has been used to validate the idea of C5 as a target in aHUS (de Jorge, ibid) and other diseases related to complement dysregulation. The C5b-specific monoclonal antibody eculizamab has been successfully used to treat aHUS (Gruppo and Rother, (2009) N Engl J Med 360; 5 p 544) and other complement-mediated diseases (e.g. Paroxysmal Nocturnal Haemoglobinuria (PNH) (Hillmen et al, (2013) Br. J Haem 162:62)). Thus, the methods and compositions of the invention can be used to modulate the expression of C5 and so prevent or treat diseases associated with complement dysregulation by targeted degradation of C5 through use of the dTAG insertion strategy described herein.

Alpha-1-antitrypsin (A1AT) deficiency occurs in about 1 in 1500-3000 people of European ancestry but is rare in individuals of Asian descent. The alpha-1-antitrypsin protein is a protease inhibitor that is encoded by the SERPINA1 gene and serves to protect cells from the activity of proteases released by inflammatory cells, including neutrophil elastase, trypsin and proteinase-3 (PR-3). Deficiency is an autosomal co-dominant or a recessive disorder caused by mutant SERPINA1 genes in heterozygous individuals where reduced expression from the mutant allele or the expression of a mutant A1AT protein with poor inhibitory activity leads to chronic lack of inhibition of neutrophil elastase resulting in tissue damage. The most common SERPINA1 mutation comprises a Glu342Lys substitution (also referred to as the Z allele) that causes the protein to form ordered polymers in the endoplasmic reticulum of patient hepatocytes. These inclusions ultimately cause liver cirrhosis which can only be treated by liver transplantation (Yusa et at (2011) Nature 478 p. 391). The polymerization within the hepatocytes results in a severe decrease in plasma A1AT levels, leading to increased risk of this inflammatory disease. In addition, A1AT deficiency is linked to pulmonary diseases including chronic obstructive pulmonary disease (COPD), emphysema and chronic bronchitis (Tuder et at (2010) Proc Am Thorac Soc 7(6): p. 381) and potentially may have a far broader reach into the inhibition of the progression of other diseases including type 1 and type 2 diabetes, acute myocardial infarction, rheumatoid arthritis, inflammatory bowel disease, cystic fibrosis, transplant rejection, graft versus host disease and multiple sclerosis (Lewis (2012) Mol Med 18(1) p. 957). Population studies have suggested a minimum ATA1 plasma threshold of approximately 0.5 mg/mL (normal plasma levels are approximately 0.9-1.75 mg/ML in a non-inflammatory state) to avoid these diseases, and current therapies mostly act to reduce symptoms through the use of bronchodilators and the like, although the use of weekly infusions of A1AT (Zemaira®) is also an option for emphysema patients with a demonstrated severe lack of plasma A1AT. Severe lung disease associated with A1AT also is ultimately treated by transplant. Clinical trials for the treatment of A1AT deficiency involve a variety of approaches including the delivery of concentrated A1AT protein, use of an AAV construct comprising an A1AT gene by IM injection, and the use of A1AT in HIV, to list just a few. Thus, the compositions and methods of the invention can be used to treat or prevent diseases related to A1AT deficiency by targeted degradation of alpha-1-antitrypsin protein through use of the dTAG insertion strategy described herein, thereby eliminating the hepatic aggregates that can lead to cirrhosis.

Another liver target of interest includes any protein(s) that is(are) involved in the regulation of iron content in the body. Iron is essential for the hemoglobin production, but in excess can result in the production of reactive oxygen species. In patients that are dependent on blood transfusions (e.g. certain hemophilias, hemoglobinopathies), secondary iron overload is common. The iron-regulatory hormone hepcidin, and its receptor and iron channel ferroportin control the dietary absorption, storage, and tissue distribution of iron by promoting its cellular uptake. The regulation of hepcidin is done at a transcriptional level, and is sensitive to iron concentrations in the plasma where increased hepcidin expression leads to lower plasma iron concentrations. Through a series of receptor-ligand interactions, involving a receptor known as hemojuvelin, the hepcidin gene is upregulated by a SMAD transcription factor. Iron-related hepcidin down regulation in turn is regulated by a protease known as TMPRSS6, which cleaves hemojuvelin and prevents the upregulation of hepcidin (Ganz (2011) Blood 117:4425). Down regulation of TMPSS6 expression by use of an inhibitory RNA targeting the TMRSS6 mRNA has been shown to cause a decrease in iron overload in mouse models (Schmidt et al (2013) Blood 121:1200). Thus, the methods and compositions of the invention can be used to target TMPRSS6 for degradation through use of the dTAG insertion strategy described herein.

Other conditions related to iron utilization pathways in the body are porphyrias. These disorders result from a number of deficiencies in the enzymes involved in heme synthesis. Acute intermittent porphyia (AIP) is an autosomal dominant disorder and is the second most common porphyria, with an incidence of approximately 5-10 in 100,000 people. AIP is caused by a deficiency in hydroxymethylbilane synthase (HMB synthase (HMBS), also called porphobilinogen-deaminase), where the mutations in the HMBS gene are very heterogeneous, comprising missense and point mutations (Solis et al (1999) Mol Med 5:664). The potentially life-threatening AIP attacks can have gastrointestinal, neuropsychiatric, cardiovascular and nervous system manifestations. Attacks have several triggers, can last for several days, and often require hospitalization and can be precipitated by several seemingly unrelated factors including certain drugs, infection, caloric restriction, smoking, alcohol and hormonal fluctuations relating to the menstrual cycle (Yasuda et al (2010) Mol Ther 18(1):17). HMB synthase is part of the heme synthesis pathway, where glycine and succinyl-CoA are joined by delta-aminolaevulinate synthase 1 (ALAS-1) to make aminolevulinic acid, which is then acted upon by aminolevulinic acid dehydratase (ALAD) to make phospho-bilinogen. Phosphobilinogen is the converted to hydroxymethylbilane by HMB synthase. The pathway continues on from there, ultimately producing the heme (Ajioka et at (2006) Biochim Biophys Acta 1762:723). Regardless of the trigger, all attacks result in an elevation of the enzyme delta-aminolevulinate synthase 1 (ALAS-1). This enzyme is the first enzyme in the hepatic heme synthesis pathway and when induced, the deficiency in HMB synthase becomes rate-limiting and the aminolevulinic acid and phospho-bilinogen precursors accumulate (Yasuda, ibid). Liver transplant in AIP patients can stop the attacks, indicating that targeting the liver may be therapeutically beneficial. Additionally, in mouse models of AIP, where the mice have only 30% of normal HMB synthase levels, insertion of the transgene HMBS, encoding HMB synthase, resulted in a decrease in aminolevulinic acid and phosphobilinogen accumulation when the mice were given phenobarbital (Yasuda, ibid). Double stranded RNAs designed for the inhibition of ALAS-1 have also been shown to reduce ALAS-1 expression in vivo in a mouse AIP model and to reduce phospho-bilinogen accumulation in response to phenobarbital treatment (see U.S. Patent Publication 20130281511). Thus the methods and compositions of the invention may be used to prevent and treat AIP by targeted degradation of ALAS-1 using the dTAG insertion strategy described herein.

Non-alcoholic fatty liver disease (NAFLD) is the most common form of liver disease worldwide, with a prevalence of 15%-30% in Western populations and is caused by triglyceride accumulation within the liver. However, the prevalence increases to 58% in overweight populations and 98% in obese populations. Nonalcoholic steatohepatitis (NASH) is a more advanced form of NAFLD where liver injury has occurred, and can lead to liver failure, portal hypertension, hepatocarcinoma and cirrhosis (Schwenger and Allard (2014) World J Gastronen 20(7): 1712). Evidence appears to suggest that the hepatic triglyceride accumulation observed in NALFD is strongly associated with hepatic insulin resistance, often as a part of type 2 diabetes and metabolic syndrome (Choi et at (2017, J Biol Chem 282 (31): 22678). Acyl-CaA:diacylglycerol acyltransferase (DGAT) catalyzes the final step in triglyceride synthesis by facilitating the linkage of sn-1,2 diacylglygerol (DAG) with a long chain acyl CoA. There are two primary isoforms of DGAT, DGAT-1 and DGAT-2. DGAT-1 is primarily expressed in the small intestine while DGAT-2 exhibits primarily hepatic expression where its expression is insulin responsive. Knock down of expression of DGAT-1 or DGAT-2 using antisense oligonucleotides in rats with diet-induced NALFD significantly improved hepatic steatosis in the DGAT-2 knockdowns but not the DGAT-1 knockdowns (Choi, ibid). Thus, the materials and methods of the invention can be used to alter expression of DGAT-2 for the treatment of NASH and NALFD, and to reduce hepatic insulin resistance by targeted degradation of DGAT-2 using the dTAG insertion strategy described herein.

Further vascular targets include those involved in hereditary angioedema (HAE). HAE is an autosomal dominant disease that affects 1 in 50,000 people and is a result of decreased levels of the C1 inhibitor. Patients experience recurrent episodes of swelling in any part of the body where swelling localized to the oropharynx, larynx or abdomen carry the highest risk of morbidity and death (see Tse and Zuraw, (2013) Clev Clin J of Med 80(5):297). The disease occurs from extravasation of plasma into tissues as a result of the over production of bradykinin. The mechanism seems to involve the cleavage of prekallikrein (also known as PKK) by activate factor XII, releasing active plasma kallikrein (which activates more factor XII). Plasma kallikrein then cleaves kininogen, releasing bradykinin. The bradykinin then binds to the B2 bradykinin receptor on endothelial cells, increasing the permeability of the endothelium. Normally, the C1 inhibitor (encoded by SERPING1) controls bradykinin production by inhibiting plasma kallikrein and the activation of factor XII. HAE occurs in three types, Type I and II that are distinguished by the amount and type of C1 inhibitor present, and Type III which is tied to a Thr309Lys mutation in factor XII (Prieto et at (2009) Allergy 64(2): 284). Type I HAE has low levels of C1 inhibitor that appear to be a result of poor expression and destruction of the small amount of C1 inhibitor protein that is made. Type 1 accounts for approximately 85% of HAE patients. Type II patients have normal levels of C1 inhibitor, but the C1 inhibitor protein is ineffectual due to mutations (Tse and Zuraw, ibid). More than 250 mutations in SERPING1 have been characterized that lead to Type I HAE including small and large insertions and deletions as well as duplications (Rijavec et at (2013) PLoS One 8(2): e56712). Due to this high variability in the genetic basis of HAE, the methods and compositions of the invention can be used to prevent or treat HAE by targeting downstream players in the manifestation of HAE. For example, targeting prekallikrein (KLKB1, expressed in hepatocytes) to effect a decrease in prekallikrein (abbreviated PKK) expression can result in a decrease in bradykinin production without regard to the type of mutation upstream that is causing the HAE, and thus result in a decrease in plasma extravasation. Thus, the methods and compositions of the invention may be used to cause a decrease in the expression of KLKB1 to prevent or treat HAE by targeted degradation of KLKB1 using the dTAG insertion strategy described herein.

Target(s) may also be involved in a fibrotic disease. Fibrotic disease in various organs is the leading cause of organ dysfunction and can occur either as a reaction to another underlying disease or as the result of a predisposition towards fibrosis in an afflicted individual. The hallmark of fibrosis is the inappropriate deposition of extracellular matrix compounds such as collagens and related glycoproteins. TGF-β plays a major role in the fibrotic process, inducing fibroblasts to synthesize extracellular matrix (ECM) proteins, and it also inhibits the expression of proteins with ECM break down activity (Leask (2011) J Cell Commun Signal 5:125). There is a class of ECM regulatory proteins known as the CNN proteins (so-called because the first three members are described, namely CYR61 (cysteine-rich 61/CCN1), CTGF (connective tissue growth factor/CCN2), and NOV (nephroblastoma overexpressed/CCN3). These proteins regulate a variety of cellular functions including cell adhesion, migration, apoptosis, survival and gene expression. TGF-β strongly upregulates the CCN2 expression which acts synergistically as a co-factor with TGF-β and seems to be involved in pericyte activation, a process which appears to be essential in fibrosis (Leask ibid). CCN2 is overexpressed in fibrotic tissue, including pulmonary tissue and is also found in the plasma of patients with systemic sclerosis (scleroderma). Also, knock down of CCN2 expression through use of antisense oligonucleotides (ASO) reduced chemical-induced liver fibrosis, ureteral obstruction-induced renal fibrosis, fibrotic scarring in cutaneous wounds, and renal interstitial fibrogenesis following partial nephrectomy (Jun and Lau (2013) Nat Rev Drug Discov. 10(12): 945-963). In addition to its pro-fibrotic role, CCN2 may be important in cancer, especially in metastasis. It may promote tumor growth by inducing angiogenesis, and high levels of CCN2 in breast cancer cells is a marker of bone metastasis potential (Jun and Lau, ibid). Experimental models that knock down CCN2 expression in various models of fibrosis, cancer, cardiovascular disease and retinopathy through the use of CCN2 modulating compounds such as monoclonal antibodies or inhibitory RNAs have shown impact of clinical progression of a number of these diseases. (Jun and Lau ibid). Thus, the methods and compositions of the invention can be used to prevent or treat fibrosis, cancer, vascular disease and retinopathy by decreasing expression of CCN2 by targeted degradation of CCN2 using the dTAG insertion strategy described herein.

In other embodiments, the target(s) are involved in an autoimmune disease. Autoimmune diseases as a class are common, and affect more than 23 million people in the United States alone. There are several different kinds with many different levels of severity and prognoses. Generally, they are characterized by the production of auto-antibodies against various self-antigens leading to an immune response against one's own body. Autoimmune disease of the gut can lead to conditions such as ulcerative colitis and inflammatory/irritable bowel disease (e.g., Crohn's disease). The cell surface glycoprotein intercellular adhesion molecule 1 (ICAM-1) is expressed on endothelial cells and upregulated in inflammatory states, serving as a binding protein for leukocytes during transmigration into tissues. Specific ICAM-1 alleles have been found to be associated with Crohn's disease (e.g. K469E allele, exon 6) or with ulcerative colitis (e.g. G241R, exon 4) and may preferentially participate in the chronic inflammatory induction found in these diseases (Braun et at (2001) Clin Immunol. 101(3): 357-60). Knock out of ICAM in mouse models of vascular and diabetic disease have demonstrated the usefulness of this therapeutic approach (see Bourdillon et at (2000) Ather Throm Vasc Bio 20:2630 and Okada et at (2003) Diabetes 52:2586, respectively). Thus, the methods and compositions of this invention may be used for the general reduction of ICAM expression in inflammatory diseases by targeted degradation of ICAM using the dTAG insertion strategy described herein.

Another common disease that has been more recently recognized as an autoimmune disease is diabetes. Glucagon, a peptide hormone released by the α-cell of pancreatic islets, plays a key role in regulating hepatic glucose production and has a profound hyperglycemic effect. In addition, glucagon activates multiple enzymes required for gluconeogenesis, especially the enzyme system for converting pyruvate to phosphoenolpyruvate, the rate-limiting step in gluconeogenesis. It has been proposed that hyperglucagonemia is a causal factor in the pathogenesis of diabetes based on the following observations: 1) diabetic hyperglycemia, from animal to human studies, is consistently accompanied by relative or absolute hyperglucagonemia; 2) infusion of somatostatin inhibits endogenous glucagon release, which in turn reduces blood glucose levels in dogs with diabetes induced by alloxan or diazoxide; and 3) chronic glucagon infusion leads to hepatic insulin resistance in humans (see Liang et at (2004) Diabetes 53(2):410). The glucagon receptor (encoded by the GCGR gene) is expressed predominantly in the liver, and treatment of diabetic (db/db) mice with antisense RNA targeting the glucagon receptor causes a significant reduction in serum glucose levels, triglycerides and fatty acids in comparison with controls (Liang et al, ibid). Similarly, glucocorticoids (GCs) increase hepatic gluconeogenesis and play an important role in the regulation of hepatic glucose output. In db/db mice, a reduction in glucocorticoid receptor (GCCR) expression through the use of targeted antisense RNAs caused ~40% decrease in fed and fasted glucose levels and 50% reduction in plasma triglycerides (see Watts et at (2005) Diabetes 54(6):1846). Thus, the methods and compositions of the invention may be used to prevent or treat diabetes through targeting the glucagon receptor and/or the glucocorticoid receptor by decreasing expression of the glucagon receptor and/or glucocorticoid receptor by targeted degradation using the dTAG insertion strategy described herein.

Another potential target in type 2, insulin resistant diabetes is protein tyrosine phosphatase 1B (PTP-1B). Insulin resistance is defined as the diminished ability of cells to respond to insulin in terms of glucose uptake and utilization in tissues. One of the most important phosphatases regulating insulin signaling is the PTP-1B which inhibits insulin receptor and insulin receptor substrate 1 by direct dephosphorylation. Mice that are PTP-1B −/− (mutated at both alleles) are hypersensitive to insulin and resistant to weight gain on high fat diets (see Fernandez-Ruiz et at (2014) PLoS One 9(2):e90344). Thus this target may be useful for both diabetes treatment and obesity. Developing inhibitory small molecules specific for this enzyme is problematic because of the highly conserved active site pocket, but antisense oligonucleotides directed PTP-1B has been shown to reduce PTP-1B mRNA expression in liver and adipose tissues by about 50% and to produce glucose lowering effects in hyperglycemic, insulin-resistant ob/ob and db/db mice, experiments that were repeated in non-human primates (see Swarbrick et at (2009) Endocrin 150:1670). Thus, the methods and compositions of the invention can be used to target the PTP-1B by targeted degradation of PTP-1B using the dTAG insertion strategy described herein, leading to increased insulin sensitivity.

A high risk factor for developing type diabetes insulin resistant diabetes is obesity. Worldwide, more than 1 billion people are estimated to be overweight (body mass index (BMI)≥25 kg/m2, and more than 300 million of these are considered obese (BMI≥30 kg/m2), meaning that obesity is one of the greatest threats to public health today (Lagerros and Rossner (2013) Ther Adv Gastroenterol 6(1):77). Obesity is highly associated with co-morbidities such as insulin resistant type II diabetes, dyslipidemia, hypertension and cardiovascular disease. Treatment of obesity typically starts with modification of diet and exercise, but often with a decrease in caloric consumption, a parallel and confounding decrease in energy expenditure by the body is observed (Yu et al, (2013) PLoS One 8(7):e66923). Fibroblast growth factor receptor 4 (FGFR4) has been shown to have an anti-obesity effect in mouse obesity models. FGFR4 is mainly expressed in the liver, and it and its ligand FGF19 (in humans) regulate bile acid metabolism. FGFR4/FGF19 regulate the expression of cholesterol 7 alpha-hydroxylase and its activity. In addition, FGFR4 and FGF19 seem to be involved in lipid, carbohydrate or energy metabolism. Hepatic FGFR4 expression is decreased by fasting, and increased by insulin. FGFR4 null mice also show changes in lipid profiles in comparison with wild type mice in response to different nutritional conditions. Treatment of obese mice with FGF 19 increased metabolic rate and improved adiposity, liver steatosis, insulin sensitivity and plasma lipid levels, and also inhibited hepatic fatty acid synthesis and gluconeogenesis while increasing glycogen synthesis. Antisense reduction of FGFR4 in obese mice also lead to reduced body weight and adiposity, improvement in insulin sensitivity and liver steatosis, and increased plasma FGF15 (the mouse equivalent of FGF19) levels without any overt toxicity (Yu et al, ibid). Thus, the methods and compositions of the invention can be used to treat obesity by reducing the expression of FGFR4 by targeted degradation using the dTAG insertion strategy described herein.

Multiple sclerosis (MS) is a chronic, disabling, autoimmune disease of the central nervous system that is characterized by inflammation, demyelination and axonal destruction. The flare ups associated with relapsing MS (occurring in 85-95 percent of patients) are thought to be tied to the entry of activated lymphocytes into the brain. Currently available treatments are only able to inhibit the rate of relapses by about 30%. Inflammatory responses induce the expression of vascular adhesion molecule-1 (VCAM-1) on the endothelium of the vasculature, and the adhesion of the lymphocytes to VCAM-1 is a necessary step that then allows the activated cells to pass through into the brain. VCAM-1 adherence by the lymphocytes is mediated by binding of very late antigen-4 (VLA-4, also known as 4p131 integrin) on the surface of the activated lymphocyte (Wolf et at (2013) PLos One 8(3): e58438). Disruption of this interaction has been the idea behind the therapeutic use of anti-VLA-4 specific antibodies and small molecule antagonists (Wolf et al, ibid). Thus, the materials and methods of the invention can be used to target VCAM-1 or VLA-4 expression by targeted degradation using the dTAG insertion strategy described herein.

Another disease of interest is Cushing's disease/syndrome (CS). In this disease, patients have elevated serum levels of glucocorticoid due to increased expression by the adrenal gland. CS is an uncommon condition with an incidence rate between 1.8 and 2.4 patients/million per year. The most common cause of endogenous CS is an ACTH-producing pituitary adenoma, seen in 70% of patients with CS. Cortisol-producing adrenal adenomas and ectopic ACTH-producing tumors are less common, each accounting for ~10-15% of cases. The first-line treatment for patients with pituitary derived CS is transsphenoidal pituitary surgery (TSS) and unilateral adrenalectomy for cortisol-producing adrenal adenoma. Unilateral adrenalectomy is curative in almost all patients with cortisol-producing adrenal adenoma and permanent adrenal insufficiency is rare. Conversely, hypopituitarism is common after TSS, with a range between 13 and 81% (see Ragnarsson and Johannsson (2013) Eur J Endocrin 169:139). In some patients however, surgical resection is not successful and so pharmacological treatment is indicated. One approach is to inhibit the activity of the hypercortisolemia by targeting the glucocorticoid receptor (GCCR), for example, using Mifepristone (also known as RU 486), a GCCR antagonist (see Johanssen and Allolio (2007) Eur J Endocrin 157:561). However, RU 486 has several other activities (most notably, induction of an abortion in pregnant patients). Thus, the methods and compositions of the invention may be used to target the GCCR by decreasing expression by targeted degradation using the dTAG insertion strategy described herein.

Transthyretin Amyloidoses (TTRA) is one of several degenerative diseases suspected to be linked to misfolded and aggregated protein (amyloids). Transthyretin (TTR) is a tetramer produced in the liver and secreted into the bloodstream that serves to transport holo-retinal binding protein. However, upon conformational changes, it becomes amyloidogenic. Partial unfolding exposes stretches of hydrophobic residues in an extended conformation that efficiently misassemble into largely unstructured spherical aggregates that ultimately before cross-β sheet amyloid structures (see Johnson et at (2012) J Mol Biol 421(2-3): 183). TTRA can occur in patients in both sporadic and autosomal dominant inherited forms which include familial amyloid polyneuropathy (FAP) and familial amyloid cardiomyopathy (FAC).

These inherited forms are usually earlier onset and relate to over 100 point mutations described in the TTR gene. Generally, the more destabilizing of the protein that the mutation is, the more likely it is to have some amount of amyloid pathology. The amyloid formed causes selective destruction of cardiac tissue in FAC or peripheral and central nervous tissue in FAP. Some new therapeutic strategies for treating these diseases such as inhibitory RNA strategies center on trying to decrease the amount of TTR to decrease the aggregation potential of the protein (Johnson et al, ibid). Thus the methods and compositions of the invention can be used to target TTR in an effort to reduce the quantity of the pathological forms of the TTR protein and/or to decrease TTR concentration in general by targeted degradation using the dTAG insertion strategy described herein.

Muscular diseases can also be approached using the methods of the invention. Spinal muscular atrophy is an autosomal recessive disease caused by a mutation in the SMN1 gene which encodes the 'survival of motor neuron' (SMN) protein and is characterized by general muscle wasting and movement impairment. The SMN protein is involved in the assembly of components of the spliceosome machinery, and several defects in the SMN1 gene are associated with splicing defects that cause exon 7 of the mature mRNA to be specifically excluded. These defects are especially prevalent in spinal motor neurons, and can cause spinal muscular atrophy. The severity of SMN1 defects can be modified by a paralogue of SMN1 known as SMN2. The SMN2 gene sequence differs from SMN1 in only a few single nucleotide polymorphisms in exons 7 and 8 and several others in the intronic sequences. Thus the methods and compositions of the invention can be used to target SMN1 in an effort to reduce the quantity of the pathological forms of the SMN1 protein and/or to decrease SMN1 concentration in general by targeted degradation using the dTAG insertion strategy described herein.

Dysregulation of the secretion of growth hormone (GH) can lead to a condition known as acromegaly, a disorder of disproportionate skeletal, tissue, and organ growth which first becomes evident at about 40 years of age (Roberts and Katznelson (2006) US Endocrine Disease: 71). It occurs an annual incidence of approximately 5 cases per million, and diagnosis requires a determination of dysregulation of GH secretion and elevated IGF 1 levels. The inability to suppress GH secretion during the 2 hours post an oral glucose load is generally used for diagnosis of acromegaly. Normal regulation of GH secretion is carried out by the pituitary gland. Hypothalamic GH-releasing hormone (GHRH), ghrelin and somatostatin regulate GH production by anterior pituitary somatotroph cells. The gene encoding the GH receptor or GHR is widely expressed and when a GH molecule interacts with a GHR dimer, signal proceeds via JAK2-dependent and independent intracellular signal transduction pathways (see Melmed (2009) J Clin Invest 119(11):3189). Circulating GH stimulates hepatic secretion of insulin-like growth factor-1 (IGF-1). Acromegaly occurs when benign pituitary tumors cause an increase in GH secretion and thus in IGF-1 secretion. One GHR mutation that is tied to acromegaly has an in-frame deletion in exon 3 that causes a deletion of 22 amino acids in the protein. This mutated receptor, known as d3-GHR, results in enhanced GH responsiveness. Current therapies focus on the normalization of GH and IGF-1 levels, often through surgical removal of the pituitary tumors. Since secretion of IGF-1 is induced by GH, targeting of the GHR is an attractive target for the methods and compositions of the invention. Thus, the methods and compositions of the invention may be used to target GHR by decreasing expression by targeted degradation using the dTAG insertion strategy described herein.

Another disease associated with muscle wasting is myotonic dystrophy, which is a chronic disease characterized by muscle wasting, cataracts, heart conduction defects, endocrine changes, multiorgan damage and myotonia (prolonged muscle contraction following voluntary contraction). Myotonic dystrophy occurs at an incidence rate of approximately 13 per 100,000 people, and there are two forms of the disease, Myotonic Dystrophy Type 1 (also called Steinert's disease, MMD1 or DM1, and is the most common) and Myotonic Dystrophy Type 2 (MMD2 or DM2). Both are inherited autosomal dominant diseases caused by abnormal expansions in the 3' non-coding regions of two genes (CTG in the DMPK gene (encoding dystrophia myotonica protein kinase) for type 1, and CCTG in the ZNF9 gene (encoding cellular nucleic acid-binding protein) in type 2) and DM1 is the most common form of muscular dystrophy in adults. These mutations result in toxic intranuclear accumulation of the mutant transcripts in RNA inclusions or foci (see Caillet-Boudin et al, (2014) Front. Mol. Neurosci doi: 10.3389). Type 1 patients have CTG copy numbers greater than 50 and have variable phenotypes, ranging from asymptomatic to severe. Antisense RNA techniques have been used to cause the specific destruction of the mutant DMPK transcripts in vitro which caused no effect on the proliferation rate of DM1 myoblasts but restored their differentiation (Furling et at (2003) Gene Therapy 10:795). Thus, the methods and compositions of the invention can be used to target the dystrophia myotonica protein kinas or cellular nucleic acid binding protein by targeted degradation using the dTAG insertion strategy described herein.

Chronic pain is a major health concern affecting 80 million Americans at some time in their lives with significant associated morbidity and effects on individual quality of life. Chronic pain can result from a variety of inflammatory and nerve damaging events that include cancer, infectious diseases, autoimmune-related syndromes and surgery. Voltage-gated sodium channels (VGSCs) are fundamental in regulating the excitability of neurons and overexpression of these channels can produce abnormal spontaneous firing patterns which underpin chronic pain. There are at least nine different VGSC subtypes in the nervous system, and each subtype can be functionally classified as either tetrodotoxin-sensitive or tetrodotoxin-resistant. Neuronal sodium channel subtypes including Nav1.3, Nav1.7, Nav1.8, and Nav1.9 have been implicated in the processing of nociceptive information. The VGSC Nav1.8 is a tetrodotoxin-resistant sodium channel with a distribution restricted to primary afferent neurons and the majority of Nav1.8-containing afferents transmit nociceptive signals to pain processing areas of the spinal cord. Changes in the expression, trafficking and redistribution of Nav1.8 (encoded by PN3) following inflammation or nerve injury are thought to be a major contributor to the sensitization of afferent nerves and the generation of pain (see Schuelert and McDougall (2012) Arthritis Res Ther 14:R5). Rodent models of osteoarthritis have demonstrated that inhibition of Nav1.8 channels on peripheral nerves, with synaptic connections in the spinal cord, is a promising treatment of nociceptive sensory processing and could be helpful to achieve more pronounced and longer lasting analgesia. Thus, the methods and compositions of the invention can be used to treat chronic pain by decreasing localized expression of NAV1.8 by targeted degradation using the dTAG insertion strategy described herein.

Cancer may also be targeted as described herein. Cancer is a generic term used to describe a number of specific diseases that are united by a lack of cellular growth regulation. Since there are so many forms, involving a myriad of different cell types, there are also numerous specific gene targets that are involved in cancer. For example, the clusterin protein (also known as apolipoprotein J), encoded by the CLU gene, is a heterodimeric protein assembled following the proteolytic cleavage into the two chains of the primary polypeptide CLU gene product. In recent years, it has been found that there are two forms of clusterin, a secretory and heavily glycosylated form (sCLU) and a nuclear form (nCLU), where nCLU is first synthesized as a pre nuclear form (pnCLU) that is found in the cell cytoplasm. The differences between the two CLU forms are tied to alternative splicing of the CLU message and the selection of the starting ATG during message translation. The translation of sCLU utilized the first AUG in the full length CLU mRNA whereas the translation of pnCLU is initiated from a second in-frame AUG following the splice-dependent removal of the transcribed leader section and Exon 1 from the full length mRNA. The sCLU form appears to promote cell survival while the nCLU form is associated with apoptosis. Overexpression of the sCLU form of the protein has been found in many tumor types, including prostate, skin, pancreatic, breast, lung, and colon tumors, as well as oesophageal squamous cell carcinoma and neuroblastoma. In addition, the progression of some cancer types towards high grade and metastatic forms leads to an elevation of sCLU levels (Shannan et at (2006) Cell Death Dif 13: 12). Use of specific antisense oligonucleotides (ASO) designed to cause silencing sCLU expression in combination with standard treatments has been carried out in Phase I studies of breast and prostate cancer, with an increase in apoptosis observed only in the patients that received both the ASO and the standard therapeutic agent (Shannan ibid). Thus, the methods and compositions of the invention can be used to treat cancers marked with an increase in sCLU expression by targeted degradation using the dTAG insertion strategy described herein.

Another protein that appears to have an oncogenic role is eukaryotic translation initiation factor 4E (eIF-4E). eIF3-4E binds to the M7GpppN cap (where N is any nucleotide) of a eukaryotic mRNA and is the rate limiting member for the formation of the eIF-4F complex. eIF-4E normally complexes with eIF-4G in the eIF-4F complex, and under normal physiologic conditions, the availability of eIF-4E is negatively regulated by the binding of a family of inhibitory proteins known as 4E-BPs which act to sequester eIF-4E from eIF-4G. Since eIF-4E is expressed normally at low levels, mRNAs compete for the available eIF-4E to be translated. mRNAs with short, unstructured 5' UTRs are thought to be more competitive for translation since they are less dependent on the unwinding activity found in the eIF-4F complex. mRNAs that are highly structural then are more dependent on eIF-4E binding for translation, and thus when eIF3-4E is overexpressed, these mRNAs are more easily translated. Growth-promoting gene products such as cyclin D1, VEGF, c-myc, FGF2, heparanase, ODC and MMP9 have these complex 5' UTRs (Mamane et at (2004) Oncogene 23:3172, Fischer (2009) Cell Cycle 8(16):2535). Additionally, eIF-4E may serve a role in modification of the nuclear pore complex and cause an increase in translocation of these same mRNAs into the cytoplasm (Culjikovic-Kraljacic et at (2012) Cell Reports 2 p. 207). eIF-4E has been implicated in oncogenic cellular transformation and is overexpressed in several cancer types including acute myeloid leukemia, colon, breast, bladder, lung, prostate, gastrointestinal tract, head and neck cancers, Hodgkin's lymphoma and neuroblastoma and elevated levels are associated with increasing grade of disease. Targeting of eIF-4E has been attempted by several different approaches, including overexpression of 4E-BPs and peptides derived there from, the development of small molecule inhibitors to prevent eIF-4E:eIFG interaction, and antisense oligos (ASO) specific for eIF-4E (Jia et at (2012) Med Res Rev 00, No. 00:1-29). ASO administration has demonstrated a knock down of eIF-4E expression in tumor cells in vitro, and in xenograft tumors in mouse models in vivo. Expression levels of eIF-4E were decreased by 80% in these mouse models without any decrease in overall protein translation and without any obvious toxicity, while increasing chemosensitivity to chemotherapeutic agents, increasing cancer cell apoptosis and suppressing tumor growth (Jia ibid). Thus, the methods and compositions of the invention may be used for the treatment or prevention of various cancers. Expression of eIF-4F can be modulated by degradation using the dTAG insertion strategy described herein.

Vascular endothelial receptor (VEGF), acting via its receptor VEGFR has a role in normal development, and also in the development of pathological angiogenesis in cancer. In humans, there are five distinct VEGF family members: VEGF-A (also known as VEGF); placenta growth factor (PIGF), VEGF-B, VEGF-C and VEGF-D. VEGF-A also has three common subtypes: VEGF-121. VEGF-165 and VEGF-189. The various VEGFs have differing roles in angiogenesis with VEGF-A primarily being involved in normal angiogenesis and also in tumor growth and metastasis, while VEGF-C and VEGF-D are involved in normal lymphangiogenesis and in malignant lymph node metastasis. In addition, the VEGF-A subtypes may also have specific growth promoting activity in hormone responsive tumors. Based on this knowledge, a number of antibodies and small molecule kinase inhibitors which suppress the VEGF-VEGFR interaction directly or the signal transduction pathways activated by the interaction. However, these therapeutics often have significant and potentially troublesome side effect profiles, such that active research is occurring to develop inhibitors with increased specificity (Shibuya, (2014) Biomol Ther 11(1): 1-9). Thus, the methods and compositions of the invention may be used to prevent or treat cancer in a subject by targeting specific VEGF proteins by degradation using the dTAG insertion strategy described herein.

Another protein that plays a role in several cancers is kinesin spindle protein (KSP), encoded by the KIF11 gene. The most successful anti-cancer therapies currently in use target microtubules where these agents have been used for the treatment of breast, lung, ovarian, bladder, and head and neck cancers. Microtubules are part of the mitotic spindle, and thus targeting them is successful in inhibiting rapidly dividing cancer cells, but microtubules are also part of the cytoskeleton, such that treatment with these agents also is associated with serious side effects. Kinesin, specifically kinesin spindle protein, is a motor protein that binds to spindle fibers and serves to force the spindle fibers apart during chromosome segregation in cell division. Thus, targeting KSP using a KSP-specific anti-mitotic agent will only target dividing cells, and might have fewer side effects. Agents that deplete KSP selectively lead to cell cycle arrest in mitosis, which after a prolonged period, leads to apoptosis. KSP is also abundant in dividing tissues, and is highly expressed in tumors of the breast, colon, lung, ovary and uterus (Sarli and Giannis, (2008) Clin Cancer Res 14:7583). In addition, clinical trials are underway using RNA interference targeted to KSP and VEGF simultaneously in cancer patients with liver involvement (Tabernero et al, (2013) Cancer Discovery 3:406). Thus, the methods and compositions of the invention may be used to treat or prevent cancers by targeted degradation of the kinesin spindle protein (KSP) using the dTAG insertion strategy described herein.

Heat shock protein 27 (HSP 27, also known as heat shock protein beta-1 or HSPB1) is another protein that is implicated in cancer. HSP 27, encoded by the HSPB1 gene, is a heat shock protein that was initially characterized in response to heat shock as a small chaperonin that facilitates proper refolding of damaged proteins. However, ongoing investigation revealed that it also is involved in responses to cellular stress conditions such as oxidative stress, and chemical stress, appears to have anti-apoptotic activity, and is able to regulate actin cytoskeletal dynamics during heat shock and other stress conditions (Vidyasagar et at (2012) Fibrogen Tis Rep 5(7)). In addition, suppression of HSP 27 may play a role in long term dormancy of cancers as research has revealed that HSP 27 is upregulated in angiogenic breast cancer cells, and suppression of HSP 27 in vivo leads to long term tumor dormancy (Straume et at (2012) Proc Natl Acad Sci USA 109(22): 8699-8704). Increased expression of heat shock proteins in tumor cells is related to loss of p53 functions and to the upregulation of proto-oncogenes such as c-myc. HSP 27's anti-apoptotic activity protects tumor cells and also has been shown to be associated with chemotherapy resistance in breast cancer and leukemia (Vidyasagar ibid). Thus, HSP 27 may be a suitable target for cancer therapeutics, where inhibitors of the protein may be used in combination with known chemotherapies to enhance their activities. The HSP 27 inhibitor quercetin has been shown to significantly reduce tumor volumes in vivo when combined with traditional chemotherapeutic agents in comparison with the agents alone. In addition, HSP 27 inhibitory ASOs are currently be evaluated in clinical studies in lung, ovarian, breast and pancreatic cancers (Vidyasagar, ibid). Thus, the methods and compositions of the invention may be used to treat cancers by inhibition of HSP 27 expression through targeted degradation of HSP 27 using the dTAG insertion strategy described herein.

Several kinases have been the target of research into anti-cancer therapeutics since they are often key regulators of cell growth. However, downstream in the signaling pathway, the effect of mutant kinases is often seen in the upregulation of the Signal Transduction and Activator of Transcription 3 protein, or Stat3, encoded by the STAT3 gene. Additionally, it appears that both Hepatitis B and C activate Stat3, and both are associated with the development of hepatic cancer. Thus it may be that the HepB and HepC viruses subvert Stat3 signaling pathways and promote hepatocyte transformation (Li et al, (2006) Clin Cancer Res 12(23):7140).

RAS proteins are a family of proteins that play a role in cell differentiation, proliferation, and survival. Various members of the RAS protein family have been implicated in cancer as aberrant RAS signaling has been found to play a role in approximately 30% of all cancers. The KRAS protein (also known as V-Ki-ras2 Kirsten rat sarcoma viral oncogene homolog) is a GTPase that performs an essential function in normal tissue signaling KRAS is an attractive cancer target, as frequent point mutations in the KRAS gene render the protein constitutively active. Thus, KRAS may be a suitable target for cancer therapeutics, where small molecules targeting the function of the KRAS protein may be used for therapeutic advantages, including in combination with known chemotherapies to enhance their activities. In one embodiment, the methods and compositions of the invention may be used to treat cancers by modulation of KRAS expression through targeted degradation of KRAS using the dTAG insertion strategy described herein.

All the various Stat proteins are transcription factors that primarily mediate signaling from cytokine and growth factor receptors. For example, IL6 and IL11 bind to their respective receptor subunits and trigger homodimerization of gp130, the transmembrane receptor that triggers Stat3 activation. Following activation via phosphorylation of the growth factor receptors, Stat3 proteins dimerize and traverse into the nucleus and bind to DNA in a sequence specific manner, up regulating many genes that are involved in cell proliferation. Tumor cells of various types often have kinase mutations that lead to overexpression of Stat3 so a decrease in Stat3 expression has the potential to be beneficial in cancers of multiple origins without regard to each specific mutant kinase (Jarnicki et at (2010) Cell Div 5:14). Stat3 contributes to malignancy by several mechanisms. It inhibits apoptosis by upregulating the pro-survival/anti-apotatic Bcl2 proteins and promotes proliferation primarily by stimulating expression of cyclinB1, cdc2, c-myc, VEGF, H1F1α and cyclin D1 as well as through its repression of the cell cycle inhibitor p21. Stat3 also promotes tumor metastasis through the induction of extracellular matrix-degrading metalloproteinases including MMP-2 and MMP-9. In normal physiological states, Stat3 functioning is inhibited by the transcriptional inhibitor Socs3, which is normally induced by Stat3 to maintain growth balance in the cell. However, in a malignant cell, Stat3 overexpression can overcome Socs3 inhibition. Thus, the methods and compositions of the invention can be used to inhibit Stat3 functioning and prevent or treat cancer by targeted degradation of Stat3 using the dTAG insertion strategy described herein.

Prostate cancer (PCa) is an androgen-dependent disease that remains one of the leading causes of death in the United States, and is the leading cause of death from cancer in men. While several studies have been done that suggest that up to 42% of prostate cancer cases have a genetic link (Mazaris and Tsiotras (2013) Nephro Urol Mon 5(3):792-800), several types of inheritance patterns have been observed (e.g. X-linked, autosomal dominant, autosomal recessive) suggesting that there is not one sole gene or gene mutation that leads to inheritance of PCa. This cancer is dependent upon the activity of the androgen receptor for growth and progression (Mahmoud et at (2013) PLoS One 8(10): e78479). Typically, PCa can be a slow to progress disease that can be treated using fairly conservative approaches, but in about 25-30% of the cases, the cancer can be an aggressive one leading to patient death. In the case of metastatic disease 70-80% of patients respond initially to androgen-deprivation therapy but in later stages, the tumor becomes hormone refractory and more aggressive, leading to a worsening prognosis (Mazaris and Tsiotras ibid). Hormone refractory PCa is not dependent on circulating androgen, but rather is driven by inappropriate activation of the androgen receptor (AR, encoded by the AR gene) through such mechanisms as AR amplification, deregulation of growth factors, and co-amplification of AR cofactors. Additionally, mutations in the AR ligand binding domain can cause the AR to be super-sensitive to very low circulating androgen levels or to be sensitive to an expanded set of ligands such as estrogens, progestins, adrenyl steroids and antiandrogens. Tumor cells that have undergone these types of mutations in the AR ligand binding domain may no longer be sensitive to anti-androgen therapies despite the reliance of the cancer on the activity of the AR. Normally the AR is present in the cytoplasm and is bound by heat shock proteins to prevent its activation. Upon exposure to androgen, the receptor is able to dimerize and travel into the cell nucleus to promote expression of several growth related genes. Thus the methods and compositions of the invention may be used to treat PCa at all stages by targeting degradation of the androgen receptor using the dTAG insertion strategy described herein.

C. Genomic In-Frame Insertion of dTAGs

As described above, the methods of the present invention are based on the genomic insertion of a dTAG in-frame with a gene expressing an endogenous protein of interest. As contemplated herein, the 5'- or 3' in-frame insertion of a nucleic acid sequence encoding a dTAG results, upon expression of the resultant nucleic acid sequence, in an endogenous protein-dTAG hybrid protein that can be targeted for degradation by the administration of a specific heterobifunctional compound.

In-frame insertion of the nucleic acid sequence encoding the dTAG can be performed or achieved by any known and effective genomic editing processes. In one aspect, the present invention utilizes the CRISPR-Cas9 system to produce knock-in endogenous protein-dTAG fusion proteins that are produced from the endogenous locus and are readily degraded in a ligand-dependent, reversible, and dose-responsive, fashion. In certain embodiments, the CRISPR-Cas9 system is employed in order to insert an expression cassette for dTAG present in a homologous recombination (HR) "donor" sequence with the dTAG nucleic acid sequence serving as a "donor" sequence inserted into the genomic locus of a protein of interest during homologous recombination following CRISPR-Cas endonucleation. The HR targeting vector contains homology arms at the 5' and 3'end of the expression cassette homologous to the genomic DNA surrounding the targeting gene of interest locus. By fusing the nucleic acid sequence encoding the dTAG in frame with the target gene of interest, the resulting fusion protein contains a dTAG that is targeted by a heterobifunctional compound.

The present invention provides for insertion of an exogenous dTAG sequence (also called a "donor sequence" or "donor" or "transgene") in frame with the target gene of interest, and the resulting fusion protein contains a dTAG that is targeted by a heterobifunctional compound. It will be readily apparent that the donor sequence need not be identical to the genomic sequence where it is placed. A donor sequence can contain a non-homologous sequence flanked by two regions of homology to allow for efficient HR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, for example, the dTAGs of the present invention, said sequences can be present in a donor nucleic acid molecule and flanked by regions of homology to sequence in the region of interest. Alternatively, a donor molecule may be integrated into a cleaved target locus via non-homologous end joining (NHEJ) mechanisms. See, e.g., U.S. 2011/0207221 and U.S. 2013/0326645, incorporated herein by reference.

The donor dTAG encoding sequence for insertion can be DNA or RNA, single-stranded and/or double-stranded and can be introduced into a cell in linear or circular form. See, e.g., U.S. 2010/0047805, U.S. 2011/0281361, and 2011/0207221, incorporated herein by reference. The donor sequence may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. Proc. Natl. Acad. Sci. 84, (1987):4959-4963 and Nehls et al. Science, 272, (1996): 886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

The donor polynucleotide encoding a dTAG can be introduced into a cell as part of a vector molecule having additional sequences such as, for example, CRISPR-Cas sequences, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The present invention takes advantage of well-characterized insertion strategies, for example the CRISPR-Cas9 system. In general, the "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus. (See, e.g., Ruan, J. et al. "Highly efficient CRISPR/Cas9-mediated transgene knockin at the H11 locus in pigs." Sci. Rep. 5, (2015):14253; and Park A, Won S T, Pentecost M, Bartkowski W, and Lee B "CRISPR/Cas9 Allows Efficient and Complete Knock-In of a Destabilization Domain-Tagged Essential Protein in a Human Cell Line, Allowing Rapid Knockdown of Protein Function." PLoS ONE 9(4), (2014): e95101, both incorporated herein by reference).

The Cas nuclease is a well-known molecule. For example, the protein sequence encoded by the Cas-9 nuclease gene may be found in the SwissProt database under accession number

```
Q99ZW2-(SEQ. ID. NO.: 52):
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFEI

RLEESFLVEEDKKHERHPIFGNIVDEVAYHEKYPTIYHLRKKLVDSTDKA

DLRLIYLALAHMIKFRGHFLIEGDLNPDNSDVDKLFIQLVQTYNQLFEEN

PINASGVDAKAILSARLSKSRRLENLIAQLPGEKKNGLFGNLIALSLGLT

PNFKSNFDLAEDAKLQLSKDTYDDDLDNLLAQIGDQYADLFLAAKNLSDA

ILLSDILRVNTEITKAPLSASMIKRYDEHHQDLTLLKALVRQQLPEKYKE

IFFDQSKNGYAGYIDGGASQEEFYKFIKPILEKMDGTEELLVKLNREDLL

RKQRTFDNGSIPHQIHLGELHAILRRQEDFYPFLKDNREKIEKILTFRIP
```

-continued

```
YYVGPLARGNSRFAWMTRKSEETITPWNFEEVVDKGASAQSFIERMTNFD

KNLPNEKVLPKHSLLYEYFTVYNELTKVKYVTEGMRKPAFLSGEQKKAIV

DLLFKTNRKVTVKQLKEDYFKKIECFDSVEISGVEDRFNASLGTYHDLLK

IIKDKDFLDNEENEDILEDIVLTLTLFEDREMIEERLKTYAHLFDDKVMK

QLKRRRYTGWGRLSRKLINGIRDKQSGKTILDFLKSDGFANRNFMQLIHD

DSLTFKEDIQKAQVSGQGDSLHEHIANLAGSPAIKKGILQTVKVVDELVK

VMGRHKPENIVIEMARENQTTQKGQKNSRERMKRIEEGIKELGSQILKEH

PVENTQLQNEKLYLYYLQNGRDMYVDQELDINRLSDYDVDHIVPQSFLKD

DSIDNKVLTRSDKNRGKSDNVPSEEVVKKMKNYWRQLLNAKLITQRKFDN

LTKAERGGLSELDKAGFIKRQLVETRQITKHVAQILDSRMNTKYDENDKL

IREVKVITLKSKLVSDFRKDFQFYKVREINNYHHAHDAYLNAVVGTALIK

KYPKLESEFVYGDYKVYDVRKMIAKSEQEIGKATAKYFFYSNIMNFFKTE

ITLANGEIRKRPLIETNGETGEIVWDKGRDFATVRKVLSMPQVNIVKKTE

VQTGGFSKESILPKRNSDKLIARKKDWDPKKYGGFDSPTVAYSVLVVAKV

EKGKSKKLKSVKELLGITIMERSSFEKNPIDFLEAKGYKEVKKDLIIKLP

KYSLFELENGRKRMLASAGELQKGNELALPSKYVNFLYLASHYEKLKGSP

EDNEQKQLFVEQHKHYLDEIIEQISEFSKRVILADANLDKVLSAYNKHRD

KPIREQAENIIHLFTLTNLGAPAAFKYFDTTIDRKRYTSTKEVLDATLIH

QSITGLYETRIDLSQLGGD.
```

In some embodiments, the CRISPR/Cas nuclease or CRISPR/Cas nuclease system includes a non-coding RNA molecule (guide) RNA, which sequence-specifically binds to DNA, and a Cas protein (e.g., Cas9), with nuclease functionality (e.g., two nuclease domains). Further included is the donor nucleotide encoding a dTAG for in-frame insertion into the genomic locus of the protein of interest.

In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*.

In some embodiments, a Cas nuclease and gRNA (including a fusion of crRNA specific for the target sequence and fixed tracrRNA), and a donor sequence encoding a dTAG are introduced into the cell. In general, target sites at the 5' end of the gRNA target the Cas nuclease to the target site, e.g., the gene, using complementary base pairing. In some embodiments, the target site is selected based on its location immediately 5' of a protospacer adjacent motif (PAM) sequence, such as typically NGG, or NAG. In this respect, the gRNA is targeted to the desired sequence by modifying the first 20 nucleotides of the guide RNA to correspond to the target DNA sequence.

In some embodiments, the CRISPR system induces DSBs at the target site, followed by homologous recombination of the donor sequence encoding a dTAG into the genomic locus of a protein of interest, as discussed herein. In other embodiments, Cas9 variants, deemed "nickases" are used to nick a single strand at the target site. In some aspects, paired nickases are used, e.g., to improve specificity, each directed by a pair of different gRNAs targeting sequences such that upon introduction of the nicks simultaneously, a 5' overhang is introduced.

In general, a CRISPR system is characterized by elements that promote the formation of a CRISPR complex at the site of a target sequence. Typically, in the context of formation of a CRISPR complex, "target sequence" generally refers to a sequence to which a guide sequence is designed to have complementarity, where hybridization between the target sequence and a guide sequence promotes the formation of a CRISPR complex, and wherein insertion of the donor sequence encoding a dTAG is to take place. Full complementarity is not necessarily required, provided there is sufficient complementarity to cause hybridization and promote formation of a CRISPR complex.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wildtype tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of the CRISPR complex. As with the target sequence, in some embodiments, complete complementarity is not necessarily needed. In some embodiments, the tracr sequence has at least 50%, 60%, 70%, 80%, 90%, 95% or 99% of sequence complementarity along the length of the tracr mate sequence when optimally aligned. In some embodiments, one or more vectors driving expression of one or more elements of the CRISPR system are introduced into the cell such that expression of the elements of the CRISPR system direct formation of the CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. In some embodiments, CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises a regulatory element operably linked to an enzyme-coding sequence encoding a CRISPR RNA-guided endonuclease. In some embodiments, a vector comprises a regulatory element operably linked to an enzyme-coding sequence encoding the CRISPR enzyme, such as a Cas protein. Non-limiting examples of Cas proteins include Cas1, Cas IB, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csxl5, Csf1, Csf2, Csf3, Csf4, Cpf1, homologs thereof, or modified versions thereof. (see WO 2015/200334, incorporated herein by reference). These enzymes are known; for example, the amino acid sequence of S. pyogenes Cas9 protein may be found in the SwissProt database under accession number Q99ZW2 (incorporated herein by reference).

Cas proteins generally comprise at least one RNA recognition or binding domain. Such domains can interact with guide RNAs (gRNAs, described in more detail below). Cas proteins can also comprise nuclease domains, for example endonuclease domains (e.g., DNase or RNase domains), DNA binding domains, helicase domains, protein-protein interaction domains, dimerization domains, and other domains. A nuclease domain possesses catalytic activity for nucleic acid cleavage. Cleavage includes the breakage of the covalent bonds of a nucleic acid molecule. Cleavage can produce blunt ends or staggered ends, and it can be single-stranded or double-stranded.

Examples of Cas proteins include Cas1, Cas IB, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx1O, Csx16, CsaX, Csx3, Csx1, Csx15, Csf1, Csf2, Csf3, Csf4, and Cul966, and homologs or modified versions thereof (see WO 2015/200334, incorporated herein by reference).

Any Cas protein that induces a nick or double-strand break into a desired recognition site can be used in the methods and compositions disclosed herein.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of the CRISPR complex to a target sequence may be assessed by any suitable assay. For example, the components of the CRISPR system sufficient to form the CRISPR complex, including the guide sequence to be tested, may be provided to the cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of the CRISPR complex, including the guide sequence to be tested and a control guide sequence different from the test guide sequence, and comparing binding or rate of cleavage at the target sequence between the test and control guide sequence reactions.

A guide sequence may be selected to target any target sequence. In some embodiments, the target sequence is a sequence within a genome of a cell, and in particular, a protein of interest targeted for controlled degradation through the engineering of an endogenous protein-dTAG hybrid. Exemplary target sequences include those that are unique in the target genome which provide for insertion of the dTAG donor nucleic acid in an in-frame orientation. In some embodiments, a guide sequence is selected to reduce the degree of secondary structure within the guide sequence. Secondary structure may be determined by any suitable polynucleotide folding algorithm.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences.

As contemplated herein, the CRISPR-Cas system is used to insert a nucleic acid sequence encoding a dTAG in-frame with the genomic sequence encoding a protein of interest in a eukaryotic, for example, human cell. In some embodiments, the method comprises allowing the CRISPR complex to bind to the genomic sequence of the targeted protein of interest to effect cleavage of the genomic sequence, wherein the CRISPR complex comprises the CRISPR enzyme complexed with a guide sequence hybridized to a target sequence within said target polynucleotide, wherein said guide sequence is linked to a tracr mate sequence which in turn hybridizes to a tracr sequence.

In some aspects, the methods include modifying expression of a polynucleotide in a eukaryotic cell by introducing a nucleic acid encoding a dTAG.

In some aspects, the polypeptides of the CRISPR-Cas system and donor sequence are administered or introduced to the cell. The nucleic acids typically are administered in the form of an expression vector, such as a viral expression vector. In some aspects, the expression vector is a retroviral expression vector, an adenoviral expression vector, a DNA plasmid expression vector, or an AAV expression vector. In some aspects, one or more polynucleotides encoding CRISPR-Cas system and donor sequence delivered to the cell. In some aspects, the delivery is by delivery of more than one vectors.

Methods of delivering nucleic acid sequences to cells as described herein are described, for example, in U.S. Pat. Nos. 8,586,526; 6,453,242; 6,503,717; 6,534,261; 6,599, 692; 6,607,882; 6,689,558; 6,824,978; 6,933,113; 6,979,539; 7,013,219; and 7,163,824, the disclosures of all of which are incorporated by reference herein in their entireties.

The various polynucleotides as described herein may also be delivered using vectors containing sequences encoding one or more of compositions described herein. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties.

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 1991/17424 and WO 1991/16024. Delivery can be to cells (e.g. in vitro or ex vivo administration) or target tissues (e.g. in vivo administration).

In some embodiments, delivery is via the use of RNA or DNA viral based systems for the delivery of nucleic acids. Viral vectors in some aspects may be administered directly to patients (in vivo) or they can be used to treat cells in vitro or ex vivo, and then administered to patients. Viral-based systems in some embodiments include retroviral, lentivirus, adenoviral, adeno-associated and herpes simplex virus vectors for gene transfer. The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66, (1992):2731-2739; Johann et al., *J. Virol.* 66, (1992):1635-1640; Sommerfelt et al., *J. Virol.* 176, (1990):58-69; Wilson et al., *J. Virol.* 63, (1989):2374-2378; Miller et al., *J. Virol.* 65, (1991):2220-2224; and PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160, (1987):38-47; U.S. Pat. No. 4,797,368; WO 1993/24641; Kotin, Human Gene Therapy 5, (1994):793-801; Muzyczka, *J. Clin. Invest.* 94, (1994): 1351. Construction of recombinant AAV vectors is described in a number of publications, including U.S. Pat. No. 5,173,414; Tratschin et al., *Mol. Cell. Biol.* 5, (1985): 3251-3260; Tratschin, et al., *Mol. Cell. Biol.* 4, (1984):2072-2081; Hermonat & Muzyczka, *PNAS* 81, (1984):6466-6470; and Samulski et al., *J. Virol.* 63, (1989):3822-3828.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., Blood 85, (1995):3048-305; Kohn et al., *Nat. Med.* 1, (1995):1017-1023; Malech et al., *PNAS* 94(22), (1997):12133-12138). PA317/pLASN was the first therapeutic vector used in a gene therapy trial. (Blaese et al., *Science* 270, (1995):475-480). Transduction efficiencies of 50% or greater have been observed for MFG-S packaged vectors. (Ellem et al., *Immunol Immunother.* 44(1), (1997):10-20; and Dranoff et al., *Hum. Gene Ther.* 1, (1997):111-112).

Vectors suitable for introduction of polynucleotides described herein also include non-integrating lentivirus vectors (IDLV). See, for example, Naldini et al. *Proc. Natl. Acad. Sci.* 93, (1996):11382-11388; Dull et al. *J Virol.* 72, (1998):8463-8471; Zuffery et al. *J. Virol.* 72, (1998):9873-9880; Follenzi et al. *Nature Genetics* 25, (2000):217-222; and U.S. 2009/0117617.

Recombinant adeno-associated virus vectors (rAAV) may also be used to deliver the compositions described herein. All vectors are derived from a plasmid that retains only the AAV inverted terminal repeats flanking the transgene expression cassette. Efficient gene transfer and stable transgene delivery are key features for this vector system. (Wagner et al., *Lancet* 351, (1998):9117 1702-3, and Kearns et al., *Gene Ther.* 9, (1996):748-55). Other AAV serotypes, including AAV1, AAV3, AAV4, AAV5, AAV6, AAV8, AAV9 and AAVrh10, pseudotyped AAV such as AAV2/8, AAV2/5 and AAV2/6 and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7, (1998):1083-1089). Additional examples of the use of adenovirus vectors for gene transfer in clinical trials include Rosenecker et al., *Infection* 24(1), (1996):5-10; Sterman et al., *Hum. Gene Ther.* 9(7), (1998):1083-1089; Welsh et al., *Hum. Gene Ther.* 2, (1995):205-218; Alvarez et al., *Hum. Gene Ther.* 5, (1997):597-613; Topf et al., *Gene Ther.* 5, (1998):507-513; Sterman et al., *Hum. Gene Ther.* 7, (1998): 1083-1089.

Packaging cells are used to form virus particles that are capable of infecting a host cell. Such cells include 293 cells, which package adenovirus, and $\psi^2$ cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

The vector can be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci.* 92, (1995):9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Vectors can be delivered in vivo by administration to an individual subject, typically by systemic administration (e.g., intravenous, intraperitoneal, intramuscular, intrathecal, intratracheal, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

In some embodiments, the polypeptides of the CRISPR-Cas system are synthesized in situ in the cell as a result of the introduction of polynucleotides encoding the polypeptides into the cell. In some aspects, the polypeptides of the CRISP-Cas system could be produced outside the cell and then introduced thereto. Methods for introducing a CRISPR-Cas polynucleotide construct into animal cells are known and include, as non-limiting examples stable transformation methods wherein the polynucleotide construct is integrated into the genome of the cell, transient transformation methods wherein the polynucleotide construct is not integrated into the genome of the cell, and virus mediated methods, as described herein. Preferably, the CRISPR-Cas polynucleotide is transiently expressed and not integrated into the genome of the cell. In some embodiments, the CRISPR-Cas polynucleotides may be introduced into the cell by for example, recombinant viral vectors (e.g. retroviruses, adenoviruses), liposome and the like. For example, in some aspects, transient transformation methods include microinjection, electroporation, or particle bombardment. In some embodiments, the CRISPR-Cas polynucleotides may be included in vectors, more particularly plasmids or virus, in view of being expressed in the cells.

In some embodiments, non-CRISPR-CAS viral and non-viral based gene transfer methods can be used to insert nucleic acids encoding a dTAG in frame in the genomic locus of a protein of interest in mammalian cells or target tissues. Such methods can be used to administer nucleic acids encoding components of a ZFP, ZFN, TALE, and/or TALEN system to cells in culture, or in a host organism including a donor sequence encoding a dTAG for in-frame insertion into the genomic locus of a protein of interest.

Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256, (1992):808-813; Nabel & Feigner, *TIBTECH* 11, (1993): 211-217; Mitani & Caskey, *TIBTECH* 11, (1993): 162-166; Dillon. *TIBTECH* 11, (1993): 167-173; Miller, Nature 357, (1992):455-460; Van Brunt, Biotechnology 6(10), (1988): 1149-1154; Vigne, *Restorative Neurology and Neuroscience* 8, (1995):35-36; Kremer & Perricaudet, *British Medical Bulletin* 51(1), (1995):31-44; and Yu et al., Gene Therapy 1, (1994): 13-26.

The preparation of lipid:nucleic acid complexes, including targeted liposomes such as immunolipid complexes, is well known to one of skill in the art (see, e.g., Crystal, Science 270, (1995):404-410; Blaese et al., Cancer *Gene Ther.* 2, (1995):291-297; Behr et al., *Bioconjugate Chem.* 5, (1994):382-389; Remy et al., *Bioconjugate Chem.* 5, (1994): 647-654; Gao et al., Gene Therapy 2, (1995):710-722; Ahmad et al., Cancer Res. 52, (1992):4817-4820; and U.S. Pat. Nos. 4,186,183, 4,217,344, 4,235,871, 4,261,975, 4,485,054, 4,501,728, 4,774,085, 4,837,028, and 4,946, 787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al *Nature Biotechnology* 27(7), (2009):643).

D. Heterobifunctional Compounds

The present application includes the use of a heterobifunctional compound which has (i) a moiety that binds to a ubiquitin ligase and (ii) a targeting moiety which binds to a dTAG which has been fused to an endogenous protein intended for ubiquitination and proteasomal degradation. In one embodiment the heterobifunctional compound binds to a dTAG that is mutated to have selectivity over the corresponding endogenous protein (i.e. the dTAG Targeting Ligand binds dTAG but does not significantly bind to the naturally occurring (and in some embodiments, will not significantly bind to a mutant or variant protein expressed by the host)).

Strategies harnessing the ubiquitin proteasome pathway (UPP) to selectively target and degrade proteins have been employed for post-translational control of protein function. Heterobifunctional compounds, are composed of a target protein-binding ligand and an E3 ubiquitin ligase ligand. Heterobifunctional compounds, are capable of induced proteasome-mediated degradation of selected proteins via their recruitment to E3 ubiquitin ligase and subsequent ubiquitination. These drug-like molecules offer the possibility of reversible, dose-responsive, tunable, temporal control over protein levels. An early description of such compounds was provided in U.S. Pat. No. 7,041,298, titled "Proteolysis Targeting Chimeric Pharmaceutical," filed in September 2000 by Deshales et al. and granted in May 2006. The publication by Sakamoto et al. (*PNAS* 98(15) (2001): 8554-8559), titled "PROTACS: Chimeric Molecules that Target Proteins to the Skp1-Cullin F Box Complex for Ubiquitination and Degradation," describes a heterobifunctional compound consisting of a small molecule binder of MAP-AP-2 linked to a peptide capable of binding the F-box protein β-TRCP, the disclosure of which is also provided in U.S. Pat. No. 7,041,298. The publication by Sakamoto et al. (*Molecular and Cellular Proteomics* 2 (2003):1350-1358), titled "Development of PROTACS to Target Cancer-promoting Proteins for Ubiquitination and Degradation," describes an analogous heterobifunctional compound (PROTAC2) that instead of degrading MAP-AP-2 degrades estrogen and androgen receptors. The publication by Schneekloth et al. (JACS 126 (2004):3748-3754), titled "Chemical Genetic Control of Protein Levels: Selective in vivo Targeted Degradation," describes an analogous heterobifunctional compound (PROTAC3) that targets the FK506 binding protein (FKBP12) and shows both PROTAC2 and PROTAC3 hit their respective targets with green fluorescent protein (GFP) imaging. The publication by Schneekloth et al. (*ChemBioChem* 6 (2005)40-46) titled "Chemical Approaches to Controlling Intracellular Protein Degradation" described the state of the field at the time, using the technology. The publication by Schneekloth et al. (*BMCL* 18(22) (2008): 5904-5908), titled "Targeted Intracellular Protein Degradation Induced by a Small Molecule: En Route to Chemical Proteomics," describes a heterobifunctional compound that consist of two small molecules linked by PEG that in vivo degrades the androgen receptor by concurrently binding the androgen receptor and Ubiquitin E3 ligase. WO 2013/170147 to Crews et al., titled "Compounds Useful for Promoting Protein Degradation and Methods Using Same," describes compounds comprising a protein degradation moiety covalently bound to a linker, wherein the ClogP of the compound is equal to or higher than 1.5. A review of the foregoing publications by Buckley et al. (*Angew. Chem. Int. Ed.* 53 (2014):2312-2330) is titled "Small-Molecule Control of Intraceullular Protein Levels through Modulation of the Ubiquitin Proteasome System." WO 2015/160845 assigned to Arvinas Inc., titled "Imide Based Modulators of Proteolysis and Associated methods of Use," describes the use of Degron technology with thalidomide to utilize cereblon as the E3 ligase protein. The following publication by J. Lu et al. (*Chemistry and Biol.* 22(6) (2015):755-763), titled "Hijacking the E3 Ubiquitin Ligase Cereblon to efficiently Target BDR4," similarly describes thalidomide based compounds useful for degrading BDR4. Additional publications describing this technology include Bondeson et al. (*Nature Chemical Biology* 11 (2015):611-617), Gustafson et al. (*Angew. Chem. Int. Ed.* 54 (2015):9659-9662), Buckley et al. (*ACS Chem. Bio.* 10 (2015):1831-1837), U.S. 2016/0058872 assigned to Arvinas Inc. titled "Imide Based Modulators of Proteolysis and Associated Methods of Use", U.S. 2016/0045607 assigned to Arvinas Inc. titled "Estrogen-related Receptor Alpha Based PROTAC Compounds and Associated Methods of Use", U.S. 2014/0356322 assigned to Yale University, GlaxoSmithKline, and Cambridge Enterprise Limited University of Cambridge titled "Compounds and Methods for the Enhanced Degradation of Targeted Proteins & Other Polypeptides by an E3 Ubiquitin Ligase", Lai et al. (*Angew. Chem. Int. Ed.* 55 (2016):807-810), Toure et al. (*Angew. Chem. Int. Ed.* 55 (2016):1966-1973), and US 2016/0176916 assigned to Dana Farber Cancer Institute titled "Methods to Induce Targeted Protein Degradation Through Bifunctional Molecules."

Other descriptions of targeted protein degradation technology include Itoh et al. (*JACS* 132(16) (2010):5820-5826), titled "Protein Knockdown Using Methyl Bestatin-Ligand Hybrid Molecules: Design and Synthesis of Inducers of Ubiquitination-Mediated Degradation of Cellular Retinoic Acid-Binding Proteins," which describes a small molecule linked to a peptide that utilizes E3 ubiquitin ligase to degraded retinoic acid-binding proteins, and Winter et al. (*Science* 348 (2015):1376-1381), titled "Phthalimide Conjugation as a Strategy for in vivo Target Protein Degradation," describes thalidomide based targeted protein degradation technology.

Heterobifunctional compounds useful for present invention may be any heterobifunctional compound capable of binding to a dTAG to induce degradation. Heterobifunctional compounds are generally known in the art, for example, see U.S. Pat. No. 7,041,298; Sakamoto et al. (*PNAS*, 2001, 98(15): 8554-8559); Sakamoto et al. (*Molecular and Cellular Proteomics* 2 (2003)1350-1358); Schneekloth et al. (*JACS* 126 (2004):3748-3754); Schneekloth et al. (*ChemBioChem* 6 (2005):40-46); Schneekloth et al. (*BMCL* 18(22) (2008):5904-5908); WO 2013/170147; Buckley et al. (*Angew. Chem. Int. Ed.* 53 (2014):2312-2330); WO 2015/160845; Lu et al. (*Chemistry and Biol.* 22(6) (2015):755-763); Bondeson et al. (*Nature Chemical Biology* 11 (2015): 611-617); Gustafson et al. (*Angew. Chem. Int. Ed.* 54 (2015): 9659-9662); Buckley et al. (*ACS Chem. Bio.* 10 (2015): 1831-1837); U.S. 2016/0058872 assigned to Arvinas Inc. titled "Imide Based Modulators of Proteolysis and Associated Methods of Use", U.S. 2016/0045607 assigned to Arvinas Inc. titled "Estrogen-related Receptor Alpha Based PROTAC Compounds and Associated Methods of Use", U.S. 2014/0356322 assigned to Yale University, GlaxoSmithKline, and Cambridge Enterprise Limited University of Cambridge titled "Compounds and Methods for the Enhanced Degradation of Targeted Proteins & Other Polypeptides by an E3 Ubiquitin Ligase", U.S. 2016/0176916 assigned to Dana-Farber Cancer Institute, Inc. titled "Methods to Induce Targeted Protein Degradation Through Bifunctional Molecules", Lai et al. (*Angew. Chem. Int. Ed.* 55 (2016):807-810); Toure et al. (*Angew. Chem. Int. Ed.* 55

(2016):1966-1973); Itoh et al. (JACS 132(16) (2010):5820-5826); and Winter et al. (*Science* 348 (2015):1376-1381), each of which is incorporated herein by reference.

In general, heterobifunctional compounds suitable for use in the present application have the general structure:

Degron-Linker-dTAG Targeting Ligand wherein the Linker is covalently bound to a Degron and a dTAG Targeting Ligand, the Degron is a compound capable of binding to a ubiquitin ligase such as an E3 Ubiquitin Ligase (e.g., cereblon), and the dTAG Targeting Ligand is capable of binding to the dTAG on the endogenous protein-dTAG hybrid protein.

In certain embodiments, the present application utilizes a compound of Formula I or Formula II:

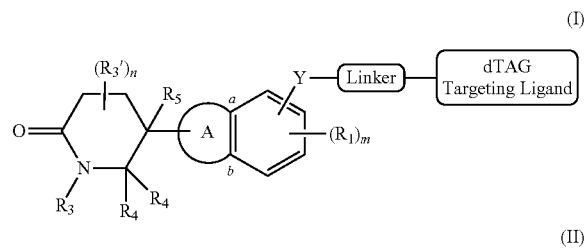
(I)

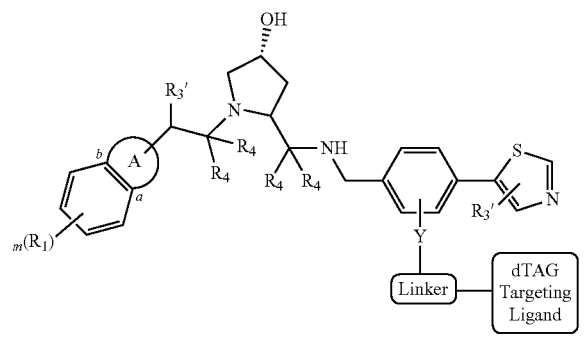
(II)

wherein:
the Linker is a group that covalently binds to the dTAG Targeting Ligand and Y; and the dTAG Targeting Ligand is capable of binding to a dTAG target or being bound by a dTAG target that allows tagging to occur.

In certain embodiments, the present application provides a compound of Formula (I), or an enantiomer, diastereomer, stereoisomer, or pharmaceutically acceptable salt thereof, wherein:
the Linker (L) is a group that covalently binds to the dTAG Targeting Ligand and Y; and the dTAG Targeting Ligand is capable of binding to or binds to a dTAG;

and wherein X1, X2, Y, $R_1$, $R_2$, $R_2'$, $R_3$, $R_3'$, $R_4$, $R_5$, m and n are each as defined herein.

In certain embodiments, the present application provides a compound of Formula (II), or an enantiomer, diastereomer, stereoisomer, or pharmaceutically acceptable salt thereof, wherein:
the Linker is a group that covalently binds to the dTAG Targeting Ligand and Y; and the dTAG Targeting Ligand is capable of binding to or binds to a dTAG;

and wherein $X_1$, $X_2$, Y, $R_1$, $R_2$, $R_2'$, $R_3$, $R_3'$, $R_4$, $R_5$, m and n are each as defined herein.

In certain embodiments, the present invention uses a compound of Formula III, Formula IV, Formula V, Formula VI, Formula VII, Formula VIII, and Formula IX:

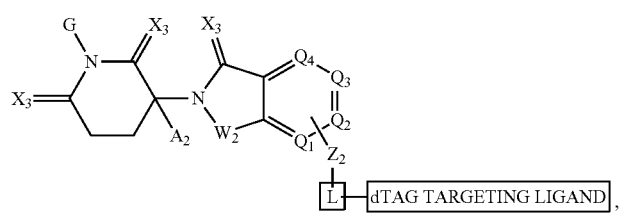
(III)

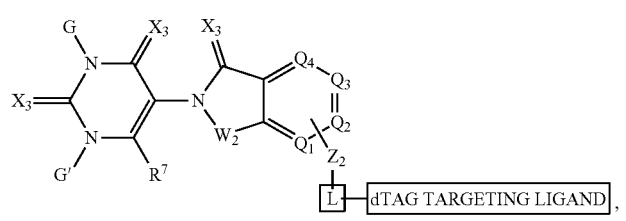
(IV)

(V)

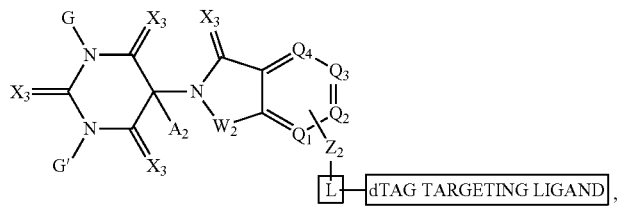

(VI)

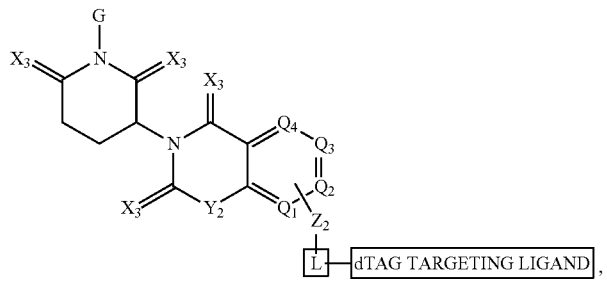

(VII)

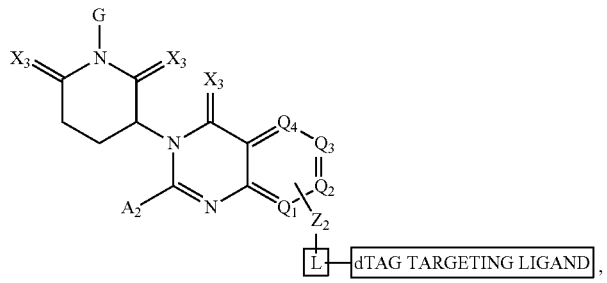

(VIII)

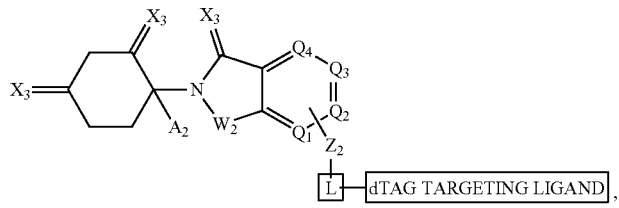

(IX)

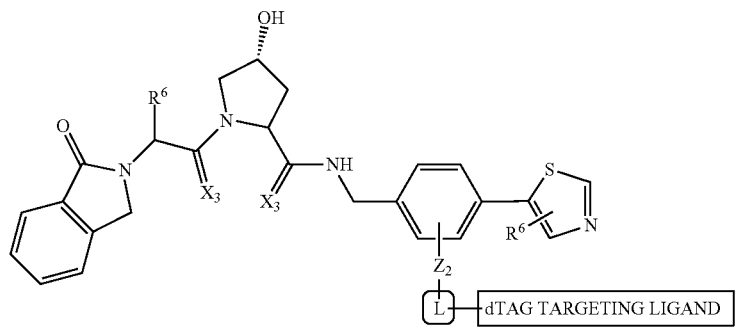

wherein:
the Linker (L) is a group that covalently binds to the dTAG Targeting Ligand and $Z_2$;
the dTAG Targeting Ligand is capable of binding to a target dTAG or being bound by a target dTAG;
$Z_2$ is a bond, alkyl, —O, —C(O)NR$_2$, —NR$^6$C(O), —NH, or —NR$^6$;
$R^6$ is H, alkyl, —C(O)alkyl, or —C(O)H;
$X_3$ is independently selected from O, S, and CH$_2$;
$W_2$ is independently selected from the group CH$_2$, CHR, C=O, SO$_2$, NH, and N-alkyl;

$Y_2$ is independently selected from the group NH, N-alkyl, N-aryl, N-hetaryl, N-cycloalkyl, N-heterocyclyl, O, and S;

G and G' are independently selected from the group H, alkyl, OH, CH$_2$-heterocyclyl optionally substituted with R', and benzyl optionally substituted with R';

$Q_1$, $Q_2$, $Q_3$, and $Q_4$ are independently selected from CH, N, CR', and N-oxide.

$A_2$ is independently selected from the group alkyl, cycloalkyl, Cl and F;

R[7] is selected from: CONR'R", OR', NR'R", SR', SO$_2$R', SO$_2$NR'R", CR'R"—, —CR'NR'R"—, -aryl, -hetaryl, -alkyl, -cycloalkyl, -heterocyclyl, —P(O)(OR')R", P(O)R'R", —OP(O)(OR')R", —OP(O)R'R", —Cl, —F, —Br, —I, —CF$_3$, —CN, NR'SO$_2$NR'R", —NR-'CONR'R", —CONR'COR", —NR'C(=N—CN)NR'R", —C(=N—CN)NR'R", —NR'C(=N—CN)R", —NR'C(=C—NO$_2$)NR'R", —SO$_2$NR'COR", —NO$_2$, CO$_2$R', —C(C=N—OR')R", —CR'=CR'R", —CCR', —S(C=O)(C=N—R')R", —SF$_5$ and —OCF$_3$ R' and R" are independently selected from a bond, H, alkyl, cycloalkyl, aryl, heteroaryl, heterocyclyl Non-limiting examples of dTAG Targeting Ligands for use in the present invention include:

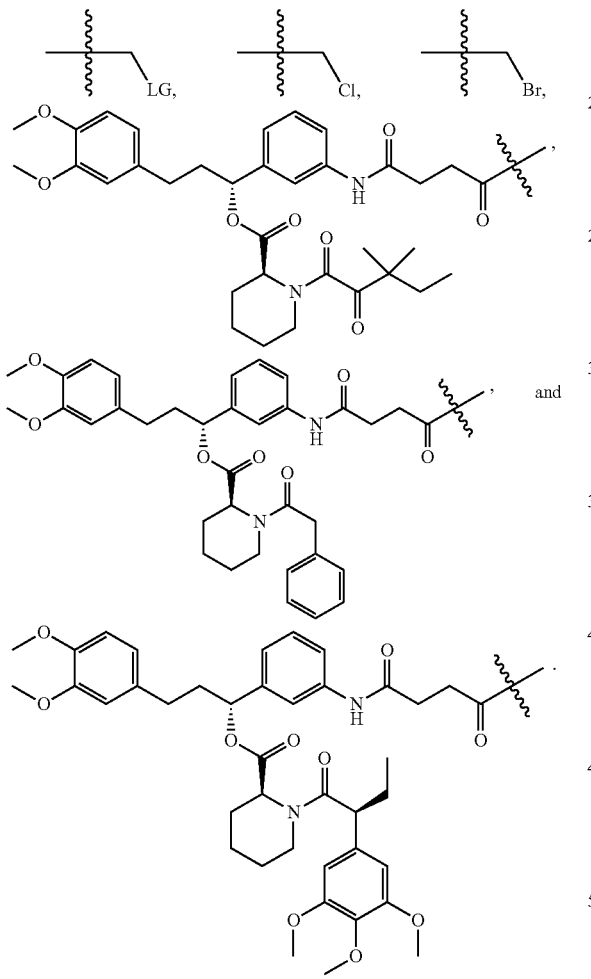

In some embodiments the dTAG Targeting Ligand targets a mutated endogenous target or a non-endogenous target.

Degron

The Degron is a compound moiety that links a dTAG, through the Linker and dTAG Targeting Ligand, to a ubiquitin ligase for proteosomal degradation. In certain embodiments, the Degron is a compound that is capable of binding to or binds to a ubiquitin ligase. In further embodiments, the Degron is a compound that is capable of binding to or binds to a E3 Ubiquitin Ligase. In further embodiments, the Degron is a compound that is capable of binding to or binds to cereblon. In further embodiments, the Degron is a thalidomide or a derivative or analog thereof.

In certain embodiments, the Degron is a moiety of Formula D, Formula D0, or Formula D':

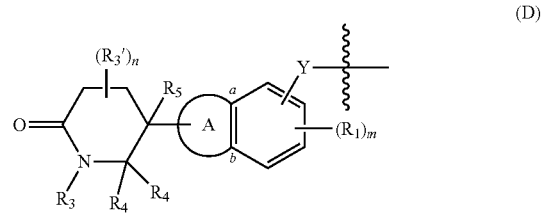

(D)

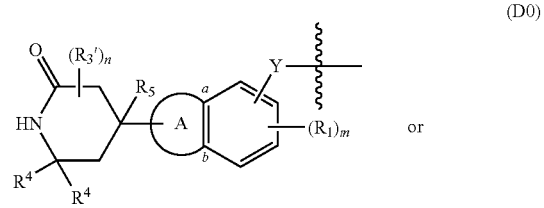

(D0)

or

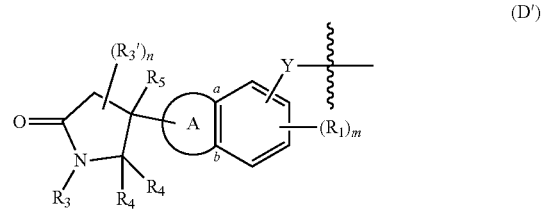

(D')

or an enantiomer, diastereomer, or stereoisomer thereof, wherein:

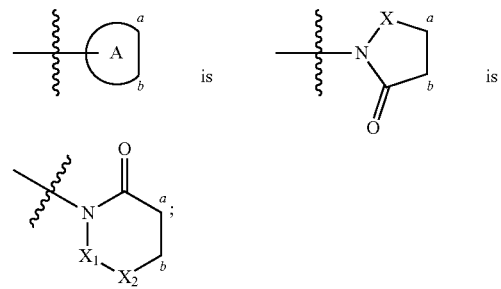

Y is a bond, (CH$_2$)$_{1-6}$, (CH$_2$)$_{0-6}$—O, (CH$_2$)$_{0-6}$—C(O)NR$_2$', (CH$_2$)$_{0-6}$—NR$_2$'C(O), (CH$_2$)$_{0-6}$—NH, or (CH$_2$)$_{0-6}$—NR$_2$;

X is C(O) or C(R$_3$)$_2$;

X$_1$—X$_2$ is C(R$_3$)=N or C(R$_3$)$_2$—C(R$_3$)$_2$;

each R$_1$ is independently halogen, OH, C$_1$-C$_6$ alkyl, or C$_1$-C$_6$ alkoxy;

R$_2$ is C$_1$-C$_6$ alkyl, C(O)—C$_1$-C$_6$ alkyl, or C(O)—C$_3$-C$_6$ cycloalkyl;

R$_2$' is H or C$_1$-C$_6$ alkyl;

each R$_3$ is independently H or C$_1$-C$_3$ alkyl;

each R$_3$' is independently C$_1$-C$_3$ alkyl;

each R$_4$ is independently H or C$_1$-C$_3$ alkyl; or two R$_4$, together with the carbon atom to which they are attached, form C(O), a C$_3$-C$_6$ carbocycle, or a 4-, 5-, or 6-membered heterocycle comprising 1 or 2 heteroatoms selected from N and O;

R$_5$ is H, deuterium, C$_1$-C$_3$ alkyl, F, or C;

m is 0, 1, 2 or 3; and n is 0, 1 or 2;

wherein the compound is covalently bonded to another moiety (e.g., a compound, or a Linker) via

In certain embodiments, the Degron is a moiety of Formula D, wherein

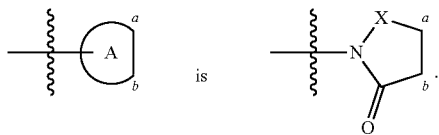

In certain embodiments, the Degron is a moiety of Formula D, wherein

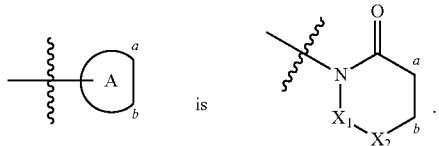

In certain embodiments, the Degron is a moiety of Formula D, wherein X is C(O).

In certain embodiments, the Degron is a moiety of Formula D, wherein X is $C(R_3)_2$; and each $R_3$ is H. In certain embodiments, X is $C(R_3)_2$; and one of $R_3$ is H, and the other is $C_1$-$C_3$ alkyl selected from methyl, ethyl, and propyl. In certain embodiments, X is $C(R_3)_2$; and each $R_3$ is independently selected from methyl, ethyl, and propyl.

In certain embodiments, the Degron is a moiety of Formula D, wherein $X_1$—$X_2$ is $C(R_3)$=N.

In certain embodiments, $X_1$—$X_2$ is CH=N. In certain embodiments, $X_1$—$X_2$ is $C(R_3)$=N; and $R_3$ is $C_1$-$C_3$ alkyl selected from methyl, ethyl, and propyl. In certain embodiments, $X_1$—$X_2$ is $C(CH_3)$=N.

In certain embodiments, the Degron is a moiety of Formula D, wherein $X_1$—$X_2$ is $C(R_3)_2$—$C(R_3)_2$; and each $R_3$ is H. In certain embodiments, $X_1$—$X_2$ is $C(R_3)_2$—$C(R_3)_2$; and one of $R_3$ is H, and the other three $R_3$ are independently $C_1$-$C_3$ alkyl selected from methyl, ethyl, and propyl. In certain embodiments, $X_1$—$X_2$ is $C(R_3)_2$—$C(R_3)_2$; and two of the $R_3$ are H, and the other two $R_3$ are independently $C_1$-$C_3$ alkyl selected from methyl, ethyl, and propyl. In certain embodiments, $X_1$—$X_2$ is $C(R_3)_2$—$C(R_3)_2$; and three of the $R_3$ are H, and the remaining $R_3$ is $C_1$-$C_3$ alkyl selected from methyl, ethyl, and propyl.

In certain embodiments, the Degron is a moiety of Formula D, wherein Y is a bond.

In certain embodiments, the Degron is a moiety of Formula D, wherein Y is $(CH_2)_1$, $(CH_2)_2$, $(CH_2)_3$, $(CH_2)_4$, $(CH_2)_5$, or $(CH_2)_6$. In certain embodiments, Y is $(CH_2)_1$, $(CH_2)_2$, or $(CH_2)_3$. In certain embodiments, Y is $(CH_2)_1$ or $(CH_2)_2$.

In certain embodiments, the Degron is a moiety of Formula D, wherein Y is O, $CH_2$—O, $(CH_2)_2$—O, $(CH_2)_3$—O, $(CH_2)_4$—O, $(CH_2)_5$—O, or $(CH_2)_6$—O. In certain embodiments, Y is O, $CH_2$—O, $(CH_2)_2$—O, or $(CH_2)_3$—O. In certain embodiments, Y is O or $CH_2$—O. In certain embodiments, Y is O.

In certain embodiments, the Degron is a moiety of Formula D, wherein Y is $C(O)NR_2'$, $CH_2$—$C(O)NR_2'$, $(CH_2)_2$—$C(O)NR_2'$, $(CH_2)_3$—$C(O)NR_2'$, $(CH_2)_4$—$C(O)NR_2'$, $(CH_2)_5$—$C(O)NR_2'$, or $(CH_2)_6$—$C(O)NR_2'$. In certain embodiments, Y is $C(O)NR_2'$, $CH_2$—$C(O)NR_2'$, $(CH_2)_2$—$C(O)NR_2'$, or $(CH_2)_3$—$C(O)NR_2'$. In certain embodiments, Y is $C(O)NR_2'$ or $CH_2$—$C(O)NR_2'$. In certain embodiments, Y is $C(O)NR_2'$.

In certain embodiments, the Degron is a moiety of Formula D, wherein Y is $NR_2'C(O)$, $CH_2$—$NR_2'C(O)$, $(CH_2)_2$—$NR_2'C(O)$, $(CH_2)_3$—$NR_2'C(O)$, $(CH_2)_4$—$NR_2'C(O)$, $(CH_2)_5$—$NR_2'C(O)$, or $(CH_2)_6$—$NR_2'C(O)$. In certain embodiments, Y is $NR_2'C(O)$, $CH_2$—$NR_2'C(O)$, $(CH_2)_2$—$NR_2'C(O)$, or $(CH_2)_3$—$NR_2'C(O)$. In certain embodiments, Y is $NR_2'C(O)$ or $CH_2$—$NR_2'C(O)$. In certain embodiments, Y is $NR_2'C(O)$.

In certain embodiments, the Degron is a moiety of Formula D, wherein $R_2'$ is H. In certain embodiments, the Degron is a moiety of Formula D, wherein $R_2'$ is selected from methyl, ethyl, propyl, butyl, i-butyl, t-butyl, pentyl, i-pentyl, and hexyl. In certain embodiments, $R_2'$ is $C_1$-$C_3$ alkyl selected from methyl, ethyl, and propyl.

In certain embodiments, the Degron is a moiety of Formula D, wherein Y is NH, $CH_2$—NH, $(CH_2)_2$—NH, $(CH_2)_3$—NH, $(CH_2)_4$—NH, $(CH_2)_5$—NH, or $(CH_2)_6$—NH. In certain embodiments, Y is NH, $CH_2$—NH, $(CH_2)_2$—NH, or $(CH_2)_3$—NH. In certain embodiments, Y is NH or $CH_2$—NH. In certain embodiments, Y is NH.

In certain embodiments, the Degron is a moiety of Formula D, wherein Y is $NR_2$, $CH_2$—$NR_2$, $(CH_2)_2$—$NR_2$, $(CH_2)_3$—$NR_2$, $(CH_2)_4$—$NR_2$, $(CH_2)_5$—$NR_2$, or $(CH_2)_6$—$NR_2$. In certain embodiments, Y is $NR_2$, $CH_2$—$NR_2$, $(CH_2)_2$—$NR_2$, or $(CH_2)_3$—$NR_2$. In certain embodiments, Y is $NR_2$ or $CH_2$—$NR_2$.

In certain embodiments, Y is $NR_2$.

In certain embodiments, the Degron is a moiety of Formula D, wherein $R_2$ is selected from methyl, ethyl, propyl, butyl, i-butyl, t-butyl, pentyl, i-pentyl, and hexyl. In certain embodiments, $R_2$ is $C_1$-$C_3$ alkyl selected from methyl, ethyl, and propyl.

In certain embodiments, the Degron is a moiety of Formula D, wherein $R_2$ is selected from C(O)-methyl, C(O)-ethyl, C(O)-propyl, C(O)-butyl, C(O)-i-butyl, C(O)-t-butyl, C(O)-pentyl, C(O)-i-pentyl, and C(O)-hexyl. In certain embodiments, $R_2$ is C(O)—$C_1$-$C_3$ alkyl selected from C(O)-methyl, C(O)-ethyl, and C(O)-propyl.

In certain embodiments, the Degron is a moiety of Formula D, wherein $R_2$ is selected from C(O)-cyclopropyl, C(O)-cyclobutyl, C(O)-cyclopentyl, and C(O)-cyclohexyl. In certain embodiments, $R_2$ is C(O)-cyclopropyl.

In certain embodiments, the Degron is a moiety of Formula D, wherein $R_3$ is H.

In certain embodiments, the Degron is a moiety of Formula D, wherein $R_3$ is $C_1$-$C_3$ alkyl selected from methyl, ethyl, and propyl. In certain embodiments, $R_3$ is methyl.

In certain embodiments, the Degron is a moiety of Formula D, wherein n is 0.

In certain embodiments, the Degron is a moiety of Formula D, wherein n is 1.

In certain embodiments, the Degron is a moiety of Formula D, wherein n is 2.

In certain embodiments, the Degron is a moiety of Formula D, wherein each $R_3'$ is independently $C_1$-$C_3$ alkyl selected from methyl, ethyl, and propyl.

In certain embodiments, the Degron is a moiety of Formula D, wherein m is 0.

In certain embodiments, the Degron is a moiety of Formula D, wherein m is 1.

In certain embodiments, the Degron is a moiety of Formula D, wherein m is 2.

In certain embodiments, the Degron is a moiety of Formula D, wherein m is 3.

In certain embodiments, the Degron is a moiety of Formula D, wherein each $R_1$ is independently selected from halogen (e.g., F, Cl, Br, and I), OH, $C_1$-$C_6$ alkyl (e.g., methyl, ethyl, propyl, butyl, i-butyl, t-butyl, pentyl, i-pentyl, and hexyl), and $C_1$-$C_6$ alkoxy (e.g., methoxy, ethoxy, propoxy, butoxy, i-butoxy, t-butoxy, and pentoxy). In further embodiments, the Degron is a moiety of Formula D, wherein each $R_1$ is independently selected from F, Cl, OH, methyl, ethyl, propyl, butyl, i-butyl, t-butyl, methoxy, and ethoxy.

In certain embodiments, the Degron is a moiety of Formula D, wherein each $R_4$ is H.

In certain embodiments, the Degron is a moiety of Formula D, wherein one of $R_4$ is H, and the other $R_4$ is $C_1$-$C_3$ alkyl selected from methyl, ethyl, and propyl.

In certain embodiments, the Degron is a moiety of Formula D, wherein each $R_4$ is independently $C_1$-$C_3$ alkyl selected from methyl, ethyl, and propyl.

In certain embodiments, the Degron is a moiety of Formula D, wherein two $R_4$, together with the carbon atom to which they are attached, form C(O).

In certain embodiments, the Degron is a moiety of Formula D, wherein two $R_4$, together with the carbon atom to which they are attached, form cyclopropyl, cyclobutyl, cyclopentyl, or cyclohexyl.

In certain embodiments, the Degron is a moiety of Formula D, wherein two $R_4$, together with the carbon atom to which they are attached, form a 4-, 5-, or 6-membered heterocycle selected from oxetane, azetidine, tetrahydrofuran, pyrrolidine, piperidine, piperazine, and morpholine. In certain embodiments, two $R_4$, together with the carbon atom to which they are attached, form oxetane.

In certain embodiments, the Degron is a moiety of Formula D, wherein $R_5$ is H, deuterium, or $C_1$-$C_3$ alkyl. In further embodiments, $R_5$ is in the (S) or (R) configuration. In further embodiments, $R_5$ is in the (S) configuration. In certain embodiments, the Degron is a moiety of Formula D, wherein the compound comprises a racemic mixture of (S)—$R_5$ and (R)—$R_5$.

In certain embodiments, the Degron is a moiety of Formula D, wherein $R_5$ is H.

In certain embodiments, the Degron is a moiety of Formula D, wherein $R_5$ is deuterium.

In certain embodiments, the Degron is a moiety of Formula D, wherein $R_5$ is $C_1$-$C_3$ alkyl selected from methyl, ethyl, and propyl. In certain embodiments, $R_5$ is methyl.

In certain embodiments, the Degron is a moiety of Formula D, wherein $R_5$ is F or Cl. In further embodiments, $R_5$ is in the (S) or (R) configuration. In further embodiments, $R_5$ is in the (R) configuration. In certain embodiments, the Degron is a moiety of Formula D, wherein the compound comprises a racemic mixture of (S)—$R_5$ and (R)—$R_5$. In certain embodiments, $R_5$ is F.

In certain embodiments, the Degron is selected from the structures in FIG. 21, wherein X is H, deuterium, $C_1$-$C_3$ alkyl, or halogen; and R is the attachment point for the Linker.

Figure 22:
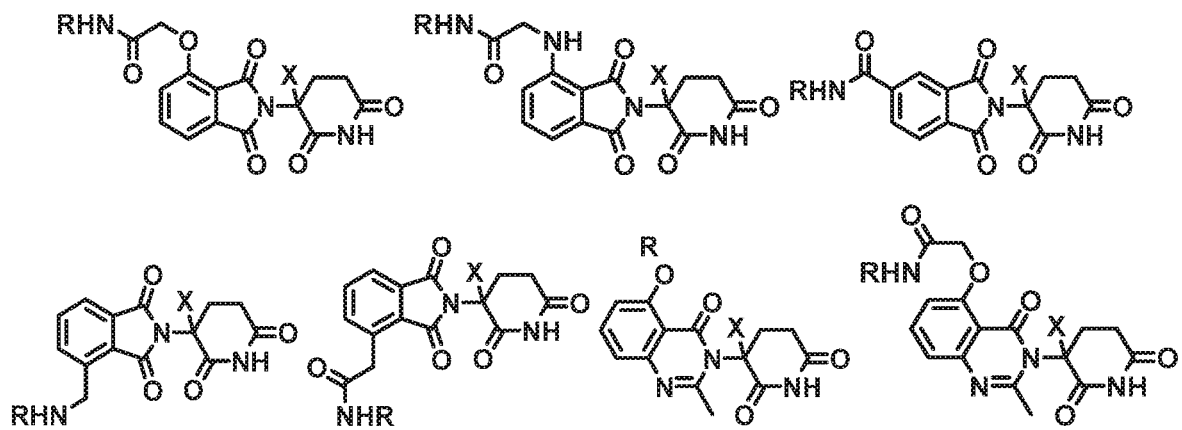
FIG. 22 provides additional examples of Degron moieties for use in the present invention, wherein R is the point of attachment for the Linker and X is as defined herein.

In certain embodiments, the Degron is selected from the structures in FIG. 22.

Figure 23:
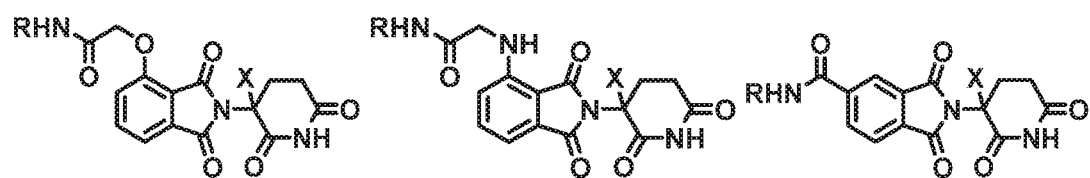
FIG. 23 provides additional examples of Degron moieties for use in the present invention, wherein R is the point of attachment for the Linker and X is as defined herein.

In certain embodiments, the Degron is selected from the structures in FIG. 23.

Linker

The Linker is a bond or a chemical group that links a dTAG Targeting Ligand with a Degron. In certain embodiments the Linker is a carbon chain. In certain embodiments, the carbon chain optionally includes one, two, three, or more heteroatoms selected from N, O, and S. In certain embodiments, the carbon chain comprises only saturated chain carbon atoms. In certain embodiments, the carbon chain optionally comprises two or more unsaturated chain carbon atoms (e.g., C=C or C≡C). In certain embodiments, one or more chain carbon atoms in the carbon chain are optionally substituted with one or more substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl)$_2$, CN, $C_3$-$C_8$ cycloalkyl, heterocyclyl, phenyl, and heteroaryl).

In certain embodiments, the Linker includes at least 5 chain atoms (e.g., C, O, N, and S).

In certain embodiments, the Linker comprises less than 20 chain atoms (e.g., C, O, N, and S). In certain embodiments, the Linker comprises 5, 6, 7, 8, 9, 10, 11, 12, 13, 14, 15, 16, 17, 18, or 19 chain atoms (e.g., C, O, N, and S). In certain embodiments, the Linker comprises 5, 7, 9, 11, 13, 15, 17, or 19 chain atoms (e.g., C, O, N, and S). In certain embodiments, the Linker comprises 5, 7, 9, or 11 chain atoms (e.g., C, O, N, and S). In certain embodiments, the Linker comprises 6, 8, 10, 12, 14, 16, or 18 chain atoms (e.g., C, O, N, and S). In certain embodiments, the Linker comprises 6, 8, 10, or 12 chain atoms (e.g., C, O, N, and S).

In certain embodiments, the Linker is a carbon chain optionally substituted with non-bulky substituents (e.g., oxo, $C_1$-$C_6$ alkyl, $C_2$-$C_6$ alkenyl, $C_2$-$C_6$ alkynyl, $C_1$-$C_3$ alkoxy, OH, halogen, $NH_2$, $NH(C_1$-$C_3$ alkyl), $N(C_1$-$C_3$ alkyl)$_2$, and CN). In certain embodiments, the non-bulky substitution is located on the chain carbon atom proximal to the Degron (i.e., the carbon atom is separated from the carbon atom to which the Degron is bonded by at least 3, 4, or 5 chain atoms in the Linker).

In certain embodiments, the Linker is of Formula L0:

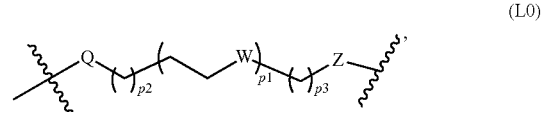

(L0)

or an enantiomer, diastereomer, or stereoisomer thereof, wherein
  p1 is an integer selected from 0 to 12;
  p2 is an integer selected from 0 to 12;
  p3 is an integer selected from 1 to 6;
  each W is independently absent, $CH_2$, O, S, NH or $NR_5$;
  Z is absent, $CH_2$, O, NH or $NR_5$;
  each $R_5$ is independently $C_1$-$C_3$ alkyl; and
  Q is absent or —$CH_2C(O)NH$—,
wherein the Linker is covalently bonded to the Degron with the

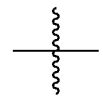

next to Q, and covalently bonded to the dTAG Targeting Ligand with the next to Z, and wherein the total number of chain atoms in the Linker is less than 20.

In certain embodiments, the Linker-dTAG Targeting Ligand (TL) has the structure of Formula L1 or L2:

(L1)

(L2)

or an enantiomer, diastereomer, or stereoisomer thereof, wherein:
p1 is an integer selected from 0 to 12;
p2 is an integer selected from 0 to 12;
p3 is an integer selected from 1 to 6;
each W is independently absent, $CH_2$, O, S, NH or $NR_5$;
Z is absent, $CH_2$, O, NH or $NR_5$;
each $R_5$ is independently $C_1$-$C_3$ alkyl; and
TL is a dTAG Targeting Ligand,
wherein the Linker is covalently bonded to the Degron with In certain embodiments, p1 is an integer selected from 0 to 10.
In certain embodiments, p1 is an integer selected from 2 to 10.
In certain embodiments, p1 is selected from 1, 2, 3, 4, 5, and 6.
In certain embodiments, p1 is selected from 1, 3, and 5.
In certain embodiments, p1 is selected from 1, 2, and 3.
In certain embodiments, p1 is 3.
In certain embodiments, p2 is an integer selected from 0 to 10.
In certain embodiments, p2 is selected from 0, 1, 2, 3, 4, 5, and 6.
In certain embodiments, p2 is an integer selected from 0 and 1.
In certain embodiments, p3 is an integer selected from 1 to 5.
In certain embodiments, p3 is selected from 2, 3, 4, and 5.
In certain embodiments, p3 is selected from 1, 2, and 3.
In certain embodiments, p3 is selected from 2 and 3.
In certain embodiments, at least one W is $CH_2$.
In certain embodiments, at least one W is O.
In certain embodiments, at least one W is S.
In certain embodiments, at least one W is NH.

In certain embodiments, at least one W is $NR_5$; and $R_5$ is $C_1$-$C_3$ alkyl selected from methyl, ethyl, and propyl.
In certain embodiments, W is O.
In certain embodiments, Z is absent.
In certain embodiments, Z is $CH_2$.
In certain embodiments, Z is O.
In certain embodiments, Z is NH.
In certain embodiments, Z is $NR_5$; and $R_5$ is $C_1$-$C_3$ alkyl selected from methyl, ethyl, and propyl.
In certain embodiments, Z is part of the dTAG Targeting Ligand that is bonded to the Linker, namely, Z is formed from reacting a functional group of the dTAG Targeting Ligand with the Linker.
In certain embodiments, W is $CH_2$, and Z is $CH_2$.
In certain embodiments, W is O, and Z is $CH_2$.
In certain embodiments, W is $CH_2$, and Z is O.
In certain embodiments, W is O, and Z is O.
In certain embodiments, the Linker-dTAG Targeting Ligand has the structure selected from Table L:

TABLE L wherein Z, TL, and p1 are each as described above.

Any one of the Degrons described herein can be covalently bound to any one of the Linkers described herein.

In certain embodiments, the present application includes the Degron-Linker (DL) having the following structure:

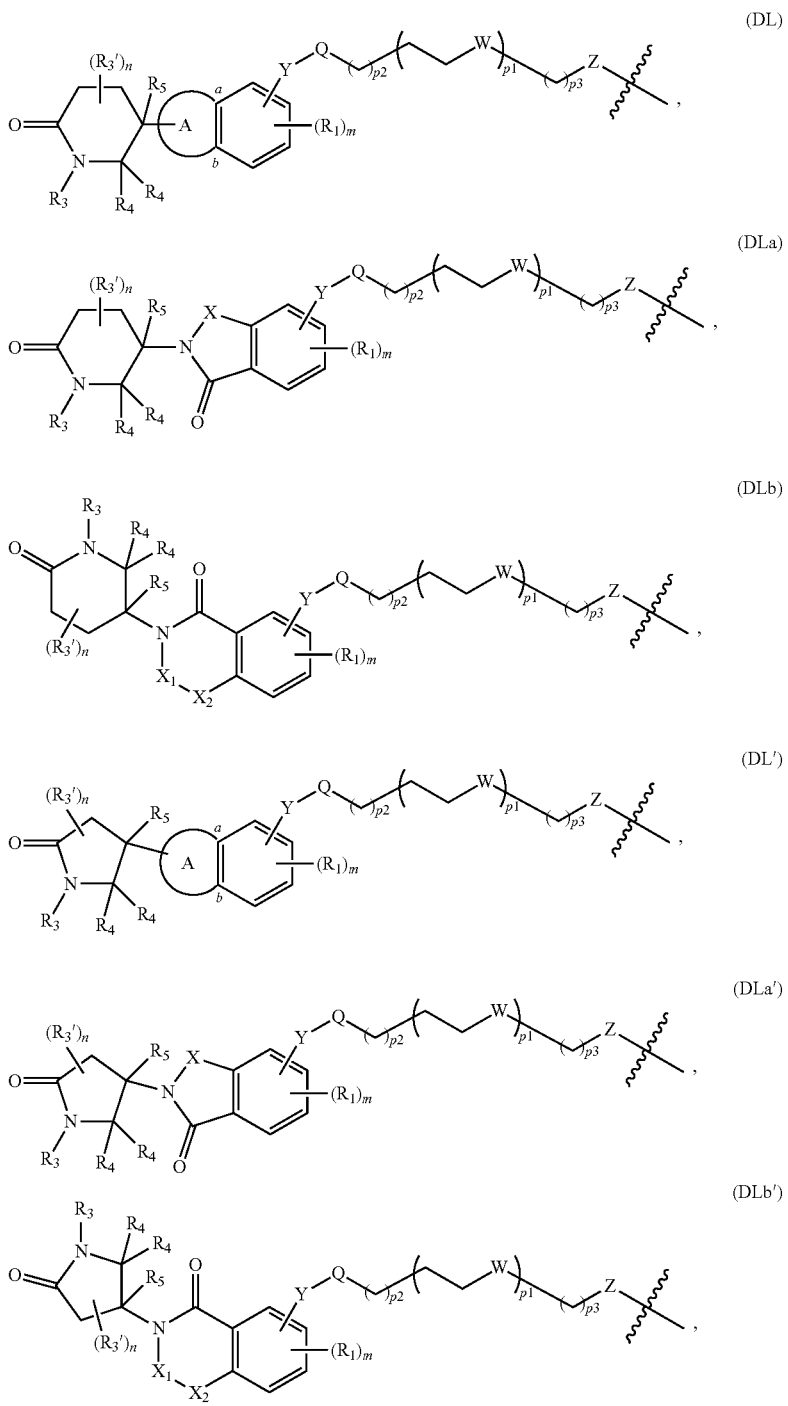
wherein each of the variables is as described above in Formula DO and Formula LO, and a dTAG Targeting Ligand is covalently bonded to the DL with the
next to Z.

In certain embodiments, the present application includes to the Degron-Linker (DL) having the following structure:

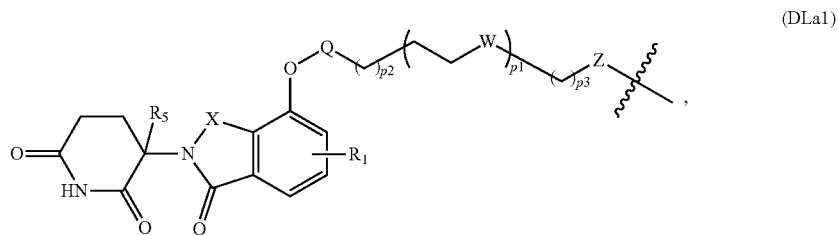
(DLa1)

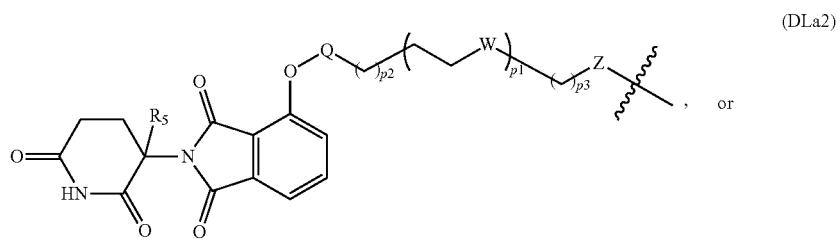
(DLa2), or

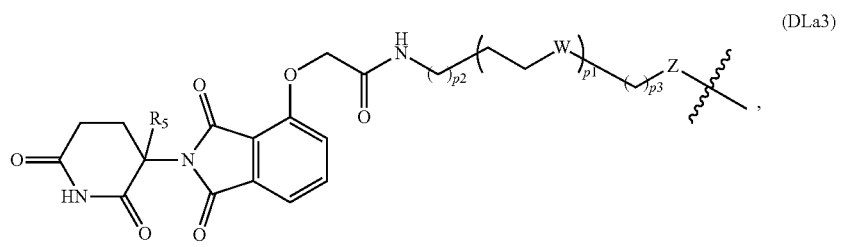
(DLa3), wherein each of the variables is as described above in Formula D and Formula LO, and a dTAG Targeting Ligand is covalently bonded to the DL with the

next to Z.

Some embodiments of the present application relate to a bifunctional compound having the following structure:

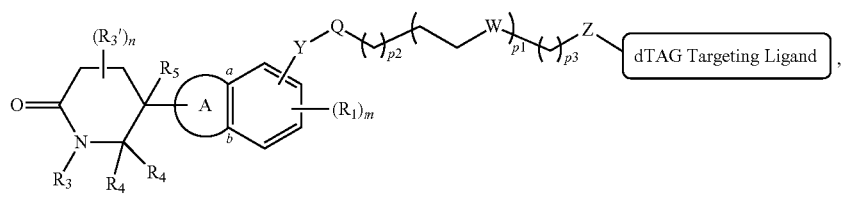,

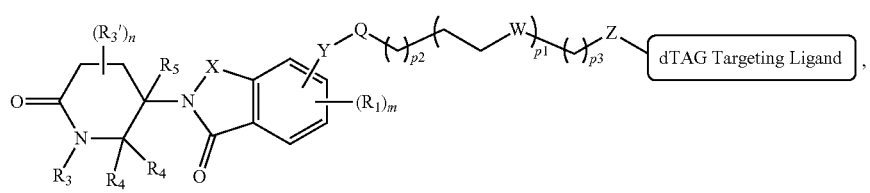,

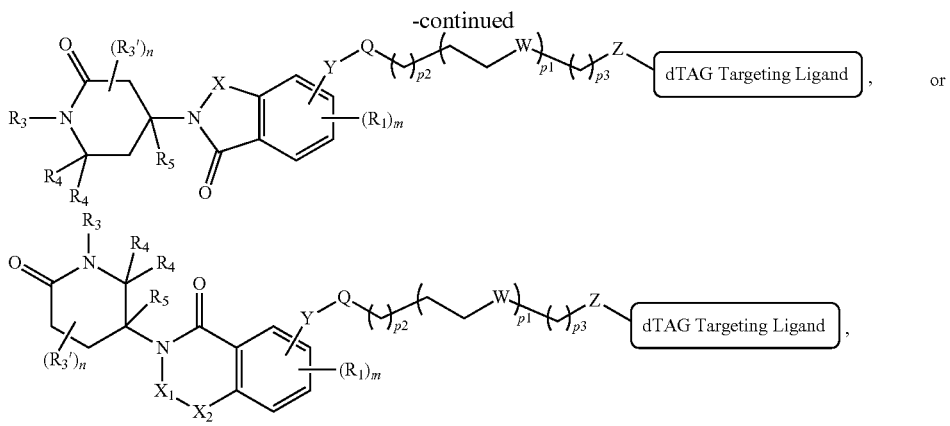

or an enantiomer, diastereomer, or stereoisomer thereof, wherein each of the variables is as described above in Formula D and Formula LO, and the dTAG Targeting Ligand is described herein below.

Further embodiments of the present application relate to a bifunctional compound having the following structure:

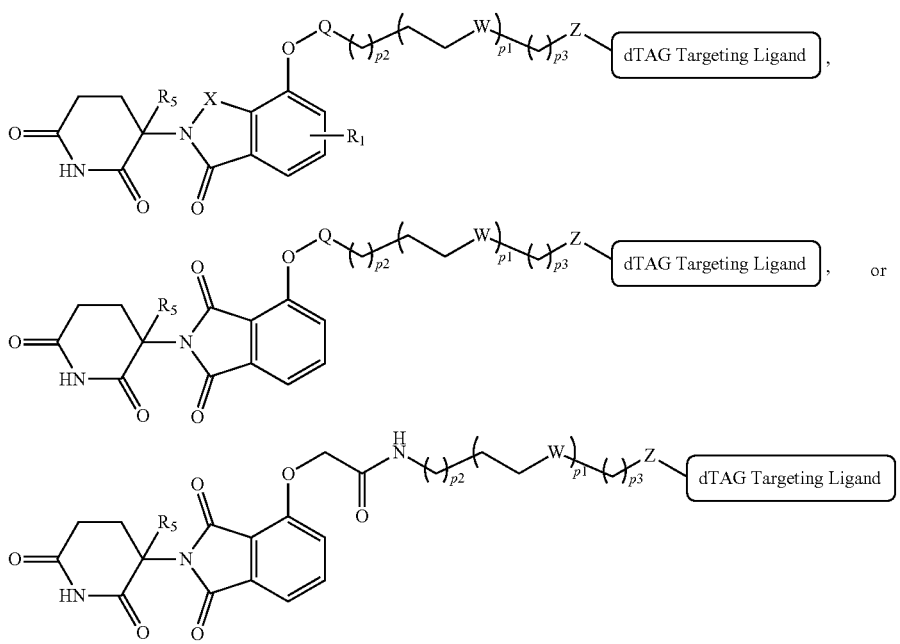

or an enantiomer, diastereomer, or stereoisomer thereof, wherein each of the variables is as described above in Formula D and Formula LO, and the dTAG Targeting Ligand is described herein below.

Certain embodiments of the present application relate to bifunctional compounds having one of the following structures:

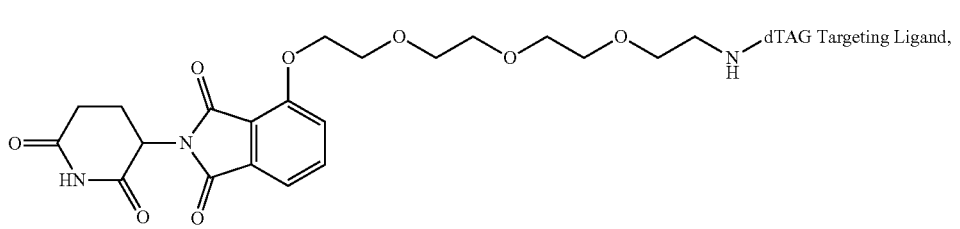

(DL1-TL)

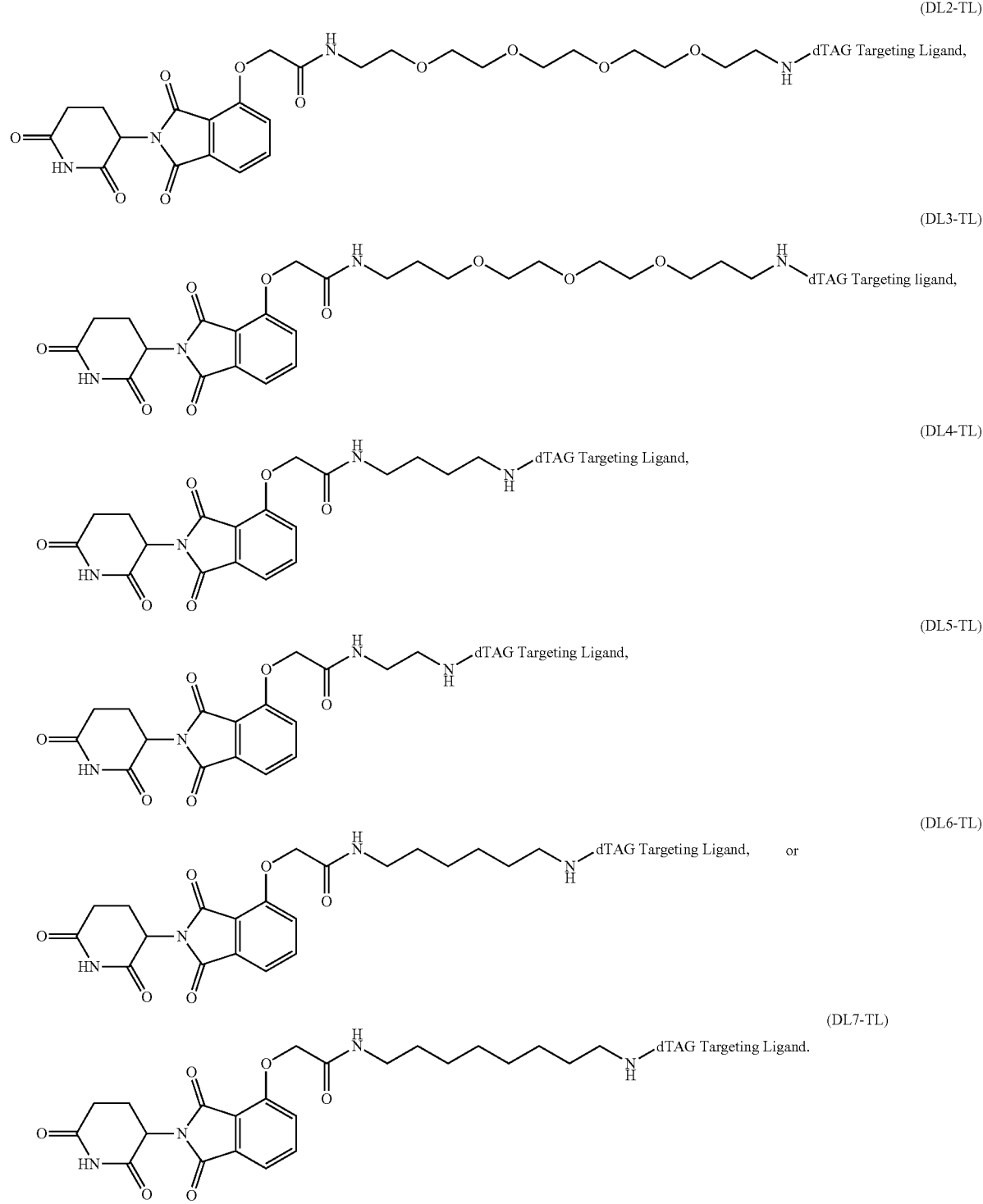

In certain embodiments, the Linker may be a polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In certain embodiments, the Linker is designed and optimized based on SAR (structure-activity relationship) and X-ray crystallography of the dTAG Targeting Ligand with regard to the location of attachment for the Linker.

In certain embodiments, the optimal Linker length and composition vary by target and can be estimated based upon X-ray structures of the original dTAG Targeting Ligand bound to its target. Linker length and composition can be also modified to modulate metabolic stability and pharmacokinetic (PK) and pharmacodynamics (PD) parameters.

In certain embodiments, where the dTAG Targeting Ligand binds multiple targets, selectivity may be achieved by varying Linker length where the ligand binds some of its targets in different binding pockets, e.g., deeper or shallower binding pockets than others.

In an additional embodiment, the heterobifunctional compounds for use in the present invention include a chemical Linker (L). In certain embodiments, the Linker group L is a group comprising one or more covalently connected structural units of A (e.g., -A$_1$ ... A$_q$-), wherein A$_1$ is a group coupled to at least one of a Degron, a dTAG Targeting Ligand, or a combination thereof.

In certain embodiments, A$_1$ links a Degron, a dTAG Targeting Ligand, or a combination thereof directly to another Degron, Targeting Ligand, or combination thereof. In other embodiments, A$_1$ links a Degron, a dTAG Targeting Ligand, or a combination thereof indirectly to another Degron, dTAG Targeting Ligand or combination thereof through A$_q$.

In certain embodiments, A$_1$ to A$_q$ are, each independently, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $SiR^{L1}R^{L2}$, $P(O)R^{L1}$, $P(O)OR^{L1}$, —$NR^{L3}C$(=NCN)$NR^{L4}$, $NR^{L3}C$(=NCN), $NR^{L3}C$(=$CNO_2$)$NR^{L4}$, $C_{3-11}$cycloalkyl optionally substituted with 0-6 $R^{L1}$ and/or $R^{L2}$ groups, $C_{3-11}$heteocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently, can be linked to other A groups to form a cycloalkyl and/or heterocyclyl moiety which can be further substituted with 0-4 $R^{L5}$ groups; wherein $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, CH=CH($C_{1-8}$alkyl), $C(C_{1-8}alkyl)$=CH($C_{1-8}$alkyl), $C(C_{1-8}alkyl)$=$C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-8}alkyl)_2$, NH $SO_2NH_2$.

In certain embodiments, q is an integer greater than or equal to 0. In certain embodiments, q is an integer greater than or equal to 1.

In certain embodiments, e.g., where q is greater than 2, A$_q$ is a group which is connected to a Degron, and A$_1$ and A$_q$ are connected via structural units of A (number of such structural units of A: q–2).

In certain embodiments, e.g., where q is 2, A$_q$ is a group which is connected to A$_1$ and to a Degron moiety.

In certain embodiments, e.g., where q is 1, the structure of the Linker group L is -A$_1$-, and A$_1$ is a group which is connected to a Degron moiety and a dTAG Targeting Ligand moiety.

In additional embodiments, q is an integer from 1 to 100, 1 to 90, 1 to 80, 1 to 70, 1 to 60, 1 to 50, 1 to 40, 1 to 30, 1 to 20, or 1 to 10.

Figure 24:
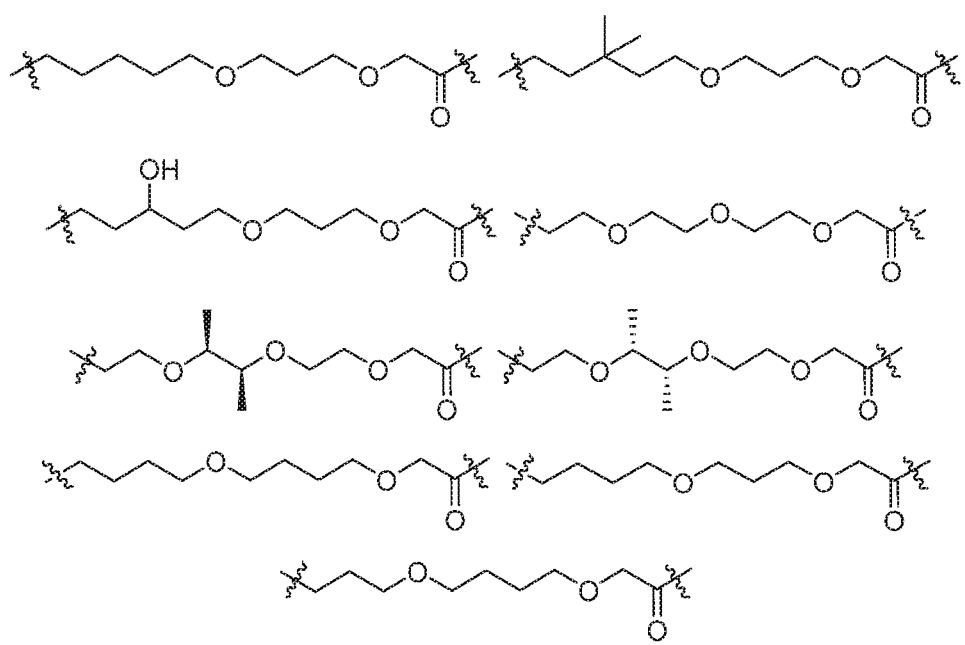
FIG. 24 provides examples of Linker moieties for use in the present invention.

In certain embodiments, the Linker (L) is selected from the structures in FIG. 24.

Figure 25:
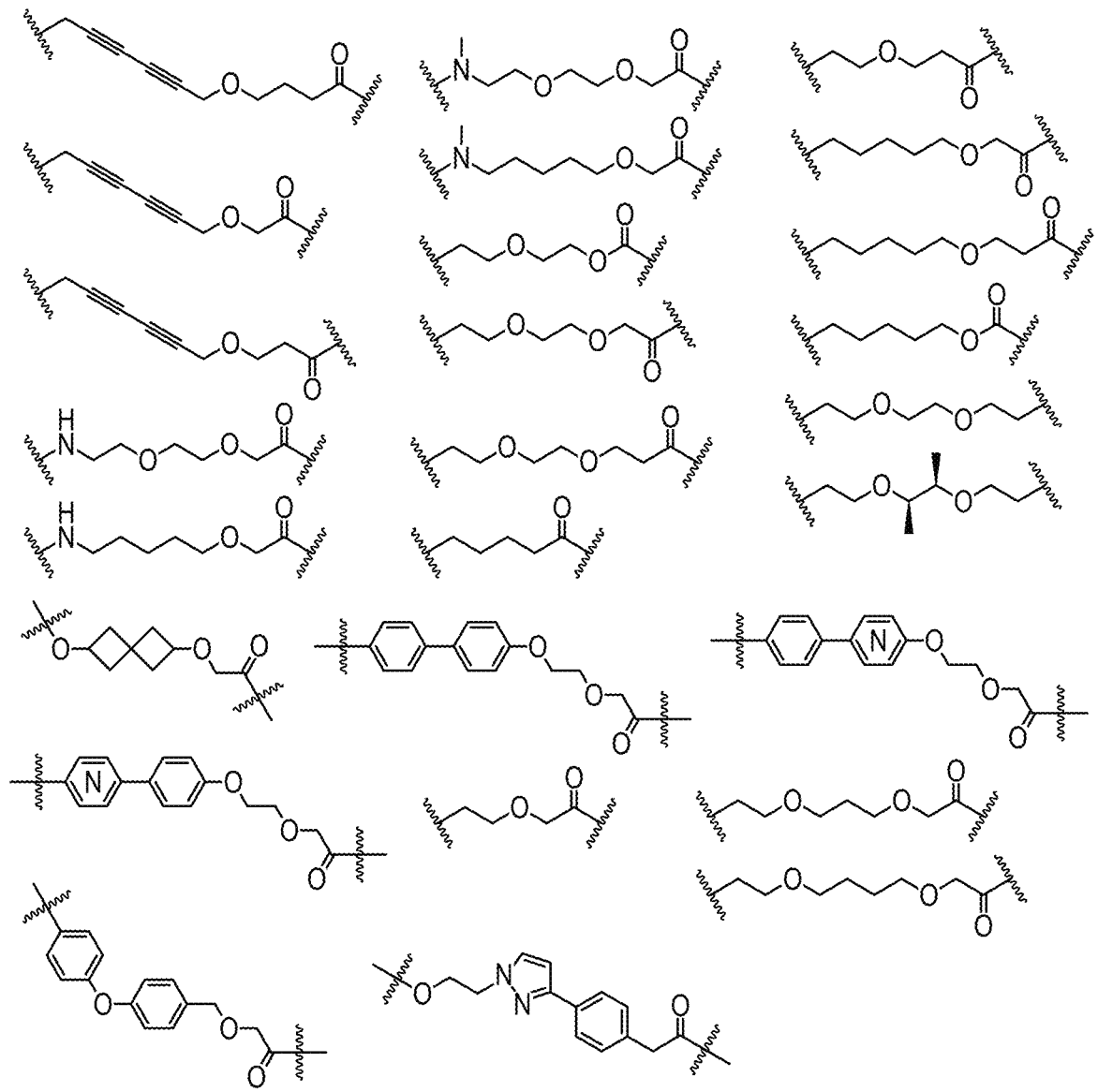
FIG. 25 provides additional examples of Linker moieties for use in the present invention.

In other embodiments the Linker (L) is selected from the structures in FIG. 25, wherein

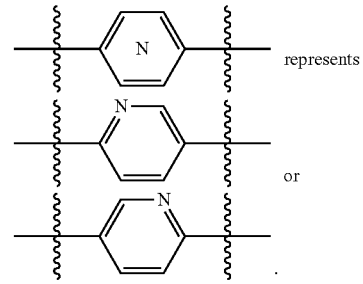

represents or

In additional embodiments, the Linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interspersed with optionally substituted, O, N, S, P or Si atoms. In certain embodiments, the Linker is substituted with an aryl, phenyl, benzyl, alkyl, alkylene, or heterocycle group. In certain embodiments, the Linker may be asymmetric or symmetrical.

In any of the embodiments of the compounds described herein, the Linker group may be any suitable moiety as described herein. In one embodiment, the Linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

Although the Degron group and dTAG Targeting Ligand group may be covalently linked to the Linker group through any group which is appropriate and stable to the chemistry of the Linker, the Linker is independently covalently bonded to the Degron group and the dTAG Targeting Ligand group preferably through an amide, ester, thioester, keto group, carbamate (urethane), carbon or ether, each of which groups may be inserted anywhere on the Degron group and dTAG Targeting Ligand group to provide maximum binding of the Degron group on the ubiquitin ligase and the dTAG Targeting Ligand group on the target dTAG. (It is noted that in certain aspects where the Degron group targets Ubiquitin Ligase, the target protein for degradation may be the ubiquitin ligase itself). The Linker may be linked to an optionally substituted alkyl, alkylene, alkene or alkyne group, an aryl group or a heterocyclic group on the Degron and/or dTAG Targeting Ligand groups.

Figure 26:
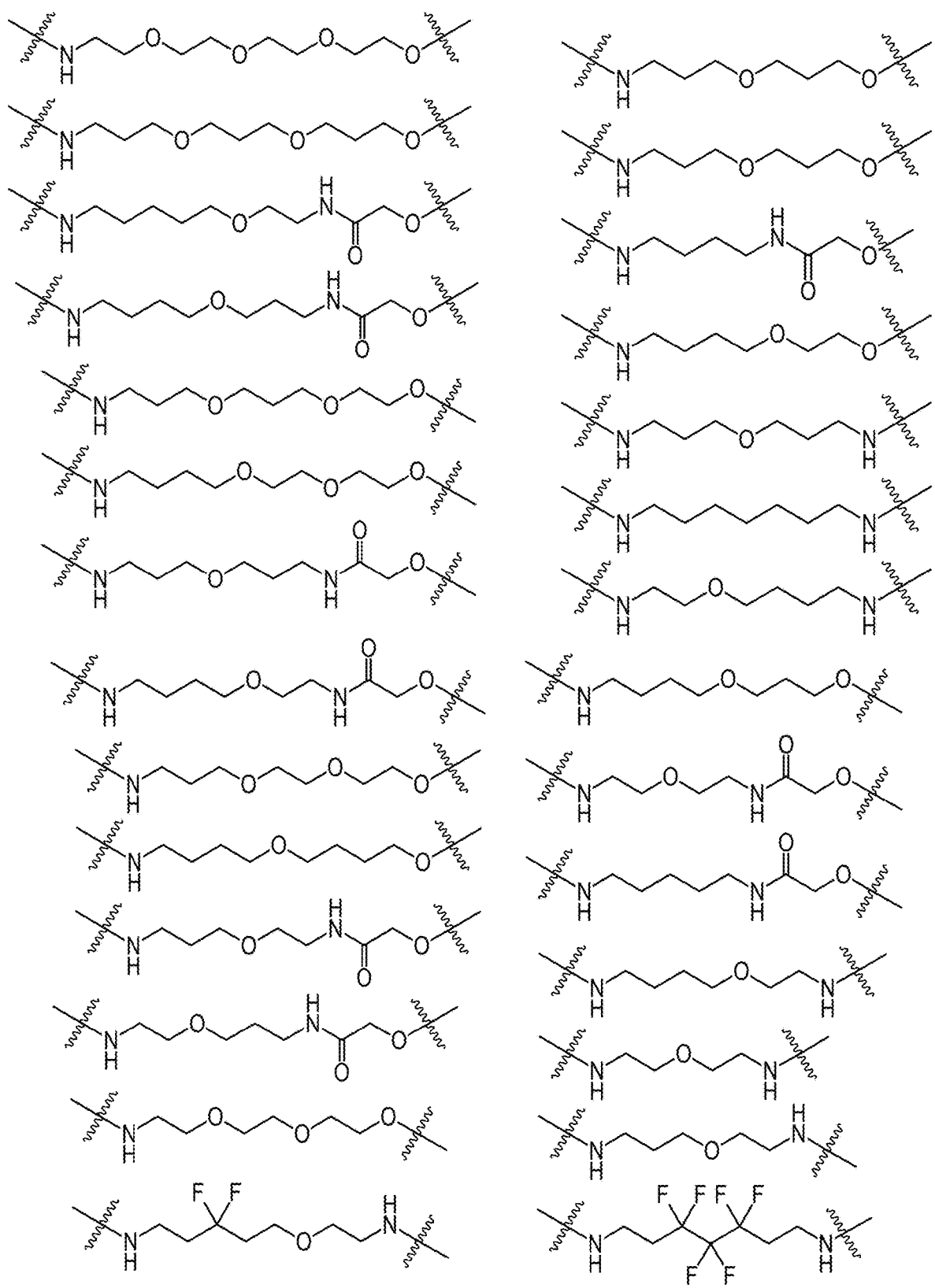
FIG. 26 provides examples of heteroaliphatic Linker moieties for use in the present invention.

In certain embodiments, "L" can be linear chains with linear atoms from 4 to 24, the carbon atom in the linear chain can be substituted with oxygen, nitrogen, amide, fluorinated carbon, etc., such as the structures in FIG. 26.

Figure 27:
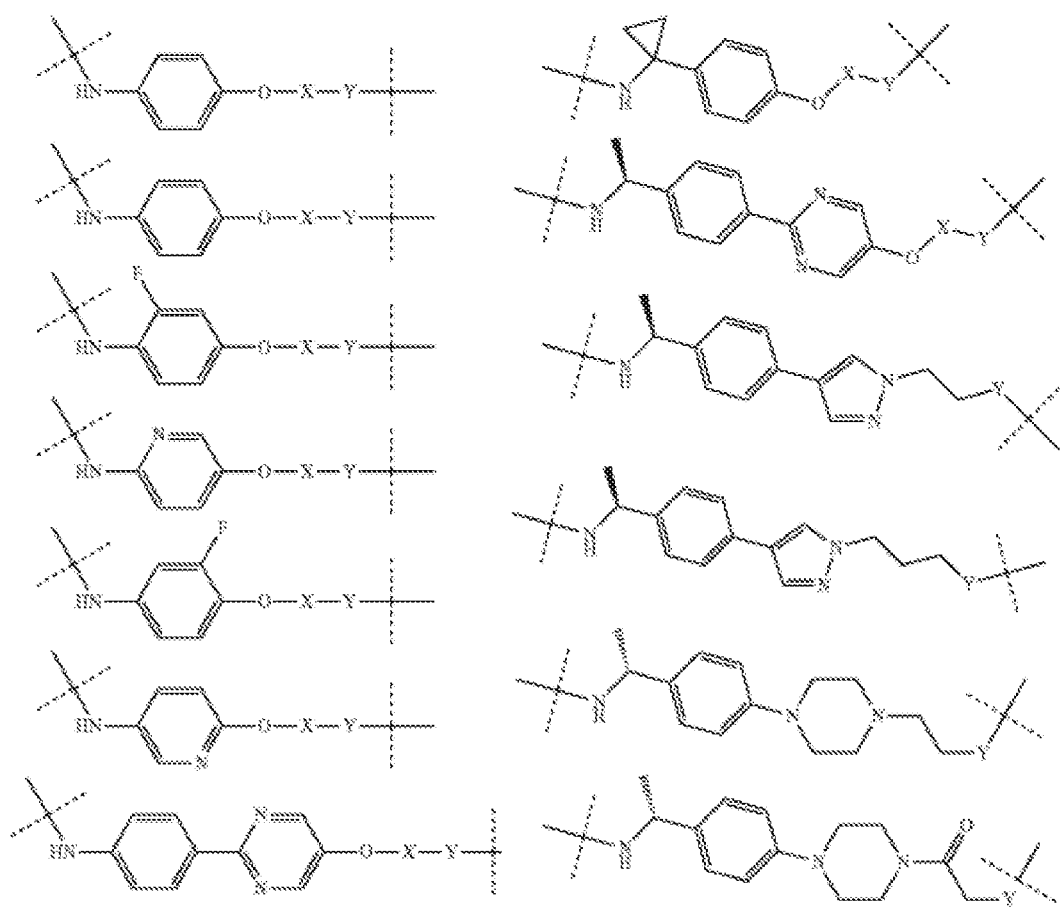
FIG. 27 provides examples of aromatic Linker moieties for use in the present invention.
Figure 28A:
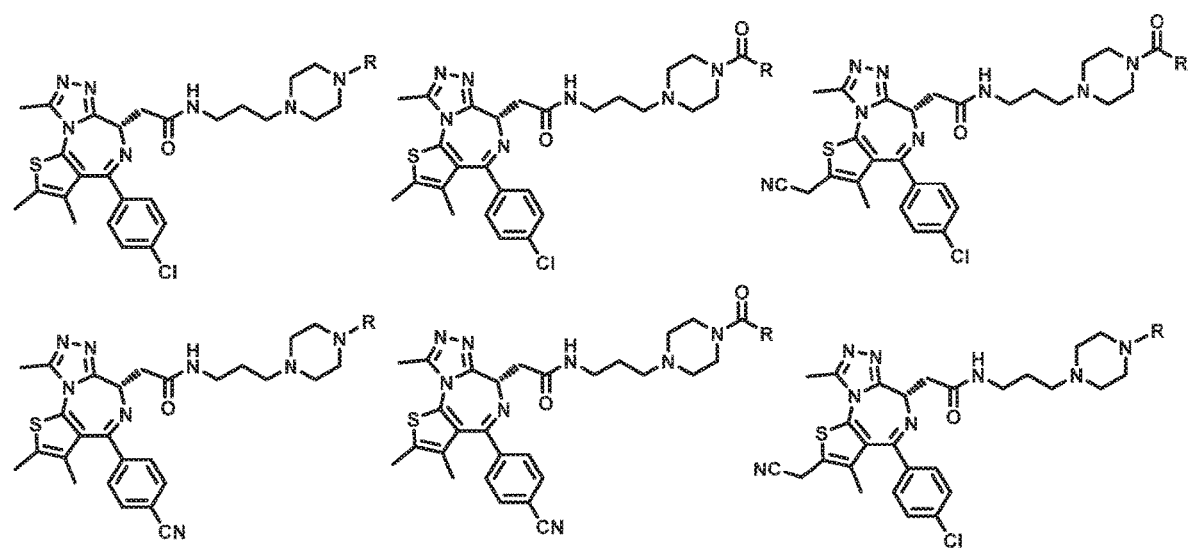
FIG. 28A, FIG. 28B, FIG. 28C, FIG. 28D, FIG. 28E, FIG. 28F, and FIG. 28G provide dTAG Targeting Ligands for use in the present invention, wherein R is the point at which the Linker is attached.
Figure 28B:
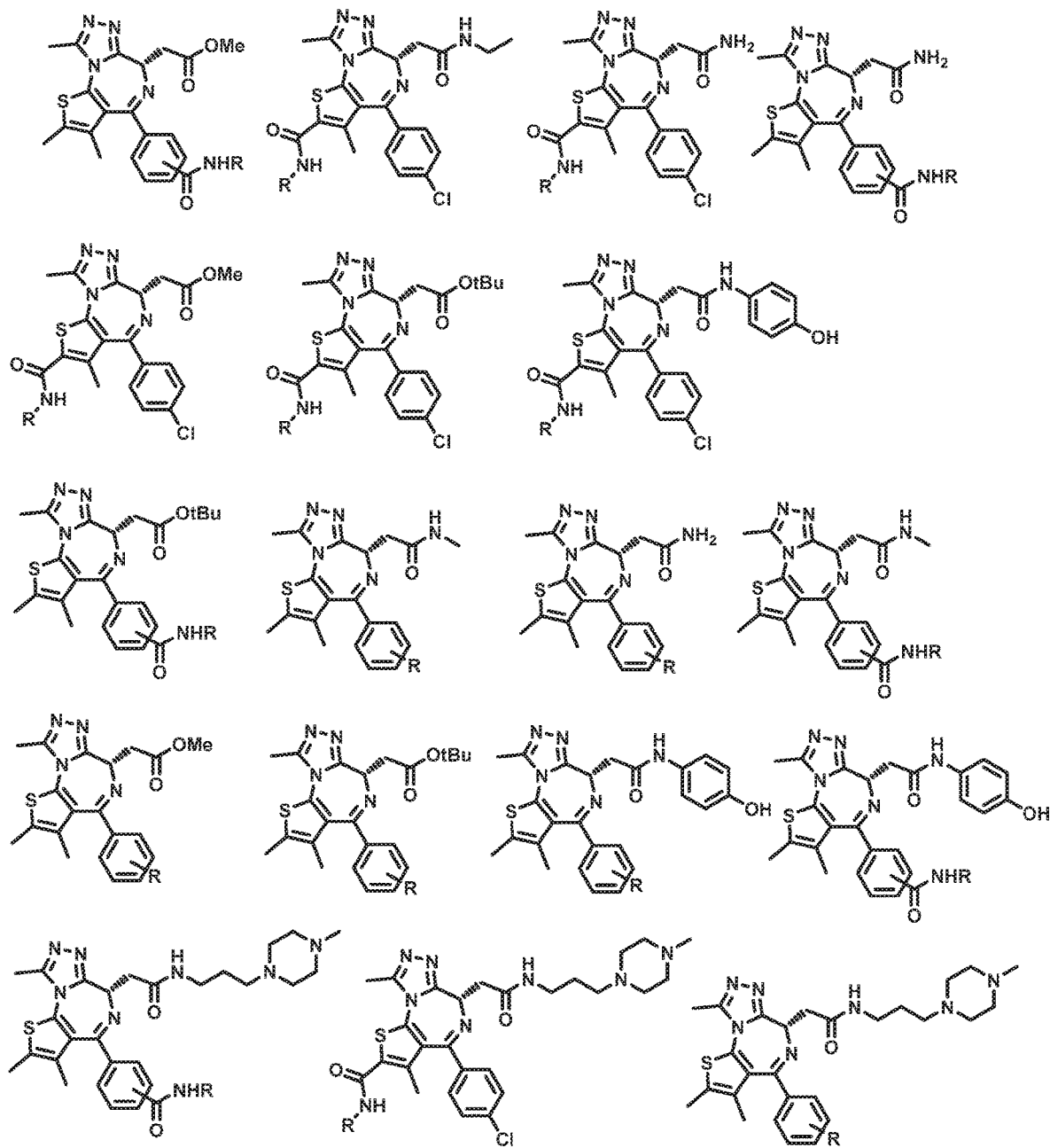
Figure 28C:
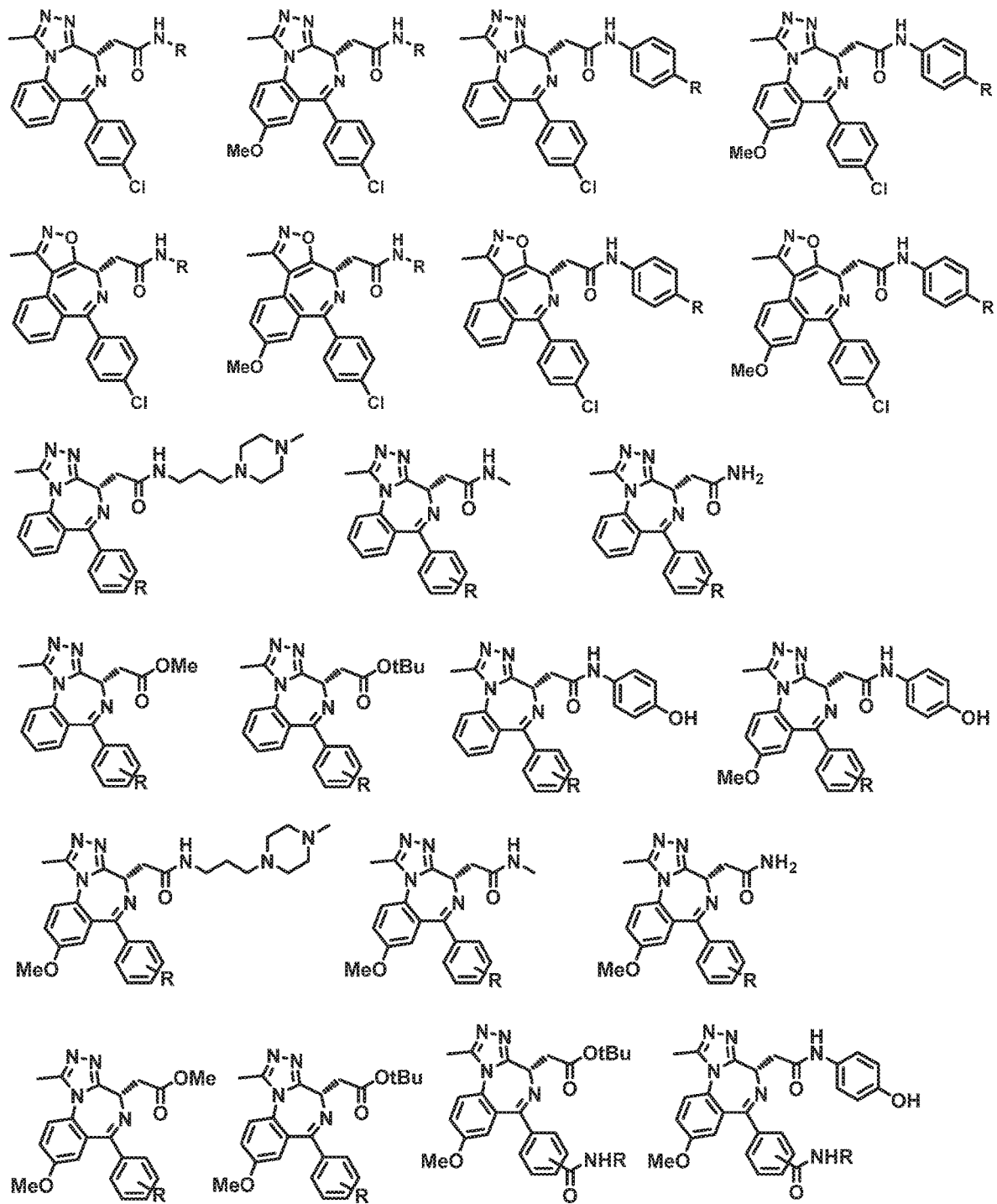
Figure 28D:
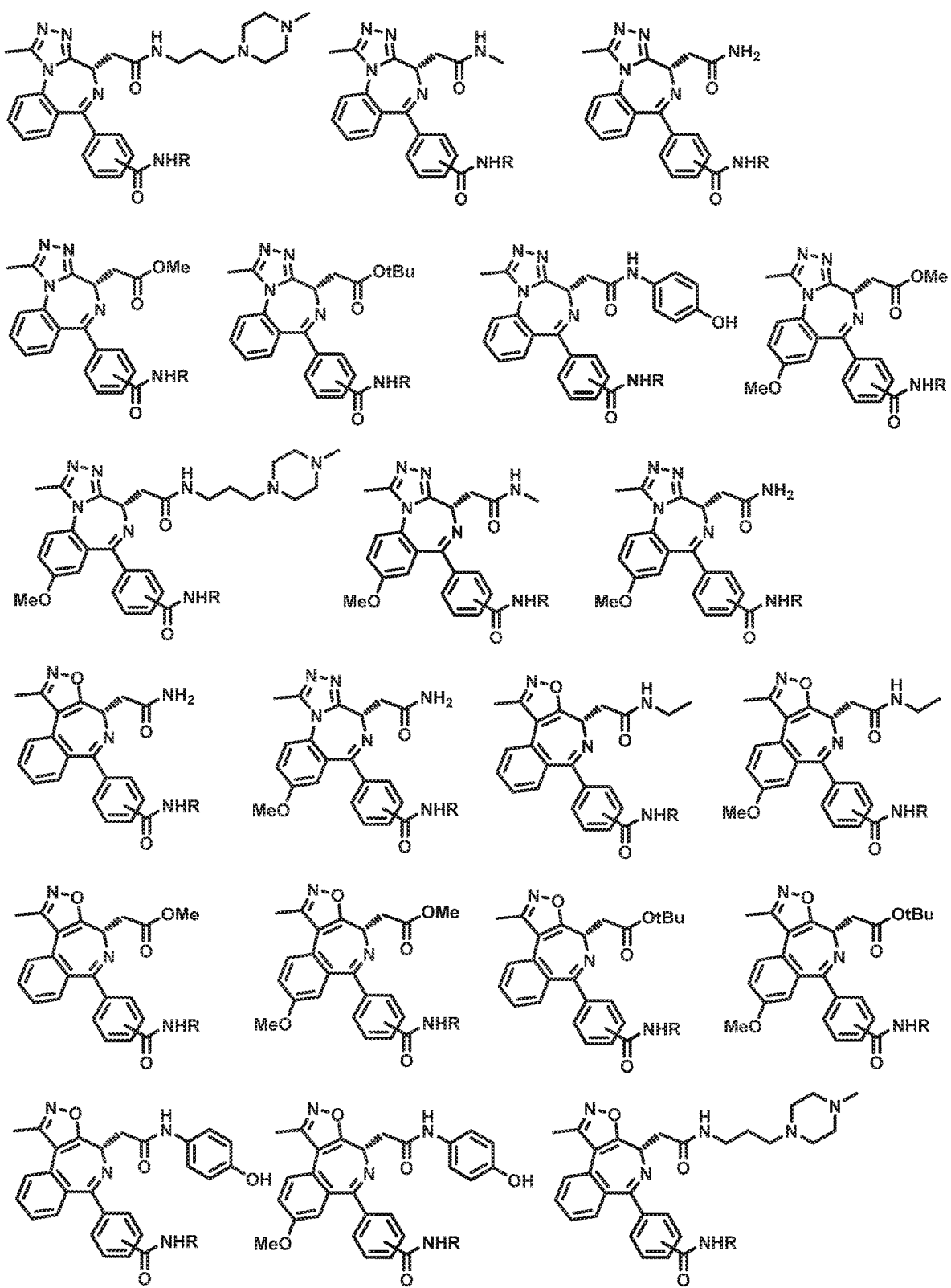
Figure 28E:
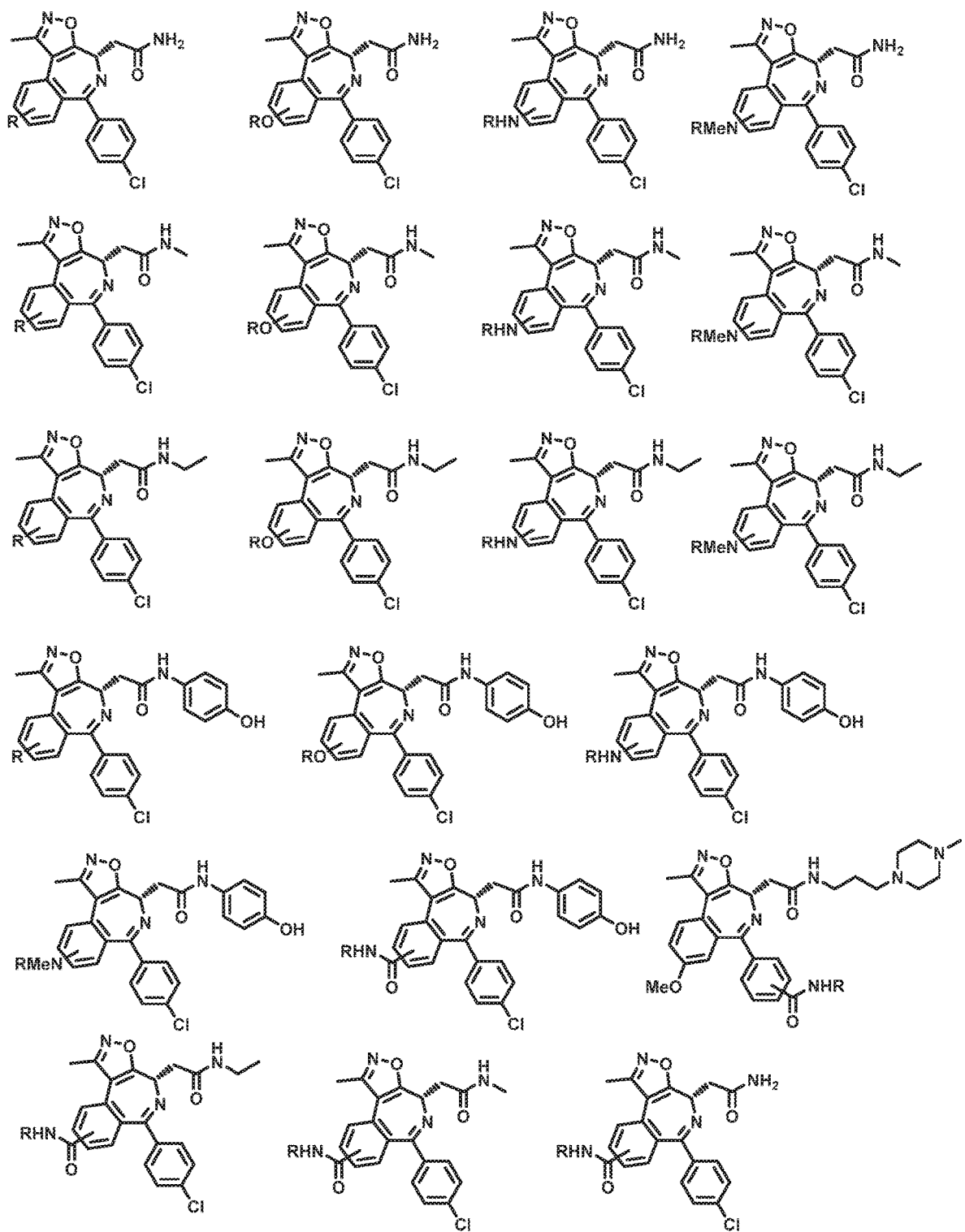
Figure 28F:
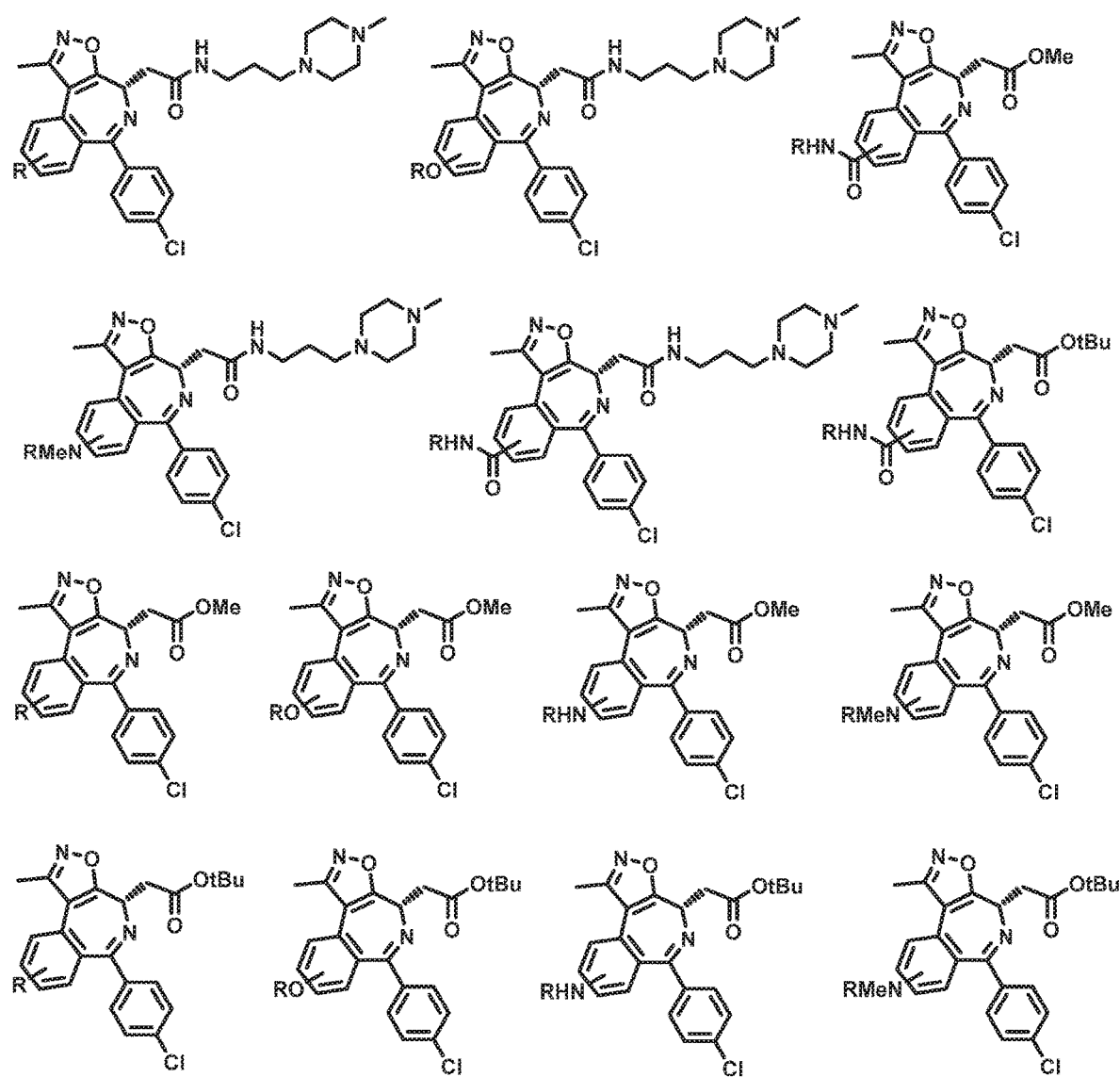
Figure 28G:
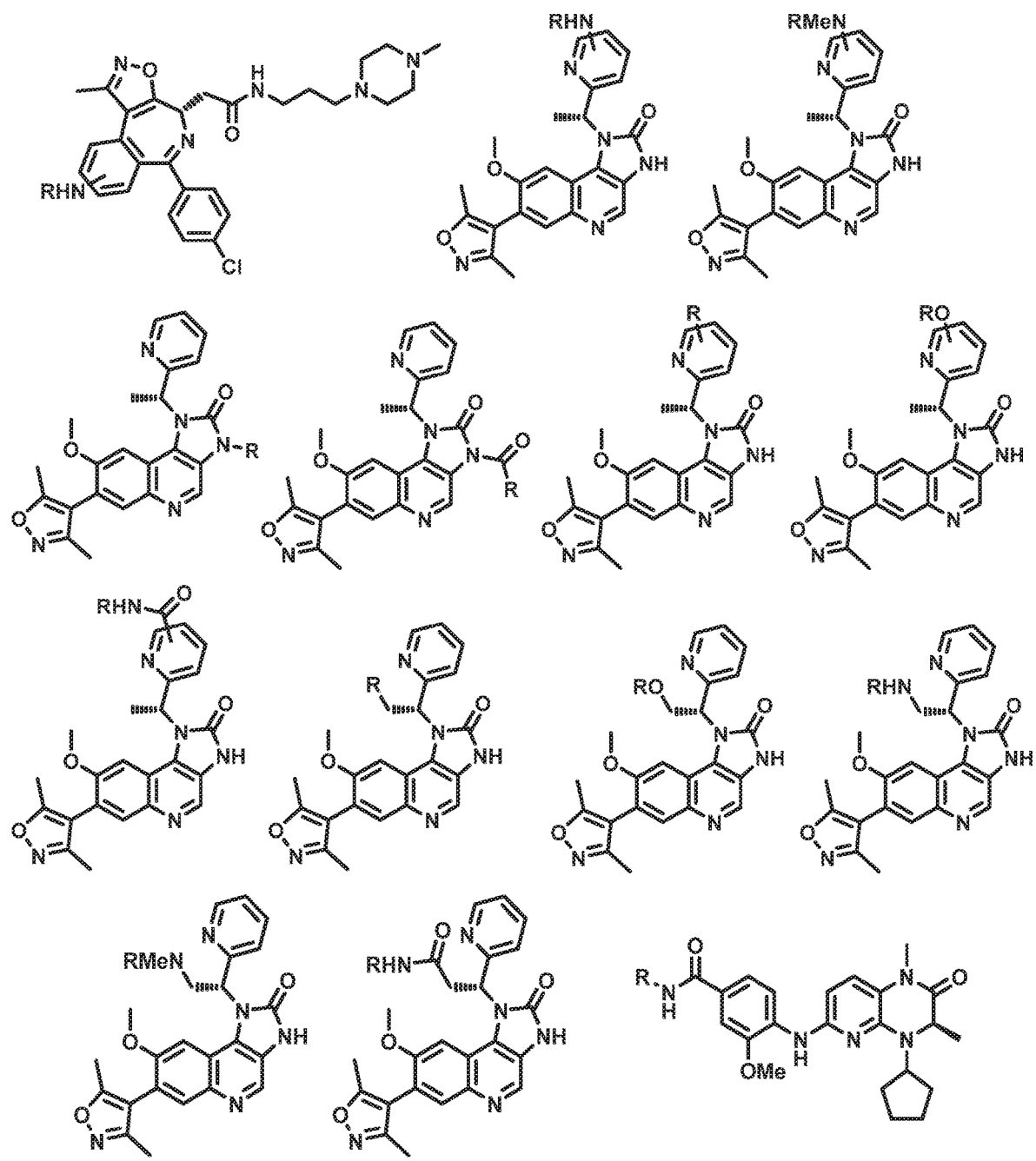
Figure 29A:
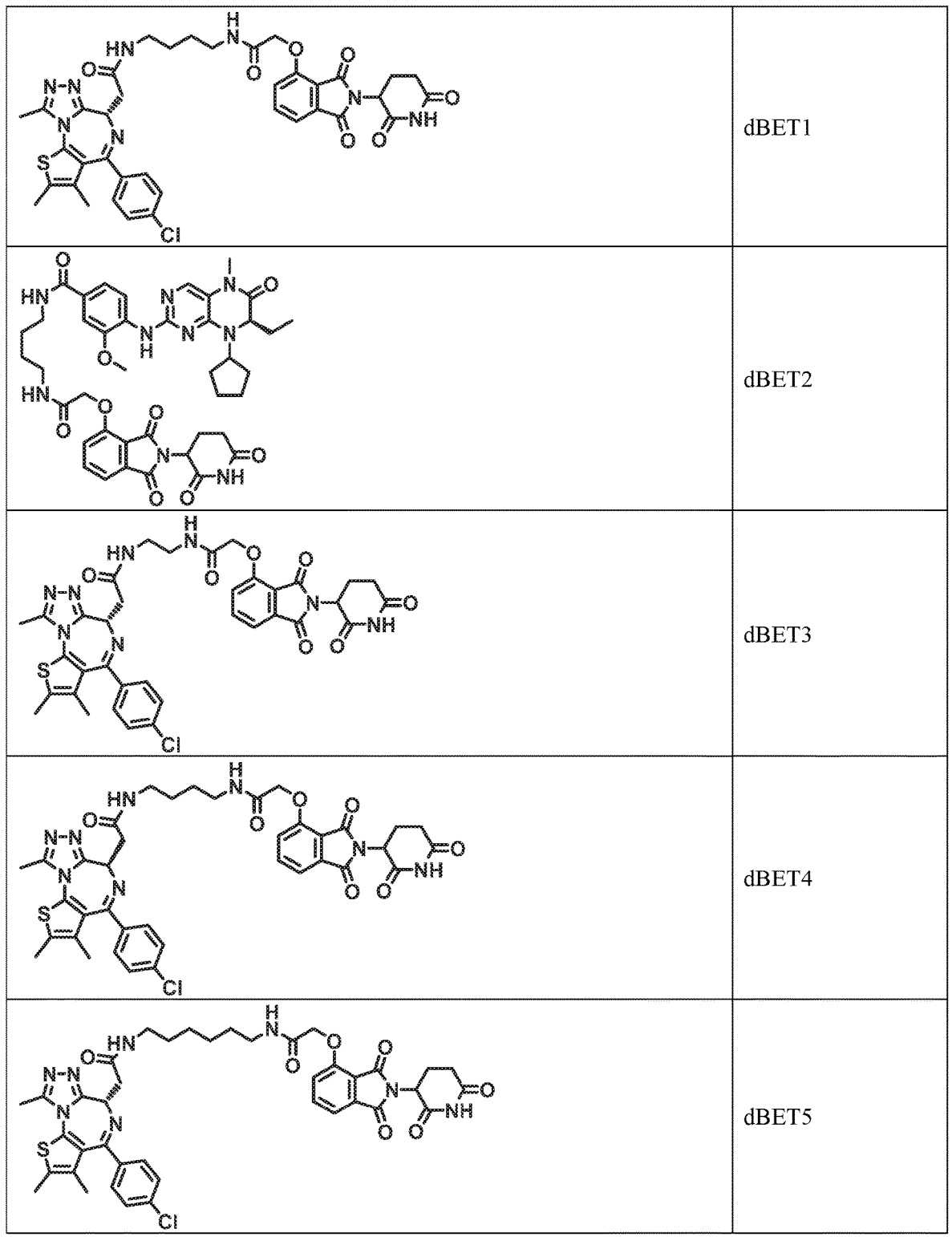
FIG. 29A, FIG. 29B, FIG. 29C, FIG. 29D, FIG. 29E, FIG. 29F, FIG. 29G, and FIG. 29H provide specific heterobifunctional compounds for use in the present invention.
Figure 29B:
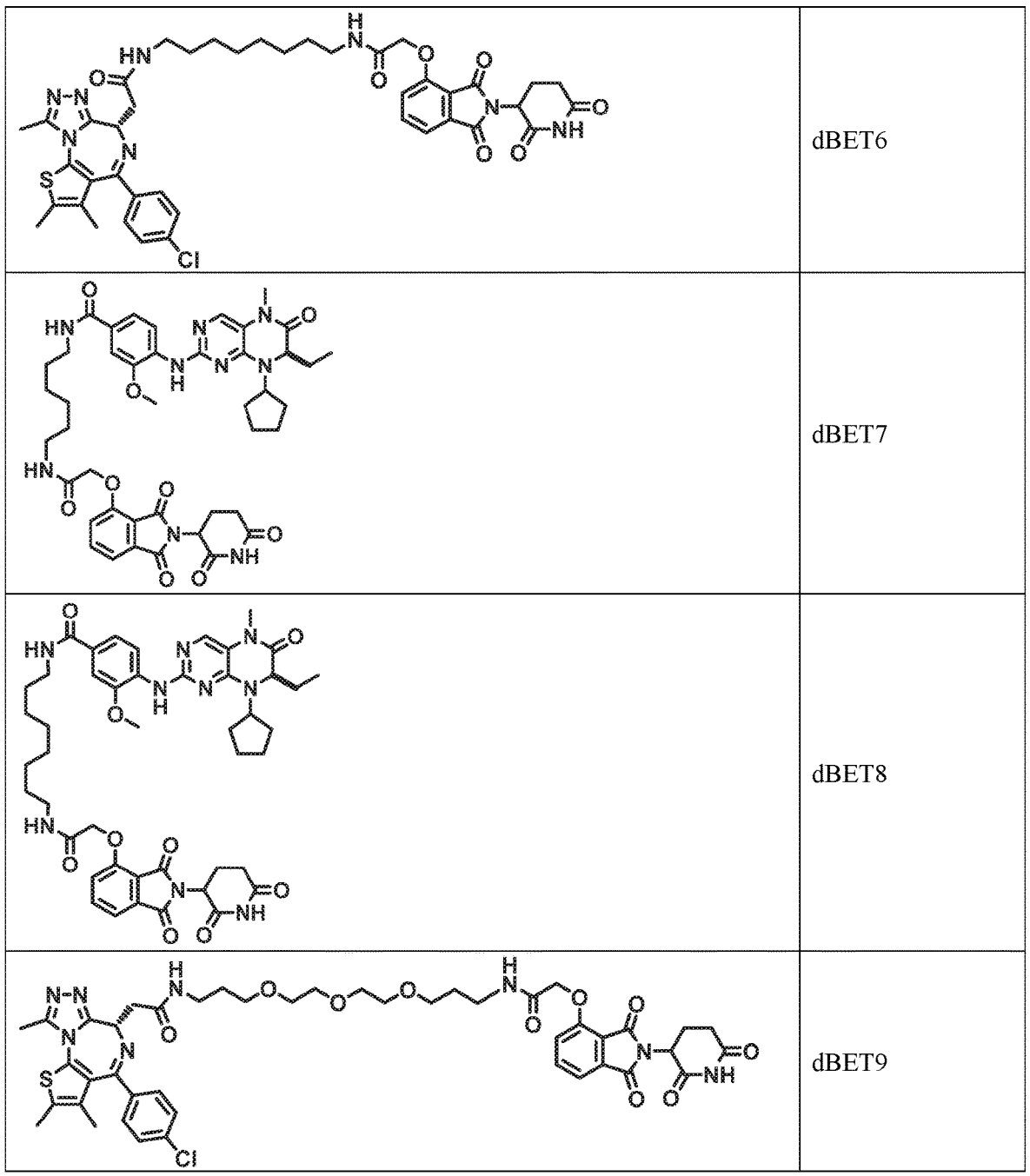
Figure 29C:
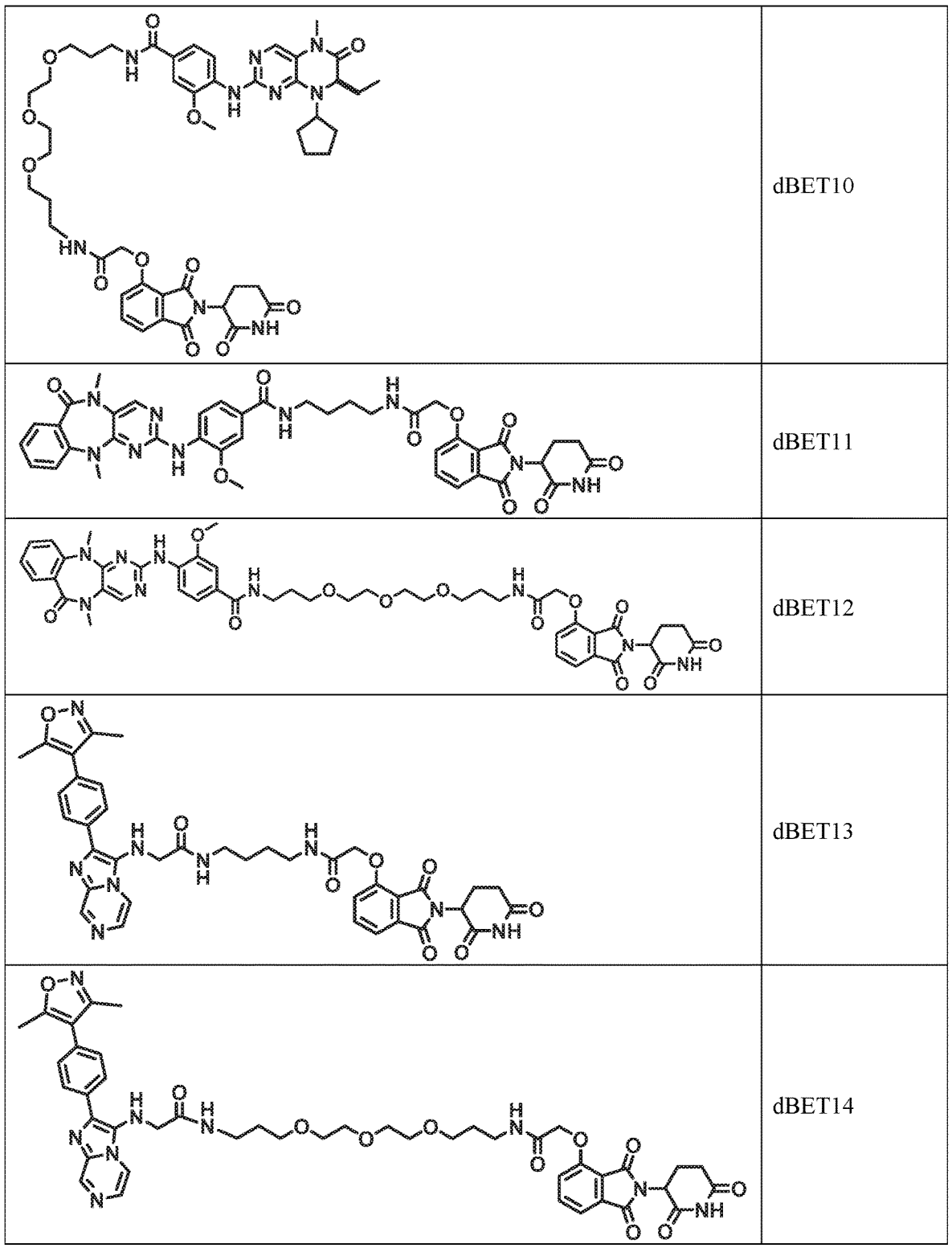
Figure 29D:
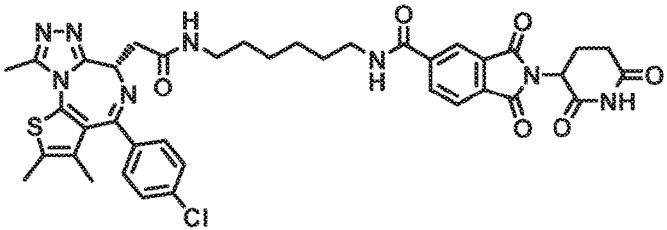
Figure 29D:
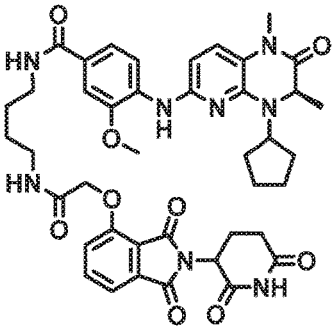
Figure 29D:
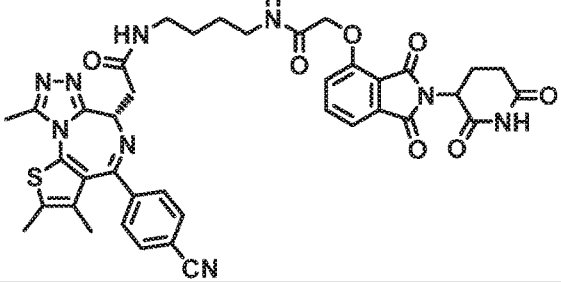
Figure 29D:
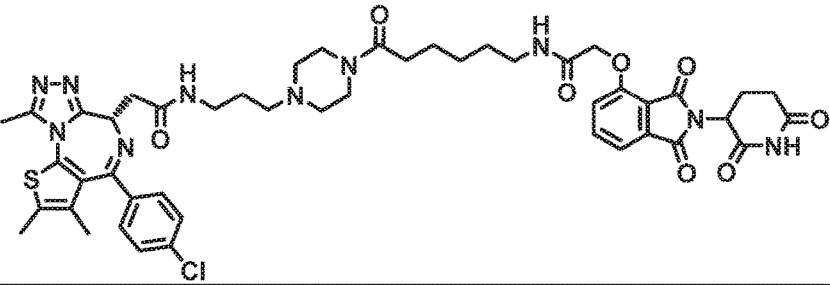
Figure 29D:
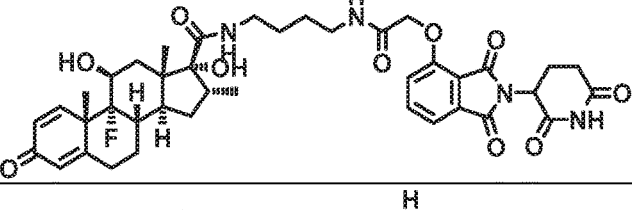
Figure 29D:
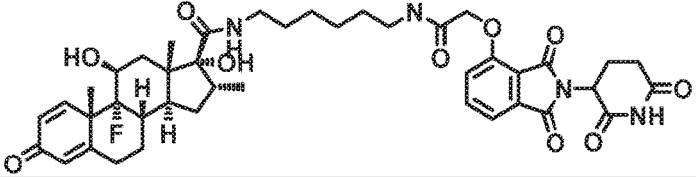
Figure 29E:
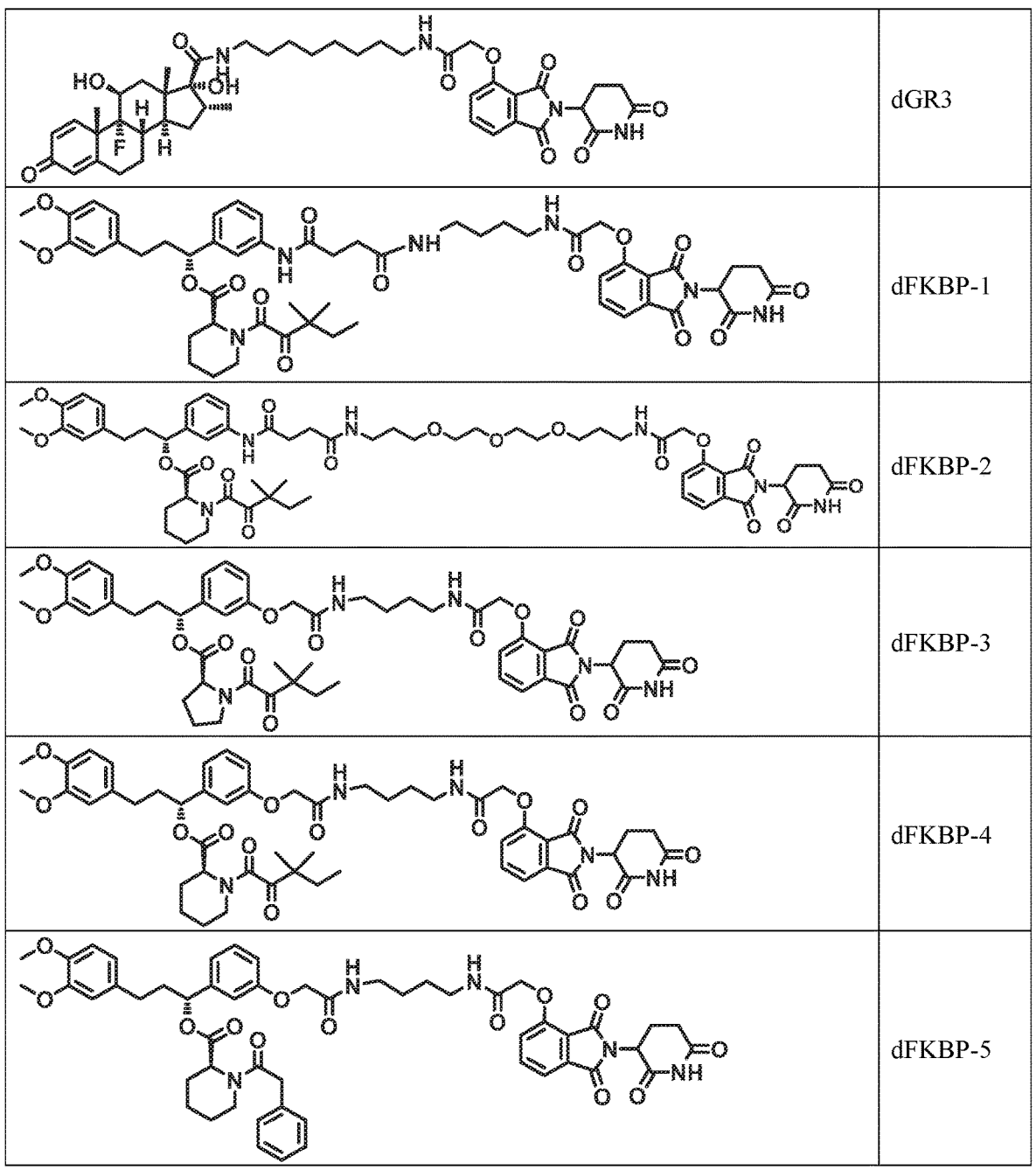
Figure 29F:
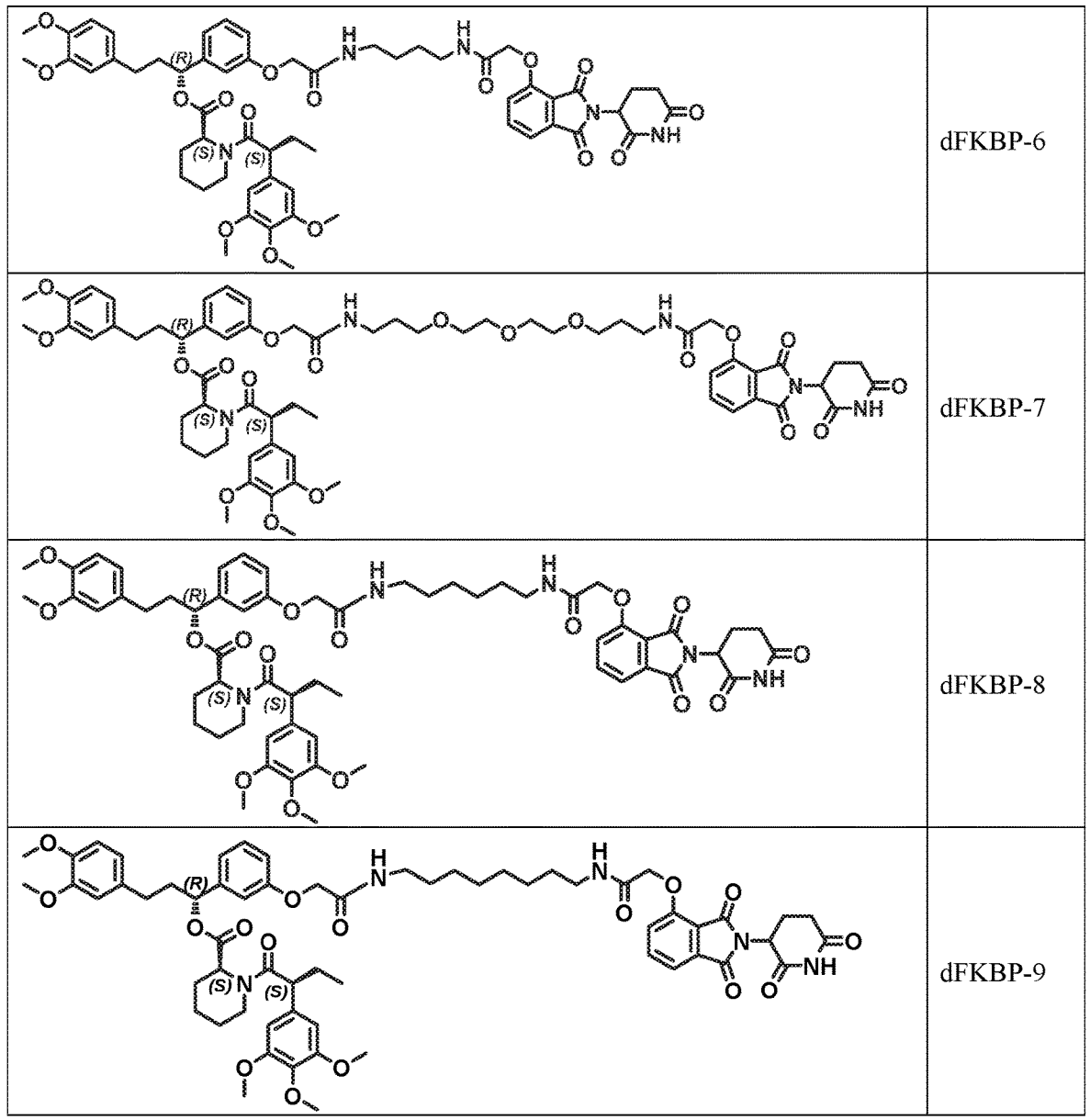
Figure 29G:
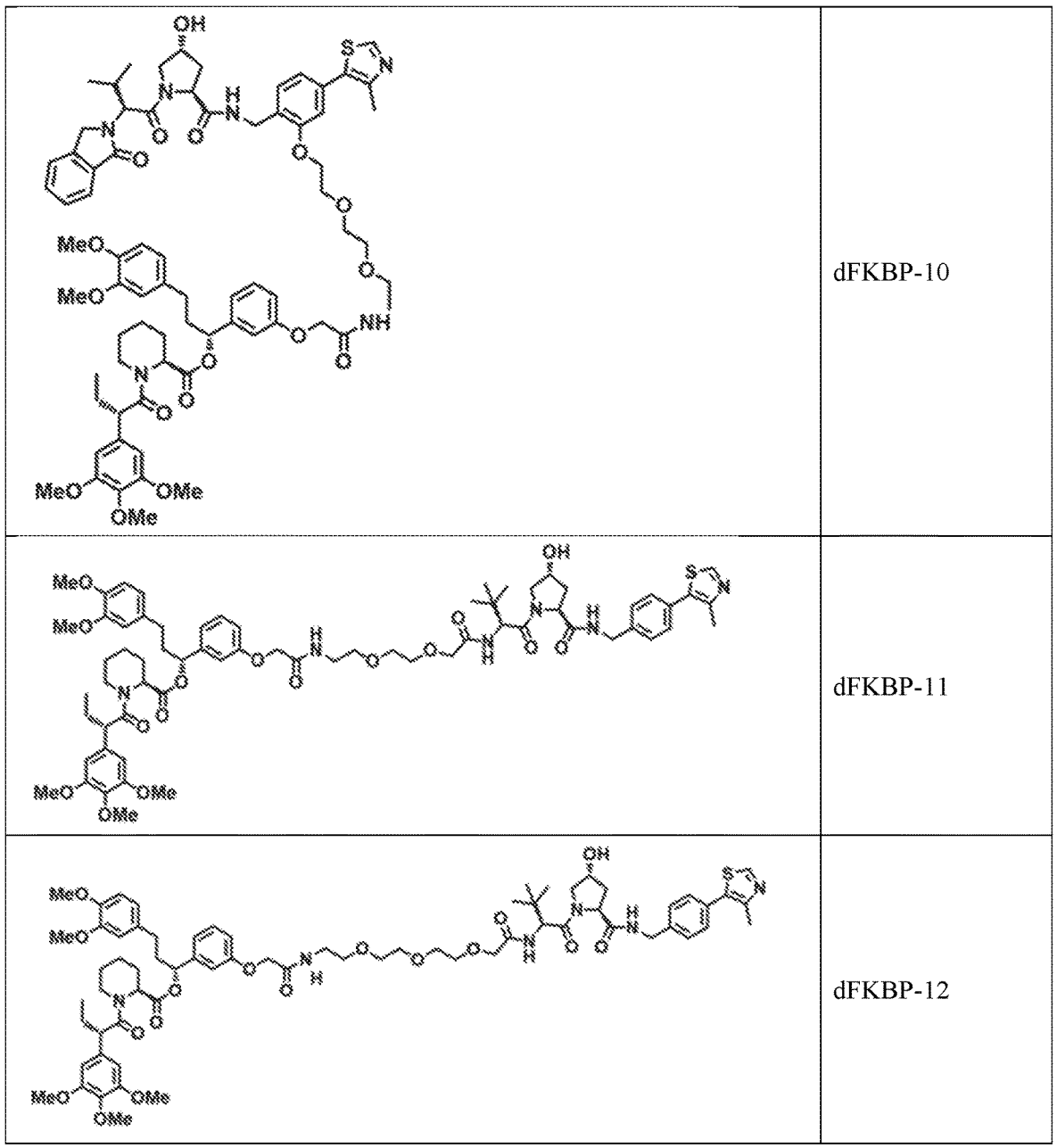
Figure 29H:
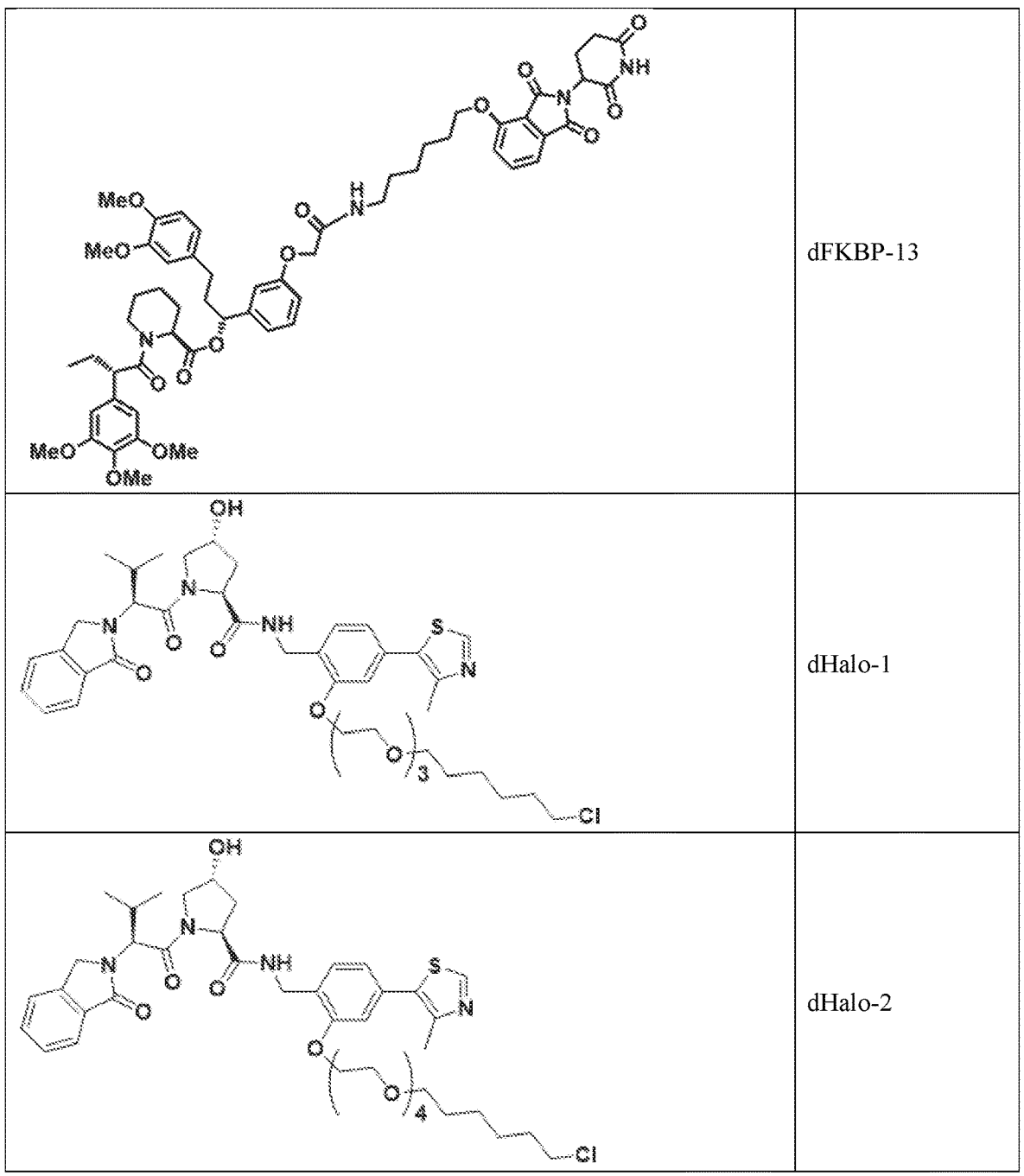
Figure 30A:
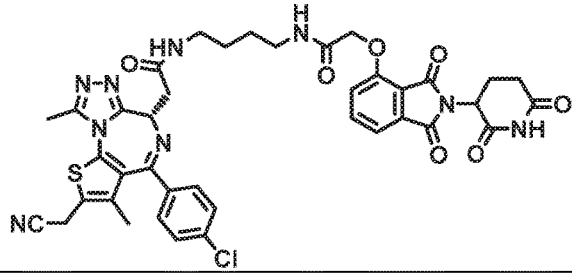
FIG. 30A, FIG. 30B, FIG. 30C, FIG. 30D, FIG. 30E, FIG. 30F, FIG. 30G, FIG. 30H, FIG. 30I, FIG. 30J, FIG. 30K, FIG. 30L, FIG. 30M, FIG. 30N, FIG. 30O, and FIG. 30P provides specific heterobifunctional compounds for use in the present invention, wherein X in the above structures is a halogen chosen from F, Cl, Br, and I.
Figure 30A:
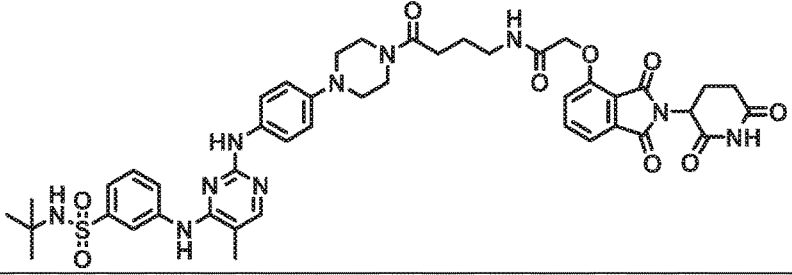
Figure 30A:
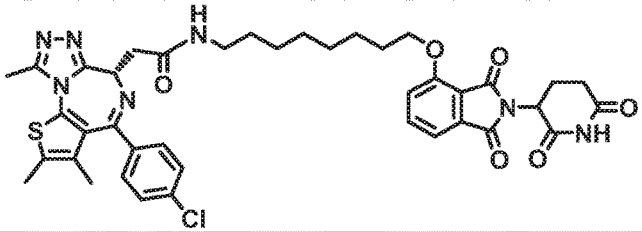
Figure 30A:
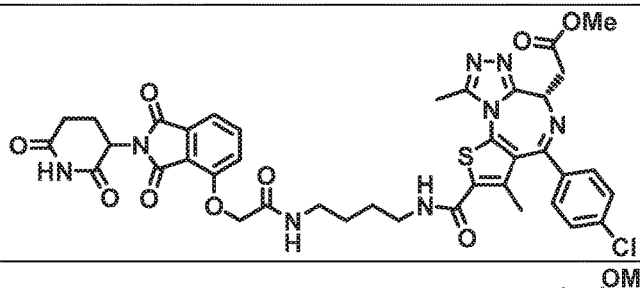
Figure 30A:
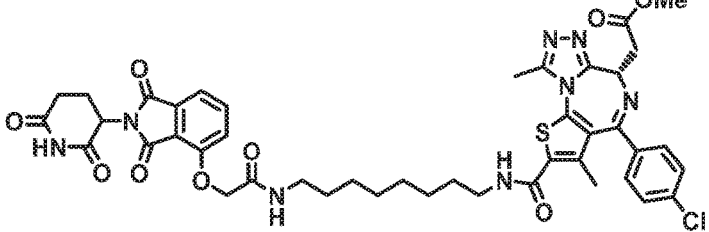
Figure 30B:
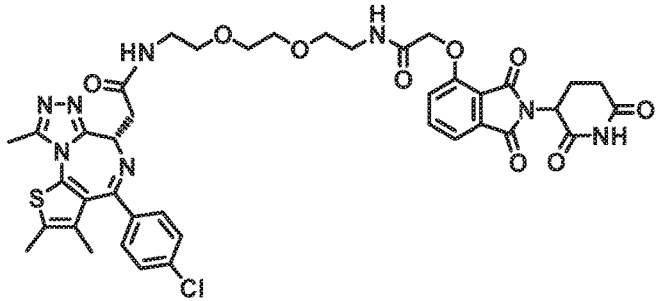
Figure 30B:
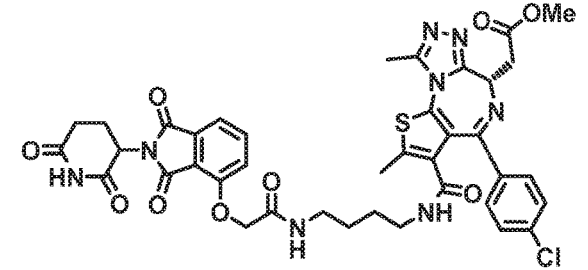
Figure 30B:
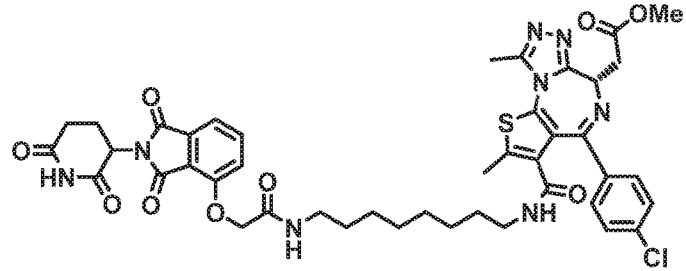
Figure 30B:
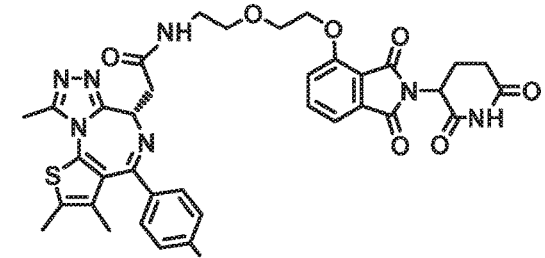
Figure 30B:
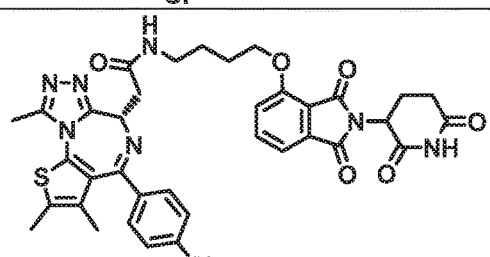
Figure 30C:
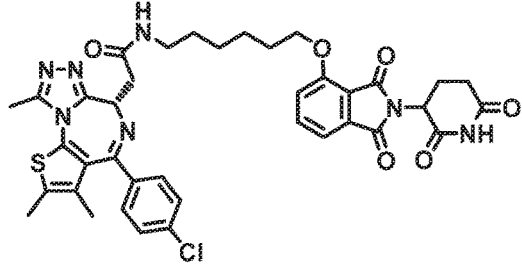
Figure 30C:
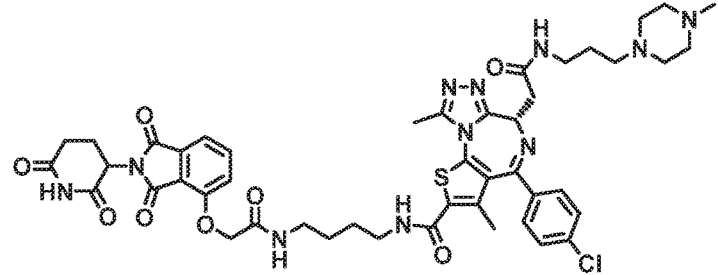
Figure 30C:
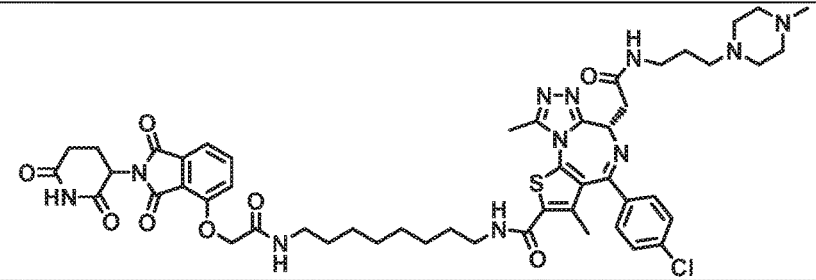
Figure 30C:
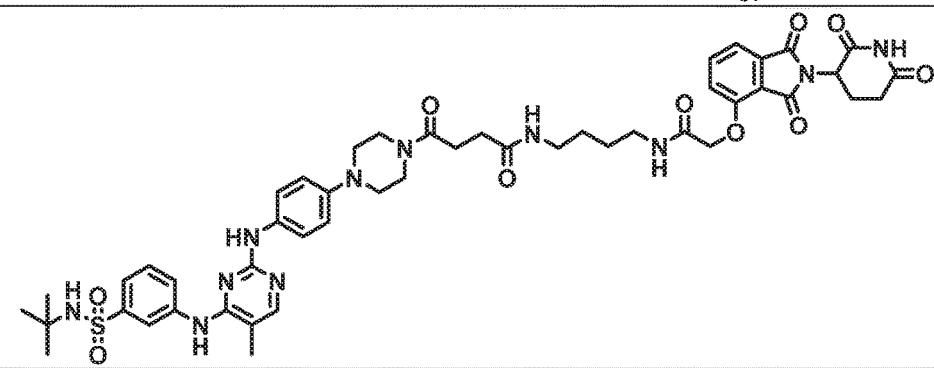
Figure 30C:
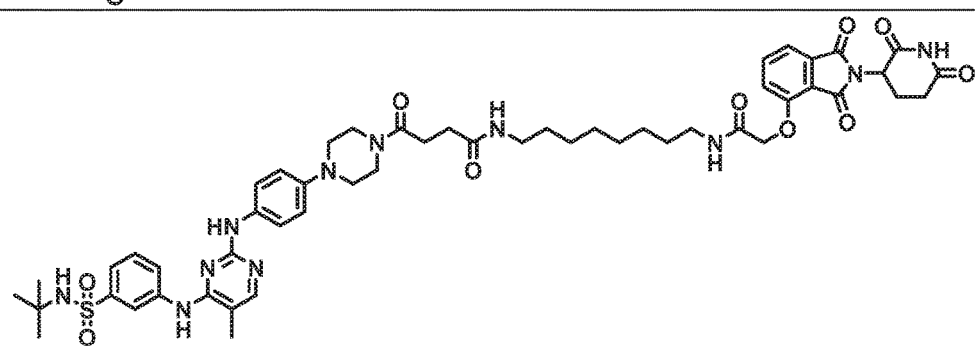
Figure 30D:
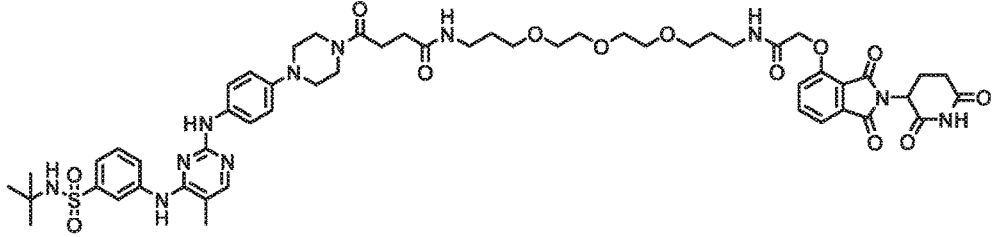
Figure 30D:
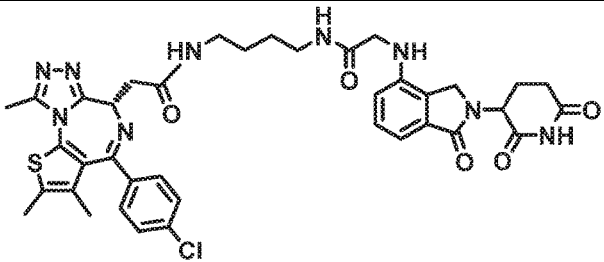
Figure 30D:
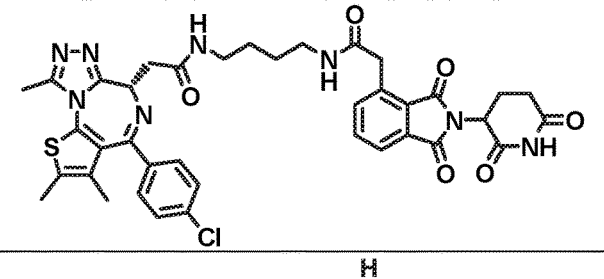
Figure 30D:
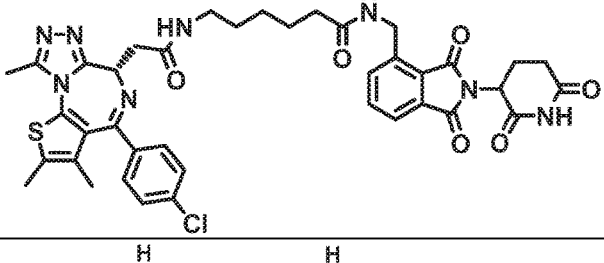
Figure 30D:
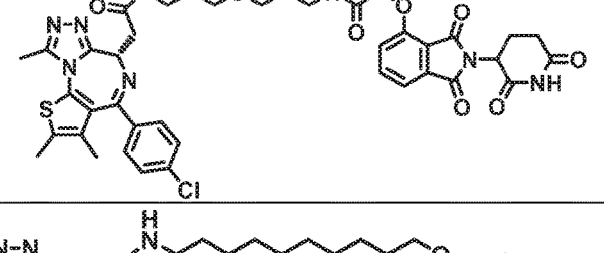
Figure 30D:
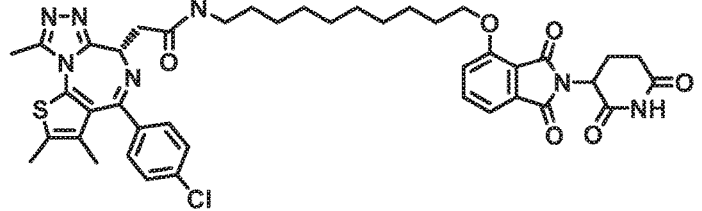
Figure 30E:
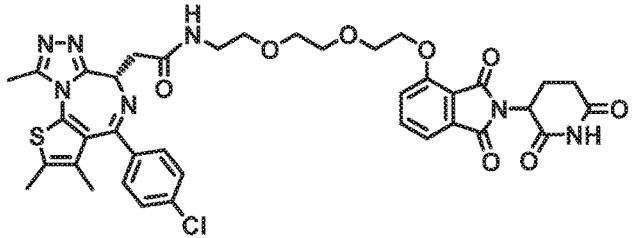
Figure 30E:
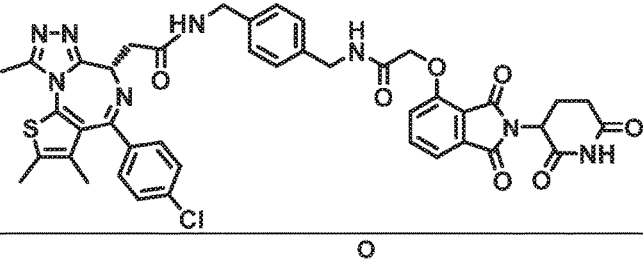
Figure 30E:
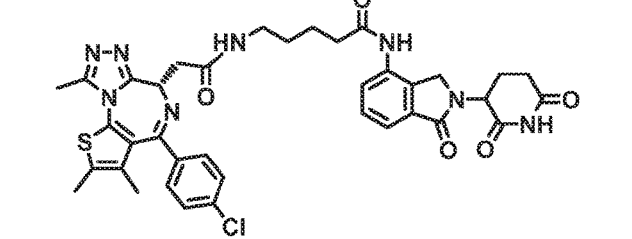
Figure 30E:
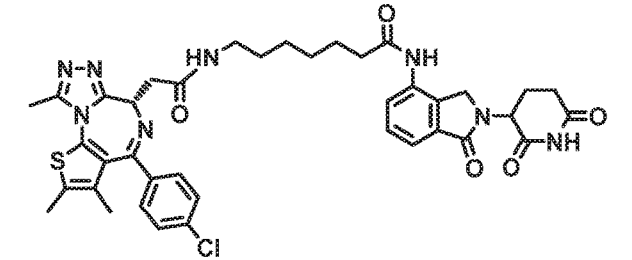
Figure 30E:
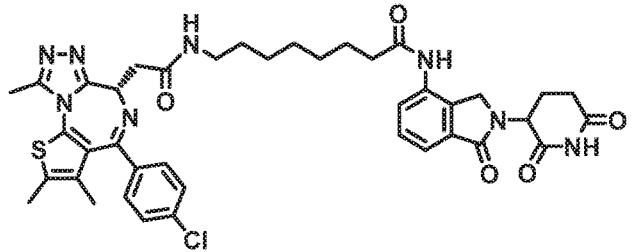
Figure 30F:
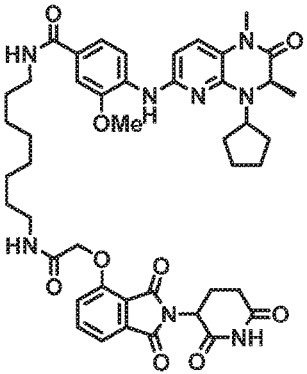
Figure 30F:
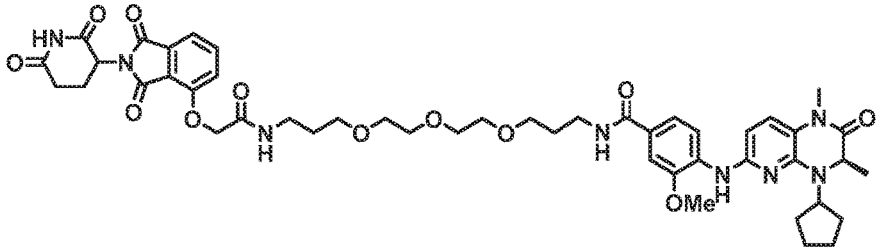
Figure 30F:
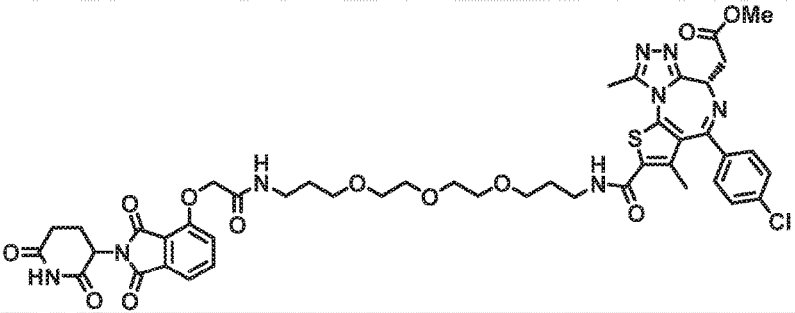
Figure 30F:
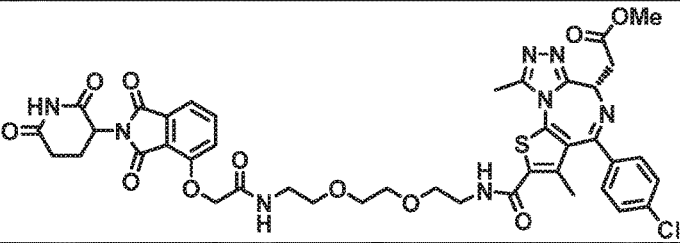
Figure 30F:
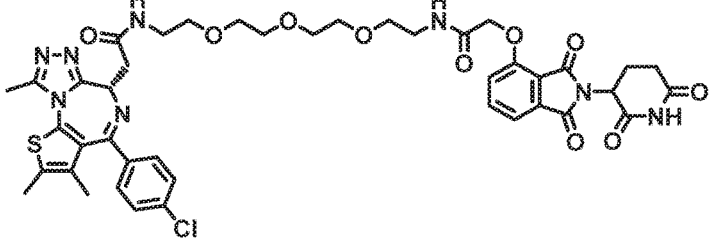
Figure 30G:
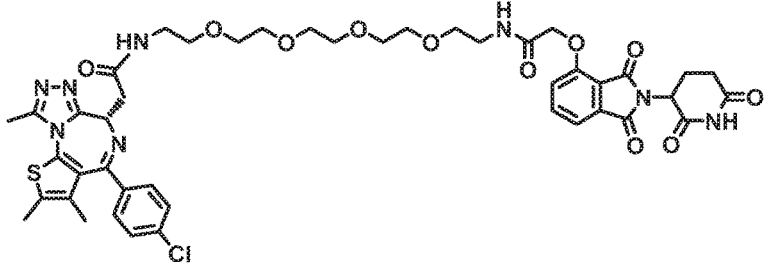
Figure 30H:
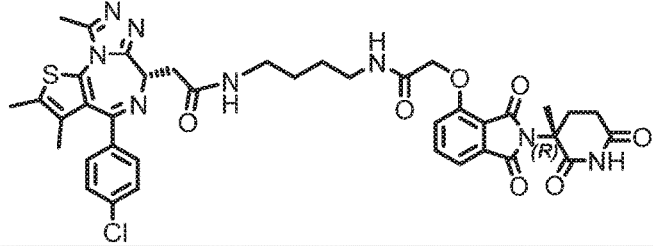
Figure 30I:
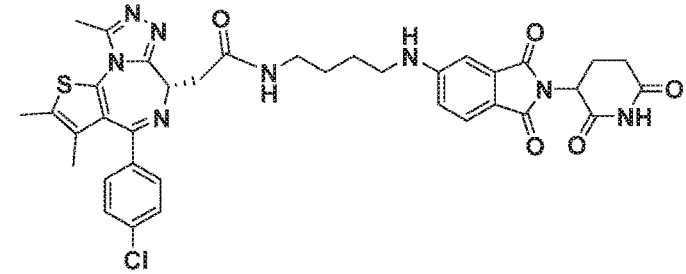
Figure 30I:
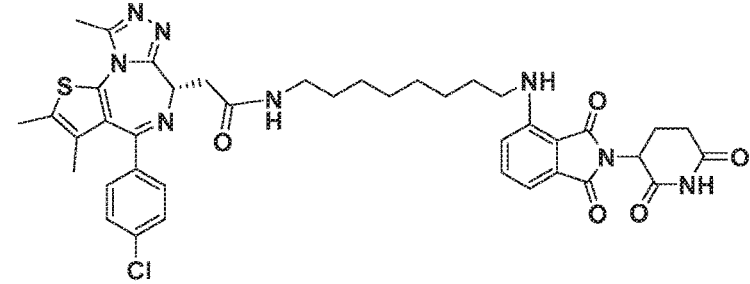
Figure 30I:
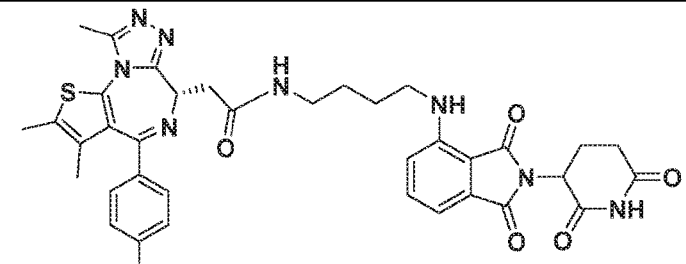
Figure 30I:
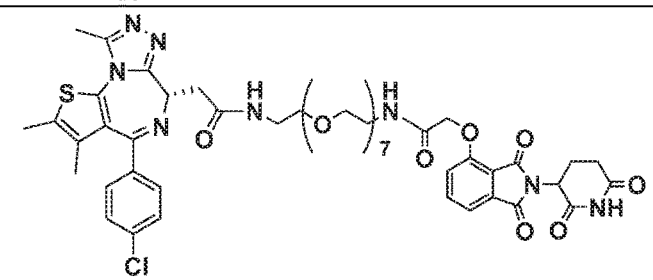
Figure 30I:
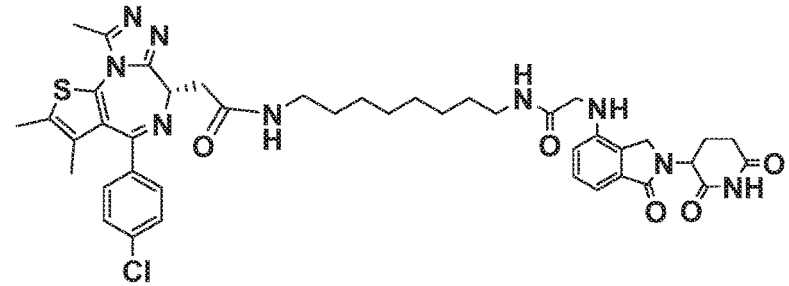
Figure 30J:
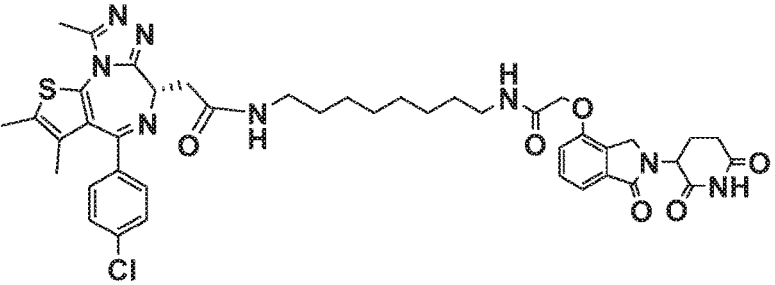
Figure 30J:
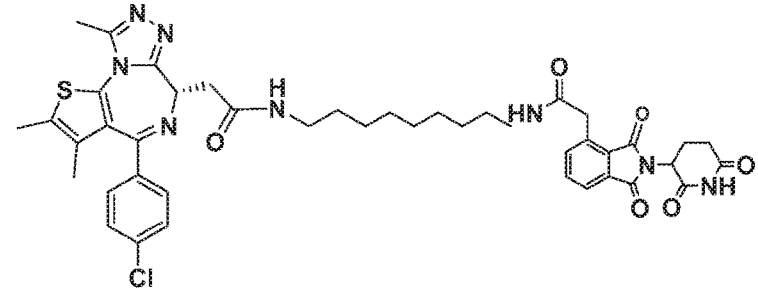
Figure 30J:
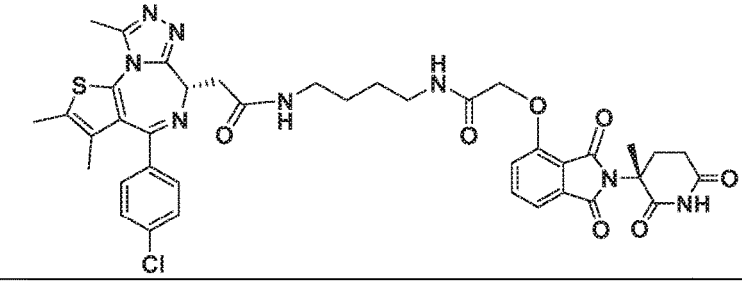
Figure 30J:
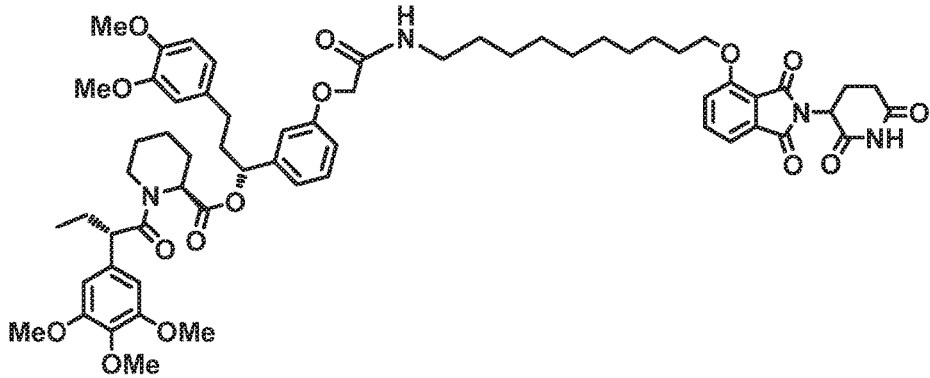
Figure 30K:
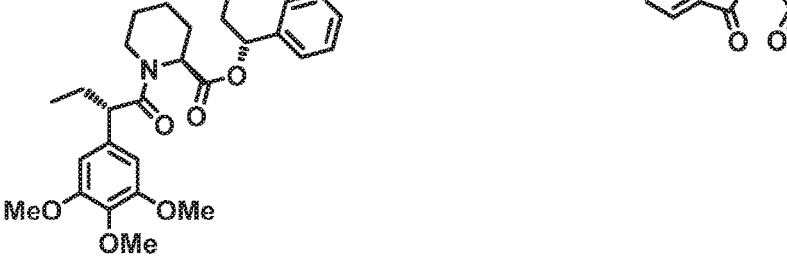
Figure 30L:
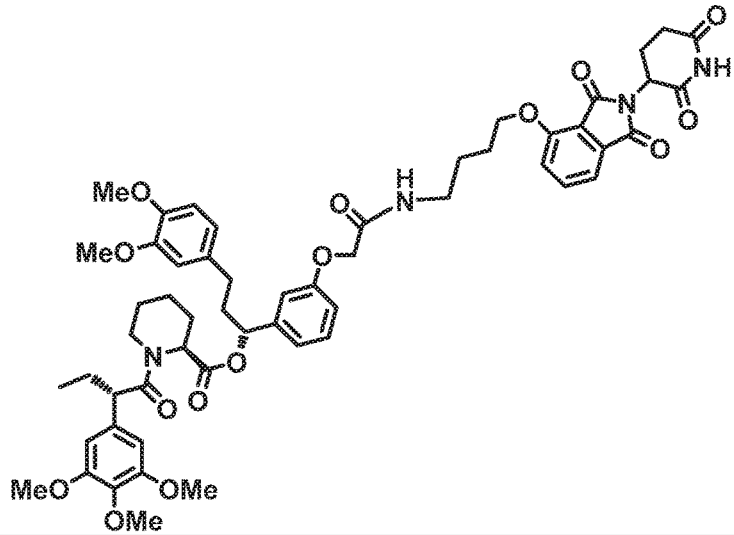
Figure 30L:
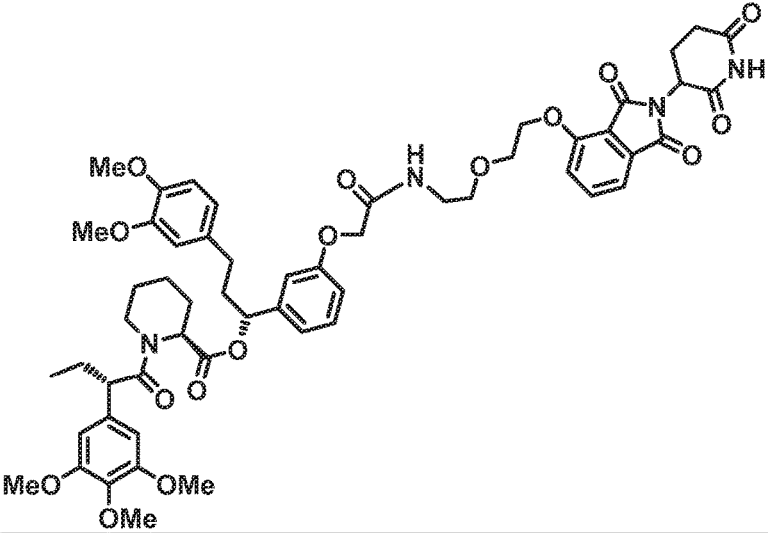
Figure 30L:
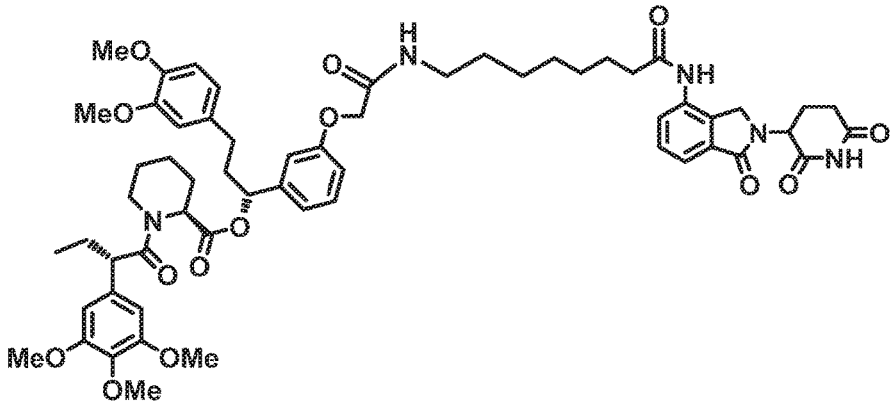
Figure 30M:
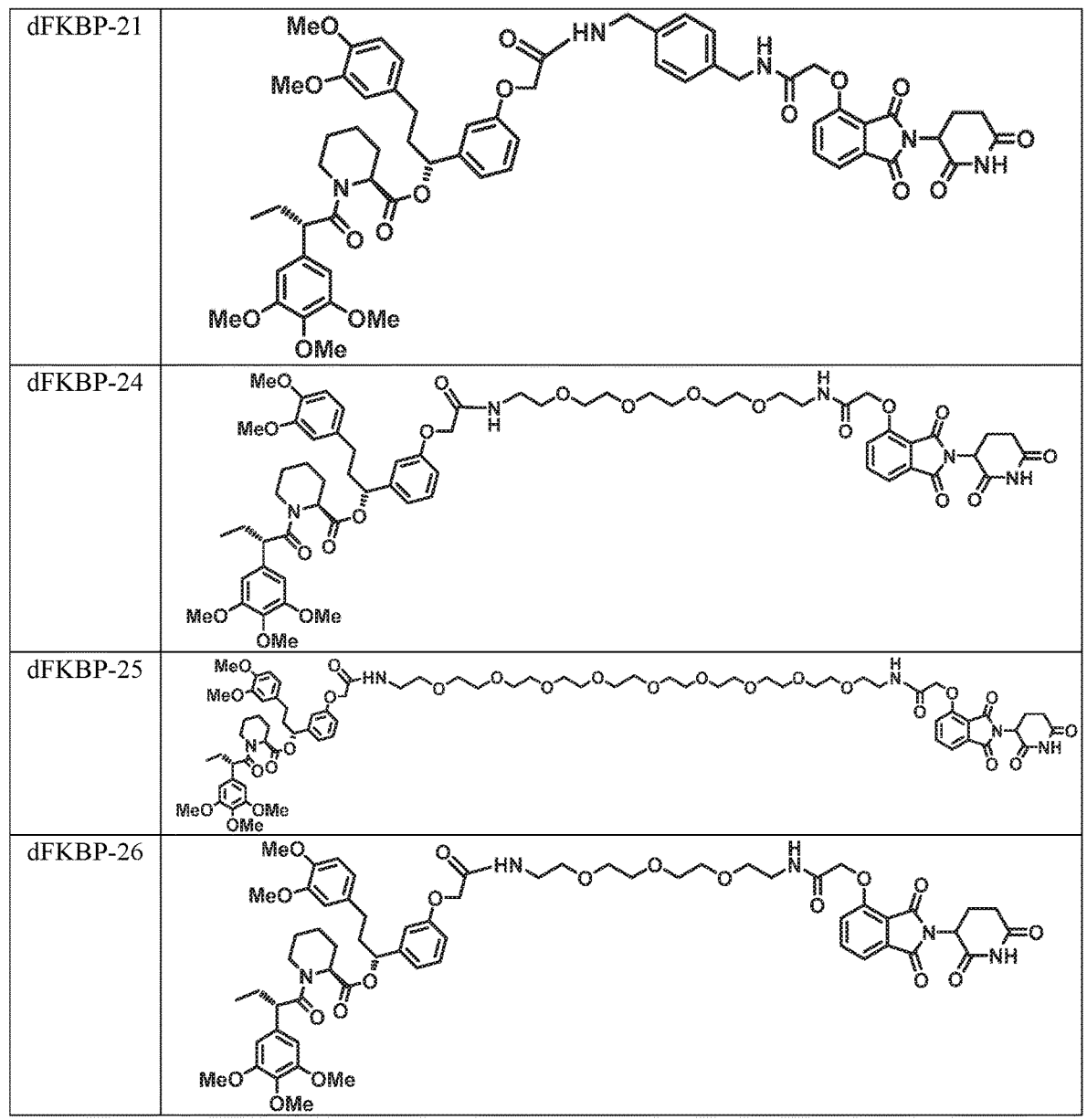
Figure 30N:
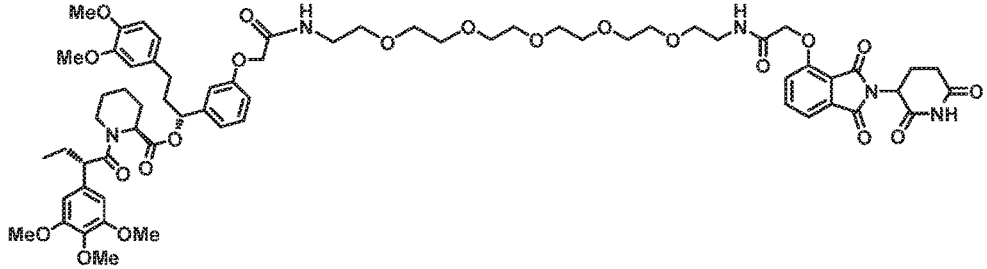
Figure 30O:
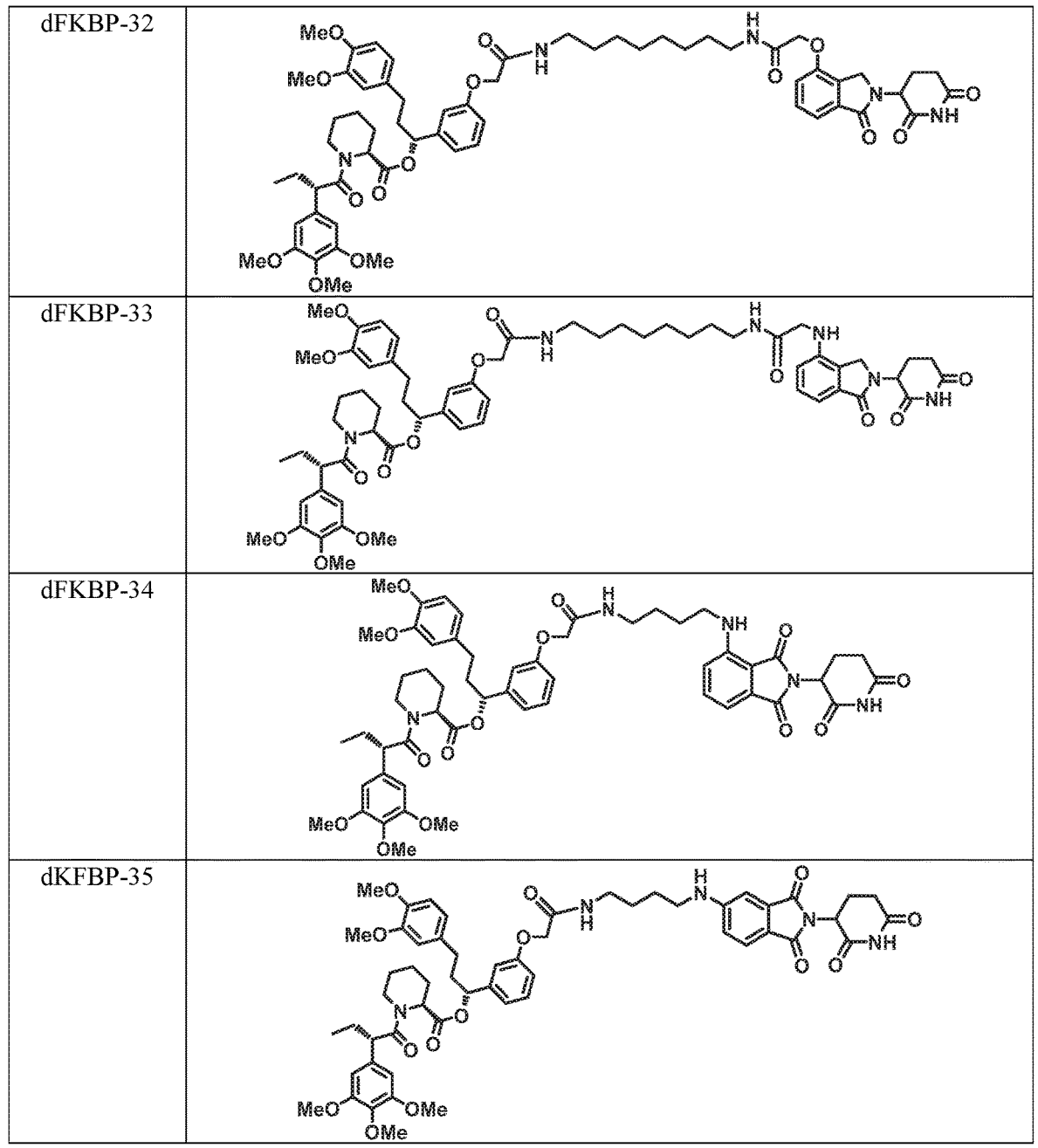
Figure 30P:
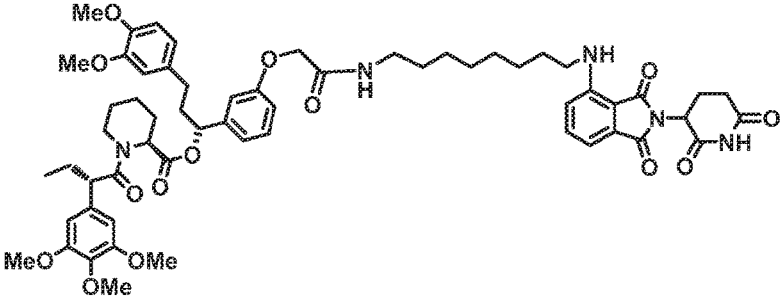
Figure 30P:
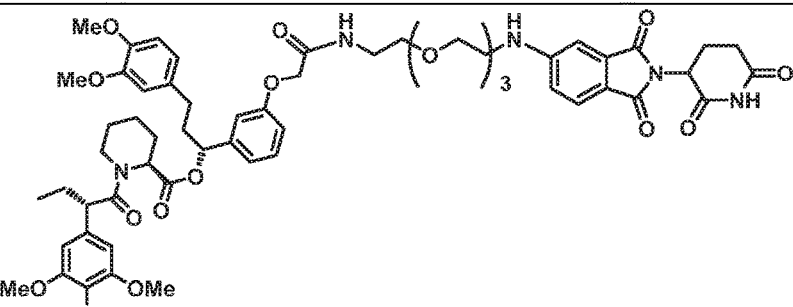
Figure 30P:
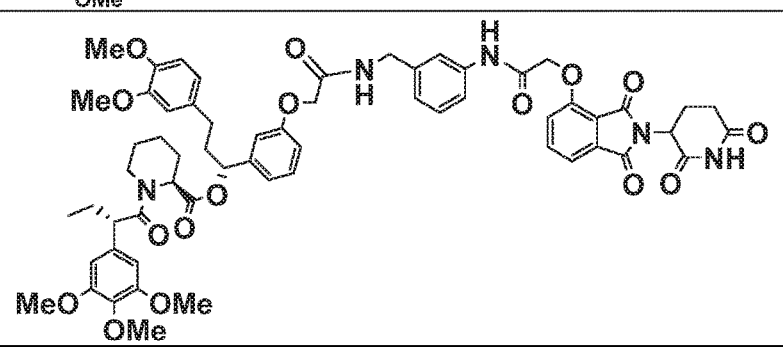
Figure 30P:
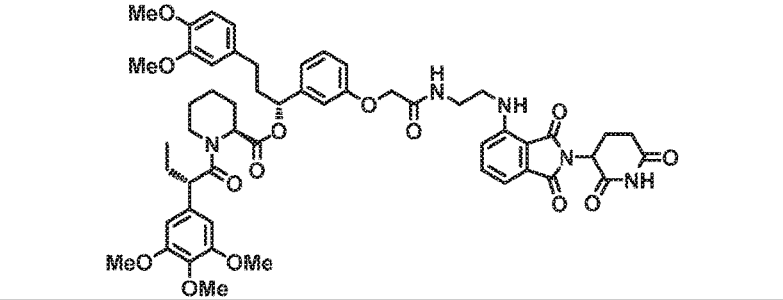
Figure 31A:
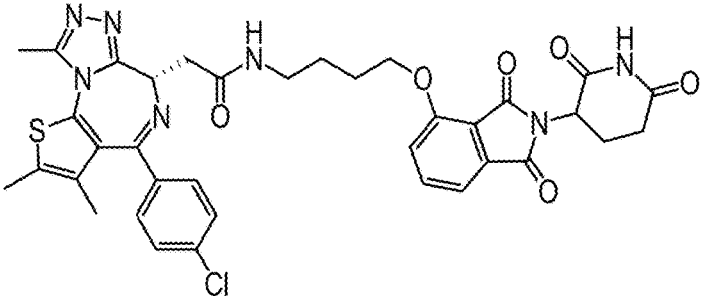
FIG. 31A, FIG. 31B, FIG. 31C, FIG. 31D, FIG. 31E, FIG. 31F, FIG. 31G, FIG. 31H, FIG. 31I, and FIG. 31J provide specific heterobifunctional compounds for use in the present invention.
Figure 31A:
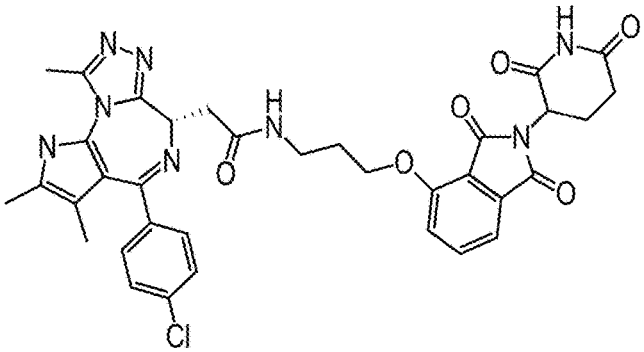
Figure 31A:
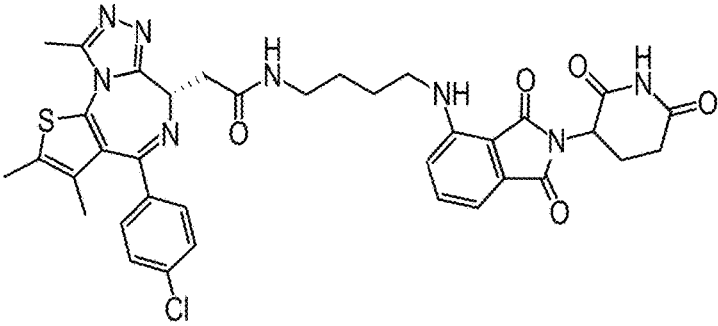
Figure 31A:
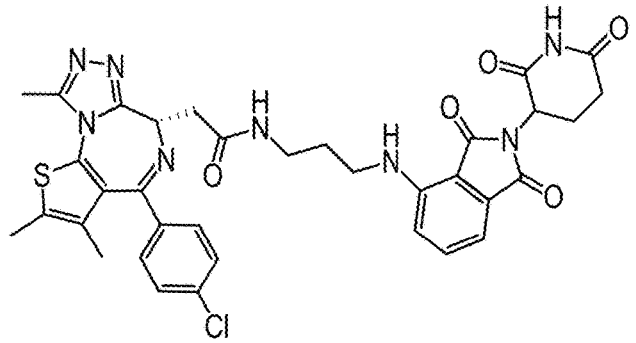
Figure 31B:
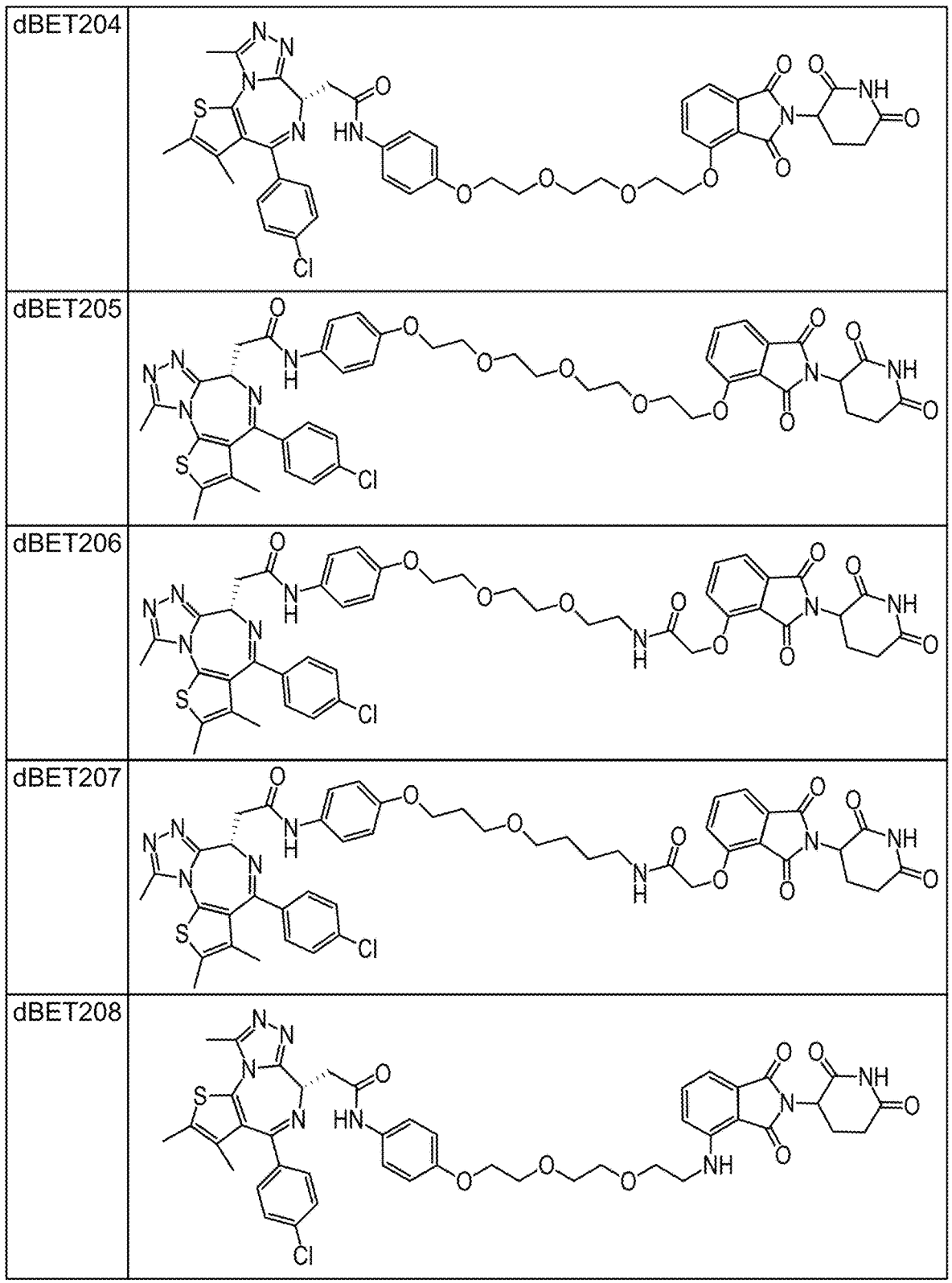
Figure 31C:
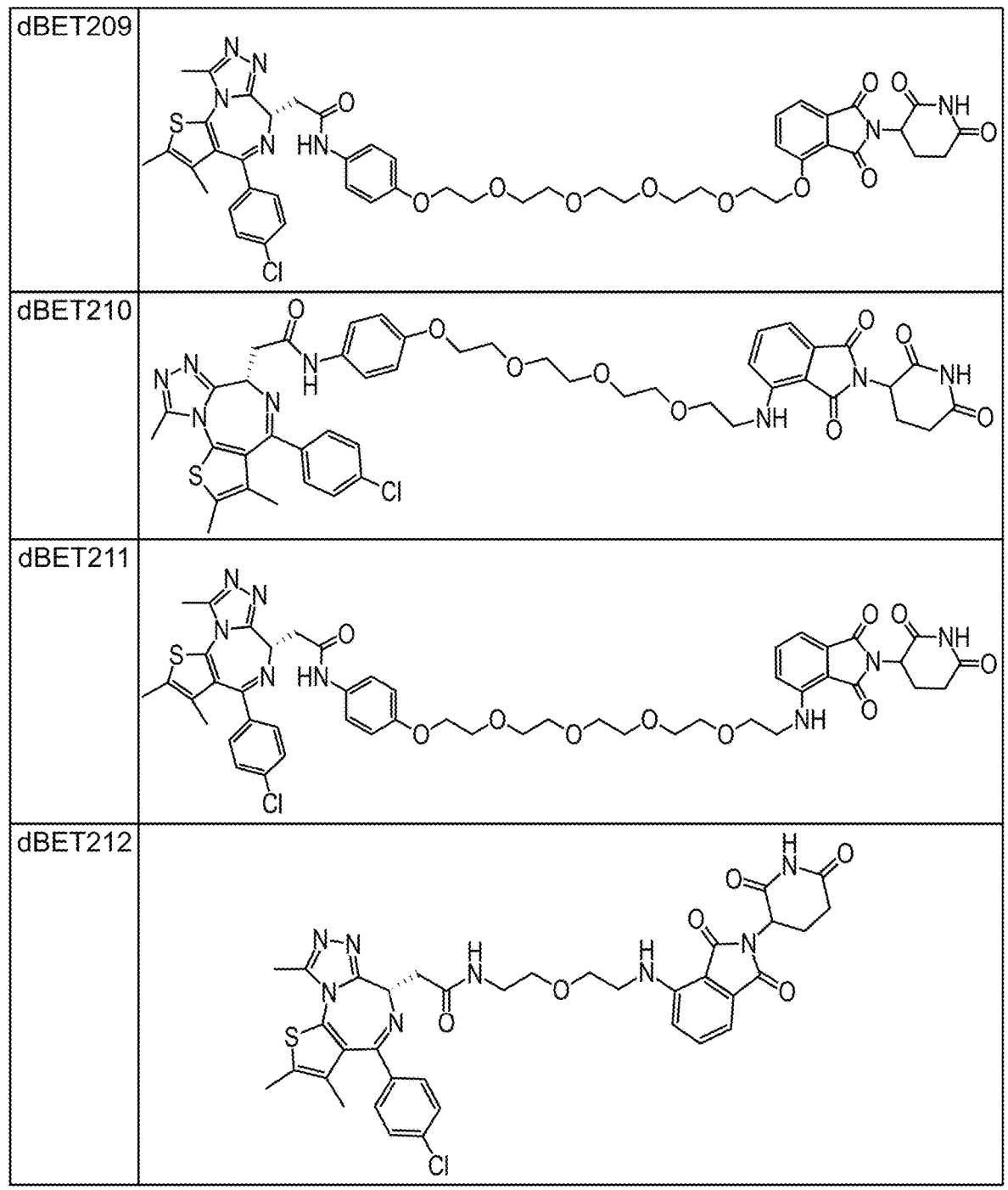
Figure 31D:
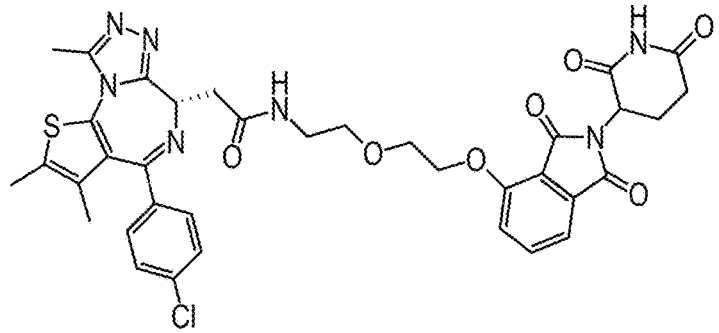
Figure 31E:
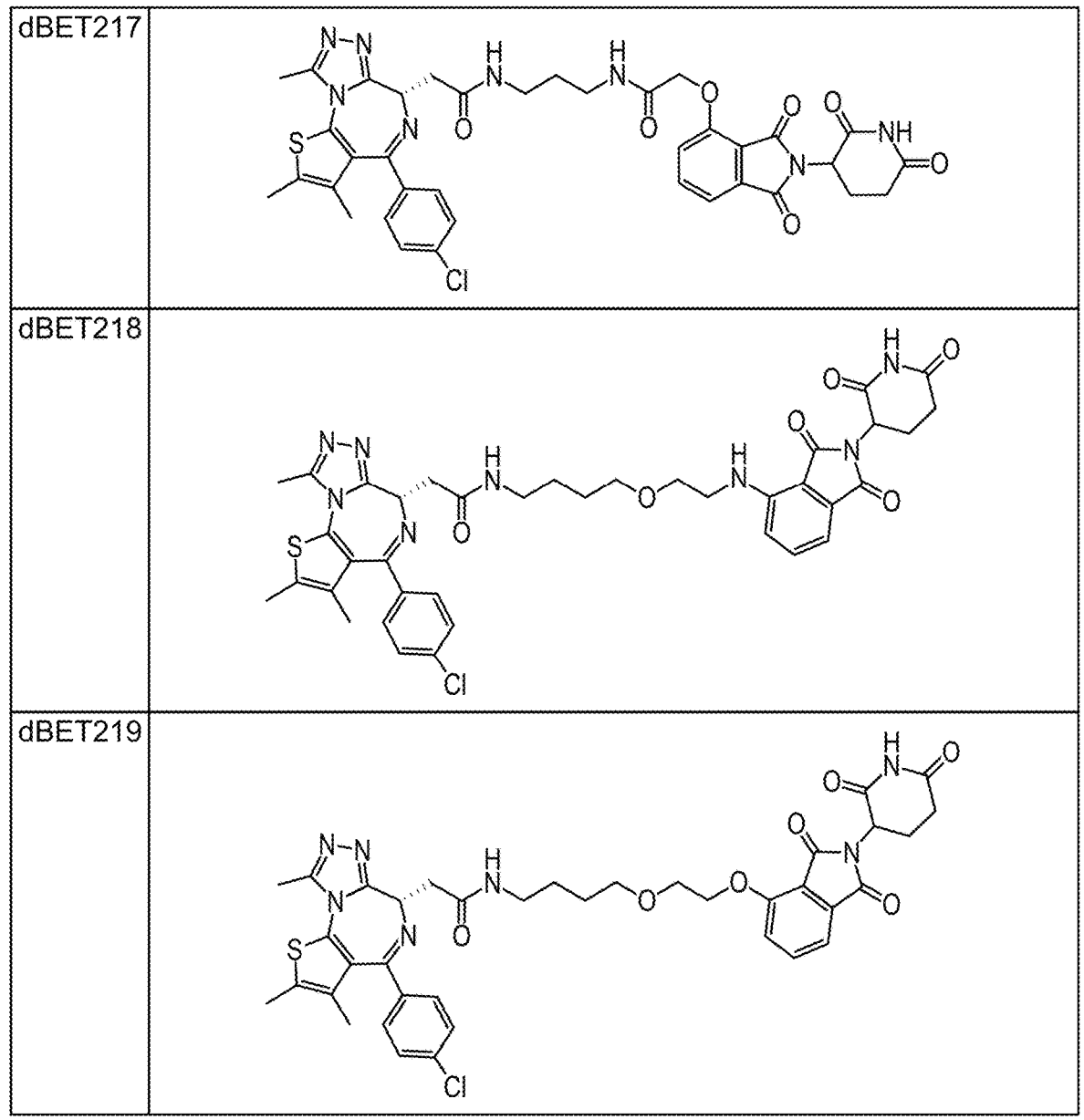
Figure 31F:
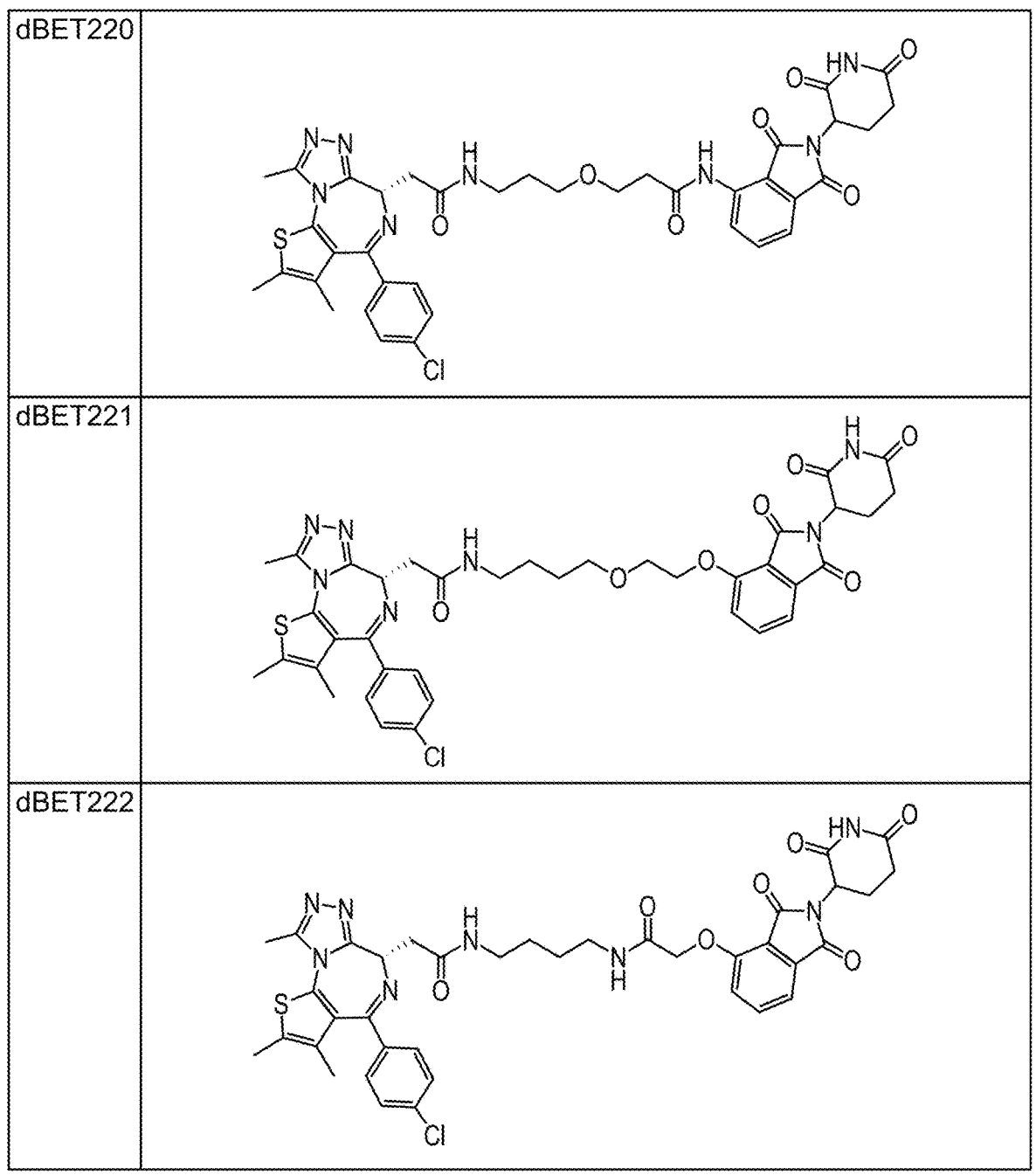
Figure 31G:
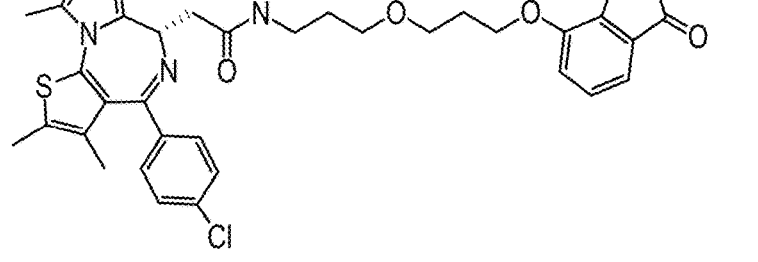
Figure 31H:
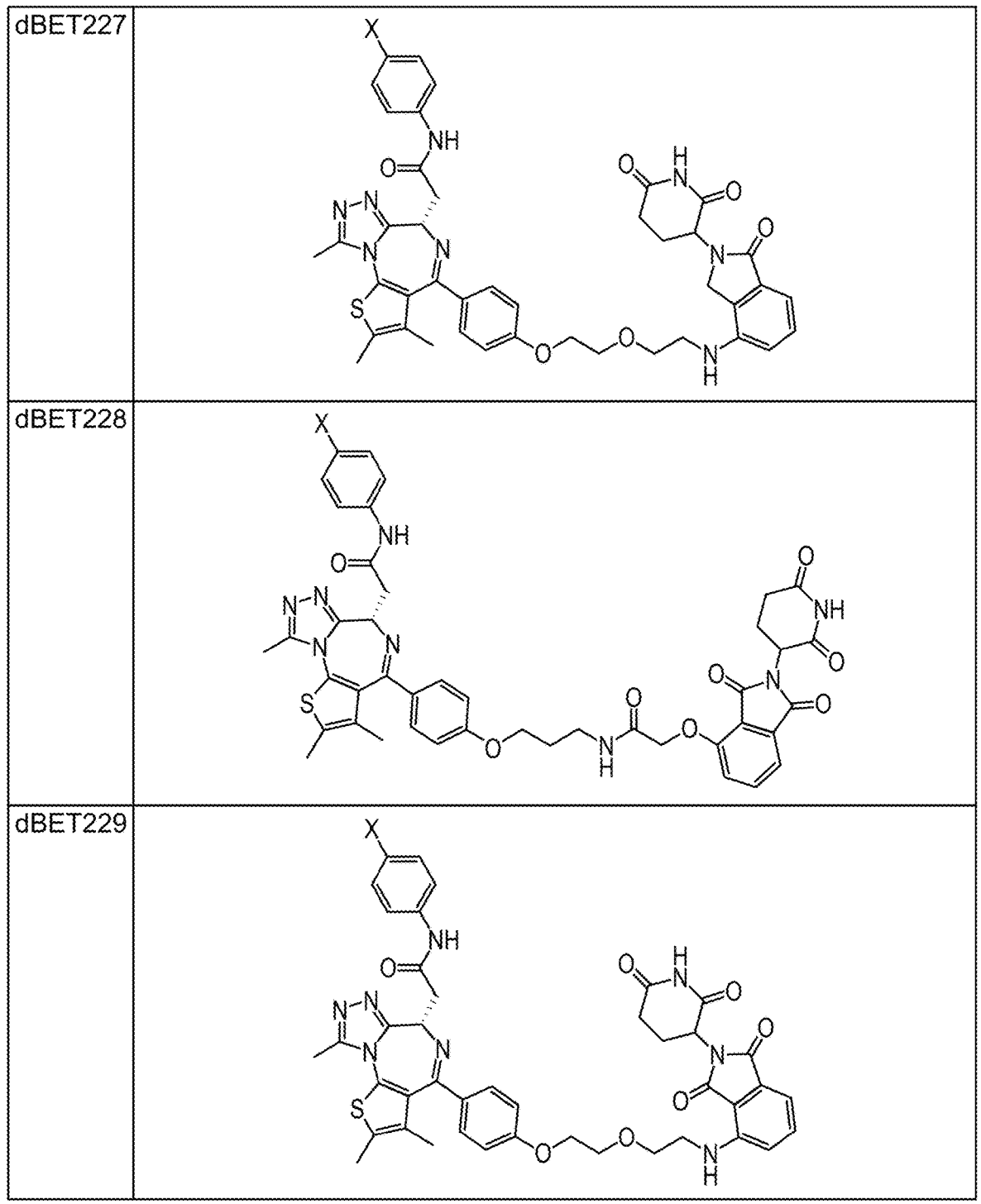
Figure 31I:
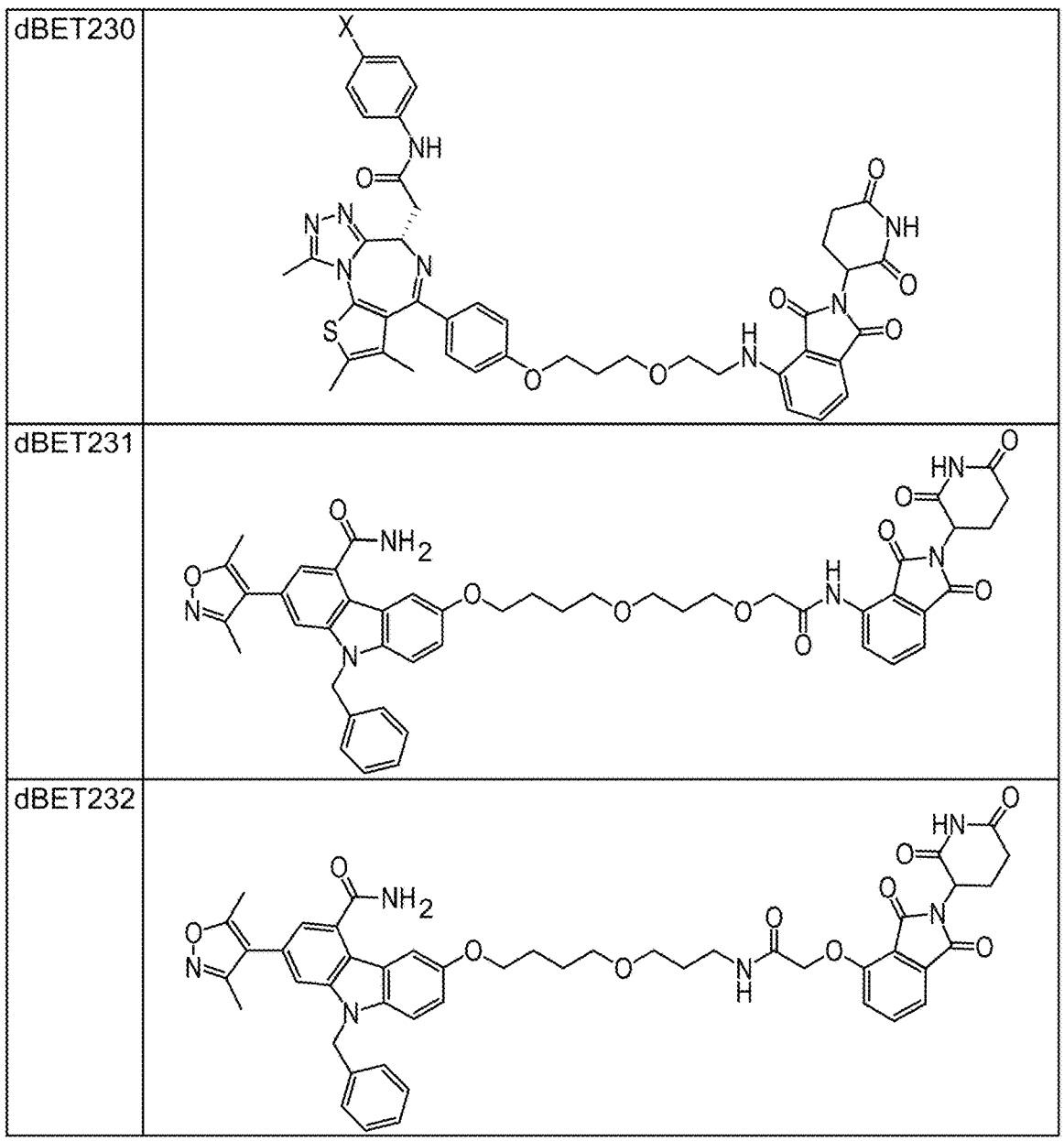
Figure 31J:
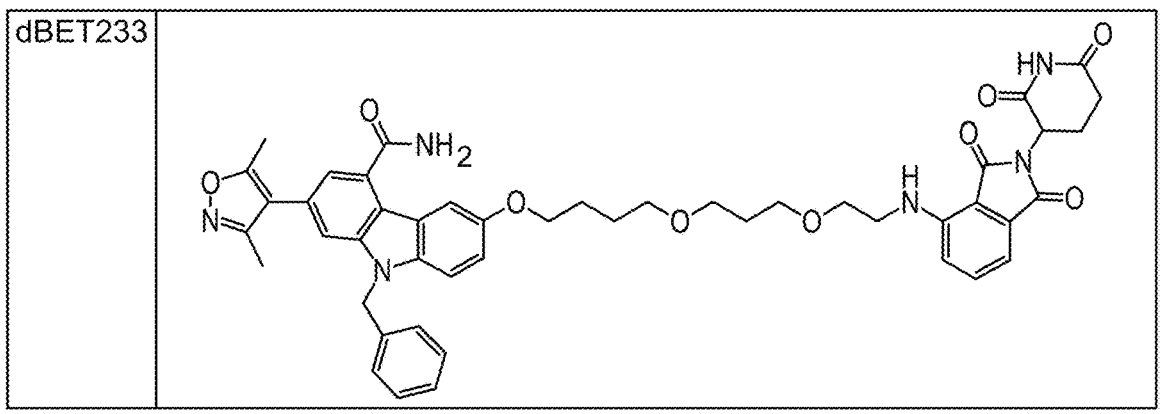
Figure 32B:
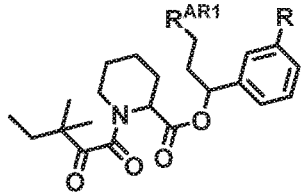
Figure 32B:
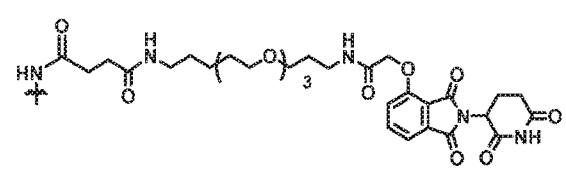
Figure 32B:
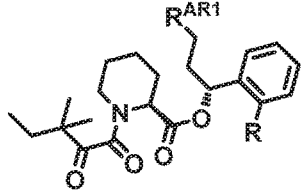
Figure 32B:
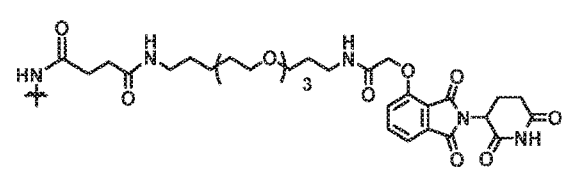
Figure 32B:
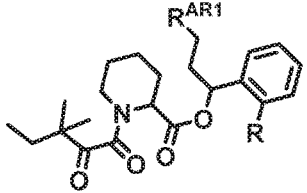
Figure 32B:
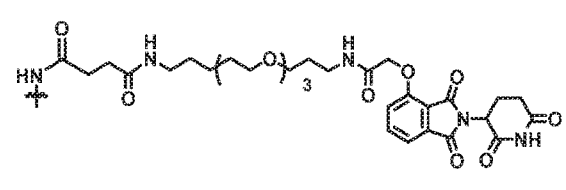
Figure 32B:
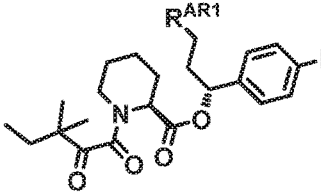
Figure 32B:
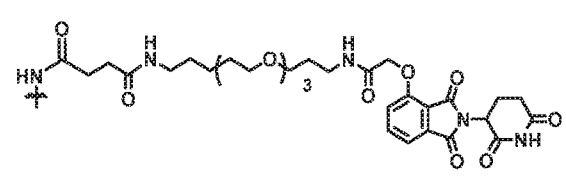
Figure 32B:
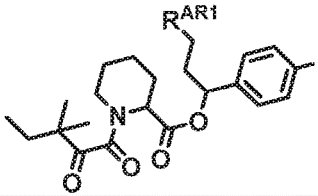
Figure 32B:
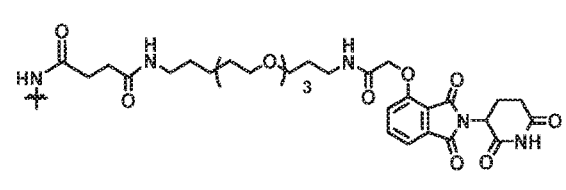
Figure 32B:
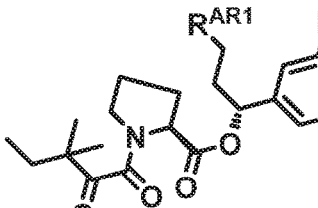
Figure 32B:
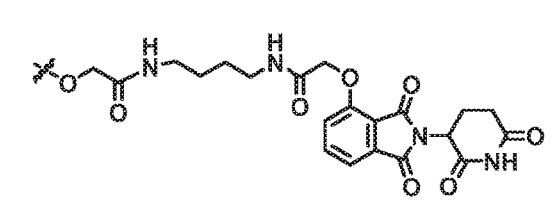
Figure 32B:
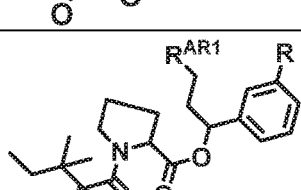
Figure 32B:
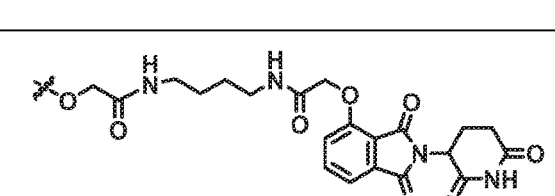
Figure 32D:
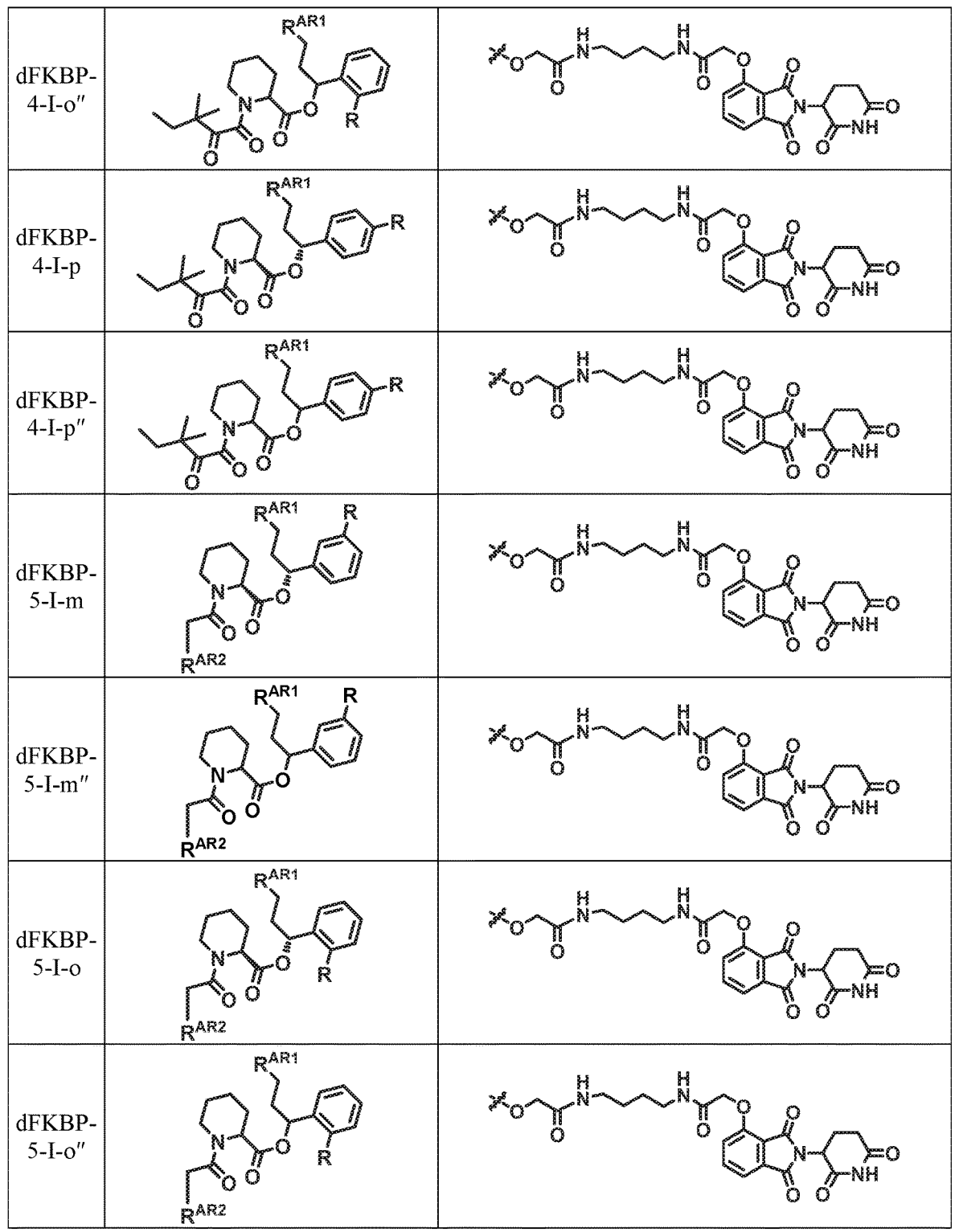
Figure 32I:
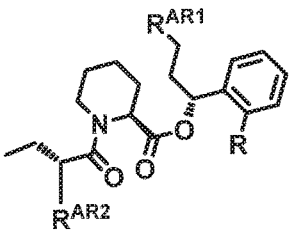
Figure 32I:
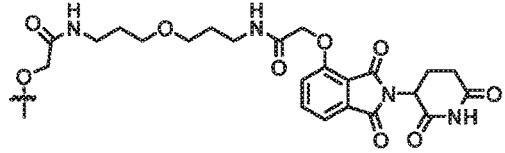
Figure 32I:
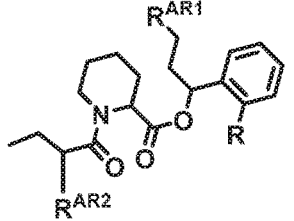
Figure 32I:
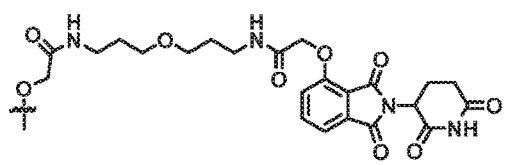
Figure 32I:
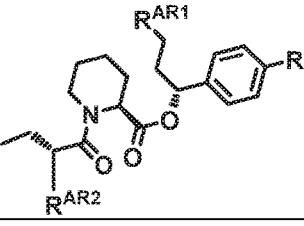
Figure 32I:
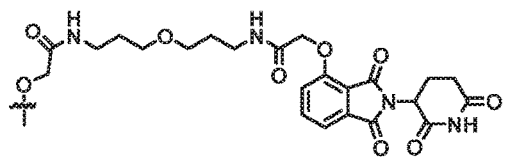
Figure 32I:
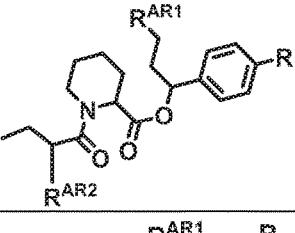
Figure 32I:
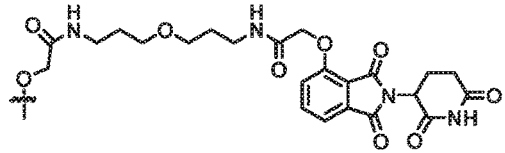
Figure 32I:
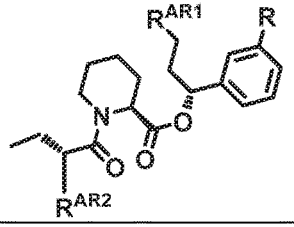
Figure 32I:
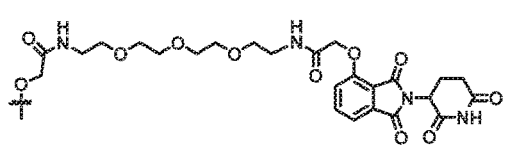
Figure 32I:
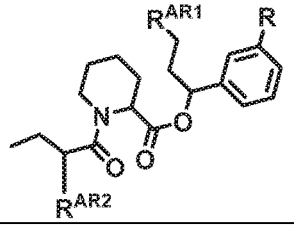
Figure 32I:
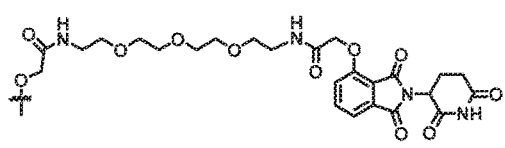
Figure 32I:
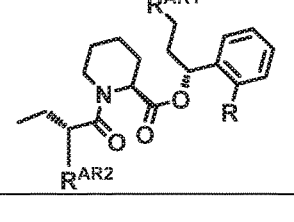
Figure 32I:
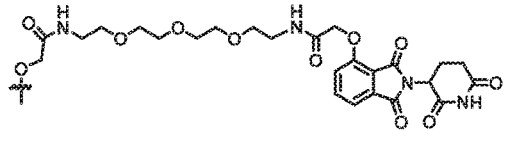
Figure 32J:
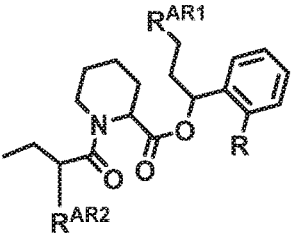
Figure 32J:
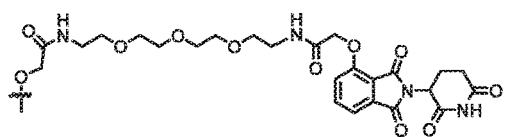
Figure 32J:
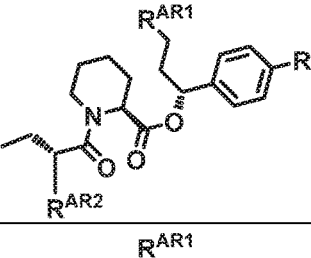
Figure 32J:
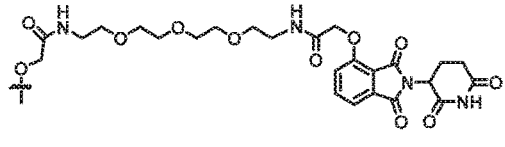
Figure 32J:
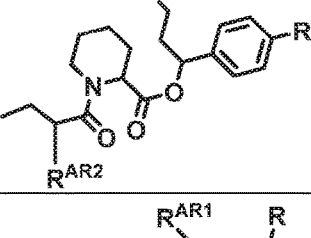
Figure 32J:
Figure 32J:
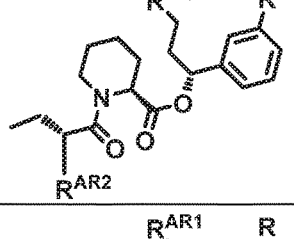
Figure 32J:
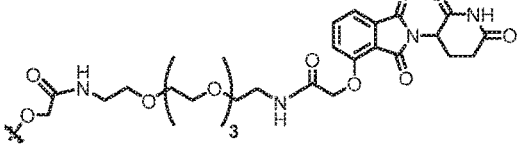
Figure 32J:
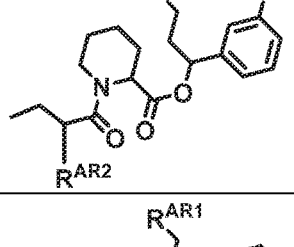
Figure 32J:
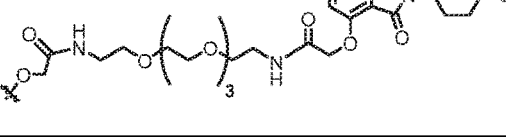
Figure 32J:
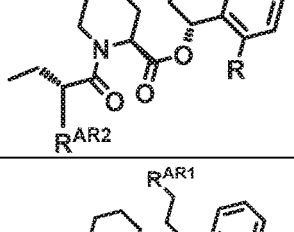
Figure 32J:
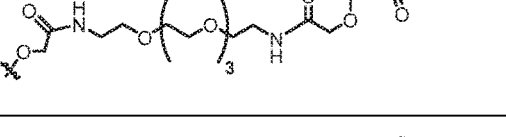
Figure 32J:
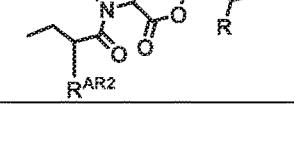
Figure 32J:
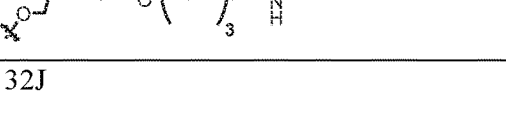
Figure 32K:
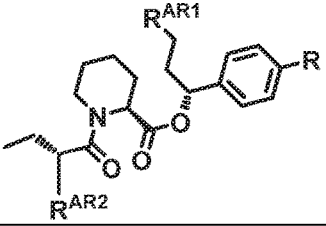
Figure 32K:
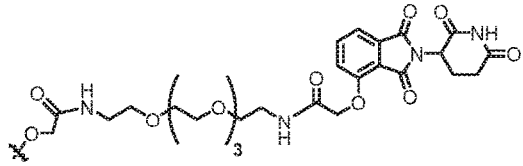
Figure 32K:
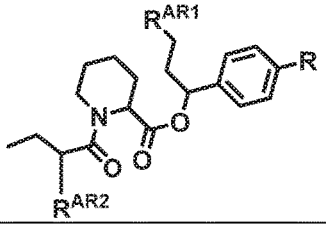
Figure 32K:
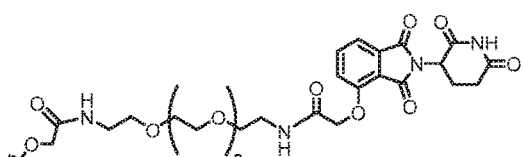
Figure 32K:
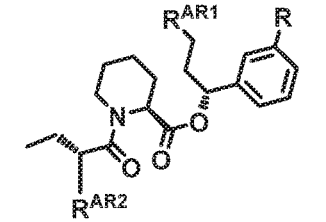
Figure 32K:
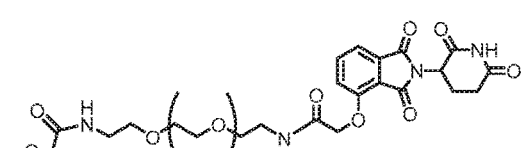
Figure 32K:
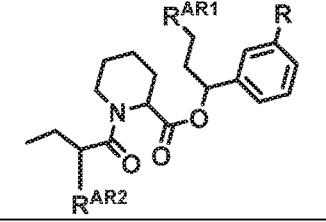
Figure 32K:
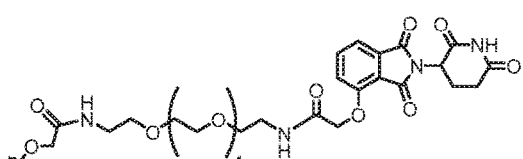
Figure 32K:
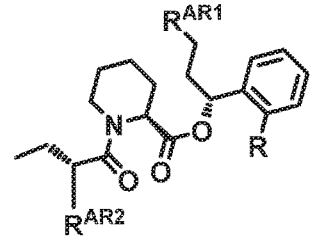
Figure 32K:
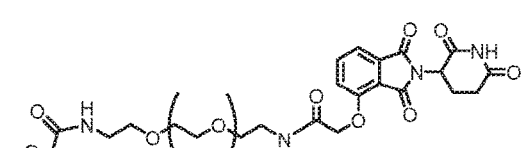
Figure 32K:
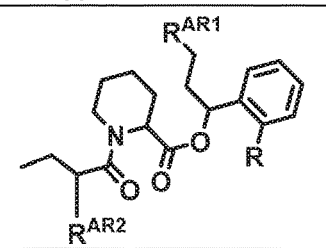
Figure 32K:
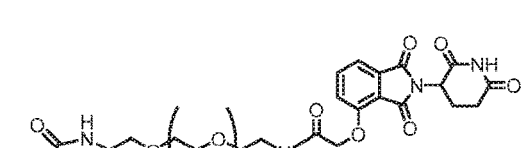
Figure 32M:
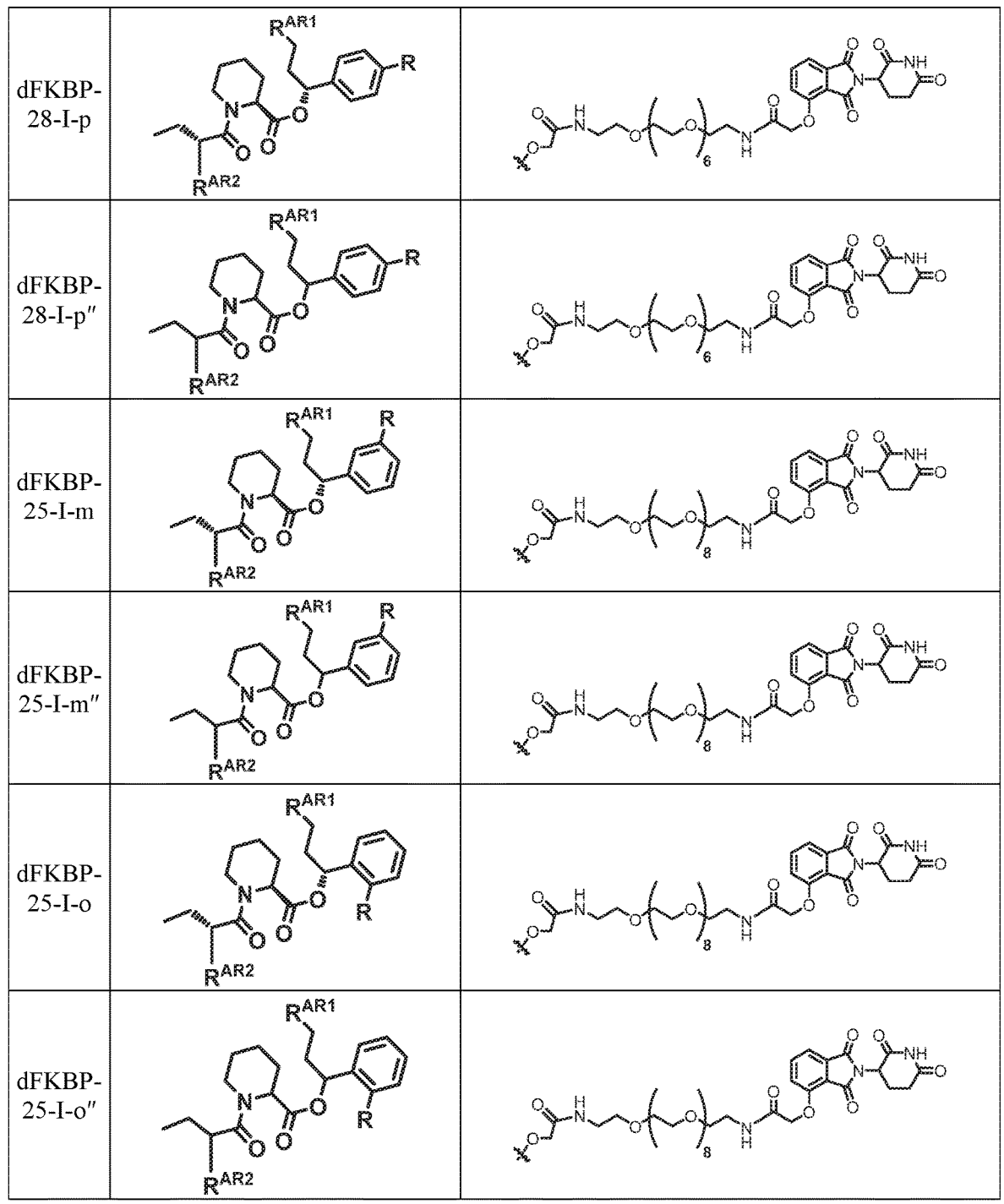
Figure 32N:
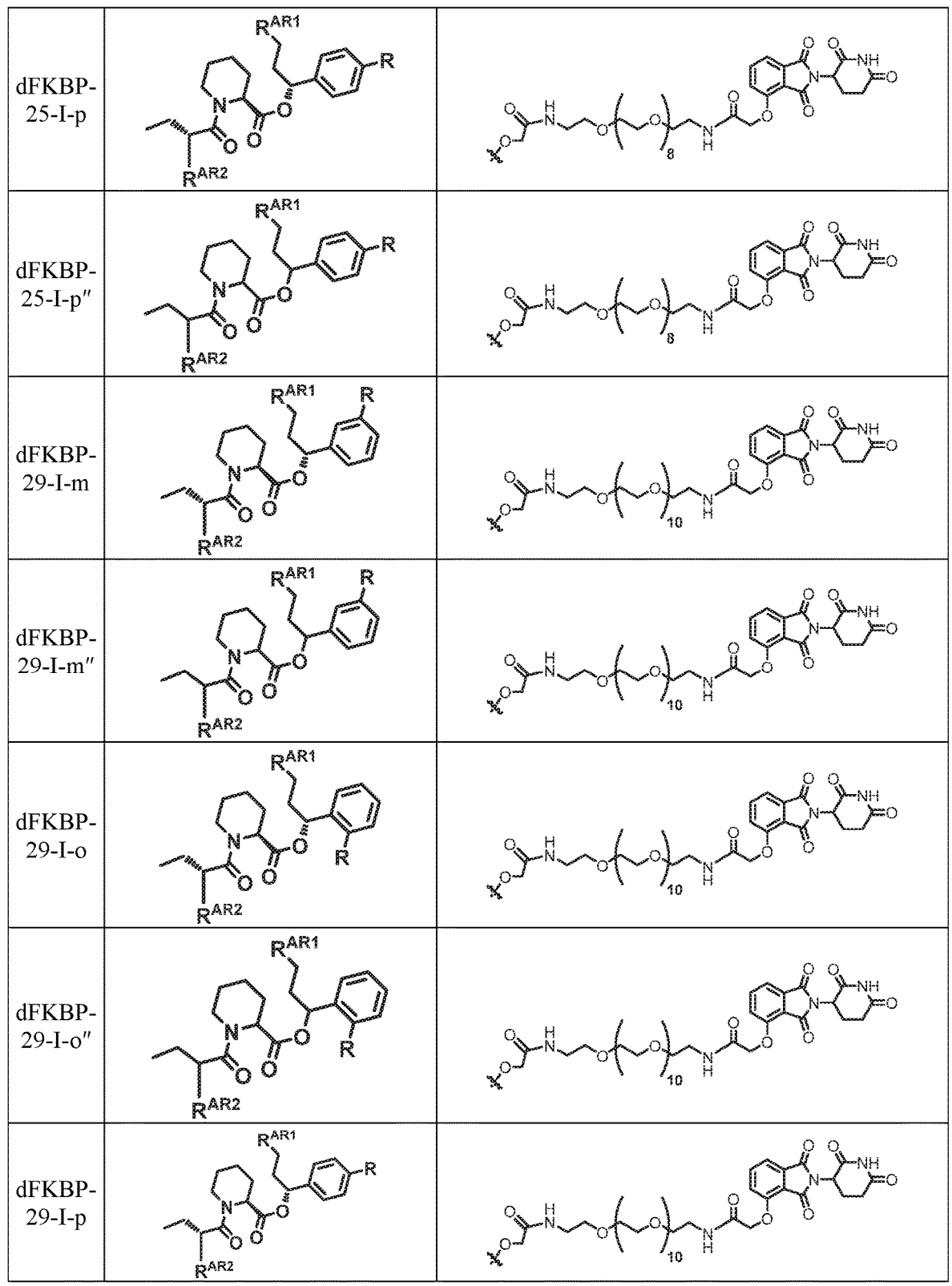
Figure 32O:
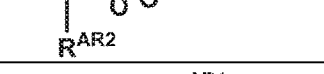
Figure 32P:
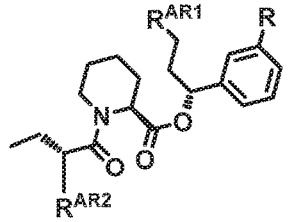
Figure 32P:
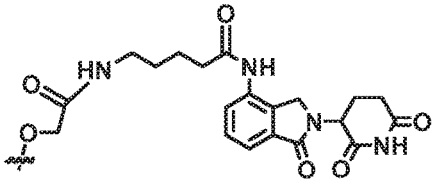
Figure 32P:
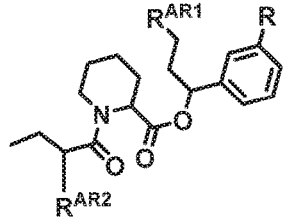
Figure 32P:
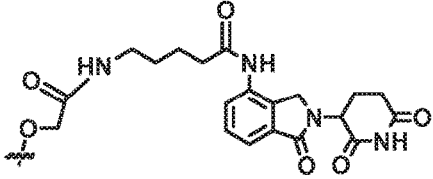
Figure 32P:
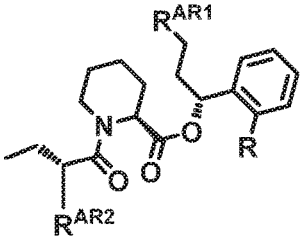
Figure 32P:
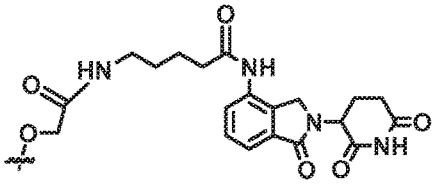
Figure 32P:
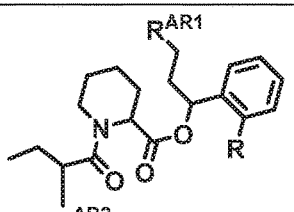
Figure 32P:
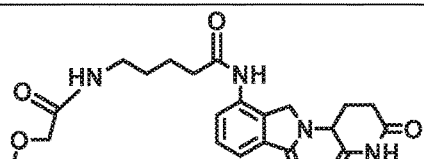
Figure 32P:
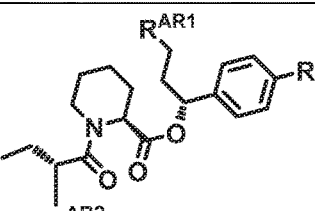
Figure 32P:
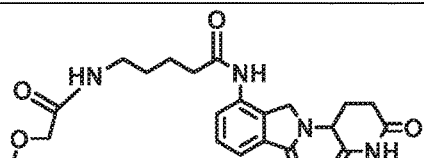
Figure 32Q:
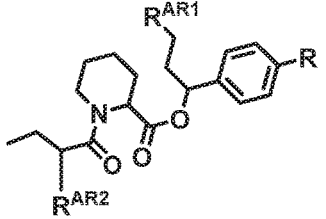
Figure 32R:
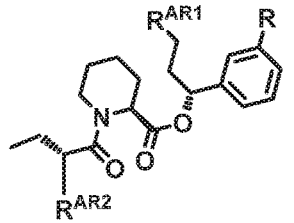
Figure 32R:
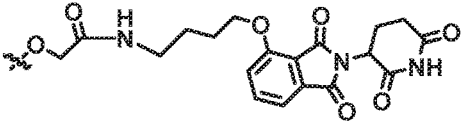
Figure 32R:
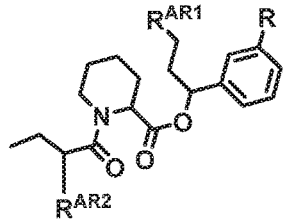
Figure 32R:
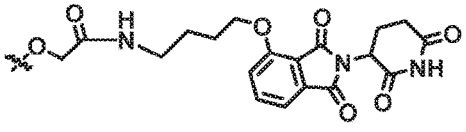
Figure 32R:
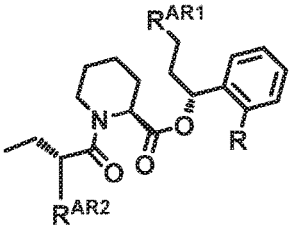
Figure 32R:
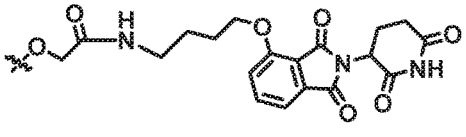
Figure 32R:
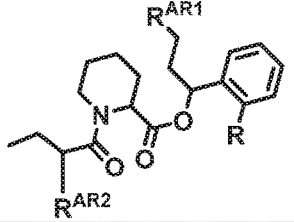
Figure 32R:
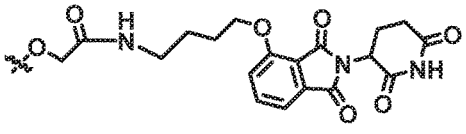
Figure 32R:
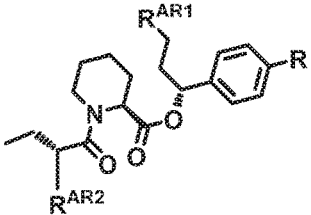
Figure 32R:
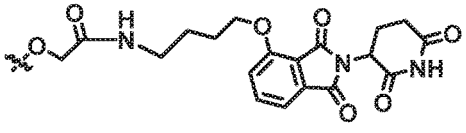
Figure 32R:
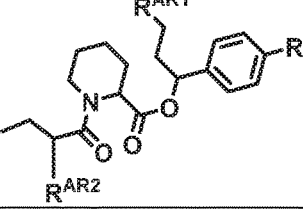
Figure 32R:
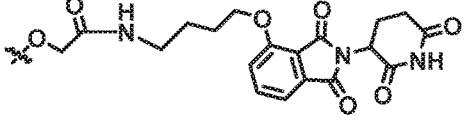
Figure 32S:
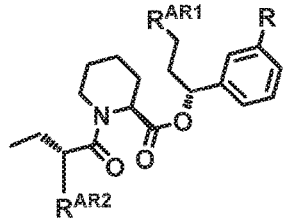
Figure 32T:
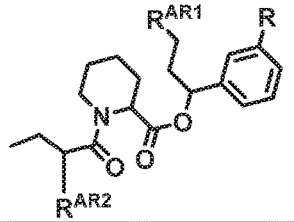
Figure 32T:
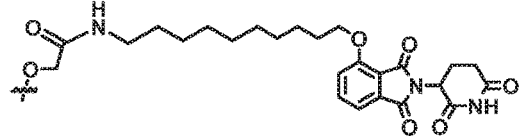
Figure 32T:
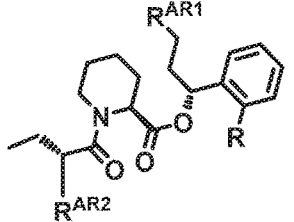
Figure 32T:
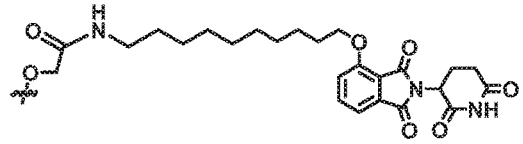
Figure 32T:
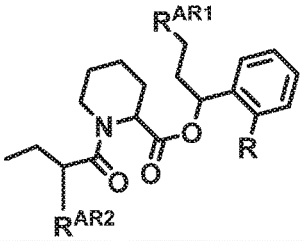
Figure 32T:
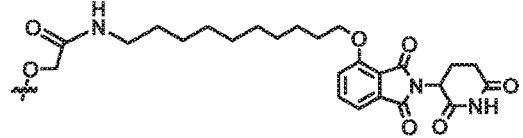
Figure 32T:
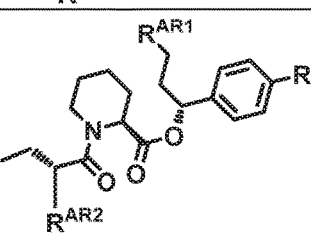
Figure 32T:
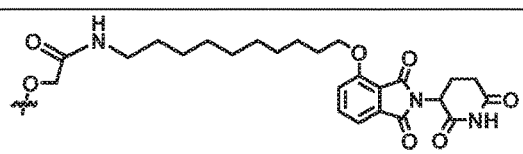
Figure 32T:
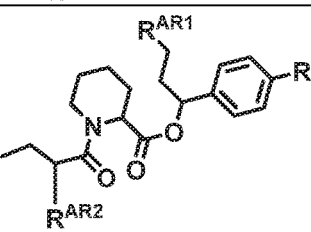
Figure 32T:
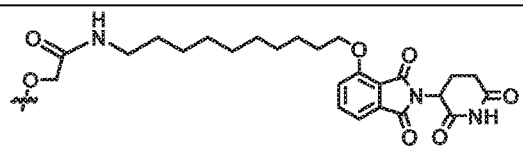
Figure 32T:
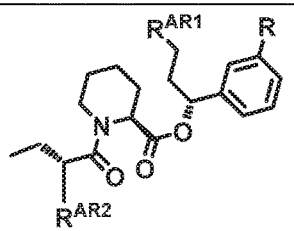
Figure 32T:
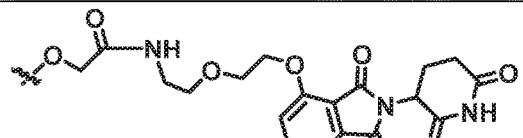
Figure 32V:
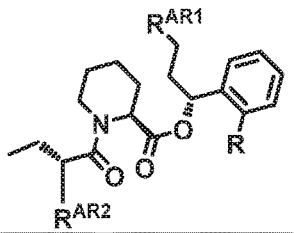
Figure 32V:
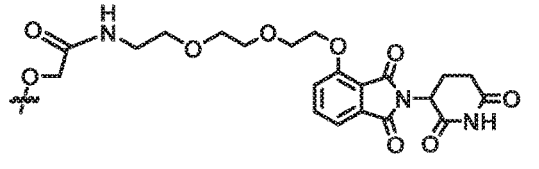
Figure 32V:
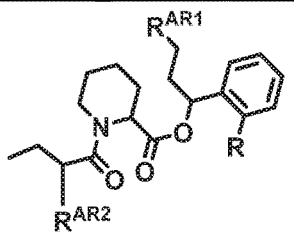
Figure 32V:
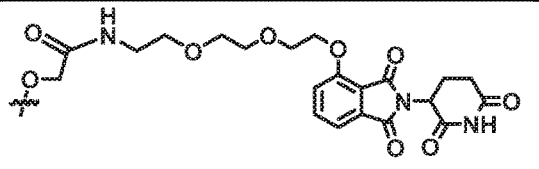
Figure 32V:
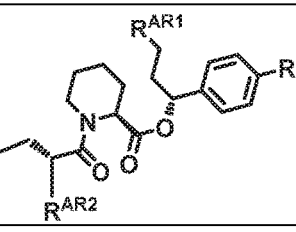
Figure 32V:
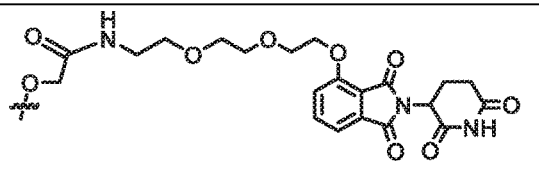
Figure 32V:
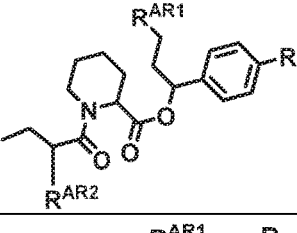
Figure 32V:
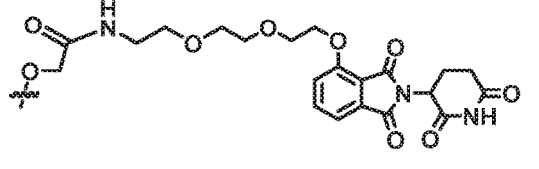
Figure 32V:
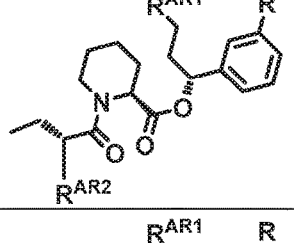
Figure 32V:
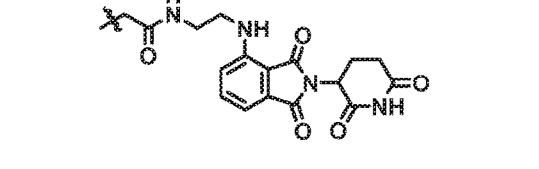
Figure 32V:
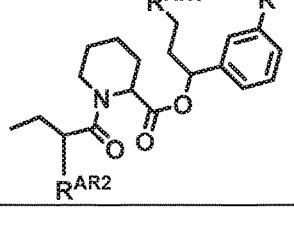
Figure 32V:
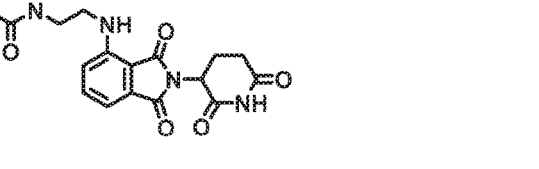
Figure 32X:
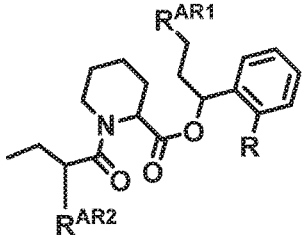
Figure 32X:
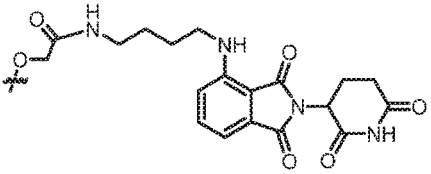
Figure 32X:
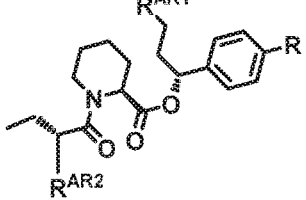
Figure 32X:
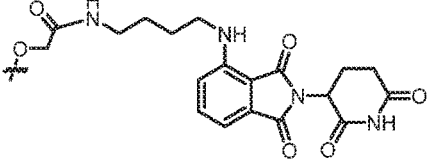
Figure 32X:
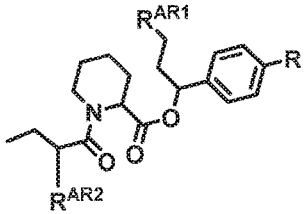
Figure 32X:
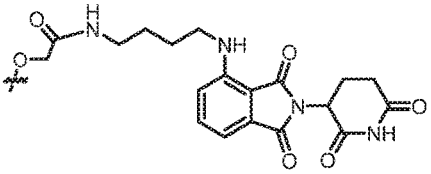
Figure 32X:
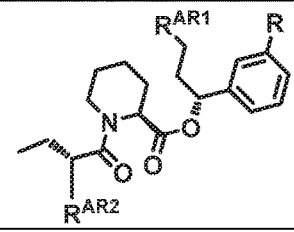
Figure 32X:
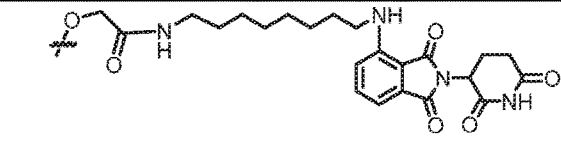
Figure 32X:
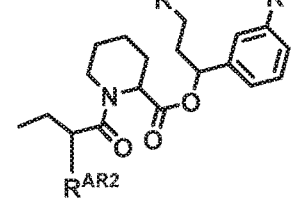
Figure 32X:
Figure 32X:
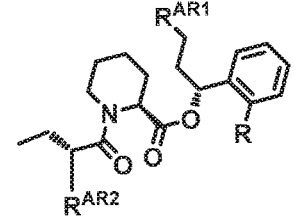
Figure 32X:
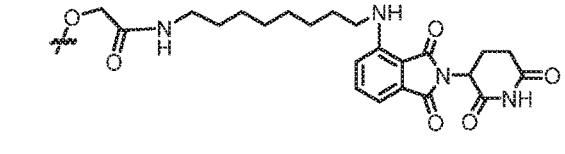
Figure 32X:
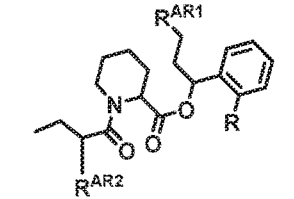
Figure 32X:
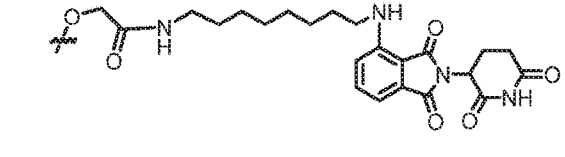
Figure 32Z:
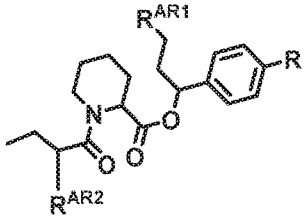
Figure 32Z:
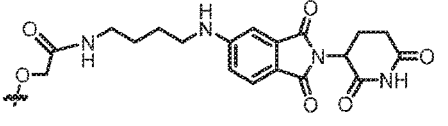
Figure 32Z:
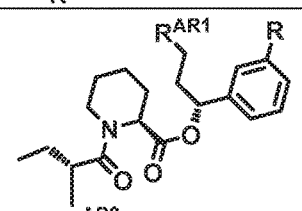
Figure 32Z:
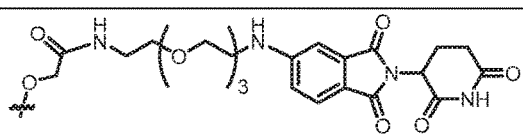
Figure 32Z:
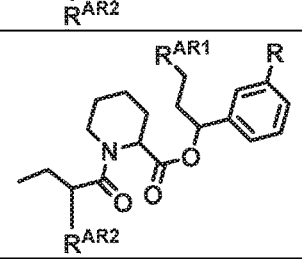
Figure 32Z:
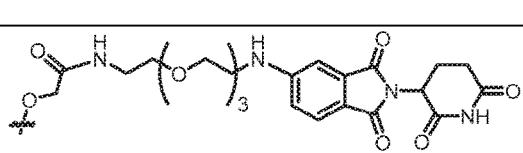
Figure 32Z:
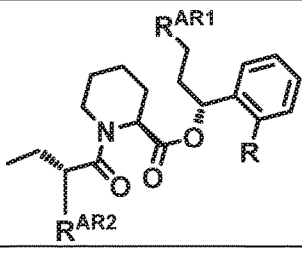
Figure 32Z:
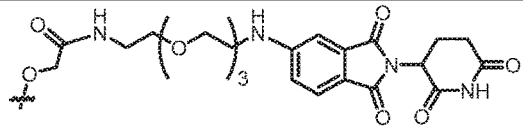
Figure 32Z:
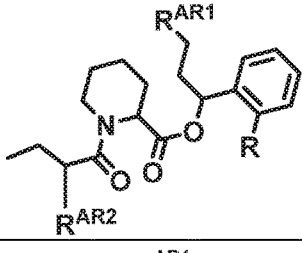
Figure 32Z:
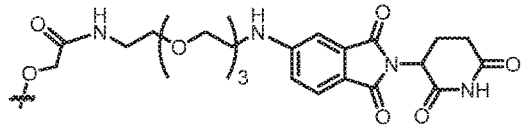
Figure 32Z:
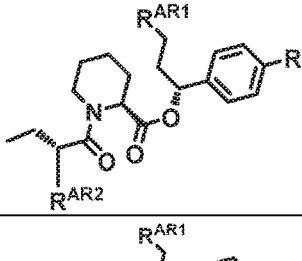
Figure 32Z:
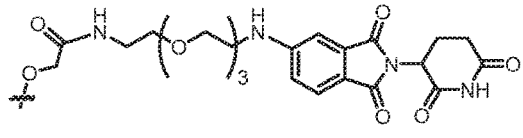
Figure 32Z:
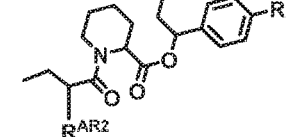
Figure 32Z:
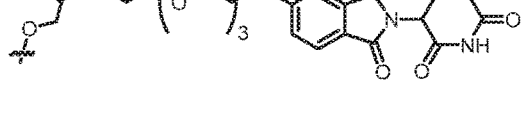
Figure 32A:
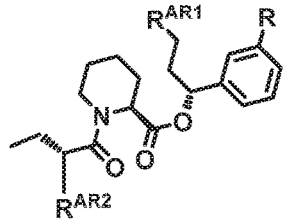
Figure 32A:
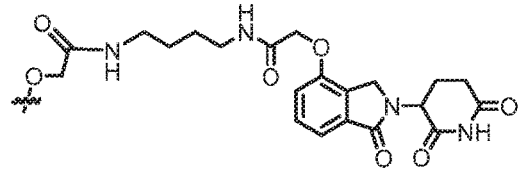
Figure 32A:
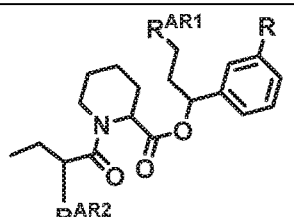
Figure 32A:
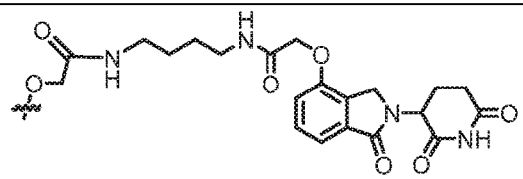
Figure 32A:
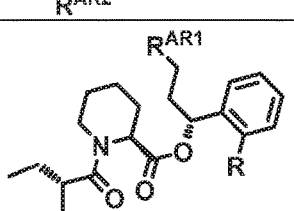
Figure 32A:
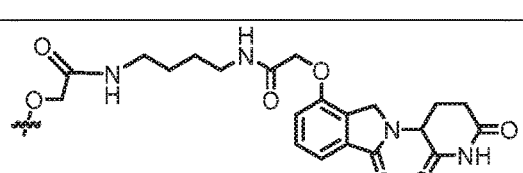
Figure 32A:
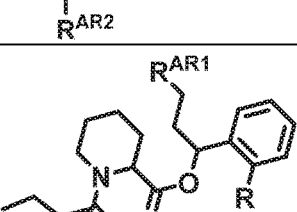
Figure 32A:
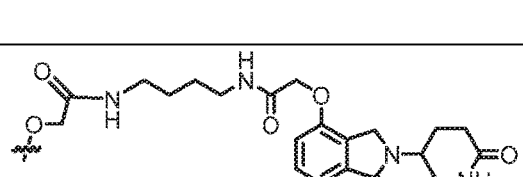
Figure 32A:
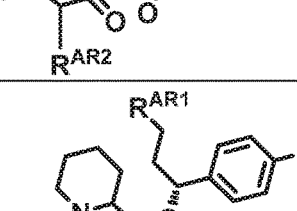
Figure 32A:
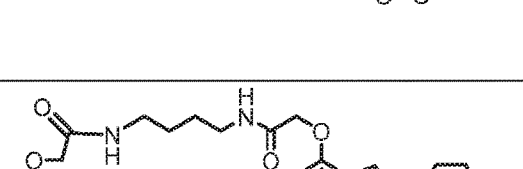
Figure 32A:
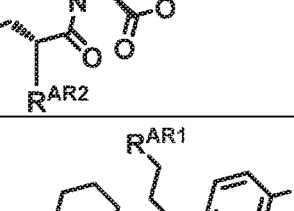
Figure 32A:
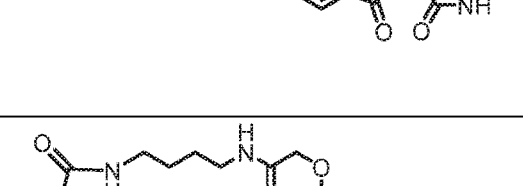
Figure 32B:
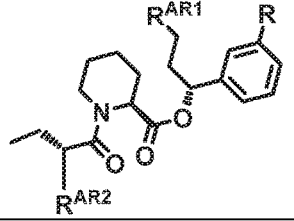
Figure 32B:
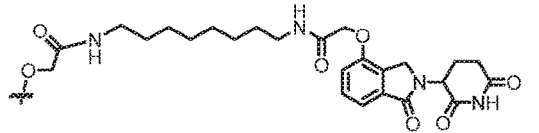
Figure 32B:
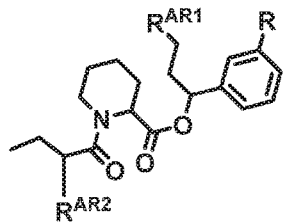
Figure 32B:
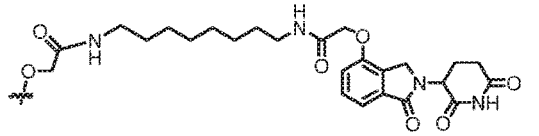
Figure 32B:
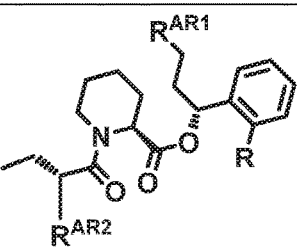
Figure 32B:
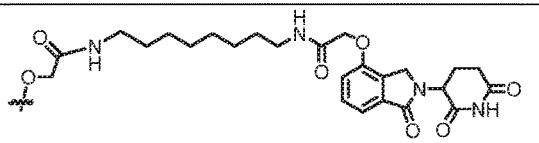
Figure 32B:
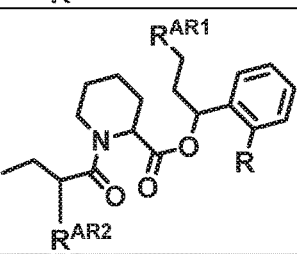
Figure 32B:
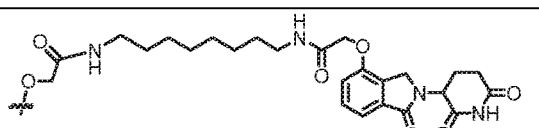
Figure 32B:
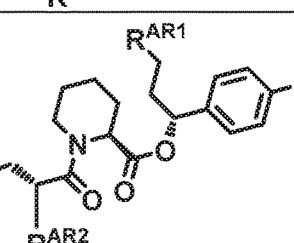
Figure 32B:
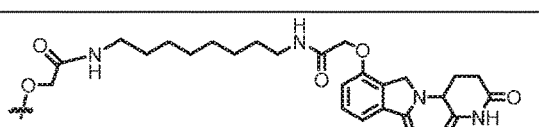
Figure 32B:
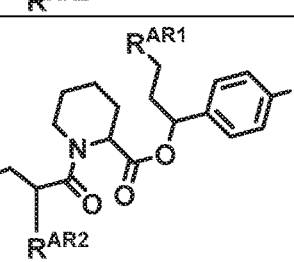
Figure 32B:
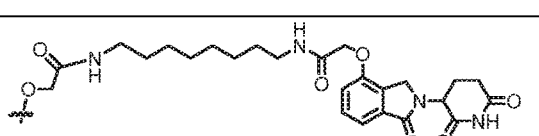
Figure 32C:
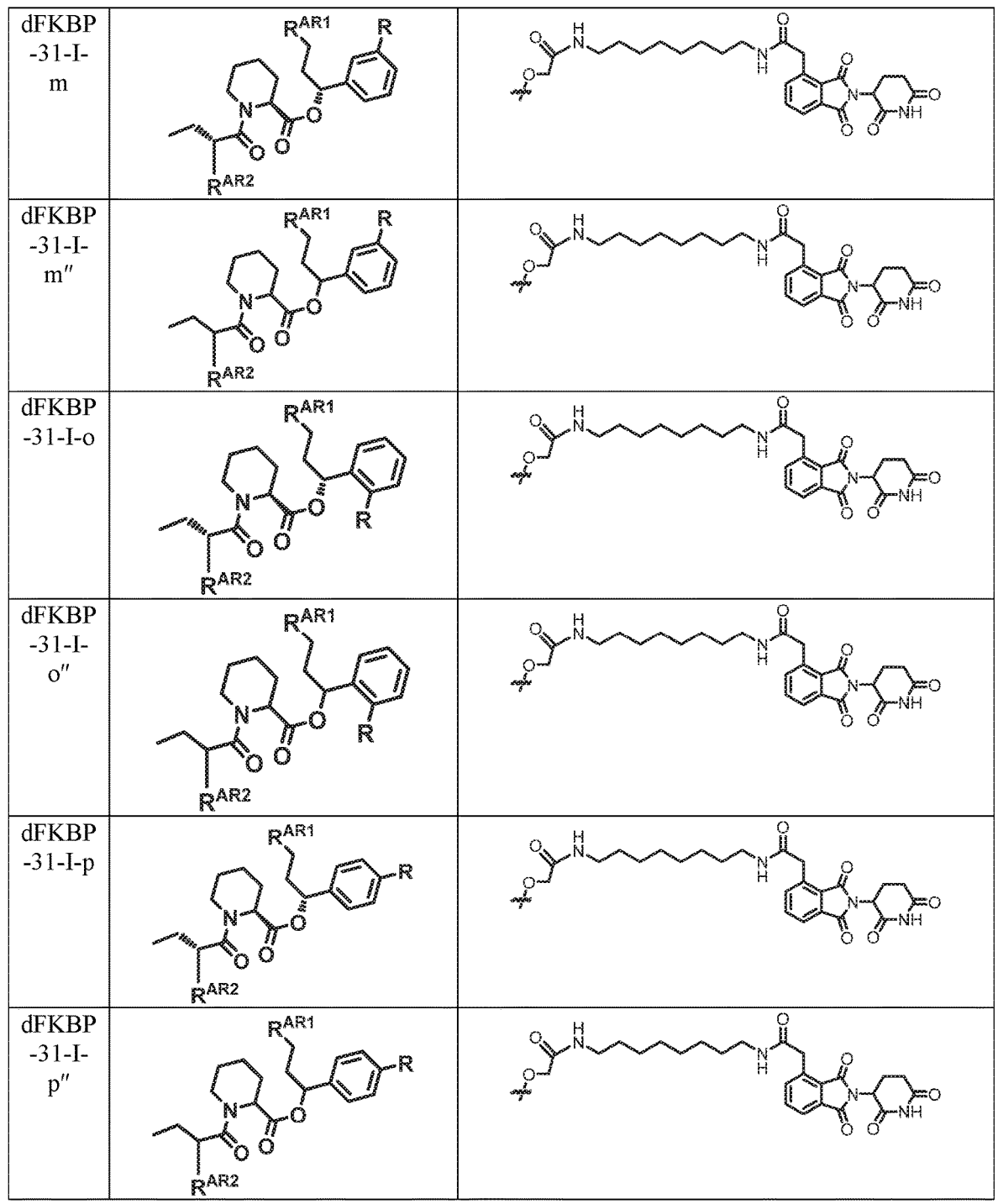
Figure 32E:
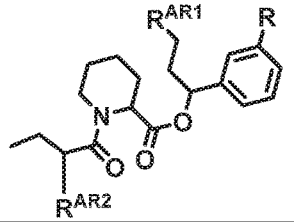
Figure 32E:
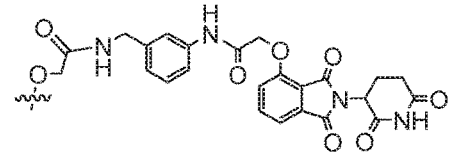
Figure 32E:
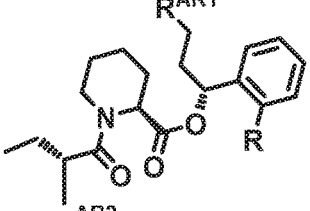
Figure 32E:
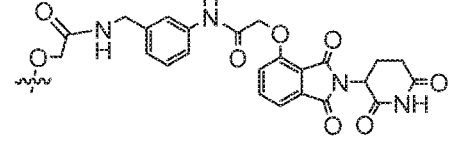
Figure 32E:
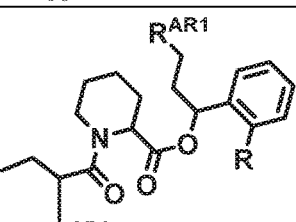
Figure 32E:
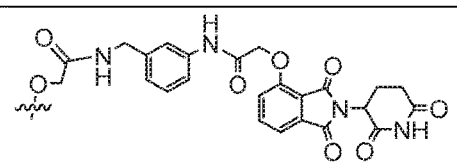
Figure 32E:
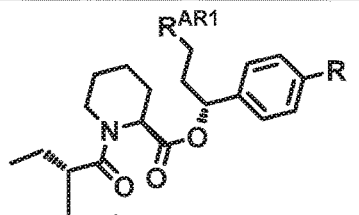
Figure 32E:
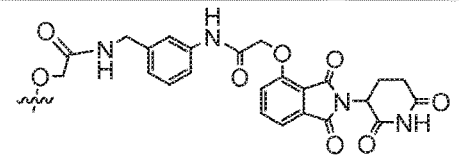
Figure 32E:
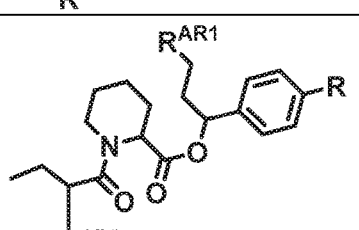
Figure 32E:
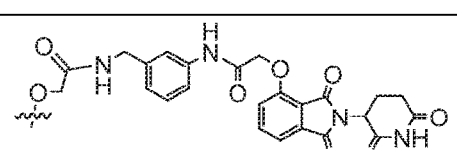
Figure 33A:
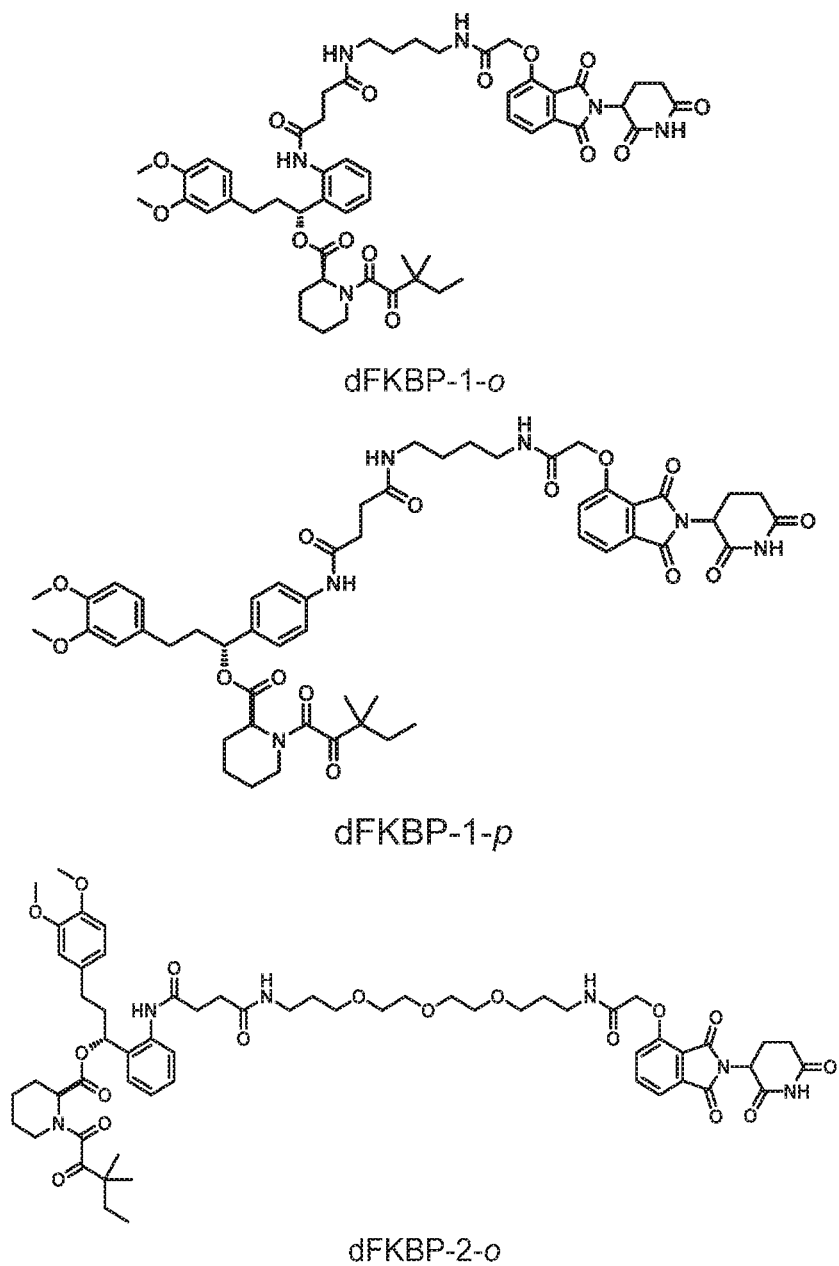
FIG. 33A, FIG. 33B, FIG. 33C, FIG. 33D, FIG. 33E, FIG. 33F, FIG. 33G, FIG. 33H, FIG. 33I, FIG. 33J, FIG. 33K, FIG. 33L, FIG. 33M, FIG. 33N, FIG. 33O, FIG. 33P, FIG. 33Q, FIG. 33R, FIG. 33S, FIG. 33T, FIG. 33U, FIG. 33V, and FIG. 33W provide additional heterobifunctional compounds for use in the present invention.
Figure 33B:
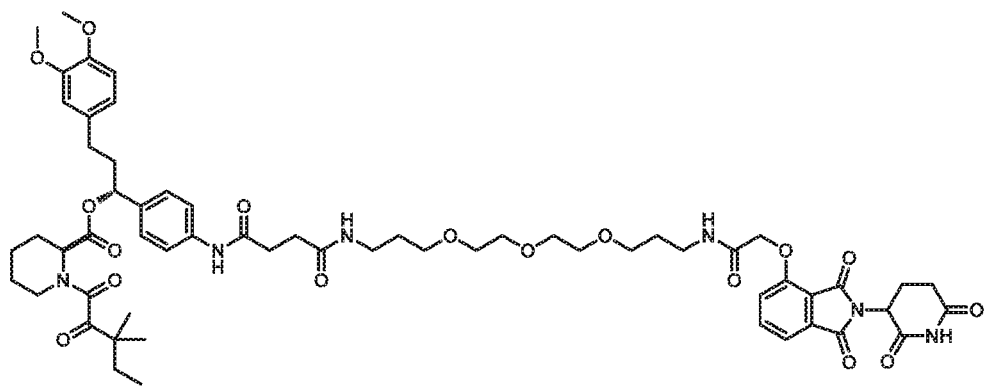
Figure 33B:
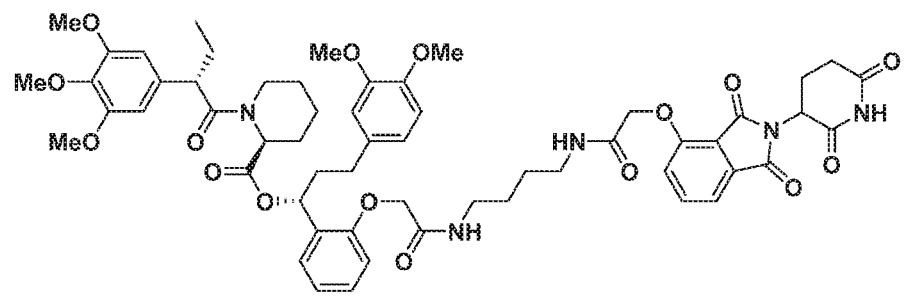
Figure 33B:
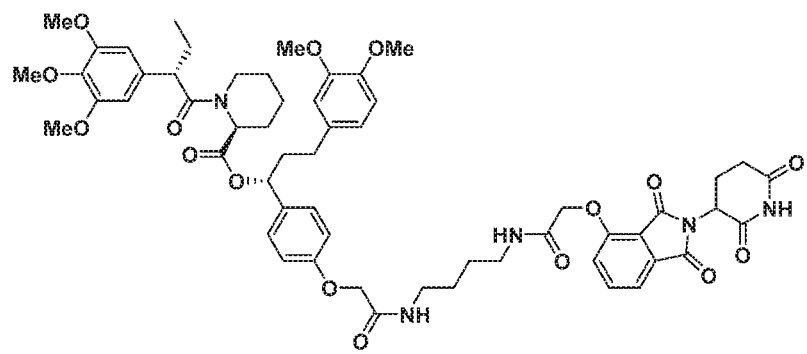
Figure 33B:
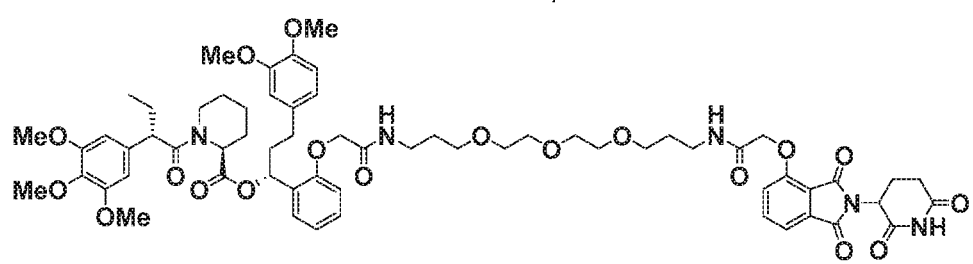
Figure 33C:
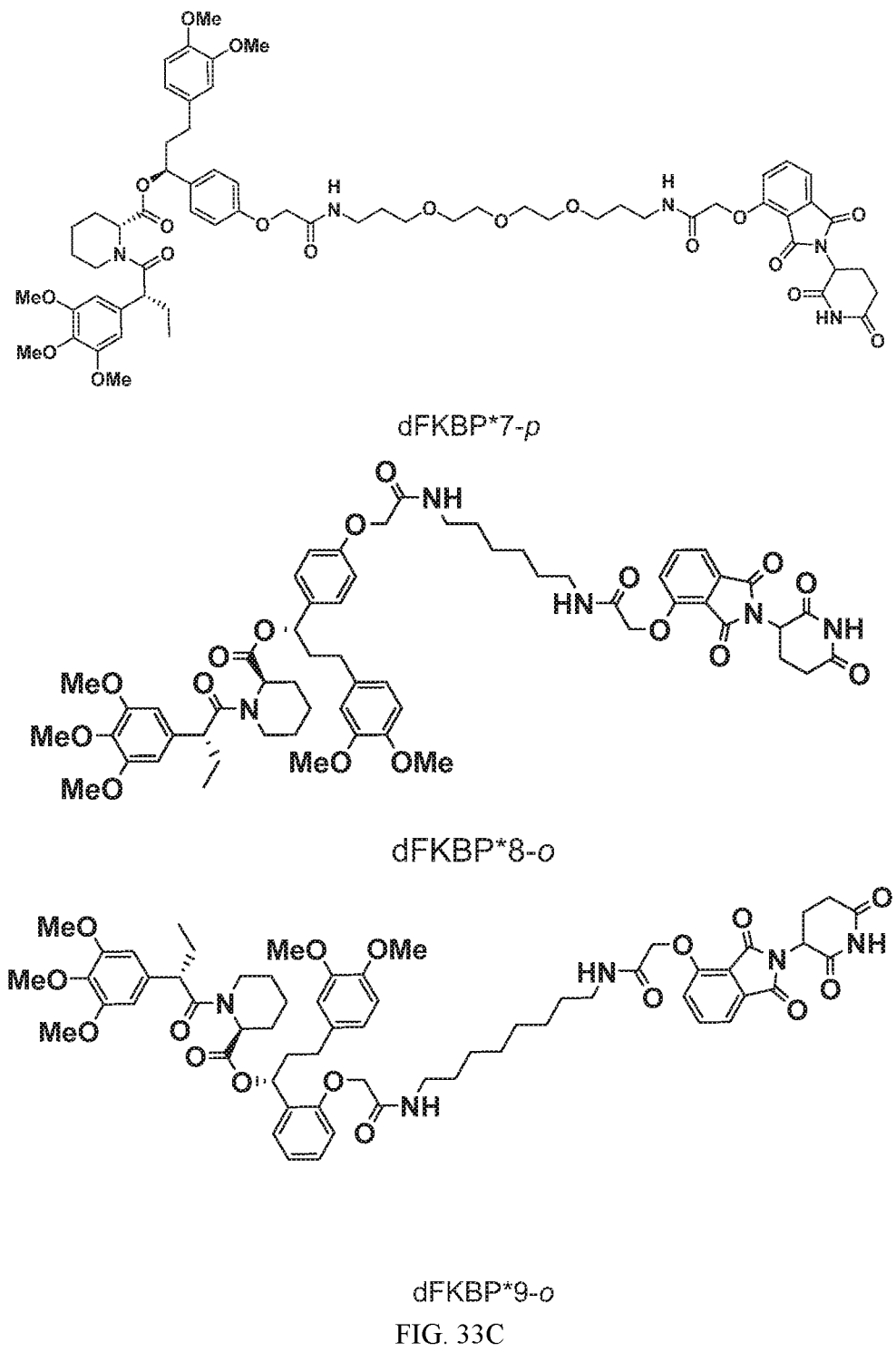
Figure 33D:
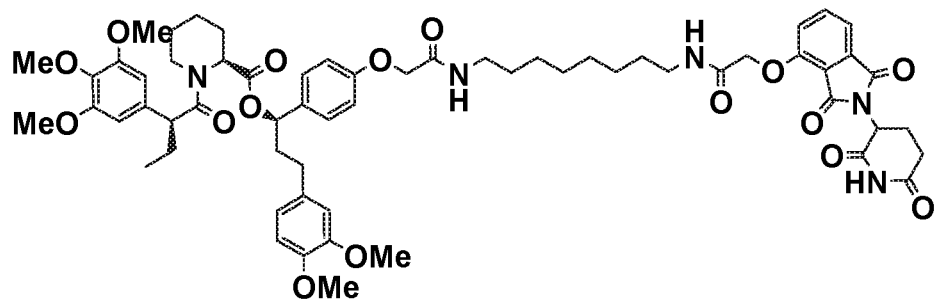
Figure 33D:
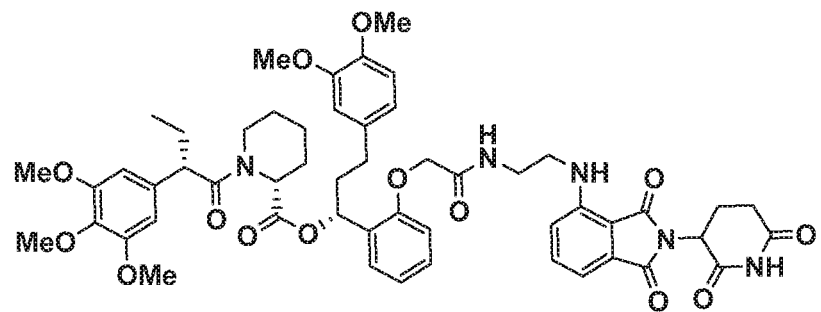
Figure 33D:
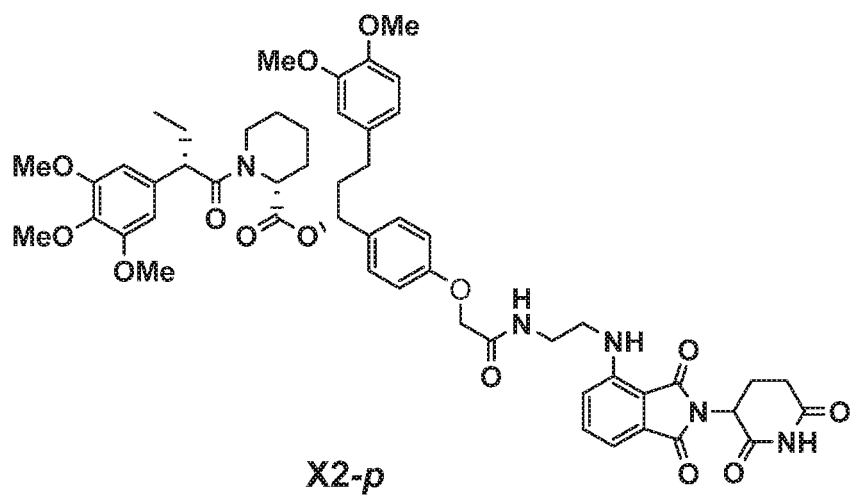
Figure 33E:
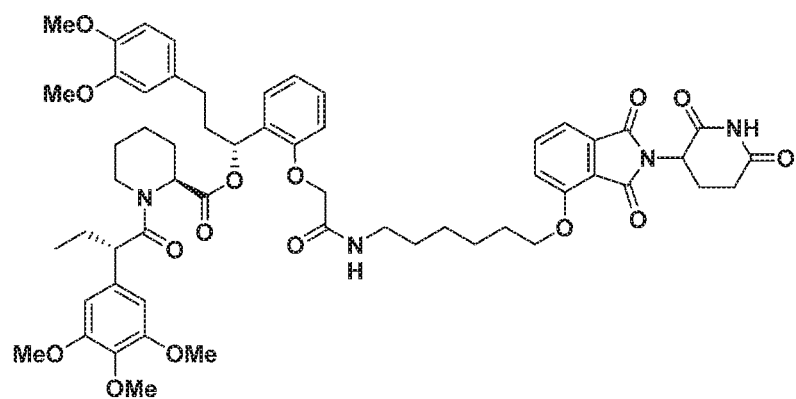
Figure 33E:
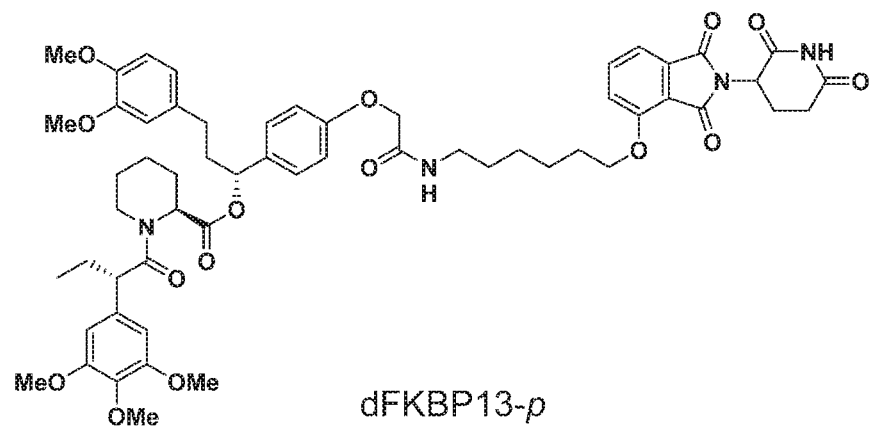
Figure 33E:
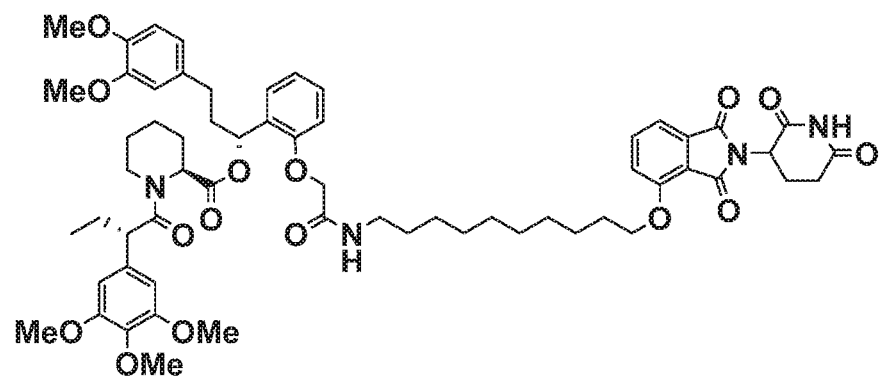
Figure 33F:
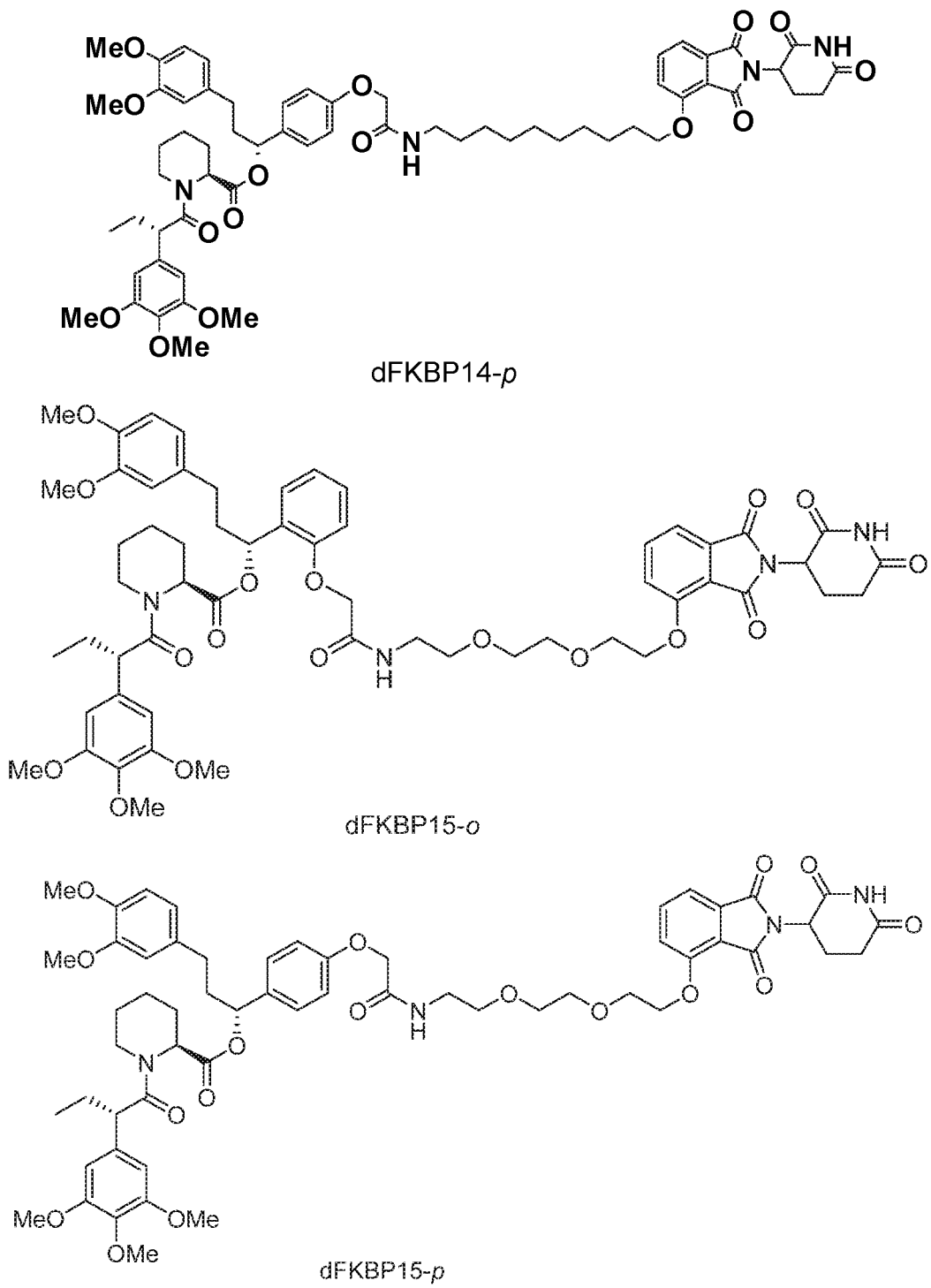
Figure 33G:
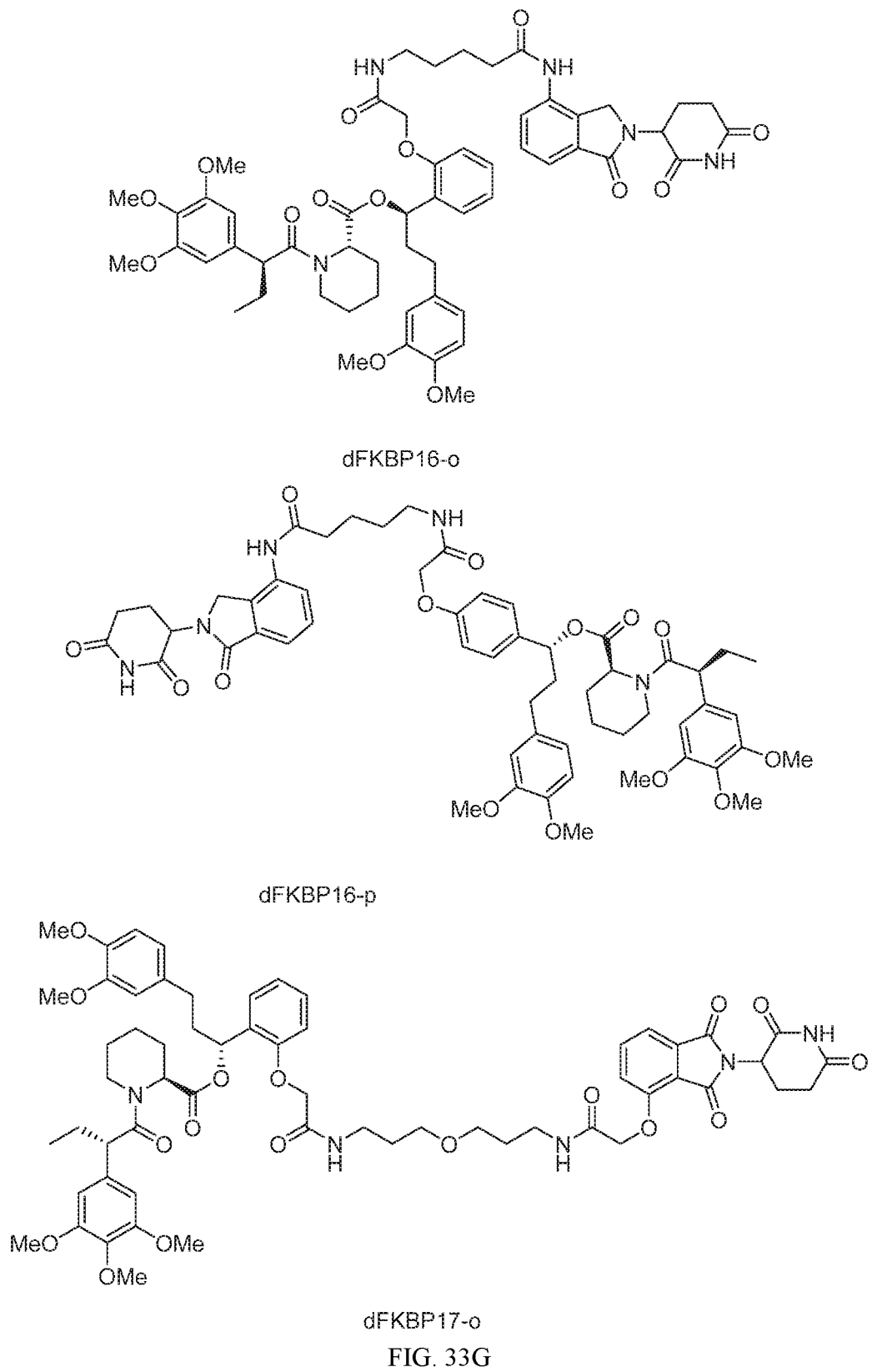
Figure 33H:
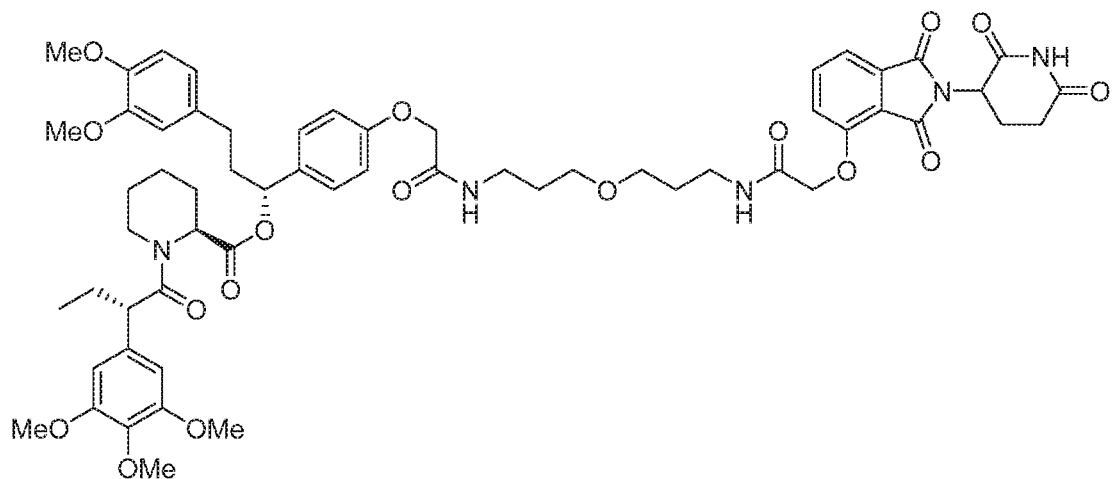
Figure 33H:
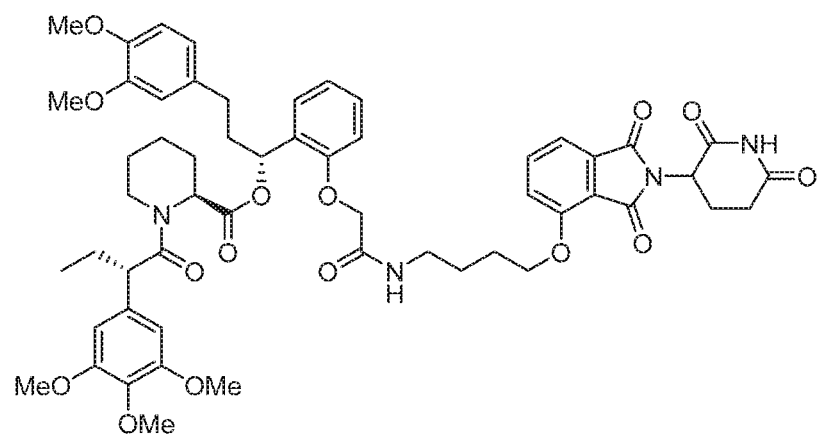
Figure 33H:
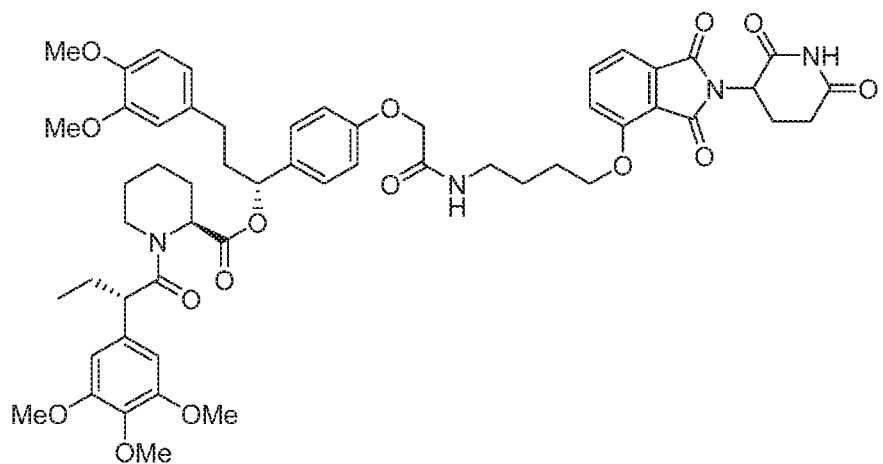
Figure 33I:
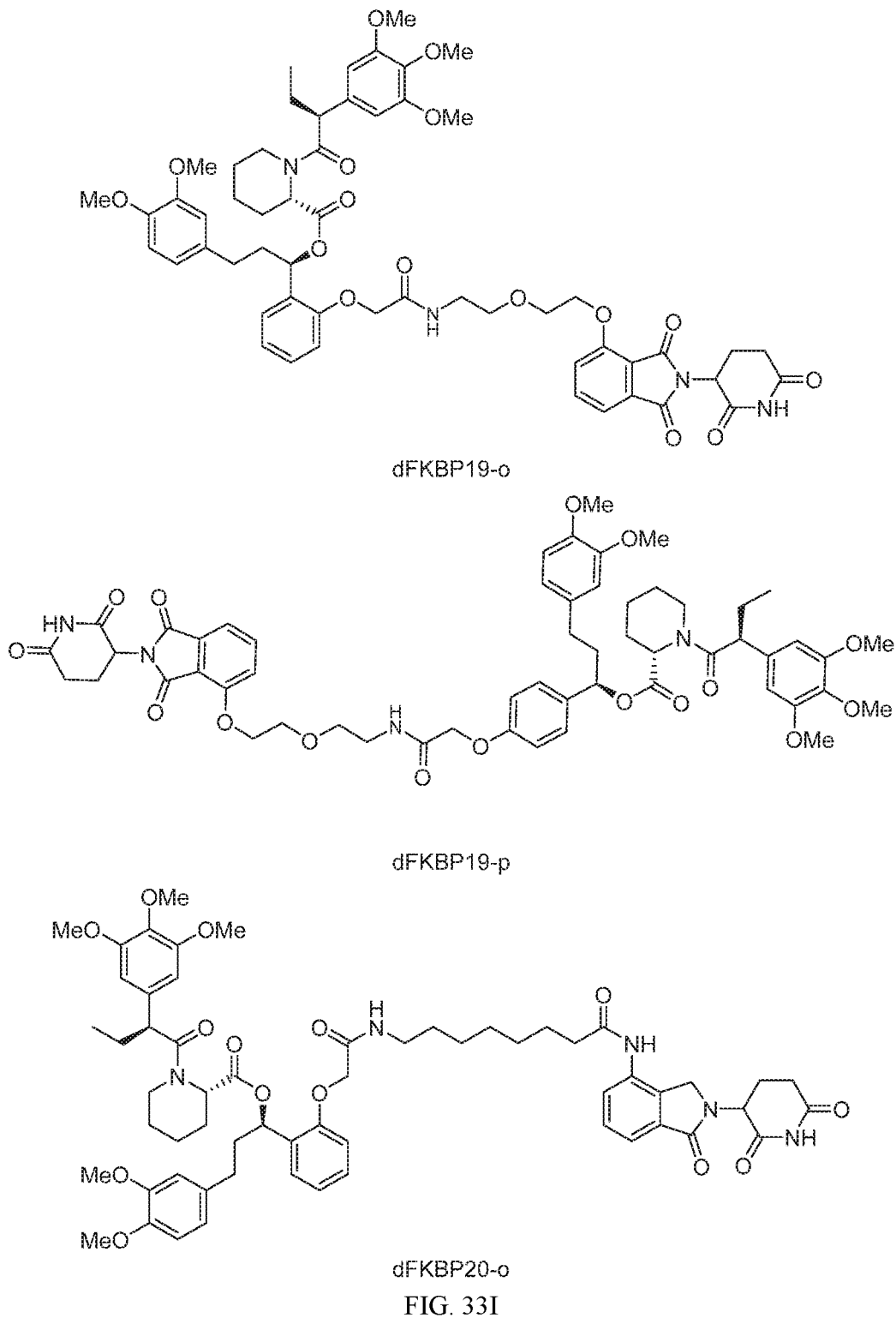
Figure 33J:
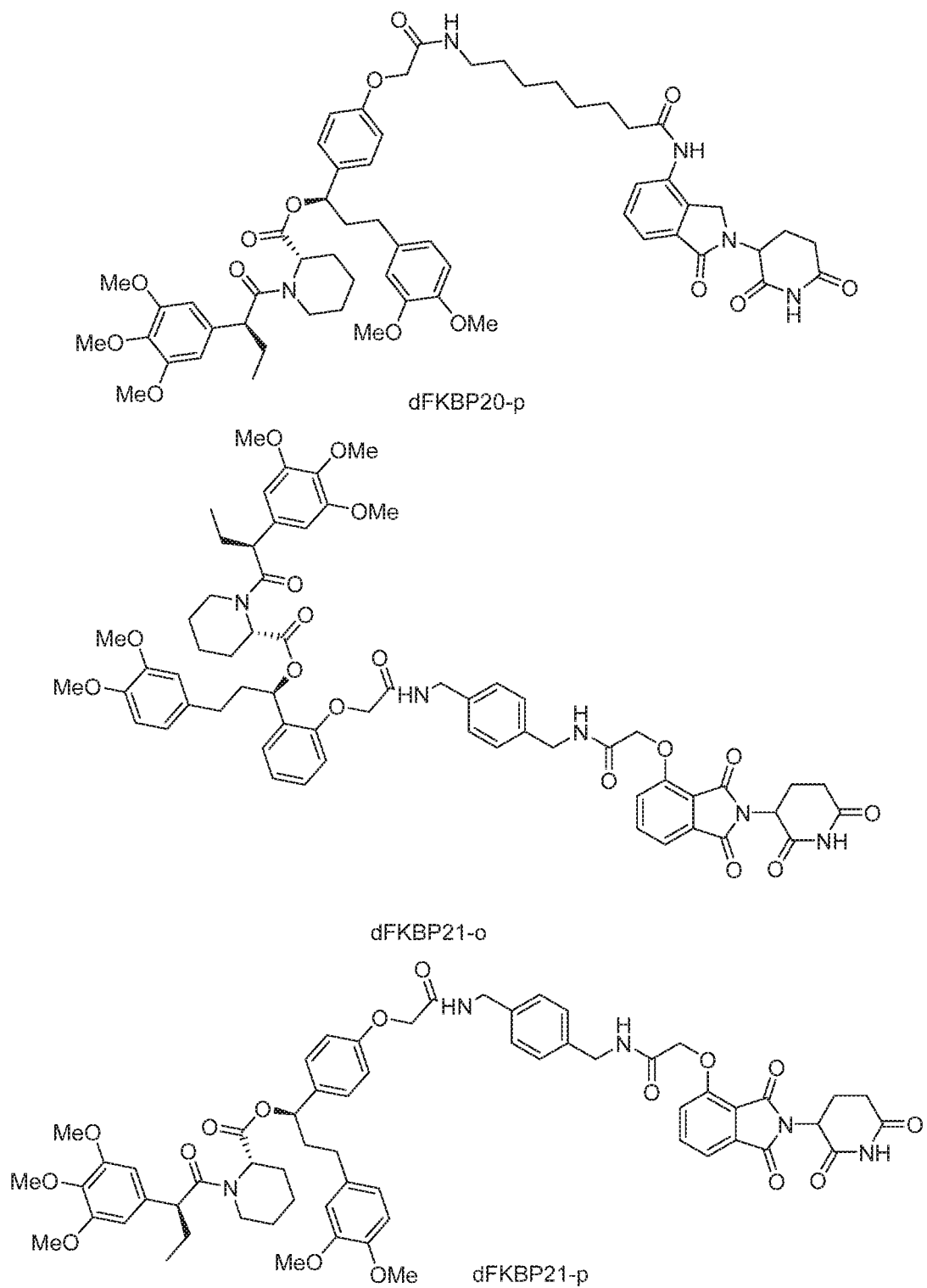
Figure 33K:
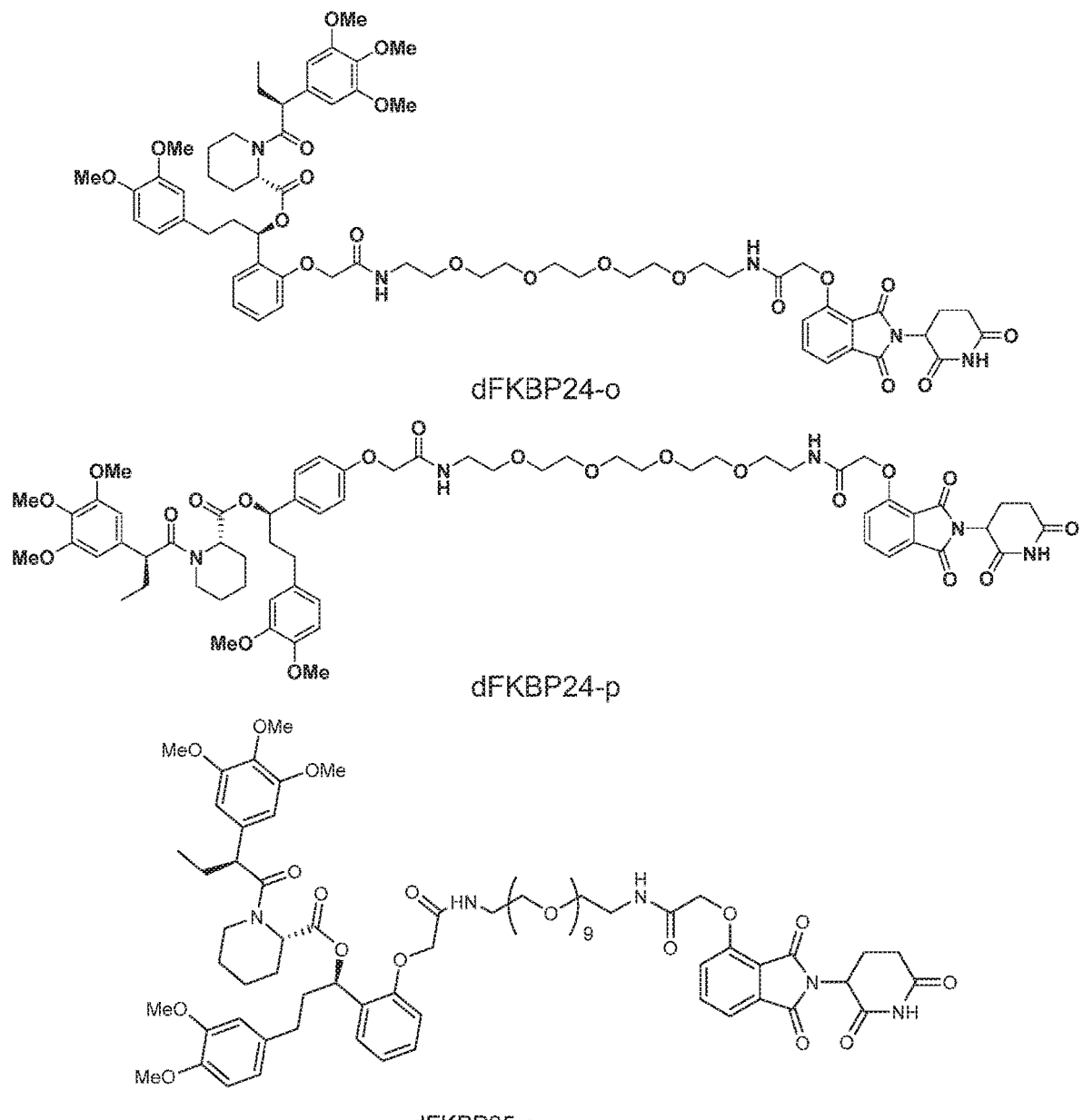
Figure 33L:
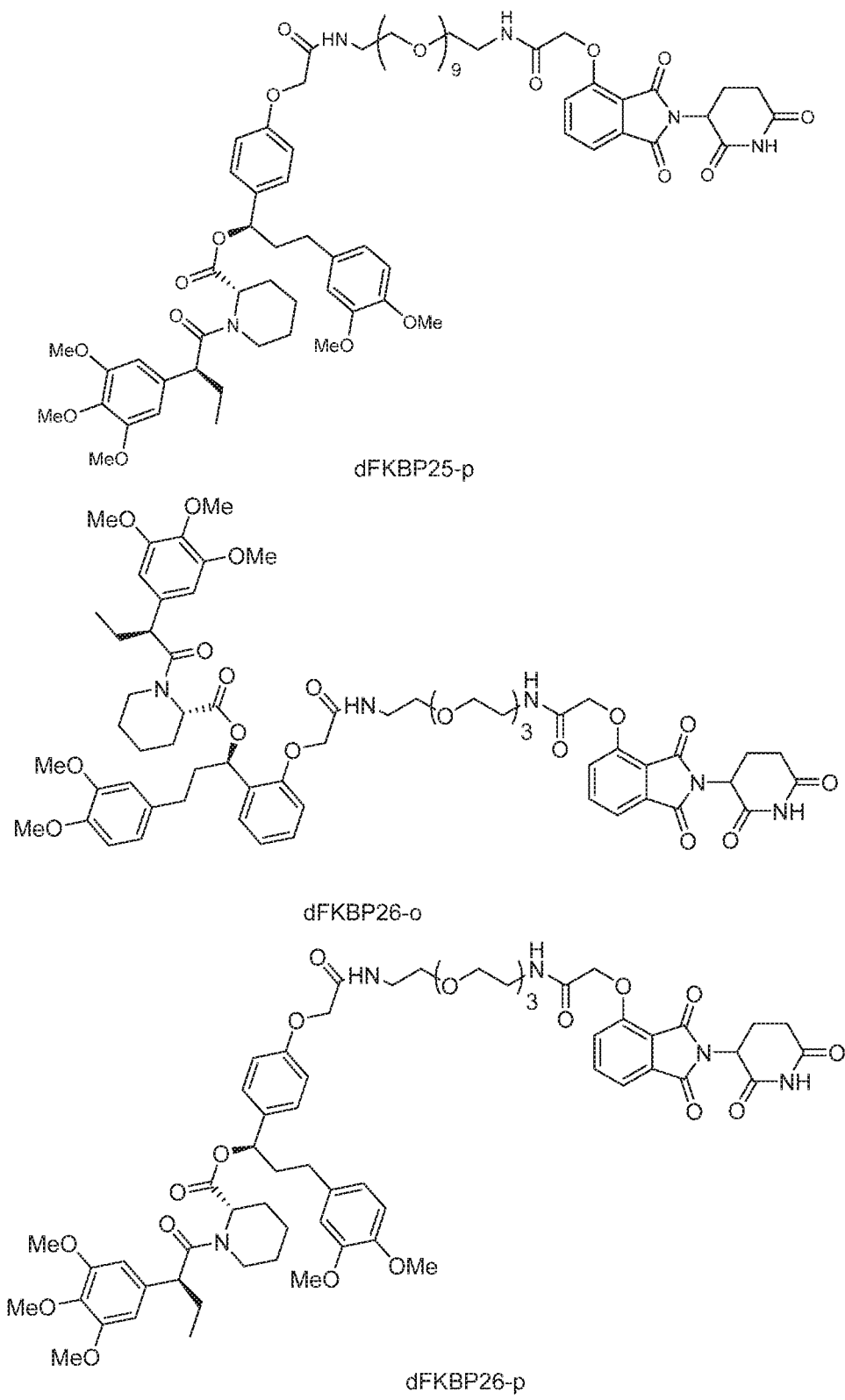
Figure 33M:
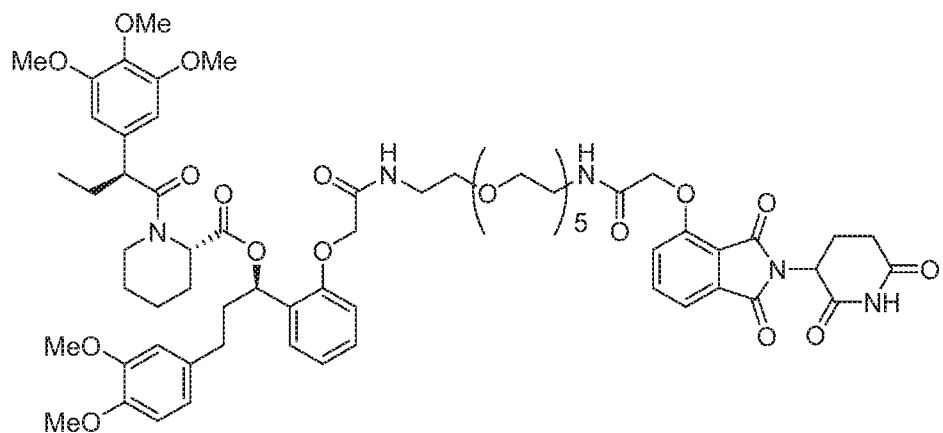
Figure 33M:
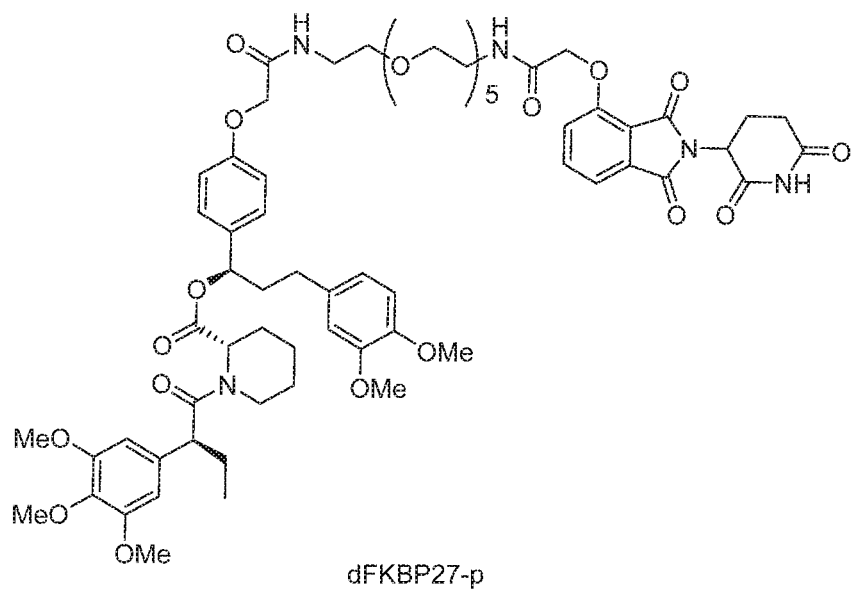
Figure 33M:
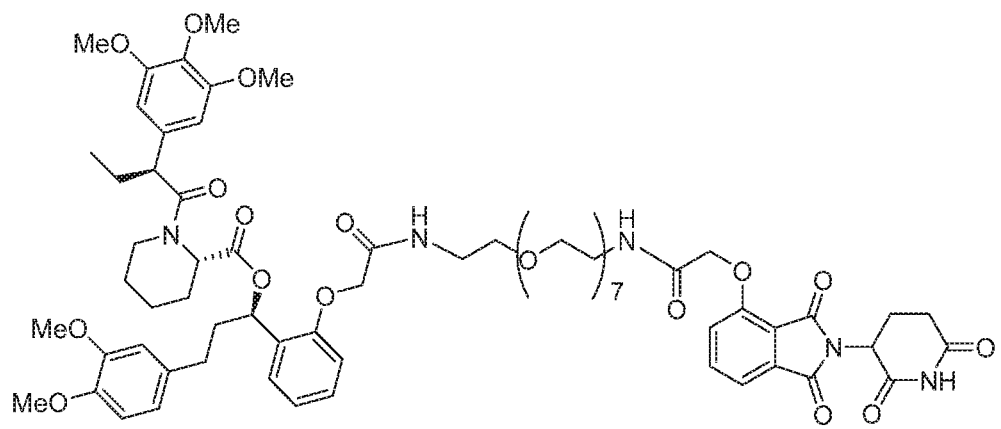
Figure 33N:
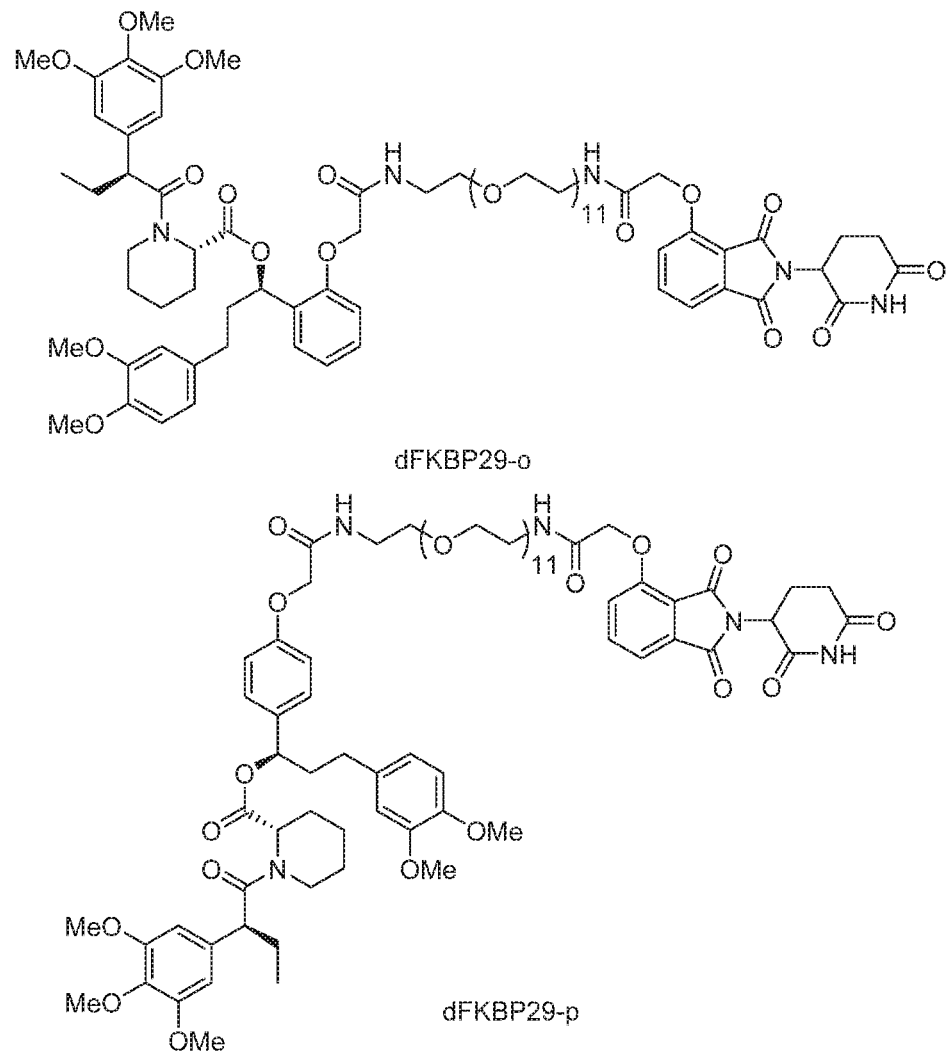
Figure 33O:
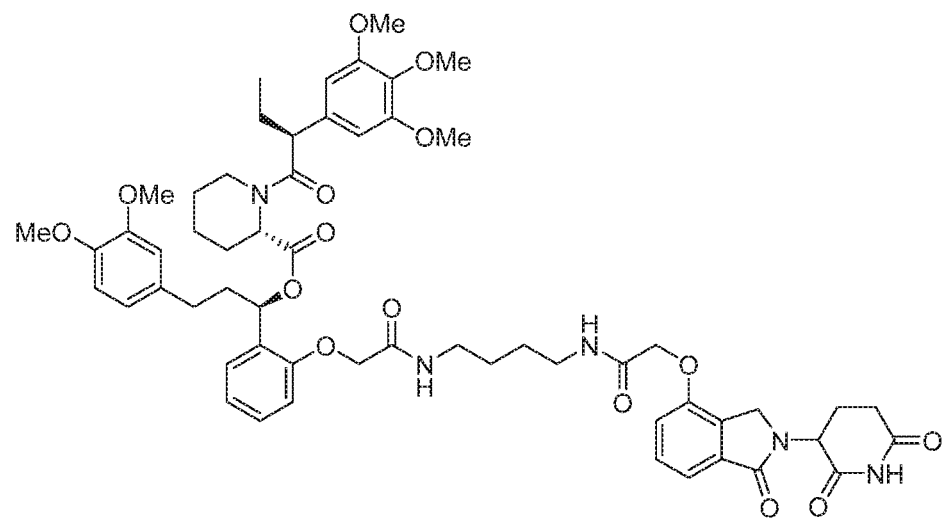
Figure 33O:
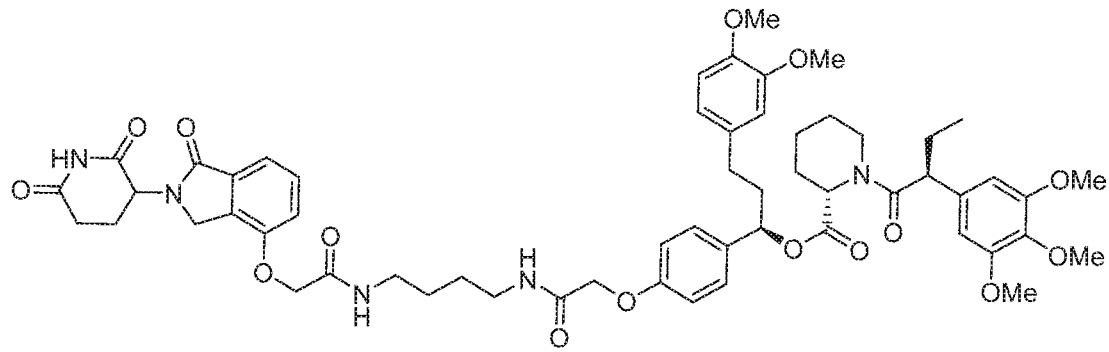
Figure 33O:
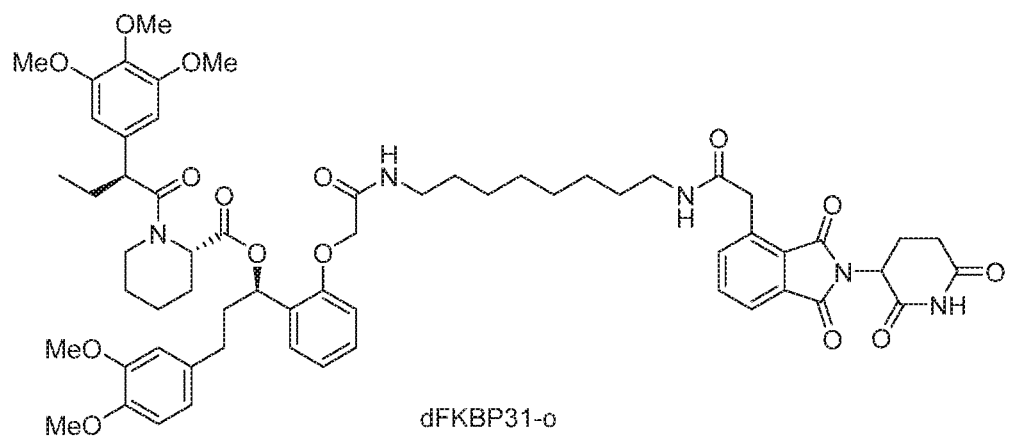
Figure 33P:
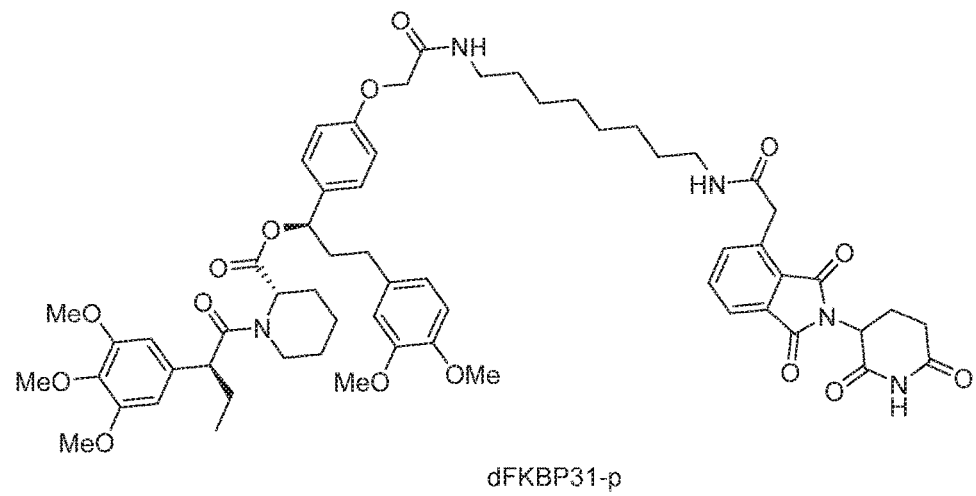
Figure 33P:
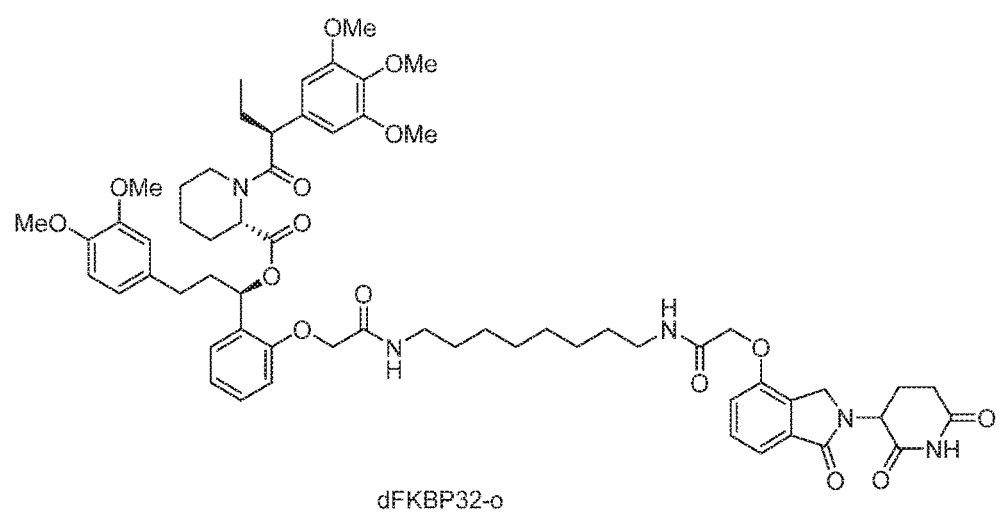
Figure 33P:
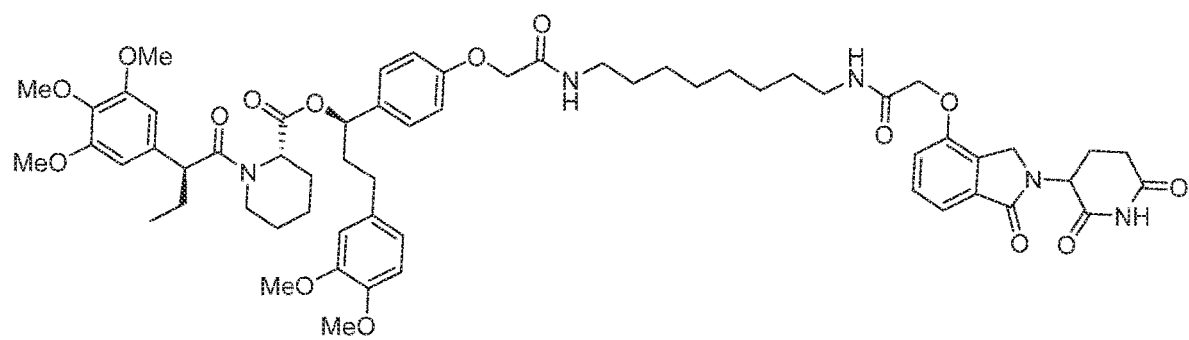
Figure 33Q:
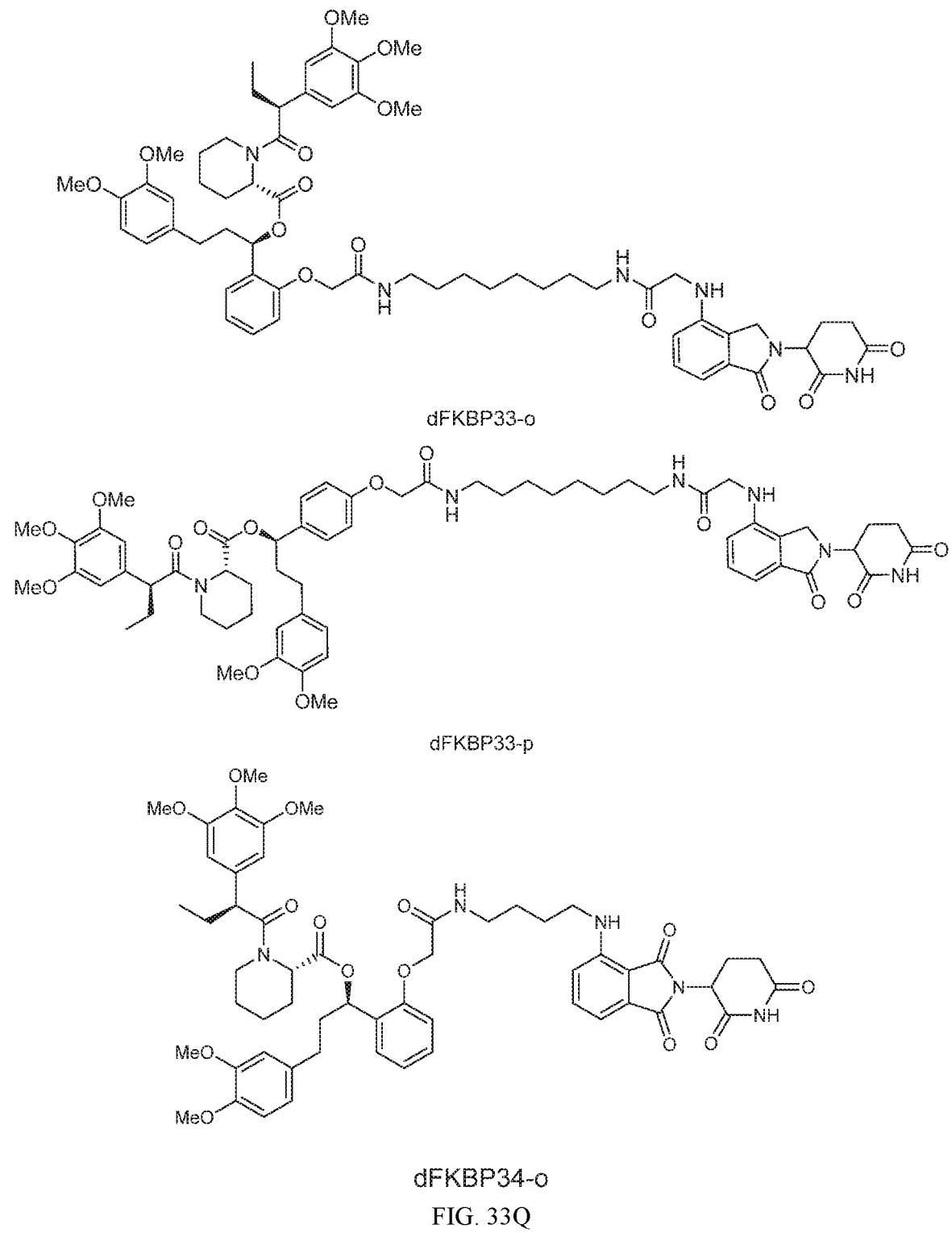
Figure 33R:
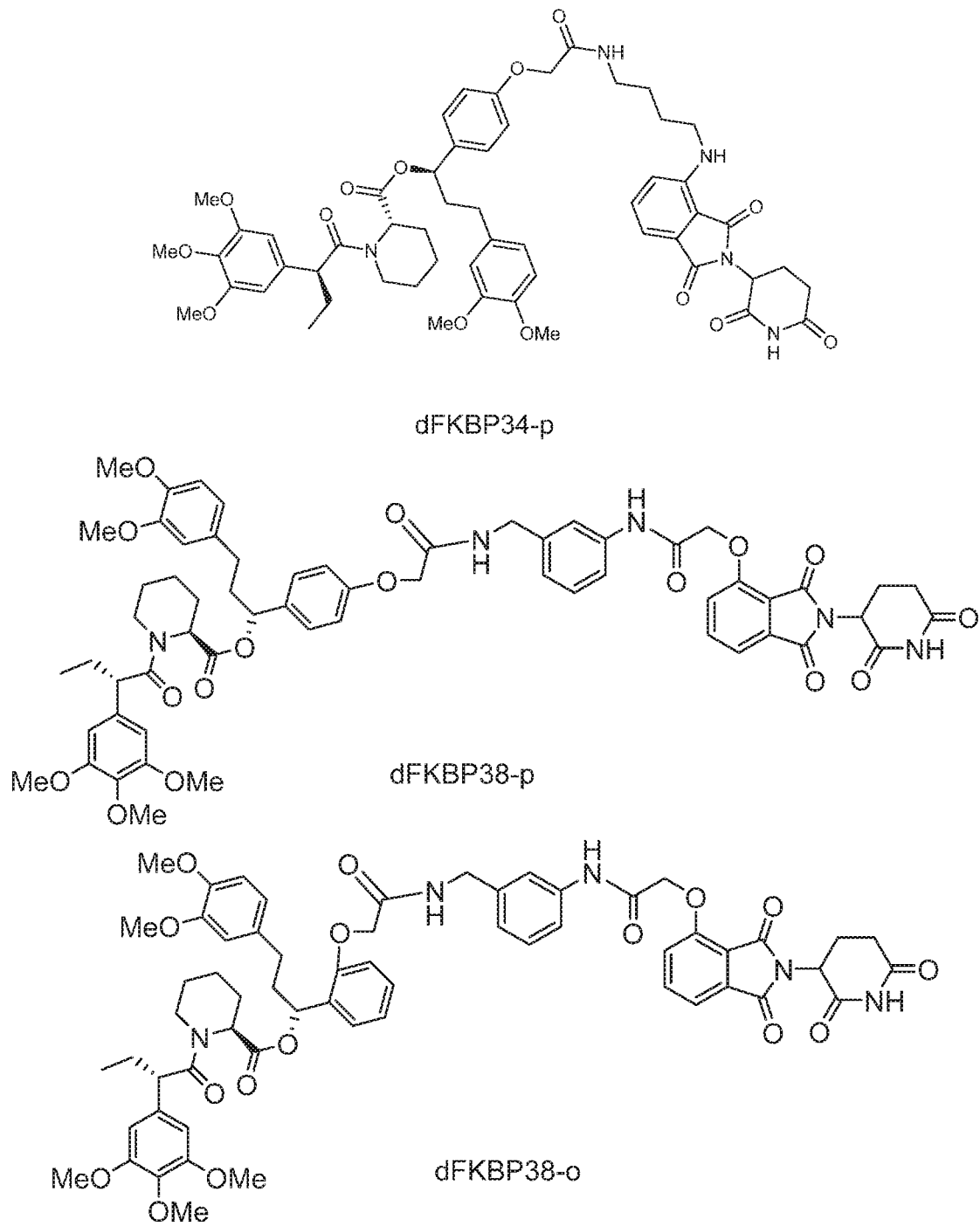
Figure 33S:
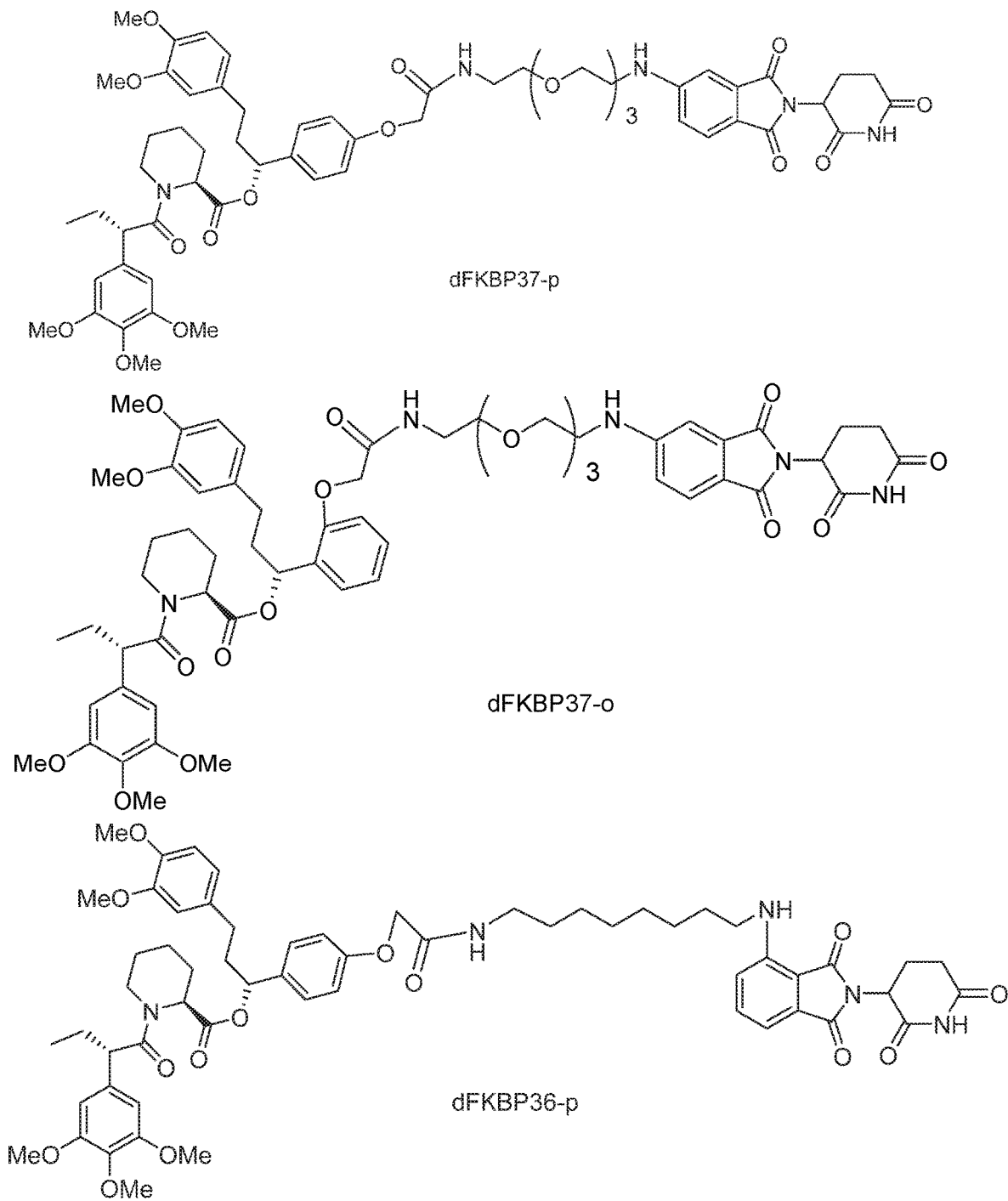
Figure 33T:
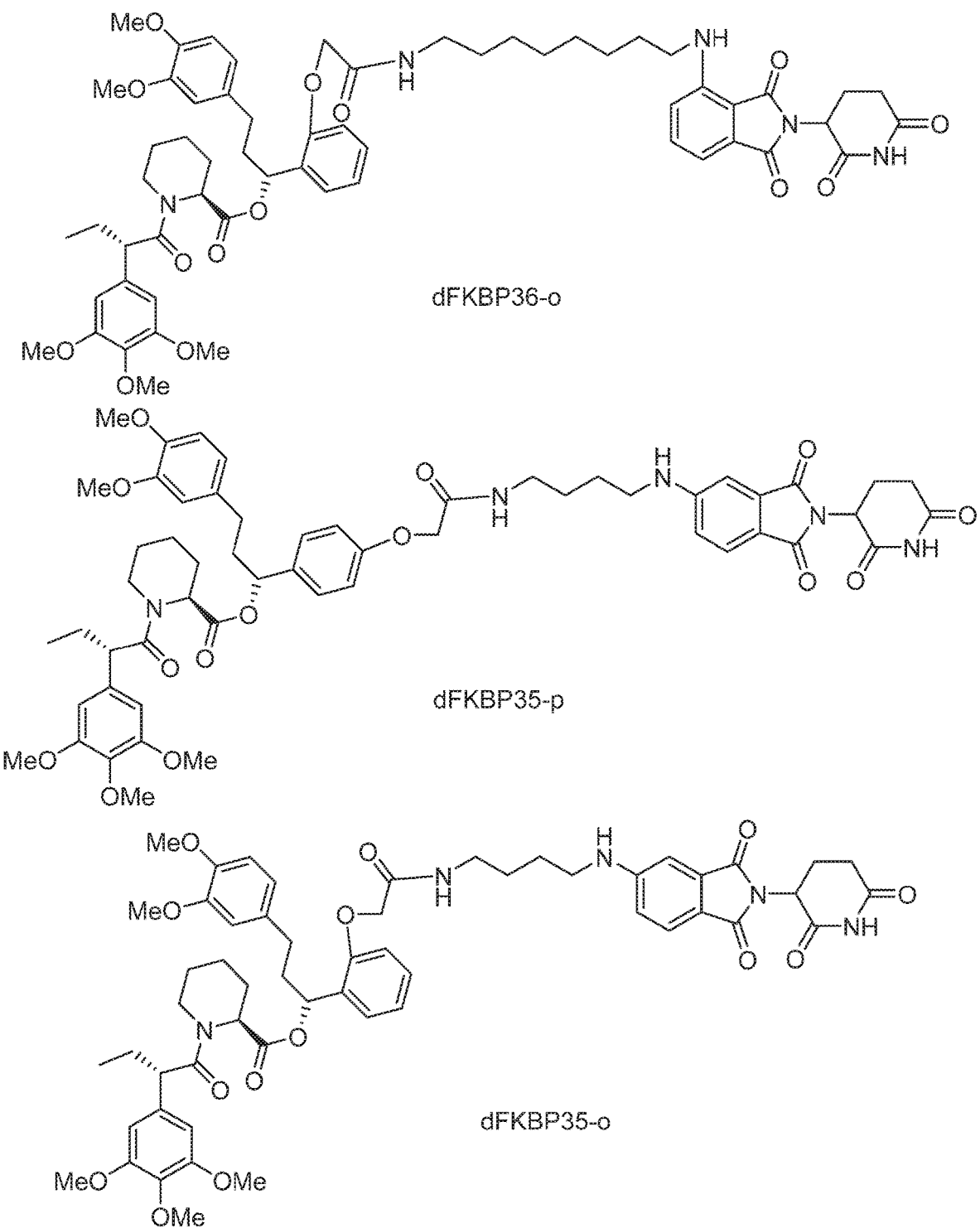
Figure 33U:
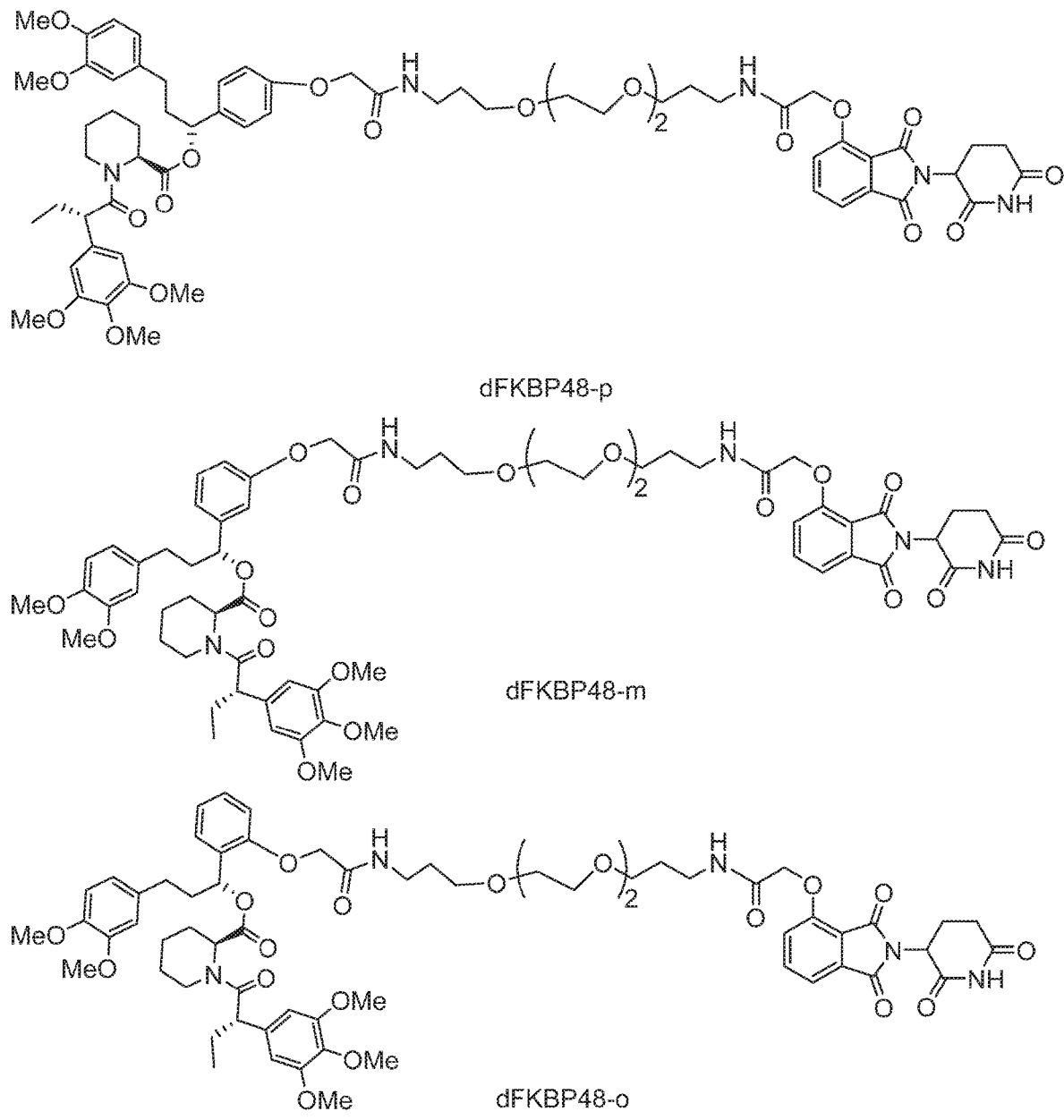
Figure 33V:
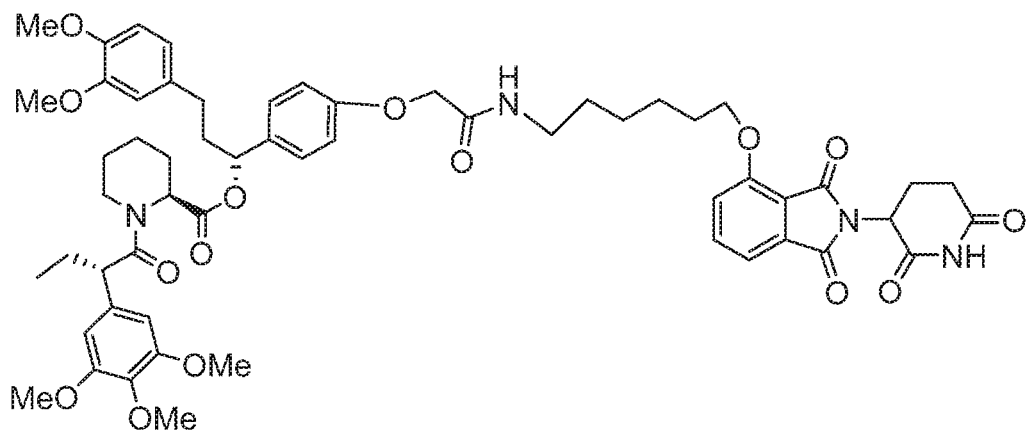
Figure 33V:
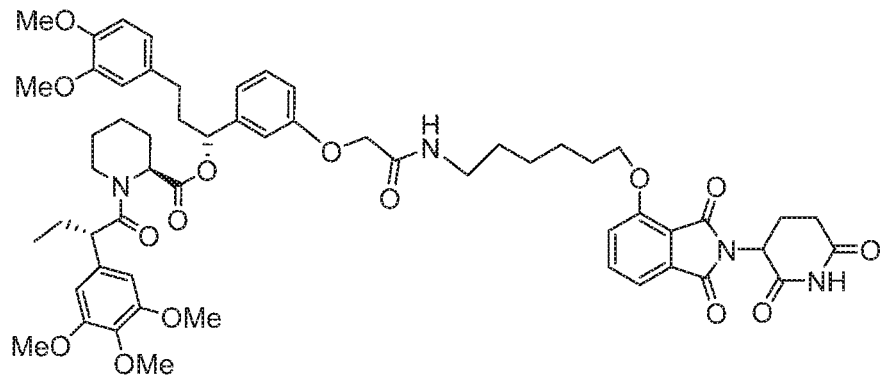
Figure 33V:
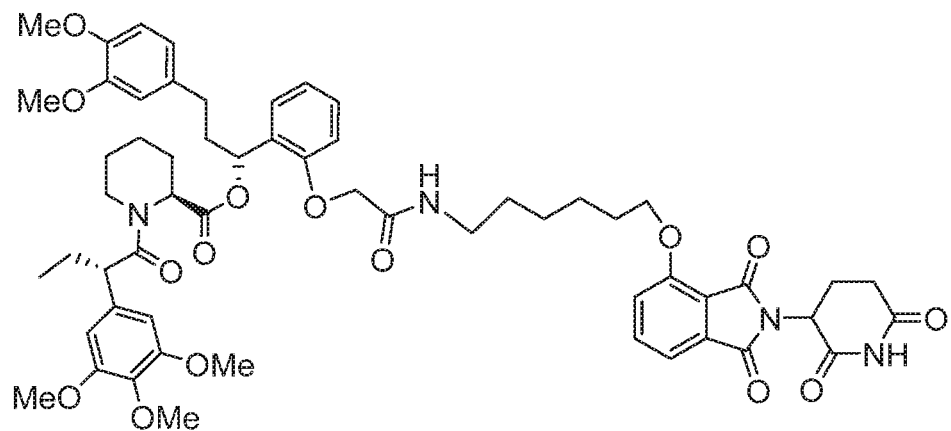
Figure 33W:
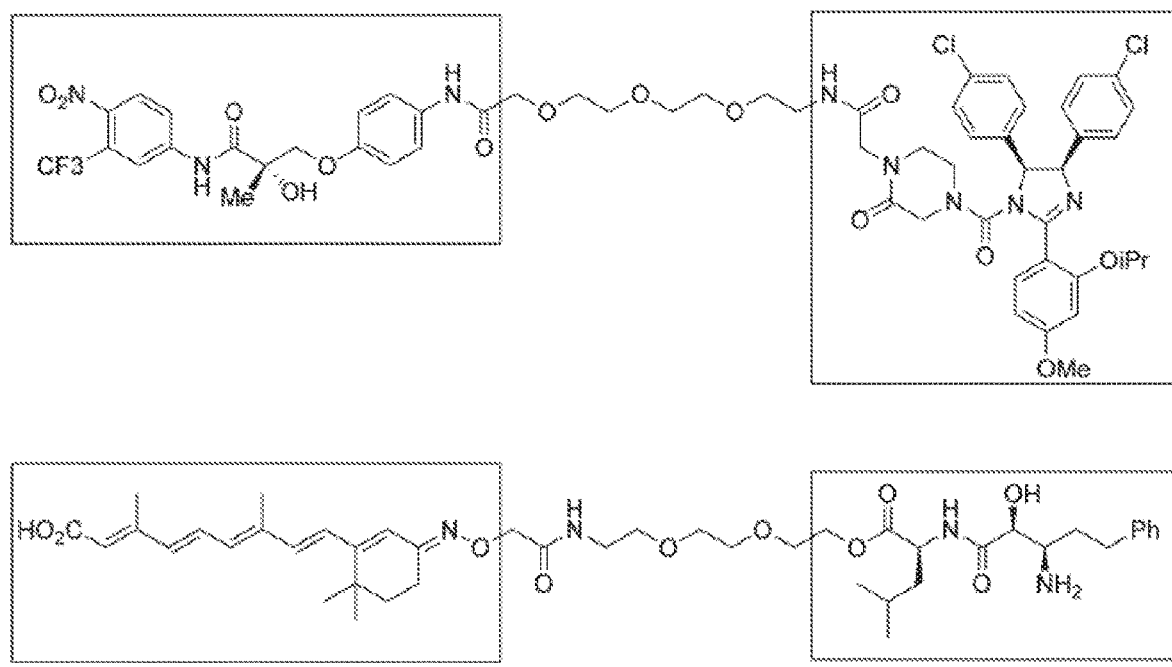

In certain embodiments, "L" can be nonlinear chains, and can be aliphatic or aromatic or heteroaromatic cyclic moieties, some examples of "L" include but not be limited to the structures of FIG. 27, wherein X and Y are independently selected from a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $SiR^{L1}R^{L2}$, $P(O)$ $R^{L1}$, $P(O)OR^{L1}$, —$NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 0-6 $R^{L1}$ and/or $R^{L2}$ groups, $C_{3-11}$heteocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 RL and/or $R^{L2}$ groups, where $R^{L1}$ or $R^{L2}$, each independently, can be linked to other A groups to form a cycloalkyl and/or heterocyclyl moiety which can be further substituted with 0-4 $R^{L5}$ groups.

dTAG Targeting Ligand

The dTAG Targeting Ligand (TL) is capable of binding to a dTAG or being bound by a dTAG target that allows tagging with ubiquitin to occur;

As contemplated herein, the genomes of the present invention include a heterobifunctional compound targeted protein (dTAG) which locates in the cytoplasm. The heterobifunctional compound targeted protein of the genome is any amino acid sequence to which a heterobifunctional compound can be bound, leading to the degradation of the protein-dTAG hybrid protein when in contact with the heterobifunctional compound. Preferably, the dTAG should not interfere with the function of the CAR. In one embodiment, the dTAG is a non-endogenous peptide, leading to heterobifunctional compound selectivity and allowing for the avoidance of off target effects upon administration of the heterobifunctional compound. In one embodiment, the dTAG is an amino acid sequence derived from an endogenous protein which has been modified so that the heterobifunctional compound binds only to the modified amino acid sequence and not the endogenously expressed protein. In one embodiment, the dTAG is an endogenously expressed protein. Any amino acid sequence domain that can be bound by a ligand for use in a heterobifunctional compound can be used as a dTAG as contemplated herewith.

In particular embodiments, the dTAGs for use in the present invention include, but are not limited to, amino acid sequences derived from endogenously expressed proteins such as FK506 binding protein-12 (FKBP12), bromodomain-containing protein 4 (BRD4), CREB binding protein (CREBBP), and transcriptional activator BRG1 (SMARCA4), or a variant thereof. As contemplated herein, "variant" means any variant such as a substitution, deletion, or addition of one or a few to plural amino acids, provided that the variant substantially retains the same function as the original sequence, which in this case is providing ligand binding for a heterobifunctional compound. In other embodiments, dTAGs for us in the present invention may include, for example, hormone receptors e.g. estrogen-receptor proteins, androgen receptor proteins, retinoid x receptor (RXR) protein, and dihydrofolate reductase (DHFR), including bacterial DHFR, bacterial dehydrogenase, and variants.

In one embodiment the dTAG is a portion of any of the proteins identified herein. For example, the dTAG can be the BD1 domain of BRD4 or the BD2 domain of BRD4. In one embodiment that Targeting Ligands identified herein to target the parent dTAG are instead used to target portion. In one embodiment, the BRD4 Targeting Ligands in Table T can be used to target the BD1 dTAG. In another embodiment, the BRD4 Targeting Ligands in Table T can be used to target the BD2 dTAG.

Some embodiments of the present application include TLs which target dTAGs including, but not limited to, those derived from Hsp90 inhibitors, kinase inhibitors, MDM2 inhibitors, compounds targeting Human BET bromodomain-containing proteins, compounds targeting cytosolic signaling protein FKBP12, HDAC inhibitors, human lysine methyltransferase inhibitors, angiogenesis inhibitors, immunosuppressive compounds, and compounds targeting the aryl hydrocarbon receptor (AHR).

In certain embodiments, the dTAG Targeting Ligand is a compound that is capable of binding to or binds to a dTAG derived from a kinase, a BET bromodomain-containing protein, a cytosolic signaling protein (e.g., FKBP12), a nuclear protein, a histone deacetylase, a lysine methyltransferase, a protein regulating angiogenesis, a protein regulating immune response, an aryl hydrocarbon receptor (AHR), an estrogen receptor, an androgen receptor, a glucocorticoid receptor, or a transcription factor (e.g., SMARCA4, SMARCA2, TRIM24).

In certain embodiments, the dTAG is derived from a kinase to which the dTAG Targeting Ligand is capable of binding or binds including, but not limited to, a tyrosine kinase (e.g., AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, IRAK4, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDGFRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES1, or ZAP70), a serine/threonine kinase (e.g., casein kinase 2, protein kinase A, protein kinase B, protein kinase C, Raf kinases, CaM kinases, AKT1, AKT2, AKT3, ALK1, ALK2, ALK3, ALK4, Aurora A, Aurora B, Aurora C, CHK1, CHK2, CLK1, CLK2, CLK3, DAPK1, DAPK2, DAPK3, DMPK, ERK1, ERK2, ERK5, GCK, GSK3, HIPK, KHS1, LKB1, LOK, MAPKAPK2, MAPKAPK, MNK1, MSSK1, MST1, MST2, MST4, NDR, NEK2, NEK3, NEK6, NEK7, NEK9, NEK11, PAK1, PAK2, PAK3, PAK4, PAK5, PAK6, PIM1, PIM2, PLK1, RIP2, RIP5, RSK1, RSK2, SGK2, SGK3, SIK1, STK33, TAO1, TAO2, TGF-beta, TLK2, TSSK1, TSSK2, ULK1, or ULK2), a cyclin dependent kinase (e.g., Cdk1-Cdk11), and a leucine-rich repeat kinase (e.g., LRRK2).

In certain embodiments, the dTAG is derived from a BET bromodomain-containing protein to which the dTAG Targeting Ligand is capable of binding or binds including, but not limited to, ASH1L, ATAD2, BAZ1A, BAZ1B, BAZ2A, BAZ2B, BRD1, BRD2, BRD3, BRD4, BRD5, BRD6, BRD7, BRD8, BRD9, BRD10, BRDT, BRPF1, BRPF3, BRWD3, CECR2, CREBBP, EP300, FALZ, GCN5L2, KIAA1240, LOC93349, MLL, PB1, PCAF, PHIP, PRKCBP1, SMARCA2, SMARCA4, SP100, SP110, SP140, TAF1, TAF1L, TIFla, TRIM28, TRIM33, TRIM66, WDR9, ZMYND11, and MLL4. In certain embodiments, a BET bromodomain-containing protein is BRD4.

In certain embodiments, the dTAG is derived from a nuclear protein to which the dTAG Targeting Ligand is capable of binding or binds including, but not limited to, BRD2, BRD3, BRD4, Antennapedia Homeodomain Protein, BRCA1, BRCA2, CCAAT-Enhanced-Binding Proteins, histones, Polycomb-group proteins, High Mobility Group Proteins, Telomere Binding Proteins, FANCA, FANCD2, FANCE, FANCF, hepatocyte nuclear factors, Mad2, NF-kappa B, Nuclear Receptor Coactivators, CREB-binding protein, p55, p107, p130, Rb proteins, p53, c-fos, c-jun, c-mdm2, c-myc, and c-rel.

In certain embodiments, the dTAG Targeting Ligand is selected from a kinase inhibitor, a BET bromodomain-containing protein inhibitor, cytosolic signaling protein FKBP12 ligand, an HDAC inhibitor, a lysine methyltransferase inhibitor, an angiogenesis inhibitor, an immunosuppressive compound, and an aryl hydrocarbon receptor (AHR) inhibitor.

In certain embodiments, the dTAG Targeting Ligand is a SERM (selective estrogen receptor modulator) or SERD (selective estrogen receptor degrader). Non-limiting examples of SERMs and SERDs are provided in WO 2014/191726 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703,810, as well as US 2015/0005286, WO 2014/205136, and WO 2014/205138 assigned to Seragon Pharmaceuticals.

Additional dTAG Targeting Ligands include, for example, any moiety which binds to an endogenous protein (binds to a target dTAG). Illustrative dTAG Targeting Ligands includes the small molecule dTAG Targeting Ligand: Hsp90 inhibitors, kinase inhibitors, HDM2 and MDM2 inhibitors, compounds targeting Human BET bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. Such small molecule target dTAG binding moieties also include pharmaceutically acceptable salts, enantiomers, solvates and polymorphs of these compositions, as well as other small molecules that may target a dTAG of interest.

In some embodiments the dTAG Targeting Ligand is an Ubc9 SUMO E2 ligase 5F6D targeting ligand including but not limited to those described in "Insights Into the Allosteric Inhibition of the SUMO E2 Enzyme Ubc9." by Hewitt, W. M., et. al. (2016) Angew. Chem. Int. Ed. Engl. 55: 5703-5707

In another embodiment the dTAG Targeting Ligand is a Tank1 targeting ligand including but not limited to those described in "Structure of human tankyrase 1 in complex with small-molecule inhibitors PJ34 and XAV939." Kirby, C. A., Cheung, A., Fazal, A., Shultz, M. D., Stams, T, (2012) Acta Crystallogr., Sect. F 68: 115-118; and "Structure-Efficiency Relationship of [1,2,4]Triazol-3-ylamines as Novel Nicotinamide Isosteres that Inhibit Tankyrases." Shultz, M. D., et al. (2013) J. Med. Chem. 56: 7049-7059.

In another embodiment the dTAG Targeting Ligand is a SH2 domain of pp60 Src targeting ligand including but not limited to those described in "Requirements for Specific Binding of Low Affinity Inhibitor Fragments to the SH2 Domain of pp60Src Are Identical to Those for High Affinity Binding of Full Length Inhibitors" Gudrun Lange, et al., J. Med. Chem. 2003, 46, 5184-5195.

In another embodiment the dTAG Targeting Ligand is a Sec7 domain targeting ligand including but not limited to those described in "The Lysosomal Protein Saposin B Binds Chloroquine." Huta, B. P., et al., (2016) Chemmedchem 11: 277.

In another embodiment the dTAG Targeting Ligand is a Saposin-B targeting ligand including but not limited to those described in "The structure of cytomegalovirus immune modulator UL141 highlights structural Ig-fold versatility for receptor binding" I. Nemcovicova and D. M. Zajonc Acta Cryst. (2014). D70, 851-862.

In another embodiment the dTAG Targeting Ligand is a Protein S100-A7 2OWS targeting ligand including but not limited to those described in "2WOS STRUCTURE OF HUMAN S100A7 IN COMPLEX WITH 2,6 ANS" DOI: 10.2210/pdb2wos/pdb; and "Identification and Characterization of Binding Sites on S100A7, a Participant in Cancer and Inflammation Pathways." Leon, R., Murray, et al., (2009) Biochemistry 48: 10591-10600.

In another embodiment the dTAG Targeting Ligand is a Phospholipase A2 targeting ligand including but not limited to those described in "Structure-based design of the first potent and selective inhibitor of human non-pancreatic secretory phospholipase A2" Schevitz, R. W., et al., Nat. Struct. Biol. 1995, 2, 458-465.

In another embodiment the dTAG Targeting Ligand is a PHIP targeting ligand including but not limited to those described in "A Poised Fragment Library Enables Rapid Synthetic Expansion Yielding the First Reported Inhibitors of PHIP(2), an Atypical Bromodomain" Krojer, T.; et al. Chem. Sci. 2016, 7, 2322-2330.

In another embodiment the dTAG Targeting Ligand is a PDZ targeting ligand including but not limited to those described in "Discovery of Low-Molecular-Weight Ligands for the AF6 PDZ Domain" Mangesh Joshi, et al. Angew. Chem. Int. Ed. 2006, 45, 3790-3795.

In another embodiment the dTAG Targeting Ligand is a PARP15 targeting ligand including but not limited to those described in "Structural Basis for Lack of ADP-ribosyltransferase Activity in Poly(ADP-ribose) Polymerase-13/Zinc Finger Antiviral Protein." Karlberg, T., et al., (2015) J. Biol. Chem. 290: 7336-7344.

In another embodiment the dTAG Targeting Ligand is a PARP14 targeting ligand including but not limited to those described in "Discovery of Ligands for ADP-Ribosyltransferases via Docking-Based Virtual Screening." Andersson, C. D., et al., (2012) J. Med. Chem. 55: 7706-7718.; "Family-wide chemical profiling and structural analysis of PARP and tankyrase inhibitors." Wahlberg, E., et al. (2012) Nat. Biotechnol. 30: 283-288.; "Discovery of Ligands for ADP-Ribosyltransferases via Docking-Based Virtual Screening." Andersson, C. D., et al. (2012) J. Med. Chem. 55: 7706-7718.

In another embodiment the dTAG Targeting Ligand is a MTH1 targeting ligand including but not limited to those described in "MTH1 inhibition eradicates cancer by preventing sanitation of the dNTP pool" Helge Gad, et. al. Nature, 2014, 508, 215-221.

In another embodiment the dTAG Targeting Ligand is a mPGES-1 targeting ligand including but not limited to those described in "Crystal Structures of mPGES-1 Inhibitor Complexes Form a Basis for the Rational Design of Potent Analgesic and Anti-Inflammatory Therapeutics." Luz, J. G., et al., (2015) J. Med. Chem. 58: 4727-4737.

In another embodiment the dTAG Targeting Ligand is a FLAP-5-lipoxygenase-activating protein targeting ligand including but not limited to those described in "Crystal structure of inhibitor-bound human 5-lipoxygenase-activating protein." Ferguson, A. D., McKeever, B. M., Xu, S., Wisniewski, D., Miller, D. K., Yamin, T. T., Spencer, R. H., Chu, L., Ujjainwalla, F., Cunningham, B. R., Evans, J. F., Becker, J. W. (2007) Science 317: 510-512.

In another embodiment the dTAG Targeting Ligand is a FA Binding Protein targeting ligand including but not limited to those described in "A Real-World Perspective on Molecular Design." Kuhn, B.; et al. J. Med. Chem. 2016, 59, 4087-4102.

In another embodiment the dTAG Targeting Ligand is a BCL2 targeting ligand including but not limited to those described in "ABT-199, a potent and selective BCL-2 inhibitor, achieves antitumor activity while sparing platelets." Souers, A. J., et al. (2013) NAT. MED. (N.Y.) 19: 202-208.

In another embodiment the dTAG Targeting Ligand is an EGFR targeting ligand. In one embodiment the dTAG Targeting Ligand is selected from erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer). The linker can be placed on these Targeting Ligands in any location that does not interfere with the Ligands binding to EGFR. Non-limiting examples of Linker binding locations are provided in Table T below. In one embodiment the EGFR targeting ligand binds the L858R mutant of EGFR. In another embodiment the EGFR targeting ligand binds the T790M mutant of EGFR. In another embodiment the EGFR targeting ligand binds the C797G or C797S mutant of EGFR. In one embodiment the EGFR targeting ligand is selected from erlotinib, gefitinib, afatinib, neratinib, and dacomitinib and binds the L858R mutant of EGFR. In another embodiment the EGFR targeting ligand is selected from osimertinib, rociletinib, olmutinib, naquotinib, nazartinib, PF-06747775, Icotinib, Neratinib, Avitinib, Tarloxotinib, PF-0645998, Tesevatinib, Transtinib, WZ-3146, WZ8040, and CNX-2006 and binds the T790M mutant of EGFR. In another embodiment the EGFR targeting ligand is EA1045 and binds the C797G or C797S mutant of EGFR.

Any protein which can bind to a dTAG Targeting Ligand group and acted on or degraded by a ubiquitin ligase is a target protein according to the present invention. In general, an endogenous target proteins for use as dTAGs may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity.

More specifically, a number of drug targets for human therapeutics represent dTAG targets to which protein target or dTAG Targeting Ligand may be bound and incorporated into compounds according to the present invention. These include proteins which may be used to restore function in numerous polygenic diseases, including for example B7.1 and B7, TINFR1m, TNFR2, NADPH oxidase, BclIBax and other partners in the apoptosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets useful as dTAGs include, for example, ecdysone 20-monooxygenase, ion channel of the GABA gated chloride channel, acetylcholinesterase, voltage-sensitive sodium channel protein, calcium release channel, and chloride channels. Still further target proteins for use as dTAGs include Acetyl-CoA carboxylase, adenylosuccinate synthetase, protoporphyrinogen oxidase, and enolpyruvylshikimate-phosphate synthase.

In one embodiment the dTAG and dTAG Targeting Ligand pair are chosen by screening a library of ligands. Such a screening is exemplified in "Kinase Inhibitor Profiling Reveals Unexpected Opportunities to Inhibit Disease-Associated Mutant Kinases" by Duong-Ly et al.; Cell Reports 14, 772-781 Feb. 2, 2016.

Haloalkane dehalogenase enzymes are another target of specific compounds according to the present invention which may be used as dTAGs. Compounds according to the present invention which contain chloroalkane peptide binding moieties (C1-C12 often about C2-C10 alkyl halo groups) may be used to inhibit and/or degrade haloalkane dehalogenase enzymes which are used in fusion proteins or related diagnostic proteins as described in PCT/US2012/063401 filed Dec. 6, 2011 and published as WO 2012/078559 on Jun. 14, 2012, the contents of which is incorporated by reference herein.

Non-limiting examples of dTAG Targeting Ligands are shown below in Table T and represent dTAG Targeting Ligands capable of targeting proteins or amino acid sequence useful as dTAGs.

TABLE T
A. BRD dTAG Targeting Ligands:
BRD dTAG Targeting Ligands as used herein include, but are not limited to:
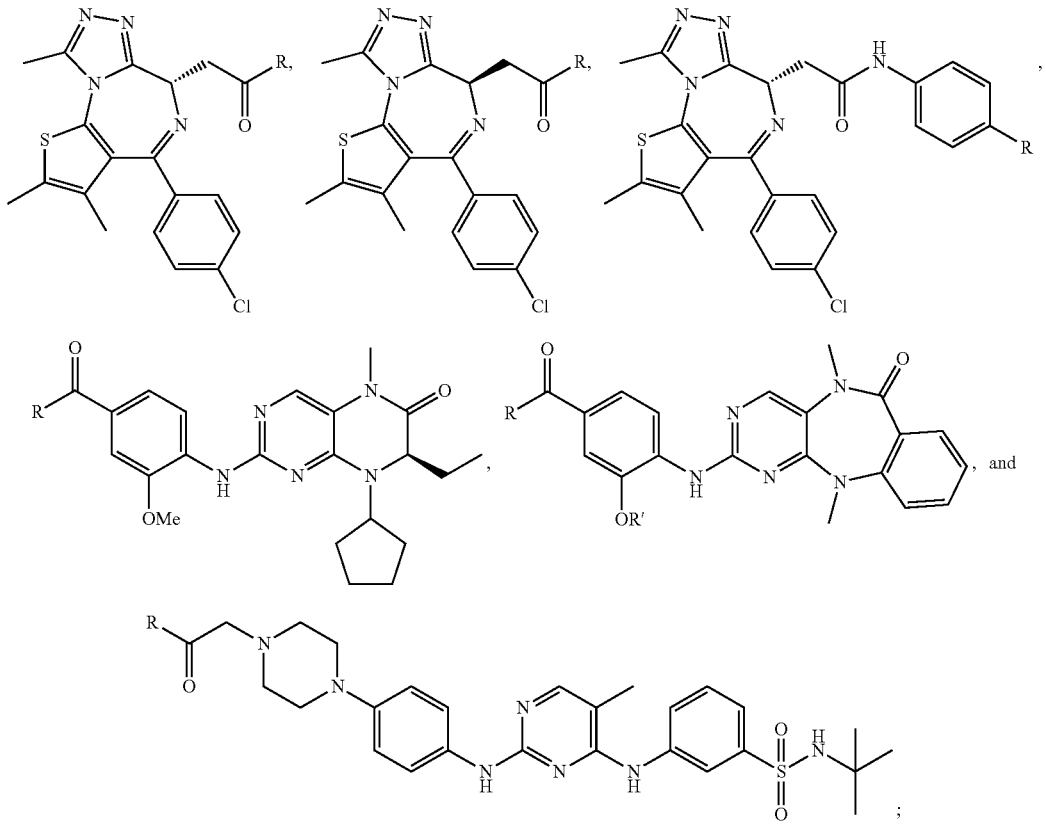
wherein:
R is the point at which the Linker is attached; and
R': is methyl or ethyl.
B. CREBBP dTAG Targeting Ligands:
CREBBP dTAG Targeting Ligands as used herein include, but are not limited to:
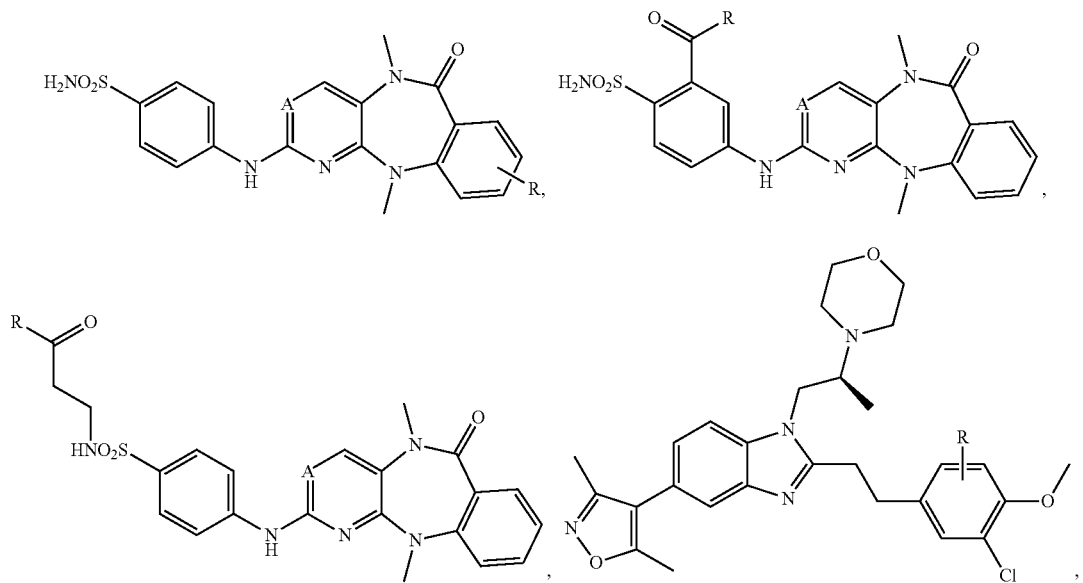

TABLE T-continued
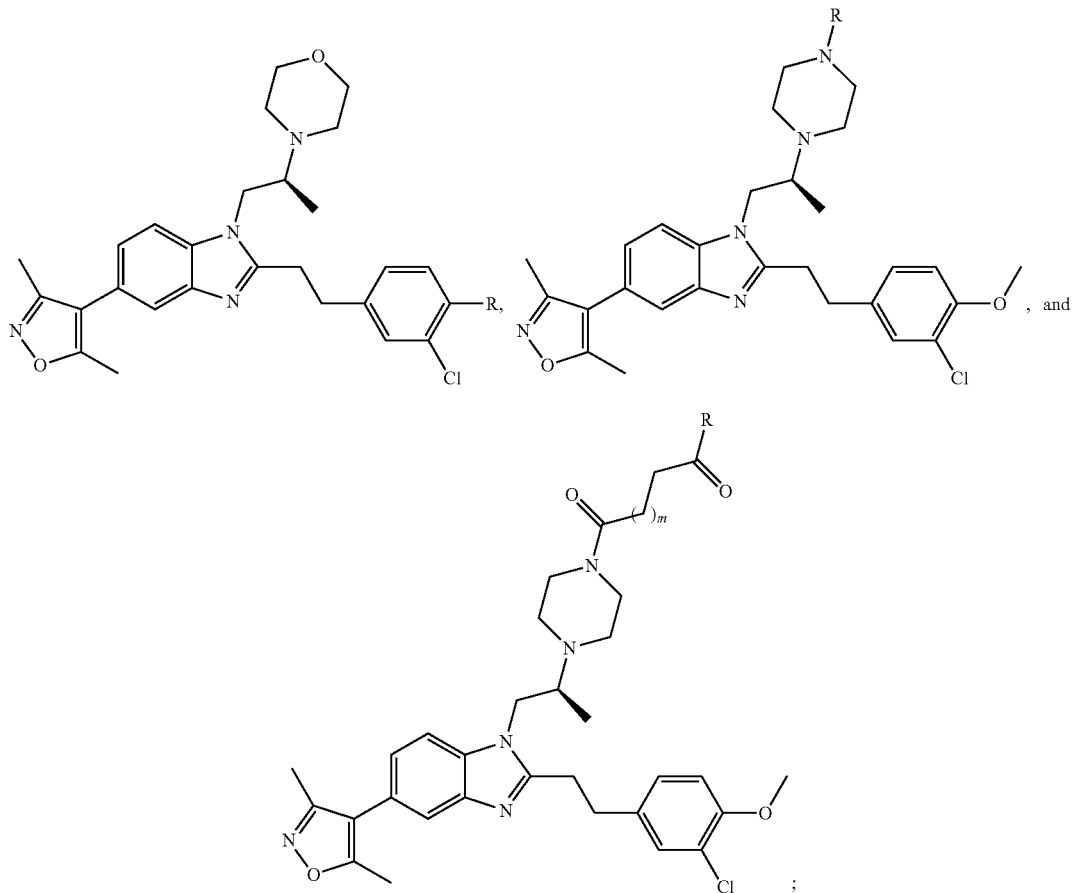
wherein:
R is the point at which the Linker is attached;
A is N or CH; and
m is 0, 1, 2, 3, 4, 5, 6, 7, or 8.
C. SMARCA4, PB1, and/or SMARCA2 dTAG Targeting Ligands:
SMARCA4, PB1, and/or SMARCA2 dTAG Targeting Ligands as used herein include, but are not limited to:
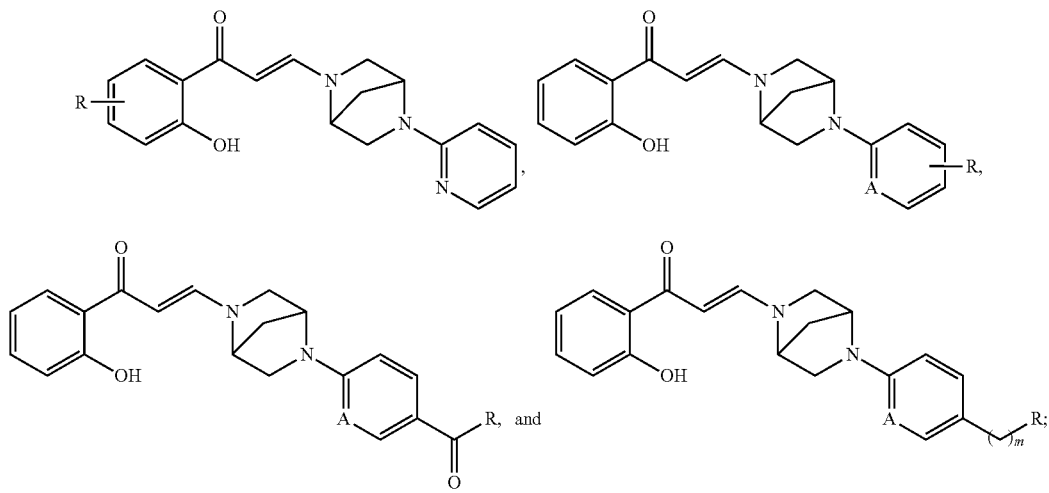
wherein:
R is the point at which the Linker is attached;
A is N or CH; and
m is 0, 1, 2, 3, 4, 5, 6, 7, or 8.

TABLE T-continued
D. TRIM24 and/or BRPF1 dTAG Targeting Ligands:
TRIM24 and/or BRPF1 dTAG Targeting Ligands as used herein include, but are not limited to:
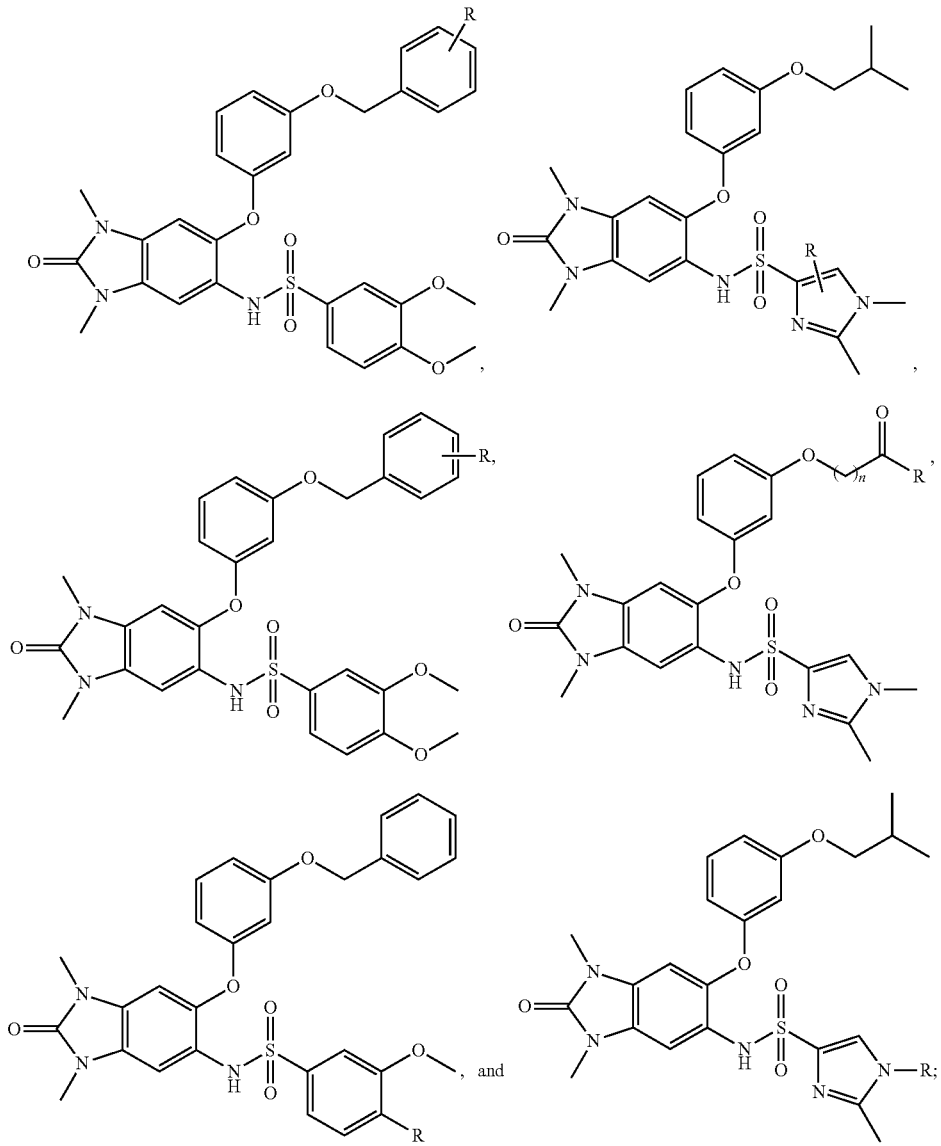
wherein:
R is the point at which the Linker is attached; and
m is 0, 1, 2, 3, 4, 5, 6, 7, or 8.
E. Glucocorticoid Receptor dTAG Targeting Ligand:
Glucocorticoid dTAG Targeting Ligands as used herein include, but are not limited to:
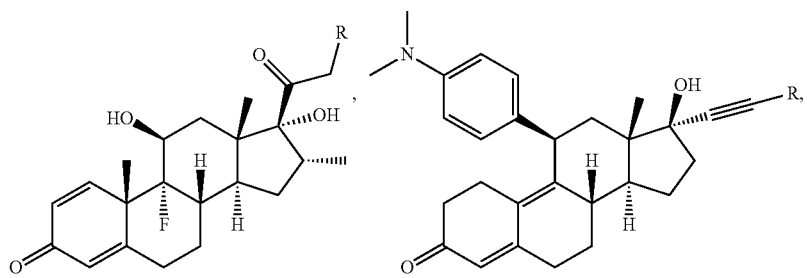

TABLE T-continued
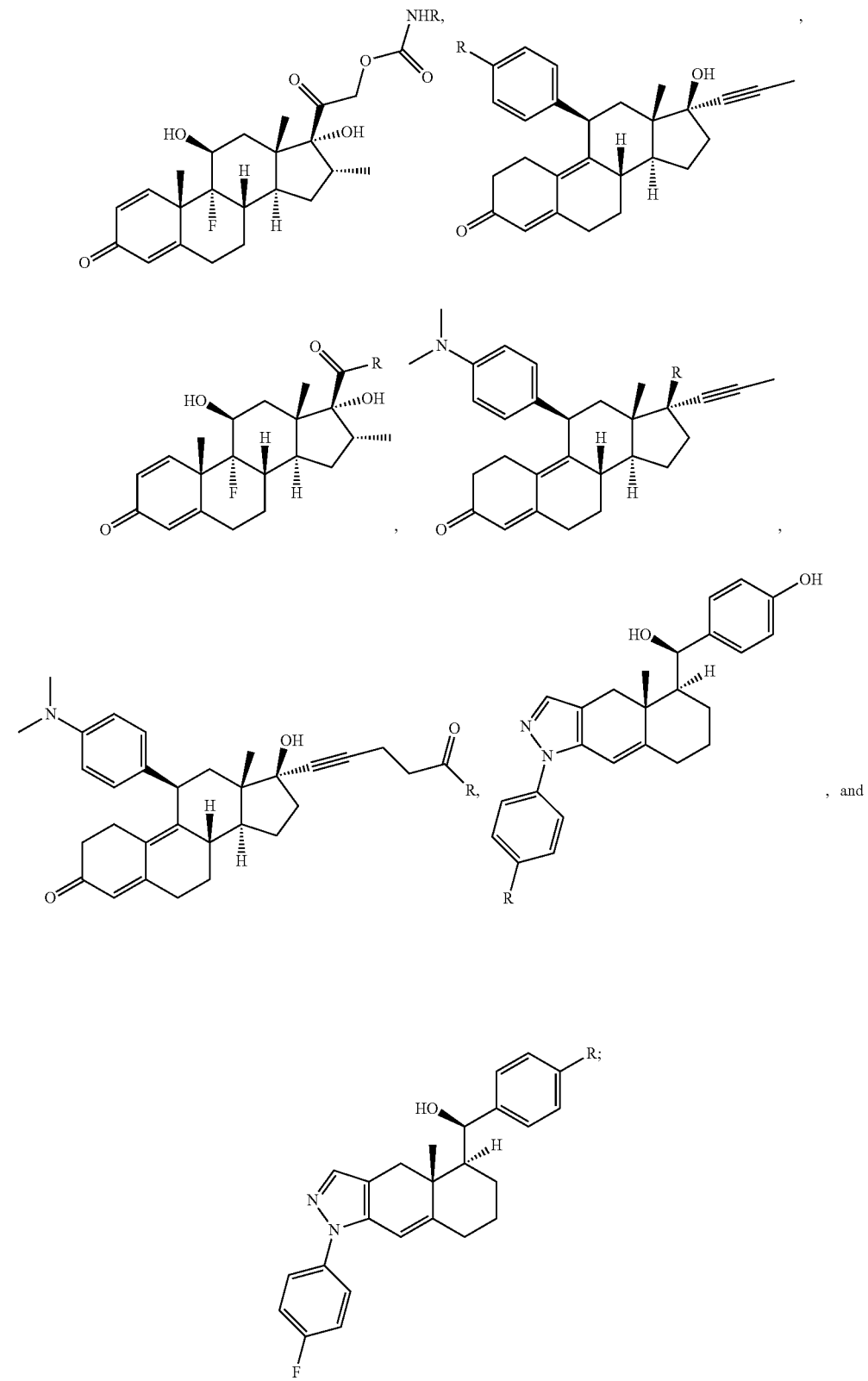
wherein:
R is the point at which the Linker is attached.

TABLE T-continued
F. Estrogen and/or Androgen Receptor dTAG Targeting Ligands:
Estrogen and/or Androgen dTAG Targeting Ligands as used herein include, but are not limited to:
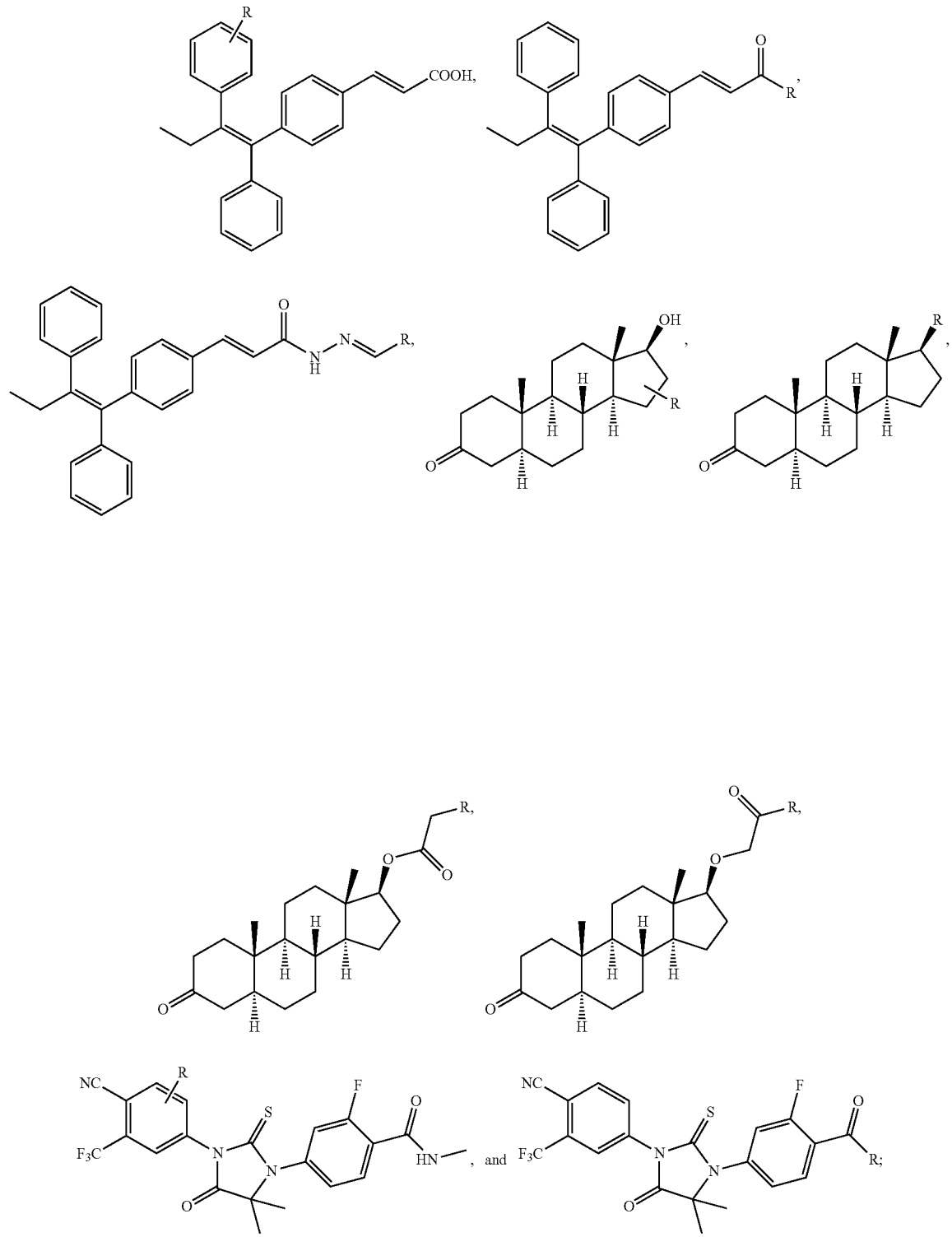
wherein:
R is the point at which the Linker is attached.

TABLE T-continued
G. DOT1L dTAG Targeting Ligands:
DOT1L dTAG Targeting Ligands as used herein include, but are not limited to:
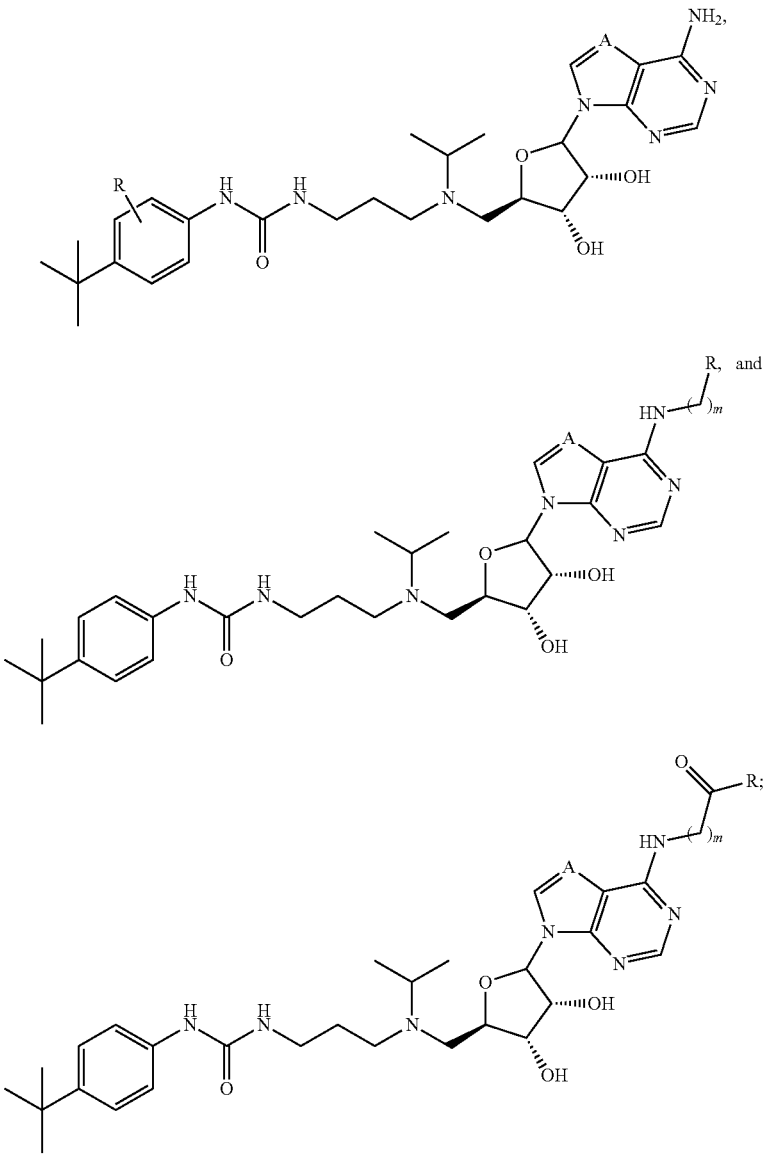
wherein:
R is the point at which the Linker is attached;
A is N or CH; and
m is 0, 1, 2, 3, 4, 5, 6, 7, or 8.
H. Ras dTAG Targeting Ligands:
Ras dTAG Targeting Ligands as used herein include, but are not limited to:
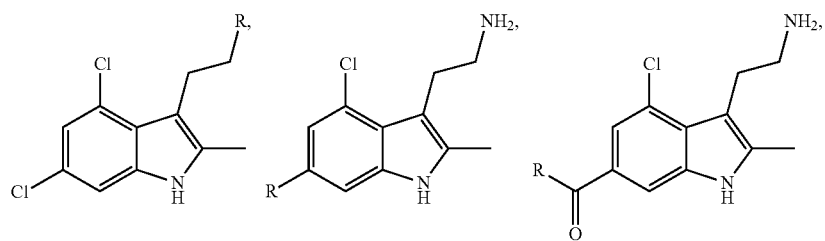

TABLE T-continued
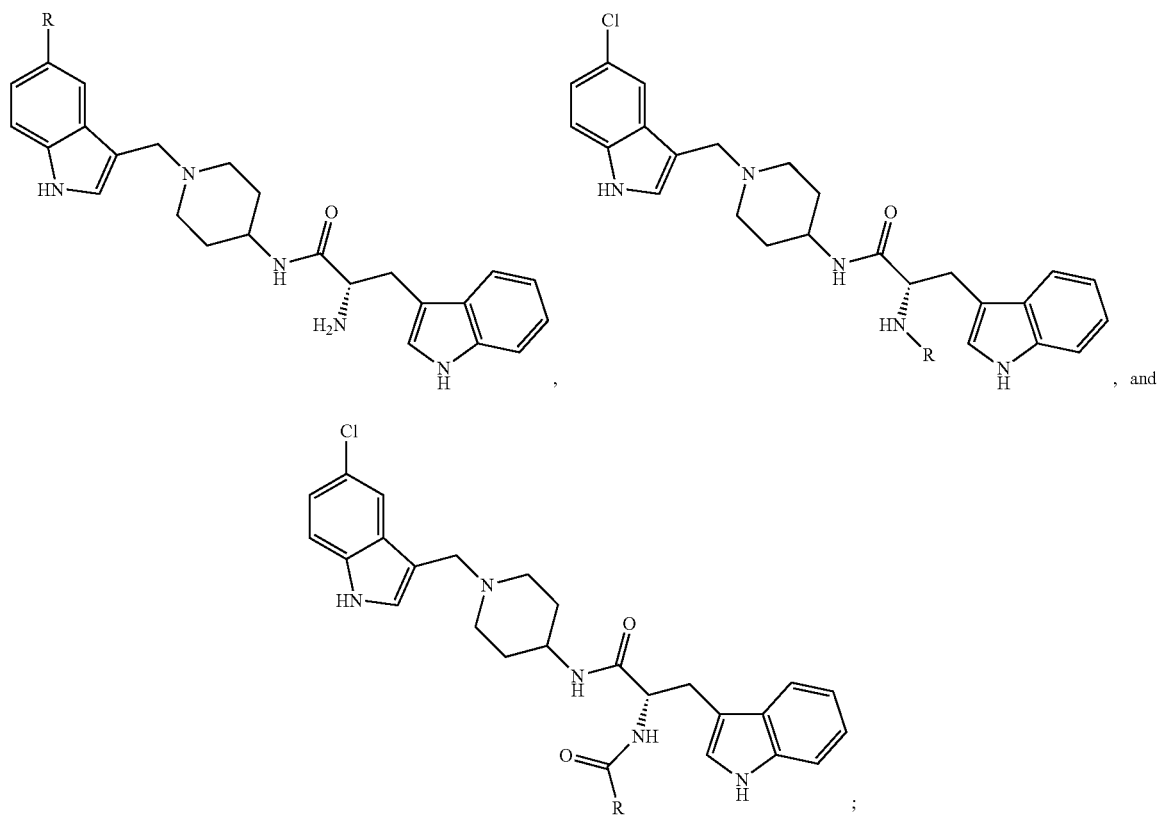
wherein:
R is the point at which the Linker is attached.
I. RasG12C dTAG Targeting Ligands:
RasG12C dTAG Targeting Ligands as used herein include, but are not limited to:
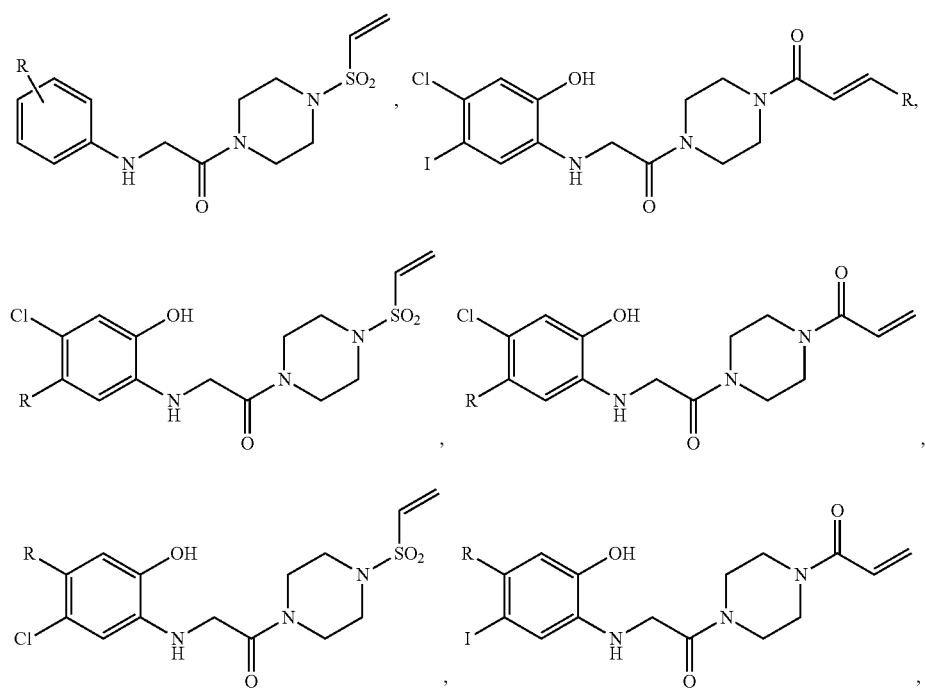

TABLE T-continued
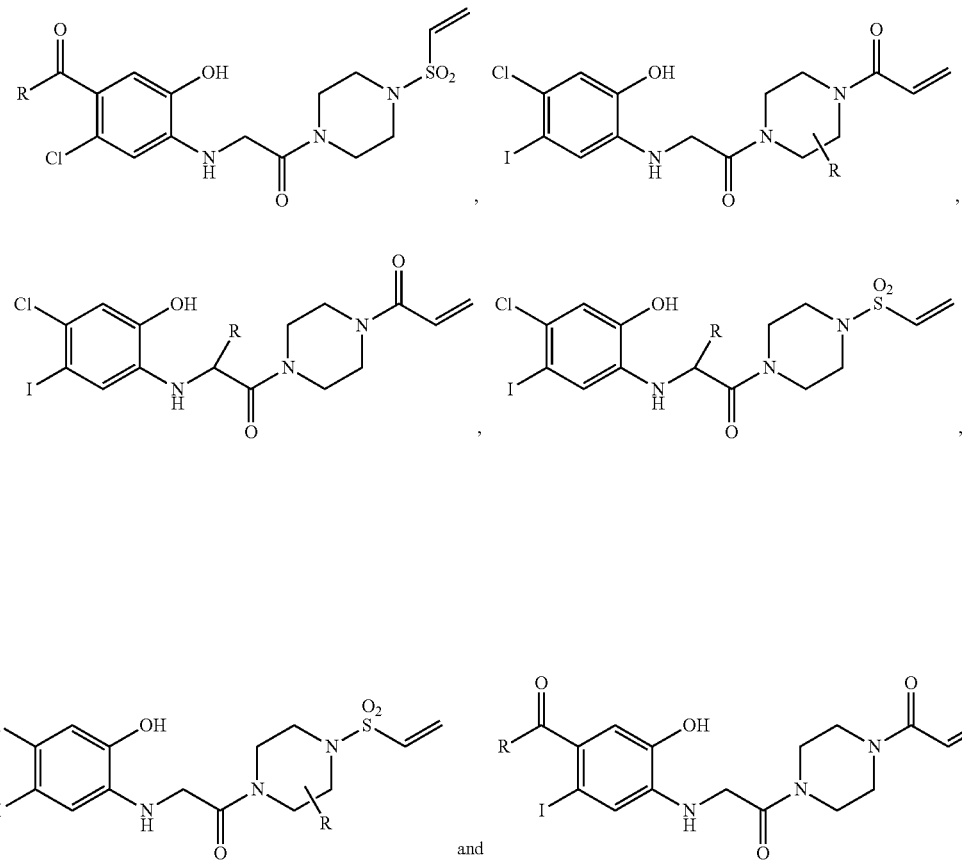
wherein:
R is the point at which the Linker is attached.
J. Her3 dTAG Targeting Ligands:
Her3 dTAG Targeting Ligands as used herein include, but are not limited to:
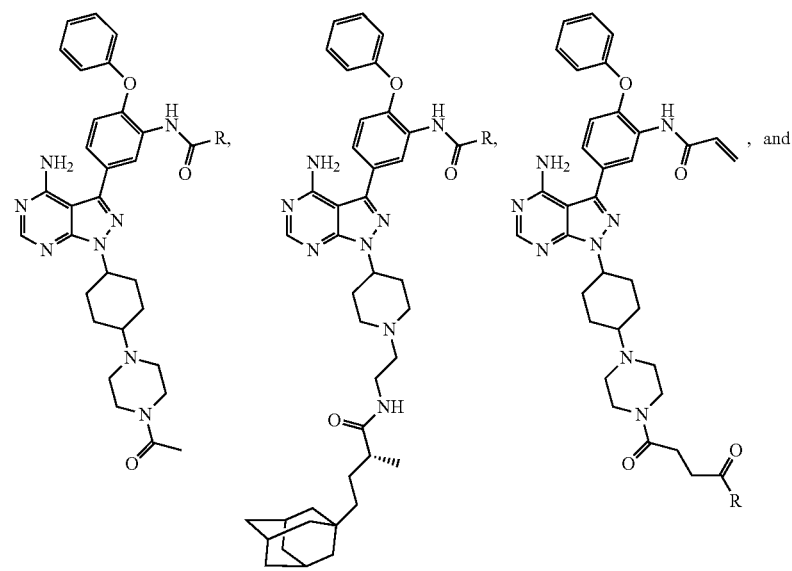

TABLE T-continued
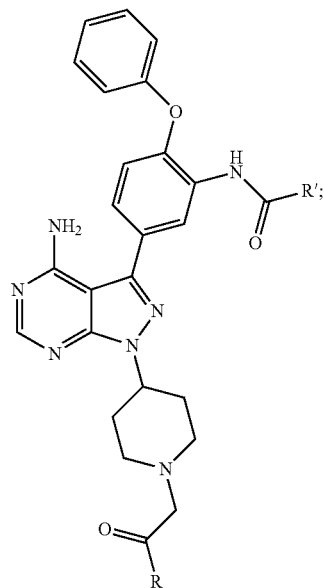
wherein:
R is the point at which the Linker is attached; and
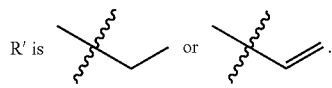
R' is ⟨structure⟩ or ⟨structure⟩.
K. Bcl-2 or Bcl-XL dTAG Targeting Ligands:
Bcl-2 or Bcl-XL dTAG Targeting Ligands as used herein include, but are not limited to:
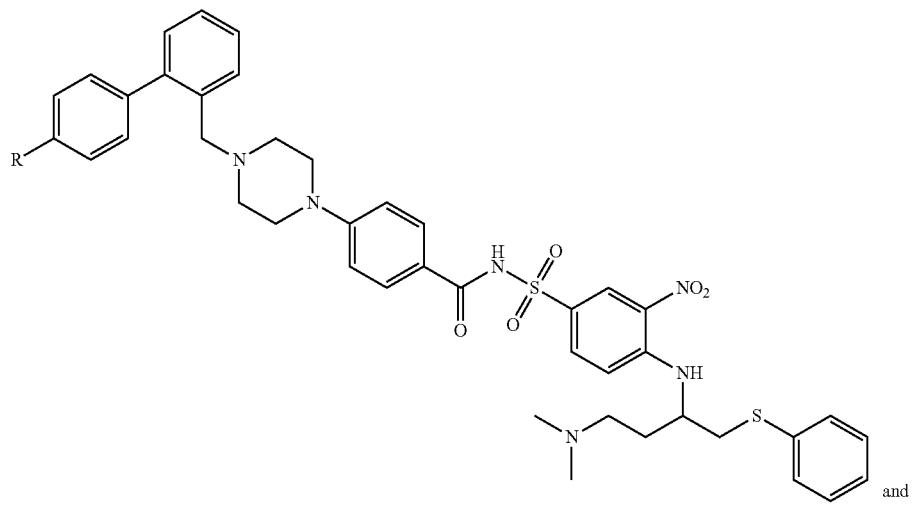
and TABLE T-continued

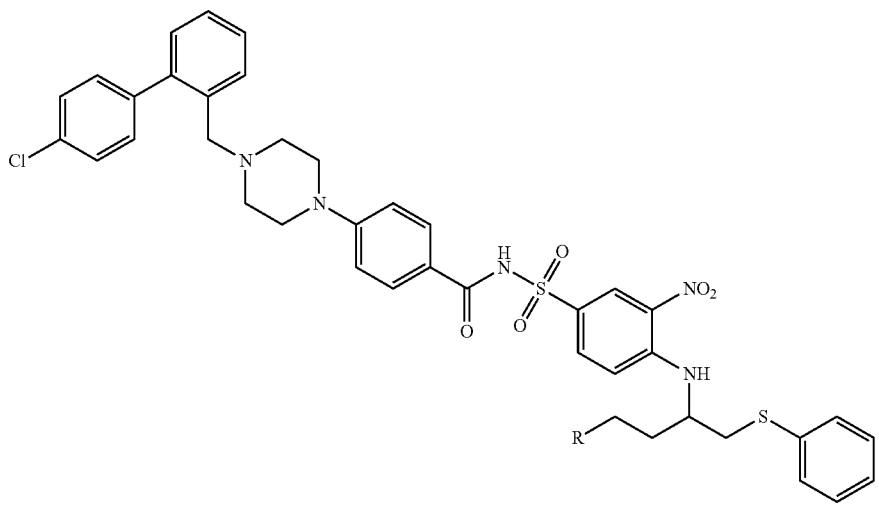

wherein:
R is the point at which the Linker is attached.

L. HDAC dTAG Targeting Ligands:

HDAC dTAG Targeting Ligands as used herein include, but are not limited to:

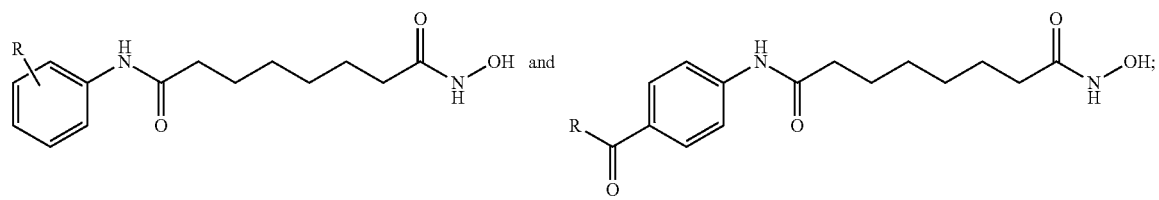

wherein:
R is the point at which the Linker is attached.

M. PPAR-gamma dTAG Targeting Ligands:

PPAR-gamma dTAG Targeting Ligands as used herein include, but are not limited to:

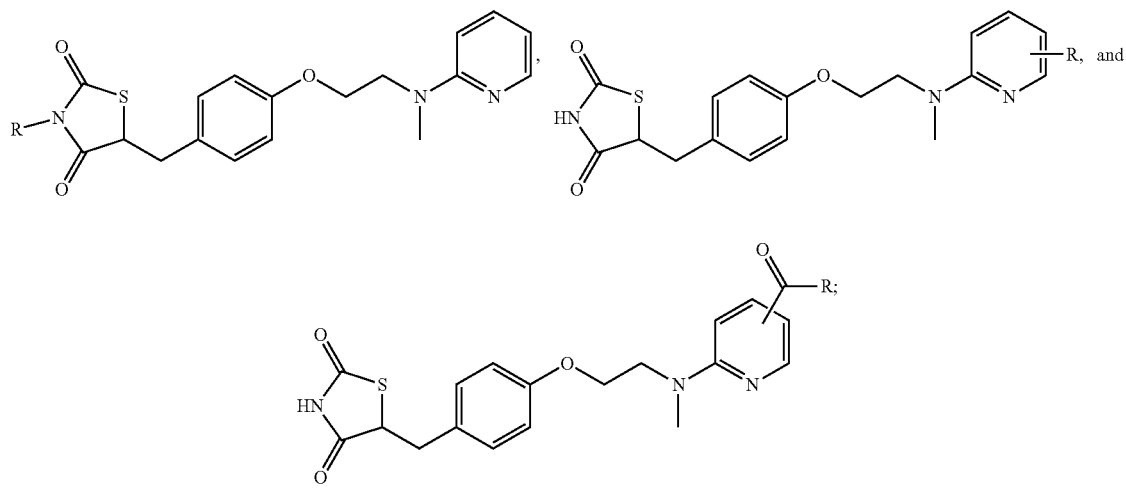

wherein:
R is the point at which the Linker is attached.

TABLE T-continued
N. RXR dTAG Targeting Ligands:
RXR dTAG Targeting Ligands as used herein include, but are not limited to:
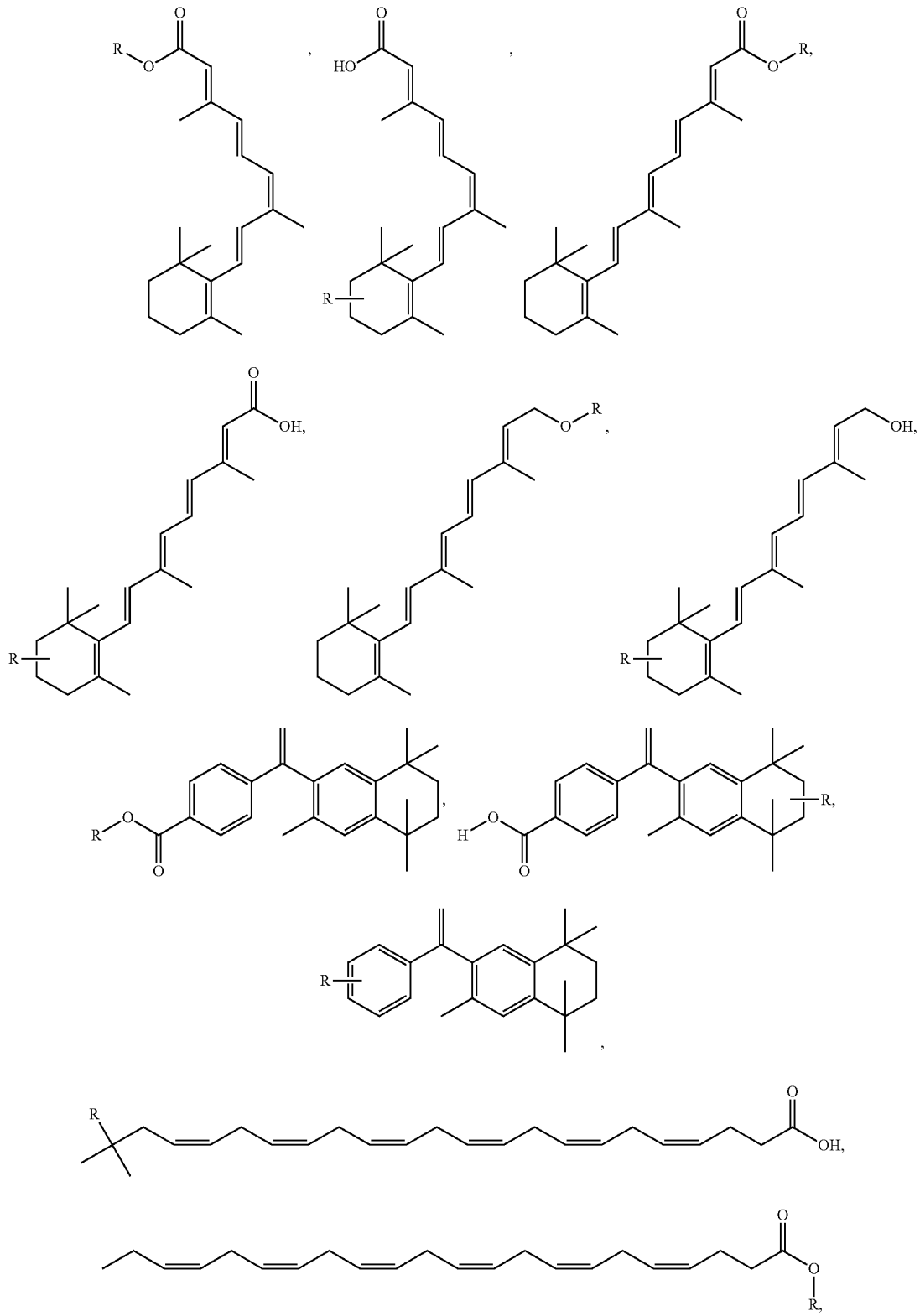

TABLE T-continued
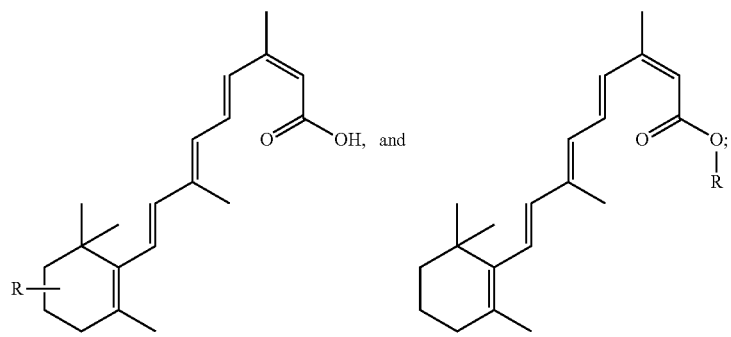
wherein:
R is the point at which the Linker is attached.
O. DHFR dTAG Targeting Ligands:
DHFR dTAG Targeting Ligands as used herein include, but are not limited to:
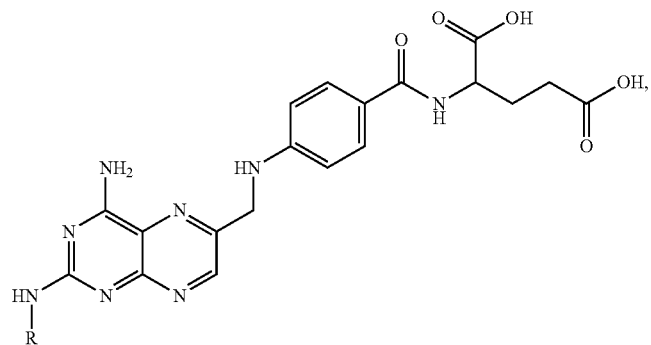
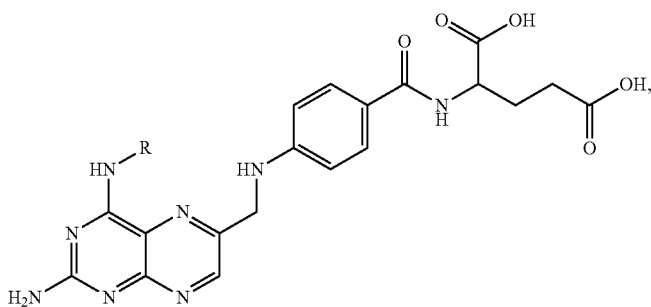
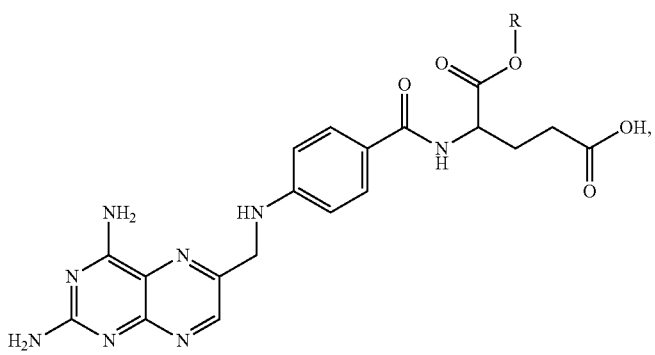

TABLE T-continued
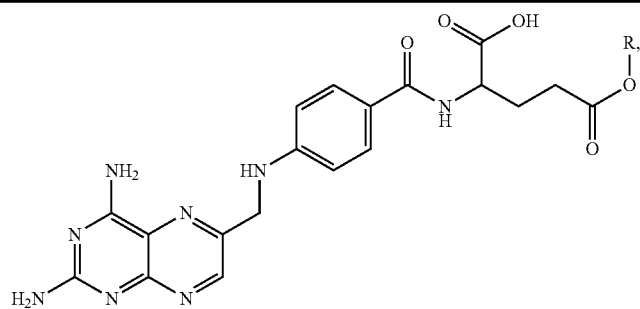
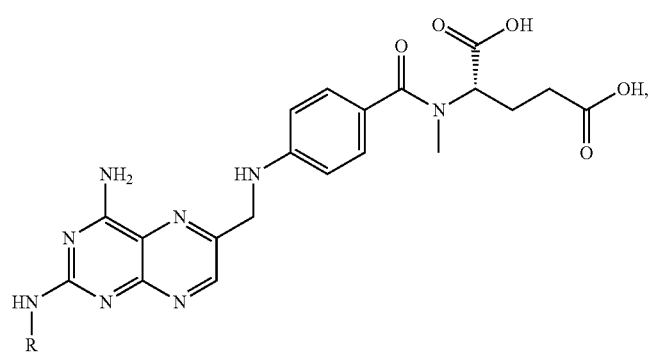
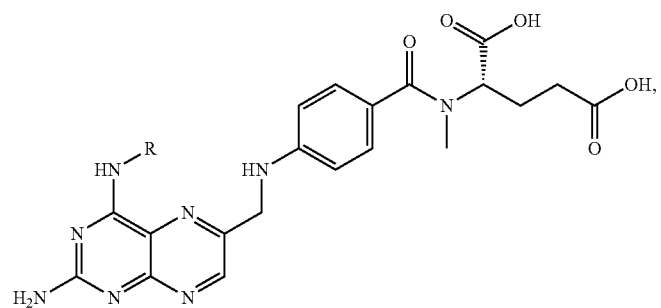
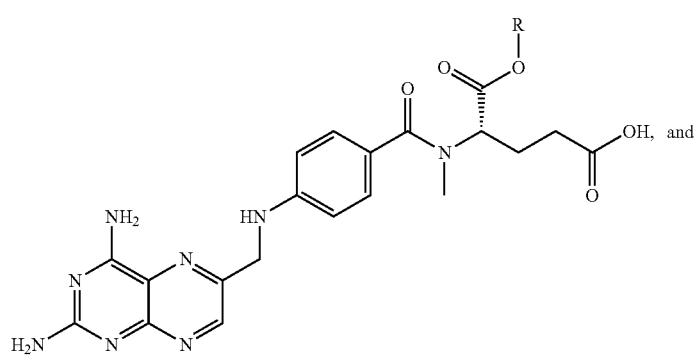
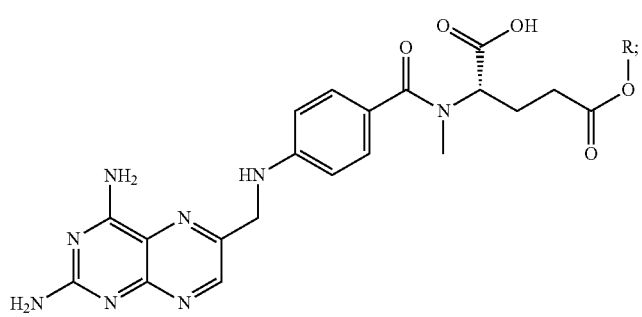

141 142
TABLE T-continued
wherein:
R is the point at which the Linker is attached.
P. EGFR dTAG Targeting Ligands:
EGFR dTAG Targeting Ligands as used herein include, but are not limited to:
1. Targeting Ligands that target L858R mutant EGFR, including erlotinib, gefitnib, afatinib, neratinib, and dacomitinib.
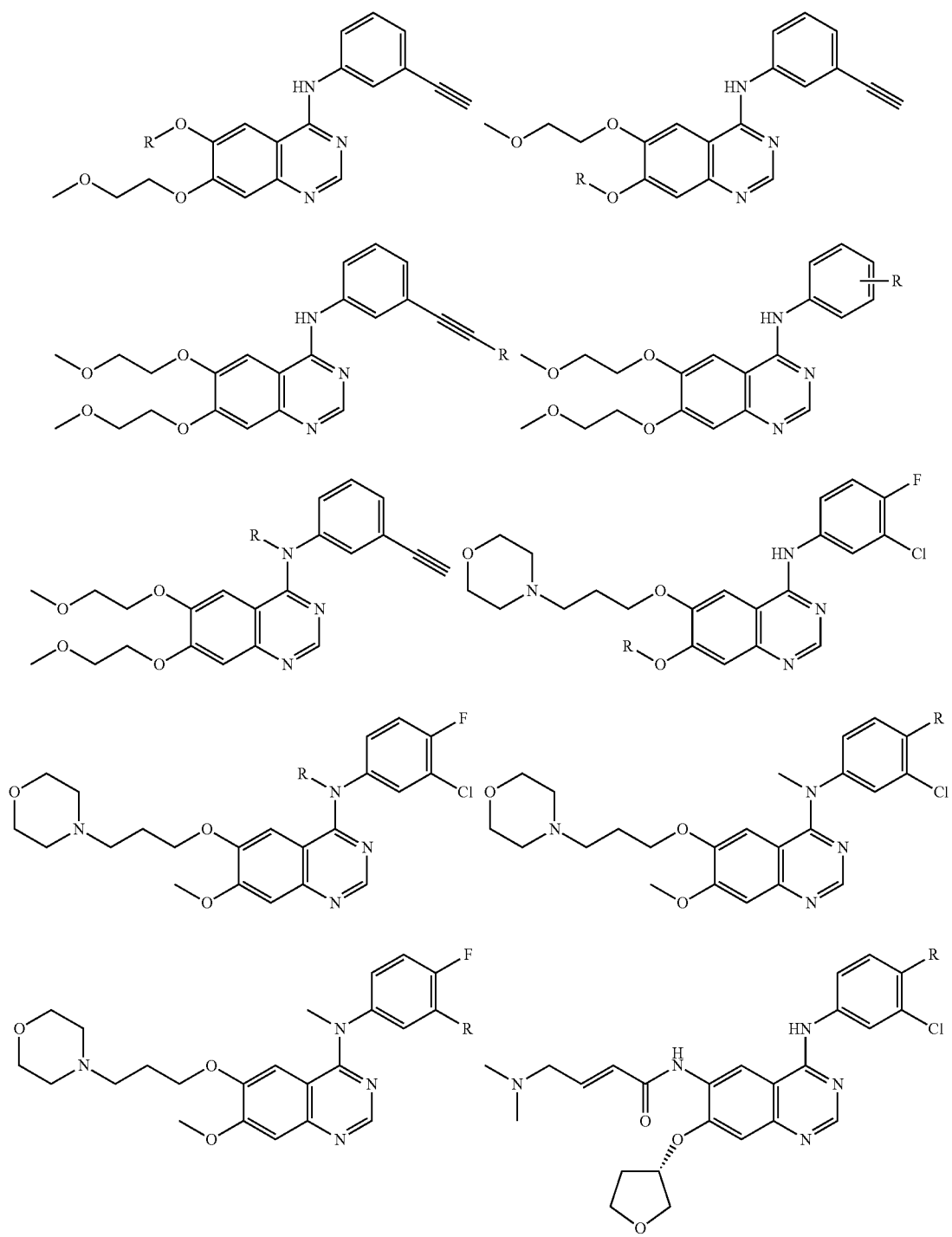

TABLE T-continued
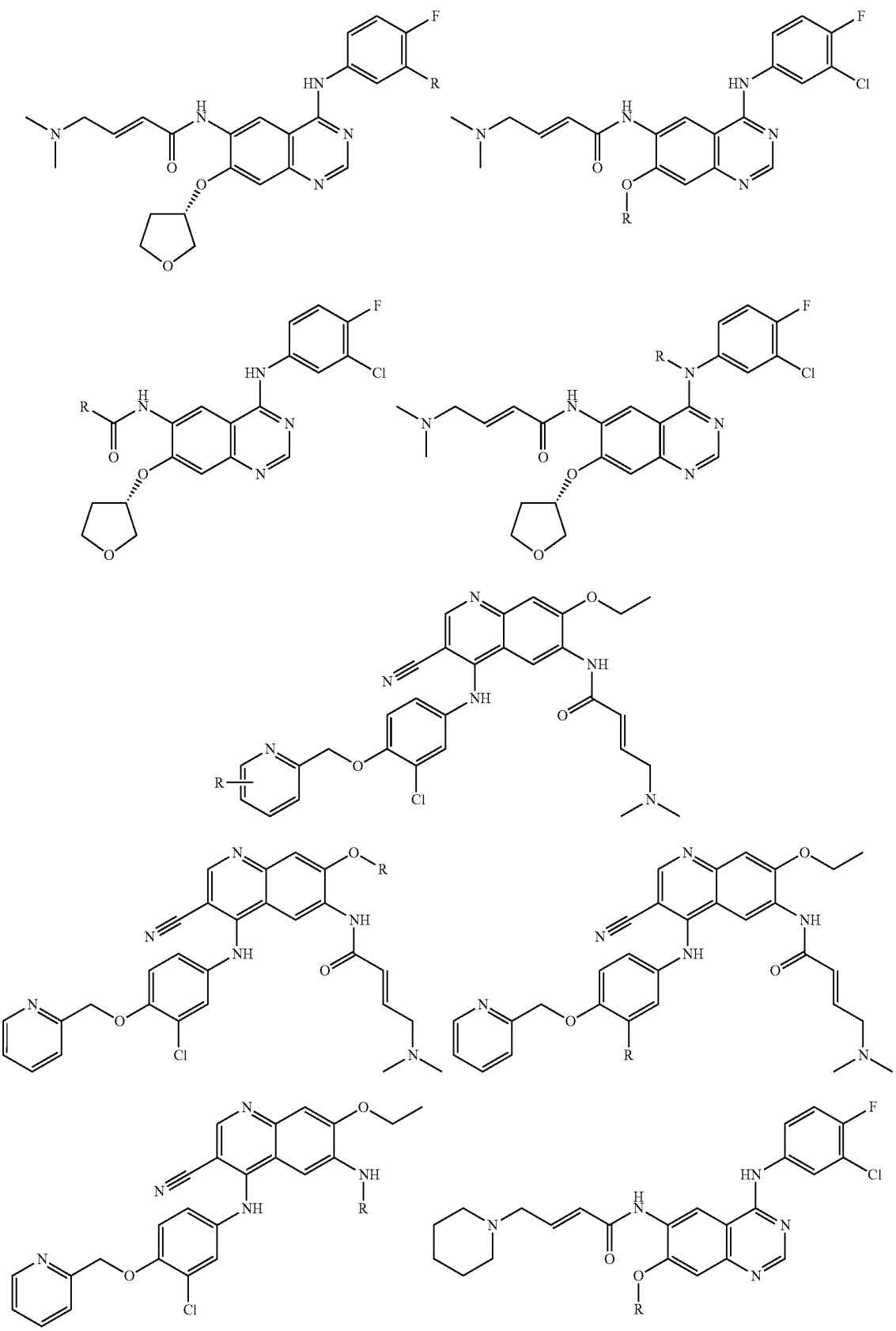

TABLE T-continued
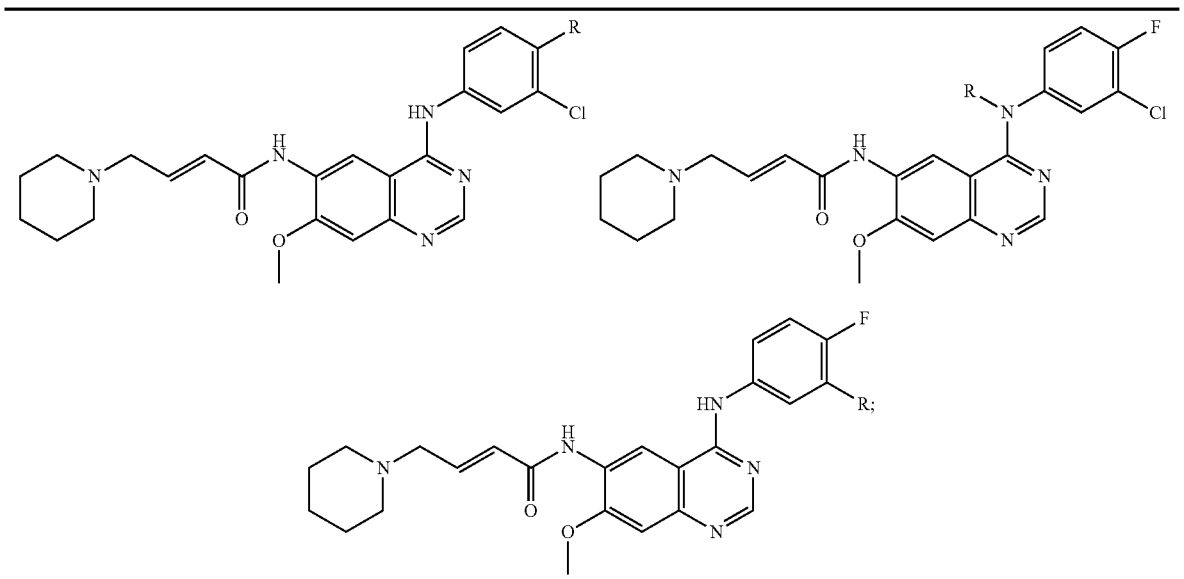
wherein:
R is the point at which the Linker is attached.
2. Targeting Ligands that target T790M mutant EGFR, including osimertinib, rociletinib, olmutinib, naquotinib, nazartinib, PF-06747775, Icotinib, Neratinib, Avitinib, Tarloxotinib, PF-0645998, Tesevatinib, Transtinib, WZ-3146, WZ8040, and CNX-2006:
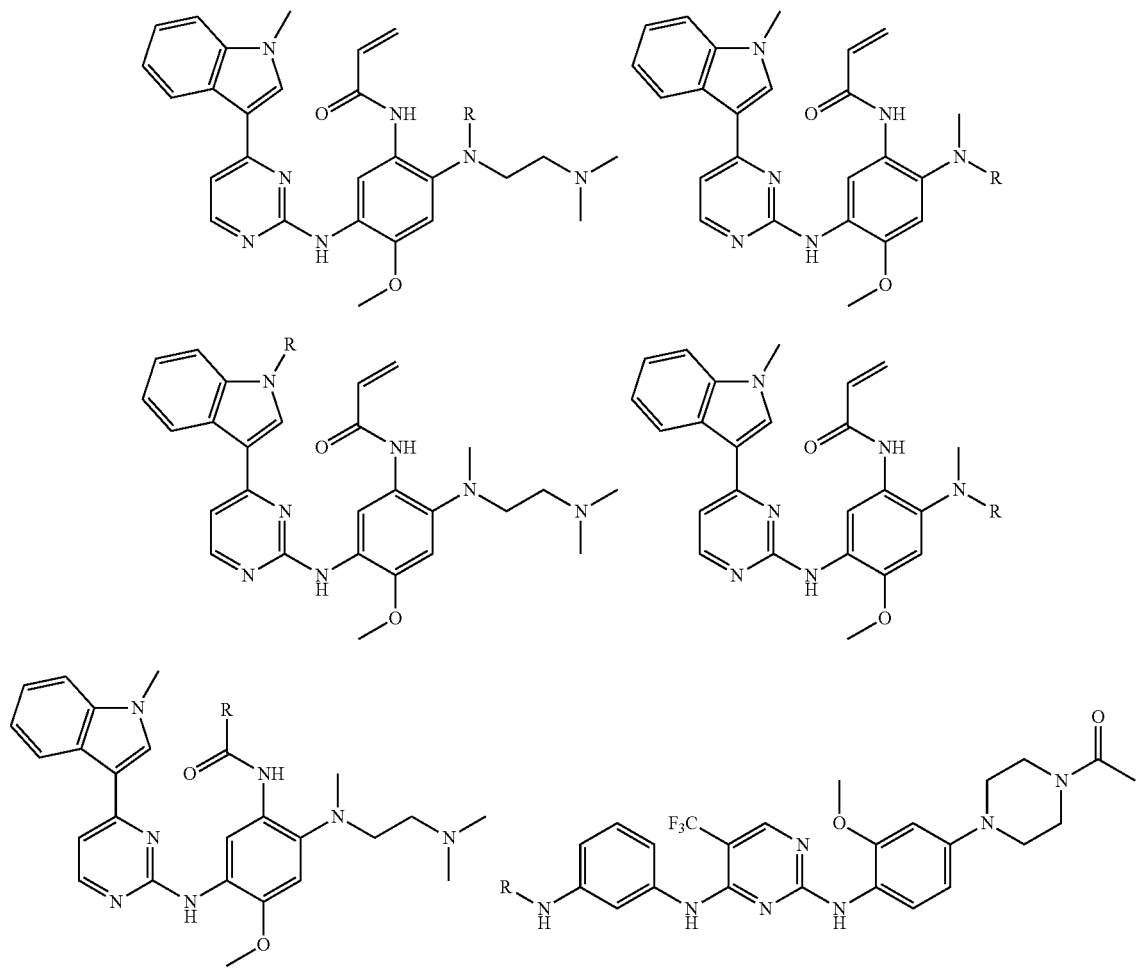

TABLE T-continued
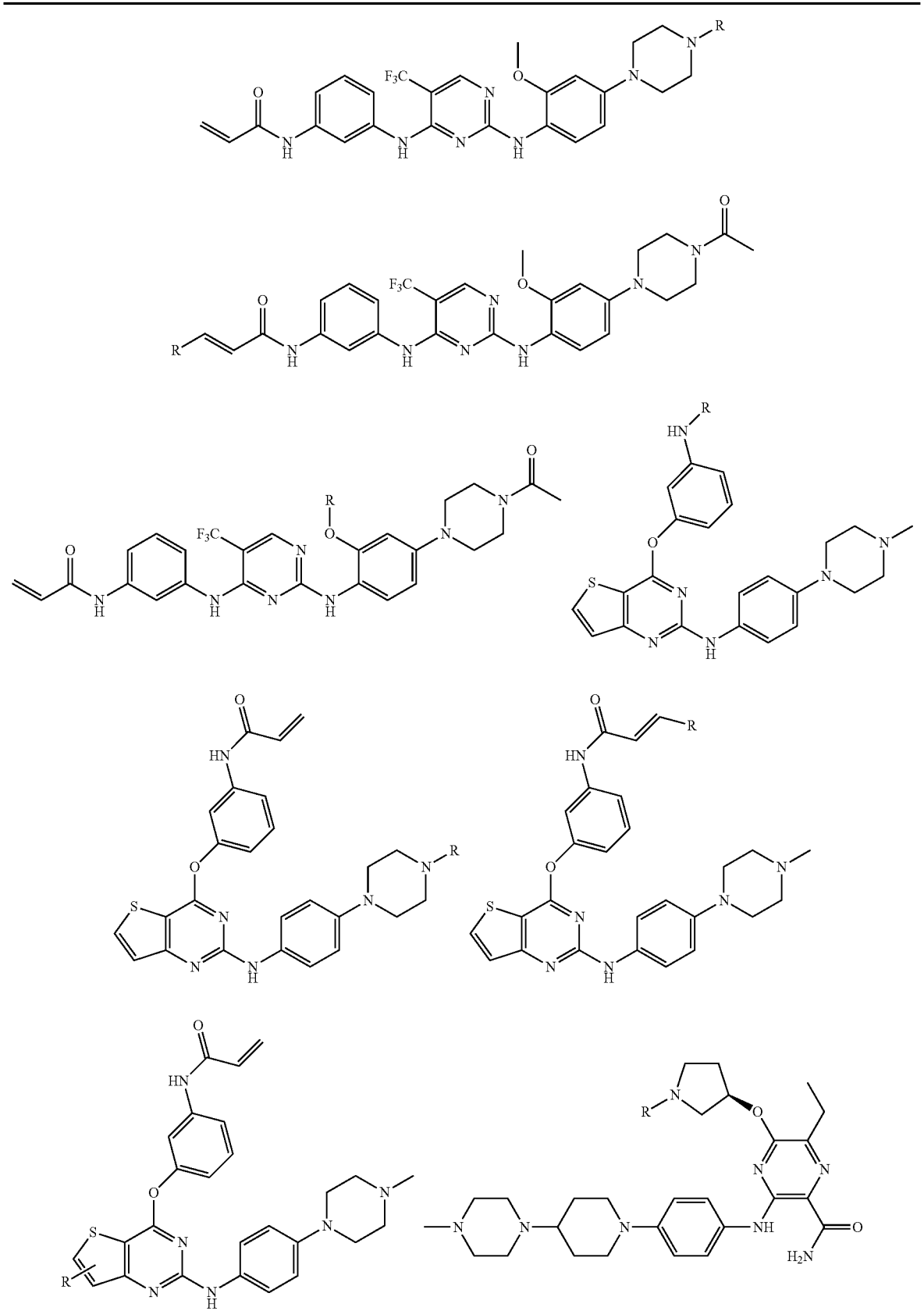

TABLE T-continued
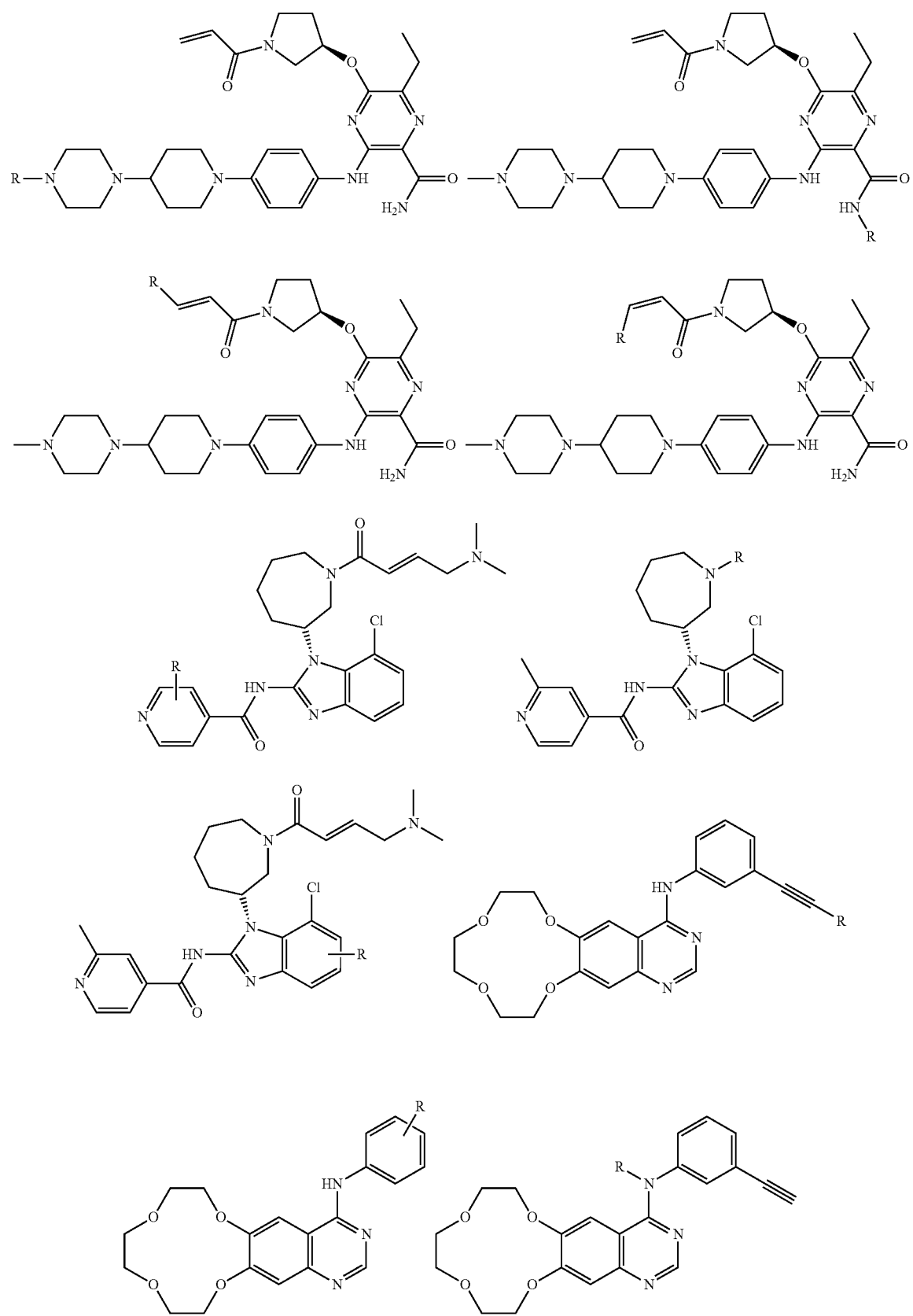

TABLE T-continued
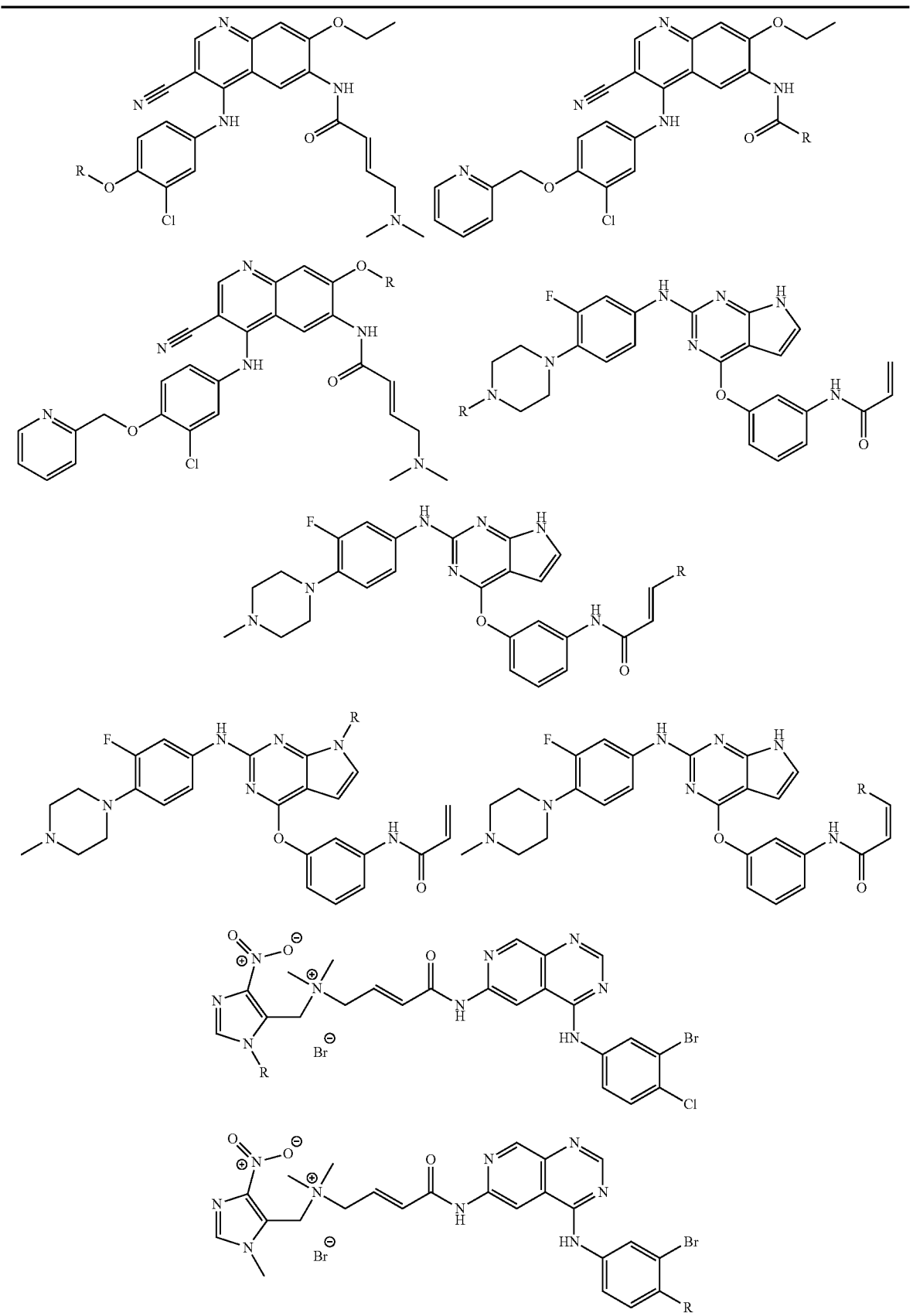

TABLE T-continued
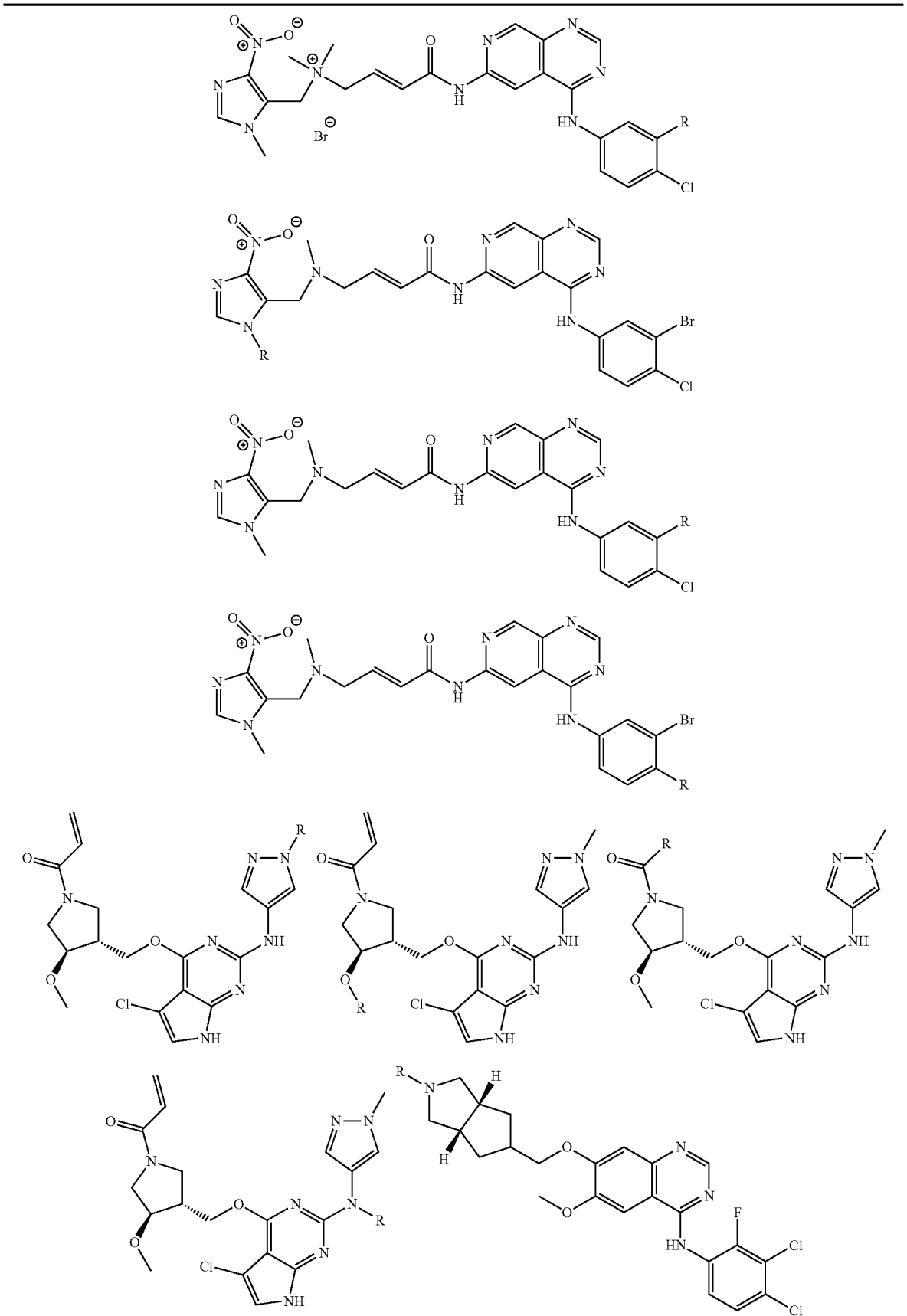

TABLE T-continued
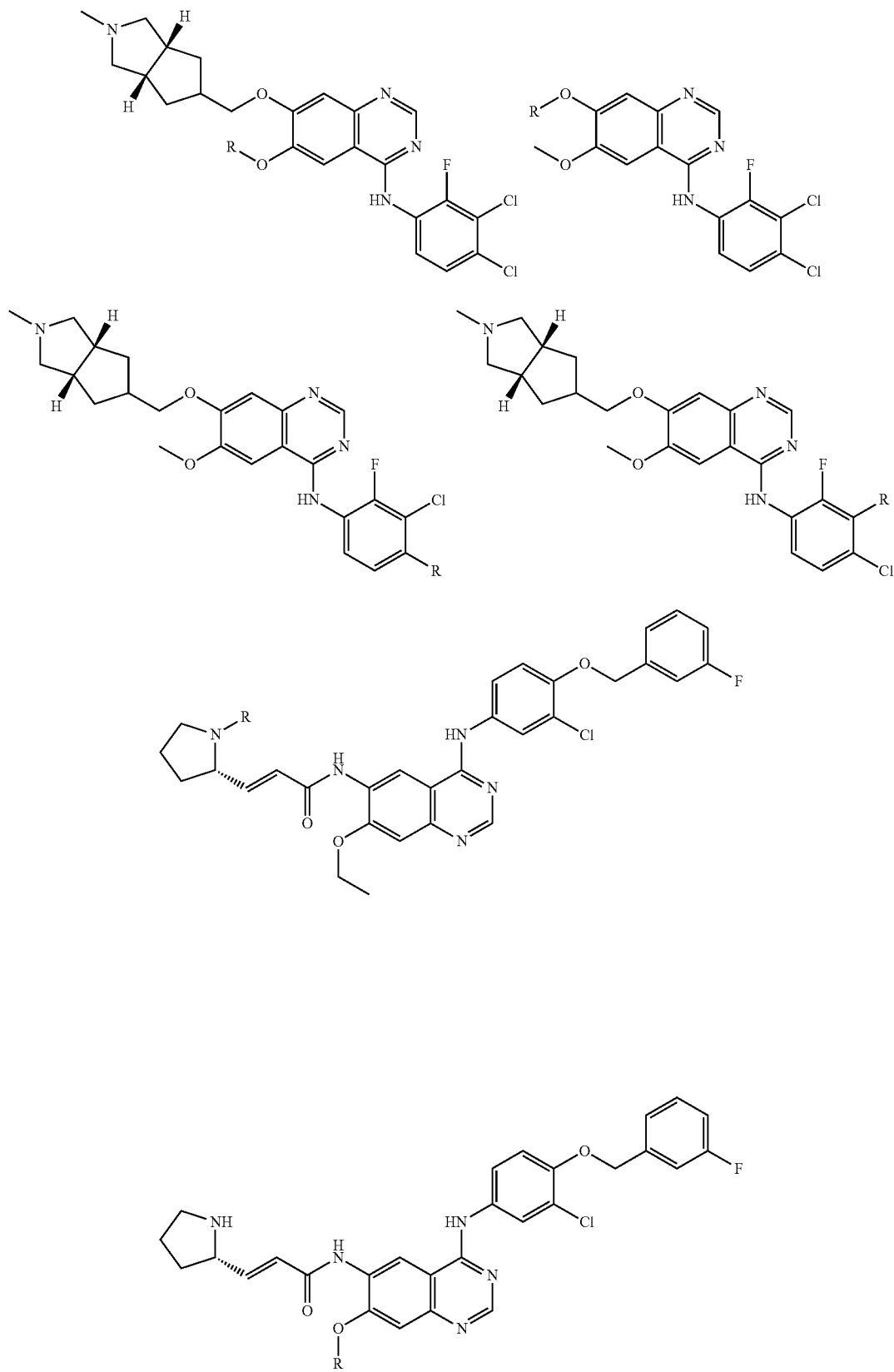

TABLE T-continued
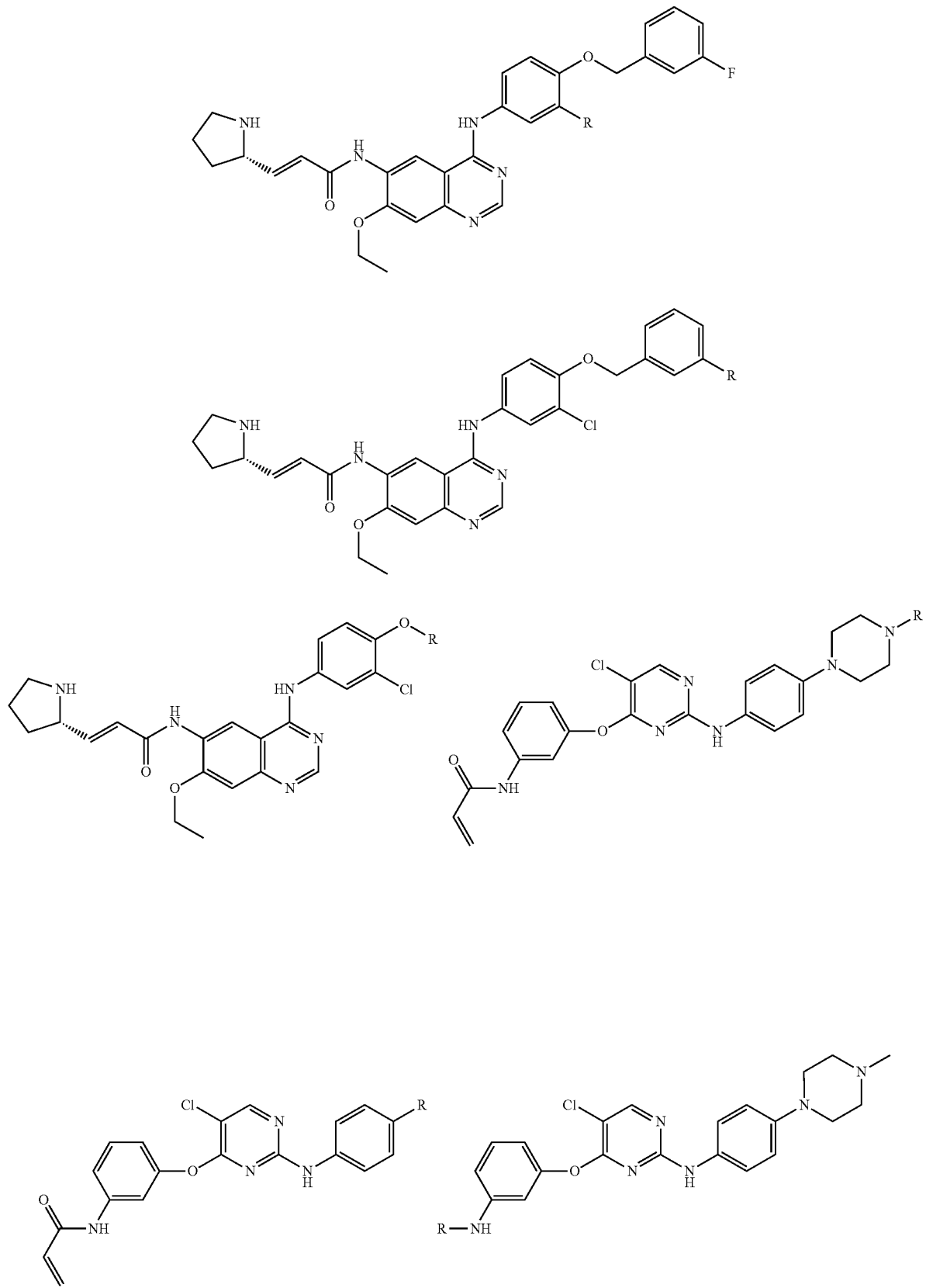

TABLE T-continued
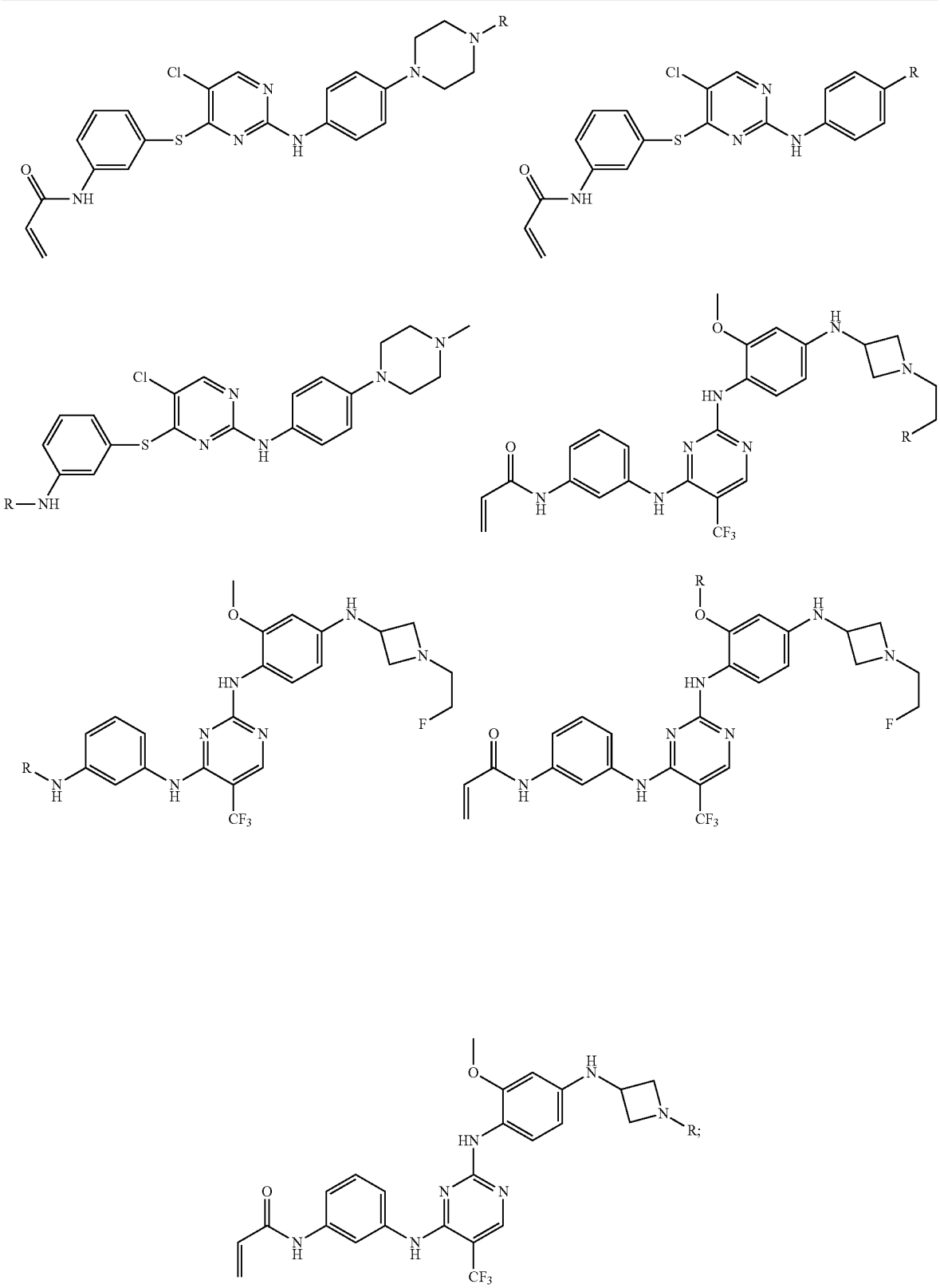
wherein:
R is the point at which the Linker is attached.

TABLE T-continued
3. Targeting Ligands that target C797S mutant EGFR, including EAI045:
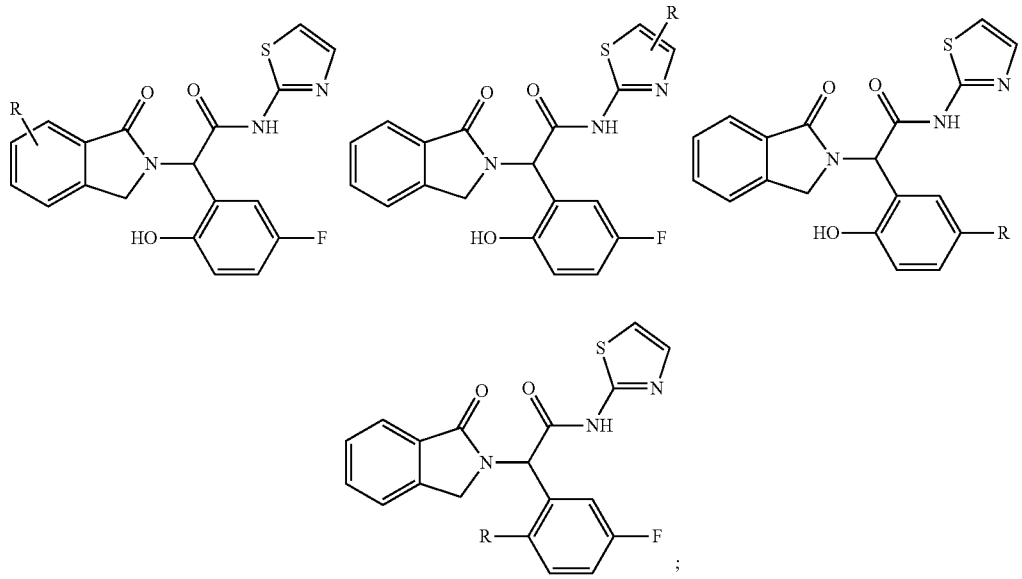
wherein:
R is the point at which the Linker is attached.
Q. BCR-ABL dTAG Targeting Ligands:
BCR-ABL dTAG Targeting Ligands as used herein include, but are not limited to:
1. Targeting Ligands that target T315I mutant BCR-ABL (PDB #3CS9), including Nilotinib and Dasatinib:
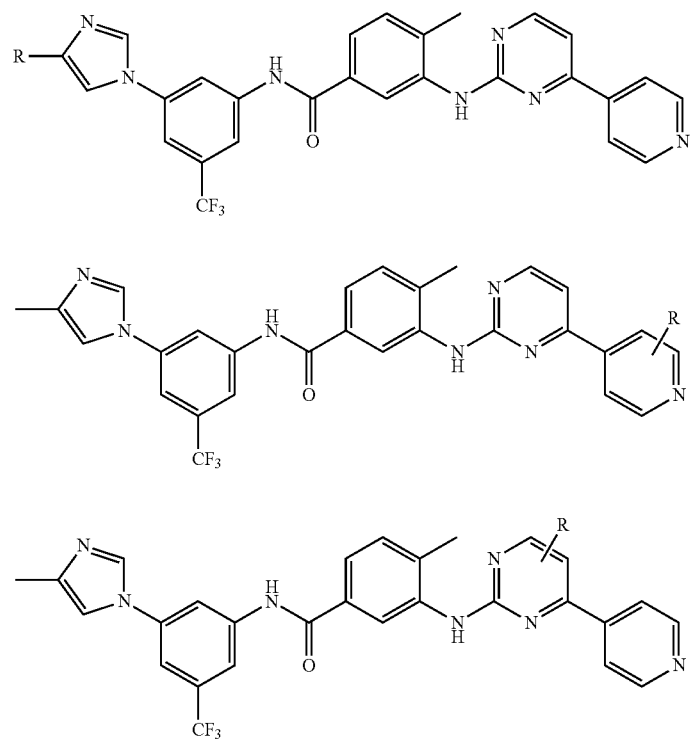

TABLE T-continued
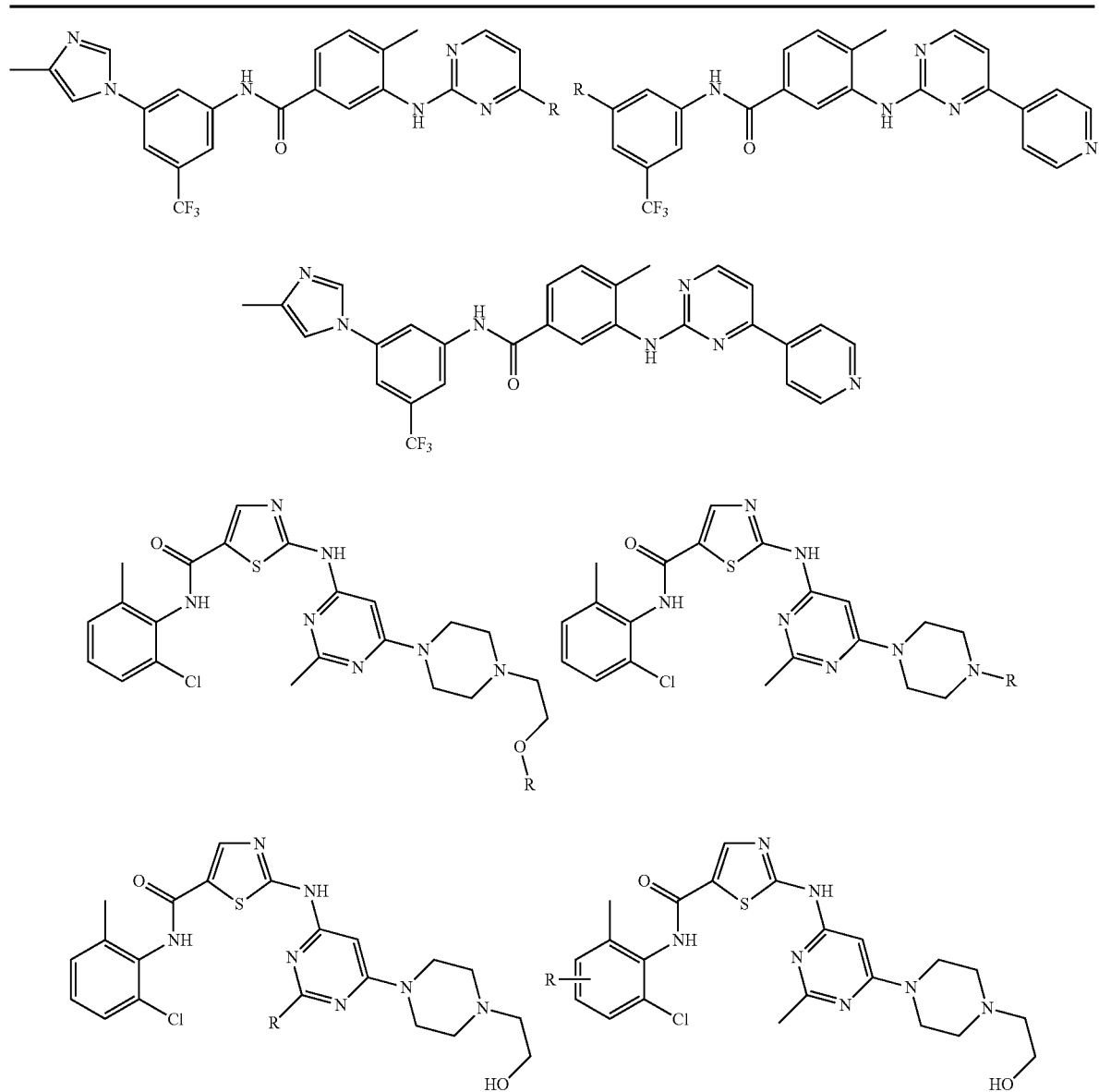
wherein:
R is the point at which the Linker is attached.
2. Targeting Ligands that target BCR-ABL, including Nilotinib, Dasatinib, Ponatinib, and Bosutinib:
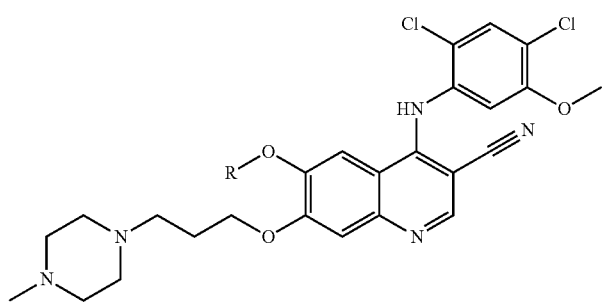

TABLE T-continued
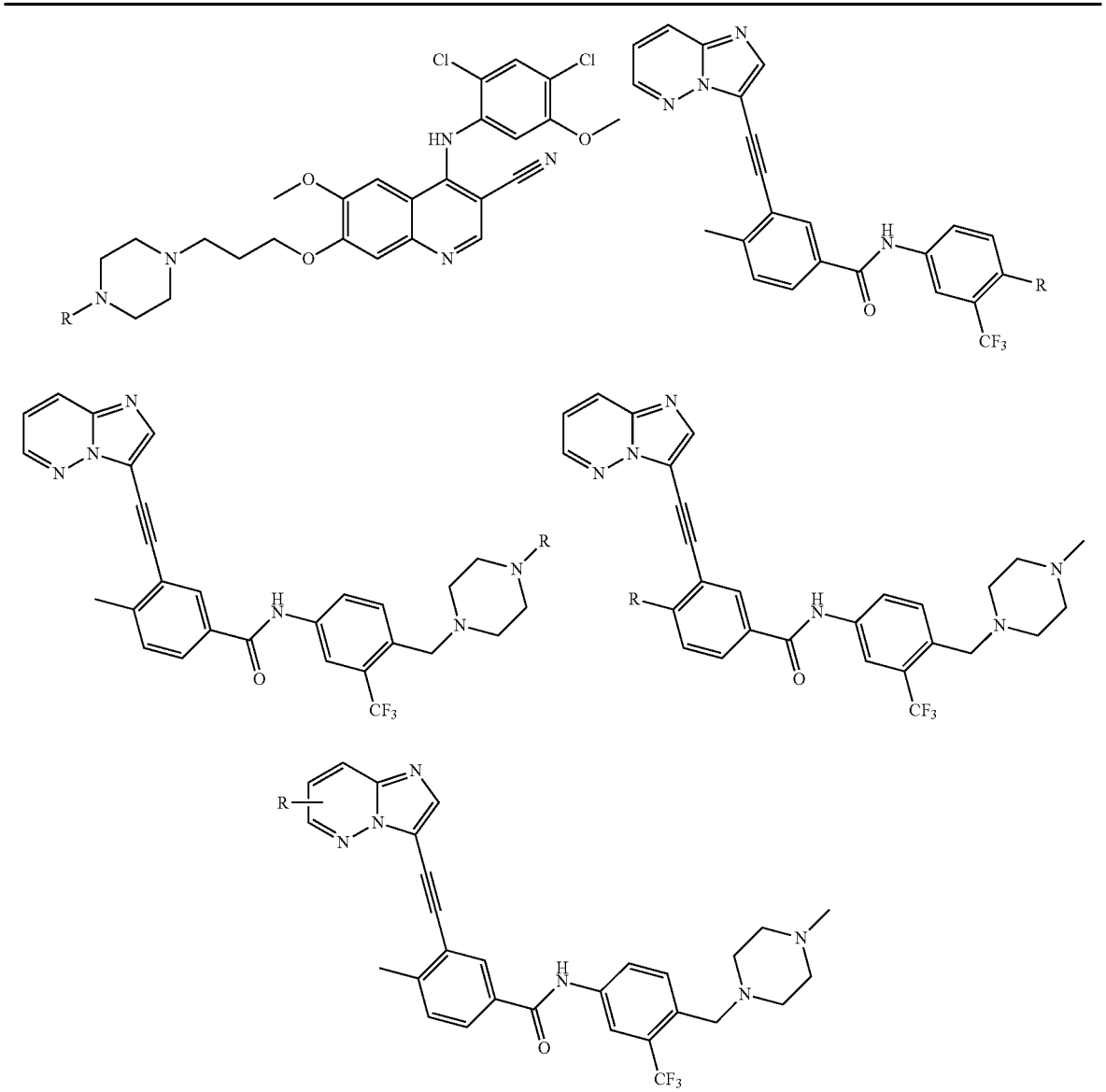
wherein:
R is the point at which the Linker is attached.
R. ALK dTAG Targeting Ligands:
ALK dTAG Targeting Ligands as used herein include, but are not limited to:
1. Targeting Ligands that target L1196M mutant ALK (PDB #4MKC), including Ceritinib:
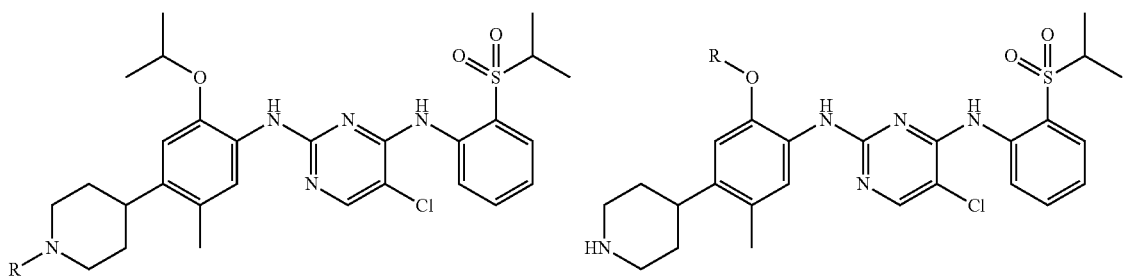

TABLE T-continued
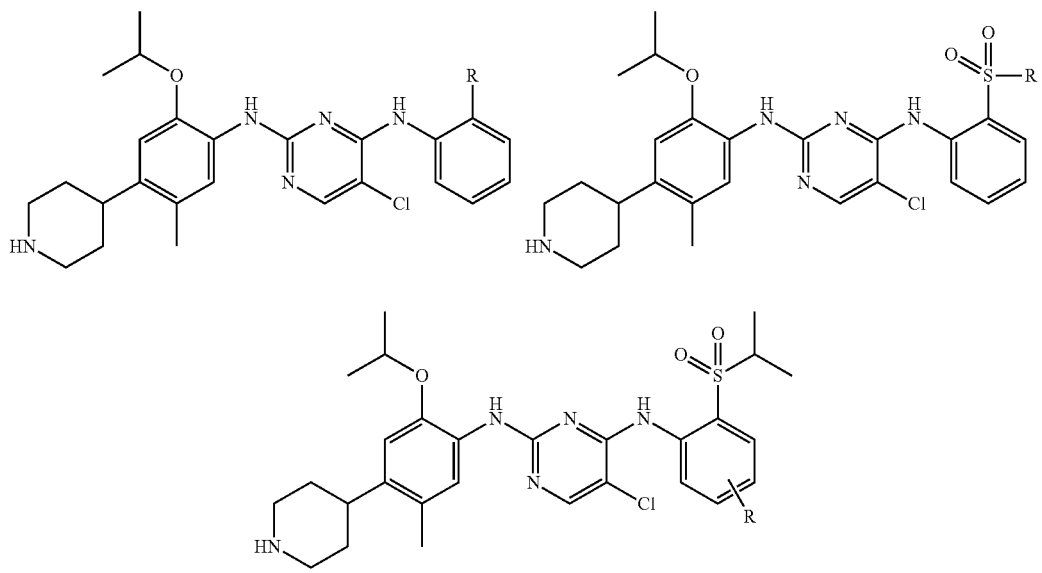
wherein:
R is the point at which the Linker is attached.
S. JAK2 dTAG Targeting Ligands:
JAK2 dTAG Targeting Ligands as used herein include, but are not limited to:
1. Targeting Ligands that target V617F mutant JAK2, including Ruxolitinib:
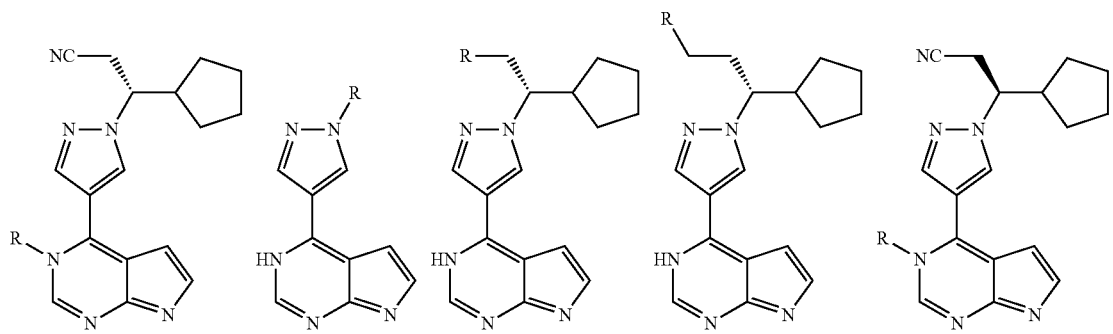
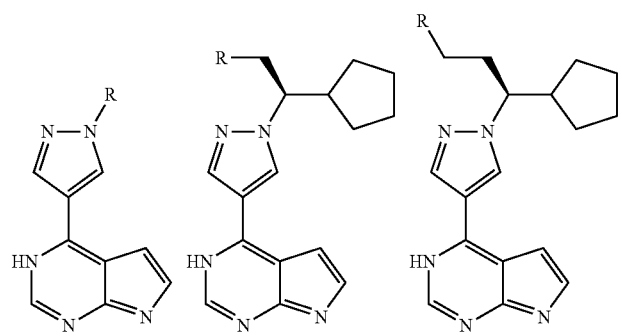
wherein:
R is the point at which the Linker is attached.

TABLE T-continued

T. BRAF dTAG Targeting Ligands:

BRAF dTAG Targeting Ligands as used herein include, but are not limited to:
1. Targeting Ligands that target V600E mutant BRAF (PBD #3OG7), including Vemurafenib:

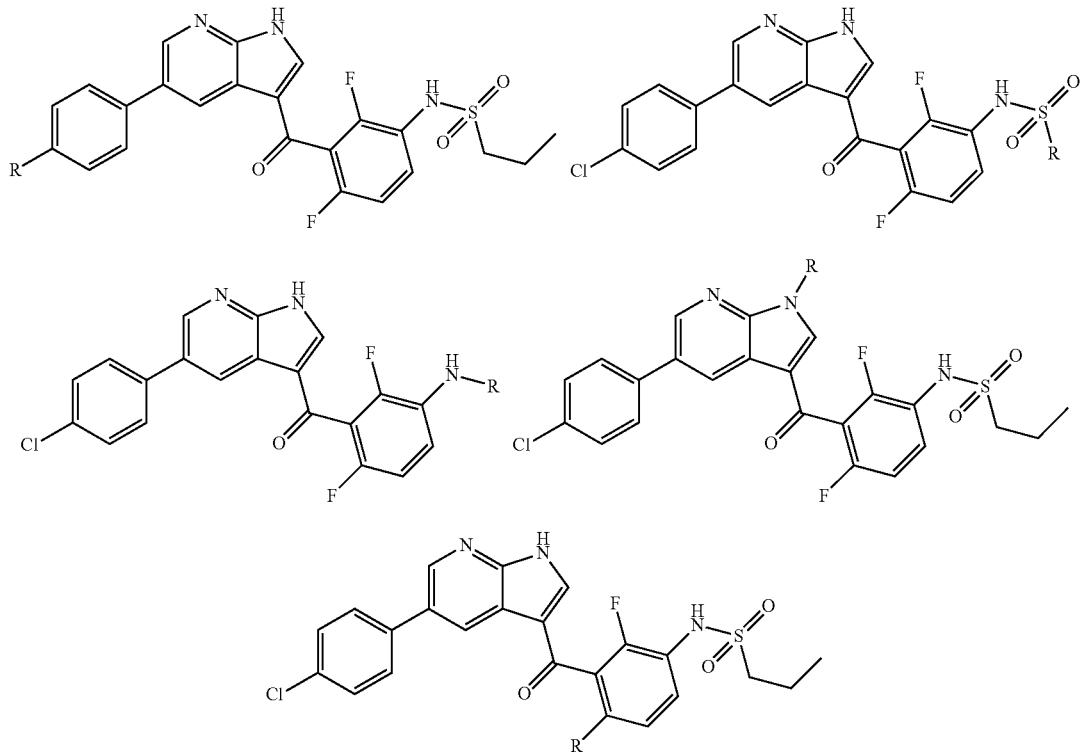

wherein:
R is the point at which the Linker is attached.

2. Targeting Ligands that target BRAF, including Dabrafenib:

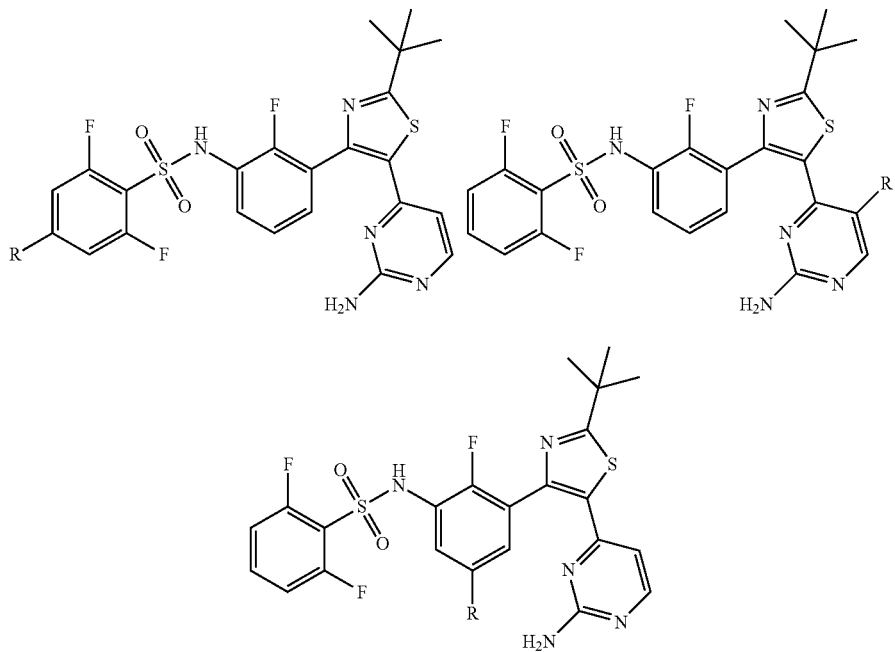

wherein:
R is the point at which the Linker is attached.

U. LRRK2 dTAG Targeting Ligands:
LRRK2 dTAG Targeting Ligands as used herein include, but are not limited to:
1. Targeting Ligands that target R1441C mutant LRRK2, including:
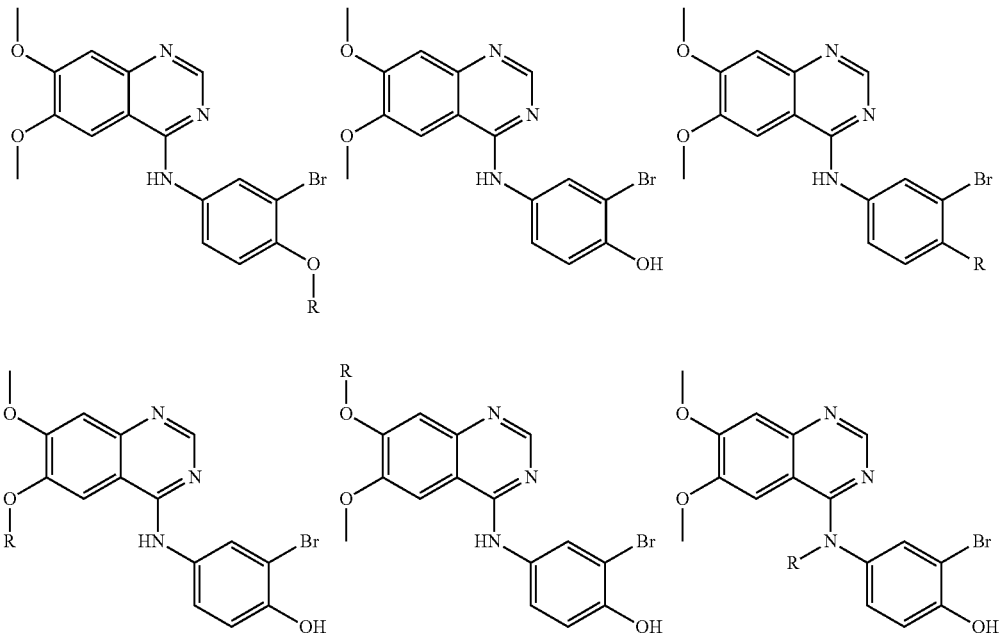
wherein:
R is the point at which the Linker is attached.
2. Targeting Ligands that target G2019S mutant LRRK2, including:
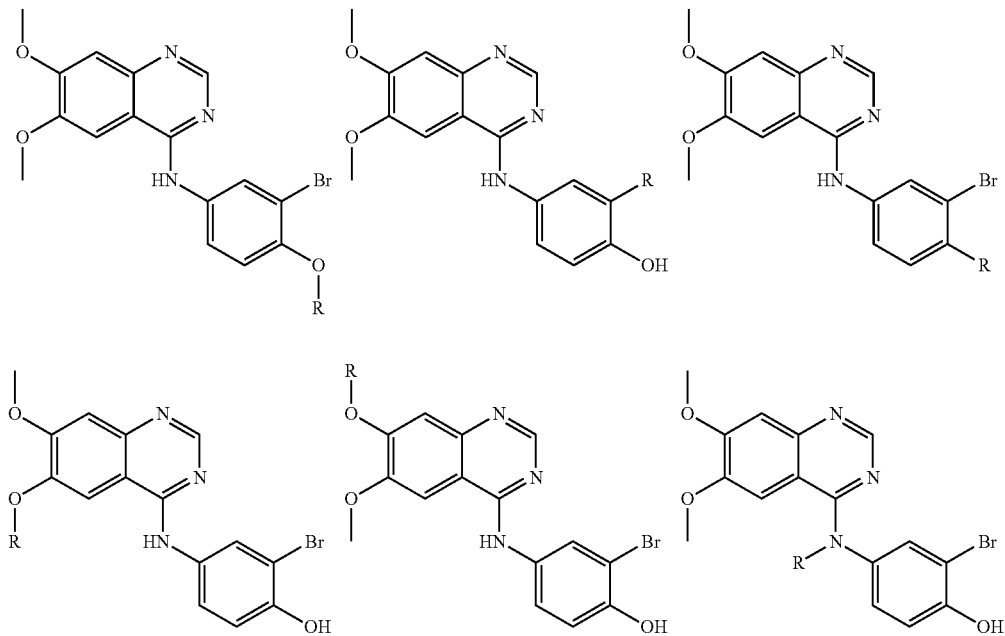
wherein:
R is the point at which the Linker is attached.

3. Targeting Ligands that target I2020T mutant LRRK2, including:

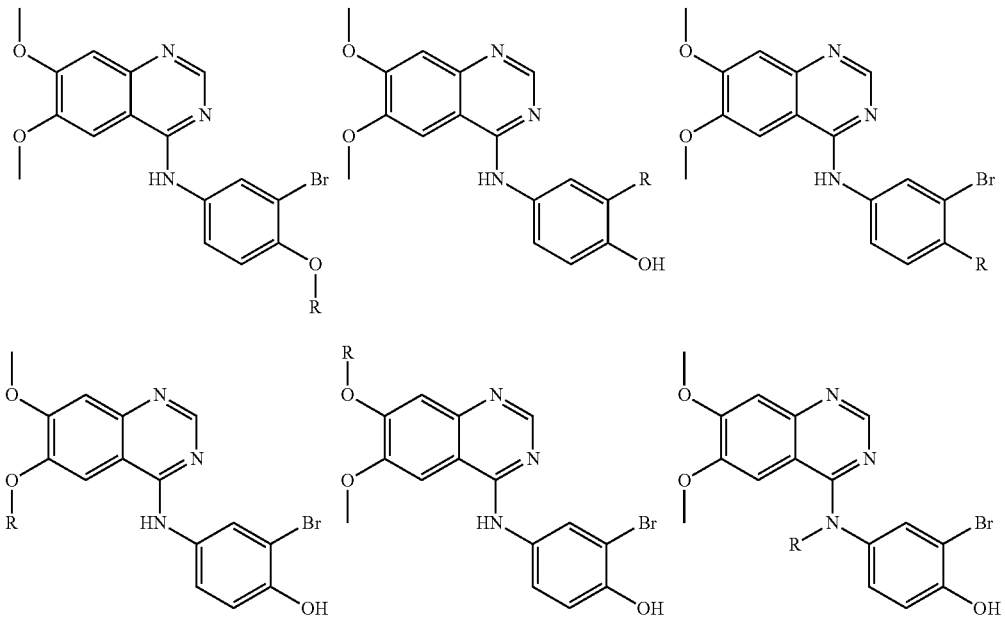

wherein:
R is the point at which the Linker is attached.

V. PDGFRα dTAG Targeting Ligands:

PDGFRα dTAG Targeting Ligands as used herein include, but are not limited to:
1. Targeting Ligands that target T674I mutant PDGFRα, including AG-1478, CHEMBL94431, Dovitinib, erlotinib, gefitinib, imatinib, Janex 1, Pazopanib, PD153035, Sorafenib, Sunitinib, WHI-P180:

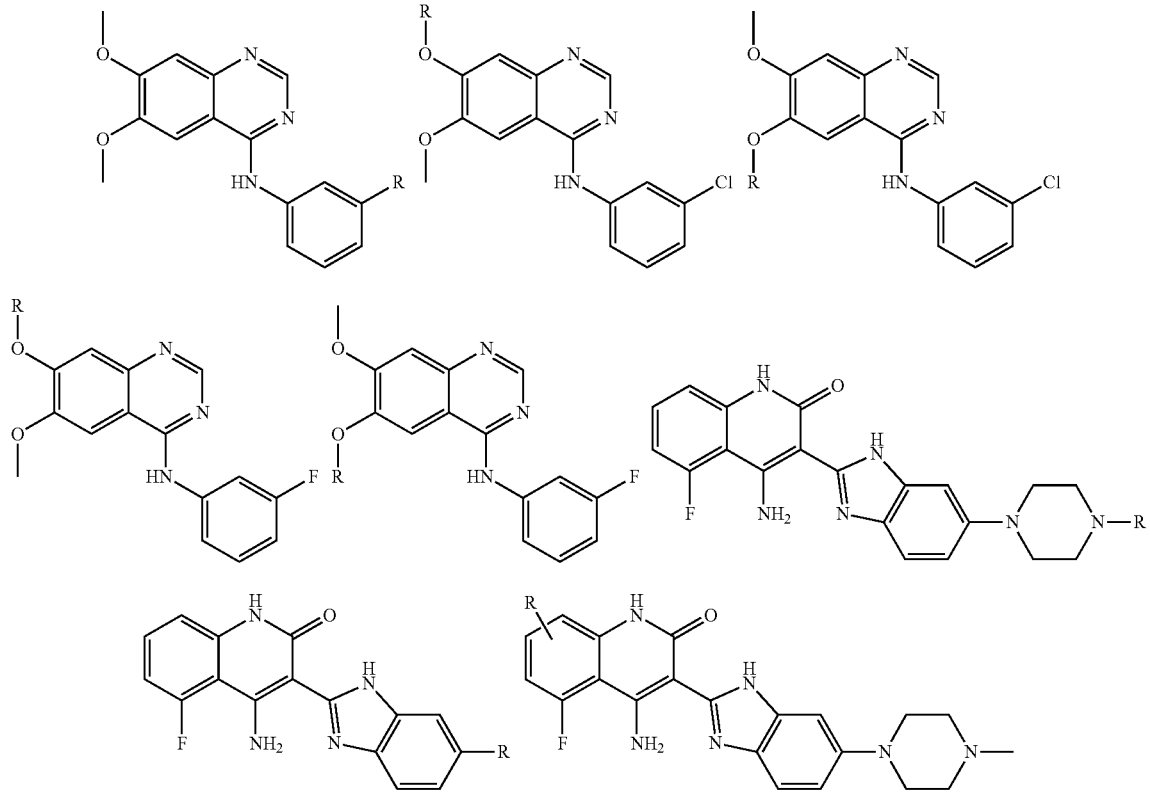

TABLE T-continued
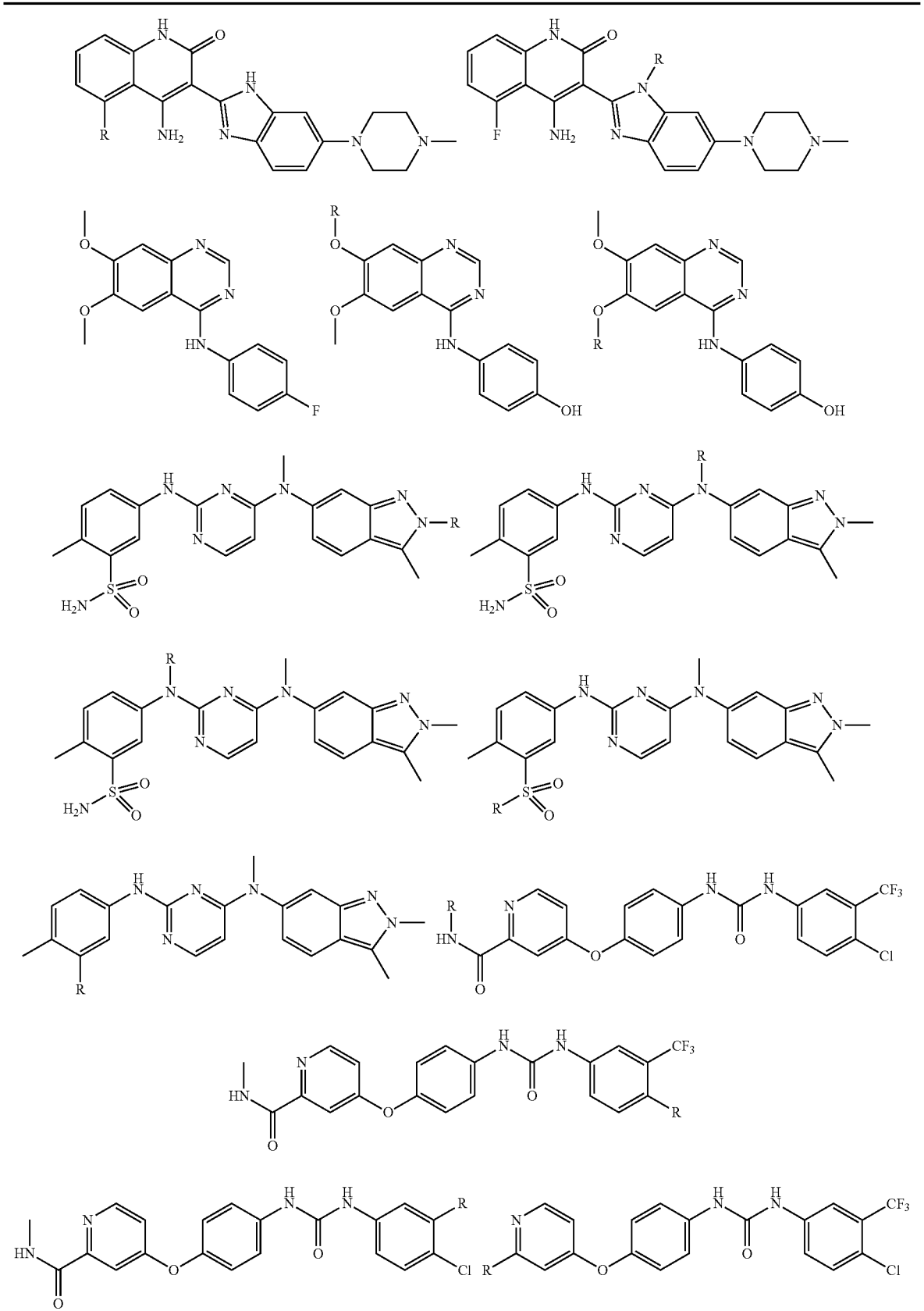

TABLE T-continued
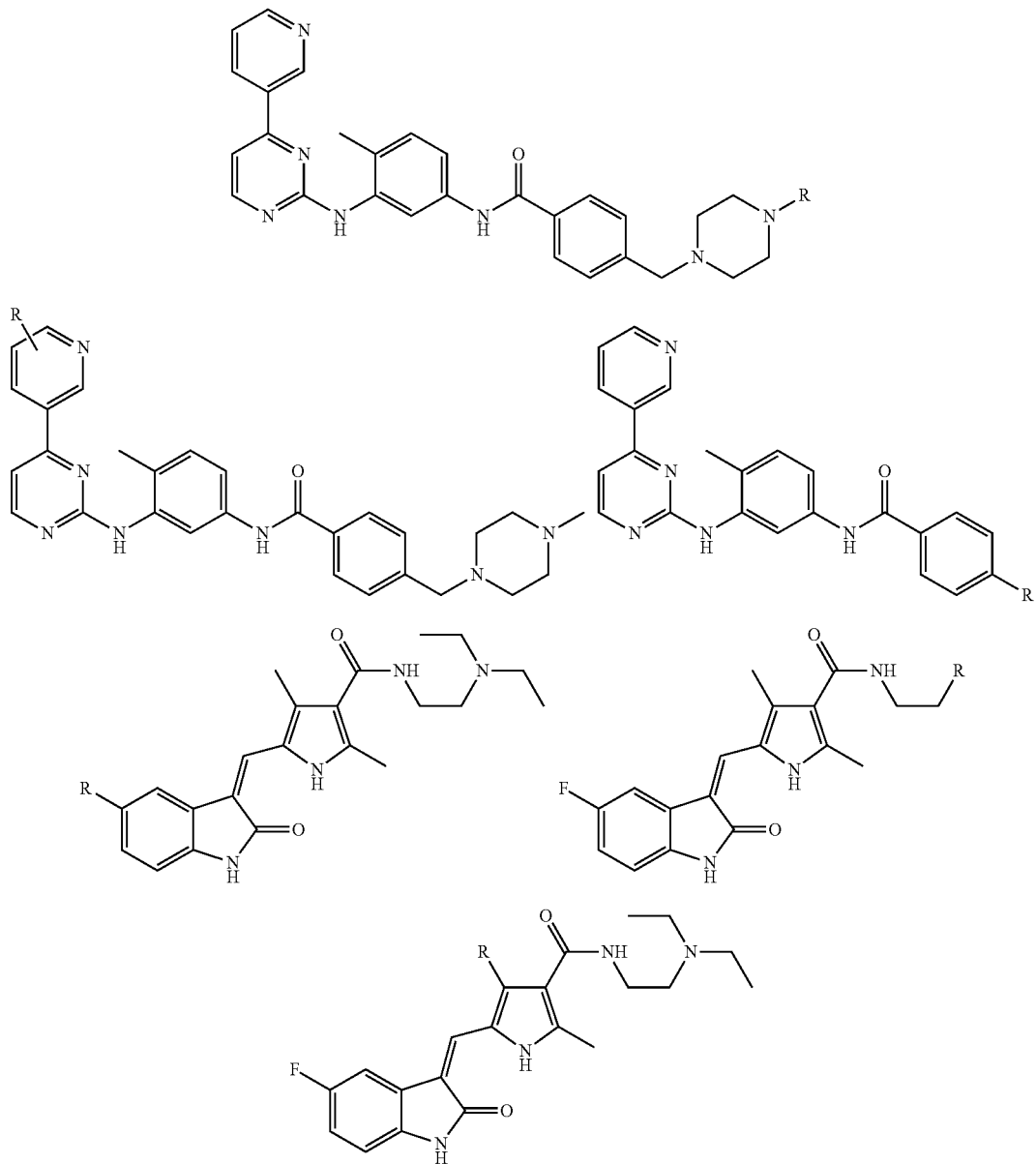
wherein:
R is the point at which the Linker is attached.
W. RET dTAG Targeting Ligands:
RET dTAG Targeting Ligands as used herein include, but are not limited to:
1. Targeting Ligands that target G691S mutant RET, including tozasertib
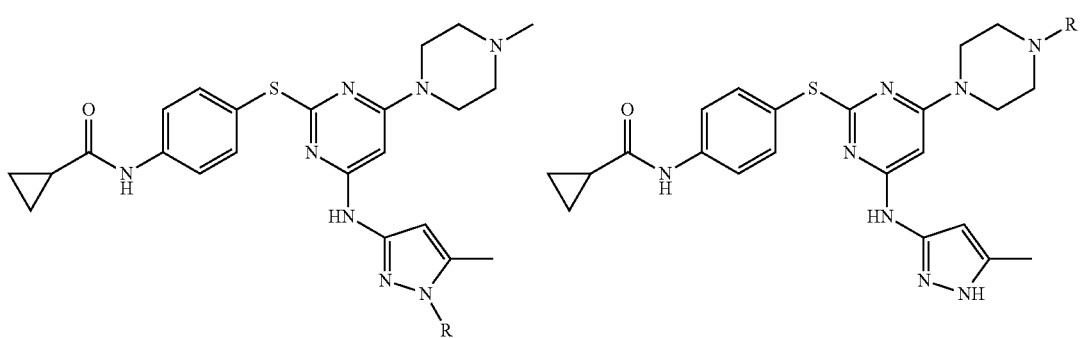

TABLE T-continued
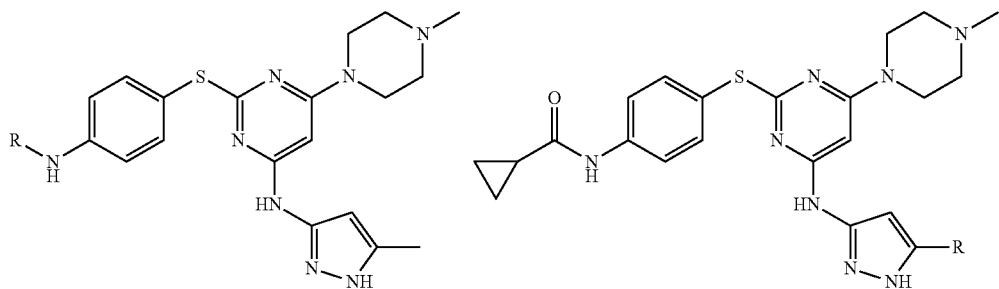
wherein:
R is the point at which the Linker is attached.
2. Targeting Ligands that target R749T mutant RET, including tozasertib
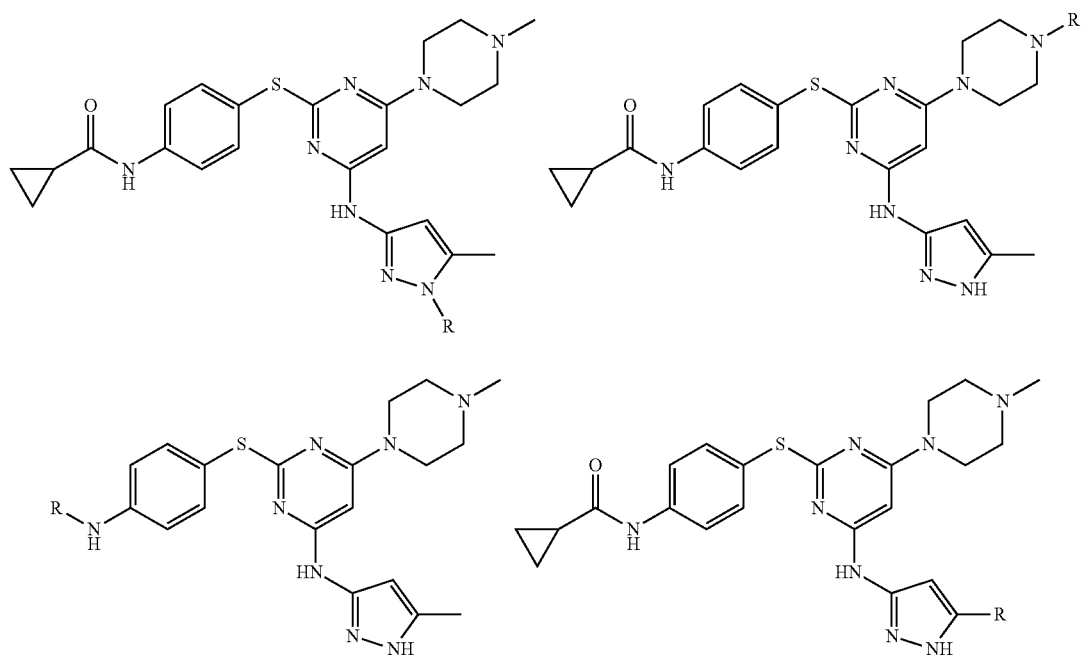
wherein:
R is the point at which the Linker is attached.
3. Targeting Ligands that target E762Q mutant RET, including tozasertib
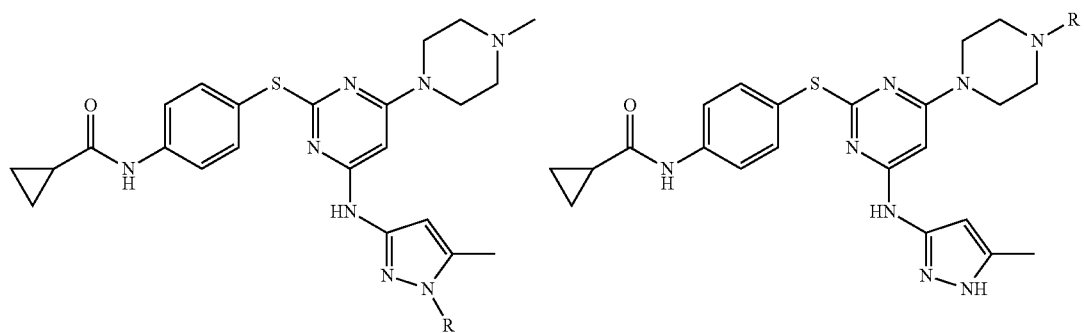

TABLE T-continued
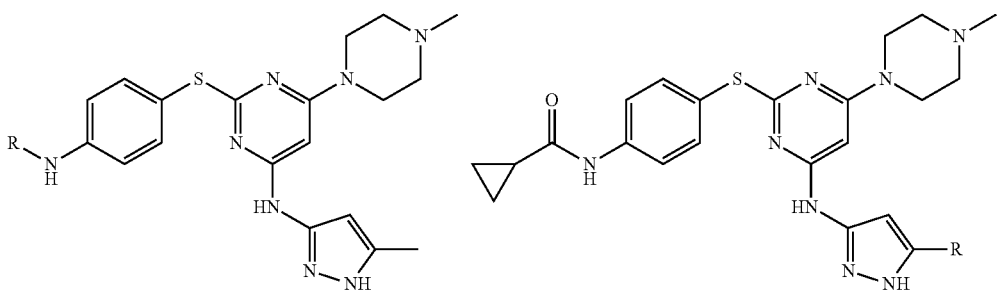
wherein:
R is the point at which the Linker is attached.
4. Targeting Ligands that target Y791F mutant RET, including tozasertib
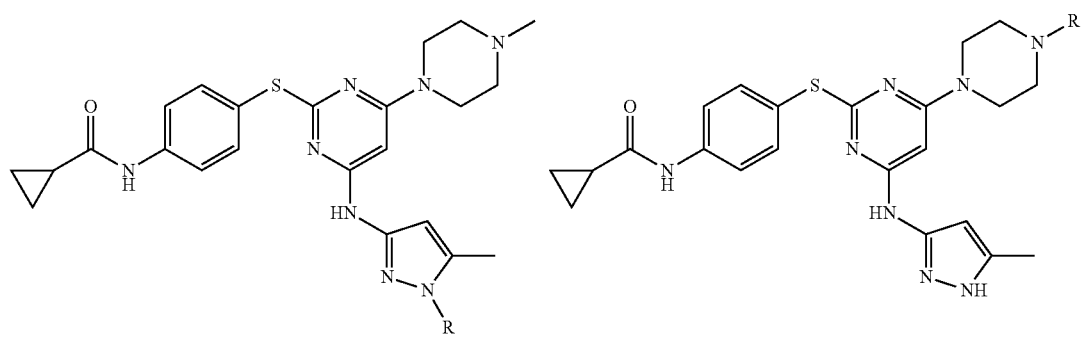
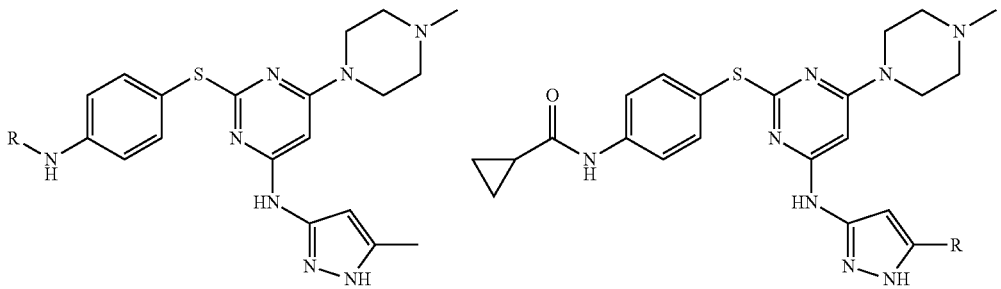
wherein:
R is the point at which the Linker is attached.
5. Targeting Ligands that target V804M mutant RET, including tozasertib
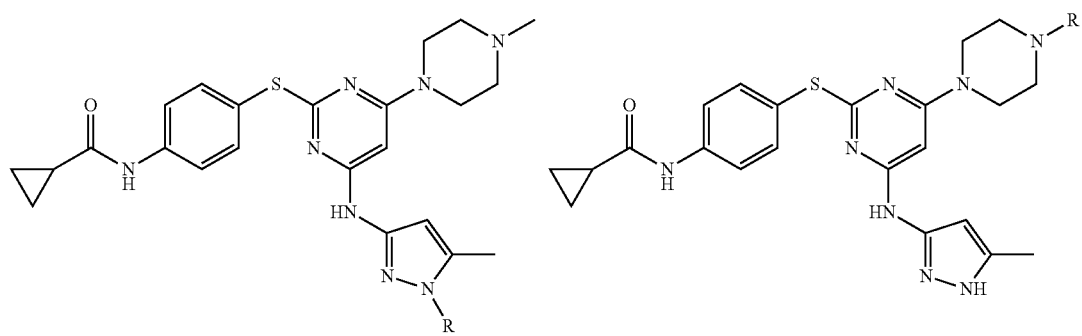

TABLE T-continued

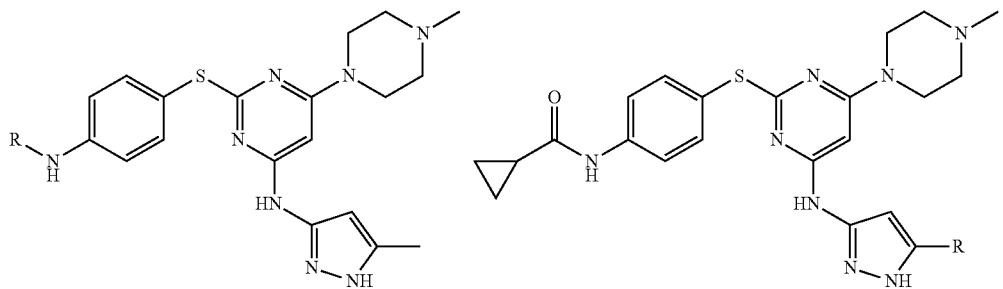

wherein:
R is the point at which the Linker is attached.
6. Targeting Ligands that target M918T mutant RET, including tozasertib

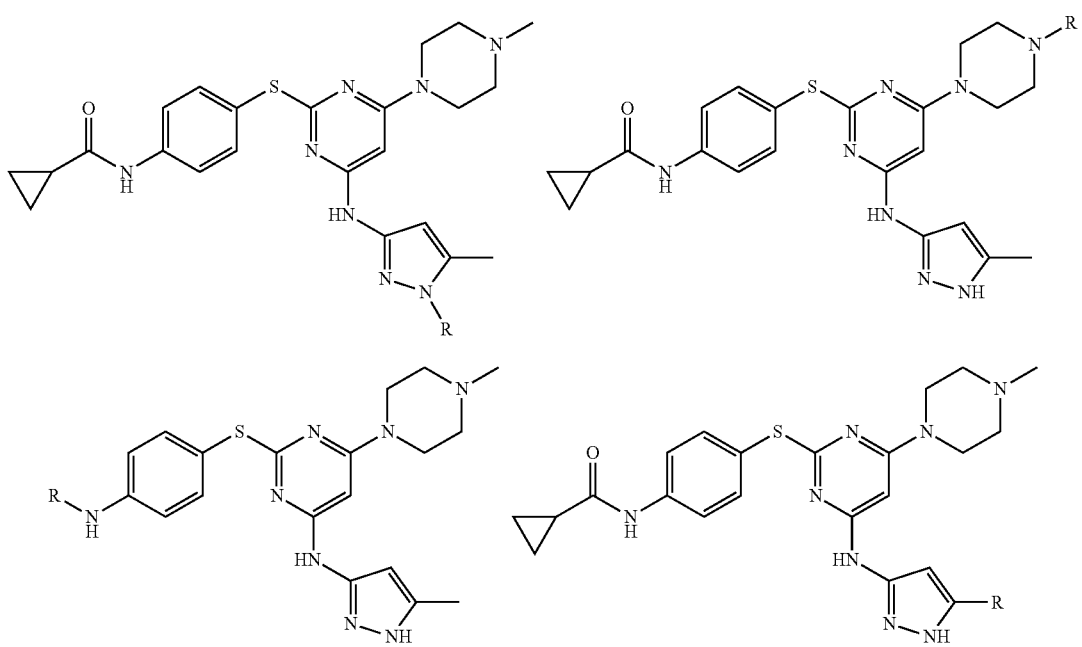

wherein:
R is the point at which the Linker is attached.

X. Heat Shock Protein 90 (HSP90) dTAG Targeting Ligands:

Heat Shock Protein 90 (HSP90) dTAG Targeting Ligands as used herein include, but are not limited to:
1. The HSP90 inhibitors identified in Vallee, et al., "Tricyclic Series of Heat Shock Protein 90 (HSP90) Inhibitors Part I: Discovery of Tricyclic Imidazo[4,5-C]Pyridines as Potent Inhibitors of the HSP90 Molecular Chaperone (2011) J. Med. Chem. 54: 7206, including YKB (N-[4-(3H-imidazo[4,5-C]Pyridin-2-yl)-9H-Fluoren-9-yl]-succinamide):

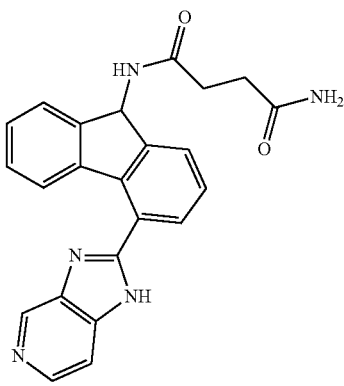 [SMILES: NC(=O)CCC(=O)NC1c2ccccc2-c2c(-c3nc4cnccc4[nH]3)cccc21]

derivatized where a Linker group L or a —(L-DEGRON) group is attached, for example, via the terminal amide group;

2. The HSP90 inhibitor p54 (modified) (8-[(2,4-dimethylphenyl)sulfanyl]-3]pent-4-yn-1-yl-3H-purin-6-amine):

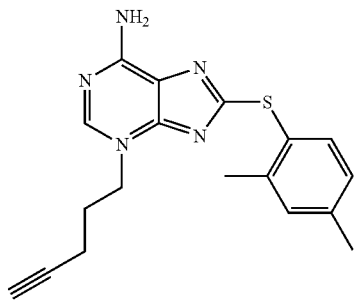

derivatized where a Linker group L or a —(L-DEGRON) group is attached, for example, via the terminal acetylene group;

3. The HSP90 inhibitors (modified) identified in Brough, et al., "4,5-Diarylisoxazole HSP90 Chaperone Inhibitors: Potential Therapeutic Agents for the Treatment of Cancer", J. MED. CHEM. vol: 51, page: 196 (2008), including the compound 2GJ (5-[2,4-dihydroxy-5-(1-methylethyl)phenyl]-n-ethyl-4-[4-(morpholin-4-ylmethyl)phenyl]isoxazole-3-carboxamide) having the structure:

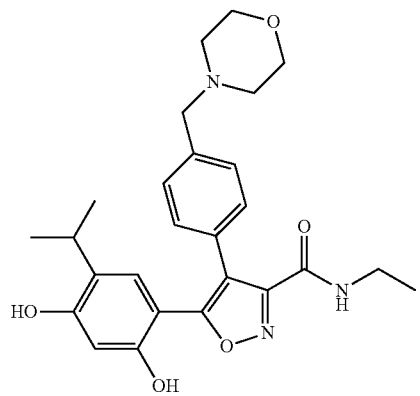 [SMILES: CCNC(=O)c1noc(-c2cc(C(C)C)c(O)cc2O)c1-c1ccc(CN2CCOCC2)cc1]

derivatized, where a Linker group L or a —(L-DEGRON) group is attached, for example, via the amide group (at the amine or at the alkyl group on the amine);

4. The HSP90 inhibitors (modified) identified in Wright, et al., Structure-Activity Relationships in Purine-Based Inhibitor Binding to HSP90 Isoforms, Chem Biol. 2004 June; 11(6):775-85, including the HSP90 inhibitor PU3 having the structure:

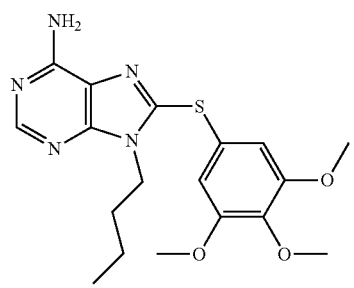 [SMILES: CCCCn1c(Sc2cc(OC)c(OC)c(OC)c2)nc2c(N)ncnc21]

derivatized where a Linker group L or —(L-DEGRON) is attached, for example, via the butyl group; and 5. The HSP90 inhibitor geldanamycin ((4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1](derivatized) or any of its derivatives (e.g. 17-alkylamino-17-desmethoxygeldanamycin ("17-AAG") or 17-(2-dimethylaminoethyl)amino-17-desmethoxygeldanamycin ("17-DMAG")) (derivatized, where a Linker group L or a —(L-DEGRON) group is attached, for example, via the amide group).

TABLE T-continued

Y. Kinase and Phosphatase dTAG Targeting Ligands:

Kinase and Phosphatase dTAG Targeting Ligands as used herein include, but are not limited to:

1. Erlotinib Derivative Tyrosine Kinase Inhibitor:

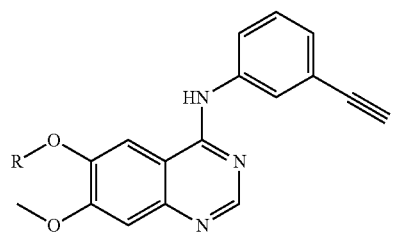

where R is a Linker group L or a —(L-DEGRON) group attached, for example, via the ether group;

2. The kinase inhibitor sunitinib (derivatized):

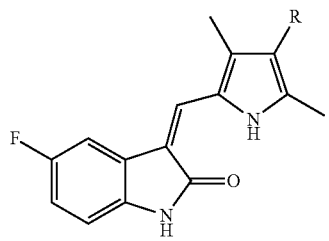

derivatized where R is a Linker group L or a —(L-DEGRON) group attached, for example, to the pyrrole moiety;

3. Kinase Inhibitor sorafenib (derivatized):

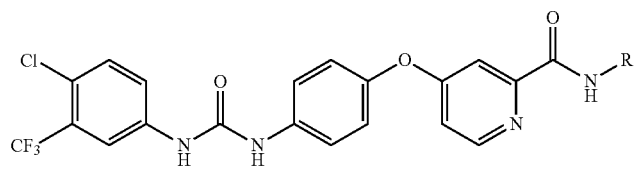

derivatized where R is a Linker group L or a —(L-DEGRON) group attached, for example, to the amide moiety;

4. The kinase inhibitor desatinib (derivatized):

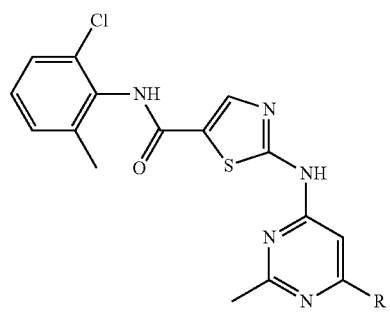

derivatized where R is a Linker group L or a —(L-DEGRON) attached, for example, to the pyrimidine;

TABLE T-continued

5. The kinase inhibitor lapatinib (derivatized):

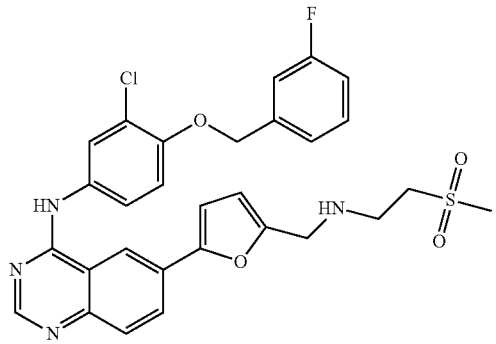 [SMILES: CS(=O)(=O)CCNCc1ccc(-c2ccc3ncnc(Nc4ccc(OCc5cccc(F)c5)c(Cl)c4)c3c2)o1]

derivatized where a Linker group L or a —(L-DEGRON) group is attached, for example, via the terminal methyl of the sulfonyl methyl group;

6. The kinase inhibitor U09-CX-5279 (derivatized):

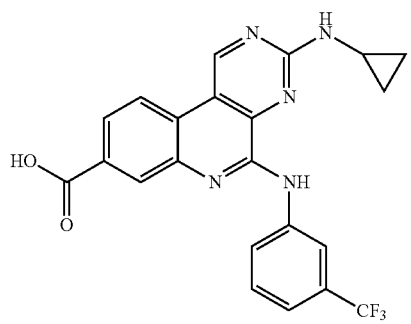 [SMILES: O=C(O)c1ccc2c(c1)nc(Nc1cccc(C(F)(F)F)c1)c1nc(NC3CC3)ncc12]

derivatized where a Linker group L or a —(L-DEGRON) group is attached, for example, via the amine (aniline), carboxylic acid or amine alpha to cyclopropyl group, or cyclopropyl group;

7. The kinase inhibitors identified in Millan, et al., Design and Synthesis of Inhaled P38 Inhibitors for the Treatment of Chronic Obstructive Pulmonary Disease, J. MED. CHEM. vol:54, page: 7797 (2011), including the kinase inhibitors Y1W and Y1X (Derivatized) having the structures:

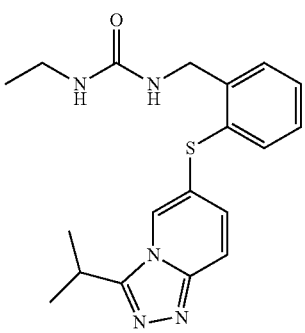 [SMILES: CCNC(=O)NCc1ccccc1Sc1ccc2nnc(C(C)C)n2c1]

YIX(1-ethyl-3-(2-{[3 -(1-methylethyl)[1,2,4]triazolo[4,3-a]pyridine-6-yl]sulfanyl}benzyl)urea, derivatized where a Linker group L or a —(L-DEGRON) group is attached, for example, via the i-propyl group;

TABLE T-continued

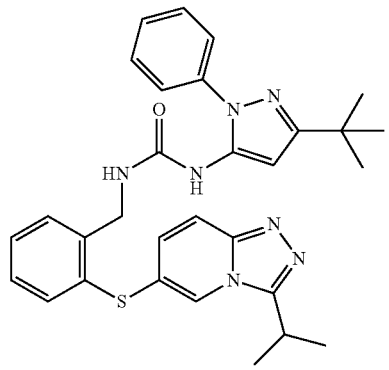 [SMILES: CC(C)c1nnc2ccc(Sc3ccccc3CNC(=O)Nc3cc(C(C)(C)C)nn3-c3ccccc3)cn12]

YIW 1-(3-tert-butyl-1-phenyl-1H-pyrazol-5-yl)-3-(2-{[3-(1-methylethyl)[1,2,4]triazolo[4,3-a]pyridin-6-yl]sulfanyl}benzyl)urea
derivatized where a Linker group L or a —(L-DEGRON) group is attached, for example, preferably via either the i-propyl group or the t-butyl group;

8. The kinase inhibitors identified in Schenkel, et al., Discovery of Potent and Highly Selective Thienopyridine Janus Kinase 2 Inhibitors J. Med. Chem., 2011, 54 (24), pp 8440-8450, including the compounds 6TP and 0TP (Derivatized) having the structures:

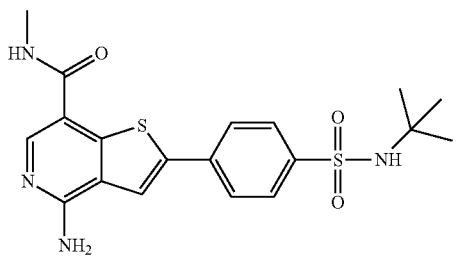 [SMILES: CNC(=O)c1cnc(N)c2cc(-c3ccc(S(=O)(=O)NC(C)(C)C)cc3)sc12]

6TP 4-amino-2-[4-(tert-butylsulfamoyl)phenyl]-N-methylthieno[3,2-c]pyridine-7-carboxamide
Thienopyridine 19
derivatized where a Linker group L or a —(L-DEGRON) group is attached, for example, via the terminal methyl group bound to amide moiety;

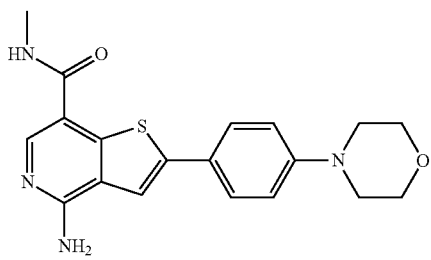 [SMILES: CNC(=O)c1cnc(N)c2cc(-c3ccc(N4CCOCC4)cc3)sc12]

0TP 4-amino-N-methyl-2-[4-(morpholin-4-yl)phenyl]thieno[3,2-c]pyridine-7-carboxamide
Thienopyridine 8
derivatized where a Linker group L or a —(L-DEGRON) group is attached, for example, via the terminal methyl group bound to the amide moiety;

TABLE T-continued

9. The kinase inhibitors identified in Van Eis, et al., "2,6-Naphthyridines as potent and selective inhibitors of the novel protein kinase C isozymes", Biorg. Med. Chem. Lett. 2011 Dec. 15; 21(24):7367-72, including the kinase inhibitor 07U having the structure:

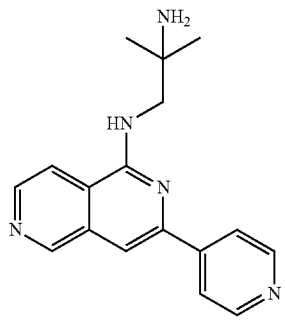 [SMILES: CC(C)(N)CNc1nc(-c2ccncc2)cc2cnccc12]

07U 2-methyl -N⁻1⁻[3-(pyridin-4-yl)-2,6-naphthyridin-1-yl]propane-1,2-diamine
derivatized where a Linker group L or a —(L-DEGRON) group is attached, for example, via the secondary amine or terminal amino group;

10. The kinase inhibitors identified in Lountos, et al., "Structural Characterization of Inhibitor Complexes with Checkpoint Kinase 2 (Chk2), a Drug Target for Cancer Therapy", J. STRUCT. BIOL. vol:176, pag: 292 (2011), including the kinase inhibitor YCF having the structure:

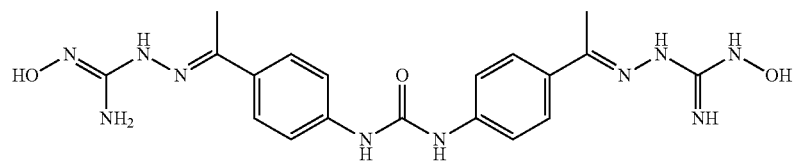 [SMILES: C/C(=N\NC(=N)NO)c1ccc(NC(=O)Nc2ccc(/C(C)=N/N/C(N)=N/O)cc2)cc1]

derivatized where a Linker group L or a —(L-DEGRON) group is attached, for example, via either of the terminal hydroxyl groups;

11. The kinase inhibitors identified in Lountos, et al., "Structural Characterization of Inhibitor Complexes with Checkpoint Kinase 2 (Chk2), a Drug Target for Cancer Therapy", J. STRUCT. BIOL. vol:176, pag: 292 (2011), including the kinase inhibitors XK9 and NXP (derivatized) having the structures:

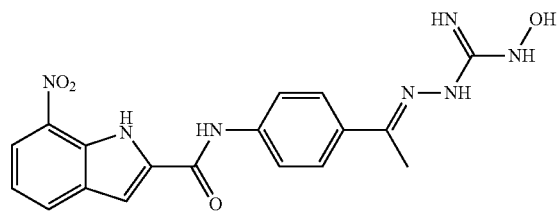 [SMILES: C/C(=N\NC(=N)NO)c1ccc(NC(=O)c2cc3cccc([N+](=O)[O-])c3[nH]2)cc1]

XK9

N-{4-[(1E)-N-(N-hydroxycarbamimidoyl)ethanehydrazonoyl]phenyl}-7-nitro-1H-indole-2-carboxamide

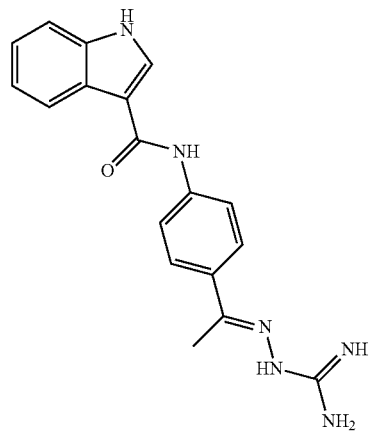 [SMILES: C/C(=N\NC(=N)N)c1ccc(NC(=O)c2c[nH]c3ccccc23)cc1]

NXP

N-{4-[(1E)-N-CARBAMIMIDOYLETHANEHYDRAZONOYL]PHENYL}-1H-INDOLE-3-CARBOXAMIDE
derivatized where a Linker group L or a —(L-DEGRON) group is attached, for example, via the terminal hydroxyl group (XK9) or the hydrazone group (NXP);

12. The kinase inhibitor afatinib (derivatized) (N-[4-[(3-chloro-4-fluorophenyl)amino]-7-[[(3S)-tetrahydro-3-furanyl]oxy]-6-quinazolinyl]-4(dimethylamino)-2-butenamide) (Derivatized where a Linker group L or a —(L-DEGRON) group is attached, for example, via the aliphatic amine group);

13. The kinase inhibitor fostamatinib (derivatized) ([6-({5-fluoro-2-[(3,4,5-trimethoxyphenyl)amino]pyrimidin-4-yl}amino)-2,2-dimethyl-3-oxo-2,3-dihydro-4H-pyrido[3,2-b]-1,4-oxazin-4-yl]methyl disodium phosphate hexahydrate) (Derivatized where a Linker group L or a —(L-DEGRON) group is attached, for example, via a methoxy group);

14. The kinase inhibitor gefitinib (derivatized) (N-(3-chloro-4-fluoro-phenyl)-7-methoxy-6-(3-morpholin-4-ylpropoxy)quinazolin-4-amine):

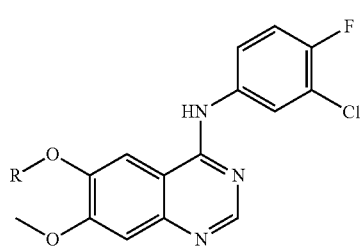

derivatized where a Linker group L or a —(L-DEGRON) group is attached, for example, via a methoxy or ether group;

15. The kinase inhibitor lenvatinib (derivatized) (4-[3-chloro-4-(cyclopropylcarbamoylamino)phenoxy]-7-methoxy-quinoline-6-carboxamide) (derivatized where a Linker group L or a —(L-DEGRON) group is attached, for example, via the cyclopropyl group);

16. The kinase inhibitor vandetanib (derivatized) (N-(4-bromo-2-fluorophenyl)-6-methoxy-7-[1-methylpiperidin-4-yl)methoxy]quinazolin-4-amine) (derivatized where a Linker group L or a —(L-DEGRON) group is attached, for example, via the methoxy or hydroxyl group);

17. The kinase inhibitor vemurafenib (derivatized) (propane-1-sulfonic acid {3-[5-(4-chlorophenyl)-1H-pyrrolo[2,3-b]pyridine-3-carbonyl]-2,4-difluoro-phenyl}-amide), derivatized where a Linker group L or a —(L-DEGRON) group is attached, for example, via the sulfonyl propyl group;

18. The kinase inhibitor Gleevec (derivatized):

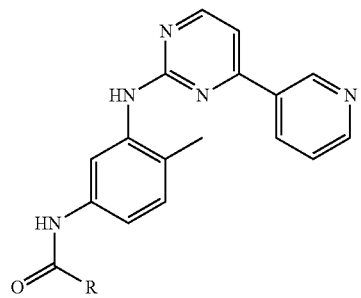

derivatized where R as a Linker group L or a —(L-DEGRON) group is attached, for example, via the amide group or via the aniline amine group;

19. The kinase inhibitor pazopanib (derivatized) (VEGFR3 inhibitor):

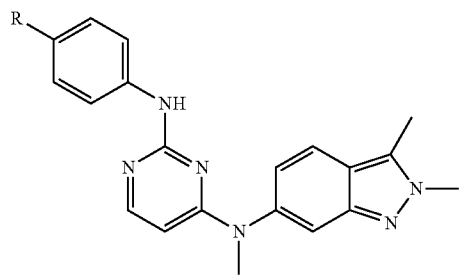

derivatized where R is a Linker group L or a —(L-DEGRON) group attached, for example, to the phenyl moiety or via the aniline amine group;

TABLE T-continued

20. The kinase inhibitor AT-9283 (Derivatized) Aurora Kinase Inhibitor

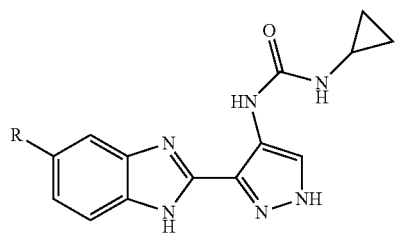

where R is a Linker group L or a —(L-DEGRON) group attached, for example, to the phenyl moiety);

21. The kinase inhibitor TAE684 (derivatized) ALK inhibitor

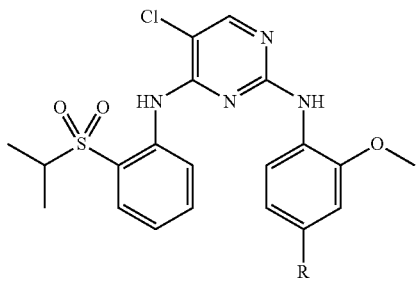

where R is a Linker group L or a —(L-DEGRON) group attached, for example, to the phenyl moiety);

22. The kinase inhibitor nilotanib (derivatized) Abl inhibitor:

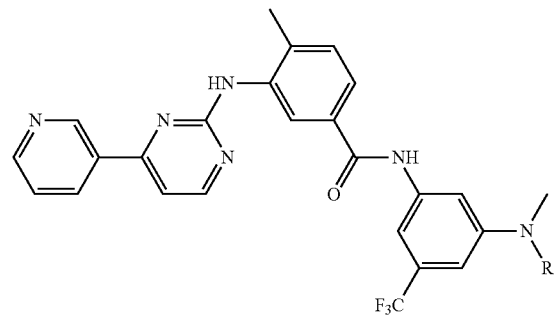

derivatized where R is a Linker group L or a —(L-DEGRON) group attached, for example, to the phenyl moiety or the aniline amine group;

23. Kinase Inhibitor NVP-BSK805 (derivatized) JAK Inhibitor

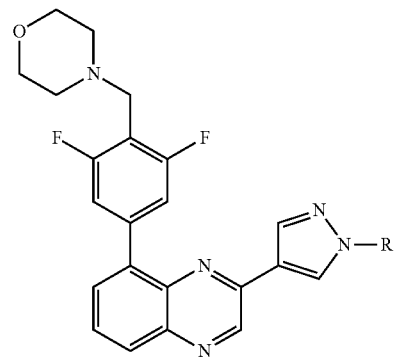

derivatized where R is a Linker group L or a —(L-DEGRON) group attached, for example, to the phenyl moiety or the diazole group;

24. Kinase Inhibitor crizotinib Derivatized Alk Inhibitor

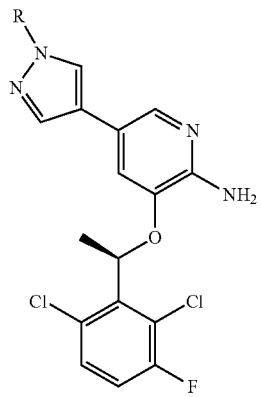

derivatized where R is a Linker group L or a —(L-DEGRON) group attached, for example, to the phenyl moiety or the diazole group;

25. Kinase Inhibitor JNJ FMS (derivatized) Inhibitor

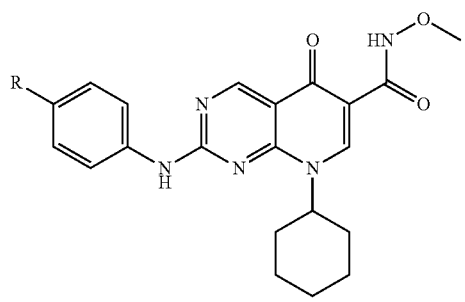

derivatized where R is a Linker group L or a —(L-DEGRON) group attached, for example, to the phenyl moiety;

26. The kinase inhibitor foretinib (derivatized) Met Inhibitor

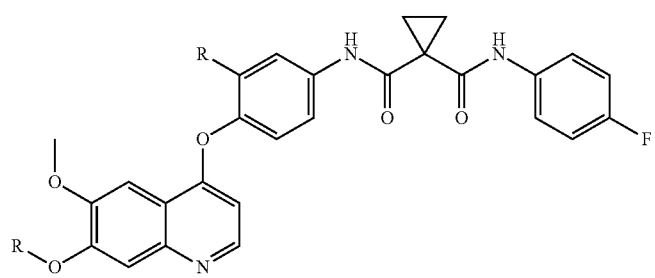

derivatized where R is a Linker group L or a —(L-DEGRON) group attached, for example, to the phenyl moiety or a hydroxyl or ether group on the quinoline moiety;

TABLE T-continued

27. The allosteric Protein Tyrosine Phosphatase Inhibitor PTP1B (derivatized):

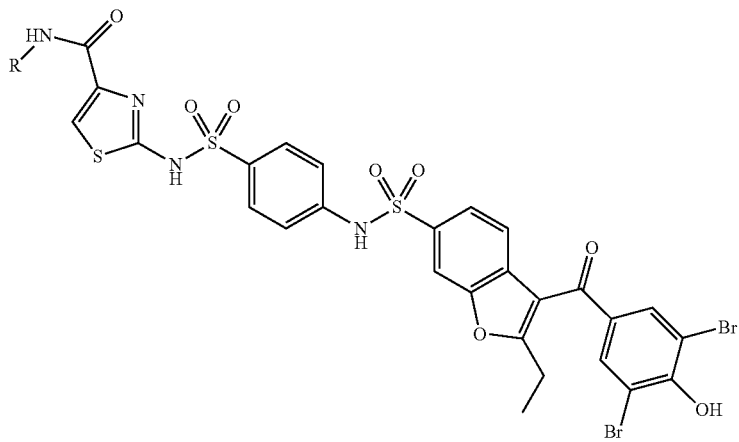

derivatized where a Linker group L or a —(L-DEGRON) group is attached, for example, at R, as indicated;

28. The inhibitor of SHP-2 Domain of Tyrosine Phosphatase (derivatized):

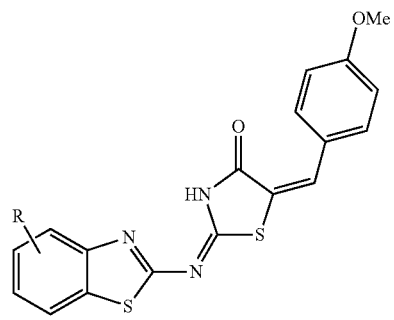

derivatized where a Linker group L or a —(L-DEGRON) group is attached, for example, at R;

29. The inhibitor (derivatized) of BRAF (BRAFV600E)/MEK:

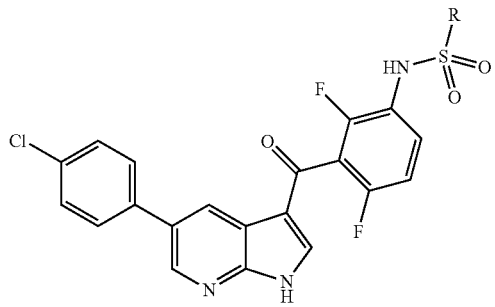

derivatized where a Linker group L or a —(L-DEGRON) group is attached, for example, at R;

30. Inhibitor (derivatized) of Tyrosine Kinase ABL

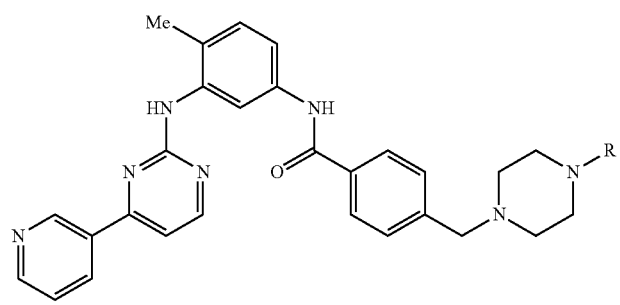

derivatized where where a Linker group L or a —(L-DEGRON) group is attached, for example, at R;

TABLE T-continued

31. The kinase inhibitor OSI-027 (derivatized) mTORC1/2 inhibitor

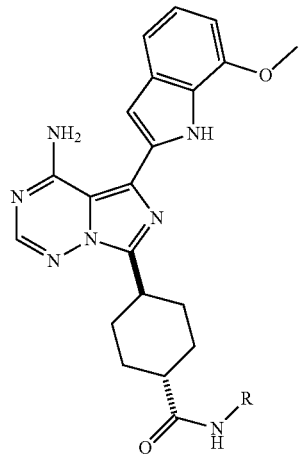

derivatized where a Linker group L or a —(L-DEGRON) group is attached, for example, at R;

32. The kinase inhibitor OSI-930 (derivatized) c-Kit/KDR inhibitor

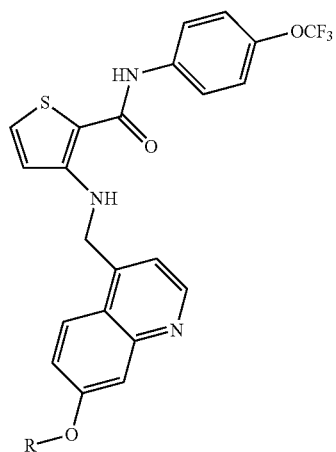

derivatized where a Linker group L or a —(L-DEGRON) group is attached, for example, at R; and 33. The kinase inhibitor OSI-906 (derivatized) IGF1R/IR inhibitor

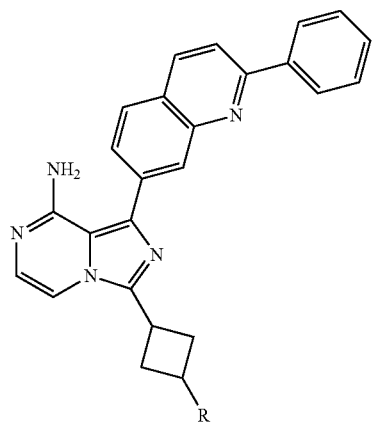

derivatized where a Linker group L or a —(L-DEGRON) group is attached, for example, at R.
Wherein, in any of the embodiments described in sections I-XVII, "R" designates a site for attachment of a Linker group L or a —(L-DEGRON) group on the piperazine moiety.

TABLE T-continued

Z. HDM2 and/or MDM2 dTAG Targeting Ligands:

HDM2 and/or MDM2 dTAG Targeting Ligands as used herein include, but are not limited to:
1. The HDM2/MDM2 inhibitors identified in Vassilev, et al., In vivo activation of the p53 pathway by small-molecule antagonists of MDM2, SCIENCE vol:303, pag: 844-848 (2004), and Schneekloth, et al., Targeted intracellular protein degradation induced by a small molecule: En route to chemical proteomics, Bioorg. Med. Chem. Lett. 18 (2008) 5904-5908, including (or additionally) the compounds nutlin-3, nutlin-2, and nutlin-1 (derivatized) as described below, as well as all derivatives and analogs thereof:

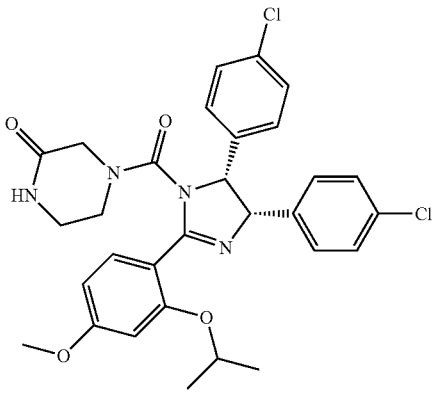 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a Linker group L or a —(L-DEGRON) group is attached, for example, at the methoxy group or as a hydroxyl group);

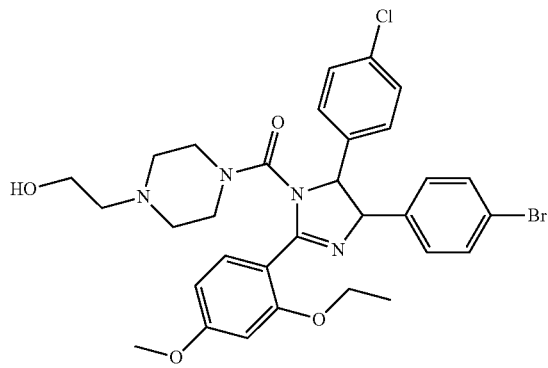 [SMILES: CCOc1cc(OC)ccc1C1=NC(c2ccc(Br)cc2)C(c2ccc(Cl)cc2)N1C(=O)N1CCN(CCO)CC1]

(derivatized where a Linker group L or a —(L-DEGRON) group is attached, for example, at the methoxy group or hydroxyl group);

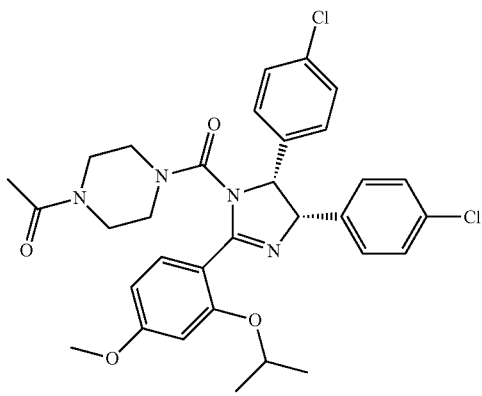 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a Linker group L or a —(L-DEGRON) group is attached, for example, via the methoxy group or as a hydroxyl group); and TABLE T-continued 2. Trans-4-Iodo-4'-Boranyl-Chalcone

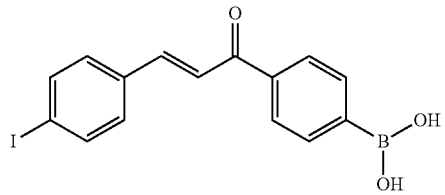 [SMILES: O=C(/C=C/c1ccc(I)cc1)c1ccc(B(O)O)cc1]

(derivatized where a Linker group L or a Linker group L or a —(L-DEGRON) group is attached,
for example, via a hydroxy group).

AA. Human BET Bromodomain-Containing Proteins dTAG Targeting Ligands:

In certain embodiments, "dTAG Targeting Ligand" can be ligands binding to Bromo- and Extra-terminal (BET) proteins BRD2, BRD3 and BRD4. Compounds targeting Human BET Bromodomain-containing proteins include, but are not limited to the compounds associated with the targets as described below, where "R" or "Linker" designates a site for Linker group L or a —(L-DEGRON) group attachment, for example:

1. JQ1, Filippakopoulos et al. Selective inhibition of BET bromodomains. Nature (2010):

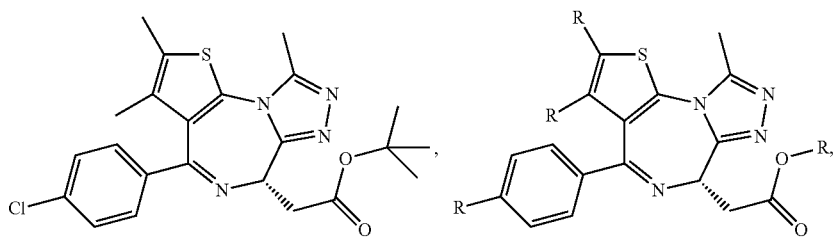

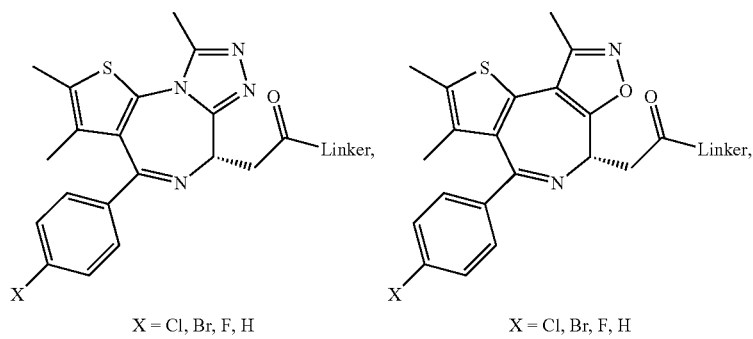

X = Cl, Br, F, H           X = Cl, Br, F, H

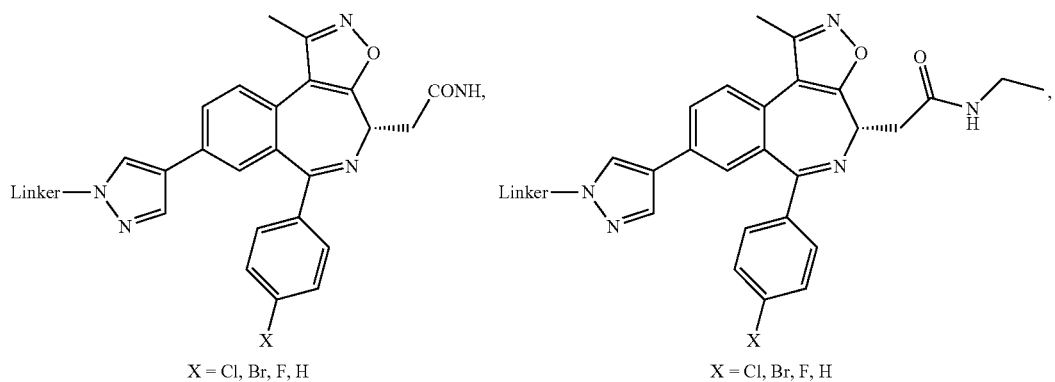

X = Cl, Br, F, H           X = Cl, Br, F, H

TABLE T-continued

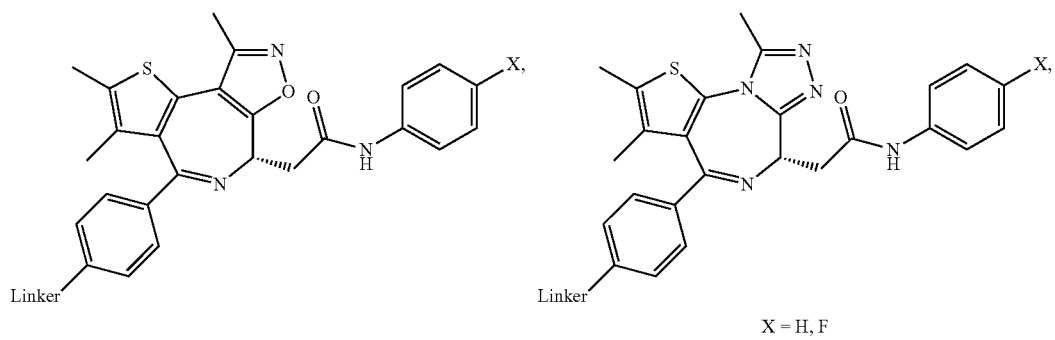

X = H, F

2. I-BET, Nicodeme et al. Suppression of Inflammation by a Synthetic Histone Mimic. Nature (2010). Chung et al. Discovery and Characterization of Small Molecule Inhibitors of the BET Family Bromodomains. J. Med Chem. (2011):

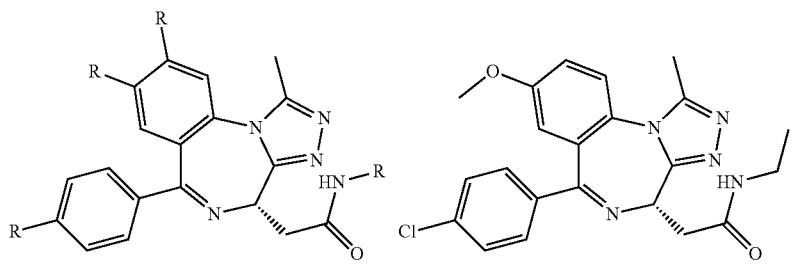

3. Compounds described in Hewings et al. 3,5-Dimethylisoxazoles Act as Acetyl-lysine Bromodomain Ligands. J Med. Chem (2011) 54 6761-6770.

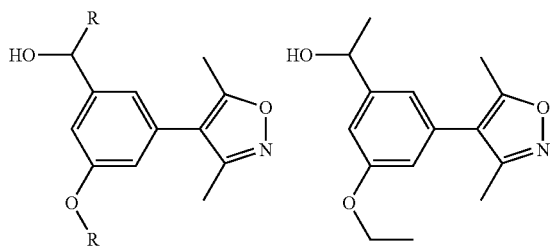

4. I-BET151, Dawson et al. Inhibition of BET Recruitment to Chromatin as an Effective Treatment for MLL-fusion Leukemia. Nature (2011):

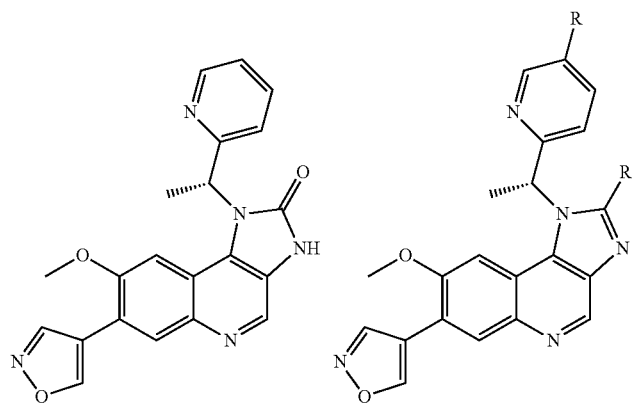

TABLE T-continued
5. Carbazole type (US 2015/0256700)
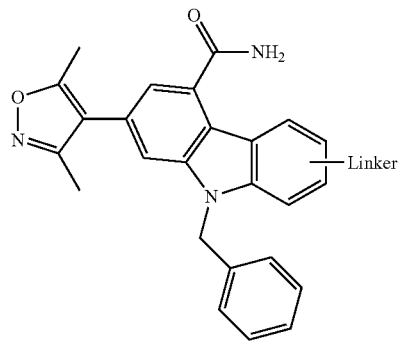
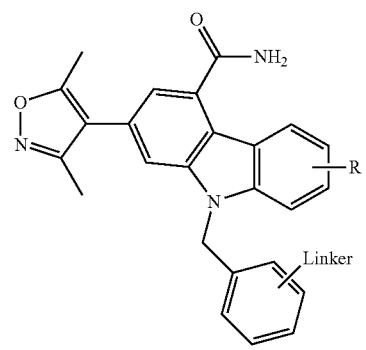
6. Pyrrolopyridone type (US 2015/0148342)
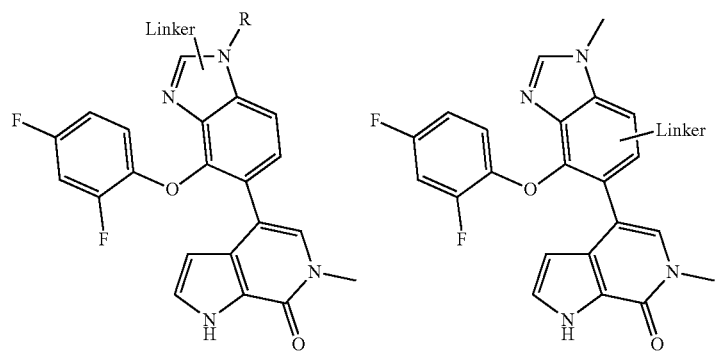
7. Tetrahydroquinoline type (WO 2015/074064)
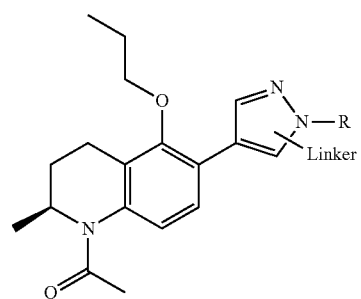

TABLE T-continued
8. Triazolopyrazine type (WO 2015/067770)
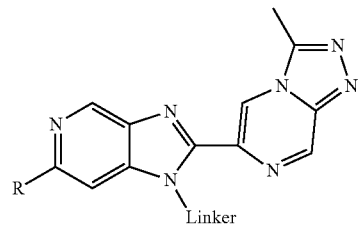
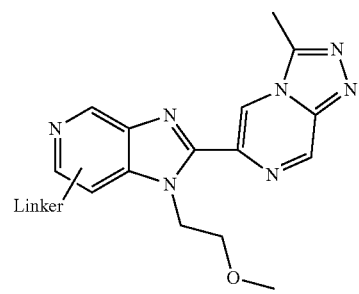
9. Pyridone type (WO 2015/022332)
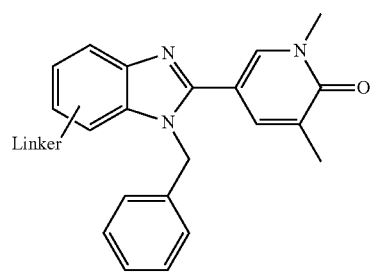
10. Quinazolinone type (WO 2015/015318)
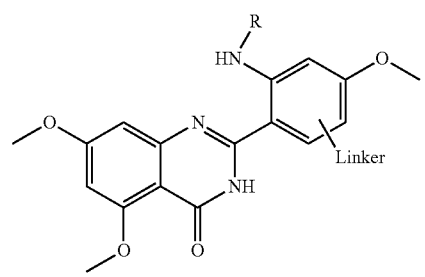

TABLE T-continued

11. Dihydropyridopyrazinone type (WO 2015/011084)

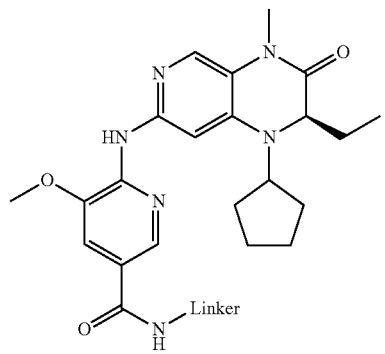

(Where R or L or Linker, in each instance, designates a site for attachment, for example, of a Linker group L or a —(L-DEGRON) group).

BB. HDAC dTAG Targeting Ligands:

HDAC dTAG Targeting Ligands as used herein include, but are not limited to:

1. Finnin, M. S. et al. Structures of Histone Deacetylase Homologue Bound to the TSA and SAHA Inhibitors. Nature 40, 188-193 (1999).

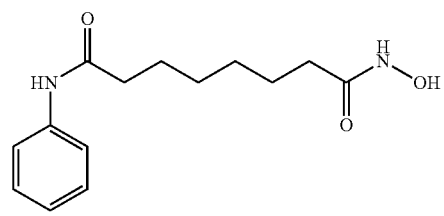 [SMILES: O=C(CCCCCCC(=O)Nc1ccccc1)NO]

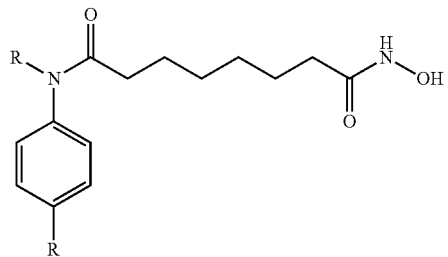

(Derivatized where "R" designates a site for attachment, for example, of a Linker group L or a —(L-DEGRON) group); and TABLE T-continued 2. Compounds as defined by formula (I) of PCT WO0222577 ("DEACETYLASE INHIBITORS") (Derivatized where a Linker group L or a —(L-DEGRON) group is attached, for example, via the hydroxyl group);

CC. Human Lysine Methyltransferase dTAG Targeting Ligands:

Human Lysine Methyltransferase dTAG Targeting Ligands as used herein include, but are not limited to:
1. Chang et al. Structural Basis for G9a-Like protein Lysine Methyltransferase Inhibition by BIX-1294. Nat. Struct. Biol. (2009) 16(3) 312.

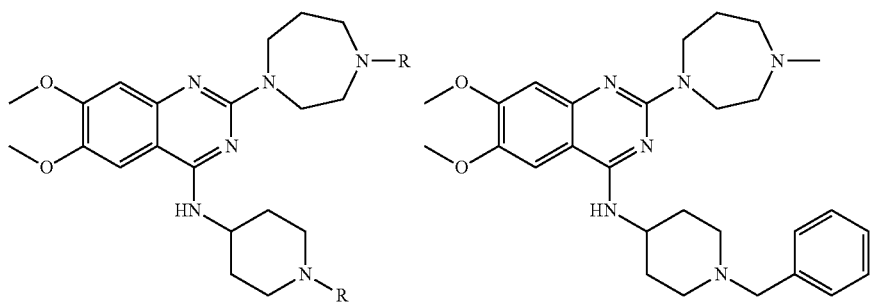

(Derivatized where "R" designates a site for attachment, for example, of a Linker group L or a —(L-DEGRON) group);
2. Liu, F. et al Discovery of a 2,4-Diamino-7-aminoalkoxyquinazoline as a Potent and Selective Inhibitor of Histone Methyltransferase G9a. J. Med. Chem. (2009) 52(24) 7950

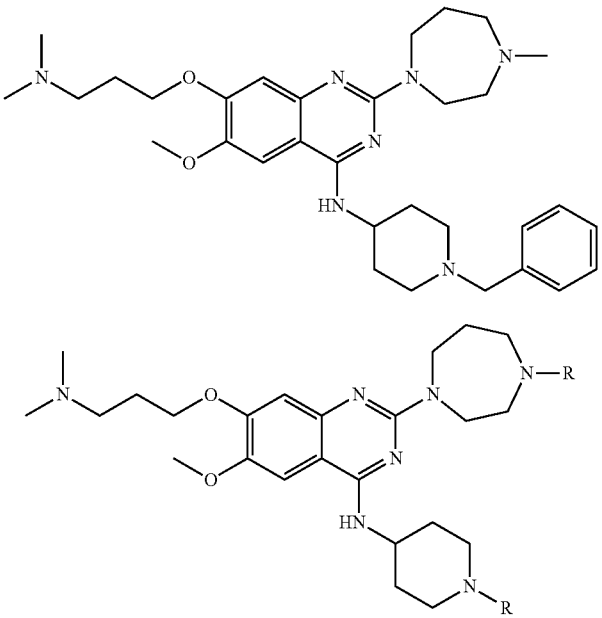

(Derivatized where "R" designates a potential site for attachment, for example, of a Linker group L or a —(L-DEGRON) group);
3. Azacitidine (derivatized) (4-amino-1-(3-D-ribofuranosyl-1,3,5-triazin-2(1H)-one) (Derivatized where a Linker group L or a —(L-DEGRON) group is attached, for example, via the hydroxy or amino groups); and
4. Decitabine (derivatized) (4-amino-1-(2-deoxy-b-D-erythro-pentofuranosyl)-1,3,5-triazin-2(1H)-one) (Derivatized where a Linker group L or a —(L-DEGRON) group is attached, for example, via either of the hydroxy groups or at the amino group).

DD. dTAG targeting ligands organized by functionality

Angiogenesis Inhibitors:
Angiogenesis inhibitors include, but are not limited to:
1. GA-1 (derivatized) and derivatives and analogs thereof, having the structure(s) and binding to Linkers as described in Sakamoto, et al., Development of Protacs to target cancer-promoting proteins for ubiquitination and degradation, Mol Cell Proteomics 2003 December; 2(12):1350-8;
2. Estradiol (derivatized), which may be bound to a Linker group L or a —(L-DEGRON) group as is generally described in Rodriguez-Gonzalez, et al., Targeting steroid hormone receptors for ubiquitination and degradation in breast and prostate cancer, Oncogene (2008) 27, 7201-7211;

TABLE T-continued

3. Estradiol, testosterone (derivatized) and related derivatives, including but not limited to DHT and derivatives and analogs thereof, having the structure(s) and binding to a Linker group L or a —(L-DEGRON) group as generally described in Sakamoto, et al., Development of Protacs to target cancer-promoting proteins for ubiquitination and degradation, Mol Cell Proteomics 2003 December; 2(12):1350-8; and 4. Ovalicin, fumagillin (derivatized), and derivatives and analogs thereof, having the structure(s) and binding to a Linker group L or a —(L-DEGRON) group as is generally described in Sakamoto, et al., Protacs: chimeric molecules that target proteins to the Skpl-Cullin-F box complex for ubiquitination and degradation Proc Natl Acad Sci USA. 2001 Jul. 17; 98(15):8554-9 and U.S. Pat. No. 7,208,157.

Immunosuppressive Compounds:

Immunosuppressive compounds include, but are not limited to:

1. AP21998 (derivatized), having the structure(s) and binding to a Linker group L or a —(L-DEGRON) group as is generally described in Schneekloth, et al., Chemical Genetic Control of Protein Levels: Selective in Vivo Targeted Degradation, J. AM. CHEM. SOC. 2004, 126, 3748-3754;

2. Glucocorticoids (e.g., hydrocortisone, prednisone, prednisolone, and methylprednisolone) (Derivatized where a Linker group L or a —(L-DEGRON) group is to bound, e.g. to any of the hydroxyls) and beclometasone dipropionate (Derivatized where a Linker group or a —(L-DEGRON) is bound, e.g. to a proprionate);

3. Methotrexate (Derivatized where a Linker group or a —(L-DEGRON) group can be bound, e.g. to either of the terminal hydroxyls);

4. Ciclosporin (Derivatized where a Linker group or a —(L-DEGRON) group can be bound, e.g. at any of the butyl groups);

5. Tacrolimus (FK-506) and rapamycin (Derivatized where a Linker group L or a —(L-DEGRON) group can be bound, e.g. at one of the methoxy groups); and 6. Actinomycins (Derivatized where a Linker group L or a —(L-DEGRON) group can be bound, e.g. at one of the isopropyl groups).

EE. Aryl Hydrocarbon Receptor (AHR) dTAG Targeting Ligands:

AHR dTAG Targeting Ligands as used herein include, but are not limited to:

1. Apigenin (Derivatized in a way which binds to a Linker group L or a —(L-DEGRON) group as is generally illustrated in Lee, et al., Targeted Degradation of the Aryl Hydrocarbon Receptor by the PROTAC Approach: A Useful Chemical Genetic Tool, Chem Bio Chem Volume 8, Issue 17, pages 2058-2062, Nov. 23, 2007); and 2. SR1 and LGC006 (derivatized such that a Linker group L or a —(L-DEGRON) is bound), as described in Boitano, et al., Aryl Hydrocarbon Receptor Antagonists Promote the Expansion of Human Hematopoietic Stem Cells, Science 10 Sep. 2010: Vol. 329 no. 5997 pp. 1345-1348.

FF. RAF dTAG Targeting Ligands:

RAF dTAG Targeting Ligands as used herein include, but are not limited to:

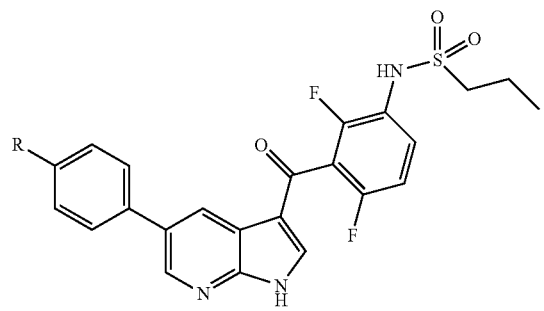

PLX4032

(Derivatized where "R" designates a site for Linker group L or —(L-DEGRON) group attachment, for example).

TABLE T-continued

GG. FKBP dTAG Targeting Ligands:

FKBP dTAG Targeting Ligands as used herein include, but are not limited to:

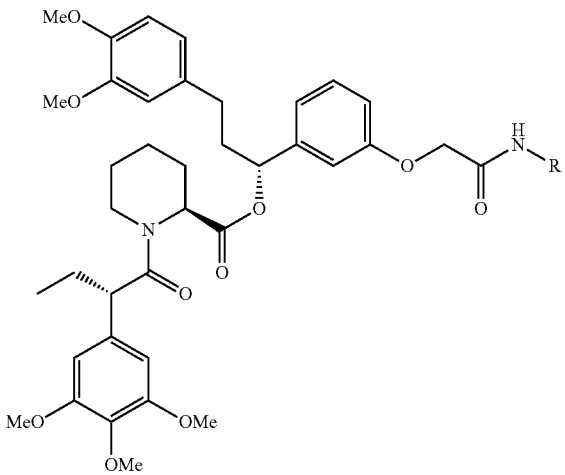

(Derivatized where "R" designates a site for a Linker group L or a —(L-DEGRON) group attachment, for example).

HH. Androgen Receptor (AR) dTAG Targeting Ligands:

AR dTAG Targeting Ligands as used herein include, but are not limited to:
1. RU59063 Ligand (derivatized) of Androgen Receptor

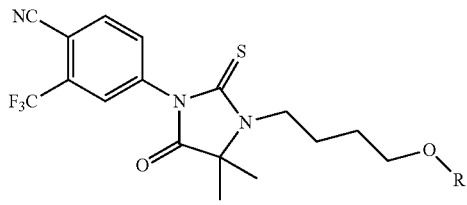

(Derivatized where "R" designates a site for a Linker group L or a —(L-DEGRON) group attachment, for example).

2. SARM Ligand (derivatized) of Androgen Receptor

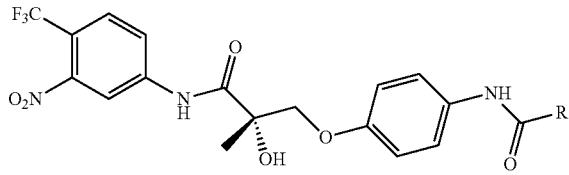

(Derivatized where "R" designates a site for a Linker group L or a —(L-DEGRON) group attachment, for example).

3. Androgen Receptor Ligand DHT (derivatized)

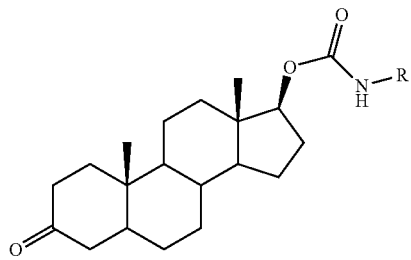

(Derivatized where "R" designates a site for a Linker group L or —(L-DEGRON) group attachment, for example).

TABLE T-continued
4. MDV3100 Ligand (derivatized)
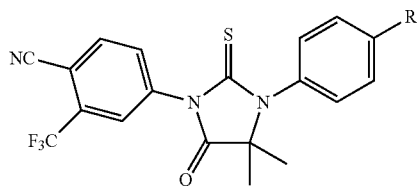
5. ARN-509 Ligand (derivatized)
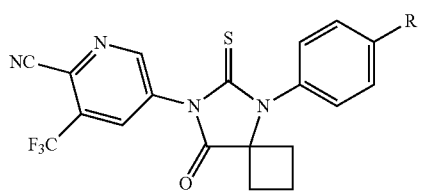
6. Hexahydrobenzisoxazoles
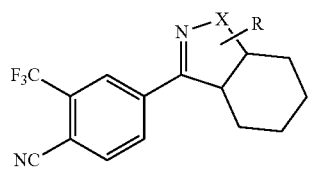
7. Tetramethylcyclobutanes
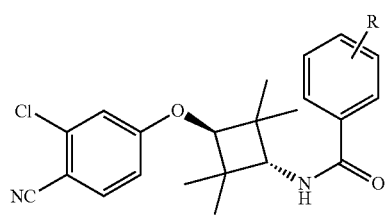
II. Estrogen Receptor (ER) dTAG Targeting Ligands:
ER dTAG Targeting Ligands as used herein include, but are not limited to:
1. Estrogen Receptor Ligand
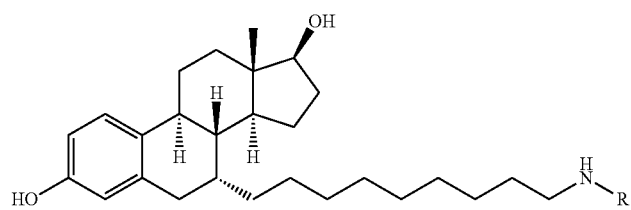
(Derivatized where "R" designates a site for Linker group L or —(L-DEGRON) group attachment).

TABLE T-continued

JJ. Thyroid Hormone Receptor (TR) dTAG Targeting Ligands:

TR dTAG Targeting Ligands as used herein include, but are not limited to:

1. Thyroid Hormone Receptor Ligand (derivatized)

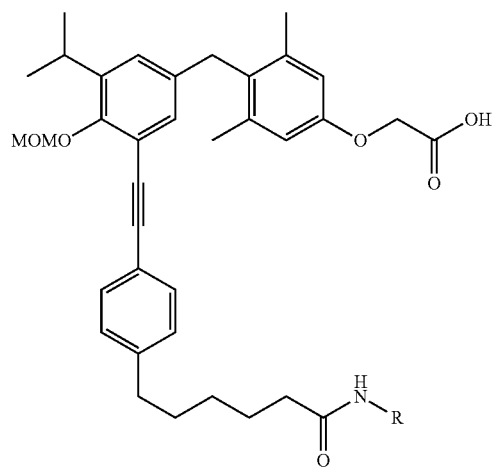

(Derivatized where "R" designates a site for Linker group L or —(L-DEGRON) group attachment and MOMO indicates a methoxymethoxy group).

KK. HIV Protease dTAG Targeting Ligands:

HIV Protease dTAG Targeting Ligands as used herein include, but are not limited to:

1. Inhibitor of HIV Protease (derivatized)

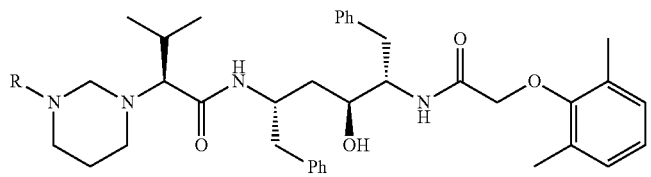

(Derivatized where "R" designates a site for Linker group L or —(L-DEGRON) group attachment).
See, J. Med. Chem. 2010, 53, 521-538.

2. Inhibitor of HIV Protease

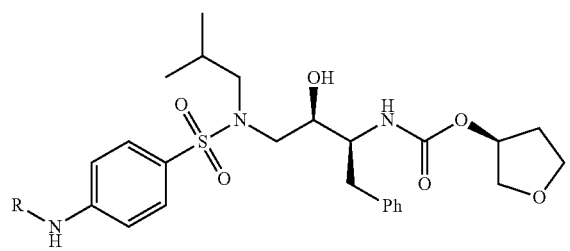

(Derivatized where "R" designates a potential site for Linker group L or —(L-DEGRON) group attachment). See, J. Med. Chem. 2010, 53, 521-538.

TABLE T-continued

LL. HIV Integrase dTAG Targeting Ligands:

HIV Integrase dTAG Targeting Ligands as used herein include, but are not limited to:

1. Inhibitor of HIV Integrase (derivatized)

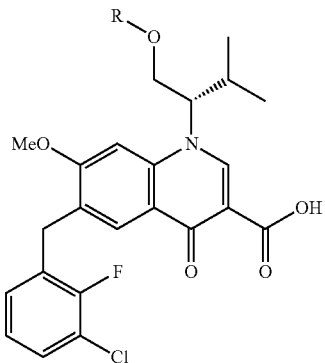

(Derivatized where "R" designates a site for Linker group L or —(L-DEGRON) group attachment).
See, J. Med. Chem. 2010, 53, 6466.

2. Inhibitor of HIV Integrase (derivatized)

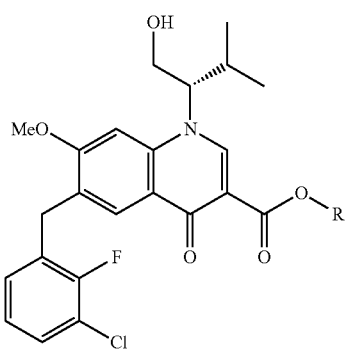

3. Inhibitor of HIV integrase (derivatized)

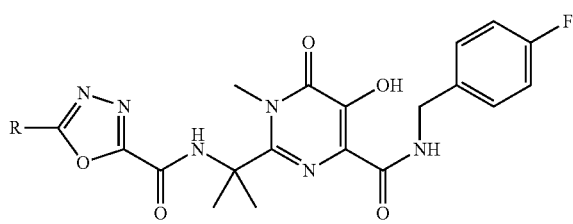

(Derivatized where "R" designates a site for Linker group L or —(L-DEGRON) group attachment).
See, J. Med. Chem. 2010, 53, 6466.

TABLE T-continued

MM. HCV Protease dTAG Targeting Ligands:

HCV Protease dTAG Targeting Ligands as used herein include, but are not limited to:
1. Inhibitors of HCV Protease (Derivatized)

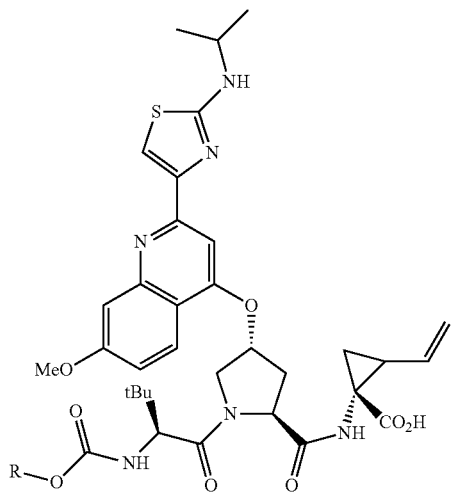

(Derivatized where "R" designates a site for Linker group L or —(L-DEGRON) group attachment).

NN. Acyl-Protein Thioesterase-1 and -2 (APT1 and APT2) dTAG Targeting

Ligands:
Acyl-Protein Thioesterase-1 and -2 (APT1 and APT2) dTAG Targeting Ligands as used herein
include, but are not limited to:
1. Inhibitor of APT1 and APT2 (Derivatized)

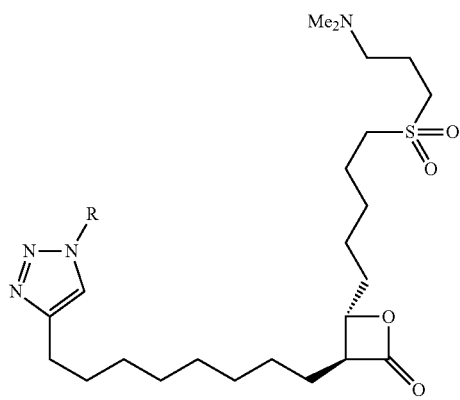

(Derivatized where "R" designates a site for Linker group L or —(L-DEGRON) group attachment). See, Angew. Chem. Int. Ed. 2011, 50, 9838-9842, where L is a Linker group as otherwise described herein and said Degron group is as otherwise described herein such that the Linker binds the Degron group to a dTAG Targeting Ligand group as otherwise described herein.

TABLE T-continued
OO. BCL2 dTAG Targeting Ligands:
BCL2 dTAG Targeting Ligands as used herein include, but are not limited to:
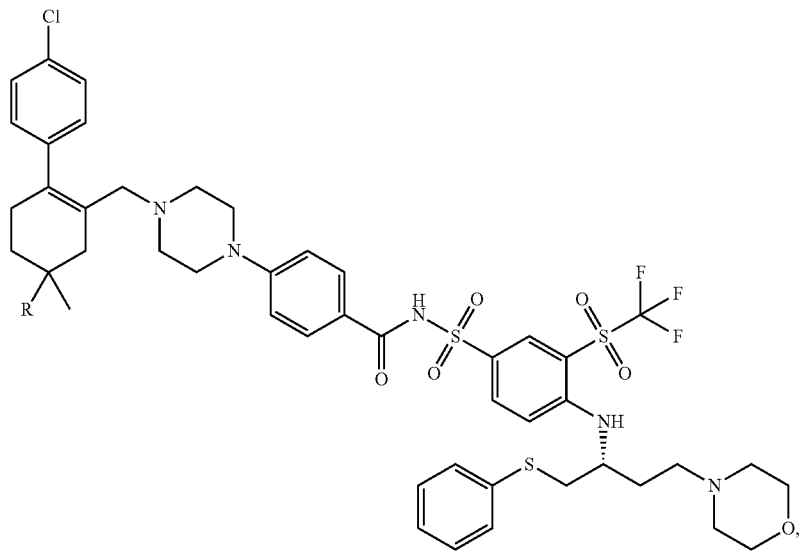
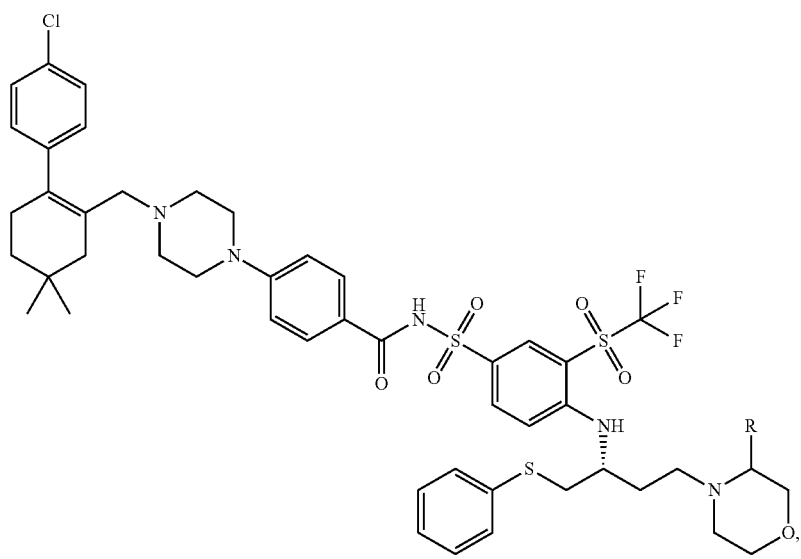

TABLE T-continued
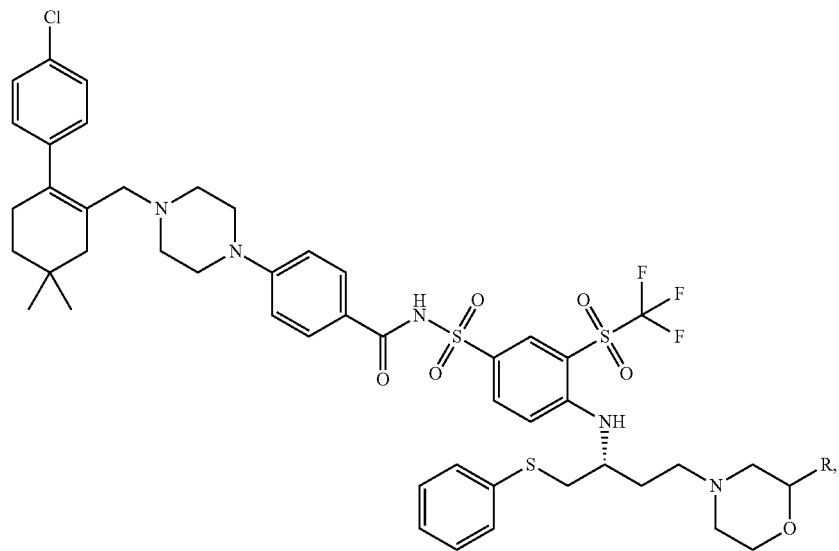
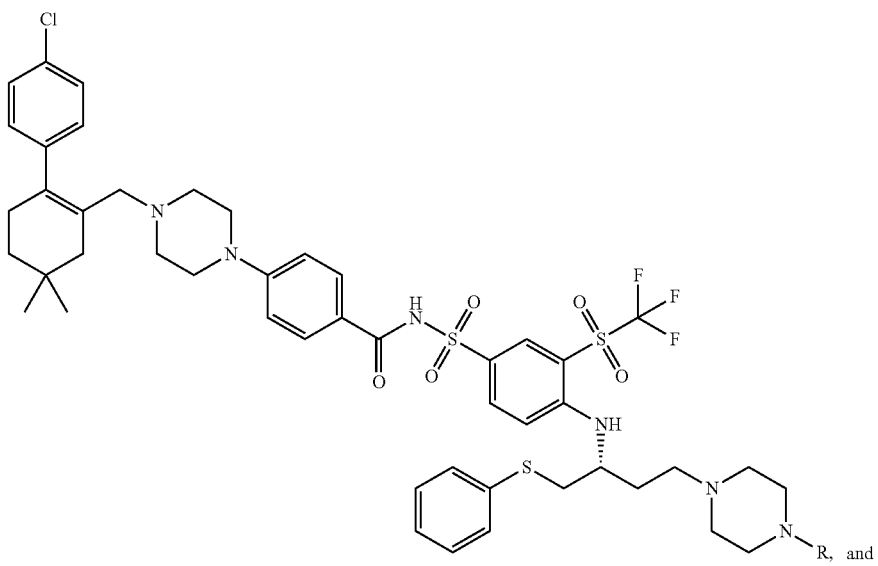
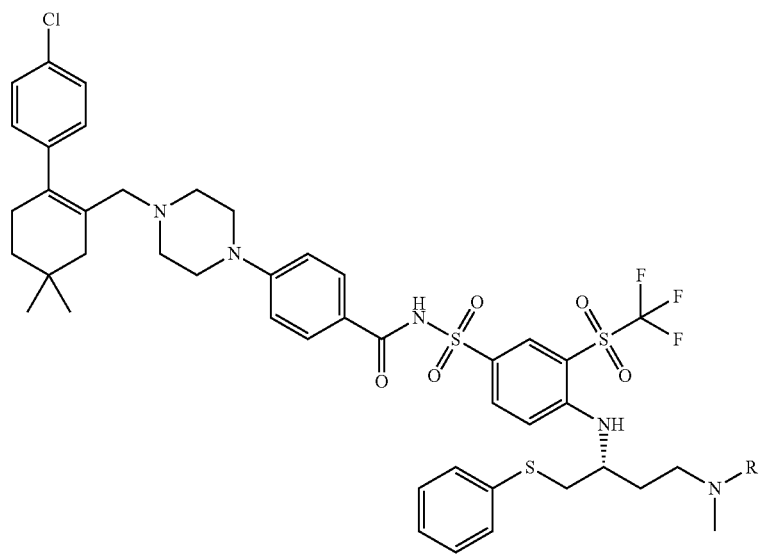

TABLE T-continued
wherein:
R is the point at which the Linker is attached.
PP. BCL-XL dTAG Targeting Ligands:
BCL-XL dTAG Targeting Ligands as used herein include, but are not limited to:
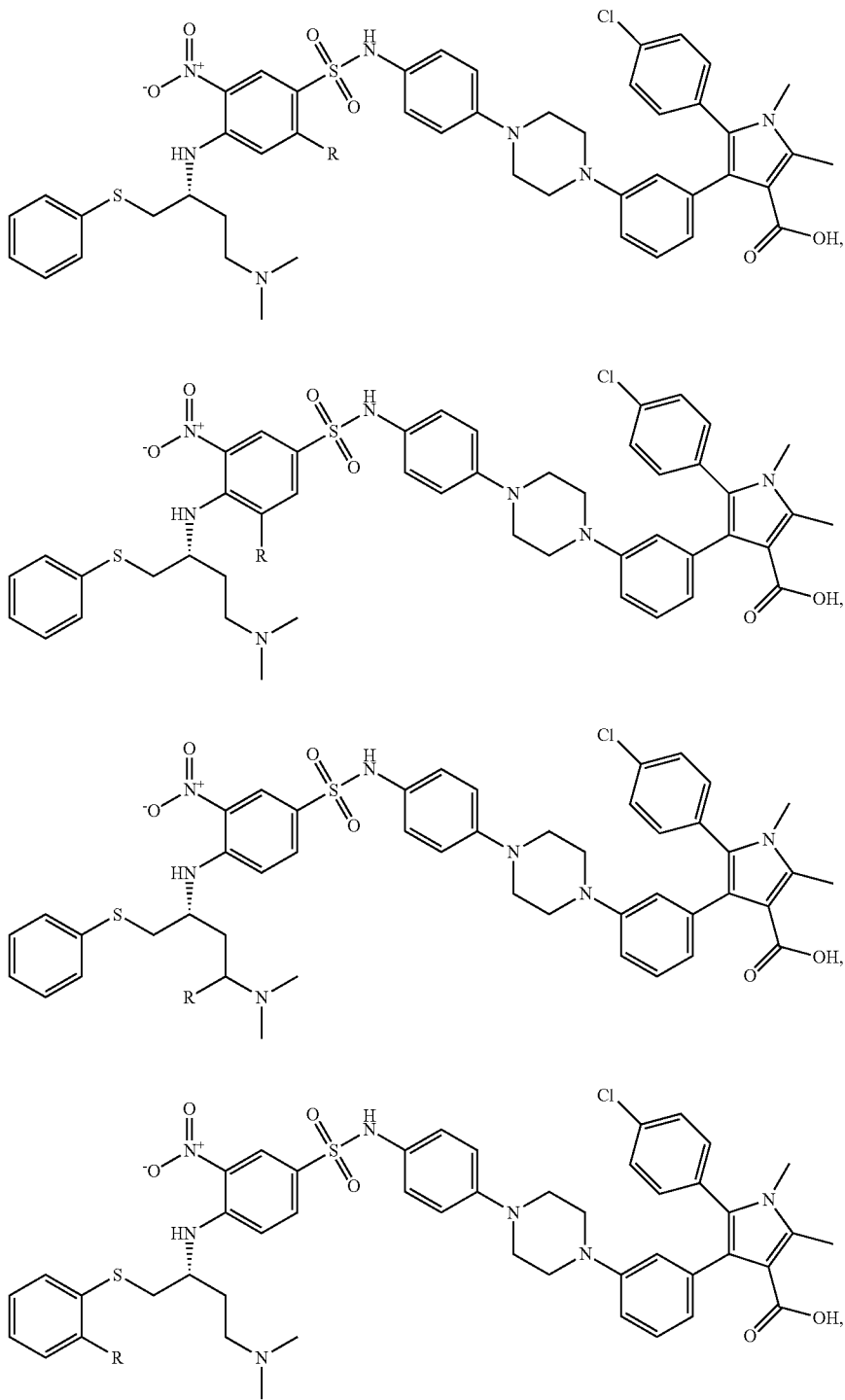

TABLE T-continued
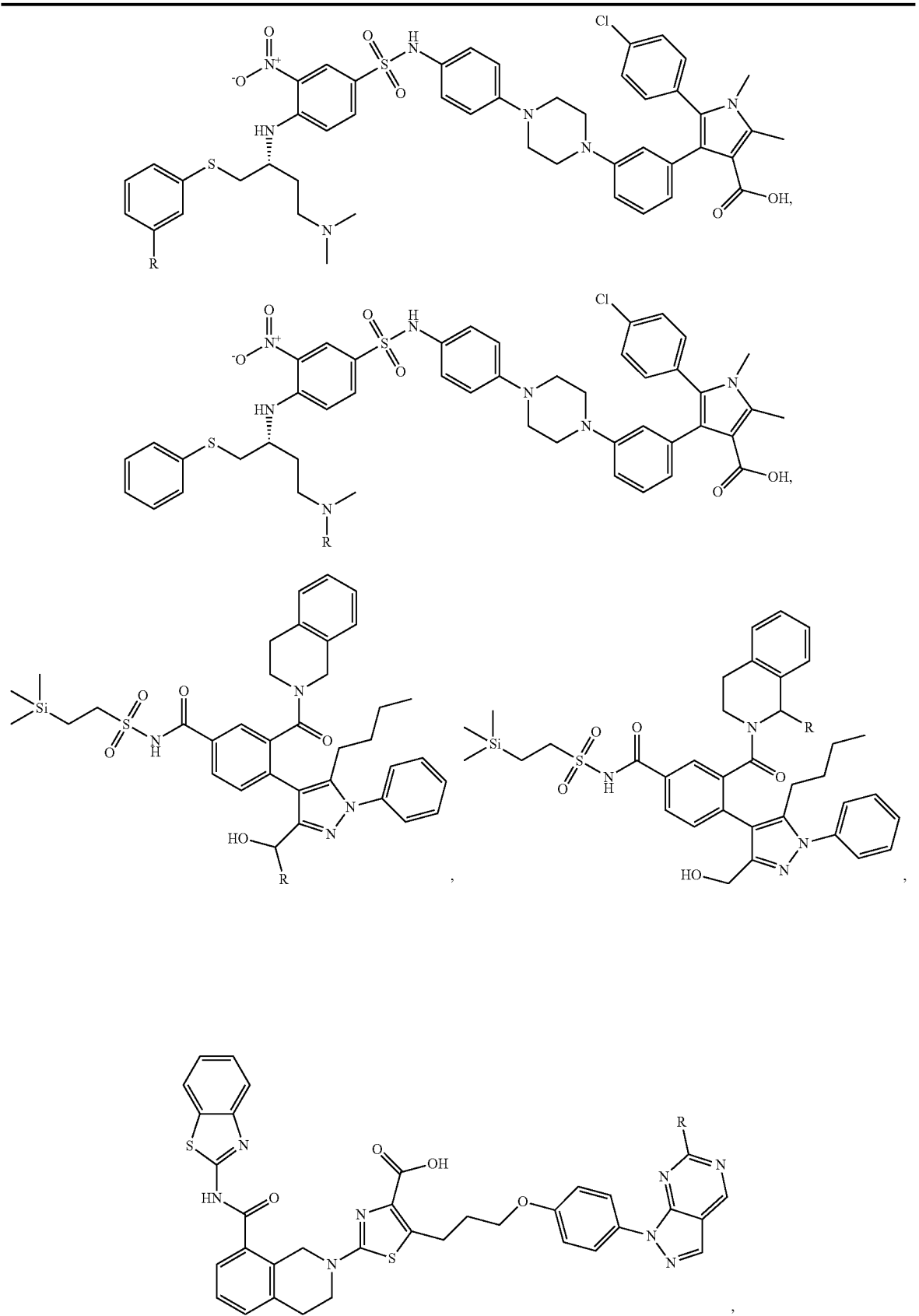

TABLE T-continued
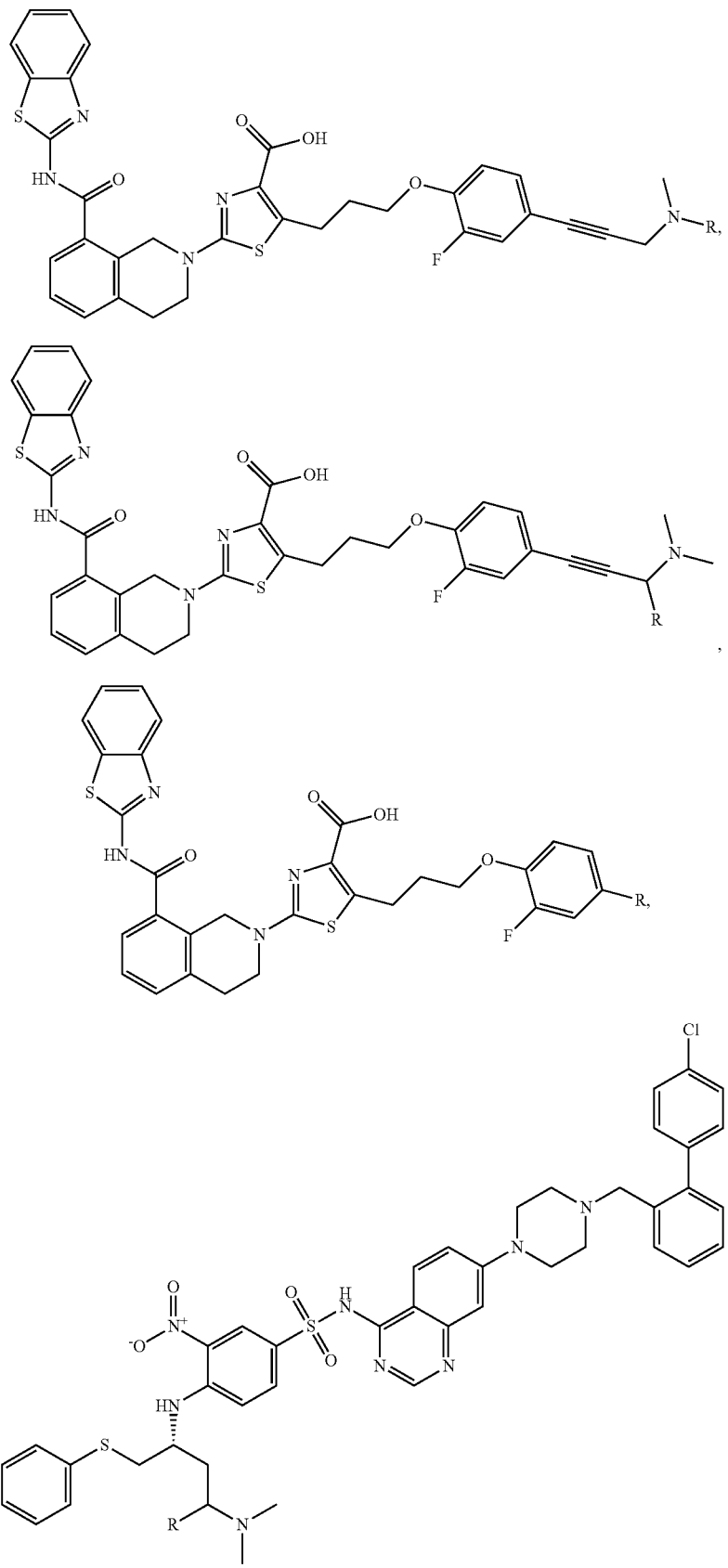

TABLE T-continued
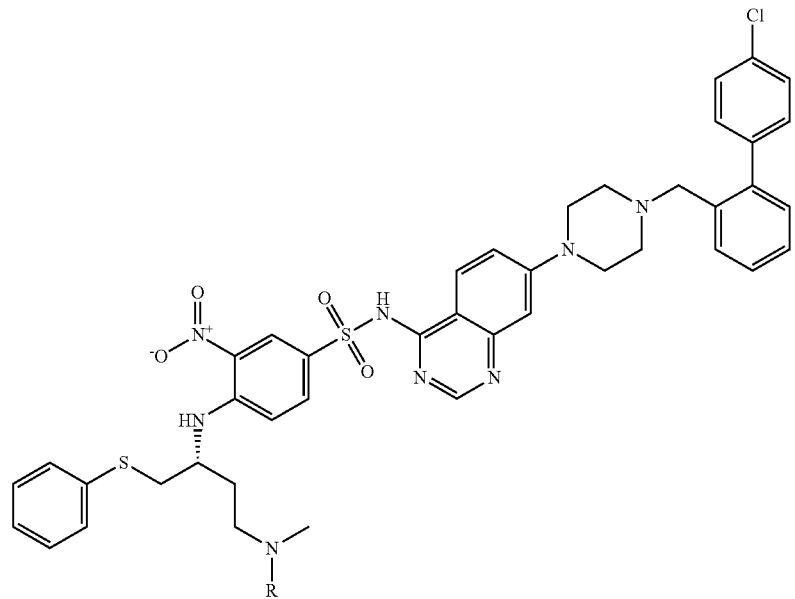
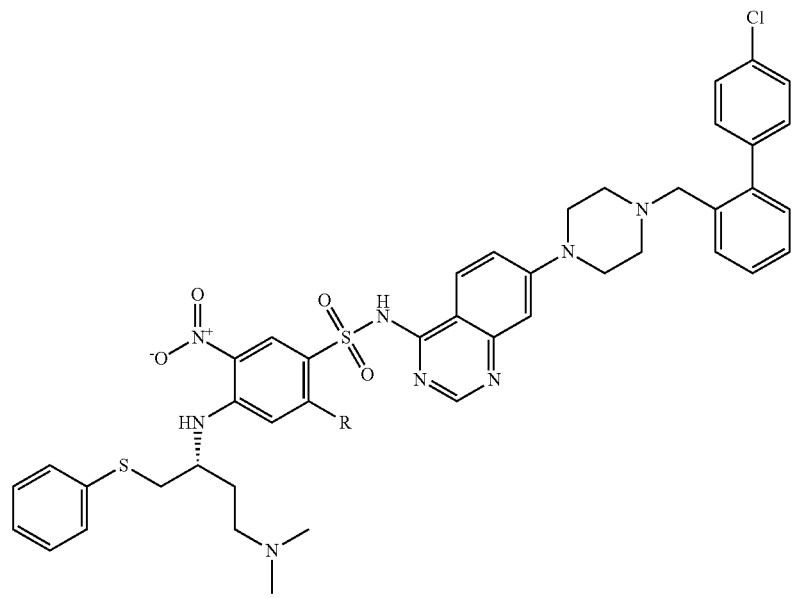

TABLE T-continued
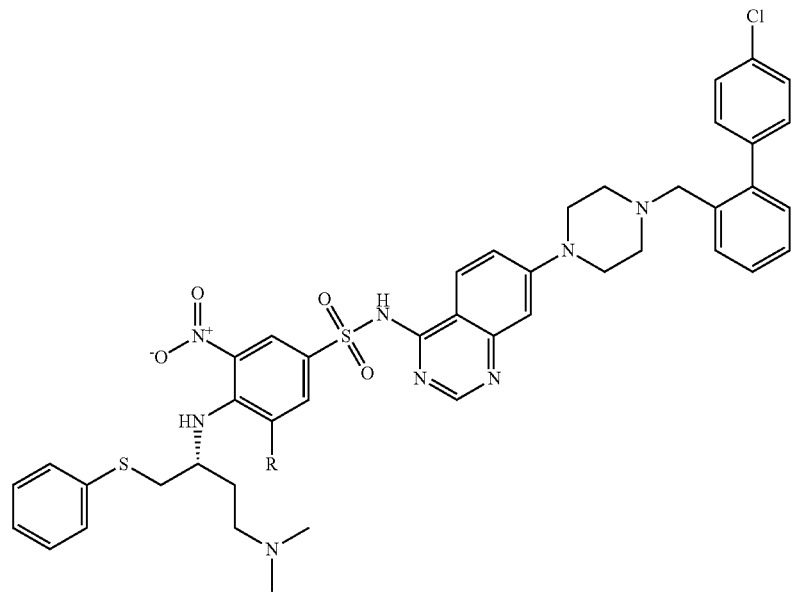
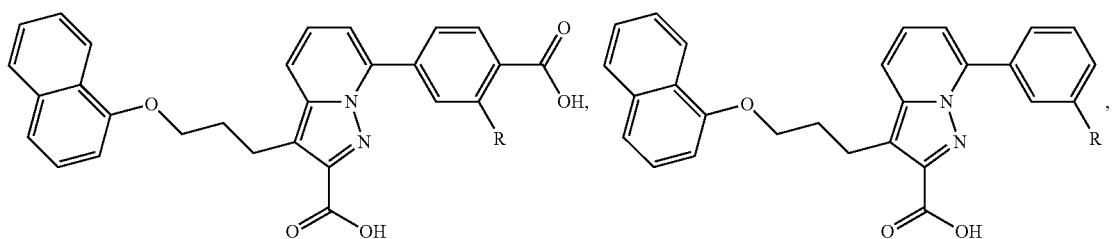
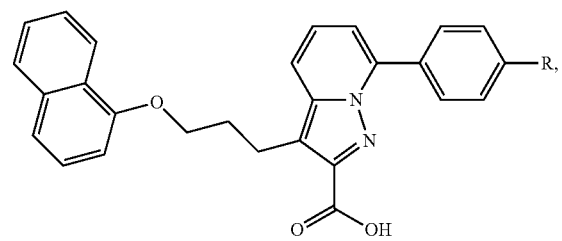

TABLE T-continued
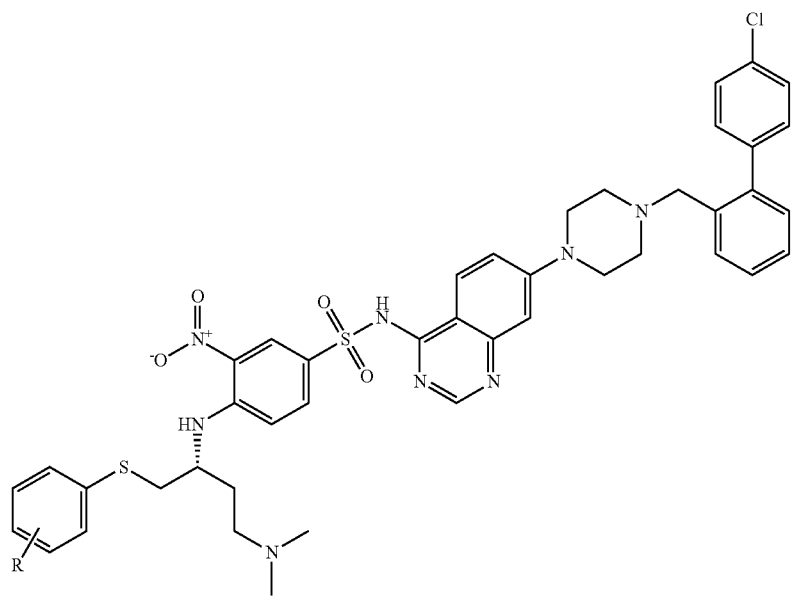
, and
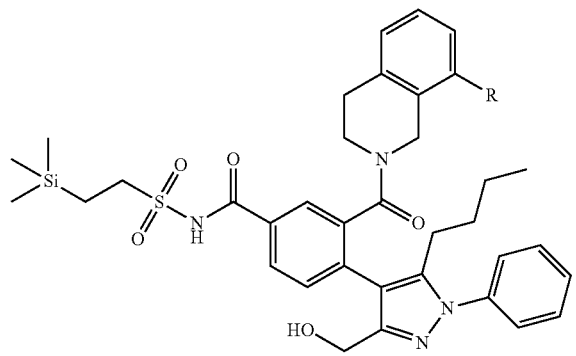
wherein:
R is the point at which the Linker is attached.
QQ. FA Binding Protein dTAG Targeting Ligands:
FA dTAG Targeting Ligands as used herein include, but are not limited to:
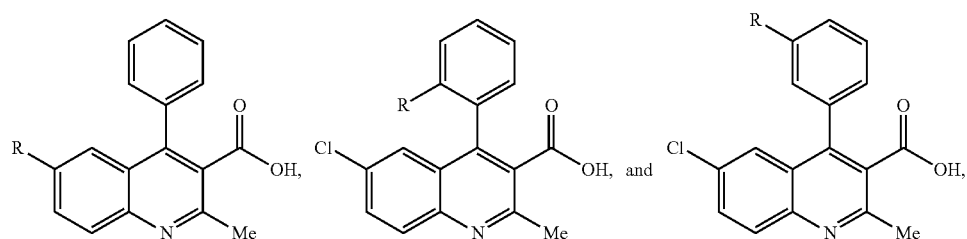
wherein:
R is the point at which the Linker is attached.

TABLE T-continued

RR. FLAP-5-Lipoxygenase Activating Protein dTAG Targeting Ligands:

FLAP-5-Lipoxygenase Activating Protein dTAG Targeting Ligands as used herein include, but are not limited to:

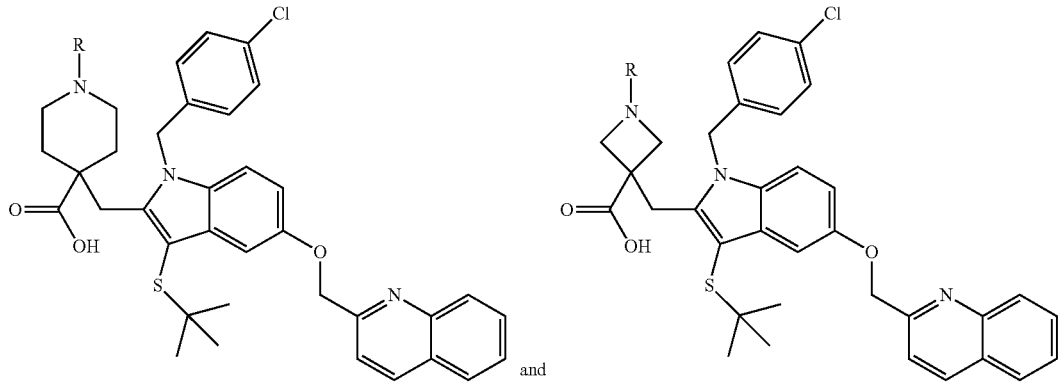

wherein:
R is the point at which the Linker is attached.

SS. HDAC6 Zn Finger Domain dTAG Targeting Ligands:

HDAC6 Zn Finger Domain dTAG Targeting Ligands as used herein include, but are not limited to:

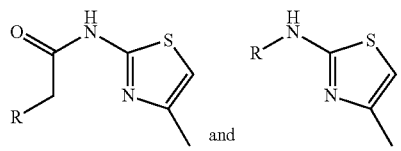

wherein:
R is the point at which the Linker is attached.

TT. Kringle Domain V 4BVV dTAG Targeting Ligands:

Kringle Domain V 4BVV dTAG Targeting Ligands as used herein include, but are not limited to:

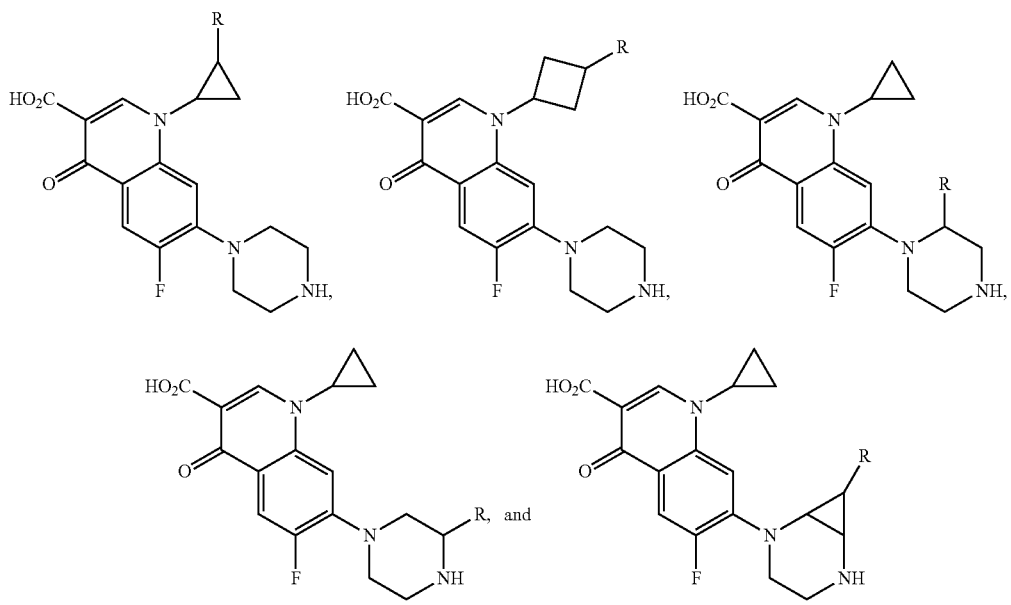

wherein:
R is the point at which the Linker is attached.

TABLE T-continued
UU. Lactoylglutathione Lyase dTAG Targeting Ligands:
Lactoylglutathione Lyase dTAG Targeting Ligands as used herein include, but are not limited to:
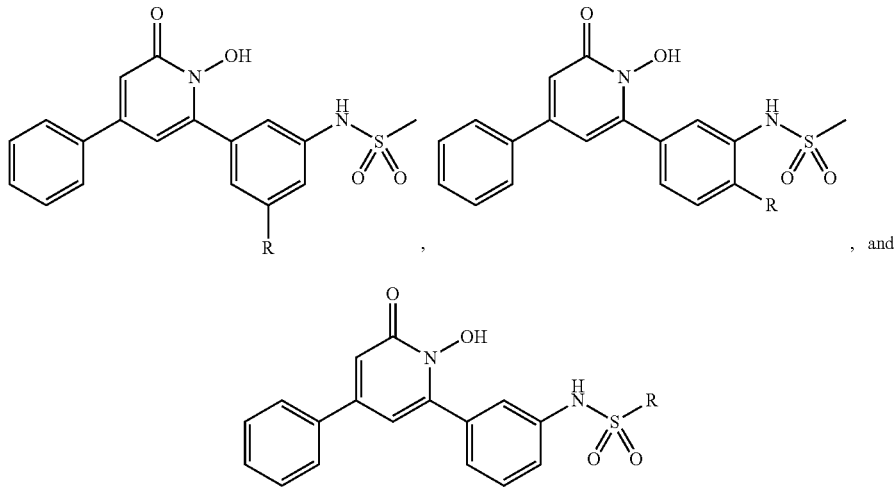
, and
wherein:
R is the point at which the Linker is attached.
VV. mPGES-1 dTAG Targeting Ligands:
mPGES-1 dTAG Targeting Ligands as used herein include, but are not limited to:
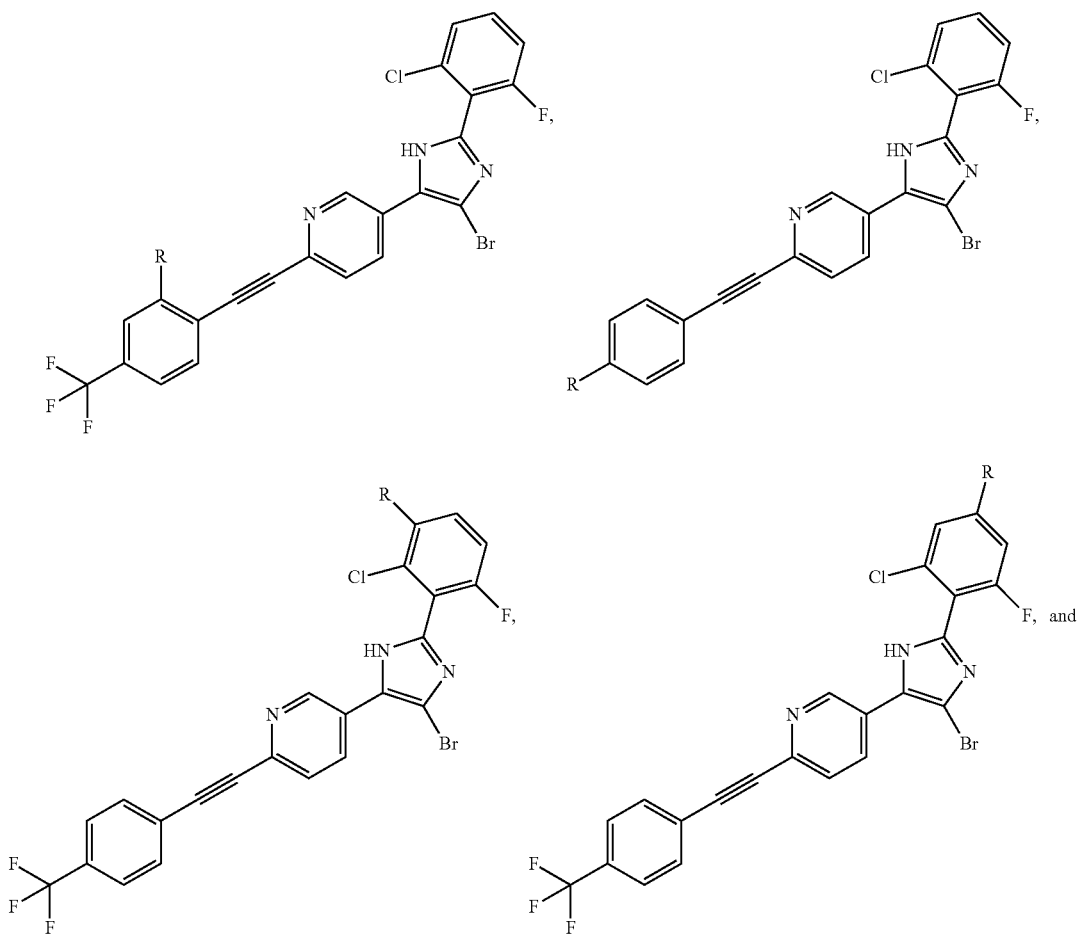

TABLE T-continued
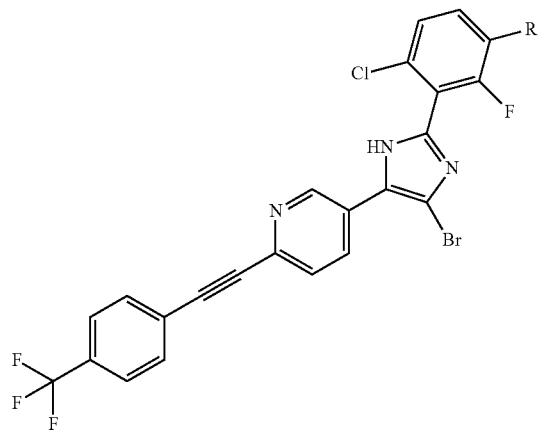
wherein:
R is the point at which the Linker is attached.
WW. MTH1 dTAG Targeting Ligands:
MTH1 dTAG Targeting Ligands as used herein include, but are not limited to:
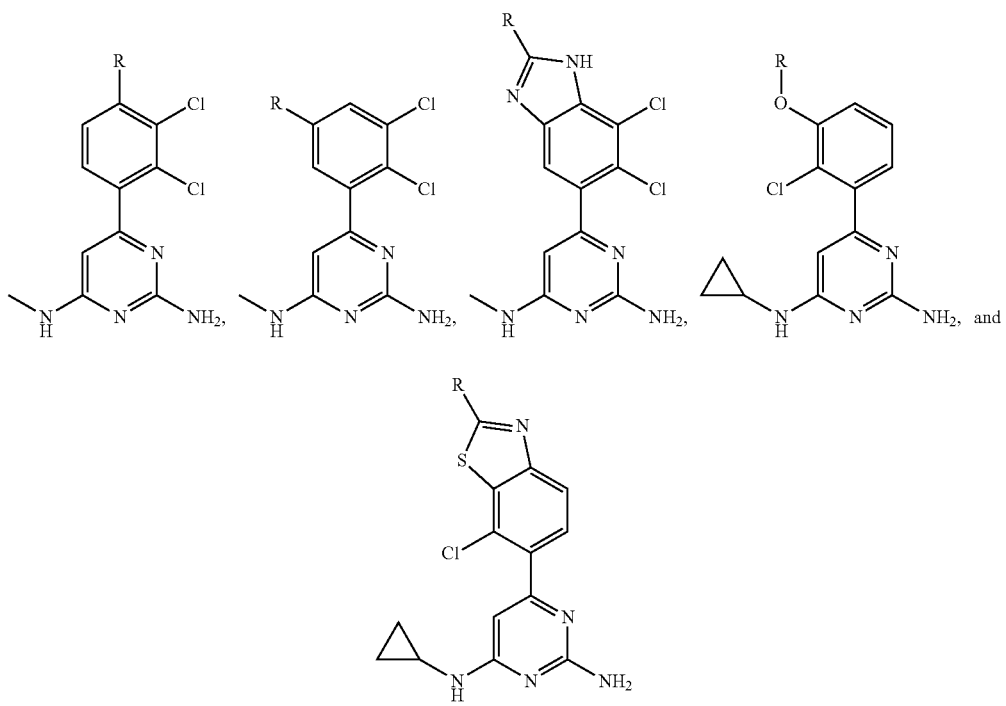
wherein:
R is the point at which the Linker is attached.
XX. PARP14 dTAG Targeting Ligands:
PARP14 dTAG Targeting Ligands as used herein include, but are not limited to:
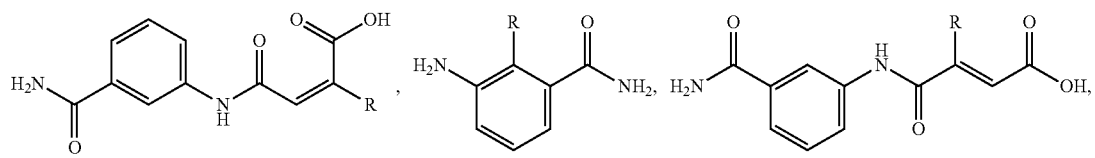

TABLE T-continued
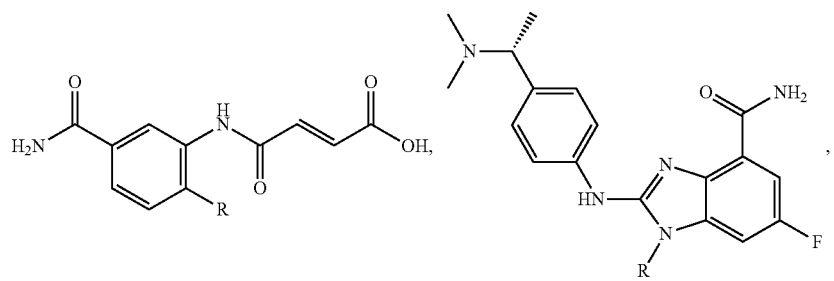
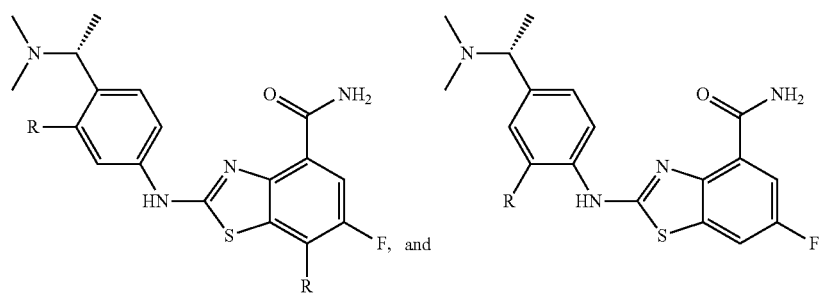
wherein:
R is the point at which the Linker is attached.
YY. PARP15 dTAG Targeting Ligands:
PARP15 dTAG Targeting Ligands as used herein include, but are not limited to:
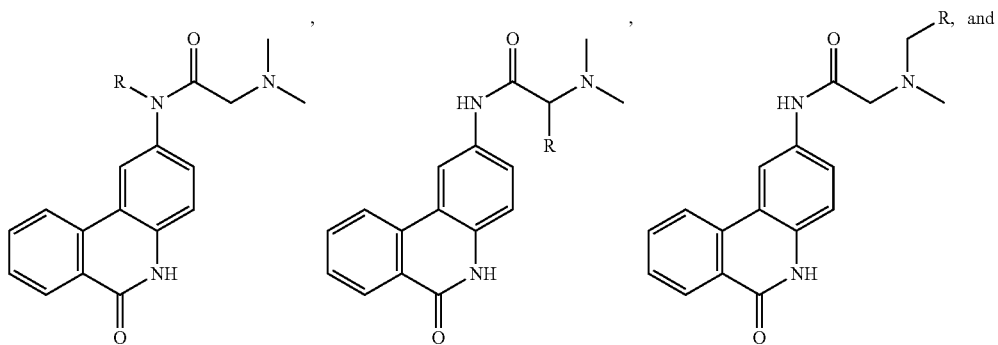
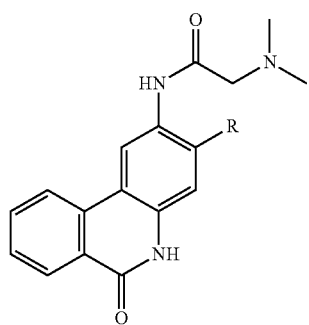
wherein:
R is the point at which the Linker is attached.

TABLE T-continued

ZZ. PDZ domain dTAG Targeting Ligands:

PDZ domain dTAG Targeting Ligands as used herein include, but are not limited to:

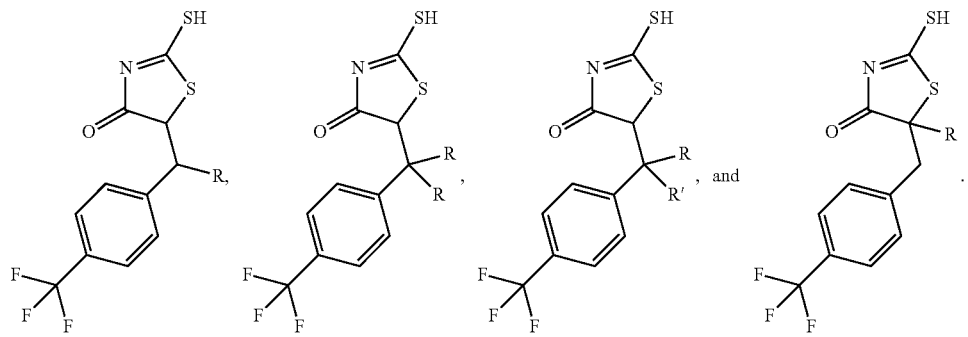

wherein:
R and R' are points at which the Linker(s) are attached.

AAA. PHIP dTAG Targeting Ligands:

PHIP dTAG Targeting Ligands as used herein include, but are not limited to:

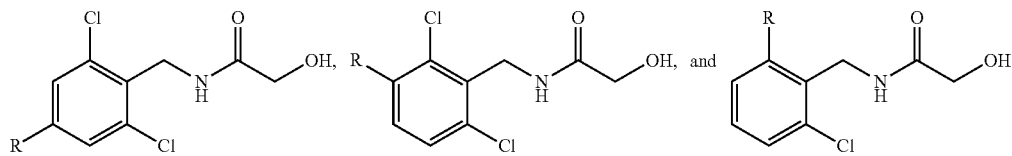

wherein:
R is the point at which the Linker is attached.

BBB. Phospholipase A2 domain dTAG Targeting Ligands:

Phospholipase A2 domain dTAG Targeting Ligands as used herein include, but are not limited to:

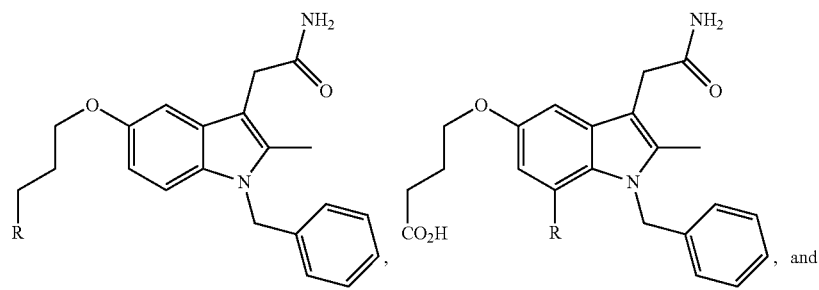

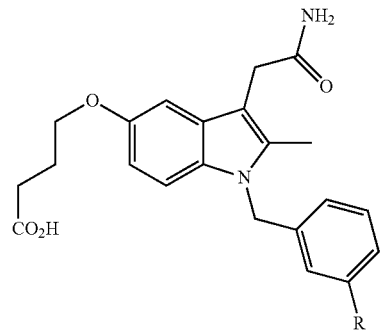

wherein:
R is the point at which the Linker is attached.

TABLE T-continued
CCC. Protein S100-A7 2WOS dTAG Targeting Ligands:
Protein S100-A7 2WOS dTAG Targeting Ligands as used herein include, but are not limited to:
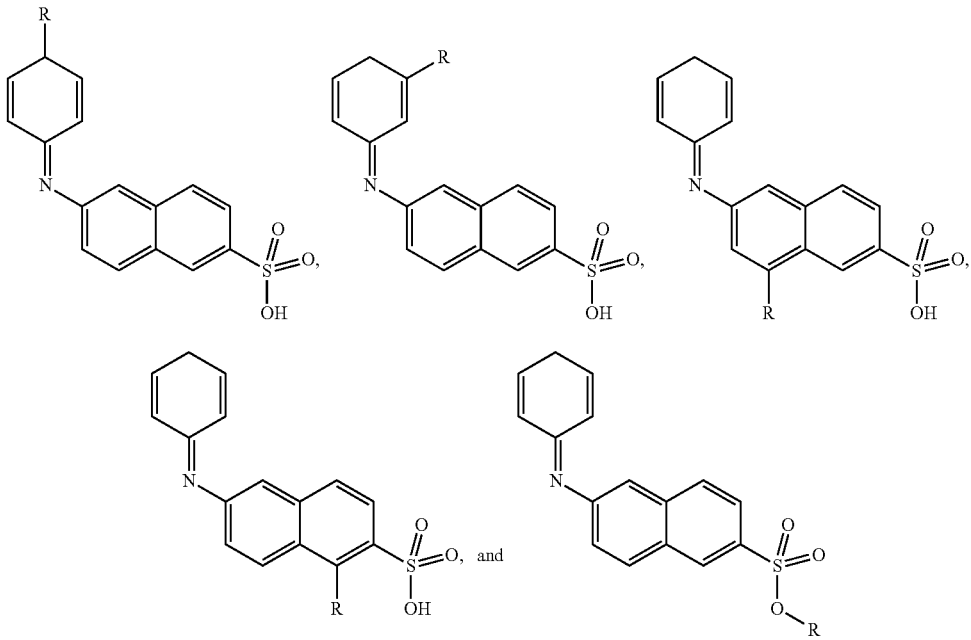
wherein:
R is the point at which the Linker is attached.
DDD. Saposin-B dTAG Targeting Ligands:
Saposin-B dTAG Targeting Ligands as used herein include, but are not limited to:
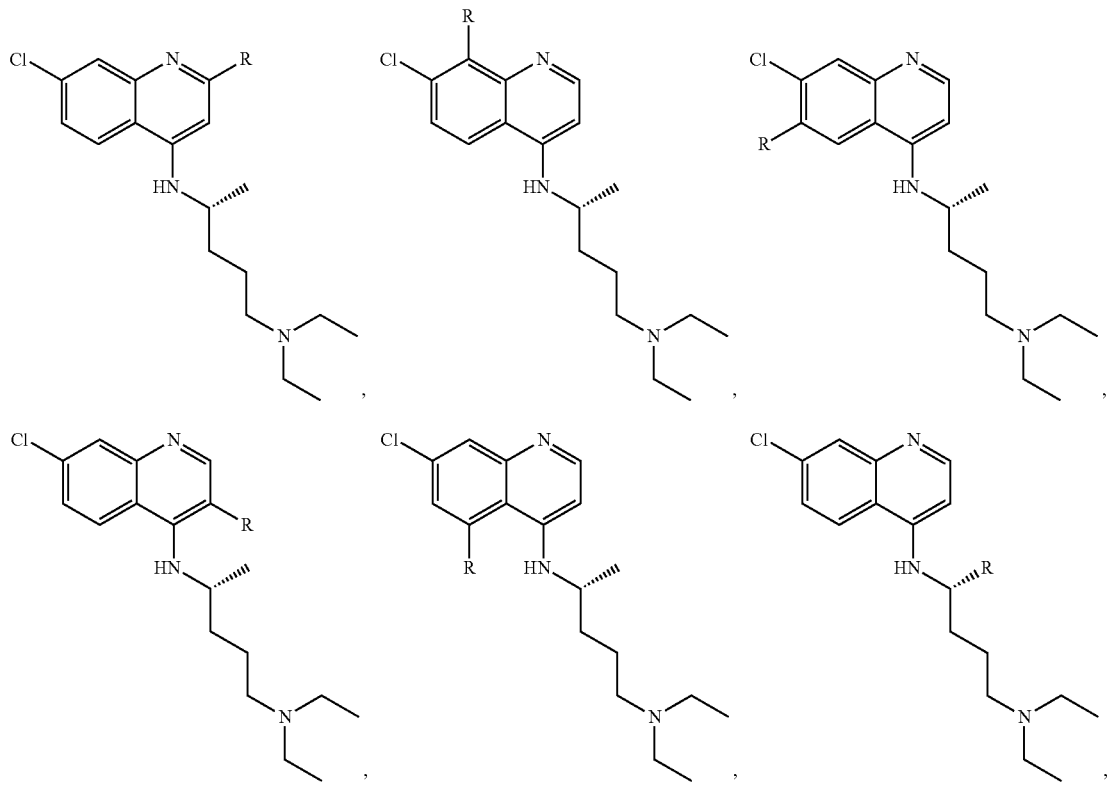

TABLE T-continued
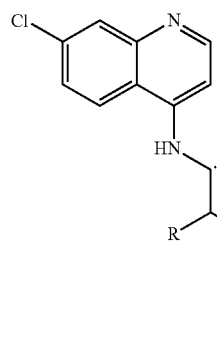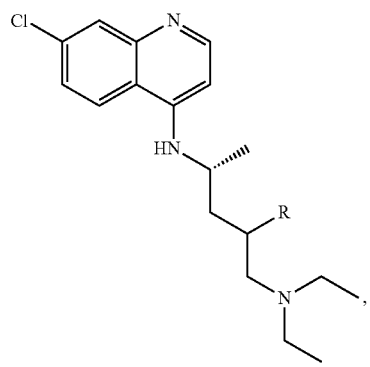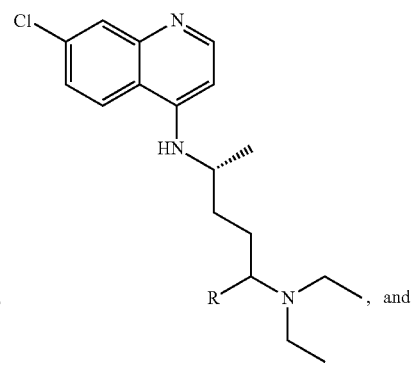
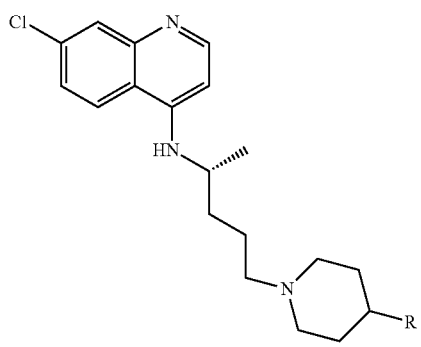
wherein:
R is the point at which the Linker is attached.
EEE. Sec7 dTAG Targeting Ligands:
Sec7 dTAG Targeting Ligands as used herein include, but are not limited to:
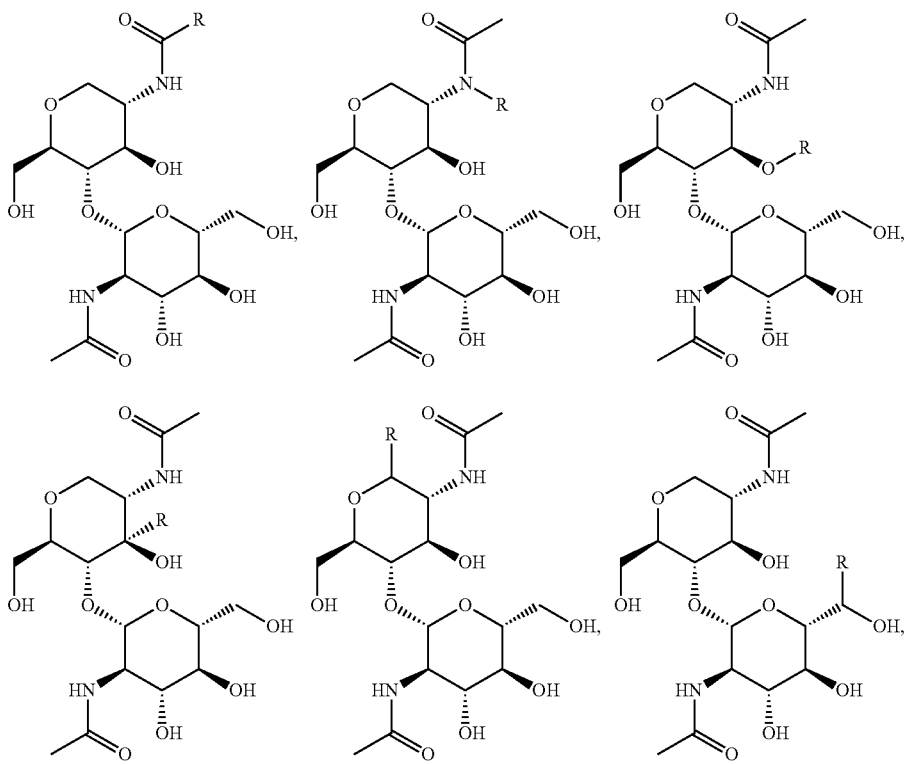

TABLE T-continued
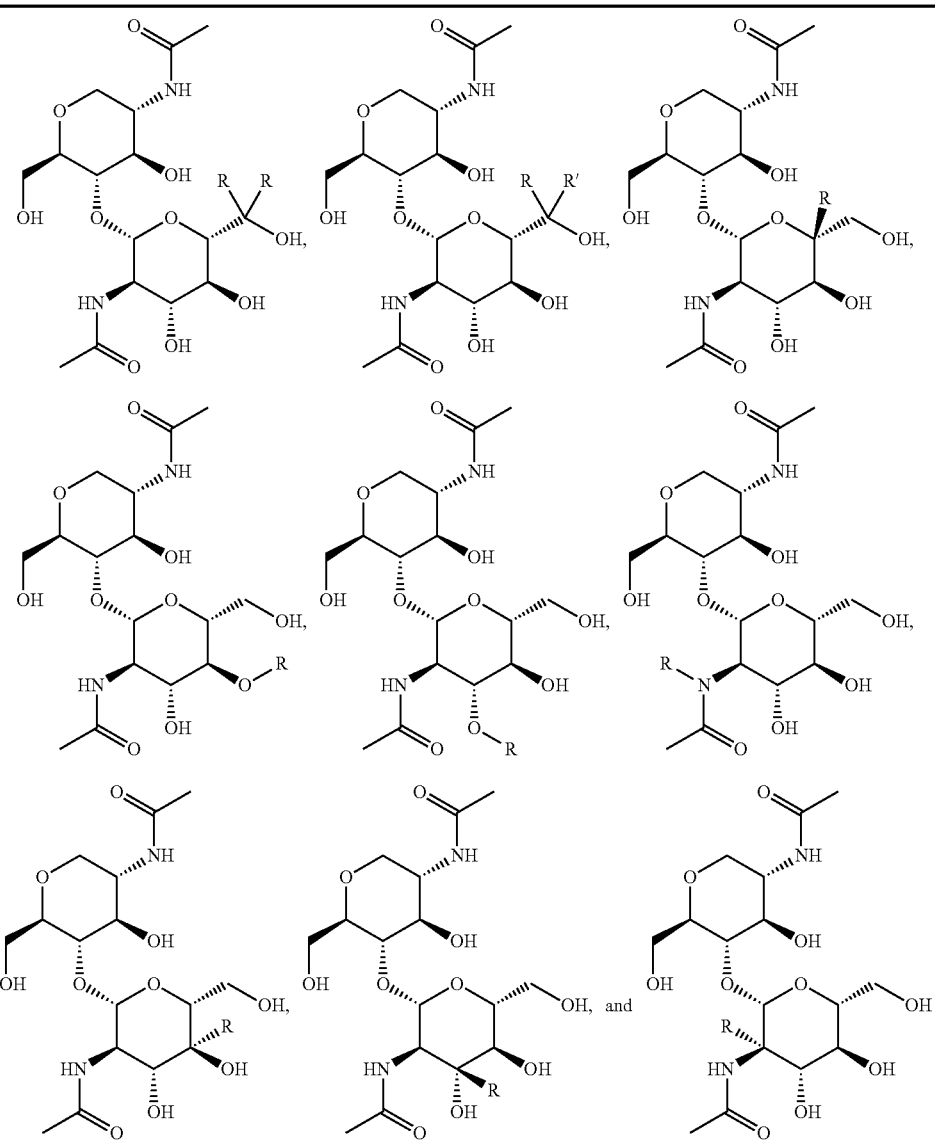
wherein:
R is the point at which the Linker is attached.
FFF. SH2 domain of pp60 Src dTAG Targeting Ligands:
SH2 domain of pp60 Src dTAG Targeting Ligands as used herein include, but are not limited to:
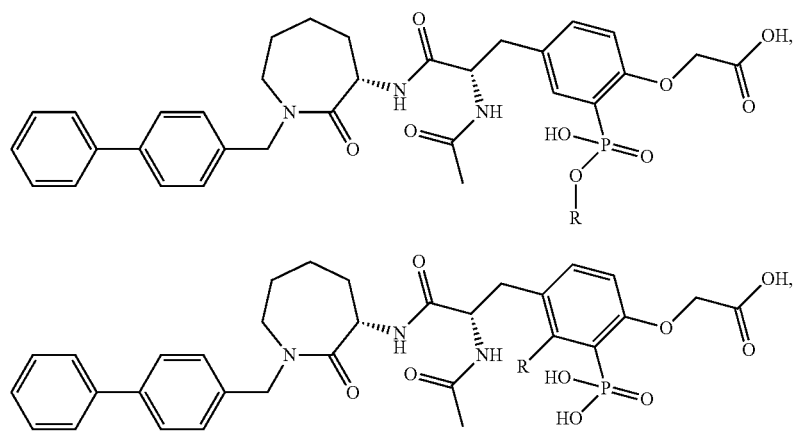

TABLE T-continued
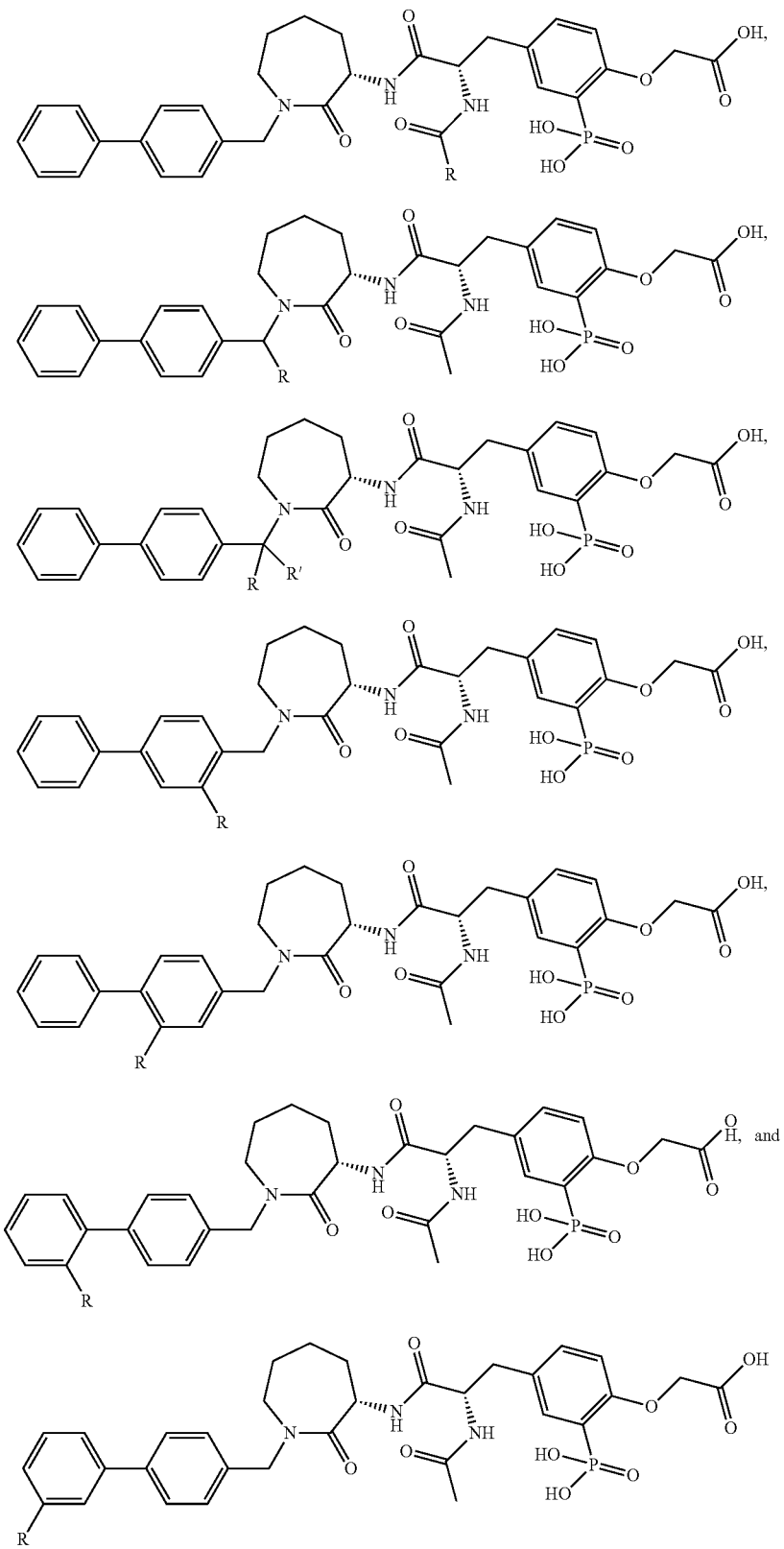
wherein:
R is the point at which the Linker is attached.

TABLE T-continued

GGG. Tank1 dTAG Targeting Ligands:

Tank1 dTAG Targeting Ligands as used herein include, but are not limited to

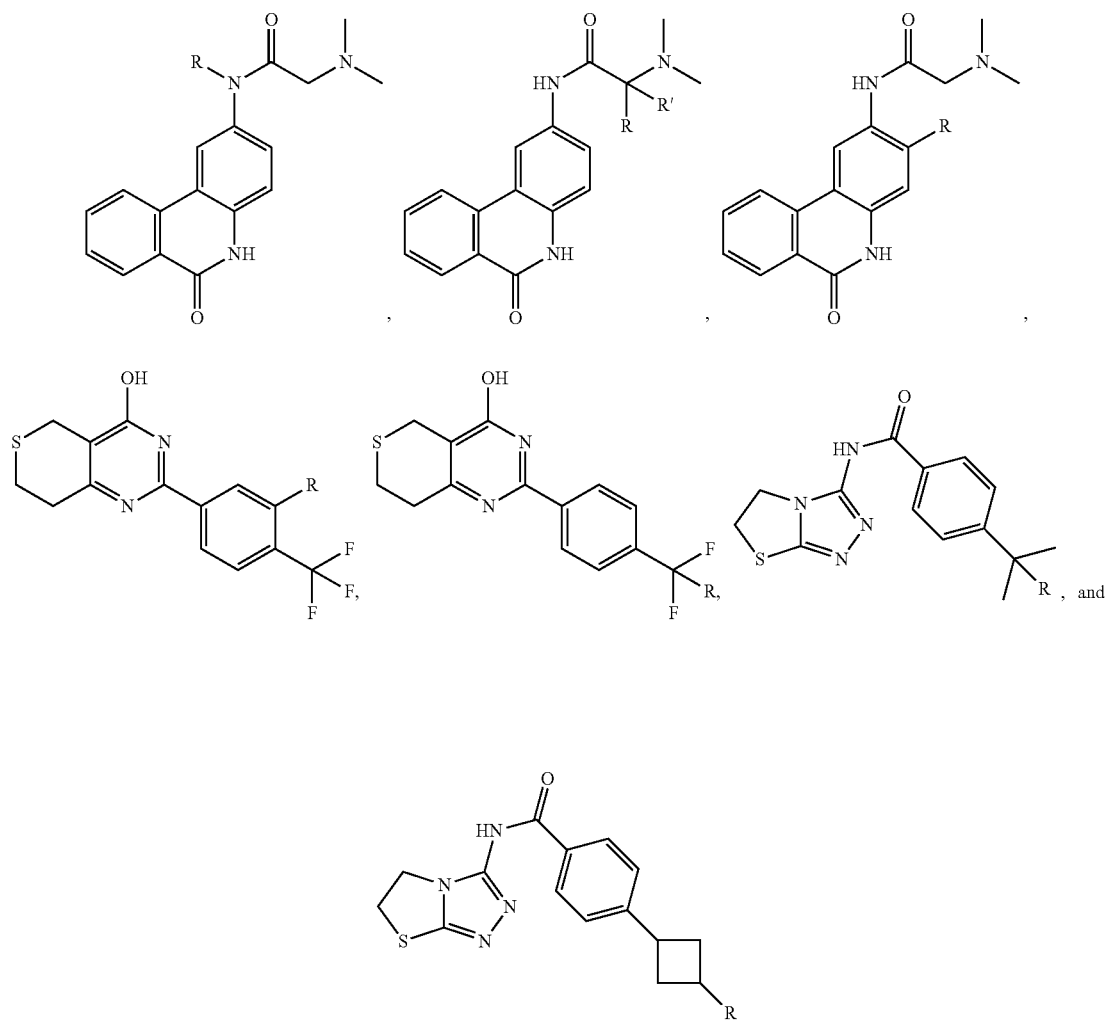

wherein:
R is the point at which the Linker is attached.

HHH. Ubc9 SUMO E2 ligase SF6D dTAG Targeting Ligands:

Ubc9 SUMO E2 ligase SF6D dTAG Targeting Ligands as used herein include, but are not limited to:

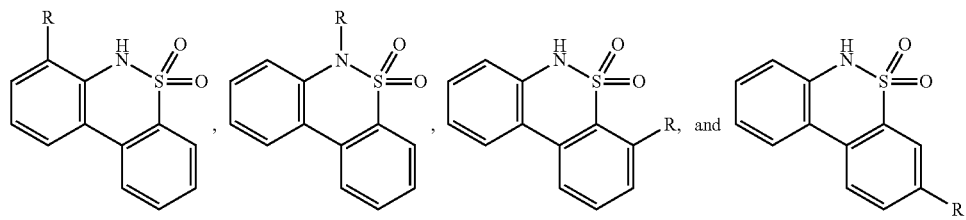

wherein:
R is the point at which the Linker is attached.

TABLE T-continued
III. Src (c-Src) dTAG Targeting Ligands:
Src dTAG Targeting Ligands as used herein include, but are not limited to:
1. Src Targenting Ligands including AP23464:
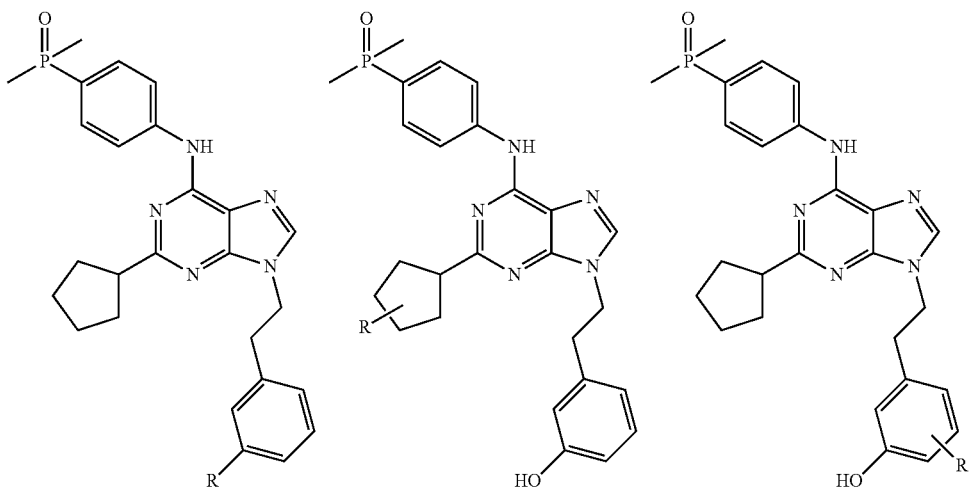
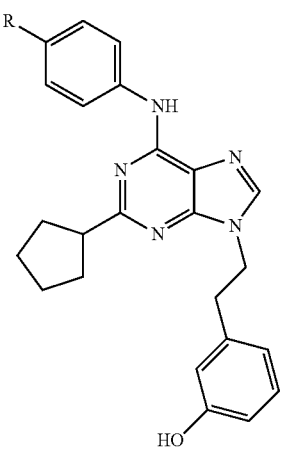
wherein:
R is the point at which the Linker is attached.
2. Src-AS1 and/or Src AS2 Targeting Ligands including:
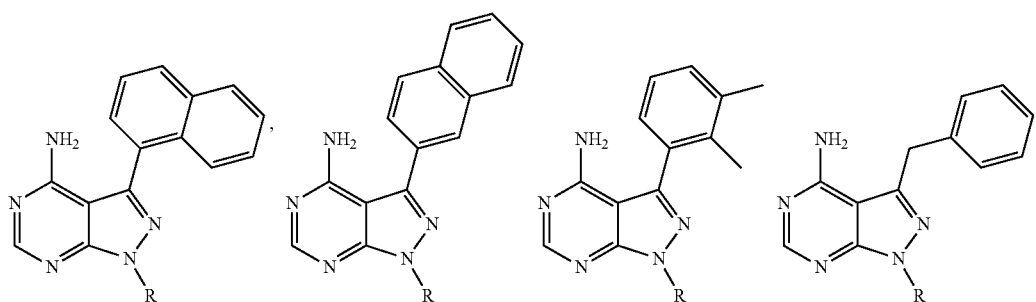

TABLE T-continued
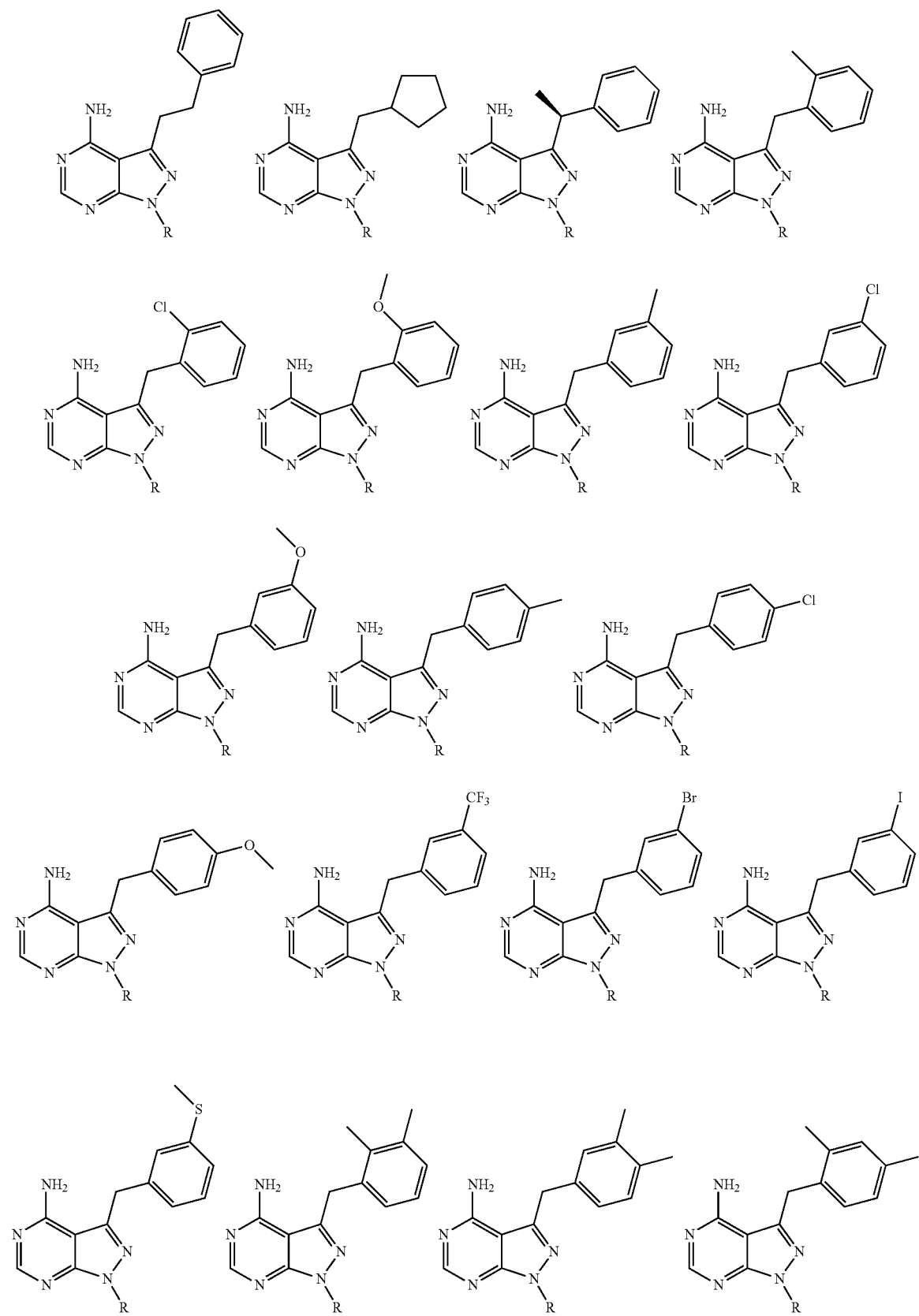

TABLE T-continued
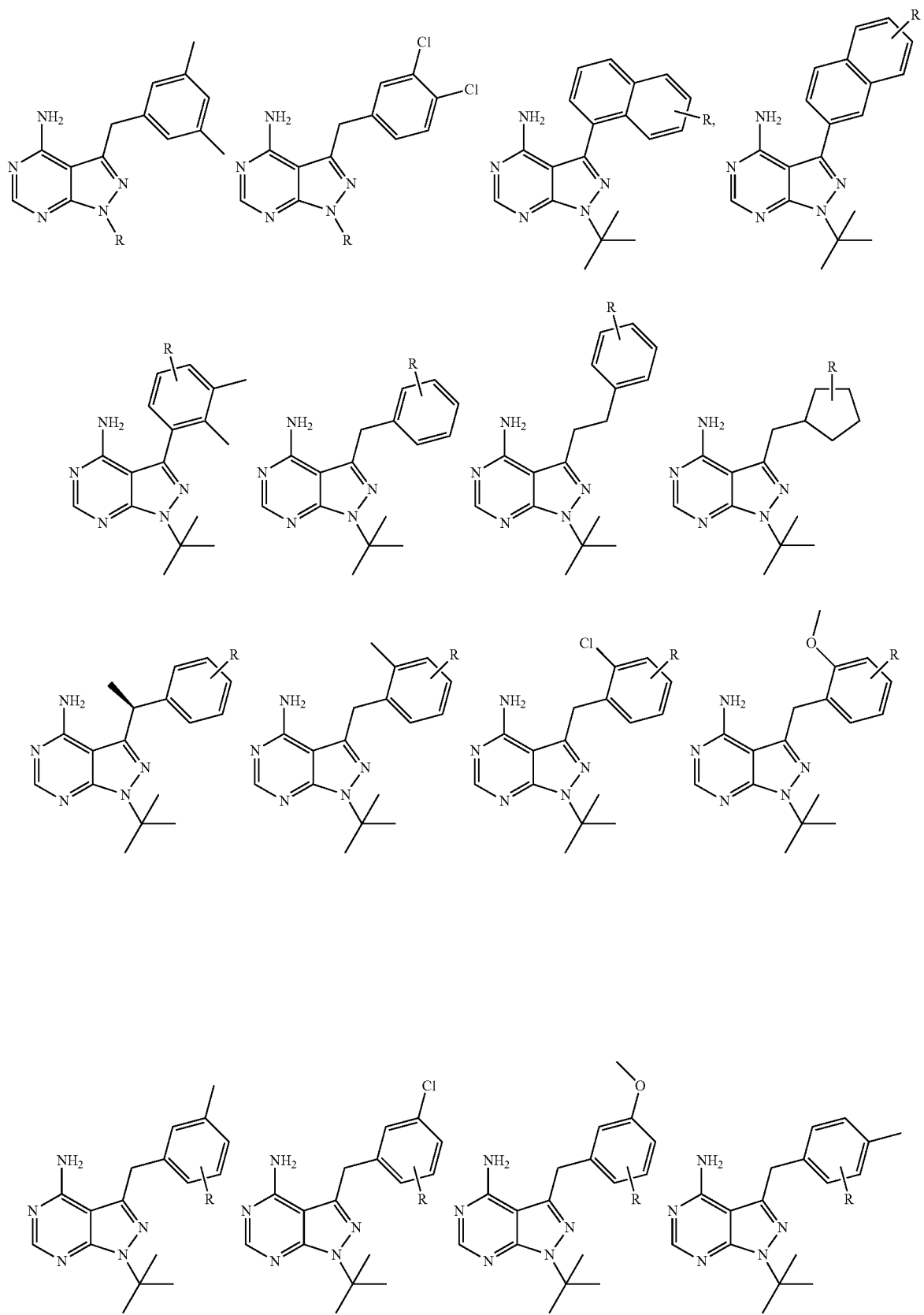

TABLE T-continued
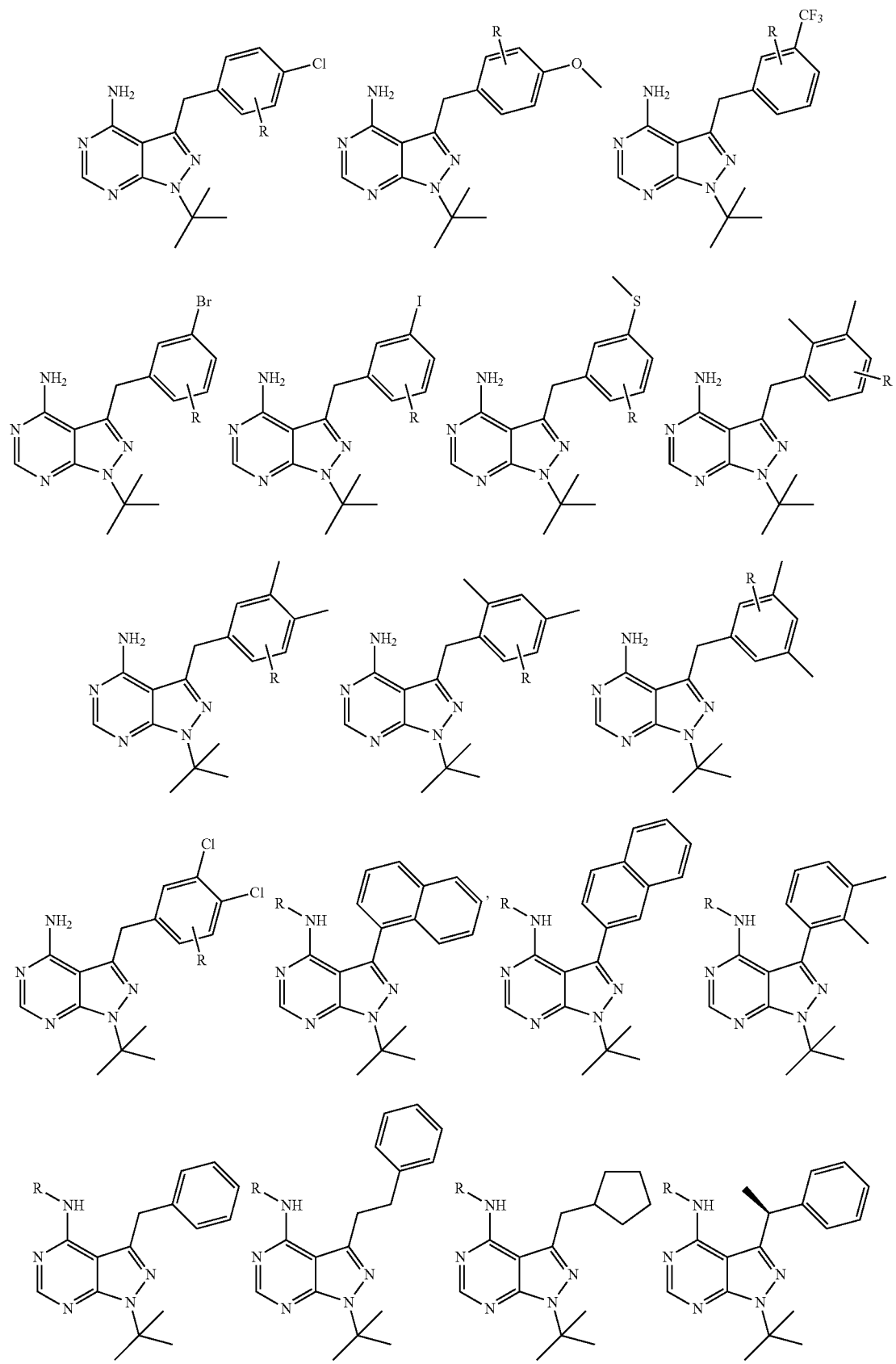

TABLE T-continued
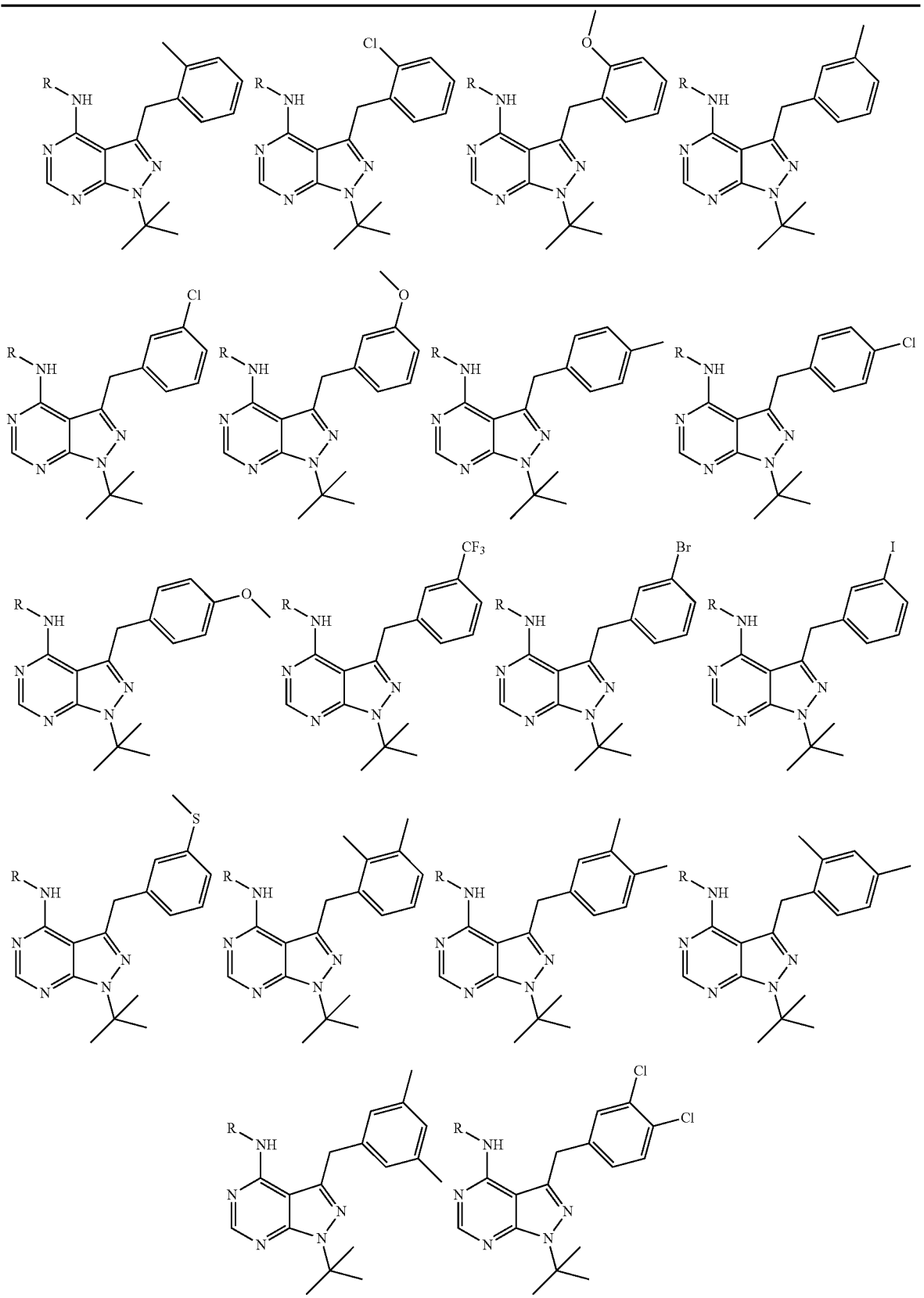
wherein:
R is the point at which the Linker is attached.

TABLE T-continued

JJJ. JAK3 dTAG Targeting Ligands:

JAK3 dTAG Targeting Ligands as used herein include, but are not limited to:
1. Targeting Ligands that target JAK3, including Tofacitinib:

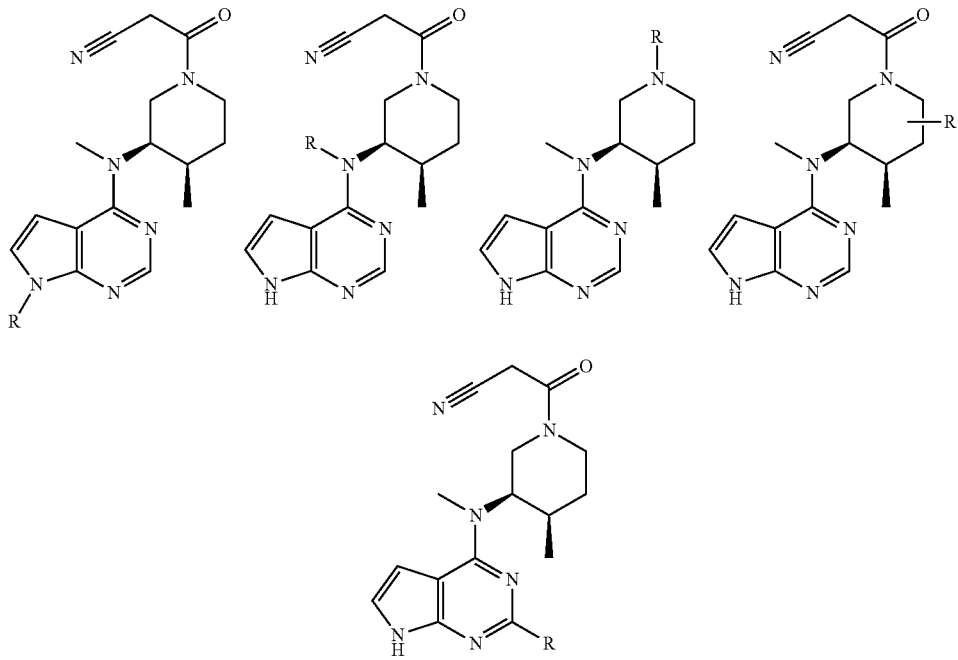

wherein:
R is the point at which the Linker is attached.

KKK. Abl dTAG Targeting Ligands:

Abl dTAG Targeting Ligands as used herein include, but are not limited to:
1. Targeting Ligands that target Abl, including Tofacitinib and Ponatinib:

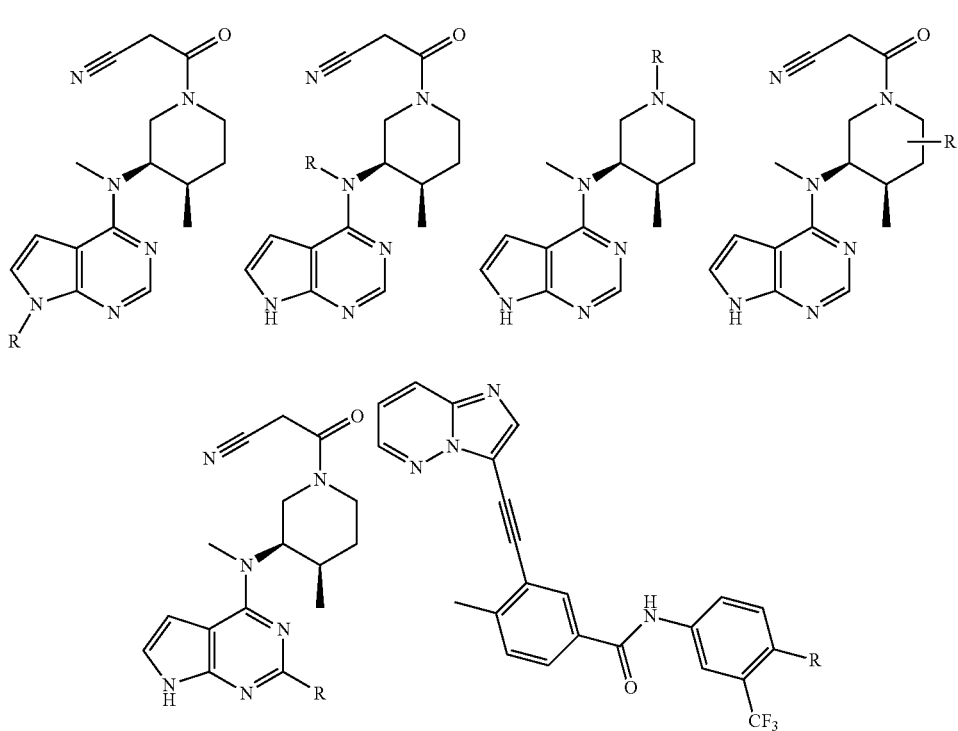

TABLE T-continued
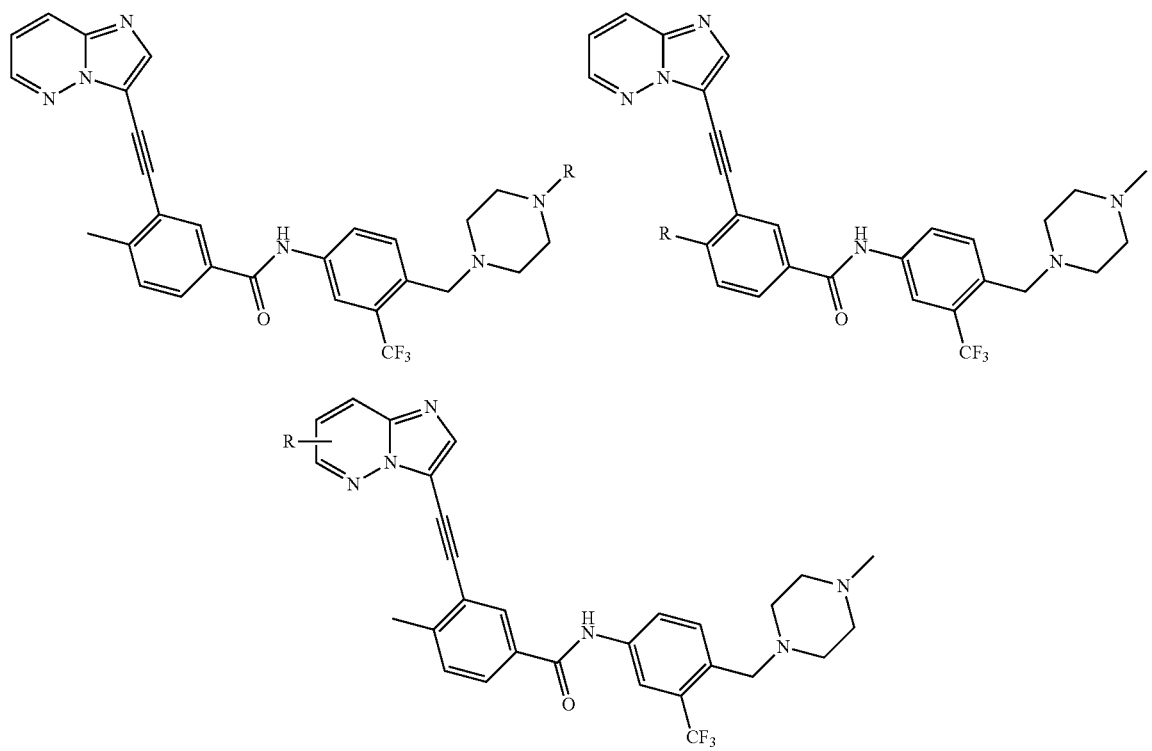
wherein:
R is the point at which the Linker is attached.
LLL. MEK1 dTAG Targeting Ligands:
MEK1 dTAG Targeting Ligands as used herein include, but are not limited to:
1. Targeting Ligands that target MEK1, including PD318088, Trametinib, and G-573:
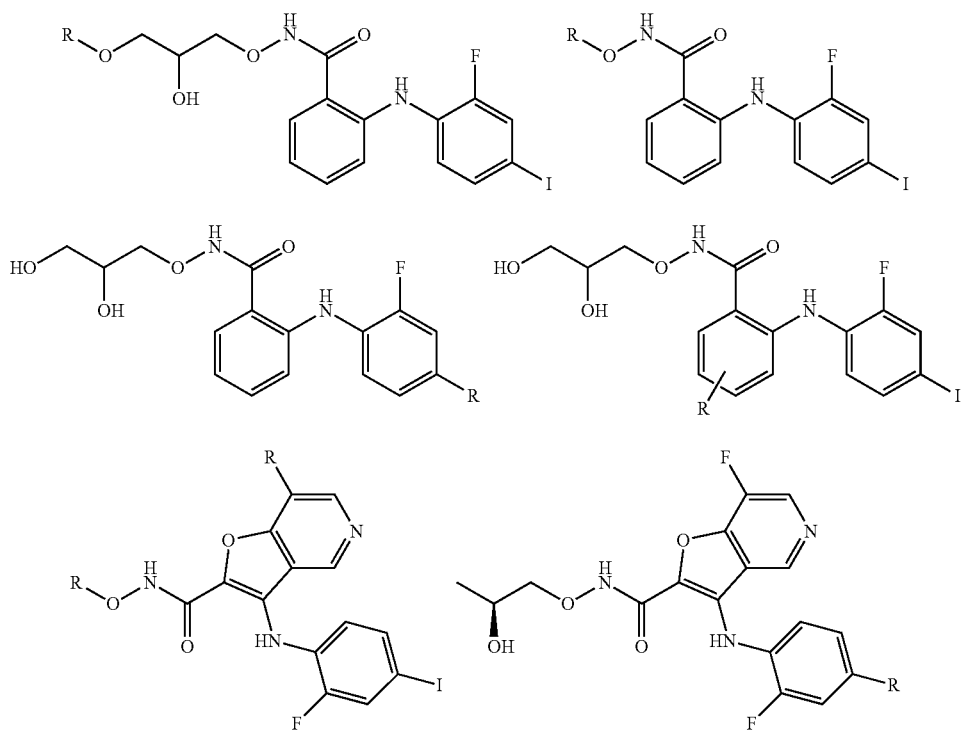

TABLE T-continued

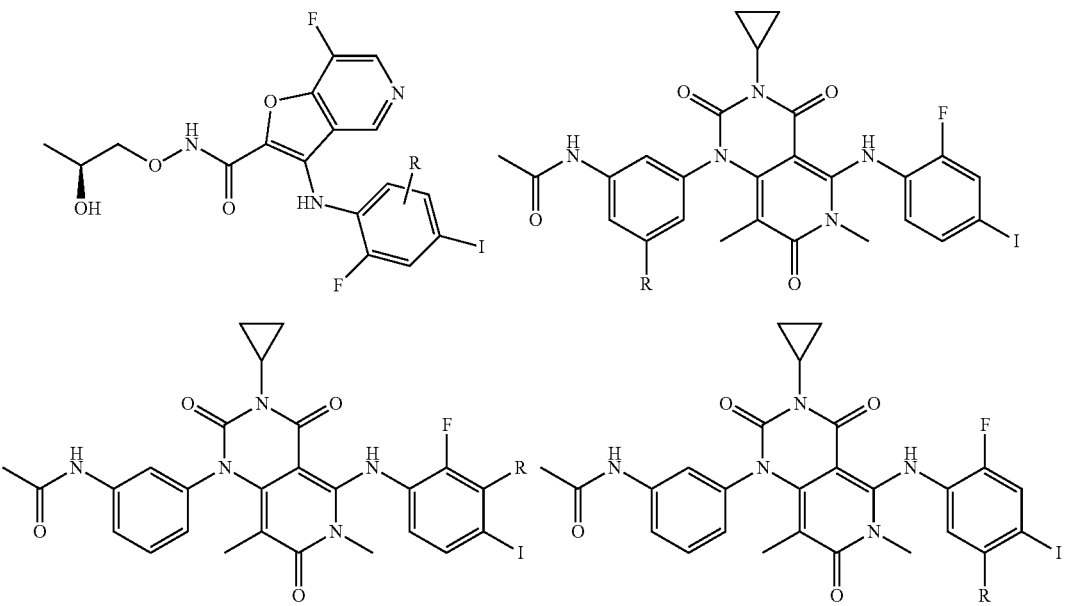

wherein:
R is the point at which the Linker is attached.

MMM. KIT dTAG Targeting Ligands:

KIT dTAG Targeting Ligands as used herein include, but are not limited to:
1. Targeting Ligands that target KIT, including Regorafenib:

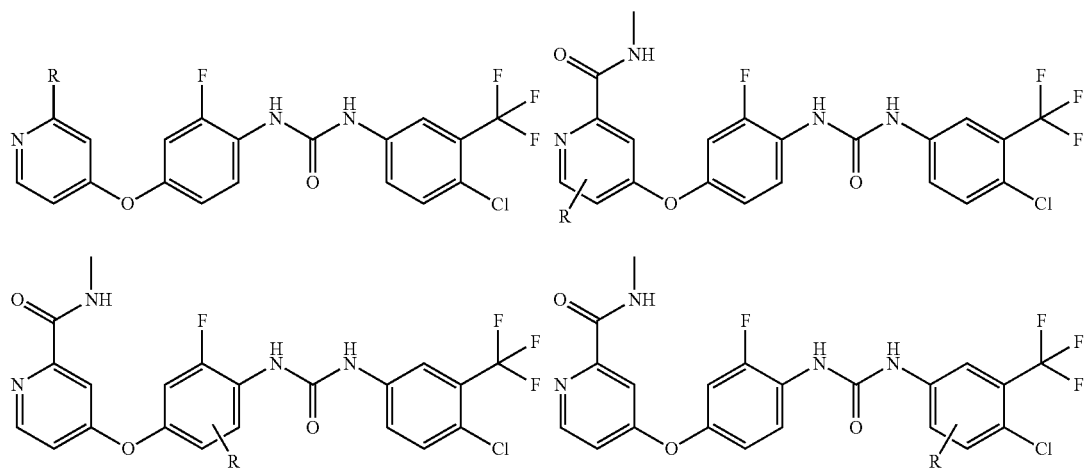

wherein:
R is the point at which the Linker is attached.

NNN. HIV Reverse Transcriptase dTAG Targeting Ligands:

HIV Reverse Transcriptase dTAG Targeting Ligands as used herein include, but are not limited to:
1. Targeting Ligands that target HIV Reverse Transcriptase, including Efavirenz, Tenofovir, Emtricitabine, Ritonavir, Raltegravir, and Atazanavir:

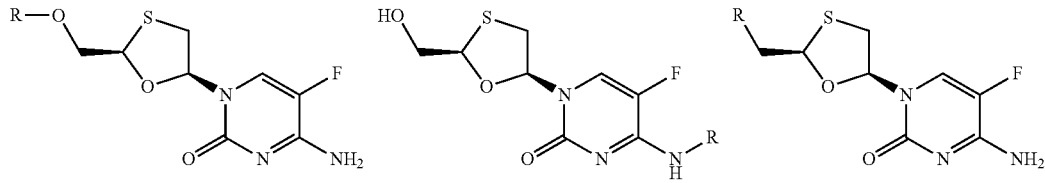

TABLE T-continued
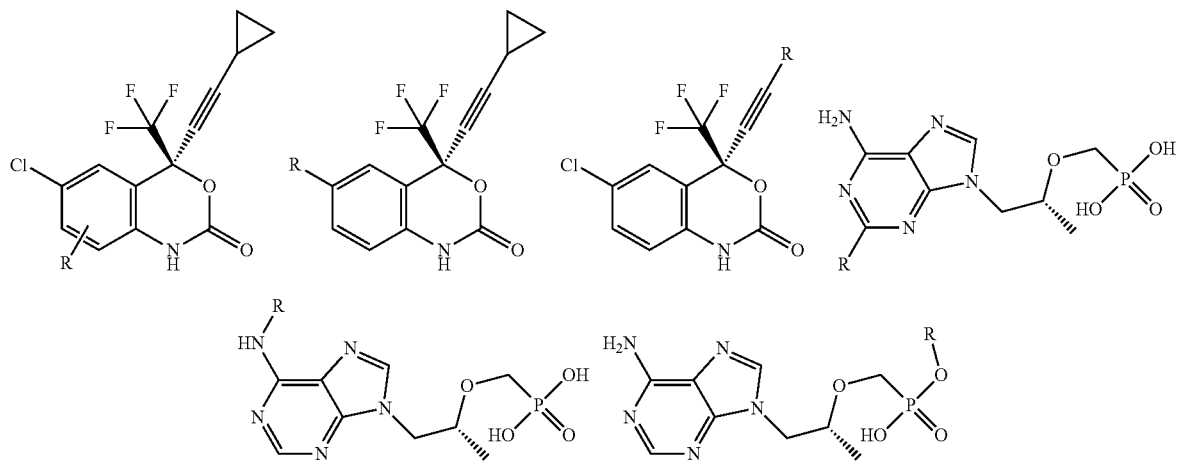
wherein:
R is the point at which the Linker is attached.
OOO. HIV Protease dTAG Targeting Ligands:
HIV Protease dTAG Targeting Ligands as used herein include, but are not limited to:
1. Targeting Ligands that target HIV Protease, including Ritonavir, Raltegravir, and Atazanavir:
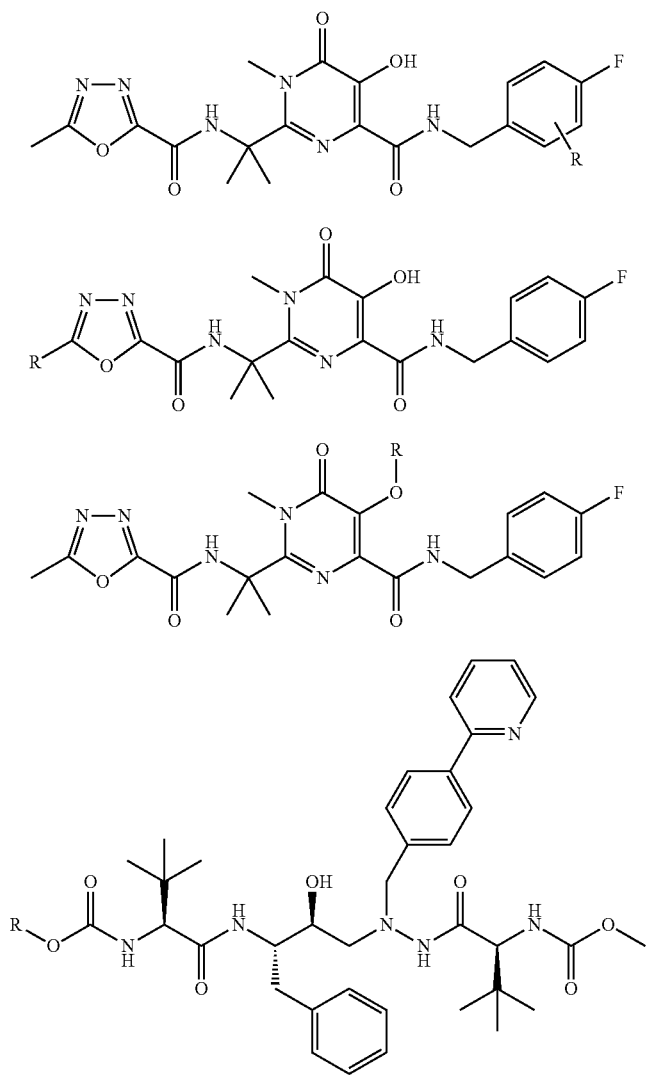

TABLE T-continued
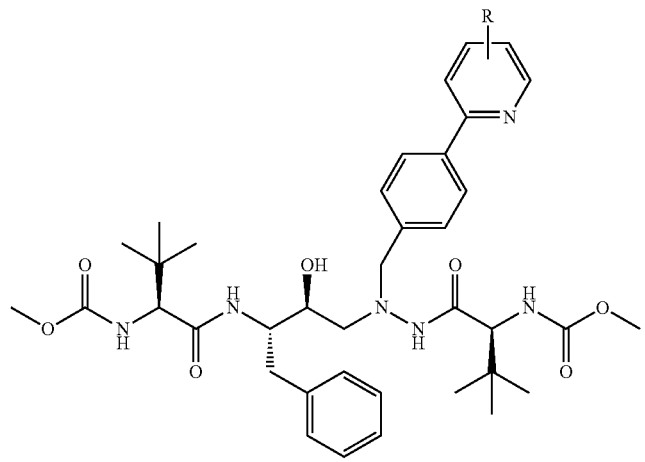
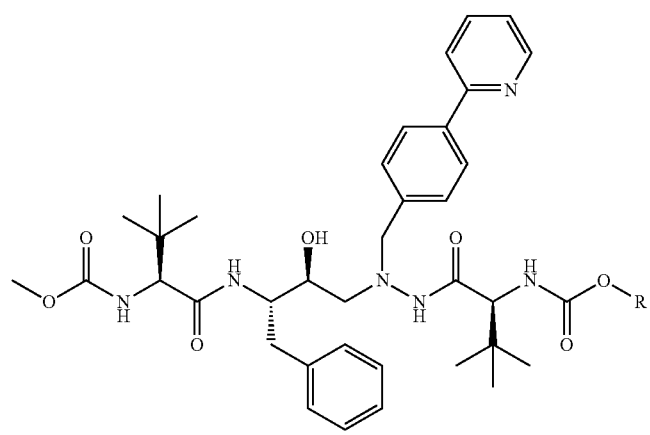
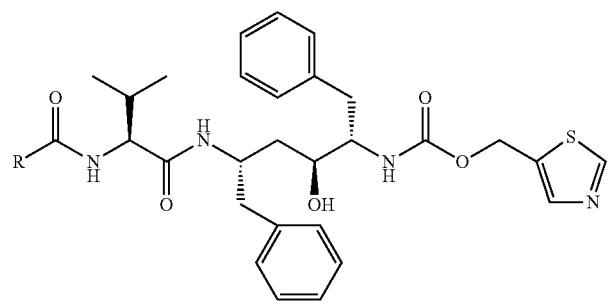
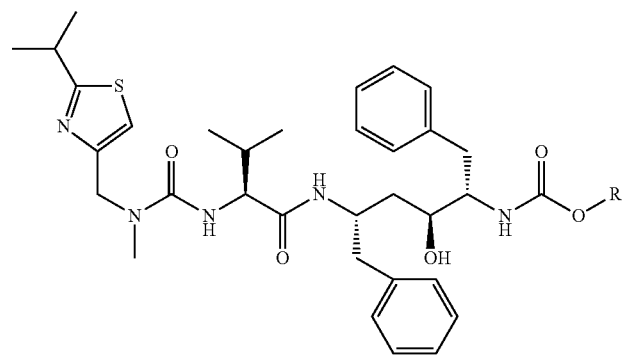

TABLE T-continued

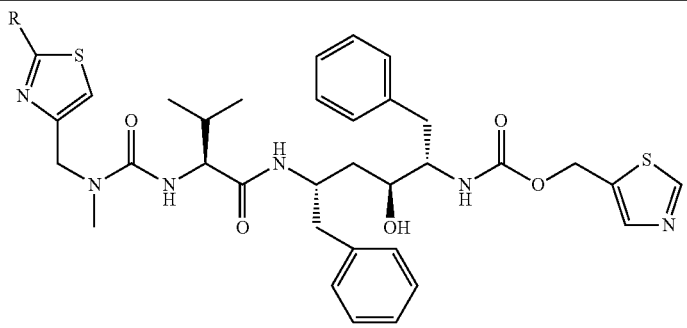

wherein:
R is the point at which the Linker is attached.

In one embodiment any of the above dTAG Targeting Ligands of Table T is used to target any dTAG described herein.

Many dTag targeting ligands are capable of binding to more than one dTAG, for example. Afatinib binds to the EGFR, the ErbB2, and the ErbB4 protein This allows for dual attack of many proteins, as exemplified in Table Z. In one embodiment, the dTAG targeting ligand is selected from the "dTAG targeting ligand" column in Table Z and the dTAG is selected from the corresponding "dTAG" row.

TABLE Z

| dTAG Targeting Ligands and corresponding dTAG | |
|---|---|
| dTAG Targeting Ligand | dTAG |
| Afatinib | EGFR, ErbB2/4 |

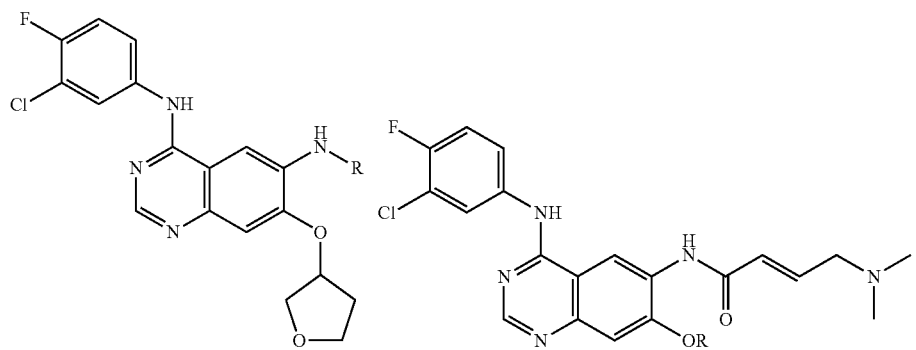

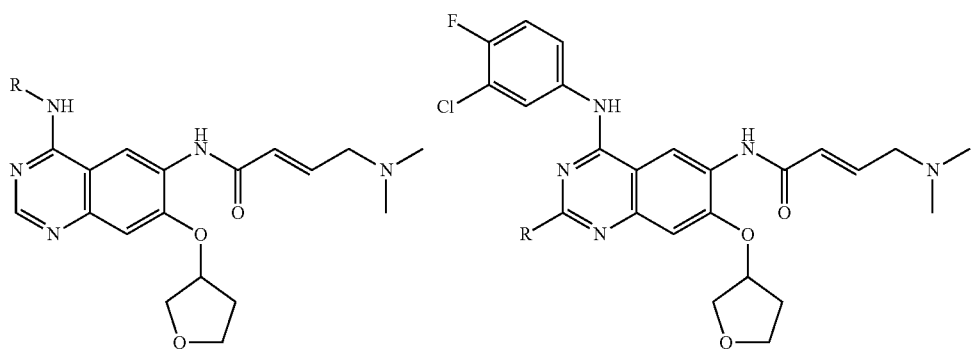

TABLE Z-continued dTAG Targeting Ligands and corresponding dTAG

| dTAG Targeting Ligand | dTAG |
|---|---|
| Axitinib | VEGFR1/2/3, PDGFRβ, Kit |
| Bosutinib | BCR-Abl, Src, Lyn, Hck |

TABLE Z-continued

| dTAG Targeting Ligand | dTAG |
|---|---|
| Cabozantinib | RET, c-Met, VEGFR1/2/3, Kit, TrkB, Flt3, Axl, Tie2 |
| Ceritinib | ALK, IGF-1R, InsR, ROS1 |

TABLE Z-continued dTAG Targeting Ligands and corresponding dTAG

| dTAG Targeting Ligand | dTAG |
|---|---|
| | |
| Crizotinib | ALK, c-Met (HGFR), ROS1, MST1R |

TABLE Z-continued dTAG Targeting Ligands and corresponding dTAG

| dTAG Targeting Ligand | dTAG |
|---|---|
| Dabrafenib | B-Raf |
| Dasatinib | BCR-Abl, Src, Lck, Lyn, Yes, Fyn, Kit, EphA2, PDGFRβ |
| Erlotinib | EGFR |

TABLE Z-continued
dTAG Targeting Ligands and corresponding dTAG
| dTAG Targeting Ligand | dTAG |
|---|---|
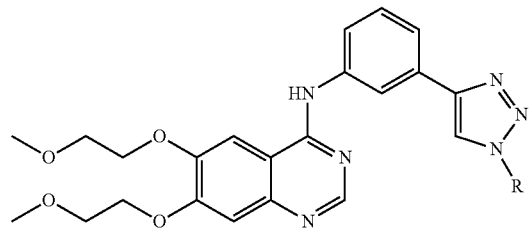
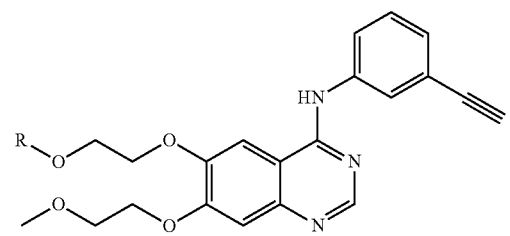
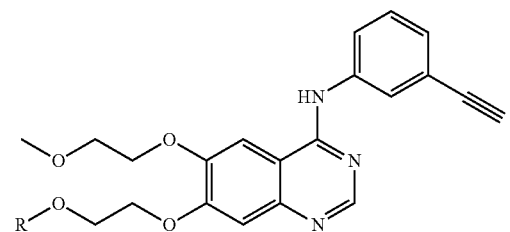
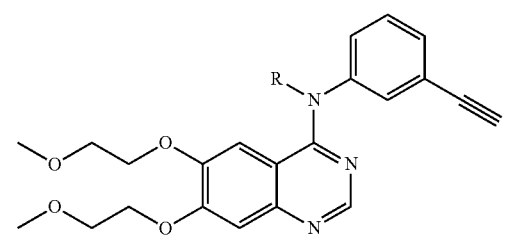

TABLE Z-continued dTAG Targeting Ligands and corresponding dTAG

| dTAG Targeting Ligand | dTAG |
|---|---|
| Everolimus (structure) | HER2— breast cancer, PNET, RCC, RAML, SEGA |

TABLE Z-continued dTAG Targeting Ligands and corresponding dTAG

| dTAG Targeting Ligand | dTAG |
|---|---|

303                                                                                                    304
TABLE Z-continued
dTAG Targeting Ligands and corresponding dTAG
| dTAG Targeting Ligand | dTAG |
|---|---|
| Gefitinib 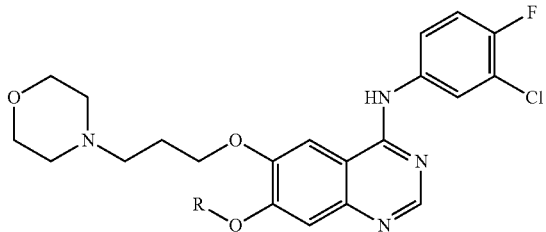 | EGFR, PDGFR |
| Ibrutinib 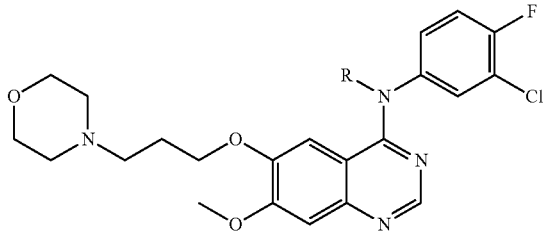 | BTK |
| Imatinib 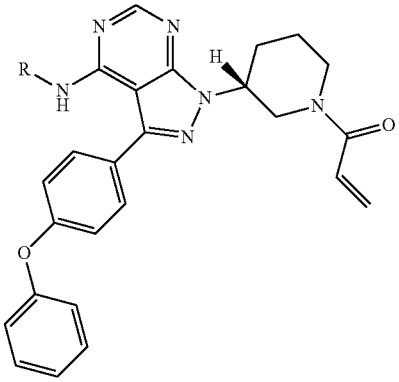 | BCR-Abl, Kit, PDGFR |

TABLE Z-continued
dTAG Targeting Ligands and corresponding dTAG
| dTAG Targeting Ligand | dTAG |
|---|---|
| Lapatinib | EGFR, ErbB2 |
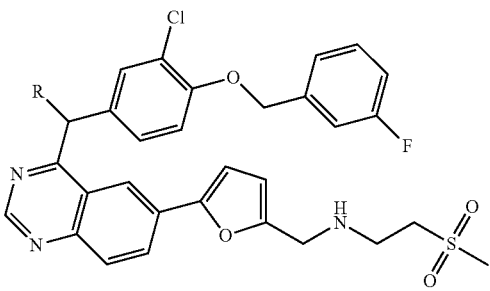
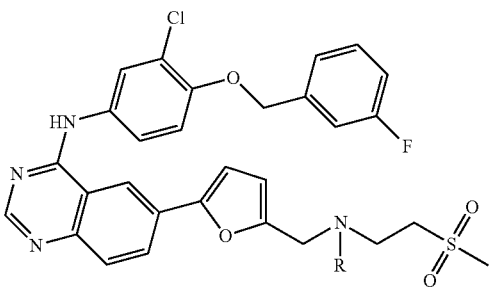
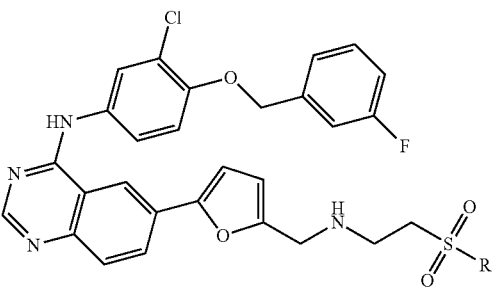
| Lenvatinib | VEGFR1/2/3, FGFR1/2/3/4, PDGFRα, Kit, RET |
|---|---|
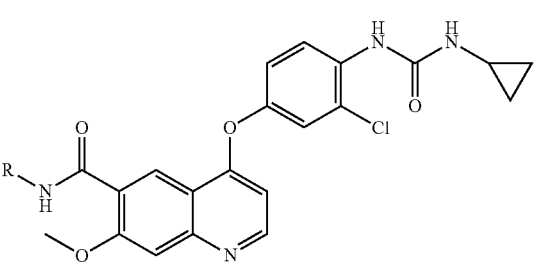
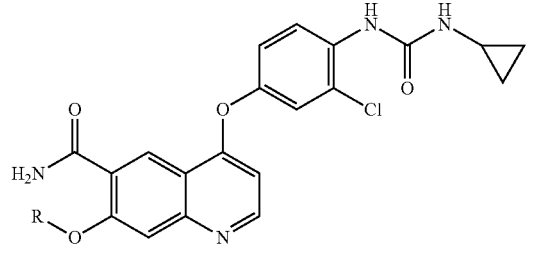

TABLE Z-continued
dTAG Targeting Ligands and corresponding dTAG
| dTAG Targeting Ligand | dTAG |
|---|---|
| 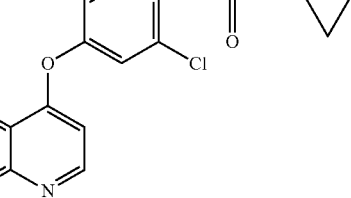 | |
| 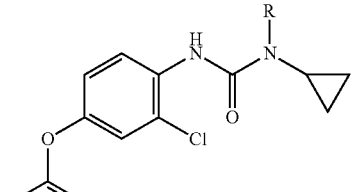<br>Nilotinib | BCR-Abl,<br>PDGFR, DDR1 |
| 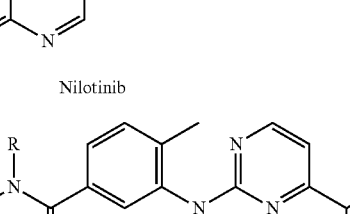 | |
|  | |

TABLE Z-continued
dTAG Targeting Ligands and corresponding dTAG
| dTAG Targeting Ligand | dTAG |
|---|---|
| Nintedanib 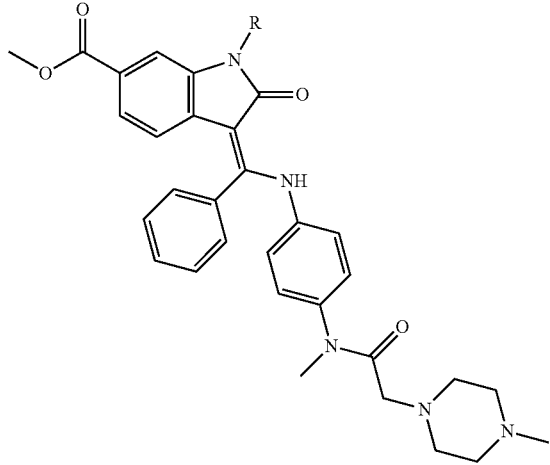 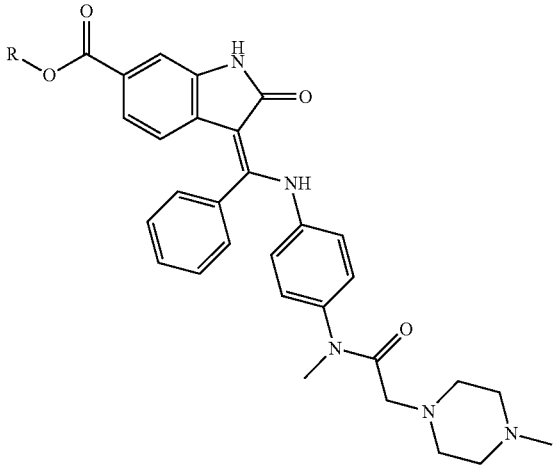 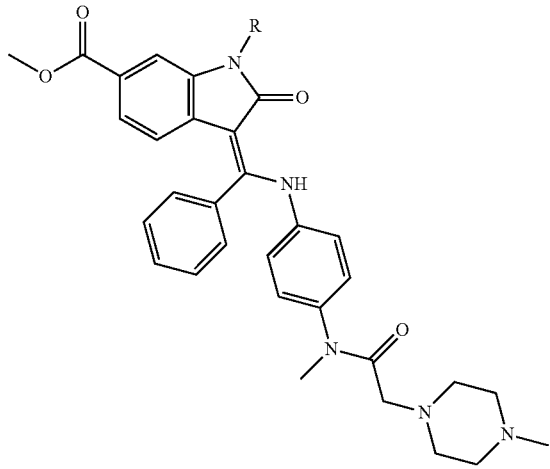 | FGFR1/2/3, Flt3, Lck, PDGFRα/β, VEGFR1/2/3 |

TABLE Z-continued
dTAG Targeting Ligands and corresponding dTAG
| dTAG Targeting Ligand | dTAG |
|---|---|
| 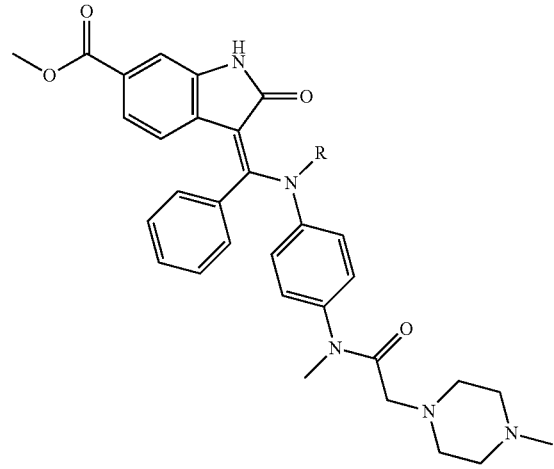 | |
| 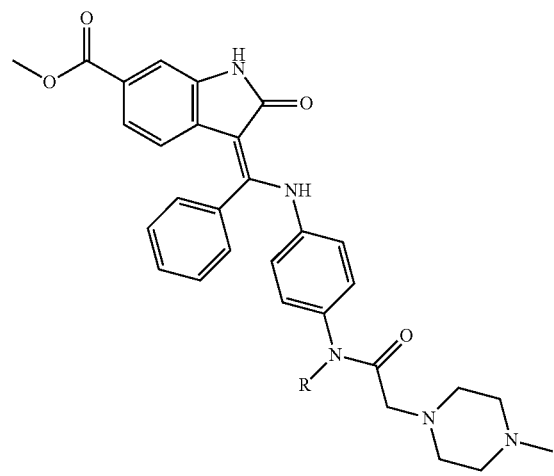 | |
| 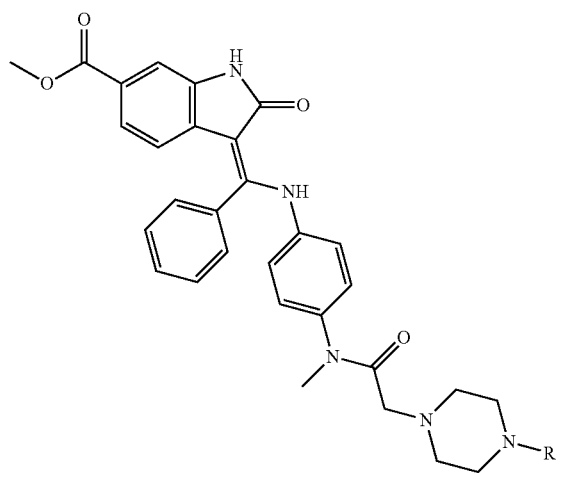 | |

TABLE Z-continued
dTAG Targeting Ligands and corresponding dTAG
| dTAG Targeting Ligand | dTAG |
|---|---|
| Palbociclib 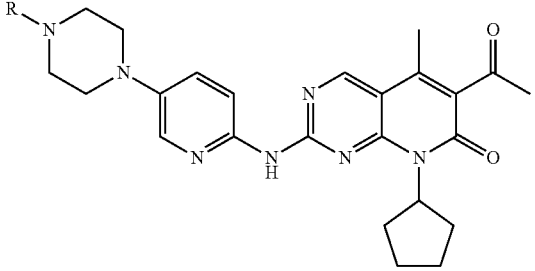 | CDK4/6 |
| Pazopanib 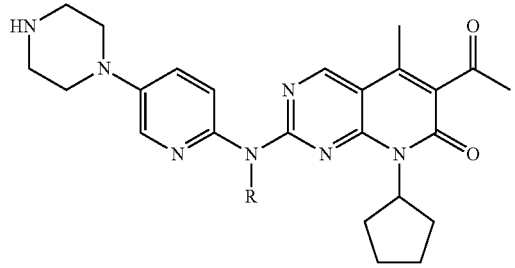 | VEGFR1/2/3, PDGFRα/β, FGFR1/3, Kit, Lck, Fms, Itk |

TABLE Z-continued
dTAG Targeting Ligands and corresponding dTAG
| dTAG Targeting Ligand | dTAG |
|---|---|
| 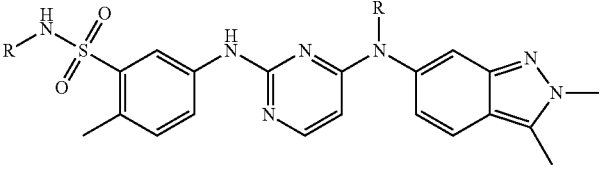 | |
| Ponatinib 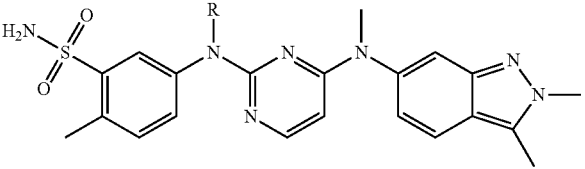 | BCR-Abl, BCR-Abl T315I, VEGFR, PDGFR, FGFR, EphR, Src family kinases, Kit, RET, Tie2, Flt3 |
| Regorafenib 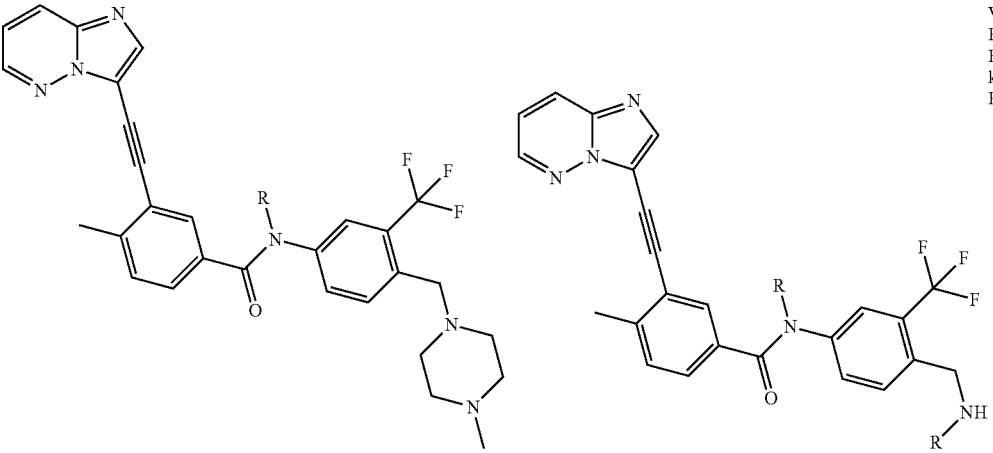 | VEGFR1/2/3, BCR-Abl, B-Raf, B-Raf (V600E), Kit, PDGFRα/β, RET, FGFR1/2, Tie2, and Eph2A |

TABLE Z-continued
dTAG Targeting Ligands and corresponding dTAG
| dTAG Targeting Ligand | dTAG |
|---|---|
| Ruxolitinib | JAK1/2 |
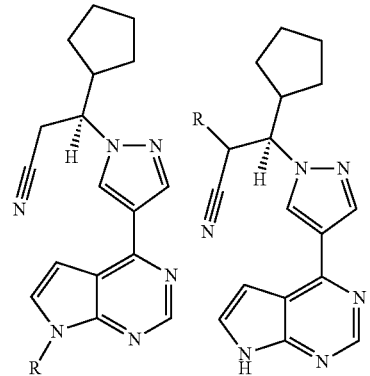
| Sirolimus | FKBP12/mTOR |
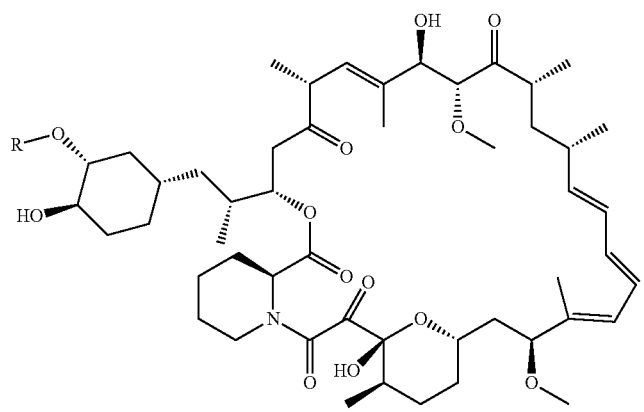
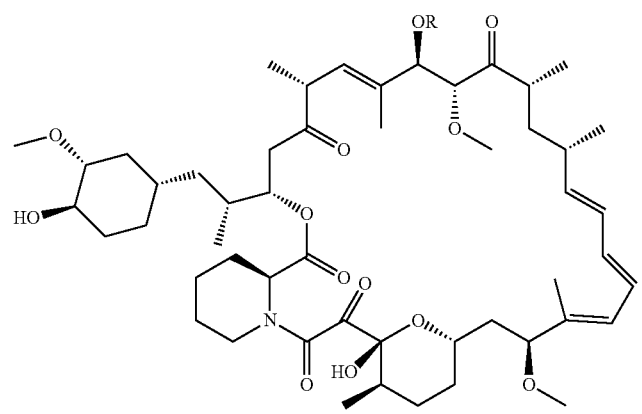

TABLE Z-continued
dTAG Targeting Ligands and corresponding dTAG
| dTAG Targeting Ligand | dTAG |
|---|---|
| 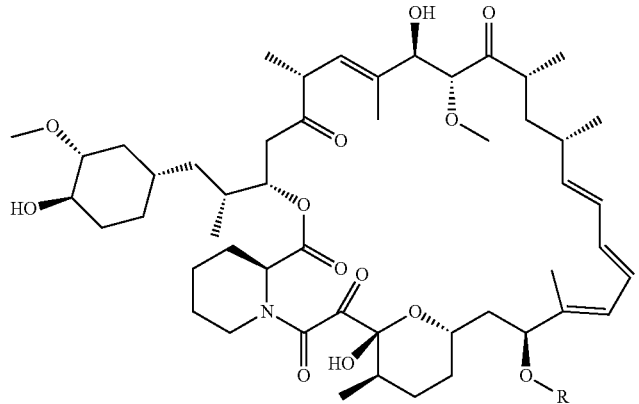 | |
| 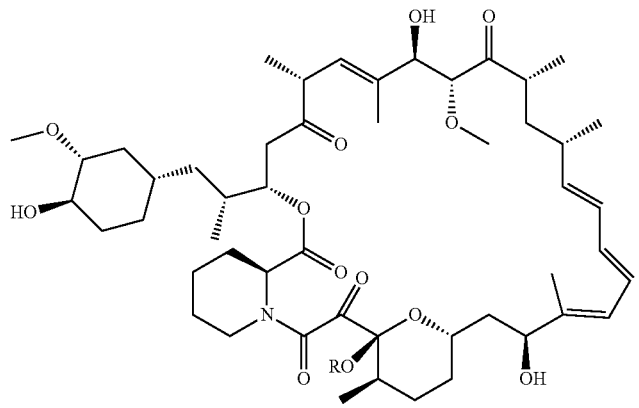 | |
| 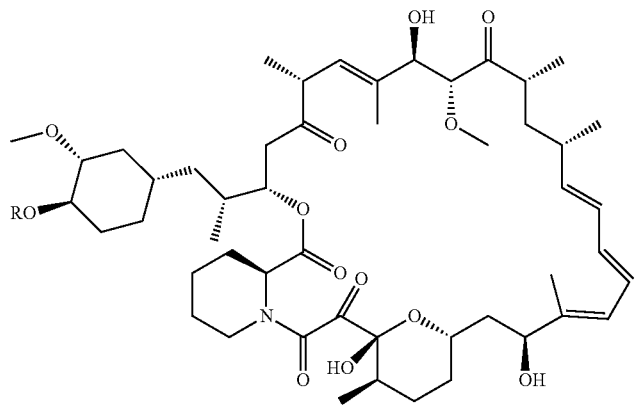<br>Sorafenib<br>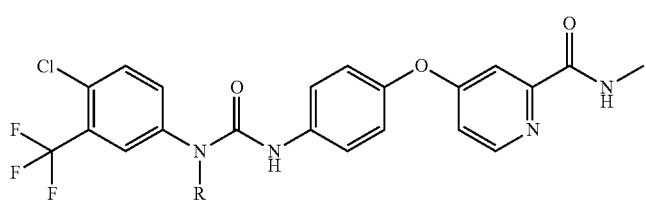 | B-Raf, CDK8, Kit, Flt3, RET, VEGFR1/2/3, PDGFR |

TABLE Z-continued dTAG Targeting Ligands and corresponding dTAG

| dTAG Targeting Ligand | dTAG |
|---|---|
| (structure) | |
| (structure) | |
| Sunitinib (structure) | PDGFRα/β, VEGFR1/2/3, Kit, Flt3, CSF-1R, RET |
| (structure) | |
| (structure) | |

TABLE Z-continued dTAG Targeting Ligands and corresponding dTAG

| dTAG Targeting Ligand | dTAG |
|---|---|
| Temsirolimus | FKBP12/mTOR |

TABLE Z-continued
dTAG Targeting Ligands and corresponding dTAG
| dTAG Targeting Ligand | dTAG |
|---|---|
| 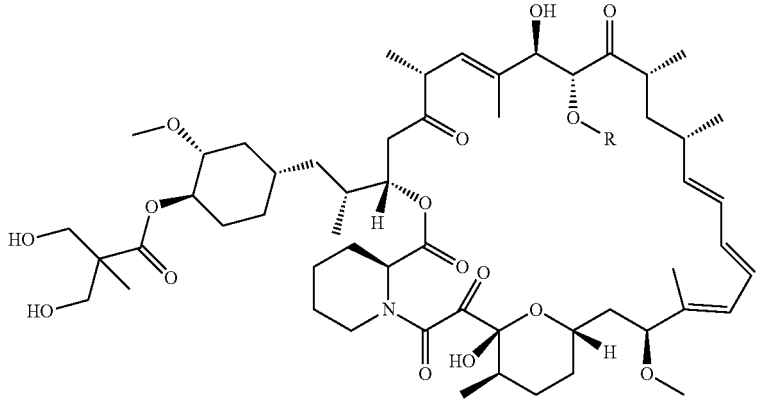 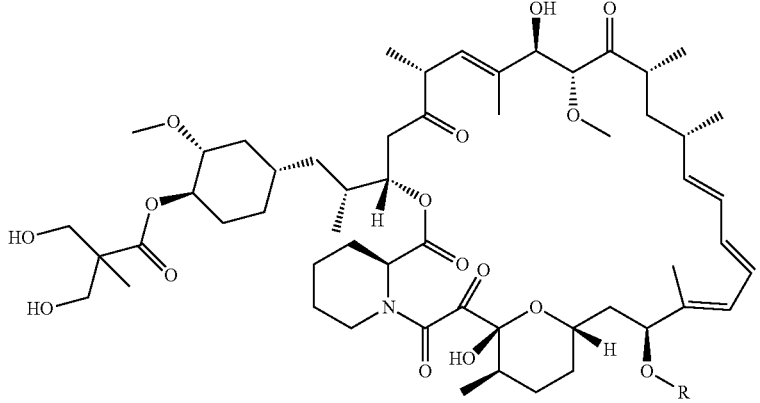 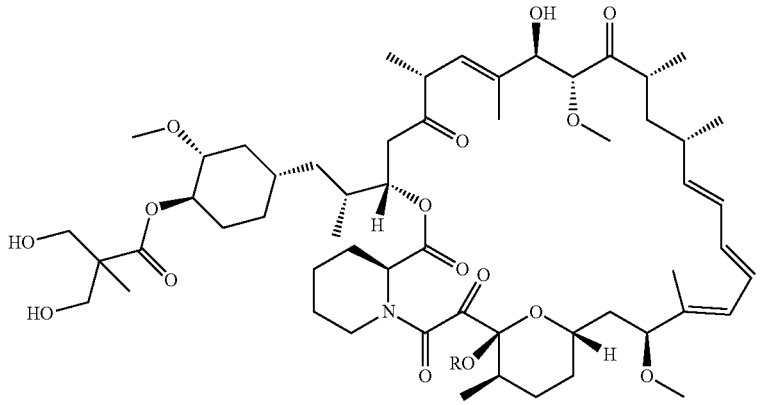<br>Tofacitinib<br>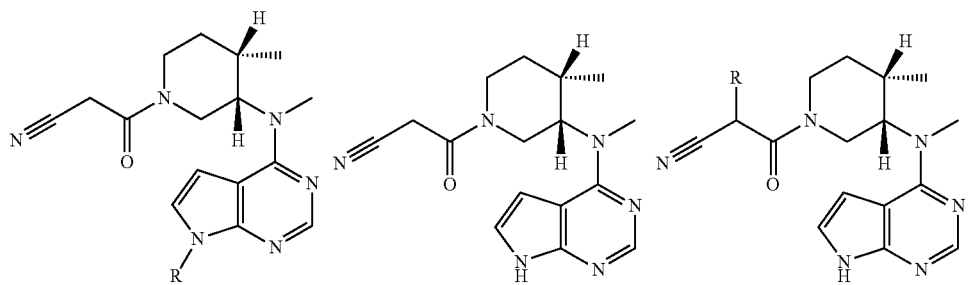 | JAK3 |

TABLE Z-continued dTAG Targeting Ligands and corresponding dTAG

| dTAG Targeting Ligand | dTAG |
|---|---|
| Trametinib | MEK1/2 |
| Vandetanib | EGFR, VEGFR, RET, Tie2, Brk, EphR |

TABLE Z-continued dTAG Targeting Ligands and corresponding dTAG

| dTAG Targeting Ligand | dTAG |
|---|---|
| 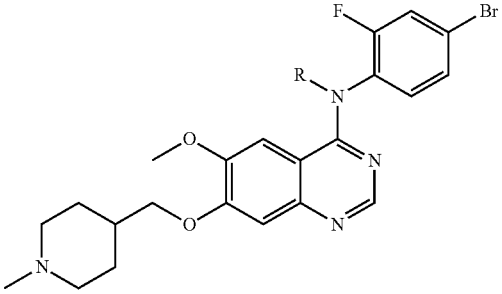<br>Vemurafenib | A/B/C-Raf and B-Raf (V600E) |
| 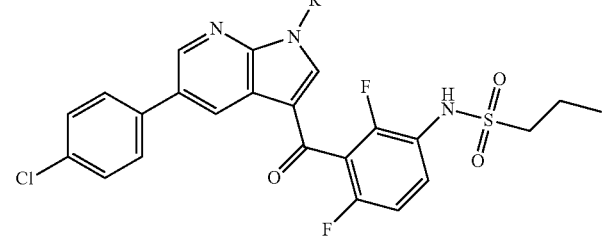 | |
| 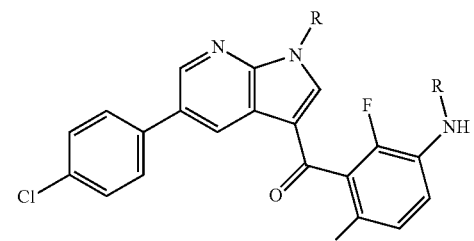 | |

In certain embodiments, the present application includes compounds containing the dTAG Targeting Ligands shown in Table 1.

TABLE 1 dTAG Targeting Ligands 1-6

| Compound | Structure |
|---|---|
| TL1 | 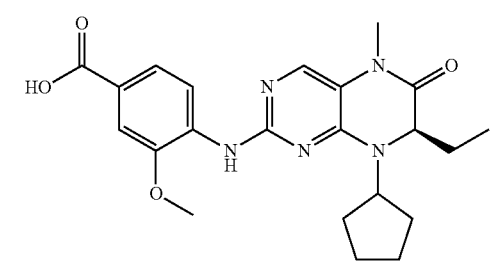 [SMILES: CC[C@@H]1C(=O)N(C)c2cnc(Nc3ccc(C(=O)O)cc3OC)nc2N1C1CCCC1]<br>Ang. Chem. Intl Ed. 50, 9378 (2011) |

TABLE 1-continued dTAG Targeting Ligands 1-6

| Compound | Structure |
|---|---|
| TL2 | 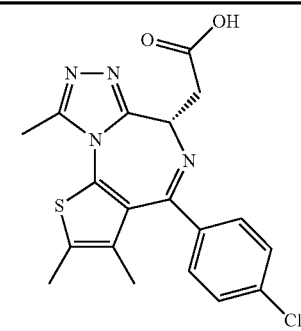 |
| TL5 | 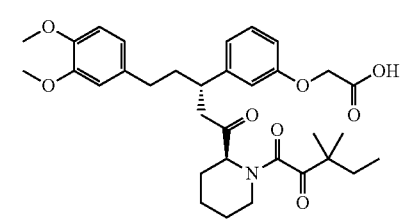 [SMILES: CCC(C)(C)C(=O)C(=O)N1CCCC[C@H]1C(=O)C[C@H](CCc1ccc(OC)c(OC)c1)c1cccc(OCC(=O)O)c1] |

TABLE 1-continued dTAG Targeting Ligands 1-6

| Compound | Structure |
|---|---|
| | JACS 115, 9925 (1993) |
| TL7 | 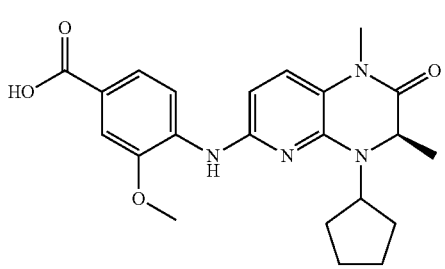 [SMILES: COc1cc(C(=O)O)ccc1Nc1ccc2c(n1)N(C1CCCC1)[C@H](C)C(=O)N2C] |
| TL3 | 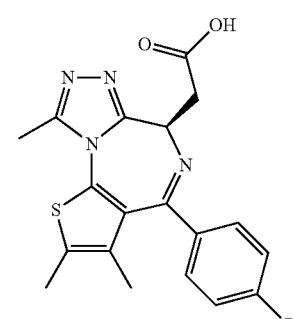 |
| TL4 | 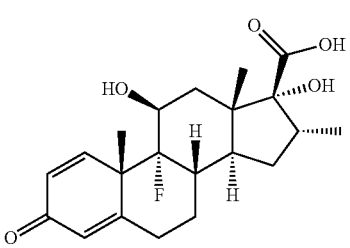 |
| TL6 | 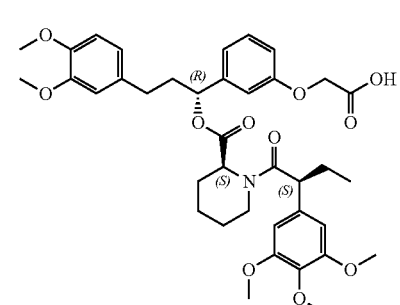 |

In certain embodiments, the dTAG Targeting Ligand is a compound of Formula TL-I:

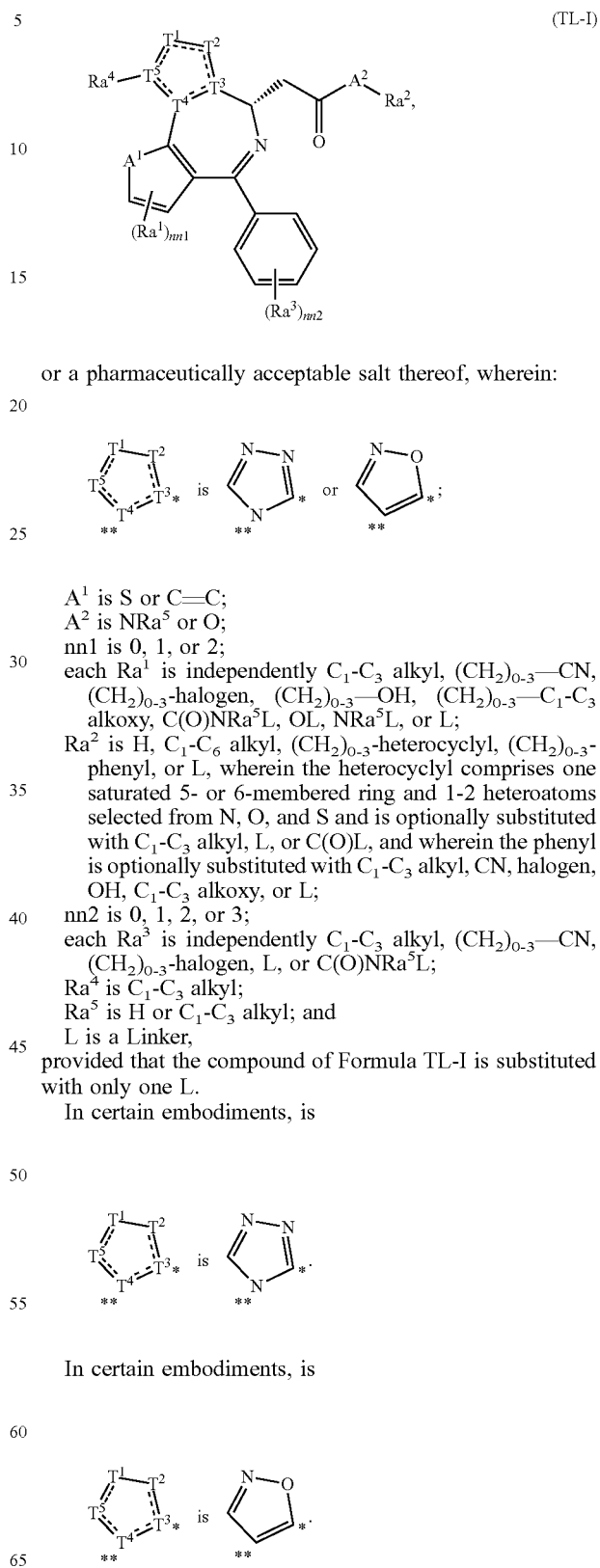

(TL-I)

or a pharmaceutically acceptable salt thereof, wherein:

$A^1$ is S or C=C;
$A^2$ is $NRa^5$ or O;
nn1 is 0, 1, or 2;
each $Ra^1$ is independently $C_1$-$C_3$ alkyl, $(CH_2)_{0-3}$—CN, $(CH_2)_{0-3}$-halogen, $(CH_2)_{0-3}$—OH, $(CH_2)_{0-3}$—$C_1$-$C_3$ alkoxy, $C(O)NRa^5L$, OL, $NRa^5L$, or L;
$Ra^2$ is H, $C_1$-$C_6$ alkyl, $(CH_2)_{0-3}$-heterocyclyl, $(CH_2)_{0-3}$-phenyl, or L, wherein the heterocyclyl comprises one saturated 5- or 6-membered ring and 1-2 heteroatoms selected from N, O, and S and is optionally substituted with $C_1$-$C_3$ alkyl, L, or C(O)L, and wherein the phenyl is optionally substituted with $C_1$-$C_3$ alkyl, CN, halogen, OH, $C_1$-$C_3$ alkoxy, or L;
nn2 is 0, 1, 2, or 3;
each $Ra^3$ is independently $C_1$-$C_3$ alkyl, $(CH_2)_{0-3}$—CN, $(CH_2)_{0-3}$-halogen, L, or $C(O)NRa^5L$;
$Ra^4$ is $C_1$-$C_3$ alkyl;
$Ra^5$ is H or $C_1$-$C_3$ alkyl; and
L is a Linker,
provided that the compound of Formula TL-I is substituted with only one L.

In certain embodiments, is

In certain embodiments, is

In certain embodiments, $A^1$ is S.

In certain embodiments, $A^1$ is C=C.

In certain embodiments, $A^2$ is $NRa^5$. In further embodiments, $Ra^5$ is H. In other embodiments, $Ra^5$ is $C_1$-$C_3$ alkyl (e.g., methyl, ethyl, propyl, or i-propyl). In further embodiments, $Ra^5$ is methyl.

In certain embodiments, $A^2$ is O.

In certain embodiments, nn1 is 0.

In certain embodiments, nn1 is 1.

In certain embodiments, nn1 is 2.

In certain embodiments, at least one $Ra^1$ is $C_1$-$C_3$ alkyl (e.g., methyl, ethyl, propyl, or i-propyl). In further embodiments, at least one $Ra^1$ is methyl. In further embodiments, two $Ra^1$ are methyl.

In certain embodiments, at least one $Ra^1$ is CN, $(CH_2)$—CN, $(CH_2)_2$—CN, or $(CH_2)_3$—CN. In further embodiments, at least one $Ra^1$ is $(CH_2)$—CN.

In certain embodiments, at least one $Ra^1$ is halogen (e.g., F, Cl, or Br), $(CH_2)$-halogen, $(CH_2)_2$-halogen, or $(CH_2)_3$-halogen. In further embodiments, at least one $Ra^1$ is $C_1$, $(CH_2)$—Cl, $(CH_2)_2$—Cl, or $(CH_2)_3$—Cl.

In certain embodiments, at least one $Ra^1$ is OH, $(CH_2)$—OH, $(CH_2)_2$—OH, or $(CH_2)_3$—OH.

In certain embodiments, at least one $Ra^1$ is $C_1$-$C_3$ alkoxy (e.g., methoxy, ethoxy, or propoxy), $(CH_2)$—$C_1$-$C_3$ alkoxy, $(CH_2)_2$—$C_1$-$C_3$ alkoxy, or $(CH_2)_3$—$C_1$-$C_3$ alkoxy. In certain embodiments, at least one $Ra^1$ is methoxy.

In certain embodiments, one $Ra^1$ is $C(O)NRa^5L$. In further embodiments, $Ra^5$ is H. In other embodiments, $Ra^5$ is $C_1$-$C_3$ alkyl (e.g., methyl, ethyl, propyl, or i-propyl).

In certain embodiments, one $Ra^1$ is OL.

In certain embodiments, one $Ra^1$ is $NRa^5L$. In further embodiments, $Ra^5$ is H. In other embodiments, $Ra^5$ is $C_1$-$C_3$ alkyl (e.g., methyl, ethyl, propyl, or i-propyl). In other embodiments, $Ra^5$ is methyl.

In certain embodiments, one $Ra^1$ is L.

In certain embodiments, $Ra^2$ is H.

In certain embodiments, $Ra^2$ is straight-chain $C_1$-$C_6$ or branched $C_3$-$C_6$ alkyl (e.g., methyl, ethyl, propyl, i-propyl, butyl, i-butyl, t-butyl, pentyl, or hexyl). In further embodiments, $Ra^2$ is methyl, ethyl, or t-butyl.

In certain embodiments, $Ra^2$ is heterocyclyl, $(CH_2)$-heterocyclyl, $(CH_2)_2$-heterocyclyl, or $(CH_2)_3$-heterocyclyl. In further embodiments, $Ra^2$ is $(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.

In certain embodiments, the heterocyclyl is substituted with $C_1$-$C_3$ alkyl (e.g., methyl, ethyl, propyl, or i-propyl).

In certain embodiments, the heterocyclyl is substituted with C(O)L.

In certain embodiments, the heterocyclyl is substituted with L.

In certain embodiments, $Ra^2$ is phenyl, $(CH_2)$-phenyl, $(CH_2)_2$-phenyl, or $(CH_2)_3$-phenyl. In further embodiments, $Ra^2$ is phenyl.

In certain embodiments, the phenyl is substituted with $C_1$-$C_3$ alkyl (e.g., methyl, ethyl, propyl, or i-propyl). In certain embodiments, the phenyl is substituted with CN. In certain embodiments, the phenyl is substituted with halogen (e.g., F, Cl, or Br). In certain embodiments, the phenyl is substituted with OH. In certain embodiments, the phenyl is substituted with $C_1$-$C_3$ alkoxy (e.g., methoxy, ethoxy, or propoxy).

In certain embodiments, the phenyl is substituted with L.

In certain embodiments, $Ra^2$ is L.

In certain embodiments, nn2 is 0.

In certain embodiments, nn2 is 1.

In certain embodiments, nn2 is 2.

In certain embodiments, nn2 is 3.

In certain embodiments, at least one $Ra^3$ is $C_1$-$C_3$ alkyl (e.g., methyl, ethyl, propyl, or i-propyl). In further embodiments, at least one $Ra^3$ is methyl.

In certain embodiments, at least one $Ra^3$ is CN, $(CH_2)$—CN, $(CH_2)_2$—CN, or $(CH_2)_3$—CN. In further embodiments, at least one $Ra^3$ is CN.

In certain embodiments, at least one $Ra^3$ is halogen (e.g., F, Cl, or Br), $(CH_2)$-halogen, $(CH_2)_2$-halogen, or $(CH_2)_3$-halogen. In further embodiments, at least one $Ra^3$ is $C_1$, $(CH_2)$—Cl, $(CH_2)_2$—Cl, or $(CH_2)_3$—Cl. In further embodiments, at least one $Ra^3$ is Cl.

In certain embodiments, one $Ra^3$ is L.

In certain embodiments, one $Ra^3$ is $C(O)NRa^5L$. In further embodiments, $Ra^5$ is H. In other embodiments, $Ra^5$ is $C_1$-$C_3$ alkyl (e.g., methyl, ethyl, propyl, or i-propyl).

In certain embodiments, $Ra^4$ is $C_1$-$C_3$ alkyl (e.g., methyl, ethyl, propyl, or i-propyl). In further embodiments, $Ra^4$ is methyl.

In certain embodiments, $Ra^5$ is H.

In certain embodiments, $Ra^5$ is $C_1$-$C_3$ alkyl (e.g., methyl, ethyl, propyl, or i-propyl). In further embodiments, $Ra^5$ is methyl.

In certain embodiments,

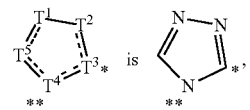

and $A^1$ is S.

In certain embodiments,

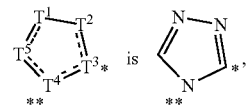

and $A^1$ is C=C.

In certain embodiments,

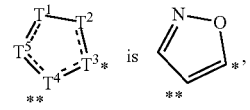

and $A^1$ is C=C.

In certain embodiments, $A^2$ is NH, and $Ra^2$ is $(CH_2)_{0-3}$-heterocyclyl. In further embodiments, $Ra^2$ is $(CH_2)_3$-heterocyclyl. In further embodiments, the heterocyclyl is piperazinyl. In further embodiments, the heterocyclyl is substituted with $C_1$-$C_3$ alkyl, L, or C(O)L.

In certain embodiments, $A^2$ is NH, and $Ra^2$ is $(CH_2)_{0-3}$-phenyl. In further embodiments, $Ra^2$ is phenyl. In further embodiments, the phenyl is substituted with OH or L.

In certain embodiments, $A^2$ is NH, and $Ra^2$ is L.

In certain embodiments, $A^2$ is NH, and $Ra^2$ is H or $C_1$-$C_6$ alkyl. In further embodiments, $Ra^2$ is $C_1$-$C_4$ alkyl.

In certain embodiments, $A^2$ is O, and $Ra^2$ is H or $C_1$-$C_6$ alkyl. In further embodiments, $Ra^2$ is $C_1$-$C_4$ alkyl.

In certain embodiments, a dTAG Targeting Ligand is a compound of Formula TL-I1:

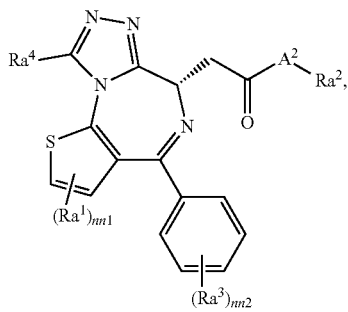

(TL-I1)

or a pharmaceutically acceptable salt thereof, wherein $A^2$, $Ra^1$, $Ra^2$, $Ra^3$, $Ra^4$, $Ra^5$, nn1, and nn2 are each as defined above in Formula TL-I.

Each of $A^2$, $Ra^1$, $Ra^2$, $Ra^3$, $Ra^4$, $Ra^5$, nn1, and nn2 may be selected from the moieties described above in Formula TL-I. Each of the moieties defined for one of $A^2$, $Ra^1$, $Ra^2$, $Ra^3$, $Ra^4$, $Ra^5$, nn1, and nn2, can be combined with any of the moieties defined for the others of $A^2$, $Ra^1$, $Ra^2$, $Ra^3$, $Ra^4$, $Ra^5$, nn1, and nn2, as described above in Formula TL-I.

In certain embodiments, a dTAG Targeting Ligand is a compound of Formula TL-I1a-TL-I1d:

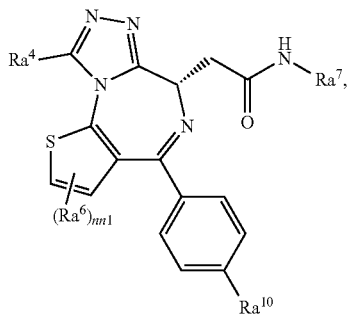

(TL-I1a)

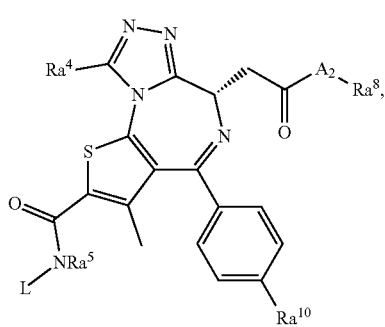

(TL-I1b)

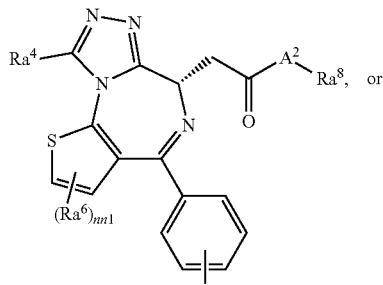

(TL-I1c)

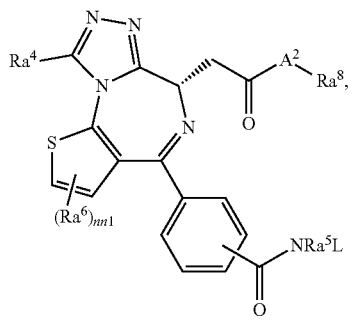

(TL-I1d)

or a pharmaceutically acceptable salt thereof, wherein:
- each $Ra^6$ is independently $C_1$-$C_3$ alkyl, $(CH_2)_{0-3}$—CN, $(CH_2)_{0-3}$-halogen, $(CH_2)_{0-3}$—OH, or $(CH_2)_{0-3}$—$C_1$-$C_3$ alkoxy;
- $Ra^7$ is $(CH_2)_{0-3}$-heterocyclyl, $(CH_2)_{0-3}$-phenyl, or L, wherein the heterocyclyl comprises one saturated 5- or 6-membered ring and 1-2 heteroatoms selected from N, O, and S and is substituted with L or C(O)L, and wherein the phenyl is substituted with L;
- $Ra^8$ is H, $C_1$-$C_6$ alkyl, $(CH_2)_{0-3}$-heterocyclyl, or $(CH_2)_{0-3}$-phenyl, wherein the heterocyclyl comprises one saturated 5- or 6-membered ring and 1-2 heteroatoms selected from N, O, and S and is optionally substituted with $C_1$-$C_3$ alkyl, and wherein the phenyl is optionally substituted with $C_1$-$C_3$ alkyl, CN, halogen, OH, or $C_1$-$C_3$ alkoxy;
- $Ra^{10}$ is $C_1$-$C_3$ alkyl, $(CH_2)_{0-3}$—CN, or $(CH_2)_{0-3}$-halogen; and
- $A^2$, $Ra^4$, $Ra^5$, nn1, and L are each as defined above in Formula TL-I.

In certain embodiments, nn1 is 0.
In certain embodiments, nn1 is 1.
In certain embodiments, nn1 is 2.
In certain embodiments, at least one $Ra^6$ is $C_1$-$C_3$ alkyl (e.g., methyl, ethyl, propyl, or i-propyl). In further embodiments, at least one $Ra^6$ is methyl. In further embodiments, two $Ra^6$ are methyl.

In certain embodiments, at least one $Ra^6$ is CN, $(CH_2)$—CN, $(CH_2)_2$—CN, or $(CH_2)_3$—CN. In further embodiments, at least one $Ra^6$ is $(CH_2)$—CN.

In certain embodiments, at least one $Ra^6$ is halogen (e.g., F, Cl, or Br), $(CH_2)$-halogen, $(CH_2)_2$-halogen, or $(CH_2)_3$-halogen. In further embodiments, at least one $Ra^6$ is $C_1$, $(CH_2)$—Cl, $(CH_2)_2$—Cl, or $(CH_2)_3$—Cl.

In certain embodiments, at least one $Ra^6$ is OH, $(CH_2)$—OH, $(CH_2)_2$—OH, or $(CH_2)_3$—OH.

In certain embodiments, at least one $Ra^6$ is $C_1$-$C_3$ alkoxy (e.g., methoxy, ethoxy, or propoxy), $(CH_2)$—$C_1$-$C_3$ alkoxy, $(CH_2)_2$—$C_1$-$C_3$ alkoxy, or $(CH_2)_3$—$C_1$-$C_3$ alkoxy. In certain embodiments, at least one $Ra^6$ is methoxy.

In certain embodiments, Ra⁷ is heterocyclyl, (CH₂)-heterocyclyl, (CH₂)₂-heterocyclyl, or (CH₂)₃-heterocyclyl. In further embodiments, Ra⁷ is (CH₂)₃-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.

In certain embodiments, the heterocyclyl is substituted with C(O)L.

In certain embodiments, the heterocyclyl is substituted with L.

In certain embodiments, Ra⁷ is phenyl, (CH₂)-phenyl, (CH₂)₂-phenyl, or (CH₂)₃-phenyl. In further embodiments, Ra⁷ is phenyl.

In certain embodiments, Ra⁷ is L.

In certain embodiments, Ra⁸ is H.

In certain embodiments, Ra⁸ is straight-chain $C_1$-$C_6$ or branched $C_3$-$C_6$ alkyl (e.g., methyl, ethyl, propyl, i-propyl, butyl, i-butyl, t-butyl, pentyl, or hexyl). In further embodiments, Ra⁸ is methyl, ethyl, or t-butyl.

In certain embodiments, Ra⁸ is heterocyclyl, (CH₂)-heterocyclyl, (CH₂)₂-heterocyclyl, or (CH₂)₃-heterocyclyl. In further embodiments, Ra⁸ is (CH₂)₃-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.

In certain embodiments, the heterocyclyl is substituted with $C_1$-$C_3$ alkyl (e.g., methyl, ethyl, propyl, or i-propyl).

In certain embodiments, Ra⁸ is phenyl, (CH₂)-phenyl, (CH₂)₂-phenyl, or (CH₂)₃-phenyl. In further embodiments, Ra⁸ is phenyl.

In certain embodiments, the phenyl is substituted with $C_1$-$C_3$ alkyl (e.g., methyl, ethyl, propyl, or i-propyl). In certain embodiments, the phenyl is substituted with CN. In certain embodiments, the phenyl is substituted with halogen (e.g., F, Cl, or Br). In certain embodiments, the phenyl is substituted with OH. In certain embodiments, the phenyl is substituted with $C_1$-$C_3$ alkoxy (e.g., methoxy, ethoxy, or propoxy).

In certain embodiments, Ra¹⁰ is $C_1$-$C_3$ alkyl (e.g., methyl, ethyl, propyl, or i-propyl).

In certain embodiments, Ra¹⁰ is CN, (CH₂)—CN, (CH₂)₂—CN, or (CH₂)₃—CN.

In certain embodiments, Ra¹ is halogen (e.g., F, Cl, or Br), (CH₂)-halogen, (CH₂)₂-halogen, or (CH₂)₃-halogen. In further embodiments, Ra¹ is $C_1$, (CH₂)—Cl, (CH₂)₂—Cl, or (CH₂)₃—Cl. In further embodiments, Ra¹⁰ is Cl.

Each of A², Ra⁴, Ra⁵, and nn1 may be selected from the moieties described above in Formula TL-I. Each of the moieties defined for one of A², Ra⁴, Ra⁵, Ra⁶, Ra⁷, Ra⁸, Ra¹⁰, and nn1, can be combined with any of the moieties defined for the others of A², Ra⁴, Ra⁵, Ra⁶, Ra⁷, Ra⁸, Ra¹⁰, and nn1, as described above and in Formula TL-I.

In certain embodiments, a dTAG Targeting Ligand is a compound of Formula TL-I2:

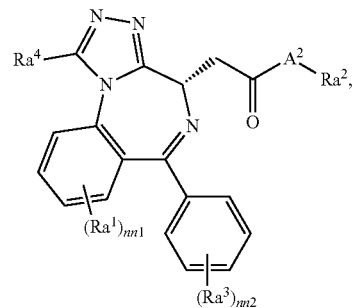

(TL-I2)

or a pharmaceutically acceptable salt thereof, wherein A², Ra¹, Ra², Ra³, Ra⁴, Ra⁵, nn1, and nn2 are each as defined above in Formula TL-I.

Each of A², Ra¹, Ra², Ra³, Ra⁴, Ra⁵, nn1, and nn2 may be selected from the moieties described above in Formula TL-I. Each of the moieties defined for one of A², Ra¹, Ra², Ra³, Ra⁴, Ra⁵, nn1, and nn2, can be combined with any of the moieties defined for the others of A², Ra¹, Ra², Ra³, Ra⁴, Ra⁵, nn1, and nn2, as described above in Formula TL-I.

In certain embodiments, a dTAG Targeting Ligand is a compound of Formula TL-I2a-TL-I2c:

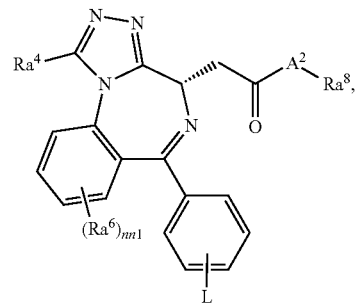

(TL-12a)

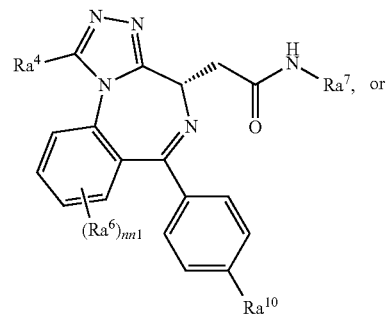

(TL-12b)

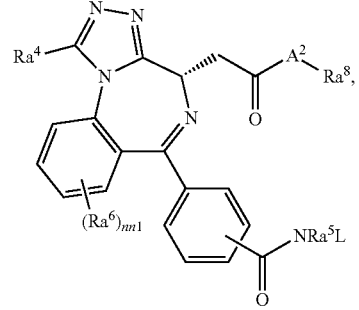

(TL-12c)

or a pharmaceutically acceptable salt thereof, wherein A², Ra⁴, Ra⁵, nn1, and L are each as defined above in Formula TL-I1, and Ra⁶, Ra⁷, Ra⁸, and Ra¹⁰ are each as defined above in Formula TL-I1a-TL-I1d.

Each of A², Ra⁴, Ra⁵, and nn1 may be selected from the moieties described above in Formula TL-I, and each of Ra⁶, Ra⁷, Ra⁸, and Ra¹⁰ may be selected from the moieties described above in Formula TL-I1a-TL-I1d. Each of the moieties defined for one of A², Ra⁴, Ra⁵, Ra⁶, Ra⁷, Ra⁸, Ra¹⁰, and nn1, can be combined with any of the moieties defined for the others of A², Ra⁴, Ra⁵, Ra⁶, Ra⁷, Ra⁸, Ra¹⁰, and nn1, as described above in Formula TL-I and TL-I1a-TL-I1d.

In certain embodiments, a dTAG Targeting Ligand is a compound of Formula TL-I3:

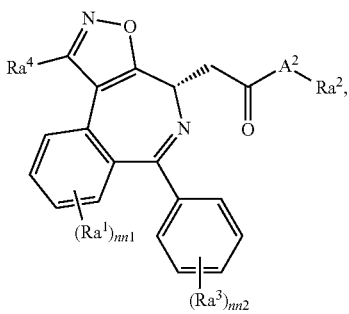

(TL-I3)

or a pharmaceutically acceptable salt thereof.

A², Ra¹, Ra², Ra³, Ra⁴, Ra⁵, nn1, and nn2 are each as defined above in Formula TL-I. Each of A², Ra¹, Ra², Ra³, Ra⁴, Ra⁵, nn1, and nn2 may be selected from the moieties described above in Formula TL-I. Each of the moieties defined for one of A², Rat, Ra², Ra³, Ra⁴, Ra⁵, nn1, and nn2, can be combined with any of the moieties defined for the others of A², Ra¹, Ra², Ra³, Ra⁴, Ra⁵, nn1, and nn2, as described above in Formula TL-I.

In certain embodiments, a dTAG Targeting Ligand is a compound of Formula TL-I3a-TL-I3c:

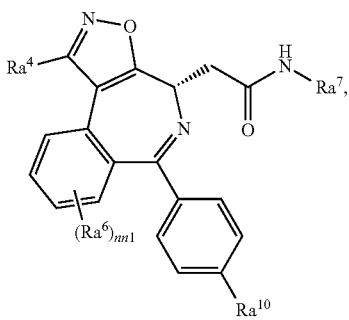

(TL-I3a)

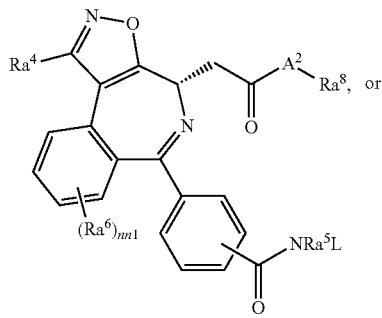

(TL-I3b)

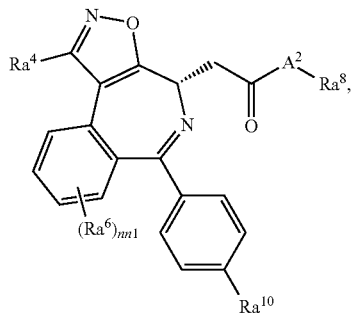

(TL-I3c)

or a pharmaceutically acceptable salt thereof, wherein:
Ra⁹ is C(O)NRa⁵L, OL, NRa⁵L, or L;
A², Ra⁴, Ra⁵, nn1, and L are each as defined above in Formula TL-I; and
Ra⁶, Ra⁷, Ra⁸, and Ra¹o are each as defined above in Formula TL-I1a-TL-I1d.

In certain embodiments, Ra⁹ is C(O)NRa⁵L. In further embodiments, Ra⁵ is H. In other embodiments, Ra⁵ is C₁-C₃ alkyl (e.g., methyl, ethyl, propyl, or i-propyl).

In certain embodiments, Ra⁹ is OL.

In certain embodiments, Ra⁹ is NRa⁵L. In further embodiments, Ra⁵ is H. In other embodiments, Ra⁵ is C₁-C₃ alkyl (e.g., methyl, ethyl, propyl, or i-propyl). In other embodiments, Ra₅ is methyl.

In certain embodiments, Ra⁹ is L.

Each of A², Ra⁴, Ra⁵, and nn1 may be selected from the moieties described above in Formula TL-I, and each of Ra⁶, Ra⁷, Ra⁸, and Ra¹o may be selected from the moieties described above in Formula TL-I1a-TL-I1d. Each of the moieties defined for one of A², Ra⁴, Ra⁵, Ra⁶, Ra⁷, Ra⁸, Ra⁹, Ra¹o, and nn1, can be combined with any of the moieties defined for the others of A², Ra⁴, Ra⁵, Ra⁶, Ra⁷, Ra⁸, Ra⁹, Ra¹⁰, and nn1, as described above and in Formula TL-I and TL-I1a-TL-I1d.

In certain embodiments, a dTAG Targeting Ligand is a compound of Formula TL-VI:

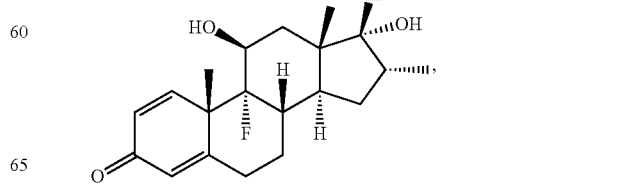

(TL-VI)

or a pharmaceutically acceptable salt thereof, wherein:

$Rf^1$ is $C(O)NRf^2L$, OL, $NRf^2L$, or L;
$Rf^2$ is independently H or $C_1$-$C_3$ alkyl; and
L is a Linker.

In certain embodiments, $Rf^1$ is $C(O)NRf^2L$. In further embodiments, $Rf^2$ is H. In other embodiments, $Rf^2$ is $C_1$-$C_3$ alkyl (e.g., methyl, ethyl, propyl, or i-propyl).

In certain embodiments, $Rf^1$ is OL.

In certain embodiments, $Rf^1$ is $NRe^4L$. In further embodiments, $Rf^2$ is H. In other embodiments, $Rf^2$ is $C_1$-$C_3$ alkyl (e.g., methyl, ethyl, propyl, or i-propyl). In other embodiments, $Rf^2$ is methyl.

In certain embodiments, $Rf^1$ is L.

In certain embodiments, a dTAG Targeting Ligand is a compound of Formula TL-VII:

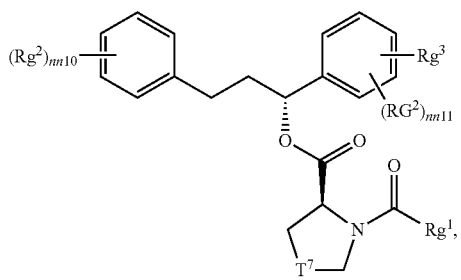

(TL-VII)

or a pharmaceutically acceptable salt thereof, wherein:
$T^7$ is $CH_2$ or $CH_2CH_2$;
$Rg^1$ is $C(O)Rg^5$ or $(CH_2)_{1-3}Rg^6$;
nn10 is 0, 1, 2, or 3;
nn11 is 0, 1, 2, or 3;
each $Rg^2$ is independently $C_1$-$C_3$ alkyl, $C_1$-$C_3$ alkoxy, CN, or halogen; $Rg^3$ is $C(O)NRg^4L$, OL, $NRg^4L$, L, O—$(CH_2)_{1-3}$—$C(O)NRg^4L$, or NHC(O)—$(CH_2)_{1-3}$—$C(O)NRg^4L$;
$Rg^4$ is H or $C_1$-$C_3$ alkyl;
$Rg^5$ is $C_1$-$C_6$ alkyl;
$Rg^6$ is phenyl optionally substituted with $C_1$-$C_3$ alkyl, $C_1$-$C_3$ alkoxy, CN, or halogen; and
L is a Linker.

In certain embodiments, $T^7$ is $CH_2$.
In certain embodiments, $T^7$ is $CH_2CH_2$.
In certain embodiments, $Rg^1$ is $C(O)Rg^5$.
In certain embodiments, $Rg^1$ is $(CH_2)$—$Rg^6$, $(CH_2)_2$—$Rg^6$, or $(CH_2)_3$—$Rg^6$.
In certain embodiments, $Rg^5$ is straight-chain $C_1$-$C_6$ or branched $C_3$-$C_6$ alkyl (e.g., methyl, ethyl, propyl, i-propyl, butyl, i-butyl, t-butyl, pentyl, or hexyl).
In certain embodiments, $Rg^6$ is unsubstituted phenyl.
In certain embodiments, $Rg^6$ is phenyl substituted with one, two, three, or more substituents independently selected from $C_1$-$C_3$ alkyl (e.g., methyl, ethyl, propyl, or i-propyl), $C_1$-$C_3$ alkoxy (e.g., methoxy, ethoxy, or propoxy), CN, and halogen (e.g., F, Cl, or Br).

In certain embodiments, nn10 is 0.
In certain embodiments, nn10 is 1.
In certain embodiments, nn10 is 2.
In certain embodiments, nn10 is 3.
In certain embodiments, nn11 is 0.
In certain embodiments, nn11 is 1.
In certain embodiments, nn11 is 2.
In certain embodiments, nn11 is 3.

In certain embodiments, at least one $Rg^2$ is $C_1$-$C_3$ alkyl (e.g., methyl, ethyl, propyl, or i-propyl). In further embodiments, at least one $Rg^2$ is methyl.

In certain embodiments, at least one $Rg^2$ is $C_1$-$C_3$ alkoxy (e.g., methoxy, ethoxy, or propoxy). In further embodiments, at least one $Rg^2$ is methoxy.

In certain embodiments, at least one $Rg^2$ is CN.

In certain embodiments, at least one $Rg^2$ is halogen (e.g., F, Cl, or Br).

In certain embodiments, $Rg^3$ is $C(O)NRg^4L$. In further embodiments, $Rg^4$ is H. In other embodiments, $Rg^4$ is $C_1$-$C_3$ alkyl (e.g., methyl, ethyl, propyl, or i-propyl).

In certain embodiments, $Rg^3$ is OL.

In certain embodiments, $Rg^3$ is $NRg^4L$. In further embodiments, $Rg^4$ is H. In other embodiments, $Rg^4$ is $C_1$-$C_3$ alkyl (e.g., methyl, ethyl, propyl, or i-propyl). In other embodiments, $Rg^4$ is methyl.

In certain embodiments, $Rg^3$ is L.

In certain embodiments, $Rg^3$ is O—$(CH_2)$—$C(O)NRg^4L$, O—$(CH_2)_2$—$C(O)NRg^4L$, or O—$(CH_2)_3$—$C(O)NRg^4L$. In further embodiments, $Rg^3$ is O—$(CH_2)$—$C(O)NRg^4L$. In further embodiments, $Rg^4$ is H. In other embodiments, $Rg^4$ is $C_1$-$C_3$ alkyl (e.g., methyl, ethyl, propyl, or i-propyl).

In certain embodiments, $Rg^3$ is NHC(O)—$(CH_2)$—$C(O)NRg^4L$, NHC(O)—$(CH_2)_2$—$C(O)NRg^4L$, or NHC(O)—$(CH_2)_3$—$C(O)NRg^4L$. In further embodiments, $Rg^3$ is NHC(O)—$(CH_2)$—$C(O)NRg^4L$, NHC(O)—$(CH_2)_2$—$C(O)NRg^4L$. In further embodiments, $Rg^3$ is NHC(O)—$(CH_2)_2$—$C(O)NRg^4L$. In further embodiments, $Rg^4$ is H. In other embodiments, $Rg^4$ is $C_1$-$C_3$ alkyl (e.g., methyl, ethyl, propyl, or i-propyl).

In certain embodiments, the dTAG Targeting Ligand is selected from the structures of FIG. 28, wherein R is the point at which the Linker is attached.

In certain embodiments, the dTAG Targeting Ligands or targets are chosen based on existence (known dTAG binding moieties) and ability to develop potent and selective ligands with functional positions that can accommodate a Linker. Some embodiments relate to dTAG Targeting Ligands with less selectivity, which may benefit from degradation coupled with proteomics as a measure of compound selectivity or target ID.

Some embodiments of the present application relate to degradation or loss of 30% to 100% of the CAR. Certain embodiments relate to the loss of 50-100% of the CAR. Other embodiments relate to the loss of 75-95% of the CAR.

Non-limiting examples of heterobifunctional compounds for use in the present invention include those of FIGS. 29, 30, 31, and 32.

FIG. 29, provides specific heterobifunctional compounds for use in the present invention.

FIG. 30, provides specific heterobifunctional compounds for use in the present invention, wherein X in the above structures is a halogen chosen from F, Cl, Br, and I.

FIG. 31, provides specific heterobifunctional compounds for use in the present invention.

FIG. 32, provides heterobifunctional compounds for use in the present invention,
wherein:

$R^{AR1}$ is selected from:

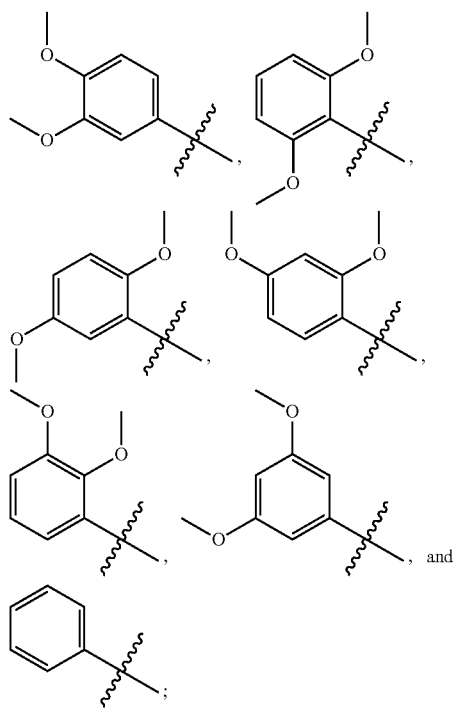

and $R^{AR2}$ is selected from:

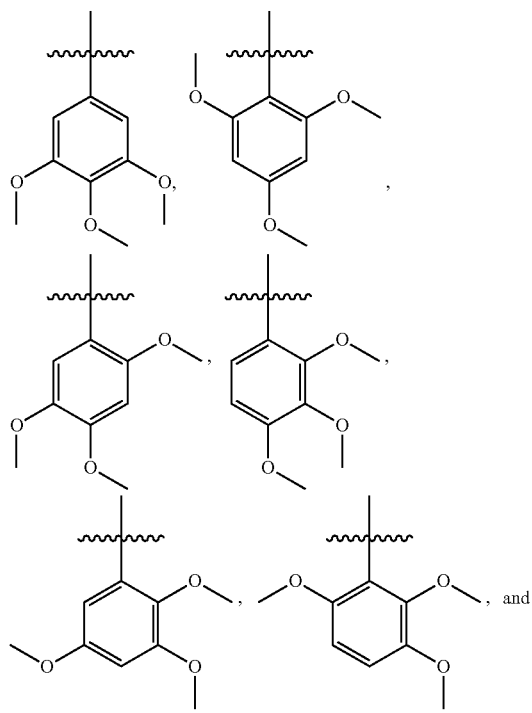

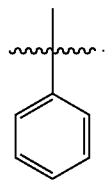

and

Additional compounds for use in the present invention include the structures of FIG. 33.

Some of the foregoing heterobifunctional compounds include one or more asymmetric centers, and thus can exist in various isomeric forms, e.g., stereoisomers and/or diastereomers. Thus, compounds and pharmaceutical compositions thereof may be in the form of an individual enantiomer, diastereomer, or geometric isomer, or may be in the form of a mixture of stereoisomers. In certain embodiments, the compounds of the application are enantiopure compounds. In certain other embodiments, mixtures of stereoisomers or diastereomers are provided.

Furthermore, certain heterobifunctional compounds, as described herein may have one or more double bonds that can exist as either the Z or E isomer, unless otherwise indicated. The application additionally encompasses the compounds as individual isomers substantially free of other isomers and alternatively, as mixtures of various isomers, e.g., racemic mixtures of stereoisomers. In addition to the above-mentioned compounds per se, this application also encompasses pharmaceutically acceptable derivatives of these heterobifunctional compounds and compositions comprising one or more compounds of the application and one or more pharmaceutically acceptable excipients or additives.

Heterobifunctional compounds of the application may be prepared by crystallization of the compound under different conditions and may exist as one or a combination of polymorphs of the compound forming part of this application. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present application encompasses heterobifunctional compounds, their derivatives, their tautomeric forms, their stereoisomers, their polymorphs, their pharmaceutically acceptable salts their pharmaceutically acceptable solvates and pharmaceutically acceptable compositions containing them.

General Synthesis of the Heterobifunctional Compounds

The heterobifunctional compounds described herein can be prepared by methods known by those skilled in the art. In one non-limiting example the disclosed heterobifunctional compounds can be made by the following schemes.

Scheme 1

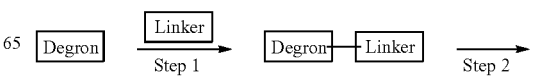

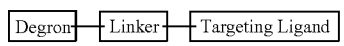

Scheme 2

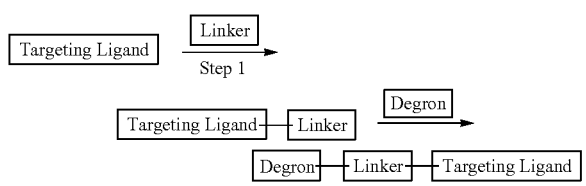

As shown in Scheme 1 heterobifunctional compounds for use in the present invention can be prepared by chemically combining a Degron and a Linker followed by subsequent addition of a dTAG Targeting Ligand. Similarly, in Scheme 2 heterobifunctional compounds for use in the present invention are prepared by chemically combing a dTAG Targeting Ligand and Linker first, followed by subsequent addition of a Degron. As illustrated in the above and following schemes, heterobifunctional compounds for use in the present invention can readily be synthesized by one skilled in the art in a variety of methods and chemical reactions.

Scheme 3

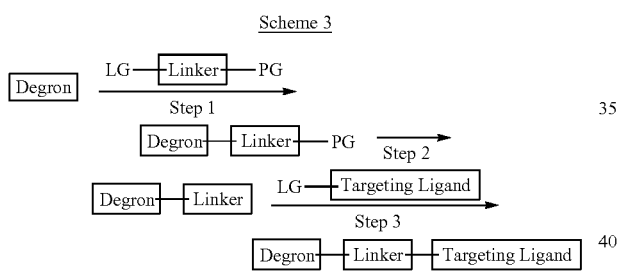

Scheme 3: In Step 1, a nucleophilic Degron displaces a leaving group on the Linker to make a Degron Linker fragment. In Step 2, the protecting group is removed by methods known in the art to free a nucleophilic site on the Linker. In Step 3, the nucleophilic Degron Linker fragment displaces a leaving group on the dTAG Targeting Ligand to form a compound for use in the present invention. In an alternative embodiment Step 1 and/or Step 2 is accomplished by a coupling reaction instead of a nucleophilic attack.

Scheme 4

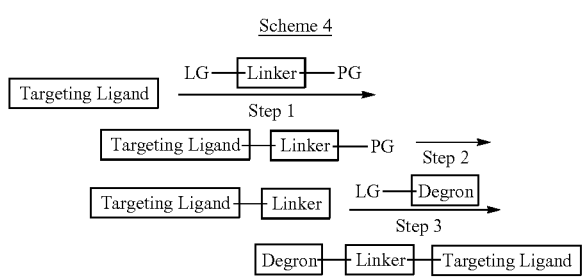

Scheme 4: In Step 1, a nucleophilic dTAG Targeting Ligand displaces a leaving group on the Linker to make a dTAG Targeting Ligand Linker fragment. In Step 2, the protecting group is removed by methods known in the art to free a nucleophilic site on the Linker. In Step 3, the nucleophilic dTAG Targeting Ligand Linker fragment displaces a leaving group on the Degron to form a compound for use in the present invention. In an alternative embodiment Step 1 and/or Step 2 is accomplished by a coupling reaction instead of a nucleophilic attack.

Scheme 5

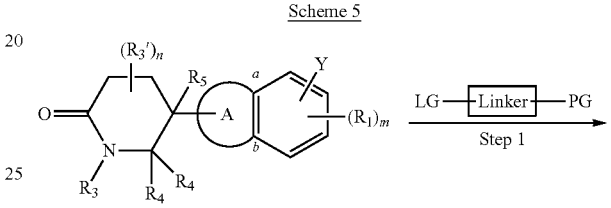

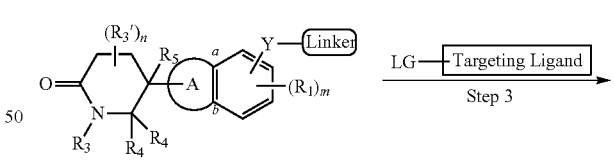

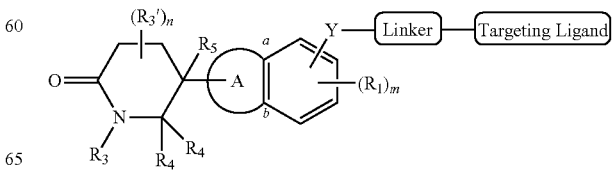

Scheme 6

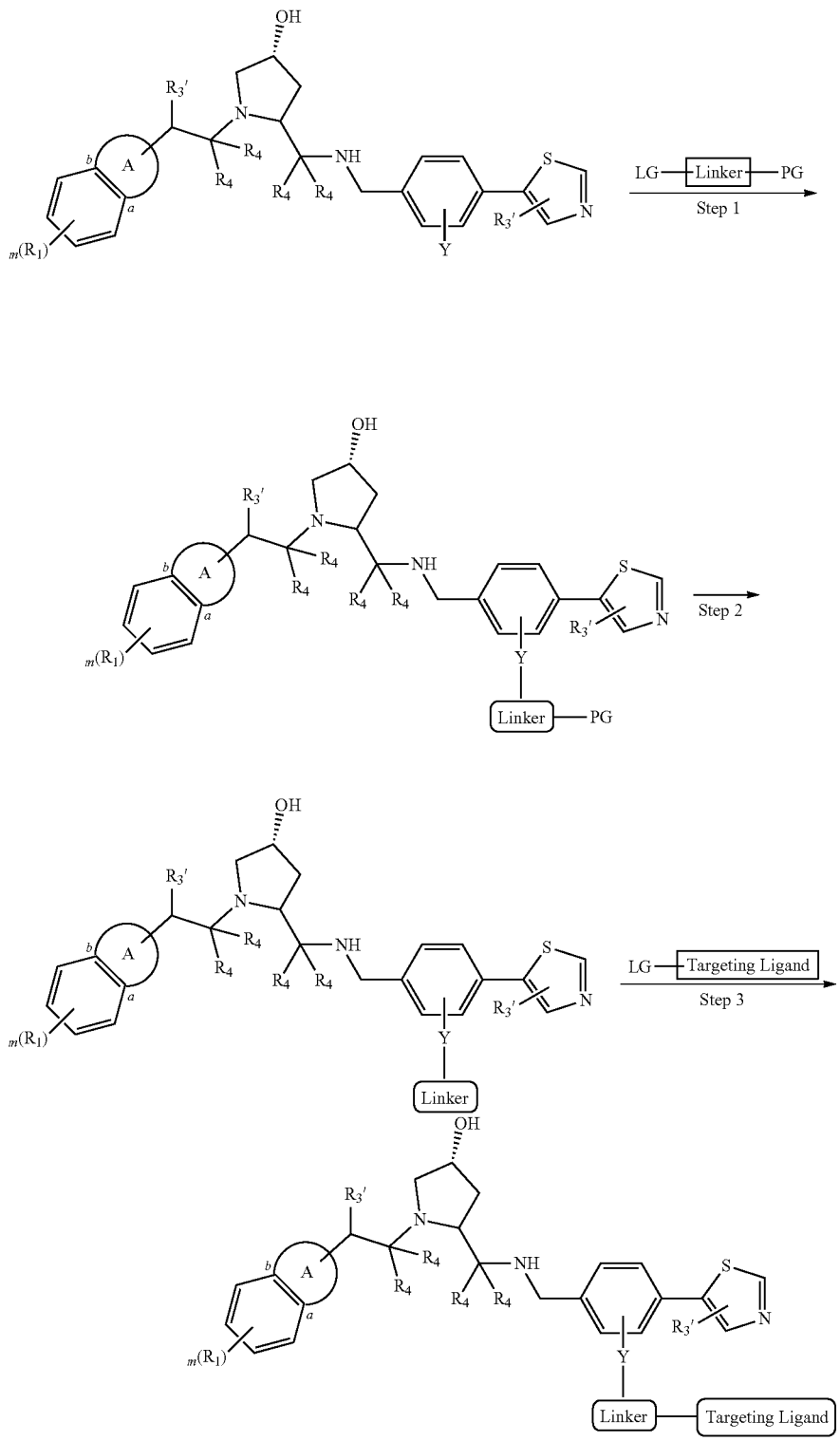

Scheme 5 and Scheme 6: In Step 1, a nucleophilic Degron displaces a leaving group on the Linker to make a Degron Linker fragment. In Step 2, the protecting group is removed by methods known in the art to free a nucleophilic site on the Linker. In Step 3, the nucleophilic Degron Linker fragment displaces a leaving group on the dTAG Targeting Ligand to form a compound of Formula I or Formula II. In an alternative embodiment Step 1 and/or Step 2 is accomplished by a coupling reaction instead of a nucleophilic attack.

Scheme 7
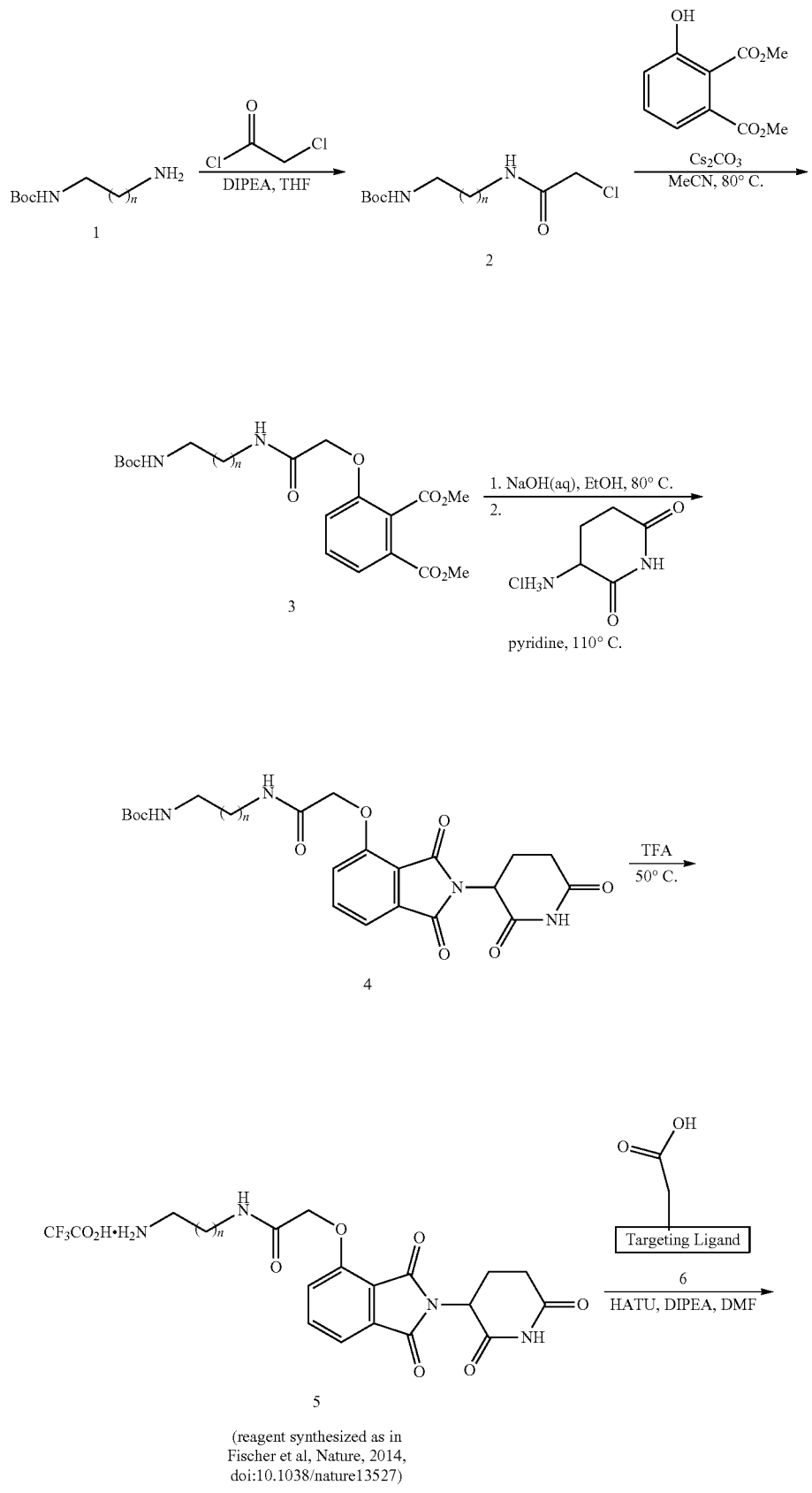

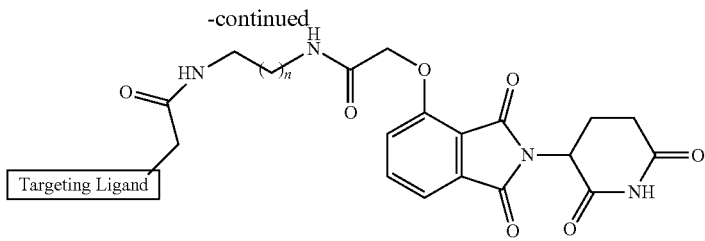

7 a) reacting tert-Butyl (2-aminoethyl)carbamate or its analog (e.g., n = 1-20) (1) or its analog (e.g., n = 1-20) with chloroacetyl chloride under suitable conditions to generate tert-butyl (2-(2-chloroacetamido)ethyl)carbamate or its analog (e.g., n = 1-20) (2);
b) reacting tert-butyl (2-(2-chloroacetamido)ethyl)carbamate or its analog (2) with dimethyl 3-hydroxyphthalate under suitable conditions to provide dimethyl 3-(2-((2-((tert-butoxycarbonyl)amino)ethyl)amino)-2-oxoethoxy)phthalate or its analog (3);
c) reacting dimethyl 3-(2-((2-((tert-butoxycarbonyl)amino)ethyl)amino)-2-oxoethoxy)phthalate or its analog (3) with strong base, followed by 3-aminopiperidine-2,6-dione hydrochloride to generate tert-butyl (2-(2-((2-(2,6-dioxopiperidin-3-yl)-1,3-dioxoisoindolin-4-yl)oxy)acetamido)ethyl)carbamate or its analog (4);
d) deprotecting compound (4) to provide diaminoethyl-acetyl-O-thalidomide trifluoroacetate or its analog (5)
e) reacting compound (5) with an acid derivative of a dTAG Targeting Ligand (compound (6)) under suitable conditions to yield a bifunctional compound (7).

In certain embodiments, the methods described above are carried out in solution phase. In certain other embodiments, the methods described above are carried out on a solid phase. In certain embodiments, the synthetic method is amenable to high-throughput techniques or to techniques commonly used in combinatorial chemistry.

Representative Synthesis of the Heterobifunctional Compounds

Unless otherwise indicated, starting materials are either commercially available or readily accessible through laboratory synthesis by anyone reasonably familiar with the art. Described generally below, are procedures and general guidance for the synthesis of compounds as described generally and in subclasses and species herein.

Synthetic Example 1': Synthesis of IMiD Derivatives and Degrons

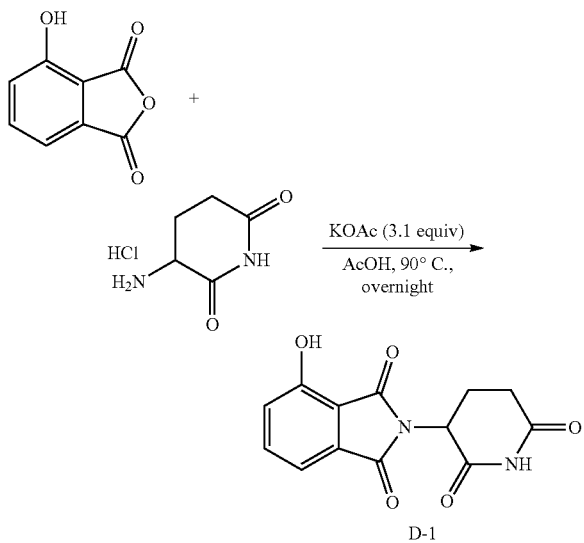

General Procedure I: IMiD Condensation 2-(2,6-dioxopiperidin-3-yl)-4-hydroxyisoindoline-1,3-dione (D-1)

In a 20 mL glass vial, a mixture of 3-hydroxyphthalic anhydride (500 mg, 3.05 mmol, 1 equiv), potassium acetate (927 mg, 9.44 mmol, 3.1 equiv) and 3-aminopiperidine-2,6-dione hydrochloride (552 mg, 3.35 mmol, 1.1 equiv) in acetic acid (10.2 mL, 0.3 M) was heated to 90° C. overnight. The black reaction mixture was cooled to room temperature and diluted to 20 mL with water, and subsequently cooled on ice for 30 min. The resulting slurry was transferred to a 50 mL Falcon tube, which was centrifuged at 3500 rpm for 5 min. The supernatant was discarded and the black solid was transferred to a 250 mL RBF with methanol and concentrated in vacuo. The residue was purified by flash column chromatography on silica gel ($CH_2Cl_2$:MeOH (9:1)) to afford the title compound as a white solid (619 mg, 74%). $^1$H NMR (400 MHz, DMSO-$d_6$) δ 11.07 (s, 1H), 7.65 (dd, J=8.4, 6.8 Hz, 1H), 7.31 (d, J=6.8 Hz, 1H), 7.24 (d, J=8.4 Hz, 1H), 5.06 (dd, J=12.8, 5.4 Hz, 1H), 2.94-2.82 (m, 1H), 2.64-2.43 (m, 2H), 2.08-1.97 (m, 1H); MS (ESI) calcd for $C_{13}H_{11}N_2O_5$ [M+H]$^+$ 275.07, found 275.26.

2-(2,6-dioxopiperidin-3-yl)-4-nitroisoindoline-1,3-dione (D-10)

General procedure I was followed using 3-nitrophthalic anhydride (300 mg, 1.55 mmol, 1 equiv), potassium acetate (473 mg, 4.82 mmol, 3.1 equiv) and 3-aminopiperidine-2,6-dione hydrochloride (281 mg, 1.71 mmol, 1.1 equiv) to afford the title compound as a light yellow solid (280 mg, 59%) following purification by flash column chromatography on silica gel ($CH_2Cl_2$:MeOH (9:1)). $^1$H NMR (500 MHz, DMSO-$d_6$) δ 11.17 (s, 1H), 8.35 (d, J=8.1 Hz, 1H), 8.24 (d, J=7.5 Hz, 1H), 8.14-8.10 (m, 1H), 5.20 (dd, J=12.9, 5.5 Hz, 1H), 2.93-2.84 (m, 1H), 2.64-2.45 (m, 2H), 2.11-2.04 (m, 1H); MS (ESI) calcd for $C_{13}H_{10}N_3O_6$ [M+H]$^+$ 304.06, found 304.19.

2-(2,6-dioxopiperidin-3-yl)-5-nitroisoindoline-1,3-dione (D-2)

General procedure I was followed using 4-nitrophthalic anhydride (300 mg, 1.55 mmol), potassium acetate (473 mg, 4.82 mmol) and 3-aminopiperidine-2,6-dione hydrochloride (281 mg, 1.71 mmol) to afford the title compound as a white solid (409 mg, 87%) following purification by flash column chromatography on silica gel (CH$_2$Cl$_2$:MeOH (30:1)). $^1$H NMR (500 MHz, DMSO-d$_6$) δ 11.18 (s, 1H), 8.68 (dd, J=8.1, 1.9 Hz, 1H), 8.56 (d, J=1.9 Hz, 1H), 8.19 (d, J=8.1 Hz, 1H), 5.24 (dd, J=12.9, 5.4 Hz, 1H), 2.90 (ddd, J=17.2, 13.9, 5.5 Hz, 1H), 2.69-2.48 (m, 2H), 2.14-2.05 (m, 1H); MS (ESI) calcd for C$_{13}$H$_{10}$N$_3$O$_6$ [M+H]$^+$ 304.06, found 304.19.

2-(2,6-dioxopiperidin-3-yl)isoindoline-1,3-dione (D-6)

General procedure I was followed using phthalic anhydride (155 mg, 1.05 mmol), potassium acetate (318 mg, 3.24 mmol) and 3-aminopiperidine-2,6-dione hydrochloride (189 mg, 1.15 mmol) to afford the title compound as a white solid (235 mg, 87%) following purification by flash column chromatography on silica gel (CH$_2$Cl$_2$:MeOH (15:1)). $^1$H NMR (500 MHz, DMSO-d$_6$) δ 11.13 (s, 1H), 8.00-7.76 (m, 4H), 5.16 (dd, J=12.8, 5.4 Hz, 1H), 2.89 (ddd, J=16.8, 13.7, 5.4 Hz, 1H), 2.65-2.42 (m, 2H), 2.12-1.99 (m, 1H); MS (ESI) calcd for C$_{13}$H$_{11}$N$_2$O$_4$ [M+H]$^+$ 259.07, found 259.23.

2-(2,5-dioxopyrrolidin-3-yl)isoindoline-1,3-dione (D-7)

General procedure I was followed using phthalic anhydride (90 mg, 0.608 mmol), potassium acetate (185 mg, 1.88 mmol) and 3-aminopyrrolidine-2,5-dione hydrochloride (101 mg, 0.668 mmol) to afford the title compound as a white solid (95 mg, 64%) following purification by flash column chromatography on silica gel (CH$_2$Cl$_2$:MeOH (14:1)). MS (ESI) calcd for C$_{12}$H$_9$N$_2$O$_4$ [M+H]$^+$ 245.06, found 245.26.

2-(2,6-dioxopiperidin-3-yl)-1,3-dioxoisoindoline-5-carboxylic acid (D-13)

General procedure I was followed using 1,2,4-benzenetricarboxylic anhydride (200 mg, 1.04 mmol), potassium acetate (317 mg, 3.23 mmol) and 3-aminopiperidine-2,6-dione hydrochloride (188 mg, 1.15 mmol) to afford the title compound as a white solid (178 mg, 57%) following purification by flash column chromatography on silica gel (CH$_2$Cl$_2$:MeOH (9:1)). MS (ESI) calcd for C$_{14}$H$_{11}$N2O6 [M+H]$^+$ 303.06, found 303.24.

2-(2,6-dioxopiperidin-3-yl)-4-fluoroisoindoline-1,3-dione (D-14)

General procedure I was followed using 3-fluorophthalic anhydride (200 mg, 1.20 mmol), potassium acetate (366 mg, 3.73 mmol) and 3-aminopiperidine-2,6-dione hydrochloride (218 mg, 1.32 mmol) to afford the title compound as a white solid (288 mg, 86%) following purification by flash column chromatography on silica gel (CH$_2$Cl$_2$:MeOH (50:1)). $^1$H NMR (500 MHz, DMSO-d$_6$) δ 11.15 (s, 1H), 7.96 (ddd, J=8.3, 7.3, 4.5 Hz, 1H), 7.82-7.71 (m, 2H), 5.17 (dd, J=13.0, 5.4 Hz, 1H), 2.90 (ddd, J=17.1, 13.9, 5.4 Hz, 1H), 2.65-2.47 (m, 2H), 2.10-2.04 (m, 1H), MS (ESI) calcd for C$_{13}$H$_{10}$FN$_2$O$_4$ [M+H]$^+$ 277.06, found 277.25.

2-(2,6-dioxopiperidin-3-yl)-4-methylisoindoline-1,3-dione (D-19)

General procedure I was followed using 3-methylphthalic anhydride (150 mg, 0.925 mmol), potassium acetate (281 mg, 2.87 mmol) and 3-aminopiperidine-2,6-dione hydrochloride (167 mg, 1.02 mmol) to afford the title compound as a white solid (168 mg, 67%) following purification by flash column chromatography on silica gel (CH$_2$Cl$_2$:MeOH (15:1)). MS (ESI) calcd for C$_{14}$H$_{13}$N$_2$O$_4$ [M+H]$^+$ 273.09, found 273.24.

2-(2,6-dioxopiperidin-3-yl)-5-fluoroisoindoline-1,3-dione (D-24)

General procedure I was followed using 4-fluorophthalic anhydride (200 mg, 1.20 mmol), potassium acetate (366 mg, 3.73 mmol) and 3-aminopiperidine-2,6-dione hydrochloride (218 mg, 1.32 mmol) to afford the title compound as a white solid (254 mg, 76%) following purification by flash column chromatography on silica gel (CH$_2$Cl$_2$:MeOH (15:1)). MS (ESI) calcd for C$_{13}$H$_{10}$FN$_2$O$_4$ [M+H]$^+$ 277.06, found 277.24.

2-(2,6-dioxopiperidin-4-yl)isoindoline-1,3-dione (D-43)

General procedure I was followed using phthalic anhydride (60 mg, 0.311 mmol), potassium acetate (95 mg, 0.963 mmol) and 4-aminopiperidine-2,6-dione hydrochloride (56 mg, 0.342 mmol) to afford the title compound as a white solid (40 mg, 43%) following purification by flash column chromatography on silica gel (CH$_2$Cl$_2$:MeOH (9:1)). MS (ESI) calcd for C$_{13}$H$_{11}$N$_2$O$_4$ [M+H]$^+$ 259.07, found 259.18.

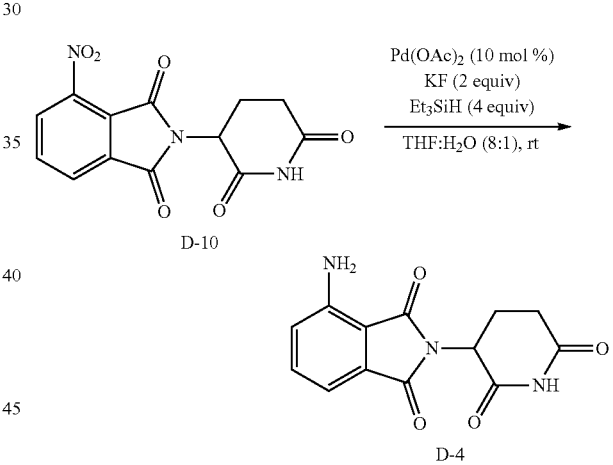

General Procedure II: Reduction of Aromatic Nitro Groups 4-amino-2-(2,6-dioxopiperidin-3-yl)isoindoline-1,3-dione (D-4)

A solution of 2-(2,6-dioxopiperidin-3-yl)-4-nitroisoindoline-1,3-dione (173 mg, 0.854 mmol), Pd(OAc)$_2$ (12.8 mg, 0.0854 mmol, 10 mol %) and potassium fluoride (66 mg, 1.71 mmol, 2 equiv) in THF:water (8:1) (5.7 mL, 0.1 M) was stirred at room temperature. Triethylsilane (365 μL, 3.41 mmol, 4 equiv) was added slowly, and the resulting black solution was stirred at room temperature for 1 hour. The reaction mixture was filtered through a pad of celite, which was washed excessively with ethyl acetate. The filtrate was concentrated in vacuo and the residue was purified by flash column chromatography on silica gel (CH$_2$Cl$_2$:MeOH (7:1)) to afford the title compound as a yellow powder (72 mg, 46%). $^1$H NMR (500 MHz, DMSO-d$_6$) δ 11.08 (s, 1H), 7.47 (dd, J=8.5, 7.0 Hz, 1H), 7.06-6.95 (m, 1H), 6.59-6.44 (m, 1H), 5.04 (dd, J=12.7, 5.4 Hz, 1H), 2.93-2.82 (m, 1H), 2.64-2.45 (m, 2H), 2.05-1.98 (m, 1H); MS (ESI) calcd for C$_{13}$H$_{11}$N$_3$O$_4$ [M+H]$^+$ 274.08, found 274.23.

2-(2,6-dioxopiperidin-3-yl)-5-nitroisoindoline-1,3-dione (D-8)

General procedure II was followed using 2-(2,6-dioxopiperidin-3-yl)-5-nitroisoindoline-1,3-dione (100 mg, 0.330 mmol), Pd(OAc)$_2$ (7.4 mg, 0.033 mmol), potassium fluoride (38 mg, 0.660 mmol) and triethylsilane (211 µL, 1.32 mmol to afford the title compound as a yellow solid (33 mg, 37%) following purification by flash column chromatography on silica gel (CH$_2$Cl$_2$:MeOH (9:1)). $^1$H NMR (500 MHz, DMSO-d$_6$) δ 11.05 (s, 1H), 7.52 (d, J=8.2 Hz, 1H), 6.94 (d, J=2.0 Hz, 1H), 6.83 (dd, J=8.2, 2.0 Hz, 1H), 6.55 (s, 2H), 5.01 (dd, J=12.8, 5.4 Hz, 1H), 2.86 (ddd, J=16.9, 13.9, 5.5 Hz, 1H), 2.68-2.43 (m, 2H), 2.03-1.93 (m, 1H); MS (ESI) calcd for C$_{13}$H$_{12}$N$_3$O$_4$ [M+H]$^+$ 274.08, found 274.59.

4-amino-2-(1-benzyl-2,6-dioxopiperidin-3-yl)isoindoline-1,3-dione (D-12)

General procedure II was followed using 2-(1-benzyl-2,6-dioxopiperidin-3-yl)-4-nitroisoindoline-1,3-dione (48 mg, 0.122 mmol), Pd(OAc)$_2$ (2.7 mg, 0.0122 mmol), potassium fluoride (14 mg, 0.244 mmol) and triethylsilane (78 µL, 0.488 mmol to afford the title compound as a yellow solid (7 mg, 16%) following purification by flash column chromatography on silica gel (0 to 100% EtOAc in hexanes). MS (ESI) calcd for C$_{20}$H$_{18}$N$_3$O$_4$ [M+H]$^+$ 364.13, found 364.34.

3-(5-amino-2-methyl-4-oxoquinazolin-3(4H)-yl)piperidine-2,6-dione (D-17)

General procedure II was followed using 3-(2-methyl-5-nitro-4-oxoquinazolin-3(4H)-yl)piperidine-2,6-dione (21 mg, 0.0664 mmol), Pd(OAc)$_2$ (1.5 mg, 0.0066 mmol), potassium fluoride (7.7 mg, 0.133 mmol) and triethylsilane (42 µL, 0.266 mmol to afford the title compound as a white solid (7 mg, 37%) following purification by preparative HPLC. MS (ESI) calcd for C$_{14}$H$_{15}$N$_4$O$_3$ [M+H]$^+$ 287.11, found 287.30.

3-(7-amino-1-oxoisoindolin-2-yl)piperidine-2,6-dione (D-41)

General procedure II was followed using 3-(7-nitro-1-oxoisoindolin-2-yl)piperidine-2,6-dione (11 mg, 0.038 mmol), Pd(OAc)$_2$ (0.9 mg, 0.0038 mmol), potassium fluoride (4.4 mg, 0.076 mmol) and triethylsilane (24 µL, 0.152 mmol to afford the title compound as a yellow solid (2 mg, 21%) following purification by flash column chromatography on silica gel (0 to 10% MeOH in CH$_2$Cl$_2$). MS (ESI) calcd for C$_{13}$H$_{14}$N$_3$O$_3$ [M+H]$^+$ 260.10, found 260.52.

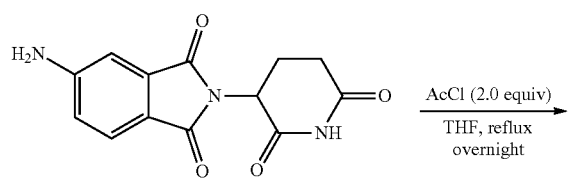

AcCl (2.0 equiv)
THF, reflux overnight

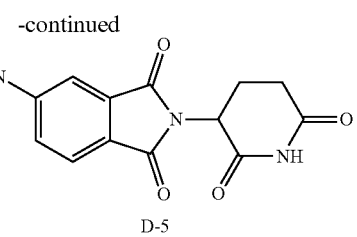

D-5

General Procedure III: Acylation of Anilines

N-(2-(2,6-dioxopiperidin-3-yl)-1,3-dioxoisoindolin-5-yl)acetamide (D-5)

In a 4 mL glass vial, a mixture of 5-amino-2-(2,6-dioxopiperidin-3-yl)isoindoline-1,3-dione (30 mg, 0.110 mmol, 1 equiv) and acetyl chloride (26 µL, 0.220 mmol, 2 equiv) in THF (1.8 mL, 0.1 M) was heated to reflux overnight. The reaction mixture was filtered, and the filter cake was washed with Et$_2$O to give the title compound as a white solid (27 mg, 47%), that was used without further purification. $^1$H NMR (500 MHz, DMSO-d$_6$) δ 11.11 (s, 1H), 10.63 (s, 1H), 8.24 (d, J=1.5 Hz, 1H), 7.91-7.83 (m, 2H), 5.11 (dd, J=12.8, 5.4 Hz, 1H), 2.88 (ddd, J=17.0, 13.8, 5.4 Hz, 1H), 2.63-2.46 (m, 2H), 2.13 (s, 3H), 2.09-2.00 (m, 1H); MS (ESI) calcd for C$_{15}$H$_{14}$N$_3$O$_5$ [M+H]$^+$ 316.09, found 316.23.

N-(2-(2,6-dioxopiperidin-3-yl)-1,3-dioxoisoindolin-4-yl)acetamide (D-3)

General procedure III was followed using 4-amino-2-(2,6-dioxopiperidin-3-yl)isoindoline-1,3-dione (50 mg, 0.183 mmol) and acetyl chloride (26 µL, 0.366 mmol) to afford the title compound as a white solid (10 mg, 17%). $^1$H NMR (500 MHz, DMSO-d$_6$) δ 11.14 (s, 1H), 9.73 (s, 1H), 8.44 (d, J=8.4 Hz, 1H), 7.83 (dd, J=8.4, 7.3 Hz, 1H), 7.62 (d, J=7.2 Hz, 1H), 5.14 (dd, J=12.9, 5.4 Hz, 1H), 2.90 (ddd, J=17.1, 13.9, 5.4 Hz, 1H), 2.66-2.45 (m, 2H), 2.19 (s, 3H), 2.14-2.00 (m, 1H); MS (ESI) calcd for C$_{15}$H$_{14}$N$_3$O$_5$ [M+H]$^+$ 316.09, found 316.27.

2-chloro-N-(2-(2,6-dioxopiperidin-3-yl)-1,3-dioxoisoindolin-5-yl)acetamide (D-32)

General procedure III was followed using 5-amino-2-(2,6-dioxopiperidin-3-yl)isoindoline-1,3-dione (10 mg, 0.0366 mmol) and chloroacetyl chloride (6 µL, 0.0732 mmol) to afford the title compound as a white solid (7.1 mg, 55%). MS (ESI) calcd for C$_{15}$H$_3$ClN$_3$O$_5$ [M+H]$^+$ 350.05, found 350.23.

2-chloro-N-(2-(2,6-dioxopiperidin-3-yl)-1-oxoisoindolin-4-yl)acetamide (D-34)

General procedure III was followed using 3-(4-amino-1-oxoisoindolin-2-yl)piperidine-2,6-dione (20 mg, 0.0771 mmol) and chloroacetyl chloride (12 µL, 0.154 mmol) to afford the title compound as a white solid (14.9 mg, 56%). $^1$H NMR (500 MHz, DMSO-d$_6$) δ 11.02 (s, 1H), 10.20 (s, 1H), 7.81 (dd, J=7.7, 1.3 Hz, 1H), 7.65-7.47 (m, 2H), 5.16 (dd, J=13.3, 5.1 Hz, 1H), 4.45-4.34 (m, 2H), 4.33 (s, 2H), 3.00-2.85 (m, 1H), 2.68-2.56 (m, 1H), 2.41-2.28 (m, 1H), 2.09-1.97 (m, 1H); MS (ESI) calcd for $C_{15}H15C_1N3O4$ [M+H]$^+$ 336.07, found 336.31.

N-(2-(2,6-dioxopiperidin-3-yl)-1-oxoisoindolin-4-yl) acrylamide (D-35)

General procedure III was followed using 3-(4-amino-1-oxoisoindolin-2-yl)piperidine-2,6-dione (20 mg, 0.0771 mmol) and acryloyl chloride (13 µL, 0.154 mmol) to afford the title compound as a white solid (18 mg, 76%). $^1$H NMR (500 MHz, DMSO-$d_6$) δ 15.77 (s, 1H), 14.81 (s, 1H), 12.65 (dd, J=7.4, 1.6 Hz, 1H), 12.37-12.18 (m, 2H), 11.28 (dd, J=17.0, 10.2 Hz, 1H), 11.06 (dd, J=17.0, 1.9 Hz, 1H), 10.57 (dd, J=10.2, 1.9 Hz, 1H), 9.91 (dd, J=13.3, 5.1 Hz, 1H), 9.24-9.05 (m, 2H), 7.67 (ddd, J=17.2, 13.7, 5.5 Hz, 1H), 7.36 (dt, J=17.3, 3.8 Hz, 1H), 7.20-7.03 (m, 1H), 6.83-6.72 (m, 1H); MS (ESI) calcd for $C_{16}H_{16}N_3O_4$ [M+H]$^+$ 314.11, found 314.24.

N-(2-(2,6-dioxopiperidin-3-yl)-1,3-dioxoisoindolin-5-yl)acrylamide (D-36)

General procedure III was followed using 5-amino-2-(2,6-dioxopiperidin-3-yl)isoindoline-1,3-dione (10 mg, 0.0366 mmol) and acryloyl chloride (6 µL, 0.0732 mmol) to afford the title compound as a white solid (8.8 mg, 73%). $^1$H NMR (500 MHz, DMSO-$d_6$) δ 11.12 (s, 1H), 10.83 (s, 1H), 8.33 (d, J=1.8 Hz, 1H), 7.99 (dd, J=8.2, 1.9 Hz, 1H), 7.90 (d, J=8.2 Hz, 1H), 6.48 (dd, J=17.0, 10.1 Hz, 1H), 6.36 (dd, J=17.0, 1.9 Hz, 1H), 5.88 (dd, J=10.0, 1.9 Hz, 1H), 5.13 (dd, J=12.8, 5.5 Hz, 1H), 2.95-2.84 (m, 1H), 2.67-2.46 (m, 2H), 2.09-2.01 (m, 1H); MS (ESI) calcd for $C_{16}H_{14}N_3O_5$ [M+H]$^+$ 328.09, found 328.23.

N-(2-(2,6-dioxopiperidin-3-yl)-1-oxoisoindolin-4-yl) acetamide (D-37)

General procedure III was followed using 3-(4-amino-1-oxoisoindolin-2-yl)piperidine-2,6-dione (20 mg, 0.0771 mmol) and acetyl chloride (11 µL, 0.154 mmol) to afford the title compound as a white solid (17 mg, 71%). MS (ESI) calcd for $C_{15}H_{16}N_3O_4$ [M+H]$^+$ 302.11, found 301.99.

N-(2-(2,6-dioxopiperidin-3-yl)-1-oxoisoindolin-4-yl) cyclopropanecarboxamide (D-38)

General procedure III was followed using 3-(4-amino-1-oxoisoindolin-2-yl)piperidine-2,6-dione (20 mg, 0.0771 mmol) and cyclopropanecarbonyl chloride (14 µL, 0.154 mmol) to afford the title compound as a white solid (19 mg, 75%). $^1$H NMR (500 MHz, DMSO-$d_6$) δ 11.01 (s, 1H), 10.06 (s, 1H), 7.84 (dd, J=7.2, 1.9 Hz, 1H), 7.66-7.38 (m, 2H), 5.14 (dd, J=13.3, 5.1 Hz, 1H), 4.52-4.30 (m, 2H), 2.92 (ddd, J=17.3, 13.6, 5.4 Hz, 1H), 2.64-2.54 (m, 1H), 2.45-2.27 (m, 1H), 2.08-1.95 (m, 1H), 1.93-1.83 (m, 1H), 0.90-0.75 (m, 4H); MS (ESI) calcd for $C_{17}H_{18}N_3O_4$ [M+H]$^+$ 328.13, found 328.00.

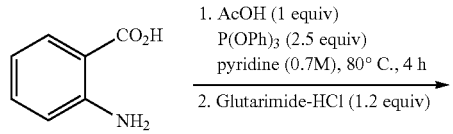

1. AcOH (1 equiv)
   P(OPh)$_3$ (2.5 equiv)
   pyridine (0.7M), 80° C., 4 h
2. Glutarimide-HCl (1.2 equiv)

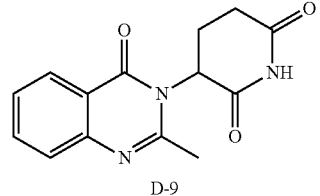

D-9

General Procedure IV: Quinazolinone Condensation

3-(2-methyl-4-oxoquinazolin-3(4H)-yl)piperidine-2,6-dione (D-9)

In a 20 mL glass vial, anthranilic acid (100 mg, 0.729 mmol, 1 equiv), acetic acid (42 µL, 0.729 mmol, 1 equiv) and P(OPh)$_3$ (479 µL, 1.82 mmol, 2.5 equiv) in pyridine (1.0 uL, 0.7 M) was heated to 90° C. After 4 hours, the reaction mixture was cooled to room temperature and 3-aminopiperidine-2,6-dione hydrochloride (144 mg, 0.875 mmol, 1.2 equiv) was added. The reaction mixture was reheated to 90° C. for 1.5 h, whereupon it was stirred at room temperature overnight. The reaction mixture was taken up in EtOAc (15 mL) and water (15 mL). The organic layer was washed with brine (2×25 mL), dried over Na$_2$SO$_4$ and concentrated in vacuo. The residue was purified by flash column chromatography on silica gel (0-5% MeOH in CH$_2$Cl$_2$) to afford the title compound as a white solid (79 mg, 40%). $^1$H NMR (500 MHz, DMSO-$d_6$) δ 11.03 (s, 1H), 8.03 (dd, J=7.9, 1.5 Hz, 1H), 7.82 (ddd, J=8.5, 7.1, 1.6 Hz, 1H), 7.62 (dd, J=8.3, 1.1 Hz, 1H), 7.50 (ddd, J=8.1, 7.1, 1.1 Hz, 1H), 5.27 (dd, J=11.5, 5.7 Hz, 1H), 2.92-2.78 (m, 1H), 2.73-2.56 (m, 5H), 2.26-2.06 (m, 1H); MS (ESI) calcd for $C_{14}H_{14}N_3O_3$ [M+H]$^+$ 272.10, found 272.33.

3-(2-methyl-4-oxoquinazolin-3(4H)-yl)pyrrolidine-2,5-dione (D-11)

General procedure IV was followed using anthranilic acid (200 mg, 1.46 mmol), acetic acid (84 µL, 1.46 mmol), P(OPh)$_3$ (959 µL, 3.65 mmol) and 3-aminopyrrolidine-2,5-dione hydrochloride (263 mg, 1.75 mmol) to afford the title compound as a white solid (25 mg, 7%) following purification by flash column chromatography on silica gel (CH$_2$Cl$_2$:MeOH (15:1)). MS (ESI) calcd for $C_{13}H_{12}N_3O_3$ [M+H]$^+$ 258.09, found 258.22.

3-(5-fluoro-2-methyl-4-oxoquinazolin-3(4H)-yl) piperidine-2,6-dione (D-66)

General procedure IV was followed using 6-fluoro anthranilic acid (100 mg, 0.645 mmol), acetic acid (37 µL, 0.644 mmol), P(OPh)$_3$ (424 µL, 1.61 mmol) and 3-aminopiperidine-2,6-dione hydrochloride (127 mg, 0.774 mmol) to afford the title compound as a white solid (70 mg, 38%) following purification by flash column chromatography on silica gel (0-10% MeOH in CH$_2$Cl$_2$). $^1$H NMR (500 MHz, DMSO-$d_6$) δ 11.03 (s, 1H), 7.84-7.76 (m, 1H), 7.44 (dd, J=8.2, 1.0 Hz, 1H), 7.25 (ddd, J=11.1, 8.2, 1.0 Hz, 1H), 5.24 (dd, J=11.3, 5.7 Hz, 1H), 2.90-2.75 (m, 1H), 2.62 (s, 3H), 2.61-2.56 (m, 2H), 2.20-2.12 (m, 1H); MS (ESI) calcd for $C_{14}H_{13}FN_3O_3$ [M+H]$^+$ 290.09, found 290.27.

3-(2-methyl-5-nitro-4-oxoquinazolin-3(4H)-yl)piperidine-2,6-dione (D-67)

General procedure IV was followed using 6-nitroanthranilic acid (100 mg, 0.549 mmol), acetic acid (31 µL, 0.549 mmol), P(OPh)₃ (361 µL, 1.37 mmol) and 3-aminopiperidine-2,6-dione hydrochloride (108 mg, 0.659 mmol) to afford the title compound as a white solid (29 mg, 17%) following purification by flash column chromatography on silica gel (0-10% MeOH in CH₂Cl₂). MS (ESI) calcd for $C_{14}H_{13}N_4O_5$ [M+H]⁺ 317.09, found 317.58.

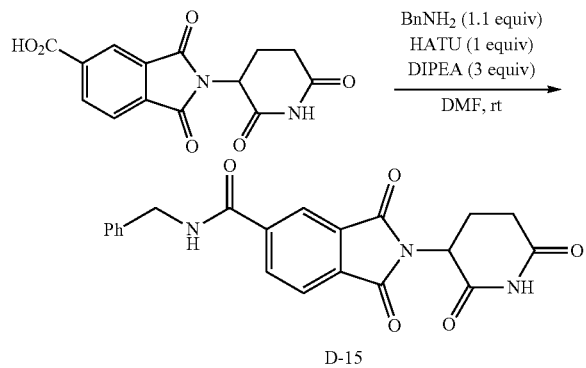

D-15

General Procedure V: Amide Coupling

N-benzyl-2-(2,6-dioxopiperidin-3-yl)-1,3-dioxoisoindoline-5-carboxamide (D-15)

In a 4 mL glass vial, 2-(2,6-dioxopiperidin-3-yl)-1,3-dioxoisoindoline-5-carboxylic acid (10 mg, 0.033 mmol, 1 equiv), HATU (13 mg, 0.033 mmol, 1 equiv), DIPEA (17 µL, 0.099 mmol, 3 equiv) and benzyl amine (4 µL, 0.036 mmol, 1.1 equiv) in DMF (331 µL, 0.1 M) was stirred at room temperature overnight. The reaction mixture was diluted with MeOH to 4 mL, filtered and then purified by preparative HPLC to afford the title compound as a white solid (6 mg, 46%). MS (ESI) calcd for $C_{21}H_{18}N_3O_5$ [M+H]⁺ 392.12, found 392.33.

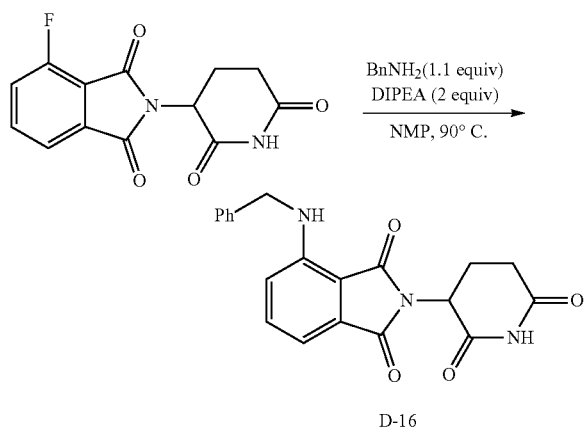

D-16

General Procedure VI: Nucleophilic Aromatic Substitution 4-(benzylamino)-2-(2,6-dioxopiperidin-3-yl)isoindoline-1,3-dione (D-16)

In a 4 mL glass vial, 2-(2,6-dioxopiperidin-3-yl)-4-fluoroisoindoline-1,3-dione (10 mg, 0.036 mmol, 1 equiv), benzyl amine (4.4 µL, 0.040 mmol, 1.1 equiv) and DIPEA (13 µL, 0.072 mmol, 2 equiv) in NMP (362 µL, 0.1 M) was heated to 90° C. overnight. The reaction mixture was cooled to room temperature and taken up in EtOAc (15 mL). The organic layer was washed with NaHCO₃(aq) (15 mL), water (15 mL) and brine (3×15 mL), and subsequently dried over Na₂SO₄ and concentrated in vacuo. The residue was purified by flash column chromatography on silica gel (0-100% EtOAc in hexanes) to afford the title compound as a yellow film (5 mg, 38%). ¹H NMR (500 MHz, Chloroform-d) δ 8.10 (s, 1H), 7.44 (dd, J=8.5, 7.1 Hz, 1H), 7.40-7.25 (m, 5H), 7.12 (d, J=7.1 Hz, 1H), 6.84 (d, J=8.5 Hz, 1H), 6.71 (t, J=5.9 Hz, 1H), 4.93 (dd, J=12.3, 5.3 Hz, 1H), 4.51 (d, J=5.9 Hz, 2H), 2.93-2.66 (m, 3H), 2.21-2.07 (m, 1H); MS (ESI) calcd for $C_{20}H_{18}N_3O_4$ [M+H]⁺ 364.13, found 364.31.

2-(2,6-dioxopiperidin-3-yl)-4-(isopropylamino)isoindoline-1,3-dione (D-18)

General procedure VI was followed using 2-(2,6-dioxopiperidin-3-yl)-4-fluoroisoindoline-1,3-dione (30 mg, 0.109 mmol), isopropylamine (10 µL, 0.119 mmol) and DIPEA (21 jaL, 0.119 mmol) to afford the title compound as a yellow film (11 mg, 32%) following purification by flash column chromatography on silica gel (0-100% EtOAc in hexanes). MS (ESI) calcd for $C_{16}H_{18}N_3O_4$ [M+H]⁺ 316.13, found 316.65.

4-(diethylamino)-2-(2,6-dioxopiperidin-3-yl)isoindoline-1,3-dione (D-21)

General procedure VI was followed using 2-(2,6-dioxopiperidin-3-yl)-4-fluoroisoindoline-1,3-dione (30 mg, 0.109 mmol), diethylamine (11 µL, 0.130 mmol) and DIPEA (32 µL, 0.181 mmol) to afford the title compound as a yellow film (28 mg, 97%) following purification by flash column chromatography on silica gel (0-100% EtOAc in hexanes). MS (ESI) calcd for $C_{17}H_{20}N_{30}O_4$ [M+H]⁺ 330.14, found 330.62.

5-(benzylamino)-2-(2,6-dioxopiperidin-3-yl)isoindoline-1,3-dione (D-25)

General procedure VI was followed using 2-(2,6-dioxopiperidin-3-yl)-5-fluoroisoindoline-1,3-dione (30 mg, 0.109 mmol), benzyl amine (13 µL, 0.119 mmol) and DIPEA (38 µL, 0.217 mmol) to afford the title compound as a yellow film (6 mg, 15%) following purification by flash column chromatography on silica gel (0-100% EtOAc in hexanes). MS (ESI) calcd for $C_{20}H_{18}N_3O_4$ [M+H]⁺ 364.13, found 364.34.

2-(2,6-dioxopiperidin-3-yl)-5-(isopropylamino)isoindoline-1,3-dione (D-26)

General procedure VI was followed using 2-(2,6-dioxopiperidin-3-yl)-5-fluoroisoindoline-1,3-dione (30 mg, 0.109 mmol), isopropyl amine (11 µL, 0.130 mmol) and DIPEA (38 µL, 0.217 mmol) to afford the title compound as a yellow film (6 mg, 17%) following purification by flash column chromatography on silica gel (0-100% EtOAc in hexanes). ¹H NMR (500 MHz, Chloroform-d) 8.00 (s, 1H), 7.53 (d, J=8.3 Hz, 1H), 6.87 (d, J=2.1 Hz, 1H), 6.64 (dd, J=8.3, 2.2 Hz, 1H), 4.86 (dd, J=12.3, 5.4 Hz, 1H), 4.30 (d, J=7.8 Hz, 1H), 2.86-2.58 (m, 3H), 2.12-2.01 (m, 1H), 1.26-1.15 (m, 6H); MS (ESI) calcd for $C_{16}H_{18}N_3O_4$ [M+H]⁺ 316.13, found 316.30.

5-(diethylamino)-2-(2,6-dioxopiperidin-3-yl)isoindoline-1,3-dione (D-27)

General procedure VI was followed using 2-(2,6-dioxopiperidin-3-yl)-5-fluoroisoindoline-1,3-dione (30 mg, 0.109 mmol), diethylamine (14 µL, 0.130 mmol) and DIPEA (38 µL, 0.217 mmol) to afford the title compound as a yellow film (6 mg, 31%) following purification by flash column chromatography on silica gel (0-100% EtOAc in hexanes). $^1$H NMR (500 MHz, Chloroform-d) δ 8.08 (s, 1H), 7.57 (d, J=8.6 Hz, 1H), 6.98 (d, J=2.4 Hz, 1H), 6.72 (dd, J=8.7, 2.4 Hz, 1H), 4.90-4.80 (m, 1H), 3.40 (q, J=7.1 Hz, 4H), 2.89-2.61 (m, 3H), 2.11-2.01 (m, 1H), 1.16 (t, J=7.1 Hz, 6H); MS (ESI) calcd for $C_{17}H_{20}N_3O_4$ [M+H]$^+$ 330.14, found 330.69.

2-(2,6-dioxopiperidin-3-yl)-5-((furan-2-ylmethyl)amino)isoindoline-1,3-dione (D-28)

General procedure VI was followed using 2-(2,6-dioxopiperidin-3-yl)-5-fluoroisoindoline-1,3-dione (50 mg, 0.181 mmol), furfurylamine (18 µL, 0.199 mmol) and DIPEA (63 µL, 0.362 mmol) to afford the title compound as a yellow film (8 mg, 13%) following purification by flash column chromatography on silica gel (0-5% MeOH in $CH_2Cl_2$). MS (ESI) calcd for $C_{18}H_{16}N_3O_4$ [M+H]$^+$ 354.11, found 354.25.

tert-butyl (2-((2-(2,6-dioxopiperidin-3-yl)-1,3-dioxoisoindolin-4-yl)amino)ethyl)carbamate (D-29)

General procedure VI was followed using 2-(2,6-dioxopiperidin-3-yl)-4-fluoroisoindoline-1,3-dione (50 mg, 0.181 mmol), 1-Boc-ethylendiamine (32 mg, 0.199 mmol) and DIPEA (63 µL, 0.362 mmol) to afford the title compound as a yellow film (31 mg, 41%) following purification by flash column chromatography on silica gel (0-10% MeOH in $CH_2Cl_2$). $^1$H NMR (500 MHz, CDCl$_3$) δ 8.08 (bs, 1H), 7.50 (dd, J=8.5, 7.1 Hz, 1H), 7.12 (d, J=7.1 Hz, 1H), 6.98 (d, J=8.5 Hz, 1H), 6.39 (t, J=6.1 Hz, 1H), 4.96-4.87 (m, 1H), 4.83 (bs, 1H), 3.50-3.41 (m, 2H), 3.41-3.35 (m, 2H), 2.92-2.66 (m, 3H), 2.16-2.09 (m, 1H), 1.45 (s, 9H); MS (ESI) calcd for $C_{20}H_{25}N_4O_6$ [M+H]$^+$ 417.18, found 417.58.

tert-butyl (2-((2-(2,6-dioxopiperidin-3-yl)-1,3-dioxoisoindolin-5-yl)amino)ethyl)carbamate (D-30)

General procedure VI was followed using 2-(2,6-dioxopiperidin-3-yl)-5-fluoroisoindoline-1,3-dione (50 mg, 0.181 mmol), 1-Boc-ethylendiamine (32 mg, 0.199 mmol) and DIPEA (63 µL, 0.362 mmol) to afford the title compound as a yellow film (22 mg, 29%) following purification by flash column chromatography on silica gel (0-10% MeOH in $CH_2Cl_2$). MS (ESI) calcd for $C_{20}H_{25}N_{40}O_6$ [M+H]$^+$ 417.18, found 417.32.

2-(2,6-dioxopiperidin-3-yl)-4-((furan-2-ylmethyl)amino)isoindoline-1,3-dione (D-31)

General procedure VI was followed using 2-(2,6-dioxopiperidin-3-yl)-4-fluoroisoindoline-1,3-dione (19.5 mg, 0.0706 mmol), furfurylamine (7 µL, 0.078 mmol) and DIPEA (25 µL, 0.141 mmol) to afford the title compound as a yellow film (19 mg, 76%) following purification by flash column chromatography on silica gel (0-2.5% MeOH in $CH_2Cl_2$). MS (ESI) calcd for $C_{18}H_{16}N_3O_4$ [M+H]$^+$ 354.11, found 354.27.

3-(5-(benzylamino)-2-methyl-4-oxoquinazolin-3(4H)-yl)piperidine-2,6-dione (D-39)

With the exception that the reaction mixture was heated to 170° C. instead of 90° C., general procedure VI was followed using 3-(5-fluoro-2-methyl-4-oxoquinazolin-3(4H)-yl)piperidine-2,6-dione (30 mg, 0.104 mmol), benzylamine (13 µL, 0.114 mmol) and DIPEA (36 µL, 0.207 mmol) to afford the title compound as a white solid (15 mg, 38%) following purification by flash column chromatography on silica gel (0-10% MeOH in $CH_2Cl_2$). $^1$H NMR (500 MHz, Chloroform-d) δ 8.73 (t, J=5.7 Hz, 1H), 8.39 (s, 1H), 7.41 (t, J=8.1 Hz, 1H), 7.39-7.19 (m, 5H), 6.77 (d, J=7.7 Hz, 1H), 6.41 (d, J=8.3 Hz, 1H), 4.67 (dd, J=11.5, 5.9 Hz, 1H), 4.43 (d, J=5.7 Hz, 2H), 3.03-2.79 (m, 2H), 2.72-2.61 (m, 1H), 2.60 (s, 3H), 2.15-2.07 (m, 1H); MS (ESI) calcd for $C_{21}H_{21}N_4O_3$ [M+H]$^+$ 377.16, found 377.02.

3-(5-(isopropylamino)-2-methyl-4-oxoquinazolin-3(4H)-yl)piperidine-2,6-dione (D-40)

With the exception that the reaction mixture was heated to 170° C. instead of 90° C., general procedure VI was followed using 3-(5-fluoro-2-methyl-4-oxoquinazolin-3(4H)-yl)piperidine-2,6-dione (30 mg, 0.104 mmol), isopropylamine (10 µL, 0.114 mmol) and DIPEA (36 µL, 0.207 mmol) to afford the title compound as a white solid (5 mg, 15%) following purification by flash column chromatography on silica gel (0-10% MeOH in $CH_2Cl_2$). $^1$H NMR (500 MHz, Chloroform-d) δ 8.31 (s, 1H), 8.21 (d, J=7.2 Hz, 1H), 7.50-7.37 (m, 1H), 6.70 (dd, J=7.9, 0.9 Hz, 1H), 6.47 (d, J=8.4 Hz, 1H), 4.65 (dd, J=11.4, 5.9 Hz, 1H), 3.69-3.56 (m, 1H), 3.03-2.80 (m, 3H), 2.58 (s, 3H), 2.14-2.03 (m, 1H), 1.27 (d, J=2.7 Hz, 3H), 1.26 (d, J=2.7 Hz, 3H); MS (ESI) calcd for $C_{17}H_{21}N_4O_3$ [M+H]$^+$ 329.16, found 329.97.

2-(2,6-dioxopiperidin-3-yl)-4-((2-hydroxyethyl)amino)isoindoline-1,3-dione (D-68)

General procedure VI was followed using 2-(2,6-dioxopiperidin-3-yl)-4-fluoroisoindoline-1,3-dione (30 mg, 0.109 mmol), aminoethanol (7 jaL, 0.119 mmol) and DIPEA (38 µL, 0.217 mmol) to afford the title compound as a yellow film (6 mg, 18%) following purification by flash column chromatography on silica gel (0-5% MeOH in $CH_2Cl_2$). $^1$H NMR (500 MHz, Chloroform-d) δ 8.26 (s, 1H), 7.50 (dd, J=8.5, 7.1 Hz, 1H), 7.12 (d, J=7.0 Hz, 1H), 6.95 (d, J=8.5 Hz, 1H), 6.50 (t, J=5.9 Hz, 1H), 4.97-4.85 (m, 1H), 3.94-3.79 (m, 2H), 3.47 (q, J=5.5 Hz, 2H), 3.03-2.68 (m, 3H), 2.19-2.04 (m, 1H); MS (ESI) calcd for $C_{15}H6N_3O_5$ [M+H]$^+$ 318.11, found 318.22.

4-(cyclopropylamino)-2-(2,6-dioxopiperidin-3-yl)isoindoline-1,3-dione (D47)

General procedure VI was followed using 2-(2,6-dioxopiperidin-3-yl)-4-fluoroisoindoline-1,3-dione (20 mg, 0.0724 mmol), cyclopropylamine (6 µL, 0.080 mmol) and DIPEA (25 µL, 0.141 mmol) to afford the title compound as a yellow film (16 mg, 70%) following purification by flash column chromatography on silica gel (0-5% MeOH in $CH_2Cl_2$). $^1$H NMR (500 MHz, Chloroform-d) δ 8.05 (s, 1H), 7.53 (dd, J=8.5, 7.1 Hz, 1H), 7.33-7.21 (m, 1H), 7.15 (dd, J=7.1, 0.7 Hz, 1H), 6.44 (bs, 1H), 4.95-4.85 (m, 1H), 2.98-2.66 (m, 3H), 2.62-2.50 (m, 1H), 2.19-2.06 (m, 1H), 0.92-0.78 (m, 2H), 0.67-0.56 (m, 2H); MS (ESI) calcd for $C_{16}H_{16}N_3O_4$ $[M+H]^+$ 314.11, found 314.54.

4-((2-(1H-indol-3-yl)ethyl)amino)-2-(2,6-dioxopiperidin-3-yl)isoindoline-1,3-dione (D-48)

General procedure VI was followed using 2-(2,6-dioxopiperidin-3-yl)-4-fluoroisoindoline-1,3-dione (20 mg, 0.0724 mmol), tryptamine (13 mg, 0.080 mmol) and DIPEA (25 µL, 0.144 mmol) to afford the title compound as a yellow film (10 mg, 33%) following purification by flash column chromatography on silica gel (0-10% MeOH in $CH_2Cl_2$). $^1H$ NMR (500 MHz, Chloroform-d) δ 8.14 (s, 1H), 8.11 (s, 1H), 7.65-7.55 (m, 1H), 7.45 (dd, J=8.6, 7.1 Hz, 1H), 7.37 (dt, J=8.2, 0.9 Hz, 1H), 7.21 (ddd, J=8.2, 7.0, 1.2 Hz, 1H), 7.16-7.04 (m, 3H), 6.88 (d, J=8.5 Hz, 1H), 6.34 (t, J=5.6 Hz, 1H), 4.89 (dd, J=12.4, 5.4 Hz, 1H), 3.59 (td, J=6.8, 5.5 Hz, 2H), 3.19-3.03 (m, 2H), 2.93-2.64 (m, 3H), 2.14-2.04 (m, 1H); MS (ESI) calcd for $C_{23}H_{21}N_4O_4$ $[M+H]^+$ 417.16, found 417.26.

2-(2,6-dioxopiperidin-3-yl)-4-((4-hydroxyphenethyl)amino)isoindoline-1,3-dione (D-49)

General procedure VI was followed using 2-(2,6-dioxopiperidin-3-yl)-4-fluoroisoindoline-1,3-dione (20 mg, 0.0724 mmol), tyramine (11 mg, 0.080 mmol) and DIPEA (25 µL, 0.144 mmol) to afford the title compound as a yellow film (15 mg, 54%) following purification by flash column chromatography on silica gel (0-5% MeOH in $CH_2Cl_2$). $^1H$ NMR (500 MHz, Chloroform-d) δ 8.20 (s, 1H), 7.51 (dd, J=8.5, 7.1 Hz, 1H), 7.17-7.08 (m, 2H), 6.90 (d, J=8.5 Hz, 1H), 6.85-6.72 (m, 2H), 4.95-4.90 (m, 1H), 3.52-3.46 (m, 2H), 2.97-2.87 (m, 2H), 2.86-2.72 (m, 2H), 2.21-2.09 (m, 1H); MS (ESI) calcd for $C_{21}H_{20}N_3O_5$ $[M+H]^+$ 394.14, found 394.25.

4-((2-(1H-imidazol-2-yl)ethyl)amino)-2-(2,6-dioxopiperidin-3-yl)isoindoline-1,3-dione (D-50)

General procedure VI was followed using 2-(2,6-dioxopiperidin-3-yl)-4-fluoroisoindoline-1,3-dione (20 mg, 0.0724 mmol), histamine (15 mg, 0.080 mmol) and DIPEA (25 µL, 0.144 mmol) to afford the title compound as a yellow film (5 mg, 19%) following purification by flash column chromatography on silica gel (0-10% MeOH in $CH_2Cl_2$). $^1H$ NMR (500 MHz, Chloroform-d) δ 8.19 (s, 1H), 7.61 (d, J=1.2 Hz, 1H), 7.47 (dd, J=8.5, 7.1 Hz, 1H), 7.07 (d, J=6.9 Hz, 1H), 6.96-6.83 (m, 2H), 6.39 (t, J=5.7 Hz, 1H), 4.97-4.79 (m, 1H), 3.59 (q, J=6.5 Hz, 2H), 2.95 (t, J=6.6 Hz, 2H), 2.92-2.62 (m, 2H), 2.16-2.04 (m, 1H); MS (ESI) calcd for $C_{18}H_{11}N_5O_4$ $[M+H]^+$ 368.14, found 368.47.

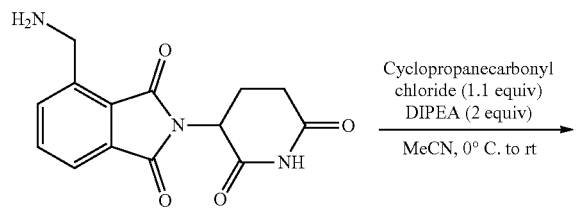

Cyclopropanecarbonyl chloride (1.1 equiv)
DIPEA (2 equiv)
MeCN, 0° C. to rt

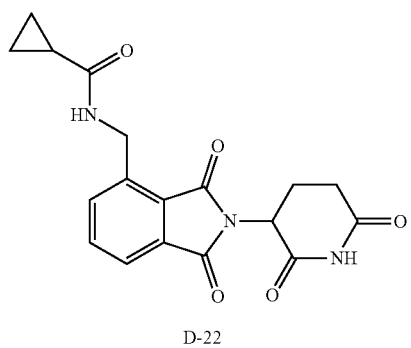

D-22

General Procedure VII: Acylation of Primary Amines

N-((2-(2,6-dioxopiperidin-3-yl)-1,3-dioxoisoindolin-4-yl)methyl)cyclopropanecarboxamide (D-22)

In a 4 mL glass vial, 4-(aminomethyl)-2-(2,6-dioxopiperidin-3-yl)isoindoline-1,3-dione (25 mg, 0.087 mmol, 1 equiv) and DIPEA (30 µL, 0.174 mmol, 2 equiv) in MeCN (250 µL, 0.35 M) was cooled to 0° C. Cyclopropanecarbonyl chloride (8.7 µL, 0.096 mmol) was added slowly and the reaction mixture was stirred at room temperature overnight. The product was isolated by filtration to afford the title compound as a white solid (4.8 mg, 15%), that was used without further purification. MS (ESI) calcd for $C_{18}H_{18}N_3O_5$ $[M+H]^+$ 356.12, found 356.32.

N-((2-(2,6-dioxopiperidin-3-yl)-1,3-dioxoisoindolin-4-yl)methyl)acetamide (D-23)

General procedure VII was followed using 4-(aminomethyl)-2-(2,6-dioxopiperidin-3-yl)isoindoline-1,3-dione (25 mg, 0.087 mmol), DIPEA (30 µL, 0.174 mmol) and acetyl chloride (7 µL, 0.096 mmol) to afford the title compound as a white solid (4.5 mg, 16%). $^1H$ NMR (500 MHz, DMSO-$d_6$) δ 11.13 (s, 1H), 8.47 (t, J=6.0 Hz, 1H), 7.88-7.76 (m, 2H), 7.70 (dt, J=7.3, 1.1 Hz, 1H), 5.15 (dd, J=12.7, 5.4 Hz, 1H), 4.69 (d, J=6.0 Hz, 2H), 2.90 (ddd, J=16.8, 13.8, 5.4 Hz, 1H), 2.64-2.44 (m, 2H), 2.15-2.01 (m, 1H), 1.92 (s, 3H); MS (ESI) calcd for $C_{16}H_{16}N_3O_5$ $[M+H]^+$ 330.11, found 330.05.

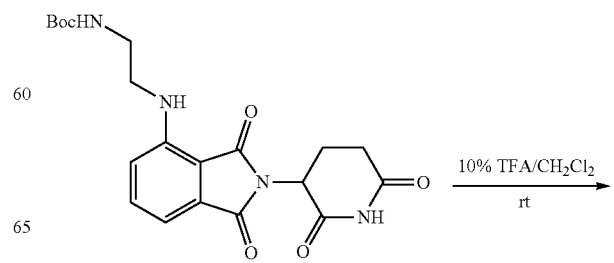

10% TFA/$CH_2Cl_2$
rt

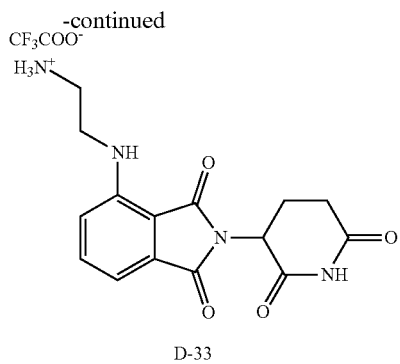

2-((2-(2,6-dioxopiperidin-3-yl)-1,3-dioxoisoindolin-4-yl)amino)ethan-1-aminium 2,2,2-trifluoroacetate (D-33)

A stirred solution of tert-butyl (2-((2-(2,6-dioxopiperidin-3-yl)-1,3-dioxoisoindolin-4-yl)amino)ethyl)carbamate (205 mg, 0.492 mmol, 1 equiv) in dichloromethane (2.25 mL) was added trifluoroacetic acid (0.250 mL). The reaction mixture was stirred at room temperature for 4 h, whereupon the volatiles were removed in vacuo. The title compound was obtained as a yellow solid (226 mg, >95%), that was used without further purification. $^1$H NMR (500 MHz, MeOD) δ 7.64 (d, J=1.4 Hz, 1H), 7.27-7.05 (m, 2H), 5.10 (dd, J=12.5, 5.5 Hz, 1H), 3.70 (t, J=6.0 Hz, 2H), 3.50-3.42 (m, 2H), 3.22 (t, J=6.0 Hz, 1H), 2.93-2.85 (m, 1H), 2.80-2.69 (m, 2H), 2.17-2.10 (m, 1H); MS (ESI) calcd for $C_{15}H_{17}N_4O_4$ [M+H]$^+$ 317.12, found 317.53.

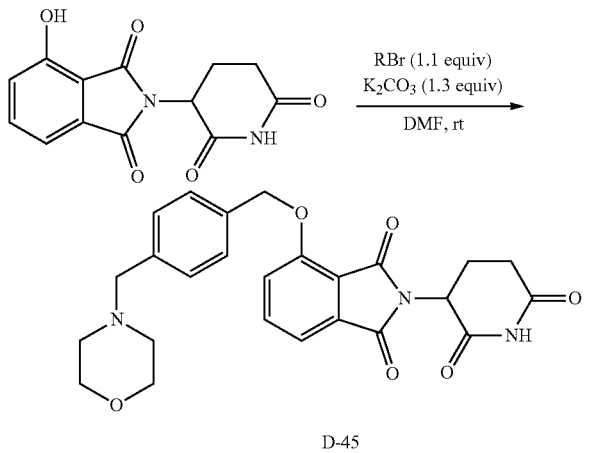

General Procedure VIII: Phenol Alkylation

2-(2,6-dioxopiperidin-3-yl)-4-((4-(morpholinomethyl)benzyl)oxy)isoindoline-1,3-dione (D-45)

In a 4 mL glass vial, 2-(2,6-dioxopiperidin-3-yl)-4-hydroxyisoindoline-1,3-dione (30 mg, 0.109 mmol, 1 equiv) and K$_2$CO$_3$ (15 mg, 0.109 mmol, 1 equiv) in DMF (365 µL, 0.3 M) was stirred at room temperature. 4-(4-(bromomethyl)benzyl)morpholine (30 mg, 0.109 mmol, 1 equiv) in DMF (200 µL) was added and the reaction mixture was stirred at room temperature for 4 days. The reaction mixture was taken up in water (15 mL) and EtOAc (15 mL), and the organic layer was washed with brine (3×15 mL), dried over Na$_2$SO$_4$ and concentrated in vacuo. The residue was purified by flash column chromatography on silica gel (0 to 10% MeOH in CH$_2$Cl$_2$) to afford the title compound as a white solid (20 mg, 40%). $^1$H NMR (500 MHz, DMSO-d$_6$) δ 11.10 (s, 1H), 7.82 (dd, J=8.5, 7.2 Hz, 1H), 7.60 (d, J=8.5 Hz, 1H), 7.50-7.42 (m, 3H), 7.35 (d, J=8.1 Hz, 2H), 5.35 (s, 2H), 5.09 (dd, J=12.8, 5.5 Hz, 1H), 3.64-3.51 (m, 4H), 3.46 (s, 2H), 2.88 (ddd, J=17.0, 14.1, 5.4 Hz, 1H), 2.63-2.47 (m, 2H), 2.38-2.31 (m, 4H), 2.07-1.99 (m, 1H); MS (ESI) calcd for $C_{25}H_{26}N_3O_6$ [M+H]$^+$ 464.18, found 464.00.

4-(benzyloxy)-2-(2,6-dioxopiperidin-3-yl)isoindoline-1,3-dione (D-46)

General procedure VIII was followed using 2-(2,6-dioxopiperidin-3-yl)-4-hydroxyisoindoline-1,3-dione (30 mg, 0.109 mmol), K$_2$CO$_3$ (15 mg, 0.109 mmol) and benzyl bromide (8 µL, 0109 mmol) to afford the title compound as a white solid (8 mg, 20%) after purification by flash column chromatography on silica gel (0 to 10% MeOH in CH$_2$Cl$_2$). $^1$H NMR (500 MHz, DMSO-d$_6$) δ 11.10 (s, 1H), 7.83 (dd, J=8.5, 7.3 Hz, 1H), 7.60 (d, J=8.5 Hz, 1H), 7.53-7.50 (m, 2H), 7.47 (d, J=7.2 Hz, 1H), 7.45-7.39 (m, 2H), 7.38-7.32 (m, 1H), 5.38 (s, 2H), 5.09 (dd, J=12.8, 5.5 Hz, 1H), 2.88 (ddd, J=16.9, 13.8, 5.5 Hz, 1H), 2.64-2.46 (m, 2H), 2.07-1.99 (m, 1H); MS (ESI) calcd for $C_{20}H_{17}N_2O_5$ [M+H]$^+$ 365.11, found 365.21.

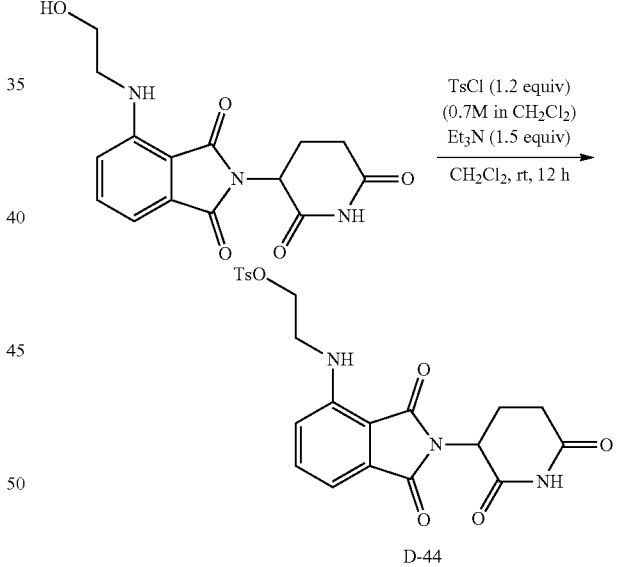

2-((2-(2,6-dioxopiperidin-3-yl)-1,3-dioxoisoindolin-4-yl)amino)ethyl 4-methylbenzene-sulfonate (D-44)

In a 4 mL glass vial, 2-(2,6-dioxopiperidin-3-yl)-4-((2-hydroxyethyl)amino)isoindoline-1,3-dione (7 mg, 0.0221 mmol, 1 equiv) and Et$_3$N (3 µL, 0.033 mmol, 1.5 equiv) in CH$_2$Cl$_2$ (200 µL) was stirred at room temperature. Tosyl chloride (6 mg, 0.026 mmol, 1.2 equiv) in CH$_2$Cl$_2$ (100 µL) was added, and the reaction mixture was stirred at room temperature overnight. The reaction mixture was concentrated in vacuo and the residue was purified by flash column chromatography on silica gel (0-10% MeOH in CH$_2$Cl$_2$) to afford the title compound as a white solid (4 mg, 40%). $^1$H NMR (500 MHz, DMSO-$d_6$) δ 11.13 (s, 1H), 7.64-7.59 (m, 2H), 7.46 (dd, J=8.6, 7.1 Hz, 1H), 7.33-7.27 (m, 2H), 7.04-6.93 (m, 2H), 6.58 (t, J=6.4 Hz, 1H), 5.09 (dd, J=12.7, 5.4 Hz, 1H), 4.15 (t, J=5.1 Hz, 2H), 3.65-3.52 (m, 2H), 2.97-2.83 (m, 1H), 2.67-2.46 (m, 2H), 2.27 (s, 3H), 2.12-2.02 (m, 1H); MS (ESI) calcd for $C_{22}H_{22}N_3O_7S$ [M+H]$^+$ 472.12, found 472.39.

(R)-4-hydroxy-2-(3-methyl-2,6-dioxopiperidin-3-yl)isoindoline-1,3-dione (D-52)

Hydroxyisobenzofuran-1,3-dione (147.08 mg, 0.896 mmol, 1 eq) was added to (R)-3-amino-3-methylpiperidine-2,6-dione hydrochloric acid (127.32 mg, 0.896 mmol, 1 eq). Pyridine (3.584 ml, 0.25 M) was then added to the mixture and it was stirred at 110° C. for 17 hours. The mixture was diluted with methanol and was condensed under reduced pressure. The crude material was purified by column chromatography (ISCO, 24 g silica column, 0 to 10% MeOH/DCM 25 minute gradient) to give a white oil (110.9 mg, 42.63% yield). $^1$H NMR (400 MHz, DMSO-$d_6$) δ 10.95 (s, 1H), 7.61 (dd, J=8.4, 7.2 Hz, 1H), 7.27-7.14 (m, 2H), 2.73-2.63 (m, 1H), 2.57-2.51 (m, 1H), 2.04-1.97 (m, 1H), 1.86 (s, 3H).
LCMS 289 (M+H).

(S)-4-hydroxy-2-(3-methyl-2,6-dioxopiperidin-3-yl)isoindoline-1,3-dione (D-53)

4-hydroxyisobenzofuran-1,3-dione (148.99 mg, 0.907 mmol, 1 eq) was added to (S)-3-amino-3-methylpiperidine-2,6-dione hydrochloric acid (128.97 mg, 0.907 mmol, 1 eq). Pyridine (3.628 ml, 0.25 M) was then added to the mixture and it was stirred at 110° C. for 17 hours. The mixture was diluted with methanol and was condensed under reduced pressure. The crude material was purified by column chromatography (ISCO, 24 g silica column, 0 to 10% MeOH/DCM 25 minute gradient) to give a white oil (150 mg, 57.4% yield). $^1$H NMR (400 MHz, DMSO-$d_6$) δ 10.95 (s, 1H), 7.62 (dd, J=8.4, 7.2 Hz, 1H), 7.27-7.16 (m, 2H), 2.75-2.62 (m, 1H), 2.55 (dd, J=14.0, 4.3 Hz, 1H), 2.05-1.96 (m, 1H), 1.86 (s, 3H). LCMS 289 (M+H).

(S)-2-((2-(3-methyl-2,6-dioxopiperidin-3-yl)-1,3-dioxoisoindolin-4-yl)oxy)acetic acid (D-55)

TFA (0.63 ml, 0.1 M) was added to tert-butyl (S)-2-((2-(3-methyl-2,6-dioxopiperidin-3-yl)-1,3-dioxoisoindolin-4-yl)oxy)acetate (25.4 mg, 0.063 mmol, 1 eq) and the mixture was stirred at 50° C. for an hour. The mixture was then diluted with methanol and condensed under reduced pressure to give a white powder (20.5 mg, 93.9% yield) that was carried forward without further purification. $^1$H NMR (500 MHz, Methanol-d4) δ 7.81-7.75 (m, 1H), 7.50 (d, J=7.3 Hz, 1H), 7.45 (d, J=8.6 Hz, 2H), 7.43-7.37 (m, 3H), 5.09 (dd, J=12.8, 5.5 Hz, 1H), 4.76 (s, 2H), 4.63 (dd, J=9.1, 5.2 Hz, 1H), 3.66-3.55 (m, 30H), 3.51-3.41 (m, 5H), 2.90-2.83 (m, 1H), 2.79-2.71 (m, 2H), 2.69 (s, 3H), 2.43 (s, 3H), 2.14 (ddt, J=10.5, 5.5, 3.2 Hz, 1H), 1.69 (s, 3H). LCMS 347 (M+H).

(R)-2-((2-(3-methyl-2,6-dioxopiperidin-3-yl)-1,3-dioxoisoindolin-4-yl)oxy)acetic acid (D-54)

TFA (1.78 ml, 0.1 M) was added to tert-butyl (R)-2-((2-(3-methyl-2,6-dioxopiperidin-3-yl)-1,3-dioxoisoindolin-4-yl)oxy)acetate (71.3 mg, 0.178 mmol, 1 eq) and the mixture was stirred at 50° C. for an hour. The mixture was then diluted with methanol and condensed under reduced pressure to give a white powder (47.2 mg, 76.63% yield) that was carried forward without further purification. $^1$H NMR (400 MHz, Methanol-d4) δ 7.72 (ddd, J=8.5, 7.3, 5.0 Hz, 1H), 7.46-7.42 (m, 1H), 7.30 (dd, J=8.6, 4.5 Hz, 1H), 4.94 (d, J=5.3 Hz, 2H), 2.81-2.56 (m, 2H), 2.24-2.07 (m, 1H), 2.00 (s, 2H), 0.90 (t, J=6.5 Hz, 2H). LCMS 347 (M+H).

4,7-dichloro-2-(2,6-dioxopiperidin-3-yl)isoindoline-1,3-dione (D-51)

4,7-dichloroisobenzofuran-1,3-dione (434.6 mg, 2.002 mmol, 1 eq) was added to 3-aminopiperidine-2,6-dione hydrochloric acid (362.6 mg, 2.203 mmol, 1.1 eq). Potassium acetate (609.07 mg, 6.206 mmol, 3.1 eq) and acetic acid (6.67 ml, 0.3 M) were then added to the mixture and it was stirred at 90° C. for 18 hours. The mixture was cooled down to room temperature, diluted with DI water and centrifuged for 5 minutes. The precipitate was diluted with methanol and was condensed under reduced pressure. The crude material was purified by column chromatography (ISCO, 12 g silica column, 0 to 10% MeOH/DCM 25 minute gradient) to give a white powder (160.4 mg, 24.5% yield). $^1$H NMR (500 MHz, DMSO-$d_6$) δ 11.15 (s, 1H), 7.91 (s, 2H), 5.17 (dd, J=12.9, 5.4 Hz, 1H), 2.88 (ddd, J=17.2, 13.9, 5.4 Hz, 1H), 2.68-2.54 (m, 1H), 2.05 (ddd, J=10.5, 5.4, 2.7 Hz, 1H). LCMS 328 (M+H).

Synthetic Example 1: Synthesis of dBET 1

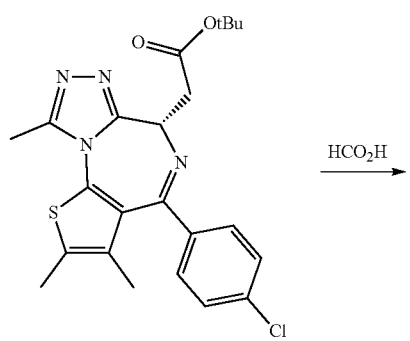

JQ1

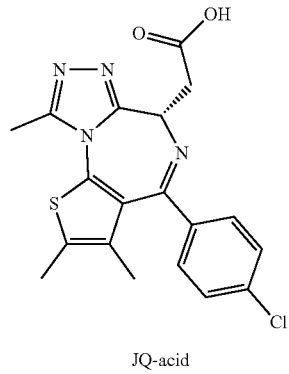

JQ-acid

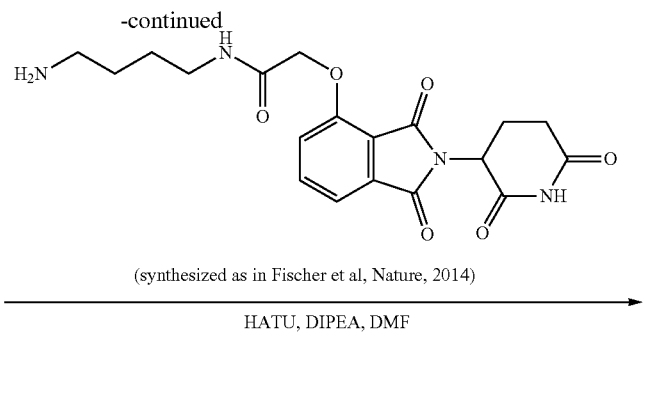

(synthesized as in Fischer et al, Nature, 2014)

HATU, DIPEA, DMF

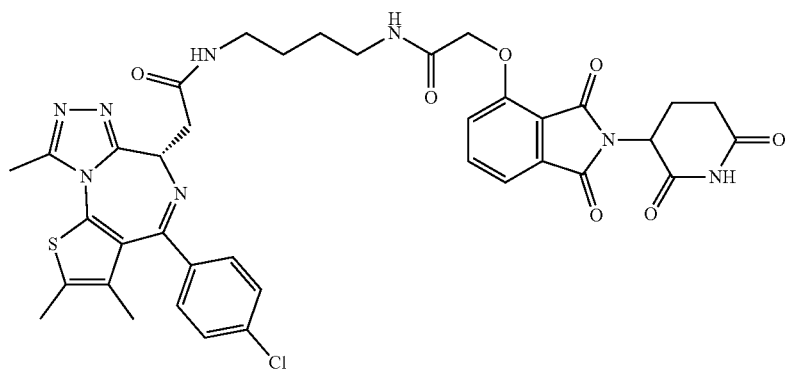

DB-2-190-2
dBET1

(1) Synthesis of JQ-Acid

JQ1 (1.0 g, 2.19 mmol, 1 eq) was dissolved in formic acid (11 mL, 0.2 M) at room temperature and stirred for 75 hours. The mixture was concentrated under reduced pressure to give a yellow solid (0.99 g, quant yield) that was used without purification. $^1$H NMR (400 MHz, Methanol-$d_4$) δ 7.50-7.36 (m, 4H), 4.59 (t, J=7.1 Hz, 1H), 3.51 (d, J=7.1 Hz, 2H), 2.70 (s, 3H), 2.45 (s, 3H), 1.71 (s, 3H). LCMS 401.33 (M+H).

N-(4-aminobutyl)-2-((2-(2,6-dioxopiperidin-3-yl)-1,3-dioxoisoindolin-4-yl)oxy)acetamidetrifluoroacetate was synthesized according to the previously published procedure (Fischer et al., Nature 512 (2014):49).

(2) Synthesis of dBET1

JQ-acid (11.3 mg, 0.0281 mmol, 1 eq) and N-(4-aminobutyl)-2-((2-(2,6-dioxopiperidin-3-yl)-1,3-dioxoisoindolin-4-yl)oxy)acetamide trifluoroacetate (14.5 mg, 0.0281 mmol, 1 eq) were dissolved in DMF (0.28 mL, 0.1 M) at room temperature. DIPEA (14.7 microliters, 0.0843 mmol, 3 eq) and HATU (10.7 mg, 0.0281 mmol, 1 eq) were then added and the mixture was stirred for 19 hours. The mixture was then purified by preparative HPLC to give dBET1 as a yellow solid (15.90 mg, 0.0202 mmol, 72%). $^1$H NMR (400 MHz, Methanol-$d_4$) δ 7.77 (dd, J=8.3, 7.5 Hz, 1H), 7.49 (d, J=7.3 Hz, 1H), 7.47-7.37 (m, 5H), 5.07 (dd, J=12.5, 5.4 Hz, 1H), 4.74 (s, 2H), 4.69 (dd, J=8.7, 5.5 Hz, 1H), 3.43-3.32 (m, 3H), 3.29-3.25 (m, 2H), 2.87-2.62 (m, 7H), 2.43 (s, 3H), 2.13-2.04 (m, 1H), 1.72-1.58 (m, 7H). $^{13}$C NMR (100 MHz, cd$_3$od) δ 174.41, 172.33, 171.27, 171.25, 169.87, 168.22, 167.76, 166.73, 166.70, 156.26, 138.40, 138.23, 137.44, 134.83, 133.92, 133.40, 132.30, 132.28, 131.97, 131.50, 129.87, 121.85, 119.31, 118.00, 69.53, 54.90, 50.54, 40.09, 39.83, 38.40, 32.12, 27.74, 27.65, 23.61, 14.42, 12.97, 11.57. LCMS 785.44 (M+H).

Synthetic Example 2: Synthesis of dBET4

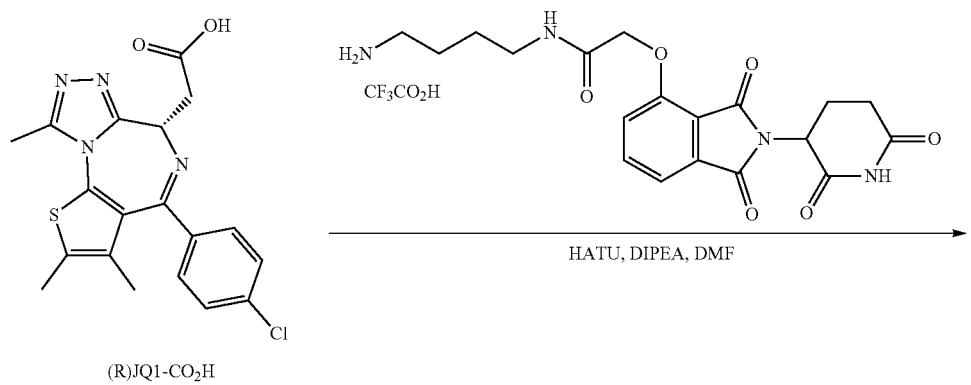

(R)JQ1-CO₂H

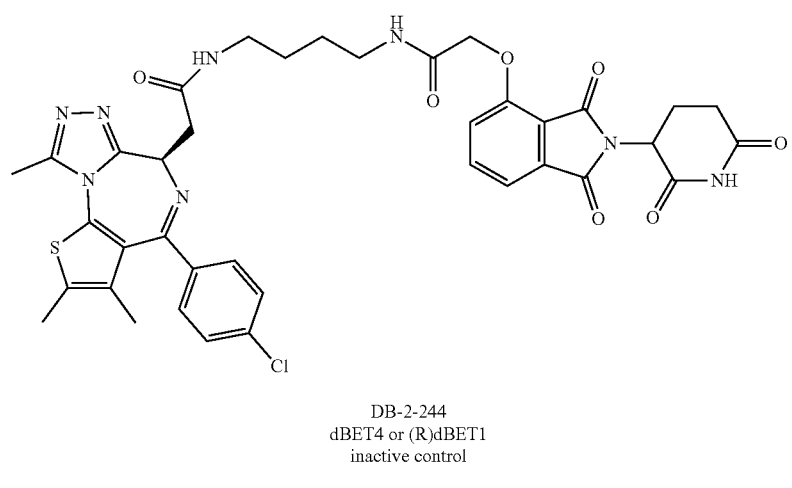

DB-2-244
dBET4 or (R)dBET1
inactive control

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.438 mL, 0.0438 mmol 1.2 eq) was added to (R)-JQ-acid (prepared from (R)-JQ1 in an analogous method to JQ-acid) (14.63 mg, 0.0365 mmol, 1 eq) at room temperature. DIPEA (19.1 microliters, 0.1095 mmol, 3 eq) and HATU (15.3 mg, 0.0402 mmol, 1.1 eq) were added and the mixture was stirred for 24 hours, then diluted with MeOH and concentrated under reduced pressure. The crude material was purified by preparative HPLC to give a yellow solid (20.64 mg, 0.0263 mmol, 72%). $^1$H NMR (400 MHz, Methanol-d₄) δ 7.79 (dd, J=8.4, 7.4 Hz, 1H), 7.51 (d, J=7.3 Hz, 1H), 7.47-7.39 (m, 5H), 5.11-5.06 (m, 1H), 4.75 (s, 2H), 4.68 (dd, J=8.8, 5.5 Hz, 1H), 3.47-3.31 (m, 5H), 2.83-2.65 (m, 7H), 2.44 (s, 3H), 2.13-2.06 (m, 1H), 1.68 (s, 3H), 1.67-1.60 (m, 4H). $^{13}$C NMR (100 MHz, cd₃od) δ 174.43, 172.40, 171.29, 169.92, 168.24, 167.82, 166.71, 156.31, 153.14, 138.38, 138.24, 137.54, 134.88, 133.86, 133.44, 132.29, 132.00, 131.49, 129.88, 122.46, 121.90, 119.38, 118.02, 69.59, 54.96, 50.55, 40.09, 39.84, 38.45, 32.14, 27.75, 27.65, 23.62, 14.41, 12.96, 11.56. MS 785.48 (M+H).

Synthetic Example 3: Synthesis of dBET3

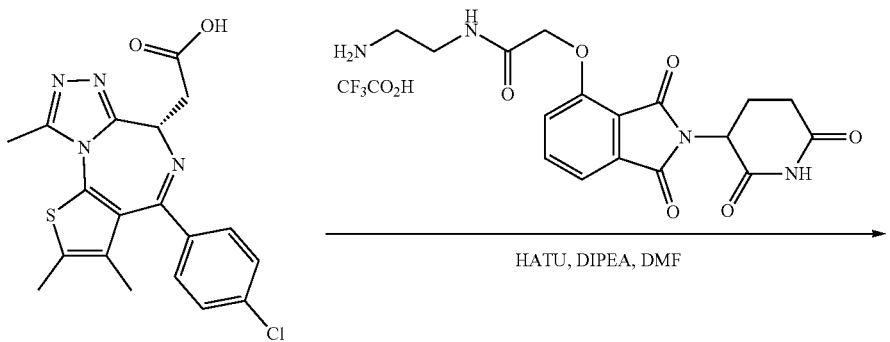

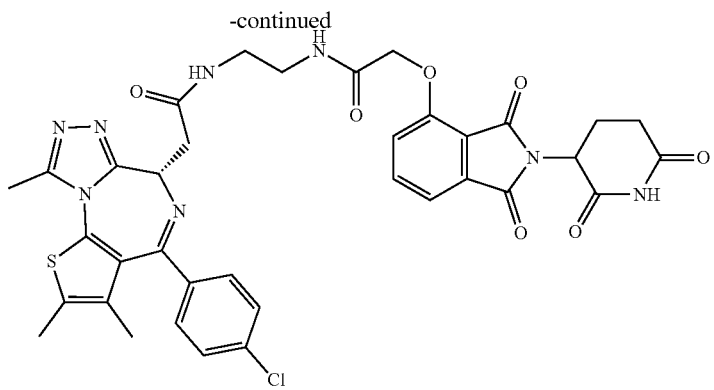

DB-2-243
dBET3

A 0.1 M solution of N-(2-aminoethyl)-2-((2-(2,6-dioxopiperidin-3-yl)-1,3-dioxoisoindolin-4-yl)oxy)acetamide trifluoroacetate in DMF (0.475 mL, 0.0475 mmol, 1.2 eq) was added to JQ-acid (15.86 mg, 0.0396 mmol, 1 eq) at room temperature. DIPEA (20.7 microliters, 0.1188 mmol, 3 eq) and HATU (16.5 mg, 0.0435 mmol, 1.1 eq) were then added and the mixture was stirred for 24 hours, then purified by reparative HPLC to give a yellow solid (22.14 mg, 0.0292 mmol, 74%). $^1$H NMR (400 MHz, Methanol-$d_4$) δ 7.82-7.75 (m, 1H), 7.52-7.32 (m, 6H), 5.04 (dd, J=11.6, 5.5 Hz, 1H), 4.76 (d, J=3.2 Hz, 2H), 4.66 (d, J=6.6 Hz, 1H), 3.58-3.35 (m, 6H), 2.78-2.58 (m, 6H), 2.48-2.41 (m, 3H), 2.11-2.02 (m, 1H), 1.70 (d, J=11.8 Hz, 3H). $^{13}$C NMR (100 MHz, cd$_3$od) δ 174.38, 171.26, 171.19, 170.26, 168.86, 168.21, 167.76, 166.72, 156.27, 153.14, 138.44, 138.36, 138.19, 134.87, 133.71, 132.31, 131.57, 131.51, 129.90, 129.86, 121.81, 119.36, 117.95, 69.48, 54.83, 50.52, 40.09, 39.76, 38.30, 32.09, 23.63, 14.40, 11.61. LCMS 757.41 (M+H).

Synthetic Example 4: Synthesis of dBET5

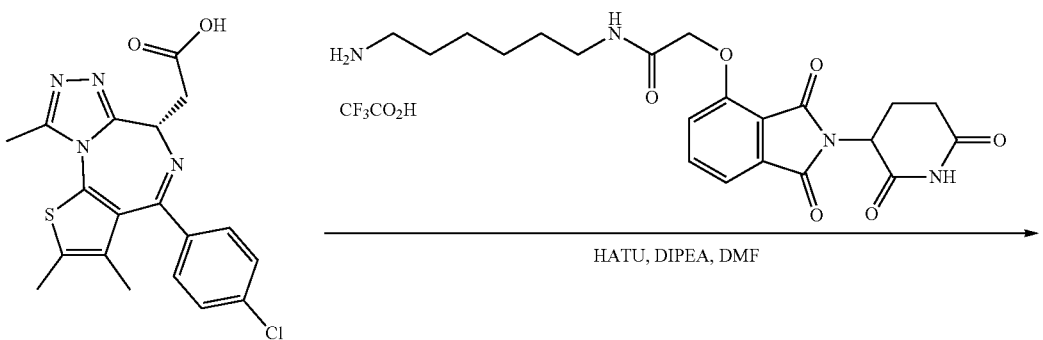

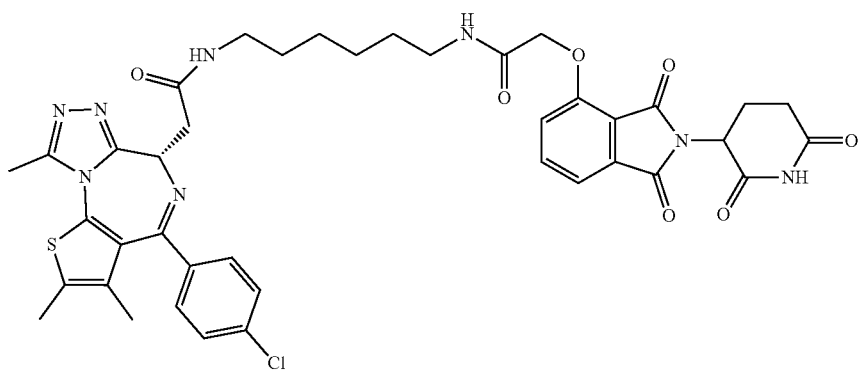

DB-2-264
dBET5

A 0.1M solution of N-(6-aminohexyl)-2-((2-(2,6-dioxopiperidin-3-yl)-1,3-dioxoisoindolin-4-yl)oxy)acetamide trifluoroacetate in DMF (0.247 mL, 0.0247 mmol, 1 eq) was added to JQ-acid (9.9 mg, 0.0247 mmol, 1 eq) at room temperature. DIPEA (12.9 microliters, 0.0741 mmol, 3 eq) and HATU (9.4 mg, 0.0247 mmol, 1 eq) were then added. the mixture was stirred for 21 hours, then diluted with MeOH and concentrated under reduced pressure. The crude material was purified by preparative HPLC to give a yellow solid (13.56 mg, 0.0167 mmol, 67%). $^1$H NMR (400 MHz, Methanol-$d_4$) δ 7.82-7.78 (m, 1H), 7.53 (dd, J=7.3, 2.0 Hz, 1H), 7.49-7.37 (m, 5H), 5.10 (dt, J=12.4, 5.3 Hz, 1H), 4.76 (s, 2H), 4.70 (dd, J=8.7, 5.5 Hz, 1H), 3.42-3.33 (m, 2H), 3.25 (dt, J=12.3, 6.0 Hz, 3H), 2.87-2.67 (m, 7H), 2.48-2.42 (m, 3H), 2.14-2.09 (m, 1H), 1.69 (d, J=4.8 Hz, 3H), 1.58 (s, 4H), 1.42 (d, J=5.2 Hz, 4H). $^{13}$C NMR (100 MHz, cd$_3$od) δ 174.51, 171.31, 171.26, 169.82, 168.27, 168.26, 167.75, 156.26, 150.46, 138.20, 134.92, 133.92, 133.47, 132.34, 132.01, 131.52, 129.88, 121.69, 119.34, 117.95, 111.42, 69.39, 54.97, 50.56, 40.39, 40.00, 38.40, 32.15, 30.46, 30.16, 27.58, 27.48, 23.64, 14.41, 12.96, 11.55. LCMS 813.38.

Synthetic Example 5: Synthesis of dBET6

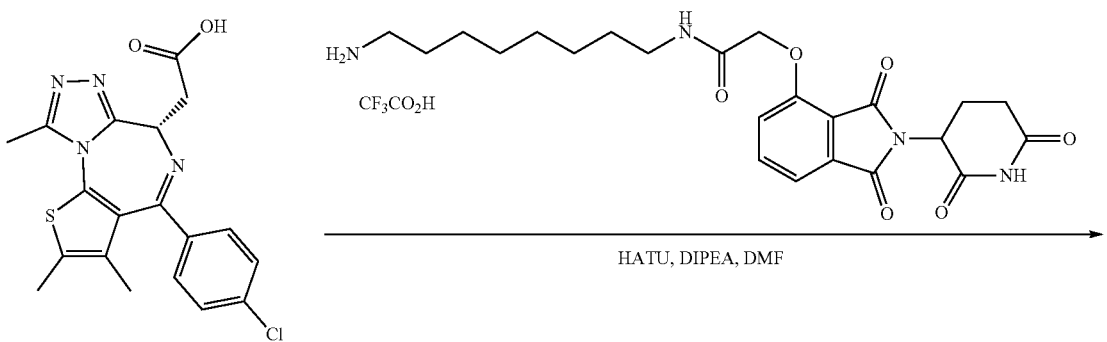

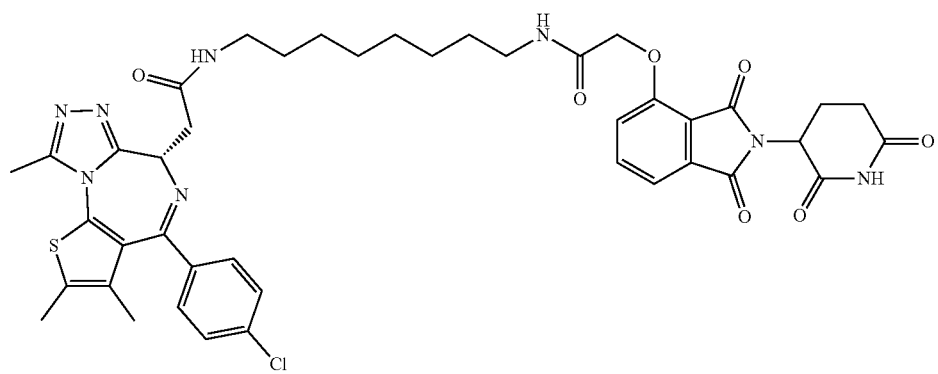

DB-2-270
dBET6

A 0.1M solution of N-(8-aminooctyl)-2-((2-(2,6-dioxopiperidin-3-yl)-1,3-dioxoisoindolin-4-yl)oxy)acetamide trifluoroacetate in DMF (0.191 mL, 0.0191 mmol, 1 eq) was added to JQ-acid (7.66 mg, 0.0191 mmol, 1 eq) at room temperature. DIPEA (10 microliters, 0.0574 mmol, 3 eq) and HATU (7.3 mg, 0.0191 mmol, 1 eq) were added and the mixture was stirred for 22 hours, diluted with MeOH, and concentrated under reduced pressure. The crude material was purified by preparative HPLC to give a cream colored solid. (8.53 mg, 0.0101 mmol, 53%). $^1$H NMR (400 MHz, Methanol-$d_4$) δ 7.80 (dd, J=8.4, 7.4 Hz, 1H), 7.53 (d, J=7.4 Hz, 1H), 7.49-7.36 (m, 5H), 5.10 (dt, J=12.3, 5.3 Hz, 1H), 4.75 (s, 2H), 4.69 (dd, J=8.8, 5.3 Hz, 1H), 3.42 (dd, J=15.0, 8.9 Hz, 1H), 3.30-3.18 (m, 4H), 2.90-2.64 (m, 7H), 2.45 (s, 3H), 2.13 (dtt, J=10.8, 5.2, 2.6 Hz, 1H), 1.71 (d, J=4.4 Hz, 3H), 1.56 (d, J=6.2 Hz, 4H), 1.33 (d, J=17.1 Hz, 8H). $^{13}$C NMR (100 MHz, cd$_3$od) δ 174.50, 172.38, 171.30, 169.81, 168.28, 167.74, 166.64, 156.25, 138.38, 138.20, 137.55, 134.92, 133.88, 133.42, 132.27, 132.02, 131.50, 129.85, 121.66, 119.30, 117.95, 69.37, 55.01, 50.58, 40.51, 40.12, 38.44, 32.18, 30.46, 30.33, 30.27, 30.21, 27.91, 27.81, 23.63, 14.42, 12.96, 11.55. LCMS 841.64 (M+H).

Synthetic Example 6: Synthesis of dBET9

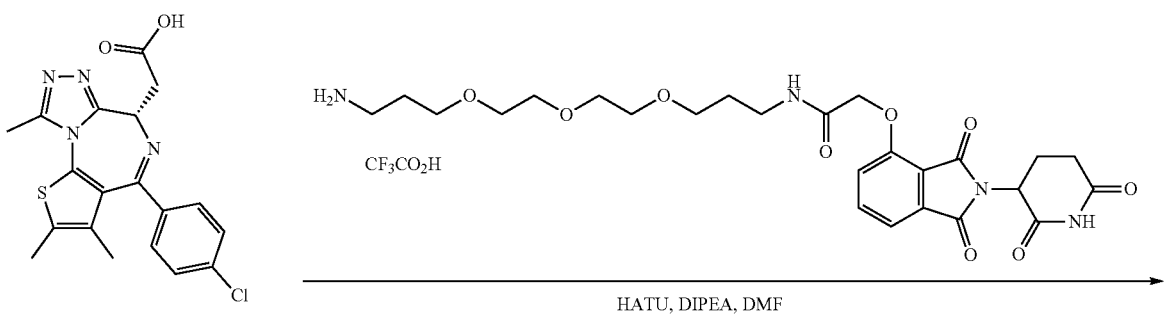

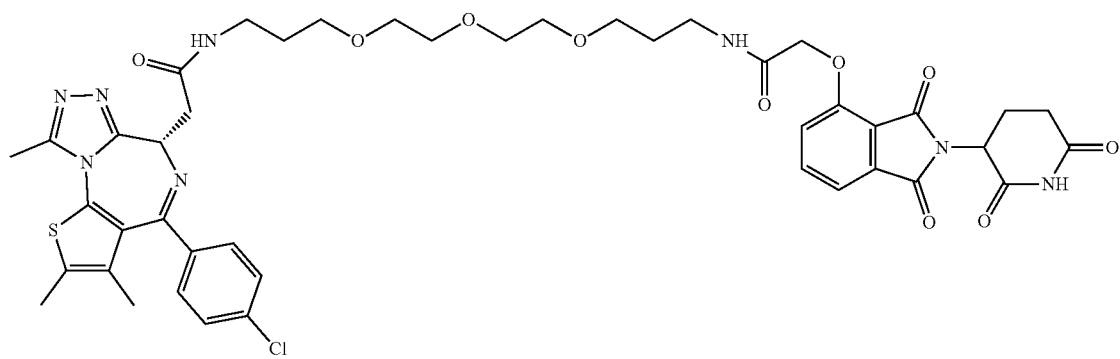

dBET9

A 0.1M solution of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (0.321 mL, 0.0321 mmol, 1 eq) was added to JQ-acid (12.87 mg, 0.0321 mmol, 1 eq) at room temperature. DIPEA (16.8 microliters, 0.0963 mmol, 3 eq) and HATU (12.2 mg, 0.0321 mmol, 1 eq) were added and the mixture was stirred for 24 hours, diluted with MeOH, and concentrated under reduced pressure. The crude material was purified by preparative HPLC to give a yellow oil. (16.11 mg, 0.0176 mmol, 55%).

$^1$H NMR (400 MHz, Methanol-$d_4$) δ 7.79 (dd, J=8.4, 7.4 Hz, 1H), 7.52 (d, J=7.2 Hz, 1H), 7.49-7.36 (m, 5H), 5.10 (dd, J=12.5, 5.5 Hz, 1H), 4.78-4.67 (m, 3H), 3.64-3.52 (m, 11H), 3.48-3.32 (m, 6H), 2.94-2.64 (m, 7H), 2.52-2.43 (m, 3H), 2.18-2.08 (m, 1H), 1.81 (p, J=6.3 Hz, 4H), 1.73-1.67 (m, 3H). LCMS 918.45 (M+H).

Synthetic Example 7: Synthesis of dBET17

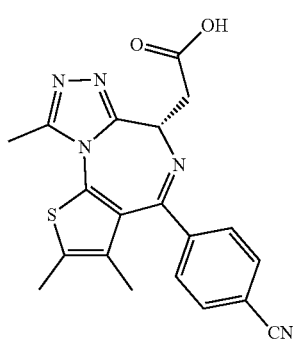
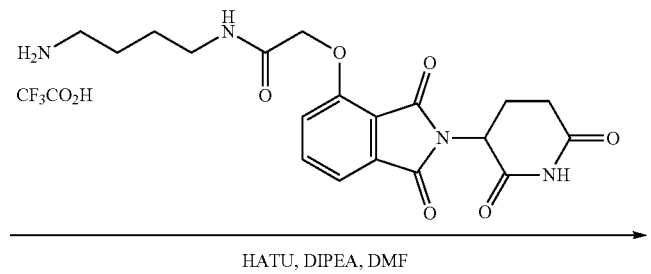
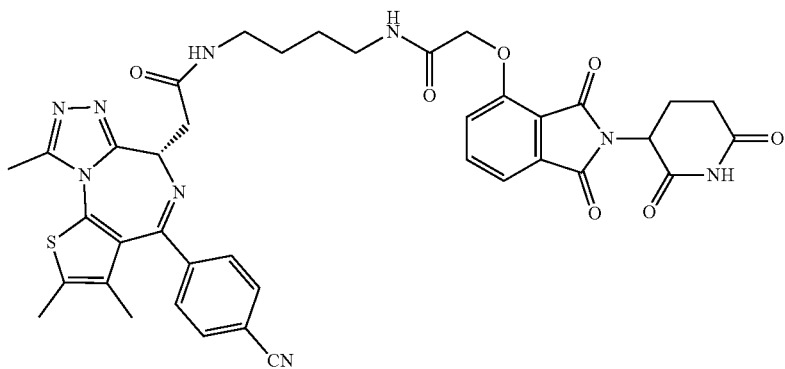

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.281 mL, 0.0281 mmol 1 eq) was added to (S)-2-(4-(4-cyanophenyl)-2,3,9-trimethyl-6H-thieno[3,2-f][1,2,4]triazolo[4,3-a][1,4]diazepin-6-yl)acetic acid (11 mg, 0.0281 mmol, 1 eq) at room temperature. DIPEA (14.7 microliters, 0.0843 mmol, 3 eq) and HATU (10.7 mg, 0.0281 mmol, 1 eq) were added and the mixture was stirred for 24 hours, diluted with EtOAc and washed with saturated sodium bicarbonate, water and brine. The organic layer was dried over sodium sulfate, filtered and condensed. Purification by column chromatography (ISCO, 4 g silica column 0-10% MeOH/DCM) gave a white solid (14.12 mg, 0.0182 mmol, 65%).

$^1$H NMR (400 MHz, Methanol-$d_4$) δ 7.82-7.72 (m, 3H), 7.61 (dd, J=8.5, 2.0 Hz, 2H), 7.51 (d, J=7.9 Hz, 1H), 7.44-7.40 (m, 1H), 5.11-5.05 (m, 1H), 4.76 (s, 2H), 4.66 (dd, J=9.0, 5.1 Hz, 1H), 3.48-3.32 (m, 4H), 3.30-3.23 (m, 1H), 2.87-2.61 (m, 7H), 2.43 (s, 3H), 2.10 (dt, J=10.7, 5.2 Hz, 1H), 1.70-1.59 (m, 7H). $^{13}$C NMR (100 MHz, cd$_3$od) δ 174.42, 172.65, 171.27, 169.92, 168.25, 167.80, 165.88, 156.31, 143.55, 138.24, 134.88, 133.92, 133.50, 133.39, 131.72, 131.46, 130.55, 121.93, 119.39, 119.21, 118.02, 115.17, 69.59, 55.50, 50.55, 40.10, 39.83, 38.86, 32.11, 27.78, 27.67, 23.62, 14.41, 12.91, 11.64. LCMS 776.39 (M+H).

Synthetic Example 8: Synthesis of dBET15

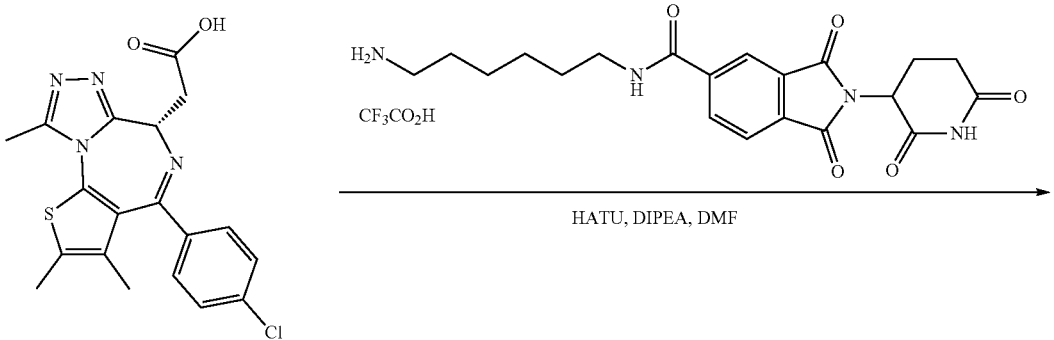

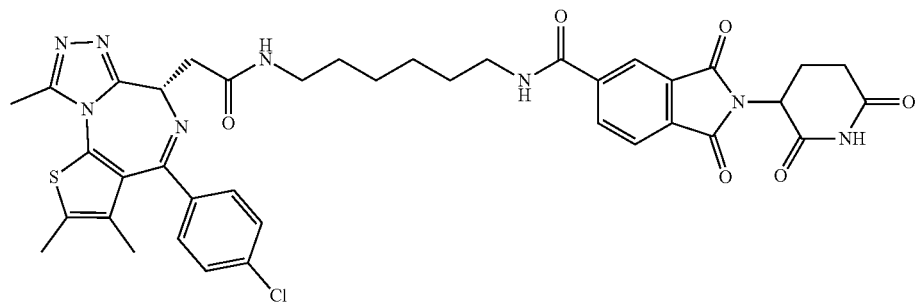

dBET15

N-(6-aminohexyl)-2-(2,6-dioxopiperidin-3-yl)-1,3-dioxoisoindoline-5-carboxamide trifluoroacetate (13.29 mg, 0.0258 mmol, 1 eq) and JQ-acid (10.3 mg, 0.0258 mmol, 1 eq) were dissolved in DMF (0.26 mL). DIPEA (13.5 microliters, 0.0775 mmol, 3 eq) was added, followed by HATU (9.8 mg, 0.0258 mmol, 1 eq) and the mixture was stirred at room temperature. After 24 hours, the material was diluted with DCM and purified by column chromatography (ISCO, 0-15% MeOH/DCM) followed by preparative HPLC to give a pale yellow solid (11.44 mg, 0.0146 mmol 57%).

$^1$H NMR (400 MHz, Methanol-$d_4$) δ 8.29-8.23 (m, 2H), 7.93 (dd, J=8.1, 4.2 Hz, 1H), 7.50-7.34 (m, 4H), 5.17-5.11 (m, 1H), 4.75-4.69 (m, 1H), 3.53-3.32 (m, 6H), 3.25 (dd, J=13.8, 6.7 Hz, 1H), 2.90-2.67 (m, 6H), 2.49-2.38 (m, 3H), 2.18-2.10 (m, 1H), 1.64 (d, J=22.4 Hz, 6H), 1.47 (s, 4H). $^{13}$C NMR (100 MHz, cd$_3$od) δ 174.48, 171.17, 168.05, 168.03, 167.99, 167.70, 166.63, 141.81, 138.40, 137.47, 135.09, 134.77, 134.74, 133.96, 133.94, 133.38, 132.24, 132.05, 131.44, 129.85, 124.57, 123.12, 123.09, 54.98, 50.78, 40.88, 40.08, 38.37, 32.13, 30.40, 30.23, 27.34, 27.26, 23.58, 14.40, 12.96, 11.54. LCMS 783.43 (M+H).

Synthetic Example 9: Synthesis of dBET2

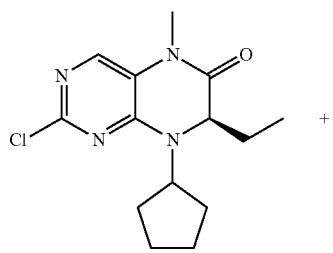

ref: ACIEE, 2011, 50, 9378

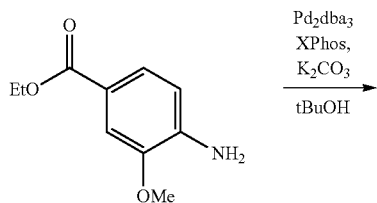

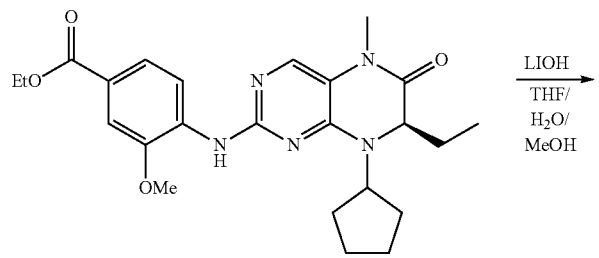

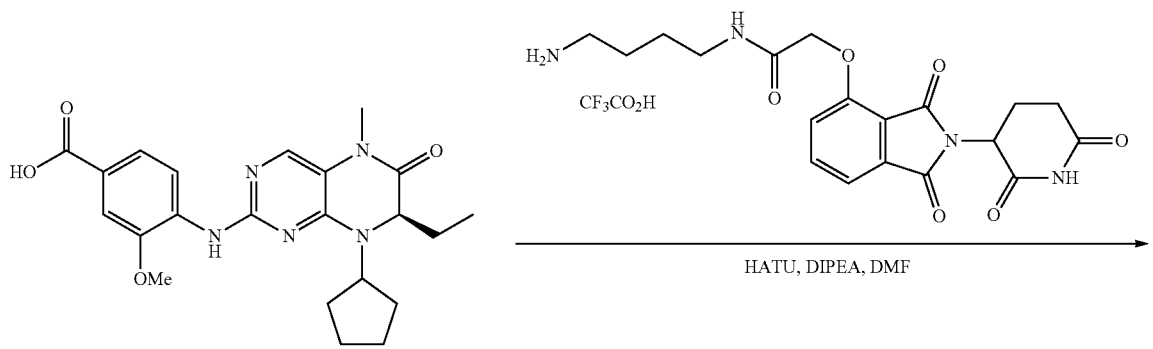

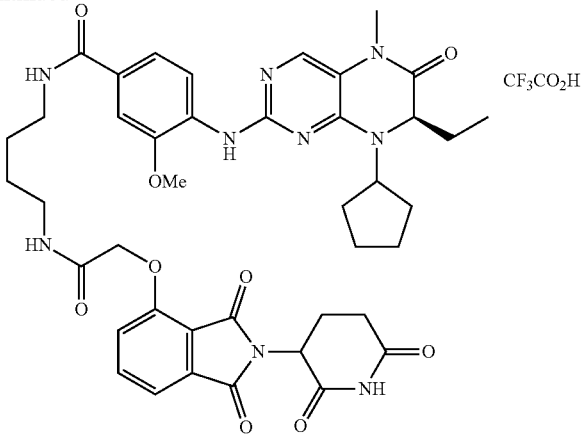

dBET2

(1) Synthesis of (R)-ethyl 4-((8-cyclopentyl-7-ethyl-5-methyl-6-oxo-5,6,7,8-tetrahydropteridin-2-yl)amino)-3-methoxybenzoate

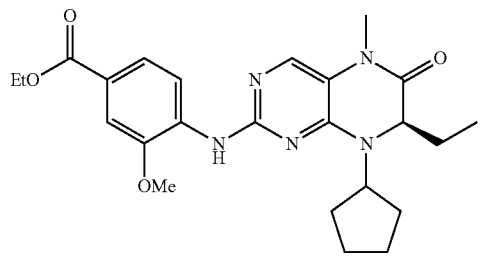 [SMILES: CC[C@@H]1C(=O)N(C)c2cnc(Nc3ccc(C(=O)O)cc3OC)nc2N1C1CCCC1]

(R)-2-chloro-8-cyclopentyl-7-ethyl-5-methyl-7,8-dihydropteridin-6(5H)-one (44.2 mg, 0.15 mmol, 1 eq), ethyl 4-amino-3-methoxybenzoate (35.1 mg, 0.18 mmol, 1.2 eq), Pd$_2$dba$_3$ (6.9 mg, 0.0075 mmol, 5 mol %), XPhos (10.7 mg, 0.0225 mmol, 15 mol %) and potassium carbonate (82.9 mg, 0.60 mmol, 4 eq) were dissolved in tBuOH (1.5 mL, 0.1 M) and heated to 100° C. After 21 hours, the mixture was cooled to room temperature, filtered through celite, washed with DCM and concentrated under reduced pressure. Purification by column chromatography (ISCO, 4 g silica column, 0-100% EtOAc/hexanes over an 18 minute gradient) gave a yellow oil (52.3 mg, 0.115 mmol, 77%). $^1$H NMR (400 MHz, Chloroform-d) δ 8.57 (d, J=8.5 Hz, 1H), 7.69 (td, J=6.2, 2.9 Hz, 2H), 7.54 (d, J=1.8 Hz, 1H), 4.52 (t, J=7.9 Hz, 1H), 4.37 (q, J=7.1 Hz, 2H), 4.23 (dd, J=7.9, 3.7 Hz, 1H), 3.97 (s, 3H), 3.33 (s, 3H), 2.20-2.12 (m, 1H), 2.03-1.97 (m, 1H), 1.86 (ddd, J=13.9, 7.6, 3.6 Hz, 4H), 1.78-1.65 (m, 4H), 1.40 (t, J=7.1 Hz, 3H), 0.88 (t, J=7.5 Hz, 3H). LCMS 454.32 (M+H).

(2) Synthesis of (R)-4-((8-cyclopentyl-7-ethyl-5-methyl-6-oxo-5,6,7,8-tetrahydropteridin-2-yl)amino)-3-methoxybenzoic acid

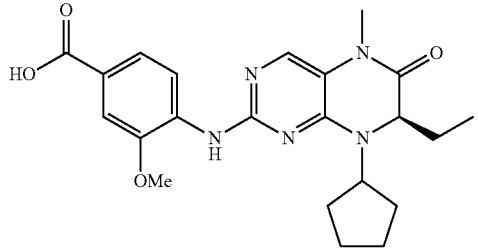

(R)-ethyl 4-((8-cyclopentyl-7-ethyl-5-methyl-6-oxo-5,6,7,8-tetrahydropteridin-2-yl)amino)-3-methoxybenzoate (73.8 mg, 0.163 mmol, 1 eq) and LiOH (11.7 mg, 0.489 mmol, 3 eq) were dissolved in MeOH (0.82 mL) THF (1.63 mL) and water (0.82 mL). After 20 hours, an additional 0.82 mL of water was added and the mixture was stirred for an additional 24 hours before being purified by preparative HPLC to give a cream colored solid (53 mg, 0.125 mmol, 76%). H NMR (400 MHz, Methanol-d$_4$) δ 7.97 (d, J=8.4 Hz, 1H), 7.67 (dd, J=8.3, 1.6 Hz, 1H), 7.64-7.59 (m, 2H), 4.38 (dd, J=7.0, 3.2 Hz, 1H), 4.36-4.29 (m, 1H), 3.94 (s, 3H), 3.30 (s, 3H), 2.13-1.98 (m, 2H), 1.95-1.87 (m, 2H), 1.87-1.76 (m, 2H), 1.73-1.57 (m, 4H), 0.86 (t, J=7.5 Hz, 3H). $^{13}$C NMR (100 MHz, cd$_3$od)$_6$ 168.67, 163.72, 153.59, 150.74, 150.60, 130.95, 127.88, 125.97, 123.14, 121.68, 116.75, 112.35, 61.76, 61.66, 56.31, 29.40, 29.00, 28.68, 28.21, 23.57, 23.41, 8.69. LCMS 426.45 (M+H).

(3) Synthesis of dBET2

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.183 mL, 0.0183 mmol 1.2 eq) was added to (R)-4-((8-cyclopentyl-7-ethyl-5-methyl-6-oxo-5,6,7,8-tetrahydropteridin-2-yl)amino)-3-methoxybenzoic acid (6.48 mg, 0.0152 mmol, 1 eq) at room temperature. DIPEA (7.9 microliters, 0.0456 mmol, 3 eq) and HATU (6.4 mg, 0.0168 mmol, 1.1 eq) were added and the mixture was stirred for 23 hours, before being purified by preparative HPLC to give a yellow solid (9.44 mg, 0.0102 mmol, 67%).
$^1$H NMR (400 MHz, Methanol-d$_4$) δ 7.84-7.77 (m, 2H), 7.58 (d, J=1.8 Hz, 2H), 7.53-7.46 (m, 2H), 7.42 (d, J=8.4 Hz, 1H), 5.11-5.05 (m, 1H), 4.76 (s, 2H), 4.48 (dd, J=6.5, 3.1 Hz, 1H), 4.33-4.24 (m, 1H), 3.95 (s, 3H), 3.49-3.35 (m, 4H), 2.97 (d, J=10.5 Hz, 3H), 2.89-2.65 (m, 5H), 2.17-1.99 (m, 4H), 1.89 (dd, J=14.5, 7.3 Hz, 2H), 1.69-1.54 (m, 6H), 1.36 (dt, J=7.6, 3.9 Hz, 1H), 0.85 (t, J=7.5 Hz, 3H). $^{13}$C NMR (100 MHz, cd$_3$od) δ 176.52, 174.48, 173.05, 171.34, 169.99, 168.91, 168.25, 167.80, 164.58, 156.34, 154.48, 153.10, 150.63, 138.22, 134.89, 133.96, 129.53, 123.93, 121.87, 120.78, 119.36, 117.99, 111.54, 69.55, 63.29, 63.10, 56.68, 50.55, 40.71, 39.86, 32.15, 29.43, 29.26, 28.73, 28.63, 27.81, 27.77, 24.25, 23.63, 8.47. LCMS 810.58 (M+H).

Synthetic Example 10: Synthesis of dBET7 mg, 0.0186 mmol, 1 eq) at room temperature. DIPEA (9.7 microliters, 0.0557 mmol, 3 eq) and HATU (7.1 mg, 0.0186 mmol, 1 eq) were added and the mixture was stirred for 19 hours, before being purified by preparative HPLC to give the desired trifluoracetate salt as a yellow solid(13.62 mg, 0.0143 mmol, 77%).
$^1$H NMR (400 MHz, Methanol-d$_4$) δ 7.80 (t, J=8.3 Hz, 2H), 7.61-7.57 (m, 2H), 7.55-7.49 (m, 2H), 7.42 (d, J=8.4 Hz, 1H), 5.13 (dd, J=12.6, 5.5 Hz, 1H), 4.75 (s, 2H), 4.48 (dd, J=6.5, 3.2 Hz, 1H), 4.33-4.24 (m, 1H), 3.97 (s, 3H), 3.40 (t, J=7.1 Hz, 2H), 3.34 (d, J=6.7 Hz, 2H), 3.30 (s, 3H), 2.98 (d, J=8.5 Hz, 1H), 2.89-2.82 (m, 1H), 2.79-2.63 (m, 3H), 2.17-2.00 (m, 4H), 1.91 (dt, J=14.4, 7.1 Hz, 3H), 1.61 (dt, J=13.4, 6.6 Hz, 7H), 1.47-1.41 (m, 3H), 0.86 (t, J=7.5 Hz, 3H). $^{13}$C NMR (100 MHz, cd$_3$od) δ 174.54, 171.37, 169.84, 168.84, 168.27, 167.74, 164.59, 156.26, 154.47, 153.18,

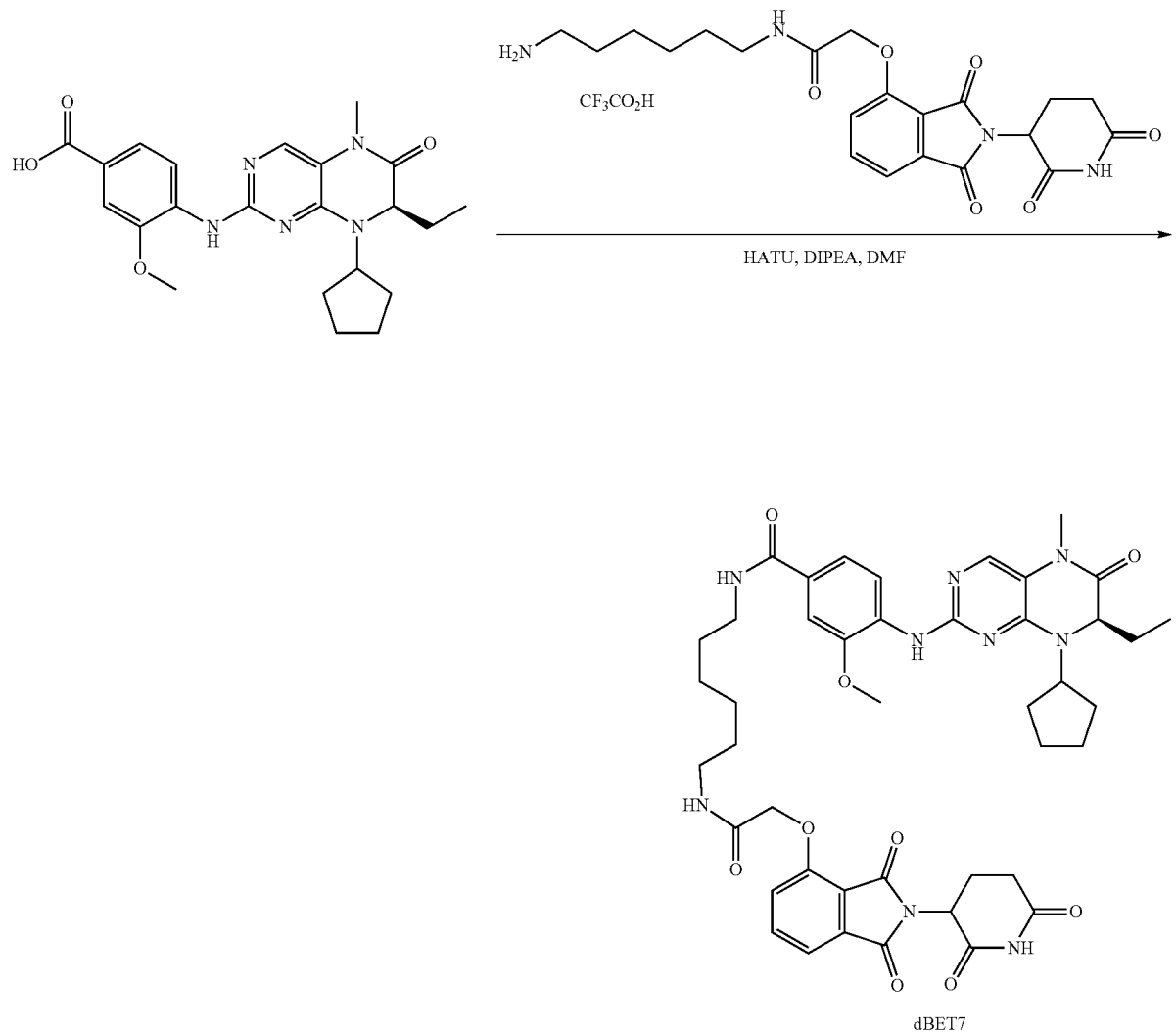

dBET7

A 0.1 M solution N-(6-aminohexyl)-2-((2-(2,6-dioxopiperidin-3-yl)-1,3-dioxoisoindolin-4-yl)oxy)acetamide trifluoroacetate in DMF (0.186 mL, 0.0186 mmol 1 eq) was added to (R)-4-((8-cyclopentyl-7-ethyl-5-methyl-6-oxo-5,6,7,8-tetrahydropteridin-2-yl)amino)-3-methoxybenzoic acid (7.9

150.69, 138.19, 134.91, 134.05, 129.47, 124.78, 124.01, 121.65, 120.77, 119.29, 117.92, 117.86, 111.55, 69.34, 63.31, 63.13, 56.67, 50.53, 40.97, 39.96, 32.16, 30.42, 30.19, 29.42, 29.26, 28.72, 28.62, 27.65, 27.46, 24.26, 23.65, 8.47. LCMS 838.60 (M+H).

Synthetic Example 11: Synthesis of dBET8

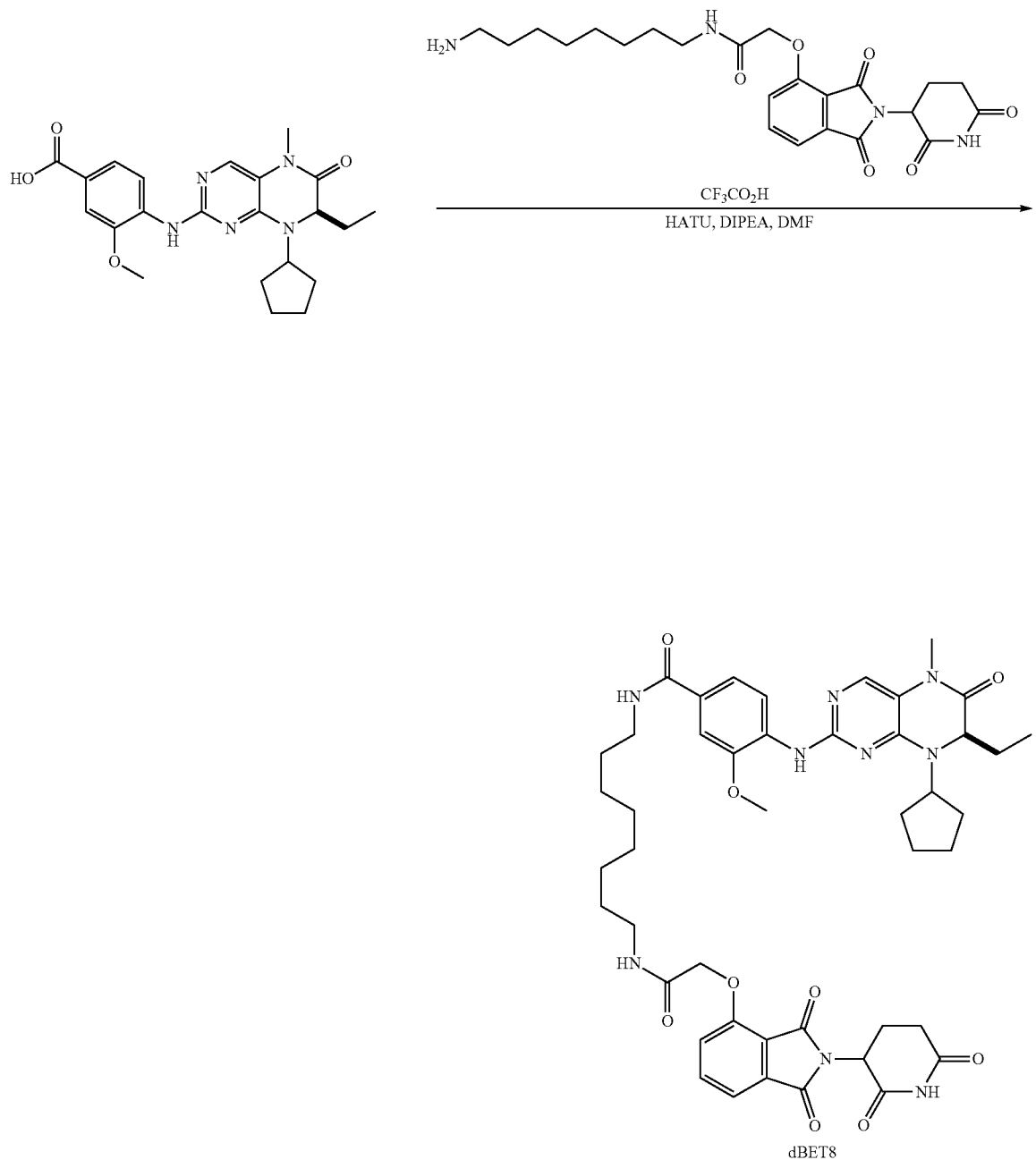

dBET8

A 0.1 M solution N-(8-aminooctyl)-2-((2-(2,6-dioxopiperdin-3-yl)-1,3-dioxoisoindolin-4-yl)oxy)acetamide trifluoroacetate in DMF (0.186 mL, 0.0186 mmol 1 eq) was added to (R)-4-((8-cyclopentyl-7-ethyl-5-methyl-6-oxo-5,6,7,8-tetrahydropteridin-2-yl)amino)-3-methoxybenzoic acid (7.9 mg, 0.0186 mmol, 1 eq) at room temperature. DIPEA (9.7 microliters, 0.0557 mmol, 3 eq) and HATU (7.1 mg, 0.0186 mmol, 1 eq) were added and the mixture was stirred for 16 hours, before being purified by preparative HPLC to give the desired trifluoracetate salt as an off-white solid(7.15 mg, 0.007296 mmol, 39%).

$^1$H NMR (400 MHz, Methanol-$d_4$) δ 7.83-7.77 (m, 2H), 7.61-7.56 (m, 2H), 7.55-7.50 (m, 2H), 7.42 (d, J=8.5 Hz, 1H), 5.13 (dd, J=12.6, 5.5 Hz, 1H), 4.75 (s, 2H), 4.49 (dd, J=6.6, 3.3 Hz, 1H), 4.33-4.24 (m, 1H), 3.97 (s, 3H), 3.39 (t, J=7.1 Hz, 2H), 3.34-3.32 (m, 2H), 3.30 (s, 3H), 3.01-2.83 (m, 2H), 2.82-2.65 (m, 3H), 2.17-2.01 (m, 4H), 1.91 (dt, J=14.2, 7.4 Hz, 1H), 1.68-1.54 (m, 7H), 1.37 (s, 7H), 0.86 (t, J=7.5 Hz, 3H). $^{13}$C NMR (100 MHz, cd$_3$od) δ 174.52, 171.35, 169.81, 168.85, 168.28, 167.74, 164.58, 156.27, 154.47, 153.89, 150.64, 138.19, 134.93, 134.18, 129.52, 129.41, 124.91, 123.83, 121.67, 120.76, 119.31, 117.95, 117.89, 111.57, 69.37, 63.37, 63.17, 56.67, 50.58, 41.12, 40.12, 32.19, 30.43, 30.28, 30.22, 30.19, 29.40, 29.25, 28.71, 28.62, 27.94, 27.75, 24.29, 23.65, 8.46. LCMS 866.56 (M+H).

Synthetic Example 12: Synthesis of dBET10

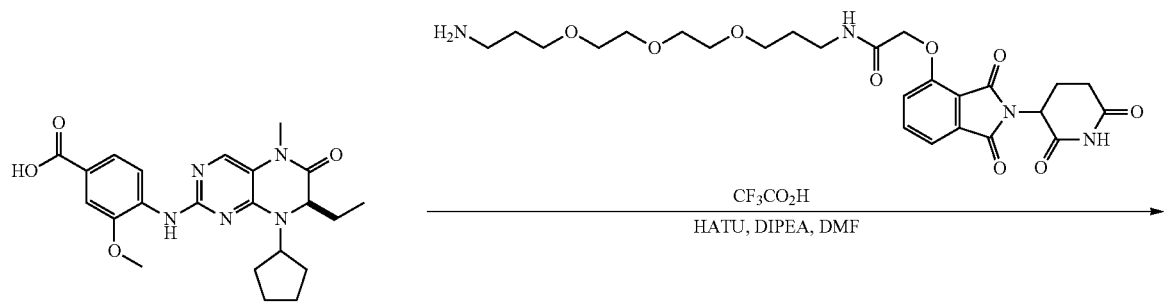

A 0.1 M solution N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (0.172 mL, 0.0172 mmol 1 eq) was added to (R)-4-((8-cyclopentyl-7-ethyl-5-methyl-6-oxo-5,6,7,8-tetrahydropteridin-2-yl)amino)-3-methoxybenzoic acid (7.3 mig, 0.0172 mmol, 1 eq) at room temperature. DIPEA (9.0 microliters, 0.0515 mmol, 3 eq) and HATU (6.5 mg, 0.0172 mmol, 1 eq) were added and the mixture was stirred for 23 hours, before being purified by preparative HPLC to give the desired trifluoracetate salt as an off-white oil (10.7 mg, 0.0101 mmol, 59%).

$^1$H NMR (400 MHz, Methanol-$d_4$) δ 7.78 (d, J=8.3 Hz, 1H), 7.75 (dd, J=8.4, 7.4 Hz, 1H), 7.56-7.51 (m, 2H), 7.49-7.44 (m, 2H), 7.36 (d, J=8.4 Hz, 1H), 5.08 (dd, J=12.4, 5.4 Hz, 1H), 4.69 (s, 2H), 4.44 (dd, J=6.7, 3.2 Hz, 1H), 4.30-4.21 (m, 1H), 3.92 (s, 3H), 3.59-3.42 (m, 12H), 3.35 (t, J=6.7 Hz, 2H), 3.25 (s, 3H), 2.95-2.64 (m, 5H), 2.13-1.95 (m, 4H), 1.91-1.71 (m, 7H), 1.65-1.48 (m, 4H), 0.81 (t, J=7.5 Hz, 3H). $^{13}$C NMR (100 MHz, cd$_3$od) δ 174.50, 171.35, 169.83, 168.77, 168.25, 167.68, 164.57, 156.26, 154.47, 153.05, 150.59, 138.19, 134.92, 133.89, 129.53, 124.57, 123.98, 121.72, 120.75, 119.26, 117.95, 117.86, 111.54, 71.51, 71.46, 71.28, 71.20, 70.18, 69.65, 69.41, 63.27, 63.07, 56.71, 50.57, 38.84, 37.59, 32.17, 30.41, 30.32, 29.46, 29.26, 28.73, 28.64, 24.27, 23.65, 8.49. LCMS 942.62 (M+H).

Synthetic Example 13: Synthesis of dBET16

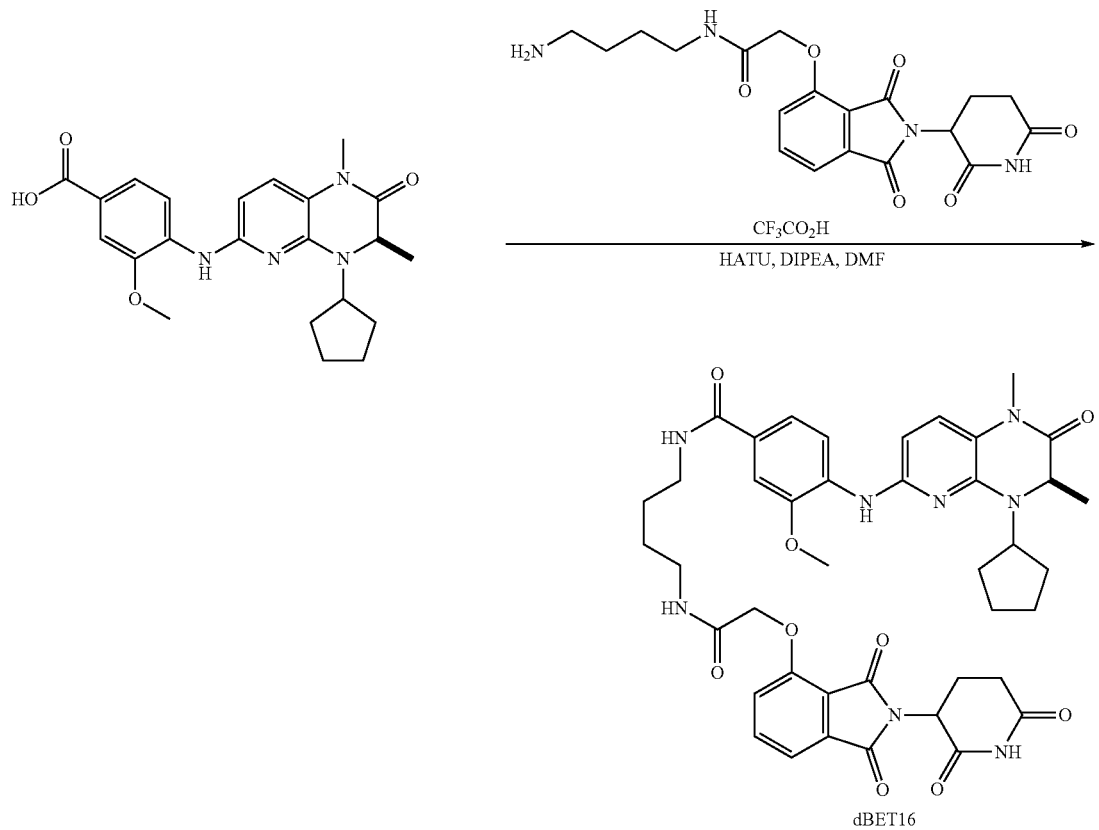

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.402 mL, 0.0402 mmol 1 eq) was added (R)-4-((4-cyclopentyl-1,3-dimethyl-2-oxo-1,2,3,4-tetrahydropyrido[2,3-b]pyrazin-6-yl)amino)-3-methoxybenzoic acid (16.55 mg, 0.0402 mmol, 1 eq) at room temperature. DIPEA (21 microliters, 0.1206 mmol, 3 eq) and HATU (15.3 mg, 0.0402 mmol, 1 eq) were added and the mixture was stirred for 21 hours, before being purified by preparative HPLC, followed by column chromatography (ISCO, 12 g $NH_2$-silica column, 0-15% MeOH/DCM, 20 min gradient) to give HPLC to give a brown solid (10.63 mg, 0.0134 mmol, 33%).

$^1$H NMR (400 MHz, Methanol-$d_4$) δ 8.22 (d, J=8.4 Hz, 1H), 7.78 (dd, J=8.4, 7.4 Hz, 1H), 7.73 7.68 (m, 1H), 7.49 (d, J=7.4 Hz, 2H), 7.46-7.39 (m, 2H), 6.98 (d, J=8.8 Hz, 1H), 5.97-5.87 (m, 1H), 5.06 (dd, J=12.6, 5.4 Hz, 1H), 4.76 (s, 2H), 3.98 (s, 3H), 3.61 (s, 2H), 3.44-3.36 (m, 4H), 2.92 (s, 1H), 2.78 (dd, J=14.3, 5.2 Hz, 1H), 2.68 (ddd, J=17.7, 8.2, 4.5 Hz, 2H), 2.36-2.26 (m, 2H), 2.10-1.90 (m, 5H), 1.76-1.62 (m, 6H), 1.31 (d, J=16.0 Hz, 4H). LCMS 795.38 (M+H).

Synthetic Example 14: Synthesis of dBET 11

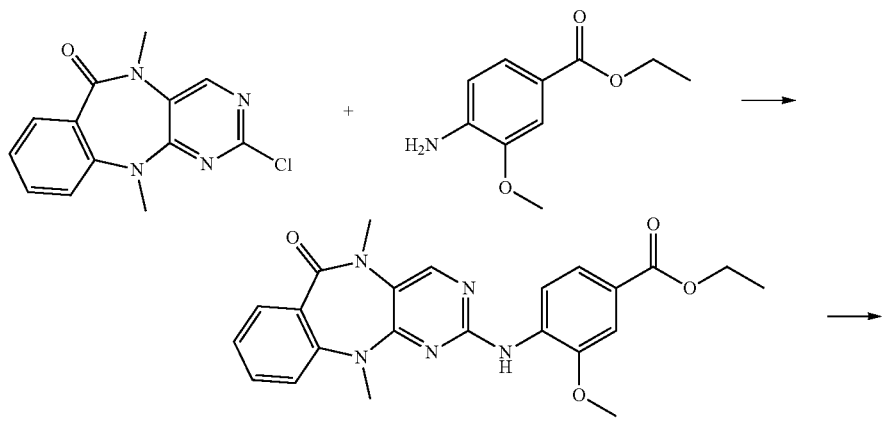

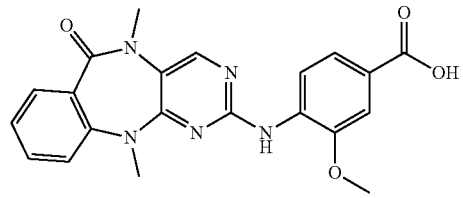
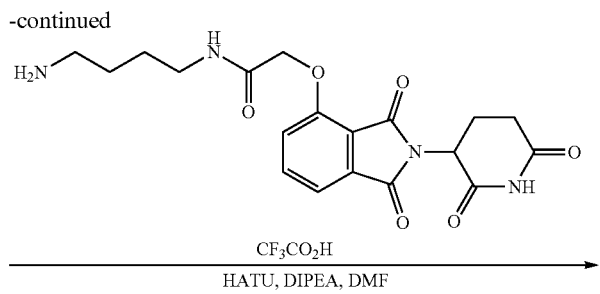
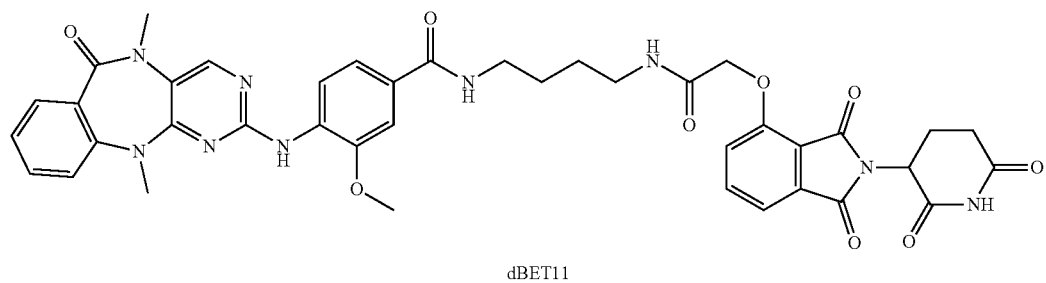

dBET11

(1) Synthesis of ethyl 4-((5,11-dimethyl-6-oxo-6,11-dihydro-5H-benzo[e]pyrimido[5,4-b][1,4]diazepin-2-yl)amino)-3-methoxybenzoate 2-chloro-5,11-dimethyl-5H-benzo[e]pyrimido[5,4-b][1,4]diazepin-6(11H)-one(82.4 mg, 0.30 mmol, 1 eq), ethyl 4-amino-3-methoxybenzoate (70.3 mg, 0.36 mmol, 1.2 eq) $Pd_2dba_3$ (13.7 mg, 0.015 mmol, 5 mol %), XPhos (21.5 mg, 0.045 mmol, 15 mol %) and potassium carbonate (166 mg, 1.2 mmol, 4 eq) were dissolved in tBuOH (3.0 mL) and heated to 100° C. After 17 hours, the mixture was cooled room temperature and filtered through celite. The mixture was purified by column chromatography (ISCO, 12 g silica column, 0-100% EtOAc/hexanes, 19 min gradient) to give an off white solid (64.3 mg, 0.148 mmol, 49%).

$^1$H NMR (400 MHz, 50% $cd_3od/cdcl_3$) δ 8.51 (d, J=8.5 Hz, 1H), 8.17 (s, 1H), 7.73 (ddd, J=18.7, 8.1, 1.7 Hz, 2H), 7.52 (d, J=1.8 Hz, 1H), 7.46-7.41 (m, 1H), 7.15-7.10 (m, 2H), 4.34 (q, J=7.1 Hz, 4H), 3.95 (s, 3H), 3.47 (s, 3H), 3.43 (s, 3H), 1.38 (t, J=7.1 Hz, 3H). $^{13}$C NMR (100 MHz, 50% $cd_3od/cdcl_3$) δ 169.28, 167.39, 164.29, 155.64, 151.75, 149.73, 147.45, 146.22, 133.88, 133.18, 132.37, 126.44, 124.29, 123.70, 123.36, 122.26, 120.58, 118.05, 116.83, 110.82, 61.34, 56.20, 38.62, 36.25, 14.51. LCMS 434.33 (M+H).

(2) Synthesis of 4-((5,11-dimethyl-6-oxo-6,11-dihydro-5H-benzo[e]pyrimido[5,4-b][1,4]diazepin-2-yl)amino)-3-methoxybenzoic acid Ethyl 4-((5,11-dimethyl-6-oxo-6,11-dihydro-5H-benzo[e]pyrimido[5,4-b][1,4]diazepin-2-yl)amino)-3-methoxybenzoate (108.9 mg, 0.251 mmol, 1 eq) and LiOH (18 mg, 18 eq) were dissolved in THF (2.5 mL) and water (1.25 mL). After 24 hours, MeOH (0.63 mL) was added to improved solubility) and stirred for an additional 24 hours before being diluted with MeOH and purified by preparative HPLC to give a light yellow solid (41.31 mg).

$^1$H NMR (400 MHz, Methanol-$d_4$) δ 8.51 (d, J=8.5 Hz, 1H), 8.22 (s, 1H), 7.73 (ddd, J=11.8, 8.1, 1.7 Hz, 2H), 7.57 (d, J=1.8 Hz, 1H), 7.49-7.44 (m, 1H), 7.19-7.11 (m, 2H), 3.97 (s, 3H), 3.48 (s, 3H), 3.45 (s, 3H). LCMS 406.32 (M+H).

(3) Synthesis of dBET11

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.190 mL, 0.0190 mmol 1 eq) was added to 4-((5,11-dimethyl-6-oxo-6,11-dihydro-5H-benzo[e]pyrimido[5,4-b][1,4]diazepin-2-yl)amino)-3-methoxybenzoic acid(7.71 mg, 0.0190 mmol, 1 eq) at room temperature. DIPEA (9.9 microliters, 0.0571 mmol, 3 eq) and HATU (7.2 mg, 0.0190 mmol, 1 eq) were added and the mixture was stirred for 22 hours, before being purified by preparative HPLC to give HPLC to give the desired trifluoracetate salt as a cream colored solid (6.72 mg, 0.00744 mmol, 39%).

$^1$H NMR (400 MHz, Methanol-$d_4$) δ 8.46 (d, J=8.3 Hz, 1H), 8.21 (s, 1H), 7.79-7.73 (m, 2H), 7.52 (d, J=7.1 Hz, 1H), 7.50-7.43 (m, 3H), 7.33 (d, J=8.2 Hz, 1H), 7.15 (dd, J=7.7, 5.9 Hz, 2H), 4.98 (dd, J=12.0, 5.5 Hz, 1H), 4.69 (s, 2H), 3.97 (s, 3H), 3.49 (s, 3H), 3.46-3.34 (m, 7H), 2.81-2.67 (m, 3H), 2.13-2.08 (m, 1H), 1.69 (dt, J=6.6, 3.5 Hz, 4H). $^{13}$C NMR (100 MHz, $cd_3od$) δ 173.40, 170.10, 169.68, 169.00, 168.85, 167.60, 167.15, 164.77, 156.01, 155.42, 151.83, 150.03, 148.21, 137.82, 134.12, 133.48, 132.58, 132.52, 128.11, 126.72, 124.54, 122.33, 121.06, 120.63, 118.77, 118.38, 117.94, 117.62, 109.67, 68.90, 56.33, 49.96, 40.16, 39.48, 38.72, 36.34, 31.82, 27.24, 23.16. LCMS 790.48 (M+H).

Synthetic Example 15: Synthesis of dBET12

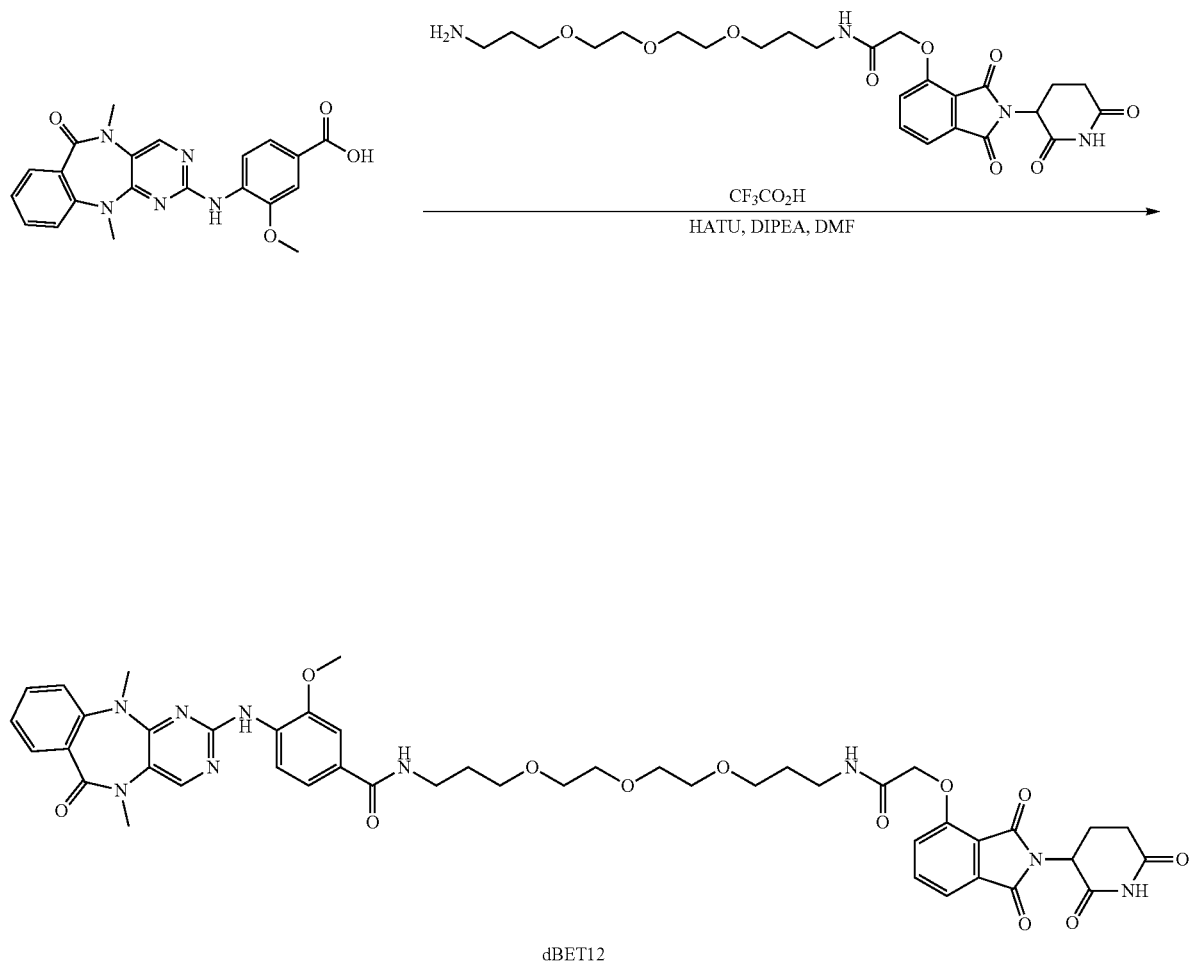

dBET12

A 0.1 M solution N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (0.186 mL, 0.0186 mmol 1 eq) was added to 4-((5,11-dimethyl-6-oxo-6,11-dihydro-5H-benzo[e]pyrimido[5,4-b][1,4]diazepin-2-yl)amino)-3-methoxybenzoic acid(7.53 mg, 0.0186 mmol, 1 eq) at room temperature. DIPEA (9.7 microliters, 0.0557 mmol, 3 eq) and HATU (7.1 mg, 0.0186 mmol, 1 eq) were added and the mixture was stirred for 22 hours, before being purified by preparative HPLC to give HPLC to give the desired trifluoracetate salt as a cream colored solid (7.50 mg, 0.00724 mmol, 39%).

$^1$H NMR (400 MHz, Methanol-$d_4$) δ 8.46 (d, J=8.9 Hz, 1H), 8.21 (s, 1H), 7.73 (dd, J=15.2, 7.8 Hz, 2H), 7.50-7.42 (m, 3H), 7.28 (d, J=8.5 Hz, 1H), 7.15 (t, J=7.7 Hz, 2H), 5.01 (dd, J=11.8, 5.8 Hz, 1H), 4.68 (s, 2H), 3.97 (s, 3H), 3.67-3.58 (m, 7H), 3.58-3.43 (m, 10H), 3.39 (t, J=6.8 Hz, 2H), 3.35 (s, 2H), 2.97 (s, 1H), 2.84-2.70 (m, 3H), 2.16-2.07 (m, 1H), 1.93-1.76 (m, 4H). LCMS 922.57 (M+H).

Synthetic Example 16: Synthesis of dBET13

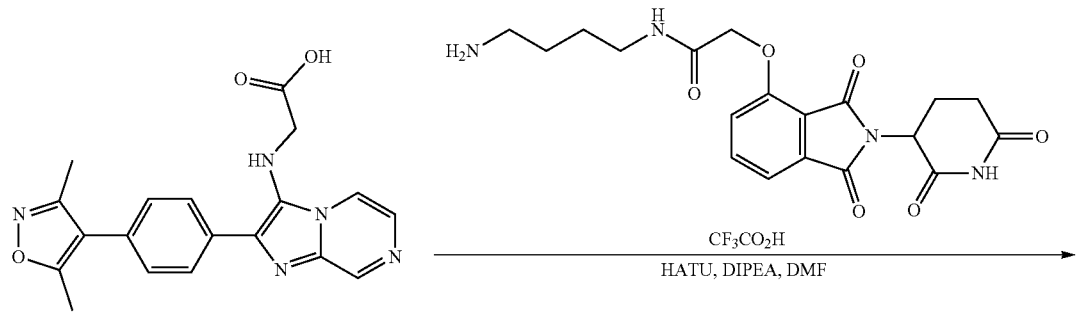

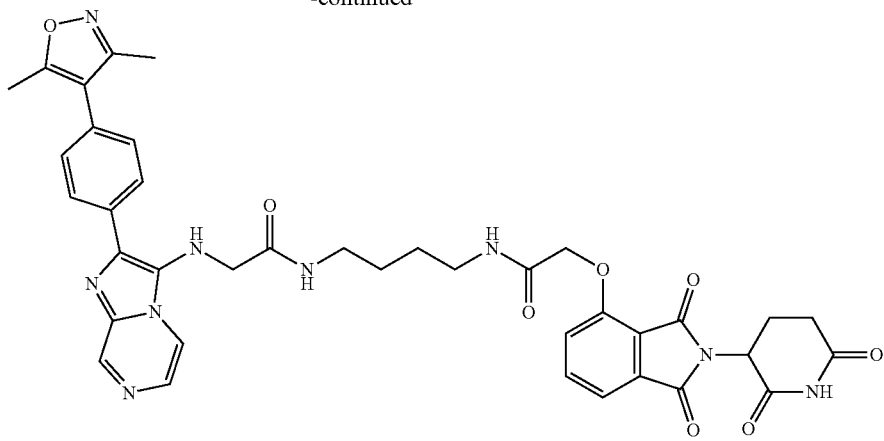

dBET13

A 0.1 M solution of N-(4-aminobutyl)-2-((2-(2,6-dioxopiperidin-3-yl)-1,3-dioxoisoindolin-4-yl)oxy)acetamide trifluoroacetate in DMF (0.501 mL, 0.0501 mmol 1 eq) was added to 2-((2-(4-(3,5-dimethylisoxazol-4-yl)phenyl)imidazo[1,2-a]pyrazin-3-yl)amino)acetic acid (synthesized as in McKeown et al, *J. Med. Chem,* 2014, 57, 9019) (18.22 mg, 0.0501 mmol, 1 eq) at room temperature. DIPEA (26.3 microliters, 0.150 mmol, 3 eq) and HATU (19.0 mg, 0.0501 mmol, 1 eq) were added and the mixture was stirred for 21 hours, before being purified by preparative HPLC to give HPLC to give the desired trifluoracetate salt as a dark yellow oil (29.66 mg, 0.0344 mmol, 69%). $^1$H NMR (400 MHz, Methanol-$d_4$) δ 9.09 (s, 1H), 8.65 (d, J=5.2 Hz, 1H), 8.14-8.06 (m, 2H), 7.94-7.88 (m, 1H), 7.80-7.74 (m, 1H), 7.59-7.47 (m, 3H), 7.40 (dd, J=8.4, 4.7 Hz, 1H), 5.11-5.06 (m, 1H), 4.72 (d, J=9.8 Hz, 2H), 3.90 (s, 2H), 3.25-3.22 (m, 1H), 3.12 (t, J=6.4 Hz, 1H), 2.96 (s, 2H), 2.89-2.79 (m, 1H), 2.76-2.62 (m, 2H), 2.48-2.42 (m, 3H), 2.29 (s, 3H), 2.10 (ddq, J=10.2, 5.3, 2.7 Hz, 1H), 1.49-1.45 (m, 2H), 1.37 (dd, J=6.7, 3.6 Hz, 2H). 13C NMR (100 MHz, cd$_3$od) δ 174.45, 171.98, 171.35, 169.88, 168.17, 167.85, 167.40, 159.88, 156.28, 141.82, 138.26, 135.85, 134.82, 133.09, 132.06, 130.75, 129.67, 122.07, 121.94, 119.30, 118.98, 118.06, 117.24, 69.56, 50.56, 40.05, 39.73, 32.13, 27.53, 23.62, 18.71, 17.28, 11.64, 10.85. LCMS 748.49 (M+H).

Synthetic Example 17: Synthesis of dBET14

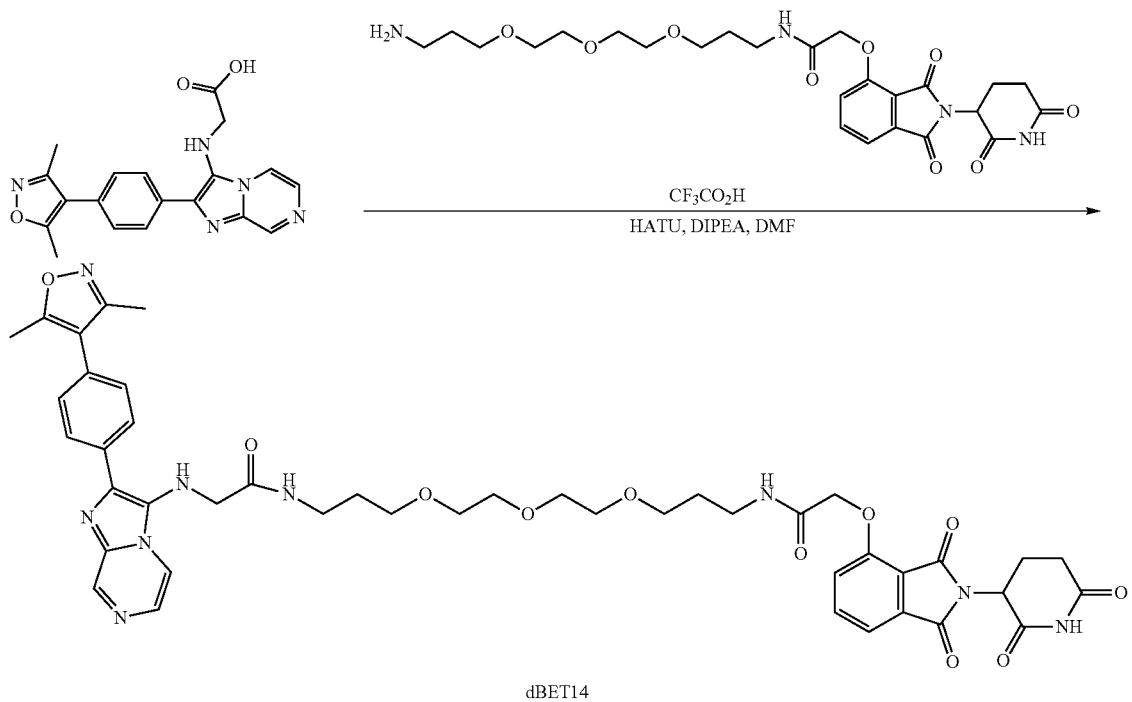

dBET14

A 0.1 M solution N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (0.510 mL, 0.0510 mmol 1 eq) was added to 2-((2-(4-(3,5- dimethylisoxazol-4-yl)phenyl)imidazo[1,2-a]pyrazin-3-yl)amino)acetic acid (synthesized as in McKeown et al, *J. Med. Chem,* 2014, 57, 9019) (18.52 mg, 0.0510 mmol, 1 eq) at room temperature. DIPEA (26.6 microliters, 0.153 mmol, 3 eq) and HATU (19.4 mg, 0.0510 mmol, 1 eq) were added and the mixture was stirred for 22 hours, before being purified by preparative HPLC to give HPLC to give the desired trifluoracetate salt as a dark yellow oil (32.63 mg, 0.0328 mmol, 64%).

$^1$H NMR (400 MHz, Methanol-$d_4$) δ 9.09 (s, 1H), 8.66 (d, J=5.4 Hz, 1H), 8.17-8.08 (m, 2H), 7.92 (d, J=5.6 Hz, 1H), 7.77 (dd, J=8.4, 7.4 Hz, 1H), 7.60-7.47 (m, 3H), 7.39 (d, J=8.4 Hz, 1H), 5.09 (dd, J=12.4, 5.5 Hz, 1H), 4.71 (s, 2H), 3.91 (s, 2H), 3.62-3.46 (m, 10H), 3.38 (dt, J=16.0, 6.4 Hz, 3H), 3.18 (t, J=6.8 Hz, 2H), 2.97 (s, 1H), 2.89-2.81 (m, 1H), 2.78-2.66 (m, 2H), 2.47 (s, 3H), 2.31 (s, 3H), 2.16-2.08 (m, 1H), 1.79 (dt, J=12.8, 6.5 Hz, 2H), 1.64 (t, J=6.3 Hz, 2H). $^{13}$C NMR (100 MHz, cd$_3$od) δ 174.48, 171.88, 171.34, 169.80, 168.22, 167.69, 167.42, 159.87, 156.24, 141.87, 138.21, 135.89, 134.88, 133.13, 132.04, 130.76, 129.67, 122.08, 121.69, 119.20, 117.94, 117.23, 71.44, 71.22, 71.10, 69.92, 69.62, 69.38, 50.57, 49.64, 38.11, 37.55, 32.16, 30.30, 30.20, 23.63, 11.67, 10.88. LCMS 880.46 (M+H).

Synthetic Example 18: Synthesis of dBET 18

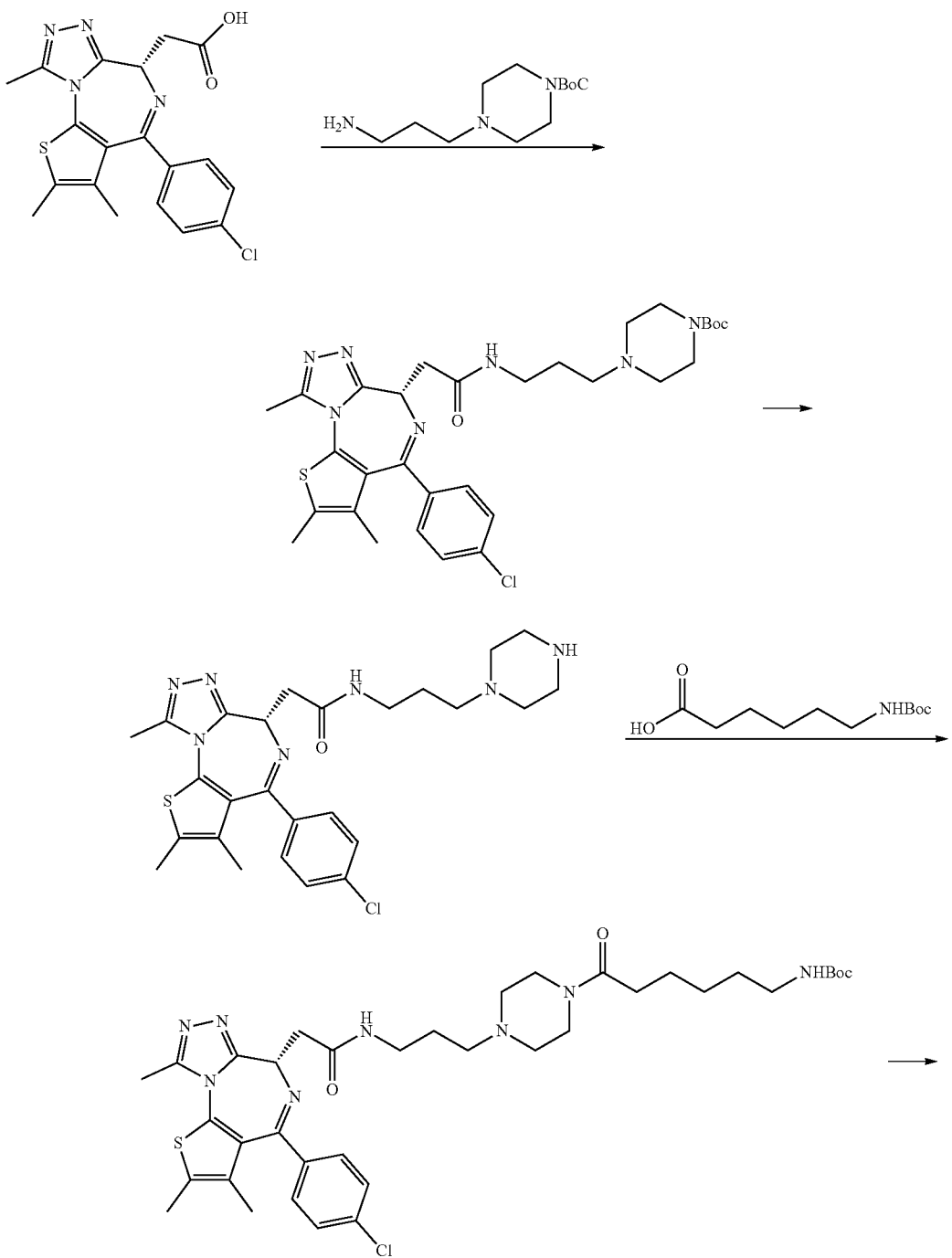

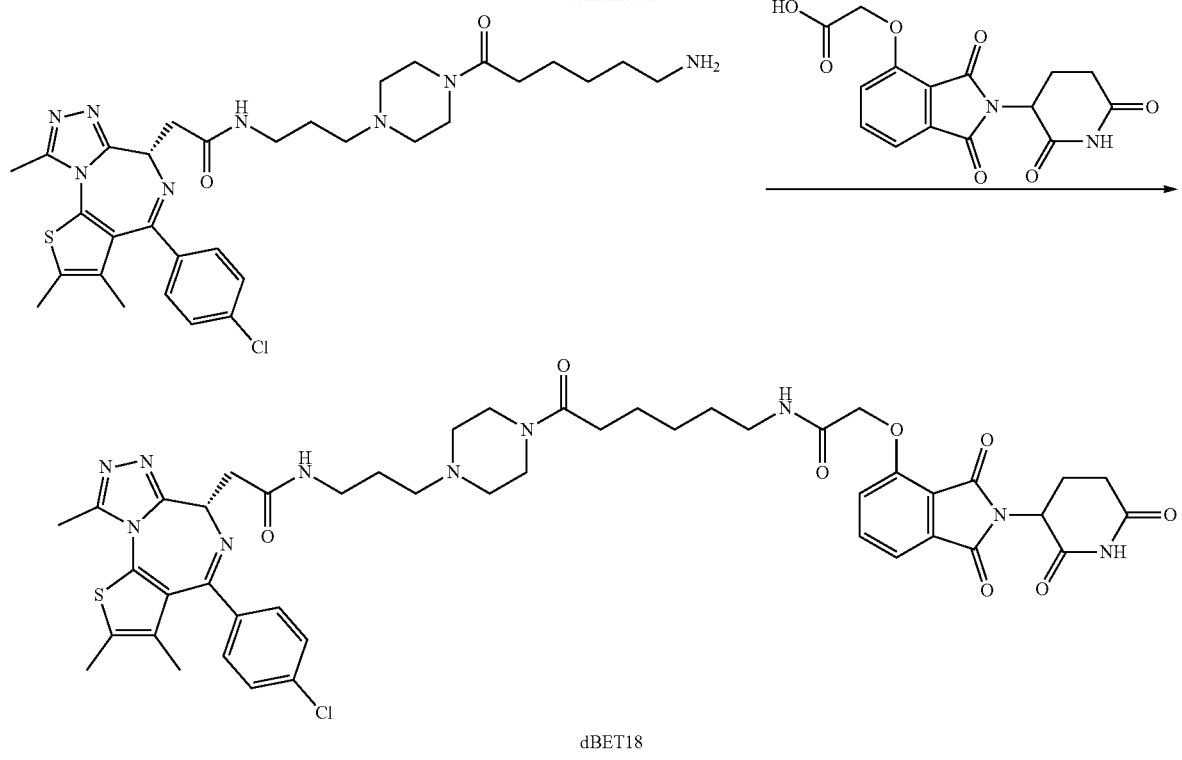

dBET18

(1) Synthesis of (S)-tert-butyl 4-(3-(2-(4-(4-chlorophenyl)-2,3,9-trimethyl-6H-thieno[3,2-f][1,2,4]triazolo[4,3-a][1,4]diazepin-6-yl)acetamido)propyl)piperazine-1-carboxylate JQ-acid (176.6 mg, 0.441 mmol, 1 eq) was dissolved in DMF (4.4 mL) at room temperature. HATU (176 mg, 0.463 mmol, 1.05 eq) was added, followed by DIPEA (0.23 mL, 1.32 mmol, 3 eq). After 10 minutes, tert-butyl 4-(3-aminopropyl)piperazine-1-carboxylate (118 mg, 0.485 mmol, 1.1 eq) was added as a solution in DMF (0.44 mL). After 24 hours, the mixture was diluted with half saturated sodium bicarbonate and extracted twice with DCM and once with EtOAc. The combined organic layer was dried over sodium sulfate, filtered and condensed. Purification by column chromatography (ISCO, 24 g silica column, 0-15% MeOH/DCM, 23 minute gradient) gave a yellow oil (325.5 mg, quant yield)

$^1$H NMR (400 MHz, Chloroform-d) δ 7.67 (t, J=5.3 Hz, 1H), 7.41-7.28 (m, 4H), 4.58 (dd, J=7.5, 5.9 Hz, 1H), 3.52-3.23 (m, 8H), 2.63 (s, 9H), 2.37 (s, 3H), 1.80-1.69 (m, 2H), 1.64 (s, 3H), 1.42 (s, 9H). $^{13}$C NMR (100 MHz, cdcl$_3$) δ 171.41, 164.35, 155.62, 154.45, 150.20, 136.92, 136.64, 132.19, 131.14, 130.98, 130.42, 129.98, 128.80, 80.24, 56.11, 54.32, 52.70, 38.96, 37.85, 28.42, 25.17, 14.43, 13.16, 11.82. LCMS 626.36 (M+H).

(2) Synthesis of (S)-2-(4-(4-chlorophenyl)-2,3,9-trimethyl-6H-thieno[3,2-f][1,2,4]triazolo[4,3-a][1,4]diazepin-6-yl)-N-(3-(piperazin-1-yl)propyl)acetamide (S)-tert-butyl 4-(3-(2-(4-(4-chlorophenyl)-2,3,9-trimethyl-6H-thieno[3,2-f][1,2,4]triazolo[4,3-a][1,4]diazepin-6-yl)acetamido)propyl)piperazine-1-carboxylate (325.5 mg) was dissolved in DCM (5 mL) and MeOH (0.5 mL). A solution of 4M HCl in dioxane (1 mL) was added and the mixture was stirred for 16 hours, then concentrated under a stream of nitrogen to give a yellow solid (231.8 mg) which was used without further purification.

$^1$H NMR (400 MHz, Methanol-d$_4$) δ 7.64-7.53 (m, 4H), 5.05 (t, J=7.1 Hz, 1H), 3.81-3.66 (m, 6H), 3.62-3.33 (m, 9H), 3.30 (p, J=1.6 Hz, 1H), 2.94 (s, 3H), 2.51 (s, 3H), 2.09 (dq, J=11.8, 6.1 Hz, 2H), 1.72 (s, 3H). $^{13}$C NMR (100 MHz, cd$_3$od) δ 171.78, 169.38, 155.83, 154.03, 152.14, 140.55, 136.33, 134.58, 134.53, 133.33, 132.73, 130.89, 130.38, 56.07, 53.54, 41.96, 37.22, 36.23, 25.11, 14.48, 13.14, 11.68. LCMS 526.29 (M+H).

(3) Synthesis of (S)-tert-butyl (6-(4-(3-(2-(4-(4-chlorophenyl)-2,3,9-trimethyl-6H-thieno[3,2-f][1,2,4]triazolo[4,3-a][1,4]diazepin-6-yl)acetamido)propyl)piperazin-1-yl)-6-oxohexyl)carbamate (S)-2-(4-(4-chlorophenyl)-2,3,9-trimethyl-6H-thieno[3,2-J][1,2,4]triazolo[4,3-a][1,4]diazepin-6-yl)-N-(3-(piperazin-1-yl)propyl)acetamide (62.1 mg) and 6-((tert-butoxycarbonyl)amino)hexanoic acid (24.0 mg, 0.1037 mmol, 1 eq) were dissolved in DMF (1 mL). DIPEA (72.2 microliters, 0.4147 mmol, 4 eq) was added, followed by HATU (39.4 mg, 0.1037 mmol, 1 eq) and the mixture was stirred for 25 hours. The mixture was diluted with half saturated sodium bicarbonate and extracted three times with DCM. The combined organic layer was dried over sodium sulfate, filtered and condensed. Purification by column chromatography (ISCO, 4 g silica column, 0-15% MeOH/DCM, 15 minute gradient) gave a yellow oil (71.75 mg, 0.0970 mmol, 94%).

$^1$H NMR (400 MHz, Chloroform-d) δ 7.61 (s, 1H), 7.43-7.28 (m, 4H), 4.63 (s, 1H), 4.61-4.56 (m, 1H), 3.82-3.21 (m, 10H), 3.11-3.01 (m, 2H), 2.61 (d, J=24.3 Hz, 9H), 2.38 (s, 3H), 2.28 (t, J=7.4 Hz, 2H), 1.73 (dq, J=13.8, 7.4 Hz, 2H), 1.63-1.55 (m, 2H), 1.53-1.24 (m, 14H). $^{13}$C NMR (100 MHz, cdcl$_3$)$_6$ 171.63, 171.11, 164.34, 156.17, 155.66, 150.21, 136.96, 136.72, 132.25, 131.14, 131.01, 130.47, 130.00, 128.85, 79.11, 56.42, 54.46, 53.06, 52.82, 45.04, 41.02, 40.47, 39.29, 38.33, 33.00, 29.90, 28.54, 26.60, 25.29, 24.86, 14.47, 13.20, 11.86. LCMS 739.37 (M+H).

(4) Synthesis of (S)—N-(3-(4-(6-aminohexanoyl) piperazin-1-yl)propyl)-2-(4-(4-chlorophenyl)-2,3,9-trimethyl-6H-thieno[3,2-f][1,2,4]triazolo[4,3-a][1,4]diazepin-6-yl)acetamide (S)-tert-butyl (6-(4-(3-(2-(4-(4-chlorophenyl)-2,3,9-trimethyl-6H-thieno[3,2-J][1,2,4]triazolo[4,3-a][1,4]diazepin-6-yl)acetamido)propyl)piperazin-1-yl)-6-oxohexyl)carbamate (71.75 mg, 0.0970 mmol, 1 eq) was dissolved in DCM (2 mL) and MeOH (0.2 mL). A solution of 4M HCl in dioxane (0.49 mL) was added and the mixture was stirred for 2 hours, then concentrated under a stream of nitrogen, followed by vacuum to give a yellow foam (59.8 mg, 0.0840 mmol, 87%).

$^1$H NMR (400 MHz, Methanol-d$_4$) δ 7.68-7.53 (m, 4H), 5.04 (d, J=6.6 Hz, 1H), 4.66 (d, J=13.6 Hz, 1H), 4.23 (d, J=13.6 Hz, 1H), 3.63-3.34 (m, 7H), 3.29-3.00 (m, 5H), 2.95 (d, J=6.0 Hz, 5H), 2.51 (d, J=9.2 Hz, 5H), 2.08 (s, 2H), 1.77-1.62 (m, 7H), 1.45 (dt, J=15.3, 8.6 Hz, 2H). $^{13}$C NMR (100 MHz, cd$_3$od) δ 173.77, 171.84, 169.35, 155.85, 153.99, 140.56, 136.40, 134.58, 133.35, 132.70, 130.39, 55.83, 53.57, 52.92, 52.70, 43.57, 40.55, 39.67, 37.33, 36.25, 33.17, 28.26, 26.94, 25.33, 25.26, 14.49, 13.15, 11.65. LCMS 639.35 (M+H).

(5) Synthesis of dBET18

(S)—N-(3-(4-(6-aminohexanoyl)piperazin-1-yl)propyl)-2-(4-(4-chlorophenyl)-2,3,9-trimethyl-6H-thieno[3,2-f][1,2,4]triazolo[4,3-a][1,4]diazepin-6-yl)acetamide dihydrochloride (20.0 mg, 0.0281 mmol, 1 eq) and 2-((2-(2,6-dioxopiperidin-3-yl)-1,3-dioxoisoindolin-4-yl)oxy)acetic acid (9.32 mg, 0.0281 mmol, 1 eq) were dissolved in DMF (0.281 mL). DIPEA (19.6 microliters, 0.1124 mmol, 4 eq) was added, followed by HATU (10.7 mg, 0.0281 mmol, 1 eq). After 24 hours, the mixture was diluted with MeOH and purified by preparative HPLC to give the desired trifluoracetate salt.

$^1$H NMR (400 MHz, Methanol-d$_4$) δ 7.83-7.79 (m, 1H), 7.54 (d, J=7.1 Hz, 1H), 7.45 (q, J=8.8 Hz, 5H), 5.12 (dd, J=12.5, 5.4 Hz, 1H), 4.76 (s, 2H), 4.68 (t, J=7.3 Hz, 1H), 3.59-3.32 (m, 8H), 3.28-3.18 (m, 4H), 2.87 (ddd, J=19.0, 14.7, 5.3 Hz, 2H), 2.80-2.65 (m, 6H), 2.44 (d, J=6.8 Hz, 5H), 2.33-2.25 (m, 1H), 2.14 (dd, J=9.8, 4.9 Hz, 1H), 2.06-1.89 (m, 3H), 1.70 (s, 3H), 1.61 (dq, J=14.4, 7.3, 6.9 Hz, 4H), 1.45-1.37 (m, 2H). $^{13}$C NMR (100 MHz, cd$_3$od) δ 174.52, 173.97, 173.69, 171.44, 169.88, 168.26, 167.83, 166.72, 156.36, 138.28, 137.84, 134.89, 133.52, 132.12, 131.83, 131.38, 129.89, 121.87, 119.32, 118.01, 69.52, 55.64, 55.03, 52.79, 50.58, 43.69, 39.77, 38.57, 36.89, 33.47, 32.16, 29.93, 27.34, 25.76, 25.45, 23.63, 14.39, 12.94, 11.66. LCMS 953.43 (M+H).

Synthetic Example 19: Synthesis of dBET19

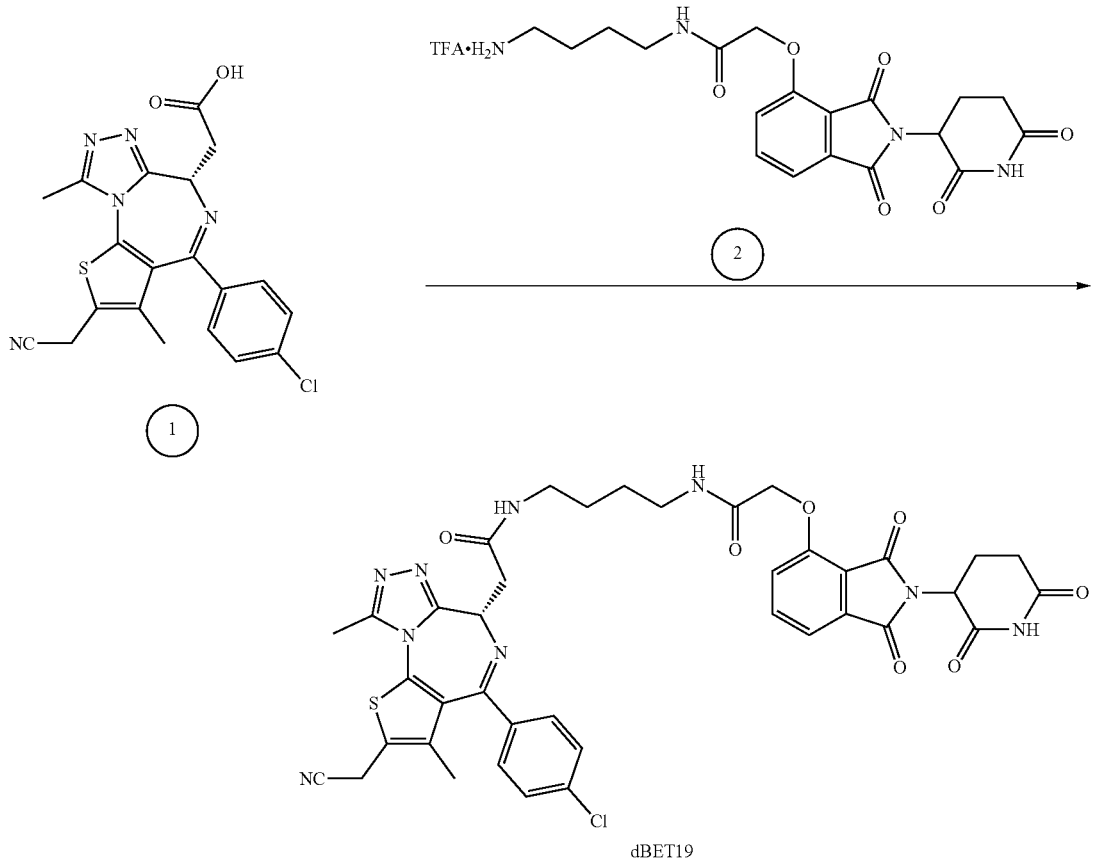

dBET19

A 0.1 M solution of N-(4-aminobutyl)-2-((2-(2,6-dioxopiperidin-3-yl)-1,3-dioxoisoindolin-4-yl)oxy)acetamide trifluoroacetate in DMF (235 microliters, 0.0235 mmol, 1 eq) was added to (S)-2-(4-(4-chlorophenyl)-2-(cyanomethyl)-3,9-dimethyl-6H-thieno[3,2-J][1,2,4]triazolo[4,3-a][1,4]diazepin-6-yl)acetic acid (10 mg, 0.0235 mmol, 1 eq) at room temperature. DIPEA (12.3 microliters, 0.0704 mmol, 3 eq) and HATU (8.9 µg, 0.0235 mmol, 1 eq) were added and the mixture was stirred for 18.5 hours. The mixture was then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a white solid (12.96 mg, 0.0160 mmol, 68%). $^1$H NMR (400 MHz, Chloroform-d) δ 7.80 (dd, J=8.4, 7.4 Hz, 1H), 7.55-7.37 (m, 6H), 5.14-5.06 (m, 1H), 4.77 (d, J=1.5 Hz, 2H), 4.64 (dd, J=8.0, 5.6 Hz, 1H), 3.45-3.32 (m, 5H), 3.29-3.21 (m, 2H), 2.83 2.66 (m, 6H), 2.58 (s, 3H), 2.14-2.06 (m, 1H), 1.71-1.57 (m, 4H). LCMS 810.30, M+H).

Synthetic Example 20: Synthesis of dBET20

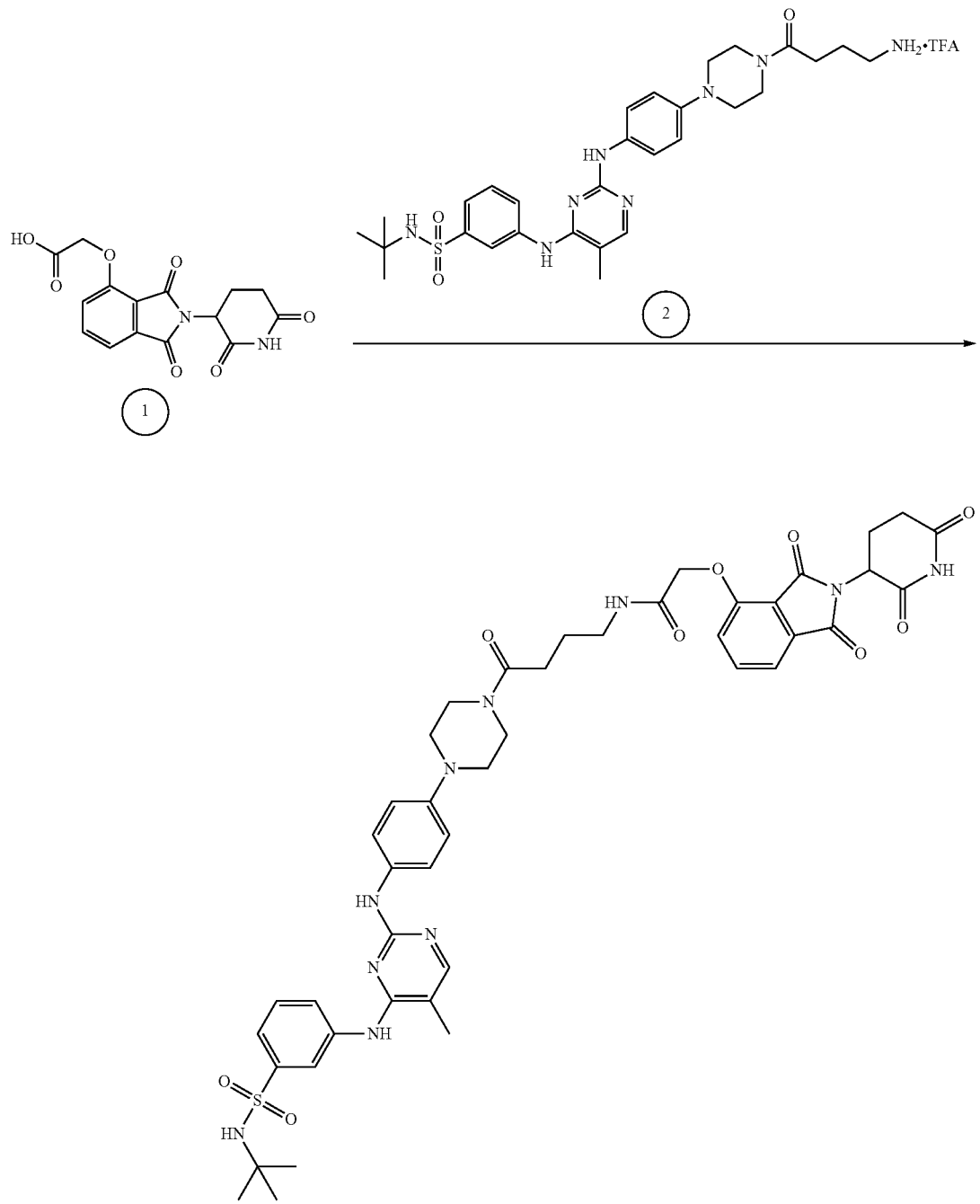

dBET20

3-((2-((4-(4-(4-aminobutanoyl)piperazin-1-yl)phenyl)amino)-5-methylpyrimidin-4-yl)amino)-N-(tert-butyl)benzenesulfonamide trifluoroacetate (7.41 mg, 0.0107 mmol, 1 eq) and 2-((2-(2,6-dioxopiperidin-3-yl)-1,3-dioxoisoindolin-4-yl)oxy)acetic acid (3.6 mg, 0.0107 mmol, 1 eq) were dissolved in DMF (214 microliters, 0.05M) at room temperature. DIPEA (5.6 microliters, 0.0321 mmol, 3 eq) and HATU (4.1 mg, 0.0107 mmol, 1 eq) were added. After 22.5 hours, the mixture was diluted with MeOH and purified by preparative HPLC to give the desired product as a brown residue (6.27 mg, 0.00701 mmol, 65%). $^1$H NMR (500 MHz, Methanol-$d_4$) δ 8.06 (s, 1H), 7.84-7.75 (m, 3H), 7.65 (s, 1H), 7.55 (t, J=7.8 Hz, 2H), 7.45 (d, J=8.4 Hz, 1H), 7.25-7.20 (m, 2H), 6.99 (d, J=8.8 Hz, 2H), 5.11 (dd, J=12.5, 5.4 Hz, 1H), 4.78 (s, 2H), 3.79-3.66 (m, 4H), 3.40 (t, J=6.6 Hz, 2H), 3.24-3.13 (m, 4H), 2.82-2.68 (m, 3H), 2.52 (t, J=7.4 Hz, 2H), 2.24-2.19 (m, 3H), 2.12 (dd, J=10.2, 5.1 Hz, 1H), 1.92 (dd, J=13.4, 6.4 Hz, 2H), 1.18 (s, 9H). LCMS 895.63 (M+H).

Synthetic Example 21: Synthesis of dBET21

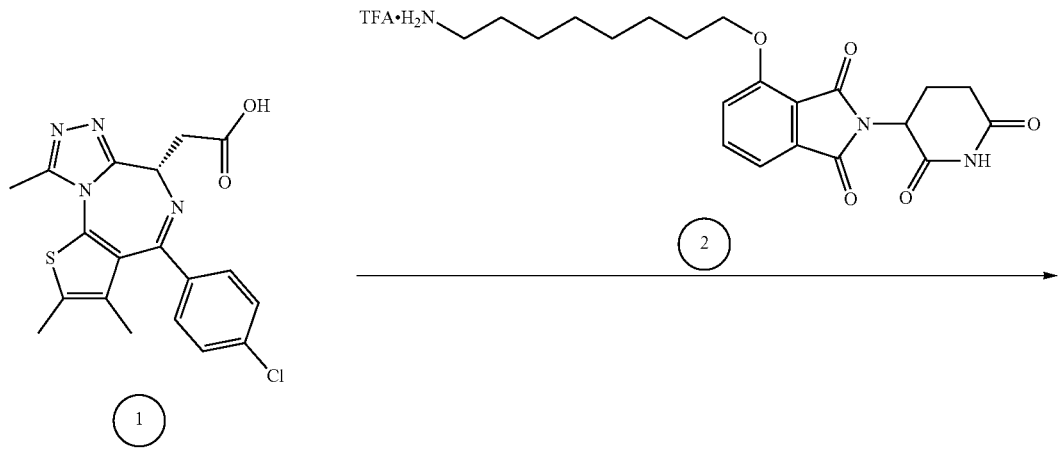

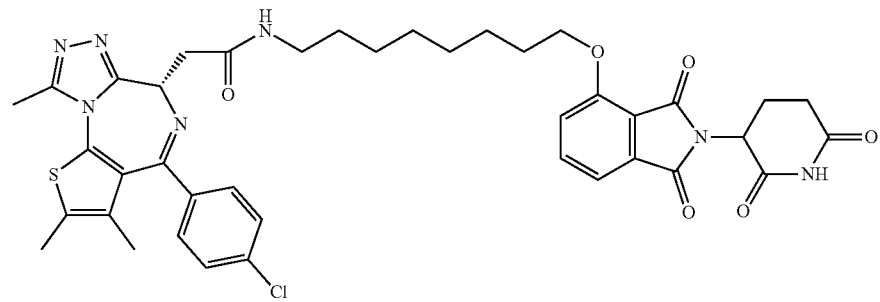

dBET21

A 0.1 M solution of 4-((10-aminodecyl)oxy)-2-(2,6-dioxopiperidin-3-yl)isoindoline-1,3-dione trifluoroacetate in DMF (232 microliters, 0.0232 mmol, 1 eq) was added to JQ-acid (9.3 mg, 0.0232 mmol, 1 eq) at room temperature. DIPEA (12.1 microliters, 0.0696 mmol, 3 eq) and HATU (8.8 mg, 0.0232 mmol, 1 eq) were added and the mixture was stirred for 18 hours. The mixture was then diluted with EtOAc and washed with saturated sodium bicarbonate, water and brine. The organic layer was dried over sodium sulfate, filtered and concentrated under reduced pressure. Purification by preparative HPLC followed by column chromatography (ISCO, 4 g silica column, 0-10% MeOH/DCM, 25 minute gradient) gave the desired product as an off-white residue (1.84 mg, 0.00235 mmol, 10%). $^1$H NMR (500 MHz, Methanol-$d_4$) δ 7.77-7.73 (m, 1H), 7.50-7.33 (m, 6H), 5.09 (dd, J=12.5, 5.5 Hz, 1H), 4.62 (s, 1H), 4.21 (t, J=6.4 Hz, 2H), 3.36 (s, 2H), 2.87-2.67 (m, 6H), 2.44 (s, 3H), 1.88-1.82 (m, 2H), 1.70 (s, 3H), 1.58 (s, 4H), 1.29 (s, 8H). LCMS 784.51 (M+H).

Synthetic Example 22: Synthesis of dBET22

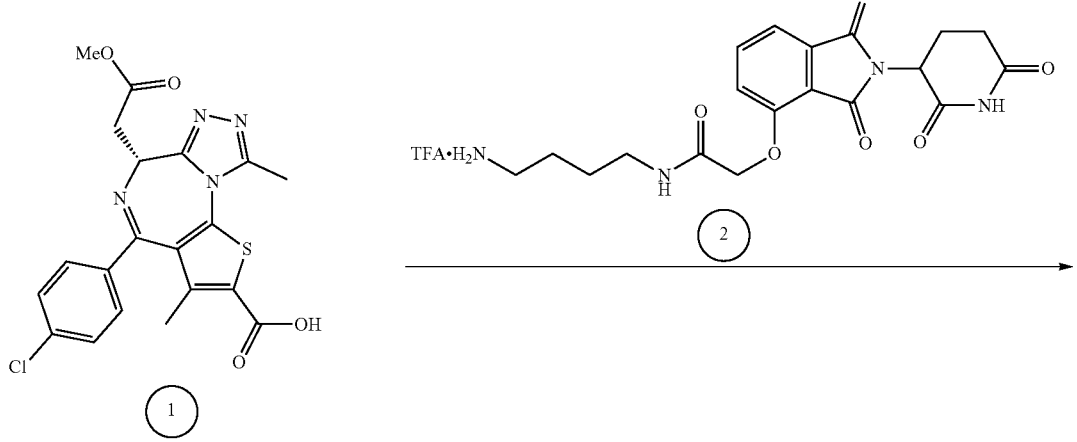

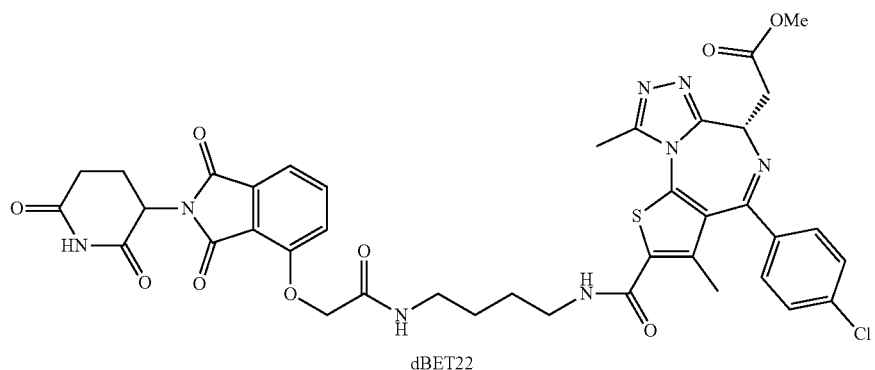

dBET22

A 0.1 M solution of N-(4-aminobutyl)-2-((2-(2,6-dioxopiperidin-3-yl)-1,3-dioxoisoindolin-4-yl)oxy)acetamide trifluoroacetate in DMF (247 microliters, 0.0247 mmol, 1 eq) was added to (S)-4-(4-chlorophenyl)-6-(2-methoxy-2-oxoethyl)-3,9-dimethyl-6H-thieno[3,2-J][1,2,4]triazolo[4,3-a][1,4]diazepine-2-carboxylic acid (10.98 mg, 0.0247 mmol, 1 eq) at room temperature. DIPEA (12.9 microliters, 0.0740 mmol, 3 eq) and HATU (9.4 mg, 0.0247 mmol, 1 eq) were added. The mixture was then stirred for 21 hours, then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a white solid (9.79 mg, 0.0118 mmol, 48%). $^1$H NMR (400 MHz, Methanol-$d_4$) δ 7.80 (dd, J=8.4, 7.4 Hz, 1H), 7.51 (dd, J=7.1, 1.5 Hz, 1H), 7.48-7.34 (m, 5H), 5.11 (ddd, J=12.4, 5.4, 3.5 Hz, 1H), 4.76 (s, 2H), 4.69 (td, J=7.2, 1.4 Hz, 1H), 3.76 (s, 3H), 3.55 (d, J=7.2 Hz, 2H), 3.48-3.33 (m, 4H), 2.93-2.82 (m, 1H), 2.78-2.64 (m, 5H), 2.14-2.07 (m, 1H), 1.96 (d, J=0.9 Hz, 3H), 1.66 (s, 4H). LCMS 829.39 (M+H).

Synthetic Example 23: Synthesis of dBET23

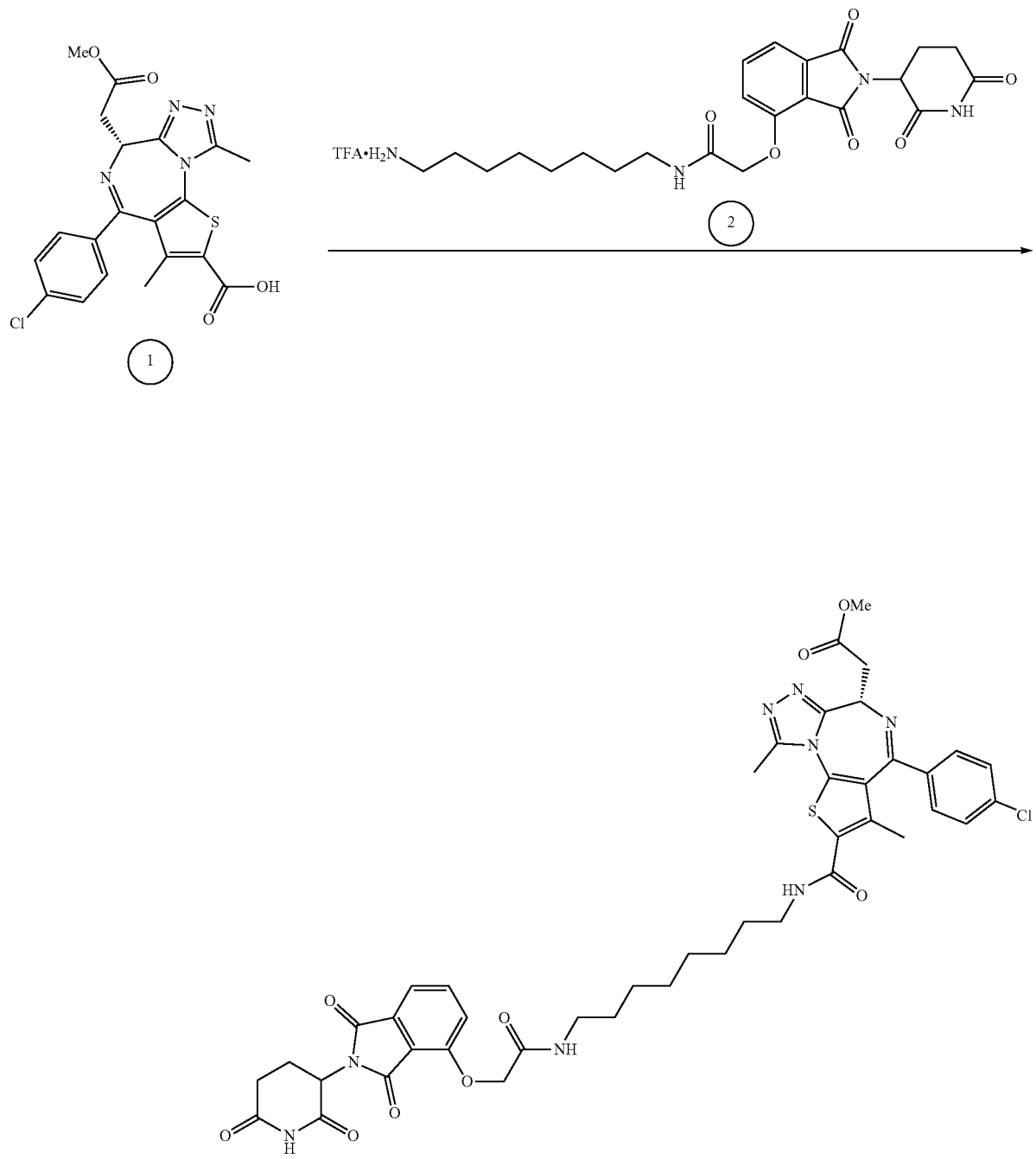

dBET23

A 0.1 M solution of N-(8-aminooctyl)-2-((2-(2,6-dioxopiperidin-3-yl)-1,3-dioxoisoindolin-4-yl)oxy)acetamide trifluoroacetate in DMF (220 microliters, 0.0220 mmol, 1 eq) was added to (S)-4-(4-chlorophenyl)-6-(2-methoxy-2-oxoethyl)-3,9-dimethyl-6H-thieno[3,2-J][1,2,4]triazolo[4,3-a][1,4]diazepine-2-carboxylic acid (9.87 mg, 0.0220 mmol, 1 eq) at room temperature. DIPEA (11.5 microliters, 0.0660 mmol, 3 eq) and HATU (8.4 mg, 0.0220 mmol, 1 eq) were added. The mixture was then stirred for 21 hours, then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a white solid (8.84 mg, 0.00998 mmol, 45%). $^1$H NMR (400 MHz, Methanol-$d_4$) δ 7.81 (dd, J=8.4, 7.4 Hz, 1H), 7.53 (d, J=7.3 Hz, 1H), 7.50-7.39 (m, 5H), 5.12 (dd, J=12.6, 5.4 Hz, 1H), 4.75 (s, 2H), 4.68 (t, J=7.2 Hz, 1H), 3.76 (s, 3H), 3.54 (d, J=7.2 Hz, 2H), 3.39-3.32 (m, 3H), 3.29 (s, 1H), 2.90-2.83 (m, 1H), 2.79-2.68 (m, 5H), 2.14 (dd, J=8.9, 3.7 Hz, 1H), 1.99 (s, 3H), 1.65-1.53 (m, 4H), 1.36 (d, J=6.5 Hz, 8H). LCMS 885.47 (M+H).

Synthetic Example 24: Synthesis of dBET24

Step 1: Synthesis of tert-butyl (2-(2-(2-(2-((2-(2,6-dioxopiperidin-3-yl)-1,3-dioxoisoindolin-4-yl)oxy)acetamido)ethoxy)ethoxy)ethyl)carbamate 2-((2-(2,6-dioxopiperidin-3-yl)-1,3-dioxoisoindolin-4-yl)oxy)acetic acid (200 mg, 0.602 mmol, 1 eq) was dissolved in DMF (6.0 mL, 0.1M). HATU (228.9 mg, 0.602 mmol, 1 eq), DIPEA (0.315 mL, 1.81 mmol, 3 eq) and N-Boc-2,2'-(ethylenedioxy)diethylamine (0.143 mL, 0.602 mmol, 1 eq) were added sequentially. After 6 hours, additional HATU (114 mg, 0.30 mmol, 0.5 eq) were added to ensure completeness of reaction. After an additional 24 hours, the mixture was diluted with EtOAc, and washed with saturated sodium bicarbonate, water and twice with brine. The combined organic layer was dried over sodium sulfate, filtered and concentrated under reduced pressure. Purification by column chromatography (ISCO, 12 g silica column, 0-15% MeOH/DCM, 15 minute gradient) gave the desired product as a yellow oil (0.25 g, 0.44 mmol, 74%). $^1$H NMR (400 MHz, Methanol-$d_4$) δ 7.82-7.75 (m, 1H), 7.51 (d, J=7.4 Hz, 1H), 7.41 (d, J=8.5 Hz, 1H), 5.13 (dd, J=12.4, 5.5 Hz, 1H), 4.76 (s, 2H), 3.66-3.58 (m, 6H), 3.53-3.45 (m, 4H), 3.19 (t, J=5.6 Hz, 2H), 2.95-2.83 (m, 1H), 2.80-2.67 (m, 2H), 2.19-2.12 (m, 1H), 1.41 (s, 9H). LCMS 563.34 (M+H).

Step 2: Synthesis of N-(2-(2-(2-aminoethoxy)ethoxy)ethyl)-2-((2-(2,6-dioxopiperidin-3-yl)-1,3-dioxoisoindolin-4-yl)oxy)acetamide trifluoroacetate tert-butyl (2-(2-(2-(2-((2-(2,6-dioxopiperidin-3-yl)-1,3-dioxoisoindolin-4-yl)oxy)acetamido)ethoxy)ethoxy)ethyl)carbamate (0.25 g, 0.44 mmol, 1 eq) was dissolved in TFA (4.5 mL) and heated to 50° C. After 3 hours, the mixture was cooled to room temperature, diluted with MeOH, and concentrated under reduced pressure. Purification by preparative HPLC gave the desired product as a tan solid (0.197 g, 0.342 mmol, 77%). $^1$H NMR (400 MHz, Methanol-$d_4$) δ 7.81 (ddd, J=8.4, 7.4, 1.1 Hz, 1H), 7.55-7.50 (m, 1H), 7.43 (d, J=8.5 Hz, 1H), 5.13 (dd, J=12.7, 5.5 Hz, 1H), 4.78 (s, 2H), 3.74-3.66 (m, 6H), 3.64 (t, J=5.4 Hz, 2H), 3.52 (t, J=5.3 Hz, 2H), 3.14-3.08 (m, 2H), 2.89 (ddd, J=17.5, 13.9, 5.2 Hz, 1H), 2.80-2.66 (m, 2H), 2.16 (dtd, J=13.0, 5.7, 2.7 Hz, 1H). LCMS 463.36 (M+H).

Step 2: Synthesis of dBET24

A 0.1 M solution of N-(2-(2-(2-aminoethoxy)ethoxy)ethyl)-2-((2-(2,6-dioxopiperidin-3-yl)-1,3-dioxoisoindolin-4-yl)oxy)acetamide trifluoroacetate in DMF (0.324 mL, 0.0324 mmol, 1 eq) was added to JQ-acid (13.0 mg, 0.324 mmol, 1 eq). DIPEA 16.9 microliters, 0.0972 mmol, 3 eq) and HATU (12.3 mg, 0.0324 mmol, 1 eq) were then added and the mixture was stirred for 18 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-10% MeOH/DCM, 25 minute gradient) gave the desired product as an off-white solid (20.0 mg, 0.0236 mmol, 73%). $^1$H NMR (400 MHz, Methanol-$d_4$) δ 7.77-7.72 (m, 1H), 7.49 (d, J=7.4 Hz, 1H), 7.45-7.35 (m, 5H), 5.09 (ddd, J=12.3, 5.4, 3.7 Hz, 1H), 4.76 (s, 2H), 4.60 (dd, J=8.9, 5.3 Hz, 1H), 3.68-3.62 (m, 6H), 3.59 (t, J=5.6 Hz, 2H), 3.54-3.48 (m, 2H), 3.47-3.35 (m, 4H), 2.84 (ddd, J=19.4, 9.9, 4.6 Hz, 1H), 2.77-2.69 (m, 2H), 2.68 (d, J=1.8 Hz, 3H), 2.43 (s, 3H), 2.12 (dt, J=9.8, 5.3 Hz, 1H), 1.68 (s, 3H). LCMS 845.39 (M+H).

Synthetic Example 25: Synthesis of dBET25

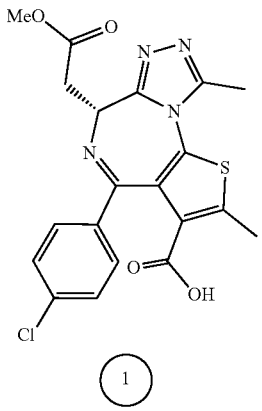

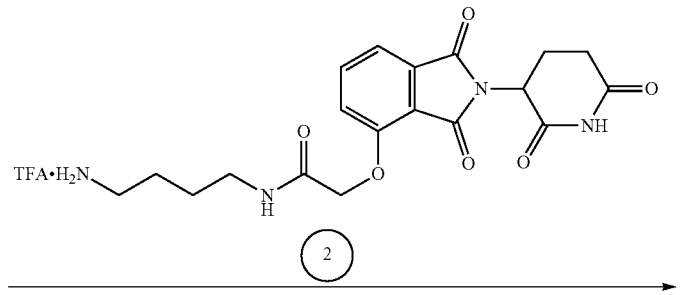

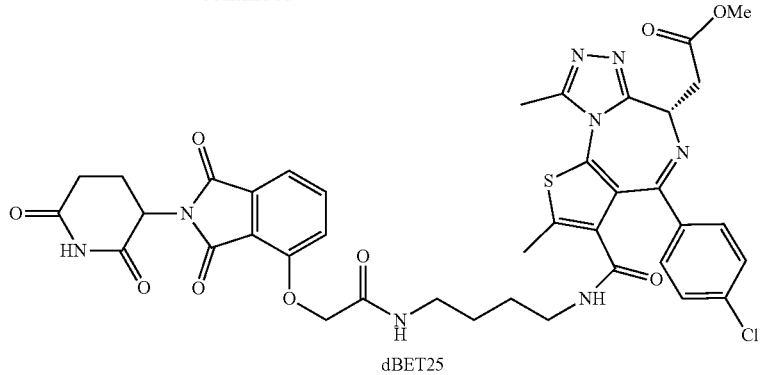

dBET25

A 0.1 M solution of N-(4-aminobutyl)-2-((2-(2,6-dioxopiperidin-3-yl)-1,3-dioxoisoindolin-4-yl)oxy)acetamide trifluoroacetate in DMF (183 microliters, 0.0183 mmol, 1 eq) was added to (S)-4-(4-chlorophenyl)-6-(2-methoxy-2-oxoethyl)-2,9-dimethyl-6H-thieno[3,2-f][1,2,4]triazolo[4,3-a][1,4]diazepine-3-carboxylic acid (8.16 mg, 0.0183 mmol, 1 eq) at room temperature. DIPEA (9.6 microliters, 0.0550 mmol, 3 eq) and HATU (7.0 mg, 0.0183 mmol, 1 eq) were added. The mixture was then stirred for 23 hours, then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a yellow solid (4.39 mg, 0.00529 mmol, 29%). $^1$H NMR (400 MHz, Methanol-$d_4$) δ 7.82 (dd, J=8.4, 7.4 Hz, 1H), 7.55 (d, J=7.3 Hz, 1H), 7.45 (d, J=8.2 Hz, 1H), 7.43-7.31 (m, 4H), 5.16-5.10 (m, 1H), 4.77 (d, J=1.5 Hz, 2H), 4.56 (s, 1H), 3.74 (d, J=1.8 Hz, 3H), 3.66-3.60 (m, 1H), 3.50 (dd, J=16.5, 7.3 Hz, 1H), 3.37-3.32 (m, 1H), 3.28 (s, 3H), 2.85 (t, J=7.2 Hz, 2H), 2.75 (d, J=7.8 Hz, 1H), 2.71 (d, J=0.9 Hz, 3H), 2.59 (d, J=1.0 Hz, 3H), 2.18-2.10 (m, 1H), 1.36-1.24 (m, 4H). LCMS 829.38 (M+H).

Synthetic Example 26: Synthesis of dBET26

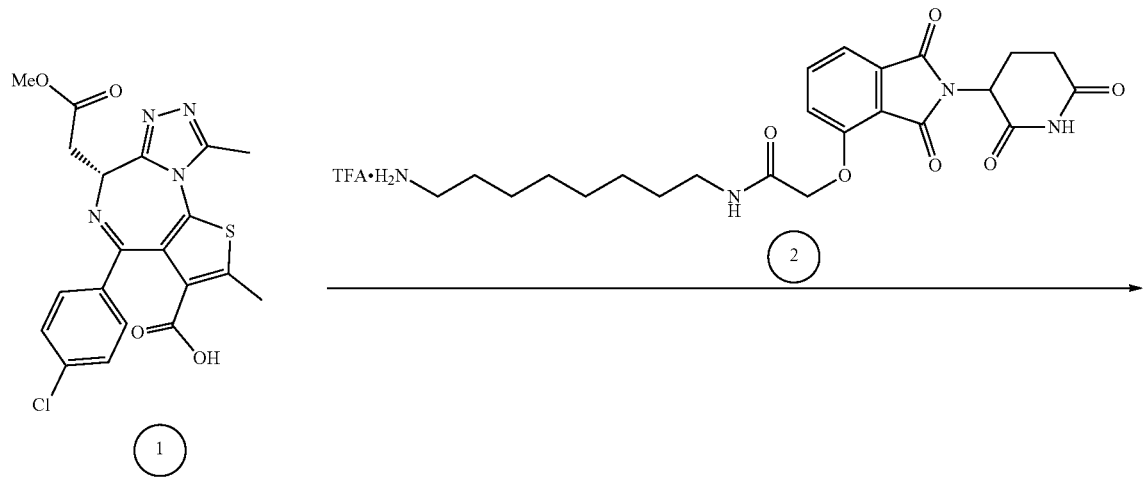

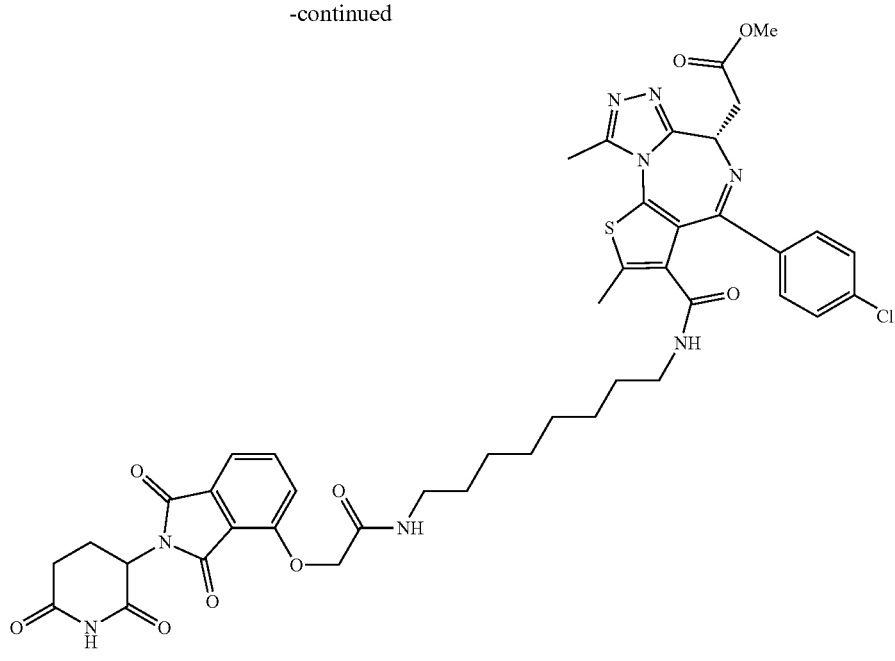

dBET26

A 0.1 M solution of N-(8-aminooctyl)-2-((2-(2,6-dioxopiperidin-3-yl)-1,3-dioxoisoindolin-4-yl)oxy)acetamide trifluoroacetate in DMF (186 microliters, 0.0186 mmol, 1 eq) was added to (S)-4-(4-chlorophenyl)-6-(2-methoxy-2-oxoethyl)-2,9-dimethyl-6H-thieno[3,2-j][1,2,4]triazolo[4,3-a][1,4]diazepine-3-carboxylic acid (8.26 mg, 0.0186 mmol, 1 eq) at room temperature. DIPEA (9.7 microliters, 0.0557 mmol, 3 eq) and HATU (7.1 mg, 0.0186 mmol, 1 eq) were added. The mixture was then stirred for 23 hours, then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a cream colored solid (6.34 mg, 0.00716 mmol, 38%). $^1$H NMR (400 MHz, Methanol-$d_4$) δ 7.83-7.78 (m, 1H), 7.53 (dd, J=7.3, 2.2 Hz, 1H), 7.45-7.38 (m, 3H), 7.32 (dd, J=8.5, 1.3 Hz, 2H), 5.16-5.08 (m, 1H), 4.76 (s, 2H), 4.56 (s, 1H), 3.75 (s, 3H), 3.66 (dd, J=15.9, 8.7 Hz, 1H), 3.50 (dd, J=16.9, 6.9 Hz, 1H), 3.32 (d, J=2.8 Hz, 4H), 2.84-2.74 (m, 3H), 2.70 (d, J=1.1 Hz, 3H), 2.66-2.54 (m, 3H), 2.14 (d, J=5.3 Hz, 1H), 1.62-1.22 (m, 12H). LCMS 885.48 (M+H).

Synthetic Example 27: Synthesis of dBET27

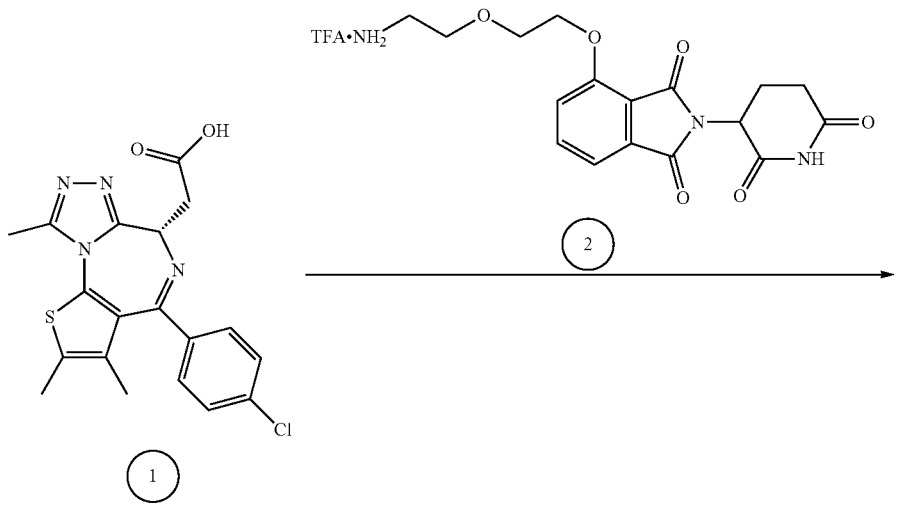

-continued

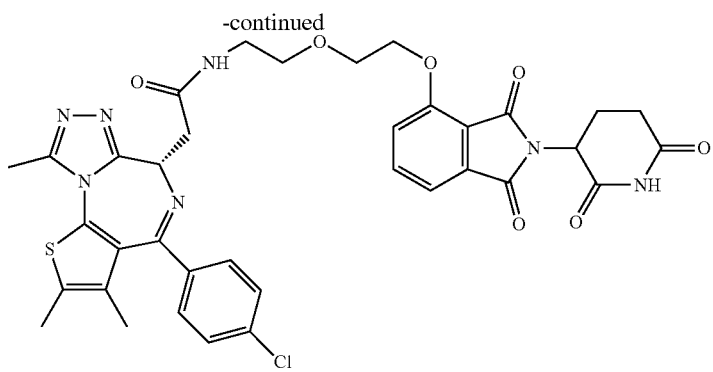

dBET27

A 0.1 M solution of 4-(2-(2-aminoethoxy)ethoxy)-2-(2,6-dioxopiperidin-3-yl)isoindoline-1,3-dione trifluoroacetate in DMF (257 microliters, 0.0257 mmol, 1 eq) was added to JQ-acid (10.3 mg, 0.0257 mmol, 1 eq). DIPEA (13.4 microliters, 0.0771 mmol, 3 eq) and HATU (9.8 mg, 0.0257 mmol, 1 eq) were then added and the mixture was stirred for 18 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-10% MeOH/DCM, 25 minute gradient) gave the desired product as a white solid (14.53 mg, 0.0195 mmol, 76%). $^1$H NMR (400 MHz, Methanol-$d_4$) δ 7.75 (ddd, J=8.5, 7.3, 1.3 Hz, 1H), 7.47-7.30 (m, 6H), 5.00 (ddd, J=25.4, 12.2, 5.2 Hz, 1H), 4.61 (td, J=9.4, 5.0 Hz, 1H), 4.36 (q, J=4.8 Hz, 2H), 3.96-3.89 (m, 2H), 3.74 (q, J=5.6 Hz, 2H), 3.53-3.41 (m, 3H), 3.30-3.24 (m, 1H), 2.78-2.53 (m, 6H), 2.41 (d, J=3.9 Hz, 3H), 2.09-1.98 (m, 1H), 1.67 (d, J=5.0 Hz, 3H).

Synthetic Example 28: Synthesis of dBET28

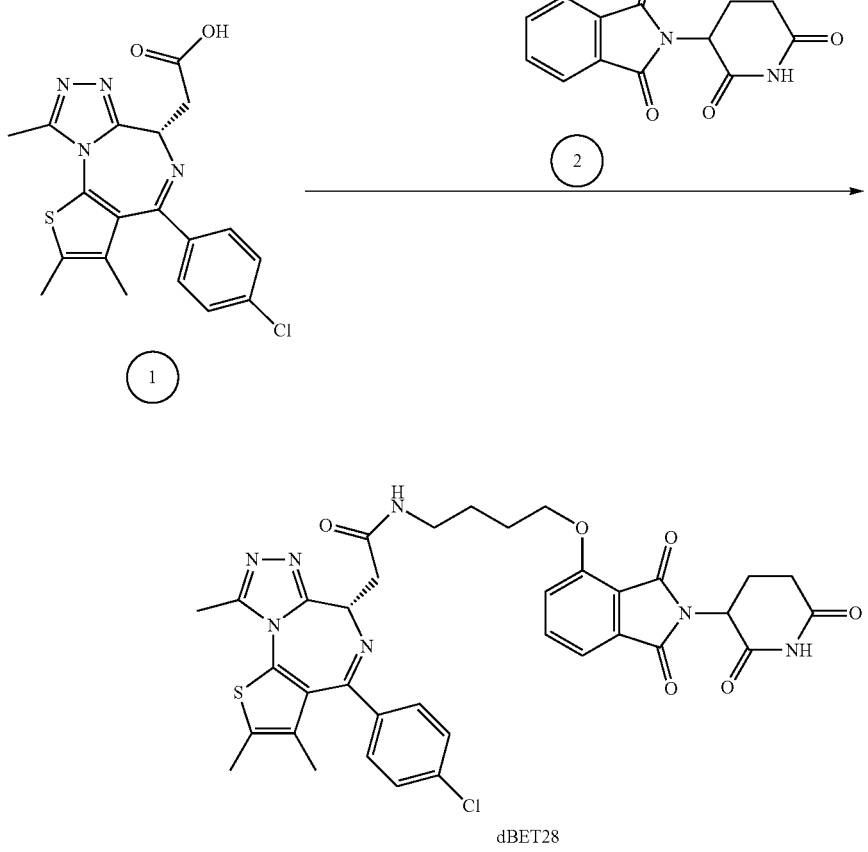

dBET28

A 0.1 M solution of 4-(4-aminobutoxy)-2-(2,6-dioxopiperidin-3-yl)isoindoline-1,3-dione trifluoroacetate in DMF (202 microliters, 0.0202 mmol, 1 eq) was added to JQ-acid (8.1 mg, 0.0202 mmol, 1 eq). DIPEA (10.6 microliters, 0.0606 mmol, 3 eq) and HATU (7.7 mg, 0.0202 mmol, 1 eq) were then added and the mixture was stirred for 18.5 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-10% MeOH/DCM, 25 minute gradient) gave the desired product as a cream colored solid (10.46 mg, 0.0144 mmol, 71%). $^1$H NMR (400 MHz, Methanol-d$_4$) δ 7.76 (t, J=7.5 Hz, 1H), 7.43 (td, J=6.5, 2.5 Hz, 4H), 7.34 (t, J=8.8 Hz, 2H), 5.08-4.98 (m, 1H), 4.64 (td, J=9.1, 5.0 Hz, 1H), 4.26 (t, J=5.3 Hz, 2H), 3.57-3.32 (m, 4H), 2.84-2.59 (m, 6H), 2.45-2.37 (m, 3H), 2.08-2.01 (m, 1H), 2.00-1.91 (m, 2H), 1.82 (dq, J=13.8, 6.9 Hz, 2H), 1.68 (d, J=11.7 Hz, 3H). LCMS 728.38 (M+H).

Synthetic Example 29: Synthesis of dBET29

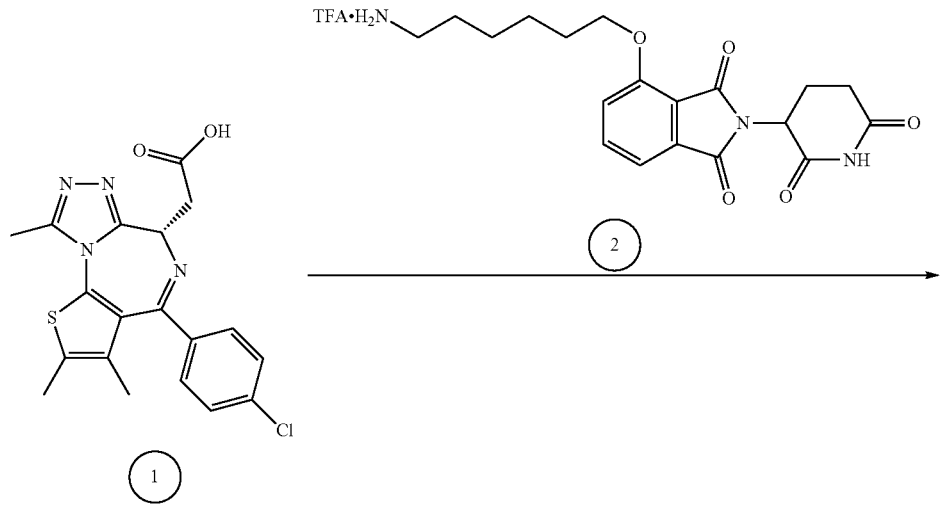

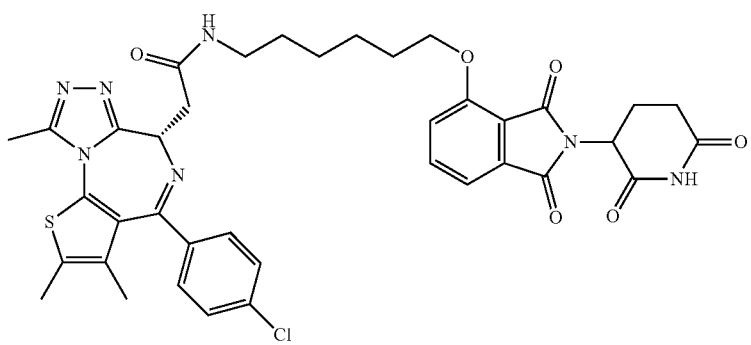

dBET29

A 0.1 M solution of 4-((6-aminohexyl)oxy)-2-(2,6-dioxopiperidin-3-yl)isoindoline-1,3-dione in DMF (205 microliters, 0.0205 mmol, 1 eq) was added to JQ-acid (8.2 mg, 0.0205 mmol, 1 eq). DIPEA (10.7 microliters, 0.0614 mmol, 3 eq) and HATU (7.8 mg, 0.0205 mmol, 1 eq) were then added and the mixture was stirred for 19 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-10% MeOH/DCM, 25 minute gradient) gave the desired product as a white solid (8.04 mg, 0.0106 mmol, 52%). 1H NMR (400 MHz, Methanol-$d_4$) δ 7.75-7.71 (m, 1H), 7.51-7.34 (m, 6H), 5.07 (ddd, J=12.1, 5.4, 2.4 Hz, 1H), 4.62 (dd, J=9.0, 5.2 Hz, 1H), 4.22 (t, J=6.4 Hz, 2H), 3.44-3.32 (m, 2H), 3.29-3.21 (m, 2H), 2.88-2.65 (m, 6H), 2.43 (s, 3H), 2.13-2.06 (m, 1H), 1.86 (dt, J=13.9, 6.7 Hz, 2H), 1.68 (s, 3H), 1.59 (dq, J=14.2, 7.0 Hz, 4H), 1.54-1.45 (m, 2H). LCMS 756.40 (M+H).

Synthetic Example 30: Synthesis of dBET30

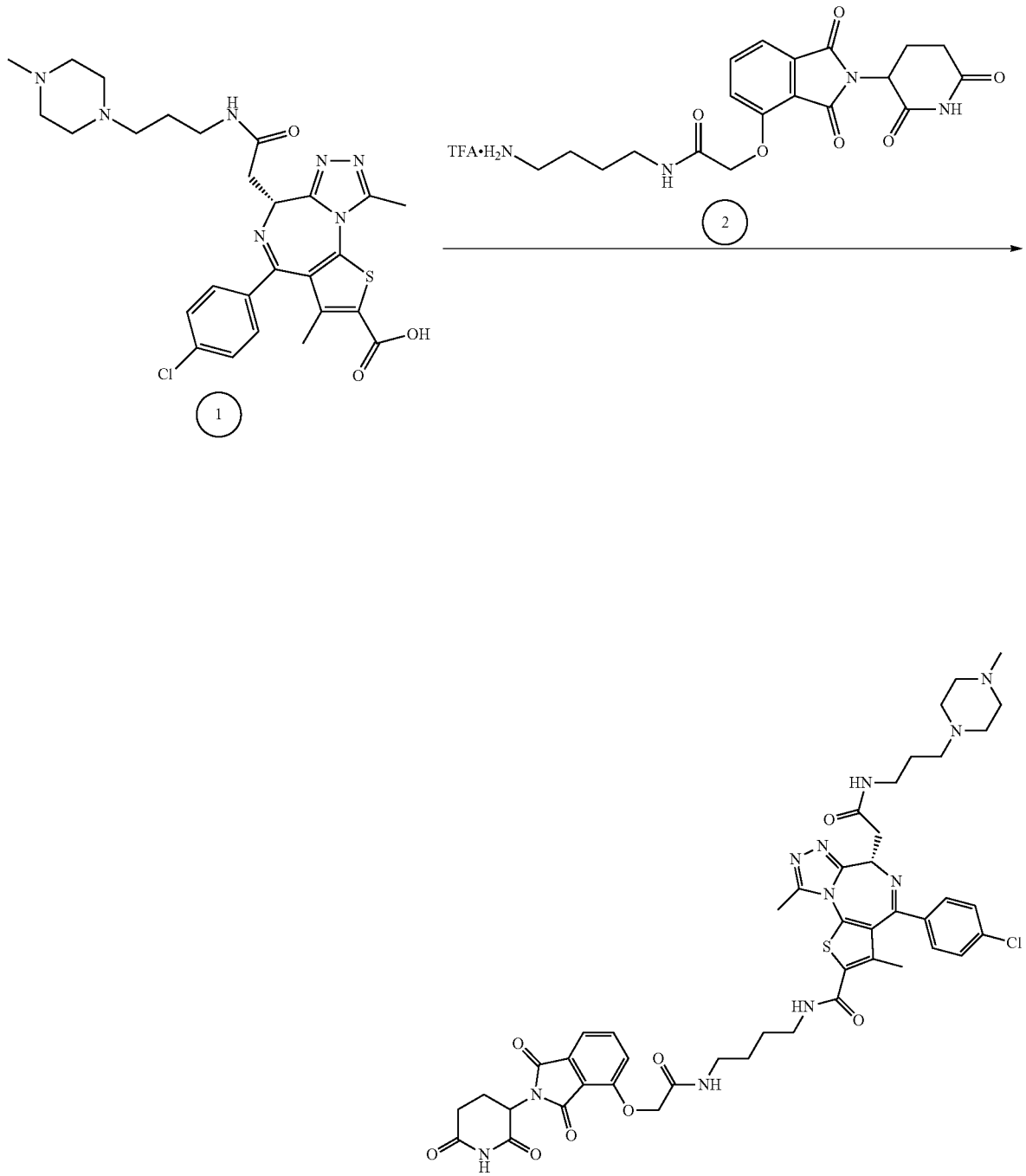

dBET30

A 0.1 M solution of N-(4-aminobutyl)-2-((2-(2,6-dioxopiperidin-3-yl)-1,3-dioxoisoindolin-4-yl)oxy)acetamide trifluoroacetate in DMF (163 microliters, 0.0163 mmol, 1 eq) was added to (S)-4-(4-chlorophenyl)-3,9-dimethyl-6-(2-((3-(4-methylpiperazin-1-yl)propyl)amino)-2-oxoethyl)-6H-thieno[3,2][1,2,4]triazolo[4,3-a][1,4]diazepine-2-carboxylic acid (9.31 mg, 0.0163 mmol, 1 eq) at room temperature. DIPEA (8.5 microliters, 0.0490 mmol, 3 eq) and HATU (6.2 mg, 0.0163 mmol, 1 eq) were added. The mixture was then stirred for 23.5 hours, then purified by preparative HPLC to give the desired product as a yellow oil (11.48 mg, 0.0107 mmol, 66%). $^1$H NMR (400 MHz, Methanol-$d_4$) δ 7.82-7.78 (m, 1H), 7.54-7.35 (m, 6H), 5.09 (td, J=12.7, 5.4 Hz, 1H), 4.77-4.70 (m, 3H), 3.56-3.31 (m, 12H), 3.23 (dd, J=8.0, 6.0 Hz, 3H), 3.05 (d, J=3.2 Hz, 2H), 2.93-2.81 (m, 5H), 2.78-2.63 (m, 5H), 2.15-2.05 (m, 2H), 1.96-1.86 (m, 4H), 1.68 (s, 4H). LCMS 954.55 (M+H).

Synthetic Example 31: Synthesis of dBET31

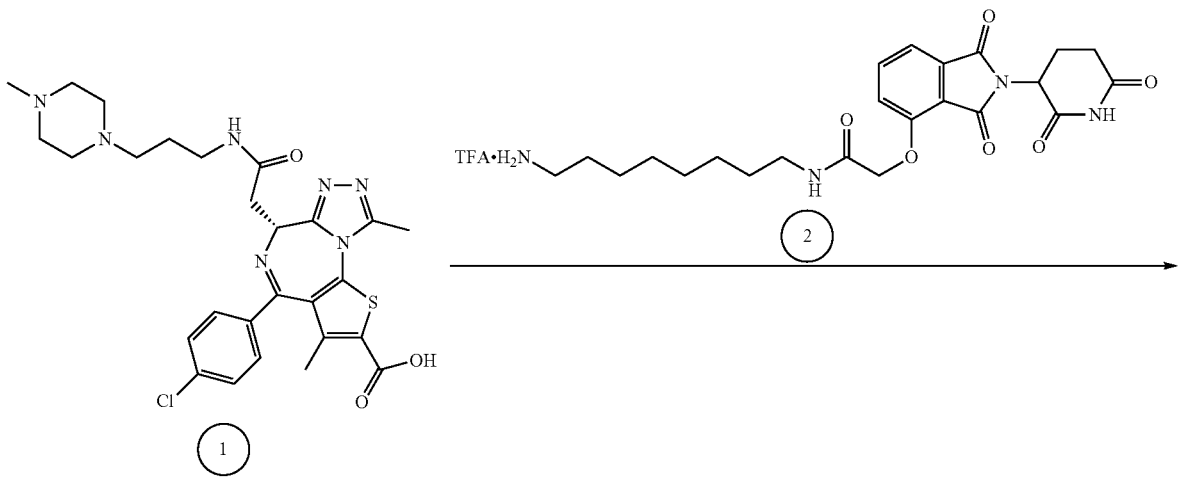

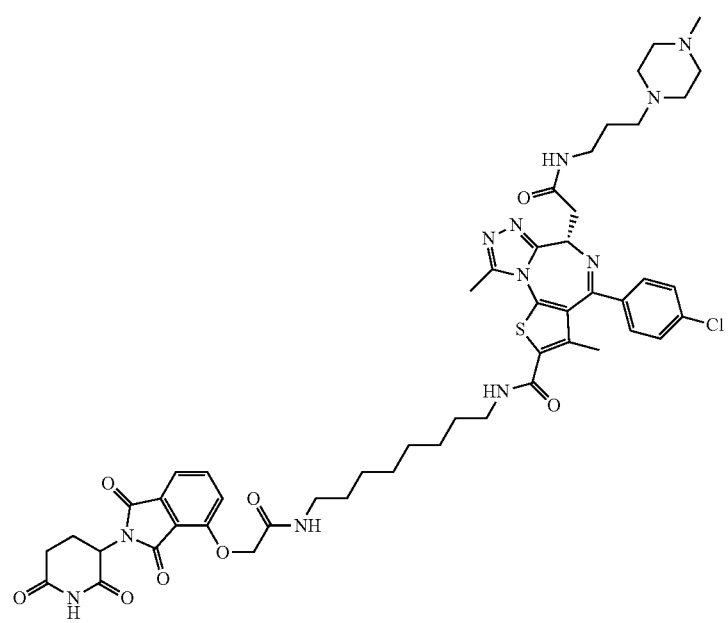

dBET31

A 0.1 M solution of N-(8-aminooctyl)-2-((2-(2,6-dioxopiperidin-3-yl)-1,3-dioxoisoindolin-4-yl)oxy)acetamide trifluoroacetate in DMF (153 microliters, 0.0153 mmol, 1 eq) was added to (S)-4-(4-chlorophenyl)-3,9-dimethyl-6-(2-((3-(4-methylpiperazin-1-yl)propyl)amino)-2-oxoethyl)-6H-thieno[3,2-f][1,2,4]triazolo[4,3-a][1,4]diazepine-2-carboxylic acid (8.7 mg, 0.0153 mmol, 1 eq) at room temperature. DIPEA (7.9 microliters, 0.0458 mmol, 3 eq) and HATU (5.8 mg, 0.0153 mmol, 1 eq) were added. The mixture was then stirred for 25 hours, then purified by preparative HPLC to give the desired product as a nice brown (not like poop brown, kind of like brick) oil (9.52 mg, 0.00847 mmol, 55%). $^1$H NMR (400 MHz, Methanol-$d_4$) δ 7.81 (dd, J=8.4, 7.4 Hz, 1H), 7.59-7.40 (m, 6H), 5.12 (dd, J=12.5, 5.4 Hz, 1H), 4.75 (s, 2H), 4.71 (t, J=7.4 Hz, 1H), 3.53-3.34 (m, 8H), 3.29-3.11 (m, 6H), 3.03-2.61 (m, 13H), 2.15 (s, 1H), 2.01-1.84 (m, 5H), 1.59 (s, 4H), 1.37 (s, 8H). LCMS 1010.62 (M+H).

Synthetic Example 32: Synthesis of dBET32

A 0.1 M solution of N-(4-aminobutyl)-2-((2-(2,6-dioxopiperidin-3-yl)-1,3-dioxoisoindolin-4-yl)oxy)acetamide trifluoroacetate in DMF (180 microliters, 0.0180 mmol, 1 eq) was added to 4-(4-(4-((4-((3-(N-(tert-butyl)sulfamoyl)phenyl)amino)-5-methylpyrimidin-2-yl)amino)phenyl)piperazin-1-yl)-4-oxobutanoic acid (10.7 mg, 0.0180 mmol, 1 eq) at room temperature. DIPEA (9.4 microliters, 0.0539 mmol, 3 eq) and HATU (6.8 mg, 0.0180 mmol, 1 eq) were added and the mixture was stirred for 19 hours. The mixture was then diluted with methanol and purified by preparative HPLC to give the desired product as a brown oil (4.40 mg, 0.00449 mmol, 25%). $^1$H NMR (500 MHz, Methanol-$d_4$) δ 8.08 (d, J=13.6 Hz, 1H), 7.84-7.76 (m, 3H), 7.63 (s, 1H), 7.57-7.51 (m, 2H), 7.41 (d, J=8.4 Hz, 1H), 7.22 (td, J=6.7, 2.2 Hz, 2H), 7.03-6.97 (m, 2H), 5.14 (dd, J=12.5, 5.5 Hz, 1H), 4.76 (d, J=16.8 Hz, 2H), 3.72 (dt, J=10.0, 5.2 Hz, 4H), 3.34-3.33 (m, 1H), 3.23-3.12 (m, 5H), 2.97 (dd, J=8.8, 4.0 Hz, 3H), 2.80-2.69 (m, 4H), 2.64 (dd, J=7.6, 5.5 Hz, 1H), 2.50 (t, J=6.8 Hz, 1H), 2.22 (dd, J=2.4, 0.9 Hz, 3H), 2.17-2.11 (m, 1H), 1.67-1.52 (m, 4H), 1.18 (d, J=0.8 Hz, 9H). LCMS 980.64 (M+H).

Synthetic Example 33: Synthesis of dBET33

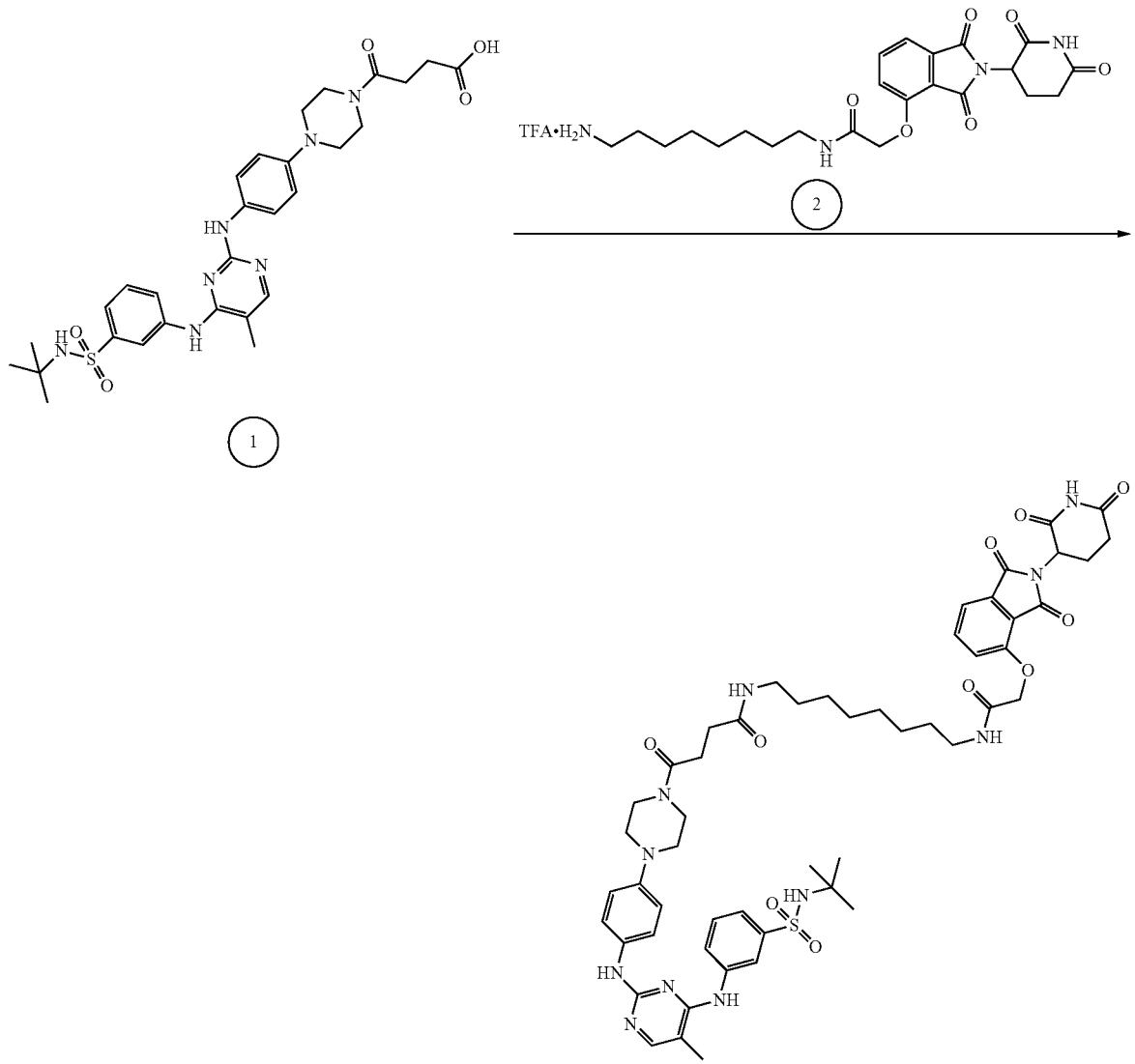

dBET33

A 0.1 M solution of N-(8-aminooctyl)-2-((2-(2,6-dioxopiperidin-3-yl)-1,3-dioxoisoindolin-4-yl)oxy)acetamide trifluoroacetate in DMF (188 microliters, 0.0188 mmol, 1 eq) was added to 4-(4-(4-((4-(3-(N-(tert-butyl)sulfamoyl)phenyl)amino)-5-methylpyrimidin-2-yl)amino)phenyl)piperazin-1-yl)-4-oxobutanoic acid (10.8 mg, 0.0188 mmol, 1 eq) at room temperature. DIPEA (9.8 microliters, 0.0564 mmol, 3 eq) and HATU (7.1 mg, 0.0188 mmol, 1 eq) were added and the mixture was stirred for 23 hours. The mixture was then diluted with methanol and purified by preparative HPLC to give the desired product as a brown residue (7.41 mg, 0.00715 mmol, 38%). $^1$H NMR (500 MHz, Methanol-$d_4$) δ 8.06 (s, 1H), 7.80 (ddd, J=10.5, 7.6, 3.2 Hz, 3H), 7.65 (d, J=4.5 Hz, 1H), 7.57-7.51 (m, 2H), 7.41 (dd, J=8.4, 2.9 Hz, 1H), 7.25 (td, J=6.7, 2.9 Hz, 2H), 7.02 (t, J=8.0 Hz, 2H), 5.16-5.09 (m, 1H), 4.75 (d, J=9.5 Hz, 2H), 3.76 (dq, J=16.0, 5.3 Hz, 4H), 3.29-3.12 (m, 7H), 3.00-2.67 (m, 7H), 2.51 (t, J=6.8 Hz, 1H), 2.22 (d, J=3.1 Hz, 3H), 2.13 (dtd, J=10.4, 5.7, 3.1 Hz, 1H), 1.59-1.52 (m, 2H), 1.51-1.43 (m, 2H), 1.32 (t, J=16.6 Hz, 8H), 1.18 (d, J=1.3 Hz, 9H). LCMS 1036.69 (M+H).

Synthetic Example 34: Synthesis of dBET34

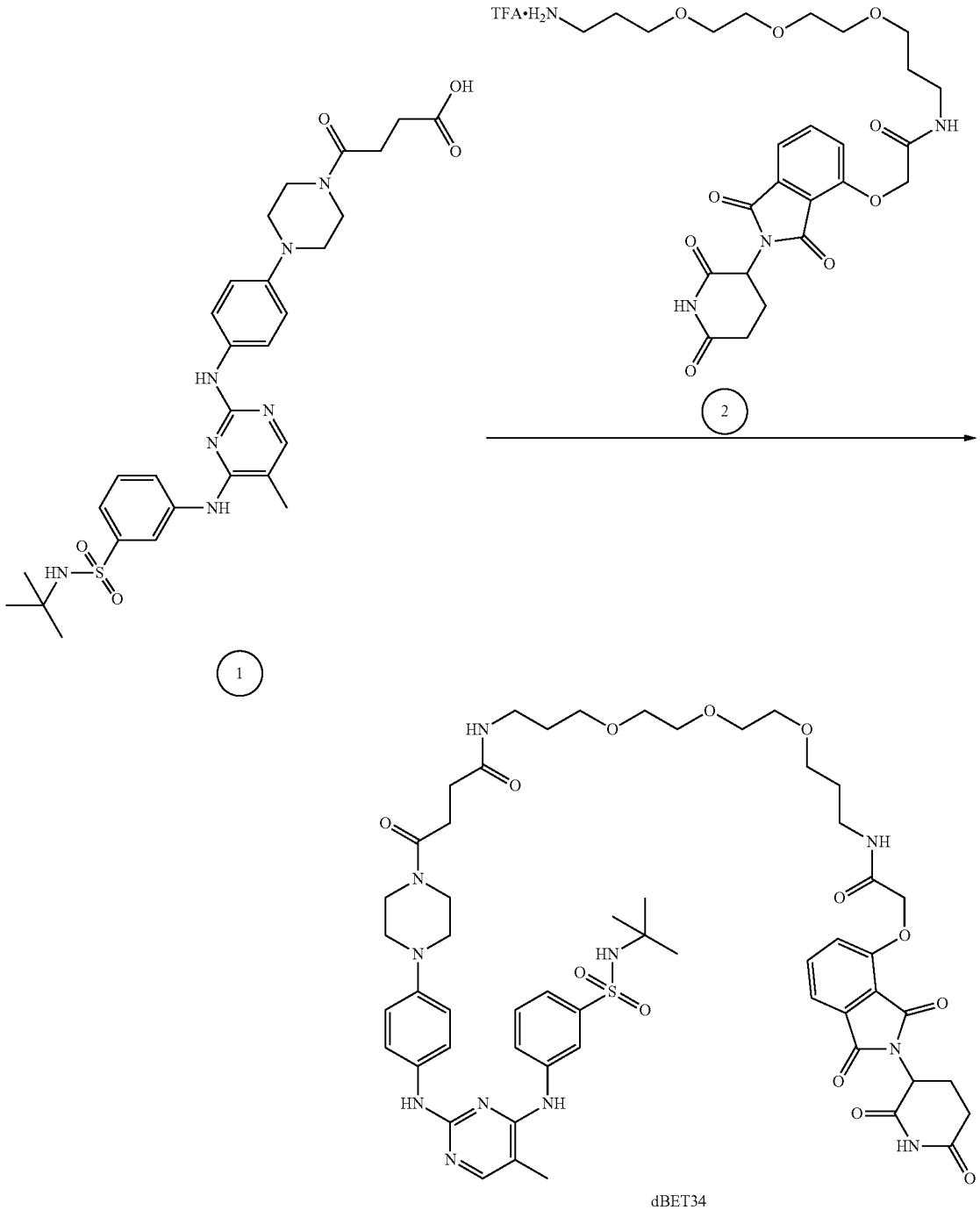

dBET34

A 0.1 M solution of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (173 microliters, 0.0173 mmol, 1 eq) was added to 4-(4-(4-((4-((3-(N-(tert-butyl)sulfamoyl)phenyl)amino)-5-methylpyrimidin-2-yl)amino)phenyl)piperazin-1-yl)-4-oxobutanoic acid (10.3 µg, 0.0173 mmol, 1 eq) at room temperature. DIPEA (9.0 microliters, 0.0519 µmol, 3 eq) and HATU (6.6 mg, 0.0173 mmol, 1 eq) were added and the mixture was stirred for 25 hours. The mixture was then diluted with methanol and purified by preparative HPLC to give the desired product as a brown residue (7.99 mg, 0.00718 µmol, 42o). $^1$H NMR (500 MHz, Methanol-$d_4$) δ 8.06 (s, 1H), 7.83-7.76 (i, 3H), 7.65 (s, 1H), 7.58-7.50 (m, 2H), 7.43 (dd, J=17.7, 8.4 Hz, 1H), 7.27-7.21 (i, 2H), 7.02 (t, J=8.0 Hz, 2H), 5.13 (dt, J=12.7, 5.2 Hz, 1H), 4.76 (d, J=12.4 Hz, 2H), 3.73 (q, J=6.3 Hz, 4H), 3.63 3.49 (i, 10H), 3.41 (q, J=6.6 Hz, 2H), 3.27-3.15 (i, 5H), 3.01-2.81 (i, 4H), 2.79-2.63 (i, 5H), 2.50 (t, J=6.8 Hz, 1H), 2.22 (d, J=2.3 Hz, 3H), 2.17-2.11 (m, 1H), 1.88-1.70 (m, 4H), 1.18 (d, J=1.2 Hz, 9H). LCMS 1112.74 (M+H).

Synthetic Example 35: Synthesis of dBET35

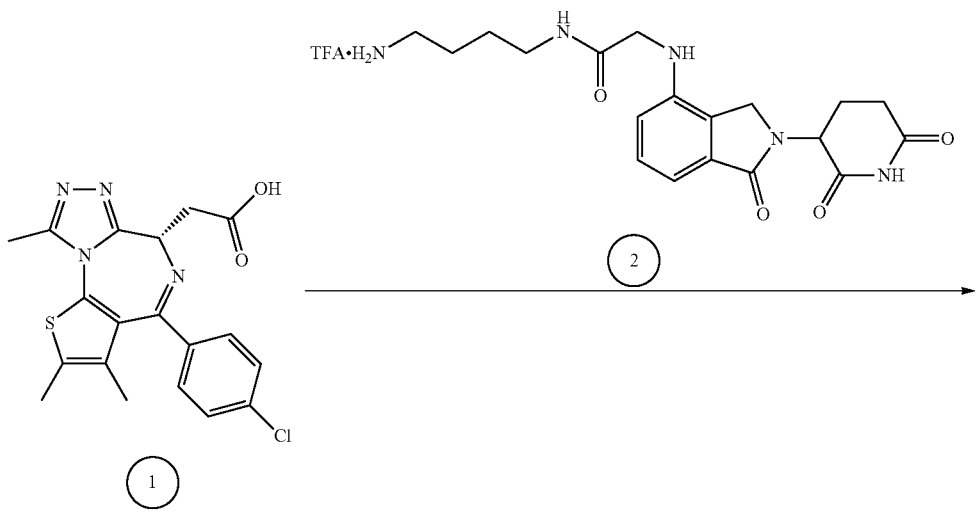

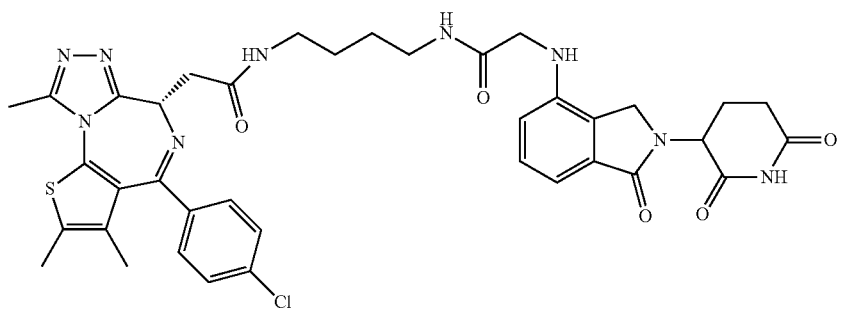

dBET35

A 0.1 M solution of N-(4-aminobutyl)-2-((2-(2,6-dioxopiperidin-3-yl)-1-oxoisoindolin-4-yl)amino)acetamide trifluoroacetate in DMF (185 microliters, 0.0185 mmol, 1 eq) was added to JQ-acid (7.4 mg, 0.0185 mmol, 1 eq). DIPEA (9.6 microliters, 0.0554 mmol, 3 eq) and HATU (7.0 mg, 0.0185 mmol, 1 eq) were then added and the mixture was stirred for 17 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-15% MeOH/DCM, 25 minute gradient) gave the desired product as a white solid (2.71 mg, 0.00351 mmol, 19%). $^1$H NMR (500 MHz, Methanol-$d_4$) δ 7.48-7.37 (m, 4H), 7.34 (t, J=7.8 Hz, 1H), 7.14 (dd, J=7.4, 2.4 Hz, 1H), 6.67 (d, J=8.1 Hz, 1H), 5.14 (td, J=13.5, 5.2 Hz, 1H), 4.66-4.60 (m, 1H), 4.59 (d, J=8.3 Hz, 2H), 4.43-4.31 (m, 2H), 3.88 (s, 2H), 3.25 (dd, J=14.8, 7.1 Hz, 4H), 2.94-2.72 (m, 3H), 2.68 (d, J=4.9 Hz, 3H), 2.49-2.40 (m, 4H), 2.21-2.12 (m, 1H), 1.68 (s, 3H), 1.53 (s, 4H). LCMS 770.51 (M+H).

Synthetic Example 36: Synthesis of dBET36

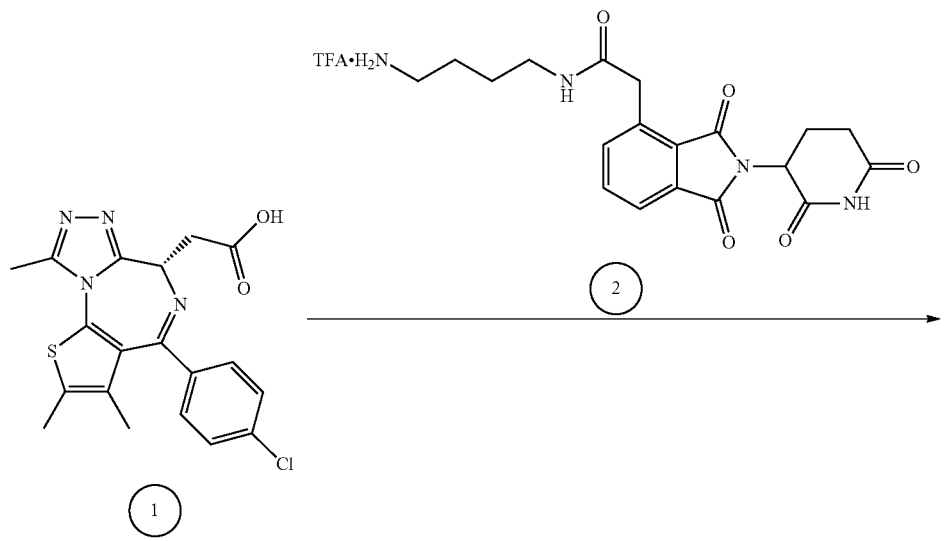

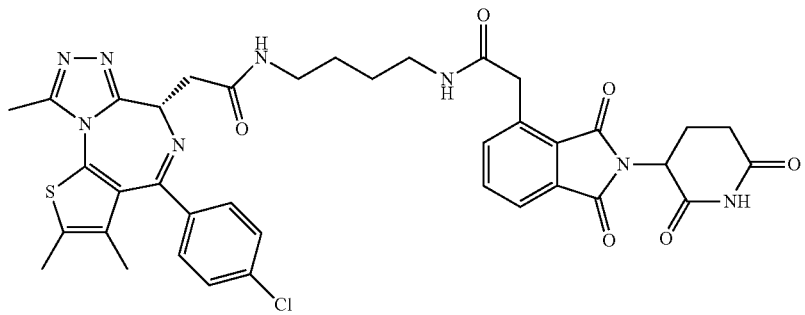

dBET36

A 0.1 M solution of N-(4-aminobutyl)-2-(2-(2,6-dioxopiperidin-3-yl)-1,3-dioxoisoindolin-4-yl)acetamide trifluoroacetate in DMF (222 microliters, 0.0222 mmol, 1 eq) was added to JQ-acid (8.9 mg, 0.0222 mmol, 1 eq). DIPEA (11.6 microliters, 0.0666 mmol, 3 eq) and HATU (8.4 mg, 0.0222 mmol, 1 eq) were then added and the mixture was stirred for 17.5 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-15% MeOH/DCM, 25 minute gradient) gave the desired product as a white solid (12.42 mg, 0.0156 mmol, 70%). $^1$H NMR (500 MHz, Methanol-$d_4$) δ 7.80-7.74 (m, 2H), 7.68 (d, J=6.8 Hz, 1H), 7.42 (q, J=8.7 Hz, 4H), 5.11 (dt, J=12.3, 4.6 Hz, 1H), 4.63 (dd, J=8.8, 5.5 Hz, 1H), 4.10-4.00 (m, 2H), 3.39 (ddd, J=14.9, 8.8, 2.5 Hz, 1H), 3.30-3.21 (m, 5H), 2.88-2.76 (m, 1H), 2.74-2.65 (m, 5H), 2.44 (s, 3H), 2.15-2.08 (m, 1H), 1.69 (s, 3H), 1.63-1.55 (m, 4H). LCMS 769.49 (M+H).

Synthetic Example 37: Synthesis of dBET37 sodium sulfate, filtered and concentrated under reduced pressure. Purification by column chromatography (ISCO, 4 g silica column, 0-15% MeOH/DCM, 25 minute gradient) gave the desired product as a white solid (11.83 mg, 0.0151 mmol, 77%). $^1$H NMR (500 MHz, Methanol-$d_4$) δ 7.78-7.74 (m, 2H), 7.71 (dd, J=5.3, 3.5 Hz, 1H), 7.42 (q, J=8.5 Hz, 4H), 5.13 (dd, J=12.6, 5.5 Hz, 1H), 4.82 (s, 2H), 4.63 (dd, J=8.8, 5.5 Hz, 1H), 3.40 (ddd, J=15.0, 8.8, 1.6 Hz, 1H), 3.30-3.21 (m, 3H), 2.86 (ddd, J=18.4, 14.6, 4.8 Hz, 1H), 2.74 (ddd, J=13.8, 10.1, 2.8 Hz, 2H), 2.69 (s, 3H), 2.44 (s, 3H), 2.30 (t, J=7.4 Hz, 2H), 2.13 (dtd, J=12.9, 4.9, 2.3 Hz, 1H), 1.74-1.64 (m, 5H), 1.59 (p, J=7.0 Hz, 2H), 1.46-1.38 (m, 2H). LCMS 783.47 (M+H).

Synthetic Example 38: Synthesis of dBET38

Step 1: Synthesis of tert-butyl (3-(3-(2-((2-(2,6-dioxopiperidin-3-yl)-1,3-dioxoisoindolin-4-yl)oxy)acetamido)propoxy)propyl)carbamate tert-butyl (3-(3-aminopropoxy)propyl)carbamate (134.5 mg, 0.579 mmol, 1 eq) was dissolved in DMF (5.79 ml, 0.05

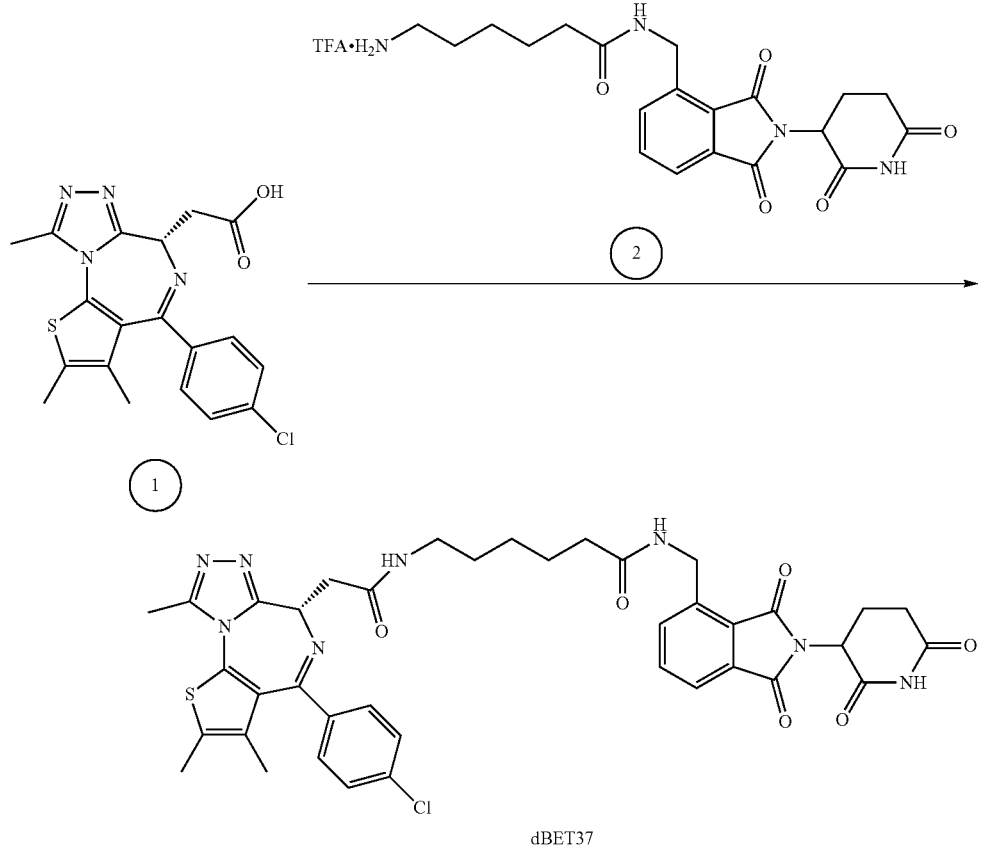

dBET37

A 0.1 M solution of 6-amino-N-((2-(2,6-dioxopiperidin-3-yl)-1,3-dioxoisoindolin-4-yl)methyl)hexanamide trifluoroacetate in DMF (195 microliters, 0.0195 mmol, 1 eq) was added to JQ-acid (7.8 mg, 0.0195 mmol, 1 eq). DIPEA (10.2 microliters, 0.0584 mmol, 3 eq) and HATU (7.4 mg, 0.0195 mmol, 1 eq) were then added and the mixture was stirred for 18 hours at room temperature. The mixture was then diluted with EtOAc and washed with saturated sodium bicarbonate, water and brine. The organic layer was then dried over M) then added to 2-((2-(2,6-dioxopiperidin-3-yl)-1,3-dioxoisoindolin-4-yl)oxy)acetic acid (192.38 mg, 0.579 mmol, 1 eq). DIPEA (0.28 ml, 1.74 mmol, 3 eq) and HATU (153.61 mg, 0.579 mmol, 1 eq) were added and the mixture was stirred for 18 hours at room temperature. The mixture was then diluted with EtOAc and washed with saturated sodium bicarbonate, water then brine. The organic layer was dried over sodium sulfate, filtered and condensed to give a yellow oil (157.1 mg). The crude material was purified by column chromatography (ISCO, 12 g silica column, 0 to 15% MeOH/DCM 25 minute gradient) to give a yellow oil (121.3 mg, 0.222 mmol, 38.27%). $^1$H NMR (400 MHz, Methanol-$d_4$) δ 7.78 (dd, J=8.4, 7.4 Hz, 1H), 7.50 (d, J=7.3 Hz, 1H), 7.41 (d, J=8.5 Hz, 1H), 5.13 (dd, J=12.4, 5.5 Hz, 1H), 4.75 (s, 2H), 3.53-3.37 (m, 6H), 3.14-3.07 (m, 2H), 2.94-2.88 (m, 1H), 2.79-2.68 (m, 2H), 2.16 (ddd, J=12.8, 6.6, 2.7 Hz, 1H), 1.81 (p, J=6.4 Hz, 2H), 1.73-1.65 (m, 2H), 1.40 (s, 9H). LCMS 547.6 (M+H).

Step 2: Synthesis of N-(3-(3-aminopropoxy)propyl)-2-((2-(2,6-dioxopuperidin-3-yl)-1,3-dioxoisoindolin-4-yl)oxy)acetamide trifluoroacetate salt TFA (2.22 ml, 0.1 M) was added to tert-butyl (3-(3-(2-((2-(2,6-dioxopiperidin-3-yl)-1,3-dioxoisoindolin-4-yl)oxy)acetamido)propoxy)propyl)carbamate (121.3 mg, 0.222 mmol, 1 eq) and the mixture was stirred at 50° C. for 2 hours. The mixture was then dissolved in MeOH and concentrated under reduced pressure to give a brown oil (114.1 mg) that was carried forward without further purification. $^1$H NMR (400 MHz, Methanol-$d_4$) δ 7.81-7.74 (m, 1H), 7.50 (d, J=7.3 Hz, 1H), 7.41 (d, J=8.5 Hz, 1H), 5.12 (dd, J=12.7, 5.5 Hz, 1H), 4.76 (s, 2H), 3.57-3.52 (m, 2H), 3.48 (t, J=5.9 Hz, 2H), 3.40 (t, J=6.6 Hz, 2H), 3.06 (t, J=6.5 Hz, 2H), 2.87 (ddd, J=14.1, 10.1, 7.0 Hz, 1H), 2.79-2.65 (m, 2H), 2.15 (dtd, J=12.8, 5.5, 2.6 Hz, 1H), 1.92 (dt, J=11.7, 5.9 Hz, 2H), 1.81 (p, J=6.3 Hz, 2H). LCMS 447.2 (M+H).

Step 3: Synthesis of dBET38

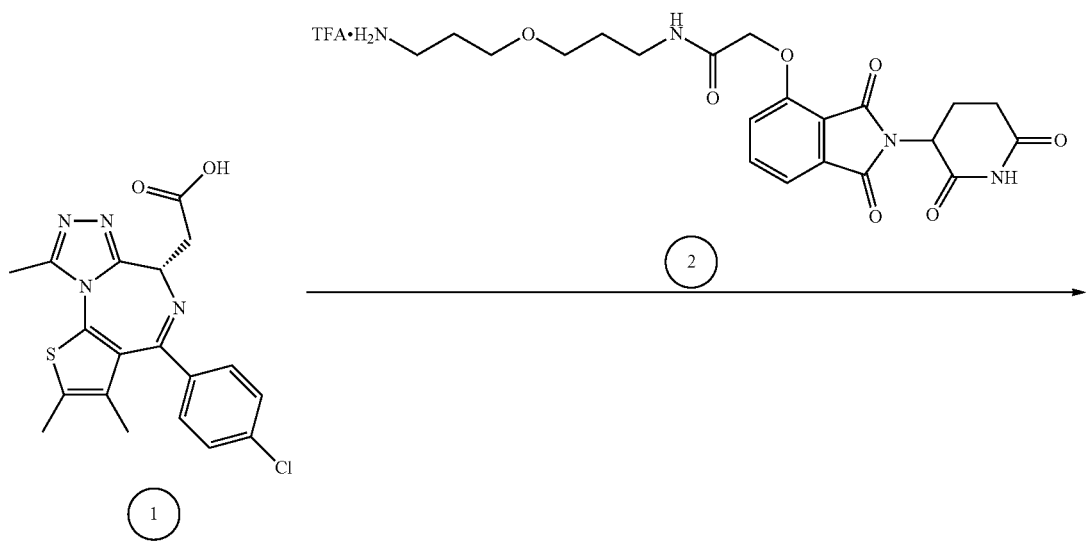

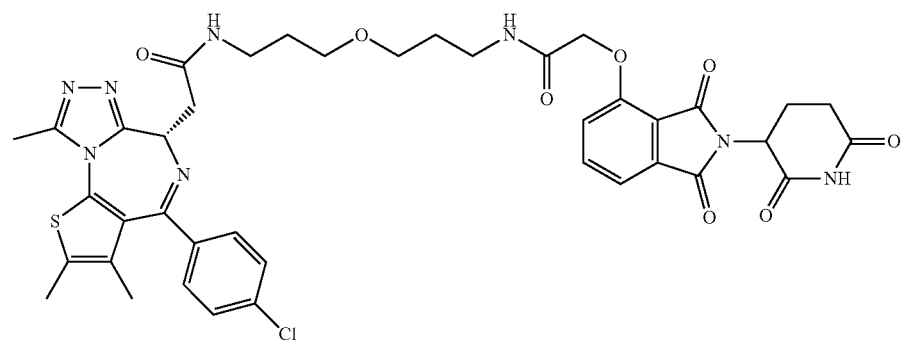

dBET38

A 0.1 M solution of N-(3-(3-aminopropoxy)propyl)-2-((2-(2,6-dioxopiperidin-3-yl)-1,3-dioxoisoindolin-4-yl)oxy) acetamide trifluoroacetate in DMF (0.215 mL, 0.0215 mmol, 1 eq) was added to JQ-acid (8.6 mg, 0.0215 mmol, 1 eq) at room temperature. DIPEA (11.2 microliters, 0.0644 mmol, 3 eq) and HATU (8.2 mg, 0.0215 mmol, 1 eq) were added. After 19 hours, the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-15% MeOH/DCM, 25 minute gradient) gave the desired product as a cream colored solid (10.6 mg, 0.0127 mmol, 59%). $^1$H NMR (500 MHz, Methanol-$d_4$) δ 7.79-7.74 (m, 1H), 7.50 (d, J=8.1 Hz, 1H), 7.46-7.36 (m, 5H), 5.11 (ddd, J=12.4, 5.5, 1.7 Hz, 1H), 4.73 (s, 2H), 4.62 (ddd, J=8.7, 5.4, 1.4 Hz, 1H), 3.50 (q, J=6.3 Hz, 4H), 3.43 (t, J=6.5 Hz, 2H), 3.41-3.32 (m, 3H), 3.29-3.24 (m, 1H), 2.85 (ddd, J=18.3, 14.6, 4.2 Hz, 1H), 2.77-2.65 (m, 5H), 2.43 (s, 3H), 2.17-2.09 (m, 1H), 1.80 (h, J=6.4 Hz, 4H), 1.68 (s, 3H). LCMS 829.32 (M+H).

Synthetic Example 39: Synthesis of dBET39

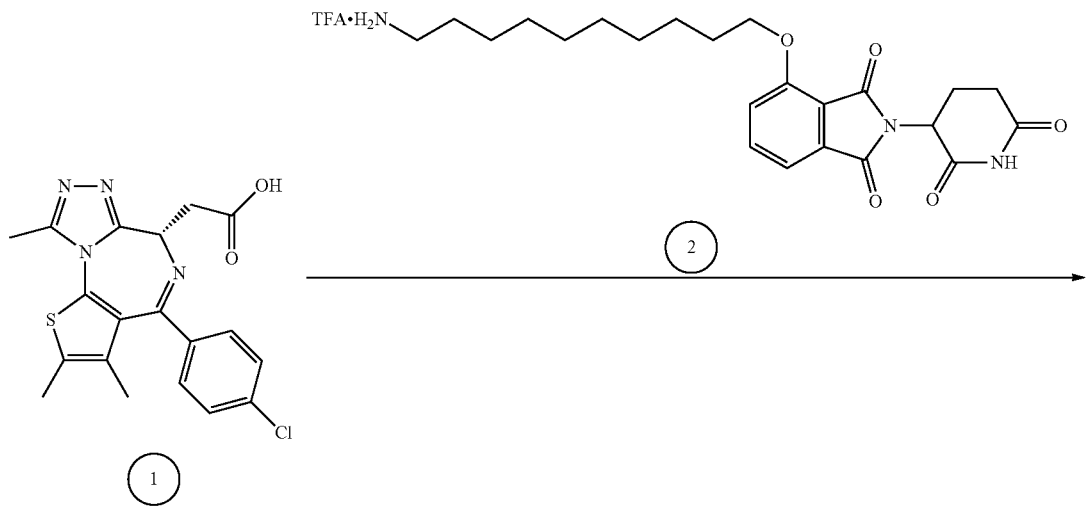

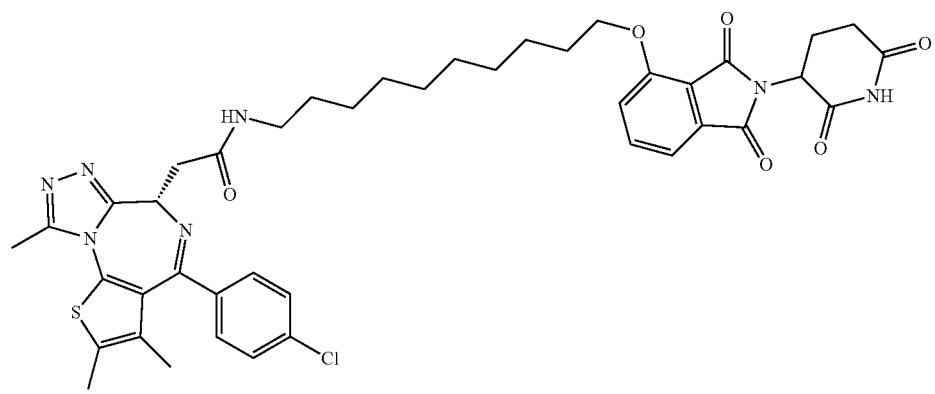

dBET39

A 0.1 M solution of 4-(2-(2-(21-aminodecyl)oxy)-2-(2,6-dioxopiperidin-3-yl)isoindoline-1,3-dione trifluoroacetate in DMF (0.212 mL, 0.0212 mmol, 1 eq) was added to JQ-acid (8.5 ig, 0.0212 mmol, 1 eq) at room temperature. DIPEA (11.1 microliters, 0.0636 mmol, 3 eq) and HATU (8.1 mg, 0.0212 mmol, 1 eq) were added. After 19 hours, the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-15% MeOH/DCM, 25 minute gradient) and preparative PLC gave the desired product (0.39 mg, 0.00048 mmol, 2.30). $^1$H NMR (500 MHz, Methanol-$d_4$) δ 7.77-7.73 (m, 1H), 7.56-7.31 (i, 6H), 5.11-5.06 (i, 1H), 4.62 (dd, J=9.2, 5.0 Hz, 1H), 4.58 (s, 2H), 4.21 (t, J=6.3 Hz, 2H), 3.42-3.38 (m, 1H), 3.24-3.20 (m, 1H), 2.90-2.68 (i, 6H), 2.45 (d, J=6.7 Hz, 3H), 2.11 (s, 1H), 1.83 (dd, J=14.7, 6.6 Hz, 2H), 1.70 (s, 3H), 1.61-1.49 (m, 4H), 1.32 (d, J=23.2 Hz, 10H). LCMS 812.60 (M+H).

Synthetic Example 40: Synthesis of dBET4O 0-10% MeOH/DCM, 25 minute gradient) and preparative HPLC gave the desired product as a brown oil (4.74 mg, 0.00601 mmol, 25%). $^1$H NMR (500 MHz, Methanol-$d_4$) δ 7.77-7.67 (m, 1H), 7.52-7.36 (m, 5H), 5.09-5.03 (m, 1H), 4.64 (d, J=4.8 Hz, 1H), 4.40-4.32 (m, 2H), 3.97-3.88 (m, 2H), 3.81-3.74 (m, 2H), 3.69-3.60 (m, 5H), 3.55-3.38 (m, 4H), 2.89-2.54 (m, 6H), 2.45 (d, J=5.9 Hz, 3H), 2.11 (s, 1H), 1.70 (d, J=8.6 Hz, 3H). LCMS 788.42 (M+H).

Synthetic Example 41: Synthesis of dBET41

Step 1: Synthesis of tert-butyl (4-((2-((2-(2,6-dioxopiperidin-3-yl)-1,3-dioxoisoindolin-4-yl)oxy)acetamido)methyl)benzyl)carbamate tert-butyl (4-(aminomethyl)benzyl)carbamate (183.14 mg, 0.755 mmol, 1 eq) was dissolved in DMF (15.1 ml, 0.05 M) and added to 2-((2-(2,6-dioxopiperidin-3-yl)-1,3-dioxoisoindolin-4-yl)oxy)acetic acid (250.90 mg, 0.755 mmol, 1 eq). DIPEA (0.374 ml, 2.265 mmol, 3 eq) and HATU (296.67 mg, 0.755 mmol, 1 eq) were added and the mixture

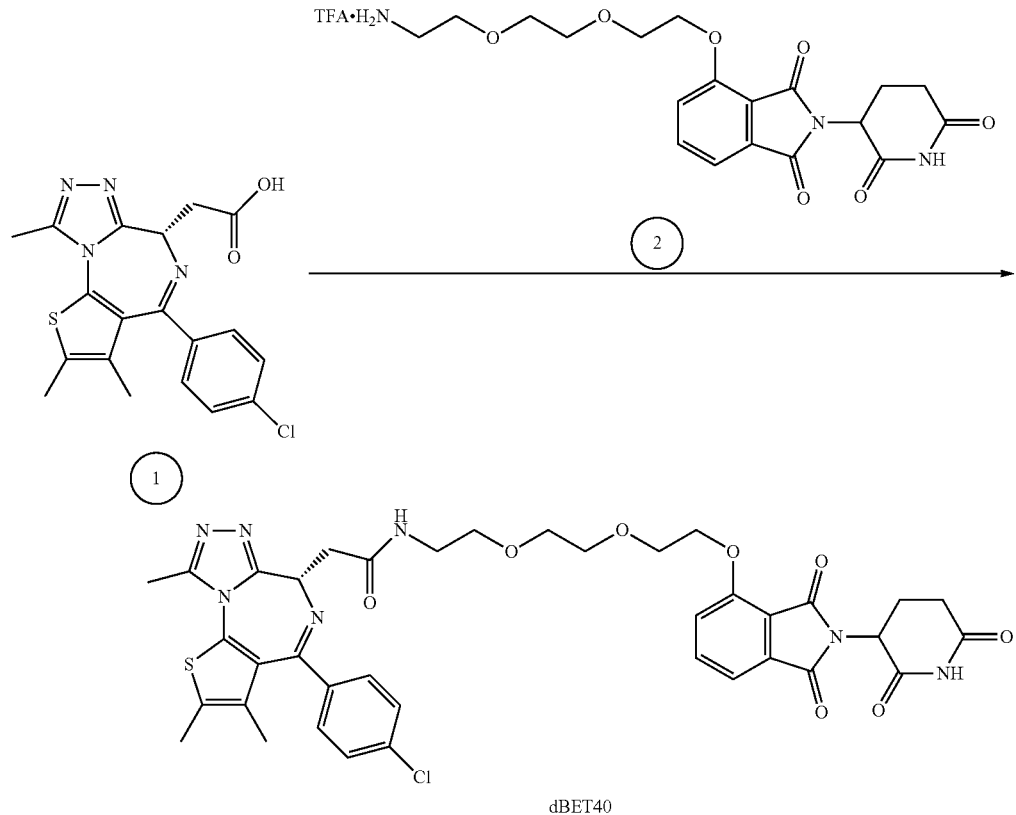

dBET40

A 0.1 M solution of 4-(2-(2-(2-aminoethoxy)ethoxy)ethoxy)-2-(2,6-dioxopiperidin-3-yl)isoindoline-1,3-dione trifluoroacetate in DMF (0.242 mL, 0.0242 mmol, 1 eq) was added to JQ-acid (9.7 mg, 0.0242 mmol, 1 eq) at room temperature. DIPEA (12.6 microliters, 0.0726 mmol, 3 eq) and HATU (9.2 mg, 0.0242 mmol, 1 eq) were added. After 22 hours, the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, was stirred for 20 hours at room temperature. The mixture was then diluted with EtOAc and washed with saturated sodium bicarbonate, water then brine. The organic layer was dried over sodium sulfate, filtered and condensed to give a light brown oil. The crude material was purified by column chromatography (ISCO, 12 g silica column, 0 to 15% MeOH/DCM 25 minute gradient) to give a light brown oil (373.1 mg, 0.678 mmol, 89.8%). $^1$H NMR (500 MHz, DMSO-$d_6$) δ 11.10 (s, 2H), 8.48 (t, J=5.8 Hz, 1H), 7.80 (dd, J=8.4, 7.3 Hz, 1H), 7.49 (d, J=7.2 Hz, 1H), 7.40 (d, J=8.6 Hz, 1H), 7.26-7.08 (m, 4H), 5.11 (dd, J=12.9, 5.4 Hz, 1H), 4.86 (s, 2H), 4.33 (d, J=3.9 Hz, 2H), 4.09 (d, J=5.3 Hz, 2H), 2.65-2.51 (m, 3H), 2.07-1.99 (m, 1H), 1.38 (s, 9H). LCMS 551.5 (M+H).

Step 2: Synthesis of N-(4-(aminomethyl)benzyl)-2-((2-(2,6-dioxopiperidin-3-yl)-1,3-dioxoisoindolin-4-yl)oxy)acetamide trifluoracetate salt TFA (6.77 ml, 0.1 M) was added to tert-butyl (4-((2-((2-(2,6-dioxopiperidin-3-yl)-1,3-dioxoisoindolin-4-yl)oxy)acetamido)methyl)benzyl)carbamate (373.1 mg, 0.677 mmol, 1 eq) and the mixture was stirred at 50° C. for 1.5 hours. The mixture was then dissolved in MeOH and concentrated under reduced pressure to give a brown oil (270.29 mg) that was carried forward without further purification. ¹H NMR (500 MHz, DMSO-d₆) δ 11.11 (s, 1H), 8.55 (t, J=6.2 Hz, 1H), 8.07 (s, 3H), 7.81 (dd, J=8.5, 7.3 Hz, 1H), 7.51 (d, J=7.2 Hz, 1H), 7.40 (dd, J=14.9, 8.3 Hz, 3H), 7.31 (d, J=8.2 Hz, 2H), 5.11 (dd, J=12.9, 5.4 Hz, 1H), 4.87 (s, 2H), 4.37 (d, J=6.1 Hz, 2H), 4.01 (q, J=5.8 Hz, 2H), 2.66-2.51 (m, 3H), 2.07-1.99 (m, 1H). LCMS 451.3 (M+H).

Step 3: Synthesis of dBET41

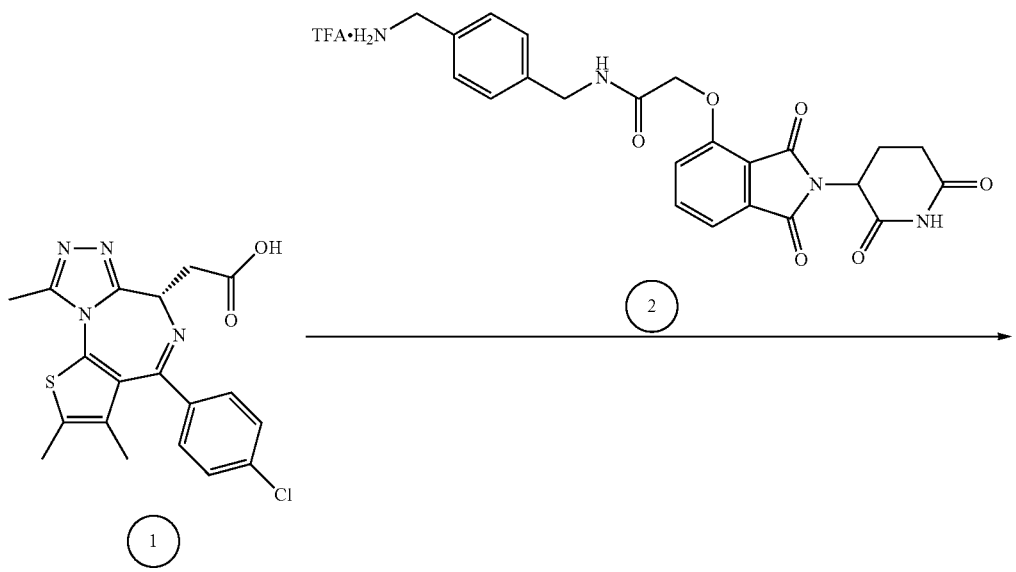

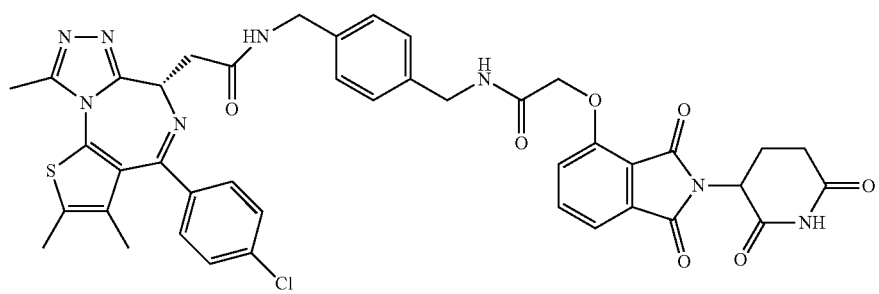

dBET41

A 0.1 M solution of N-(4-(aminomethyl)benzyl)-2-((2-(2,6-dioxopiperidin-3-yl)-1,3-dioxoisoindolin-4-yl)oxy)acetamide trifluoroacetate in DMF (0.237 mL, 0.0237 mmol, 1 eq) was added to JQ-acid (9.5 mg, 0.0237 mmol, 1 eq) at room temperature. After 23 hours, the mixture was diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a cream colored solid (11.8 mg, 0.0142 mmol, 60%). 1H NMR (500 MHz, Methanol-$d_4$) δ 7.80-7.75 (m, 1H), 7.51 (dd, J=7.3, 1.5 Hz, 1H), 7.41 (d, J=8.4 Hz, 1H), 7.36 (d, J=2.2 Hz, 4H), 7.34-7.28 (m, 4H), 5.10-5.00 (m, 1H), 4.82 (s, 2H), 4.67-4.64 (m, 1H), 4.61-4.42 (m, 4H), 4.34 (dd, J=14.9, 12.8 Hz, 1H), 3.49 (ddd, J=14.8, 9.5, 5.2 Hz, 1H), 2.83-2.75 (m, 1H), 2.73-2.61 (i, 5H), 2.44-2.39 (m, 3H), 2.06 (ddq, J=9.8, 4.7, 2.6 Hz, 1H), 1.66 (d, J=4.2 Hz, 3H). LCMS 832.92 (M+H).

Synthetic Example 42: Synthesis of dBET42

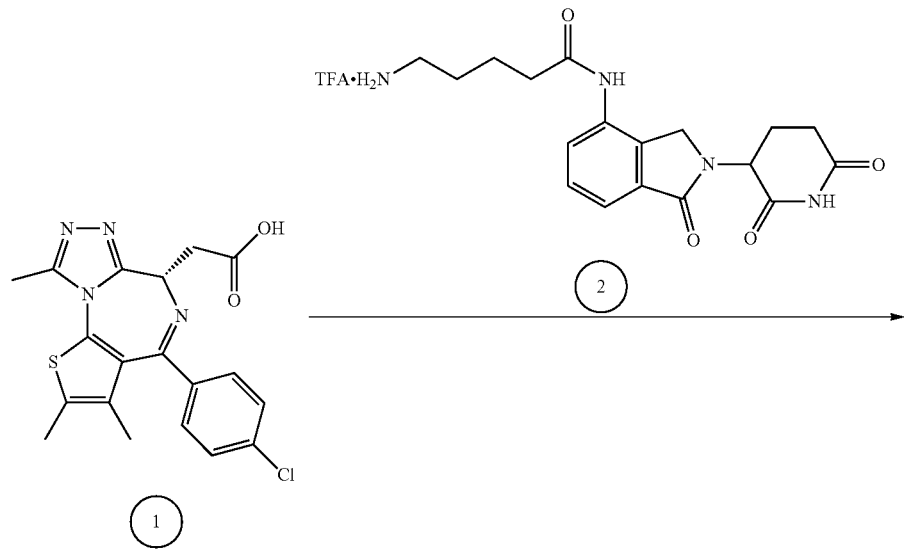

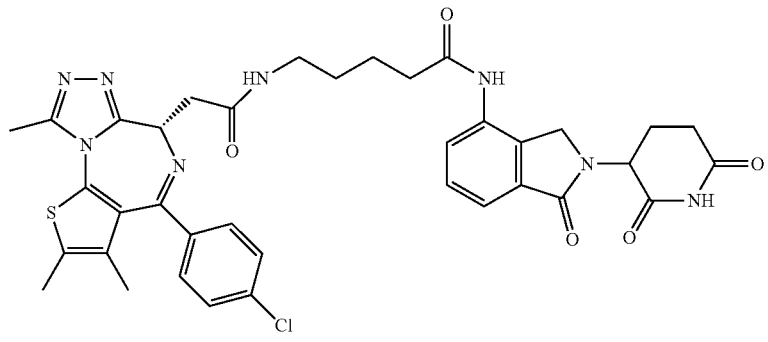

dBET42

A 0.1 M solution of 5-amino-N-(2-(2,6-dioxopiperidin-3-yl)-1-oxoisoindolin-4-yl)pentanamide trifluoroacetate in DMF (222 microliters, 0.0222 mmol, 1 eq) was added to JQ-acid (8.9 mg, 0.0222 mmol, 1 eq). DIPEA (11.6 microliters, 0.0666 mmol, 3 eq) and HATU (8.4 mg, 0.0222 mmol, 1 eq) were then added and the mixture was stirred for 24 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-10% MeOH/DCM, 25 minute gradient) gave the desired product as a white solid (12.23 mg, 0.0165 mmol, 74%). $^1$H NMR (500 MHz, Methanol-$d_4$) δ 7.76-7.71 (m, 1H), 7.66-7.62 (m, 1H), 7.51 (td, J=7.8, 2.5 Hz, 1H), 7.45-7.35 (m, 4H), 5.11 (ddd, J=13.2, 11.3, 5.2 Hz, 1H), 4.63 (ddd, J=8.8, 5.7, 3.2 Hz, 1H), 4.47 (s, 2H), 3.45-3.32 (m, 3H), 3.30-3.27 (m, 1H), 2.90-2.80 (m, 1H), 2.73-2.63 (m, 4H), 2.49 (t, J=7.4 Hz, 2H), 2.46-2.38 (m, 4H), 2.11 (ddtd, J=12.8, 10.5, 5.3, 2.3 Hz, 1H), 1.84-1.75 (m, 2H), 1.66 (dd, J=16.2, 7.6 Hz, 5H). LCMS 741.46 (M+H).

Synthetic Example 43: Synthesis of dBET43

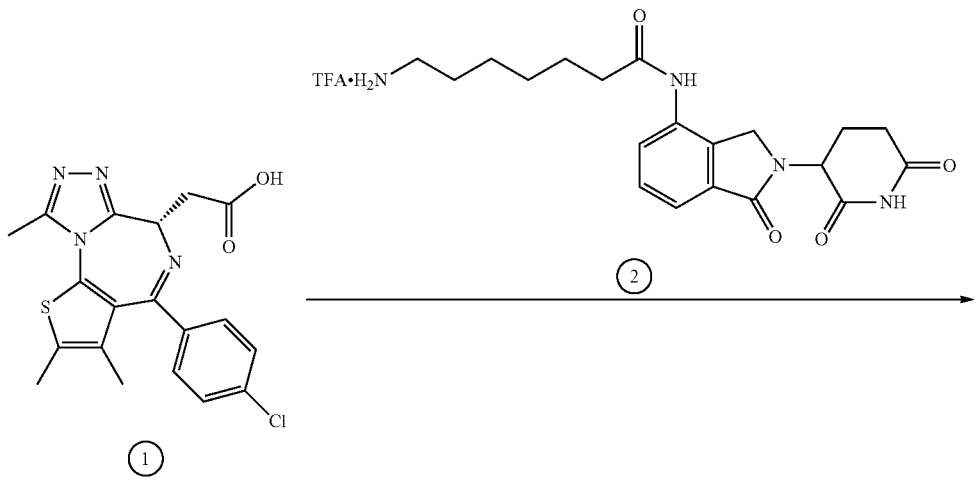

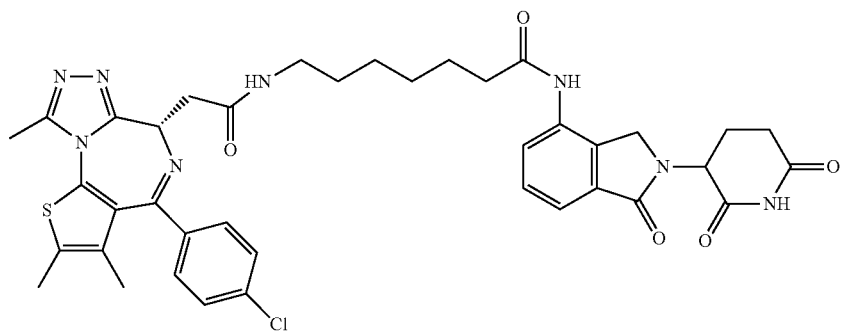

dBET43

A 0.1 M solution of 7-amino-N-(2-(2,6-dioxopiperidin-3-yl)-1-oxoisoindolin-4-yl)heptanamide trifluoroacetate in DMF (227 microliters, 0.0227 mmol, 1 eq) was added to JQ-acid (9.1 mg, 0.0227 mmol, 1 eq). DIPEA (11.9 microliters, 0.0681 mmol, 3 eq) and HATU (8.6 mg, 0.0227 mmol, 1 eq) were then added and the mixture was stirred for 25.5 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-10% MeOH/DCM, 25 minute gradient) gave the desired product as an off-white solid (12.58 mg, 0.0164 mmol, 72%). $^1$H NMR (500 MHz, Methanol-$d_4$) δ 7.71 (d, J=7.9 Hz, 1H), 7.64 (d, J=7.4 Hz, 1H), 7.51 (t, J=7.8 Hz, 1H), 7.46-7.38 (m, 4H), 5.14 (ddd, J=13.3, 5.2, 2.2 Hz, 1H), 4.62 (ddd, J=8.6, 5.6, 2.1 Hz, 1H), 4.49-4.45 (m, 2H), 3.39 (ddd, J=14.9, 8.7, 1.3 Hz, 1H), 3.30-3.24 (m, 3H), 2.93-2.83 (m, 1H), 2.79-2.65 (m, 4H), 2.50-2.40 (m, 6H), 2.16 (ddq, J=9.9, 5.2, 2.6 Hz, 1H), 1.78-1.70 (m, 2H), 1.68 (d, J=2.1 Hz, 3H), 1.63-1.57 (m, 2H), 1.50-1.42 (m, 4H). LCMS 769.55 (M+H).

Synthetic Example 44: Synthesis of dBET44

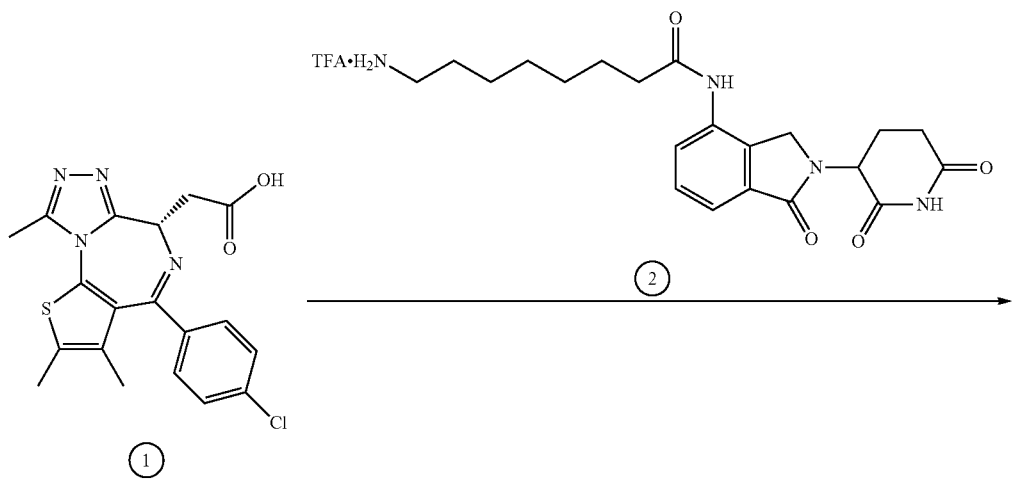

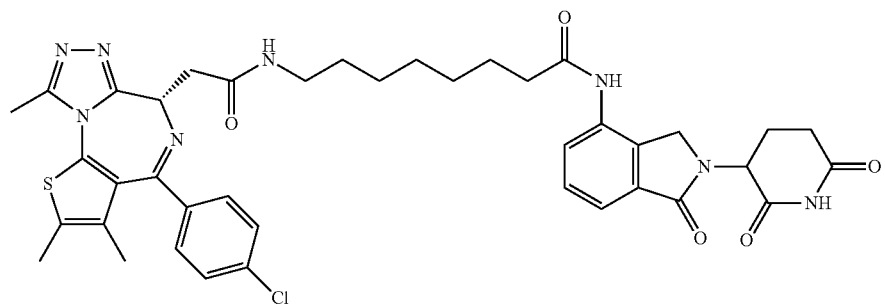

dBET44

A 0.1 M solution of 8-amino-N-(2-(2,6-dioxopiperidin-3-yl)-1-oxoisoindolin-4-yl)octanamide trifluoroacetate in DMF (217 microliters, 0.0217 mmol, 1 eq) was added to JQ-acid (8.7 mg, 0.0217 mmol, 1 eq). DIPEA (11.3 microliters, 0.0651 mmol, 3 eq) and HATU (8.3 mg, 0.0217 mmol, 1 eq) were then added and the mixture was stirred for 20.5 hours at room temperature. The mixture was then diluted with EtOAc and washed with saturated sodium bicarbonate, water and brine. The organic layer was then dried over sodium sulfate, filtered and concentrated under reduced pressure. Purification by column chromatography (ISCO, 4 g silica column, 0-10% MeOH/DCM, 25 minute gradient) gave the desired product as an cream colored solid (14.28 mg, 0.0182 mmol, 84%). $^1$H NMR (500 MHz, Methanol-$d_4$) δ 7.72-7.68 (m, 1H), 7.64 (d, J=7.5 Hz, 1H), 7.51 (t, J=7.7 Hz, 1H), 7.46-7.39 (m, 4H), 5.14 (dt, J=13.3, 5.0 Hz, 1H), 4.62 (dd, J=8.8, 5.4 Hz, 1H), 4.48-4.44 (m, 2H), 3.40 (ddd, J=14.9, 8.8, 0.9 Hz, 1H), 3.26 (dt, J=13.2, 6.9 Hz, 3H), 2.88 (ddd, J=18.7, 13.5, 5.4 Hz, 1H), 2.75 (dddd, J=17.6, 7.1, 4.5, 2.4 Hz, 1H), 2.68 (d, J=2.2 Hz, 3H), 2.49-2.39 (m, 6H), 2.17 (ddt, J=9.8, 5.3, 2.3 Hz, 1H), 1.76-1.70 (m, 2H), 1.70-1.67 (m, 3H), 1.61-1.54 (m, 2H), 1.42 (s, 6H). LCMS 783.53 (M+H).

Synthetic Example 45: Synthesis of dBET45

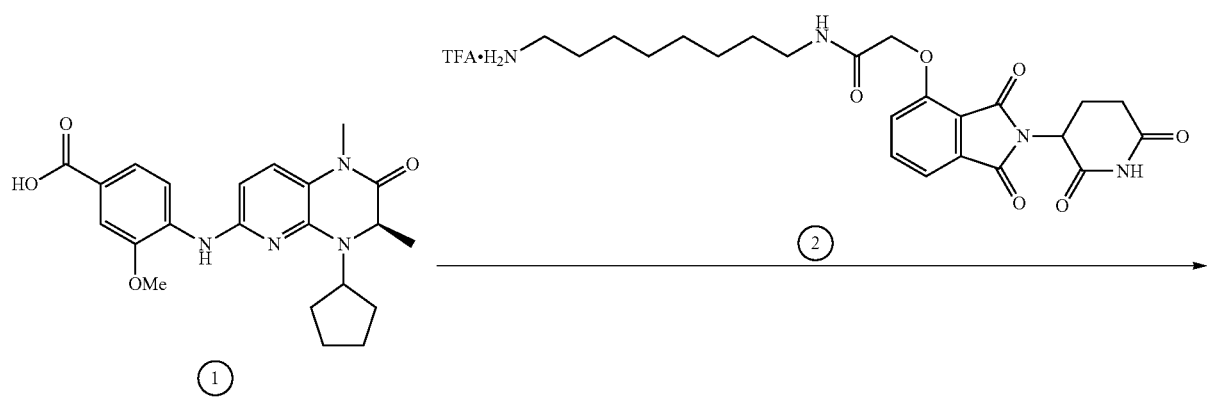

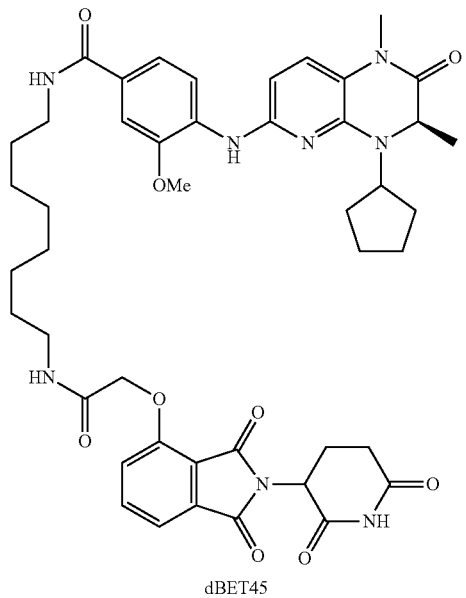

dBET45

A 0.1 M solution of N-(8-aminooctyl)-2-((2-(2,6-dioxopiperidin-3-yl)-1,3-dioxoisoindolin-4-yl)oxy)acetamide trifluoroacetate in DMF (268 microliters, 0.0268 mmol, 1 eq) was added to (R)-4-((4-cyclopentyl-1,3-dimethyl-2-oxo-1,2,3,4-tetrahydropyrido[2,3-b]pyrazin-6-yl)amino)-3-methoxybenzoic acid (11.0 mg, 0.0268 mmol, 1 eq) at room temperature. DIPEA (14.0 microliters, 0.0804 mmol, 3 eq) and HATU (10.2 mg, 0.0268 mmol, 1 eq) were then added and the mixture was stirred for 18.5 hours. The mixture was then diluted with methanol and purified by preparative HPLC to give the desired product as a dark brown solid (10.44 mg, 0.0108 mmol, 40%). $^1$H NMR (500 MHz, Methanol-$d_4$) δ 8.38 (d, J=8.4 Hz, 1H), 7.80-7.75 (m, 1H), 7.55-7.48 (m, 1H), 7.48-7.35 (m, 3H), 7.27 (d, J=8.3 Hz, 1H), 6.45 (d, J=8.2 Hz, 1H), 5.12 (dd, J=12.5, 5.5 Hz, 1H), 4.72 (d, J=5.1 Hz, 2H), 4.53 (s, 1H), 4.28 (d, J=6.8 Hz, 1H), 3.98 (d, J=4.1 Hz, 3H), 3.48-3.33 (m, 4H), 2.90-2.82 (m, 1H), 2.80-2.69 (m, 2H), 2.18-2.01 (m, 4H), 1.88-1.52 (m, 10H), 1.34 (d, J=42.9 Hz, 10H), 1.17 (d, J=6.8 Hz, 3H). LCMS 851.67 (M+H).

Synthetic Example 46: Synthesis of dBET46

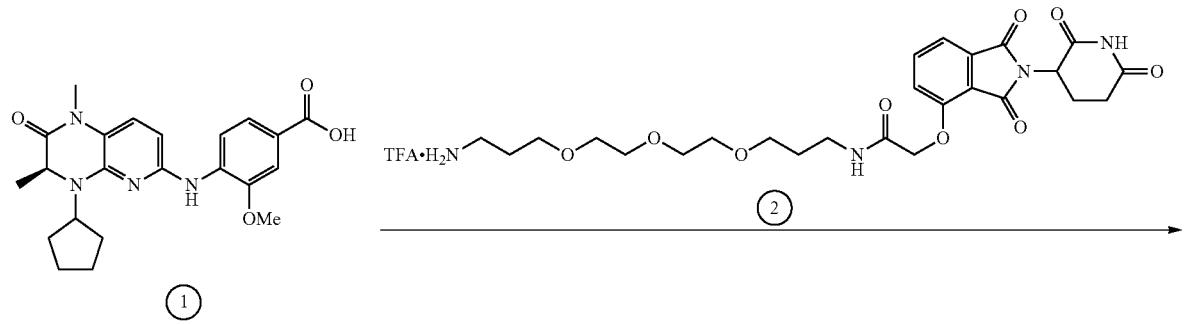

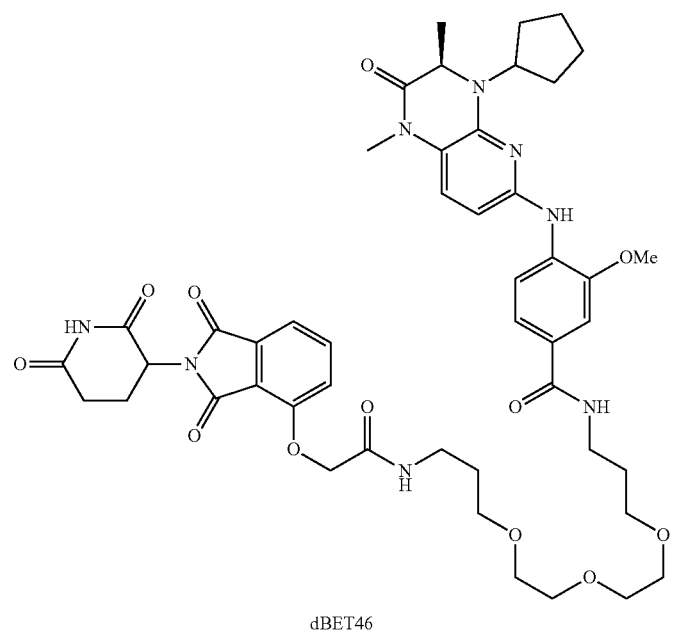

dBET46

A 0.1 M solution of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (256 microliters, 0.0256 mmol, 1 eq) was added to (R)-4-((4-cyclopentyl-1,3-dimethyl-2-oxo-1,2,3,4-tetrahydropyrido[2,3-b]pyrazin-6-yl)amino)-3-methoxybenzoic acid (10.5 mg, 0.0256 mmol, 1 eq) at room temperature. DIPEA (13.4 microliters, 0.0767 mmol, 3 eq) and HATU (9.7 mg, 0.0256 mmol, 1 eq) were then added and the mixture was stirred for 20 hours. The mixture was then diluted with methanol and purified by preparative HPLC to give the desired product as a dark brown solid (13.69 mg, 0.0132 mmol, 51%). $^1$H NMR (500 MHz, Methanol-$d_4$) δ 8.28-8.24 (m, 1H), 7.74-7.71 (m, 1H), 7.49 (dd, J=7.3, 3.7 Hz, 1H), 7.39-7.34 (m, 2H), 7.28-7.25 (m, 1H), 7.14-7.10 (m, 1H), 6.34 (d, J=8.3 Hz, 1H), 5.01-4.97 (m, 1H), 4.62 (s, 2H), 4.25 (q, J=6.7 Hz, 1H), 3.95 (d, J=5.4 Hz, 3H), 3.60 (ddd, J=9.0, 6.1, 1.6 Hz, 8H), 3.53-3.46 (m, 6H), 3.40-3.37 (m, 2H), 2.78 (td, J=11.1, 6.6 Hz, 3H), 2.16-2.00 (m, 4H), 1.84 (ddt, J=33.5, 13.0, 6.4 Hz, 7H), 1.75-1.60 (m, 6H), 1.17 (d, J=6.8 Hz, 3H). LCMS 927.74 (M+H).

Synthetic Example 47: Synthesis of dBET50

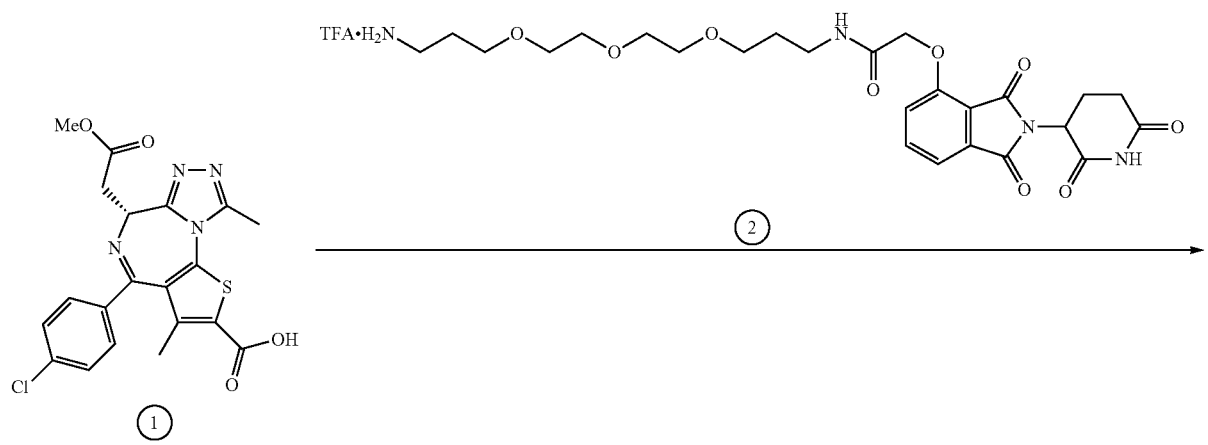

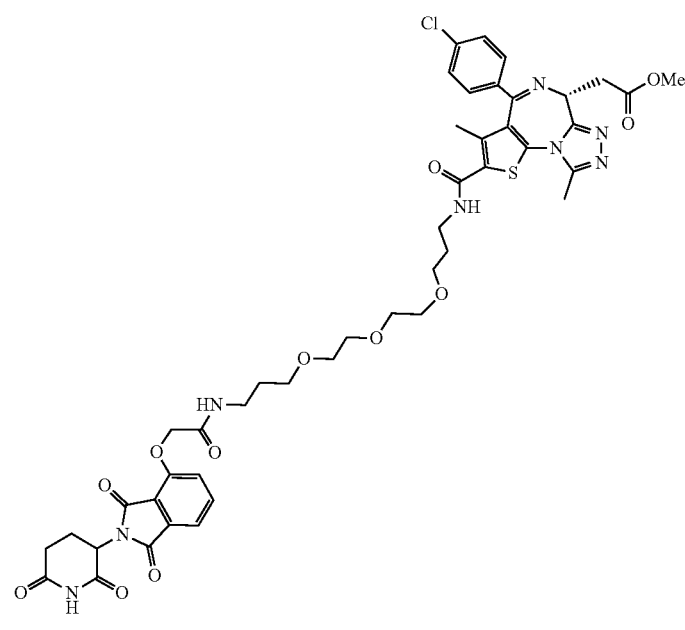

dBET50

A 0.1 M solution of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate in DMF (200 microliters, 0.0200 mmol, 1 eq) was added to (S)-4-(4-chlorophenyl)-6-(2-methoxy-2-oxoethyl)-3,9-dimethyl-6H-thieno[3,2-][1,2,4]triazolo[4,3-a][1,4]diazepine-2-carboxylic acid (8.9 mg, 0.020 mmol, 1 eq) at room temperature. DIPEA (10.5 microliters, 0.060 mmol, 3 eq) and HATU (7.6 mg, 0.020 mmol, 1 eq) were added. The mixture was then stirred for 17 hours, then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as a cream colored solid (9.31 mg, 0.00968 mmol, 48%). $^1$H NMR (500 MHz, Methanol-$d_4$) δ 7.82-7.78 (m, 1H), 7.52 (dd, J=7.1, 1.6 Hz, 1H), 7.49-7.40 (m, 5H), 5.10 (ddd, J=12.8, 5.5, 2.9 Hz, 1H), 4.74 (s, 2H), 4.67 (t, J=7.1 Hz, 1H), 3.76 (s, 3H), 3.62-3.50 (m, 14H), 3.49-3.43 (m, 2H), 3.40 (q, J=6.5 Hz, 2H), 2.87 (ddd, J=17.6, 14.0, 5.3 Hz, 1H), 2.79-2.67 (m, 5H), 2.12 (ddq, J=10.3, 5.4, 2.9 Hz, 1H), 2.00 (s, 3H), 1.86 (q, J=6.3 Hz, 2H), 1.80 (p, J=6.4 Hz, 2H). LCMS 961.67 (M+H).

Synthetic Example 48: Synthesis of dBET51

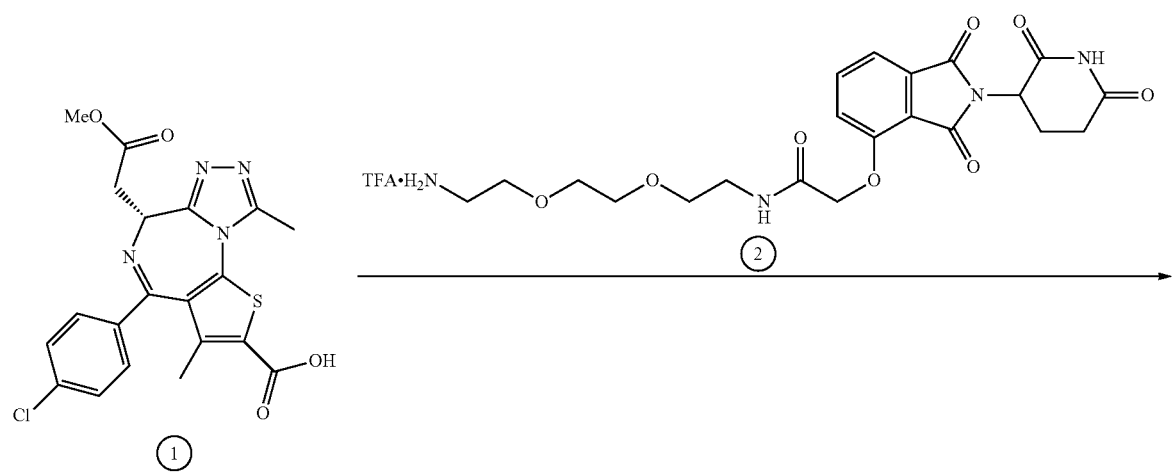

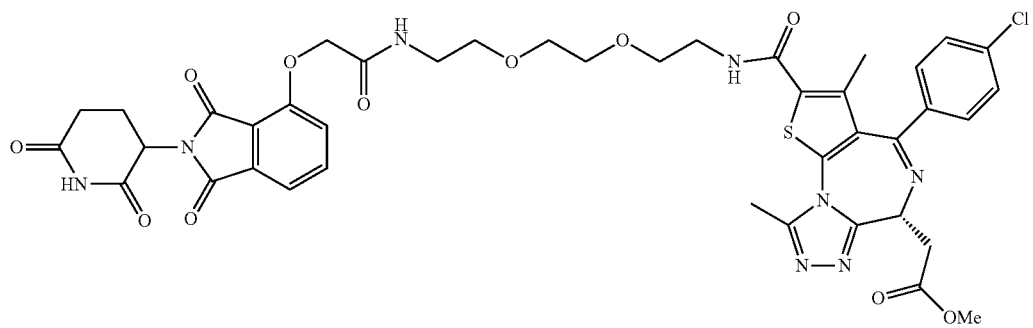

dBET51

A 0.1 M solution of N-(2-(2-(2-aminoethoxy)ethoxy)ethyl)-2-((2-(2,6-dioxopiperidin-3-yl)-1,3-dioxoisoindolin-4-yl)oxy)acetamide trifluoroacetate in DMF (200 microliters, 0.0200 mmol, 1 eq) was added to (S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxylic acid (8.9 mg, 0.020 mmol, 1 eq) at room temperature. DIPEA (10.5 microliters, 0.060 mmol, 3 eq) and HATU (7.6 mg, 0.020 mmol, 1 eq) were added. The mixture was then stirred for 17 hours, then diluted with EtOAc and washed with saturated sodium bicarbonate, water and brine. The organic layer was dried over sodium sulfate, filtered and concentrated under reduced pressure. Purification by column chromatography (ISCO, 4 g silica column, 0-10% MeOH/DCM, 25 minute gradient) gave the desired product as an off-white solid (8.38 mg, 0.00942 mmol, 47%). $^1$H NMR (500 MHz, Methanol-$d_4$) δ 7.80 (dd, J=8.4, 7.4 Hz, 1H), 7.52 (dd, J=7.2, 1.3 Hz, 1H), 7.48-7.38 (m, 5H), 5.08 (ddd, J=12.7, 5.5, 1.6 Hz, 1H), 4.74 (d, J=2.7 Hz, 2H), 4.66 (t, J=7.1 Hz, 1H), 3.75 (d, J=3.0 Hz, 3H), 3.65 (t, J=4.1 Hz, 6H), 3.59 (t, J=5.3 Hz, 2H), 3.57-3.49 (m, 4H), 3.49-3.40 (m, 2H), 2.93-2.84 (m, 1H), 2.78-2.64 (m, 5H), 2.15-2.09 (m, 1H), 2.00 (d, J=0.9 Hz, 3H). LCMS 889.58 (M+H).

Synthetic Example 49: Synthesis of dBET52

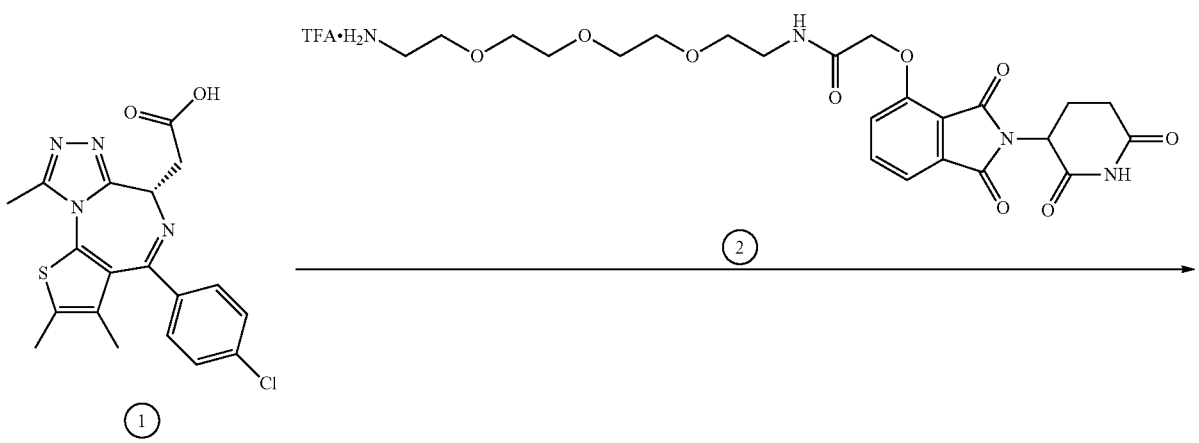

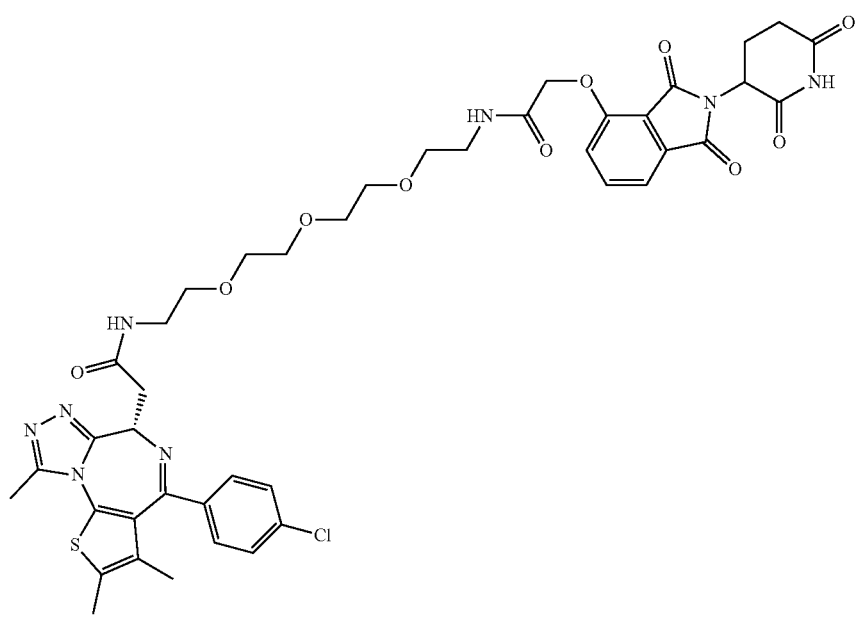

dBET52

A 0.1 M solution of N-(2-(2-(2-(2-aminoethoxy)ethoxy)ethoxy)ethyl)-2-((2-(2,6-dioxopiperidin-3-yl)-1,3-dioxoisoindolin-4-yl)oxy)acetamide trifluoroacetate in DMF (200 microliters, 0.020 mmol, 1 eq) was added to JQ-acid (8.0 mg, 0.020 mmol, 1 eq) at room temperature. DIPEA (10.5 microliters, 0.060 mmol, 3 eq) and HATU (7.6 mg, 0.020 mmol, 1 eq) were added. After 17.5 hours, the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-10% MeOH/DCM, 25 minute gradient) gave the desired product as a colorless residue (9.12 mg, 0.01025 mmol, 51%). $^1$H NMR (500 MHz, Methanol-$d_4$) δ 7.77 (t, J=7.9 Hz, 1H), 7.50 (dd, J=7.3, 1.5 Hz, 1H), 7.47-7.36 (m, 5H), 5.09 (ddd, J=13.0, 7.6, 5.5 Hz, 1H), 4.76 (s, 2H), 4.62 (dd, J=9.1, 5.1 Hz, 1H), 3.62 (ddt, J=17.3, 11.2, 6.5 Hz, 12H), 3.52-3.41 (m, 5H), 3.28 (d, J=5.1 Hz, 1H), 2.90-2.81 (m, 1H), 2.79-2.66 (m, 5H), 2.44 (s, 3H), 2.16-2.09 (m, 1H), 1.69 (s, 3H). LCMS 889.38 (M+H).

Synthetic Example 50: Synthesis of dBET53

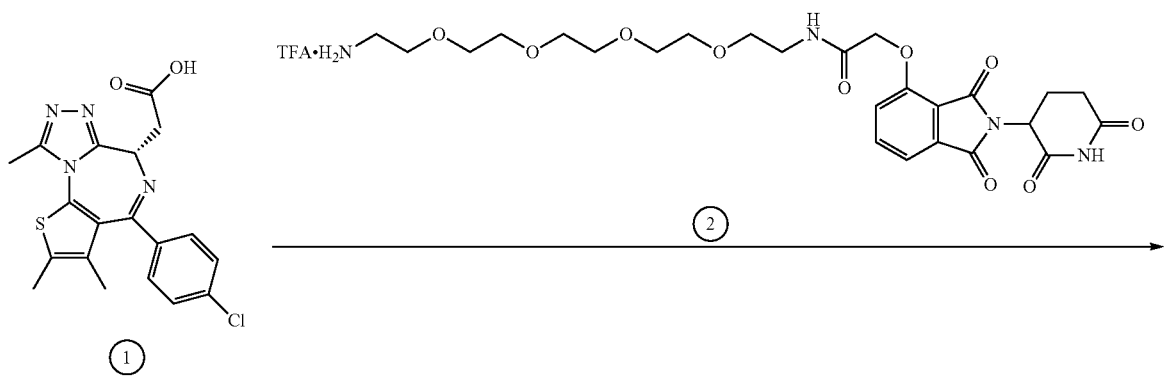

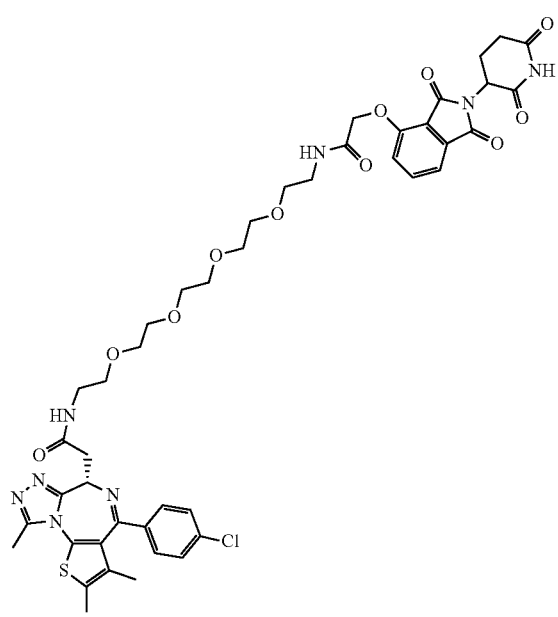

dBET53

A 0.1 M solution of N-(14-amino-3,6,9,12-tetraoxatetradecyl)-2-((2-(2,6-dioxopiperidin-3-yl)-1,3-dioxoisoindolin-4-yl)oxy)acetamide trifluoroacetate in DMF (200 microliters, 0.020 5 mmol, 1 eq) was added to JQ-acid (8.0 mg, 0.020 mmol, 1 eq) at room temperature. DIPEA (10.5 microliters, 0.060 mmol, 3 eq) and HATU (7.6 mg, 0.020 mmol, 1 eq) were added. After 17.5 hours, additional HATU (7.6 mg) and DIPEA (10.5 microliters were added) and the mixture was stirred for an additional 5 hours. The mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-10% MeOH/DCM, 25 minute gradient) gave the desired product (3.66 mg). 1H NMR (500 MHz, Methanol-$d_4$) 7.79 (dd, J=8.4, 7.4 Hz, 1H), 7.51 (d, J=7.3 Hz, 1H), 745 (d, J=7.7 Hz, 2H), 7.43-7.36 (m, 3H), 5.08 (ddd, J=12.7, 5.5, 2.2 Hz, 1H), 4.78-4.74 (m, 2H), 4.62 (dd, J=9.1, 5.1 Hz, 1H), 3.70-3.51 (m, 16H), 3.50-3.41 (m, 8H), 3.27 (dd, J=5.1, (m, 1H), 1.69 (s, 3H). LCMS 933.43 (M+H).

Synthetic Example 51: Synthesis of dBET54

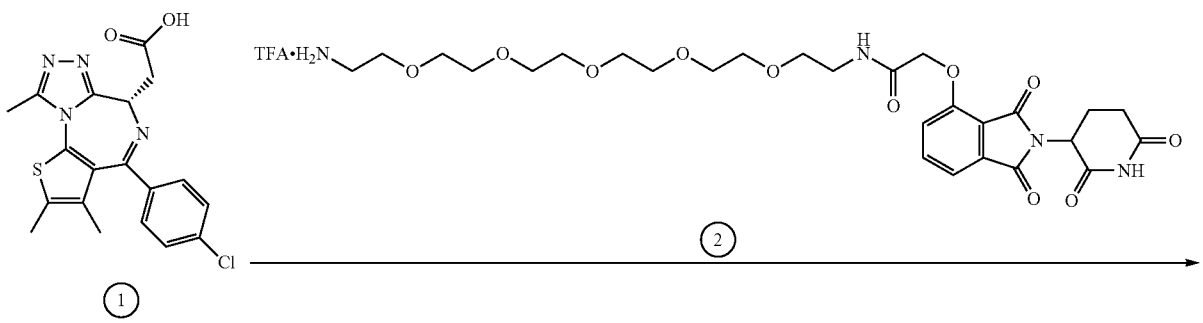

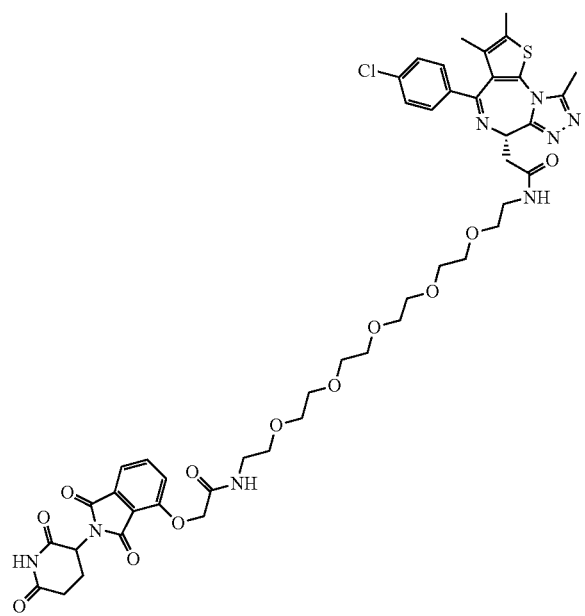

dBET54

A 0.1 M solution of N-(17-amino-3,6,9,12,15-pentaoxa-heptadecyl)-2-((2-(2,6-dioxopiperidin-3-yl)-1,3-dioxoisoindolin-4-yl)oxy)acetamide trifluoroacetate in DMF (200 microliters, 0.020 mmol, 1 eq) was added to JQ-acid (8.0 mg, 0.020 mmol, 1 eq) at room temperature. DIPEA (10.5 microliters, 0.060 mmol, 3 eq) and HATU (7.6 mg, 0.020 mmol, 1 eq) were added. After 16 hours the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-10% MeOH/DCM, 25 minute gradient) gave the desired product (6.27 mg, 0.00641 mmol, 32%). $^1$H NMR (500 MHz, Methanol-$d_4$) δ 7.81-7.76 (m, 1H), 7.51 (d, J=7.1 Hz, 1H), 7.47-7.38 (m, 5H), 5.09 (dd, J=12.6, 5.5 Hz, 1H), 4.77 (s, 2H), 4.62 (dd, J=8.8, 5.0 Hz, 1H), 3.67-3.55 (m, 20H), 3.46 (ddd, J=20.1, 10.2, 4.7 Hz, 5H), 3.28 (d, J=5.1 Hz, 1H), 2.91-2.83 (m, 1H), 2.78-2.68 (m, 5H), 2.44 (s, 3H), 2.16-2.10 (m, 1H), 1.72-1.66 (m, 3H). LCMS 977.50 (M+H).

Synthetic Example 52: Synthesis of dBET55

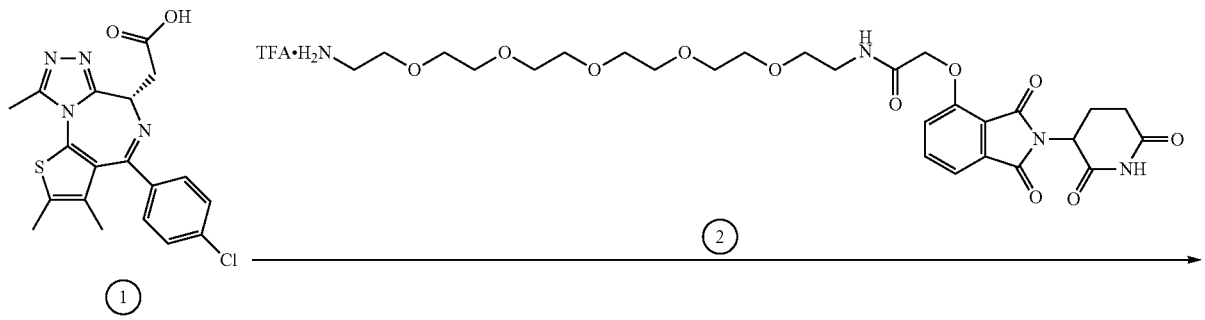

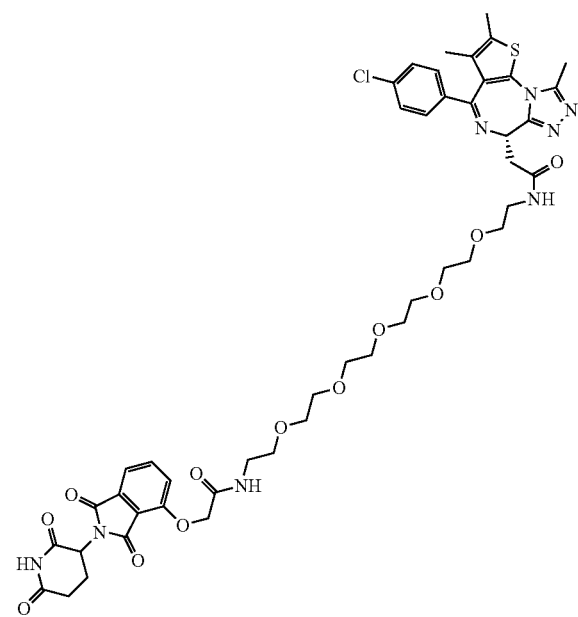

dBET55

A 0.1 M solution of N-(29-amino-3,6,9,12,15,18,21,24,27-nonaoxanonacosyl)-2-((2-(2,6-dioxopiperidin-3-yl)-1,3-dioxoisoindolin-4-yl)oxy)acetamide trifluoroacetate in DMF (200 microliters, 0.020 mmol, 1 eq) was added to JQ-acid (8.0 mg, 0.020 mmol, 1 eq) at room temperature. DIPEA (10.5 microliters, 0.060 mmol, 3 eq) and HATU (7.6 mg, 0.020 mmol, 1 eq) were added. After 18 hours the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-10% MeOH/DCM, 25 minute gradient) gave the desired product (10.55 mg, 0.00914 mmol, 46%). $^1$H NMR (500 MHz, Methanol-$d_4$) δ 7.82 (dd, J=8.4, 7.4 Hz, 1H), 7.55 (d, J=7.0 Hz, 1H), 7.49-7.41 (m, 5H), 5.13 (dd, J=12.6, 5.5 Hz, 1H), 4.80 (s, 2H), 4.65 (dd, J=9.1, 5.1 Hz, 1H), 3.68-3.58 (m, 36H), 3.53-3.44 (m, 5H), 2.94-2.86 (m, 1H), 2.81-2.70 (m, 5H), 2.46 (s, 3H), 2.19-2.13 (m, 1H), 1.74-1.69 (m, 3H). LCMS 1153.59 (M+H).

Synthetic Example 53: Synthesis of dBET56

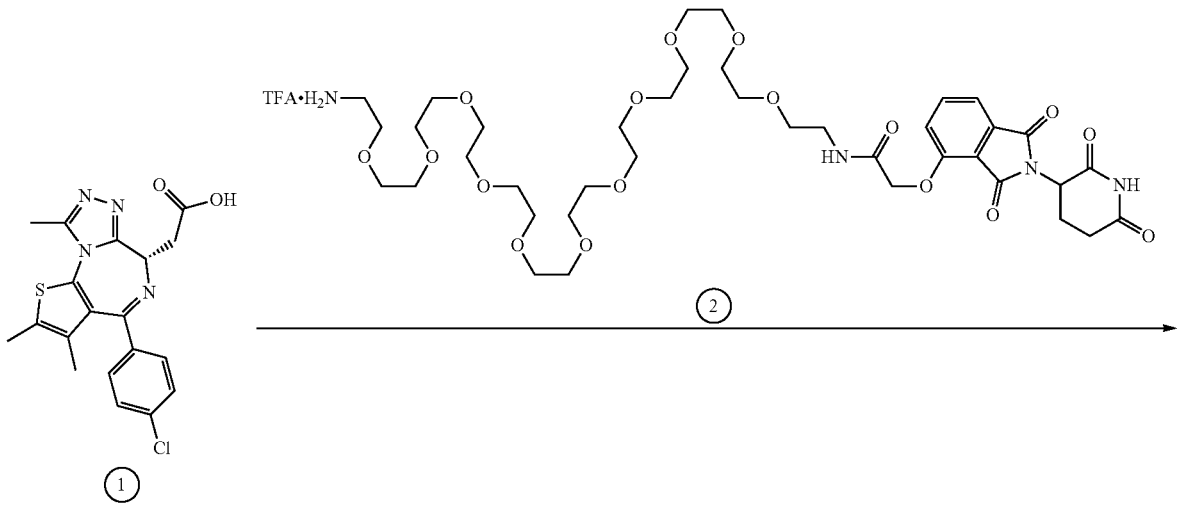

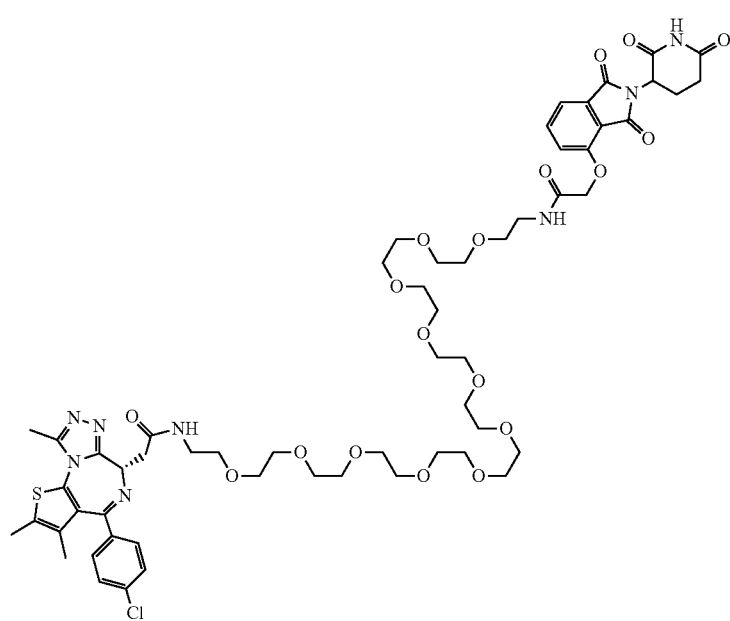

dBET56

A 0.1 M solution of N-(35-amino-3,6,9,12,15,18,21,24,27,30,33-undecaoxapentatriacontyl)-2-((2-(2,6-dioxopiperidin-3-yl)-1,3-dioxoisoindolin-4-yl)oxy)acetamide trifluoroacetate in DMF (200 microliters, 0.020 mmol, 1 eq) was added to JQ-acid (8.0 mg, 0.020 mmol, 1 eq) at room temperature. DIPEA (10.5 microliters, 0.060 mmol, 3 eq) and HATU (7.6 mg, 0.020 mmol, 1 eq) were added. After 20 hours the mixture was diluted with EtOAc and washed with saturated sodium bicarbonate, water and brine. The combined organic layer was dried over sodium sulfate, filtered and concentrated under reduced pressure. Purification by column chromatography (ISCO, 4 g silica column, 0-10% MeOH/DCM, 25 minute gradient) gave the desired product as an oily residue (9.03 mg, 0.00727 mmol, 36%). $^1$H NMR (500 MHz, Methanol-$d_4$) δ 7.81 (dd, J=8.4, 7.4 Hz, 1H), 7.53 (d, J=7.1 Hz, 1H), 7.50-7.40 (m, 5H), 5.11 (dd, J=12.6, 5.5 Hz, 1H), 4.78 (s, 2H), 4.68 (dd, J=8.6, 5.0 Hz, 1H), 3.69-3.56 (m, 44H), 3.52-3.43 (m, 5H), 3.34 (dd, J=7.9, 3.5 Hz, 1H), 2.88 (ddd, J=18.0, 14.0, 5.2 Hz, 1H), 2.79-2.68 (m, 5H), 2.46 (s, 3H), 2.17-2.12 (m, 1H), 1.71 (s, 3H). LCMS 1241.60 (M+H).

Synthetic Example 54: Synthesis of dBET57

Step 1: Synthesis of 2-(2,6-dioxopiperidin-3-yl)-4-fluoroisoindoline-1,3-dione

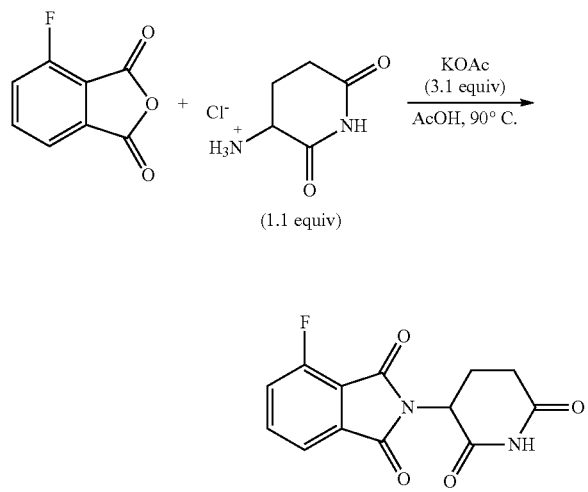

A solution of 4-fluoroisobenzofuran-1,3-dione (200 mg, 1.20 mmol, 1 equiv) in AcOH (4.0 mL, 0.3 M) was added 2,6-dioxopiperidin-3-amine hydrochloride (218 mg, 1.32 mmol, 1.1 equiv) and potassium acetate (366 mg, 3.73 mmol, 3.1 equiv). The reaction mixture was heated to 90° C. overnight, whereupon it was diluted with water to 20 mL and cooled on ice for 30 min. The resulting slurry was filtered, and the black solid was purified by flash column chromatography on silica gel (2% MeOH in CH$_2$Cl$_2$, R$_f$=0.3) to afford the title compound as a white solid (288 mg, 86%). $^1$H NMR (500 MHz, DMSO-$d_6$) δ 11.15 (s, 1H), 7.96 (ddd, J=8.3, 7.3, 4.5 Hz, 1H), 7.82-7.71 (m, 2H), 5.17 (dd, J=13.0, 5.4 Hz, 1H), 2.90 (ddd, J=17.1, 13.9, 5.4 Hz, 1H), 2.65-2.47 (m, 2H), 2.10-2.04 (m, 1H), MS (ESI) cald for C$_{13}$H$_{10}$FN$_2$O$_4$ [M+H]$^+$ 277.06, found 277.25.

Step 2: Synthesis of tert-butyl (2-((2-(2,6-dioxopiperidin-3-yl)-1,3-dioxoisoindolin-4-yl)amino)ethyl) carbamate

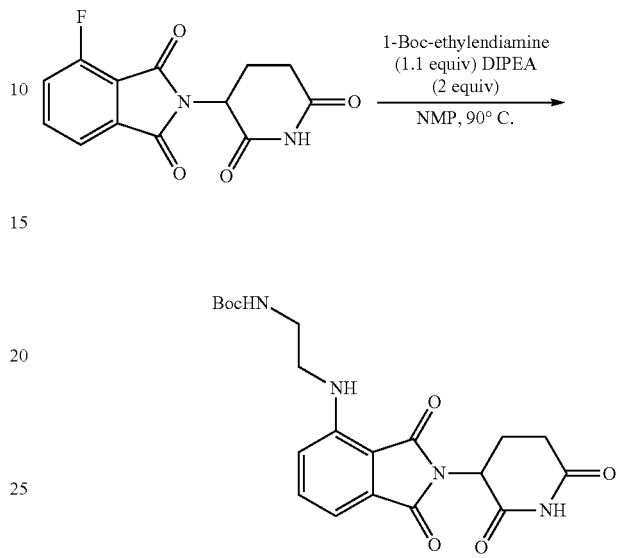

A stirred solution of 2-(2,6-dioxopiperidin-3-yl)-4-fluoroisoindoline-1,3-dione (174 mg, 0.630 mmol, 1 equiv) in DMF (6.3 mL, 0.1 M) was added DIPEA (220 µL, 1.26 mmol, 2 equiv) and 1-Boc-ethylenediamine (110 µL, 0.693 mmol, 1.1 equiv). The reaction mixture was heated to 90° C. overnight, whereupon it was cooled to room temperature and taken up in EtOAc (30 mL) and water (30 mL). The organic layer was washed with brine (3×20 mL), dried over Na$_2$SO$_4$ and concentrated in vacuo. The residue was purified by flash column chromatography on silica gel (0-10% MeOH in CH$_2$Cl$_2$) to give the title compound as a yellow solid (205 mg, 79%). $^1$H NMR (500 MHz, CDCl$_3$) δ 8.08 (bs, 1H), 7.50 (dd, J=8.5, 7.1 Hz, 1H), 7.12 (d, J=7.1 Hz, 1H), 6.98 (d, J=8.5 Hz, 1H), 6.39 (t, J=6.1 Hz, 1H), 4.96-4.87 (m, 1H), 4.83 (bs, 1H), 3.50-3.41 (m, 2H), 3.41-3.35 (m, 2H), 2.92-2.66 (m, 3H), 2.16-2.09 (m, 1H), 1.45 (s, 9H); MS (ESI) cald for C$_{20}$H$_{25}$N$_4$O$_6$ [M+H]$^+$ 417.18, found 417.58.

Step 3: Synthesis of 2-((2-(2,6-dioxopiperidin-3-yl)-1,3-dioxoisoindolin-4-yl)amino)ethan-1-aminium 2,2,2-trifluoroacetate

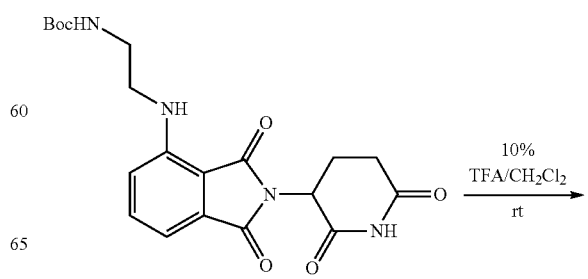

-continued

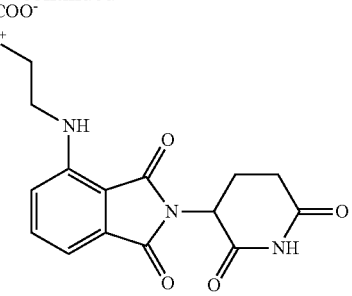

-continued

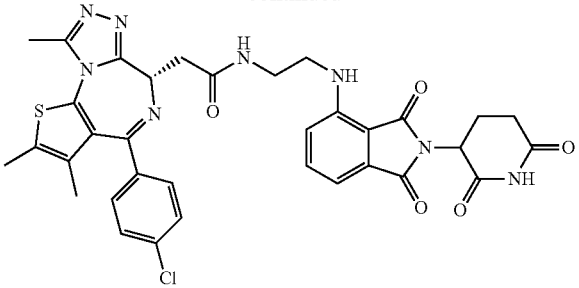

dBET57

A stirred solution of tert-butyl (2-((2-(2,6-dioxopiperidin-3-yl)-1,3-dioxoisoindolin-4-yl)amino)ethyl)carbamate (205 mg, 0.492 mmol, 1 equiv) in dichloromethane (2.25 mL) was added trifluoroacetic acid (0.250 mL). The reaction mixture was stirred at room temperature for 4 h, whereupon the volatiles were removed in vacuo. The title compound was obtained as a yellow solid (226 mg, >95%), that was used without further purification. $^1$H NMR (500 MHz, MeOD) δ 7.64 (d, J=1.4 Hz, 1H), 7.27-7.05 (m, 2H), 5.10 (dd, J=12.5, 5.5 Hz, 1H), 3.70 (t, J=6.0 Hz, 2H), 3.50-3.42 (m, 2H), 3.22 (t, J=6.0 Hz, 1H), 2.93-2.85 (m, 1H), 2.80-2.69 (m, 2H), 2.17-2.10 (m, 1H); MS (ESI) calcd for $C_{15}H_{17}N_4O_4$ [M+H]$^+$ 317.12, found 317.53.

Step 2: Synthesis of dBET57

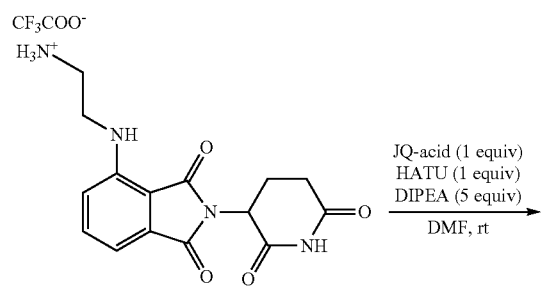

JQ-acid (1 equiv)
HATU (1 equiv)
DIPEA (5 equiv)
―――――――→
DMF, rt

JQ-acid (8.0 mg, 0.0200 mmol, 1 eq) and 2-((2-(2,6-dioxopiperidin-3-yl)-1,3-dioxoisoindolin-4-yl)amino)ethan-1-aminium 2,2,2-trifluoroacetate (8.6 mg, 0.0200 mmol, 1 equiv) were dissolved in DMF (0.200 mL, 0.1 M) at room temperature. DIPEA (17.4 μL, 0.100 mmol, 5 equiv) and HATU (7.59 mg, 0.0200 mmol, 1 equiv) were then added and the mixture was stirred at room temperature overnight. The reaction mixture was taken up in EtOAc (15 mL), and washed with satd. NaHCO$_3$(aq) (15 mL), water (15 mL) and brine (3×15 mL). The organic layer was dried over Na$_2$SO$_4$ and concentrated in vacuo. The residue was purified by flash column chromatography on silica gel (0-10% MeOH in CH$_2$Cl$_2$, R$_f$=0.3 (10% MeOH in CH$_2$Cl$_2$)) to give the title compound as a bright yellow solid (11.2 mg, 80%). $^1$H NMR (400 MHz, CDCl$_3$) δ 8.49 (bs, 0.6H), 8.39 (bs, 0.4H), 7.51-7.43 (m, 1H), 7.38 (d, J=7.8 Hz, 2H), 7.29 (dd, J=8.8, 1.7 Hz, 2H), 7.07 (dd, J=7.1, 4.9 Hz, 1H), 6.97 (dd, J=8.6, 4.9 Hz, 1H), 6.48 (t, J=5.9 Hz, 1H), 6.40 (t, J=5.8 Hz, 0.6H), 4.91-4.82 (m, 0.4H), 4.65-4.60 (m, 1H), 3.62-3.38 (m, 6H), 2.87-2.64 (m, 3H), 2.63 (s, 3H), 2.40 (s, 6H), 2.12-2.04 (m, 1H), 1.67 (s, 3H), rotamers; MS (ESI) calcd for $C_{34}H_{32}ClN_8O_5S$ [M+H]$^+$ 700.19, found 700.34.

Synthetic Example 55: Synthesis of dGR1

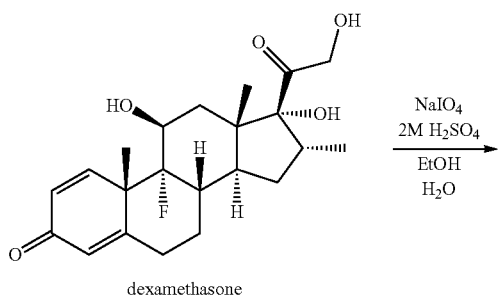

dexamethasone

NaIO$_4$
2M H$_2$SO$_4$
―――――――→
EtOH
H$_2$O

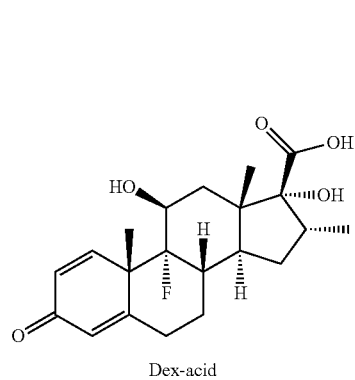
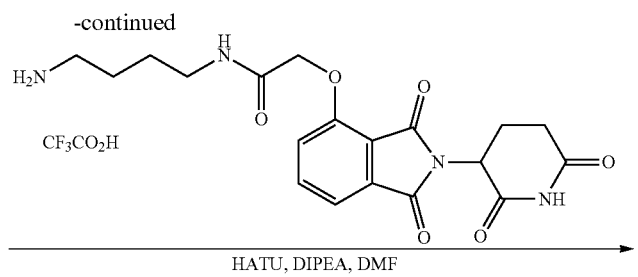
Dex-acid
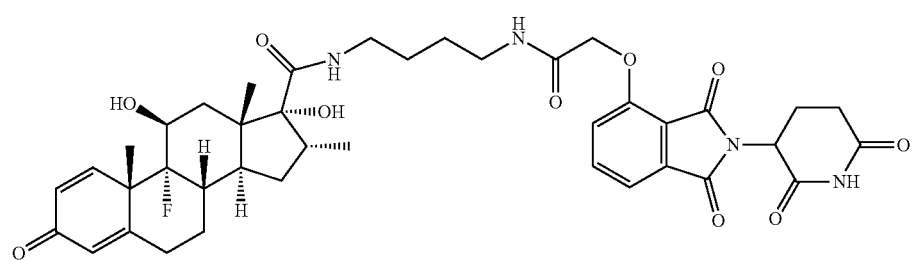
DB-2-247
dGR1
Synthetic Example 56: Synthesis of dGR2
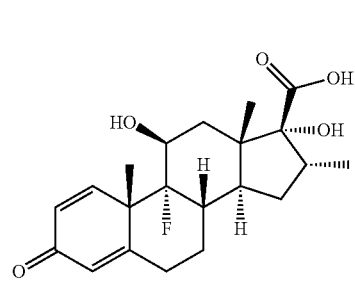
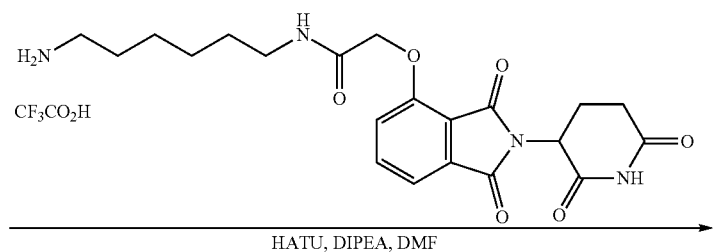
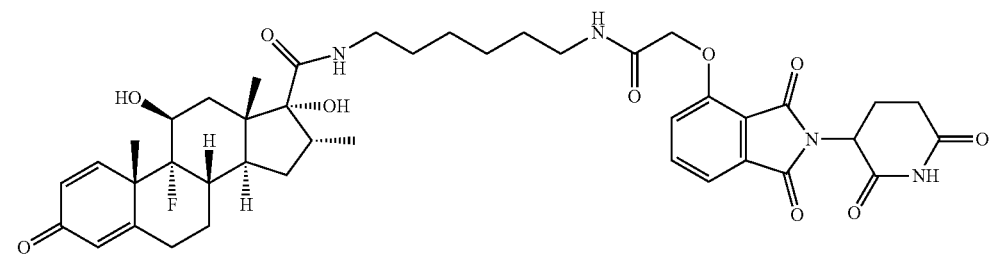
DB-2-265
dGR2

Synthetic Example 57: Synthesis of dGR3
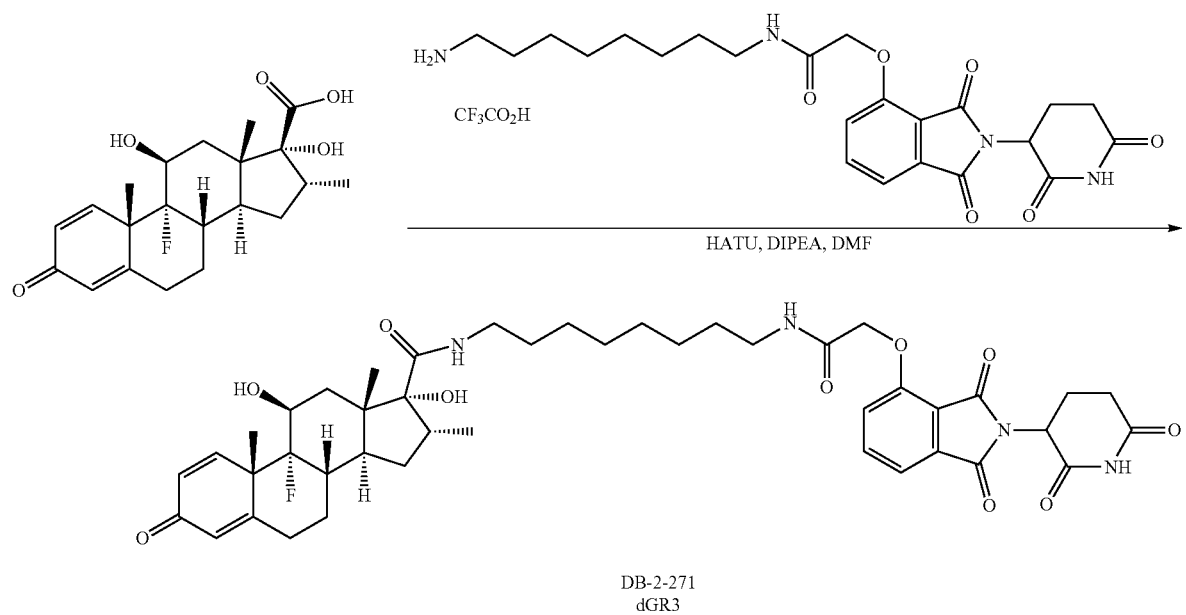
Synthetic Example 58: Synthesis of dFKBP-1
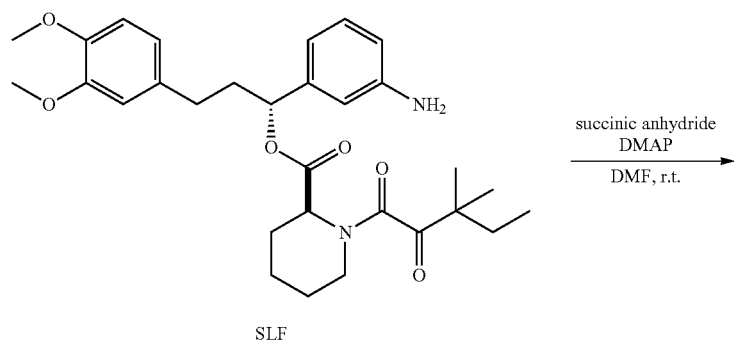
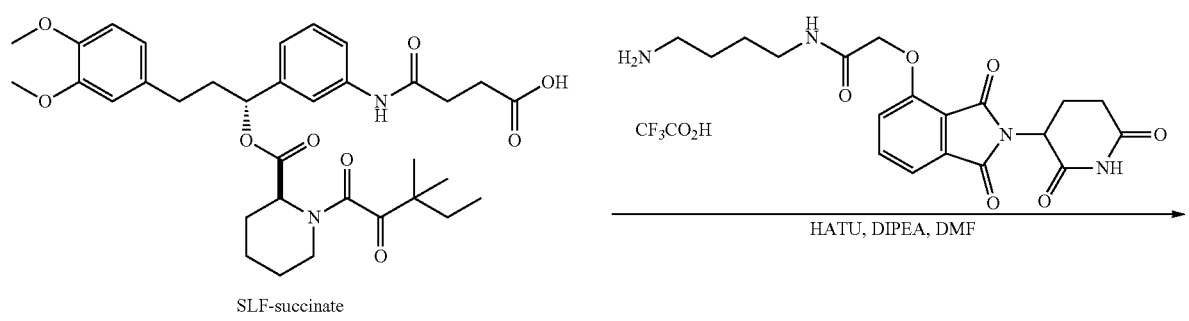

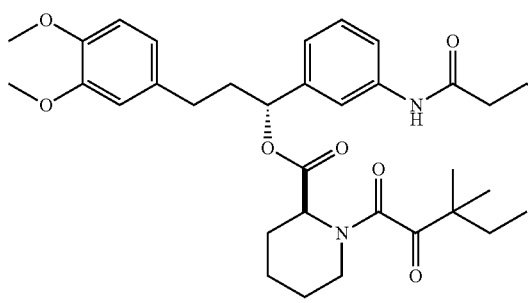

dFKBP-1

(1) Synthesis of SLF-succinate

SLF (25 mg, 2.5 mL of a 10 mg/mL solution in MeOAc, 0.0477 mmol, 1 eq) was combined with DMF (0.48 mL, 0.1 M) and succinic anhydride (7.2 mg, 0.0715 mmol, 1.5 eq) and stirred at room temperature for 24 hours. Low conversion was observed and the mixture was placed under a stream of N2 to remove the MeOAc. An additional 0.48 mL of DMF was added, along with an additional 7.2 mg succinic anhydride and DMAP (5.8 mg, 0.0477 mmol, 1 eq). The mixture was then stirred for an additional 24 hours before being purified by preparative HPLC to give SLF-succinate as a yellow oil (24.06 mg, 0.0385 mmol, 81%).

$^1$H NMR (400 MHz, Methanol-d$_4$) δ 7.62 (d, J=10.7 Hz, 1H), 7.44 (d, J=8.0 Hz, 1H), 7.26 (td, J=7.9, 2.7 Hz, 1H), 7.07-6.97 (m, 1H), 6.80 (dd, J=8.1, 2.1 Hz, 1H), 6.74-6.66 (m, 2H), 5.73 (dd, J=8.1, 5.5 Hz, 1H), 5.23 (d, J=4.8 Hz, 1H), 3.83 (s, 3H), 3.81 (s, 3H), 3.39-3.29 (m, 4H), 3.21 (td, J=13.2, 3.0 Hz, 1H), 2.68-2.50 (m, 5H), 2.37-2.19 (m, 2H), 2.12-2.02 (m, 1H), 1.79-1.61 (m, 4H), 1.49-1.30 (m, 2H), 1.27-1.05 (m, 6H), 0.82 (dt, J=41.2, 7.5 Hz, 3H). LCMS 624.72 (M+H).

(2) Synthesis of dFKBP-1

N-(4-aminobutyl)-2-((2-(2,6-dioxopiperidin-3-yl)-1,3-dioxoisoindolin-4-yl)oxy)acetamide trifluoroacetate (9.9 mg, 0.0192 mmol, 1 eq) was added to SLFsuccinate (11.98 mg, 0.0192 mmol, 1 eq) as a solution in 0.192 mL DMF (0.1 M). DIPEA (10.0 microliters, 0.0575 mmol, 3 eq) was added, followed by HATU (7.3 mg, 0.0192 mmol, 1 eq). The mixture was stirred for 17 hours, then diluted with MeOH and purified by preparative HPLC to give dFKBP-1 (7.7 mg, 0.00763 mmol, 40%) as a yellow solid.

$^1$H NMR (400 MHz, Methanol-d$_4$) δ 7.81 (s, 1H), 7.77-7.70 (m, 1H), 7.55-7.49 (m, 2H), 7.26 (dd, J=8.0, 5.3 Hz, 2H), 7.05-6.99 (m, 1H), 6.77 (d, J=8.8 Hz, 1H), 6.66 (d, J=6.8 Hz, 2H), 5.77-5.72 (m, 1H), 5.24 (d, J=4.8 Hz, 1H), 4.99 (dd, J=12.3, 5.7 Hz, 1H), 4.68-4.59 (m, 2H), 3.82 (s, 3H), 3.81 (s, 3H), 3.32 (dt, J=3.3, 1.6 Hz, 4H), 3.26-3.14 (m, 3H), 2.79 (dd, J=18.9, 10.2 Hz, 3H), 2.64-2.48 (m, 5H), 2.34 (d, J=14.4 Hz, 1H), 2.22 (d, J=9.2 Hz, 1H), 2.14-2.02 (m, 2H), 1.78-1.49 (m, 9H), 1.43-1.30 (m, 2H), 1.20-1.04 (m, 6H), 0.90-0.76 (m, 3H). 13C NMR (100 MHz, cd$_3$od) δ 208.51, 173.27, 172.64, 171.63, 169.93, 169.51, 168.04, 167.69, 167.09, 166.71, 154.92, 149.05, 147.48, 140.76, 138.89, 137.48, 133.91, 133.67, 129.36, 122.19, 120.61, 120.54, 119.82, 118.41, 118.12, 117.79, 112.12, 111.76, 68.54, 56.10, 55.98, 51.67, 46.94, 44.57, 39.32, 39.01, 38.23, 32.64, 31.55, 31.43, 26.68, 26.64, 25.08, 23.52, 23.21, 22.85, 21.27, 8.76. LCMS 1009.66 (M+H).

Synthetic Example 59: Synthesis of dFKBP-2

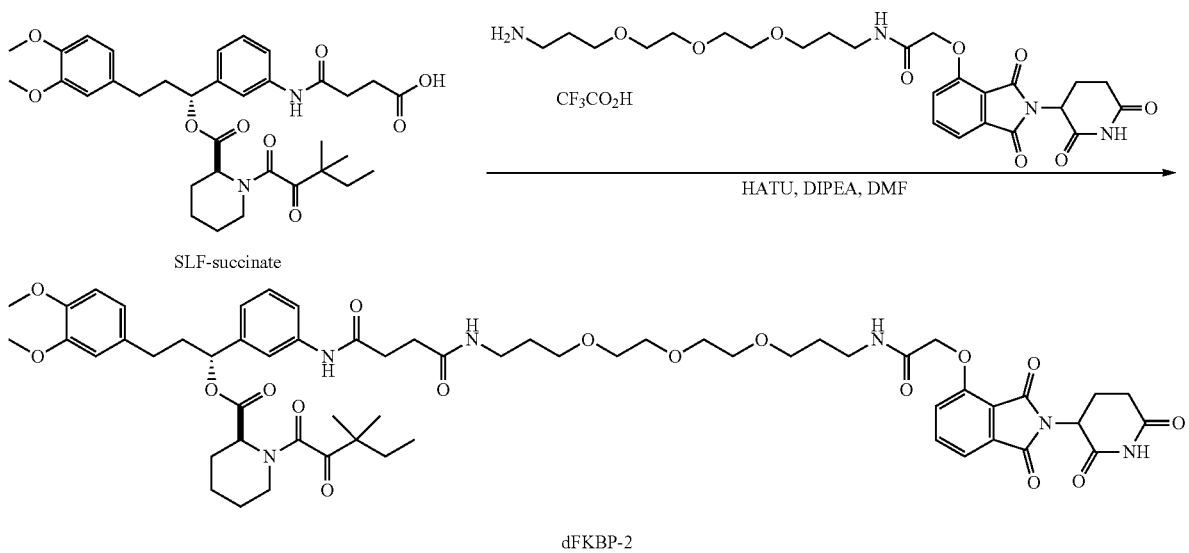

dFKBP-2

(1) Synthesis of tert-butyl (1-chloro-2-oxo-7,10,13-trioxa-3-azahexadecan-16-yl)carbamate tert-butyl (3-(2-(2-(3-aminopropoxy)ethoxy)ethoxy)propyl)carbamate (1.0 g, 3.12 mmol, 1 eq) was dissolved in THF (31 mL, 0.1 M). DIPEA (0.543 mL, 3.12 mmol, 1 eq) was added and the solution was cooled to 0° C. Chloroacetyl chloride (0.273 mL, 3.43 mmol, 1.1 eq) was added and the mixture was warmed slowly to room temperature. After 24 hours, the mixture was diluted with EtOAc and washed with saturated sodium bicarbonate, water then brine. The organic layer was dried over sodium sulfate, filtered and condensed to give a yellow oil (1.416 g) that was carried forward without further purification.

$^1$H NMR (400 MHz, Chloroform-d) δ 7.24 (s, 1H), 5.00 (s, 1H), 3.98-3.89 (m, 2H), 3.54 (dddt, J=17.0, 11.2, 5.9, 2.2 Hz, 10H), 3.47-3.40 (m, 2H), 3.37-3.31 (m, 2H), 3.17-3.07 (m, 2H), 1.79-1.70 (m, 2H), 1.67 (p, J=6.1 Hz, 2H), 1.35 (s, 9H). $^{13}$C NMR (100 MHz, cdcl$_3$) δ 165.83, 155.97, 78.75, 70.49, 70.47, 70.38, 70.30, 70.14, 69.48, 42.61, 38.62, 38.44, 29.62, 28.59, 28.40. LCMS 397.37 (M+H).

(2) Synthesis of dimethyl 3-((2,2-dimethyl-4,20-dioxo-3,9,12,15-tetraoxa-5,19-diazahenicosan-21-yl)oxy)phthalate tert-butyl (1-chloro-2-oxo-7,10,13-trioxa-3-azahexadecan-16-yl)carbamate (1.41 g, 3.12 mmol, 1 eq) was dissolved in MeCN (32 mL, 0.1 M). Dimethyl 3-hydroxyphthalate (0.721 g, 3.43 mmol, 1.1 eq) and cesium carbonate (2.80 g, 8.58 mmol, 2.75 eq) were added. The flask was fitted with a reflux condenser and heated to 80° C. for 19 hours. The mixture was cooled to room temperature and diluted water and extracted once with chloroform and twice with EtOAc. The combined organic layers were dried over sodium sulfate, filtered and concentrated under reduced pressure. The crude material was purified by column chromatography (ISCO, 24 g silica column, 0-15% MeOH/DCM 22 minute gradient) to give a yellow oil (1.5892 g, 2.78 mmol, 89% over two steps).

$^1$H NMR (400 MHz, Chloroform-d) δ 7.52 (d, J=7.8 Hz, 1H), 7.35 (t, J=8.1 Hz, 1H), 7.04 (d, J=8.3 Hz, 1H), 7.00 (t, J=5.3 Hz, 1H), 5.06 (s, 1H), 4.46 (s, 2H), 3.83 (s, 3H), 3.78 (s, 3H), 3.47 (ddd, J=14.9, 5.5, 2.8 Hz, 8H), 3.39 (dt, J=9.4, 6.0 Hz, 4H), 3.29 (q, J=6.5 Hz, 2H), 3.09 (d, J=6.0 Hz, 2H), 1.70 (p, J=6.5 Hz, 2H), 1.63 (p, J=6.3 Hz, 2H), 1.31 (s, 9H). $^{13}$C NMR (100 MHz, cdcl$_3$) δ 167.68, 167.36, 165.45, 155.93, 154.41, 130.87, 129.60, 125.01, 123.20, 117.06, 78.60, 70.40, 70.17, 70.06, 69.39, 68.67, 68.25, 52.77, 52.57, 38.38, 36.58, 29.55, 29.20, 28.34. LCMS 571.47 (M+H).

(3) Synthesis of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate Dimethyl 3-((2,2-dimethyl-4,20-dioxo-3,9,12,15-tetraoxa-5,19-diazahenicosan-21-yl)oxy)phthalate (1.589 g, 2.78 mmol, 1 eq) was dissolved in EtOH (14 mL, 0.2 M). Aqueous 3M NaOH (2.8 mL, 8.34 mmol, 3 eq) was added and the mixture was heated to 80° C. for 22 hours. The mixture was then cooled to room temperature, diluted with 50 mL DCM and 20 mL 0.5 M HCl. The layers were separated and the organic layer was washed with 25 mL water. The aqueous layers were combined and extracted three times with 50 mL chloroform. The combined organic layers were dried over sodium sulfate, filtered and condensed to give 1.53 g of material that was carried forward without further purification. LCMS 553.44.

The resultant material (1.53 g) and 3-aminopiperidine-2,6-dione hydrochloride (0.480 g, 2.92 mmol, 1 eq) were dissolved in pyridine (11.7 mL, 0.25 M) and heated to 110° C. for 17 hours. The mixture was cooled to room temperature and concentrated under reduced pressure to give crude tert-butyl (1-((2-(2,6-dioxopiperidin-3-yl)-1,3-dioxoisoindolin-4-yl)oxy)-2-oxo-7,10,13-trioxa-3-azahexadecan-16-yl)carbamate as a black sludge (3.1491 g) that was carried forward without further purification. LCMS 635.47.

The crude tert-butyl (1-((2-(2,6-dioxopiperidin-3-yl)-1,3-dioxoisoindolin-4-yl)oxy)-2-oxo-7,10,13-trioxa-3-azahexadecan-16-yl)carbamate (3.15 g) was dissolved in TFA (20 mL) and heated to 50° C. for 2.5 hours. The mixture was cooled to room temperature, diluted with MeOH and concentrated under reduced pressure. The material was purified by preparative HPLC to give N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate (1.2438 g, 1.9598 mmol, 71% over 3 steps) as a dark red oil.

$^1$H NMR (400 MHz, Methanol-d$_4$) δ 7.77 (dd, J=8.3, 7.5 Hz, 1H), 7.49 (d, J=7.3 Hz, 1H), 7.40 (d, J=8.5 Hz, 1H), 5.12 (dd, J=12.8, 5.5 Hz, 1H), 4.75 (s, 2H), 3.68-3.51 (m, 12H), 3.40 (t, J=6.8 Hz, 2H), 3.10 (t, J=6.4 Hz, 2H), 2.94-2.68 (m, 3H), 2.16 (dtd, J=12.6, 5.4, 2.5 Hz, 1H), 1.92 (p, J=6.1 Hz, 2H), 1.86-1.77 (m, 2H). $^{13}$C NMR (100 MHz, cd$_3$od) α 173.17, 169.97, 168.48, 166.87, 166.30, 154.82, 136.89, 133.41, 120.29, 117.67, 116.58, 69.96, 69.68, 69.60, 68.87, 68.12, 67.92, 49.19, 38.62, 36.14, 30.80, 28.92, 26.63, 22.22. LCMS 536.41 (M+H).

(4) Synthesis of dFKBP-2

N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate(12.5 mg, 0.0193 mmol, 1 eq) was added to SLF-succinate (12.08 mg, 0.0193 mmol, 1 eq) as a solution in 0.193 mL in DMF (0.1 M). DIPEA (10.1 microliters, 0.0580 mmol, 3 eq) and HATU (7.3 mg, 0.0193 mmol, 1 eq) were added and the mixture was stirred for 19 hours. The mixture was then diluted with MeOH and purified by preparative HPLC to give dFKBP-2 (9.34 mg, 0.00818 mmol, 42%) as a yellow oil.

$^1$H NMR (400 MHz, 50% MeOD/Chloroform-d) δ 7.76-7.70 (m, 1H), 7.58-7.45 (m, 3H), 7.26 (t, J=8.2 Hz, 2H), 7.05-6.98 (m, 1H), 6.77 (d, J=7.9 Hz, 1H), 6.71-6.63 (m, 2H), 5.73 (dd, J=8.1, 5.6 Hz, 1H), 5.23 (d, J=5.4 Hz, 1H), 5.03-4.95 (m, 1H), 4.64 (s, 2H), 3.82 (s, 3H), 3.80 (s, 3H), 3.62-3.52 (m, 8H), 3.47 (t, J=6.1 Hz, 2H), 3.44-3.33 (m, 3H), 3.27-3.14 (m, 3H), 2.84-2.70 (m, 3H), 2.64-2.47 (m, 6H), 2.34 (d, J=14.1 Hz, 1H), 2.24 (dd, J=14.3, 9.3 Hz, 2H), 2.13-2.00 (m, 2H), 1.83 (p, J=6.3 Hz, 2H), 1.67 (dtd, J=38.4, 16.8, 14.8, 7.0 Hz, 7H), 1.51-1.26 (m, 3H), 1.22-1.05 (m, 6H), 0.80 (dt, J=39.8, 7.5 Hz, 3H). $^{13}$C NMR (100 MHz, cdcl$_3$) δ 208.64, 173.39, 173.01, 171.76, 170.11, 169.62, 168.24, 167.92, 167.36, 166.69, 155.02, 149.23, 147.66, 140.94, 139.18, 137.57, 134.09, 133.91, 129.49, 122.32, 120.75, 120.52, 119.93, 118.42, 117.75, 112.33, 111.98, 70.77, 70.51, 70.40, 69.45, 69.04, 68.48, 56.20, 56.10, 51.88, 47.09, 44.78, 38.40, 37.48, 36.91, 32.80, 32.71, 31.70, 31.59, 31.55, 29.53, 29.30, 26.77, 25.22, 23.63, 23.33, 22.98, 21.43. LCMS 1141.71 (M+H).

Synthetic Example 60: Synthesis of dFKBP-3

A 0.1 M solution of N-(4-aminobutyl)-2-((2-(2,6-dioxopiperidin-3-yl)-1,3-dioxoisoindolin-4-yl)oxy)acetamide trifluoroacetate (0.233 mL, 0.0233 mmol, 1 eq) was added to 2-(3-((R)-3-(3,4-dimethoxyphenyl)-1-(((S)-1-(3,3-dimethyl-2-oxopentanoyl)pyrrolidine-2-carbonyl)oxy)propyl)phenoxy)acetic acid (13.3 mg, 0.0233 mmol, 1 eq). DIPEA (12.2 microliters, 0.0700 mmol, 3 eq) was added, followed by HATU (8.9 mg, 0.0233 mmol, 1 eq). The mixture was stirred for 23 hours, then diluted with MeOH and purified by preparative HPLC to give a white solid (10.72 mg mg, 0.0112 mmol, 48%).

$^1$H NMR (400 MHz, Methanol-$d_4$) δ 7.79-7.74 (m, 1H), 7.52 (d, J=7.4 Hz, 1H), 7.33 (d, J=8.4 Hz, 1H), 7.26 (t, J=8.1 Hz, 1H), 6.97-6.90 (m, 2H), 6.89-6.84 (m, 1H), 6.79 (dd, J=8.2, 1.9 Hz, 1H), 6.73-6.64 (m, 2H), 5.73-5.65 (m, 1H), 5.07-4.99 (m, 1H), 4.67 (s, 2H), 4.57-4.51 (m, 1H), 4.48 (dd, J=5.7, 2.5 Hz, 2H), 3.82 (d, J=1.9 Hz, 3H), 3.80 (s, 3H), 3.66-3.39 (m, 6H), 2.88-2.48 (m, 6H), 2.42-1.87 (m, 9H), 1.73-1.51 (m, 6H), 1.19-0.92 (m, 6H), 0.75 (dt, J=56.7, 7.5 Hz, 3H). LCMS 954.52 (M+H).

Example 61: Synthesis of dFKBP-4

A 0.1 M solution of N-(4-aminobutyl)-2-((2-(2,6-dioxopiperidin-3-yl)-1,3-dioxoisoindolin-4-yl)oxy)acetamide trifluoroacetate (0.182 mL, 0.0182 mmol, 1 eq) was added to 2-(3-((R)-3-(3,4-dimethoxyphenyl)-1-(((S)-1-(3,3-dimethyl-2-oxopentanoyl)piperidine-2-carbonyl)oxy)propyl)phenoxy)acetic acid (10.6 mg, 0.0182 mmol, 1 eq). DIPEA (9.5 microliters, 0.0545 mmol, 3 eq) was added, followed by HATU (6.9 mg, 0.0182 mmol, 1 eq). The mixture was stirred for 26 hours, then diluted with MeOH and purified by preparative HPLC to give a white solid (9.74 mg, 0.01006 mmol, 55%).

$^1$H NMR (400 MHz, Methanol-$d_4$) δ 7.75 (dd, J=8.3, 7.4 Hz, 1H), 7.53 (d, J=2.3 Hz, 1H), 7.33-7.25 (m, 2H), 7.00-6.84 (m, 3H), 6.79 (dd, J=8.1, 2.5 Hz, 1H), 6.72-6.65 (m, 2H), 5.75-5.70 (m, 1H), 5.23 (d, J=4.9 Hz, 1H), 5.05-4.96 (m, 1H), 4.66 (s, 2H), 4.46 (s, 2H), 3.82 (s, 3H), 3.81 (s, 3H), 3.39-3.32 (m, 4H), 3.20-3.12 (m, 1H), 2.82-2.69 (m, 3H), 2.62-2.49 (m, 2H), 2.37-2.00 (m, 5H), 1.78-1.30 (m, 11H), 1.24-1.08 (m, 6H), 0.81 (dt, J=32.9, 7.5 Hz, 3H). LCMS 968.55 (M+H).

Synthetic Example 62: Synthesis of dFKBP-5

A 0.1 M solution of N-(4-aminobutyl)-2-((2-(2,6-dioxopiperidin-3-yl)-1,3-dioxoisoindolin-4-yl)oxy)acetamide trifluoroacetate (0.205 mL, 0.0205 mmol, 1 eq) was added to 2-(3-((R)-3-(3,4-dimethoxyphenyl)-1-(((S)-1-(2-phenylacetyl)piperidine-2-carbonyl)oxy)propyl)phenoxy)acetic acid (11.8 mg, 0.0205 mmol, 1 eq). DIPEA (10.7 microliters, 0.0615 mmol, 3 eq) was added, followed by HATU (7.8 mg, 0.0205 mmol, 1 eq). The mixture was stirred for 29 hours, then diluted with MeOH and purified by preparative HPLC to give a white solid (10.62 mg, 0.01106 mmol, 54%).

$^1$H NMR (400 MHz, Methanol-$d_4$) δ 7.77-7.72 (m, 1H), 7.52 (s, 1H), 7.31-7.11 (m, 7H), 6.92-6.77 (m, 4H), 6.68-6.62 (m, 2H), 5.70-5.64 (m, 1H), 5.38 (d, J=3.8 Hz, 1H), 4.99 (d, J=4.6 Hz, 1H), 4.65 (s, 2H), 4.45-4.39 (m, 2H), 3.80 (dd, J=6.7, 2.4 Hz, 8H), 3.13-3.03 (m, 1H), 2.83-2.68 (m, 3H), 2.63-2.45 (m, 3H), 2.34-1.93 (m, 6H), 1.71-1.52 (m, 7H), 1.34-1.20 (m, 3H). LCMS 960.54 (M+H).

Synthetic Example 63: Synthesis of dFKBP-6

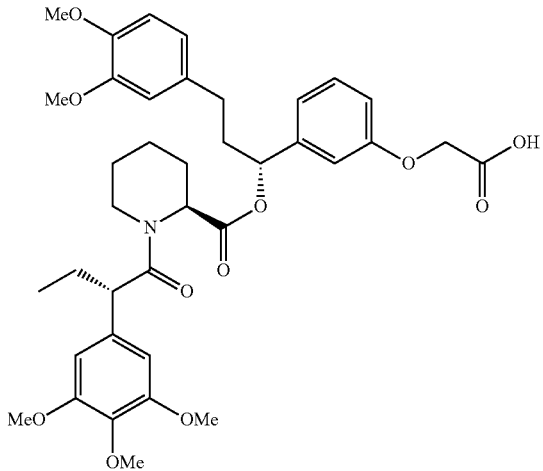
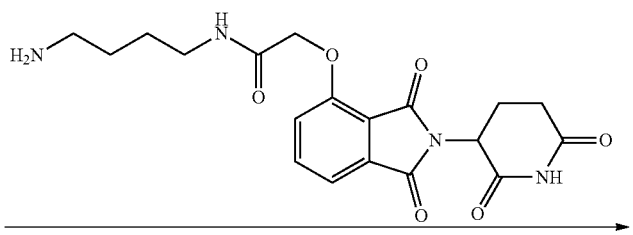

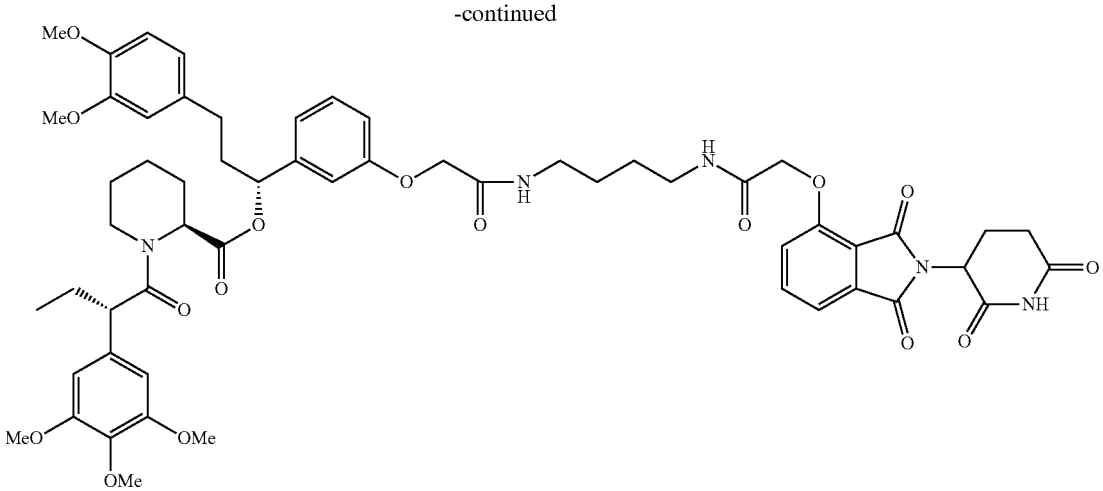

dFKBP*6

N-(4-aminobutyl)-2-((2-(2,6-dioxopiperidin-3-yl)-1,3-dioxoisoindolin-4-yl)oxy)acetamide trifluoroacetate(11.9 mg, 0.0231 mmol, 1 eq) is added to 2-(3-((R)-3-(3,4-dimethoxyphenyl)-1-(((S)-1-((S)-2-(3,4,5-trimethoxyphenyl)butanoyl)piperidine-2-carbonyl)oxy)propyl)phenoxy)acetic acid (16.0 mg, 0.0231 mmol, 1 eq) as a solution in 0.231 mL DMF (0.1 M). DIPEA (12.1 microliters, 0.0692 mmol, 3 eq) and HATU (8.8 mg, 0.0231 mmol, 1 eq) are added and the mixture is stirred for 21 hours. The mixture is diluted with EtOAc and washed with saturated sodium bicarbonate, water and brine. The organic layer is dried over sodium sulfate, filtered and concentrated under reduced pressure. The crude material is purified by column chromatography.

The above synthetic scheme can also be used to provide the analogous ortho or para bonding configuration in the dFKBP structures herein by choice of starting material, as illustrated below. Any of these positional isomers can be used in the present invention to degrade FKBP. For example:

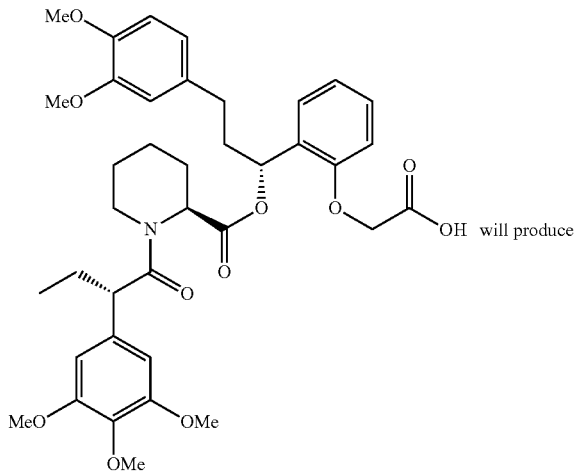 will produce

487
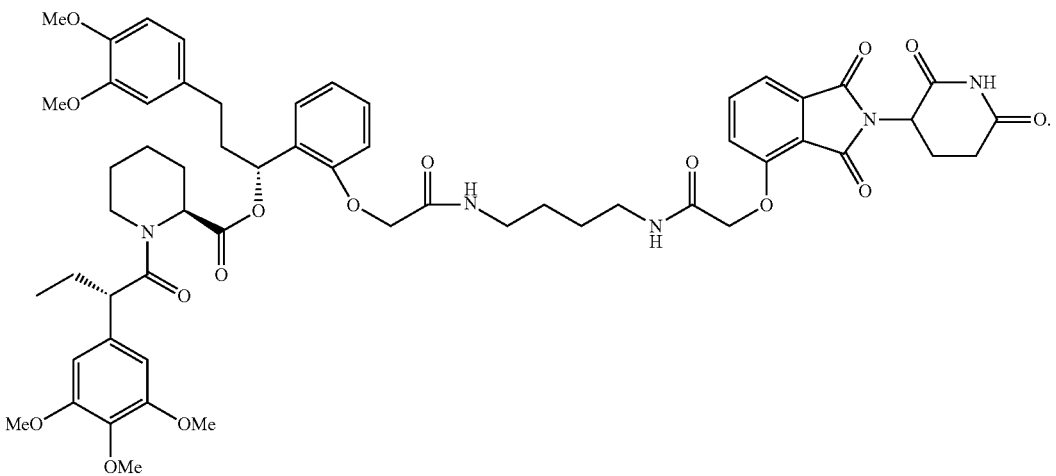
dFKBP6-o
Similarly use of
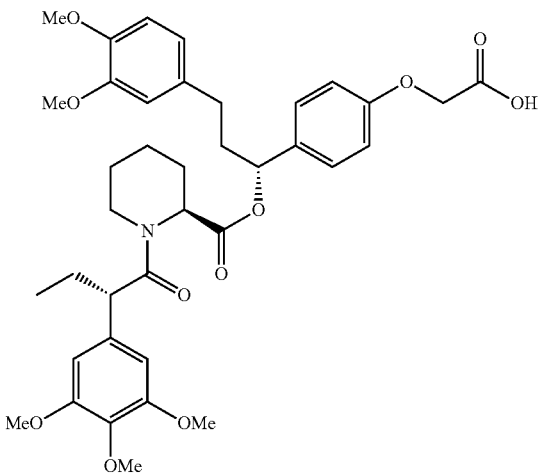
will produce
488
dFKBP6-p
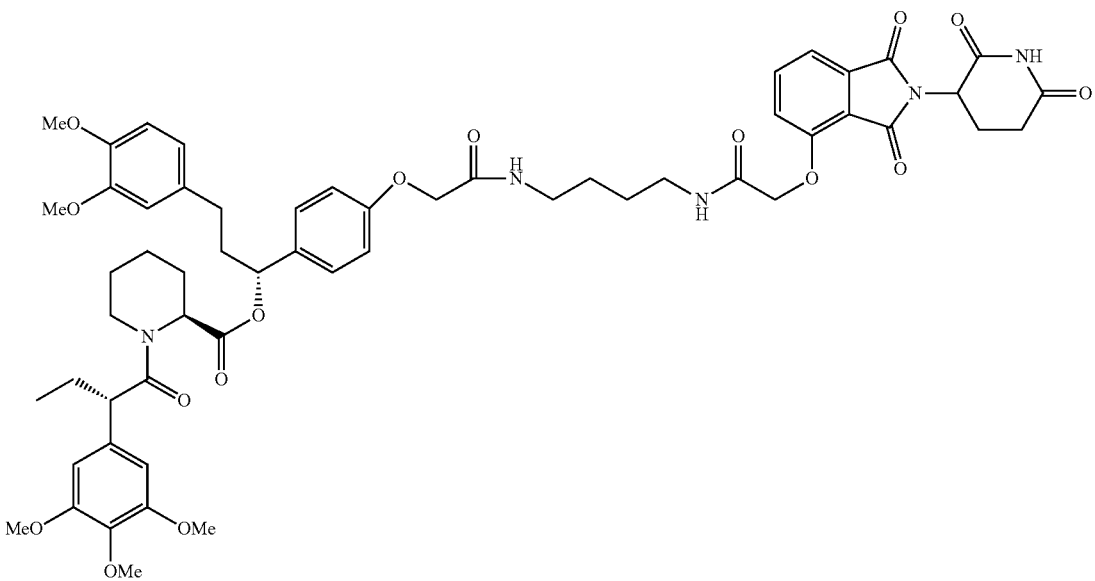

Synthetic Example 64: Synthesis of dFKBP-7

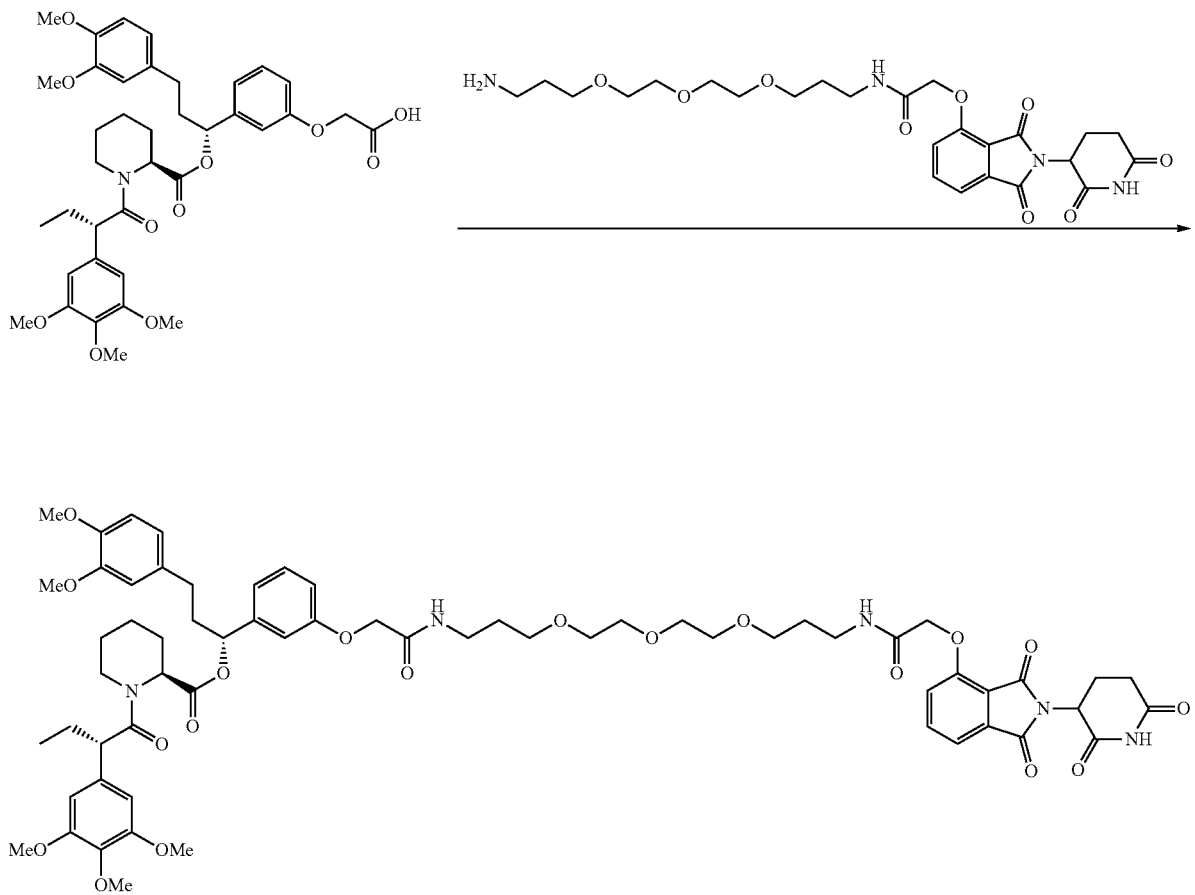

dFKBP*7

N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoracetate (12.3 mg, 0.0189 mmol, 1 eq) is added to 2-(3-((R)-3-(3,4-dimethoxyphenyl)-1-(((S)-1-((S)-2-(3,4,5-trimethoxyphenyl)butanoyl) piperidine-2-carbonyl)oxy)propyl)phenoxy)acetic acid (13.1 mg, 0.0189 mmol, 1 eq) as a solution in 0.189 mL DMF (0.1 M). DIPEA (9.9 microliters, 0.0566 mmol, 3 eq) and HATU (7.2 mg, 0.0189 mmol, 1 eq) are added and the mixture is stirred for 17 hours. The mixture is diluted with EtOAc and washed with saturated sodium bicarbonate, water and brine. The organic layer is dried over sodium sulfate, filtered and concentrated under reduced pressure. The crude material is purified by column chromatography.

Synthetic Example 65: Synthesis of dFKBP-8

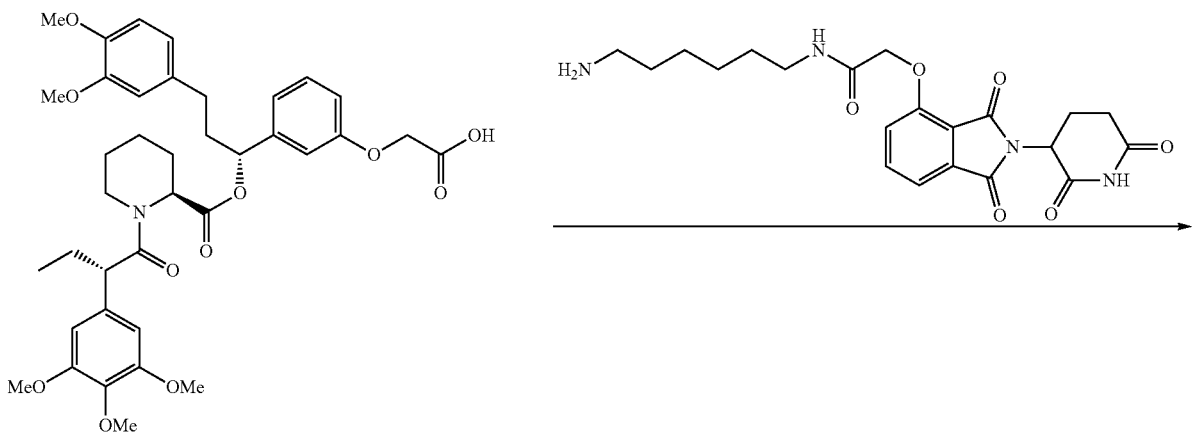

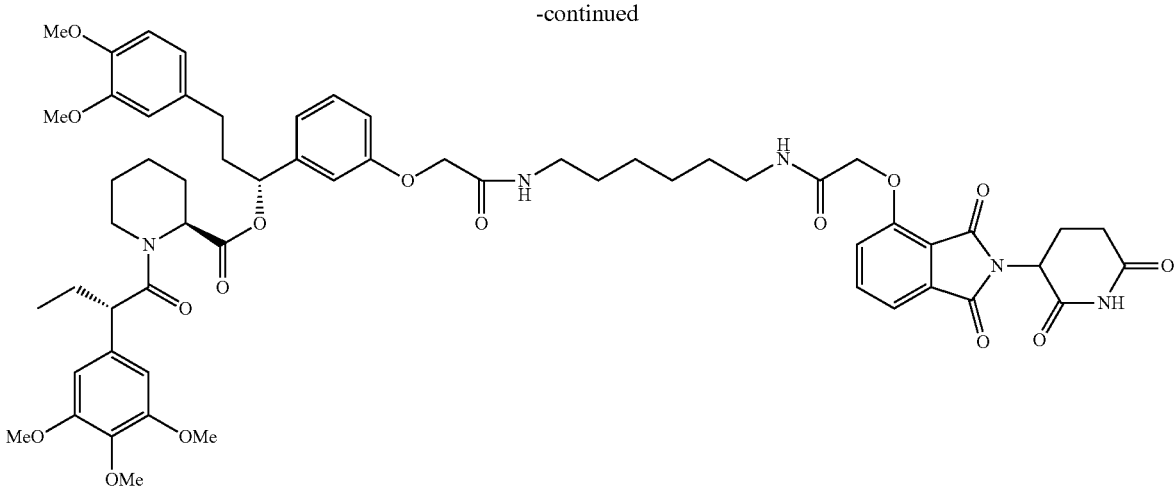

dFKBP*8

N-(6-aminohexyl)-2-((2-(2,6-dioxopiperidin-3-yl)-1,3-dioxoisoindolin-4-yl)oxy)acetamide trifluoracetate (12.7 mg, 0.0233 mmol, 1.3 eq) is added to 2-(3-((R)-3-(3,4-dimethoxyphenyl)-1-(((S)-1-((S)-2-(3,4,5-trimethoxyphenyl)butanoyl)piperidine-2-carbonyl)oxy)propyl)phenoxy)acetic acid (12.4 mg, 0.0179 mmol, 1 eq) as a solution in 0.233 mL DMF (0.1 M). DIPEA (9.3 microliters, 0.0537 mmol, 3 eq) and HATU (6.8 mg, 0.0179 mmol, 1 eq) are added and the mixture is stirred for 22 hours. The mixture is diluted with EtOAc and washed with saturated sodium bicarbonate, water and brine. The organic layer is dried over sodium sulfate, filtered and concentrated under reduced pressure. The crude material is purified by column chromatography.

Synthetic Example 66: Synthesis of dFKBP-9

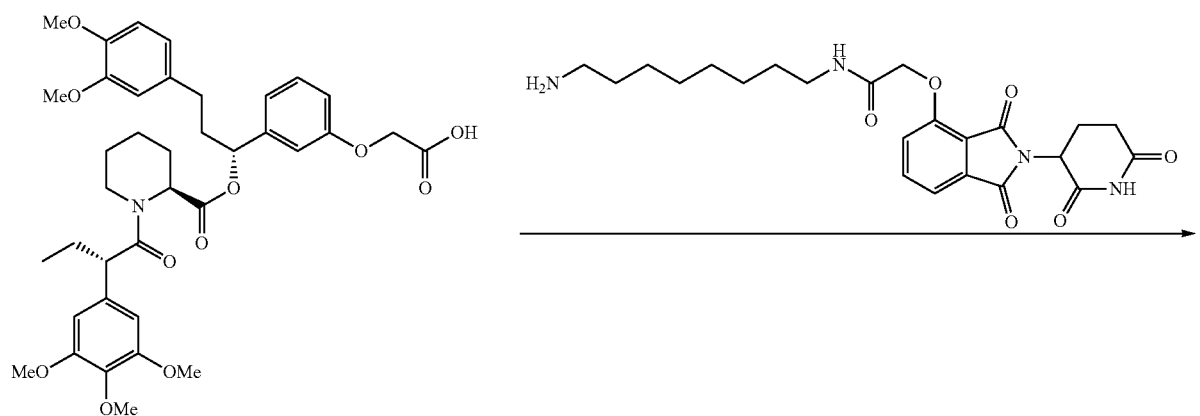

-continued

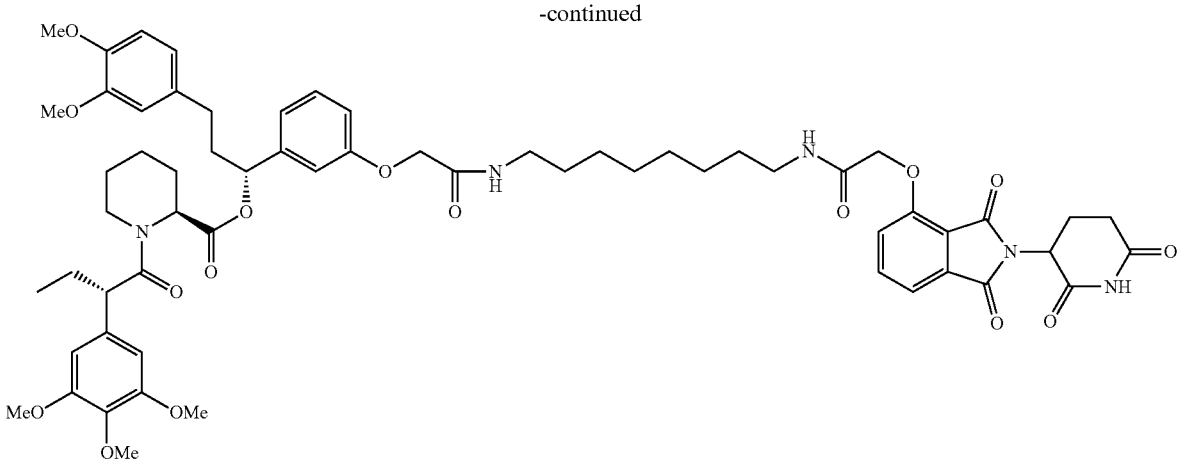

dFKBP*9

N-(8-aminooctyl)-2-((2-(2,6-dioxopiperidin-3-yl)-1,3-dioxoisoindolin-4-yl)oxy)acetamide trifluoroacetate (10.4 mg, 0.0181 mmol, 1 eq) is added to 2-(3-((R)-3-(3,4-dimethoxyphenyl)-1-(((S)-1-((S)-2-(3,4,5-trimethoxyphenyl)butanoyl)piperidine-2-carbonyl)oxy)propyl)phenoxy)acetic acid (12.5 mg, 0.0181 mmol, 1 eq) as a solution in 0.181 mL DMF (0.1 M). DIPEA (9.5 microliters, 0.0543 mmol, 3 eq) and HATU (6.9 mg, 0.0181 mmol, 1 eq) are added and the mixture is stirred for 22 hours. The mixture is diluted with EtOAc and washed with saturated sodium bicarbonate, water and brine. The organic layer is dried over sodium sulfate, filtered and concentrated under reduced pressure. The crude material is purified by column chromatography.

Synthetic Example 67: Synthesis of dFKBP

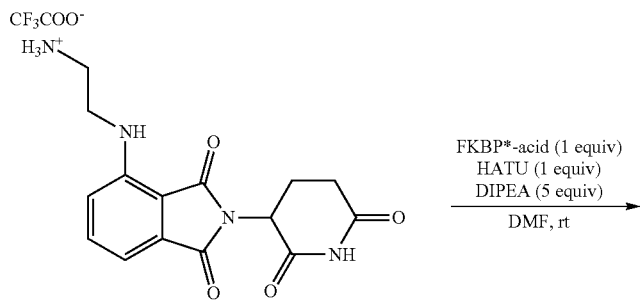

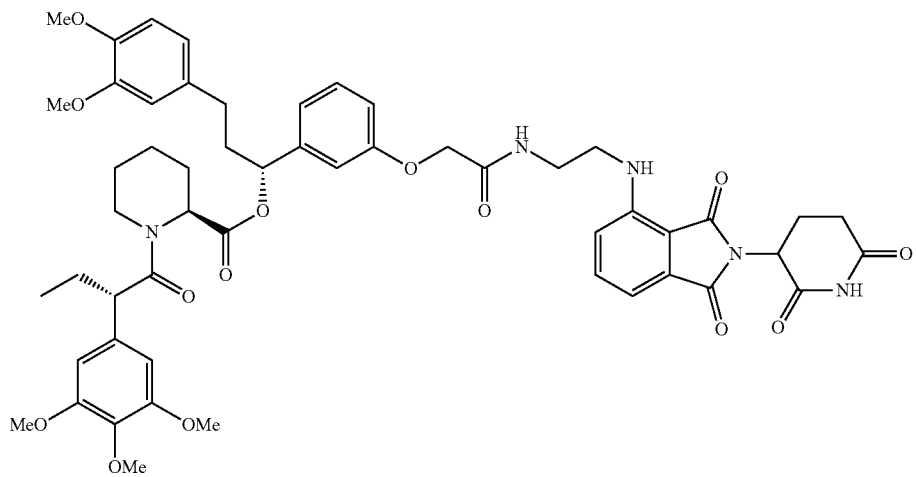

X2

X₂

FKBP*-acid (14.0 mg, 0.0202 mmol, 1 eq) and 2-((2-(2,6-dioxopiperidin-3-yl)-1,3-dioxoisoindolin-4-yl)amino)ethan-1-aminium 2,2,2-trifluoroacetate (8.7 mg, 0.0202 mmol, 1 equiv) are dissolved in DMF (0.202 mL, 0.1 M) at room temperature. DIPEA (17.6 OL, 0.101 mmol, 5 equiv) and HATU (7.6 mg, 0.0200 mmol, 1 equiv) are then added and the mixture is stirred at room temperature overnight. The reaction mixture is taken up in EtOAc (15 mL), and washed with satd. NaHCO₃(aq) (15 mL), water (15 mL) and brine (3×15 mL). The organic layer is dried over Na₂SO₄ and concentrated in vacuo. The crude material is purified by column chromatography.

Synthetic Example 68: Synthesis of diaminoethyl-acetyl-O-thalidomide trifluoroacetate

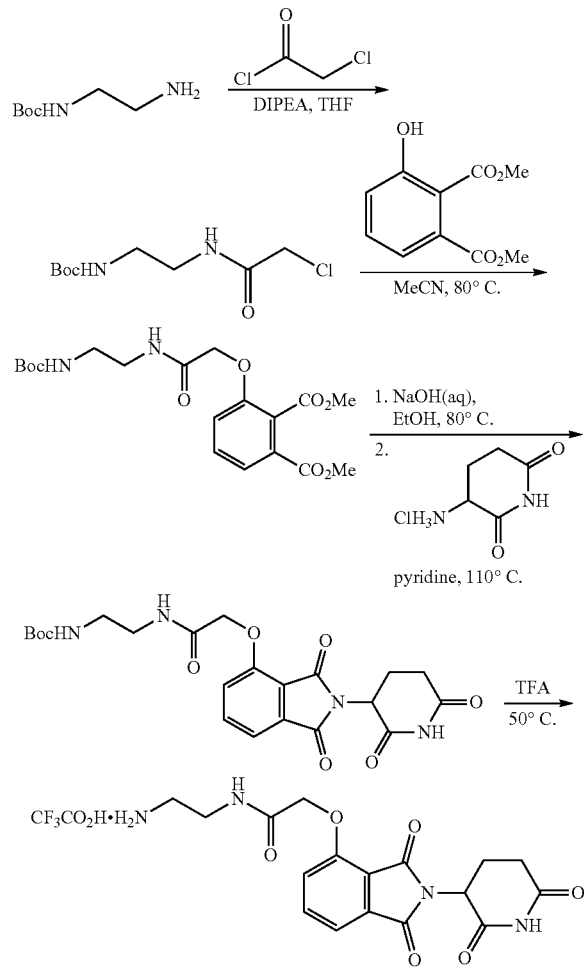

(1) Synthesis of tert-Butyl (2-(2-chloroacetamido)ethyl)carbamate

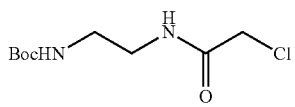 [SMILES: CC(C)(C)OC(=O)NCCNC(=O)CCl]

tert-butyl (2-aminoethyl)carbamate (0.40 mL, 2.5 mmol, 1 eq) was dissolved in THF (25 mL, 0.1 M) and DIPEA (0.44 mL, 2.5 mmol, 1 eq) at 0° C. Chloroacetyl chloride (0.21 mL, 2.75 mmol, 1.1 eq) was added and the mixture was allowed to warm to room temperature. After 22 hours, the mixture was diluted with EtOAc and washed with saturated sodium bicarbonate, water and brine. The organic layer was dried with sodium sulfate, filtered and concentrated under reduced pressure to give a white solid (0.66 g, quantitative yield) that carried forward to the next step without further purification. ¹H NMR (400 MHz, Chloroform-d) δ 7.16 (s, 1H), 4.83 (s, 1H), 4.04 (s, 2H), 3.42 (q, J=5.4 Hz, 2H), 3.32 (q, J=5.6 Hz, 2H), 1.45 (s, 9H). LCMS 237.30 (M+H).

(2) Synthesis of dimethyl 3-(2-((2-((tert-butoxycarbonyl)amino)ethyl)amino)-2-oxoethoxy)phthalate

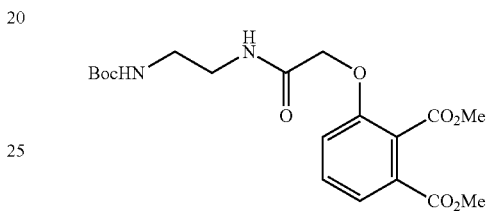

tert-butyl (2-(2-chloroacetamido)ethyl)carbamate (0.66 g, 1 eq) was dissolved in MeCN (17 mL, 0.15 M). Dimethyl 3-hydroxyphthalate (0.578 g, 2.75 mmol, 1.1 eq) and cesium carbonate (2.24 g, 6.88 mmol, 2.75 eq) were then added. The flask was fitted with a reflux condenser and heated to 80° C. for 32 hours. The mixture was then cooled to room temperature, diluted with EtOAc and washed three times with water. The organic layer was dried over sodium sulfate, filtered and concentrated under reduced pressure. Purification by column chromatography (ISCO, 4 g silica column, 0-15% MeOH/DCM over a 15 minute gradient) gave a yellow solid (0.394 g, 0.960 mmol, 38% over 2 steps). ¹H NMR (400 MHz, Chloroform-d) δ 7.65-7.56 (m, 1H), 7.50-7.41 (m, 1H), 7.27 (s, 1H), 7.11 (dd, J=8.4, 4.1 Hz, 2H), 5.17 (s, 1H), 4.57 (d, J=6.3 Hz, 2H), 3.94 (s, 2H), 3.88 (s, 2H), 3.40 (p, J=5.8 Hz, 4H), 3.32-3.19 (m, 4H), 1.39 (d, J=5.7 Hz, 13H). ¹³C NMR (100 MHz, cdcl₃) δ 168.37, 168.23, 165.73, 156.13, 154.71, 131.24, 130.09, 124.85, 123.49, 117.24, 79.42, 68.48, 53.22, 52.83, 40.43, 39.54, 28.44. LCMS 411.45 (M+H).

(3) Synthesis of diaminoethyl-acetyl-O-thalidomide trifluoroacetate

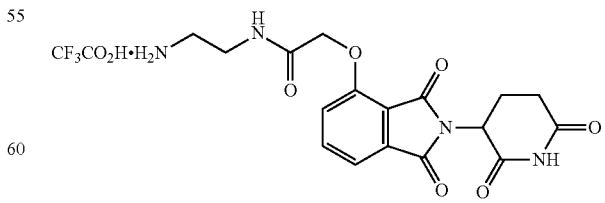

Dimethyl 3-(2-((2-((tert-butoxycarbonyl)amino)ethyl)amino)-2-oxoethoxy)phthalate (0.39 g, 0.970 mmol, 1 eq) was dissolved in EtOH (9.7 mL, 0.1 M). Aqueous 3M NaOH (0.97 mL, 2.91 mmol, 3 eq) was added and the mixture was heated to 80° C. for 3 hours. The mixture was cooled to room temperature, diluted with 50 mL DCM, 5 mL 1 M HCl and 20 mL water. The layers were separated and the organic layer was washed with 20 mL water. The combined aqueous layers were then extracted 3 times with 50 mL chloroform. The combined organic layers were dried over sodium sulfate, filtered and concentrated under reduced pressure to give a yellow solid (0.226 g) that was carried forward without further purification. LCMS 383.36.

The resultant yellow solid (0.226 g) and 3-aminopiperidine-2,6-dione hydrochloride (0.102 g, 0.6197 mmol, 1 eq) were dissolved in pyridine (6.2 mL, 0.1 M) and heated to 110° C. for 16 hours. The mixture was cooled to room temperature and concentrated under reduced pressure to give tert-butyl (2-(2-((2-(2,6-dioxopiperidin-3-yl)-1,3-dioxoisoindolin-4-yl)oxy)acetamido)ethyl)carbamate as a poorly soluble black tar (0.663 g) which was carried forward without purification (due to poor solubility). LCMS 475.42 (M+H).

The crude tert-butyl (2-(2-((2-(2,6-dioxopiperidin-3-yl)-1,3-dioxoisoindolin-4-yl)oxy)acetamido)ethyl)carbamate was dissolved in TFA (10 mL) and heated to 50° C. for 3.5 hours, then concentrated under reduced pressure. Purification by preparative HPLC gave a red oil (176.7 mg, 0.362 mmol, 37% over 3 steps). $^1$H NMR (400 MHz, Methanol-$d_4$) δ 7.85-7.76 (m, 1H), 7.57-7.50 (m, 1H), 7.48-7.41 (m, 1H), 5.13 (dd, J=12.6, 5.5 Hz, 1H), 4.81 (s, 2H), 3.62 (td, J=5.6, 1.8 Hz, 2H), 3.14 (t, J=5.8 Hz, 2H), 2.97 (s, 1H), 2.80-2.66 (m, 2H), 2.15 (dddd, J=10.1, 8.0, 5.8, 2.8 Hz, 1H). $^{13}$C NMR (100 MHz, cd$_3$od) δ 173.09, 170.00, 169.99, 166.78, 166.62, 154.93, 136.88, 133.46, 120.71, 117.93, 116.77, 68.29, 49.17, 39.37, 38.60, 30.73, 22.19. LCMS 375.30 (M+H for free base).

Synthetic Example 69: Synthesis of diaminobutyl-acetyl-O-thalidomide trifluoroacetate

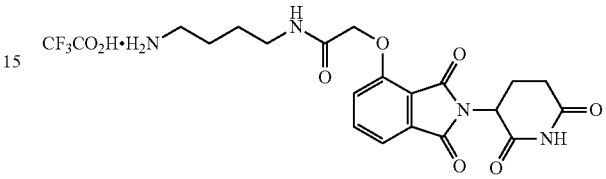

Diaminobutyl-acetyl-O-thalidomide trifluoroacetate was prepared according to the procedure in Fischer et al. *Nature*, 2014, 512, 49-53.

Synthetic Example 70: Synthesis of diaminohexyl-acetyl-O-thalidomide trifluoroacetate

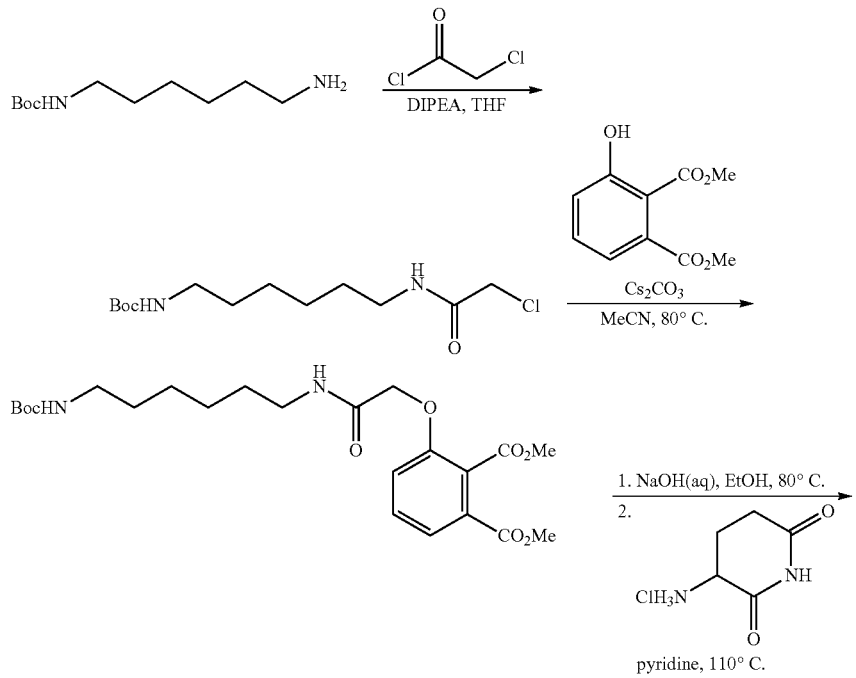

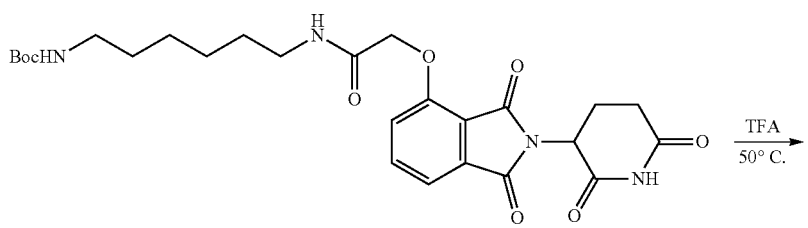

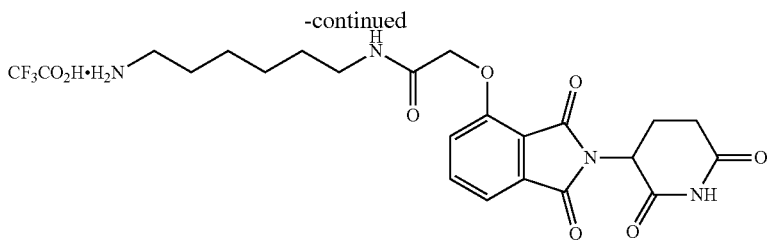

(1) Synthesis of tert-butyl (6-(2-chloroacetamido)hexyl)carbamate

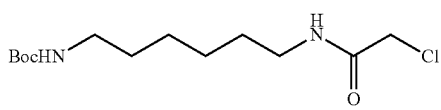 [SMILES: CC(C)(C)OC(=O)NCCCCCCNC(=O)CCl]

tert-butyl (6-aminohexyl)carbamate (0.224 mL, 1.0 mmol, 1 eq) was dissolved in THF (10 mL, 0.1 M). DIPEA (0.17 mL, 1.0 mmol, 1 eq) was added and the mixture was cooled to 0° C. Chloroacetyl chloride (88 microliters, 1.1 mmol, 1.1 eq) was added and the mixture was warmed to room temperature and stirred for 18 hours. The mixture was then diluted with EtOAc and washed with saturated sodium bicarbonate, water and brine. The organic layer was dried over sodium sulfate, filtered and concentrated under reduced pressure to give a white solid (0.2691 g, 0.919 mmol, 92%). $^1$H NMR (400 MHz, Chloroform-d) δ 6.60 (s, 1H), 4.51 (s, 1H), 4.05 (s, 2H), 3.30 (q, J=6.9 Hz, 2H), 3.11 (d, J=6.7 Hz, 2H), 1.57-1.46 (m, 4H), 1.44 (s, 9H), 1.38-1.32 (m, 4H). LCMS 293.39 (M+H).

(2) Synthesis of dimethyl 3-(2-((6-(((tert-butoxycarbonyl)amino)hexyl)amino)-2-oxoethoxy)phthalate

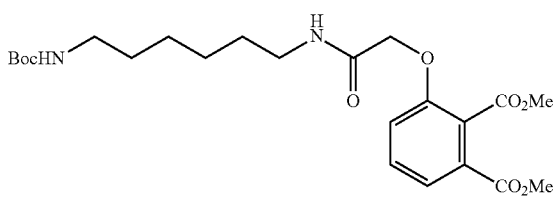 [SMILES: COC(=O)c1cccc(OCC(=O)NCCCCCCNC(=O)OC(C)(C)C)c1C(=O)OC]

tert-butyl (6-(2-chloroacetamido)hexyl)carbamate (0.2691 g, 0.919 mmol, 1 eq) was dissolved in MeCN (9.2 mL, 0.1 M). Dimethyl 3-hydroxyphthalate (0.212 g, 1.01 mmol, 1.1 eq) and cesium carbonate (0.823 g, 2.53 mmol, 2.75 eq) were added. The flask was fitted with a reflux condenser and heated to 80° C. for 14 hours. The mixture was cooled to room temperature and diluted with EtOAc, washed three times with water and back extracted once with EtOAc. The combined organic layers were dried over sodium sulfate, filtered and concentrated under reduced pressure. The crude material was purified by column chromatography (ISCO, 12 g silica column, 0-15% MeOH/DCM 15 minute gradient) to give a yellow oil (0.304 g, 0.651 mmol, 71%). $^1$H NMR (400 MHz, Chloroform-d) δ 7.66-7.58 (m, 1H), 7.44 (td, J=8.2, 1.6 Hz, 1H), 7.15-7.08 (m, 1H), 6.96 (s, 1H), 4.56 (s, 2H), 3.92 (t, J=1.6 Hz, 3H), 3.88 (t, J=1.6 Hz, 3H), 3.27 (q, J=6.9 Hz, 2H), 3.10-3.00 (m, 2H), 1.41 (s, 13H), 1.33-1.22 (m, 4H). $^{13}$C NMR (100 MHz, cdcl$_3$) δ 167.97, 167.37, 165.58, 155.95, 154.37, 130.97, 129.74, 124.94, 123.26, 116.81, 78.96, 68.04, 52.89, 52.87, 52.69, 52.67, 40.41, 38.96, 29.88, 29.13, 28.39, 26.33, 26.30. LCMS 467.49.

(3) Synthesis of diaminohexyl-acetyl-O-thalidomide trifluoroacetate

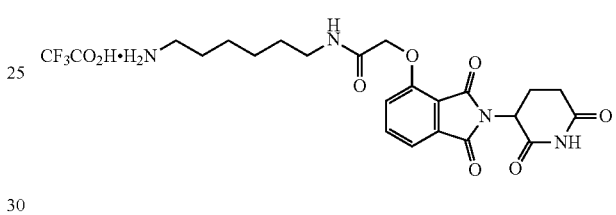

Dimethyl 3-(2-((6-(((tert-butoxycarbonyl)amino)hexyl)amino)-2-oxoethoxy)phthalate (0.304 g, 0.651 mmol, 1 eq) was dissolved in EtOH (6.5 mL, 0.1 M). Aqueous 3M NaOH (0.65 mL, 1.953 mmol, 3 eq) was added and the mixture was heated to 80° C. for 18 hours. The mixture was cooled to room temperature and diluted with 50 mL DCM and 10 mL 0.5 M HCl. The layers were separated and the organic layer was washed with 20 mL water. The combined aqueous layers were then extracted 3 times with chloroform. The combined organic layers were dried over sodium sulfate, filtered and concentrated under reduced pressure to give a yellow foam (0.290 g) that was carried forward without further purification. LCMS 439.47.

The resultant yellow solid (0.290 g) and 3-aminopiperidine-2,6-dione hydrochloride (0.113 g, 0.69 mmol, 1 eq) were dissolved in pyridine (6.9 mL, 0.1 M) and heated to 110° C. for 17 hours. The mixture was cooled to room temperature and concentrated under reduced pressure to give tert-butyl (6-(2-((2-(2,6-dioxopiperidin-3-yl)-1,3-dioxoisoindolin-4-yl)oxy)acetamido)hexyl)carbamate as a black solid (0.4216 g) which was carried forward without purification (due to poor solubility). LCMS 531.41 (M+H).

The crude tert-butyl (6-(2-((2-(2,6-dioxopiperidin-3-yl)-1,3-dioxoisoindolin-4-yl)oxy)acetamido)hexyl)carbamate (0.4216 g) was dissolved in TFA (10 mL) and heated to 50° C. for 2 hours. The mixture was concentrated under reduced pressure, then concentrated under reduced pressure. Purification by preparative HPLC gave a brown solid (379.2 mg). $^1$H NMR (400 MHz, Methanol-d$_4$) δ 7.79 (dd, J=8.4, 7.4 Hz, 1H), 7.52 (d, J=7.2 Hz, 1H), 7.42 (d, J=8.4 Hz, 1H), 5.13 (dd, J=12.6, 5.5 Hz, 1H), 4.75 (s, 2H), 3.32 (t, J=7.6 Hz, 2H), 2.96-2.89 (m, 2H), 2.89-2.65 (m, 3H), 2.16 (ddt, J=10.4, 5.4, 2.9 Hz, 1H), 1.63 (dp, J=20.6, 7.1 Hz, 4H), 1.51-1.34 (m, 4H). $^{13}$C NMR (100 MHz, cd$_3$od) δ 174.57, 171.42, 169.90, 168.24, 167.79, 156.23, 138.23, 134.87, 121.69, 119.22, 117.98, 69.36, 50.53, 40.64, 39.91, 32.14, 30.01, 28.44, 27.23, 26.96, 23.63. LCMS 431.37 (M+H).

Synthetic Example 71: Synthesis of diaminooctyl-acetyl-O-thalidomide trifluoroacetate

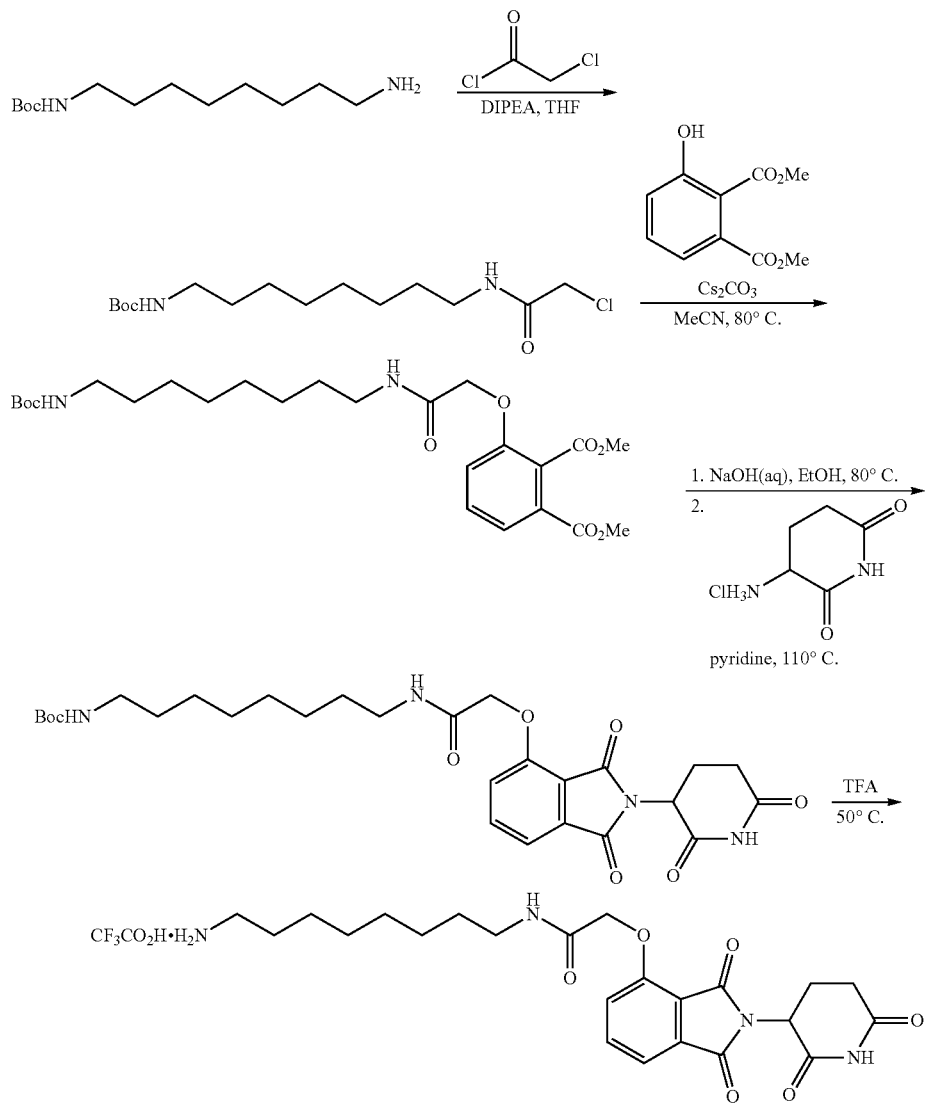

(1) Synthesis of tert-Butyl (8-(2-chloroacetamido)octyl)carbamate

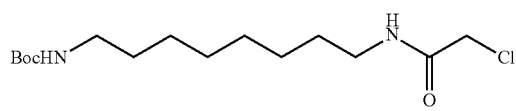 [SMILES: CC(C)(C)OC(=O)NCCCCCCCCNC(=O)CCl]

Octane-1,8-diamine (1.65 g, 11.45 mmol, 5 eq) was dissolved in chloroform (50 mL). A solution of di-tert-butyl dicarbonate (0.54 g, 2.291 mmol, 1 eq) in chloroform (10 mL) was added slowly at room temperature and stirred for 16 hours before being concentrated under reduced pressure. The solid material was resuspended in a mixture of DCM, MeOH, EtOAc and 0.5 N $NH_3$ (MeOH), filtered through celite and concentrated under reduced pressure. Purification by column chromatography (ISCO, 12 g $NH_2$-silica column, 0-15% MeOH/DCM over a 15 minute gradient) gave a mixture (1.75 g) of the desired product and starting material which was carried forward without further purification.

This mixture was dissolved in THF (72 mL) and DIPEA (1.25 mL, 7.16 mmol) and cooled to 0° C. Chloroacetyl chloride (0.63 mL, 7.88 mmol) was added and the mixture was allowed to warm to room temperature. After 16 hours, the mixture was diluted with EtOAc and washed with saturated sodium bicarbonate, water and brine. The resultant mixture was purified by column chromatography (ISCO, dry load onto silica, 24 g column, 0-100% EtOAc/hexanes, over a 21 minute gradient) to give a white solid (0.56 g, 1.745 mmol, 76% over 2 steps). $^1$H NMR (400 MHz, Chloroform-d) δ 6.55 (s, 1H), 4.48 (s, 1H), 4.05 (s, 2H), 3.30 (q, J=6.9 Hz, 2H), 3.10 (d, J=6.2 Hz, 2H), 1.44 (s, 12H), 1.31 (s, 9H). $^{13}$C NMR (100 MHz, cdcl$_3$) δ 165.86, 156.14, 77.36, 42.86, 40.73, 40.00, 30.18, 29.44, 29.26, 28.59, 26.86, 26.82. LCMS 321.34 (M+H).

(2) Synthesis of dimethyl 3-(2-((8-((tert-butoxycarbonyl)amino)octyl)amino)-2-oxoethoxy)phthalate

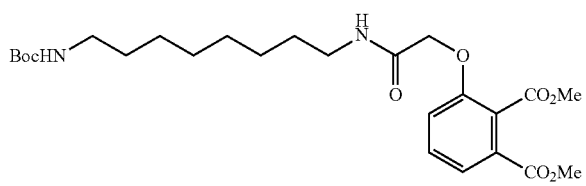 [SMILES: COC(=O)c1cccc(OCC(=O)NCCCCCCCCNC(=O)OC(C)(C)C)c1C(=O)OC]

tert-butyl (8-(2-chloroacetamido)octyl)carbamate (0.468 g, 1.46 mmol, 1 eq) was dissolved in MeCN (15 mL, 0.1 M). Dimethyl 3-hydroxyphthalate (0.337 g, 1.60 mmol, 1.1 eq) and cesium carbonate (1.308 g, 4.02 mmol, 2.75 eq) were added. The flask was fitted with a reflux condenser and heated to 80° C. for 18 hours. The mixture was cooled to room temperature and diluted water and extracted once with chloroform and twice with EtOAc. The combined organic layers were dried over sodium sulfate, filtered and concentrated under reduced pressure.

The crude material was purified by column chromatography (ISCO, 24 g silica column, 0-15% MeOH/DCM 20 minute gradient) to give a yellow oil (0.434 g, 0.878 mmol, 60%). $^1$H NMR (400 MHz, Chloroform-d) δ 7.57 (dd, J=7.9, 0.8 Hz, 1H), 7.40 (t, J=8.1 Hz, 1H), 7.07 (dd, J=8.4, 0.7 Hz, 1H), 6.89 (t, J=5.3 Hz, 1H), 4.63 (s, 1H), 4.52 (s, 2H), 3.88 (s, 3H), 3.83 (s, 3H), 3.22 (q, J=6.9 Hz, 2H), 3.01 (q, J=6.4 Hz, 2H), 1.36 (s, 12H), 1.20 (s, 9H). $^{13}$C NMR (100 MHz, cdcl$_3$) δ 167.89, 167.29, 165.54, 155.97, 154.38, 130.95, 129.69, 124.96, 123.23, 116.86, 78.82, 68.05, 52.83, 52.82, 52.66, 52.64, 40.54, 39.06, 29.97, 29.19, 29.10, 29.06, 28.40, 26.66, 26.61. LCMS 495.42 (M+H).

(3) Synthesis of diaminooctyl-acetyl-O-thalidomide trifluoroacetate

Dimethyl 3-(2-((8-((tert-butoxycarbonyl)amino)octyl)amino)-2-oxoethoxy)phthalate (0.434 g, 0.878 mmol, 1 eq) was dissolved in EtOH (8.8 mL, 0.1 M) Aqueous 3M NaOH (0.88 mL, 2.63 mmol, 3 eq) was added and the mixture was heated to 80° C. for 24 hours. The mixture was cooled to room temperature and diluted with 50 mL DCM and 10 mL 0.5 M HCl. The layers were separated and the organic layer was washed with 20 mL water. The combined aqueous layers were then extracted 3 times with chloroform. The combined organic layers were dried over sodium sulfate, filtered and concentrated under reduced pressure to give a yellow solid (0.329 g) that was carried forward without further purification. LCMS 467.41.

The resultant yellow solid (0.329 g) and 3-aminopiperidine-2,6-dione hydrochloride (0.121 g, 0.734 mmol, 1 eq) were dissolved in pyridine (7.3 mL, 0.1 M) and heated to 110° C. for 20 hours. The mixture was cooled to room temperature and concentrated under reduced pressure to give tert-butyl (8-(2-((2-(2,6-dioxopiperidin-3-yl)-1,3-dioxoisoindolin-4-yl)oxy)acetamido) octyl) carbamate as a black tar (0.293 g) which was carried forward without purification (due to poor solubility). LCMS 559.45 (M+H).

The crude tert-butyl (8-(2-((2-(2,6-dioxopiperidin-3-yl)-1,3-dioxoisoindolin-4-yl)oxy)acetamido)octyl)carbamate (0.293 g) was dissolved in TFA (10 mL) and heated to 50° C. for 4 hours. The mixture was concentrated under reduced pressure, then concentrated under reduced pressure. Purification by preparative HPLC gave a brown residue (114.69 mg, 23% over 3 steps). $^1$H NMR (400 MHz, Methanol-d$_4$) δ 7.84-7.78 (m, 1H), 7.54 (d, J=7.3 Hz, 1H), 7.43 (d, J=8.5 Hz, 1H), 5.13 (dd, J=12.5, 5.5 Hz, 1H), 4.76 (s, 2H), 3.32 (d, J=4.1 Hz, 1H), 3.30 (d, J=3.3 Hz, 1H), 2.94-2.84 (m, 3H), 2.80-2.70 (m, 2H), 2.19-2.12 (m, 1H), 1.67-1.55 (m, 4H), 1.40-1.34 (m, 8H). $^{13}$C NMR (100 MHz, cd$_3$od) δ 174.57, 171.37, 169.85, 168.26, 167.78, 156.26, 138.22, 134.91, 121.70, 119.28, 117.97, 69.37, 50.57, 40.76, 40.08, 32.17, 30.19, 30.05, 30.01, 28.52, 27.68, 27.33, 23.63. LCMS 459.41 (M+H).

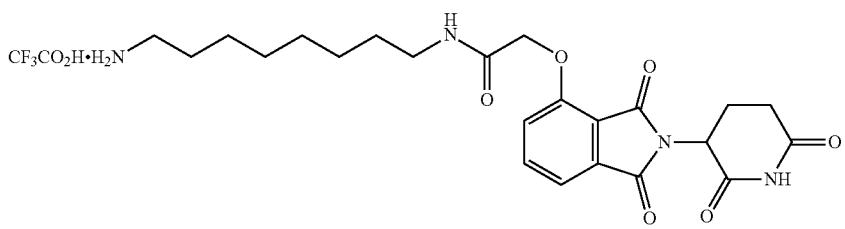

Synthetic Example 72: Synthesis of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate

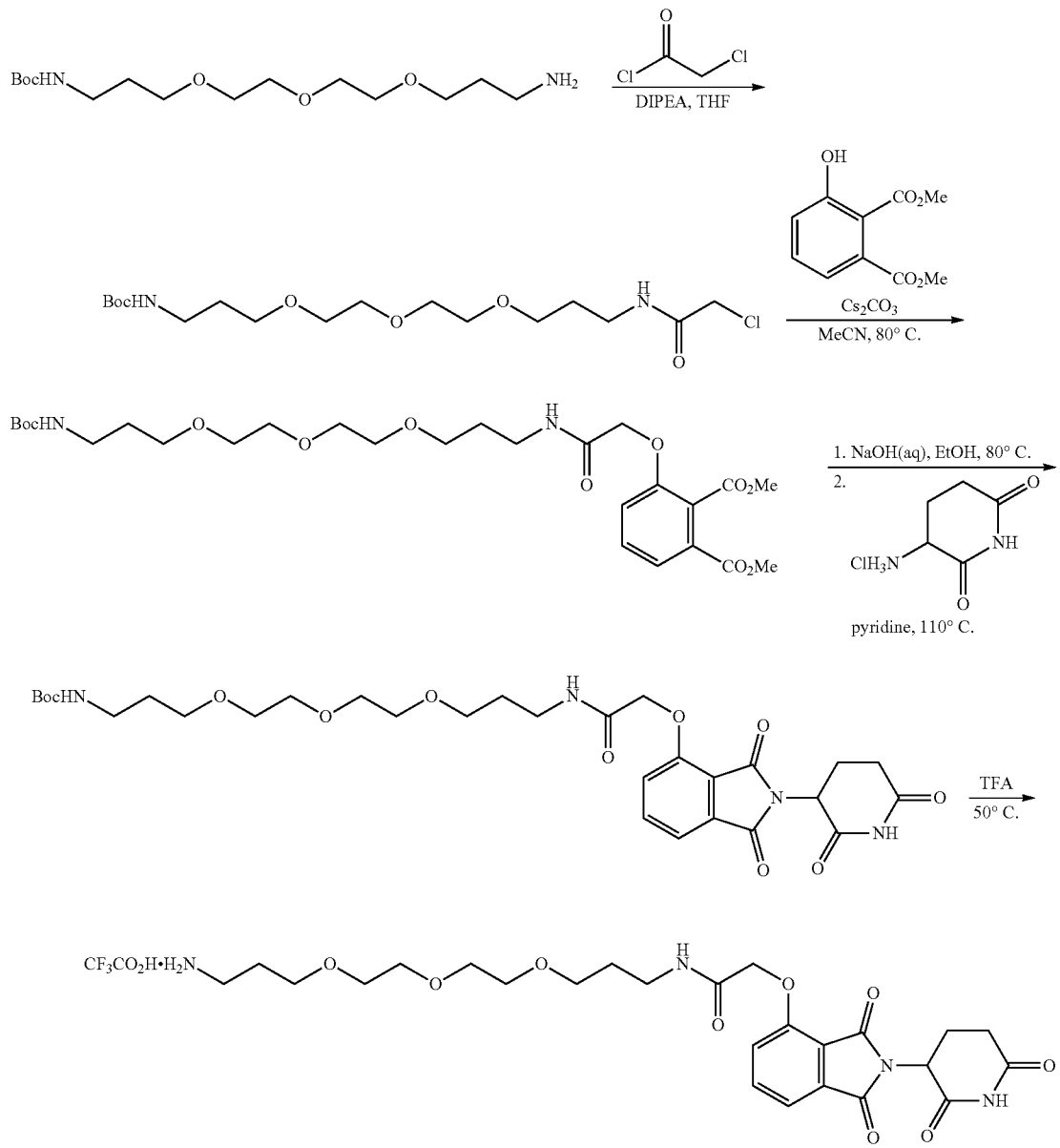

(1) Synthesis of tert-butyl (1-chloro-2-oxo-7,10,13-trioxa-3-azahexadecan-16-yl)carbamate

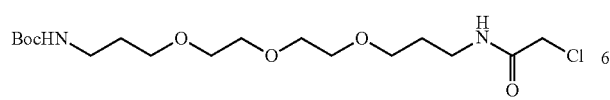

tert-butyl (3-(2-(2-(3-aminopropoxy)ethoxy)ethoxy)propyl)carbamate (1.0 g, 3.12 mmol, 1 eq) was dissolved in THF (31 mL, 0.1 M). DIPEA (0.543 mL, 3.12 mmol, 1 eq) was added and the solution was cooled to 0° C. Chloroacetyl chloride (0.273 mL, 3.43 mmol, 1.1 eq) was added and the mixture was warmed slowly to room temperature. After 24 hours, the mixture was diluted with EtOAc and washed with saturated sodium bicarbonate, water then brine. The organic layer was dried over sodium sulfate, filtered and condensed to give a yellow oil (1.416 g) that was carried forward without further purification. $^1$H NMR (400 MHz, Chloroform-d) δ 7.24 (s, 1H), 5.00 (s, 1H), 3.98-3.89 (m, 2H), 3.54 (dddt, J=17.0, 11.2, 5.9, 2.2 Hz, 10H), 3.47-3.40 (m, 2H), 3.37-3.31 (m, 2H), 3.17-3.07 (m, 2H), 1.79-1.70 (m, 2H), 1.67 (p, J=6.1 Hz, 2H), 1.35 (s, 9H). $^{13}$C NMR (100 MHz, cdcl$_3$) δ 165.83, 155.97, 78.75, 70.49, 70.47, 70.38, 70.30, 70.14, 69.48, 42.61, 38.62, 38.44, 29.62, 28.59, 28.40. LCMS 397.37 (M+H).

(2) Synthesis of dimethyl 3-((2,2-dimethyl-4,20-dioxo-3,9,12,15-tetraoxa-5,19-diazahenicosan-21-yl)oxy)phthalate

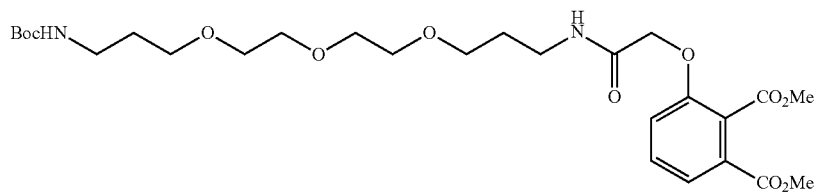 [SMILES: COC(=O)c1cccc(OCC(=O)NCCCOCCOCCOCCCNC(=O)OC(C)(C)C)c1C(=O)OC]

tert-butyl (1-chloro-2-oxo-7,10,13-trioxa-3-azahexadecan-16-yl)carbamate (1.41 g, 3.12 mmol, 1 eq) was dissolved in MeCN (32 mL, 0.1 M). Dimethyl 3-hydroxyphthalate (0.721 g, 3.43 mmol, 1.1 eq) and cesium carbonate (2.80 g, 8.58 mmol, 2.75 eq) were added. The flask was fitted with a reflux condenser and heated to 80° C. for 19 hours. The mixture was cooled to room temperature and diluted water and extracted once with chloroform and twice with EtOAc. The combined organic layers were dried over sodium sulfate, filtered and concentrated under reduced pressure. The crude material was purified by column chromatography (ISCO, 24 g silica column, 0-15% MeOH/DCM 22 minute gradient) to give a yellow oil (1.5892 g, 2.78 mmol, 89% over two steps). $^1$H NMR (400 MHz, Chloroform-d) δ 7.52 (d, J=7.8 Hz, 1H), 7.35 (t, J=8.1 Hz, 1H), 7.04 (d, J=8.3 Hz, 1H), 7.00 (t, J=5.3 Hz, 1H), 5.06 (s, 1H), 4.46 (s, 2H), 3.83 (s, 3H), 3.78 (s, 3H), 3.47 (ddd, J=14.9, 5.5, 2.8 Hz, 8H), 3.39 (dt, J=9.4, 6.0 Hz, 4H), 3.29 (q, J=6.5 Hz, 2H), 3.09 (d, J=6.0 Hz, 2H), 1.70 (p, J=6.5 Hz, 2H), 1.63 (p, J=6.3 Hz, 2H), 1.31 (s, 9H). $^{13}$C NMR (100 MHz, cdcl$_3$) δ 167.68, 167.36, 165.45, 155.93, 154.41, 130.87, 129.60, 125.01, 123.20, 117.06, 78.60, 70.40, 70.17, 70.06, 69.39, 68.67, 68.25, 52.77, 52.57, 38.38, 36.58, 29.55, 29.20, 28.34. LCMS 571.47 (M+H).

(3) Synthesis of N-(3-(2-(2-(3-aminopropoxy)ethoxy)ethoxy)propyl)-2-((2-(2,6-dioxopiperidin-3-yl)-1,3-dioxoisoindolin-4-yl)oxy)acetamide trifluoroacetate dimethyl 3-((2,2-dimethyl-4,20-dioxo-3,9,12,15-tetraoxa-5,19-diazahenicosan-21-yl)oxy)phthalate (1.589 g, 2.78 mmol, 1 eq) was dissolved in EtOH (14 mL, 0.2 M). Aqueous 3M NaOH (2.8 mL, 8.34 mmol, 3 eq) was added and the mixture was heated to 80° C. for 22 hours. The mixture was then cooled to room temperature, diluted with 50 mL DCM and 20 mL 0.5 M HCl. The layers were separated and the organic layer was washed with 25 mL water. The aqueous layers were combined and extracted three times with 50 mL chloroform. The combined organic layers were dried over sodium sulfate, filtered and condensed to give 1.53 g of material that was carried forward without further purification. LCMS 553.44.

The resultant material (1.53 g) and 3-aminopiperidine-2,6-dione hydrochloride (0.480 g, 2.92 mmol, 1 eq) were dissolved in pyridine (11.7 mL, 0.25 M) and heated to 110° C. for 17 hours. The mixture was cooled to room temperature and concentrated under reduced pressure to give crude tert-butyl (1-((2-(2,6-dioxopiperidin-3-yl)-1,3-dioxoisoindolin-4-yl)oxy)-2-oxo-7,10,13-trioxa-3-azahexadecan-16-yl)carbamate as a black sludge (3.1491 g) that was carried forward without further purification. LCMS 635.47.

The crude tert-butyl (1-((2-(2,6-dioxopiperidin-3-yl)-1,3-dioxoisoindolin-4-yl)oxy)-2-oxo-7,10,13-trioxa-3-azahexadecan-16-yl)carbamate (3.15 g) was dissolved in TFA (20 mL) and heated to 50° C. for 2.5 hours. The mixture was cooled to room temperature, diluted with MeOH and concentrated under reduced pressure. The material was purified by preparative HPLC to give N-(3-(2-(2-(3-aminopropoxy)ethoxy)propyl)-2-((2-(2,6-dioxopiperidin-3-yl)-1,3-dioxoisoindolin-4-yl)oxy)acetamide trifluoroacetate (1.2438 g, 1.9598 mmol, 71% over 3 steps) as a dark red oil. $^1$H NMR (400 MHz, Methanol-d$_4$) δ 7.77 (dd, J=8.3, 7.5 Hz, 1H), 7.49 (d, J=7.3 Hz, 1H), 7.40 (d, J=8.5 Hz, 1H), 5.12 (dd, J=12.8, 5.5 Hz, 1H), 4.75 (s, 2H), 3.68-3.51 (m, 12H), 3.40 (t, J=6.8 Hz, 2H), 3.10 (t, J=6.4 Hz, 2H), 2.94-2.68 (m, 3H), 2.16 (dtd, J=12.6, 5.4, 2.5 Hz, 1H), 1.92 (p, J=6.1 Hz, 2H), 1.86-1.77 (m, 2H). $^{13}$C NMR (100 MHz, cd$_3$od) δ 173.17, 169.97, 168.48, 166.87, 166.30, 154.82, 136.89, 133.41, 120.29, 117.67, 116.58, 69.96, 69.68, 69.60, 68.87, 68.12, 67.92, 49.19, 38.62, 36.14, 30.80, 28.92, 26.63, 22.22. LCMS 536.41 (M+H).

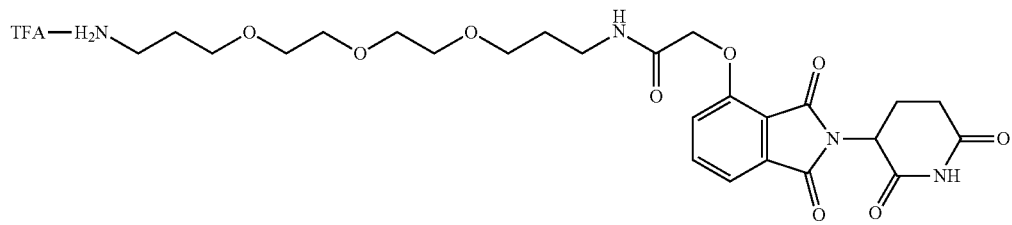

Synthetic Example 73: Synthesis of N-(6-aminohexyl)-2-(2,6-dioxopiperidin-3-yl)-1,3-dioxoisoindoline-5-carboxamide

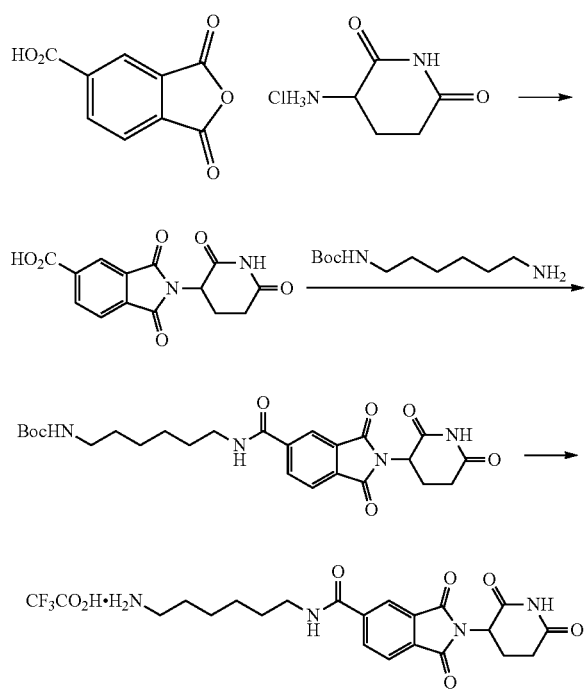

(1) Synthesis of 2-(2,6-dioxopiperidin-3-yl)-1,3-dioxoisoindoline-5-carboxylic acid

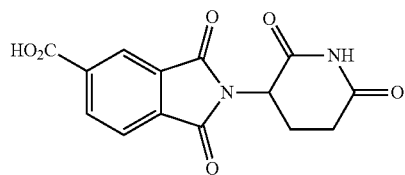 [SMILES: O=C1CCC(N2C(=O)c3ccc(C(=O)O)cc3C2=O)C(=O)N1]

1,3-dioxo-1,3-dihydroisobenzofuran-5-carboxylic acid (0.192 g, 1 mmol, 1 eq) and 3-aminopiperidine-2,6-dione hydrochloride (0.165 g, 1 mmol, 1 eq) were dissolved in DMF (2.5 mL) and acetic acid (5 mL) and heated to 80° C. for 24 hours. The mixture was then concentrated under reduced pressure and diluted with EtOH, from which a precipitate slowly formed. The precipitate was washed twice with EtOH to give a white solid (84.8 mg, 0.28 mmol, 28%). $^1$H NMR (400 MHz, DMSO-$d_6$) 13.74 (s, 1H), 11.12 (s, 1H), 8.39 (dd, J=7.8, 1.4 Hz, 1H), 8.26 (s, 1H), 8.04 (d, J=7.8 Hz, 1H), 5.18 (dd, J=12.8, 5.4 Hz, 1H), 2.93-2.88 (m, 1H), 2.84 (d, J=4.7 Hz, 0H), 2.66-2.50 (m, 2H), 2.12-1.99 (m, 1H). LCMS 303.19 (M+H).

(2) Synthesis of tert-butyl (6-(2-(2,6-dioxopiperidin-3-yl)-1,3-dioxoisoindoline-5-carboxamido)hexyl)carbamate 2-(2,6-dioxopiperidin-3-yl)-1,3-dioxoisoindoline-5-carboxylic acid (22.7 mg, 0.0751 mmol, 1 eq) and HATU (31.4 mg, 0.0826 mmol, 1.1 eq) were dissolved in DMF (0.75 mL). After 5 minutes, DIPA (39.2 microliters, 0.225 mmol, 3 eq) was added. After an additional 5 minutes, tert-butyl (6-aminohexyl)carbamate (19.5 mg, 0.0901 mmol, 1.2 eq) was added as a solution in DMF (0.75 mL). The mixture was stirred for 20 hours, then diluted with EtOAc. The organic layer was washed three times with brine, dried over sodium sulfate and concentrated under reduced pressure. Purification by column chromatography (ISCO, 4 g column, 0-10% MeOH/DCM, 25 minute gradient) to give a yellow oil (17.18 mg, 0.03432 mmol, 46%). $^1$H NMR (400 MHz, Chloroform-d) δ 8.29 (d, J=6.2 Hz, 2H), 8.16 (s, 1H), 7.94 (d, J=8.4 Hz, 1H), 6.91 (s, 1H), 5.00 (dd, J=12.4, 5.3 Hz, 1H), 4.58 (s, 1H), 3.47 (q, J=6.7 Hz, 2H), 3.14 (q, J=8.5, 7.3 Hz, 2H), 2.97-2.69 (m, 3H), 2.17 (ddd, J=10.4, 4.8, 2.6 Hz, 1H), 1.65 (p, J=6.9 Hz, 2H), 1.53-1.32 (m, 15H). $^{13}$C NMR (100 MHz, cdcl$_3$) δ 174.69, 170.77, 167.86, 166.67, 165.27, 156.49, 141.06, 133.95, 133.71, 132.13, 124.21, 122.27, 77.36, 49.71, 39.75, 31.54, 30.27, 29.22, 28.57, 25.70, 25.37, 22.73. LCMS 501.28 (M+H).

(3) Synthesis of N-(6-aminohexyl)-2-(2,6-dioxopiperidin-3-yl)-1,3-dioxoisoindoline-5-carboxamide tert-butyl (6-(2-(2,6-dioxopiperidin-3-yl)-1,3-dioxoisoindoline-5-carboxamido)hexyl)carbamate (17.18 mg, 0.343 mmol, 1 eq) was dissolved in TFA (1 mL) and heated to 50° C. for 2 hours. The mixture was concentrated under reduced pressure to give a yellow oil (13.29 mg) which was deemed sufficiently pure without further purification. $^1$H NMR (400 MHz, Methanol-$d_4$) δ 8.27 (dd, J=9.3, 1.3 Hz, 2H), 7.99 (d, J=7.6 Hz, 1H), 5.18 (dd, J=12.5, 5.4 Hz, 1H), 3.48-3.40 (m, 2H), 2.96-2.84 (m, 3H), 2.76 (ddd, J=17.7, 8.1, 3.7 Hz, 2H), 2.20-2.12 (m, 1H), 1.75-1.63 (m, 4H), 1.53-1.43 (m, 4H). LCMS 401.31 (M+H).

Synthetic Example 74: Synthesis of 2-((2-(2,6-di-oxopiperidin-3-yl)-1,3-dioxoisoindolin-4-yl)oxy) acetic acid

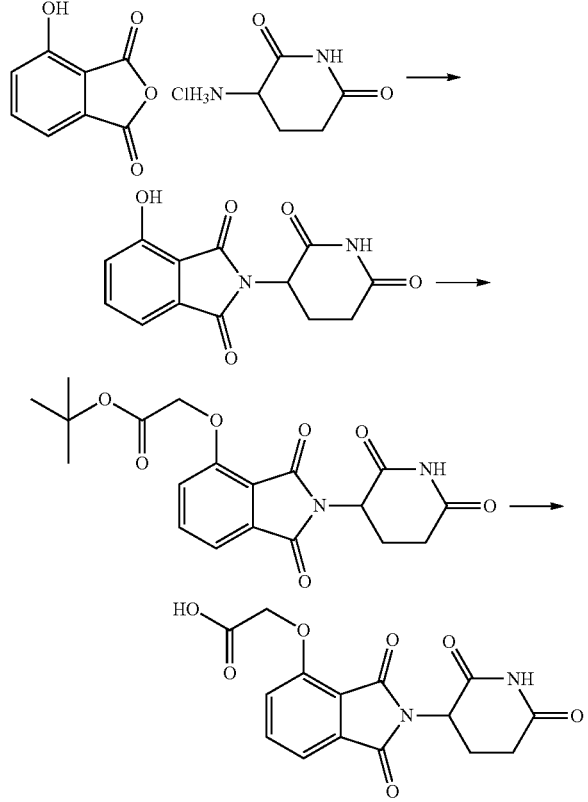

(1) Synthesis of 2-(2,6-dioxopiperidin-3-yl)-4-hydroxyisoindoline-1,3-dione

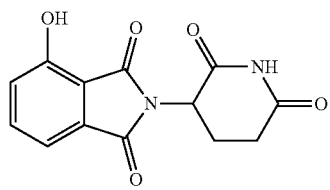 [SMILES: O=C1CCC(N2C(=O)c3cccc(O)c3C2=O)C(=O)N1]

4-hydroxyisobenzofuran-1,3-dione (0.773 g, 4.71 mmol, 1 eq) and 3-aminopiperidine-2,6-dione hydrochloride (0.775 g, 4.71 mmol, 1 eq) were dissolved in pyridine (19 mL) and heated to 110° C. for 16 hours. The mixture was concentrated under reduced pressure and purified by column chromatography (ISCO, 12 g silica column, 0-10% MeOH/DCM, 25 minute gradient) to give an off white solid (1.14 g, 4.16 mmol, 88%). $^1$H NMR (400 MHz, DMSO-d$_6$) δ 11.19 (s, 1H), 11.07 (s, 1H), 7.65 (dd, J=8.3, 7.3 Hz, 1H), 7.31 (d, J=7.2 Hz, 1H), 7.24 (d, J=8.4 Hz, 1H), 5.07 (dd, J=12.8, 5.4 Hz, 1H), 2.88 (ddd, J=17.7, 14.2, 5.4 Hz, 1H), 2.63-2.50 (m, 2H), 2.11-1.95 (m, 1H). LCMS 275.11 (M+H).

(2) Synthesis of tert-butyl 2-((2-(2,6-dioxopiperi-din-3-yl)-1,3-dioxoisoindolin-4-yl)oxy)acetate

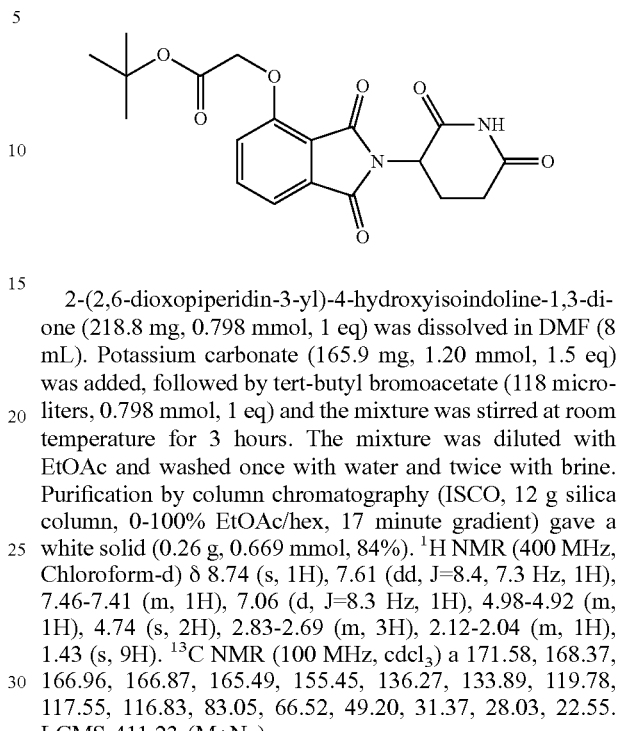

2-(2,6-dioxopiperidin-3-yl)-4-hydroxyisoindoline-1,3-dione (218.8 mg, 0.798 mmol, 1 eq) was dissolved in DMF (8 mL). Potassium carbonate (165.9 mg, 1.20 mmol, 1.5 eq) was added, followed by tert-butyl bromoacetate (118 microliters, 0.798 mmol, 1 eq) and the mixture was stirred at room temperature for 3 hours. The mixture was diluted with EtOAc and washed once with water and twice with brine. Purification by column chromatography (ISCO, 12 g silica column, 0-100% EtOAc/hex, 17 minute gradient) gave a white solid (0.26 g, 0.669 mmol, 84%). $^1$H NMR (400 MHz, Chloroform-d) δ 8.74 (s, 1H), 7.61 (dd, J=8.4, 7.3 Hz, 1H), 7.46-7.41 (m, 1H), 7.06 (d, J=8.3 Hz, 1H), 4.98-4.92 (m, 1H), 4.74 (s, 2H), 2.83-2.69 (m, 3H), 2.12-2.04 (m, 1H), 1.43 (s, 9H). $^{13}$C NMR (100 MHz, cdcl$_3$) a 171.58, 168.37, 166.96, 166.87, 165.49, 155.45, 136.27, 133.89, 119.78, 117.55, 116.83, 83.05, 66.52, 49.20, 31.37, 28.03, 22.55. LCMS 411.23 (M+Na).

(3) Synthesis of 2-((2-(2,6-dioxopiperidin-3-yl)-1,3-dioxoisoindolin-4-yl)oxy)acetic acid

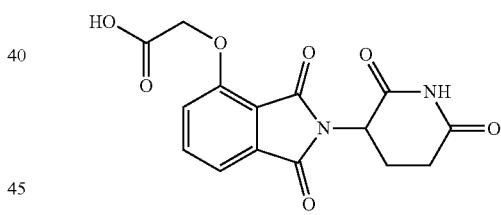

tert-butyl 2-((2-(2,6-dioxopiperidin-3-yl)-1,3-dioxoisoindolin-4-yl)oxy)acetate (47.5 mg, 0.122 mmol, 1 eq) was dissolved in TFA (1.3 mL) at room temperature. After 3 hours, the mixture was diluted with DCM and concentrated under reduced pressure to yield a white solid (42.27 mg), which was deemed sufficiently pure without further purification. $^1$H NMR (400 MHz, Methanol-d$_4$) δ 7.76 (dd, J=8.5, 7.3 Hz, 1H), 7.50 (d, J=7.3 Hz, 1H), 7.34 (d, J=8.5 Hz, 1H), 5.11 (dd, J=12.5, 5.5 Hz, 1H), 4.96 (s, 2H), 2.87 (ddd, J=17.8, 14.2, 5.0 Hz, 1H), 2.80-2.65 (m, 2H), 2.18-2.09 (m, 1H). LCMS 333.15 (M+H).

Heterobifunctional Compound Pharmaceutical Compositions

In another aspect of the present application, pharmaceutical compositions are provided, which comprise any one of the heterobifunctional compounds described herein (or a prodrug, pharmaceutically acceptable salt or other pharmaceutically acceptable derivative thereof), and optionally comprise a pharmaceutically acceptable carrier. According to the present application, a pharmaceutically acceptable derivative includes, but is not limited to, pharmaceutically acceptable salts, esters, salts of such esters, or a pro-drug or other adduct or derivative of a compound of this application which upon administration to a patient in need is capable of providing, directly or indirectly, a heterobifunctional compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J Pharmaceutical Sciences* 66 (1977): 1-19, incorporated herein by reference. The salts can be prepared in situ during the final isolation and purification of the heterobifunctional compounds of the application, or separately by reacting a free base or free acid function with a suitable reagent, as described generally below. For example, a free base function can be reacted with a suitable acid. Furthermore, where the heterobifunctional compounds of the application carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters that hydrolyze in vivo and include those that break down readily in the human body to leave the parent heterobifunctional compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the heterobifunctional compounds of the present application which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the application. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, (1987), both of which are incorporated herein by reference.

As described above, the pharmaceutical heterobifunctional compound compositions of the present application additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Sixteenth Edition, E. W. Martin (Mack Publishing Co., Easton, Pa., (1980)) discloses various carriers used in formulating pharmaceutical compositions and known techniques for the preparation thereof. Except insofar as any conventional carrier medium is incompatible with the compounds of the application, such as by producing any undesirable biological effect or otherwise interacting in a deleterious manner with any other component(s) of the pharmaceutical composition, its use is contemplated to be within the scope of this application. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner.

Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active heterobifunctional compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active heterobifunctional compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The present application encompasses pharmaceutically acceptable topical formulations of inventive compounds. The term "pharmaceutically acceptable topical formulation", as used herein, means any formulation which is pharmaceutically acceptable for intradermal administration of a compound of the application by application of the formulation to the epidermis. In certain embodiments of the application, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, *Remington's Pharmaceutical Sciences,* 16th Edition, (1980) and 17th Edition, (1985), both published by Mack Publishing Company, Easton, Pa., the disclosures of which are incorporated herein by reference in their entireties. In certain other embodiments, the topical formulations of the application may comprise excipients. Any pharmaceutically acceptable excipient known in the art may be used to prepare the inventive pharmaceutically acceptable topical formulations. Examples of excipients that can be included in the topical formulations of the application include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the application include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the application include, but are not limited to, vitamin E oil, allatoin, dimethicone, glycerin, petrolatum, and zinc oxide.

In certain embodiments, the pharmaceutically acceptable topical formulations of the application comprise at least a compound of the application and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Maibach H. I. and Smith H. E. (eds.), *Percutaneous Penetration Enhancers*, CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (eds.), Interpharm Press Inc., Buffalo Grove, Ill. (1997). In certain exemplary embodiments, penetration agents for use with the application include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the application are creams, which may further contain saturated or unsaturated fatty acids such as stearic acid, palmitic acid, oleic acid, palmito-oleic acid, cetyl or oleyl alcohols, and stearic acid are useful. Creams of the application may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this application. Additionally, the present application contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that certain heterobifunctional compounds of present application can exist in free form for treatment, or where appropriate, as a pharmaceutically acceptable derivative thereof. According to the present application, a pharmaceutically acceptable derivative includes, but is not limited to, pharmaceutically acceptable salts, esters, salts of such esters, or a prodrug or other adduct or derivative of a compound of this application which upon administration to a patient in need is capable of providing, directly or indirectly, a compound as otherwise described herein, or a metabolite or residue thereof.

In one embodiment the heterobifunctional compound as any one of the pharmaceutical compositions described above, is administered to a host in need thereof to stop expression of a protein of interest by action on a synthetic endogenous protein-dTAG hybrid protein. Alternatively, the heterobifunctional compound as any one of the pharmaceutical compositions described above, is administered to a host in need thereof to start expression of a protein of interest by action on a synthetic endogenous protein-dTAG hybrid protein.

EXAMPLES

Examples are further provided of exemplary engineering of endogenous protein-dTAG hybrid proteins having a dTAG capable of being bound by or binding to a heterobifunctional compound, which, when exposed to the heterobifunctional compound is degraded by the ubiquitin proteasomal pathway (UPP). The examples are exemplary only and are not intended to be limited, instead serving as illustrations of a method of modulating the expression of a protein-of-interest through specific degradation of the target with a heterobifunctional compound targeting the endogenous protein-dTAG hybrid protein.

Example 1: Proprotein Convertase Subtilisin/Kexin Type 9 (PCSK9)-dTAG

To further describe the targeting of endogenous proteins of interest for degradation through the use of a dTAG as contemplated herein, the targeting of an exemplary protein of interest, the gene product of PCSK9, for insertion of a nucleic acid encoding a dTAG is illustrated.

Proprotein convertase subtilisin/kexin type 9 (PCSK9) is an enzyme that controls cholesterol homeostasis. PCSK9 regulates the expression of low density lipoprotein (LDL) receptor in the liver. LDLR binds to, and internalizes free LDL cholesterol from the blood, effectively reducing cholesterol levels. When PCSK9 is deregulated, the enzyme binds and degrades LDLR, thus increasing free blood cholesterol resulting in hypercholesterolemia. Inhibition, or degradation of PCSK9 would restore LDLC expression and effectively reduce free blood cholesterol in the liver. Since increased levels of free LDL are associated with an increased risk of cardiac disease, efforts to reduce PCKS9 expression or activity are of great interest to the community.

To engineer the endogenous protein-dTAG hybrid protein, a homologous donor construct is cloned that includes a left homology region (portion of intron 1), dTAG nucleic acid sequence (derived from the dTAG FKBP*—SEQ. ID. NO.: 2) cloned in frame with exon 1 of PCSK9, and a right homology region (portion of intron 2). The dTAG peptide is cloned in frame with a 2× glycine linker. To initiate homologous recombination, a CRISPR sgRNA is designed to target the coding sequence PCSK9 in exon 1. CAS9 expression induces a double strand break which is repaired by homologous recombination repair using the donor construct as template. The end result is a gene locus with dTAG nucleic acid cloned in frame with exon 1 of PCSK9.

Figure 2:
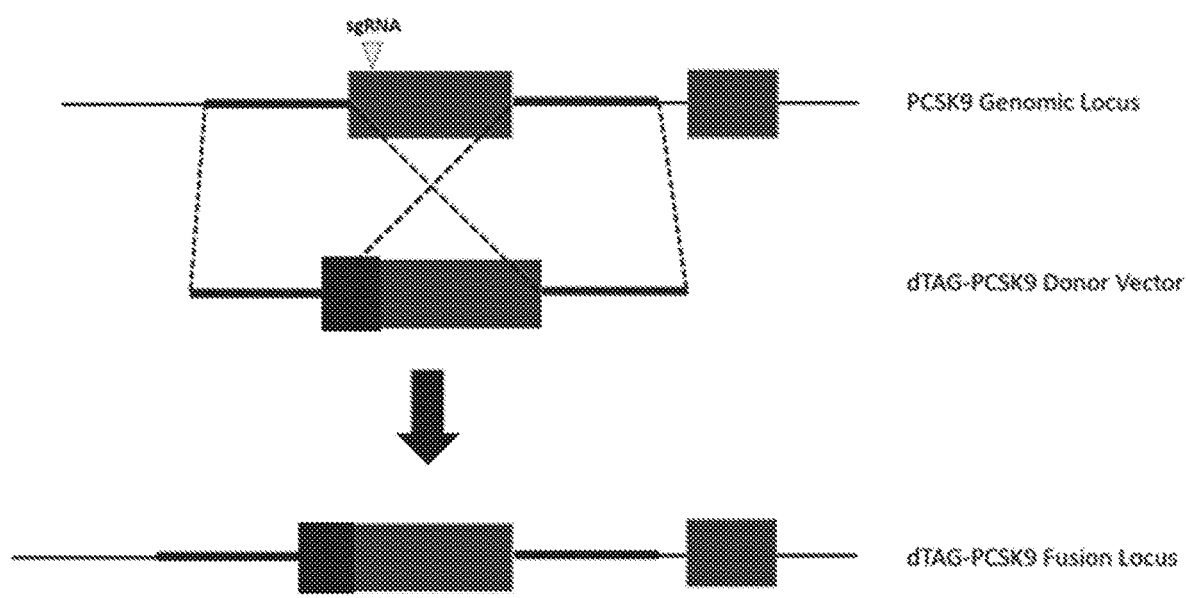
FIG. 2 is a schematic representing the genomic integration of a nucleic acid sequence encoding a dTAG into the genomic locus of the endogenous gene encoding PCSK9. Following homologous recombination, the resultant insertion results in an expression product comprising an N-terminus dTAG in frame with the proprotein convertase subtilisin/kexin type 9 (PCSK9) protein, thus providing a proprotein convertase subtilisin/kexin type 9 (PCSK9)-dTAG hybrid capable of being degraded by a heterobifunctional compound targeting the dTAG sequence.

As derived, the resultant nucleic acid sequence including the in frame dTAG nucleic acid insert results in the following genomic nucleic acid sequence, wherein lower case letters indicate intronic sequences of the PCSK9 genomic sequence, capital, underlined sequences indicate the sgRNA target (SEQ. ID. NO.: 45)
(GAGGGAGATTTGACACACACAGG), ATG indicates the transcriptional start site of the PCSK9 protein or PCSK9-dTAG hybrid, capital letters indicate the exon coding sequence of the PCSK9 protein, and capital, italicized letters indicate the in frame insertion of the FKBP* derived dTAG nucleic acid with a 2X glycine linker (GGGGGG) (SEQ. ID. NO.: 46). An illustration representing the exemplified HR strategy is provided for in FIG. 2.

```
Targeted PCSK9 Genomic Locus
                                                             (SEQ. ID. NO.: 47)
gtgtggggctgcctccccgagcttccatctgccgctggggccacaccccaggcccagggatgggaccccacagtggtcacatcatcttgc agcagaacccaggtacagctcctggagcagatggtggtcccaagcacgggtgggaccagaaaggactctcacctgggctaactcagctg cagcctcagttccctcctcacacacgacgaggaacatggactggaagcctgcccagcaggccttctgctcgatgtgcgttgtgtggcttacg tccagggagggaagcagcctctgtgctgtcttctagataagcctgtattccccgggctgtctgccaatgtatccagttgtcccgtcagcctgg aagactgagggaaaaccttgggctgcttcctgagcacctgtatccctgcagccagcccggggcctctgctaggagcagactgagcatg gcttatgggcctggcaccatctggcctctgcccaccttgctggccttgtcttgtgtctgcccttcgacattccatagcccagctcaatatctagt ggttcctctagggtggcgagcactgtttggtctccagatgtcttcaggtcggagctcacagcgctctcagccaccccttcccagtgtagcacc gggcacatggtagatgcctattgatgagtgaaagctcctaacacactcagagagcaaggactccgcctcatcccacagcctgggaggaga ggcagactgccaaggacctgctcagcatgctacagaagaaaccaaagtgcccacgggactgatcagtggagcttcctgccgagactgga ggccttagggcagggtagacagtgtgtgtgcaggctggggactcacagttcggactgtgcccagacctactagcatagtgggtgggtggg aggatgcgggactgggggccgaccttgcctgaaattcatgtgggatctcagagcagccactgaattgctctgtaggggctaaatagtggc ccccacagatacacacacccagacagagcctgtgagccagaccttatttggagaaaaggtctttgtagatgtaattaagcatctcaagatgg catcatctggattatgcggtgggctgtaagtcctgtgatgtgtctttATGAGAGAAAGGCAGAGGGAGATTTGACA

CACACAGGAGGGCCACGTGGAGACAGAGGTGGAGATTGGAGAAATGTGGCCACA

AGCCAGGGAACACCAGCAGCCACCAGAAGCCGGAAGACGTGAGGCAGGGTTCTTCC

CAGAGCCTTCGCTGCTGAGTCTGGGAATTTGTGACCGAAGCCATAAGAAGTGGGTA

CACGCCCTGAGCCTCCCACACTTGCTCACCTGTCCTGAGATGAGAATCTCTACTCTG

CAGCATATTTGGAGGATCACTGCGGGGGCCACAGAGGTGCTGTTCAGATGGCACTTC

AGAAGACTCAGGAGACCCTGGGGCAGGAGCAGTTTGACTGACAGCCCAGAGGGCTG

CCCTCTGATTCCACCTGAGGCCCTGCTTTTCCTGGCTGCAGGGGTTCCAGGGCCAGG

CCATTTCCGCTGGCGCAGGACTCTGCTAGCAGCAACCTGCCTGAAGTCTTCCTTTGG

CCTGGCTGAGAGTTTCTGAGACCTGCGCTGGAGCGGAGGTGCTTCCTTCCTTGCTTC

CTTTCTTCCTCTCTCCCTTCTCCATCCAGCAGGCTGGACCTGCCTGGCATCTGTGAGC

TCTCCCTACTTTCTCCTATACCCTAACCTTTGTCCTGCATGGGCGACTCCCCCAGTGA

GTCTCTTGCAGCTTTTACCCCAGTGCCTGCTTCTTGGAGAATCCAAACTGATCCAGTT

AGGGATGATAAAGTGTAGGGTAGGCGCTCGGTGACTGTTTTCTCTGAGGTTGTGACT

CGTGTGAGGCAGAAGCAGTCCCCGTGAGCCCTCCTGGTATCTTGTGGAGTGGAGAA

CGCTTGGACCTGGAGCCAGGAGGCCCAGACATACATCCTGTCCGAGCTGCAGCTTCC

TGTCTCTAAAATGAGCCGGCCAGCGCAGGTGGCCAGACATCACTGTTATTCTCCTTT

GAGTCTTTAAATCTTGTTGTCTTTCTTGCAGACTCGGTGAGCTGTGAAAGGCTATAAT
```

```
AGGGGCTTTATTTTACACTTTGATACTATTTTTTGAACATTCATATTATTGTTAGATA
TTGATATTCATATGAAGGAGCAGGATGACTTGGGTCCTTCTTGGCAGTAGCATTGCC
AGCTGATGGCCTTGGACAGTTACCTGCCCTCTCTAGGCCTCCCTTTCCTTGTCTATGA
AATACATTATAGAATAGGATGTAGTGTGTGAGGATTTTTTGGAGGTTAAACGAGTGA
ATATATTTAAGGCGCTTTCACCAGTGCCTGGGATGTGCTCTGTAGTTTCTGTGTGTTA
ACTATAAGGTTGACTTTATGCTCATTCCCTCCTCTCCCACAAATGtcgccttggaaagacggagg
cagcctggtggaggtgtatctcctagacaccagcatacagagtgaccaccgggaaatcgagggcagggtcatggtcaccgacttcgaga
atgtgcccgaggaggacgggacccgcttccacagacaggtaagcacggccgtctgatgggagggctgcctctgcccatatccccatcct
ggaggtgggtggggactgccaccccagagcgttgcagctgtactcctgggttgcaccccccagctgtcactgtcccctccctgccatca
gttgtgggaagggcgttcatccatccagccacctgctgatttgttataggggtggagggggggtctttctcatgtggtccttgtgttcgtcgagc
aggccagcaagtgtgacagtcatggcacccacctggcaggggtggtcagcggccgggatgccggcgtggccaagggtgccagcatgc
gcagcctgcgcgtgctcaactgccaagggaagggcacggttagcggcaccctcataggtaagtgatggcccccagacgctggtctctctcc
atctggacctggcctgggaggtggcttgggctgggcccagggagagctaatgtctcctaaccaagaatgctgtggcagcctctgccgcag
agccagagaaccagagtgccaaggctggcagggttcccagtggccacgagtgcagatgaagaaacccaggcccccaagagggtcatgc
aggtagcccagggagttcagccttgaccctgggtcaatgacctttccacagttccacactgctccccttttaaaatccggtgatgtctttatgtct
tttgttatgttatcttcaatgtggagggactcgaggtgatctaagcaaacttttttctatcttctgcttgcataccttctgagaccaggggactcactc
acttgcatgactgggccctgcaggtcacactggccaggcagatgtggtggaggaactggcagaggactttttctagactgtgactacattta
gtccacccagcggccccctatgaagtccagttgagaactaggactctgggggccggtggacagagaagag.
Resultant PCSK9-dTAG Hybrid
                                                                                              (SEQ. ID. NO.: 48)
gtgtggggctgcctccccgagcttccatctgccgctggggccacaccccaggcccagggatgggaccccacagtggtcacatcatcttgc
agcagaacccaggtacagctcctggagcagatggtggtcccaagcacgggtgggaccagaaaggactctcacctgggctaactcagctg
cagcctcagttccctcctcacacacgacgaggaacatggactggaagcctgcccagcaggccttctgctcgatgtgcgttgtgtggcttacg
tccagggagggaagcagcctctgtgctgtcttctagataagcctgtattccccgggctgtctgccaatgtatccagttgtcccgtcagcctgg
aagctctgagggaaaaccttgggctgcttcctgagcacctgtatccctgcagccagccgggcctctgctaggagcagactgagcatg
gatatggggcctggcaccatctggcctctgcccaccttgctggccttgtcttgtgtctgccccttcgacattccatagcccagctcaatatctagt
ggttcctctagggtggcgagcactgtttggtctccagatgtcttcaggtcggagctcacagcgctctcagccacccttcccagtgtagcacc
gggcacatggtagatgcctattgatgagtgaaagctcctaacacactcagagagcaaggactccgcctcatcccacagcctgggaggaga
ggcagactgccaaggacctgctcagcatgctacagaagaaaccaaagtgcccacgggactgatcagtggagcttcctgccgagactgga
ggccttagggcagggtagacagtgtgtgtgcaggctggggactcacagttcggactgtgcccagacctactagcatagtgggtgggtggg
aggatgcgggactggggccgaccttgcctgaaattcatgtgggatctcagagcagccactgaattgctctgtaggggctaaatagtggc
ccccacagatacacacacccagacagagcctgtgagccagaccttatttggagaaaaggtctttgtagatgtaattaagcatctcaagatgg
catcatctggattatgcggtgggctgtaagtcctgtgatgtgtcttt<u>ATGGGAGTGCAGGTGGAAACCATCTCCCCA</u>
<u>GGAGACGGGCGCACCTTCCCCAAGCGCGGCCAGACCTGCGTGGTGCACTACACCGGGA</u>
<u>TGCTTGAAGATGGAAAGAAAGTTGATTCCTCCCGGGACAGAAACAAGCCCTTTAAGTTTAT</u>
<u>GCTAGGCAAGCAGGAGGTGATCCGAGGCTGGGAAGAAGGGGTTGCCCAGATGAGTGTG</u>
<u>GGTCAGAGAGCCAAACTGACTATATCTCCAGATTATGCCTATGGTGCCACTGGGCACCCA</u>
<u>GGCATCATCCCACCACATGCCACTCTCGTCTTCGATGTGGAGCTTCTAAAACTGGGGGGG</u>
<u>AGAGAAAGGCAGAGGGAGATTTGACACACACAGGAGGGGCCACGTGGAGACAGAG</u>
GTGGAGATTGGAGAAATGTGGCCACAAGCCAGGGAACACCAGCAGCCACCAGAAG
CCGGAAGACGTGAGGCAGGGTTCTTCCCAGAGCCTTCGCTGCTGAGTCTGGGAATTT
```

-continued

```
GTGACCGAAGCCATAAGAAGTGGGTACACGCCCTGAGCCTCCCACACTTGCTCACCT

GTCCTGAGATGAGAATCTCTACTCTGCAGCATATTTGGAGGATCACTGCGGGGCCA

CAGAGGTGCTGTTCAGATGGCACTTCAGAAGACTCAGGAGACCCTGGGGCAGGAGC

AGTTTGACTGACAGCCCAGAGGGCTGCCCTCTGATTCCACCTGAGGCCCTGCTTTTC

CTGGCTGCAGGGGTTCCAGGGCCAGGCCATTTCCGCTGGCGCAGGACTCTGCTAGCA

GCAACCTGCCTGAAGTCTTCCTTTGGCCTGGCTGAGAGTTTCTGAGACCTGCGCTGG

AGCGGAGGTGCTTCCTTCCTTGCTTCCTTTCTTCCTCTCTCCCTTCTCCATCCAGCAG

GCTGGACCTGCCTGGCATCTGTGAGCTCTCCCTACTTTCTCCTATACCCTAACCTTTG

TCCTGCATGGGCGACTCCCCCAGTGAGTCTCTTGCAGCTTTTACCCCAGTGCCTGCTT

CTTGGAGAATCCAAACTGATCCAGTTAGGGATGATAAAGTGTAGGGTAGGCGCTCG

GTGACTGTTTTCTCTGAGGTTGTGACTCGTGTGAGGCAGAAGCAGTCCCCGTGAGCC

CTCCTGGTATCTTGTGGAGTGGAGAACGCTTGGACCTGGAGCCAGGAGGCCCAGAC

ATACATCCTGTCCGAGCTGCAGCTTCCTGTCTCTAAAATGAGCCGGCCAGCGCAGGT

GGCCAGACATCACTGTTATTCTCCTTTGAGTCTTTAAATCTTGTTGTCTTTCTTGCAG

ACTCGGTGAGCTGTGAAAGGCTATAATAGGGGCTTTATTTTACACTTTGATACTATTT

TTTGAACATTCATATTATTGTTAGATATTGATATTCATATGAAGGAGCAGGATGACT

TGGGTCCTTCTTGGCAGTAGCATTGCCAGCTGATGGCCTTGGACAGTTACCTGCCCT

CTCTAGGCCTCCCTTTCCTTGTCTATGAAATACATTATAGAATAGGATGTAGTGTGTG

AGGATTTTTGGAGGTTAAACGAGTGAATATATTTAAGGCGCTTTCACCAGTGCCTG

GGATGTGCTCTGTAGTTTCTGTGTGTTAACTATAAGGTTGACTTTATGCTCATTCCCT

CCTCTCCCACAAATGtcgccttggaaagacggaggcagcctggtggaggtgtatctcctagacaccagcatacagagtgac caccgggaaatcgagggcagggtcatggtcaccgacttcgagaatgtgcccgaggaggacgggacccgcttccacagacaggtaagca cggccgtctgatgggagggctgcctctgcccatatcccatcctggaggtgggtggggactgccaccccagagcgttgcagctgtactcct gggttgcaccccccccagctgtcactgtccctccctgccatcagttgtgggaagggcgttcatccatccagccacctgctgatttgttatag ggtgggaggggggggtctttctcatgtggtccttgtgttcgtcgagcaggccagcaagtgtgacagtcatggcacccacctggcaggggtggt cagcggccgggatgccggcgtggccaagggtgccagcatgcgcagcctgcgcgtgctcaactgccaagggaagggcacggttagcgg caccctcataggtaagtgatggccccagacgctggtctctctccatctggacctggcctgggaggtggcttgggctgggcccagggagag ctaatgtctcctaaccaagaatgctgtggcagcctctgccgcagagccagagaaccagagtgccaaggctggcagggttcccagtggcca cgagtgcagatgaagaaacccaggccccaagagggtcatgcaggtagcccagggagttcagccttgaccctgggtcaatgacctttccac agttccacactgctcccatttaaaatccggtgatgtctttatgtcttttgttatgttatcttcaatgtggagggactcgaggtgatctaagcaaactt tttctatcttctgcttgcatacctctgagaccagggggactcactcacttgcatgactgggccctgcaggtcacactggccaggcagatgtggtg gaggaactggcagaggacttttttctagactgtgactacatttagtccacccagcggcccccctatgaagtccagttgagaactaggactctgg gggccggtggacagagaagag.
```

Example 2: β-catenin (CTNNB1)-dTAG

To further describe the targeting of endogenous proteins of interest for degradation through the use of a dTAG as contemplated herein, the targeting of an exemplary protein of interest, β-catenin (CTNNB1), for dTAG insertion is illustrated.

β-catenin is encoded by the CTNNB1 gene. β-catenin regulates both cell-cell adhesion and gene transcription as a downstream effector of the WNT signaling pathway. Under normal conditions, β-catenin function and expression is mediated by phosphorylation and ubiquitin mediated destruction via the βTrCP E3 ligase. Normally, β-catenin is regulated upon binding to a repressive complex, which includes, axin, GSK3β, and APC. Upon WNT stimulation, axin is sequestered to frizzled receptors, thus releasing β-catenin from the destruction complex. The protein then translocates to the nucleus to bind TCF/LEF to activate transcriptional programs. Upon release of Wnt ligands, free beta-catenin is phosphorylated by GSK3 (and degraded through binding and ubiquitination by βTrCRP E3 ligase.

The Wnt/β-catenin pathway is frequently mutated in human cancers, with 1β-catenin mutations being observed in nearly 25% of hepatocellular carcinoma. Recurrent mutations are found within the βTrCP binding site, conferring stability to the oncogenic transcriptional regulator. While a bonafide oncology target, historical small molecule programs have failed as 1β-catenin is a relatively flat protein with few known ligands that bind with high affinity. These data suggested β-catenin as an exemplary gene to target for conditional degradation.

To engineer the endogenous protein-dTAG hybrid protein, a homologous donor construct is cloned that includes a left homology region (portion of intron 1), dTAG nucleic acid sequence (derived from the dTAG FKBP*—SEQ. ID. NO.: 2) cloned in frame with a short exon 1 of CTNNB1, intron 2, exon2, and a right homology region (portion of intron 3). The dTAG nucleic acid sequence is cloned in frame with a 2X glycine linker.

To initiate homologous recombination, a CRISPR sgRNA is designed to target the coding sequence β-catenin in exon 2. CAS9 expression induces a double strand break which is repaired by homologous recombination repair using the donor construct as template. The end result is a gene locus with a dTAG nucleic acid sequence cloned in frame with exon 1 of CTNNB1.

Figure 3:
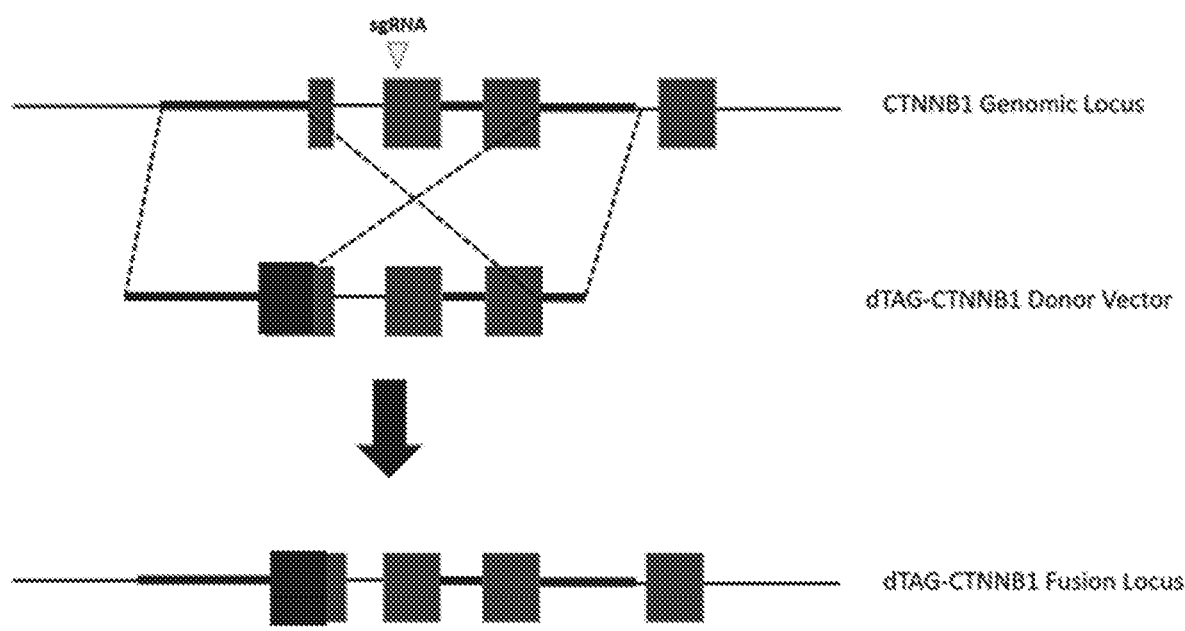
FIG. 3 is a schematic representing the genomic integration of a nucleic acid sequence encoding a dTAG into the genomic locus of the endogenous gene encoding β-catenin (CTNNB1). Following homologous recombination, the resultant insertion results in an expression product comprising an N-terminus dTAG in frame with the β-catenin (CTNNB1) protein, thus providing a β-catenin (CTNNB1)-dTAG hybrid capable of being degraded by a heterobifunctional compound targeting the dTAG sequence.

As derived, the resultant nucleic acid sequence including the in frame dTAG nucleic acid insert results in the following genomic nucleic acid sequence, wherein lower case letters indicate intronic sequences of the CTNNB1 genomic sequence, capital, underlined sequences indicate the sgRNA target (SEQ. ID. NO.: 49)
(TACCACAGCTCCTTCTCTGAGTGG), ATG indicates the transcriptional start site of the CTNNB1 protein (βcatenin) or β-catenin (CTNBB1)-dTAG hybrid, capital letters indicate the exon coding sequence of the β-catenin protein, and capital, italicized letters indicate the in frame insertion of the FKBP* derived dTAG nucleic acid with a 2X glycine linker (GGGGGG) (SEQ. ID. NO.: 46). An illustration representing the exemplified HR strategy is provided for in FIG. 3.

```
CTNNB1 Genomic Locus
                                                                              (SEQ. ID. NO.: 50)
aaataattttttgatggcactatatcagaaaacaacttgttaaagaaaatgtggagttttaaaatcccactgtacctctgttatccaaaggggatct gtgaattttttctgtgaaaggttaaaaaaggagagacctttaggaattcagagagcagctgattttttgaatagtgttttccctccctggcttttata ttacaactctgtgattttcatcaccatcctgaatatctataattaatatttatactattaataaaaagacattttggtaaggaggagttttcactgaa gttcagcagtgatggagctgtggttgaggtgtctggaggagaccatgaggtctgcgtttcactaacctggtaaaagaggatatgggttttttt gtgggtgtaatagtgacatttaacaggtatcccagtgacttaggagtattaatcaagctaaatttaaatcctaatgacttttgattaactttttttagg gtatttgaagtataccatacaactgttttgaaaatccagcgtggacaATGGCTACTCAAGgtttgtgtcattaaatctttagttactga attggggctctgcttcgttgccattaagccagtctggctgagatcccctgcttcctctctccctgcttacttgtcaggctaccttttgctccatttt ctgctcactcctcctaatggcttggtgaaatagcaaacaagccaccagcaggaatctagtctggatgactgcttctggagcctggatgcagta ccattcttccactgattcagtgagtaactgttaggtggttccctaagggattaggtatttcatcactgagctaaccctggctatcattctgcttttctt ggctgtctttcagatttgactttatttctaaaaatatttcaatgggtcatatcacagattcttttttttttaaattaaagtaacatttccaatctactaatgct aatactgtttcgtatttatagCTGATTTGATGGAGTTGGACATGGCCATGGAACCAGACAGAAAAG

CGGCTGTTAGTCACTGGCAGCAACAGTCTTACCTGGACTCTGGAATCCATTCTGGTG

CCACTACCACAGCTCCTTCTCTGAGTGGTAAAGGCAATCCTGAGGAAGAGGATGTG

GATACCTCCCAAGTCCTGTATGAGTGGGAACAGGGATTTTCTCAGTCCTTCACTCAA

GAACAAGTAGCTGgtaagagtattatattcattgccttactgaaagtcagaatgcagttttgagaactaaaaagttagtgtataata gtttaaataaaatgttgtggtgaagaaaagagagtaatagcaatgtcactttttaccatttaggatagcaaatacttaggtaaatgctgaactgtg gatagtgagtgttgaattaaccttttccagATATTGATGGACAGTATGCAATGACTCGAGCTCAGAGGG

TACGAGCTGCTATGTTCCCTGAGACATTAGATGAGGGCATGCAGATCCCATCTACAC

AGTTTGATGCTGCTCATCCCACTAATGTCCAGCGTTTGGCTGAACCATCACAGATGC

TGAAACATGCAGTTGTAAACTTGATTAACTATCAAGATGATGCAGAACTTGCCACAC

GTGCAATCCCTGAACTGACA

Resultant CTNNB1-dTAG Hybrid
                                                                              (SEQ. ID. NO.: 51)
aaataattttttgatggcactatatcagaaaacaacttgttaaagaaaatgtggagttttaaaatcccactgtacctctgttatccaaaggggatct gtgaattttttctgtgaaaggttaaaaaaggagagacctttaggaattcagagagcagctgattttttgaatagtgattccctccctggcttttata ttacaactctgtgattttcatcaccatcctgaatatctataattaatatttatactattaataaaaagacattttggtaaggaggagttttcactgaa gttcagcagtgatggagctgtggttgaggtgtctggaggagaccatgaggtctgcgtttcactaacctggtaaaagaggatatgggttttttt gtgggtgtaatagtgacatttaacaggtatcccagtgacttaggagtattaatcaagctaaatttaaatcctaatgacttttgattaactttttttagg
```

-continued

```
gtatttgaagtatacccatacaactgttttgaaaatccagcgtggacaATGGGAGTGCAGGTGGAAACCATCTCCCCA

GGAGACGGGCGCACCTTCCCCAAGCGCGGCCAGACCTGCGTGGTGCACTACACCGGGA

TGCTTGAAGATGGAAAGAAAGTTGATTCCTCCCGGGACAGAAACAAGCCCTTTAAGTTTAT

GCTAGGCAAGCAGGAGGTGATCCGAGGCTGGGAAGAAGGGGTTGCCCAGATGAGTGTG

GGTCAGAGAGCCAAACTGACTATATCTCCAGATTATGCCTATGGTGCCACTGGGCACCCA

GGCATCATCCCACCACATGCCACTCTCGTCTTCGATGTGGAGCTTCTAAAACTGGGGGGG

ATGGCTACTCAAGgtttgtgtcattaaatctttagttactgaattggggctctgcttcgttgccattaagccagtctggctgagatccc cctgcttcctctctccctgcttacttgtcaggctacctttttgctccatttctgctcactcctcctaatgcttggtgaaatagcaaacaagccacc agcaggaatctagtctggatgactgcttctggagcctggatgcagtaccattcttccactgattcagtgagtaactgttaggtggttccctaagg gattaggtatttcatcactgagctaaccctggctatcattctgcttttcttggctgtctttcagatttgactttatttctaaaaatatttcaatgggtcat atcacagattctttttttttaaattaaagtaacatttcaatctactaatgctaatactgtacgtatttatagcCTGATTTGATGGAGT

TGGACATGGCCATGGAACCAGACAGAAAAGCGGCTGTTAGTCACTGGCAGCAACAG

TCTTACCTGGACTCTGGAATCCATTCTGGTGCCACTACCACAGCTCCTTCTCTGAGTG

GTAAAGGCAATCCTGAGGAAGAGGATGTGGATACCTCCCAAGTCCTGTATGAGTGG

GAACAGGGATTTTCTCAGTCCTTCACTCAAGAACAAGTAGCTGgtaagagtattattttttcattgcctt actgaaagtcagaatgcagttttgagaactaaaaagttagtgtataatagtttaaataaaatgttgtggtgaagaaaagagagtaatagcaatgt cacttttaccatttaggatagcaaatacttaggtaaatgctgaactgtggatagtgagtgttgaattaaccttttccagATATTGATGG

ACAGTATGCAATGACTCGAGCTCAGAGGGTACGAGCTGCTATGTTCCCTGAGACATT

AGATGAGGGCATGCAGATCCCATCTACACAGTTTGATGCTGCTCATCCCACTAATGT

CCAGCGTTTGGCTGAACCATCACAGATGCTGAAACATGCAGTTGTAAACTTGATTAA

CTATCAAGATGATGCAGAACTTGCCACACGTGCAATCCCTGAACTGACA
```

In any of the below examples either dFKBP13-o and dFKBP 13-p or dFKBP7-o and dFKBP7-p can be used.

Example 3

Figure 4:
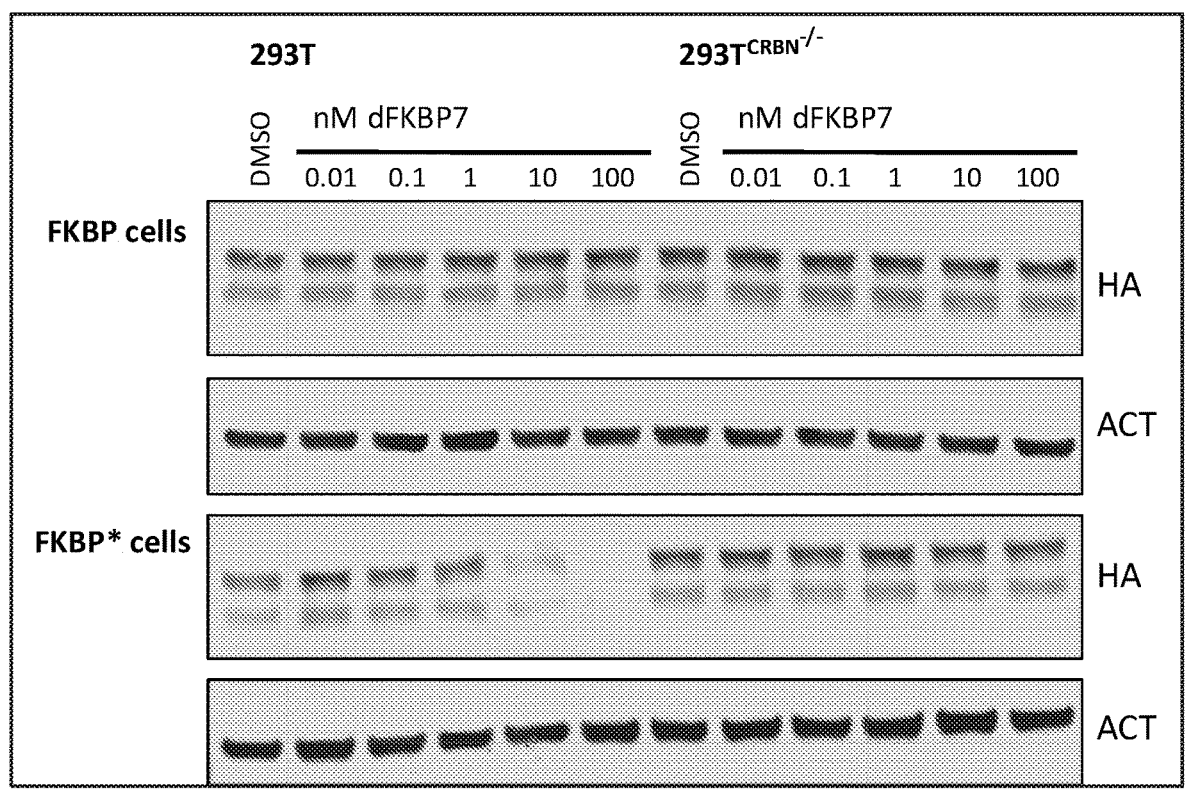
FIG. 4 is an immunoblot of cells treated with heterobifunctional compounds described in the present invention. 293FT cells (CRBN-WT or CRBN−/−) expressing either HA-tagged FKBP12WT or FKBP* were treated with indicated concentrations of dFKBP7 for 4 hours. CRBN-dependent degradation of FKBP* and not FKBPWT confirms selective activity of dFKBP7 for mutant FKBP*.

FIG. 4 illustrates an example to confirm selective degradation of FKBP*-fused proteins with dFKBP7.

The dTAG is predicated on the selectivity of FKBP* specific ligands over endogenous, wild type FKBP. In 293T cells expressing wild type FKBP12 or FKBP*, dFKBP7 induces targeted degradation only in FKBP* expressing cells. An immunoblot of cells treated with heterobifunctional compounds described in the present invention was performed. 293FT cells (CRBN-WT or CRBN−/−) expressing either HA-tagged FKBP12WT or FKBP* were treated with indicated concentrations of dFKBP7 for 4 hours. CRBN-dependent degradation of FKBP* and not FKBPWT confirms selective activity of dFKBP7 for mutant FKBP*.

Example 4

Figure 5A:
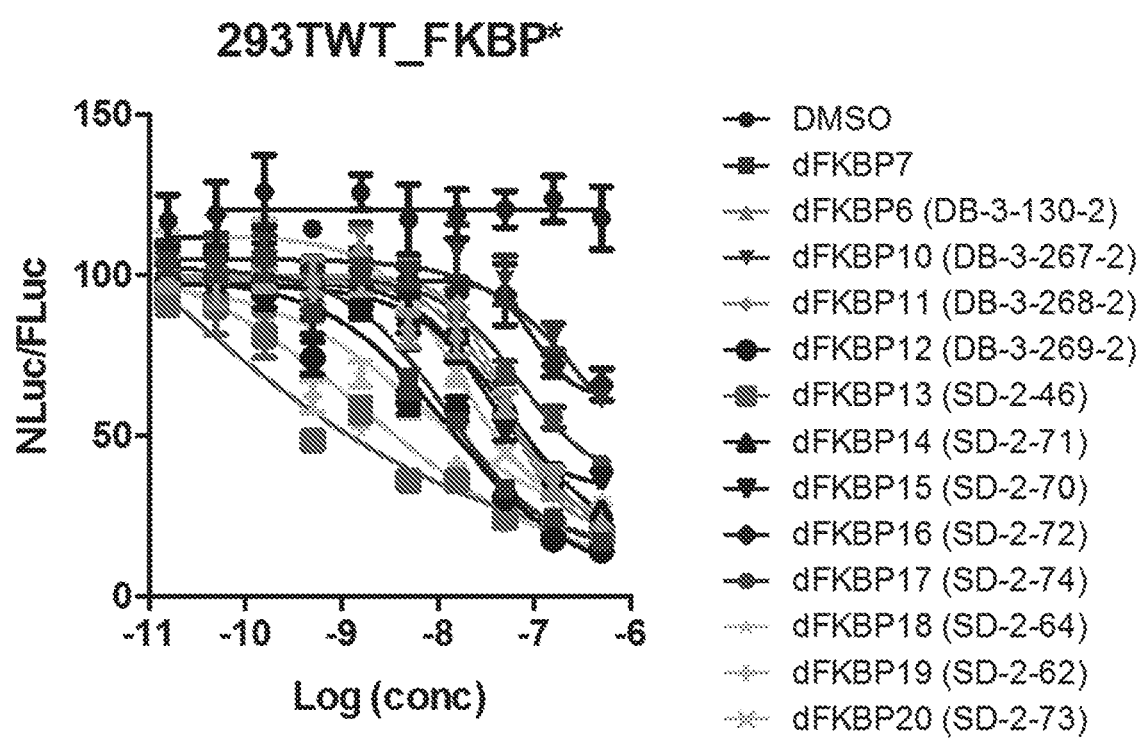
FIG. 5A and FIG. 5B are graphs measuring the activity of a panel of dFKBP heterobifunctional compounds in cells expressing FKBP* fused to Nluc. Degradation of FKBP* is measured as a signal ration (Nluc/Fluc) between NANOluc and firefly luciferase from the same multicistronic transcript in wild type (FIG. 7A) or CRBN −/− (FIG. 7B) 293FT cells treated with indicated concentrations of dFKBPs for 4 hours. A decrease in the signal ratio indicates FKBP* (Nluc) degradation.
Figure 5B:
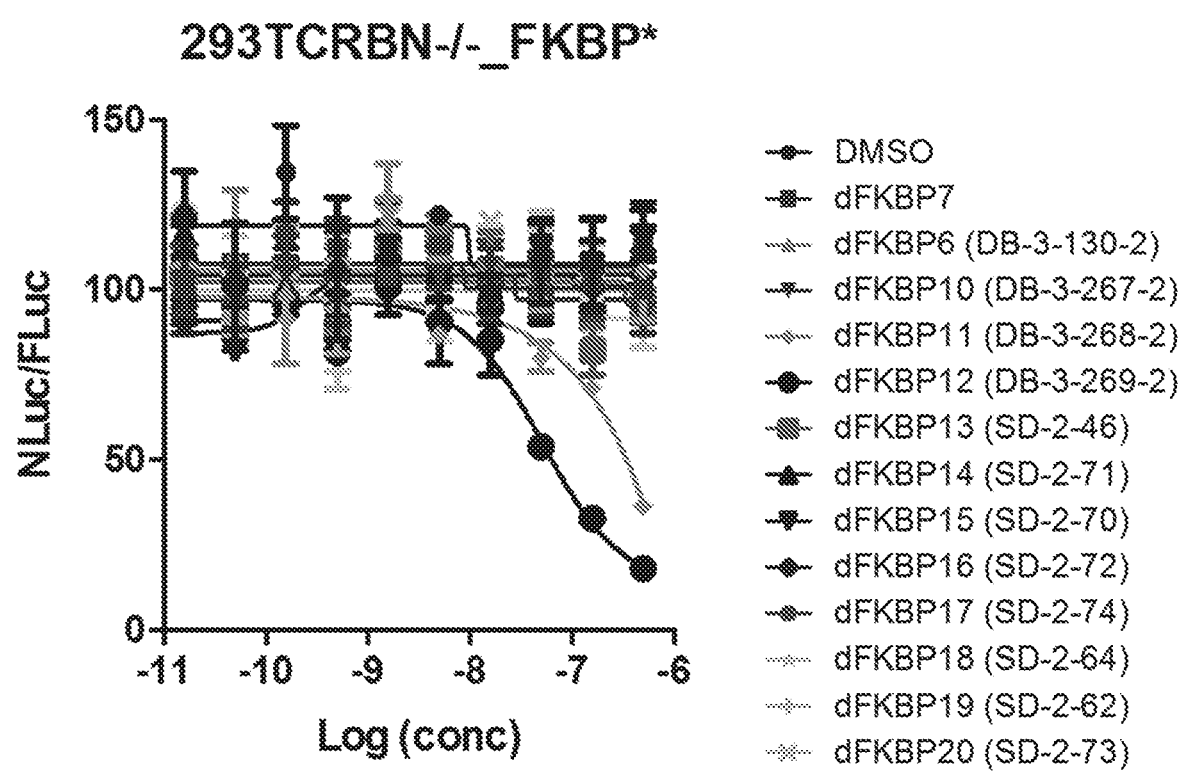

FIGS. 5A-B illustrate an example of profiling of a panel of dFKBP heterobifunctional compounds to measure differential degradation activity.

In an effort to identify potent and selective dFKPB heterobifunctional compounds, high throughput measurements of targeted FKBP* degradation were measured by surrogate levels of luciferase. Here, FKBP* is exogenously expressed as a multicistronic transcript with two types of luciferase: nano luciferase (NLuc) and firefly luciferase (FLuc) that allow for cell normalized quantification of FKBP* protein levels. Degradation of FKBP* is measured as a signal ration (Nluc/Fluc) in wild type (FIG. 4A) or CRBN −/− (FIG. 4B) 293FT cells treated with indicated concentrations of dFKBPs for 4 hours. A decrease in the signal ratio indicates FKBP* (Nluc) degradation and molecules that effectively degrade FKBP* in a cereblon dependent manner are observed (ex. dFKBP7).

Example 5

Figure 6:
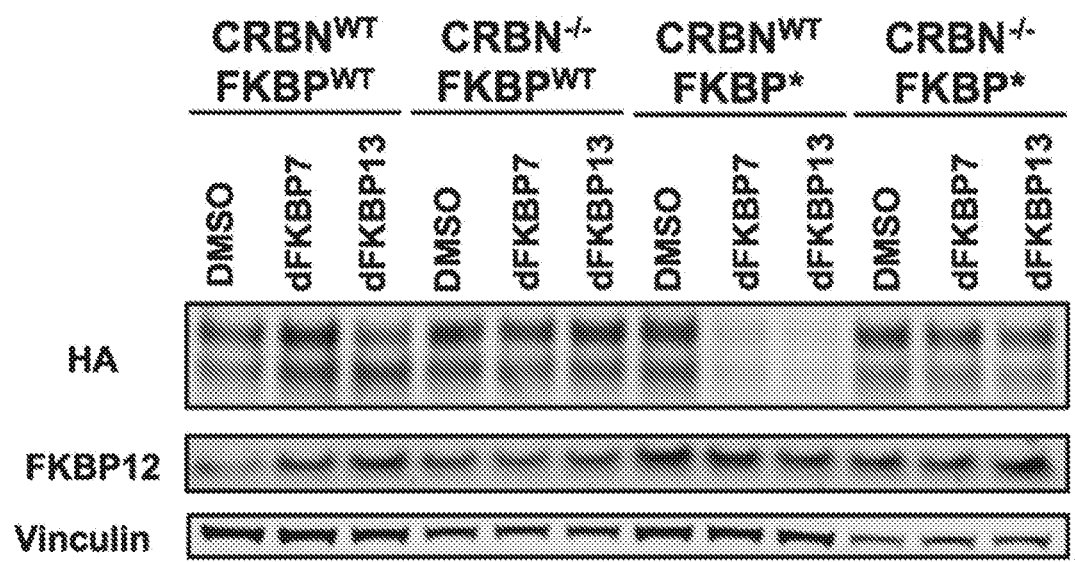
FIG. 6 is an immunoblot of cells treated with heterobifunctional compounds described in the present invention. Isogenic 293FT cells (CRBN-WT or CRBN−/−) expressing either FKBP12WT or FKBP* were treated with 100 nM of either dFKBP7 or dFKBP13 for 4 hours. CRBN-dependent degradation of FKBP* and not FKBP12WT or endogenous FKBP12 confirms selectivity of dFKBP7 and dFKBP13 for mutant FKBP*.

FIG. 6 illustrates an example of selective degradation of FKBP*-fused proteins with dFKBP7 and dFKBP13, bifunctional molecules described in the present invention.

In 293T cells expressing wild type FKBP12 or FKBP*, treatment with dFKBP7 and dFKBP13 induces targeted degradation only in FKBP* expressing cells. Isogenic 293FT cells (CRBN-WT or CRBN−/−) were engineered to expressed either FKBP12WT or FKBP*. Cells were treated with 100 nM of either dFKBP7 or dFKBP13 for 4 hours before lysates were prepared for western immunoblot analysis. CRBN-dependent degradation of FKBP* and not FKBP12WT or endogenous FKBP12 confirms selectivity of dFKBP7 and dFKBP13 for mutant FKBP*.

Example 6

Figure 7:
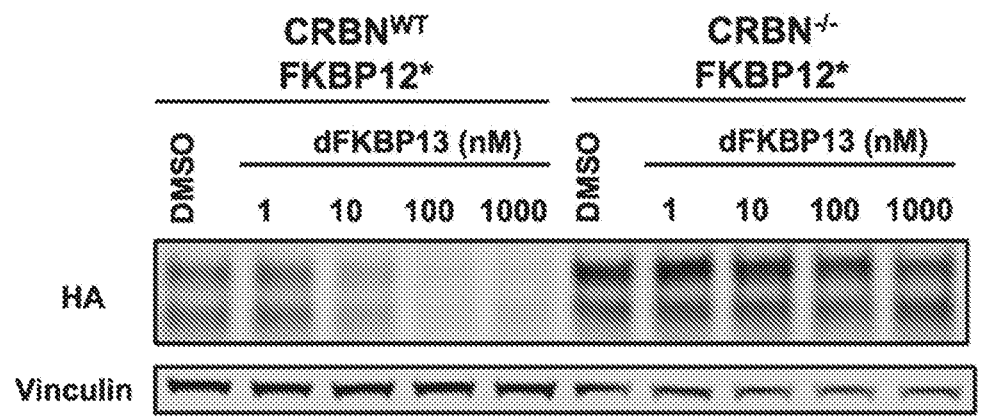
FIG. 7 is an immunoblot of cells treated with heterobifunctional compounds described in the present invention. Isogenic 293FT cells (CRBN-WT or CRBN−/−) expressing HA-tagged FKBP* were treated with the indicated dose of dFKBP13 for 4 hours. These data confirm dose- and CRBN-dependent degradation of HA-tagged FKBP* by dFKBP13.

FIG. 7 illustrates and example of dose-dependent degradation of HA-tagged FKBP12* with a bifunctional molecule dFKBP13.

In an effort to define the optimal concentration of dFKB13 heterobifunctional compound to induce degradation of FKBP*, degradation was measured upon treatment with increasing concentrations of dFKBP13. Isogenic 293FT cells (CRBN-WT or CRBN-/-) were engineered to expressed HA-tagged FKBP*. Cells were treated with the indicated dose of dFKBP13 for 4 hours before lysates were prepared for western immunoblot analysis. These data confirm dose- and CRBN-dependent degradation of HA-tagged FKBP* by dFKBP 13.

Example 7

Figure 8:
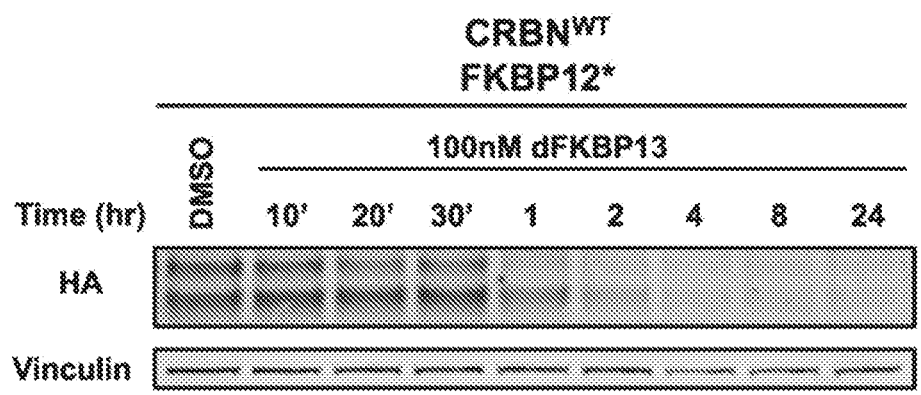
FIG. 8 is an immunoblot of cells treated with heterobifunctional compounds described in the present invention. 293FT cells (CRBN-WT) expressing HA-tagged FKBP* were treated with 100 nM dFKBP13 for the indicated times. Cells were harvested and protein lysates immunoblotted to measure the kinetics of HA-tagged FKBP* degradation induced by dFKBP13.

FIG. 8 illustrates the kinetic control of dFKBP13-dependent degradation of HA-tagged FKBP*.

To evaluate the kinetic control of targeted degradation FKBP*, dFKBP13 was administered by increased duration. 293FT cells (CRBN-WT) were engineered to express HA-tagged FKBP*. Cells were treated with 100 nM dFKBP13 for the indicated times. Cells were harvested and protein lysates immunoblotted to measure the kinetics of HA-tagged FKBP* degradation induced by dFKBP13.

Example 8

Figure 9:
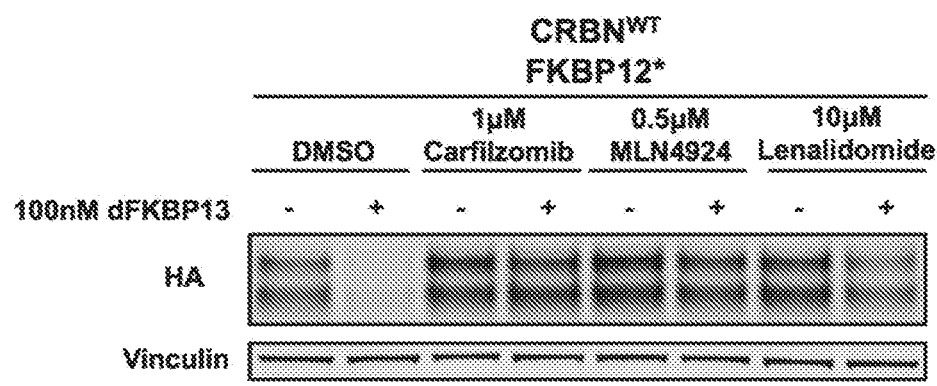
FIG. 9 is an immunoblot of cells treated with heterobifunctional compounds described in the present invention. 293FT cells (CRBN-WT) expressing FKBP* were pre-treated with 1 uM Carfilzomib (proteasome inhibitor), 0.5 uM MLN4924 (neddylation inhibitor), and 10 uM Lenalidomide (CRBN binding ligand) for two hours prior to a 4 hour treatment with dFKBP13. Degradation of HA-tagged FKBP* by dFKBP13 was rescued by the proteasome inhibitor Carfilzomib, establishing a requirement for proteasome function. Pre-treatment with the NAE1 inhibitor MLN4924 rescued HA-tagged FKBP* establishing dependence on CRL activity, as expected for cullin-based ubiquitin ligases that require neddylation for processive E3 ligase activity. Pre-treatment with excess Lenalidomide abolished dFKBP13-dependent FKBP* degradation, confirming the requirement of CRBN engagement for degradation.

FIG. 9 illustrates and example to confirm CRBN- and proteasome-dependent degradation of FKBP* by the bifunctional molecule dFKBP13.

293FT cells (CRBN-WT) were engineered to express FKBP*. Cells were pretreated with 1 uM Carfilzomib (proteasome inhibitor), 0.5 uM MLN4924 (neddylation inhibitor), and 10 uM Lenalidomide (CRBN binding ligand) for two hours prior to a 4 hour treatment with dFKBP13. Lysates were prepared and western immunoblot analysis performed. Degradation of HA-tagged FKBP* by dFKBP13 was rescued by the proteasome inhibitor Carfilzomib, establishing a requirement for proteasome function. Pre-treatment with the NAE1 inhibitor MLN4924 rescued HA-tagged FKBP* establishing dependence on CRL activity, as expected for cullin-based ubiquitin ligases that require neddylation for processive E3 ligase activity. Pre-treatment with excess Lenalidomide abolished dFKBP13-dependent FKBP* degradation, confirming the requirement of CRBN engagement for degradation.

Example 9

Figure 10A:
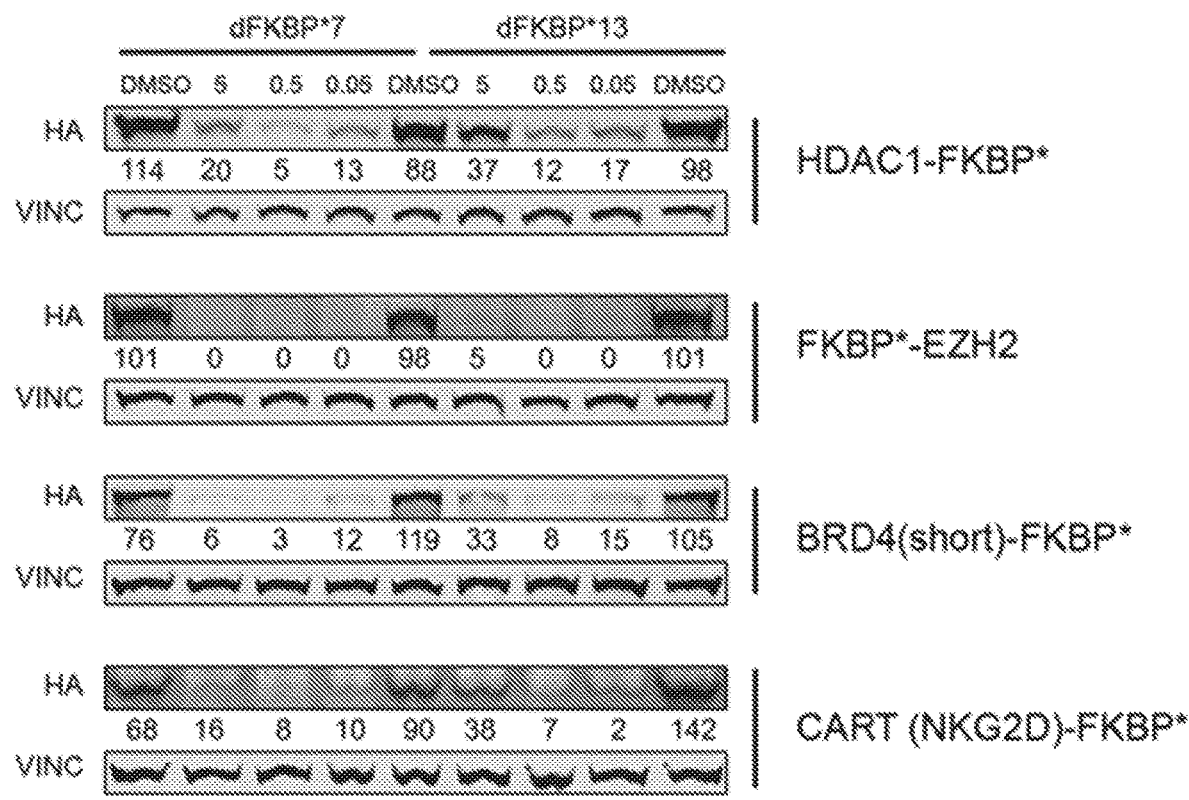
FIG. 10A and FIG. 10B are immunoblots of cells treated with heterobifunctional compounds described in the present invention. Immunoblots of MV4; 11 leukemia cells expressing indicated proteins fused to mutant FKBP* with an HA tag. Cells were treated for 16 hours with indicated concentrations of FKBP* selective heterobifunctional compounds, dFKBP7 or dFKBP13 and abundance of fusion proteins measured by western immunoblot analysis.
Figure 10B:
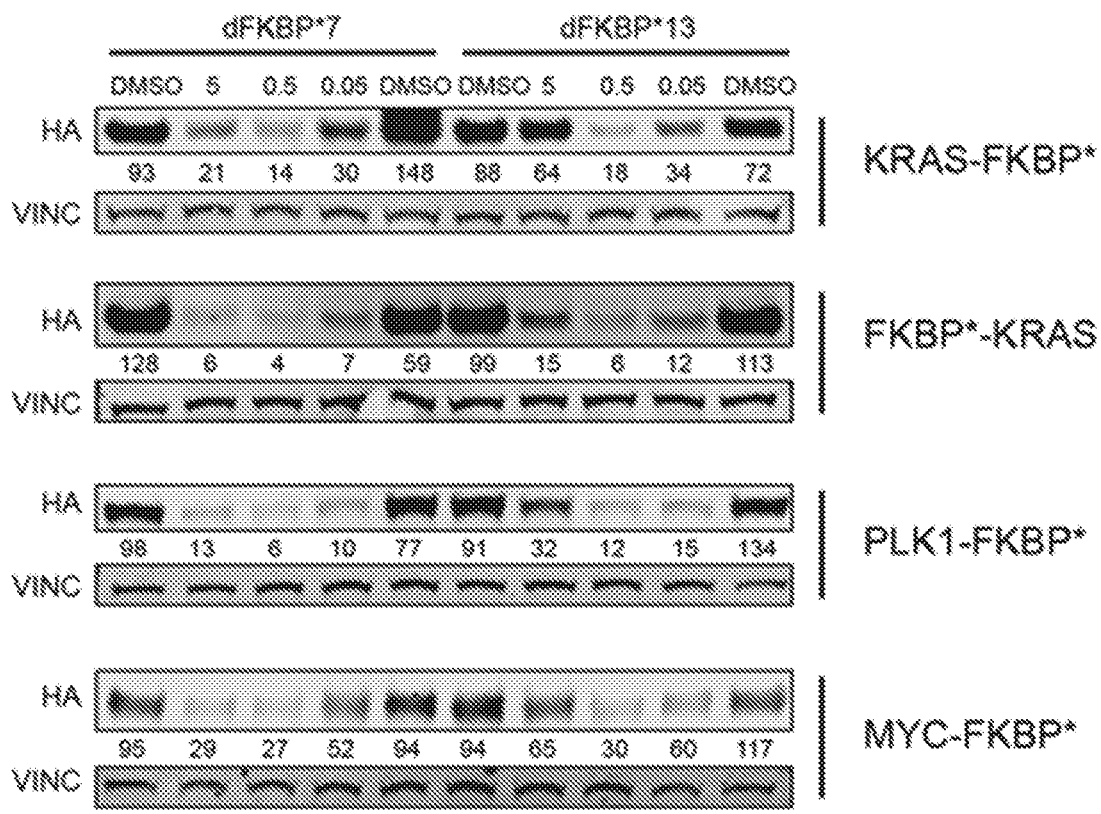

FIGS. 10A-B confirms targeted degradation of proteins of interest when fused to dTAG.

To test the general utility of the dTAG technology across several protein types, the indicated proteins fused to the dTAG in MV4;11 leukemia cells were expressed. Upon treatment with the indicated dFKBP bifunctional molecules (dFKBP7 and dFKBP13), targeted protein degradation was observed as measured by western blot. Cells were treated for 16 hours with indicated concentrations of FKBP* selective heterobifunctional compounds and degradation was observed with nanomolar concentrations.

Example 10

Figure 11:
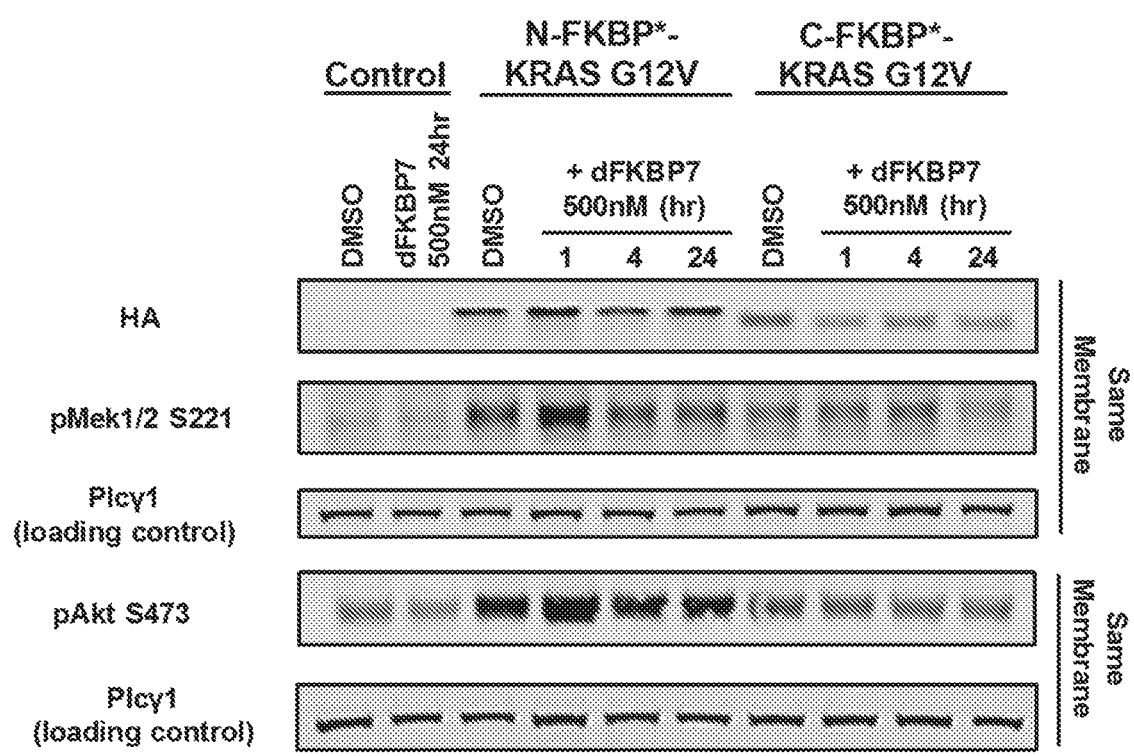
FIG. 11 is an immunoblot of NIH3T3 cells expressing KRASG12V allele fused to FKBP* in the N-terminus or C-terminus. Cells were treated with 500 nM dFKBP7 for the indicated time. Cells were harvested and immunoblotted to measure degradation of FKBP*-KRASG12V and downstream surrogates of KRAS signaling (e.g. pMEK and pAKT). The data suggest N-terminal FKBP* fusions are active and degraded upon administration of dFKBP7.

FIG. 11 illustrates an example confirming degradation of N-terminal dTAG-KRAS.

In N-terminal dTAG-KRAS, dFKBP7 treatment resulted in potent degradation as well as a downstream decrease in p-AKT signal suggesting the biological relevance of overexpressed endogenous protein-dTAG hybrid proteins. Cells were treated with 500 nM dFKBP7 for the indicated time. Cells were harvested and immunoblotted to measure degradation of FKBP*-KRAS and downstream surrogates of KRAS signaling (e.g. pMEK and pAKT). Overexpression of dTAG KRAS resulted in the activation of the relevant downstream signaling pathways as an observed increase in p-AKT signal as measured by western blot.

Example 11

Figure 12:
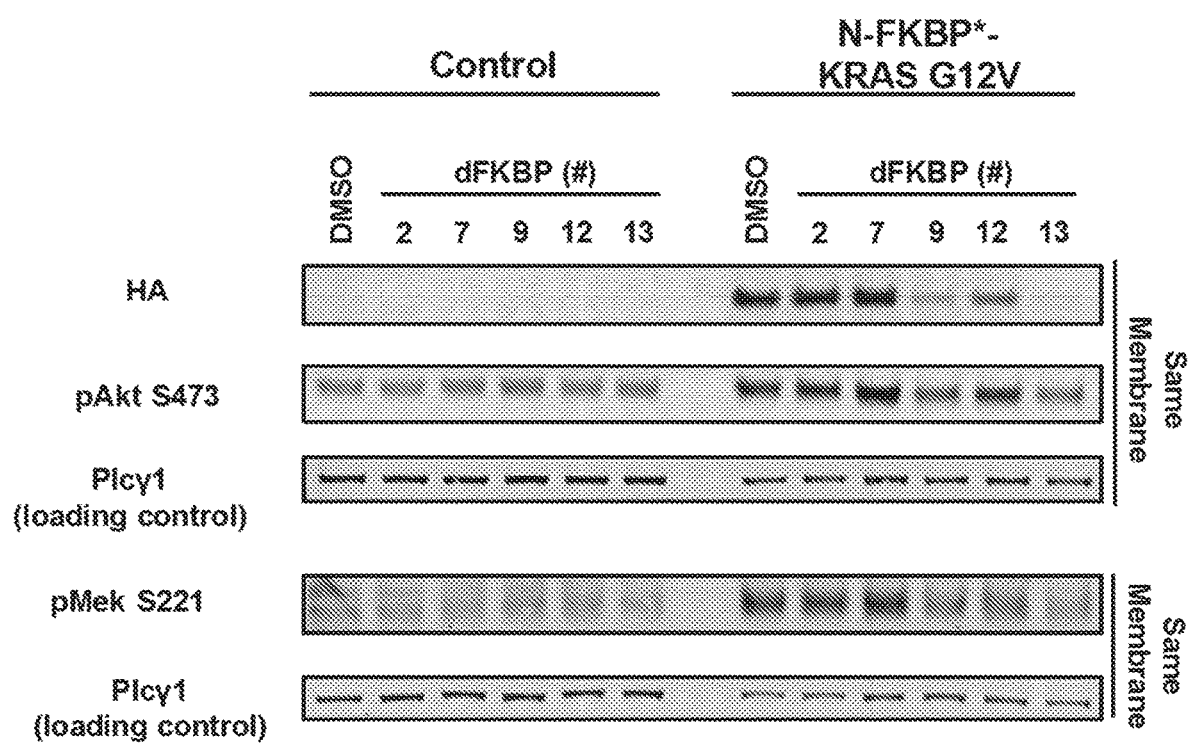
FIG. 12 is an immunoblot of NIH3T3 cells expressing FKBP* fused to the N-terminus of KRASG12V treated with 1 uM of the indicated dFKBP heterobifunctional compounds for 24 hours. Cells were harvested and immunoblotted to measure degradation of FKBP*-KRASG12V and downstream surrogates of KRAS signaling (e.g. pMEK and pAKT). The data suggest that dFKBP9, dFKBP12, and dFKBP13 induce potent degradation of FKBP*-KRASG12V and inhibition of downstream signaling.

FIG. 12 illustrates the profiling of dFKBP heterobifunctional compounds to induce degradation of dTAG-KRAS.

In an effort to identify the best performing dFKBP molecule, dTAG-KRAS degradation was profiled across a series of dFKBP molecules. Western blotting of NIH3T3 cells expressing dTAG-KRASG12V were treated with 1 μM of the indicated dFKBP heterobifunctional compounds for 24 hours. Cells were harvested and immunoblotted to measure degradation of FKBP*-KRAS and downstream surrogates of KRAS signaling (e.g. pMEK and pAKT). The data suggest that dFKBP9, dFKBP 12, and dFKBP13 induce potent degradation of FKBP*-KRAS and inhibition of downstream signaling.

Example 12

Figure 13:
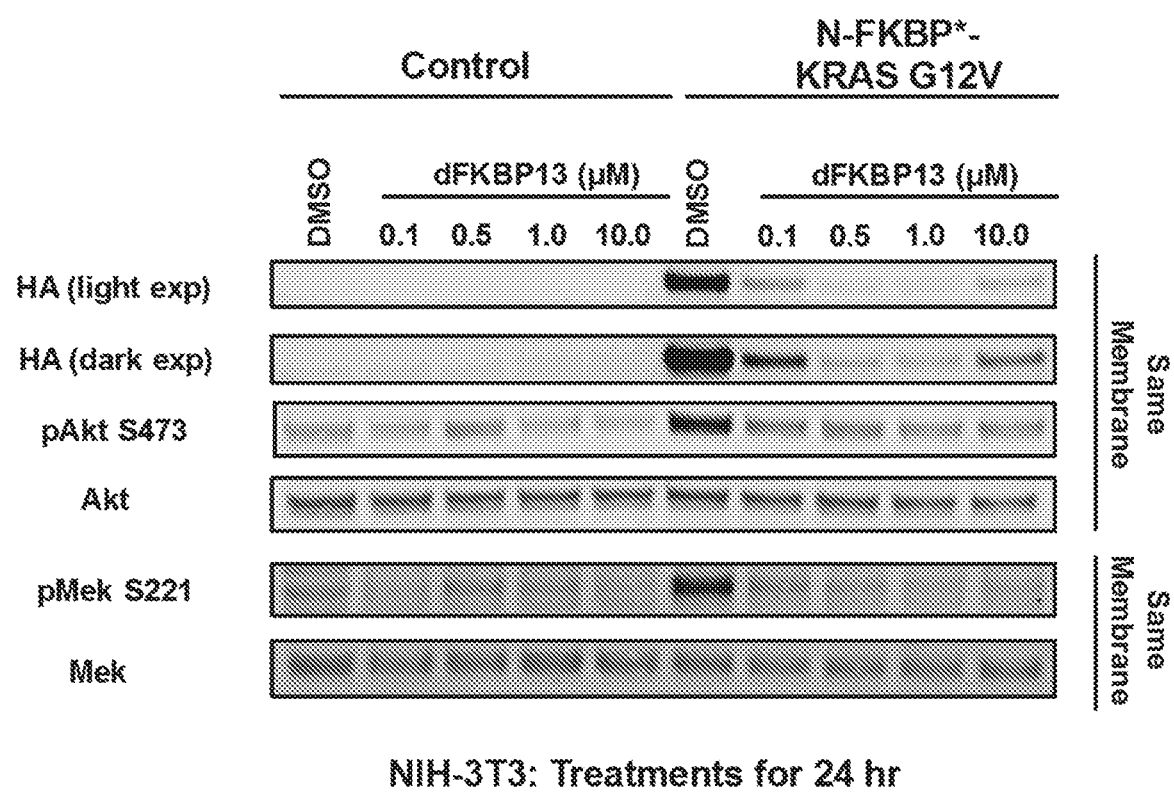
FIG. 13 is an immunoblot of NIH3T3 cells expressing FKBP* fused to the N-terminus of KRASG12V treated with the indicated concentrations of dFKBP13 for 24 hours. Cells were harvested and immunoblotted to measure degradation of FKBP*-KRASG12V and downstream surrogates of KRAS signaling (e.g. pMEK and pAKT). The data suggest that dFKBP13 induces potent degradation of FKBP*-KRASG12V and inhibits downstream signaling potently with an IC50>100 nM.

FIG. 13 illustrates an example confirming targeted degradation of dTAG-KRAS with dFKBP13.

The dFKBP13 heterobifunctional compound potently degrades dTAG-KRAS at nanomolar concentrations. Western blotting of NIH3T3 cells expressing FKBP* fused to the N-terminus of KRAS treated with the indicated concentrations of dFKBP13 for 24 hours. Cells were harvested and immunoblotted to measure degradation of FKBP*-KRAS and downstream surrogates of KRAS signaling (e.g. pMEK and pAKT). The data suggest that dFKBP13 induces potent degradation of FKBP*-KRAS and inhibits downstream signaling potently with an IC50>100 nM.

Example 13

Figure 14:
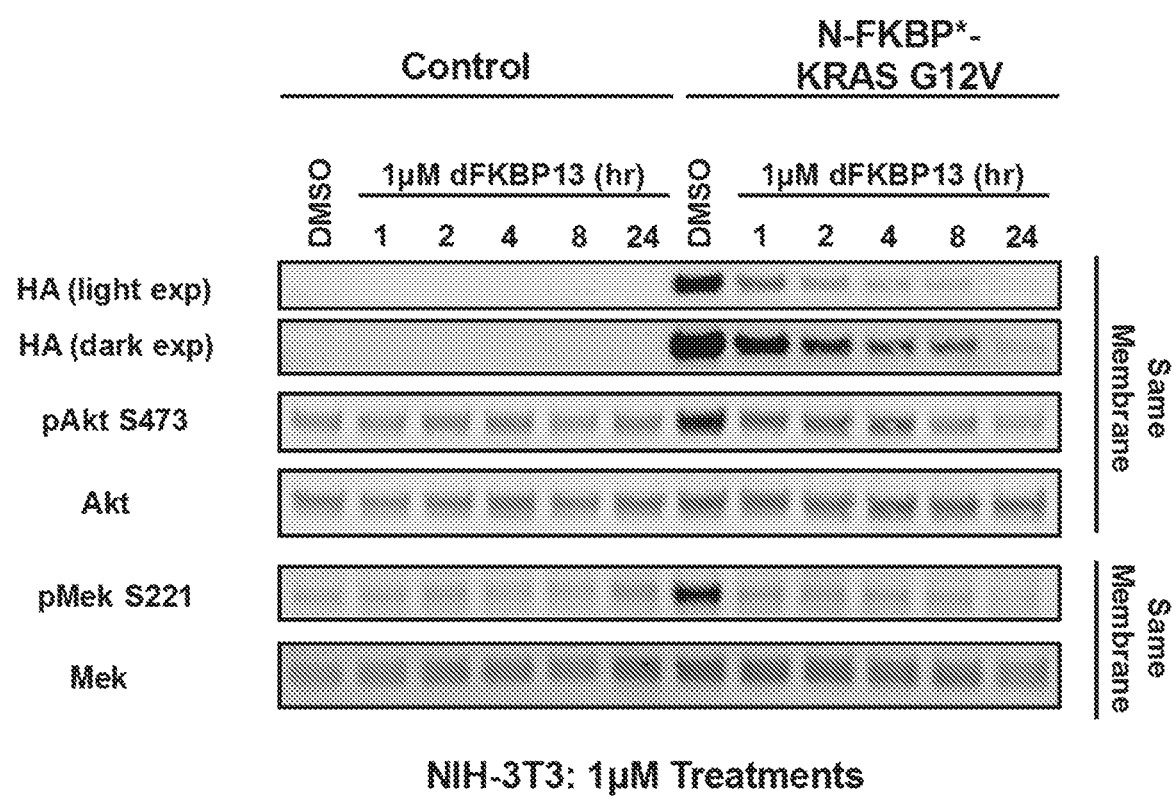
FIG. 14 is an immunoblot of NIH3T3 cells expressing FKBP* fused to the N-terminus of KRASG12V treated with 1 uM dFKBP13 for the indicated time. Cells were harvested and immunoblotted to measure degradation of FKBP*-KRASG12V and downstream surrogates of KRAS signaling (e.g. pMEK and pAKT). Data suggest that dFKBP13 induces potent degradation of FKBP*-KRASG12V and inhibition of downstream signaling as early as 1 hour post treatment.

FIG. 14 illustrates an example of the kinetic control of targeted degradation of dTAG-KRAS with dFKBP13.

To evaluate the kinetic control of targeted degradation of dTAG-KRAS, dFKBP13 was administered by increased duration. Western blotting of NIH3T3 cells expressing FKBP* fused to the N-terminus of KRAS treated with 1 μM dFKBP13 for the indicated time. Cells were harvested and immunoblotted to measure degradation of FKBP*-KRAS and downstream surrogates of KRAS signaling (e.g. pMEK and pAKT). The data suggest that dFKBP13 induces potent degradation of FKBP*-KRAS and inhibition of downstream signaling as early as 1 hour post treatment.

Example 14

Figure 15:
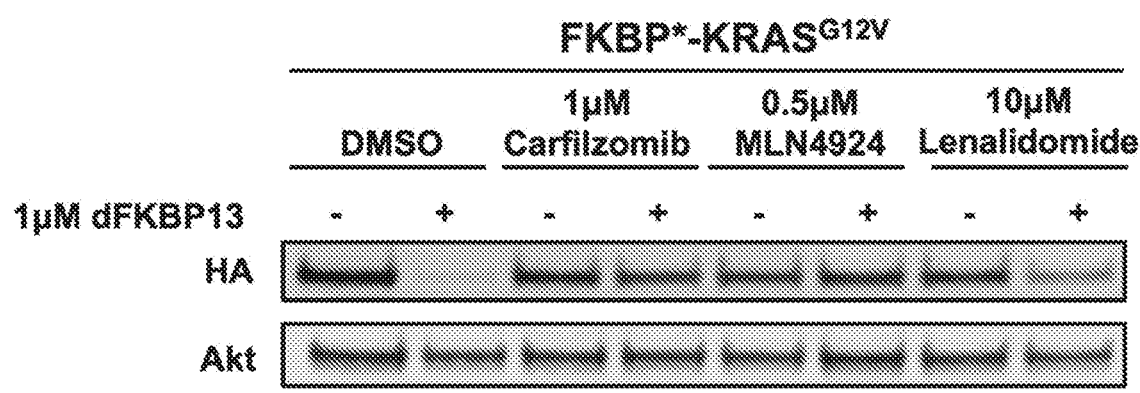
FIG. 15 is an immunoblot of NIH3 T3 cells expressing dTAG-KRASG12V pretreated with 1 uM Carfilzomib (proteasome inhibitor), 0.5 uM MLN4924 (neddylation inhibitor), and 10 uM Lenalidomide (CRBN binding ligand) for two hours prior to a 4 hour treatment with dFKBP13.

FIG. 15 illustrates and example to confirm CRBN- and proteasome-dependent degradation of dTAG-KRASG12V by the heterobifunctional compound dFKBP 13.

NIH3T3 cells (CRBN-WT) were engineered to express dTAG-KRASG12V. Cells were pretreated with 1 uM Carfilzomib (proteasome inhibitor), 0.5 uM MLN4924 (neddylation inhibitor), and 10 uM Lenalidomide (CRBN binding ligand) for two hours prior to a 4 hour treatment with dFKBP13. Lysates were prepared and western immunoblot analysis performed. Degradation of dTAG-KRASG12V by dFKBP13 was rescued by the proteasome inhibitor Carfilzomib, establishing a requirement for proteasome function. Pre-treatment with the NAE1 inhibitor MLN4924 rescued dTAG-KRASG12V expression establishing dependence on CRL activity, as expected for cullin-based ubiquitin ligases that require neddylation for processive E3 ligase activity. Pre-treatment with excess Lenalidomide abolished dFKBP13-dependent dTAG-KRASG12V degradation, confirming the requirement of CRBN engagement for degradation.

Example 15

Figure 16:
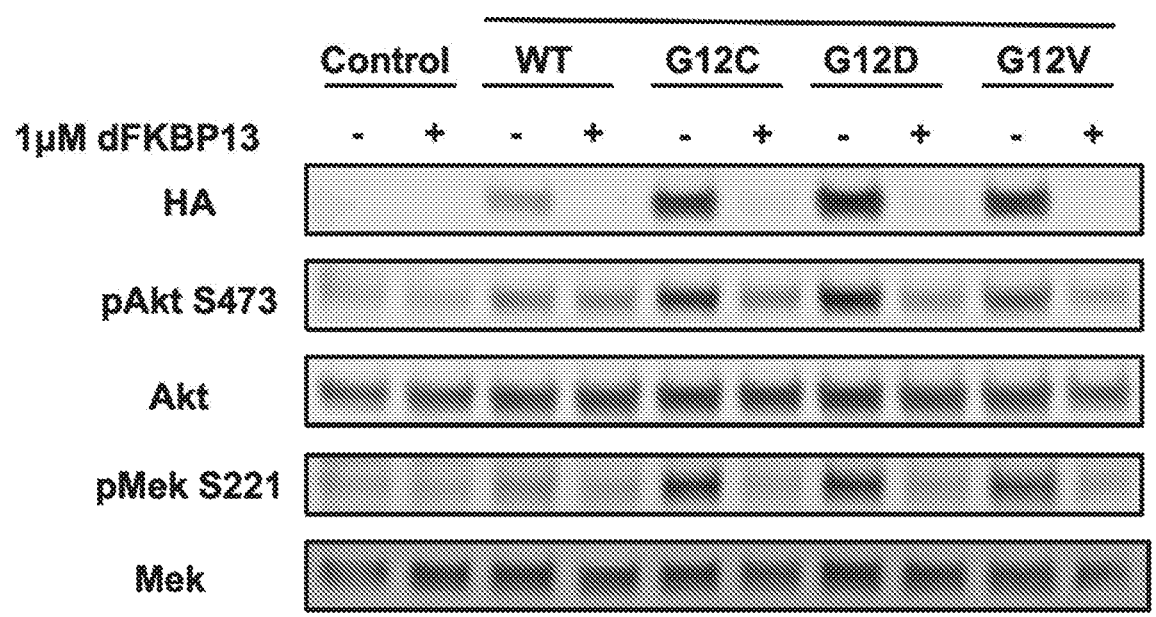
FIG. 16 is an immunoblot of NIH3T3 cells expressing KRAS alleles either WT or mutant forms of amino acid glycine 12 (G12C, G12D, and G12V) treated with 1 uM of dFKBP13 for 24 hours.

FIG. 16 illustrates an example confirming targeted degradation of oncogenic dTAG-KRAS alleles with dFKBP13.

The dFKBP13 heterobifunctional compound potently degrades dTAG-KRAS mutant alleles. NIH3T3 cells were engineered to express KRAS alleles either WT or mutant forms of amino acid glycine 12 (G12C, G12D, and G12V). Western blotting of NIH3T3 cells expressing dTAG fused to the N-terminus of KRAS alleles were treated with 1 uM of dFKBP13 for 24 hours. Cells were harvested and immunoblotted to measure degradation of dTAG-KRAS and downstream surrogates of KRAS signaling (e.g. pMEK and pAKT). The data suggest that dFKBP13 induces potent degradation of WT and mutant KRAS alleles and potently inhibits downstream signaling.

Example 16

Figure 17:
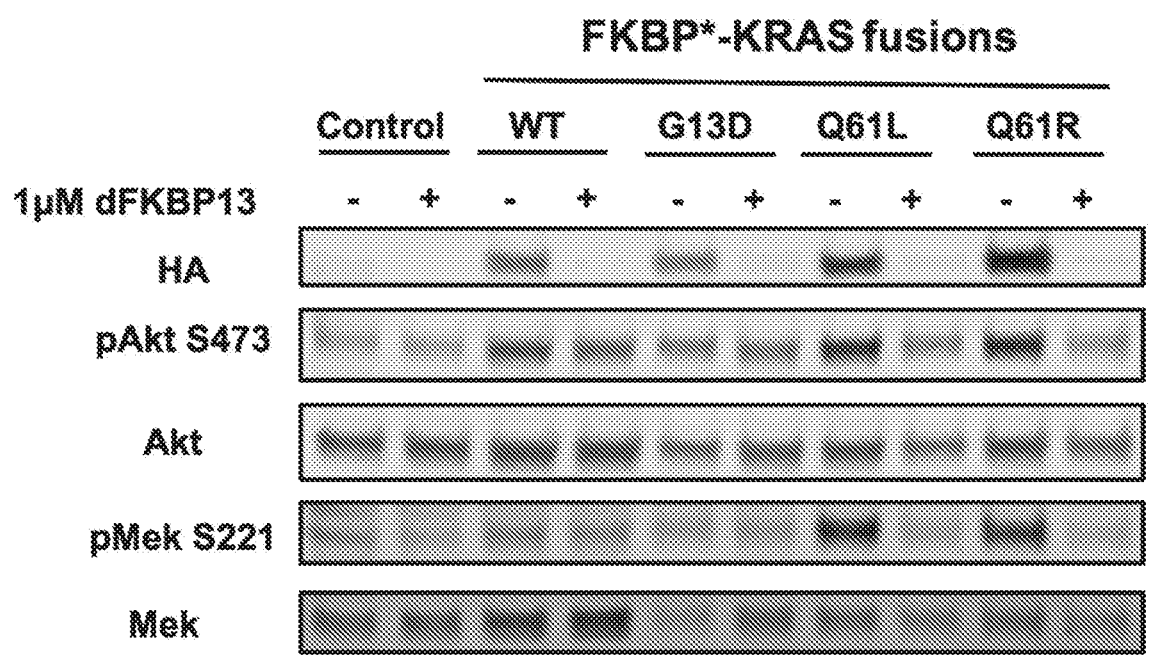
FIG. 17 is an immunoblot of NIH3T3 cells expressing either WT or mutant KRAS alleles (G13D, Q61L, and Q61R) treated with 1 uM of dFKBP13 for 24 hours.
Figure 18A:
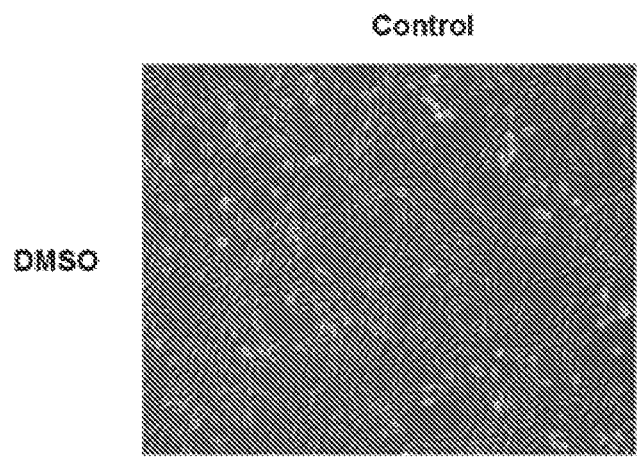
FIG. 18A, FIG. 18B, FIG. 18C, and FIG. 18D are panels of phase contrast images of control NIH3T3 cells or NIH3T3 expressing FKBP* fused to the N-terminus of KRASG12V treated with DMSO of dFKBP13 for 24 hours. Phase contrast images highlight the morphological change induced upon dFKBP13-dependent degradation of FKBP*-KRASG12V.
Figure 18B:
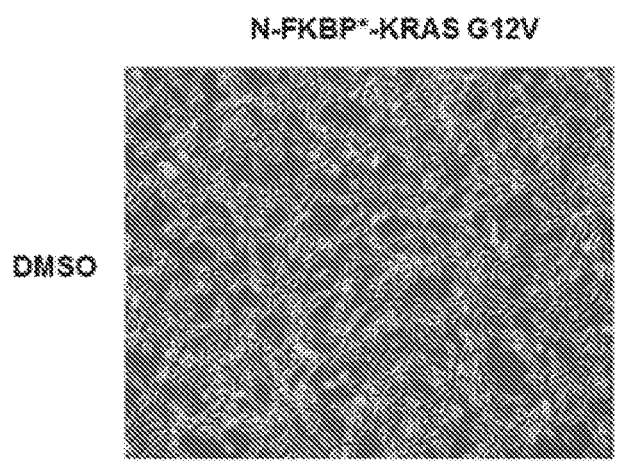
Figure 18C:
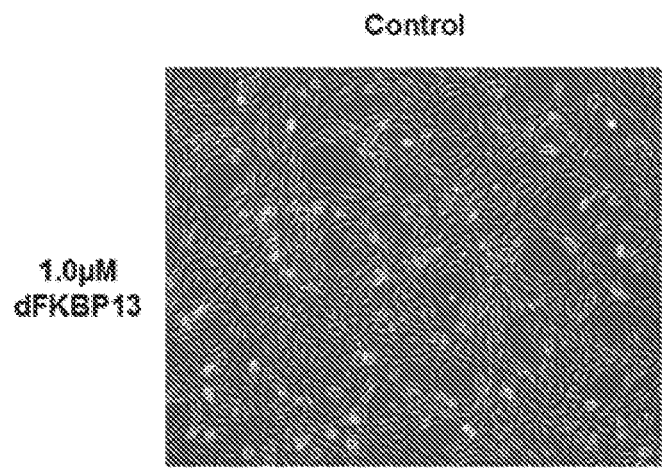
Figure 18D:
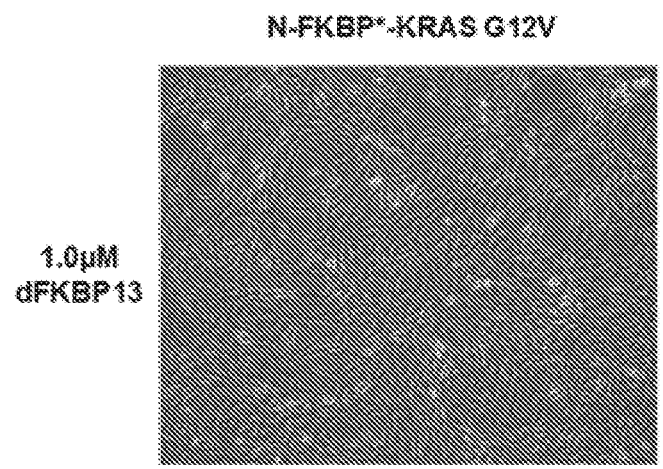
Figure 19A:
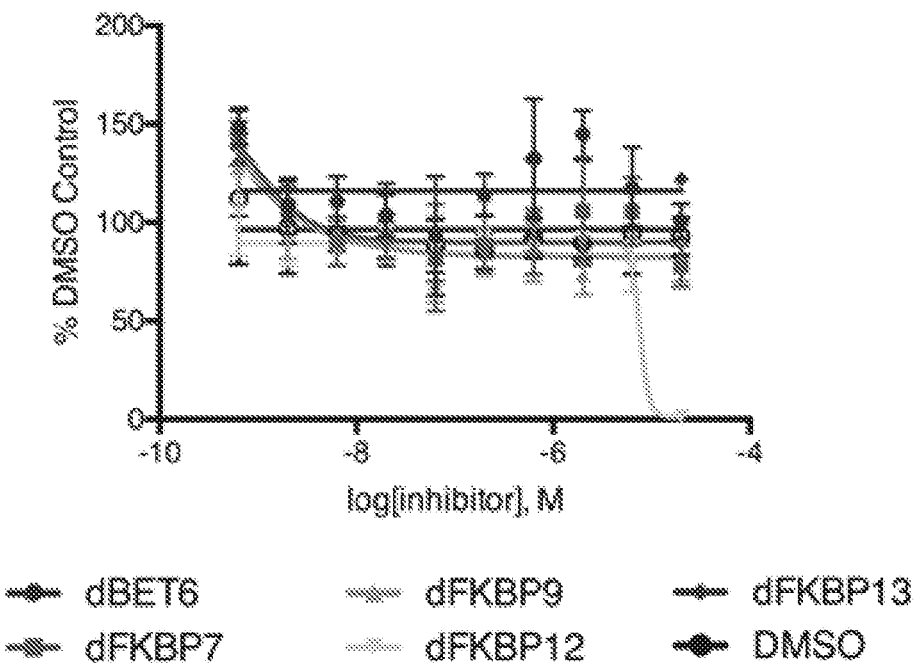
FIG. 19A, FIG. 19B, FIG. 19C, and FIG. 19D are proliferation graphs that measure the effect of dFKBP13 on the growth of NIH3T3 control cells of NIH3T3 expressing FKBP*-KRASG12V. Cells were treated with the indicated concentrations if dFKBPs for 72 hours and cell count measured using an ATPlite assay. The ATPlite 1step luminescence assay measures cell proliferation and cytotoxicity in cells based on the production of light caused by the reaction of ATP with added luciferase and D-luciferin. A decrease in signal indicates a reduction in cell number.
Figure 19B:
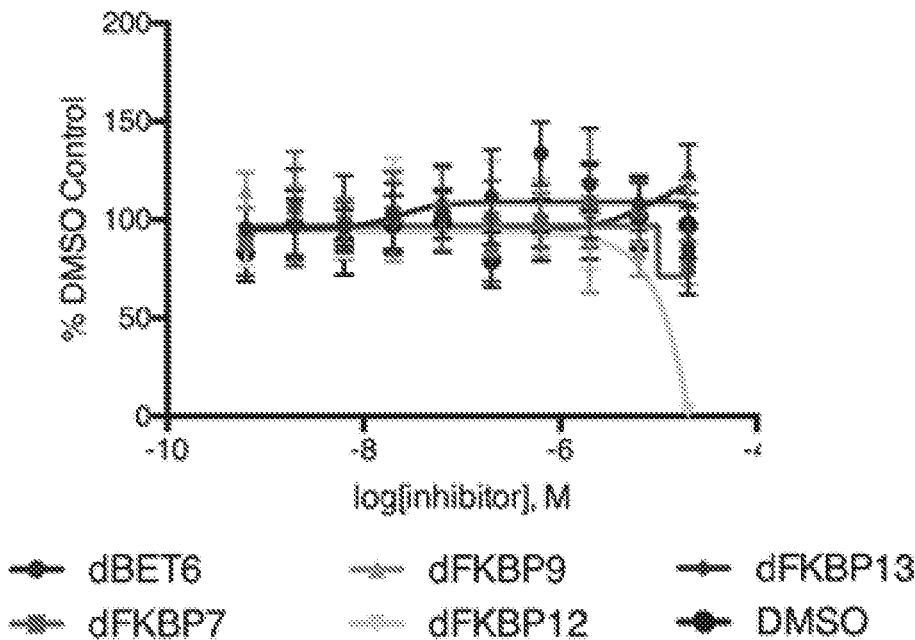
Figure 19C:
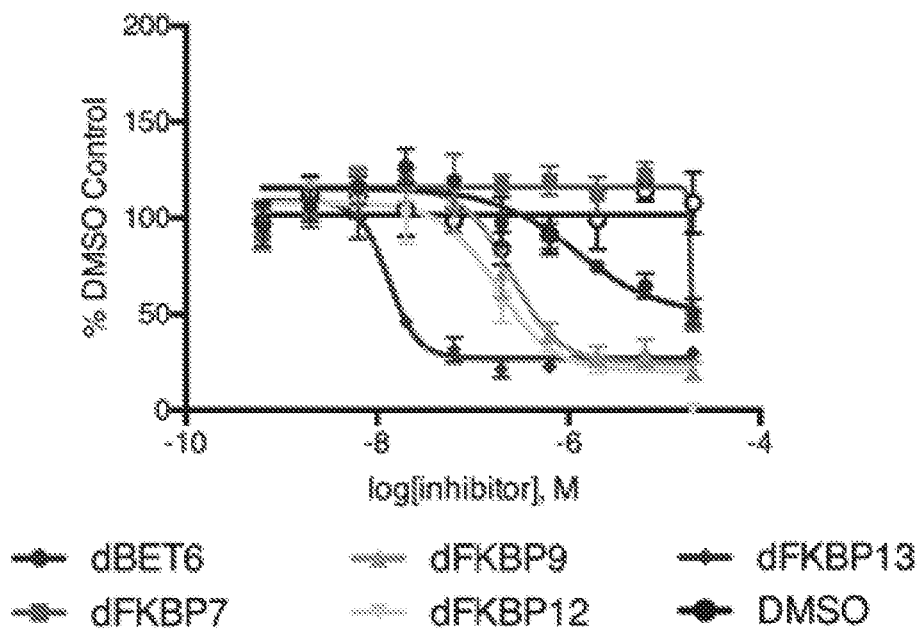
Figure 19D:
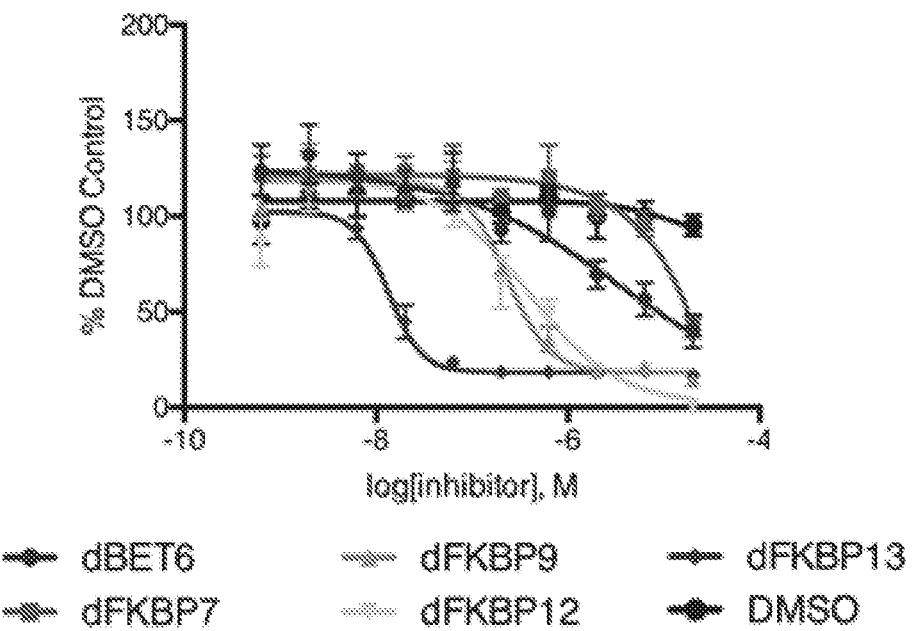

FIG. 17 illustrates an example confirming targeted degradation of oncogenic dTAG-KRAS alleles with dFKBP13.

The dFKBP13 heterobifunctional compound potently degrades dTAG-KRAS mutant alleles. NIH3T3 cells were engineered to express either WT or mutant KRAS alleles (G13D, Q61L, and Q61R). Western blotting of NIH3T3 cells expressing dTAG fused to the N-terminus of KRAS alleles were treated with 1 uM of dFKBP13 for 24 hours. Cells were harvested and immunoblotted to measure degradation of dTAG-KRAS and downstream surrogates of KRAS signaling (e.g. pMEK and pAKT). The data suggest that dFKBP13 induces potent degradation of WT and mutant KRAS alleles and potently inhibits downstream signaling.

Example 17

FIGS. 18A-D illustrates an experiment performed to confirm phenotypical changes induced upon degradation of dTAG-KRAS.

Morphological changes were observed in NIH3T3 cells upon overexpression of dTAG-KRAS as shown by phase contrast imaging. Upon treatment with dFKBP13 for 24 hours, cells morphologically revert back to the wild type (DMSO control) state.

Example 18

FIGS. 19A-D illustrates the phenotypic consequence of dTAG-KRAS degradation on the viability of NIH3T3 cells.

The ATPlite 1-step luminescence assay measures cell proliferation and cytotoxicity in cells based on the production of light caused by the reaction of ATP with added luciferase and D-luciferin. A decrease in signal indicates a reduction in cell number. To evaluate the effect of dFKBP13 on proliferation in NIH3T3 cells expressing dTAG-KRAS, viability was assessed by surrogate measurements of ATP levels. Cells were treated with the indicated concentrations of dFKBPs for 72 hours and cell viability was measured using an ATPlite assay.

Example 19

Figure 20:
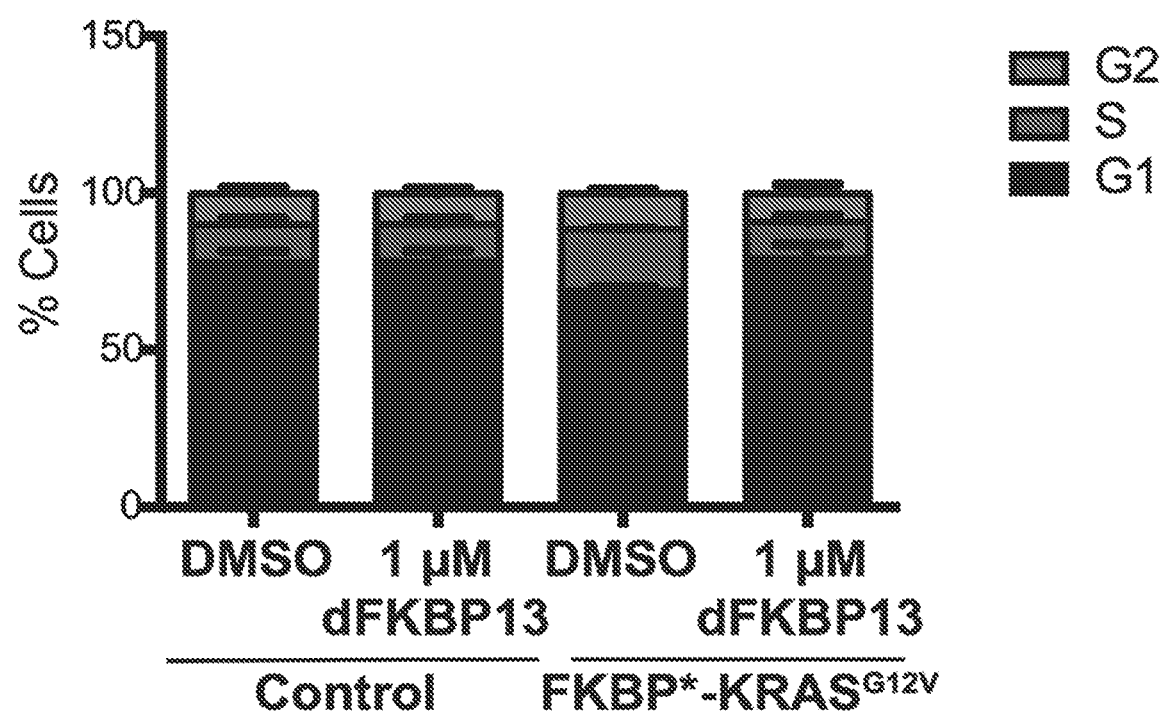
FIG. 20 is a bar graph illustrating NIH3T3 cells expressing dTAG-KRASG12V treated with dFKBP7 and dFKBP13 for 48 hours to induce targeted dTAG-KRASG12V degradation. Fixed cells were stained with propidium iodide and cell cycle analysis was performed.
Figure 21A:
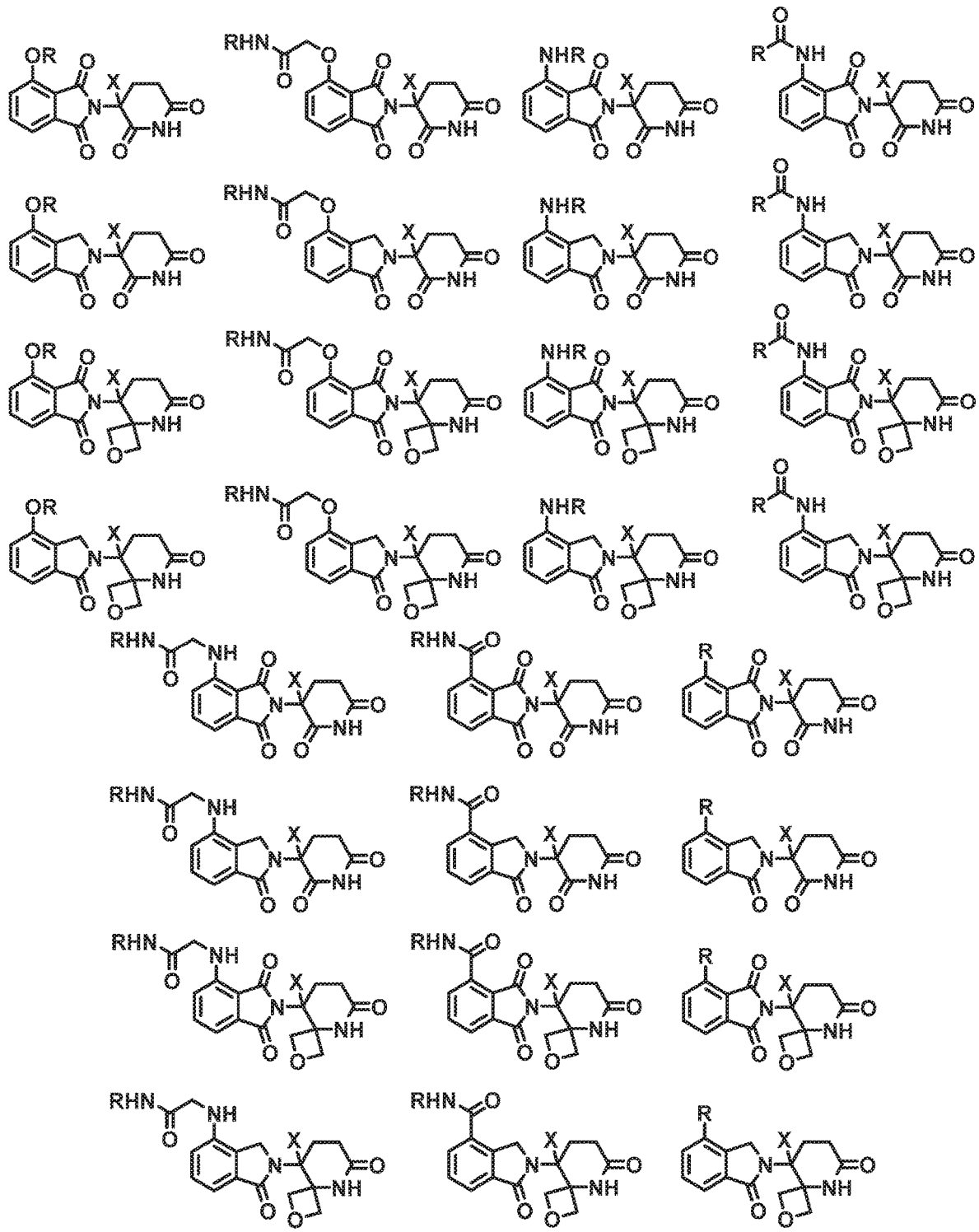
FIG. 21A, FIG. 21B, FIG. 21C, FIG. 21D, FIG. 21E, FIG. 21F, FIG. 21G, FIG. 21H, and FIG. 21I provide examples of Degron moieties for use in the present invention, wherein R is the point of attachment for the Linker and X is as defined herein.
Figure 21B:
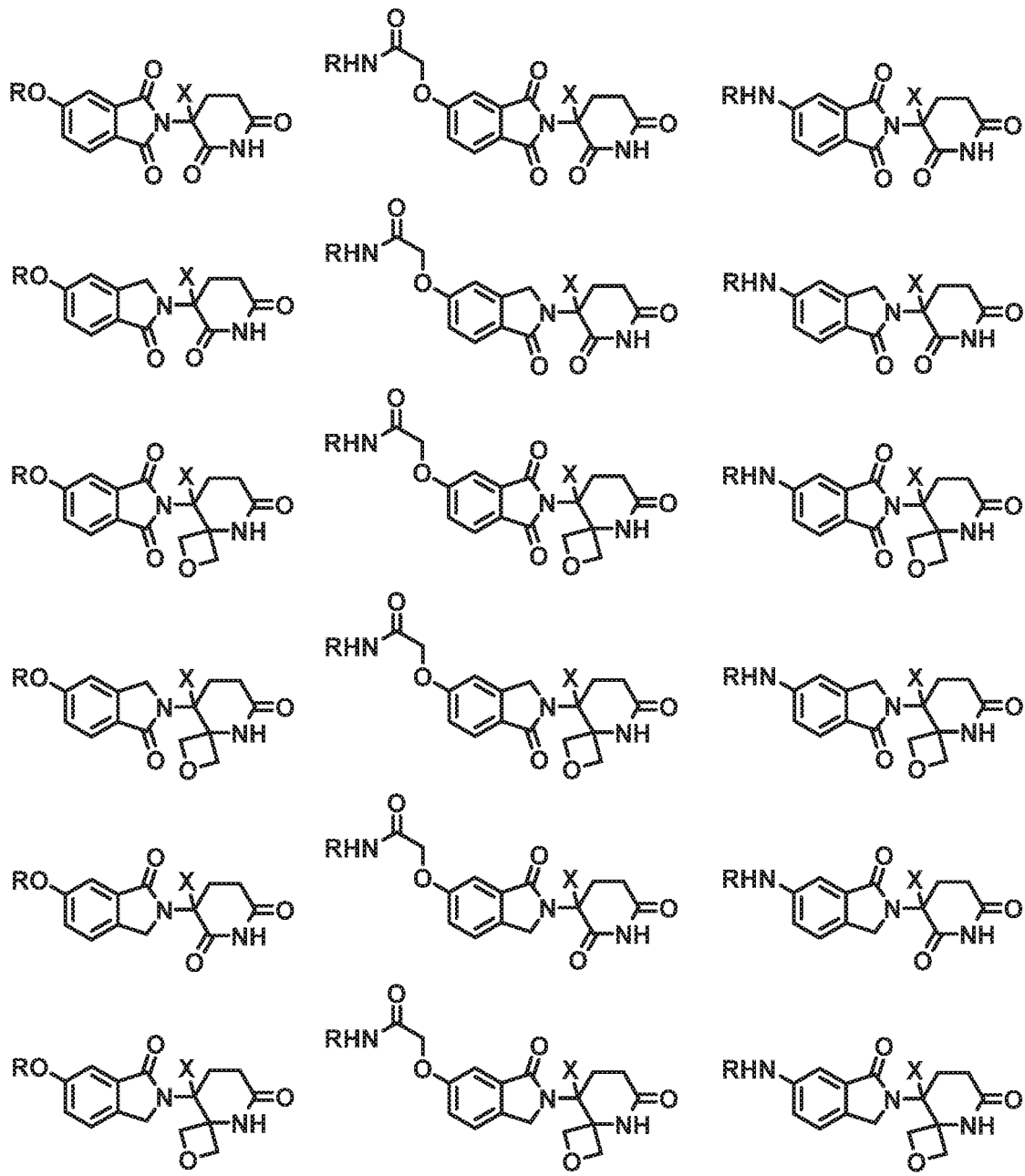
Figure 21C:
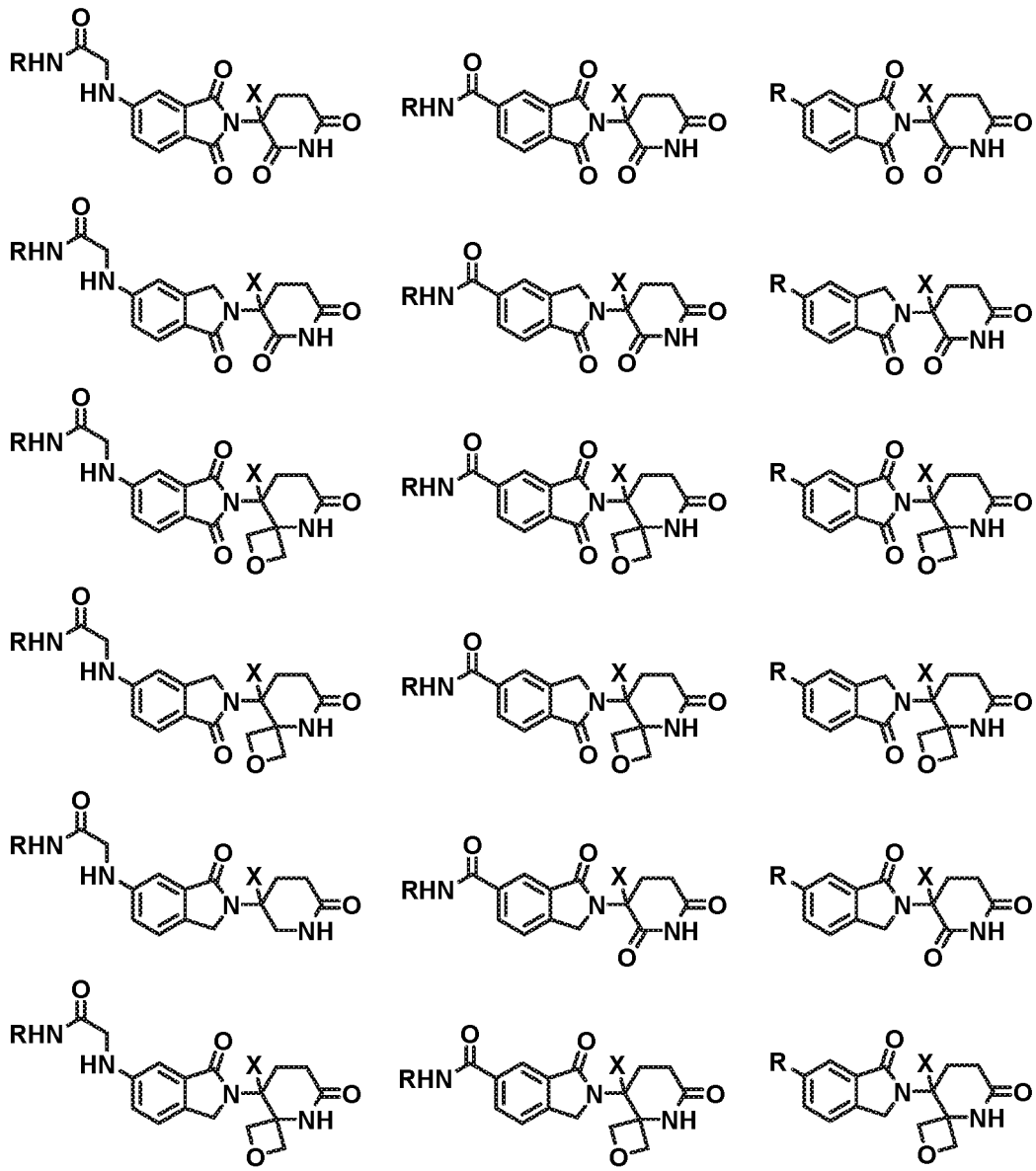
Figure 21D:
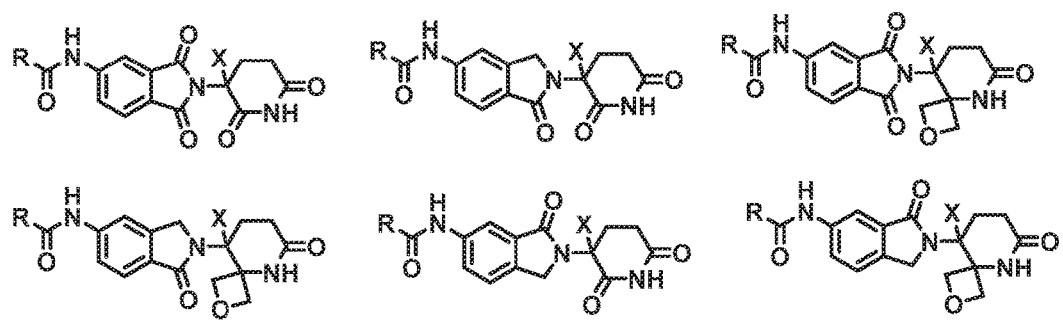
Figure 21E:
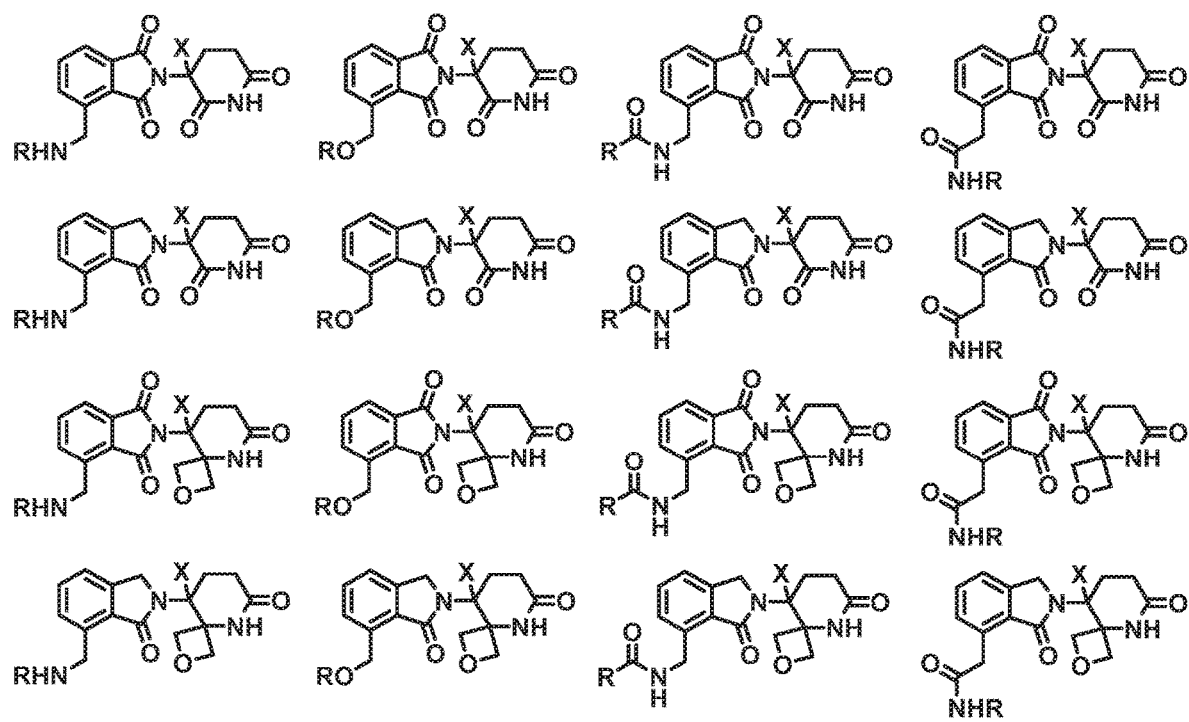
Figure 21F:
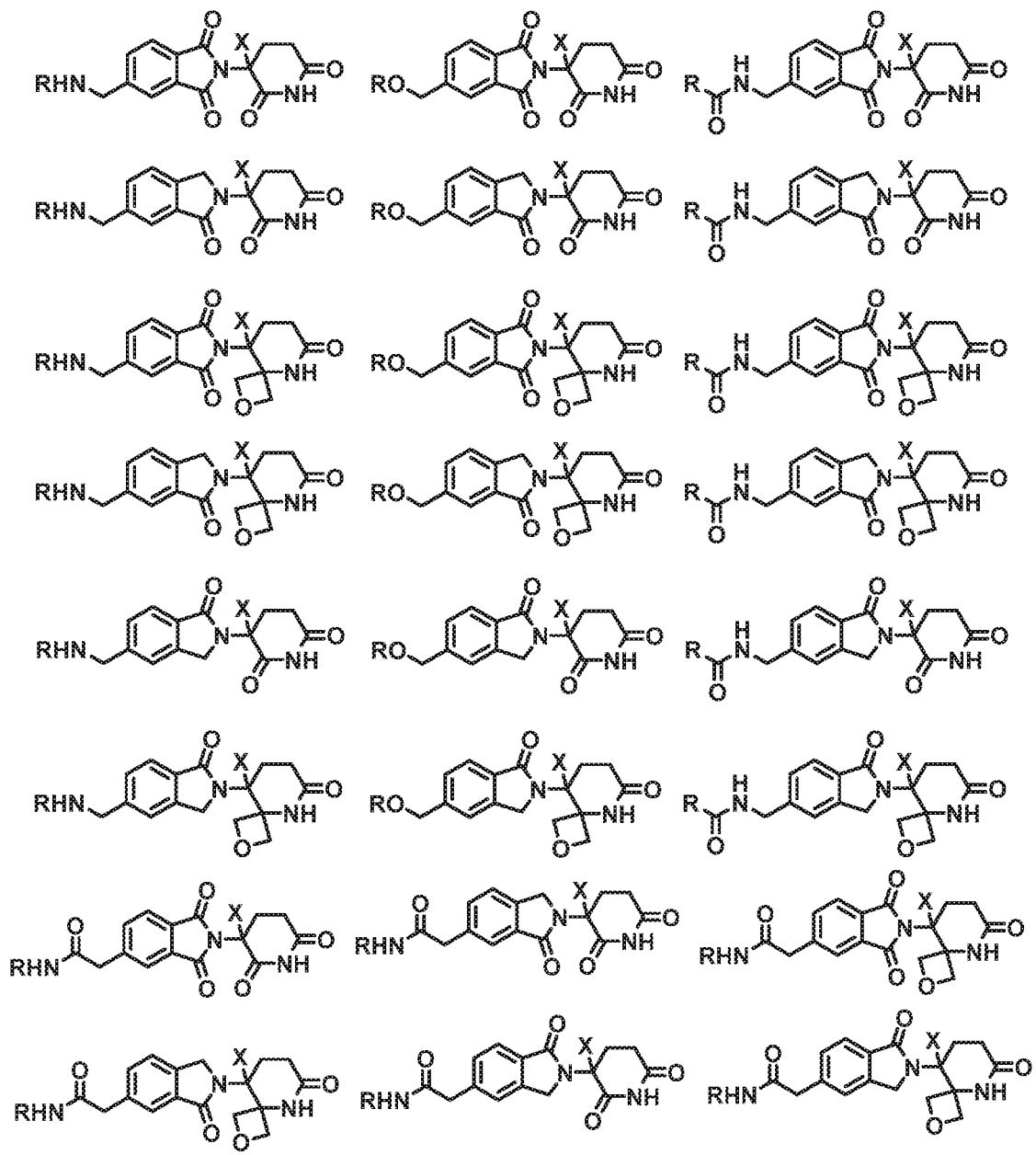
Figure 21G:
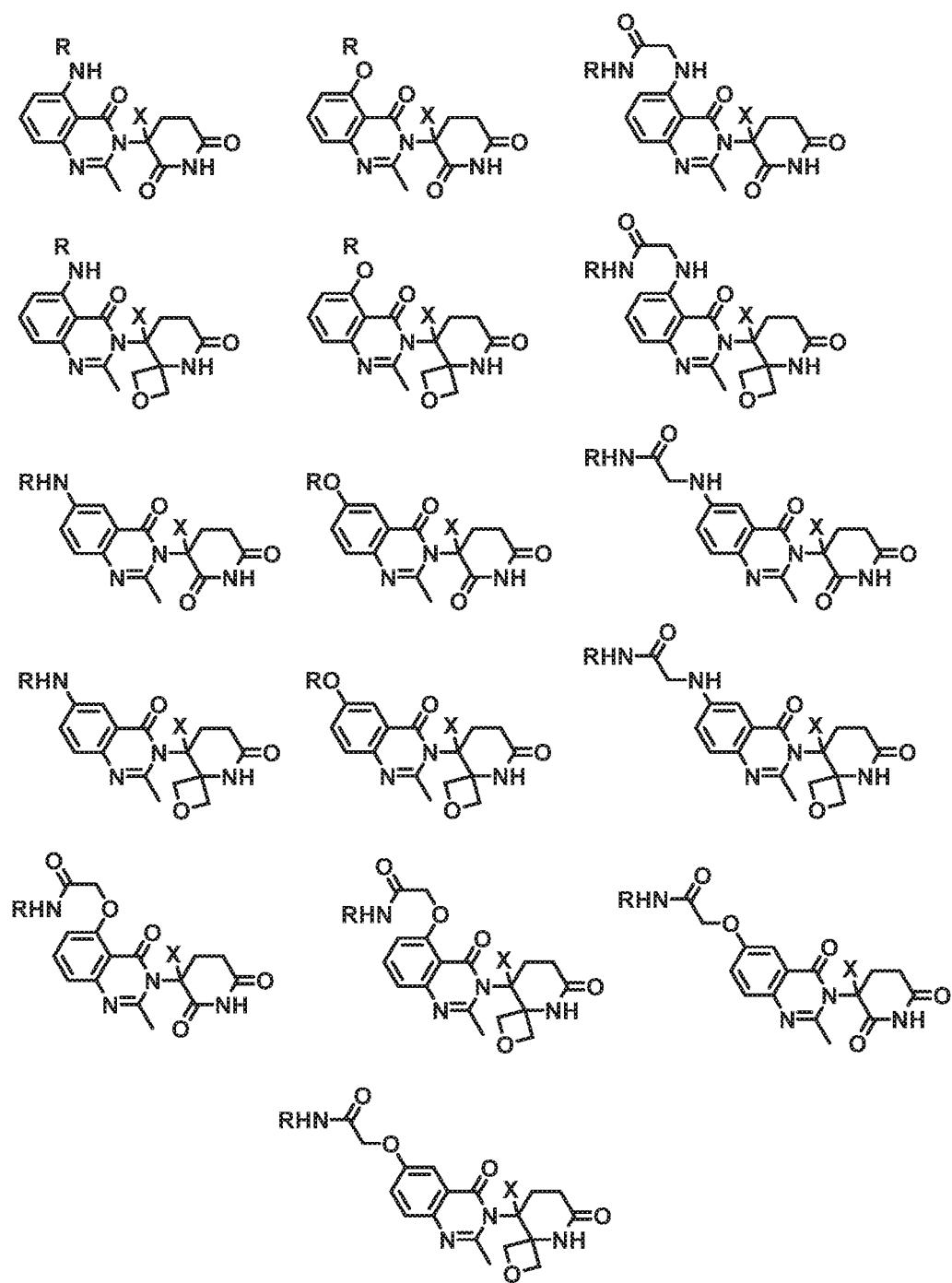
Figure 21H:
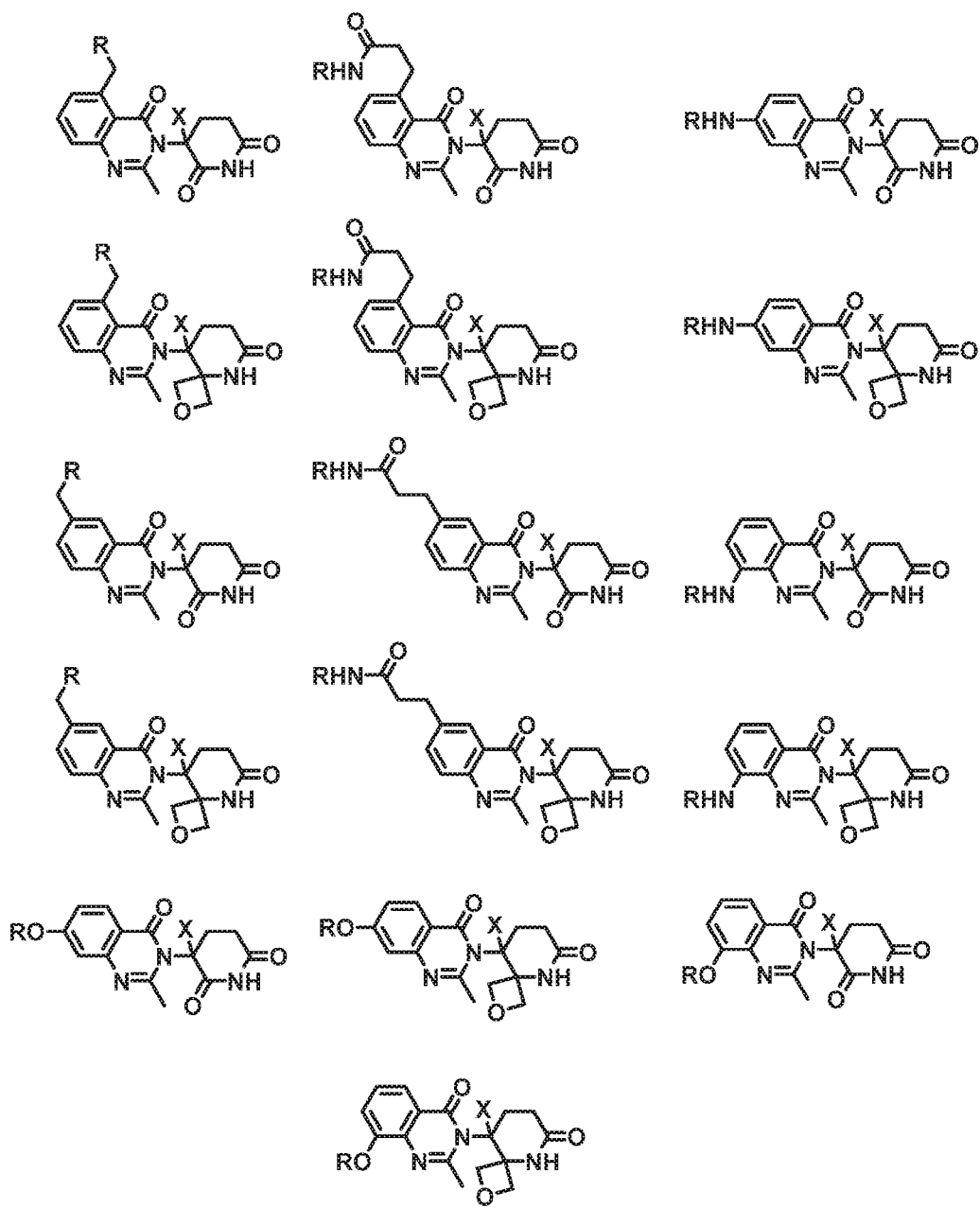
Figure 21I:
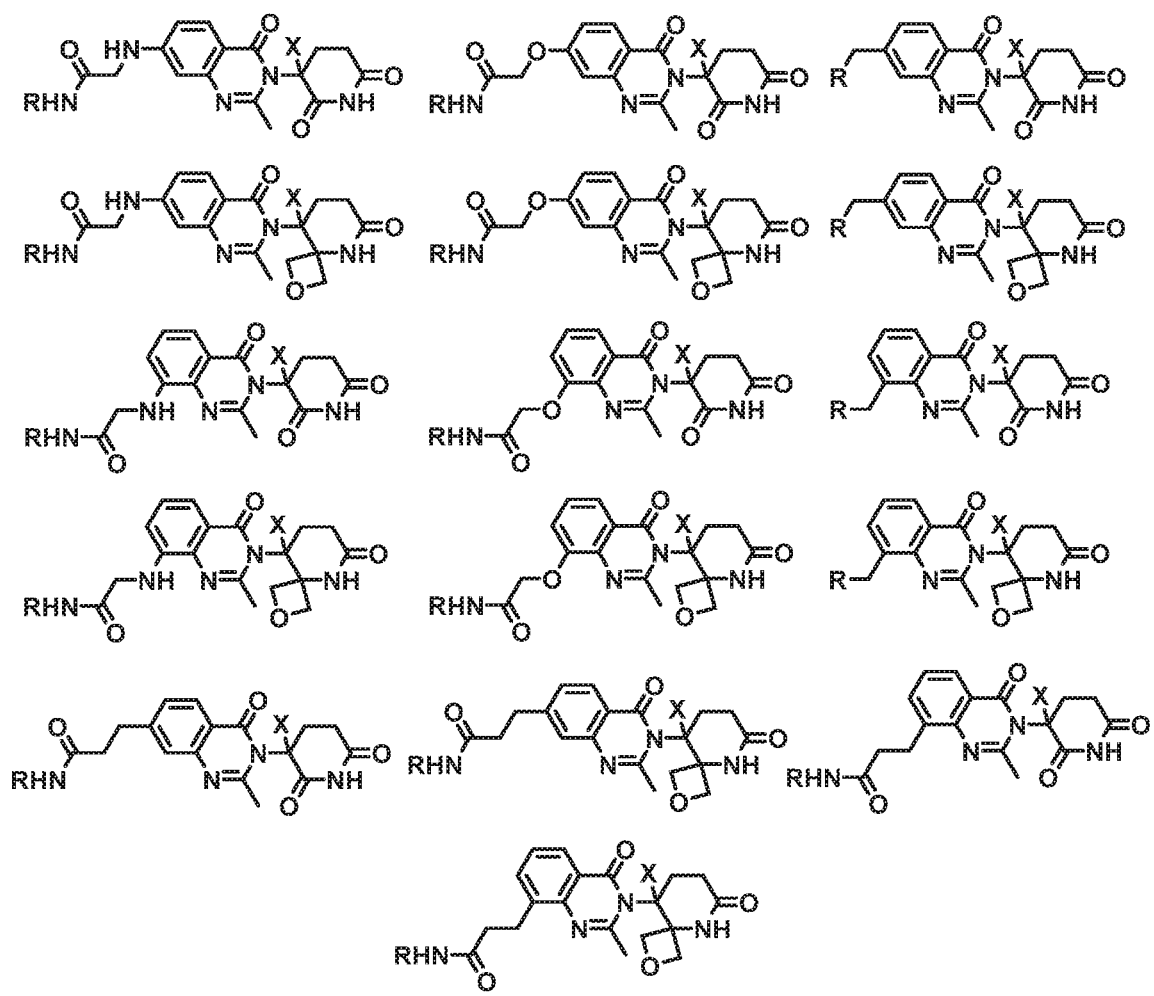

FIG. 20 illustrates the phenotypic consequence of dTAG-KRAS degradation on the cell cycle profile of NIH3T3 cells.

NIH3T3 cells were engineered to express dTAG-KRASG12V. NIH3T3 cells expressing dTAG-KRASG12V were treated with dFKBP7 and dFKBP13 for 48 hours to induce targeted dTAG-KRASG12V degradation. Fixed cells were stained with propidium iodide and cell cycle analysis was performed. Treatment with both dFKBP7 and dFKBP13 resulted in diminished S-phase entry, in agreement with the biological role of endogenous KRASG12V in driving S-phase entry. These data are consistent with the observed effect on dTAG-KRASG12V degradation on cell viability.

Example 20: Delivery of CRISPR-CAS9 and Homologous Donor Vectors to the Liver

Targeted gene therapy can be accomplished using both viral and non-viral approaches such as adeno-associated or lentivirus, or lipid-based formulations. For example, a single bicistronic vector system is used to deliver sgRNA targeting either PCKS9 or CTNNB1 with CAS9 being expressed from a neighboring promoter. Both the CRISPR vector and donor homology plasmid are encapsulated in Poly (beta-amino esters) (PBAEs) cationic polymers that provide the added specificity of cancer cell targeting vs. normal hepatocytes. PBAE nanoparticles are also biodegradable, or degrade by hydrolysis, thus releasing plasmid DNAs in the cytoplasm of tumor cells upon internalization. PBAE-encapsulated plasmid DNAs will be delivery locally via intrahepatic artery administration and systemically via intravenous injection. Upon successful recombination, and following administration of a heterobifunctional compound, local core biopsies would be taken to confirm degradation of either the PCKS9 gene product or the CTNNB1 gene product.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

We claim:

1. A transformed cell comprising:
a genomically integrated nucleic acid sequence encoding a heterobifunctional compound targeting protein (dTAG) capable of being bound by a heterobifunctional compound;
wherein the dTAG comprises an amino acid sequence derived from EGFR, BCR-ABL, ALK, JAK2, BRAF, or Src, wherein the dTAG comprises the amino acid sequence selected from SEQ. ID. NO.:53-57 and 59-63;
wherein the nucleic acid sequence encoding the dTAG is integrated genomically in-frame in a 5' or 3' orientation with a nucleic acid sequence of a gene encoding an endogenous protein;
wherein expression of the gene encoding an endogenous protein produces an endogenous protein-dTAG hybrid protein;
wherein the heterobifunctional compound is capable of binding to a) the endogenous protein-dTAG hybrid protein through the dTAG and b) a ubiquitin ligase in a manner that brings the endogenous protein-dTAG hybrid protein into proximity of the ubiquitin ligase;
wherein the endogenous protein-dTAG hybrid protein is ubiquitinated and then degraded by a proteasome.

2. The transformed cell of claim 1, wherein the cell is a human cell.

3. The transformed cell of claim 2, wherein the human cell is a liver cell.

4. The transformed cell of claim 1, wherein the nucleic acid sequence encoding the heterobifunctional compound targeting protein is inserted in frame with a gene encoding an endogenous protein associated with a disease that is a result of a gain of function mutation, amplification or increased expression, a monogenetic disease, a proteopathy, or a combination thereof.

5. The transformed cell of claim 1, further comprising a nucleic acid sequence encoding a CRISPR RNA-guided endonuclease.

6. The transformed cell of claim 5, wherein the CRISPR RNA-guided endonuclease is selected from the group consisting of Cas1, Cas IB, Cas2, Cas3, Cas4, Cas5, Cash, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cpf1.

7. The transformed cell of claim 6, wherein the nucleic acid encodes a Cas9 endonuclease comprised of an amino acid sequence of SEQ. ID. NO.: 52.

8. The transformed cell of claim 1, wherein the heterobifunctional compound targeting protein does not interfere with the function of the endogenously expressed protein.

9. A method of modulating protein expression in a subject comprising:
administering to the subject an effective amount of a heterobifunctional compound;
wherein the subject has one or more cells that have been transformed with a nucleic acid sequence encoding a heterobifunctional compound targeting protein (dTAG);
wherein the dTAG comprises an amino acid sequence derived from EGFR, BCR-ABL, ALK, JAK2, BRAF, or Src, wherein the dTAG comprises the amino acid sequence selected from SEQ. ID. NO.:53-57 and 59-63;
wherein the nucleic acid sequence encoding the dTAG is integrated genomically in-frame in a 5' or 3' orientation with a nucleic acid sequence of an endogenous protein associated with a disease;
wherein the insertion of the nucleic acid sequence encoding the dTAG into the genomic sequence results in an endogenous protein-dTAG hybrid protein upon expression;
wherein the heterobifunctional compound binds to a) the endogenous protein-dTAG hybrid protein through the dTAG and b) a ubiquitin ligase in a manner that brings the endogenous protein-dTAG hybrid protein into proximity of the ubiquitin ligase,
wherein the endogenous protein-dTAG hybrid protein is ubiquitinated and then degraded by a proteasome.

10. The method of claim 9, wherein the one or more transformed cells is a human cell.

11. The method of claim 10, wherein the human cell is a liver cell.

12. The method of claim 9, wherein the nucleic acid sequence encoding the heterobifunctional compound targeting protein is inserted in frame with a gene encoding an endogenous protein associated with a disease that is a result of a gain of function mutation, amplification or increased expression, a monogenetic disease, a proteopathy, or a combination thereof.

13. The method of claim 9, wherein the one or more transformed cells further comprises a nucleic acid sequence encoding a CRISPR RNA-guided endonuclease.

14. The method of claim 13, wherein the CRISPR RNA-guided endonuclease is selected from the group consisting of Cas1, Cas IB, Cas2, Cas3, Cas4, Cas5, Cash, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cpf1.

15. The method of claim 14, wherein the nucleic acid encodes a Cas9 endonuclease comprised of an amino acid sequence of SEQ. ID. NO.: 52.

16. The method of claim 9, wherein the heterobifunctional compound targeting protein does not interfere with the function of the endogenously expressed protein.

17. A method of reducing protein overexpression in a subject comprising:
   administering to the subject an effective amount of a heterobifunctional compound;
   wherein the subject has one or more cells that have been transformed with a nucleic acid sequence encoding a heterobifunctional compound targeting protein (dTAG);
   wherein the dTAG comprises an amino acid sequence derived from EGFR, BCR-ABL, ALK, JAK2, BRAF, or Src, wherein the dTAG comprises the amino acid sequence selected from SEQ. ID. NO.:53-57 and 59-63;
   wherein the nucleic acid sequence encoding the dTAG is integrated genomically in-frame in a 5' or 3' orientation with a nucleic acid sequence of an endogenous protein associated with a disease due to overexpression of a protein;
   wherein the insertion of the nucleic acid sequence encoding the dTAG into the genomic sequence results in an endogenous protein-dTAG hybrid protein upon expression;
   wherein the heterobifunctional compound binds to a) the endogenous protein-dTAG hybrid protein through the dTAG and b) a ubiquitin ligase in a manner that brings the endogenous protein-dTAG hybrid protein into proximity of the ubiquitin ligase, wherein the endogenous protein-dTAG hybrid protein is ubiquitinated and then degraded by a proteasome.

18. The method of claim 17, wherein the one or more transformed cells is a human cell.

19. The method of claim 18, wherein the human cell is a liver cell.

20. The method of claim 17, wherein the nucleic acid sequence encoding the heterobifunctional compound targeting protein is inserted in frame with a gene encoding an endogenous protein associated with a disease that is a result of a gain of function mutation, amplification or increased expression, a monogenetic disease, a proteopathy, or a combination thereof.

21. The method of claim 17, wherein the one or more transformed cells further comprises a nucleic acid sequence encoding a CRISPR RNA-guided endonuclease.

22. The method of claim 21, wherein the CRISPR RNA-guided endonuclease is selected from Cas1, Cas IB, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cpf1.

23. The method of claim 22, wherein the nucleic acid encodes a Cas9 endonuclease comprised of an amino acid sequence of SEQ. ID. NO.: 52.

24. The method of claim 17, wherein the heterobifunctional compound targeting protein does not interfere with the function of the endogenously expressed protein.

\* \* \* \* \*